US012577202B2

(12) United States Patent
Fleetham et al.

(10) Patent No.: US 12,577,202 B2
(45) Date of Patent: Mar. 17, 2026

(54) ORGANIC ELECTROLUMINESCENT MATERIALS AND DEVICES

(71) Applicant: Universal Display Corporation, Ewing, NJ (US)

(72) Inventors: Tyler Fleetham, Yardley, PA (US); Eric A. Margulies, Philadelphia, PA (US); Bin Ma, Plainsboro, NJ (US); Pierre-Luc T. Boudreault, Pennington, NJ (US); Bert Alleyne, Newtown, PA (US); Ting-Chih Wang, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 692 days.

(21) Appl. No.: 17/864,455

(22) Filed: Jul. 14, 2022

(65) Prior Publication Data

US 2022/0399517 A1 Dec. 15, 2022

Related U.S. Application Data

(63) Continuation-in-part of application No. 17/672,895, filed on Feb. 16, 2022, and a continuation-in-part of application No. 17/672,934, filed on Feb. 16, 2022.

(Continued)

(51) Int. Cl.

*H01L 51/50* (2006.01)
*C07D 209/86* (2006.01)

(Continued)

(52) U.S. Cl.

CPC .......... *C07D 209/86* (2013.01); *H10K 50/11* (2023.02); *H10K 85/342* (2023.02);

(Continued)

(58) Field of Classification Search

None

See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |

(Continued)

FOREIGN PATENT DOCUMENTS

| | | |
|---|---|---|
| CN | 101308905 | 11/2008 |
| CN | 108395455 | 8/2018 |

(Continued)

OTHER PUBLICATIONS

Liu, X., et al., "Isotope Effect in the Magento-Optoelectronic Response of Organic Light-Emitting Diodes Based on Donor-Acceptor Exciplexes," Adv. Mater., 2020, 32, 2004421, pp. 1-8.

(Continued)

*Primary Examiner* — Gregory D Clark

(74) *Attorney, Agent, or Firm* — DUANE MORRIS LLP

(57) ABSTRACT

The present disclosure provides for an organic electroluminescent device (OLED) including an anode; a cathode; and an emissive layer, disposed between the anode and the cathode. The emissive layer includes a phosphorescent dopant, a first host, and a second host, wherein the first host transports holes, the second host transports electrons, and the first host is fully or partially deuterated. Consumer products that include the OLED are also provided.

19 Claims, 2 Drawing Sheets

Related U.S. Application Data

(60) Provisional application No. 63/313,545, filed on Feb. 24, 2022, provisional application No. 63/229,748, filed on Aug. 5, 2021, provisional application No. 63/220,429, filed on Jul. 9, 2021, provisional application No. 63/154,320, filed on Feb. 26, 2021.

(51) Int. Cl.

| | |
|---|---|
| ***H10K 50/11*** | (2023.01) |
| ***H10K 85/30*** | (2023.01) |
| ***H10K 85/40*** | (2023.01) |
| ***H10K 85/60*** | (2023.01) |
| *H10K 101/40* | (2023.01) |

(52) U.S. Cl.

CPC ......... *H10K 85/346* (2023.02); *H10K 85/361* (2023.02); *H10K 85/40* (2023.02); *H10K 85/615* (2023.02); *H10K 85/622* (2023.02); *H10K 85/624* (2023.02); *H10K 85/652* (2023.02); *H10K 85/654* (2023.02); *H10K 85/657* (2023.02); *H10K 85/6572* (2023.02); *H10K 85/6574* (2023.02); *H10K 85/6576* (2023.02); *H10K 85/658* (2023.02); *C07B 2200/05* (2013.01); *H10K 2101/40* (2023.02)

(56) References Cited

U.S. PATENT DOCUMENTS

| | | | | |
|---|---|---|---|---|
| 5,247,190 | A | 9/1993 | Friend et al. | |
| 5,703,436 | A | 12/1997 | Forrest et al. | |
| 5,707,745 | A | 1/1998 | Forrest et al. | |
| 5,834,893 | A | 11/1998 | Bulovic et al. | |
| 5,844,363 | A | 12/1998 | Gu et al. | |
| 6,013,982 | A | 1/2000 | Thompson et al. | |
| 6,087,196 | A | 7/2000 | Sturm et al. | |
| 6,091,195 | A | 7/2000 | Forrest et al. | |
| 6,097,147 | A | 8/2000 | Baldo et al. | |
| 6,294,398 | B1 | 9/2001 | Kim et al. | |
| 6,303,238 | B1 | 10/2001 | Thompson et al. | |
| 6,337,102 | B1 | 1/2002 | Forrest et al. | |
| 6,468,819 | B1 | 10/2002 | Kim et al. | |
| 6,528,187 | B1 | 3/2003 | Okada | |
| 6,687,266 | B1 | 2/2004 | Ma et al. | |
| 6,835,469 | B2 | 12/2004 | Kwong et al. | |
| 6,921,915 | B2 | 7/2005 | Takiguchi et al. | |
| 7,087,321 | B2 | 8/2006 | Kwong et al. | |
| 7,090,928 | B2 | 8/2006 | Thompson et al. | |
| 7,154,114 | B2 | 12/2006 | Brooks et al. | |
| 7,250,226 | B2 | 7/2007 | Tokito et al. | |
| 7,279,704 | B2 | 10/2007 | Walters et al. | |
| 7,332,232 | B2 | 2/2008 | Ma et al. | |
| 7,338,722 | B2 | 3/2008 | Thompson et al. | |
| 7,393,599 | B2 | 7/2008 | Thompson et al. | |
| 7,396,598 | B2 | 7/2008 | Takeuchi et al. | |
| 7,431,968 | B1 | 10/2008 | Shtein et al. | |
| 7,445,855 | B2 | 11/2008 | Mackenzie et al. | |
| 7,534,505 | B2 | 5/2009 | Lin et al. | |
| 2002/0034656 | A1 | 3/2002 | Thompson et al. | |
| 2002/0134984 | A1 | 9/2002 | Igarashi | |
| 2002/0158242 | A1 | 10/2002 | Son et al. | |
| 2003/0138657 | A1 | 7/2003 | Li et al. | |
| 2003/0152802 | A1 | 8/2003 | Tsuboyama et al. | |
| 2003/0162053 | A1 | 8/2003 | Marks et al. | |
| 2003/0175553 | A1 | 9/2003 | Thompson et al. | |
| 2003/0230980 | A1 | 12/2003 | Forrest et al. | |
| 2004/0036077 | A1 | 2/2004 | Ise | |
| 2004/0137267 | A1 | 7/2004 | Igarashi et al. | |
| 2004/0137268 | A1 | 7/2004 | Igarashi et al. | |
| 2004/0174116 | A1 | 9/2004 | Lu et al. | |
| 2005/0025993 | A1 | 2/2005 | Thompson et al. | |
| 2005/0089715 | A1 | 4/2005 | Cosimbescu | |
| 2005/0112407 | A1 | 5/2005 | Ogasawara et al. | |
| 2005/0127823 | A1 | 6/2005 | Iwakuma | |
| 2005/0238919 | A1 | 10/2005 | Ogasawara | |
| 2005/0244673 | A1 | 11/2005 | Satoh et al. | |
| 2005/0260441 | A1 | 11/2005 | Thompson et al. | |
| 2005/0260449 | A1 | 11/2005 | Walters et al. | |
| 2006/0008670 | A1 | 1/2006 | Lin et al. | |
| 2006/0202194 | A1 | 9/2006 | Jeong et al. | |
| 2006/0240279 | A1 | 10/2006 | Adamovich et al. | |
| 2006/0251923 | A1 | 11/2006 | Lin et al. | |
| 2006/0263635 | A1 | 11/2006 | Ise | |
| 2006/0280965 | A1 | 12/2006 | Kwong et al. | |
| 2007/0190359 | A1 | 8/2007 | Knowles et al. | |
| 2007/0278938 | A1 | 12/2007 | Yabunouchi et al. | |
| 2008/0015355 | A1 | 1/2008 | Schafer et al. | |
| 2008/0018221 | A1 | 1/2008 | Egen et al. | |
| 2008/0106190 | A1 | 5/2008 | Yabunouchi et al. | |
| 2008/0124572 | A1 | 5/2008 | Mizuki et al. | |
| 2008/0220265 | A1 | 9/2008 | Xia et al. | |
| 2008/0286605 | A1 | 11/2008 | Takeda | |
| 2008/0297033 | A1 | 12/2008 | Knowles et al. | |
| 2009/0008605 | A1 | 1/2009 | Kawamura et al. | |
| 2009/0009065 | A1 | 1/2009 | Nishimura et al. | |
| 2009/0017330 | A1 | 1/2009 | Iwakuma et al. | |
| 2009/0030202 | A1 | 1/2009 | Iwakuma et al. | |
| 2009/0039776 | A1 | 2/2009 | Yamada et al. | |
| 2009/0045730 | A1 | 2/2009 | Nishimura et al. | |
| 2009/0045731 | A1 | 2/2009 | Nishimura et al. | |
| 2009/0101870 | A1 | 4/2009 | Prakash et al. | |
| 2009/0108737 | A1 | 4/2009 | Kwong et al. | |
| 2009/0115316 | A1 | 5/2009 | Zheng et al. | |
| 2009/0165846 | A1 | 7/2009 | Johannes et al. | |
| 2009/0167162 | A1 | 7/2009 | Lin et al. | |
| 2009/0179554 | A1 | 7/2009 | Kuma et al. | |
| 2010/0084967 | A1 | 4/2010 | Takeda | |
| 2011/0101312 | A1 | 5/2011 | Lecloux | |
| 2012/0181528 | A1 | 7/2012 | Takada | |
| 2014/0070204 | A1 | 3/2014 | Nagao | |
| 2014/0374728 | A1 | 12/2014 | Adamovich et al. | |
| 2015/0333271 | A1 | 11/2015 | Chung | |
| 2016/0099422 | A1 | 4/2016 | Zeng et al. | |
| 2017/0077423 | A1 | 3/2017 | Ahn | |
| 2017/0338432 | A1 | 11/2017 | Adamovich | |
| 2018/0123049 | A1 | 5/2018 | Lee | |
| 2018/0138425 | A1 | 5/2018 | Ma | |
| 2018/0301639 | A1 | 10/2018 | Zeng et al. | |
| 2019/0036055 | A1* | 1/2019 | Lin | H10K 50/81 |
| 2020/0136059 | A1 | 4/2020 | Hong et al. | |
| 2020/0168811 | A1 | 5/2020 | Wolohan | |
| 2020/0168812 | A1 | 5/2020 | Wolohan | |
| 2020/0168819 | A1 | 5/2020 | Ahn | |
| 2020/0199164 | A1 | 6/2020 | Kim | |
| 2020/0203631 | A1 | 6/2020 | Gao et al. | |
| 2021/0032278 | A1 | 2/2021 | Tsai | |
| 2021/0066613 | A1 | 3/2021 | Cheng | |
| 2021/0104682 | A1 | 4/2021 | Shin | |
| 2021/0104698 | A1 | 4/2021 | Kim | |
| 2021/0367168 | A1 | 11/2021 | Heechoon | |
| 2022/0006022 | A1 | 1/2022 | Suh | |
| 2023/0080974 | A1* | 3/2023 | Parham | H10K 85/636 257/40 |
| 2023/0139757 | A1 | 5/2023 | Tada | |
| 2023/0145235 | A1 | 5/2023 | Ukigai | |
| 2023/0189635 | A1 | 6/2023 | Heechoon | |
| 2023/0247902 | A1 | 8/2023 | No | |
| 2024/0206332 | A1 | 6/2024 | Han | |

FOREIGN PATENT DOCUMENTS

| | | |
|---|---|---|
| CN | 113502156 | 10/2021 |
| CN | 115368293 | 11/2022 |
| EP | 0650955 | 5/1995 |
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| JP | 2009231516 | 10/2009 |
| KR | 20120013173 | 2/2012 |
| KR | 1020190038303 | 4/2019 |

(56) References Cited

FOREIGN PATENT DOCUMENTS

| | | |
|---|---|---|
| KR | 10-2021-0018127 | 2/2021 |
| KR | 10-2021-0048977 | 5/2021 |
| KR | 20210092513 | 7/2021 |
| KR | 102283849 | 8/2021 |
| KR | 10-2022-0122512 | 9/2022 |
| KR | 10-2022-0149469 | 11/2022 |
| WO | 01/39234 | 5/2001 |
| WO | 02/02714 | 1/2002 |
| WO | 02015654 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008/117889 | 10/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2011/019360 | 2/2011 |
| WO | 2021/029616 | 2/2021 |
| WO | 2022/255241 | 12/2022 |

OTHER PUBLICATIONS

Third Party Observation for European Application No. EP20220158225, submitted on Aug. 29, 2023.

Laurent Aubouy et al., "Molecular engineering to improve the charge carrier balance in single-layer silole-based OLEDs", New Journal of Chemistry, Royal Society of Chemistry, GB, vol. 33, Apr. 27, 2009, pp. 1290-1300.

Hamid Pourtaghi-Zahed et al., "Synthesis and characterization of ethylene-propylene copolymer and polyethylene using [alpha]-diimine nickel catal", Journal of Polymer Research, Kluwer Academic Publishers—Consultants Bureau, NL, vol. 19, No. 11, Oct. 31, 2012, pp. 1-8.

Partial European Search Report issued on May 26, 2023 for corresponding European Patent Application No. 22186698.1.

Adachi, Chihaya et al., "Organic Electroluminescent Device Having a Hole Conductor as an Emitting Layer," Appl. Phys. Lett., 55(15): 1489-1491 (1989).

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2, N)iridium(III) Derivatives," Adv. Mater., 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1)162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

(56) References Cited

OTHER PUBLICATIONS

Mi, Bao-Xiu et al., "Thermally Stable Hole-Transporting Material for Organic Light-Emitting Diode an Isoindole Derivative," Chem. Mater., 15(16):3148-3151 (2003).
Nishida, Jun-ichi et al., "Preparation, Characterization, and Electroluminescence Characteristics of a-Diimine-type Platinum(II) Complexes with Perfluorinated Phenyl Groups as Ligands," Chem. Lett., 34(4): 592-593 (2005).
Niu, Yu-Hua et al., "Highly Efficient Electrophosphorescent Devices with Saturated Red Emission from a Neutral Osmium Complex," Chem. Mater., 17(13):3532-3536 (2005).
Noda, Tetsuya and Shirota, Yasuhiko, "5,5'-Bis(dimesitylboryl)-2,2'-bithiophene and 5,5"-Bis (dimesitylboryl)-2,2'5',2"-terthiophene as a Novel Family of Electron-Transporting Amorphous Molecular Materials," J. Am. Chem. Soc., 120 (37):9714-9715 (1998).
Okumoto, Kenji et al., "Green Fluorescent Organic Light-Emitting Device with External Quantum Efficiency of Nearly 10%," Appl. Phys. Lett., 89:063504-1-063504-3 (2006).
Palilis, Leonidas C., "High Efficiency Molecular Organic Light-Emitting Diodes Based on Silole Derivatives and Their Exciplexes," Organic Electronics, 4:113-121 (2003).
Paulose, Betty Marie Jennifer S. et al., "First Examples of Alkenyl Pyridines as Organic Ligands for Phosphorescent Iridium Complexes," Adv. Mater., 16(22):2003-2007 (2004).
Ranjan, Sudhir et al., "Realizing Green Phosphorescent Light-Emitting Materials from Rhenium(I) Pyrazolato Diimine Complexes," Inorg. Chem., 42(4):1248-1255 (2003).
Sakamoto, Youichi et al., "Synthesis, Characterization, and Electron-Transport Property of Perfluorinated Phenylene Dendrimers," J. Am. Chem. Soc., 122(8):1832-1833 (2000).
Salbeck, J. et al., "Low Molecular Organic Glasses for Blue Electroluminescence," Synthetic Metals, 91:209-215 (1997).
Shirota, Yasuhiko et al., "Starburst Molecules Based on pi-Electron Systems as Materials for Organic Electroluminescent Devices," Journal of Luminescence, 72-74:985-991 (1997).
Sotoyama, Wataru et al., "Efficient Organic Light-Emitting Diodes with Phosphorescent Platinum Complexes Containing N^C^N^—Coordinating Tridentate Ligand," Appl. Phys. Lett., 86:153505-1-153505-3 (2005).
Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).
T. Östergård et al., "Langmuir-Blodgett Light-Emitting Diodes of Poly(3-Hexylthiophene) Electro-Optical Characteristics Related to Structure," Synthetic Metals, 88:171-177 (1997).
Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).
Tang, C.W. and VanSlyke, S.A., "Organic Electroluminescent Diodes," Appl. Phys. Lett., 51(12):913-915 (1987).
Tung, Yung-Liang et al., "Organic Light-Emitting Diodes Based on Charge-Neutral Ru II PHosphorescent Emitters," Adv. Mater., 17(8)1059-1064 (2005).
Van Slyke, S. A. et al., "Organic Electroluminescent Devices with Improved Stability," Appl. Phys. Lett., 69 (15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(III) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

* cited by examiner

ORGANIC ELECTROLUMINESCENT MATERIALS AND DEVICES

CROSS-REFERENCE TO RELATED APPLICATIONS

This application is a continuation-in-part of U.S. patent application Ser. No. 17/672,895, filed on Feb. 16, 2022, which claims priority under 35 U.S.C. § 119(e) to U.S. Provisional Applications No. 63/229,748, filed on Aug. 5, 2021, No. 63/220,429, filed on Jul. 9, 2021, No. 63/154,320, filed on Feb. 26, 2021. This application is also a continuation-in-part of U.S. patent application Ser. No. 17/672,934, filed on Feb. 16, 2022, which claims priority under 35 U.S.C. § 119(e) to U.S. Provisional Applications No. 63/229,748, filed on Aug. 5, 2021, and 63/220,429, filed on Jul. 9, 2021. This application also claims priority under 35 U.S.C. § 119(e) to U.S. Provisional Application No. 63/313,545, filed on Feb. 24, 2022, the entire contents of which are incorporated herein by reference

FIELD

The present disclosure generally relates to organic light emitting diodes and related electronic devices.

BACKGROUND

Opto-electronic devices that make use of organic materials are becoming increasingly desirable for various reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials.

OLEDs make use of thin organic films that emit light when voltage is applied across the device. OLEDs are becoming an increasingly interesting technology for use in applications such as flat panel displays, illumination, and backlighting.

One application for phosphorescent emissive molecules is a full color display. Industry standards for such a display call for pixels adapted to emit particular colors, referred to as "saturated" colors. In particular, these standards call for saturated red, green, and blue pixels. Alternatively, the OLED can be designed to emit white light. In conventional liquid crystal displays emission from a white backlight is filtered using absorption filters to produce red, green and blue emission. The same technique can also be used with OLEDs. The white OLED can be either a single emissive layer (EML) device or a stack structure. Color may be measured using CIE coordinates, which are well known to the art.

SUMMARY

In one aspect, the present disclosure provides an OLED comprising an anode; a cathode; and an emissive layer, disposed between the anode and the cathode. The emissive layer comprises a phosphorescent dopant, a first host, and a second host, wherein the first host transports holes, the second host transports electrons, and the first host is fully or partially deuterated.

In yet another aspect, the present disclosure provides a consumer product comprising an OLED as described herein.

DETAILED DESCRIPTION

A. Terminology

Figure 1:
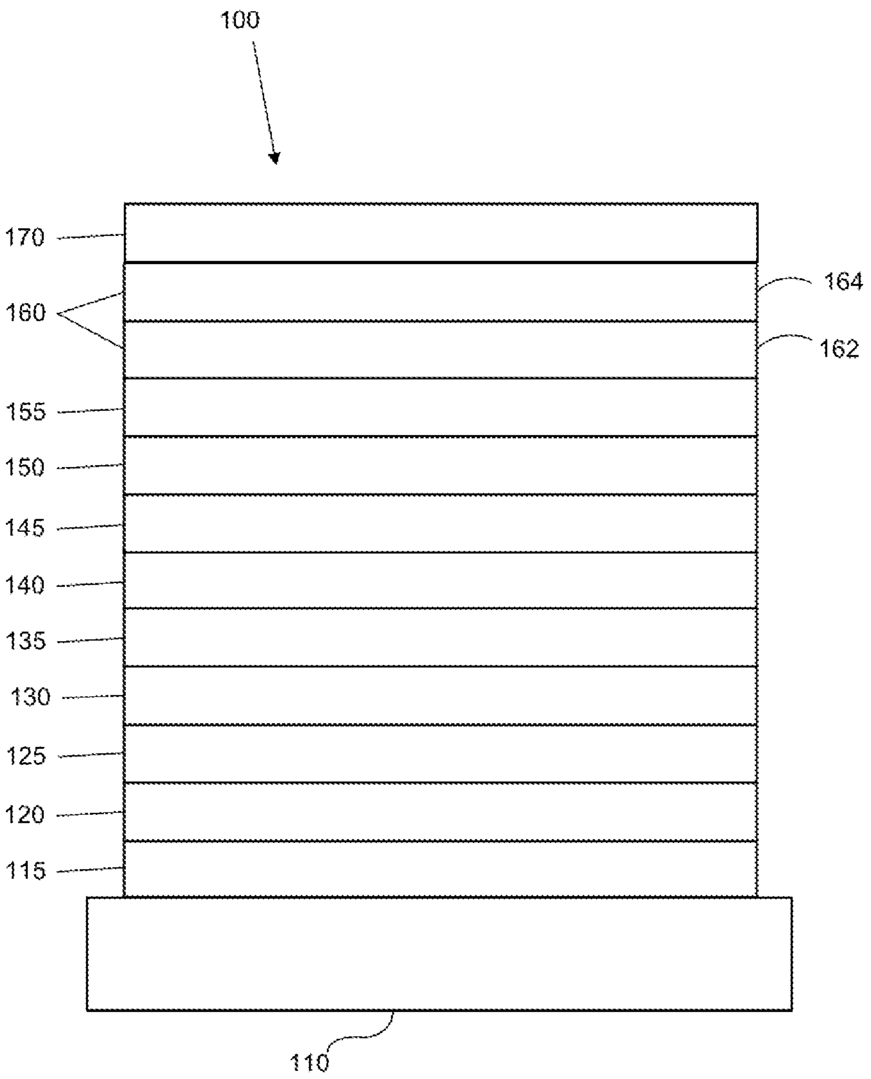
FIG. 1 shows an organic light emitting device.

Unless otherwise specified, the below terms used herein are defined as follows:

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processable" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

The terms "halo," "halogen," and "halide" are used interchangeably and refer to fluorine, chlorine, bromine, and iodine.

The term "acyl" refers to a substituted carbonyl radical ($C(O)—R_s$).

The term "ester" refers to a substituted oxycarbonyl ($—O—C(O)—R_s$ or $—C(O)—O—R_s$) radical.

The term "ether" refers to an $—OR_s$ radical.

The terms "sulfanyl" or "thio-ether" are used interchangeably and refer to a $—SR_s$ radical.

The term "selenyl" refers to a $—SeR_s$ radical.

The term "sulfinyl" refers to a $—S(O)—R_s$ radical.

The term "sulfonyl" refers to a $—SO_2—R_s$ radical.

The term "phosphino" refers to a $—P(R_s)_3$ radical, wherein each $R_s$ can be same or different.

The term "silyl" refers to a $—Si(R_s)_3$ radical, wherein each $R_s$ can be same or different.

The term "germyl" refers to a $—Ge(R_s)_3$ radical, wherein each $R_s$ can be same or different.

The term "boryl" refers to a $—B(R_s)_2$ radical or its Lewis adduct $—B(R_s)_3$ radical, wherein $R_s$ can be same or different.

In each of the above, $R_s$ can be hydrogen or a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, and combination thereof. Preferred $R_s$ is selected from the group consisting of alkyl, cycloalkyl, aryl, heteroaryl, and combination thereof.

The term "alkyl" refers to and includes both straight and branched chain alkyl radicals. Preferred alkyl groups are those containing from one to fifteen carbon atoms and includes methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, and the like. Additionally, the alkyl group may be optionally substituted.

The term "cycloalkyl" refers to and includes monocyclic, polycyclic, and spiro alkyl radicals. Preferred cycloalkyl groups are those containing 3 to 12 ring carbon atoms and includes cyclopropyl, cyclopentyl, cyclohexyl, bicyclo[3.1.1]heptyl, spiro[4.5]decyl, spiro[5.5]undecyl, adamantyl, and the like. Additionally, the cycloalkyl group may be optionally substituted.

The terms "heteroalkyl" or "heterocycloalkyl" refer to an alkyl or a cycloalkyl radical, respectively, having at least one carbon atom replaced by a heteroatom. Optionally the at least one heteroatom is selected from O, S, N, P, B, Si and Se, preferably, 0, S or N. Additionally, the heteroalkyl or heterocycloalkyl group may be optionally substituted.

The term "alkenyl" refers to and includes both straight and branched chain alkene radicals. Alkenyl groups are essentially alkyl groups that include at least one carbon-carbon double bond in the alkyl chain. Cycloalkenyl groups are essentially cycloalkyl groups that include at least one carbon-carbon double bond in the cycloalkyl ring. The term "heteroalkenyl" as used herein refers to an alkenyl radical having at least one carbon atom replaced by a heteroatom. Optionally the at least one heteroatom is selected from O, S, N, P, B, Si, and Se, preferably, O, S, or N. Preferred alkenyl, cycloalkenyl, or heteroalkenyl groups are those containing two to fifteen carbon atoms. Additionally, the alkenyl, cycloalkenyl, or heteroalkenyl group may be optionally substituted.

The term "alkynyl" refers to and includes both straight and branched chain alkyne radicals. Alkynyl groups are essentially alkyl groups that include at least one carbon-carbon triple bond in the alkyl chain. Preferred alkynyl groups are those containing two to fifteen carbon atoms. Additionally, the alkynyl group may be optionally substituted.

The terms "aralkyl" or "arylalkyl" are used interchangeably and refer to an alkyl group that is substituted with an aryl group. Additionally, the aralkyl group may be optionally substituted.

The term "heterocyclic group" refers to and includes aromatic and non-aromatic cyclic radicals containing at least one heteroatom. Optionally the at least one heteroatom is selected from O, S, N, P, B, Si, and Se, preferably, O, S, or N. Hetero-aromatic cyclic radicals may be used interchangeably with heteroaryl. Preferred hetero-non-aromatic cyclic groups are those containing 3 to 7 ring atoms which includes at least one hetero atom, and includes cyclic amines such as morpholino, piperidino, pyrrolidino, and the like, and cyclic ethers/thio-ethers, such as tetrahydrofuran, tetrahydropyran, tetrahydrothiophene, and the like. Additionally, the heterocyclic group may be optionally substituted.

The term "aryl" refers to and includes both single-ring aromatic hydrocarbyl groups and polycyclic aromatic ring systems. The polycyclic rings may have two or more rings in which two carbons are common to two adjoining rings (the rings are "fused") wherein at least one of the rings is an aromatic hydrocarbyl group, e.g., the other rings can be cycloalkyls, cycloalkenyls, aryl, heterocycles, and/or heteroaryls. Preferred aryl groups are those containing six to thirty carbon atoms, preferably six to twenty carbon atoms, more preferably six to twelve carbon atoms. Especially preferred is an aryl group having six carbons, ten carbons or twelve carbons. Suitable aryl groups include phenyl, biphenyl, triphenyl, triphenylene, tetraphenylene, naphthalene, anthracene, phenalene, phenanthrene, fluorene, pyrene, chrysene, perylene, and azulene, preferably phenyl, biphenyl, triphenyl, triphenylene, fluorene, and naphthalene. Additionally, the aryl group may be optionally substituted.

The term "heteroaryl" refers to and includes both single-ring aromatic groups and polycyclic aromatic ring systems that include at least one heteroatom. The heteroatoms include, but are not limited to O, S, N, P, B, Si, and Se. In many instances, O, S, or N are the preferred heteroatoms. Hetero-single ring aromatic systems are preferably single rings with 5 or 6 ring atoms, and the ring can have from one to six heteroatoms. The hetero-polycyclic ring systems can have two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. The hetero-polycyclic aromatic ring systems can have from one to six heteroatoms per ring of the polycyclic aromatic ring system. Preferred heteroaryl groups are those containing three to thirty carbon atoms, preferably three to twenty carbon atoms, more preferably three to twelve carbon atoms. Suitable heteroaryl groups include dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine, preferably dibenzothiophene, dibenzofuran, dibenzoselenophene, carbazole, indolocarbazole, imidazole, pyridine, triazine, benzimidazole, 1,2-azaborine, 1,3-azaborine, 1,4-azaborine, borazine, and aza-analogs thereof. Additionally, the heteroaryl group may be optionally substituted.

Of the aryl and heteroaryl groups listed above, the groups of triphenylene, naphthalene, anthracene, dibenzothiophene, dibenzofuran, dibenzoselenophene, carbazole, indolocarbazole, imidazole, pyridine, pyrazine, pyrimidine, triazine, and benzimidazole, and the respective aza-analogs of each thereof are of particular interest.

The terms alkyl, cycloalkyl, heteroalkyl, heterocycloalkyl, alkenyl, cycloalkenyl, heteroalkenyl, alkynyl, aralkyl, heterocyclic group, aryl, and heteroaryl, as used herein, are independently unsubstituted, or independently substituted, with one or more general substituents.

In many instances, the general substituents are selected from the group consisting of deuterium, halogen, alkyl, cycloalkyl, heteroalkyl, heterocycloalkyl, arylalkyl, alkoxy, aryloxy, amino, silyl, germyl, boryl, alkenyl, cycloalkenyl, heteroalkenyl, alkynyl, aryl, heteroaryl, acyl, carboxylic acid, ether, ester, nitrile, isonitrile, sulfanyl, selenyl, sulfinyl, sulfonyl, phosphino, and combinations thereof.

In some instances, the preferred general substituents are selected from the group consisting of deuterium, fluorine, alkyl, cycloalkyl, heteroalkyl, alkoxy, aryloxy, amino, silyl, boryl, alkenyl, cycloalkenyl, heteroalkenyl, aryl, heteroaryl, nitrile, isonitrile, sulfanyl, boryl, and combinations thereof.

In some instances, the more preferred general substituents are selected from the group consisting of deuterium, fluorine, alkyl, cycloalkyl, alkoxy, aryloxy, amino, silyl, aryl, heteroaryl, sulfanyl, and combinations thereof.

In yet other instances, the most preferred general substituents are selected from the group consisting of deuterium, fluorine, alkyl, cycloalkyl, aryl, heteroaryl, and combinations thereof.

The terms "substituted" and "substitution" refer to a substituent other than H that is bonded to the relevant position, e.g., a carbon or nitrogen. For example, when $R^1$ represents mono-substitution, then one $R^1$ must be other than H (i.e., a substitution). Similarly, when $R^1$ represents di-substitution, then two of $R^1$ must be other than H. Similarly, when $R^1$ represents zero or no substitution, $R^1$, for example, can be a hydrogen for available valencies of ring atoms, as in carbon atoms for benzene and the nitrogen atom in pyrrole, or simply represents nothing for ring atoms with fully filled valencies, e.g., the nitrogen atom in pyridine. The maximum number of substitutions possible in a ring structure will depend on the total number of available valencies in the ring atoms.

As used herein, "combinations thereof" indicates that one or more members of the applicable list are combined to form a known or chemically stable arrangement that one of ordinary skill in the art can envision from the applicable list. For example, an alkyl and deuterium can be combined to form a partial or fully deuterated alkyl group; a halogen and alkyl can be combined to form a halogenated alkyl substituent; and a halogen, alkyl, and aryl can be combined to form a halogenated arylalkyl. In one instance, the term substitution includes a combination of two to four of the listed groups. In another instance, the term substitution includes a combination of two to three groups. In yet another instance, the term substitution includes a combination of two groups. Preferred combinations of substituent groups are those that contain up to fifty atoms that are not hydrogen or deuterium, or those which include up to forty atoms that are not hydrogen or deuterium, or those that include up to thirty atoms that are not hydrogen or deuterium. In many instances, a preferred combination of substituent groups will include up to twenty atoms that are not hydrogen or deuterium.

The "aza" designation in the fragments described herein, i.e. aza-dibenzofuran, aza-dibenzothiophene, etc. means that one or more of the C—H groups in the respective aromatic ring can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

As used herein, "deuterium" refers to an isotope of hydrogen. Deuterated compounds can be readily prepared using methods known in the art. For example, U.S. Pat. No. 8,557,400, Patent Pub. No. WO 2006/095951, and U.S. Pat. Application Pub. No. US 2011/0037057, which are hereby incorporated by reference in their entireties, describe the making of deuterium-substituted organometallic complexes. Further reference is made to Ming Yan, et al., Tetrahedron 2015, 71, 1425-30 and Atzrodt et al., Angew. Chem. Int. Ed. (Reviews) 2007, 46, 7744-65, which are incorporated by reference in their entireties, describe the deuteration of the methylene hydrogens in benzyl amines and efficient pathways to replace aromatic ring hydrogens with deuterium, respectively.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

In some instance, a pair of adjacent substituents can be optionally joined or fused into a ring. The preferred ring is a five, six, or seven-membered carbocyclic or heterocyclic ring, includes both instances where the portion of the ring formed by the pair of substituents is saturated and where the portion of the ring formed by the pair of substituents is unsaturated. As used herein, "adjacent" means that the two substituents involved can be on the same ring next to each other, or on two neighboring rings having the two closest available substitutable positions, such as 2, 2' positions in a biphenyl, or 1, 8 position in a naphthalene, as long as they can form a stable fused ring system.

B. The OLEDs and the Devices of the Present Disclosure

In one aspect, the present disclosure is drawn to an OLED that comprises an anode; a cathode; and an emissive layer, disposed between the anode and the cathode where the emissive layer comprises a phosphorescent dopant, a first host, and a second host, wherein the first host transports holes, the second host transports electrons, and the first host is fully or partially deuterated.

In some embodiments of the inventive OLED, at least one of the following conditions is true:

(i) the second host does not comprise a carbazole or an indolocarbazole;

(ii) the second host has a HOMO level <−5.75 eV;

(iii) the second host has a HOMO level >−5.5 eV and is at least 25% deuterated;

(iv) the second host comprises biscarbazole or indolocarbazole moiety that is at least 60% deuterated;

(v) the first host comprises a hole transporting moiety that is at least 50% deuterated and the second host comprises an electron transporting moiety that is at least 50% deuterated; and (vi) the lifetime (measured as LT95) of the inventive OLED is at least 75% higher than the lifetime (LT95) of a comparative OLED where the only difference between the inventive OLED and the comparative OLED is that the first host in the comparative OLED is not deuterated.

The HOMO levels referenced herein can be measured by solution cyclic voltammetry and differential pulsed voltammetry performed using a potentiostat (e.g., CH Instruments model 6201B) using anhydrous dimethylformamide solvent and tetrabutylammonium hexafluorophosphate as the supporting electrolyte. Glassy carbon, platinum, and silver wires can be used as the working, counter, and reference electrodes, respectively. Electrochemical potentials can be referenced to an internal ferrocene-ferroconium redox couple (Fc/Fc+) by measuring the peak potential differences from differential pulsed voltammetry. The corresponding HOMO and LUMO energies can be determined by referencing the cationic and anionic redox potentials to ferrocene (4.8 eV vs. vacuum) according to literature ((a) Fink, R.; Heischkel, Y.; Thelakkat, M.; Schmidt, H.-W. *Chem. Mater.* 1998, 10, 3620-3625. (b) Pommerehne, J.; Vestweber, H.; Guss, W.; Mahrt, R. F.; Bassler, H.; Porsch, M.; Daub, *J. Adv. Mater.* 1995, 7, 551.

The lifetime measurements (LT95) of OLEDs referenced herein are the time to reduction of luminance of the OLEDs to 95% of the initial luminance at a constant current density of 80 $mA/cm^2$.

In some embodiments, the first host comprises a carbazole or indolocarbazole moiety.

In some embodiments, the first host comprises at least one moiety selected from the group consisting of naphthalene, biphenyl, triphenylene, dibenzothiophene, dibenzofuran, silyl, boryl, phenanthrene, phenanthridine, arylamine, and fluorene.

In some embodiments, the second host comprises at least one moiety selected from the group consisting of benzene, pyridine, pyrimidine, pyridazine, pyrazine, triazine, imidazole, aza-dibenzothiophene, aza-dibenzofuran, and aza-carbazole, boryl, thiazole, naphthalene, quinoline, isoquinoline, quinazoline, benzoquinazoline, benzofuran, benzoxazole, benzothiophene, benzothiazole, benzoselenophene benzimidazole, carbazole, dibenzofuran, dibenzothiophene, quinoxaline, phthalazine, phenanthrene, phenanthridine, triphenylene, and fluorene.

In some embodiments, the first host is at least 10% deuterated. In some embodiments, the first host is at least 25% deuterated. In some embodiments, the first host is at least 50% deuterated. In some embodiments, the first host is >75% deuterated. In some embodiments, the first host is >90% deuterated.

In some embodiments, the second host does not comprise a carbazole or an indolocarbazole.

In some embodiments, the second host has a HOMO level <−5.75 eV.

In some embodiments, the second host has a HOMO level >−5.5 eV and is at least 25% deuterated.

In some embodiments, the second host comprises a biscarbazole or indolocarbazole moiety that is at least 60% deuterated.

In some embodiments, the first host comprises a hole transporting moiety that is at least 50% deuterated and the second host comprises an electron transporting moiety that is at least 50% deuterated.

In some embodiments, the hole transporting moiety of the first host is selected from the group consisting of the structures of the following LIST 1:

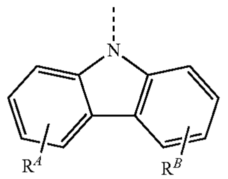
,

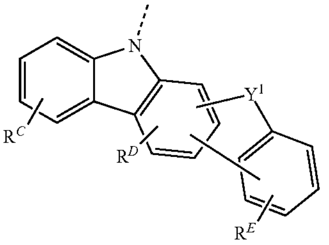
,

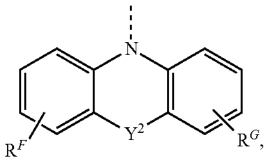
,

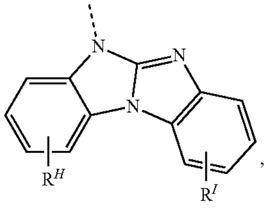
,

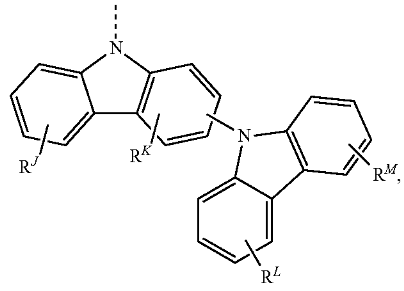
,

-continued

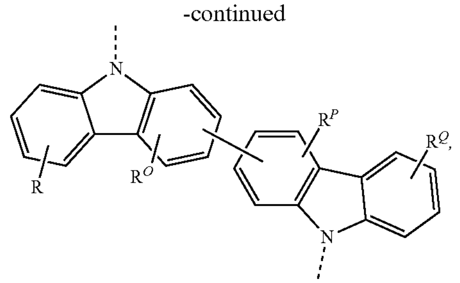

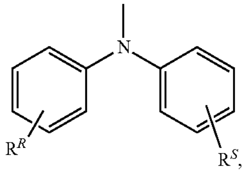

and

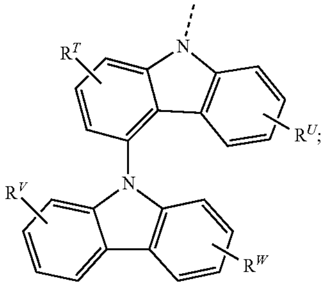

wherein:

each of $Y^1$ and $Y^2$ is independently selected from the group consisting of BR, BRR', NR, PR, P(O)R, O, S, Se, C=O, C=S, C=Se, C=NR, C=CRR', S=O, $SO_2$, CRR', SiRR', and GeRR';

each of $R^A$ to $R^W$ represents mono, up to the maximum number of allowable substitutions, or no substitution;

each R, R', and $R^A$ to $R^W$ is independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

any two adjacent of R, R', and $R^A$ to $R^W$ can be joined or fused to form a ring; and when present, at least 4 of $R^A$ and $R^B$ are D; at least 5 of $R^C$, $R^D$, and $R^E$ are D; at least 4 of $R^F$ and $R^G$ are D; at least 4 of $R^H$ and $R^I$ are D; at least 8 of $R^J$, $R^K$, $R^L$, $R^M$ are D; at least 7 of $R^N$, $R^O$, $R^P$, and $R^Q$ are D; at least 4 of $R^R$ and $R^S$ are D; and at least 7 of $R^T$, $R^U$, $R^V$, and $R^W$ are D.

In some embodiments, the electron transporting moiety of the second host is selected from the group consisting of the structures of the following LIST 2:

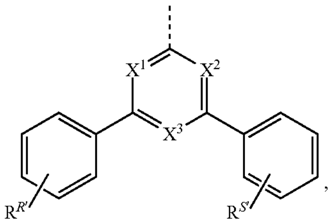

-continued

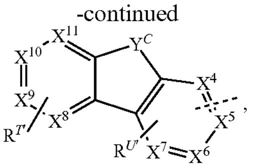

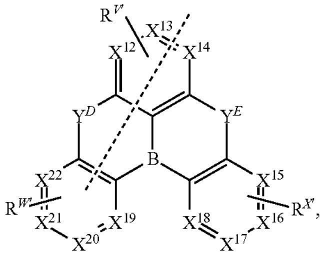

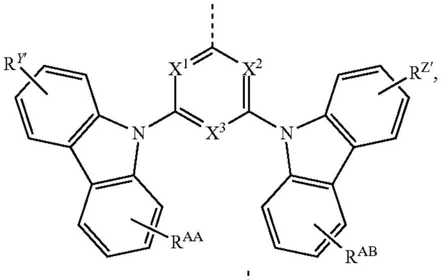

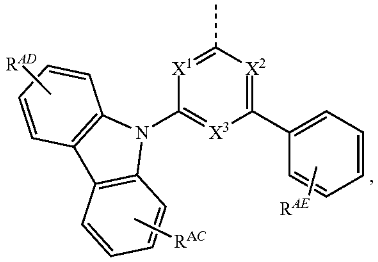

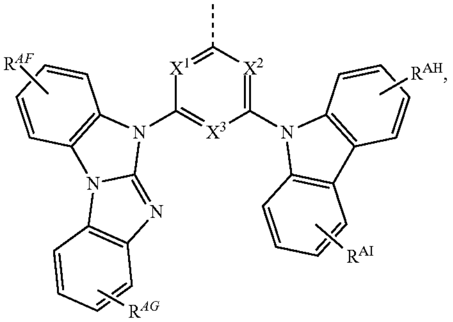

and

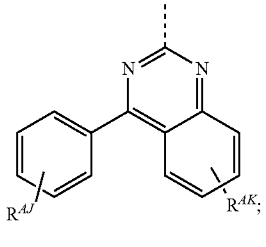

wherein:

each of $X^1$ to $X^{22}$ is independently C or N;

at least one of $X^1$ to $X^3$ is N;

at least one of $X^4$ to $X^{11}$ is N;

each of $Y^C$, $Y^D$ and $Y^E$ is independently selected from the group consisting of BR, BRR', NR, PR, P(O)R, O, S, Se, C=O, C=S, C=Se, C=NR, C=CRR', S=O, $SO_2$, CRR', SiRR', and GeRR';

each of $R^{R'}$ to $R^{Z'}$ and $R^{AA}$ to $R^{AK}$ represents mono, up to the maximum number of allowable substitutions, or no substitution;

each R, R', $R^{R'}$ to $R^{Z'}$, and $R^{AA}$ to $R^{AK}$ is independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

any two adjacent R, R', $R^{R'}$ to $R^{Z'}$, or $R^{AA}$ to $R^{AK}$ can be joined or fused to form a ring; and when present, at least 5 of $R^{R'}$ and $R_{Z'}$ are D; at least 4 of $R^{T'}$ and $R^{U'}$ are D; at least 6 of $R^{V'}$, $R^{W'}$, and $R^{X'}$ are D; at least 9 of $R^{Y'}$, $R^{Z'}$, $R^{AA}$, and $R^{AB}$ are D; at least 7 of $R^{AC}$, $R^{AD}$, and $R^{AE}$ are D; at least 9 of $R^{AF}$, $R^{AG}$, $R^{AH}$, and $R^{AI}$ are D; and at least 5 of $R^{AJ}$ and $R^{AK}$ are D.

In some embodiments, the second host is not deuterated.

In some embodiments, the first host comprises at least one deuterated fused moiety selected from the group consisting of carbazole, biscarbazole, and indolocarbazole, and the at least one deuterated fused moiety is at least 50% deuterated. In some embodiments, the at least one deuterated fused moiety is at least 70% deuterated. In some embodiments, the at least one deuterated fused moiety is at least 90% deuterated.

In some embodiments, the device has an EQE at 10 mA/cm$^2$ greater than 25%.

In some embodiments, the device has a voltage at 10 mA/cm$^2$ less than 4.5V.

In some embodiments, the device has a LT95 at 1000 nits that is greater than 30,000 hours.

In some embodiments, the first host has a HOMO level greater than −5.75 eV.

In some embodiments, the second host has a HOMO level less than −5.75 eV, and the first host has a HOMO greater than −5.6 eV. In some embodiments, the second host has a HOMO level less than −5.45 eV, and the first host has a HOMO greater than −5.3 eV.

In some embodiments, the second host has a HOMO level less than −5.75 eV, and the first host has a HOMO less than −5.8 eV but greater than −5.75 eV. In some embodiments, the second host has a HOMO level less than −5.9 eV, and the first host has a HOMO less than −5.95 eV but greater than −5.9 eV.

In some embodiments, the first host is selected from the group consisting of the structures in the following LIST 3:

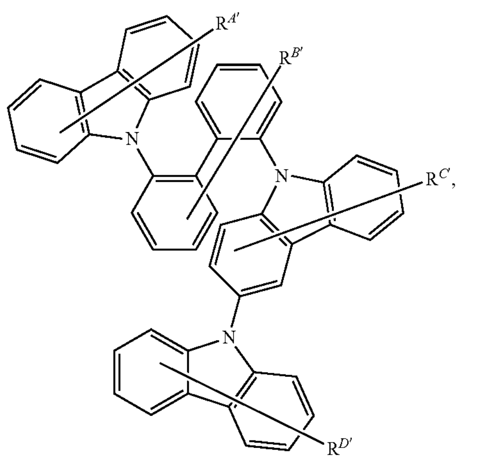

-continued

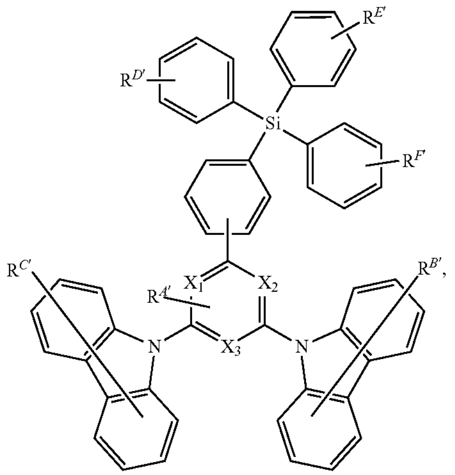

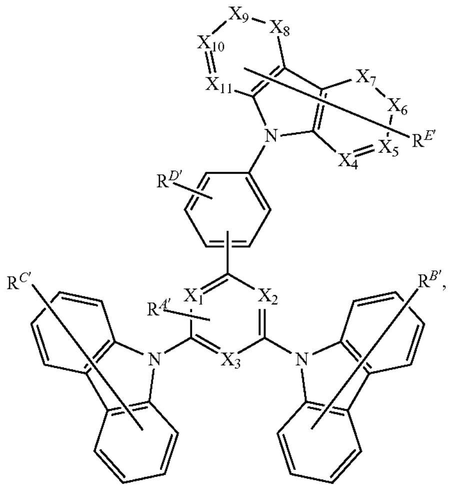

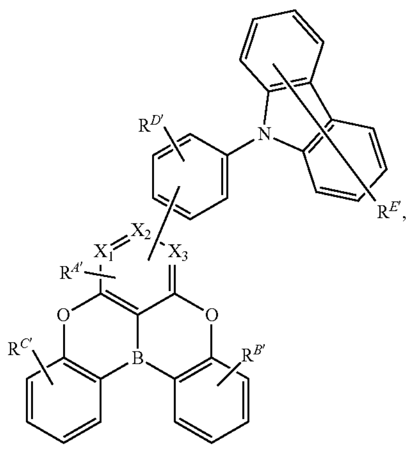

-continued
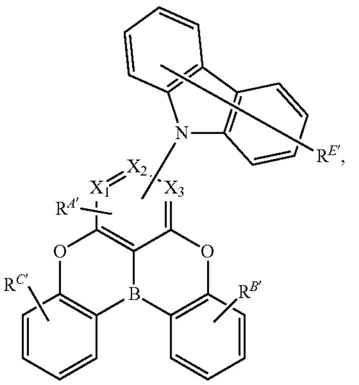
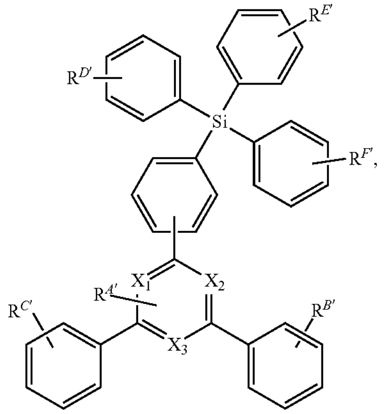
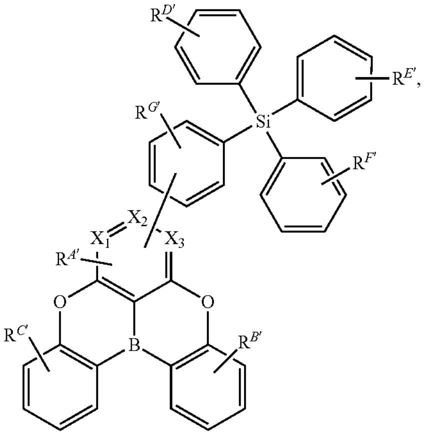
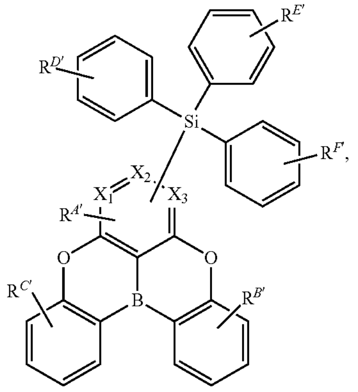
-continued
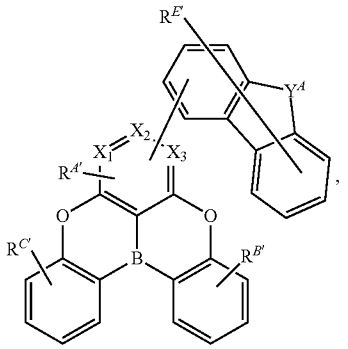
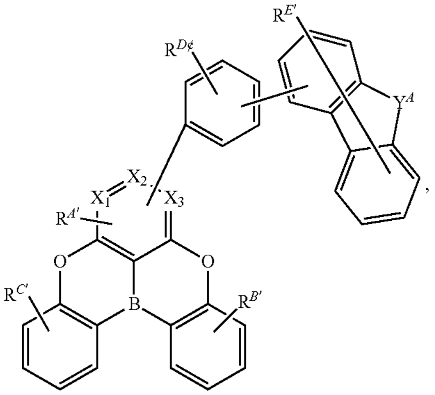
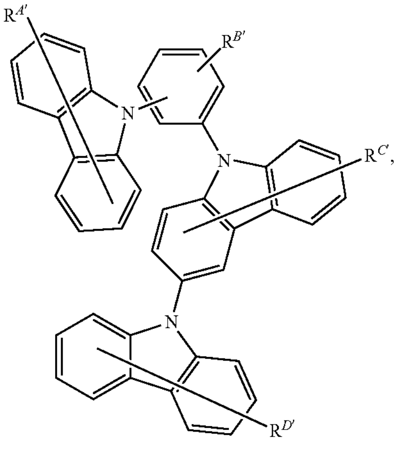
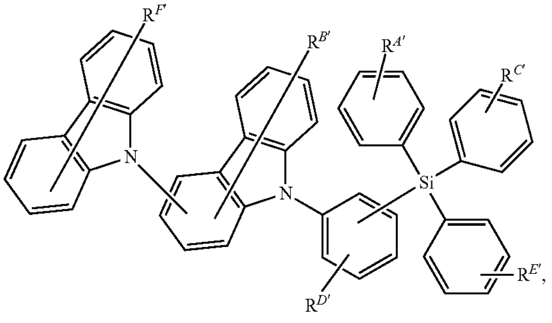

-continued
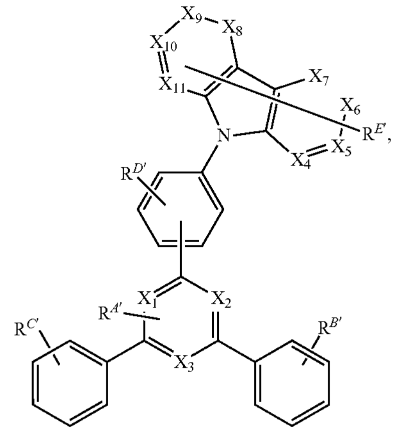
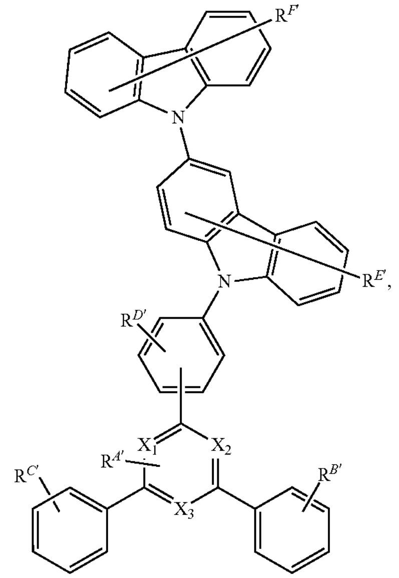
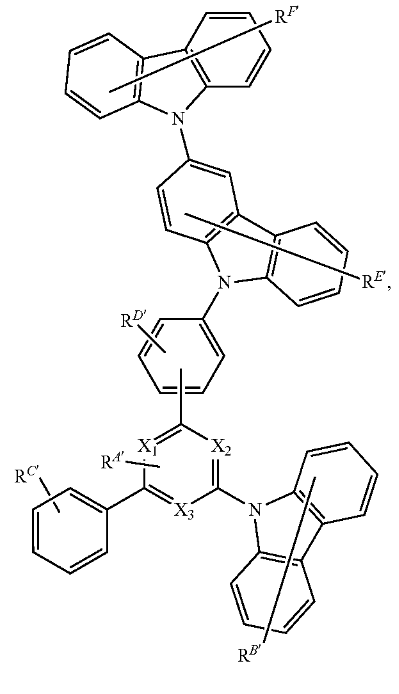
-continued
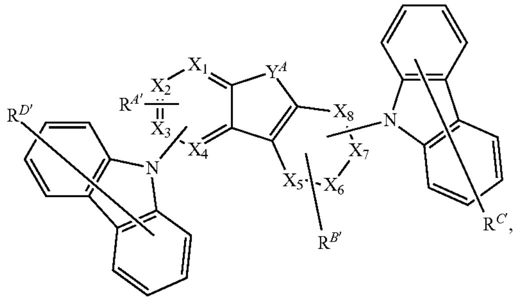
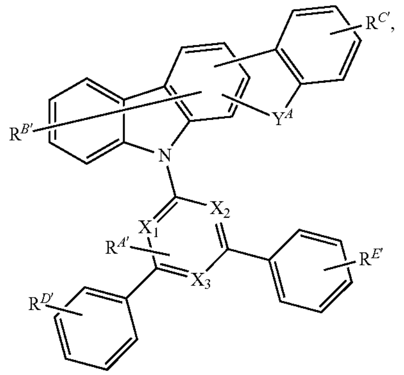
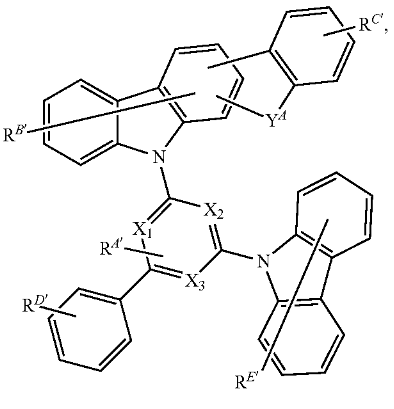
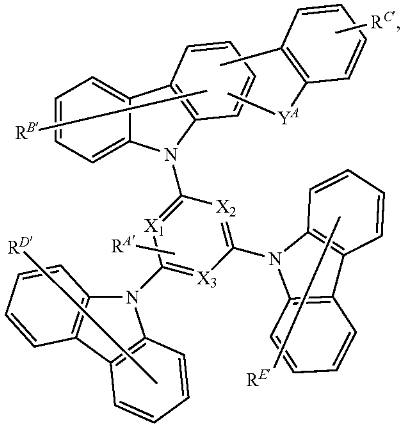

-continued
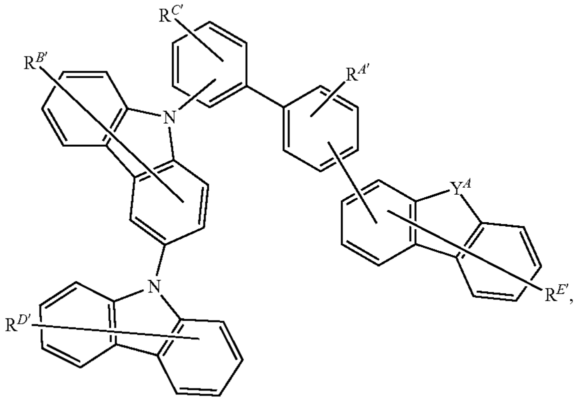
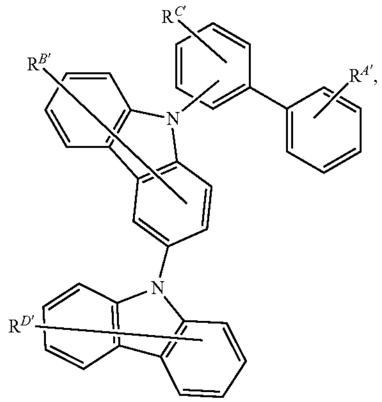
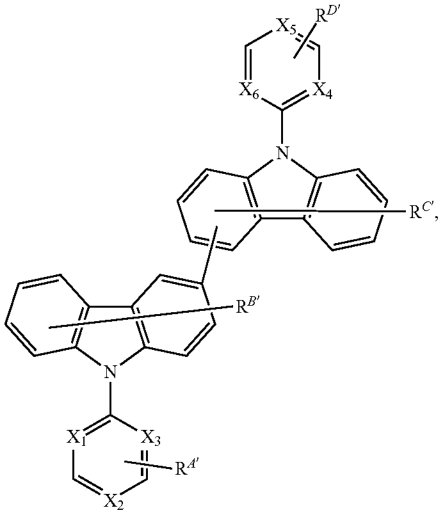
-continued
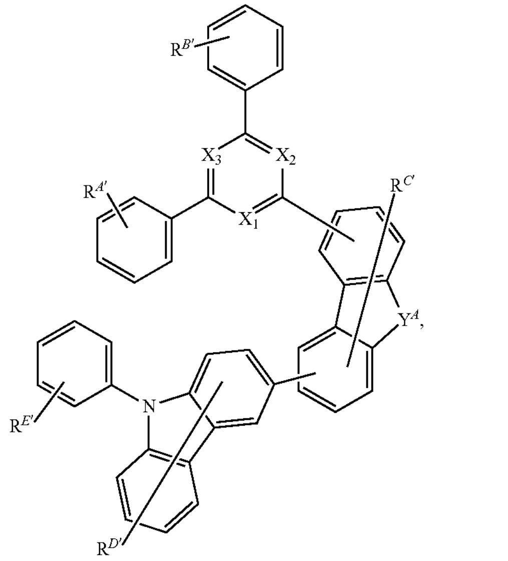
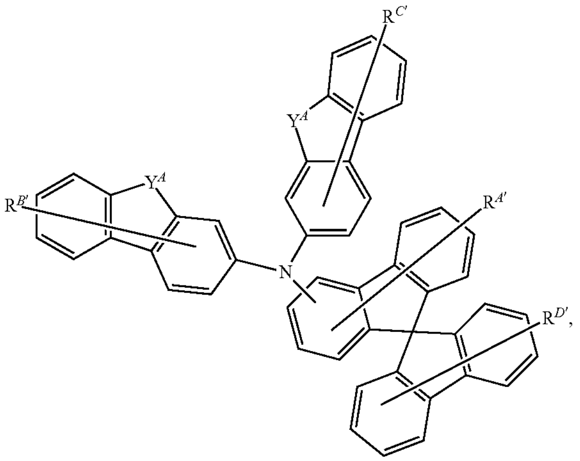
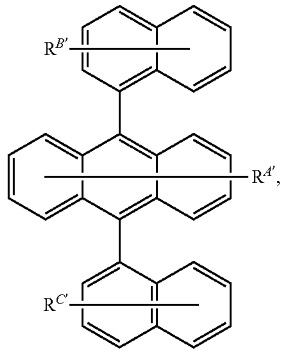
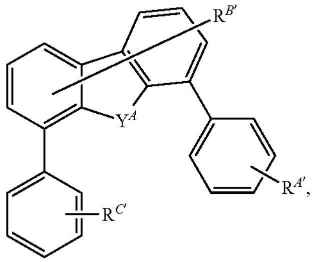

-continued
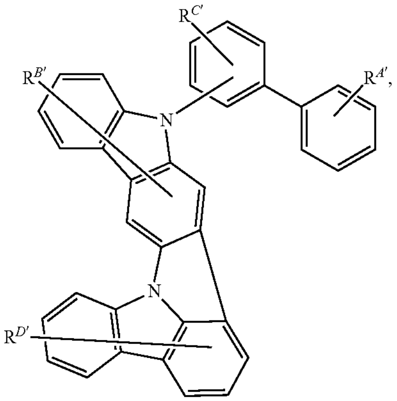
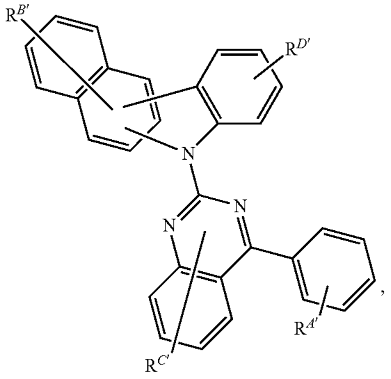
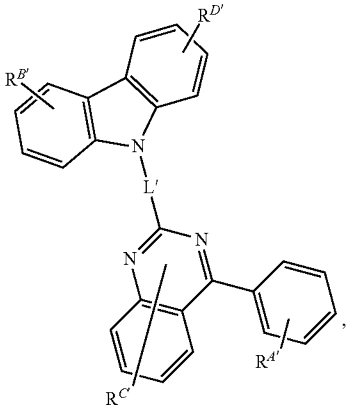
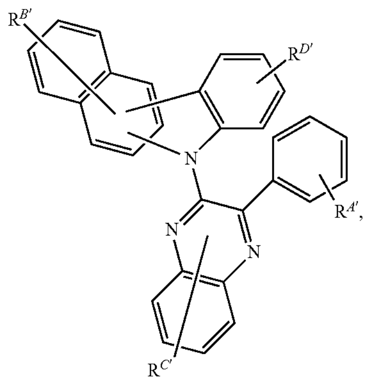
-continued
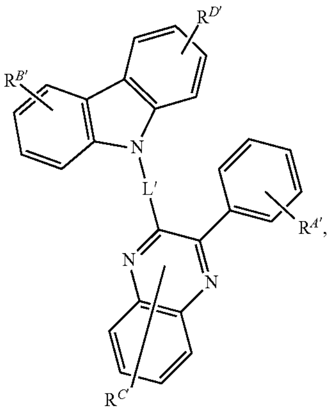
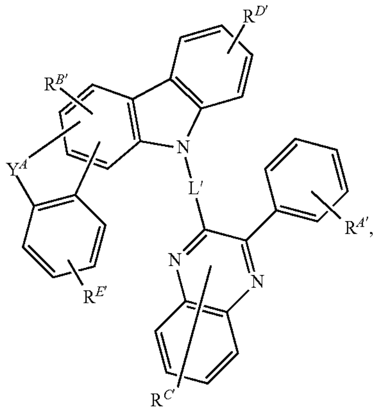
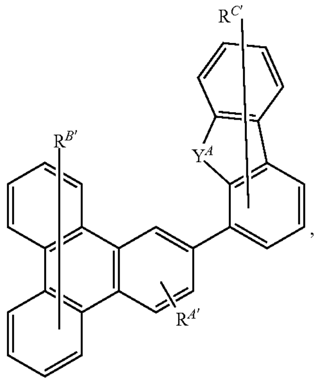
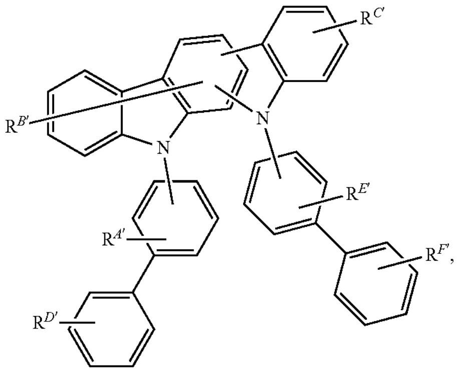

-continued
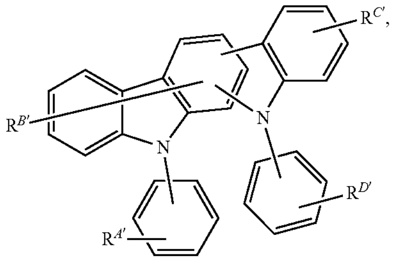
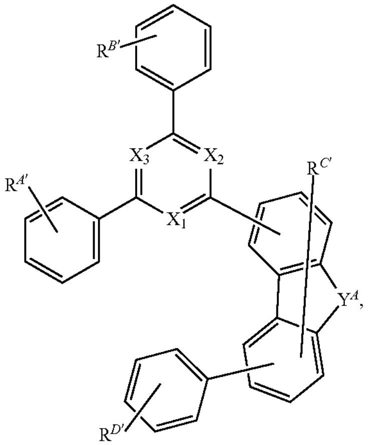
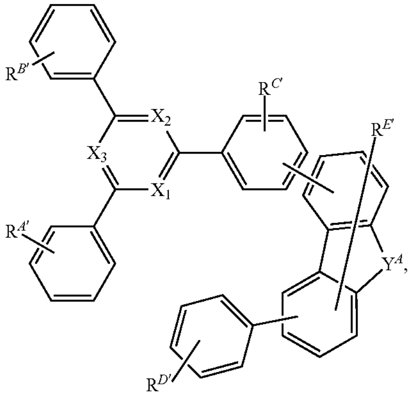
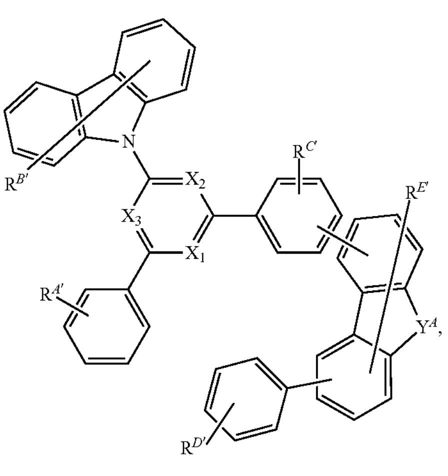
-continued
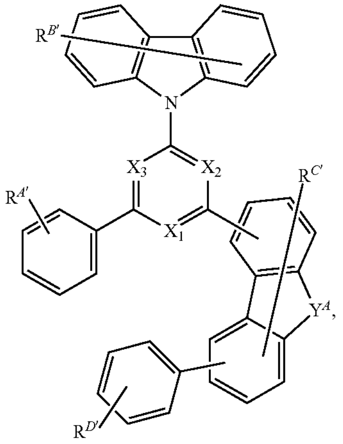
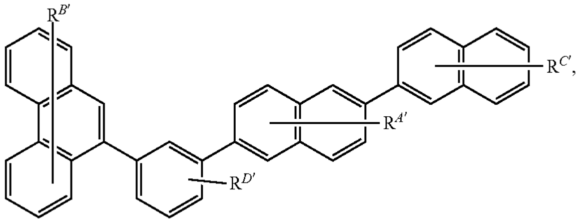
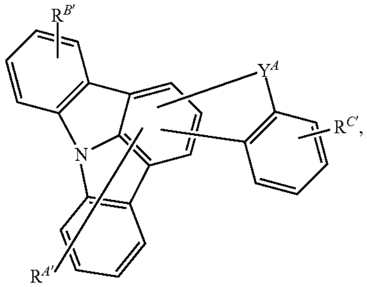
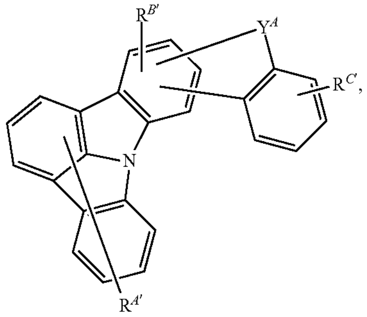
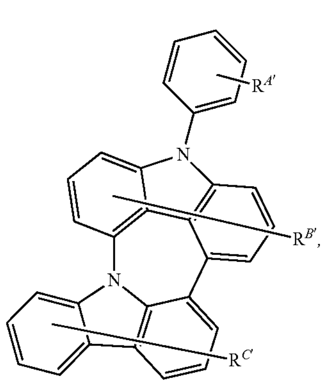

-continued

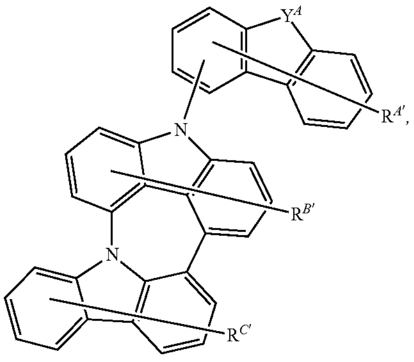

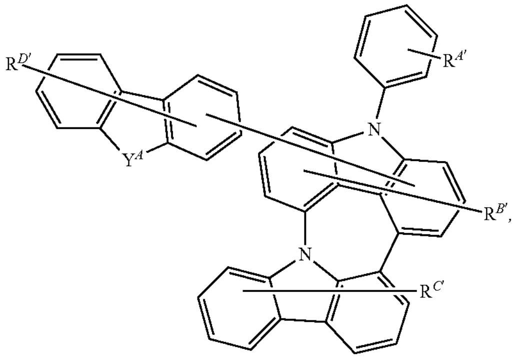

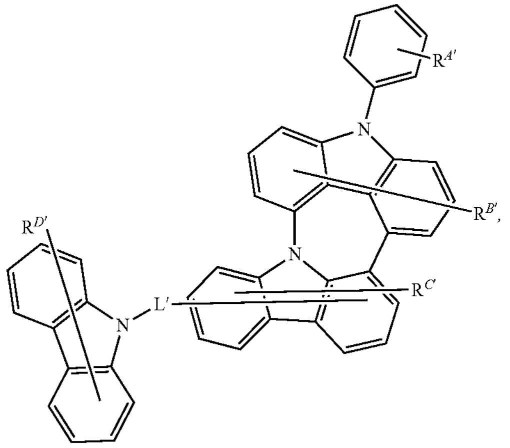

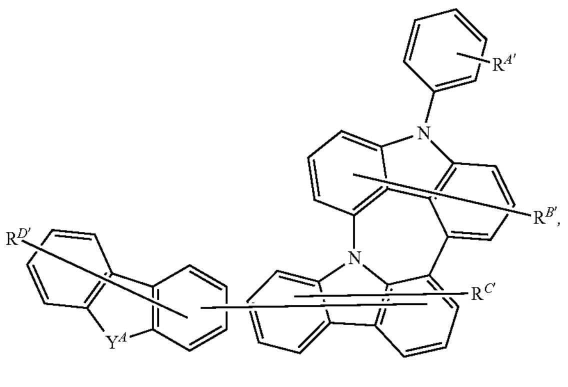

-continued

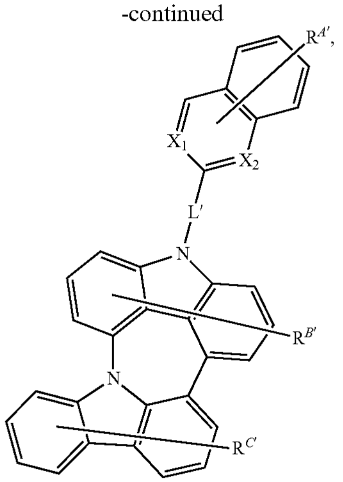

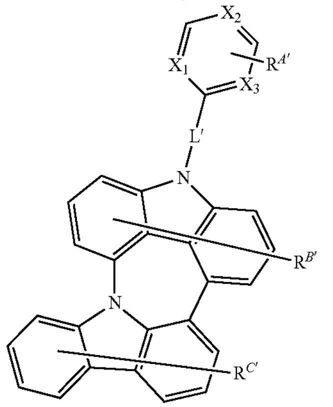

and

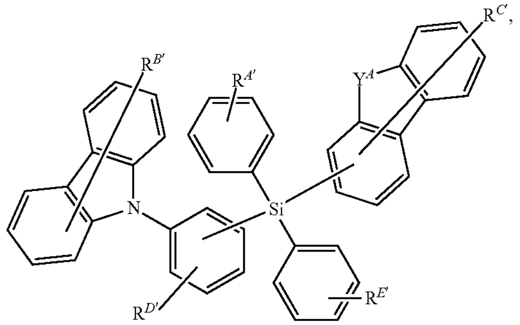

wherein:

each of $X_1$ to $X_{11}$ is independently C or N;

L' is a direct bond or an organic linker;

each $Y^A$ is independently selected from the group consisting of absent a bond, O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono, up to the maximum substitutions, or no substitutions;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

two adjacent of $R^{A'}$, $R^{B'}$, $R^{C'}$, $R^{D'}$, $R^{E'}$, $R^{F'}$, and $R^{G'}$ are optionally joined or fused to form a ring; and at least one R, R', $R^{A'}$, $R^{B'}$, $R^{C'}$, $R^{D'}$, $R^{E'}$, $R^{F'}$, or $R^{G'}$ comprises deuterium.

In some embodiments, the linker L' is selected from the group consisting of a direct bond, BR, BRR', NR, PR, P(O)R, O, S, Se, C═O, C═S, C═Se, C═NR', C═CR'R", S═O, $SO_2$, CR, CRR', SiRR', GeRR', alkylene, cycloalkyl, aryl, cycloalkylene, arylene, heteroarylene, and combinations thereof.

In some embodiments, the first host is selected from the group consisting of the structures of the following LIST 4:

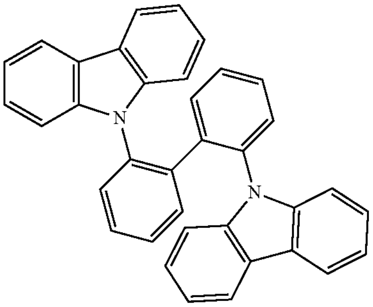

,

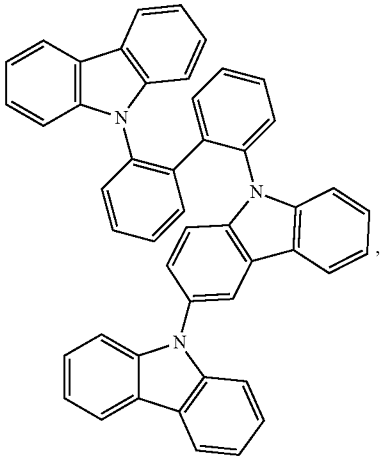

,

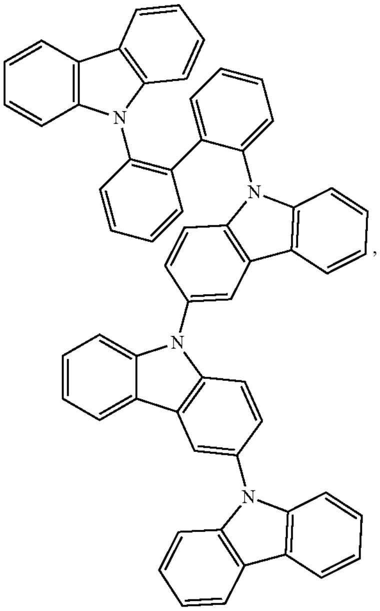

,

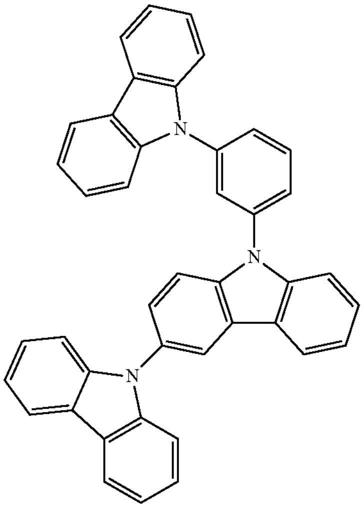

,

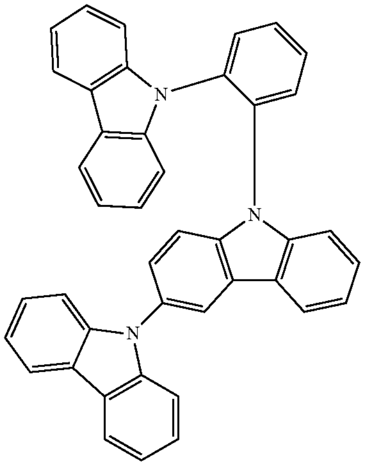

,

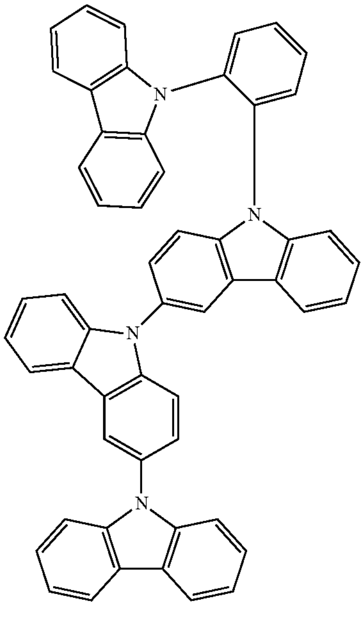

,

-continued
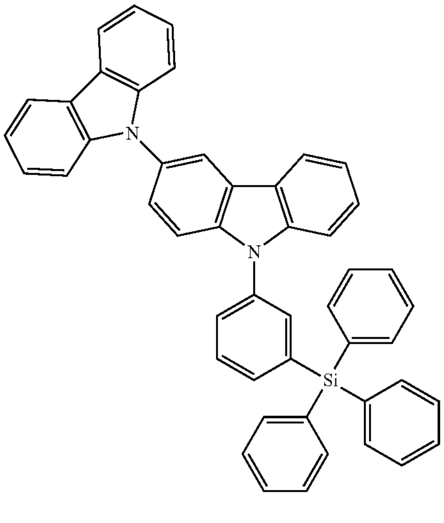
,
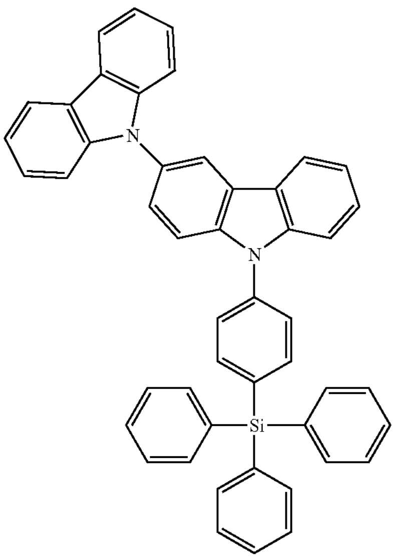
,
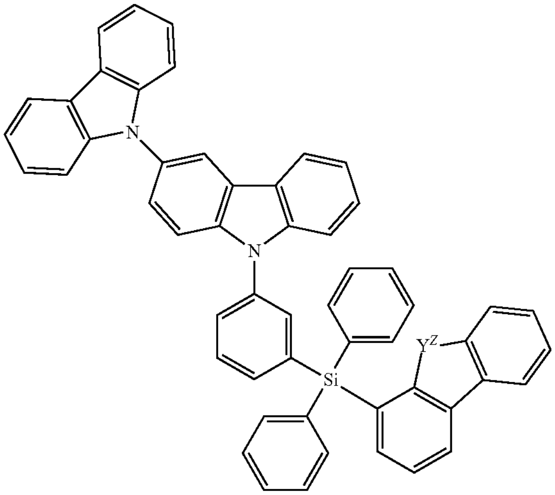
,
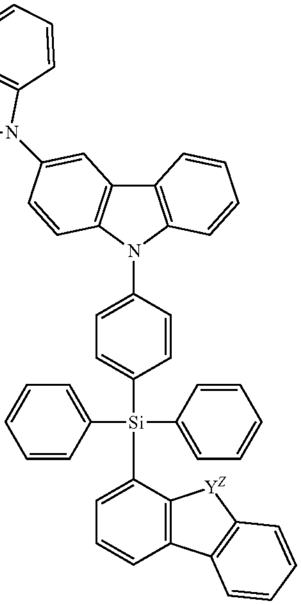
,
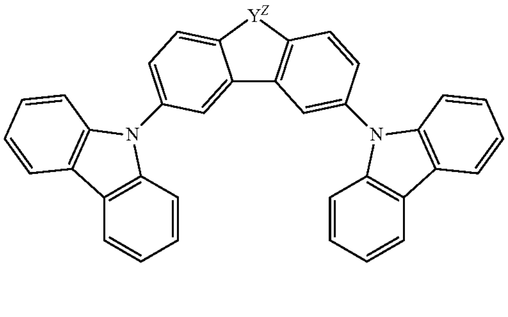
,
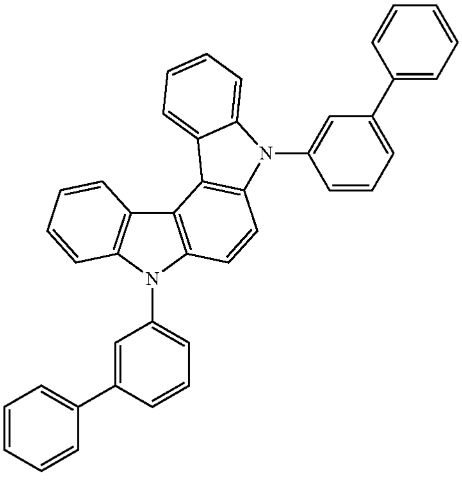
, -continued
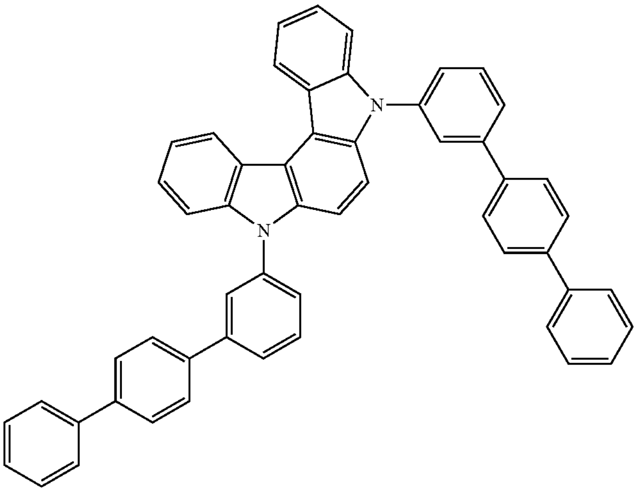
,
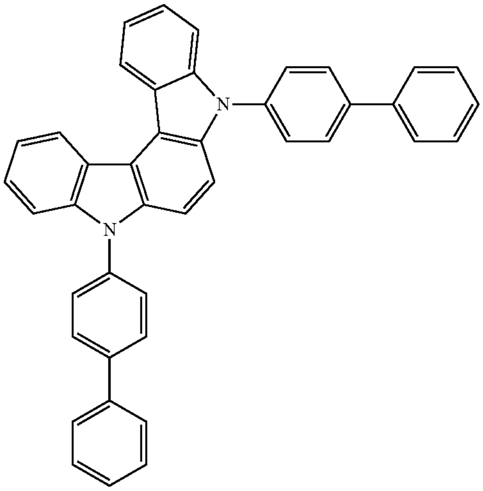
,
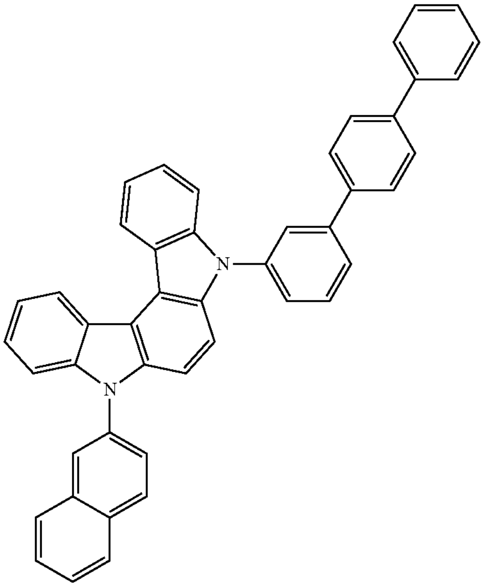
,
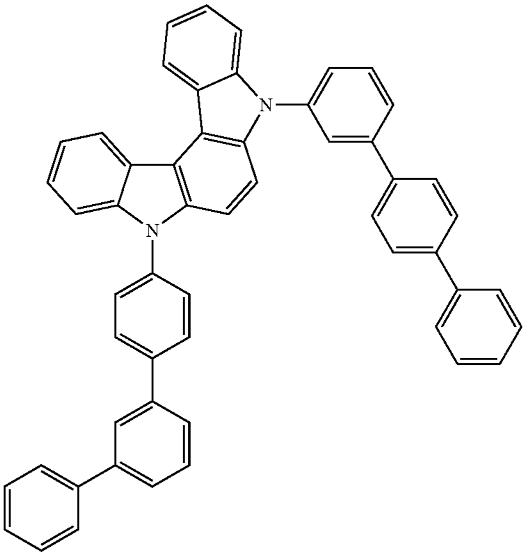
,
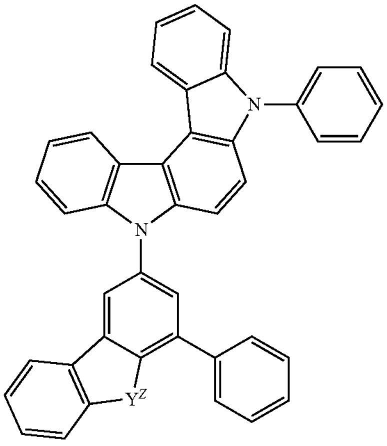
,
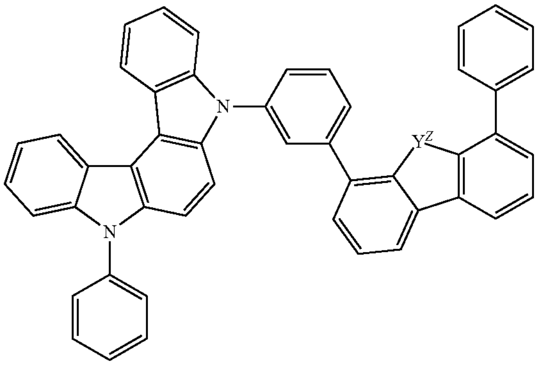
, -continued
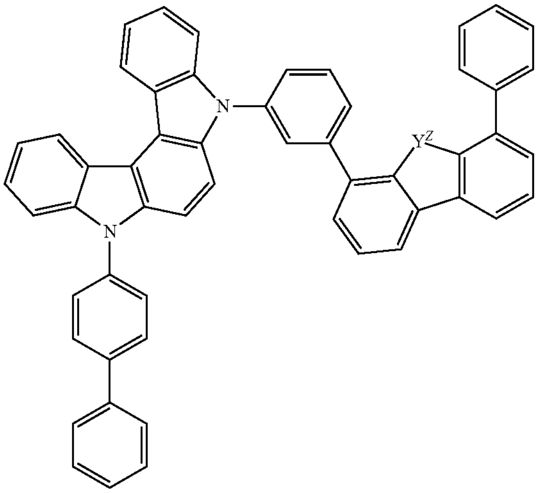
,
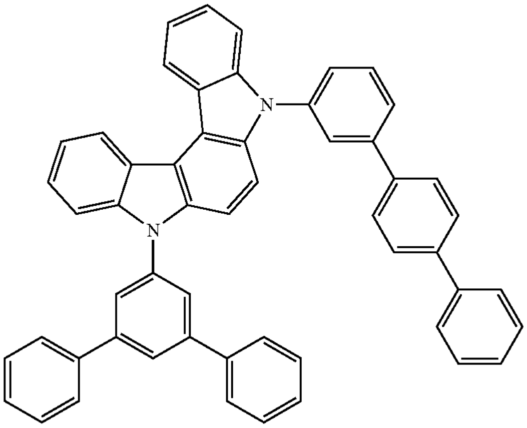
,
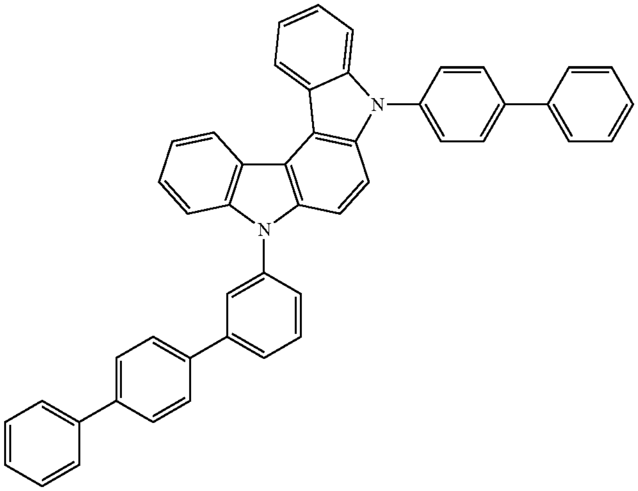
,
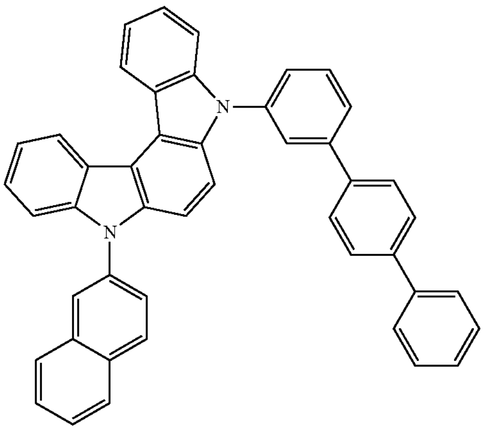
,
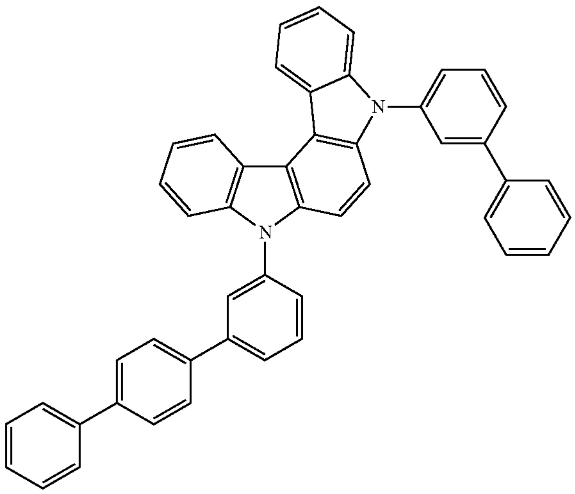
, -continued
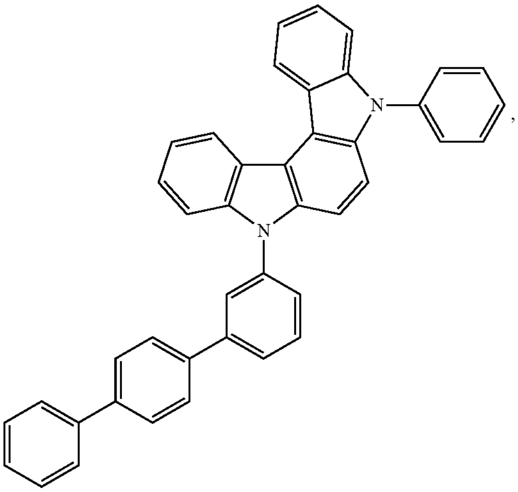
,
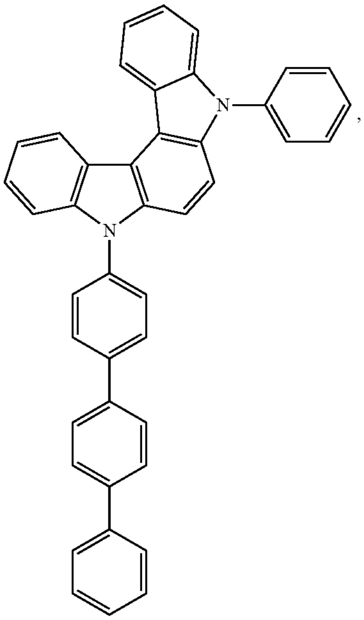
,
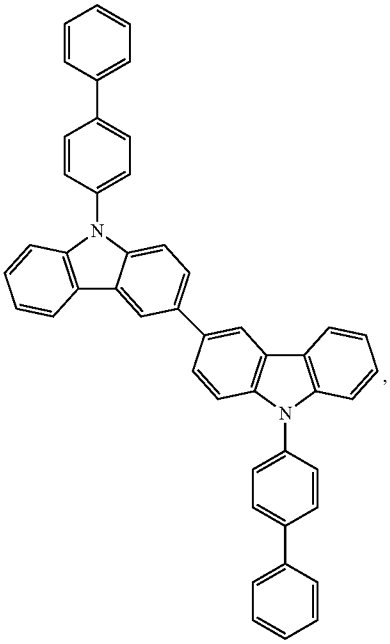
,
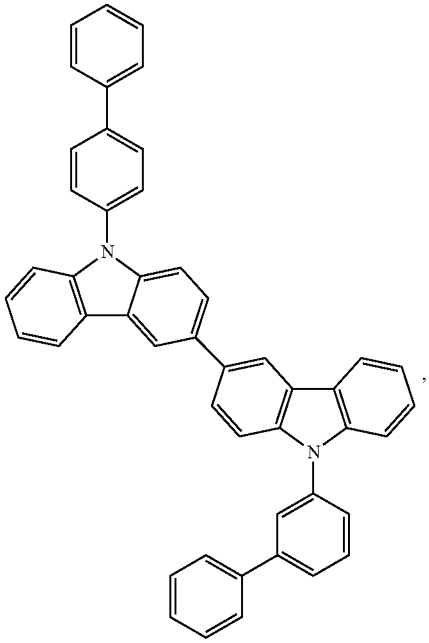
, -continued
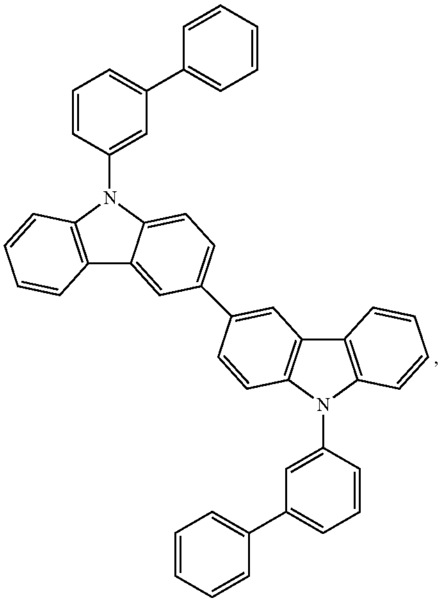
,
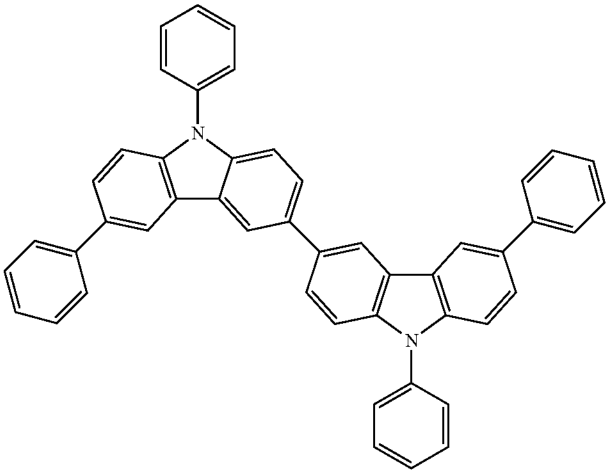
,
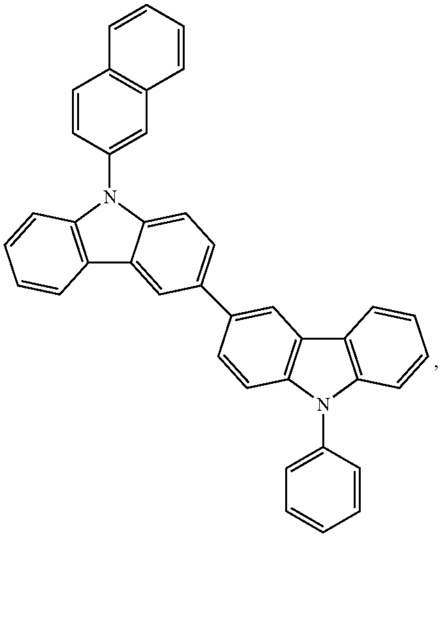
,
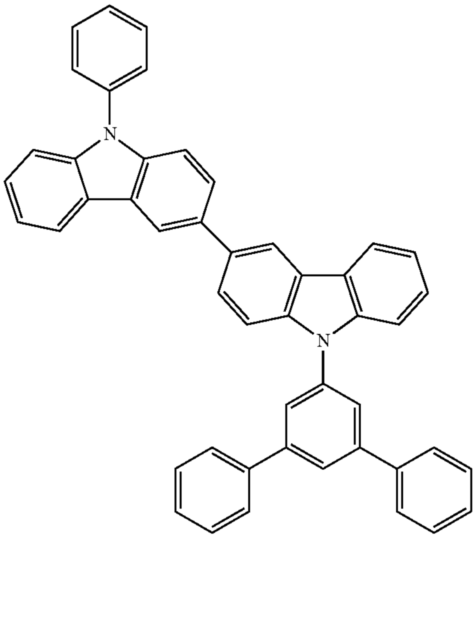
, -continued
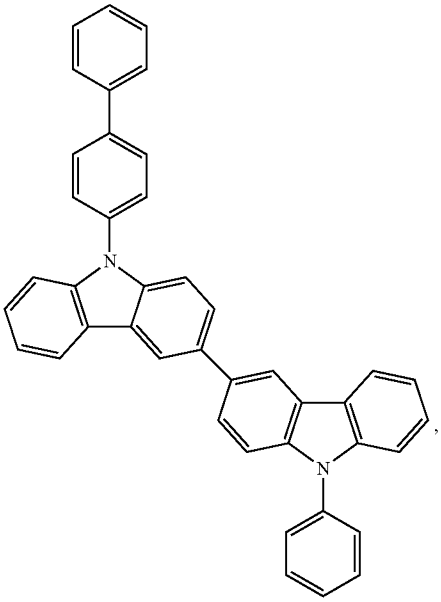
,
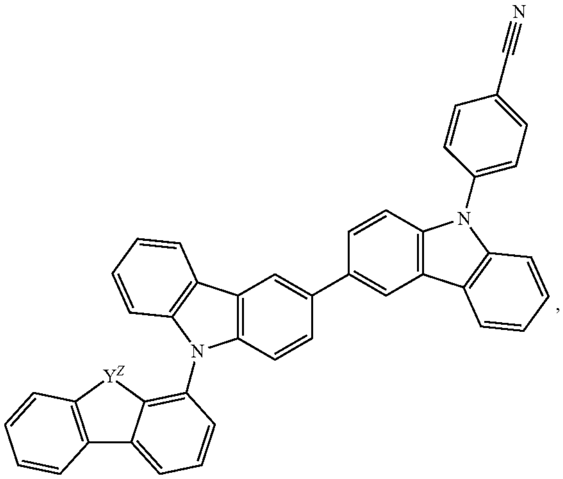
,
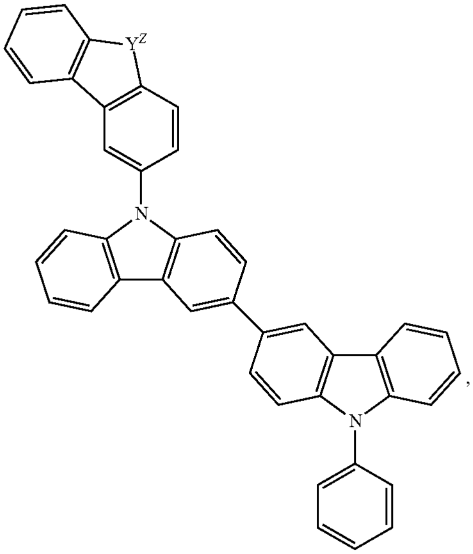
,
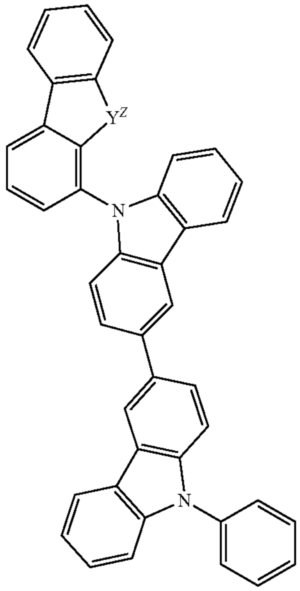
,
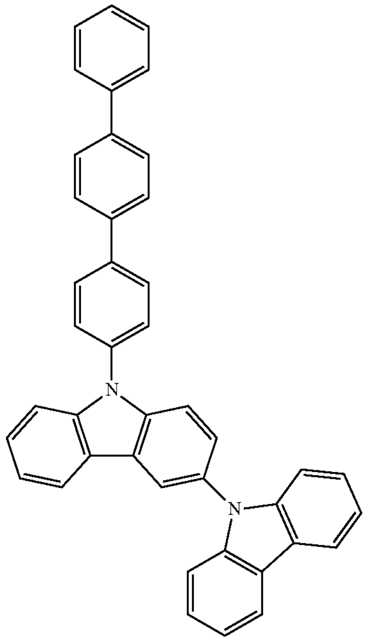
, -continued
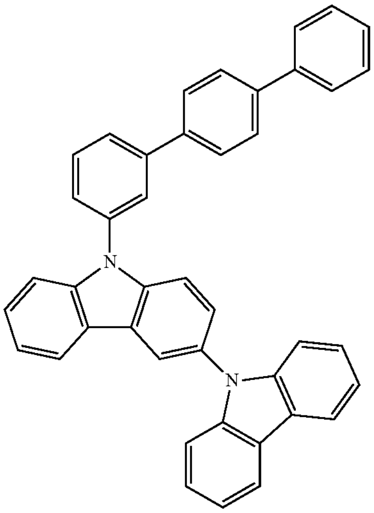,
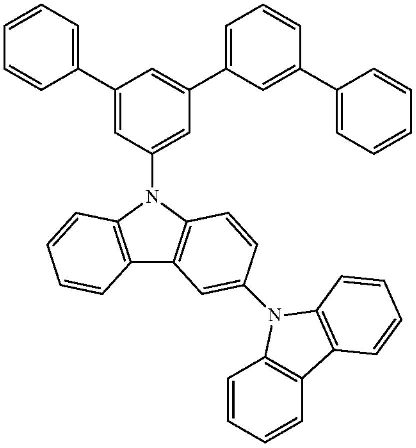,
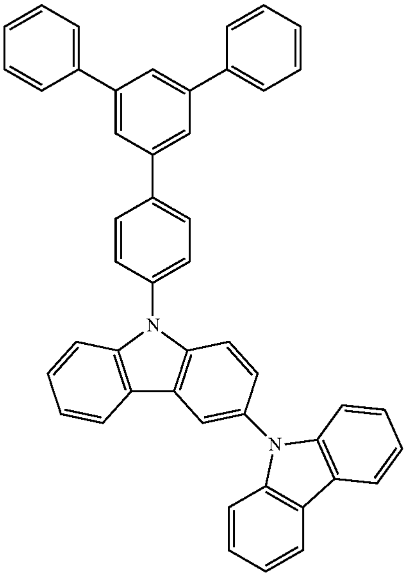,
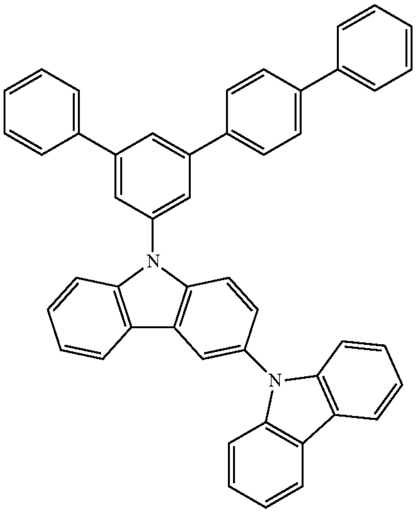,
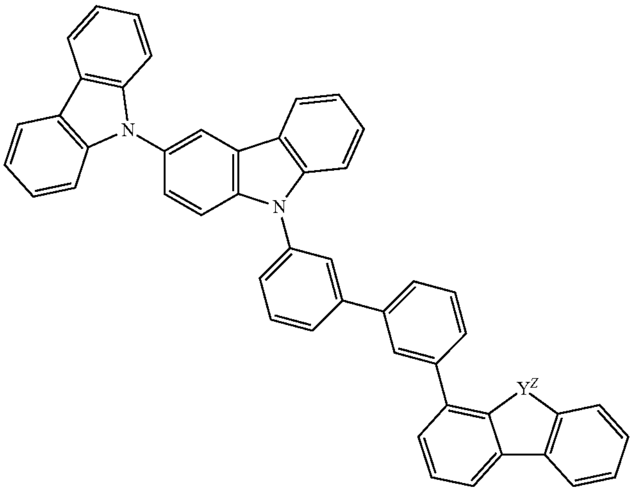,
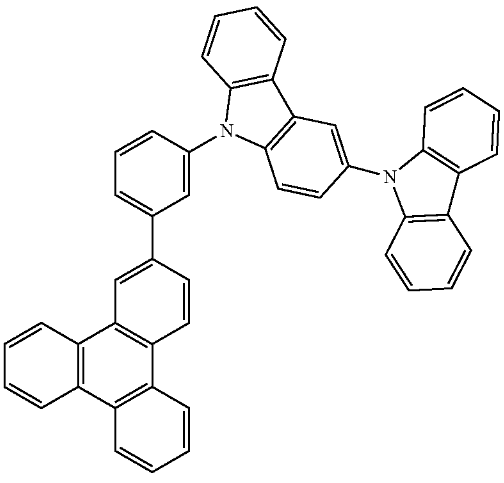, -continued
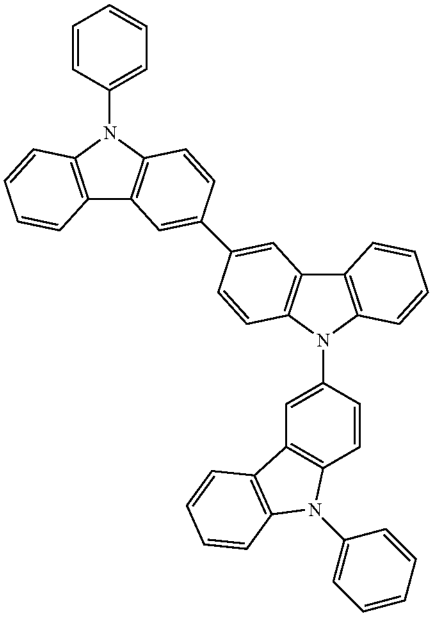
,
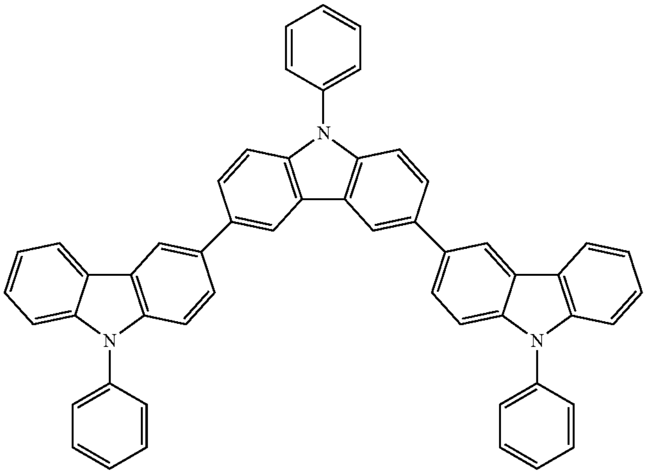
,
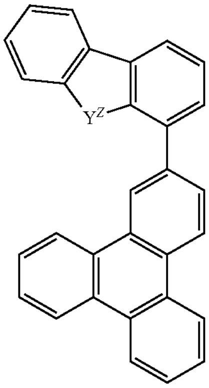
,
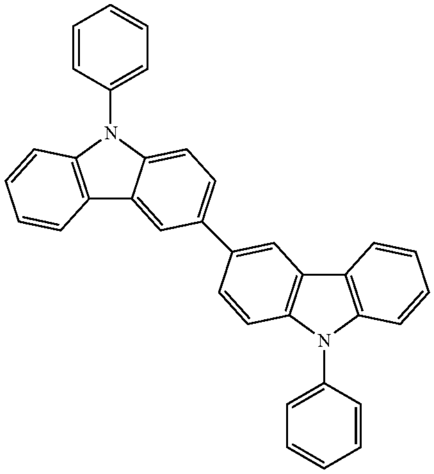
,
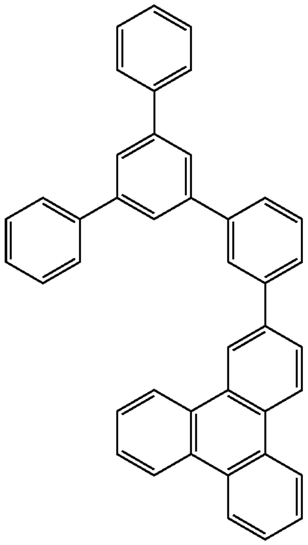
,
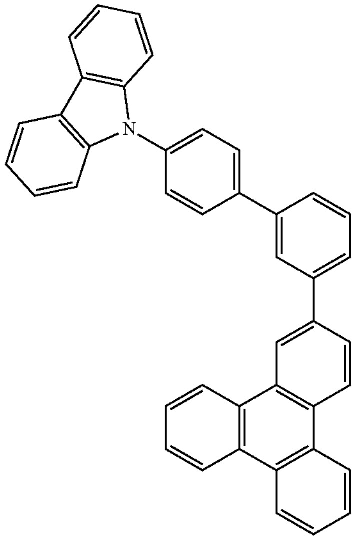
,
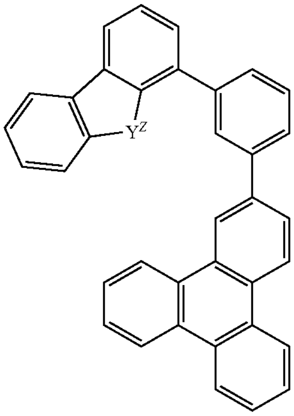
,
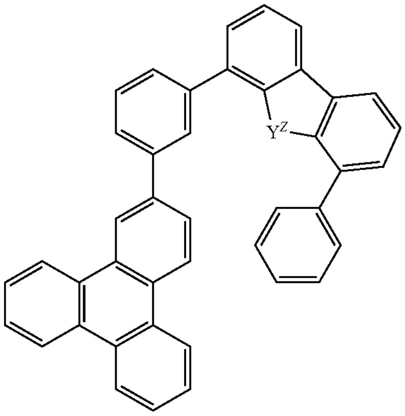
, -continued
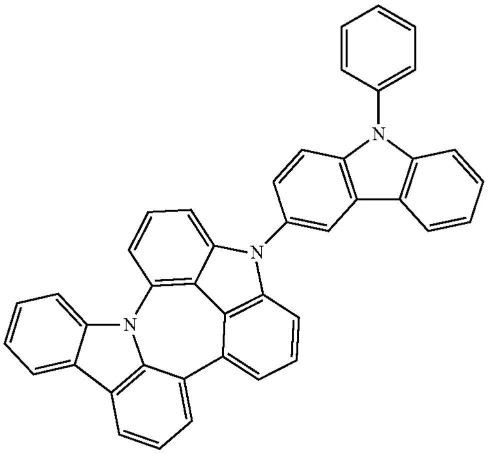
,
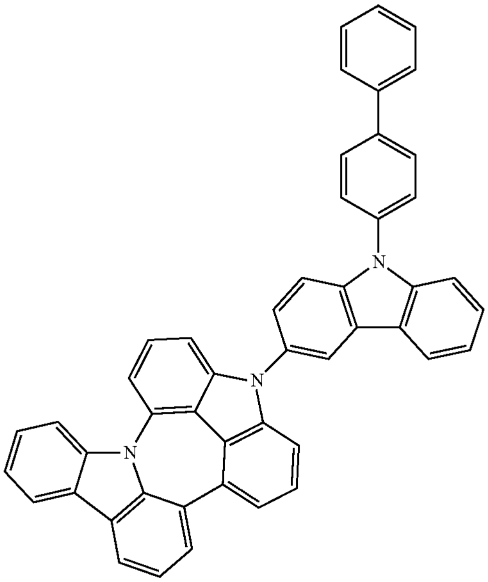
,
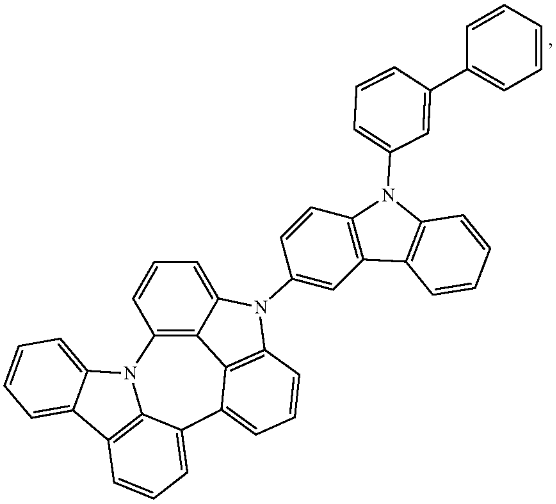
,
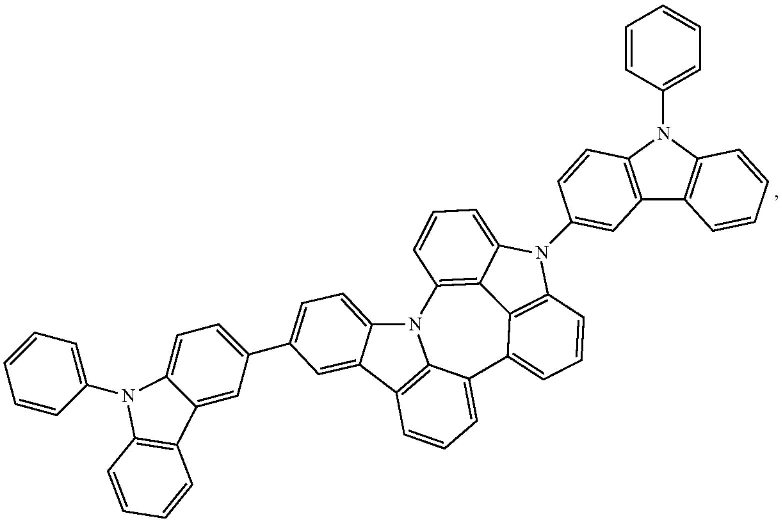
, -continued
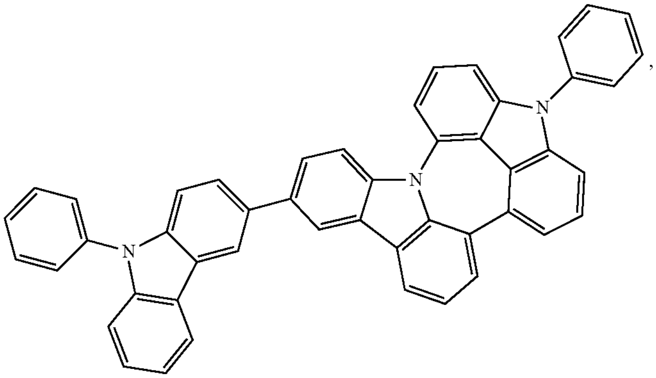
,
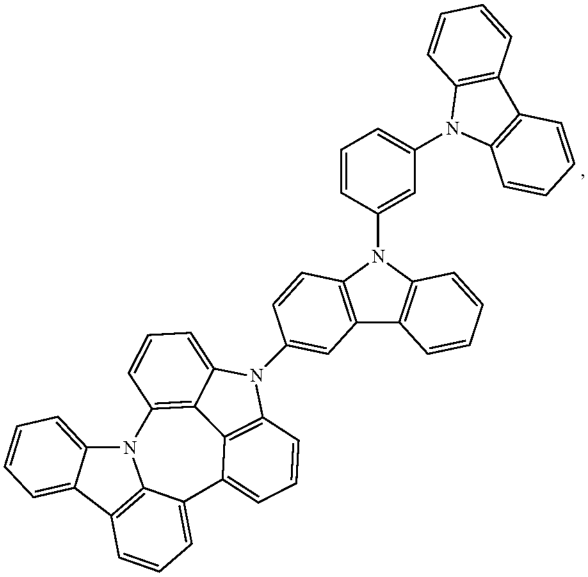
,
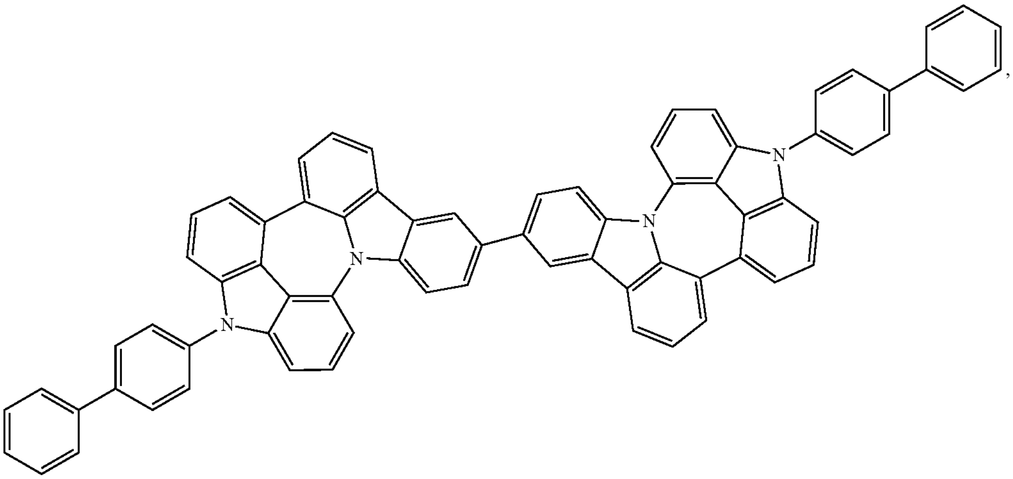
, -continued

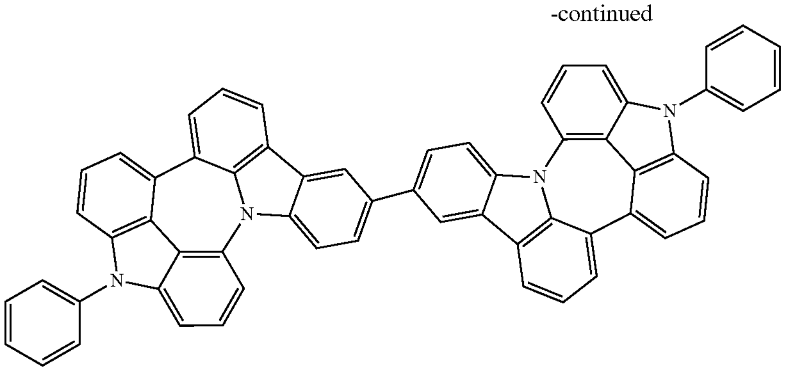

,

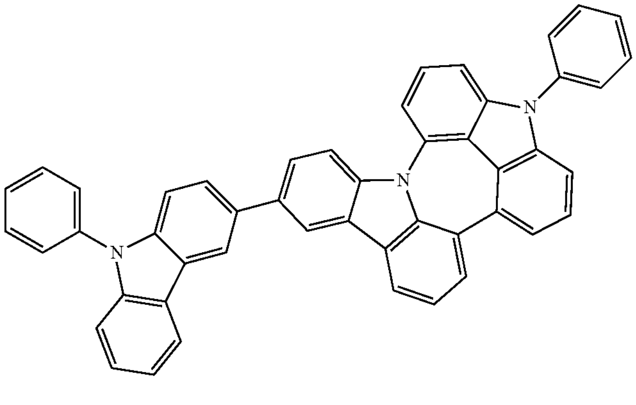

,

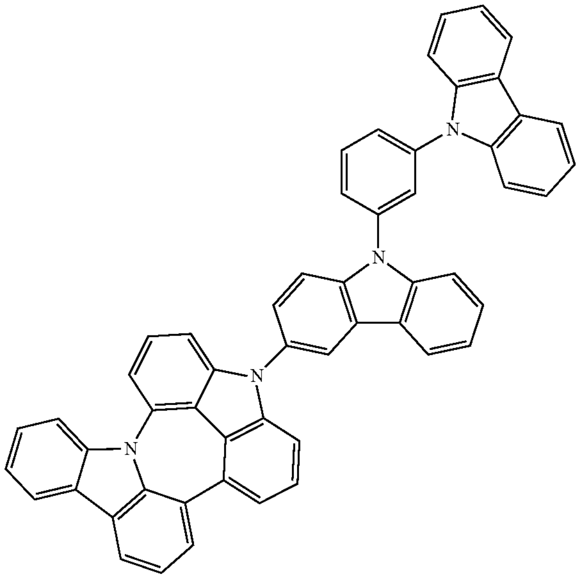

, and

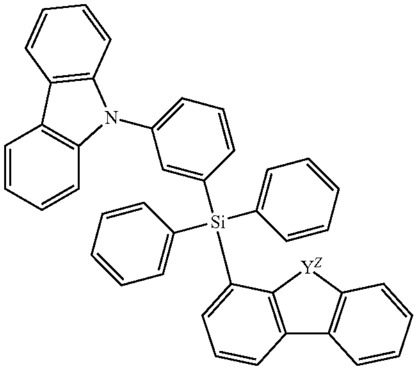

;

wherein:

$Y^Z$ is selected from the group consisting of O, S, and N-phenyl; and the first host is at least partially deuterated.

In some embodiments where the first host is one of the structures of LIST 4, at least 50% of the hydrogen atoms are replaced with deuterium. In some embodiments where the first host is one of the structures of LIST 4, at least 70% of the hydrogen atoms are replaced with deuterium. In some embodiments where the first host is one of the structures of LIST 4, at least 90% of the hydrogen atoms are replaced with deuterium.

In some embodiments, the first host is selected from the group consisting of the structures of the following LIST 5:

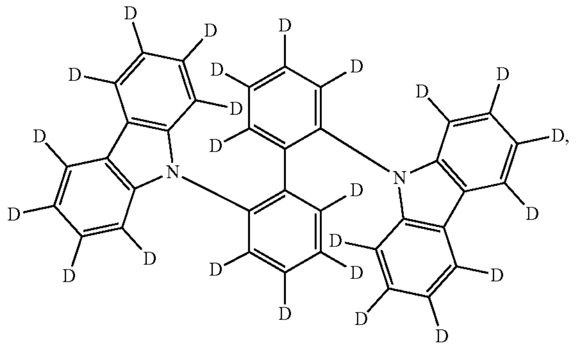
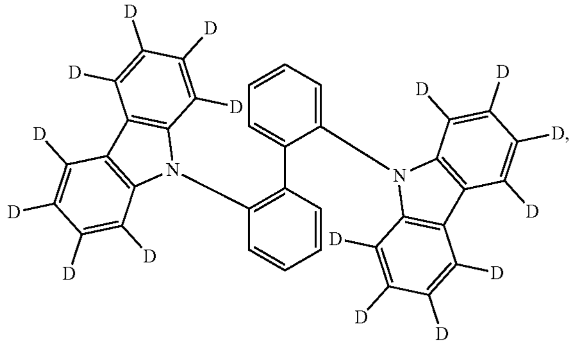
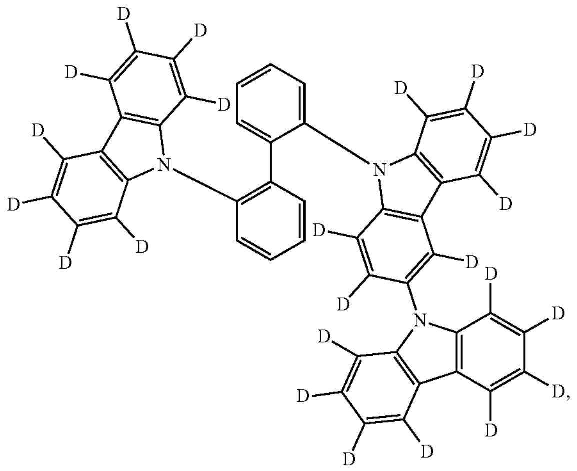
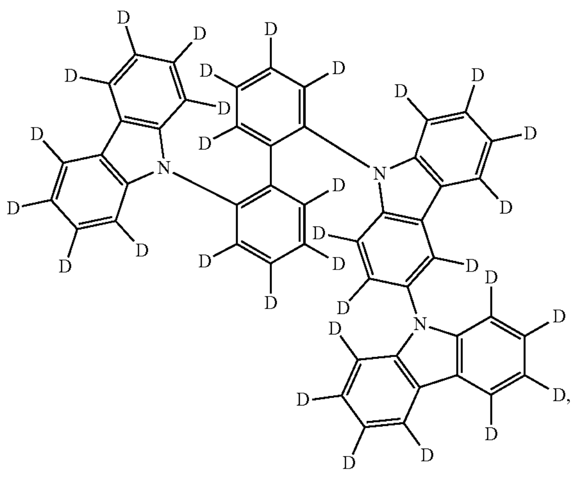
-continued
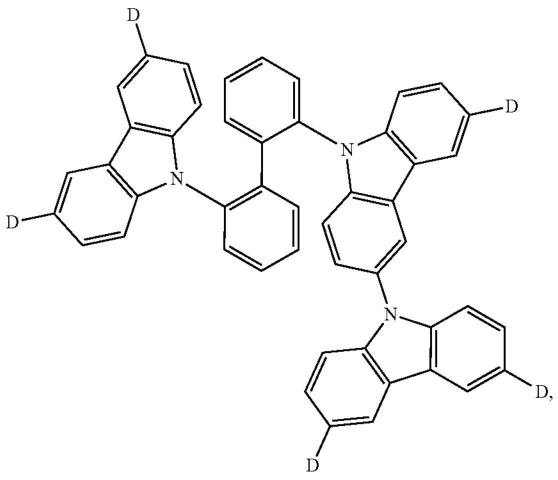
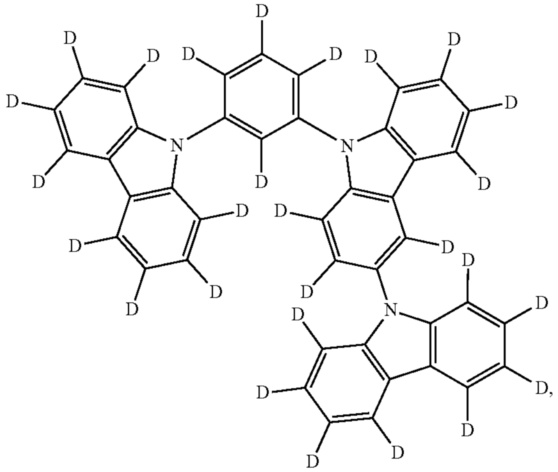
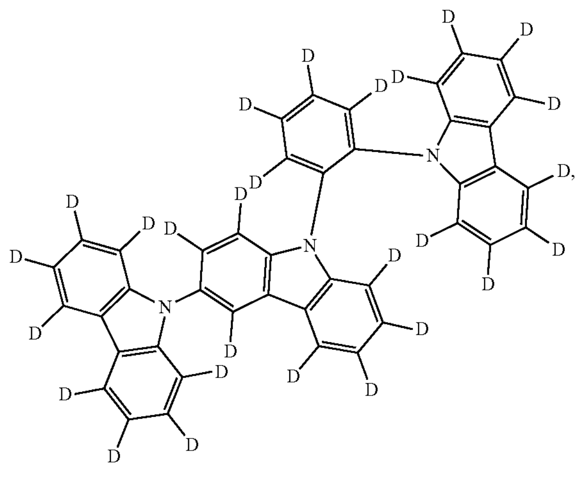

-continued
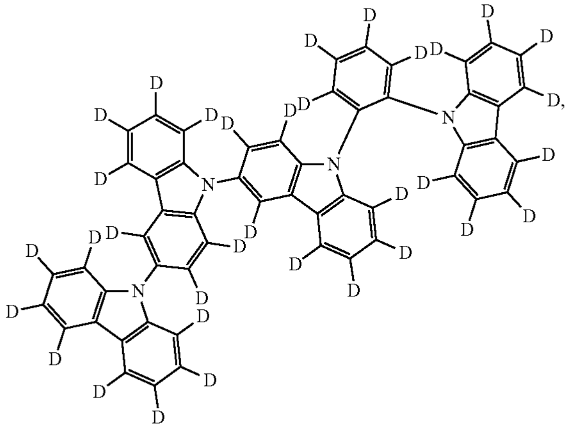
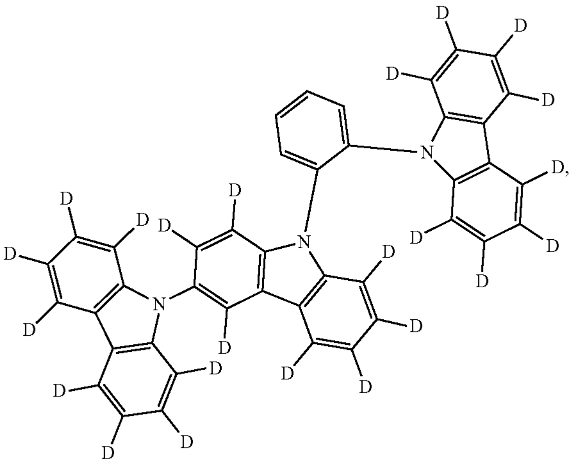
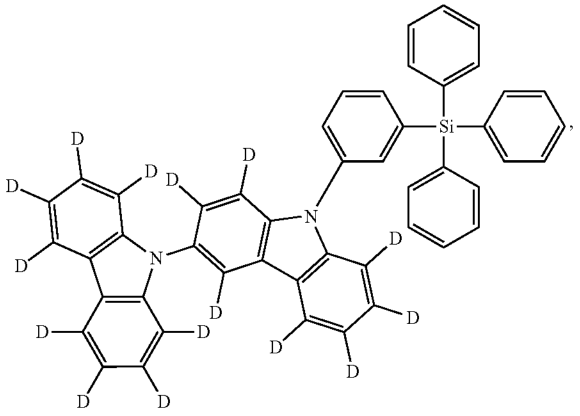
-continued
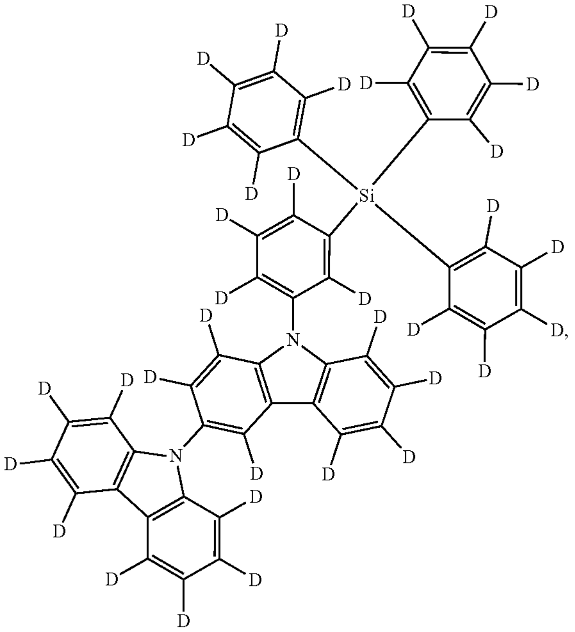
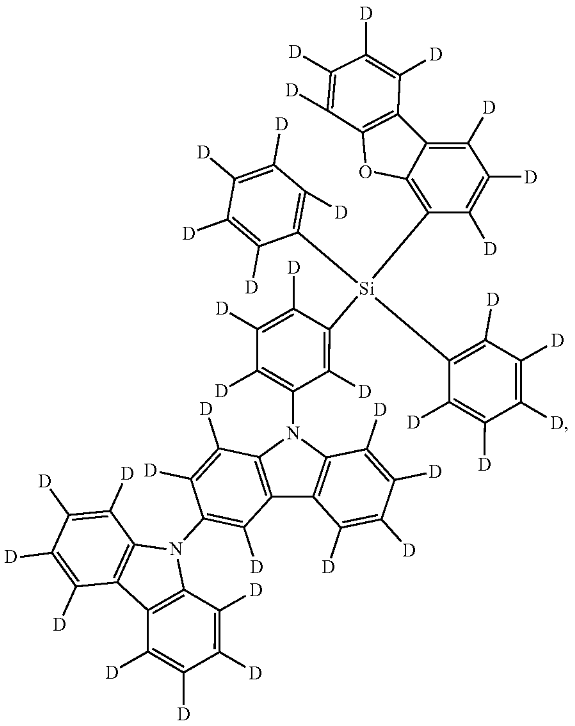

-continued
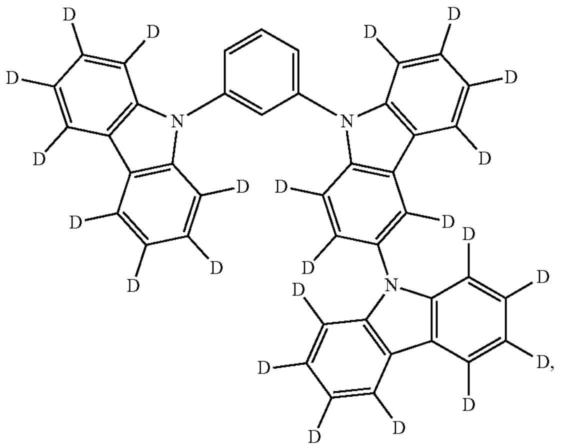
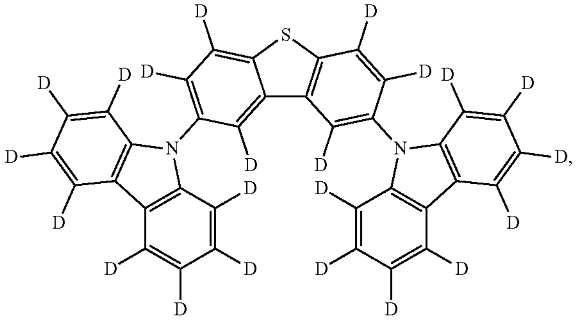
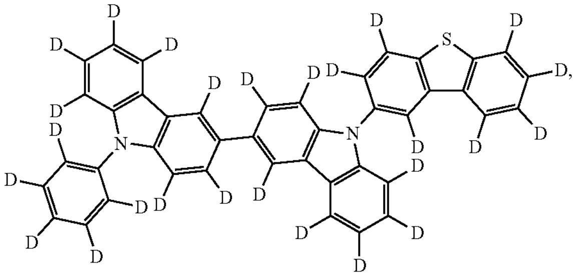
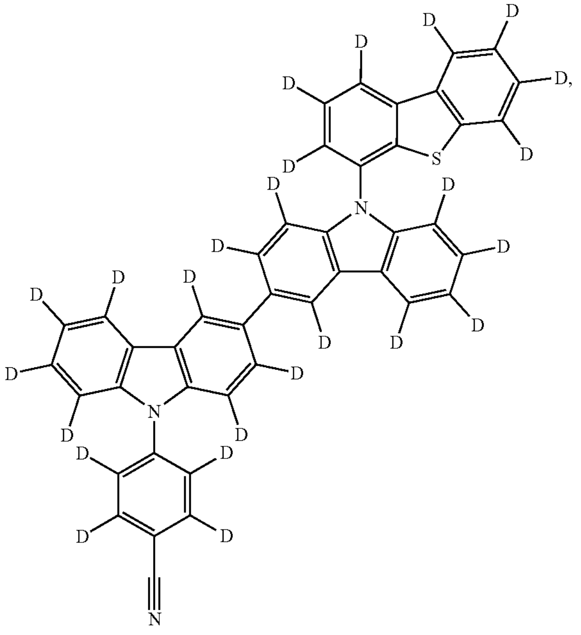
-continued
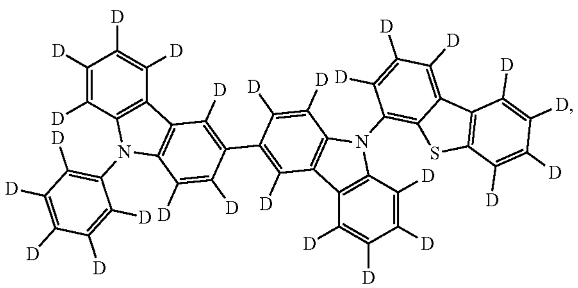
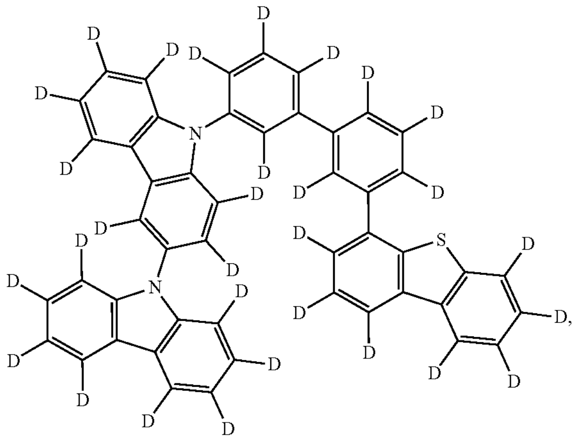
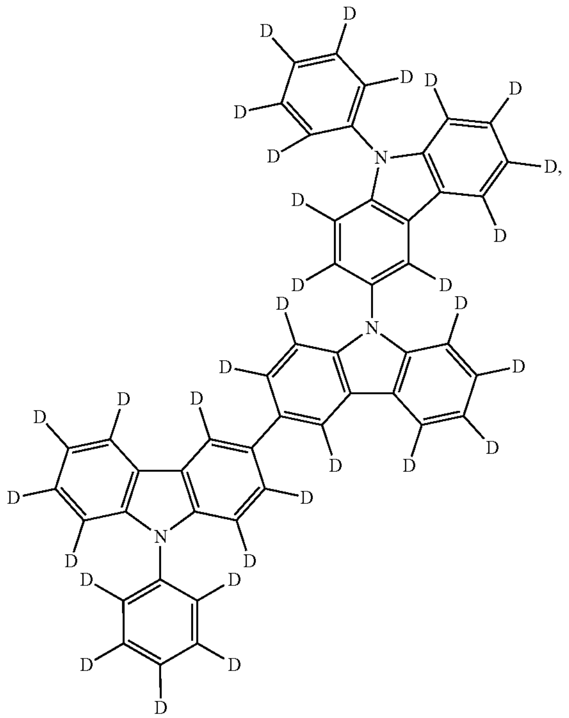

-continued
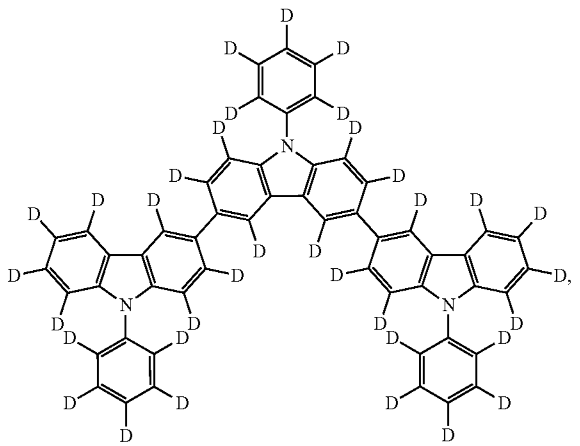
-continued
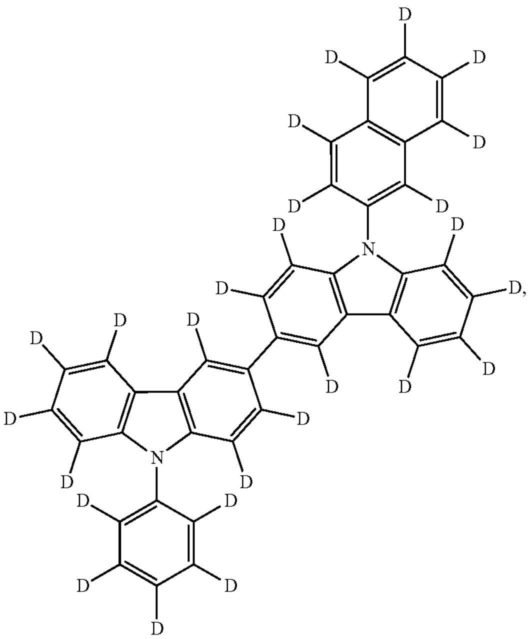
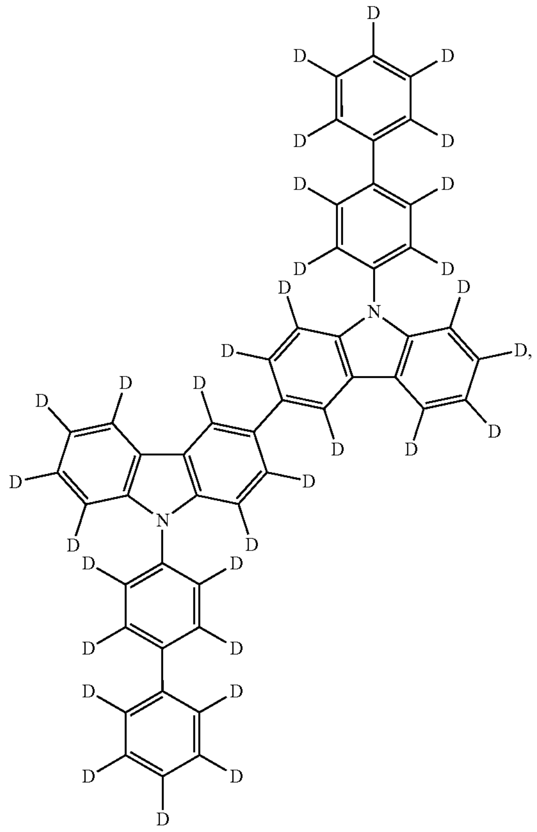
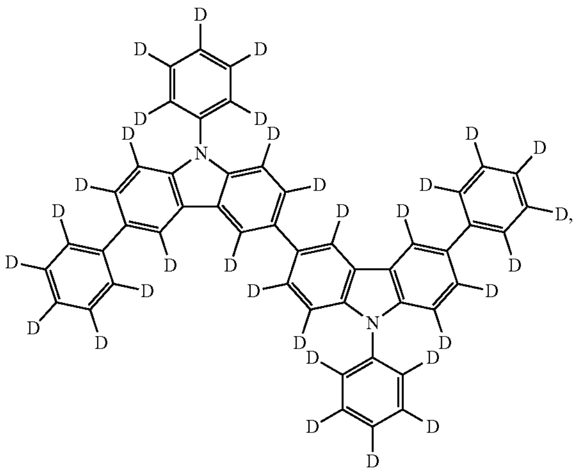

-continued
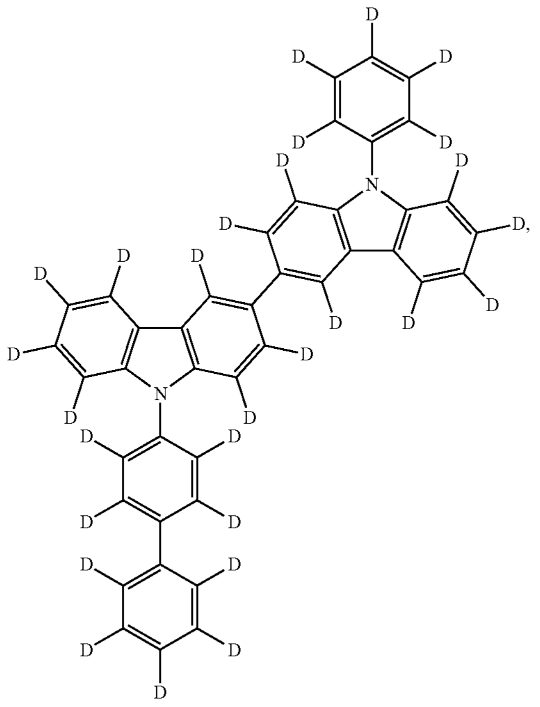
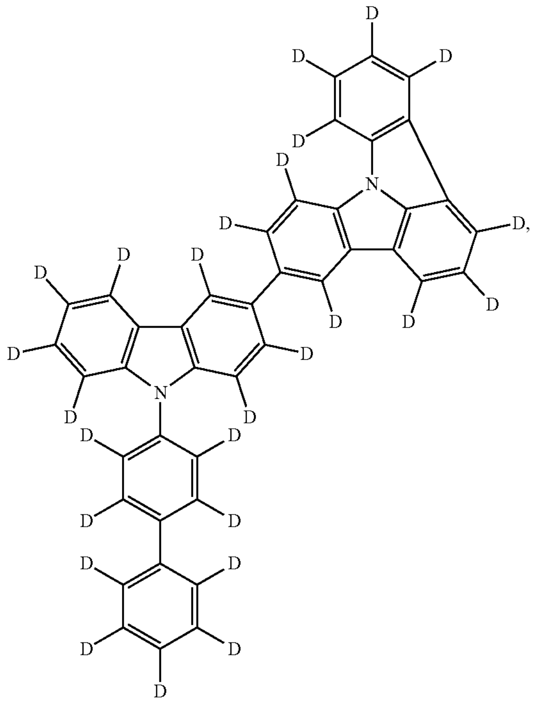
-continued
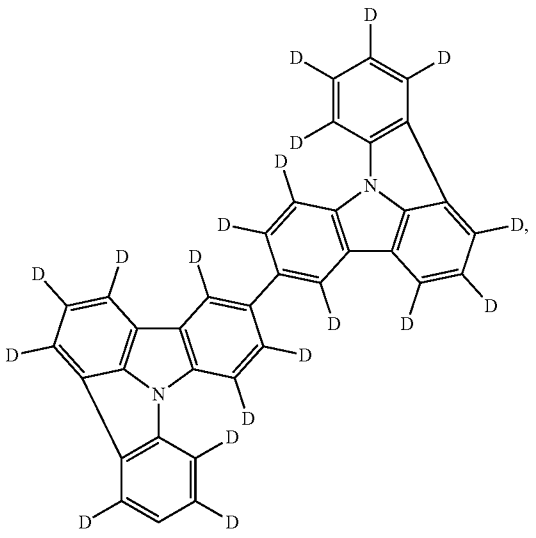
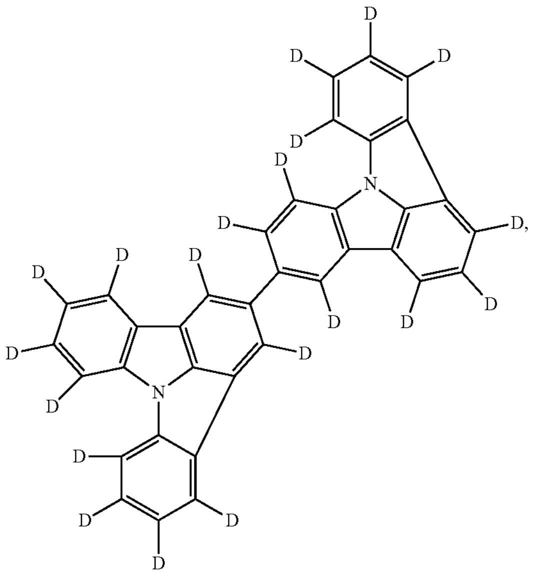
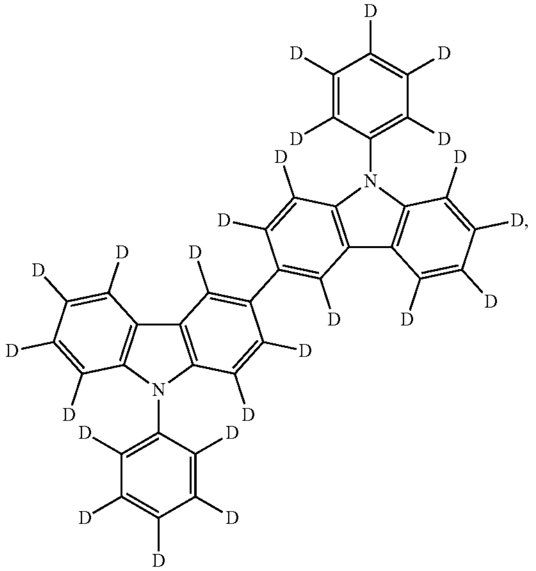

-continued
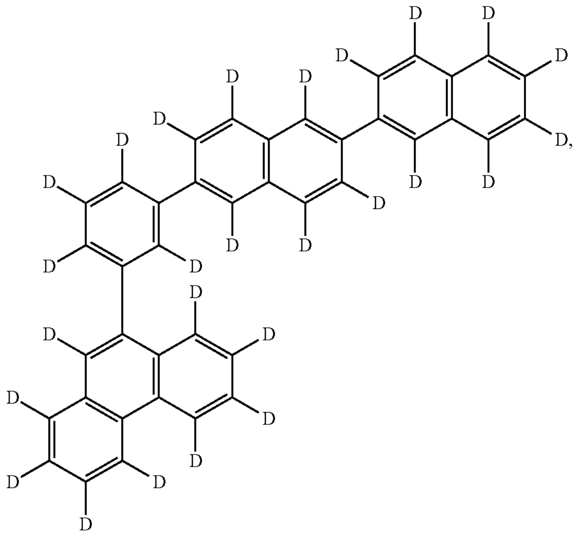
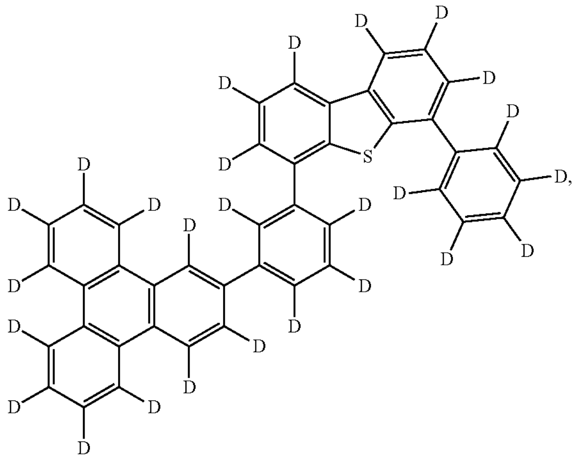
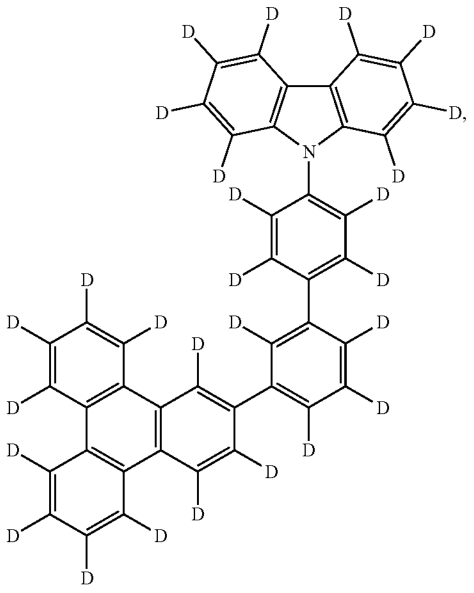
-continued
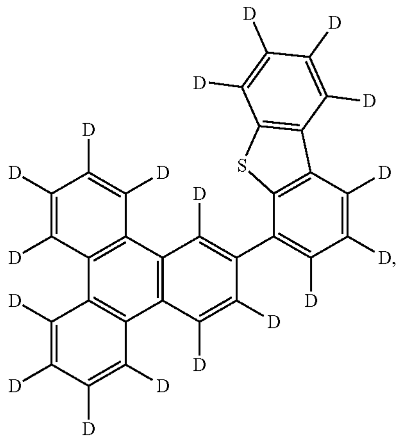
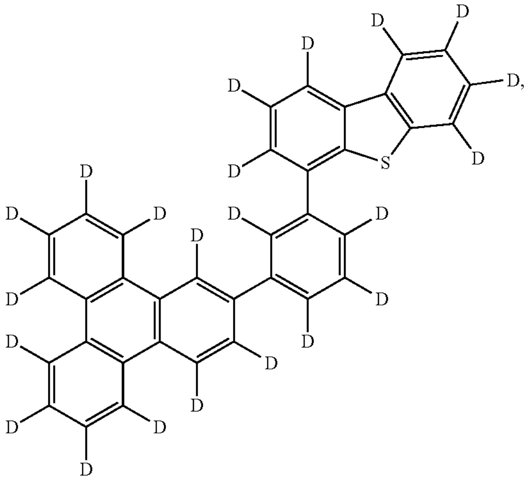

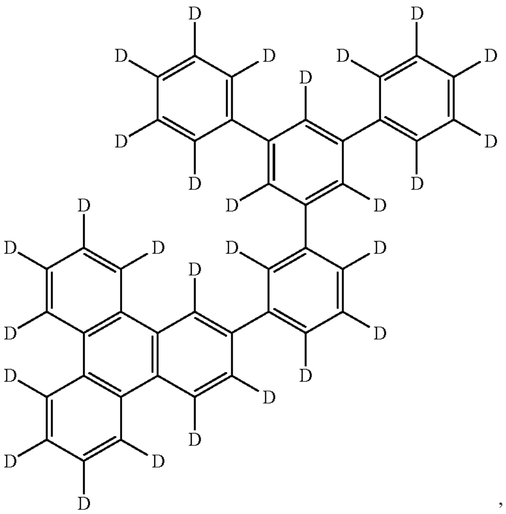
,
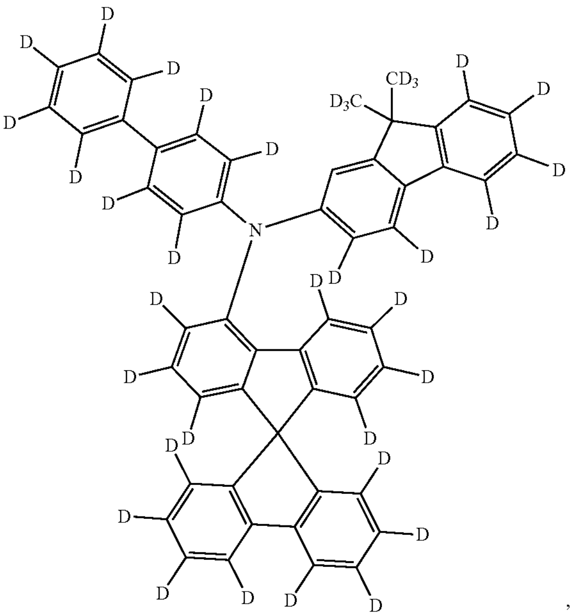
,
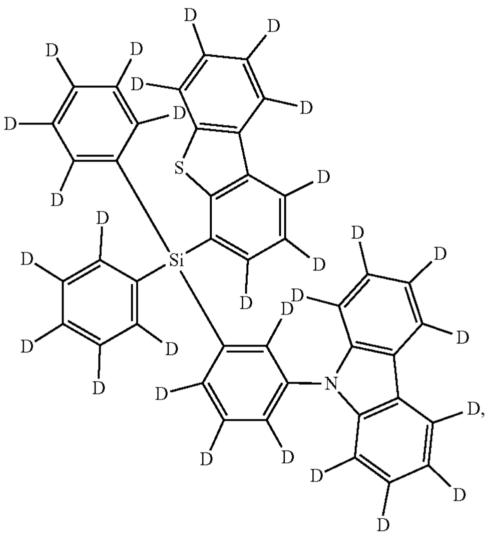
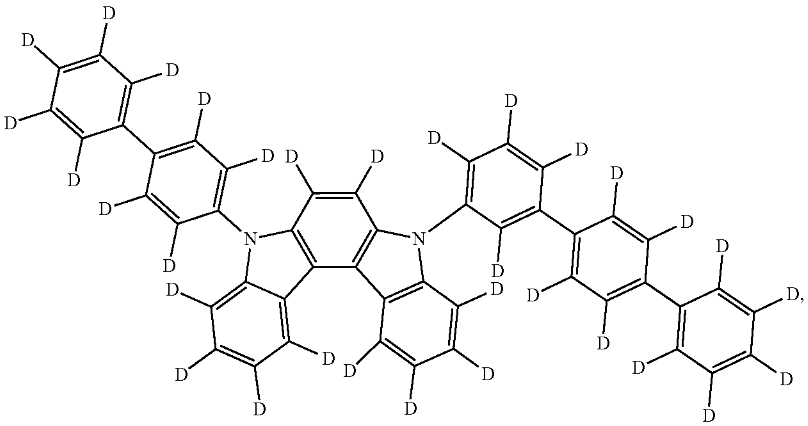

-continued
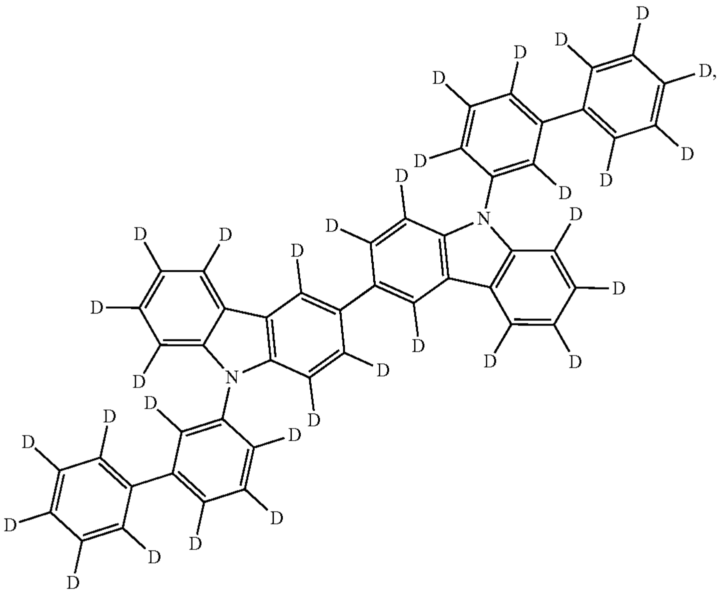
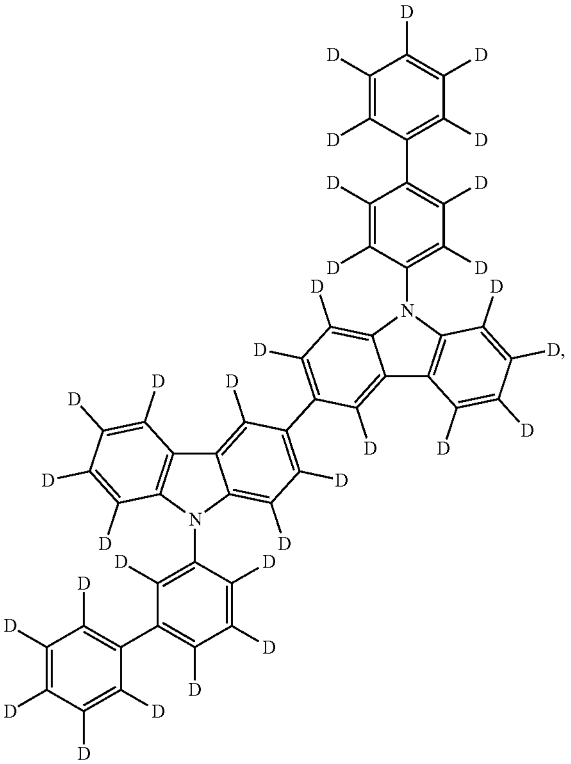

-continued
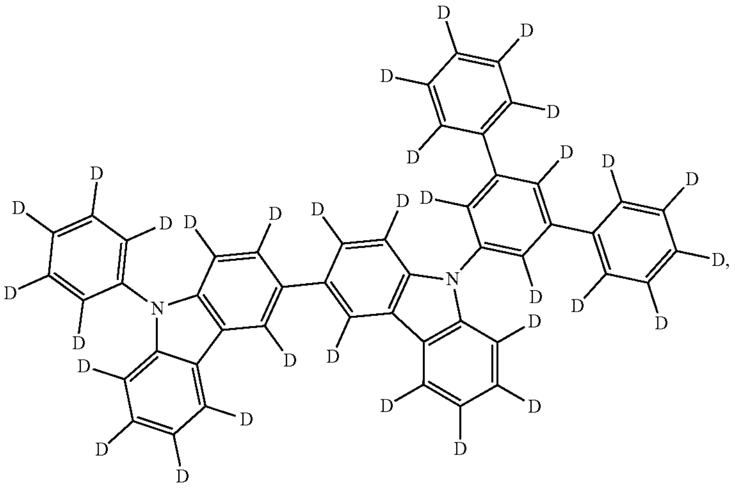
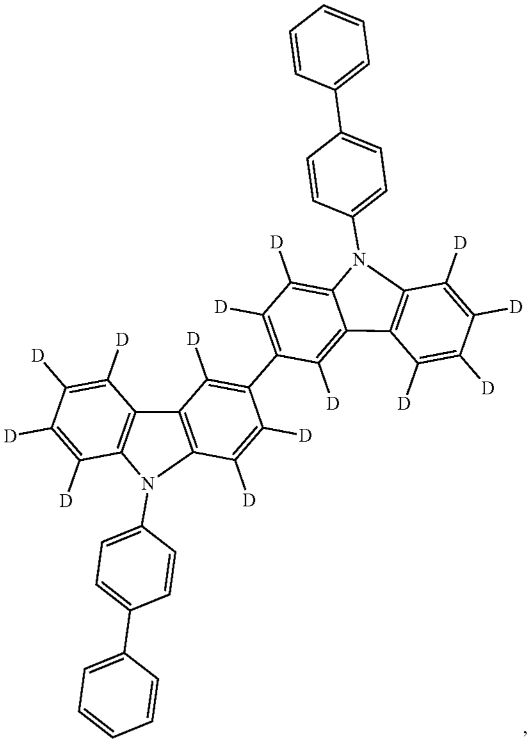
,
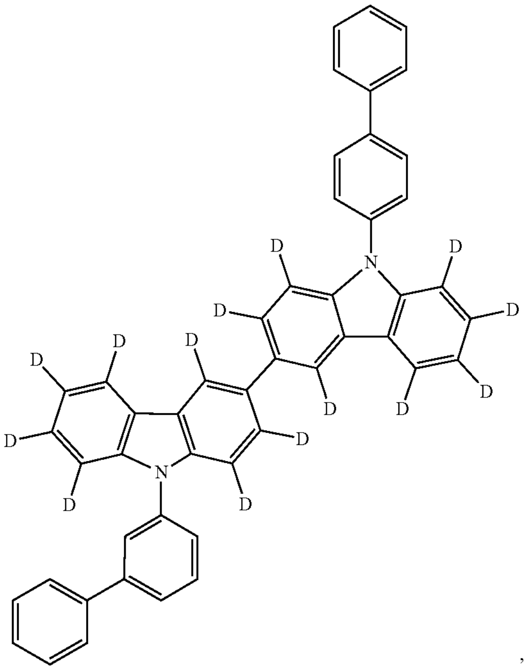
,

-continued
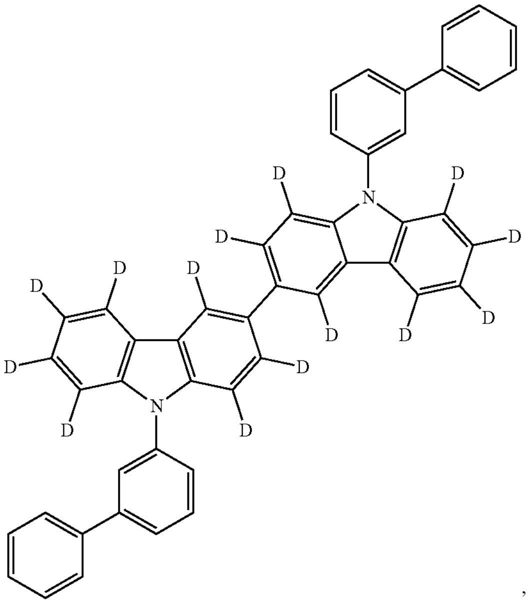
,
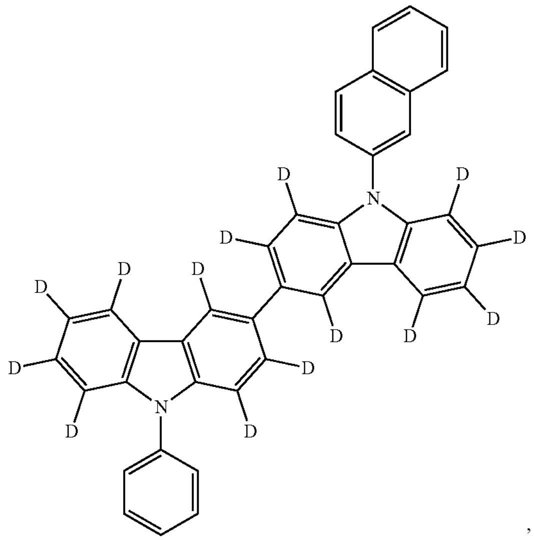
,
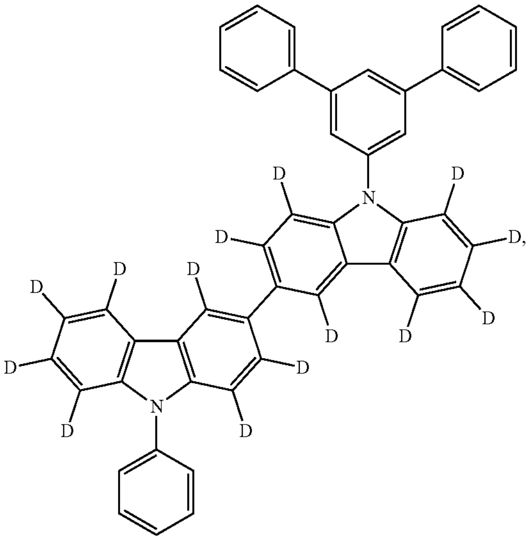
,
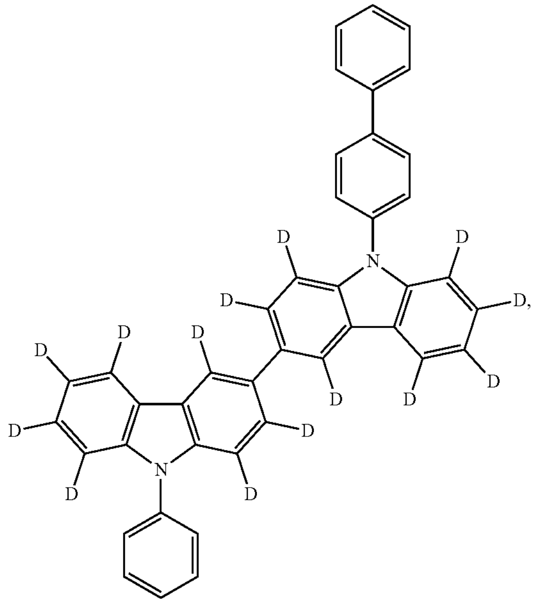
,
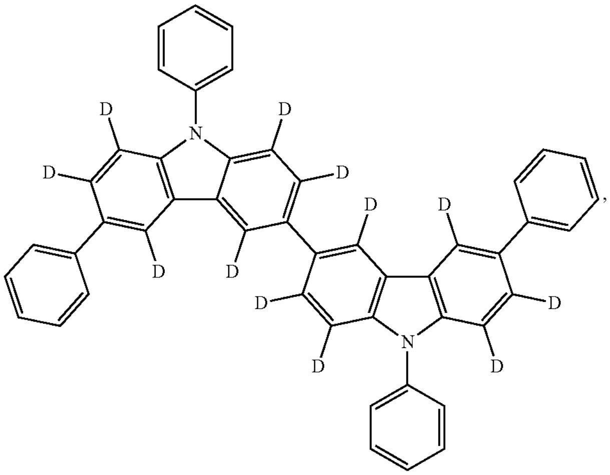
, -continued
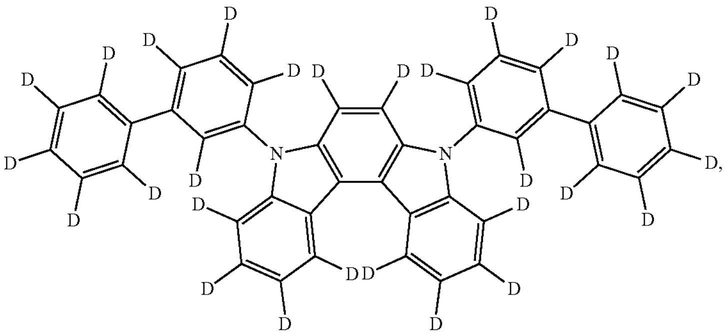
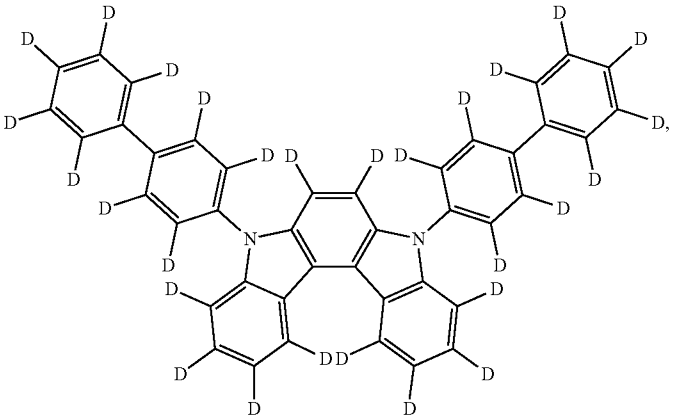
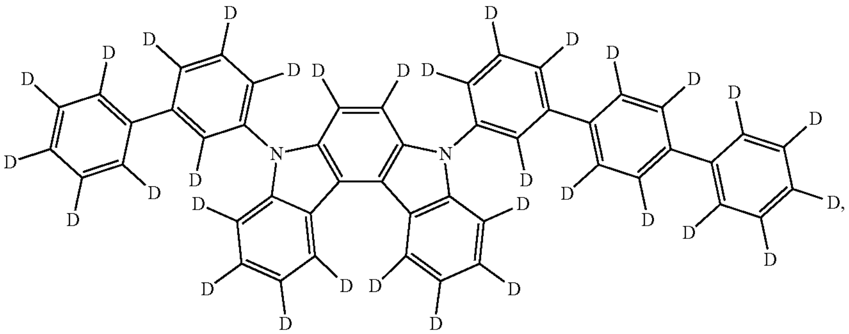
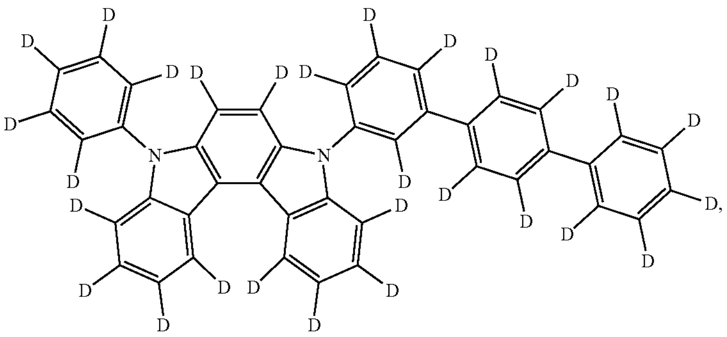

-continued
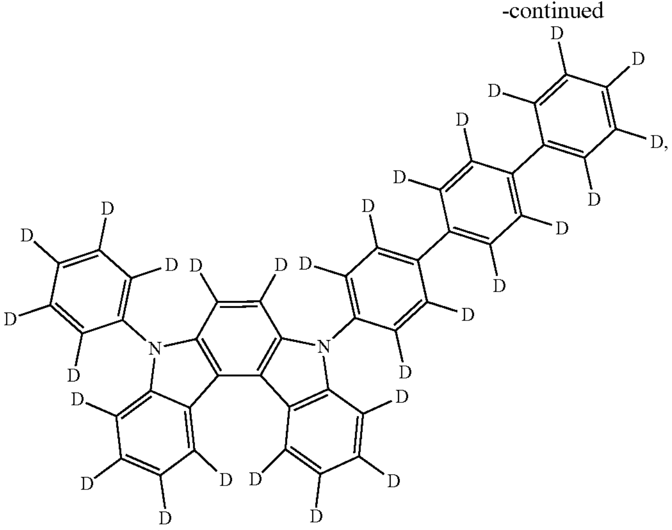
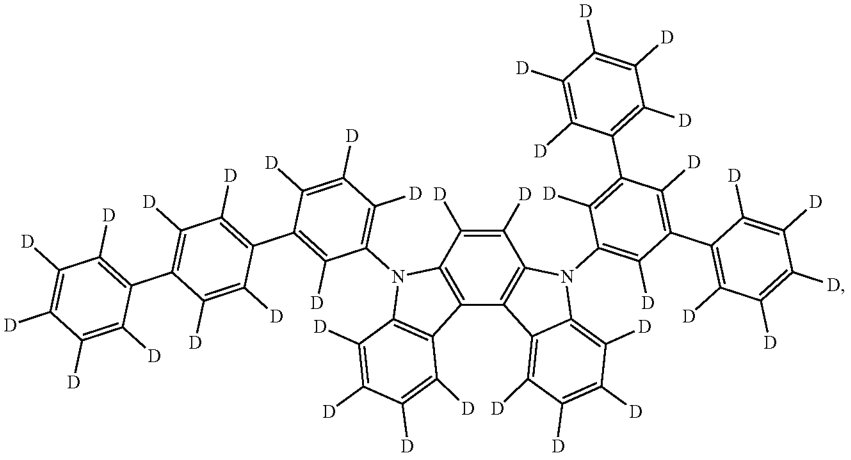
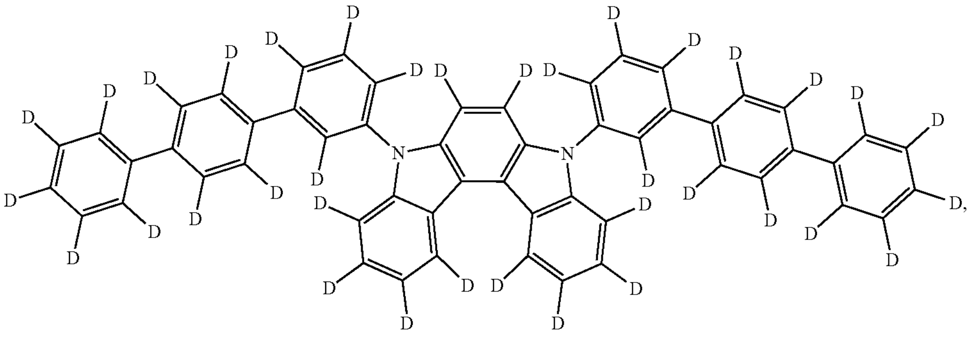
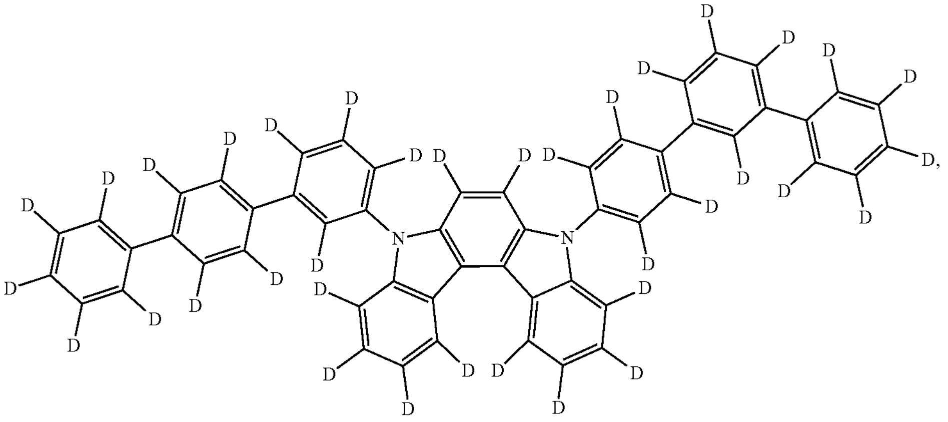

-continued
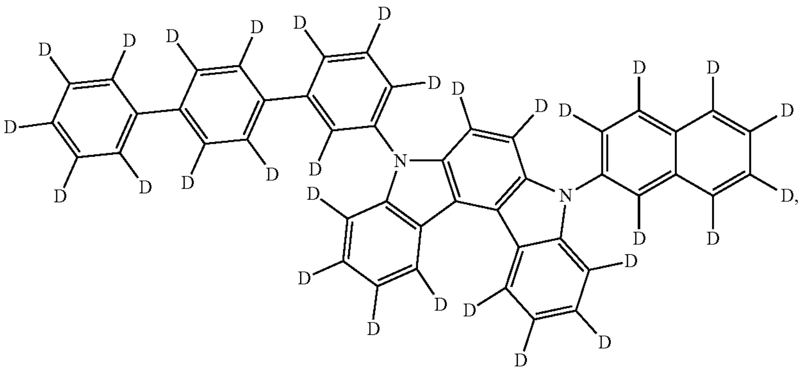
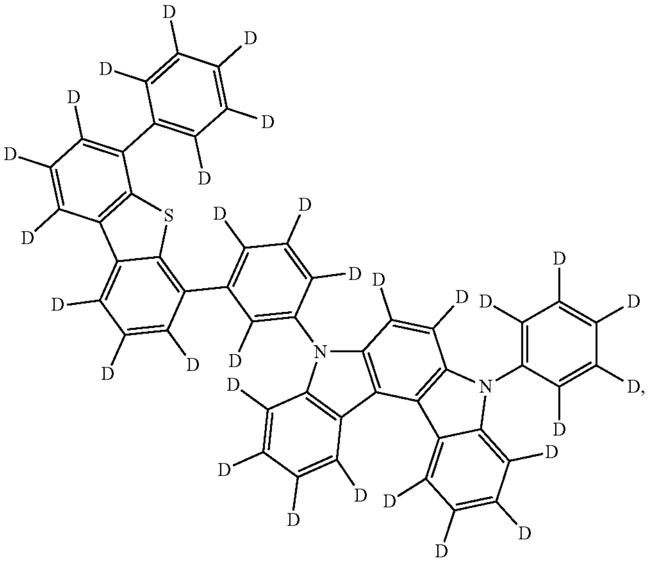
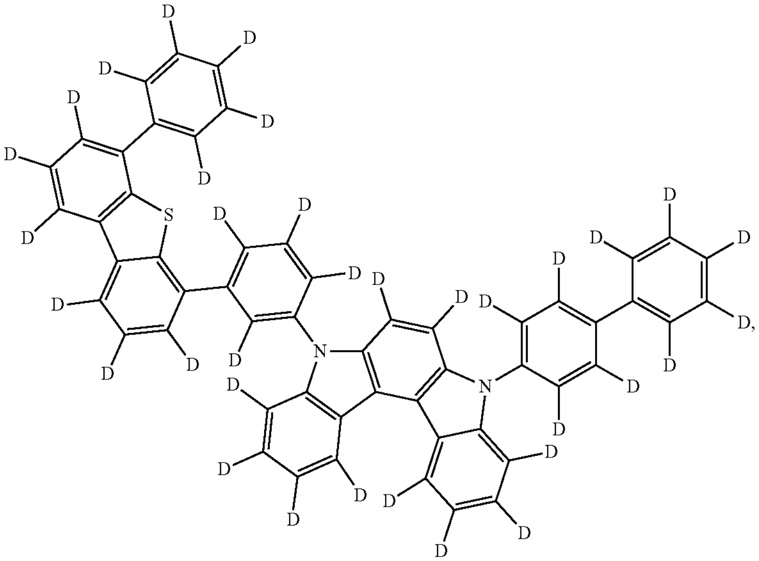

-continued
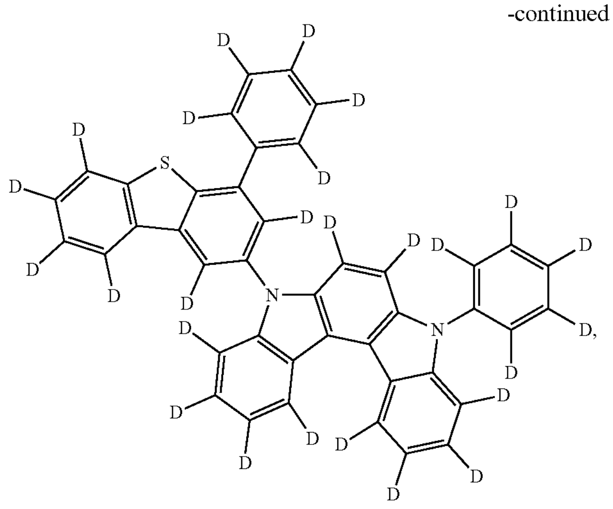
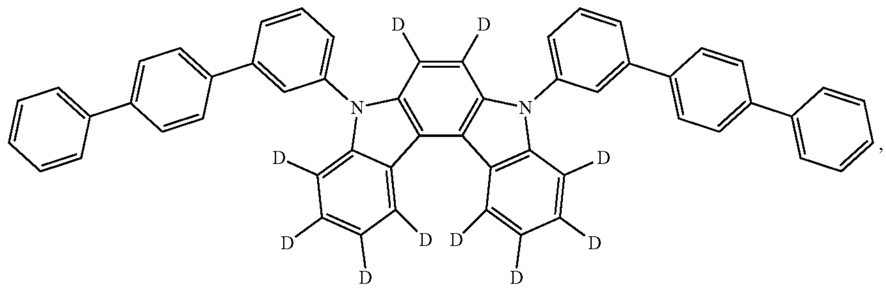
,
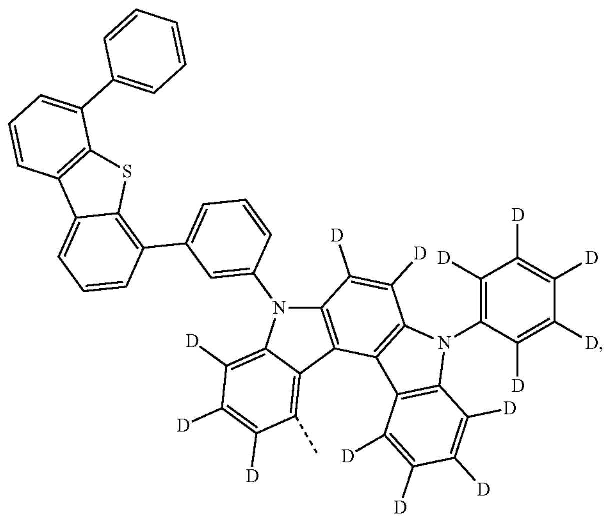
D,

-continued
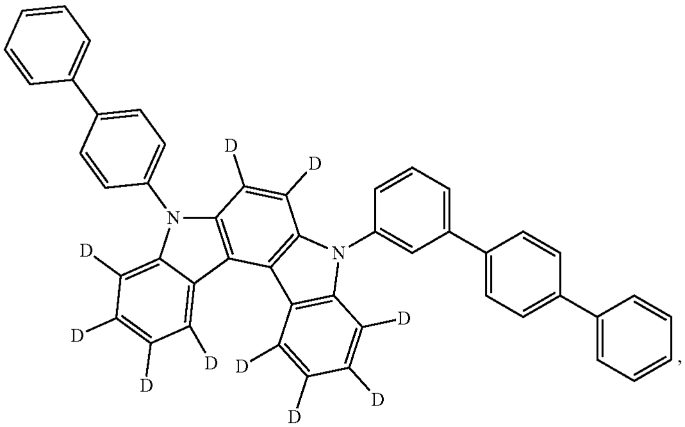
,
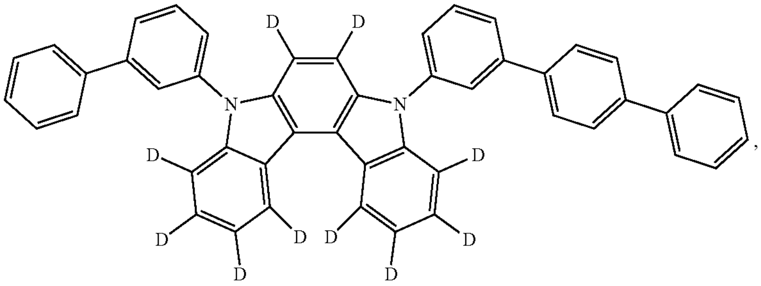
,
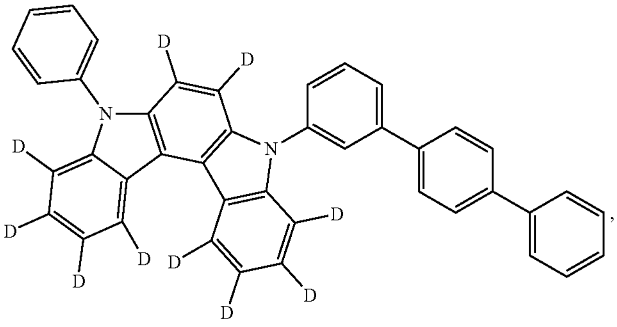
,
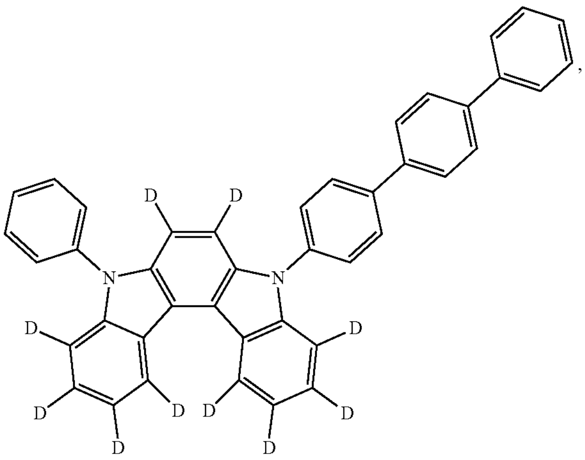
,

-continued
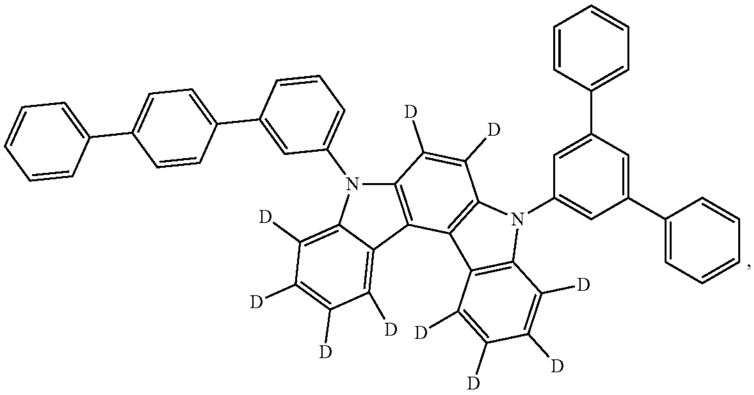
,
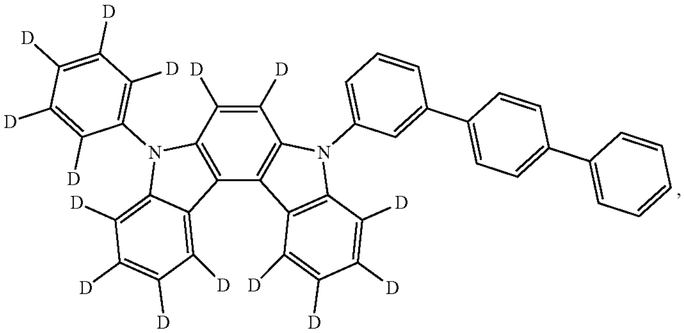
,
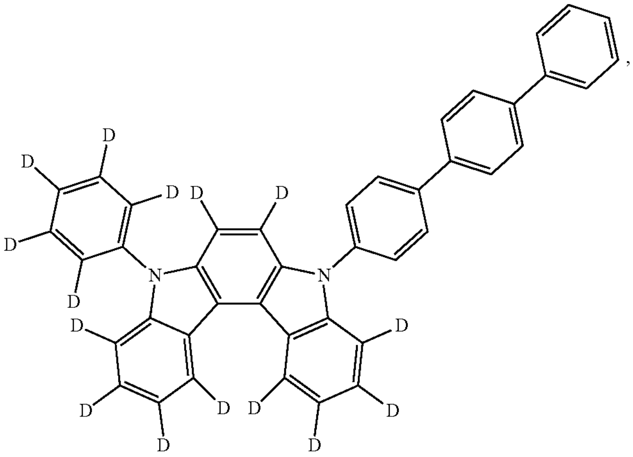
,
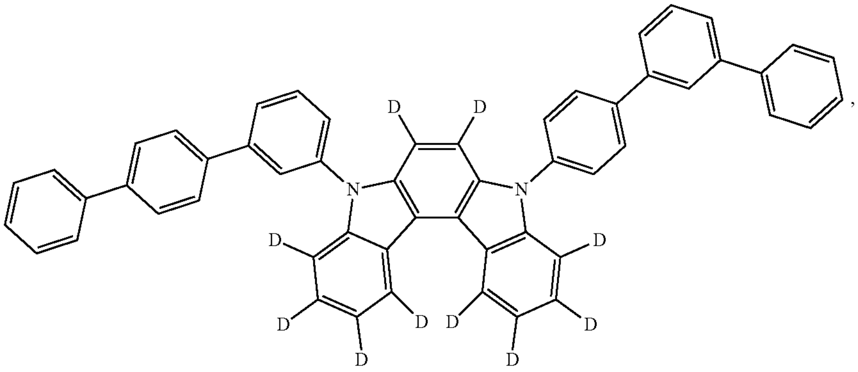
,

-continued
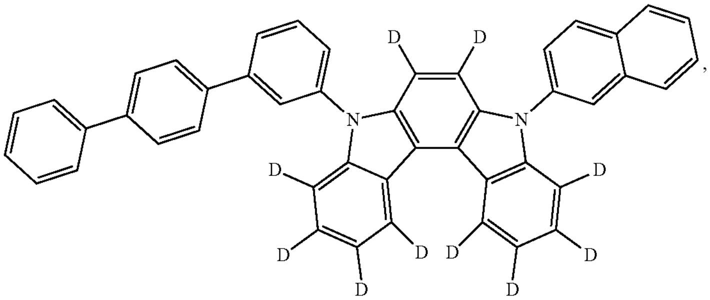
,
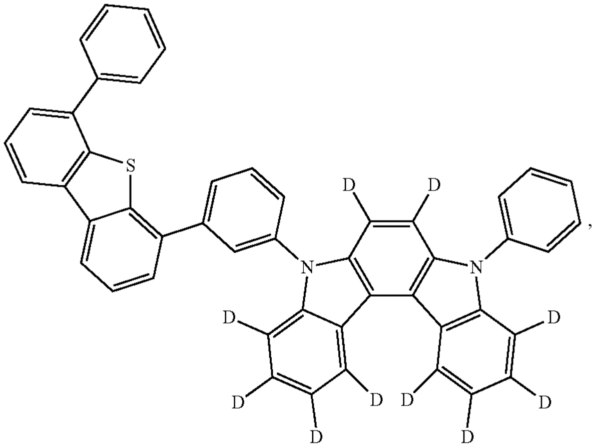
,
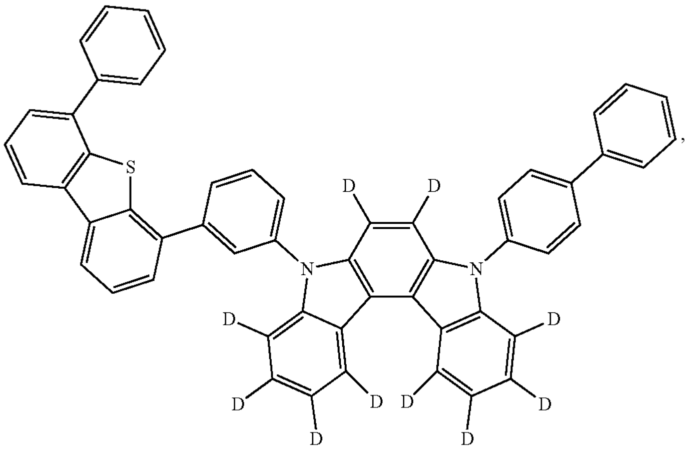
,
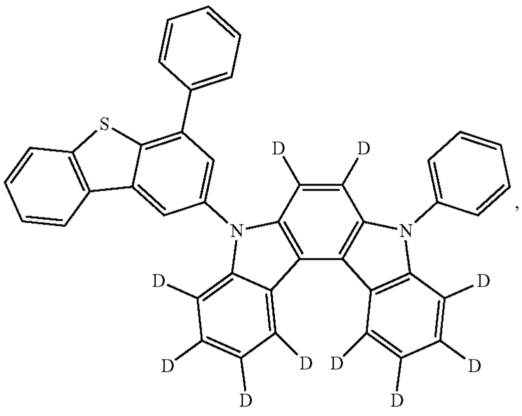
,
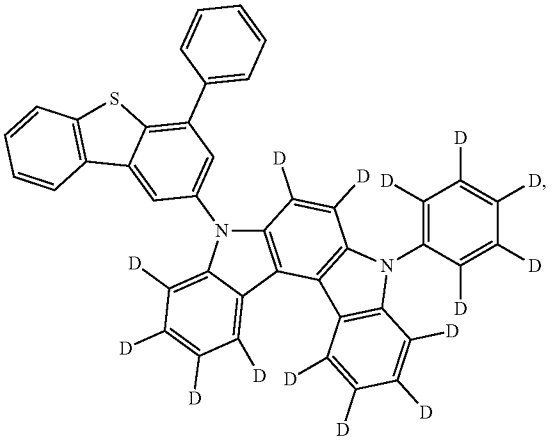
, -continued
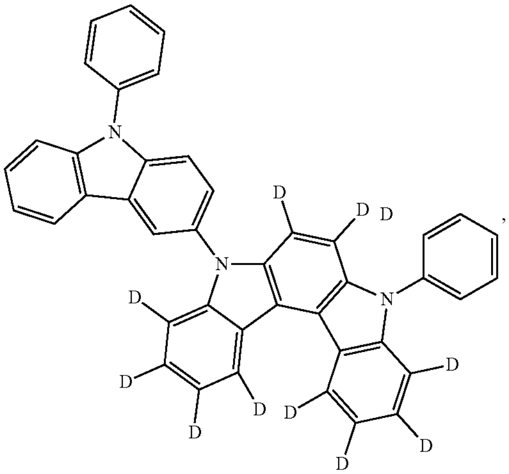
,
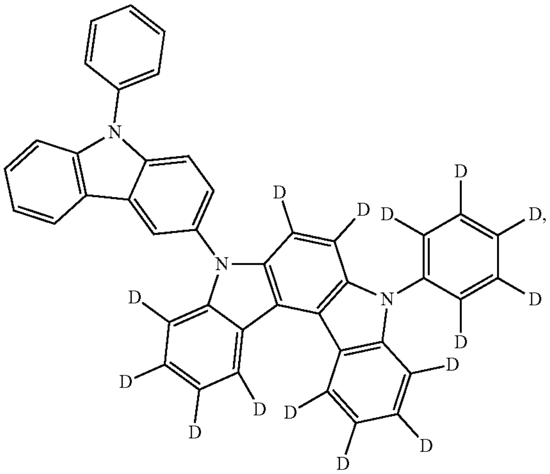
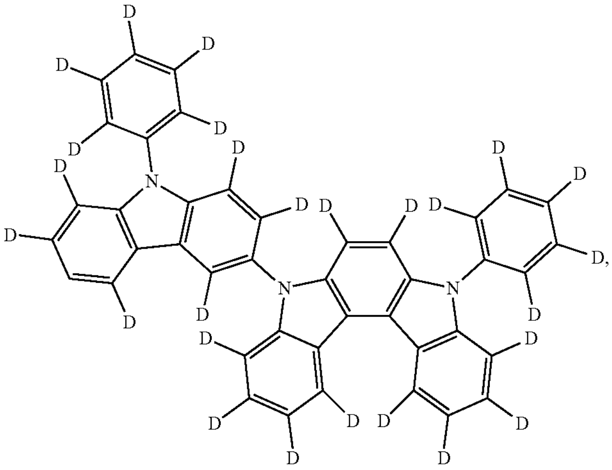
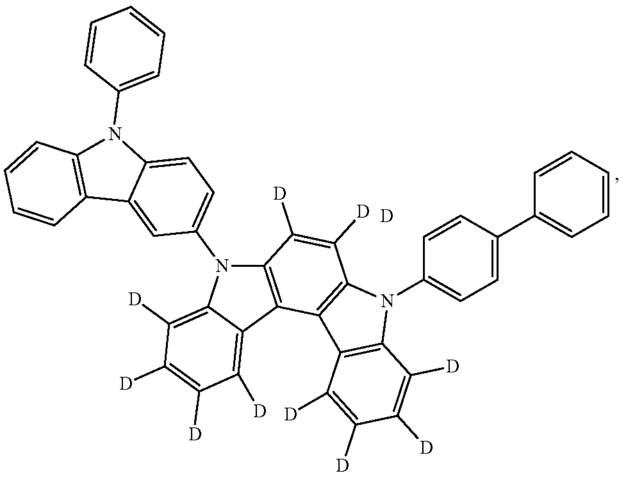
, -continued
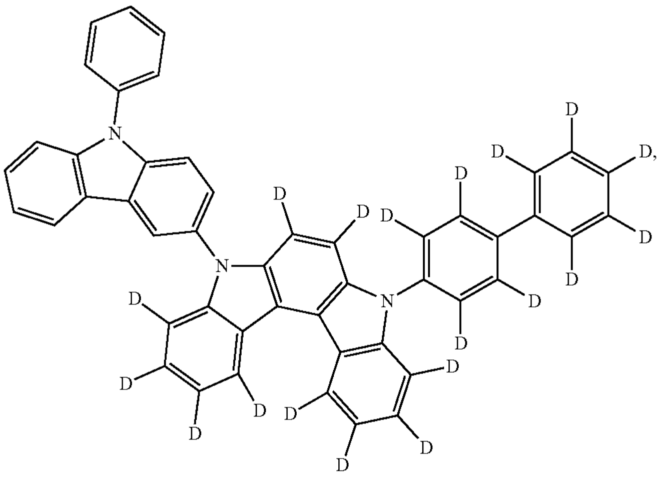
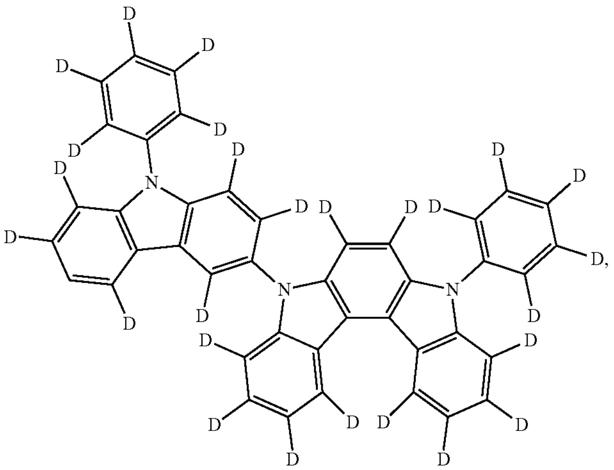
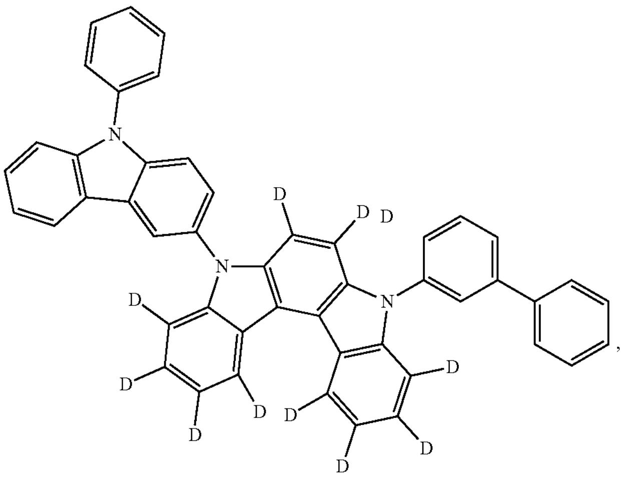

-continued
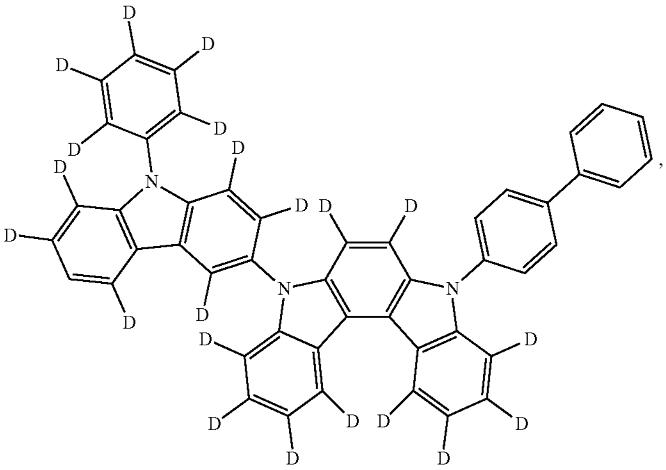
,
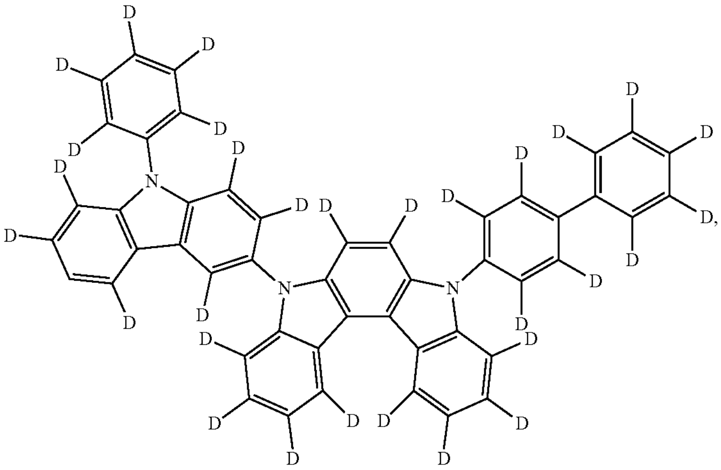
,
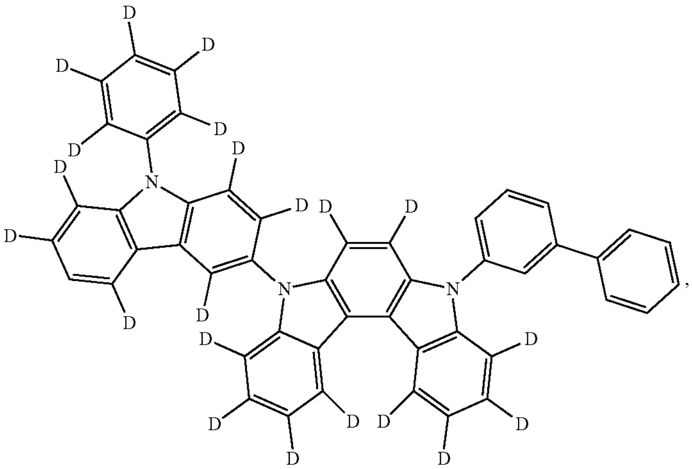
,

-continued
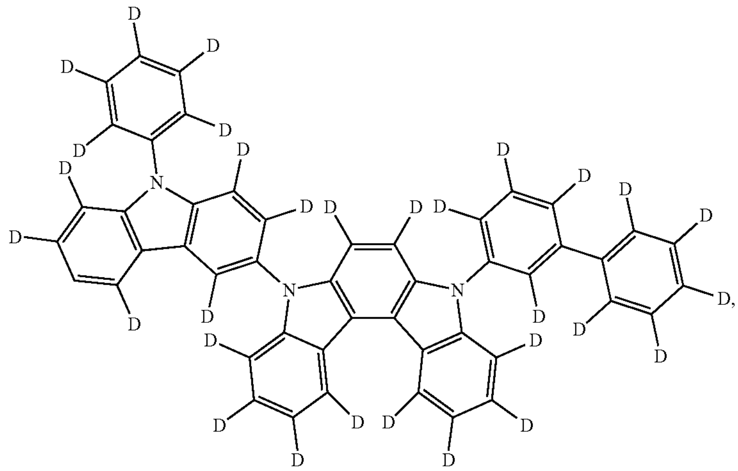
,
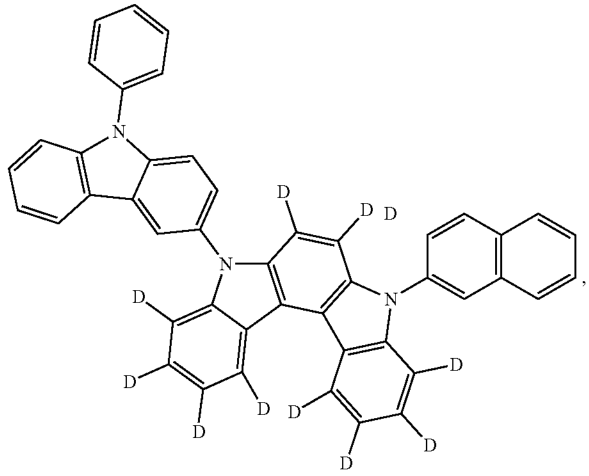
,
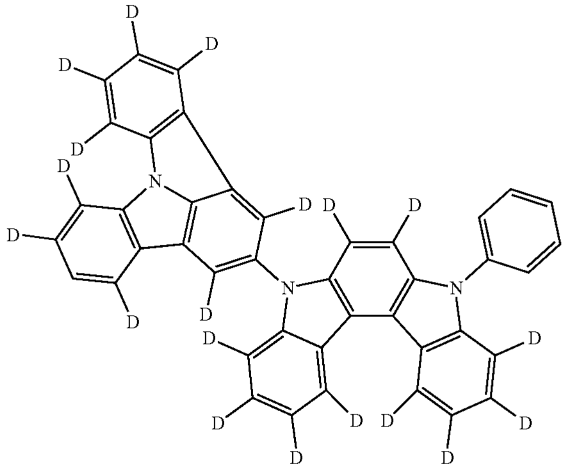
,
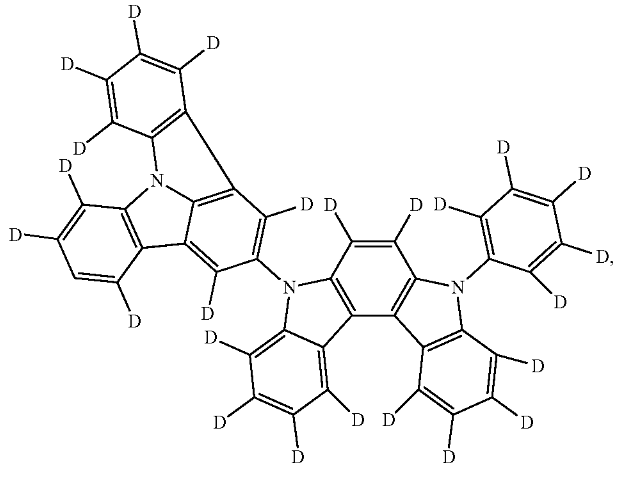
,
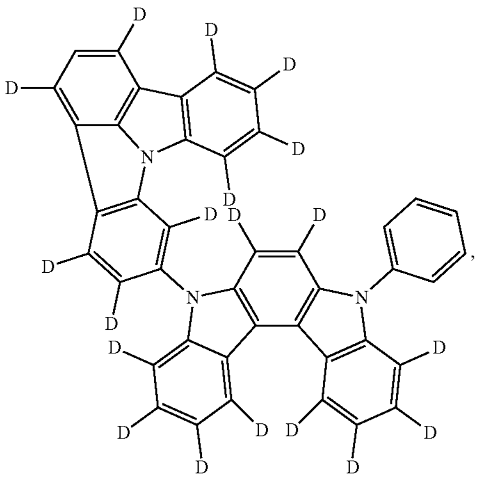
, -continued
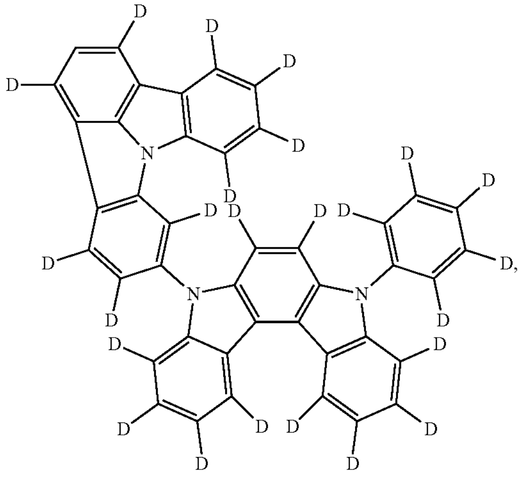
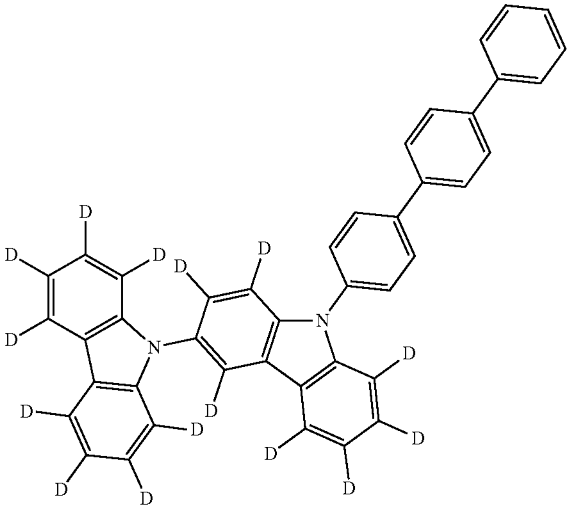
,
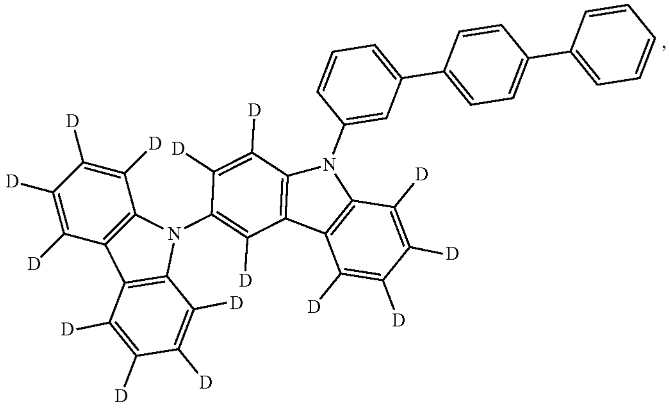
,
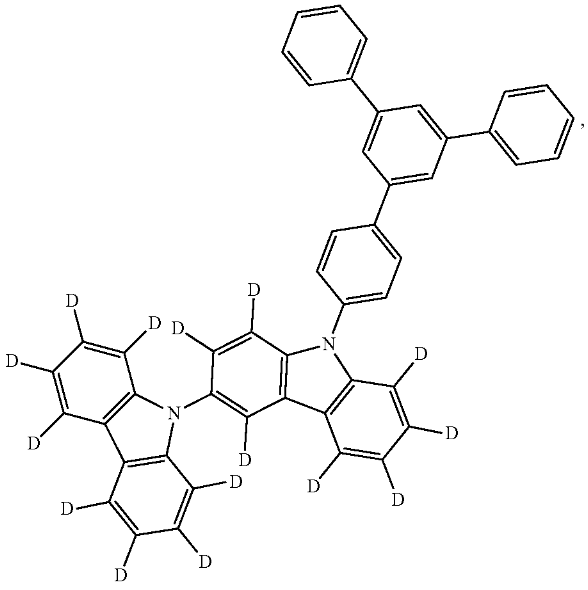
, -continued
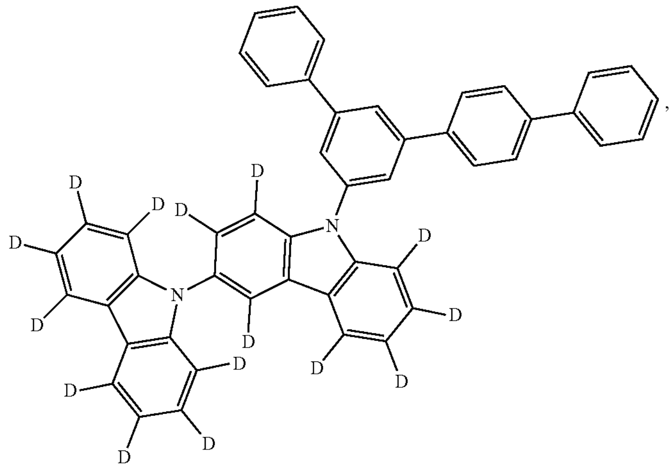
,
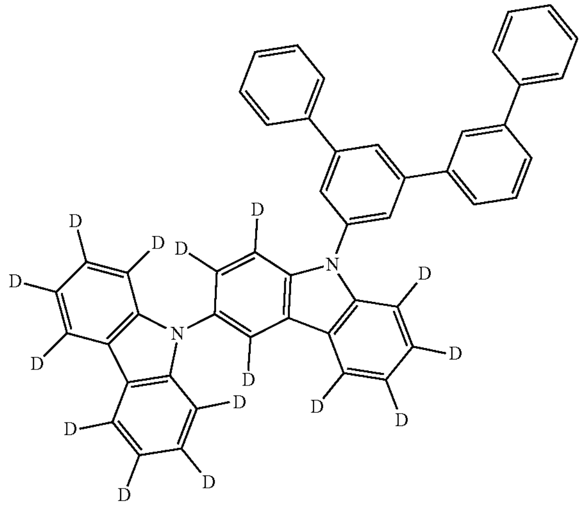
,
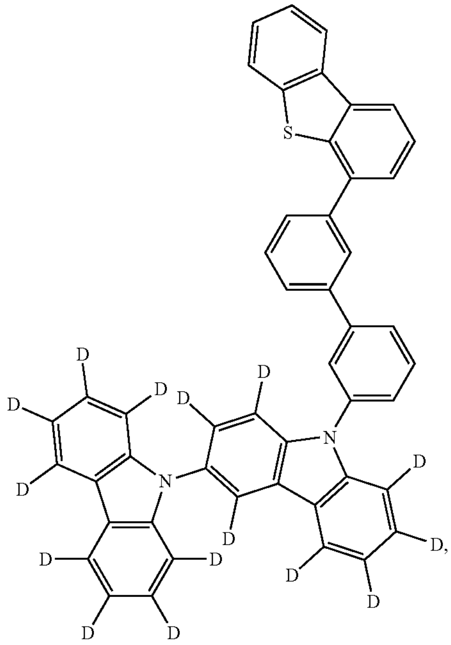
,
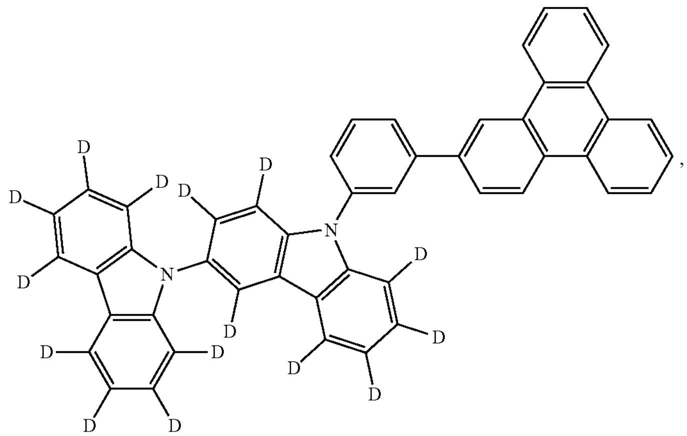
, -continued
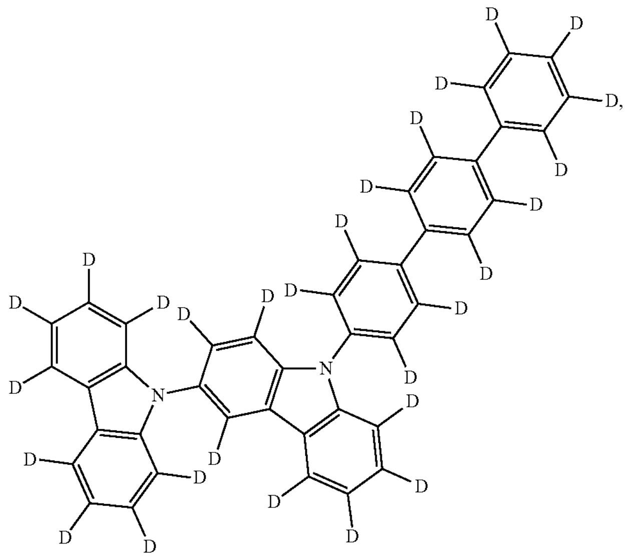
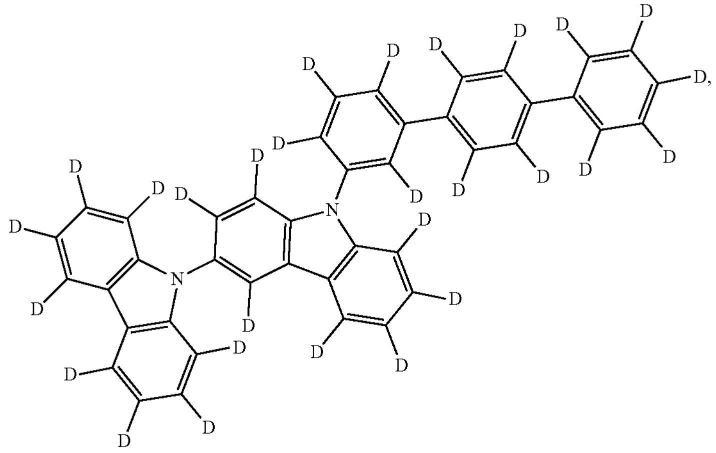
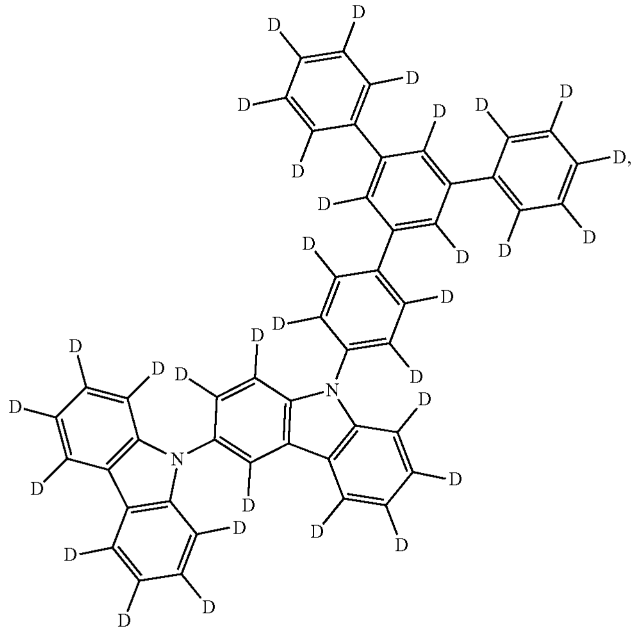

-continued
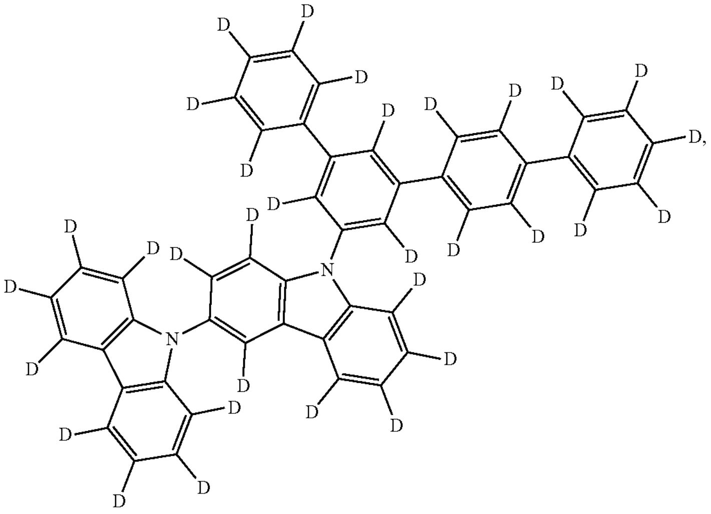
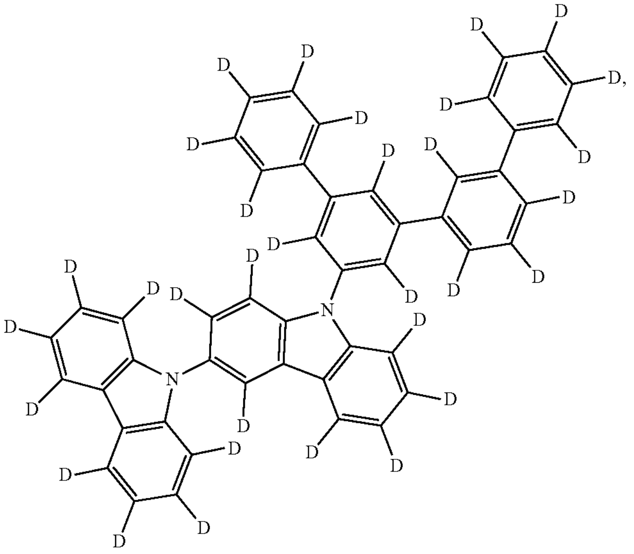
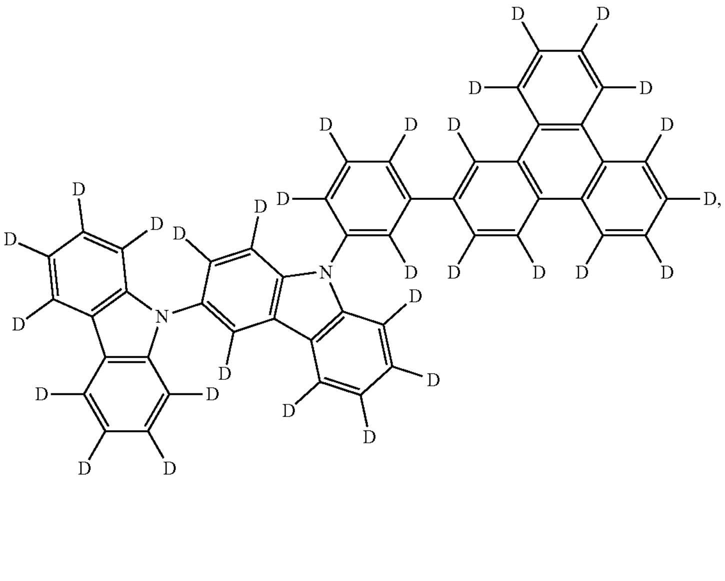
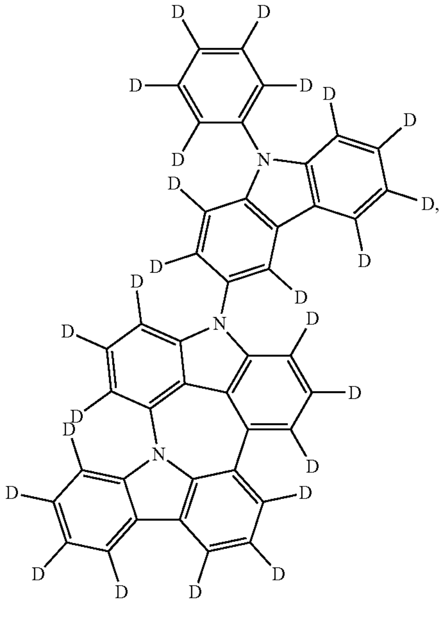

-continued
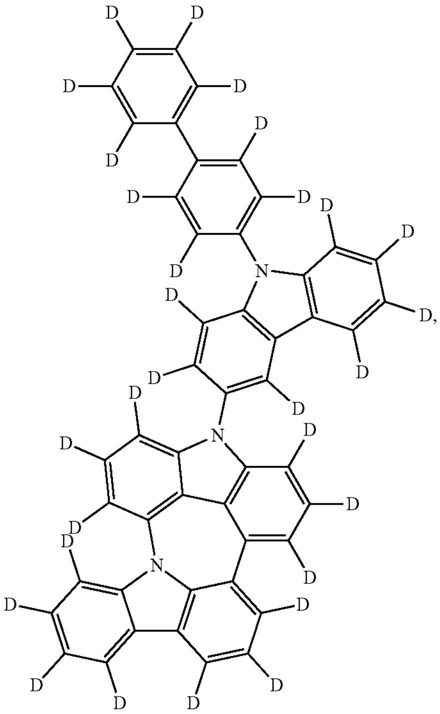
,
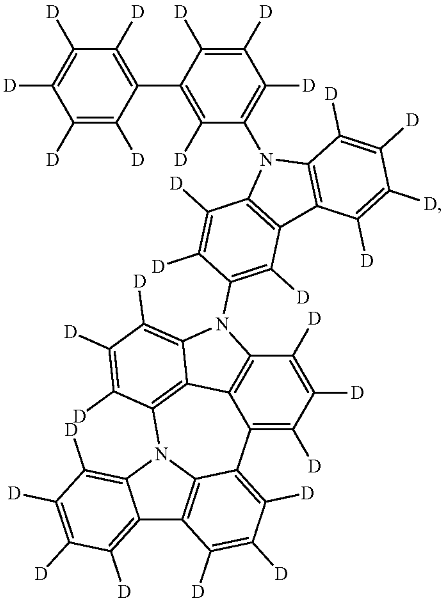
,
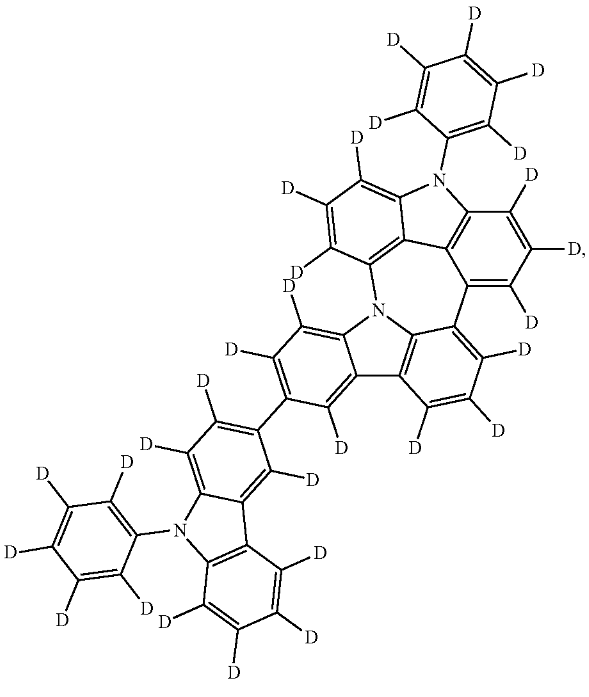
,

-continued
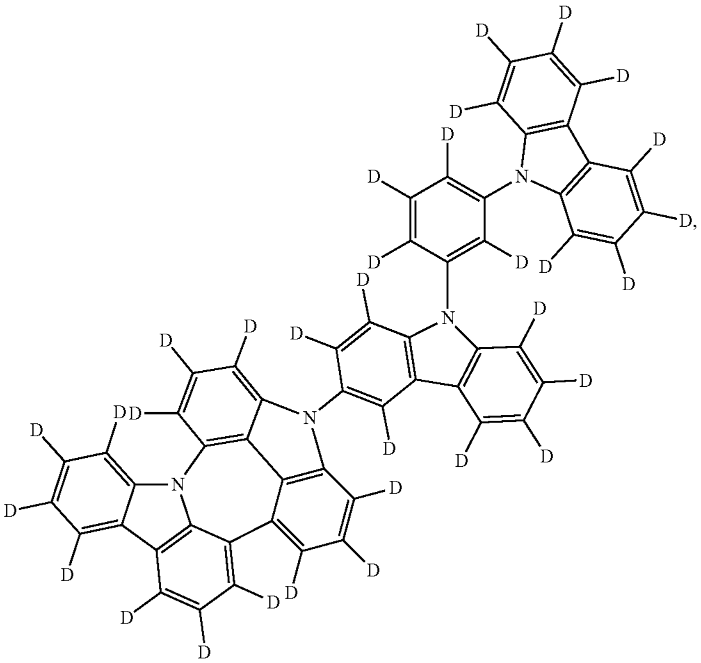
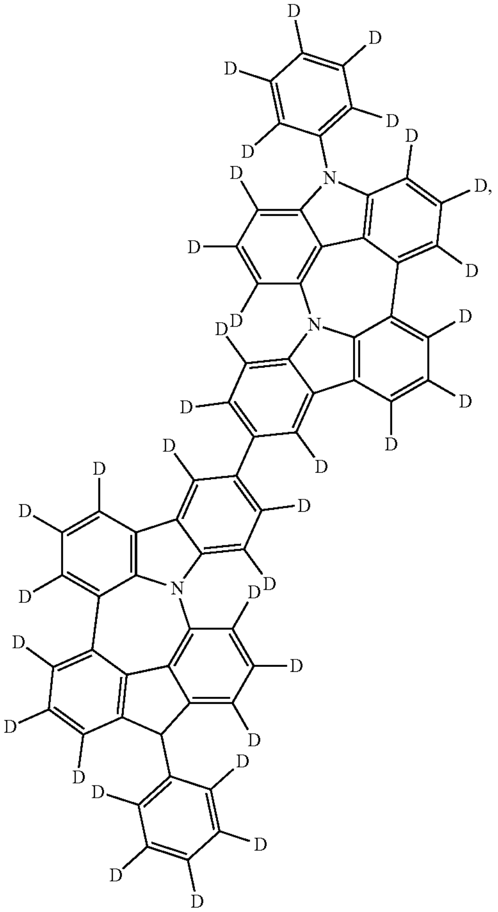
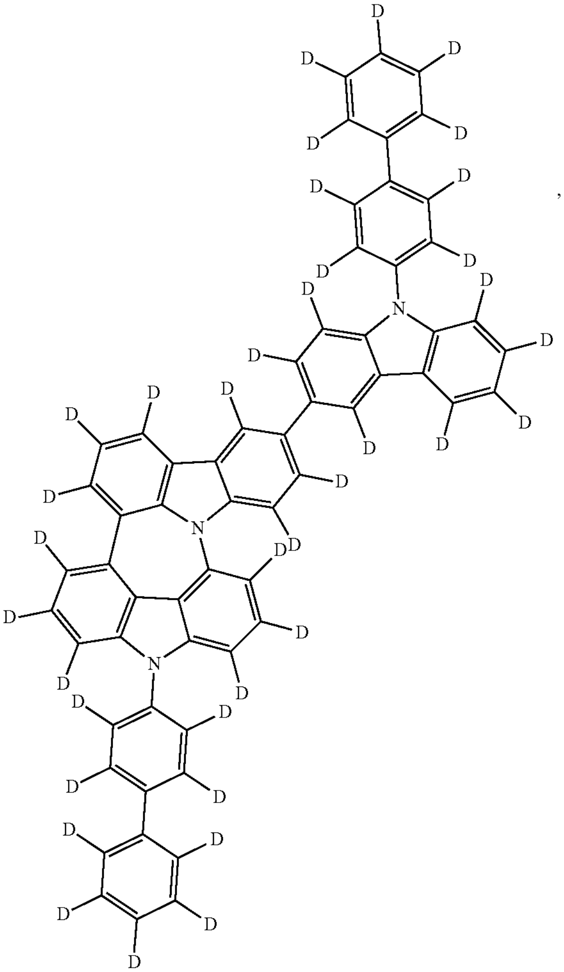
,

-continued
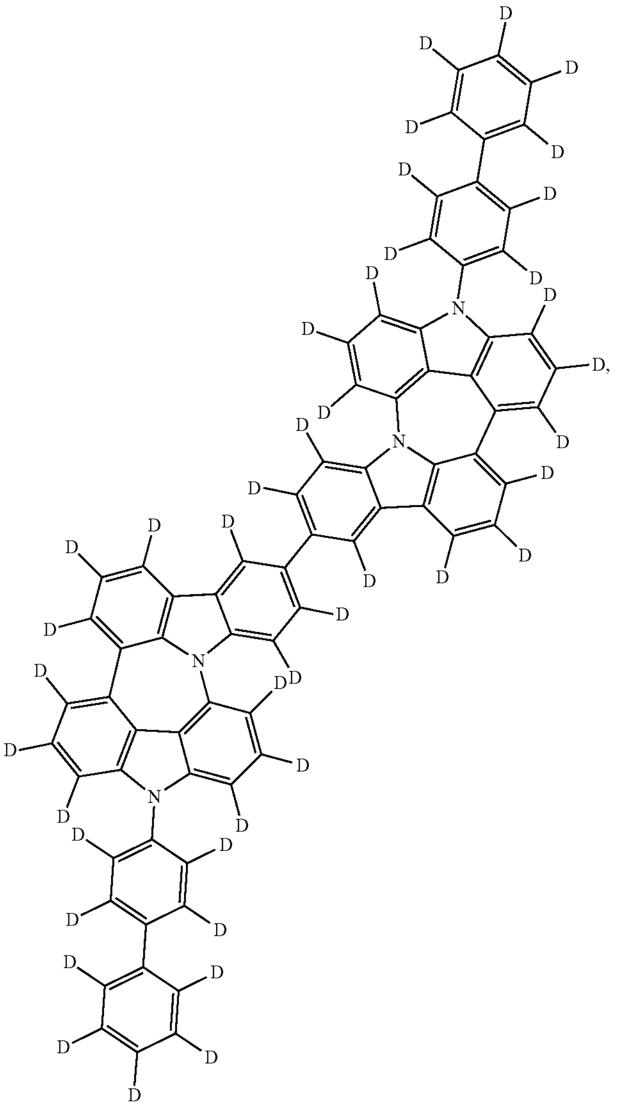
,

-continued
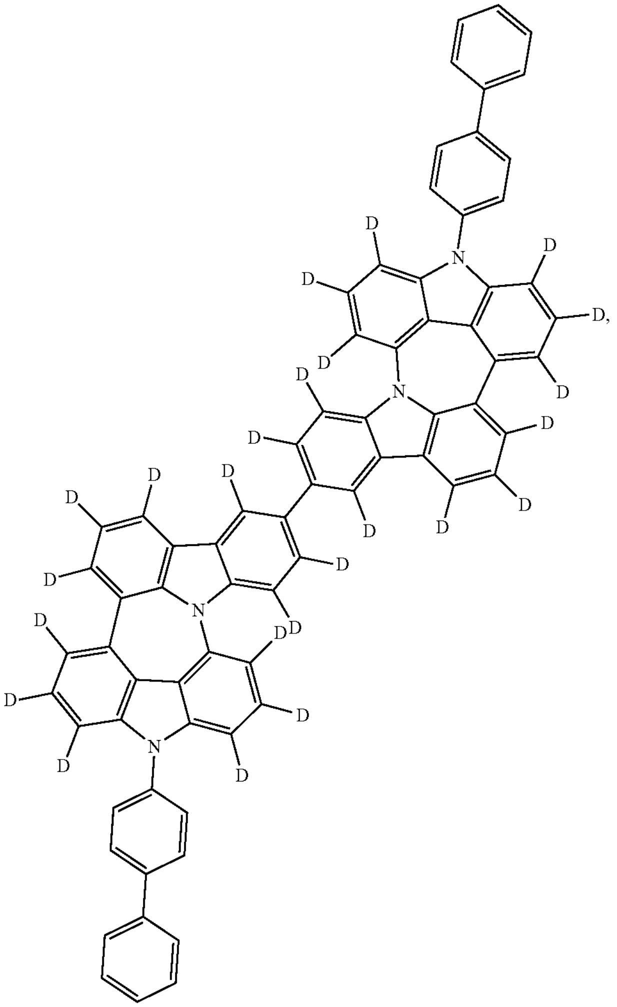
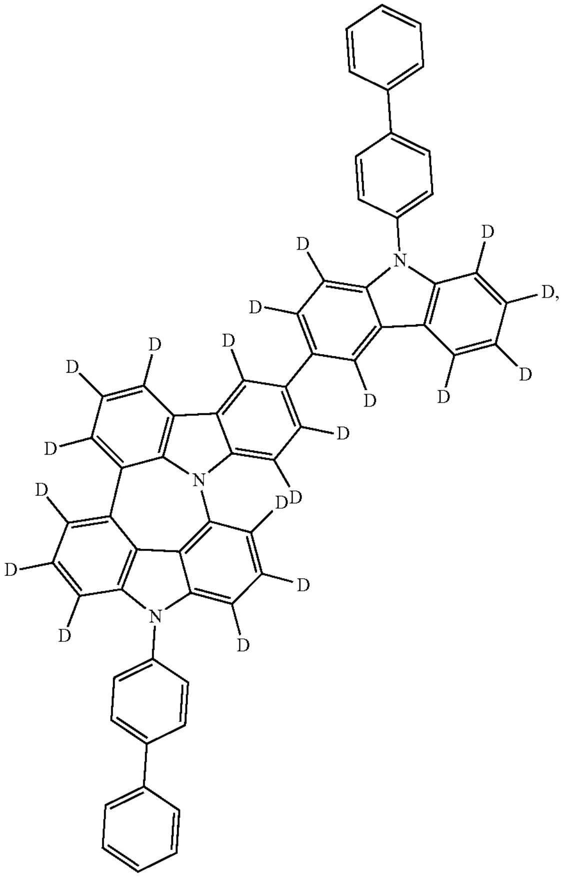
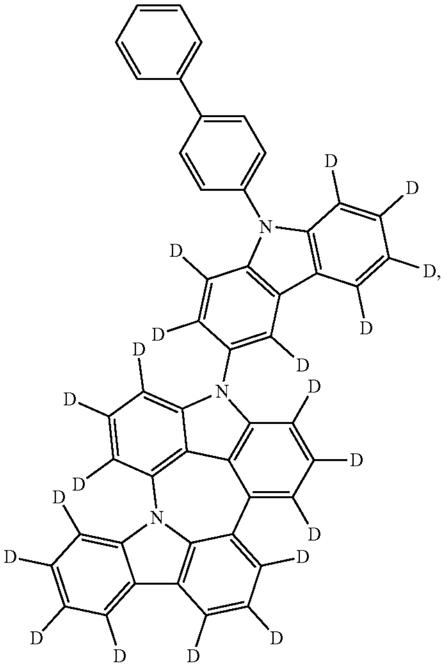

-continued
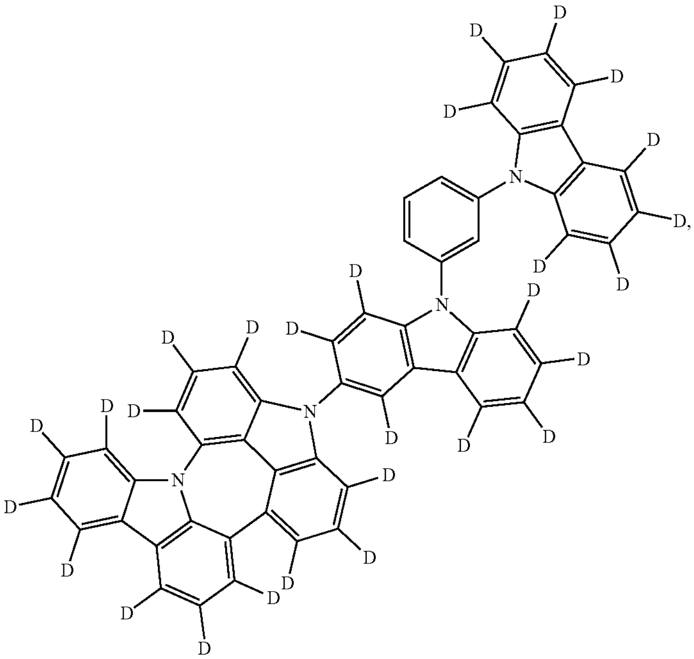
D, and
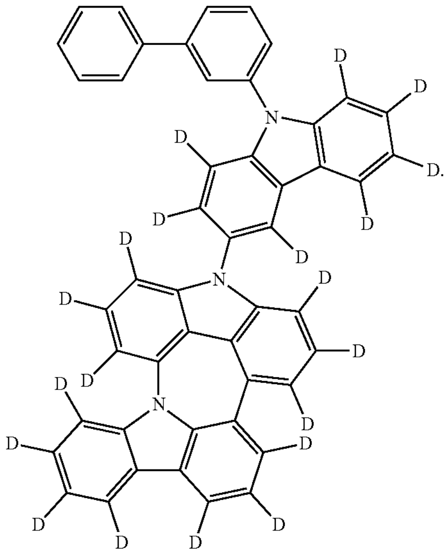
D.
In some embodiments, the second host is selected from the group consisting of the structures of the following LIST 6:
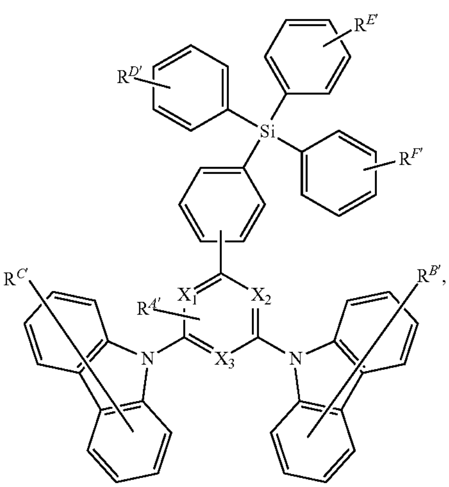
,
-continued
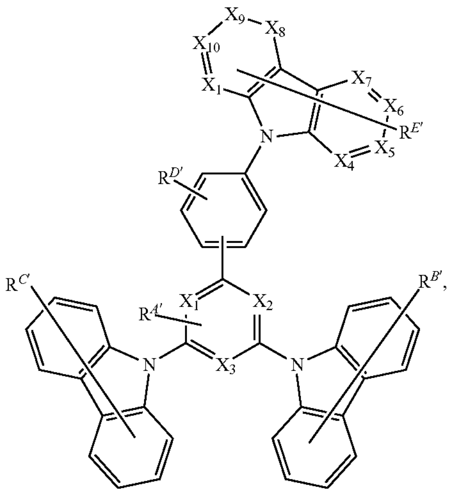
, -continued
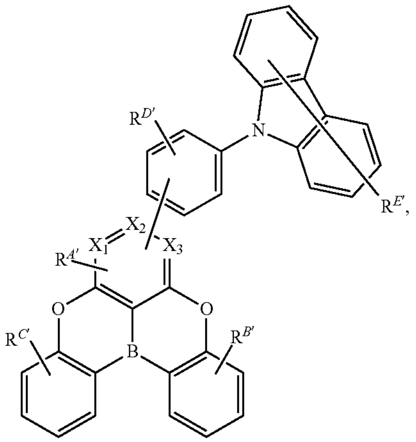
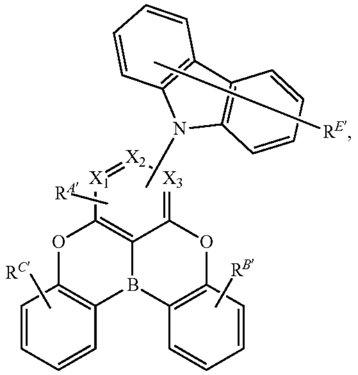
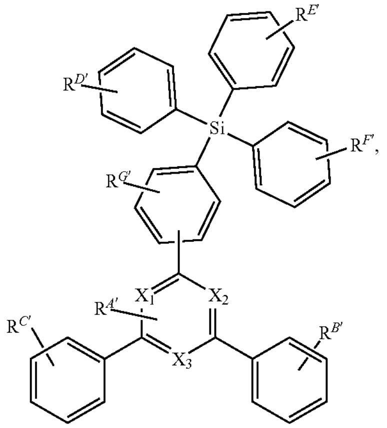
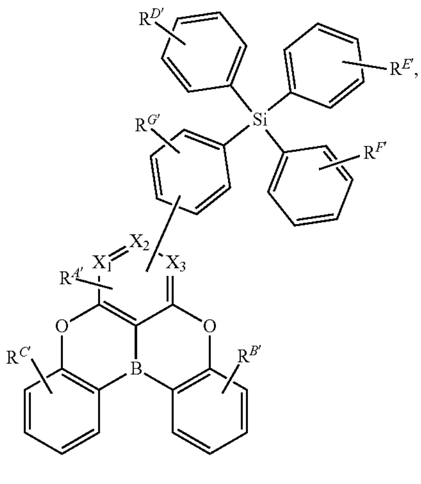
-continued
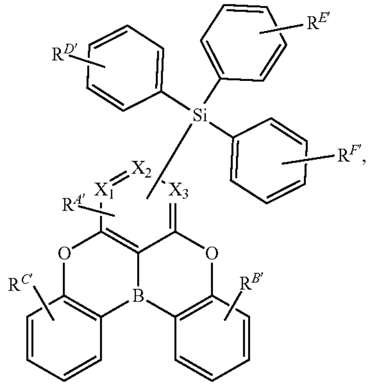
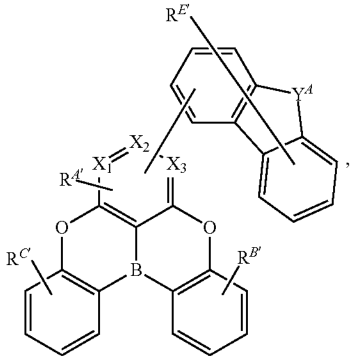
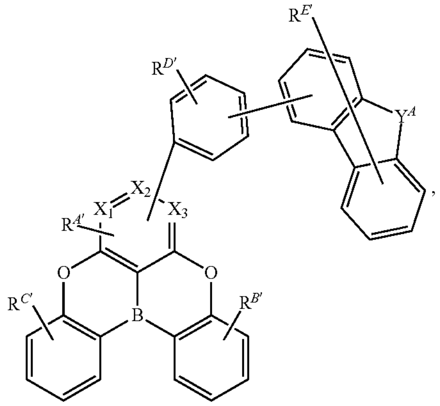
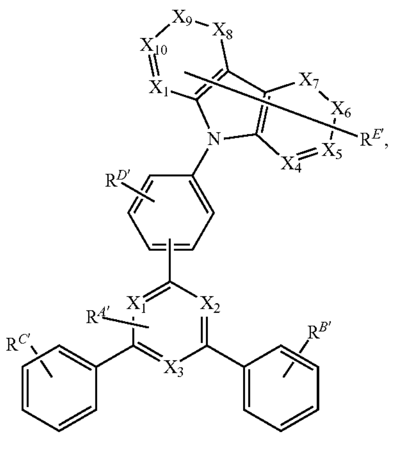

-continued
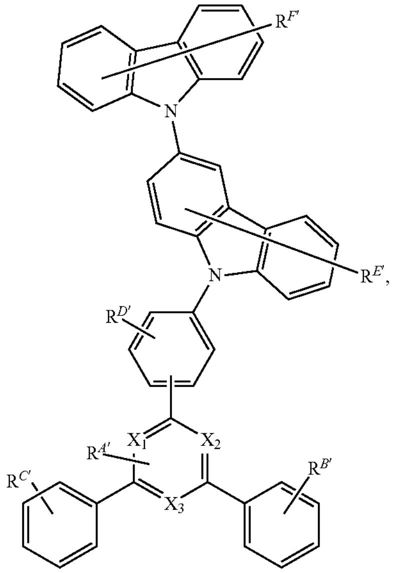
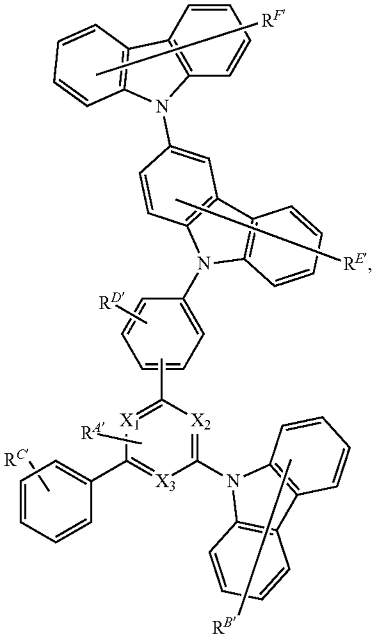
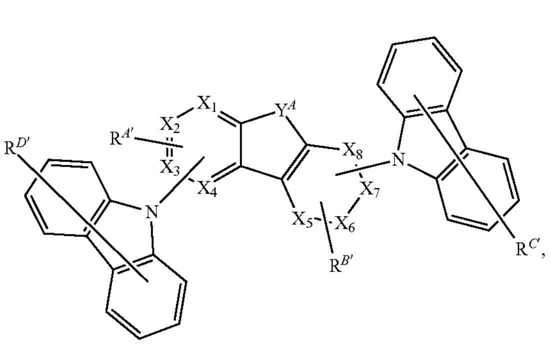
-continued
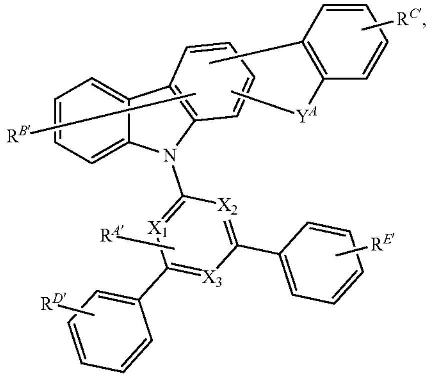
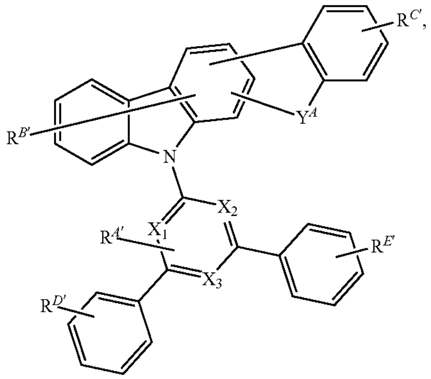
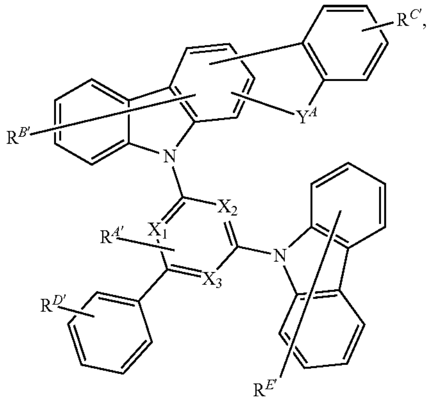
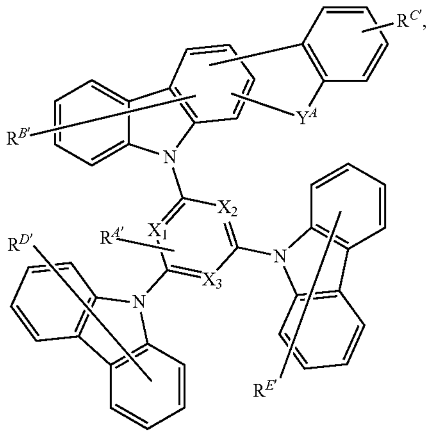

-continued
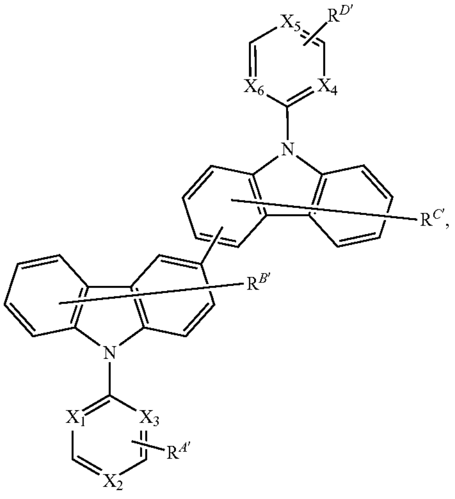
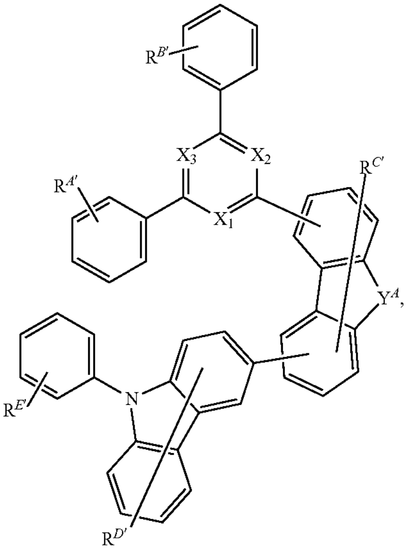
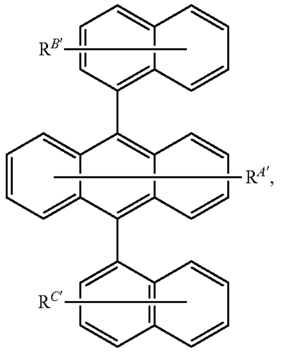
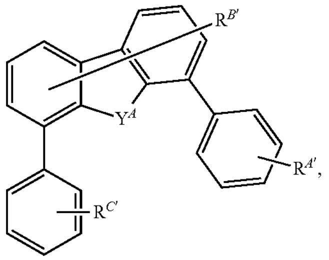
-continued
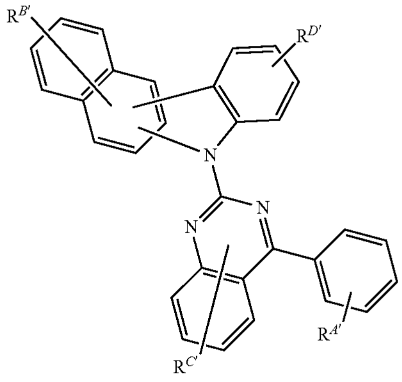
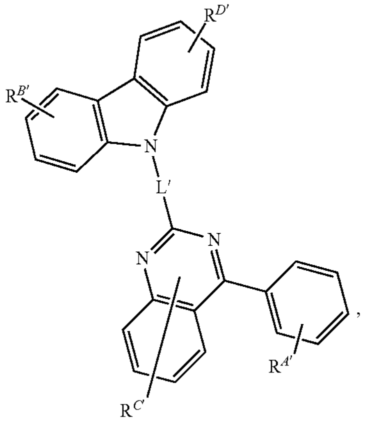
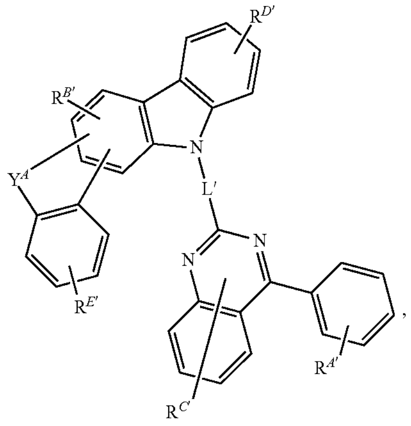
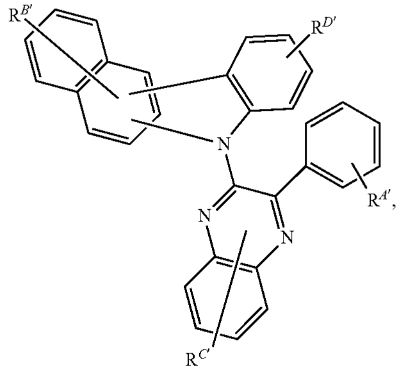

-continued
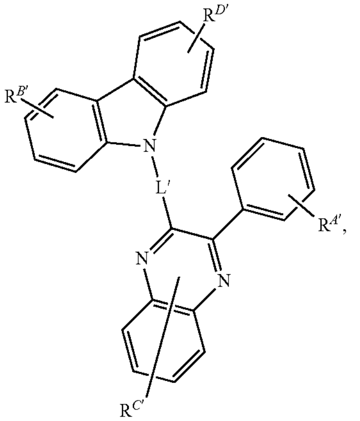
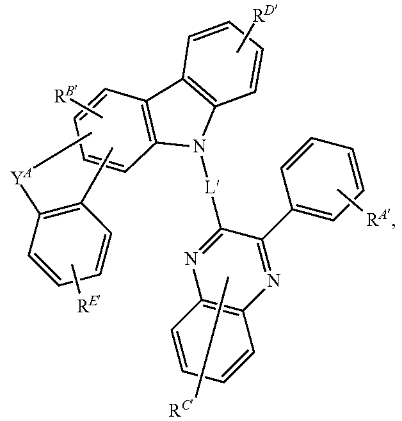
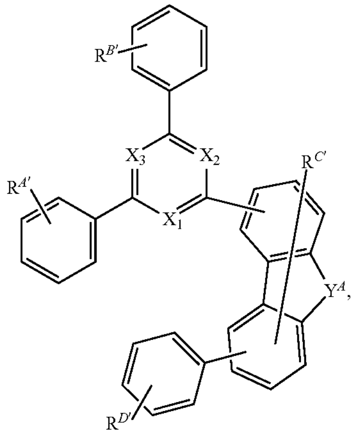
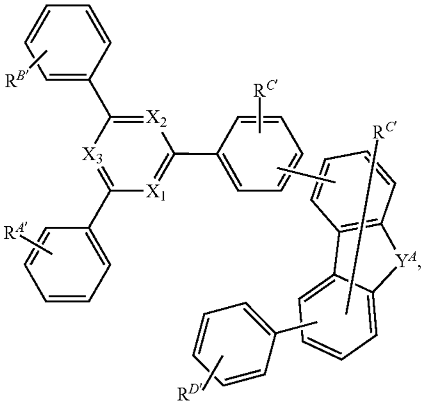
-continued
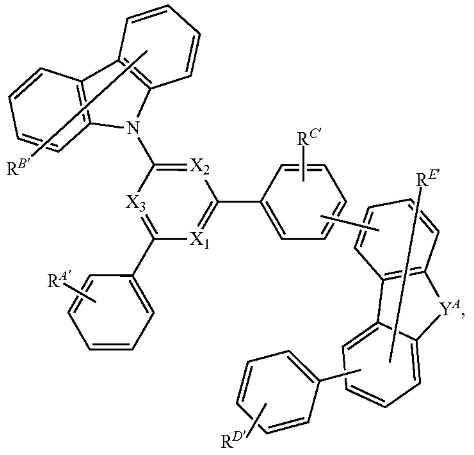
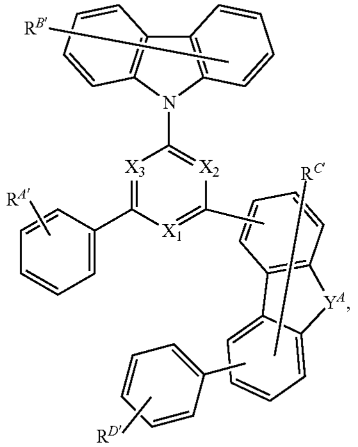
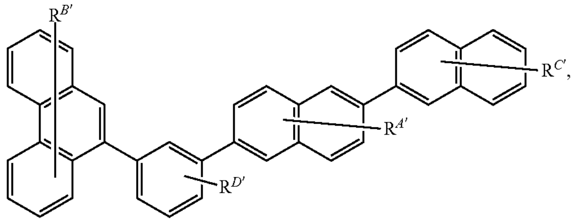
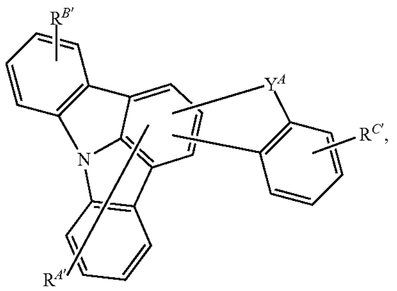

-continued

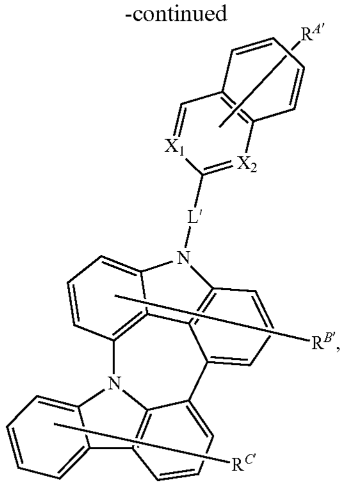

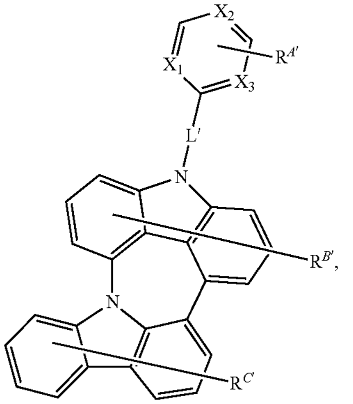

and

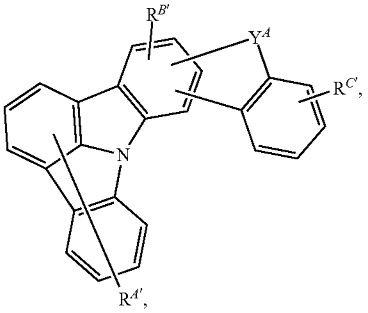

wherein:

wherein:

each of $X_1$ to $X_{11}$ is independently C or N;

L' is a direct bond or an organic linker;

each $Y^A$ is independently selected from the group consisting of absent a bond, O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono-, up to the maximum number of allowable substitutions, or no substitution;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

any two adjacent of $R^{A'}$, $R^{B'}$, $R^{C'}$, $R^{D'}$, $R^{E'}$, $R^{F'}$, and $R^{G'}$ can be joined or fused to form a ring.

In some embodiments, the linker L' is selected from the group consisting of a direct bond, BR, BRR', NR, PR, P(O)R, O, S, Se, C═O, C═S, C═Se, C═NR', C═CR'R", S═O, $SO_2$, CR, CRR', SiRR', GeRR', alkylene, cycloalkyl, aryl, cycloalkylene, arylene, heteroarylene, and combinations thereof.

In some embodiments, the second host is selected from the group consisting of the structures of the following LIST 7:

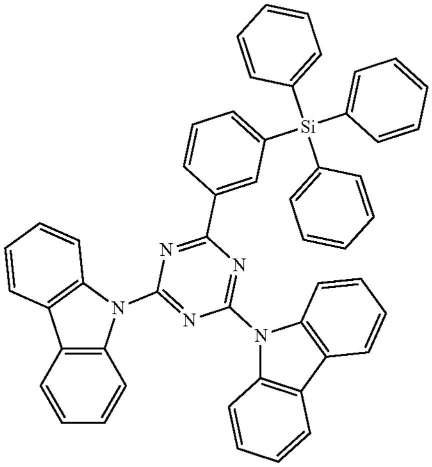

,

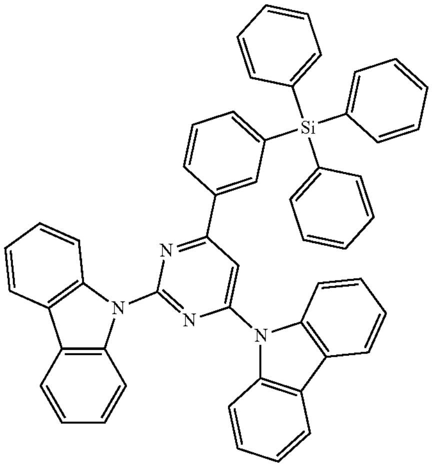

,

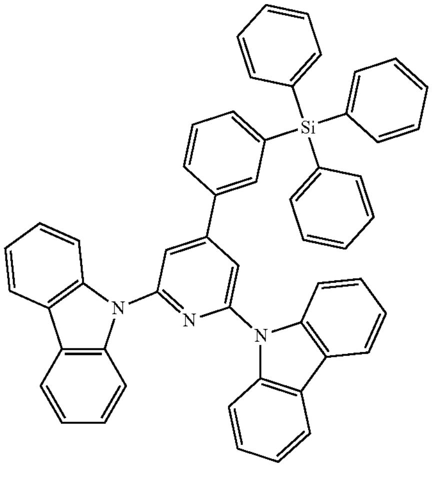

,

-continued
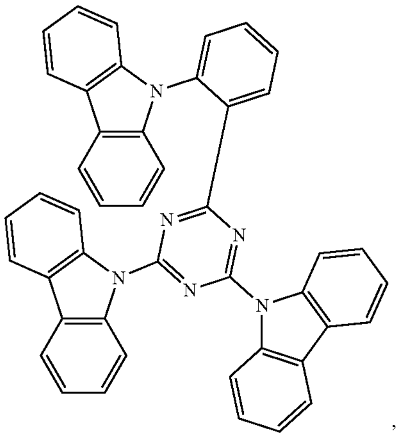
,
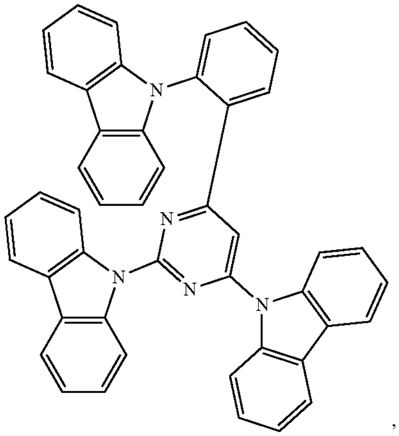
,
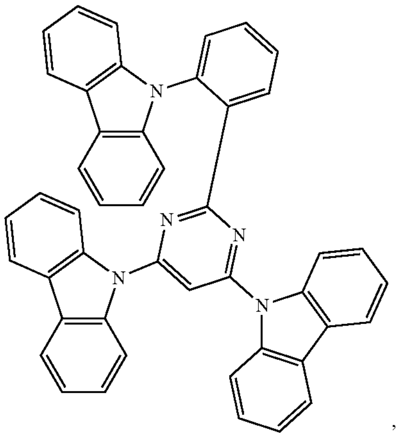
,
-continued
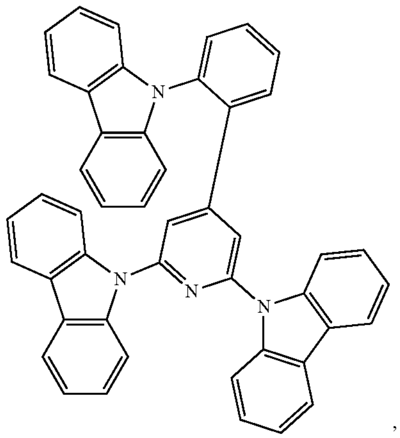
,
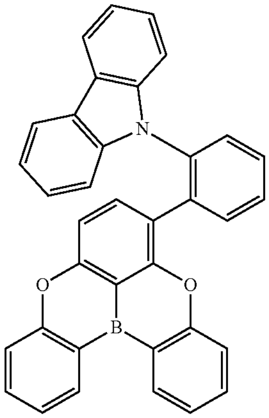
,
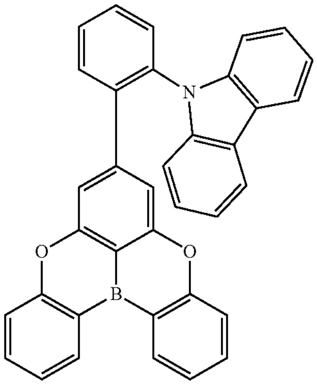
,
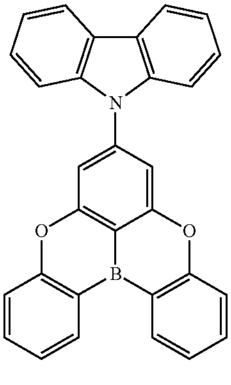
, -continued
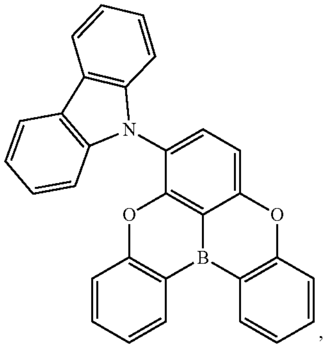
,
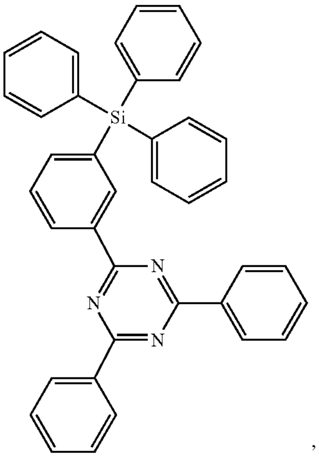
,
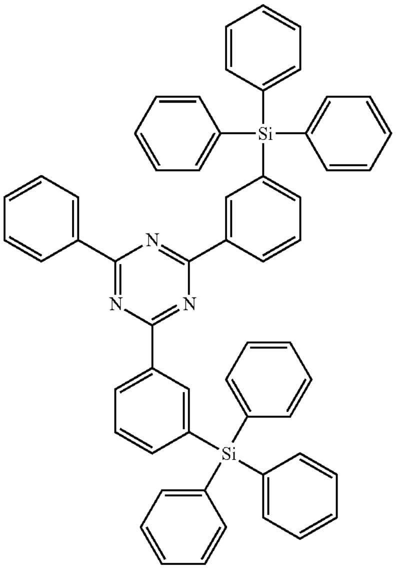
,
-continued
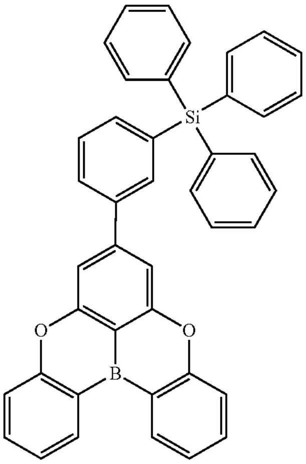
,
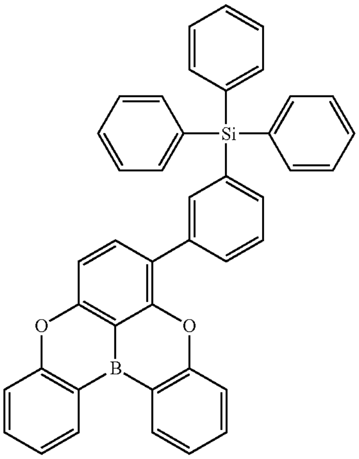
,
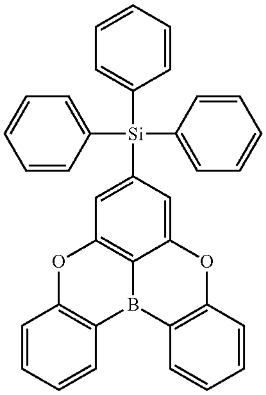
,
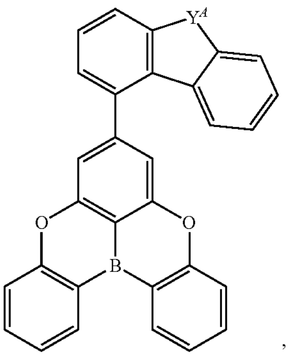
, -continued
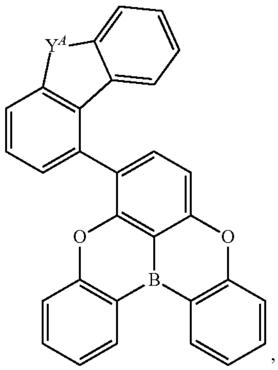
,
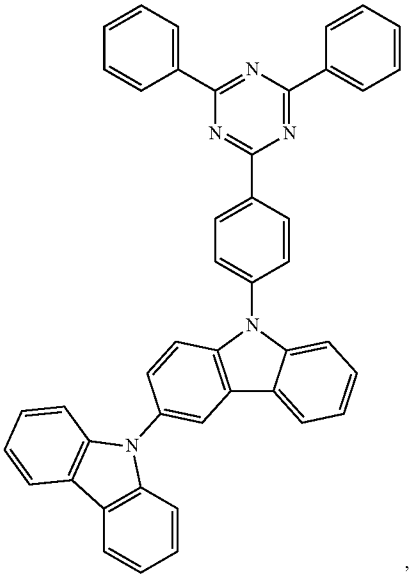
,
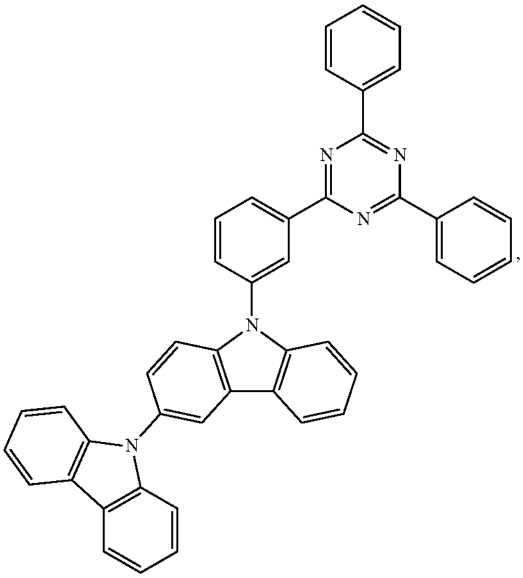
,
-continued
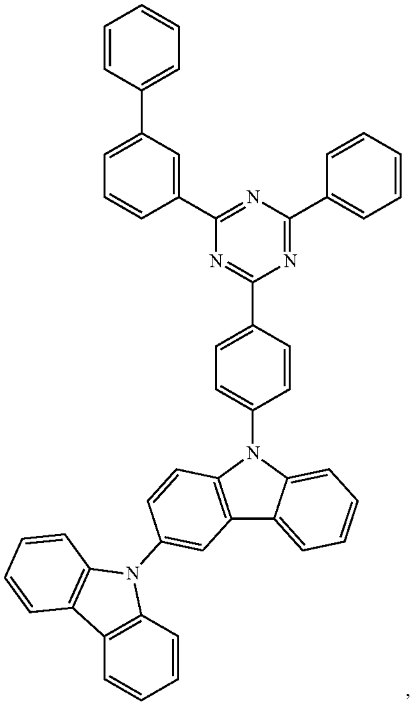
,
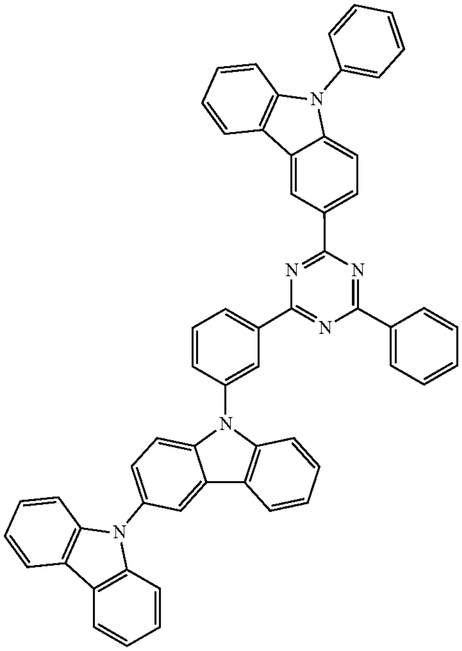
, -continued
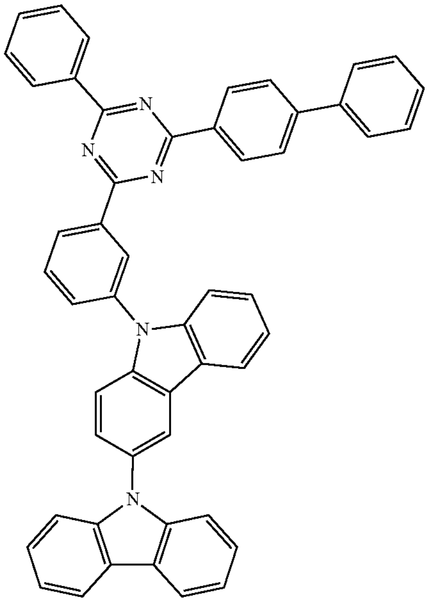
,
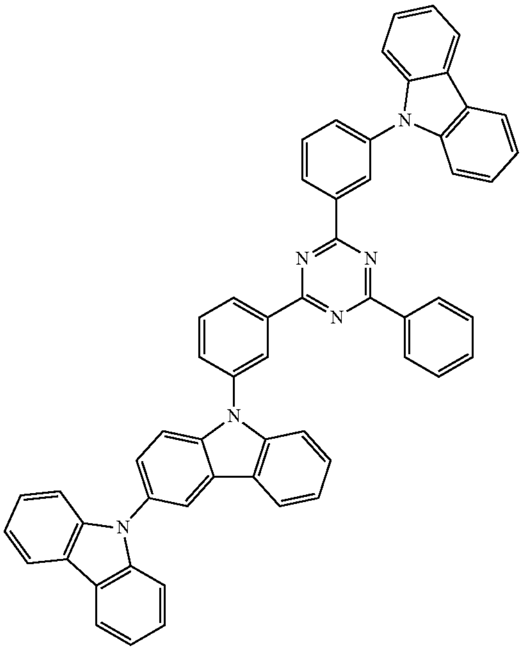
,
-continued
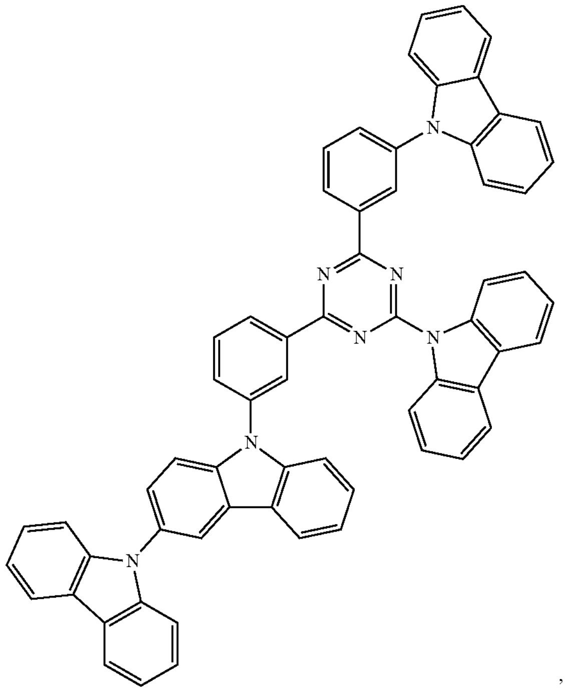
,
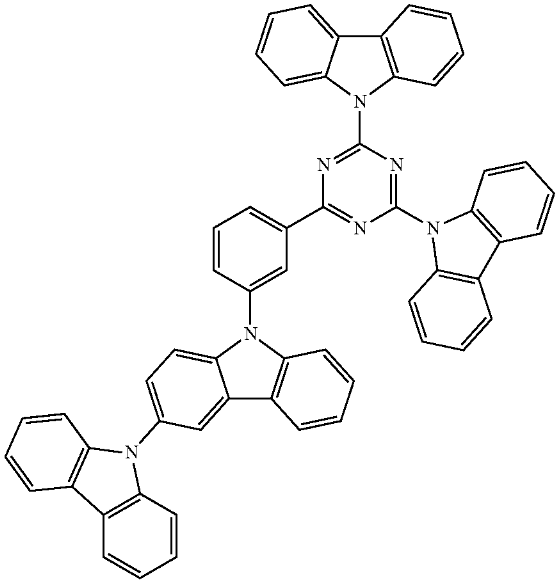
, -continued
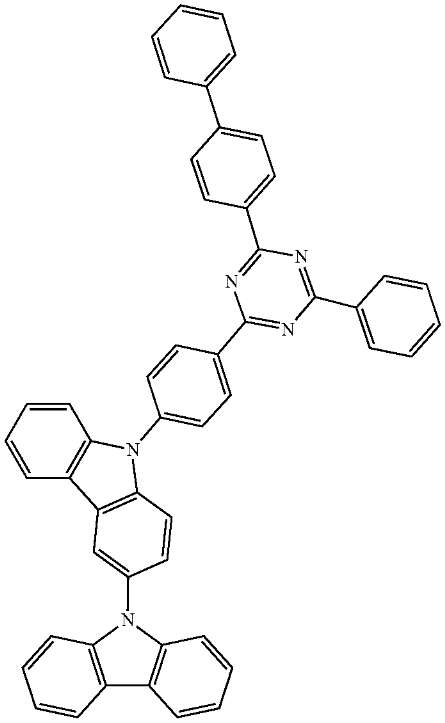
,
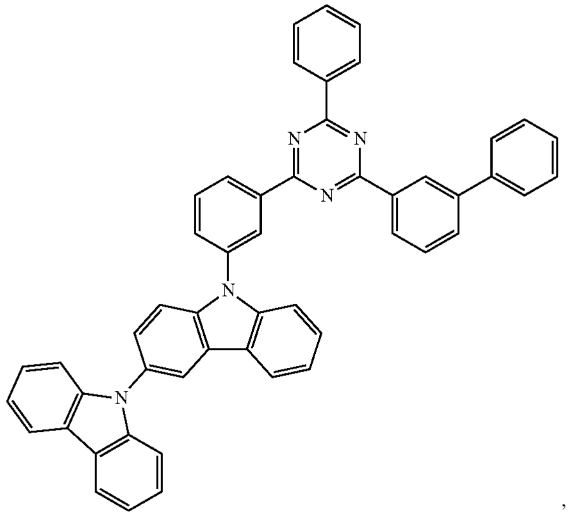
,
-continued
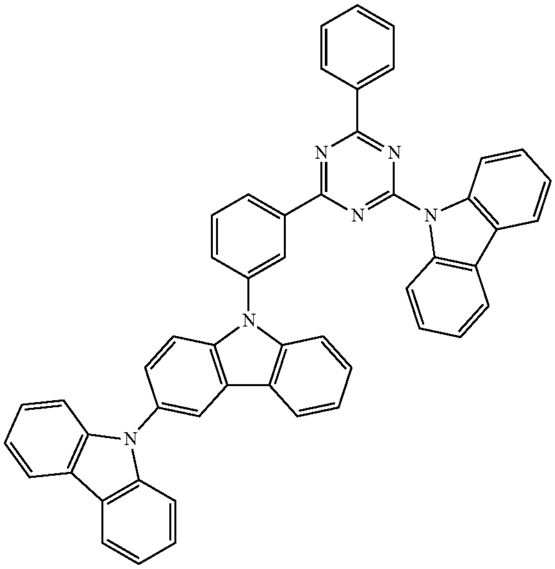
,
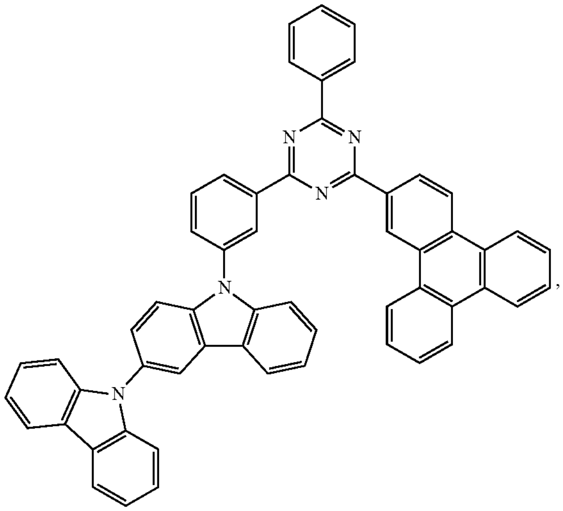
,
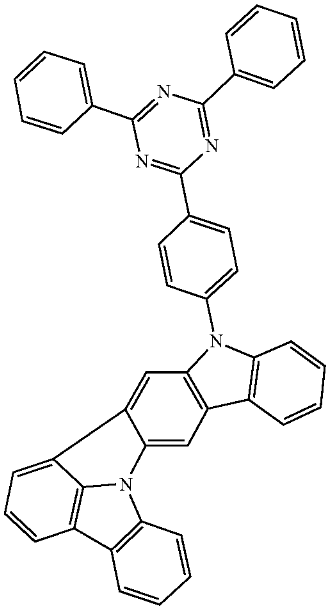
, -continued
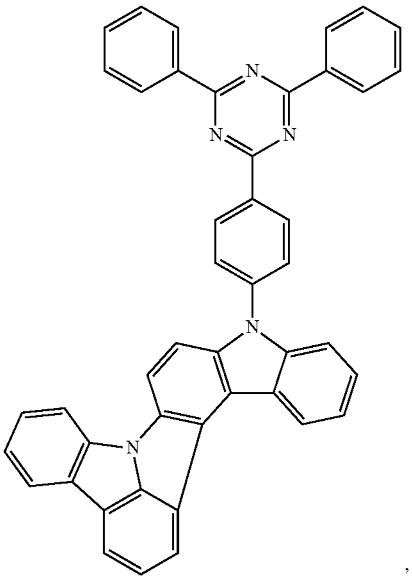
,
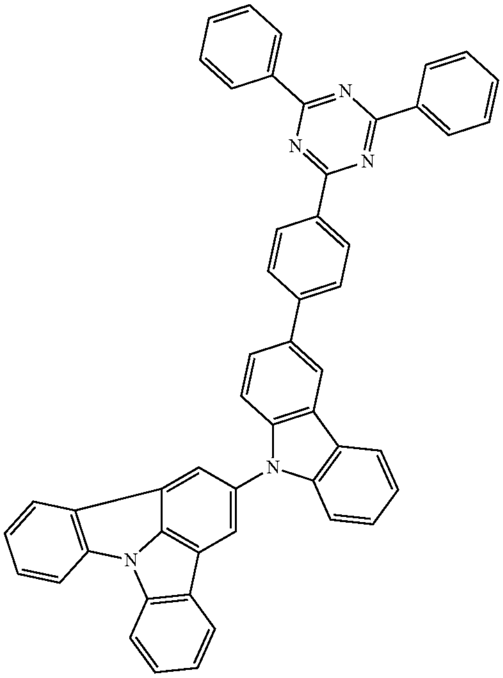
,
-continued
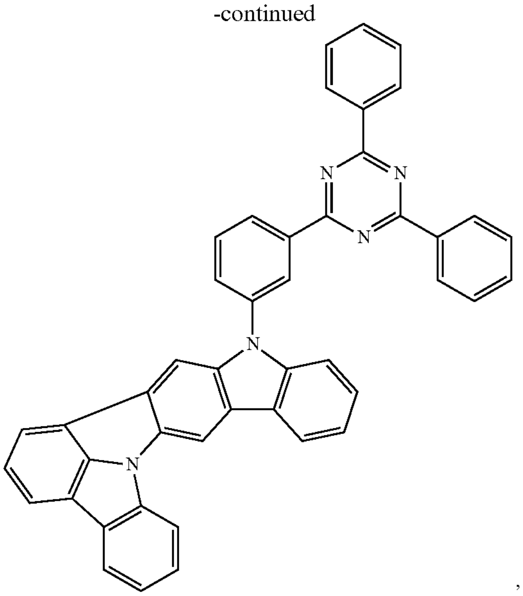
,
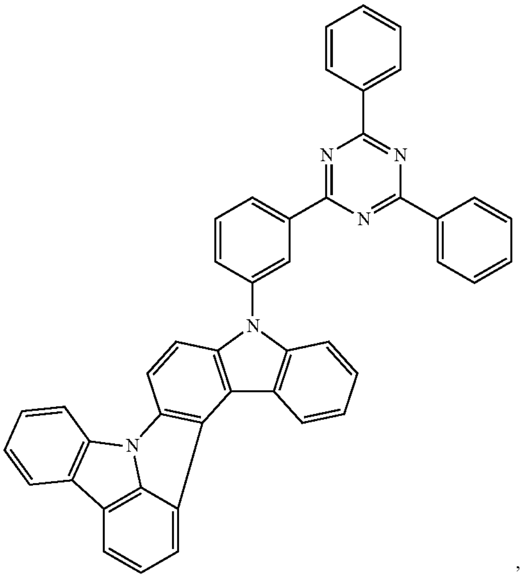
,
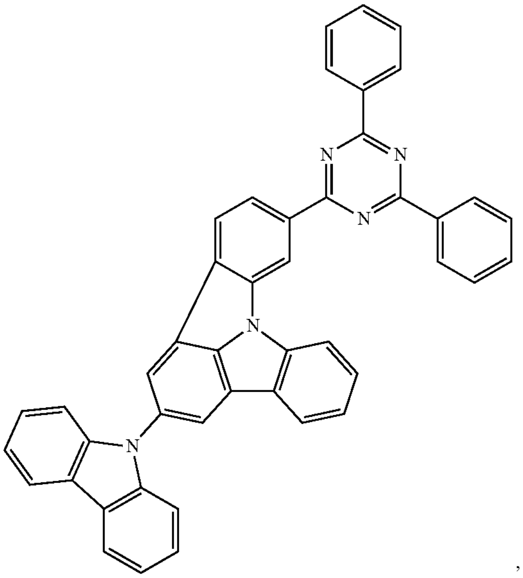
, -continued
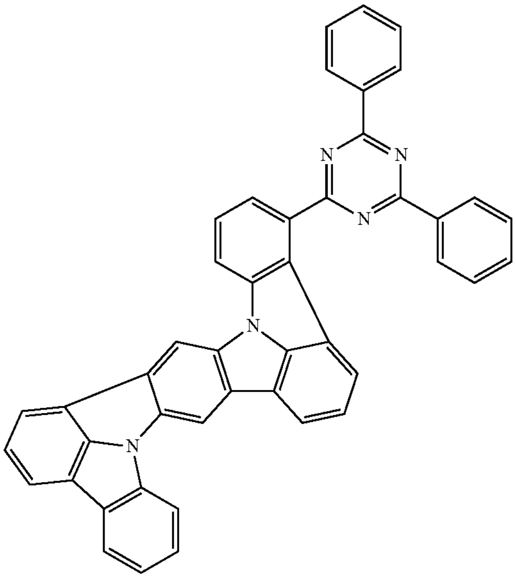
,
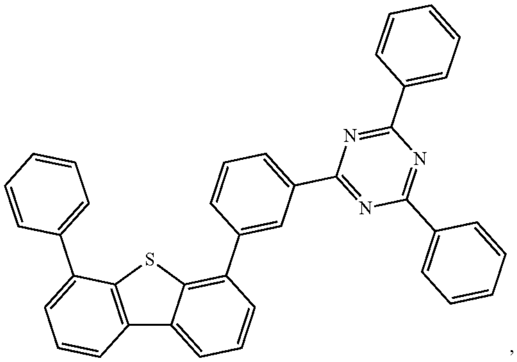
,
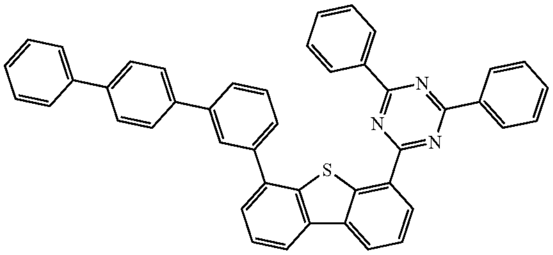
,
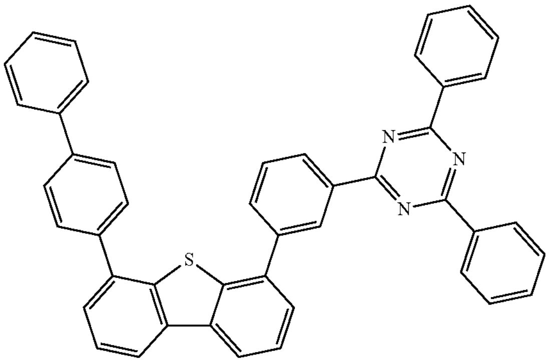
,
-continued
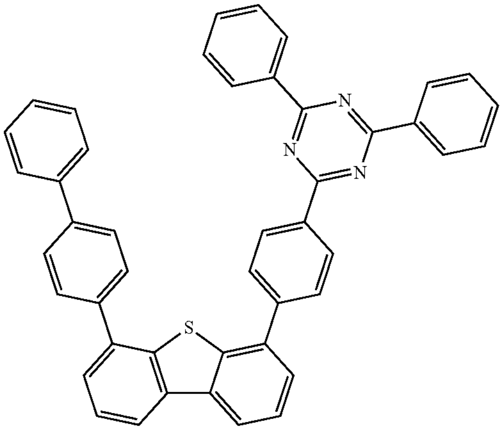
,
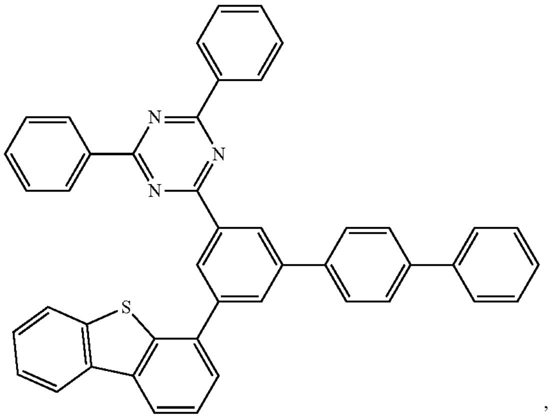
,
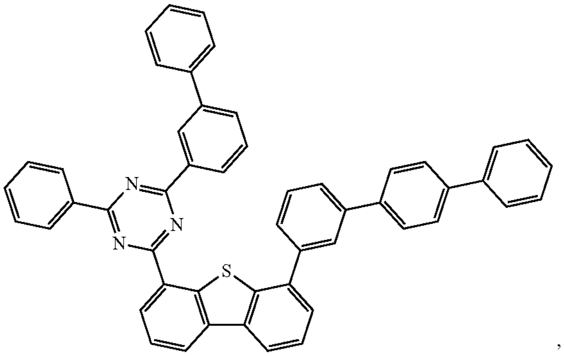
,
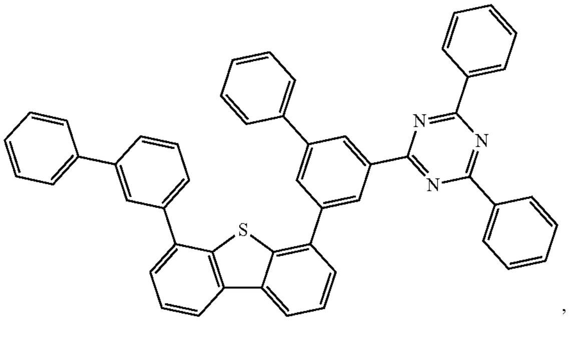
,

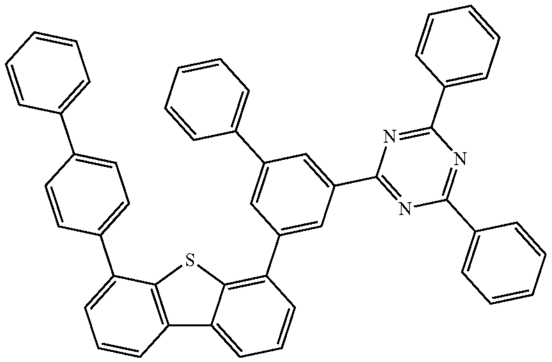
,
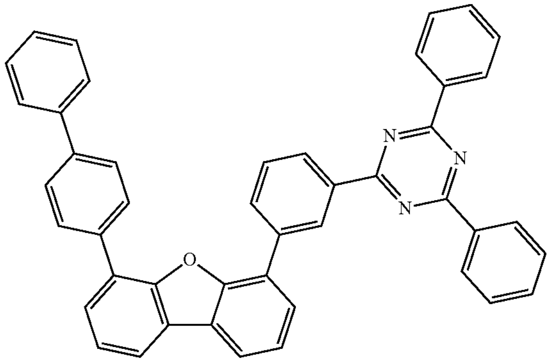
,
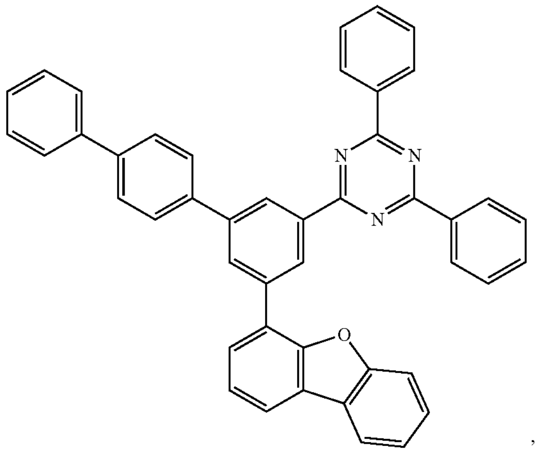
,
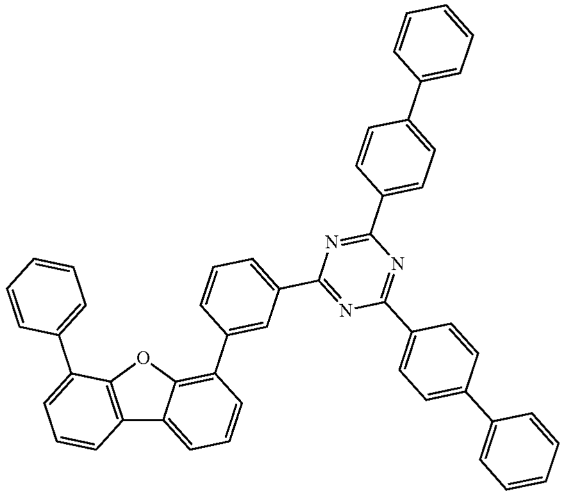
,
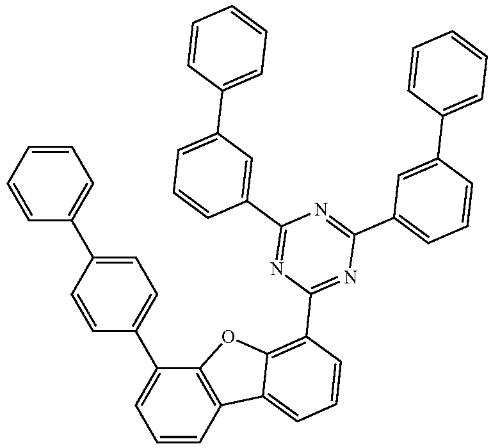
,
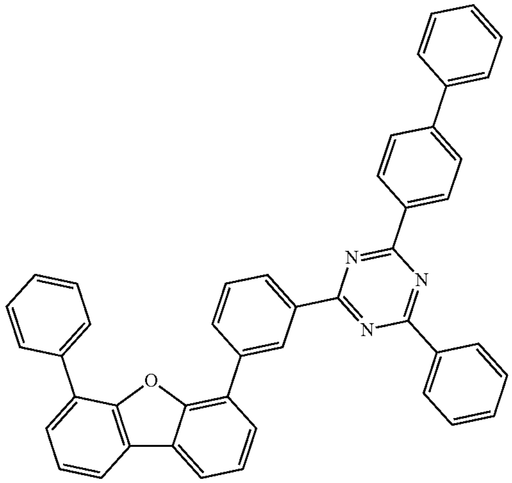
,
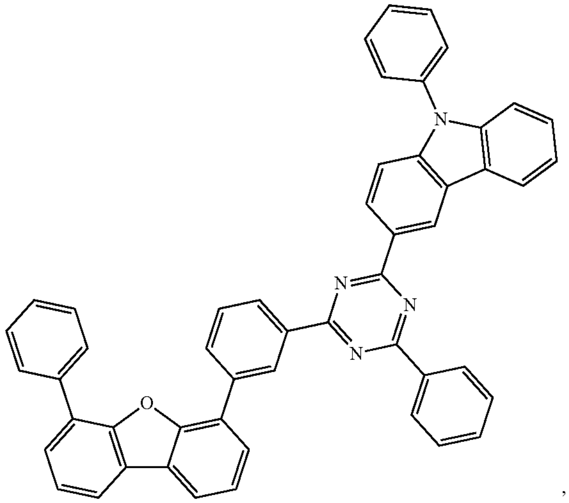
, -continued
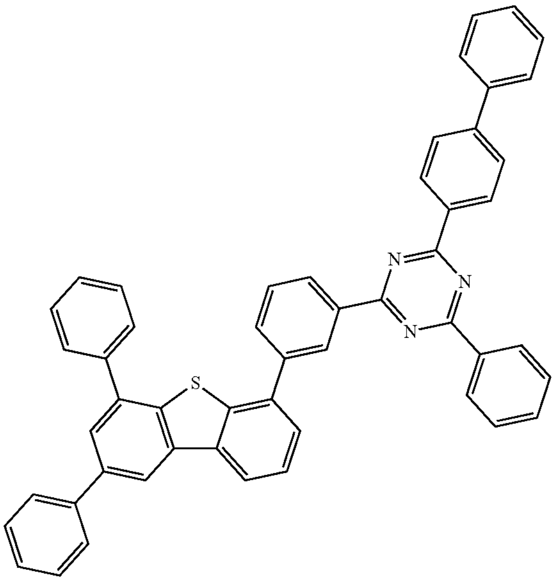
,
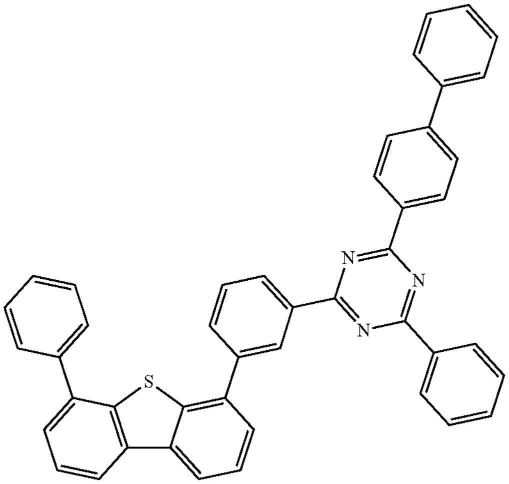
,
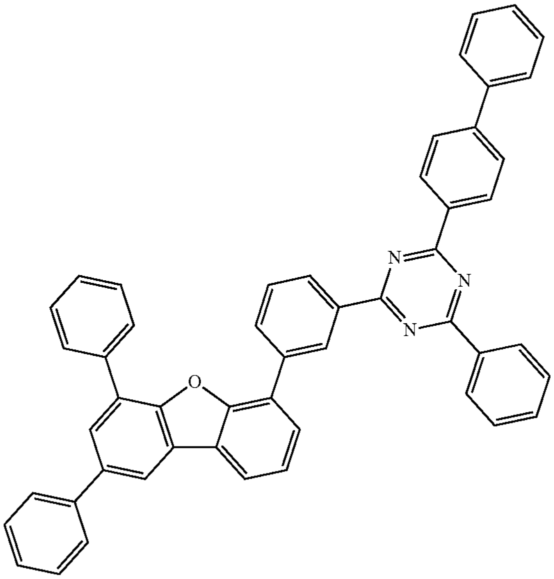
,
-continued
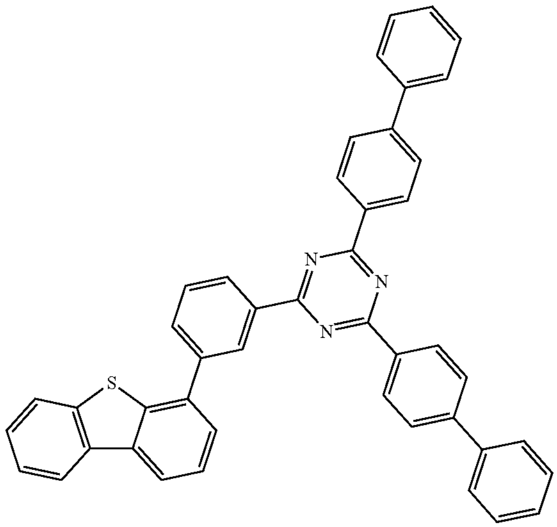
,
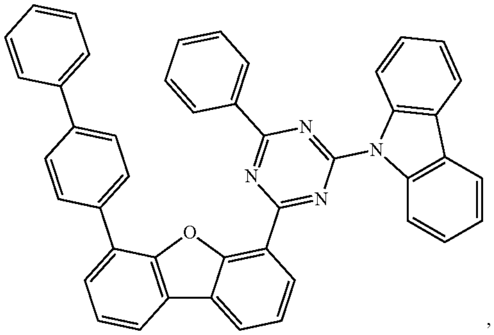
,
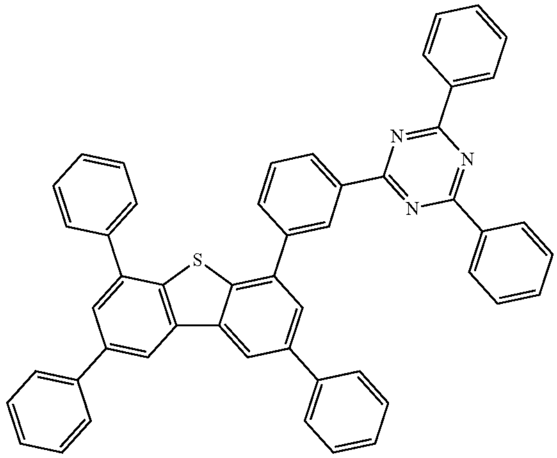
, -continued
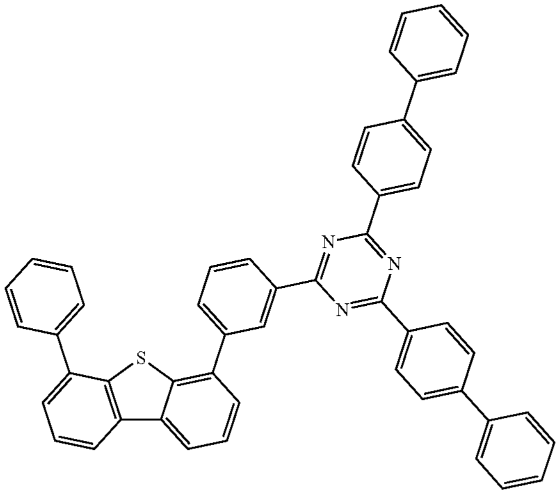
,
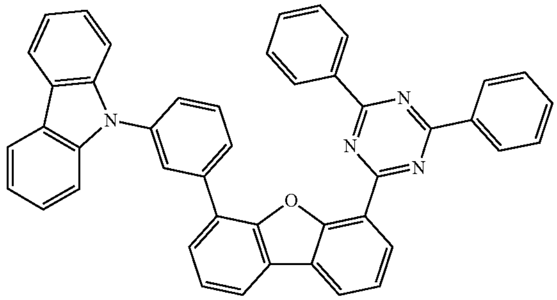
,
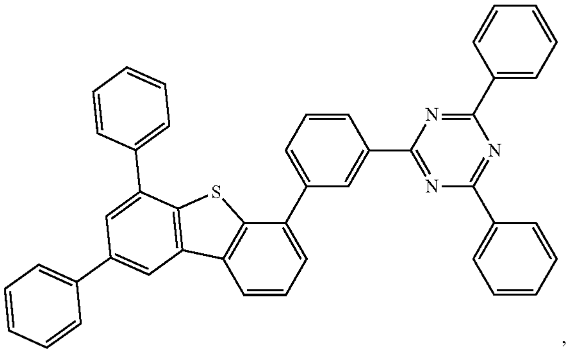
,
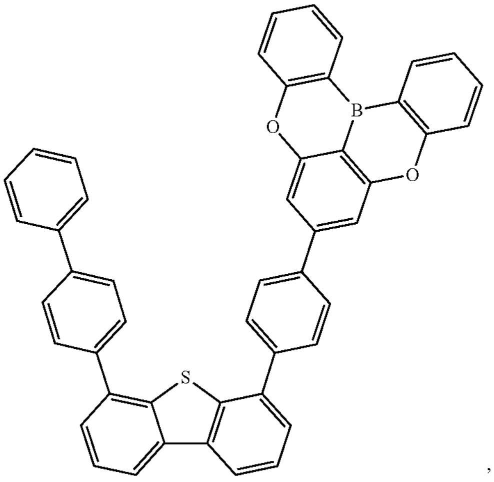
,
-continued
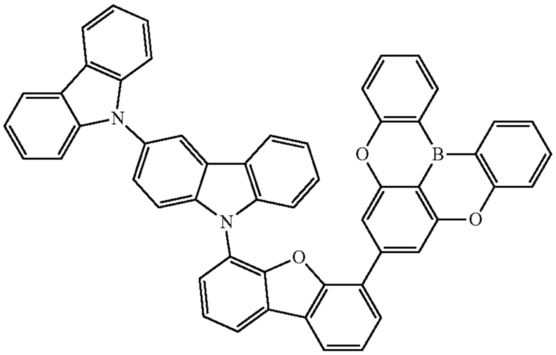
,
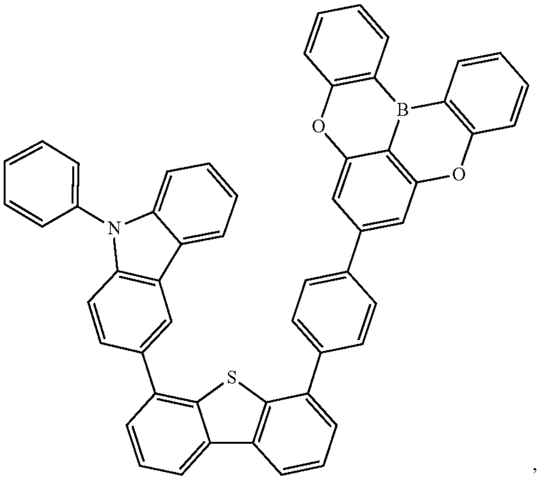
,
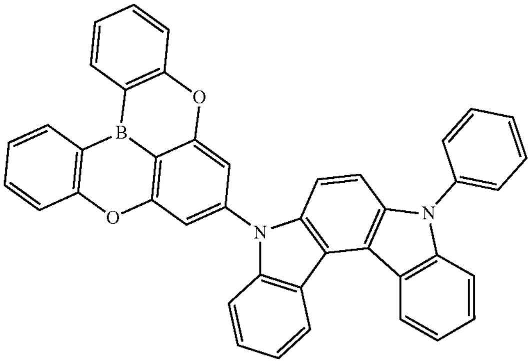
,
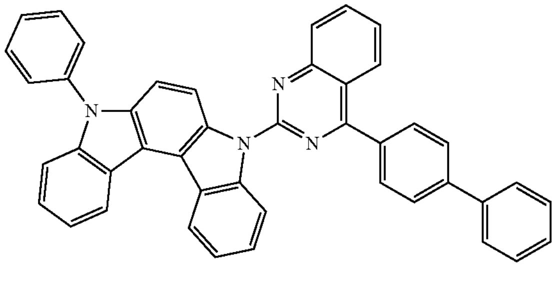
, -continued
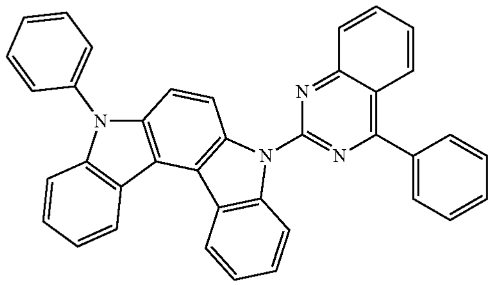
,
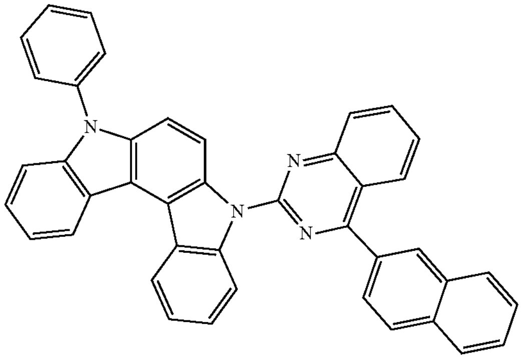
,
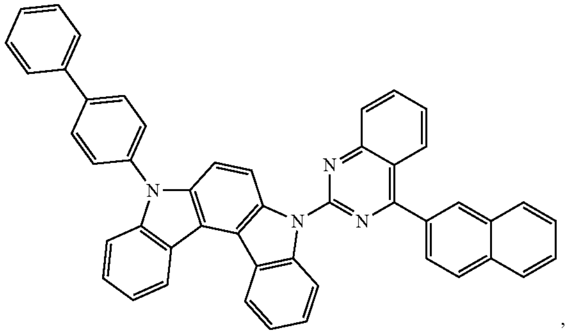
,
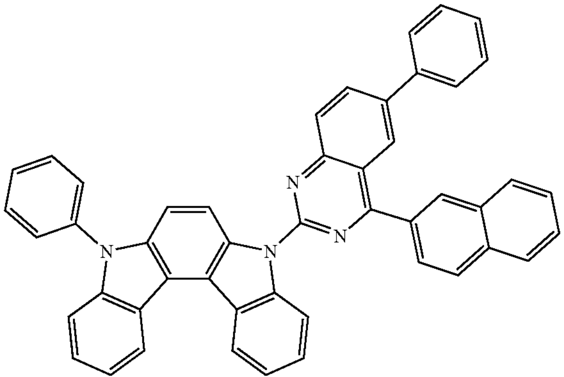
,
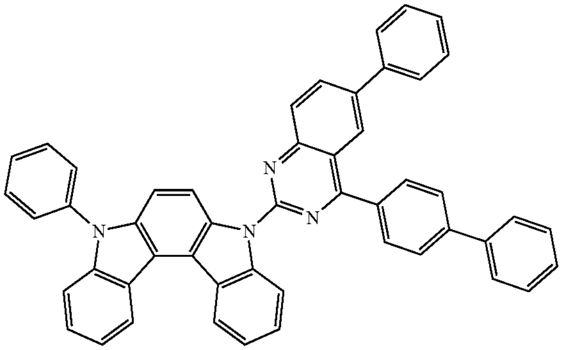
,
-continued
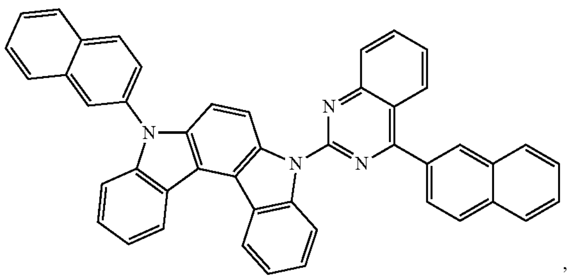
,
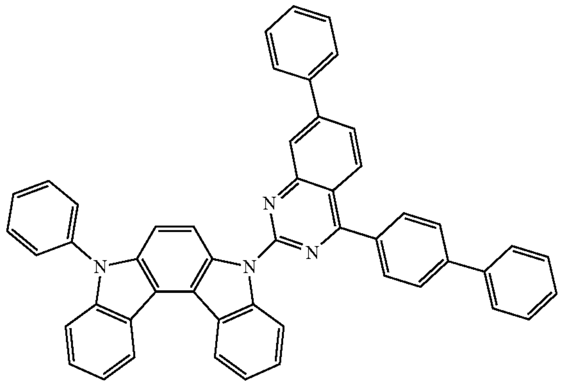
,
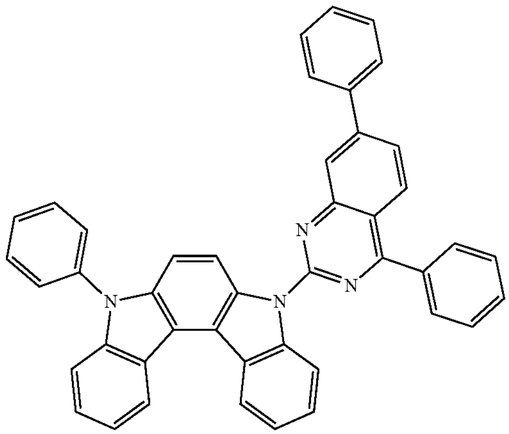
,
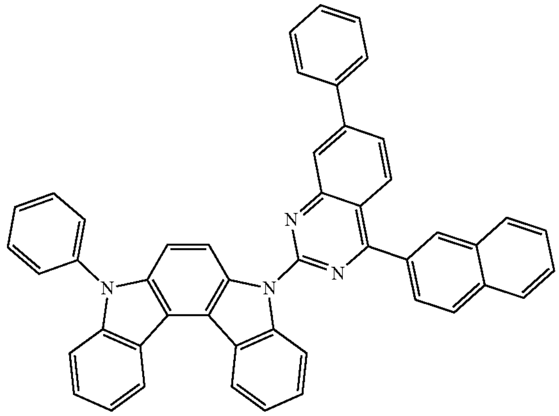
, -continued
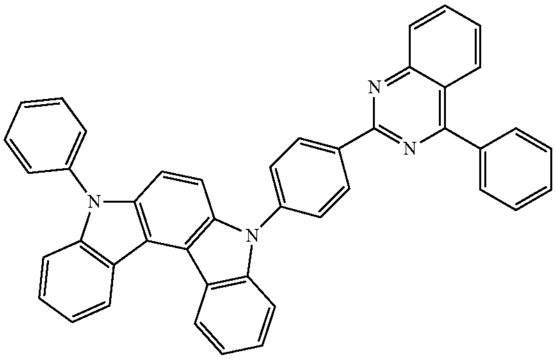
,
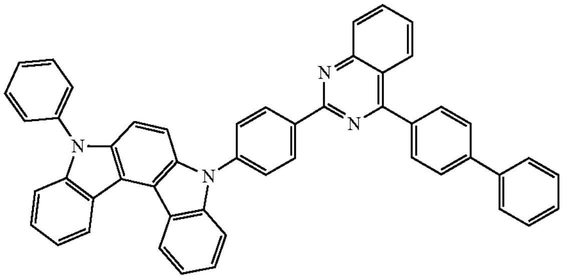
,
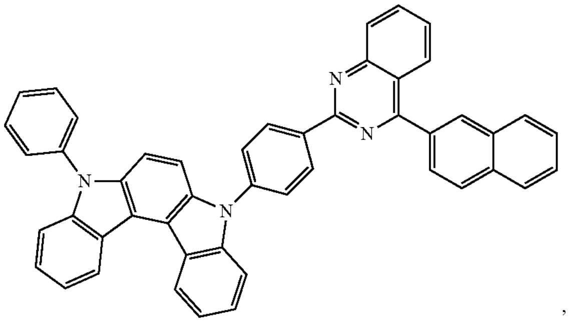
,
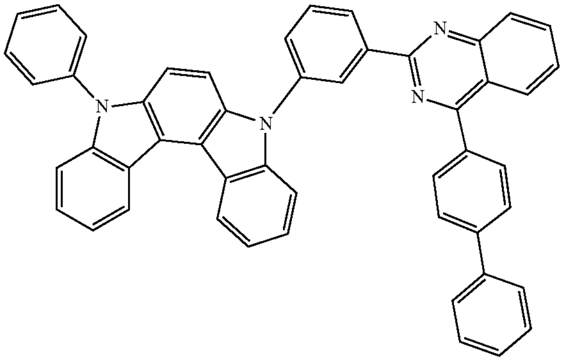
,
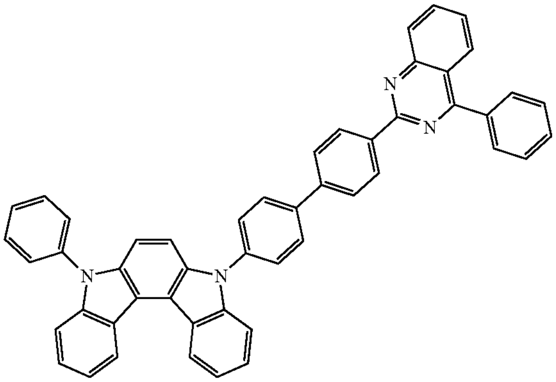
,
-continued
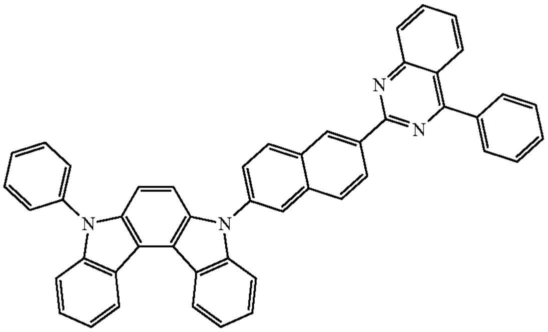
,
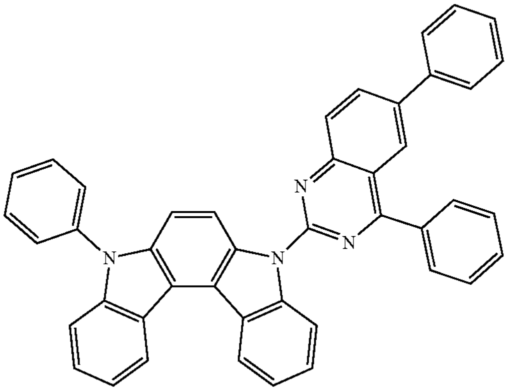
,
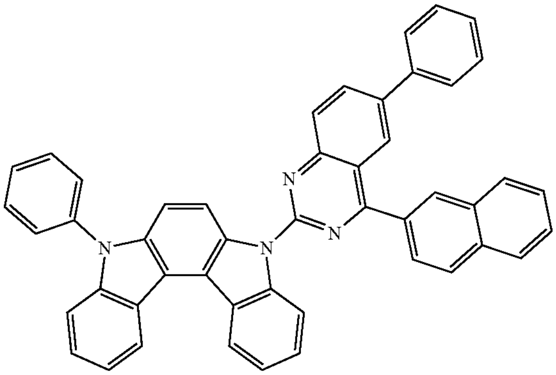
,
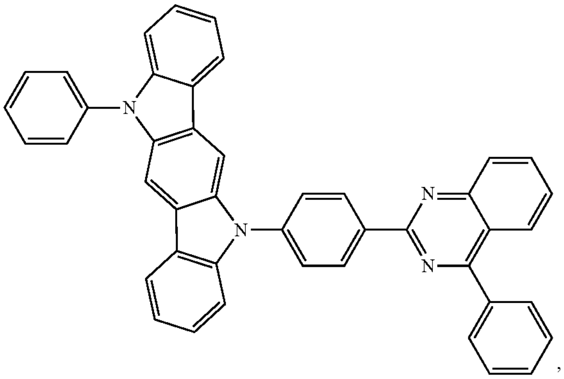
, -continued
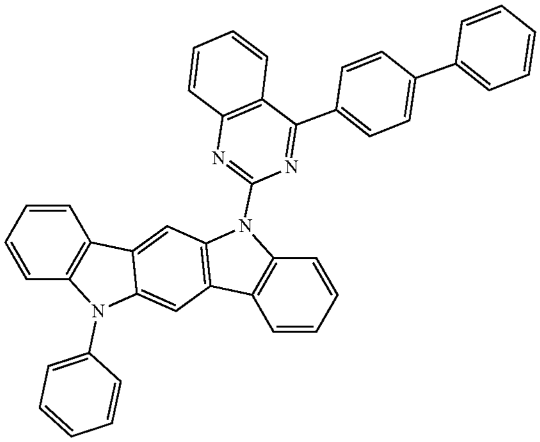
,
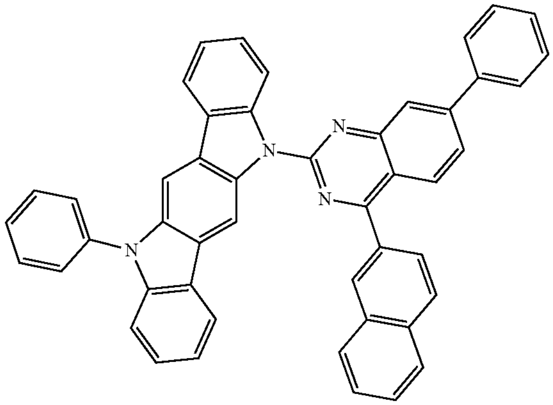
,
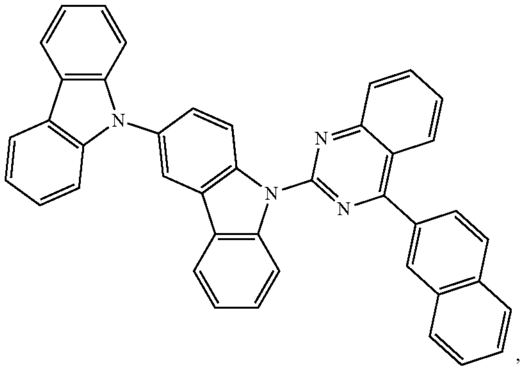
,
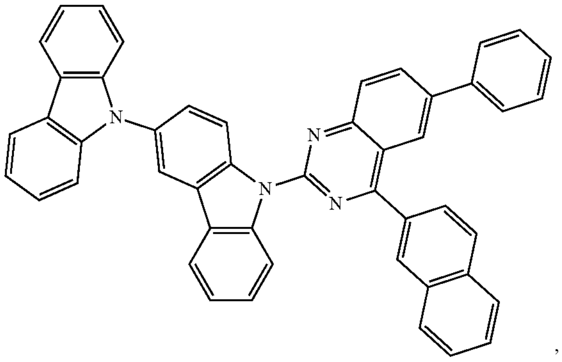
,
-continued
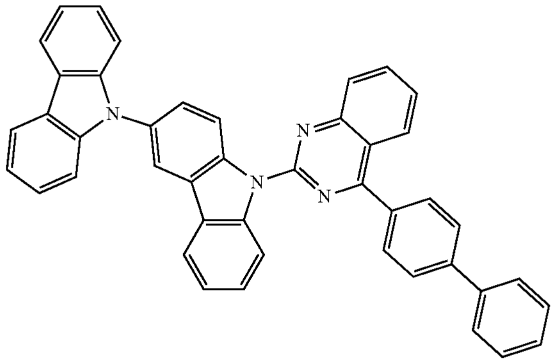
,
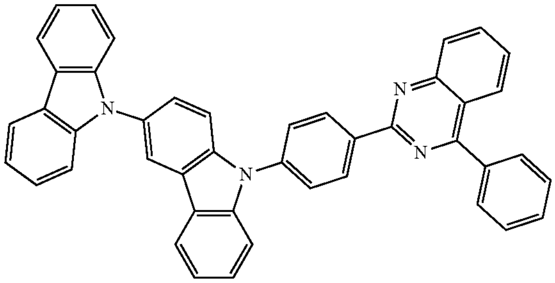
,
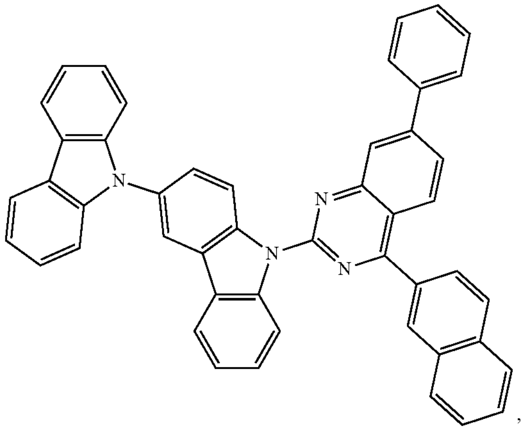
,
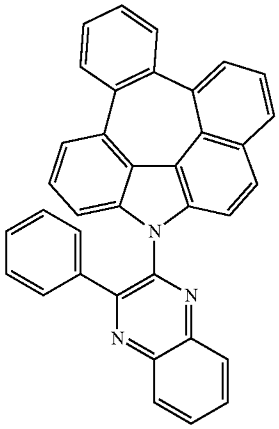
, -continued
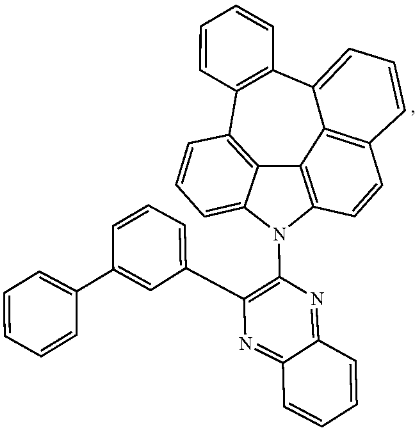
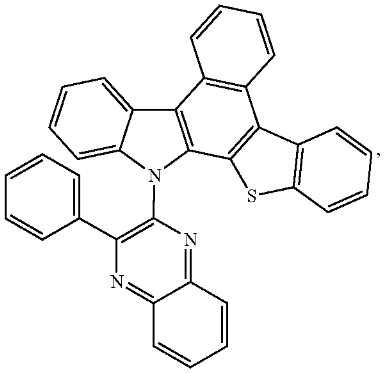
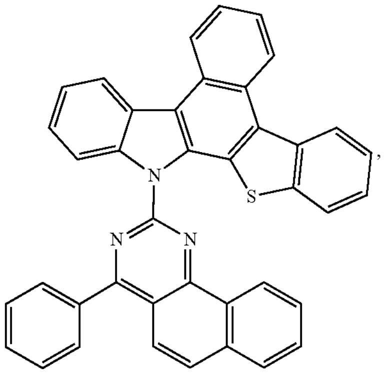
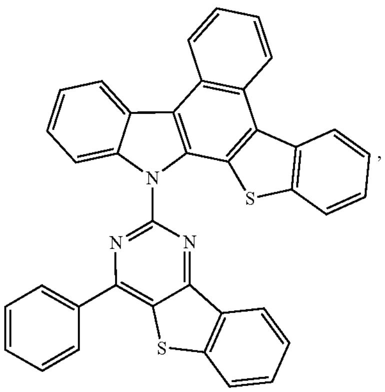
-continued
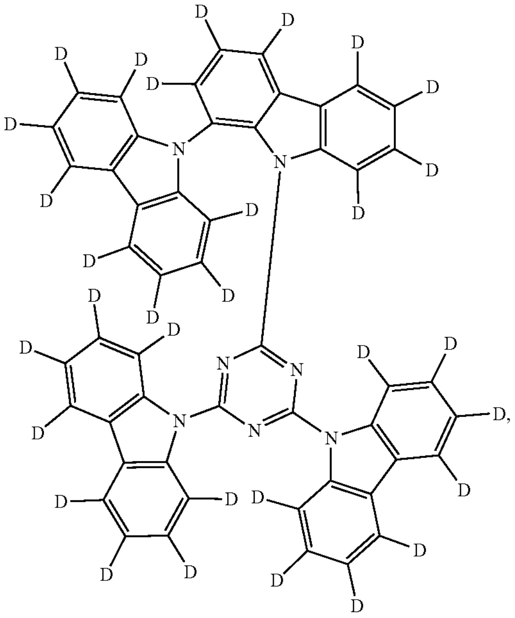
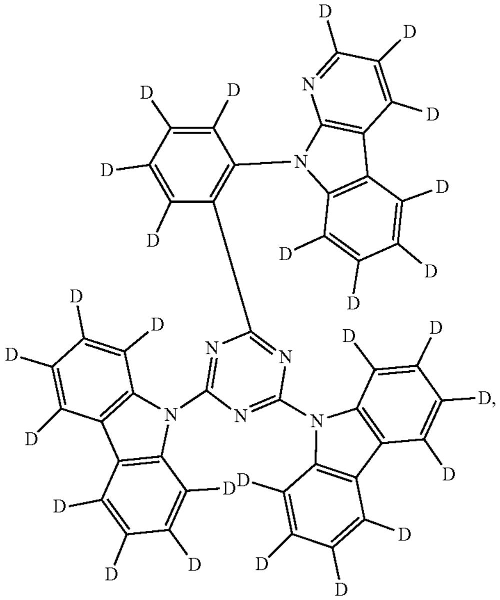

-continued
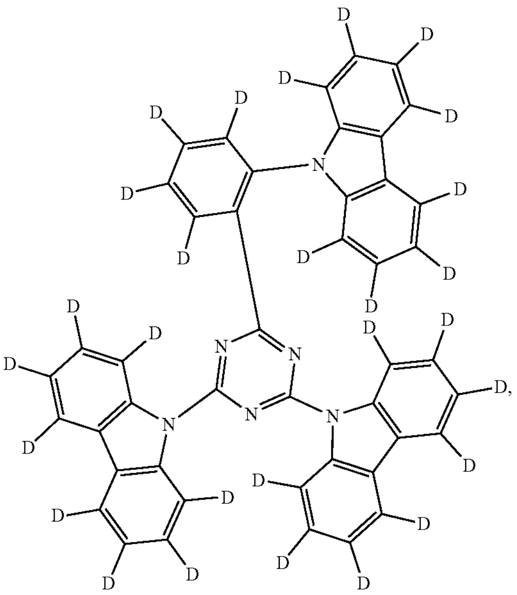
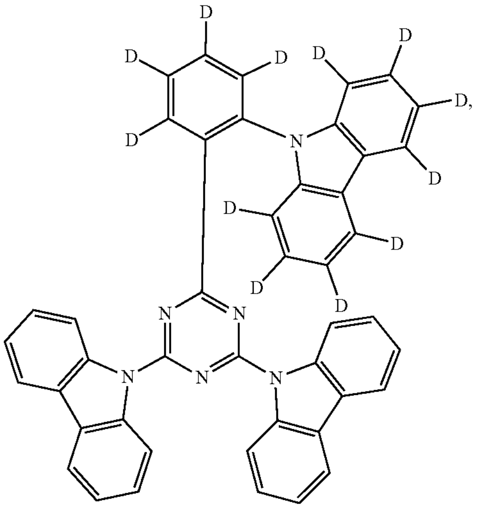
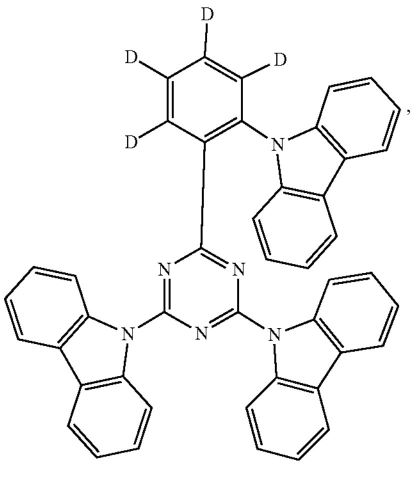
-continued
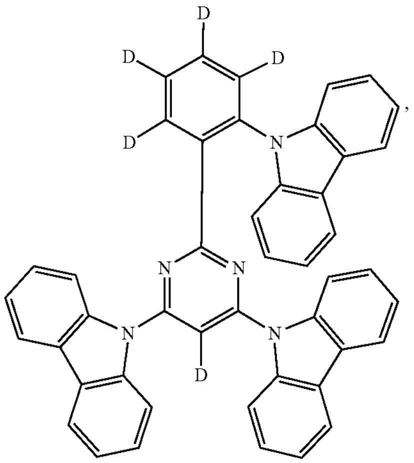
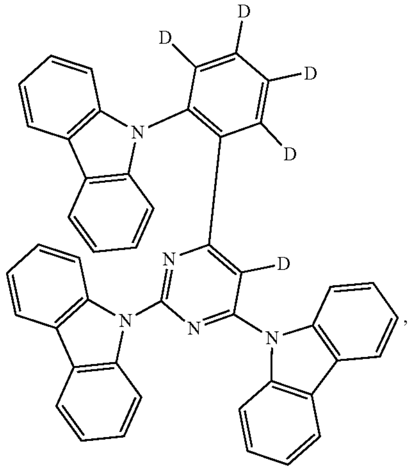
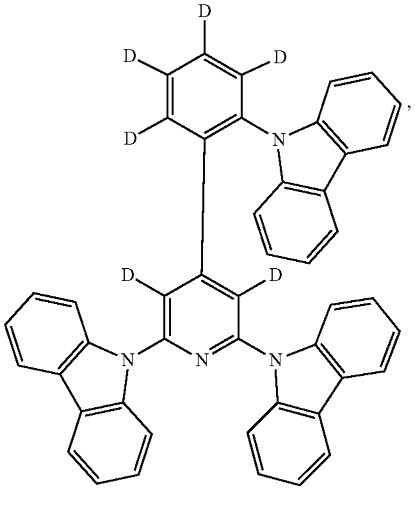

-continued
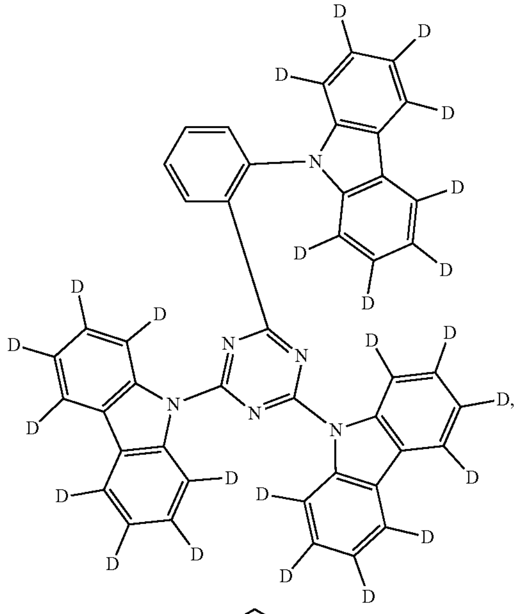
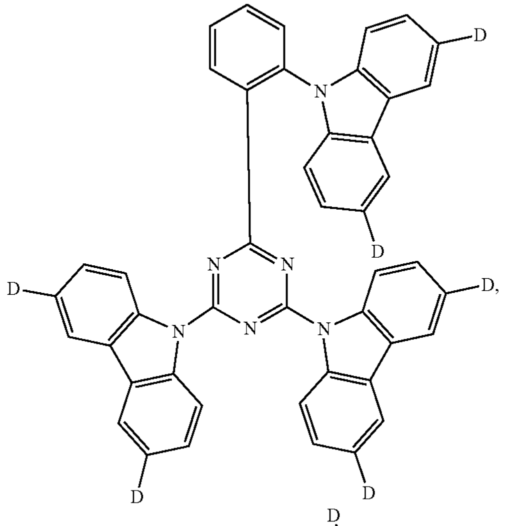
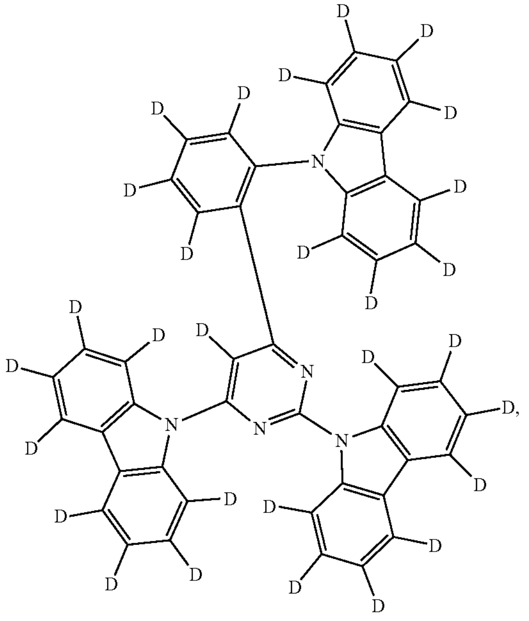
-continued
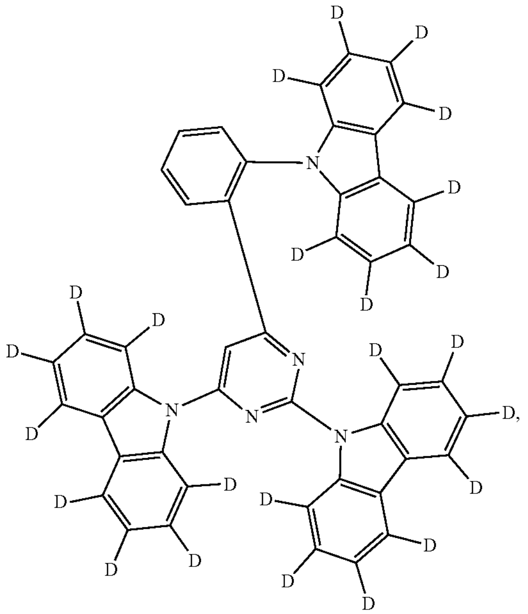
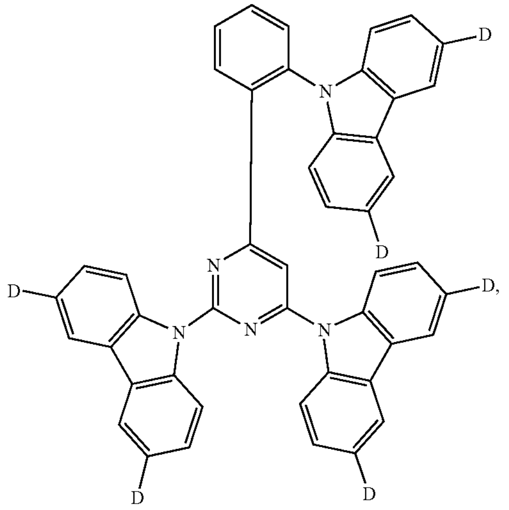
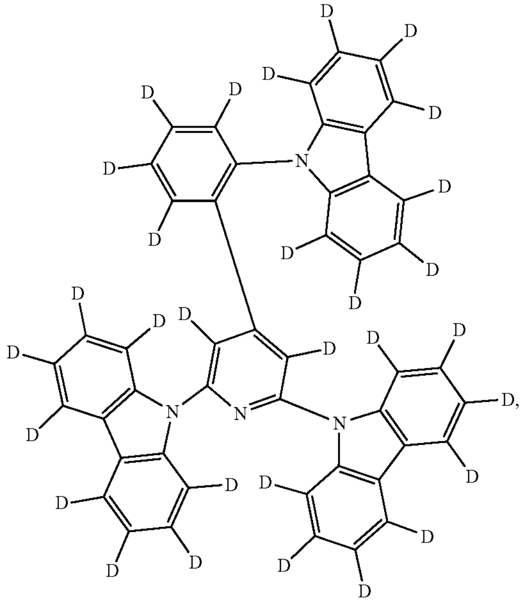

-continued
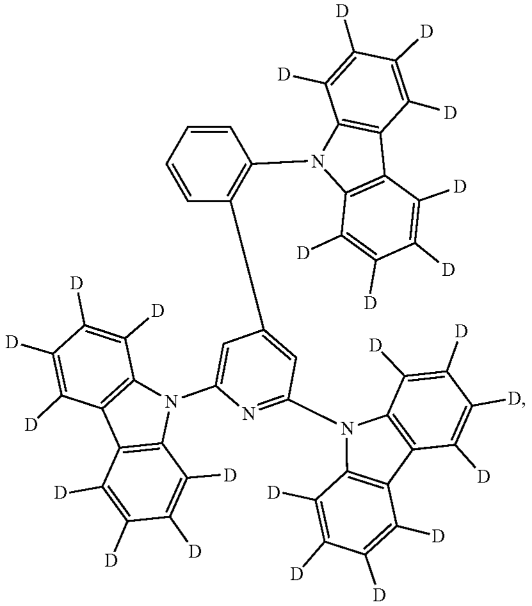
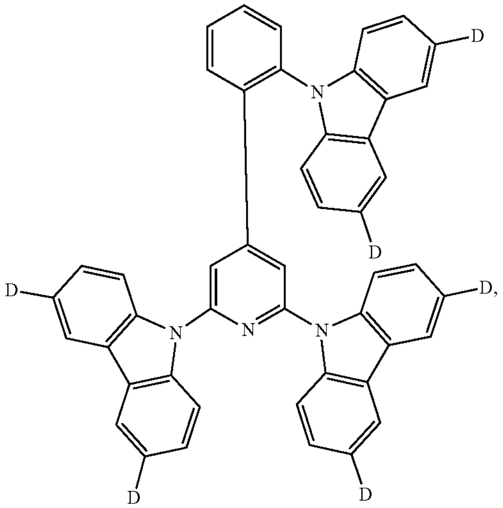
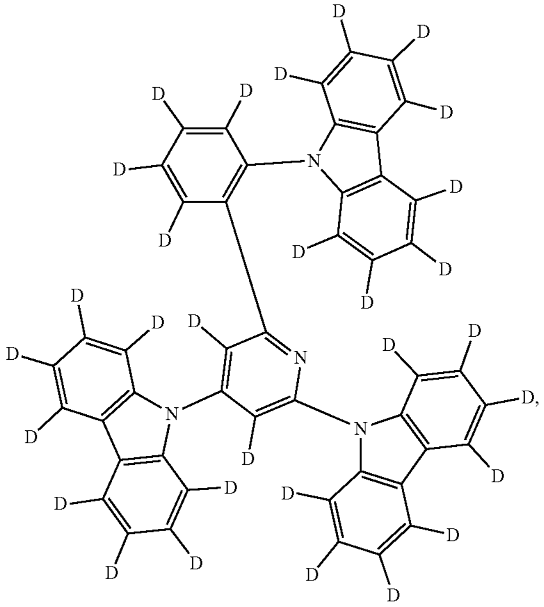
-continued
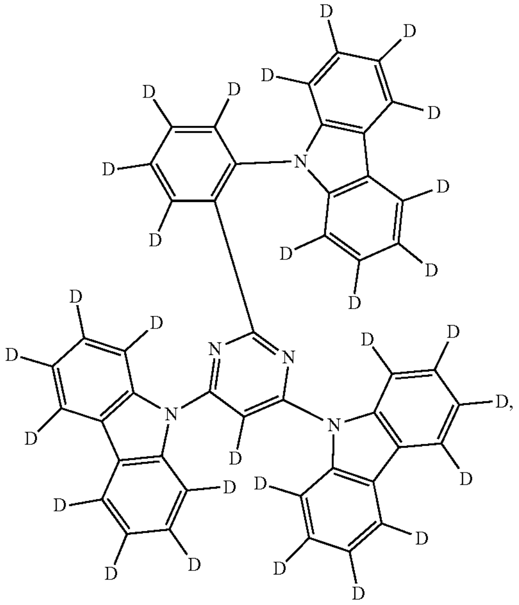
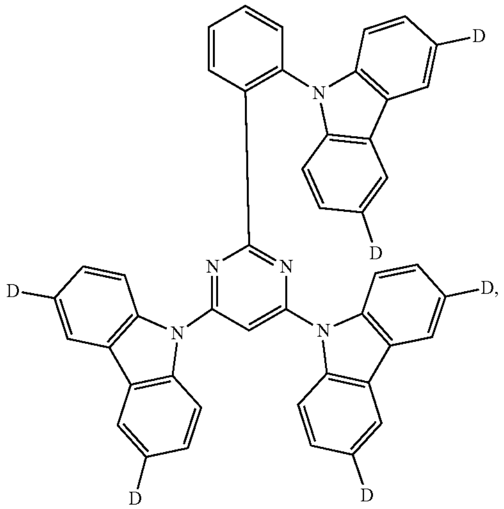
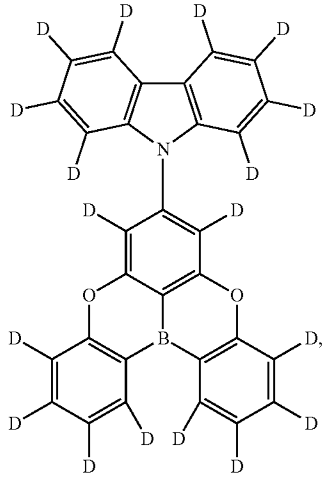

-continued
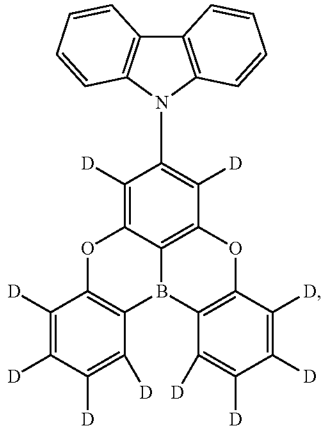
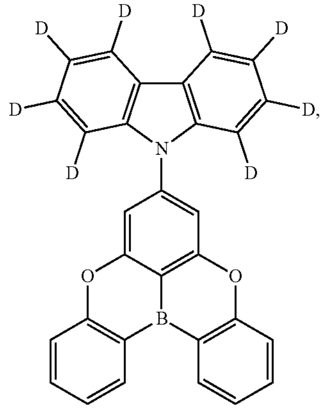
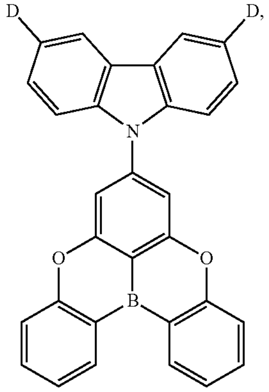
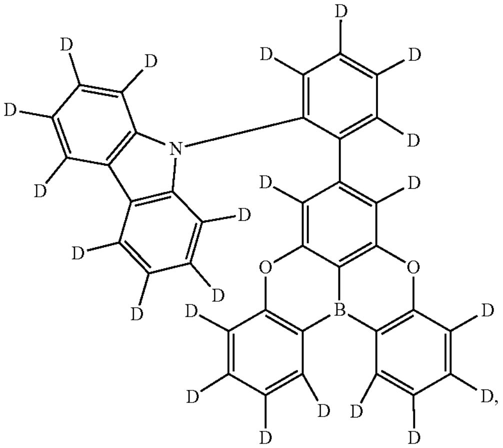
-continued
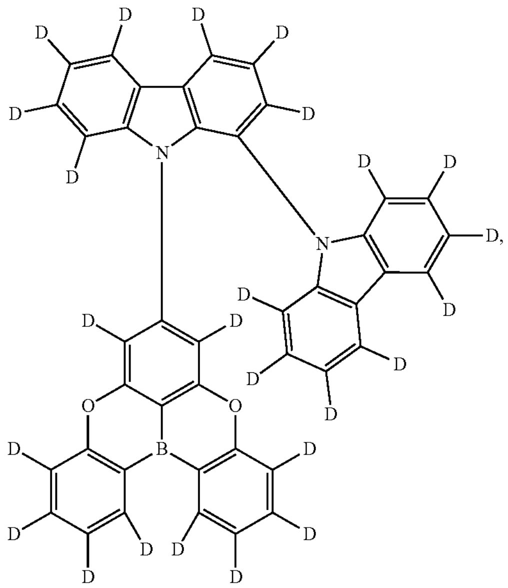
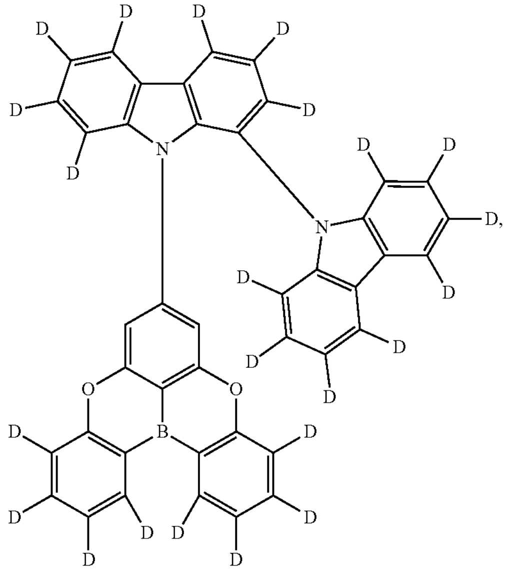
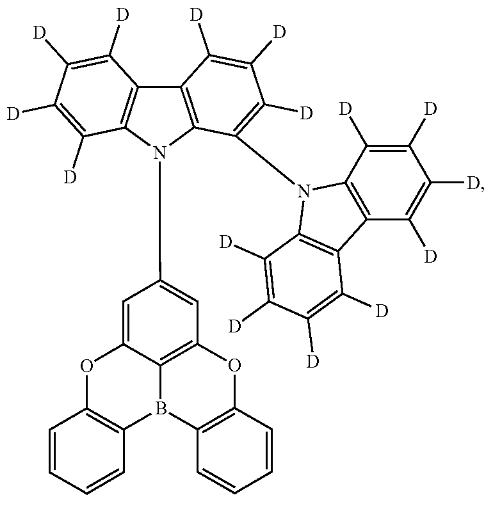

-continued
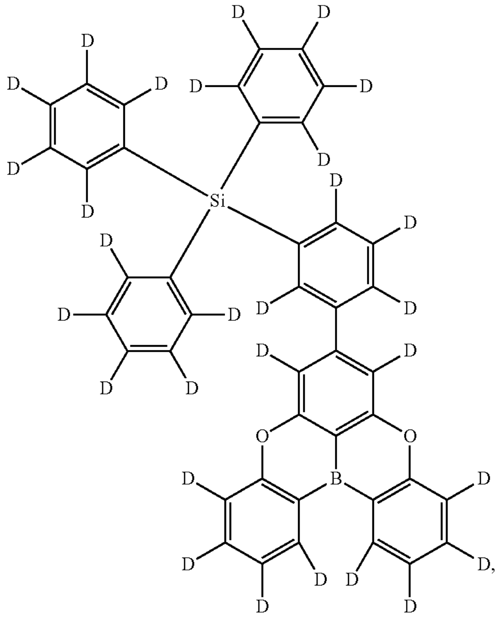
,
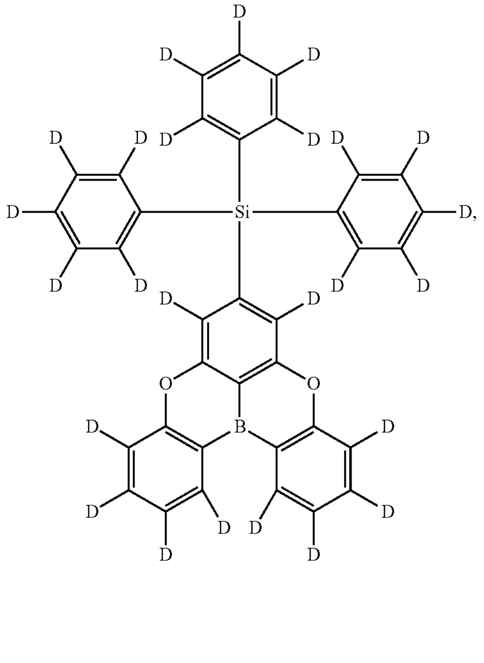
,
-continued
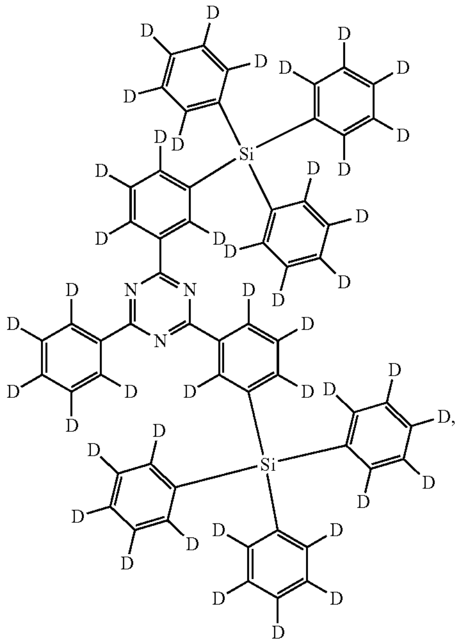
,
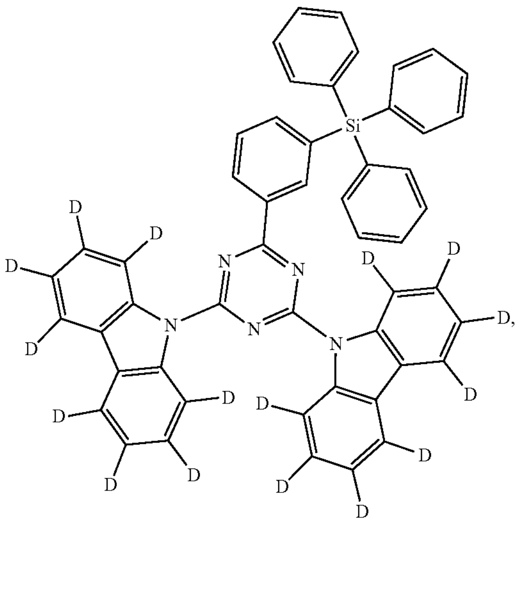
,

-continued
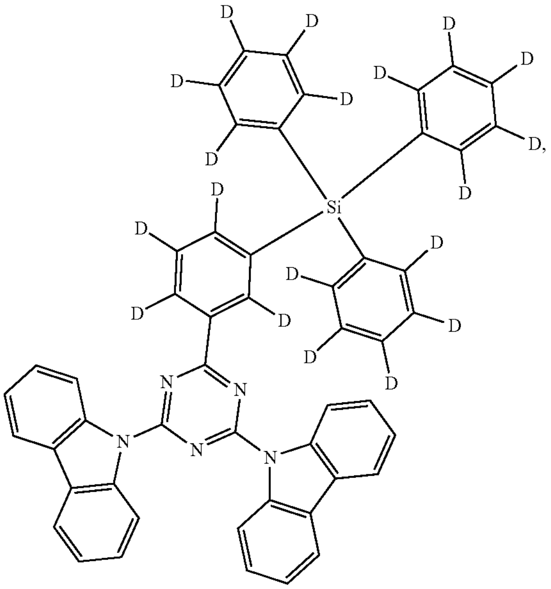
-continued
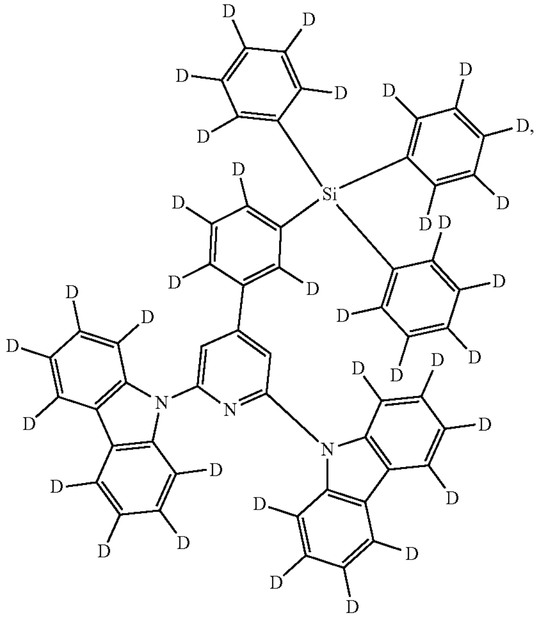
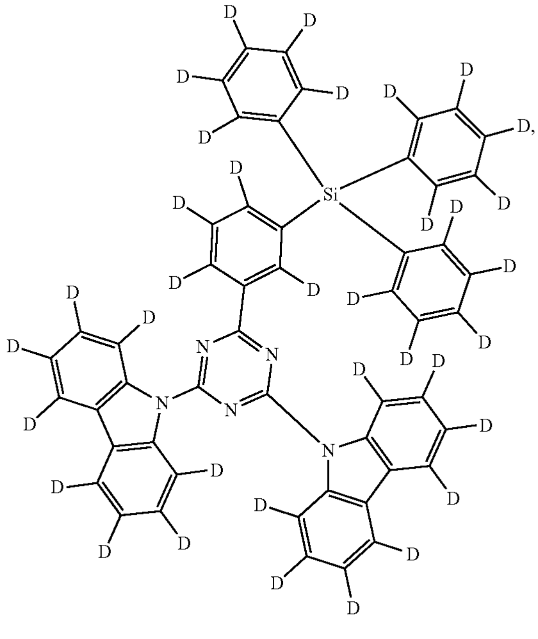
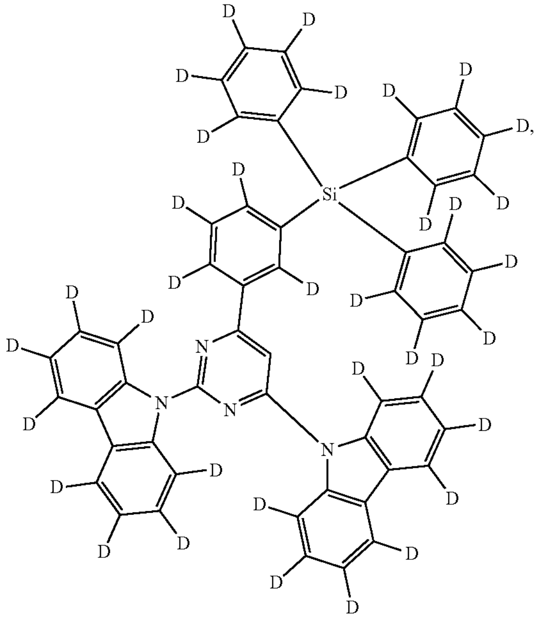

-continued
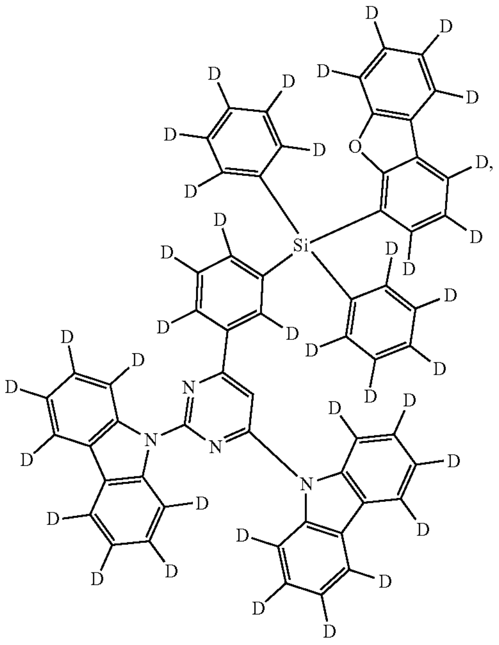
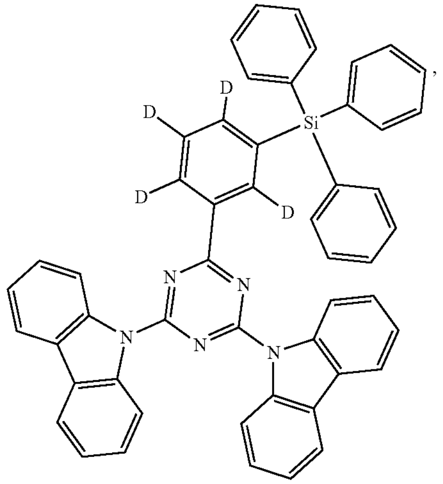
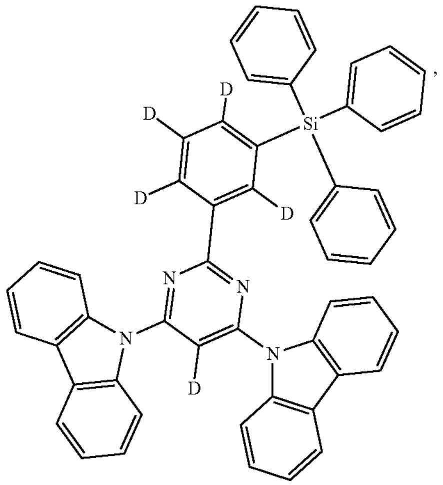
-continued
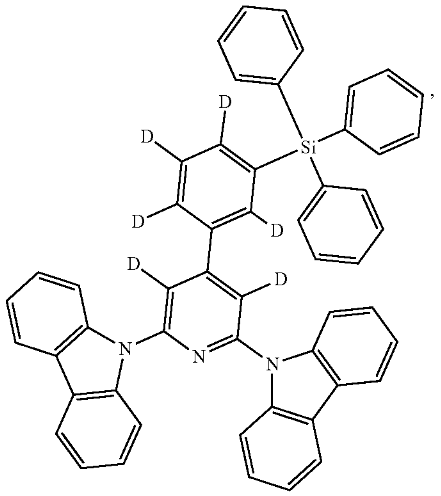
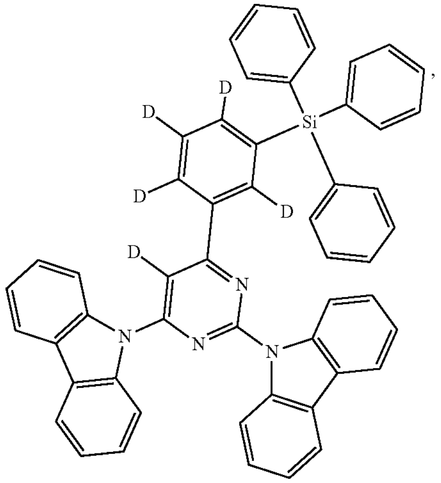
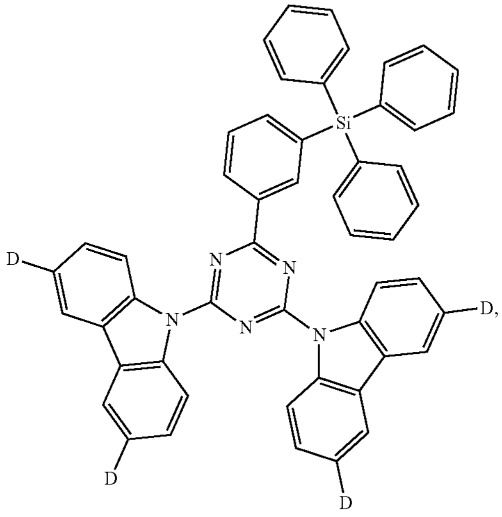

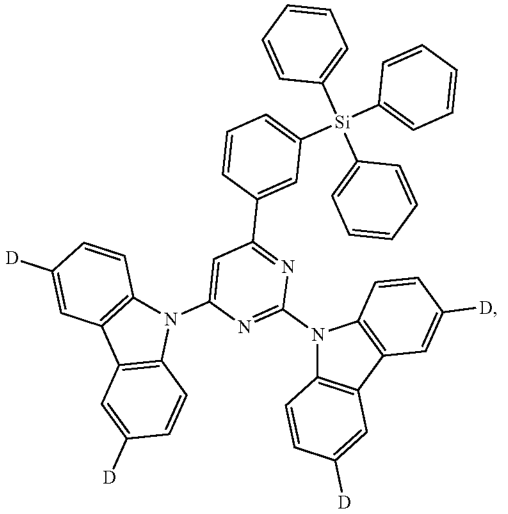
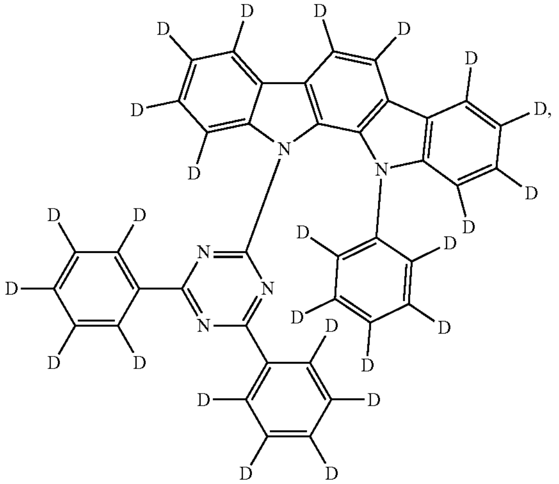
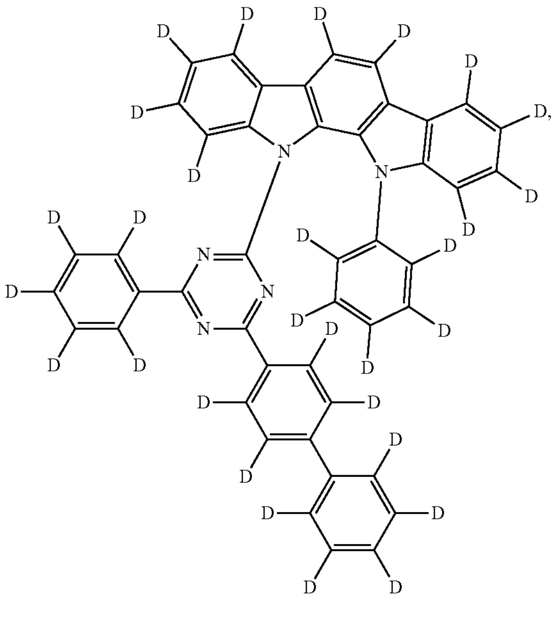
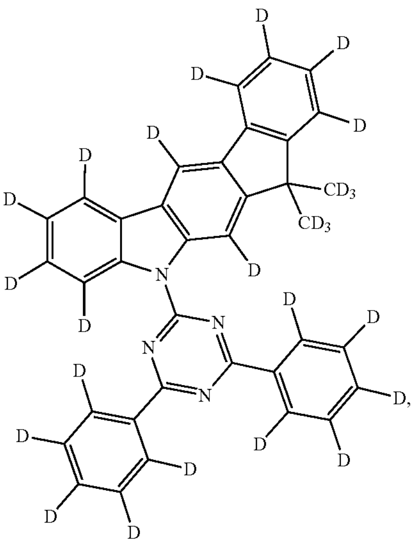
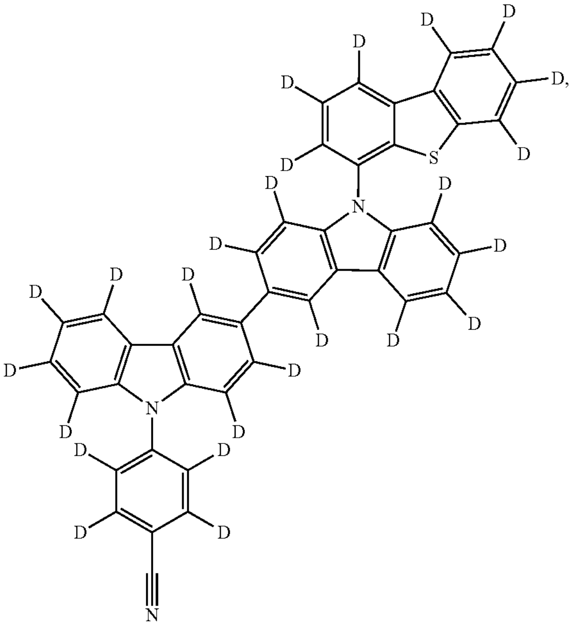
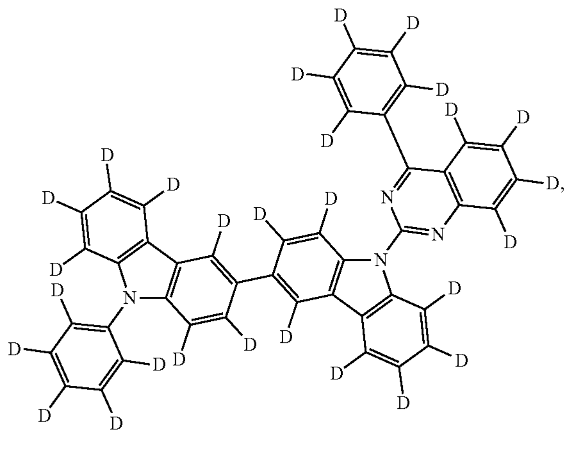

-continued
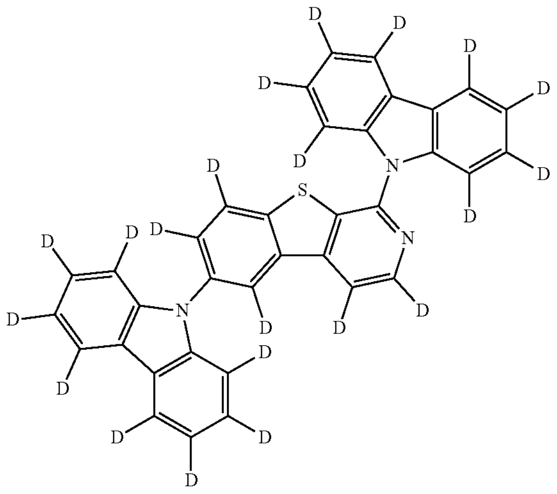
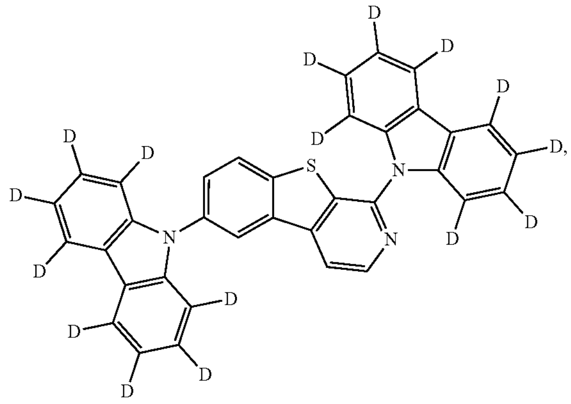
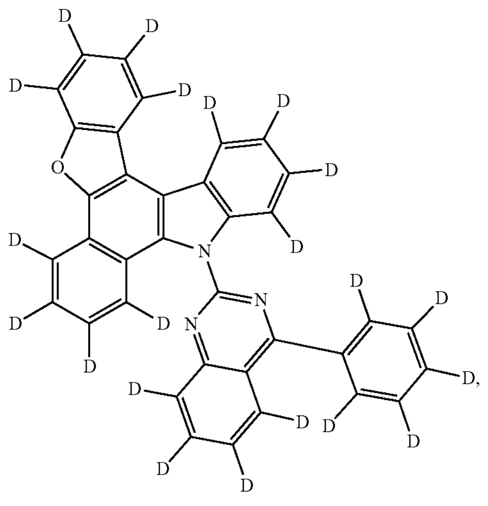
-continued
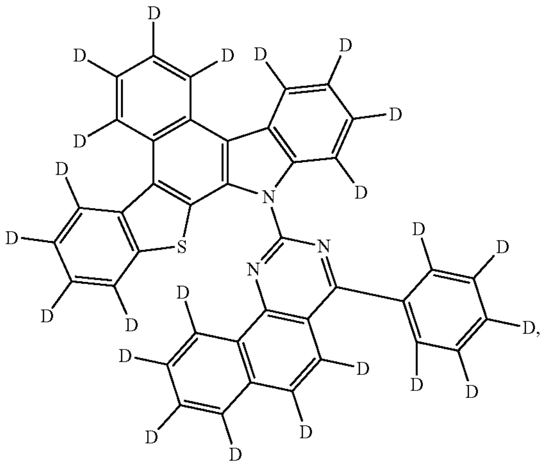
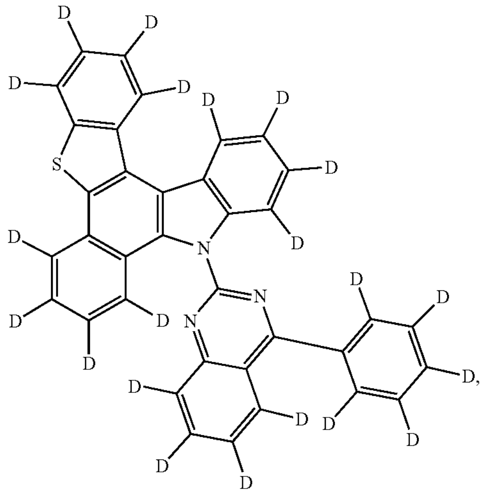
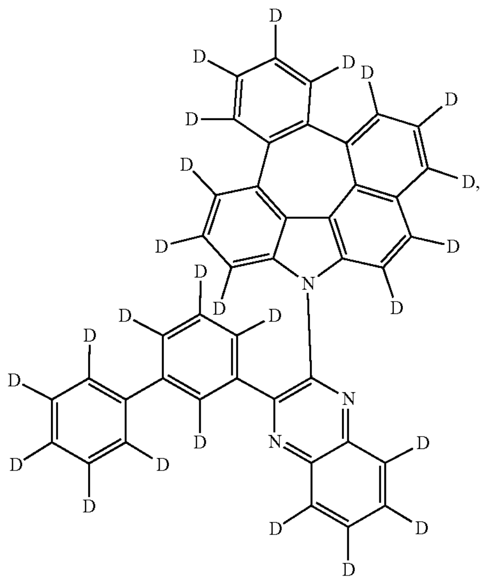

-continued
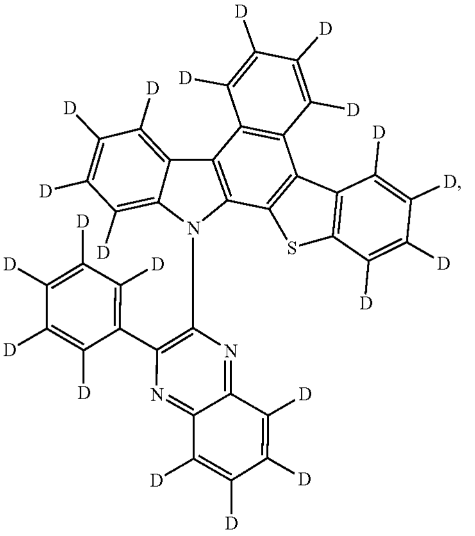
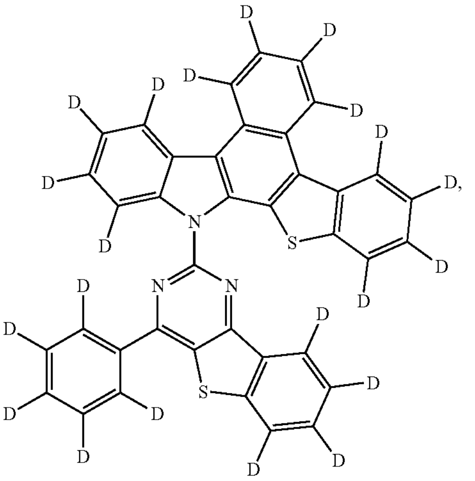
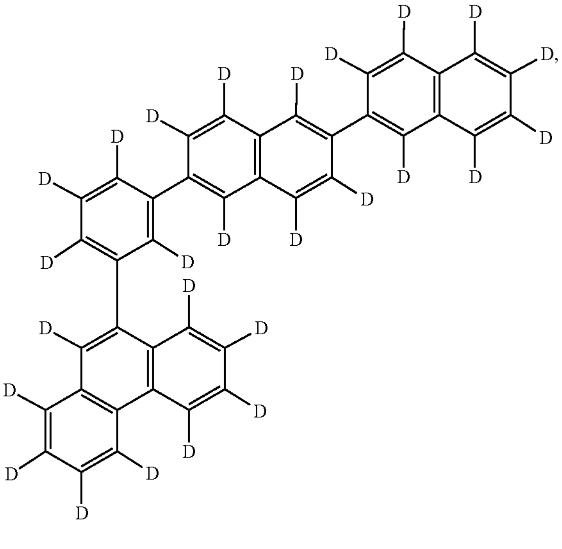
-continued
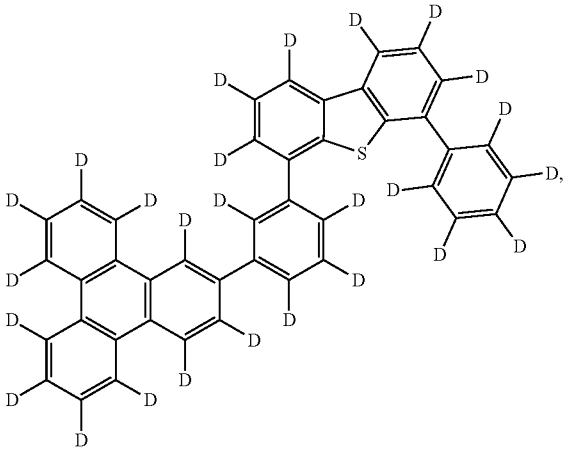
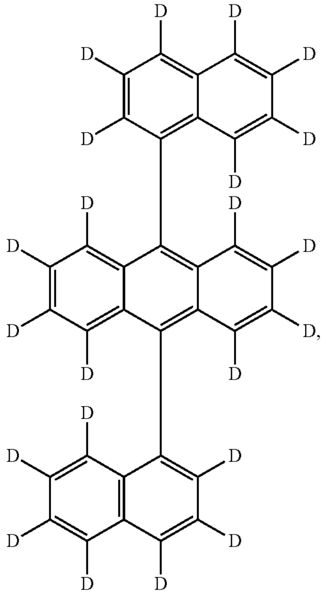
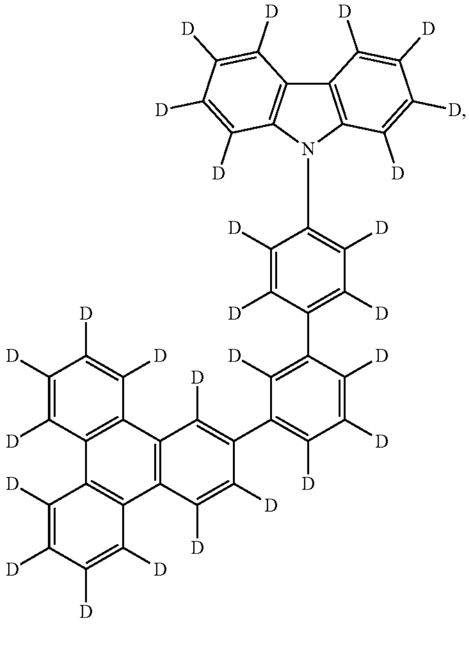

-continued
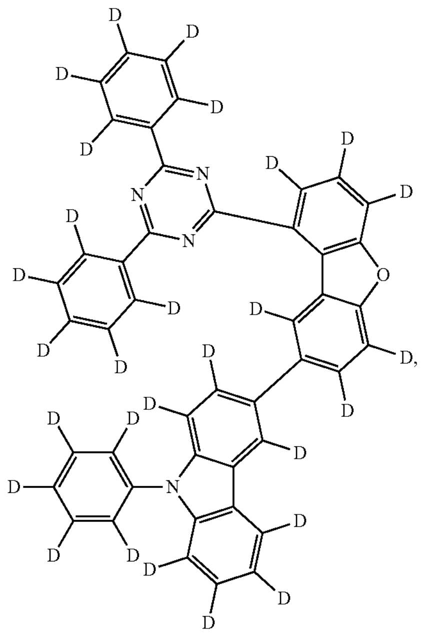
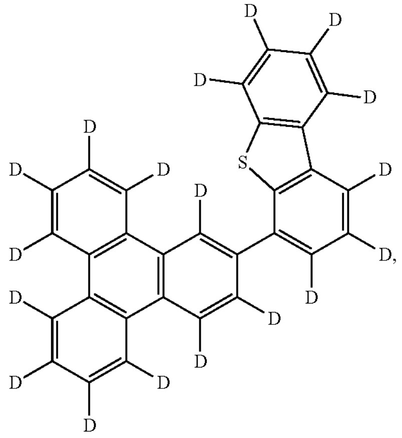
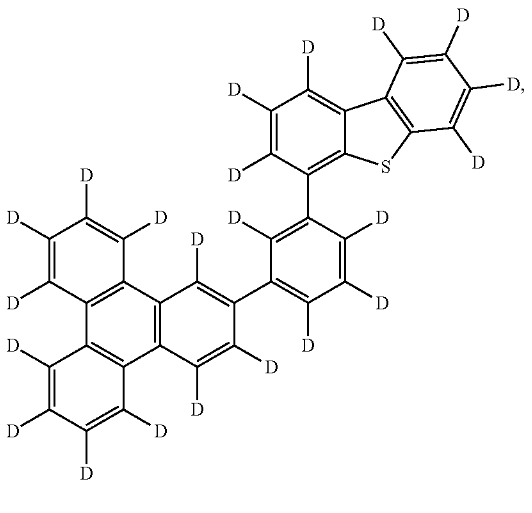
-continued
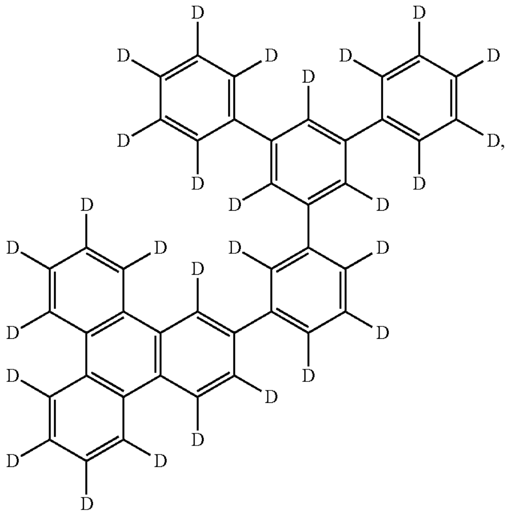
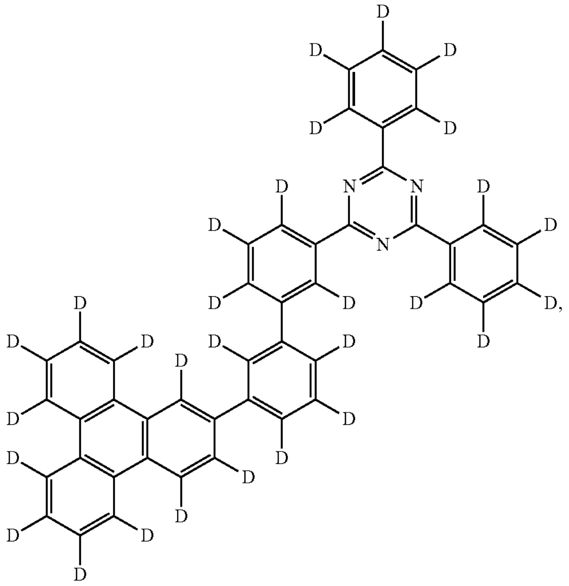
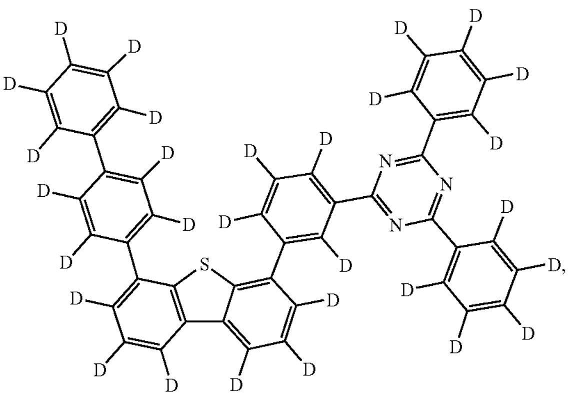

-continued
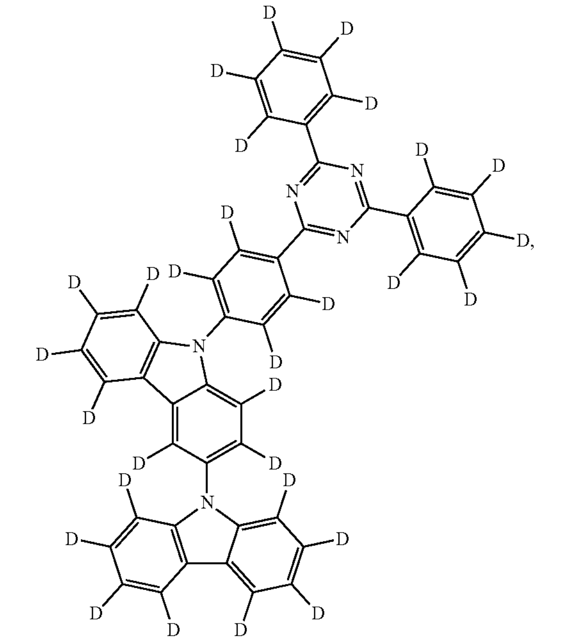
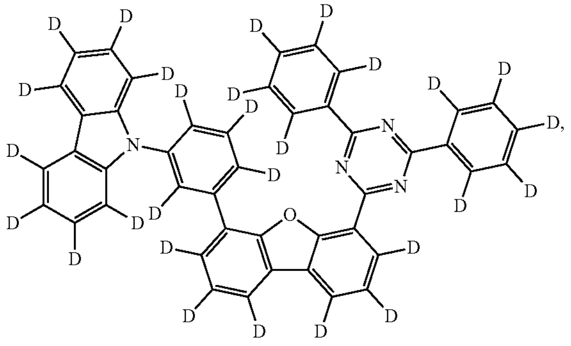
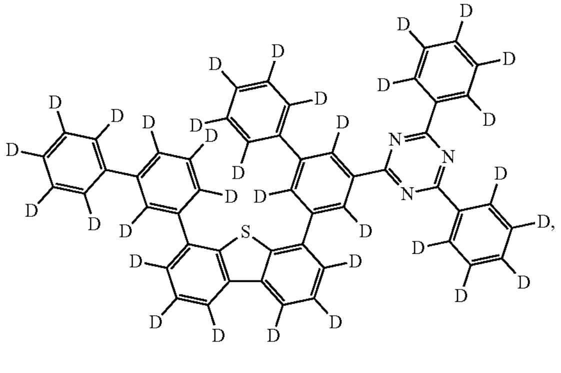
-continued
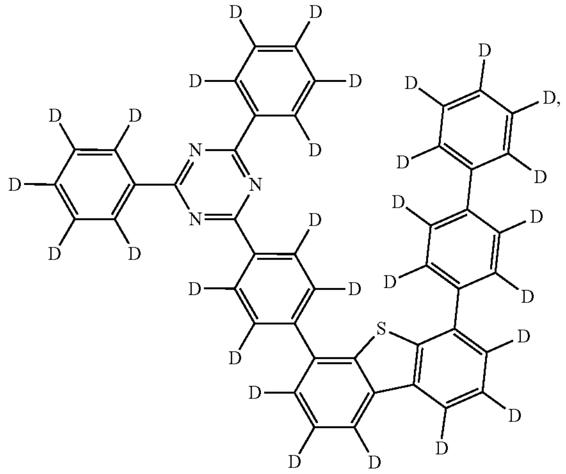
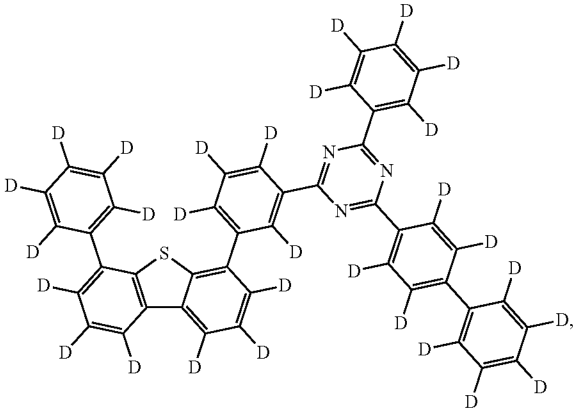
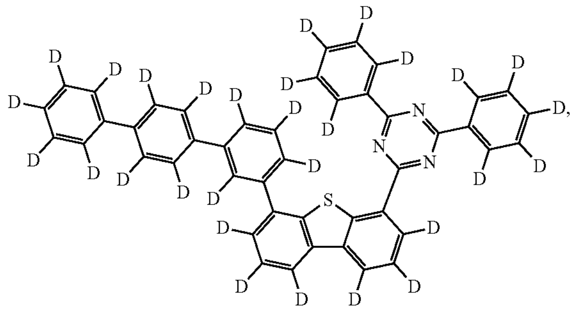
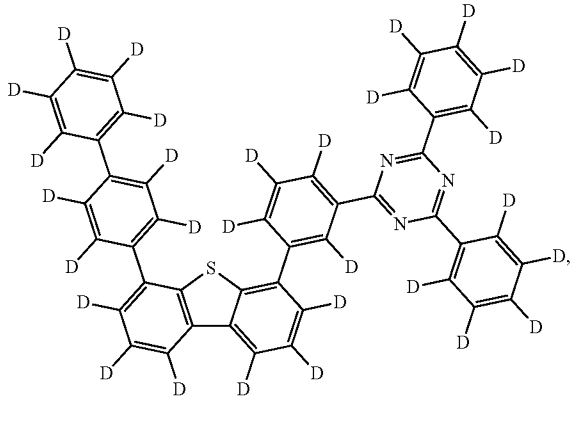

-continued
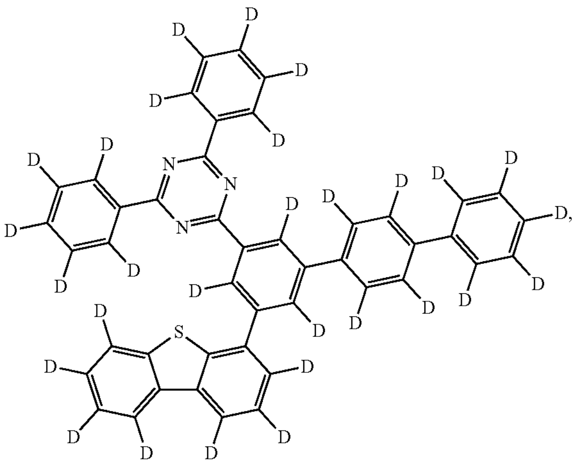
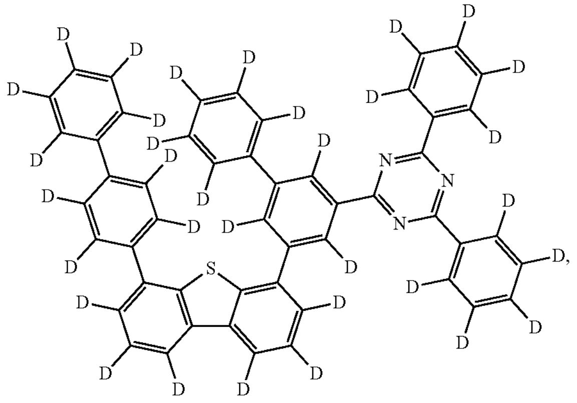
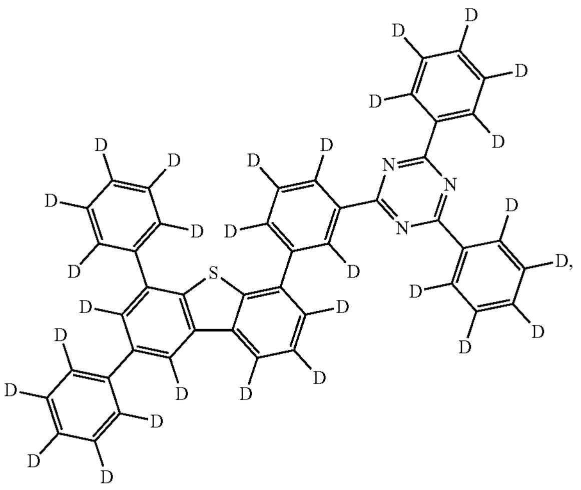
-continued
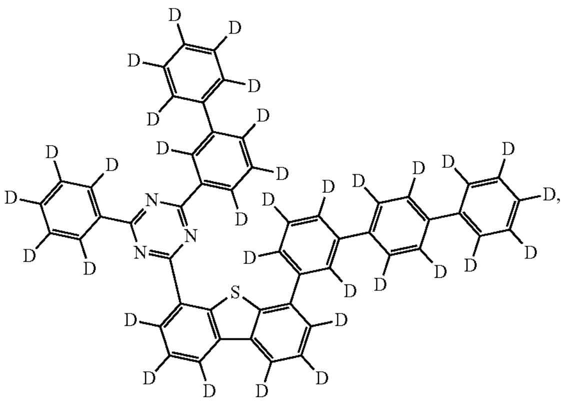
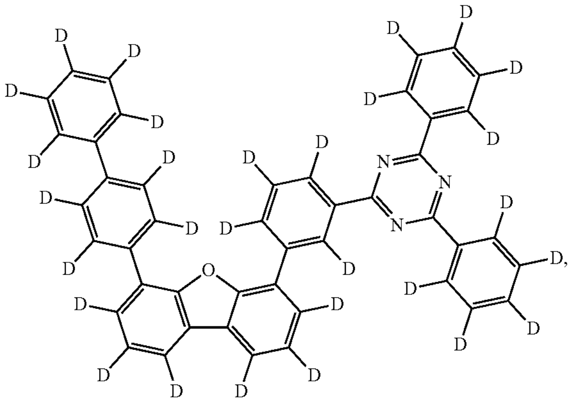
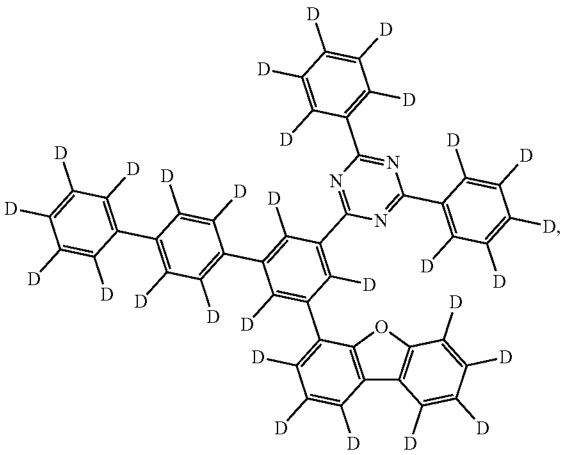

-continued
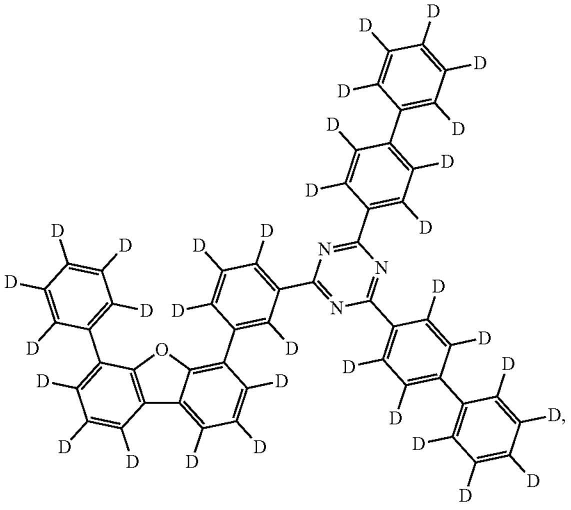
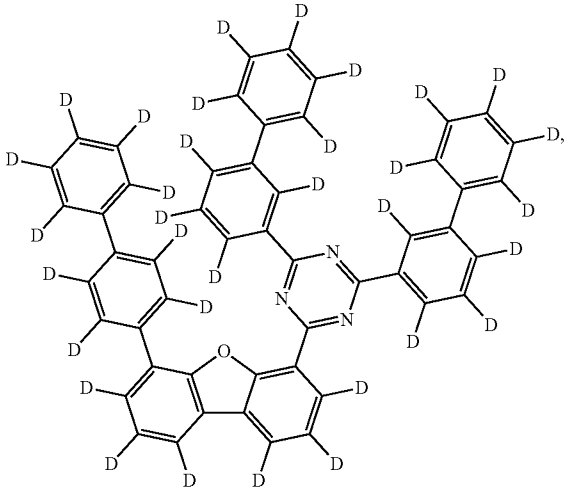
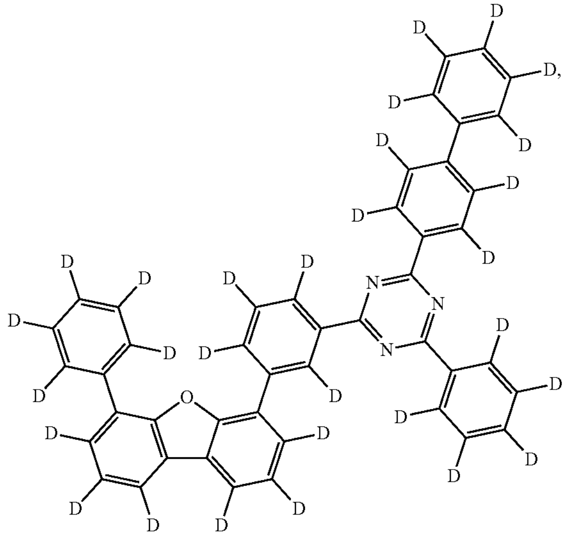
-continued
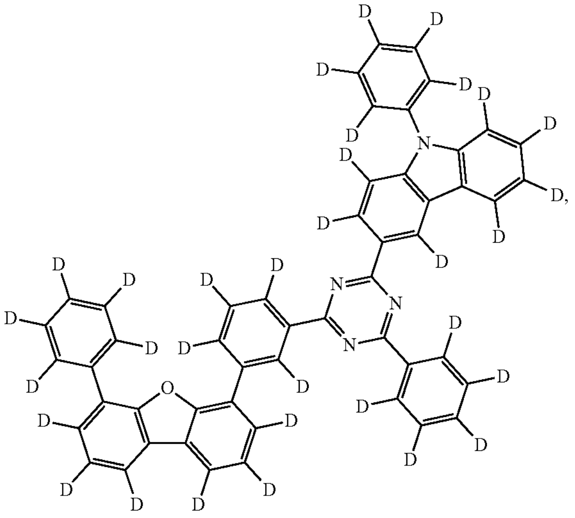
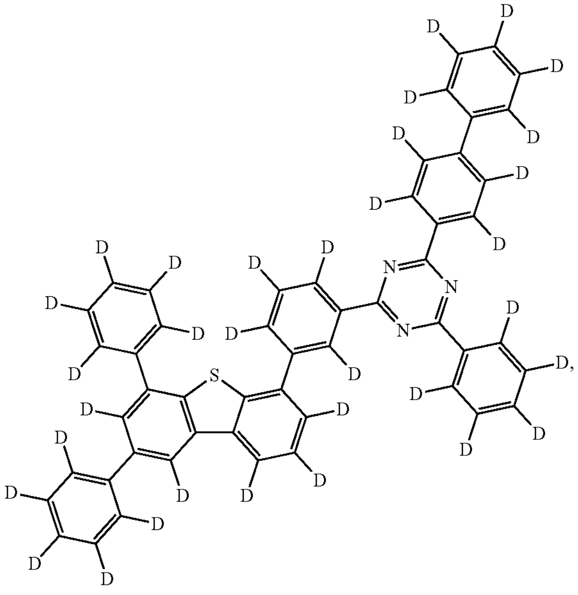

-continued
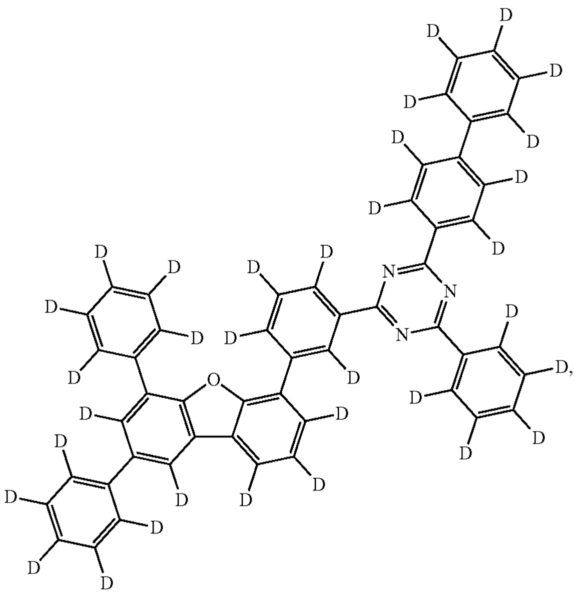
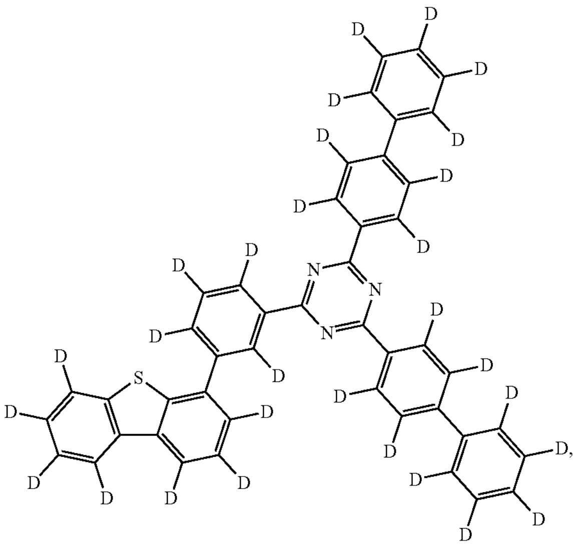
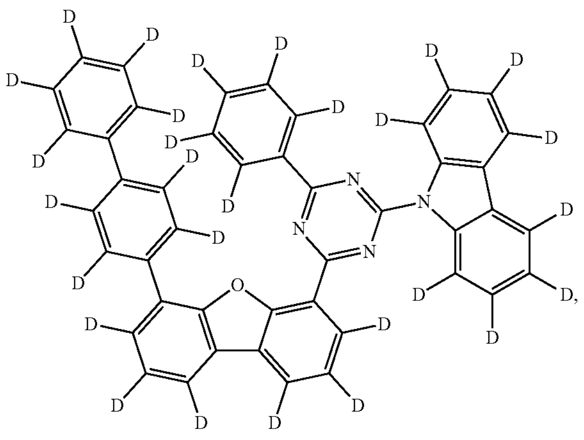
-continued
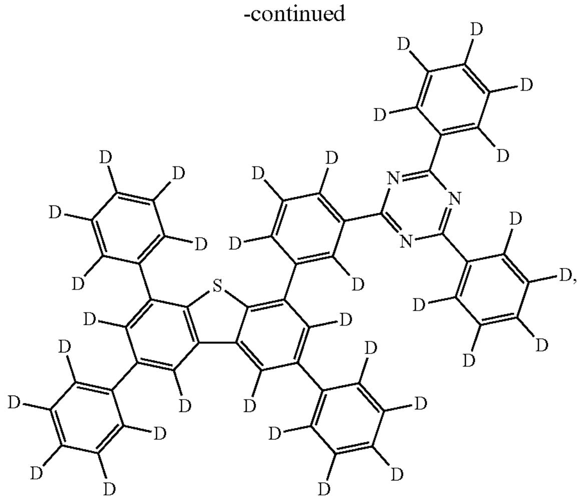
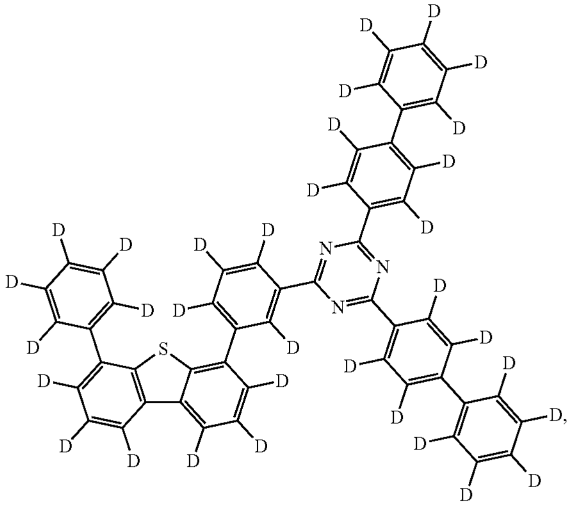
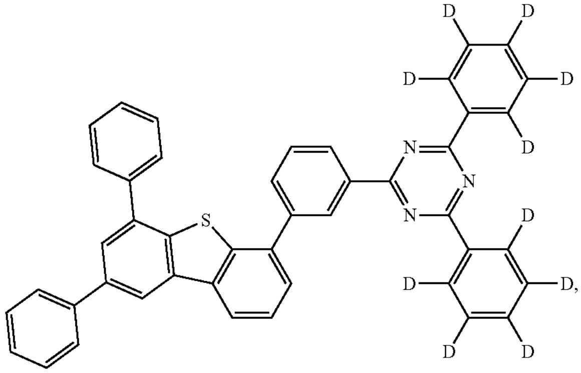
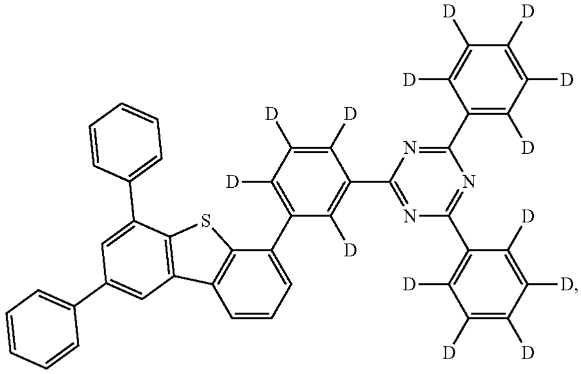

-continued
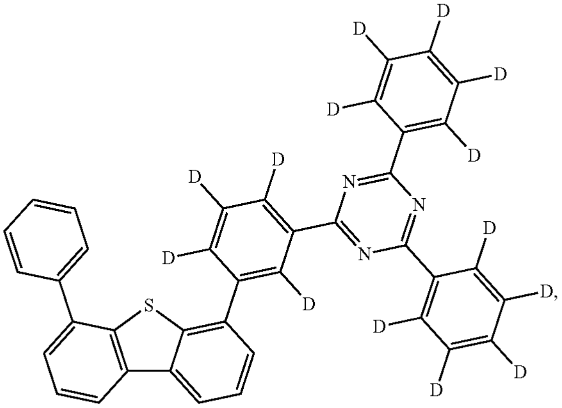
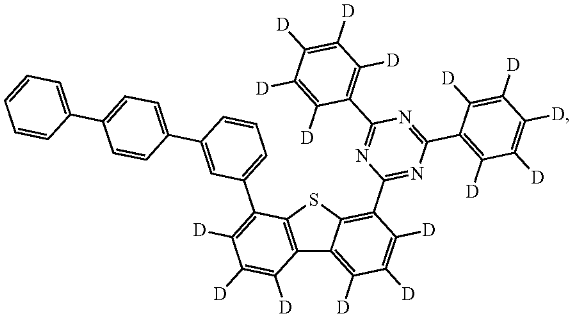
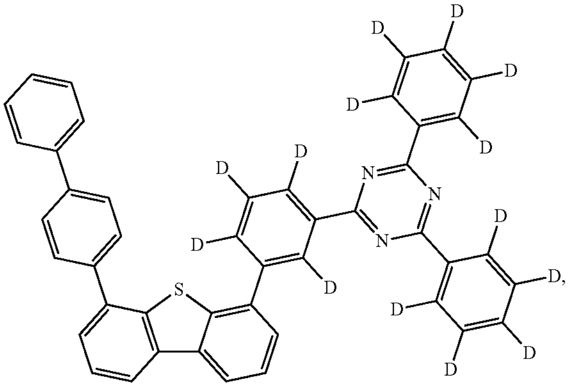
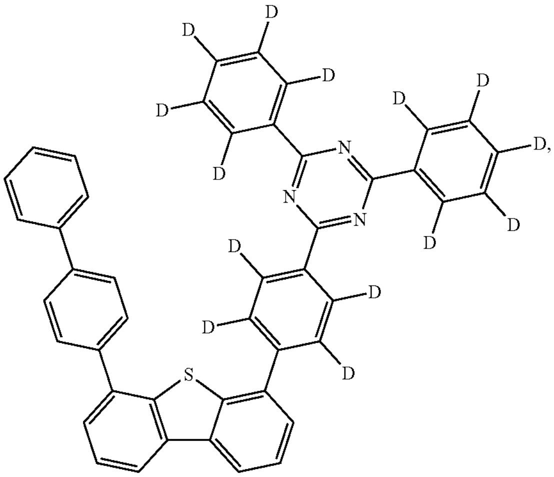
-continued
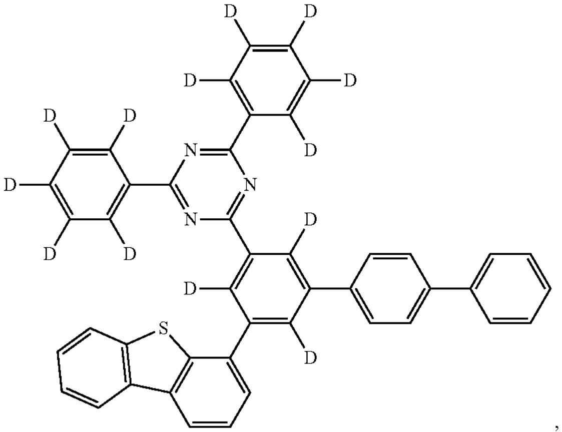
,
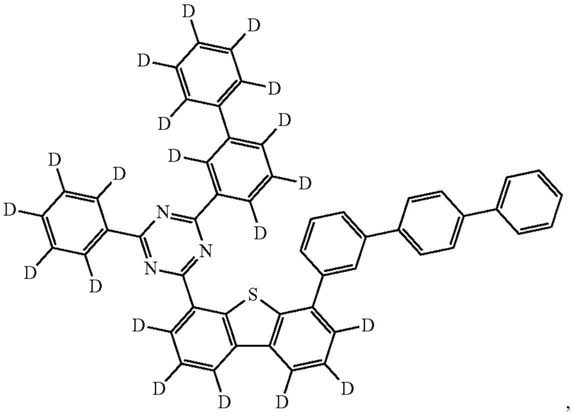
,
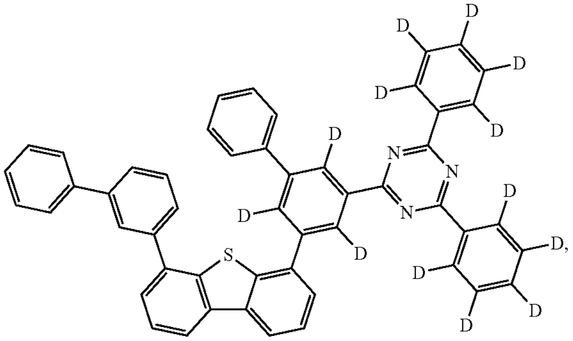
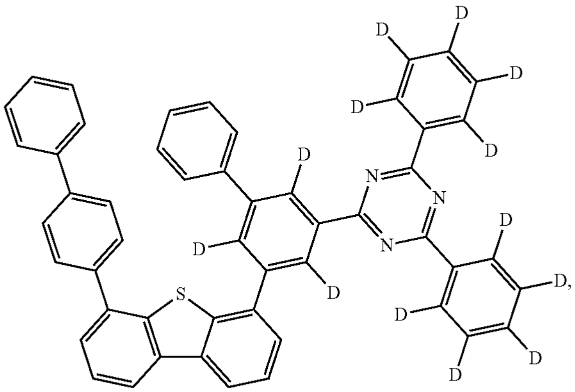

-continued
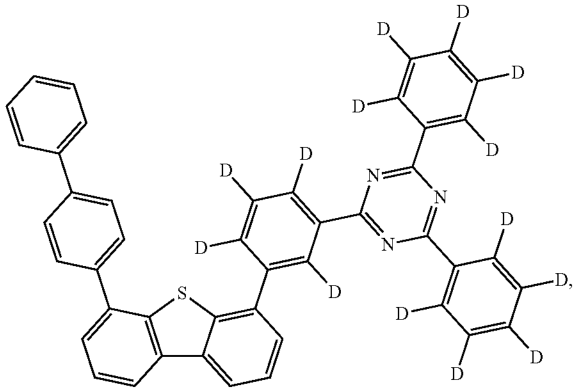
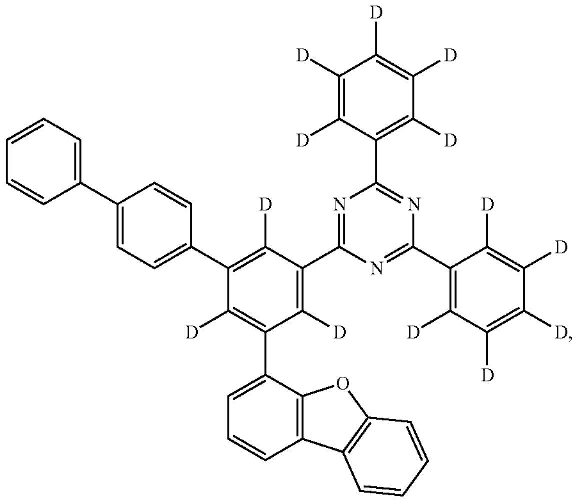
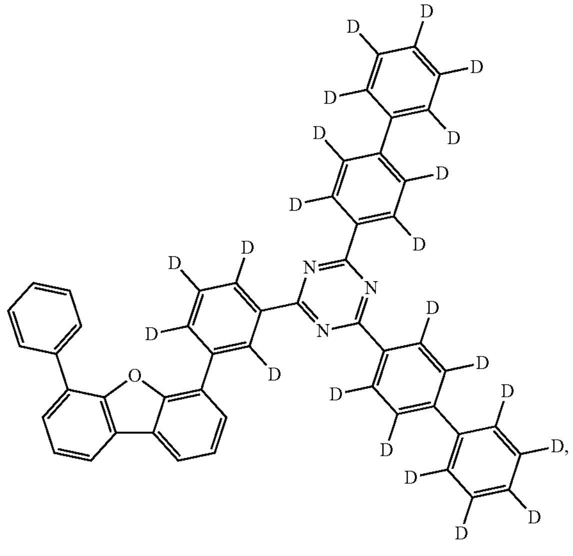
-continued
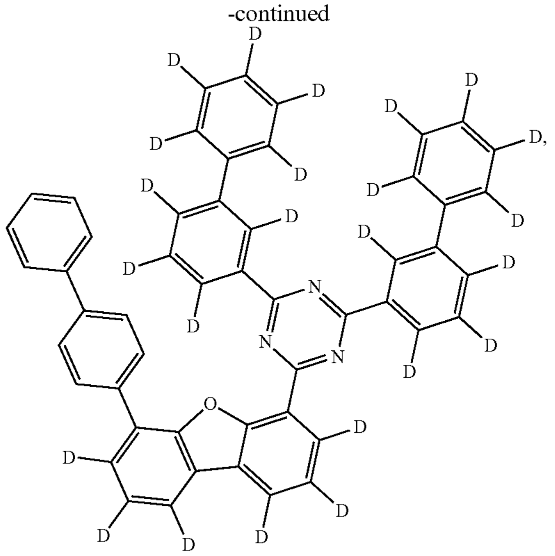
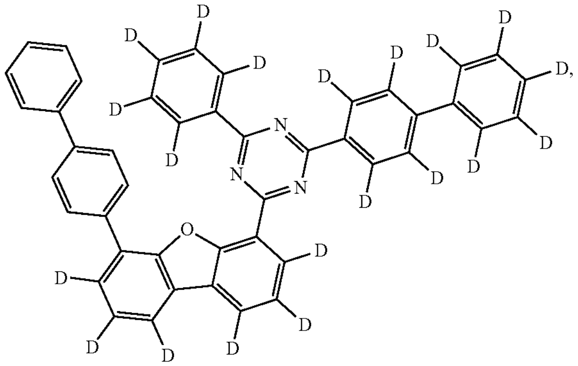
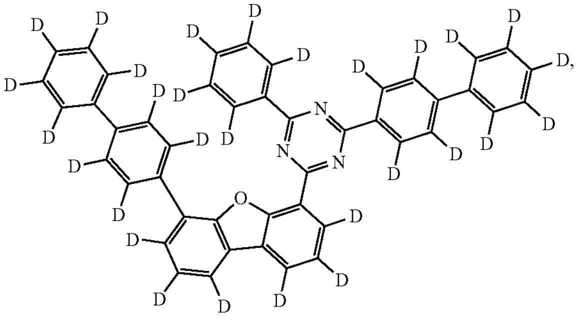

-continued
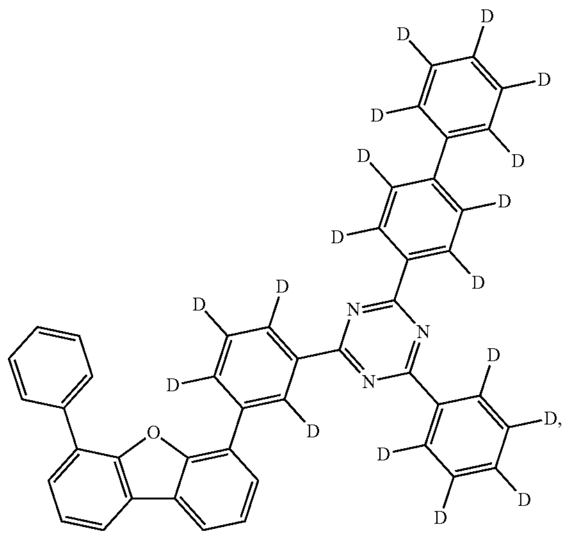
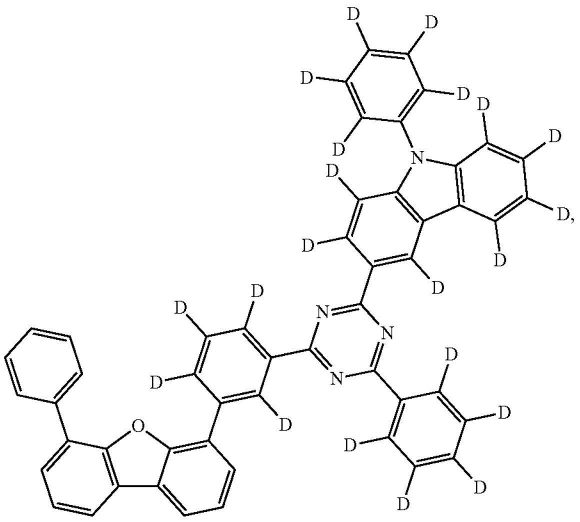
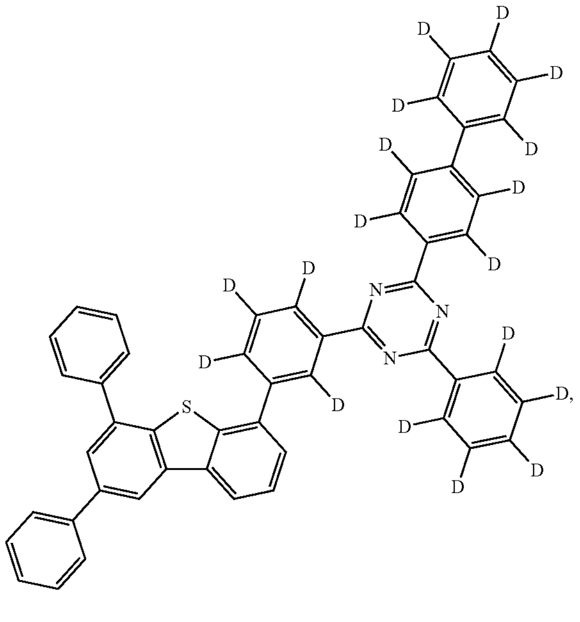
-continued
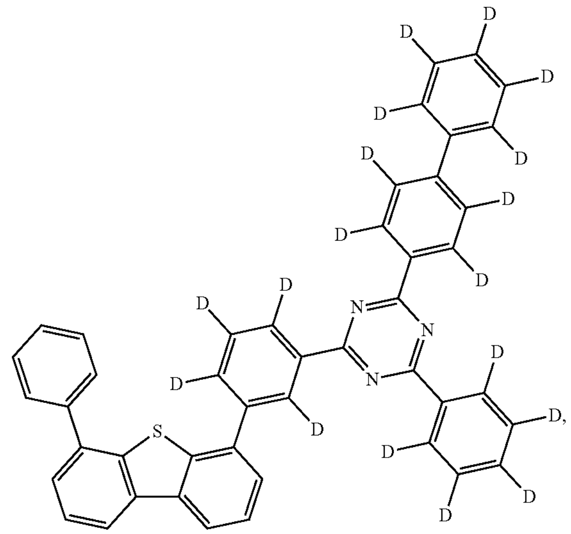
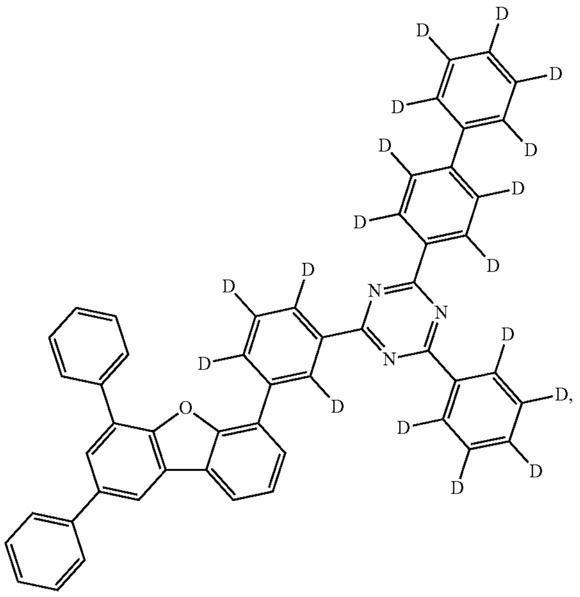
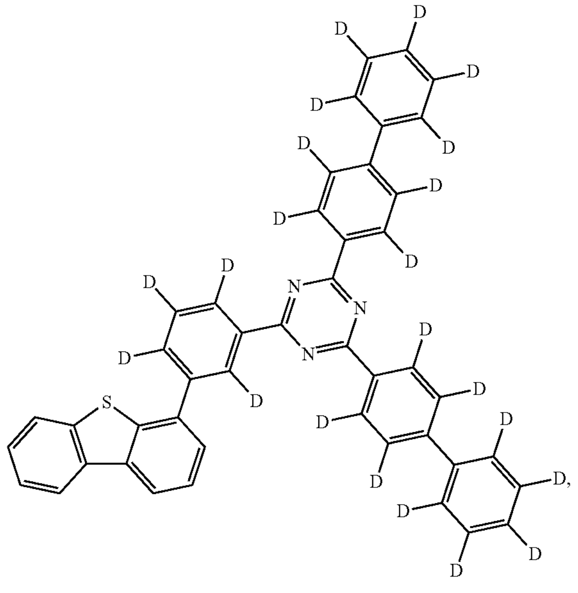

-continued
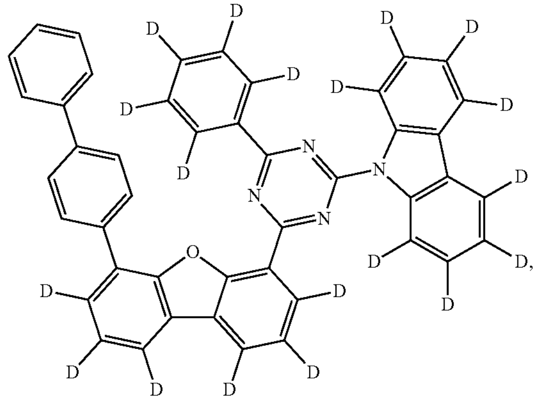
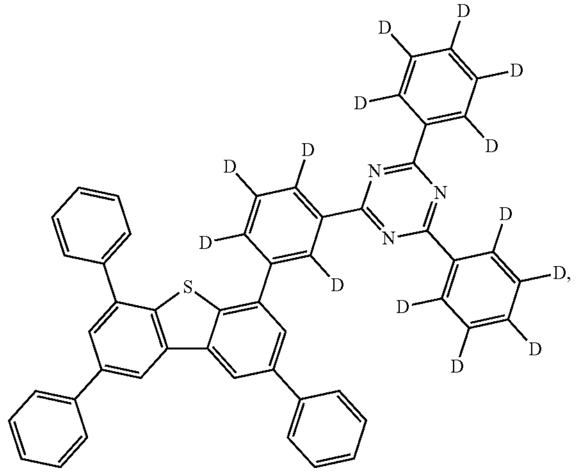
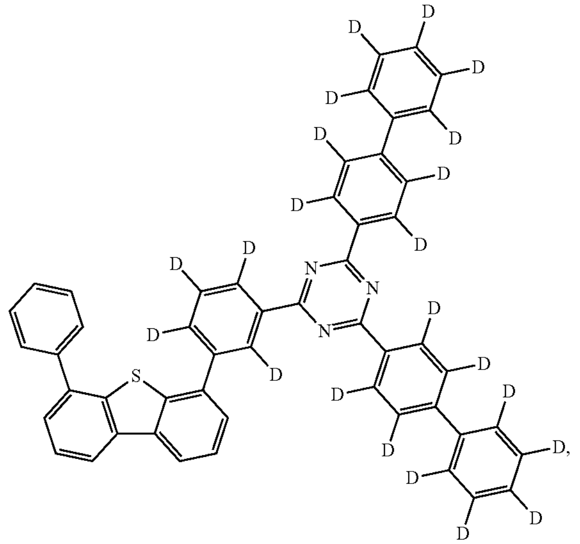
-continued
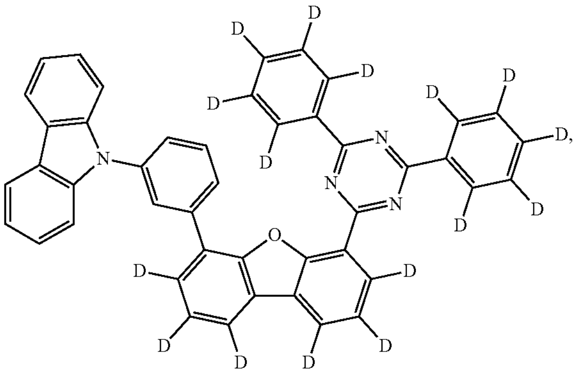
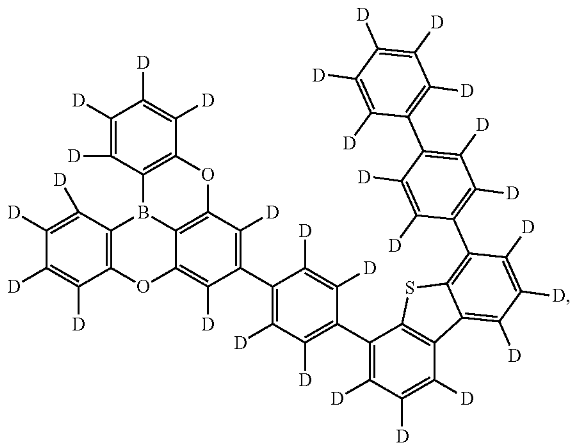
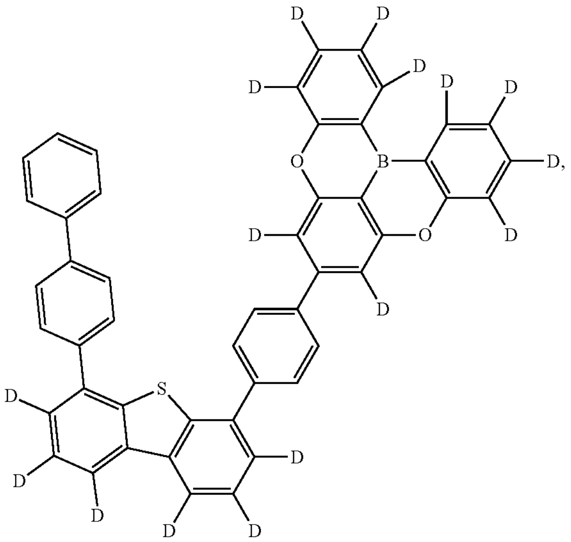

-continued
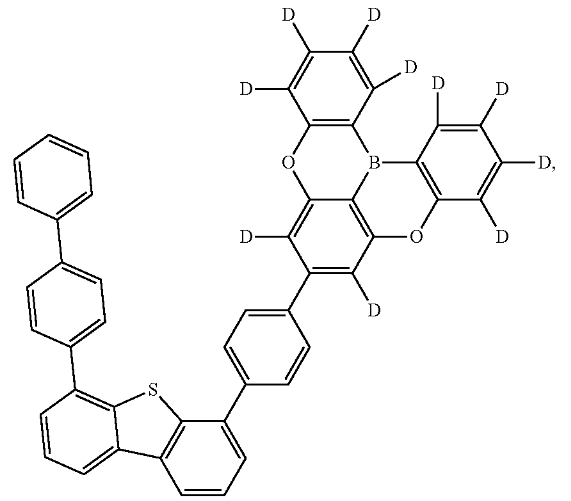
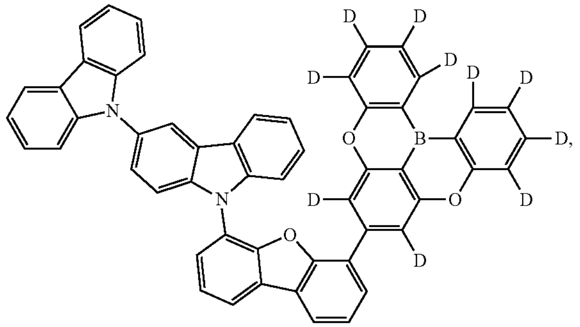
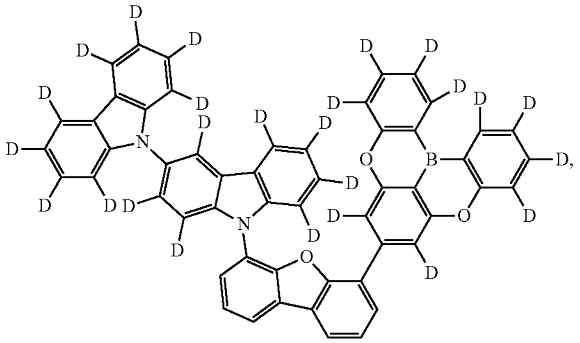
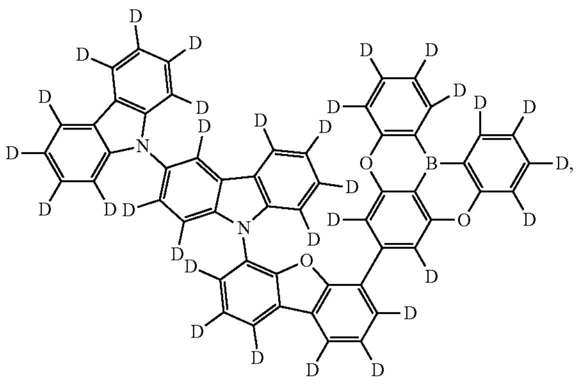
-continued
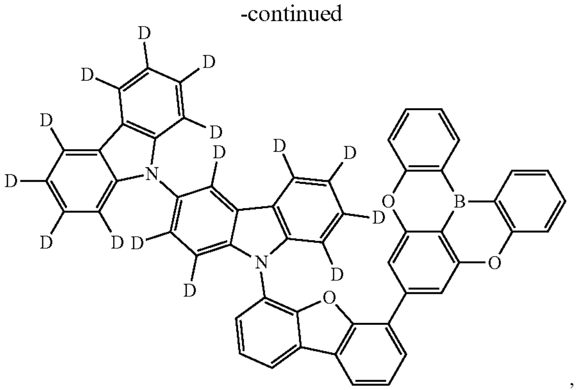
,
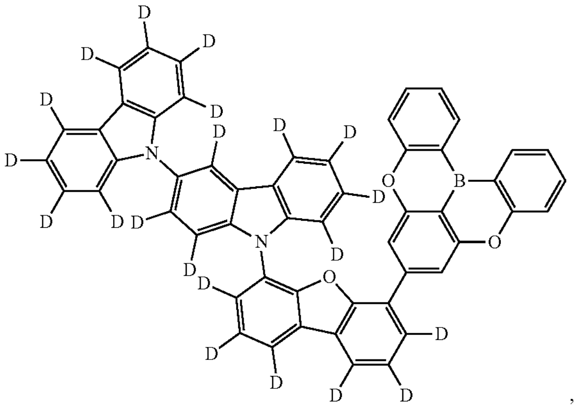
,
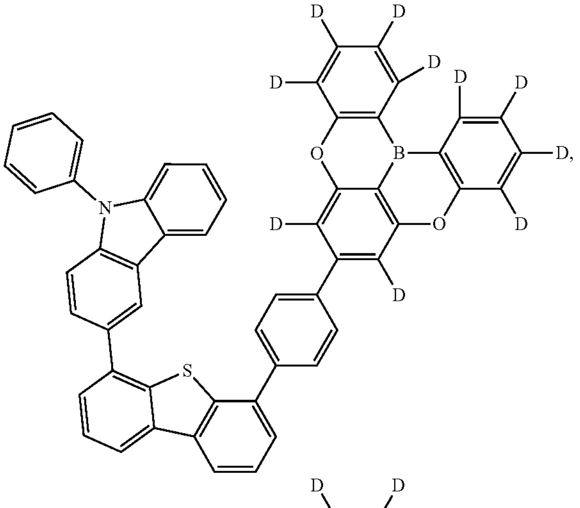
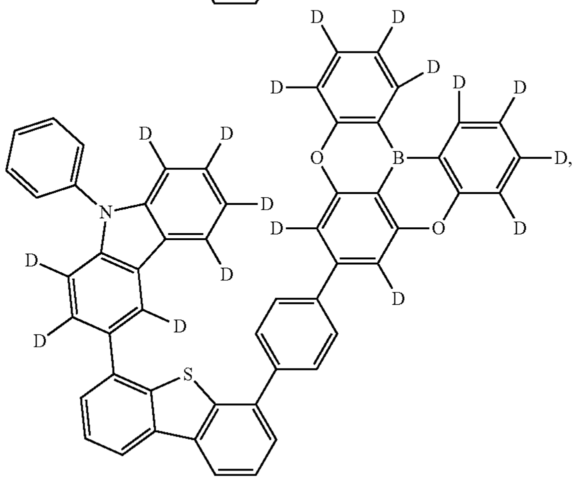

-continued
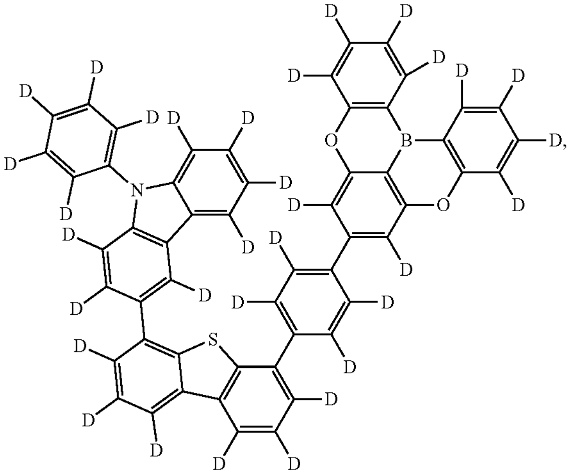
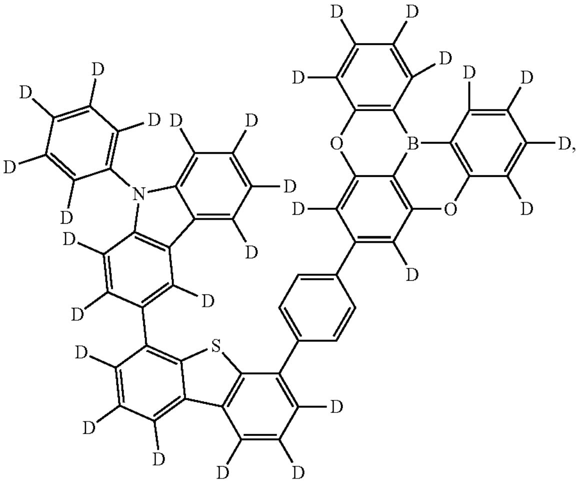
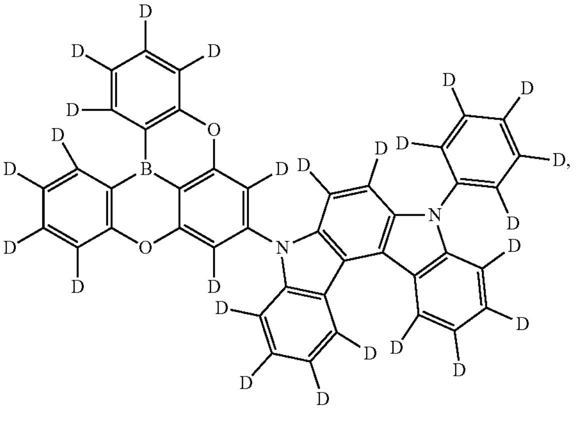
-continued
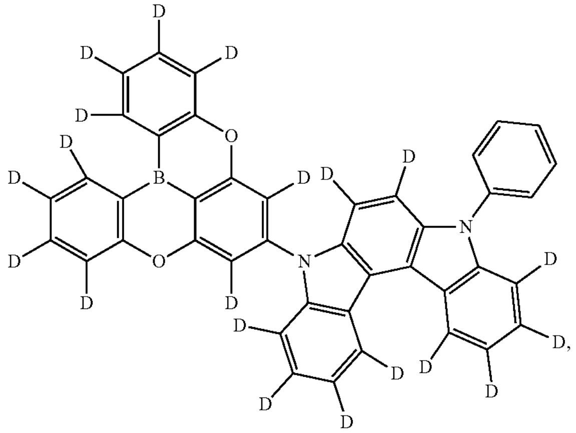
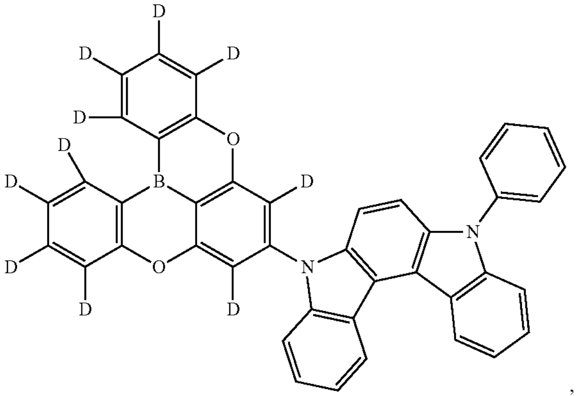
,
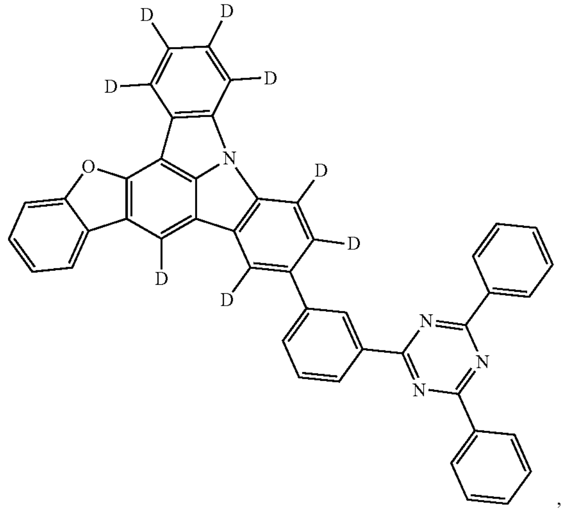
,
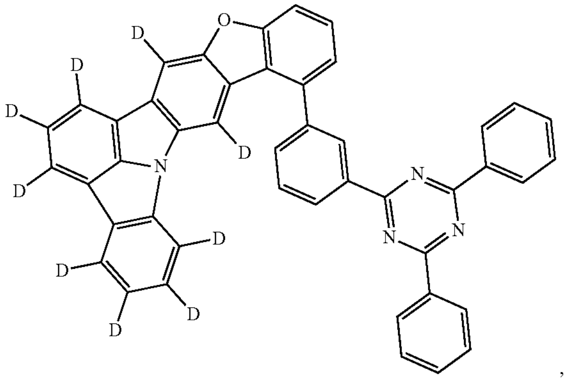
, -continued
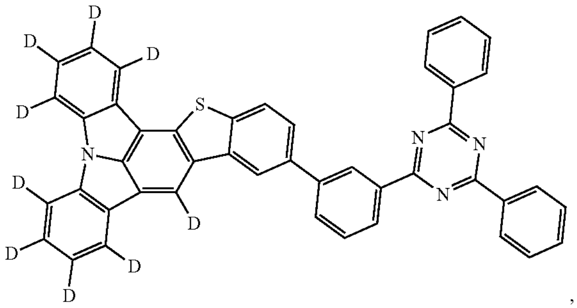
,
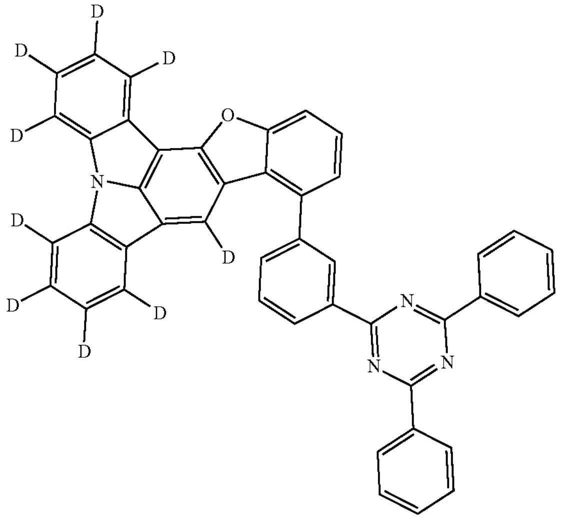
,
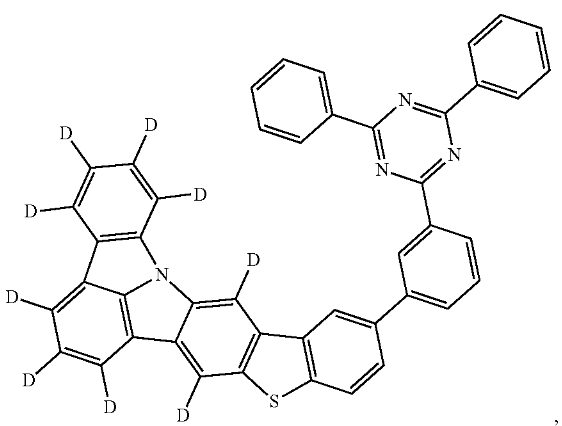
,
-continued
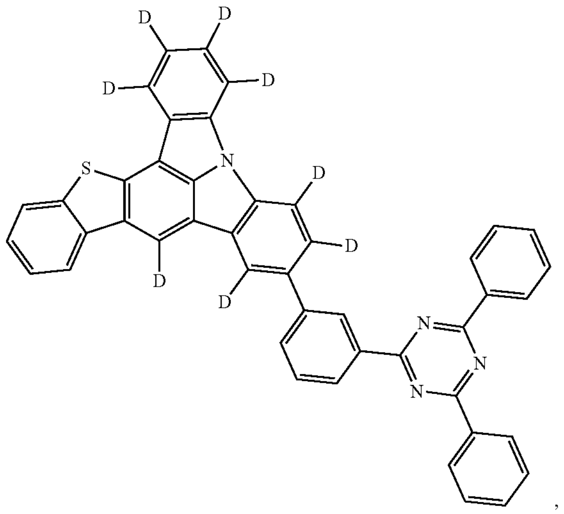
,
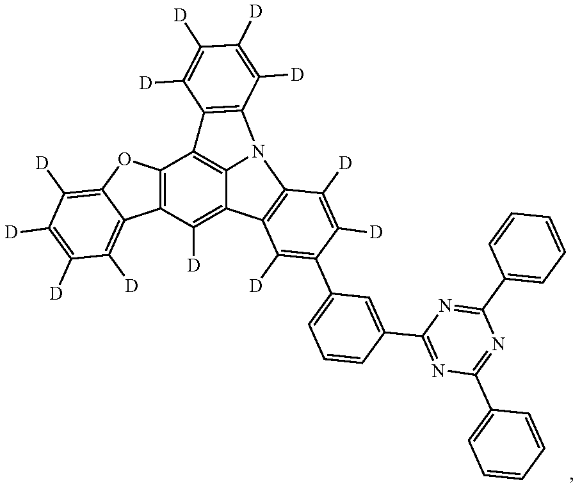
,
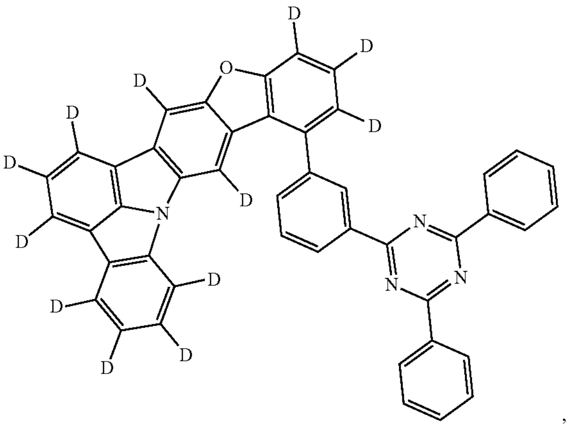
,

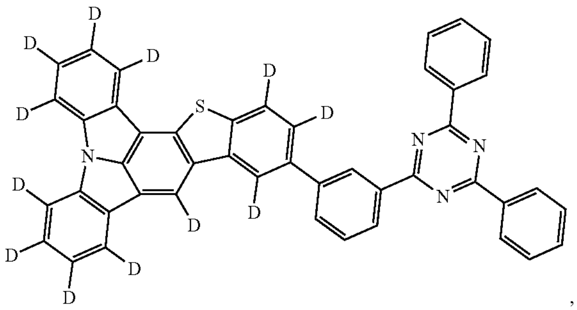
,
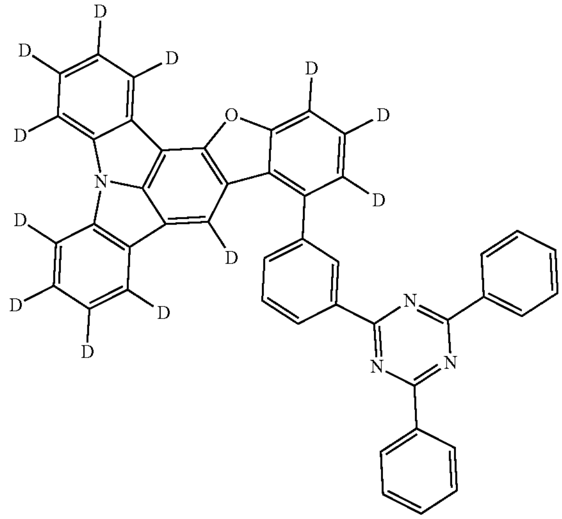
,
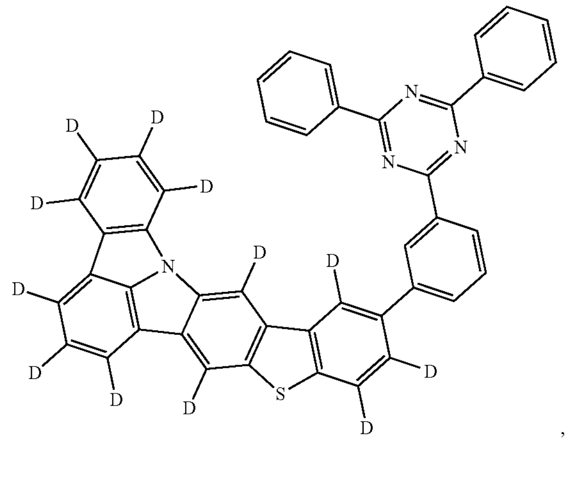
,
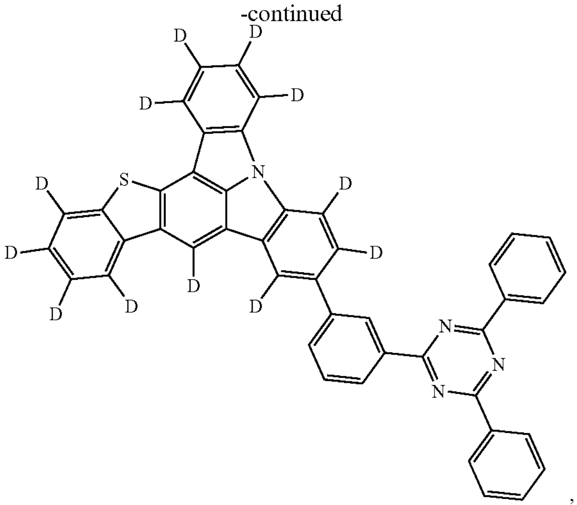
,
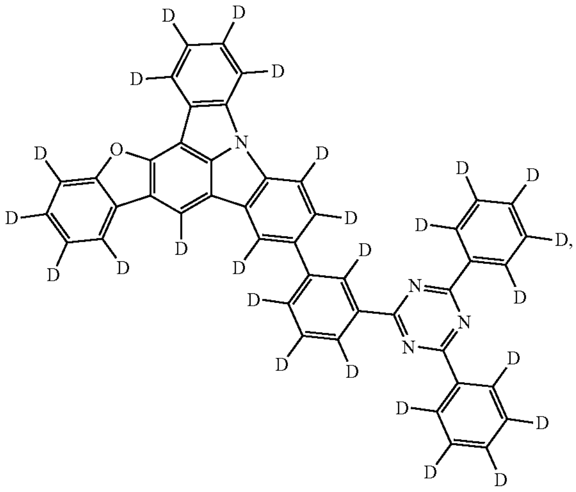
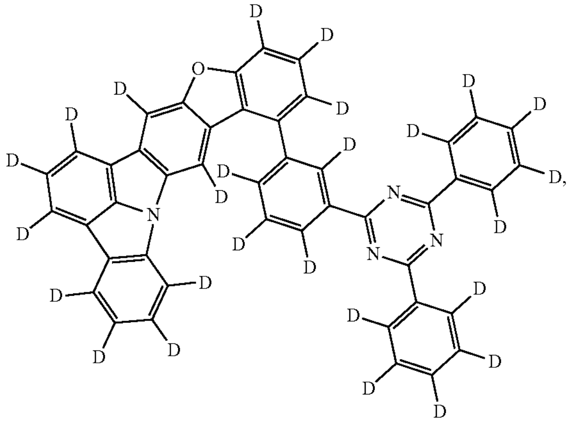
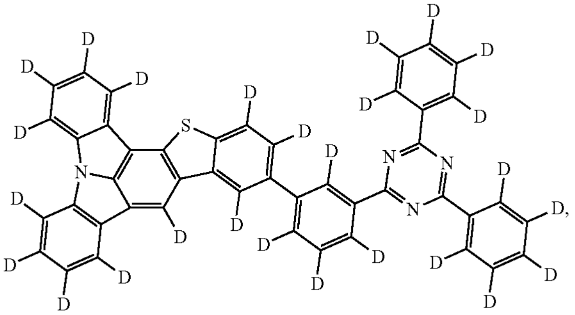

-continued
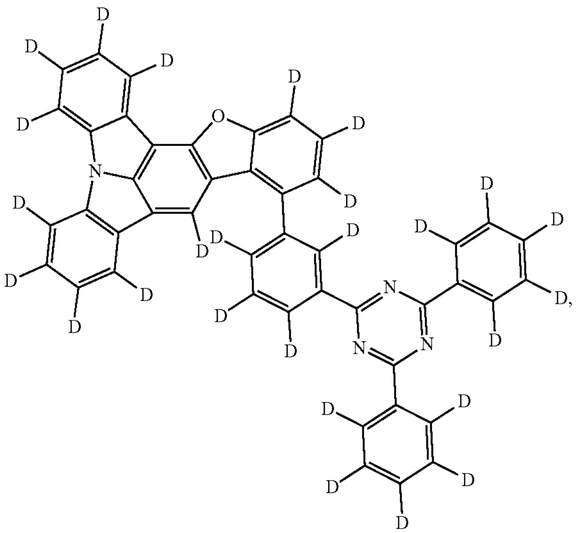
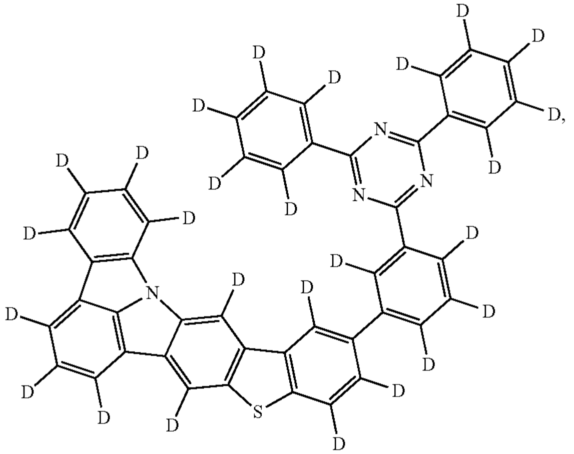
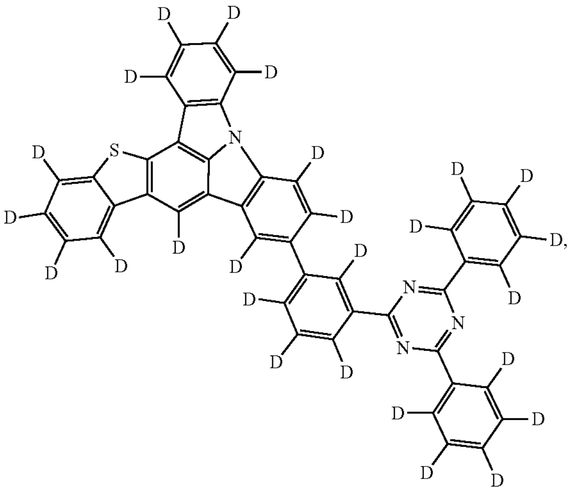
-continued
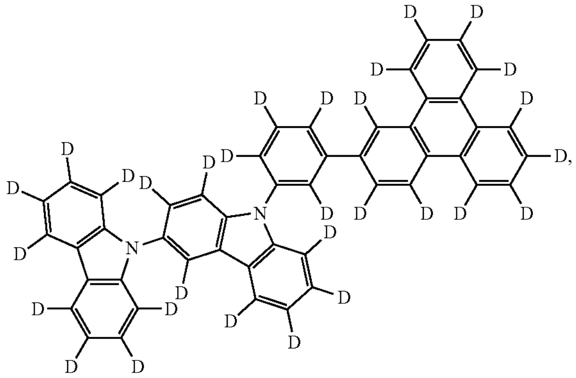
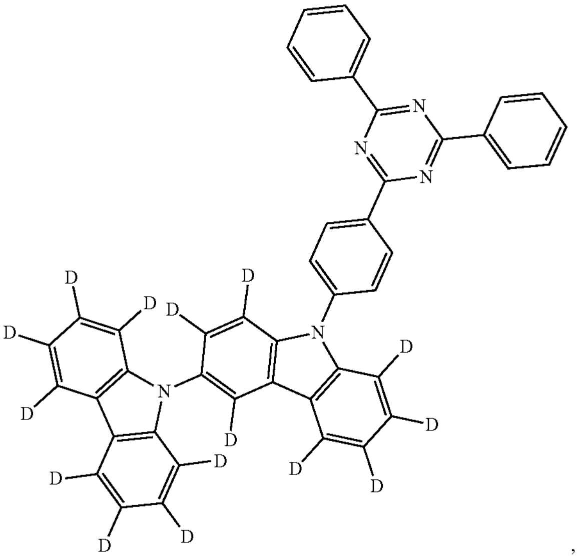
, -continued
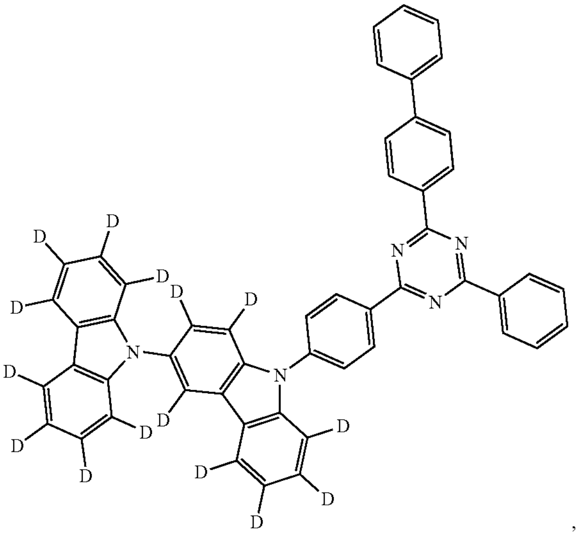
,
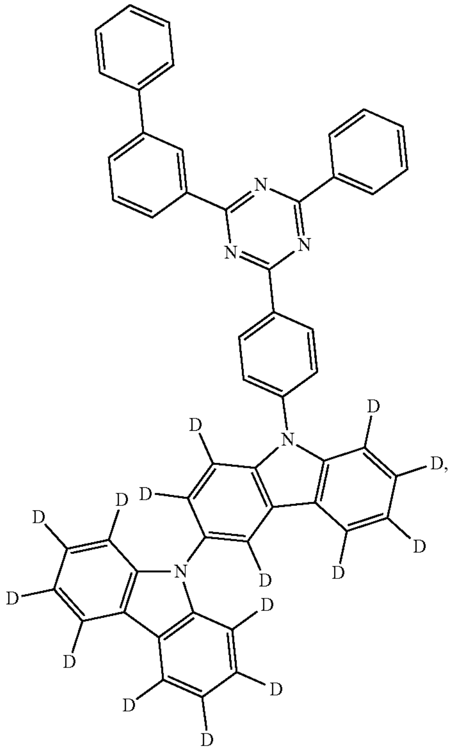
-continued
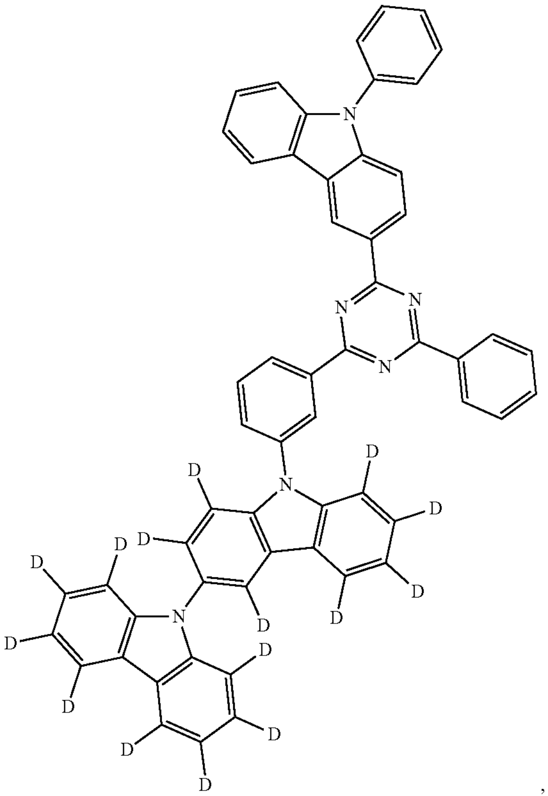
,
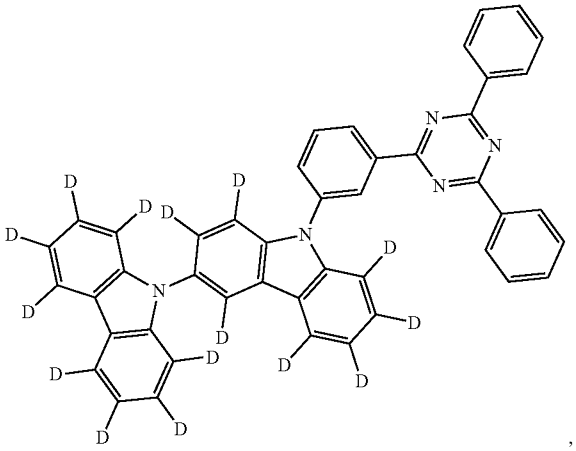
,

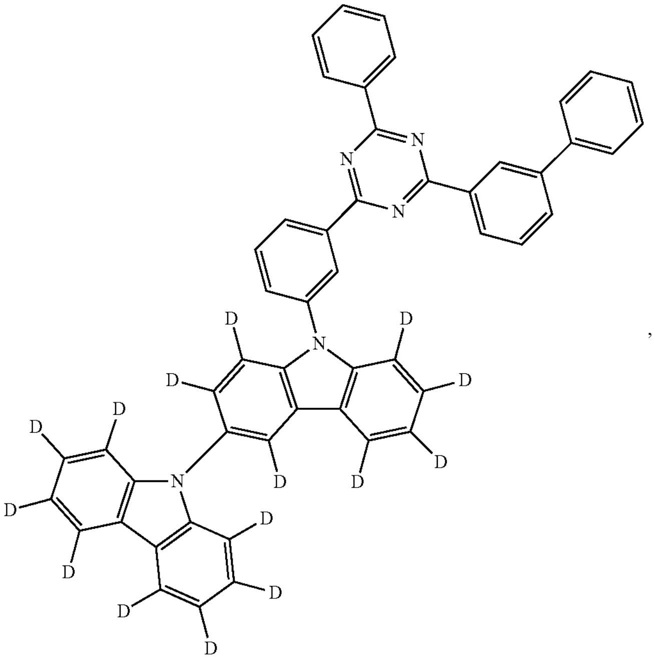
,
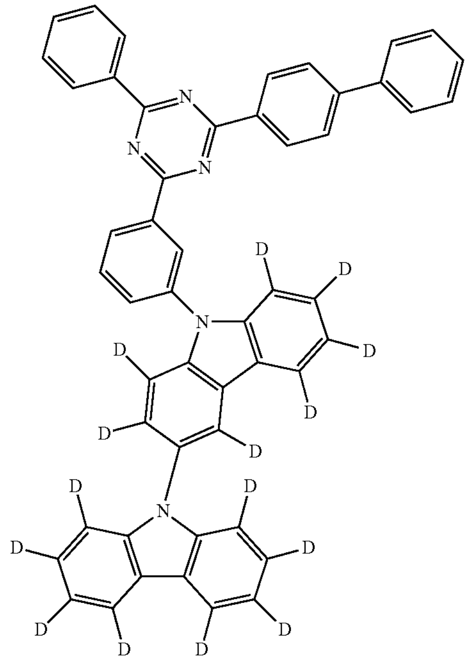
,
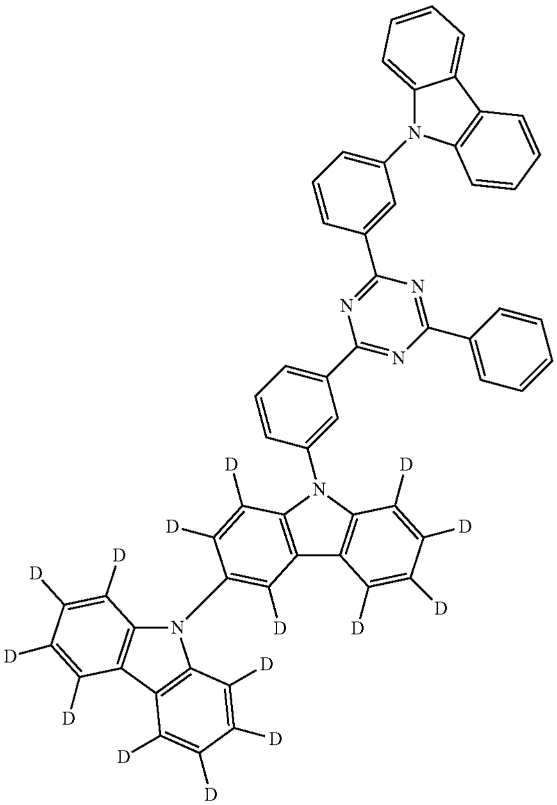
,
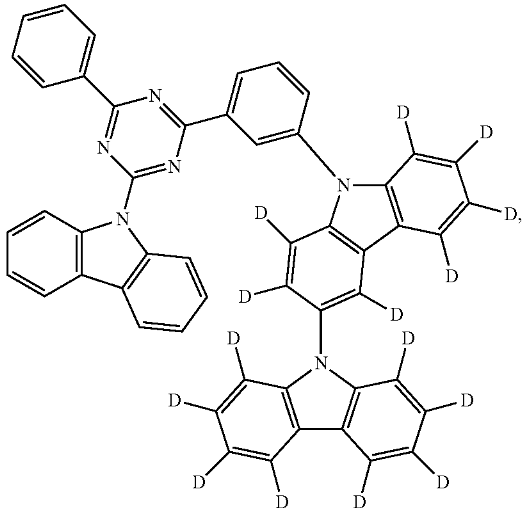
,

-continued
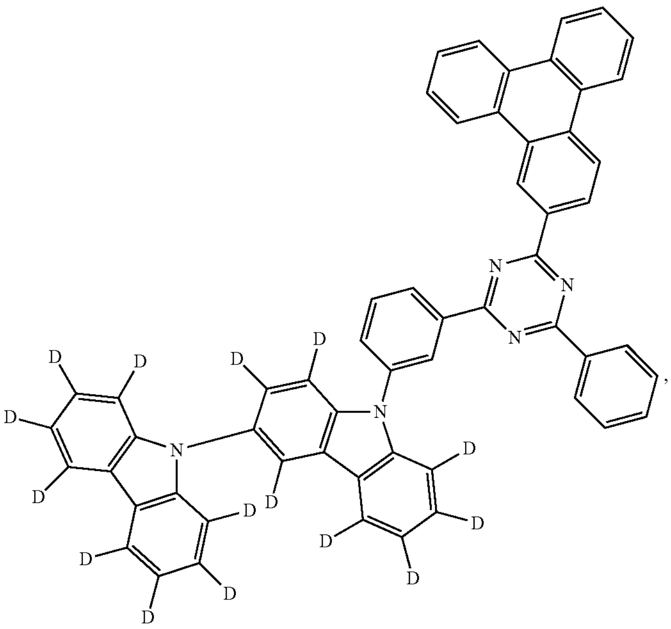
,
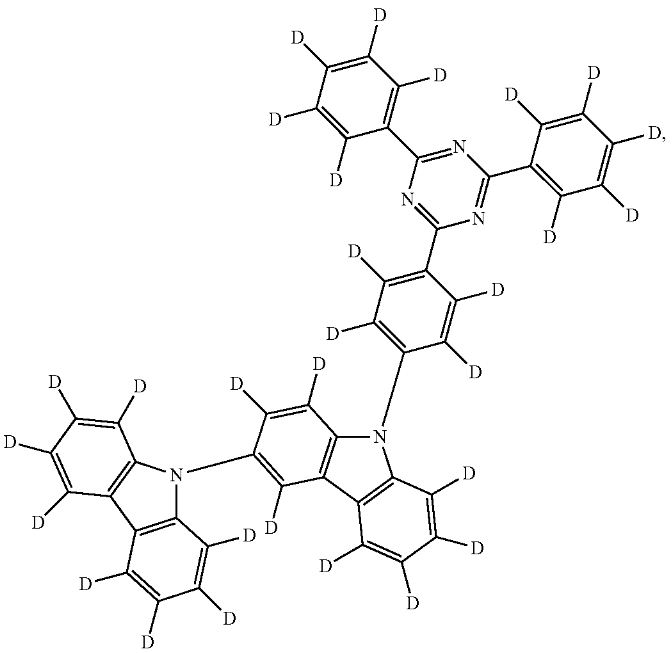

-continued
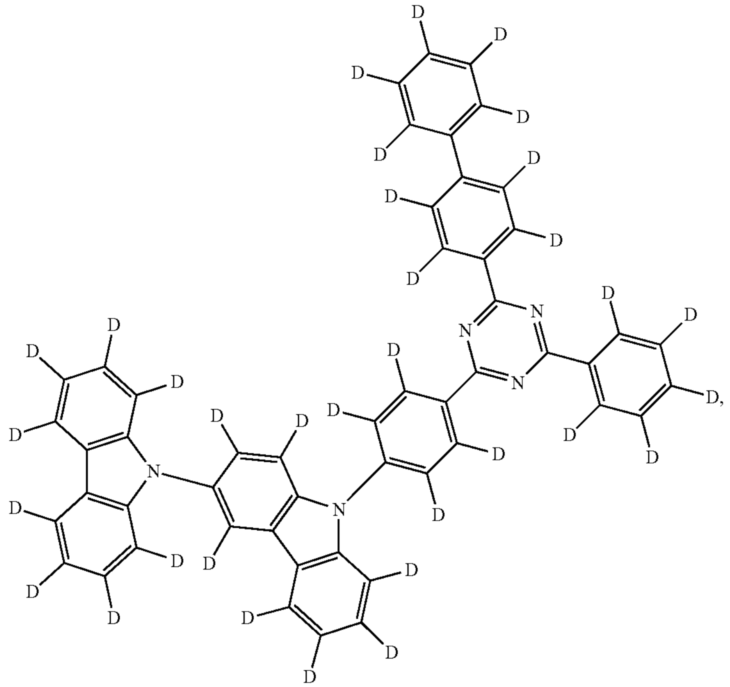
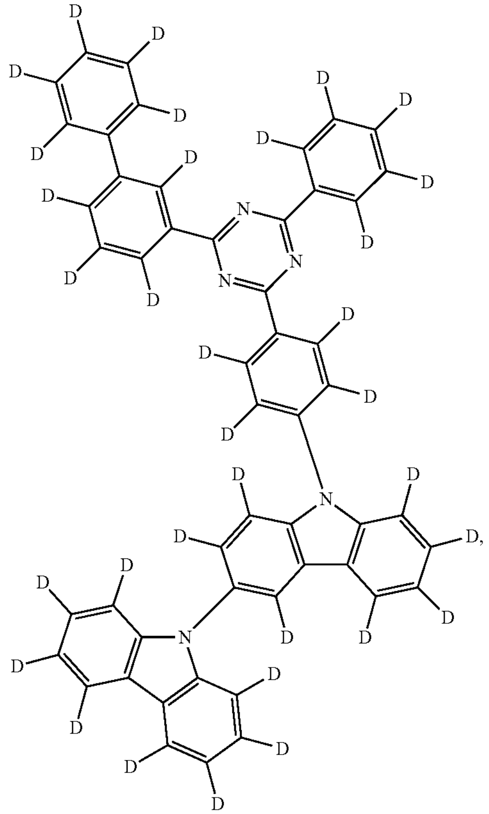
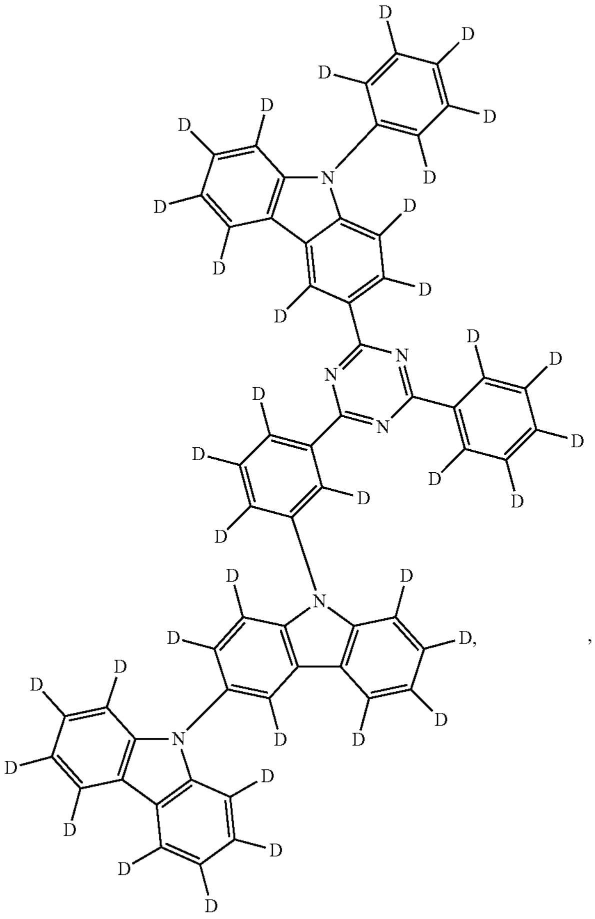
,

-continued
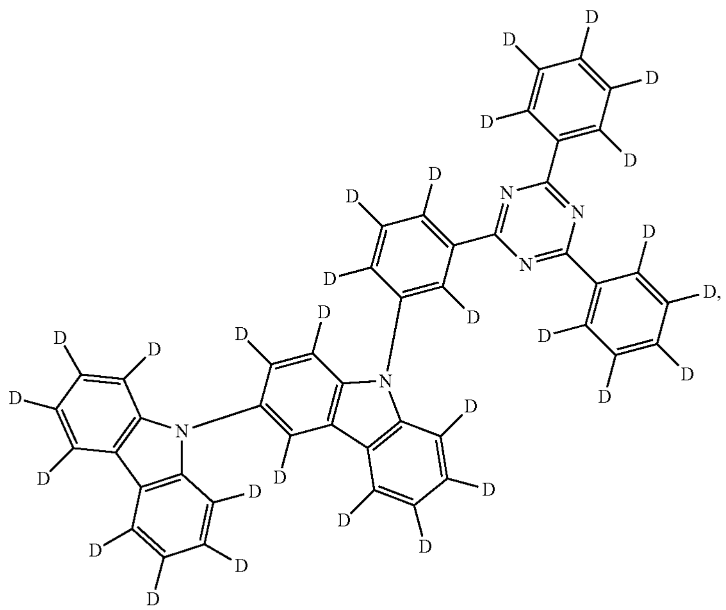
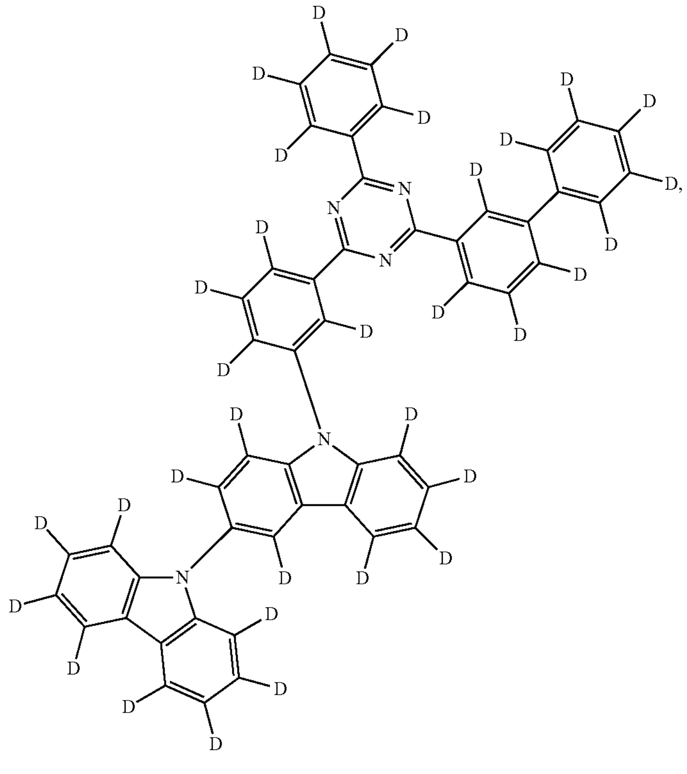

-continued
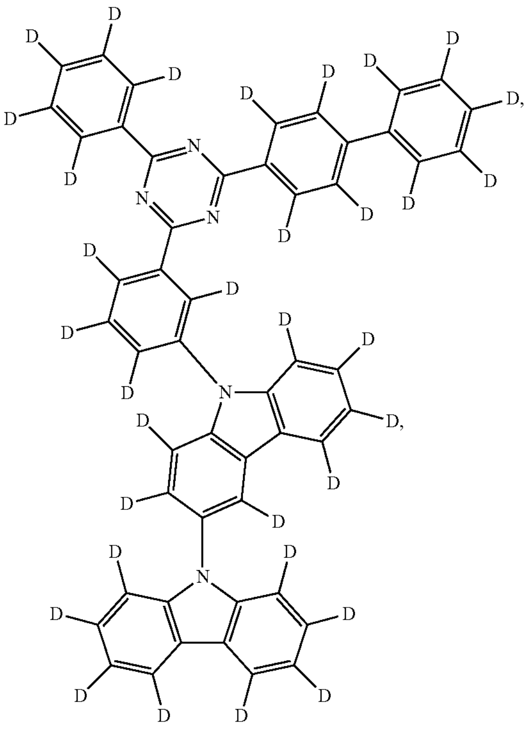
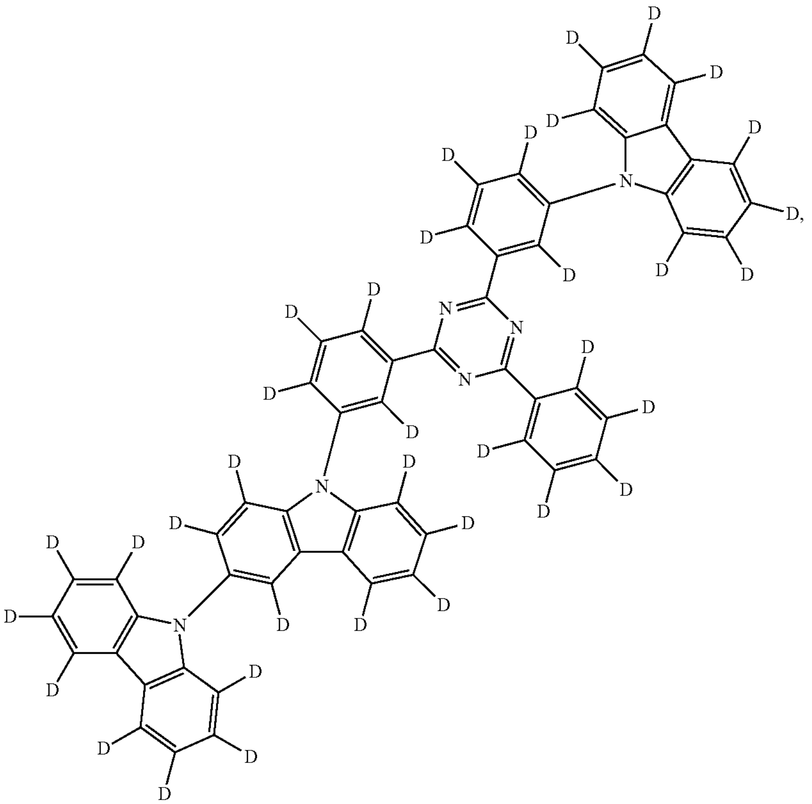

-continued
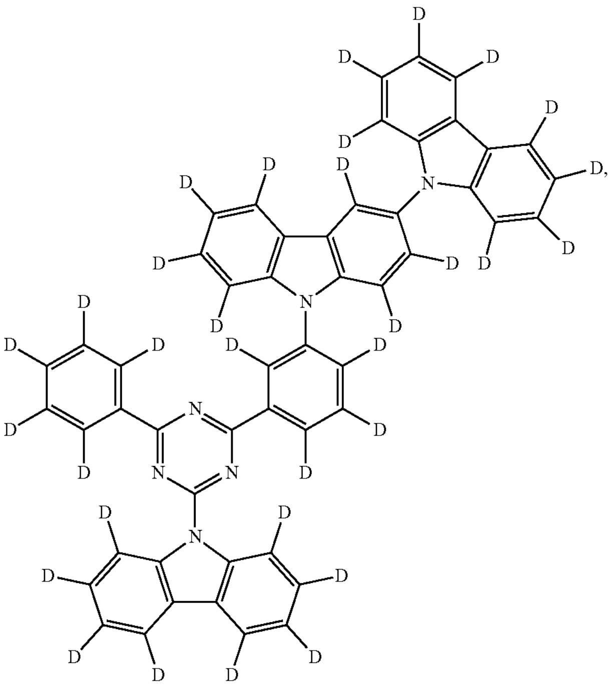
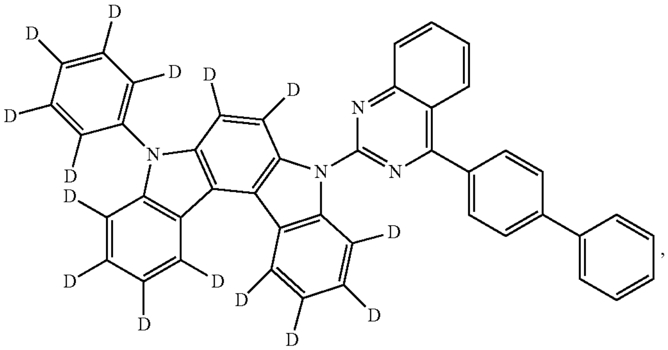
,
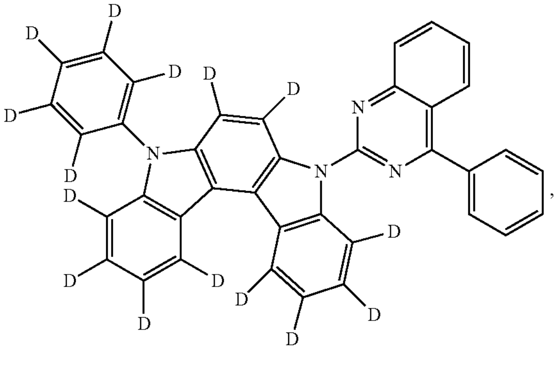
,
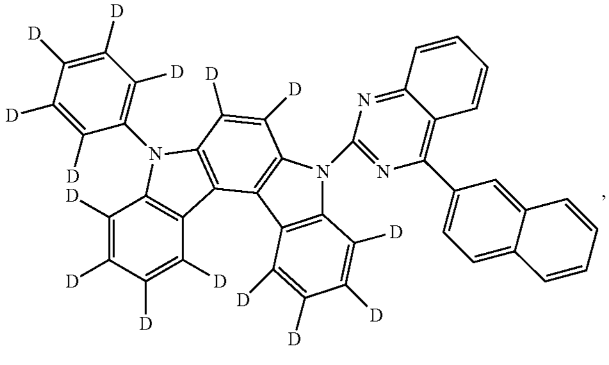
,

-continued
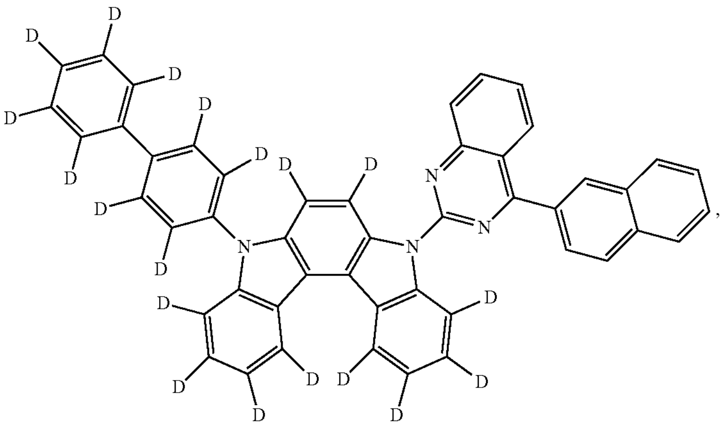
,
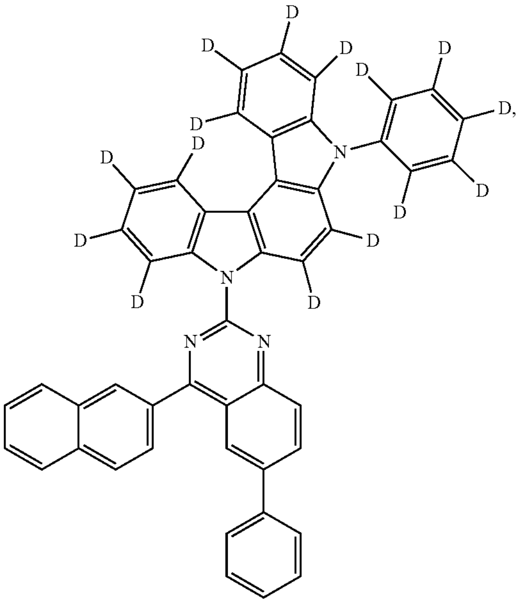
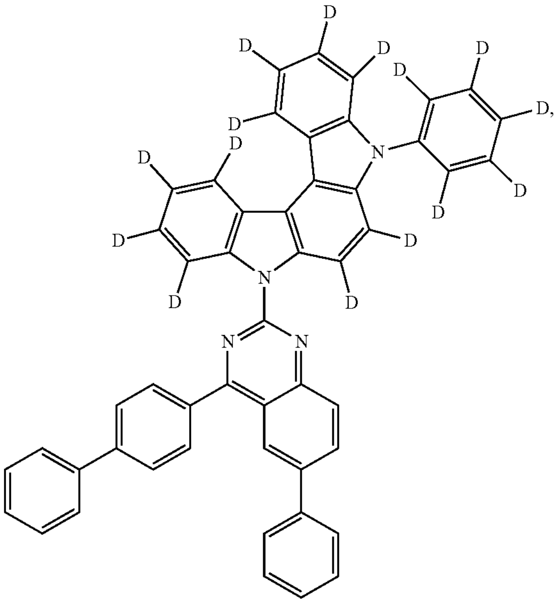
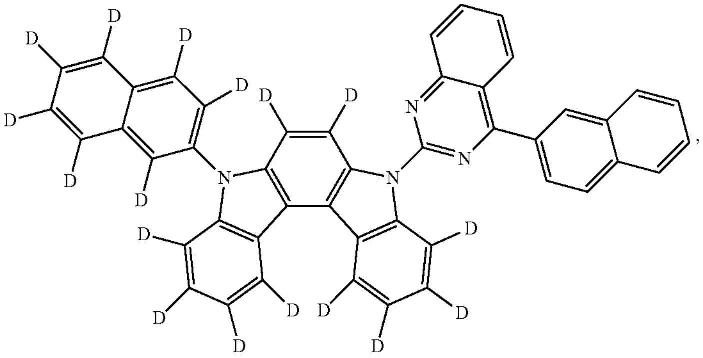
,

-continued
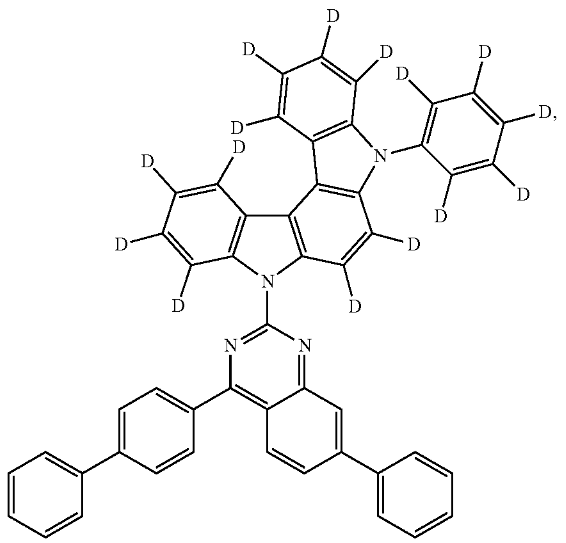
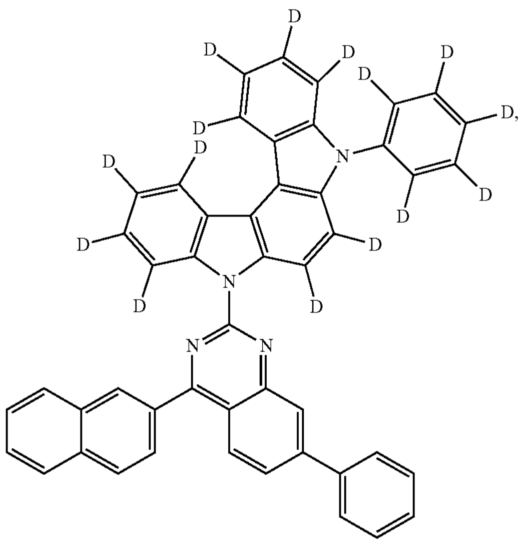
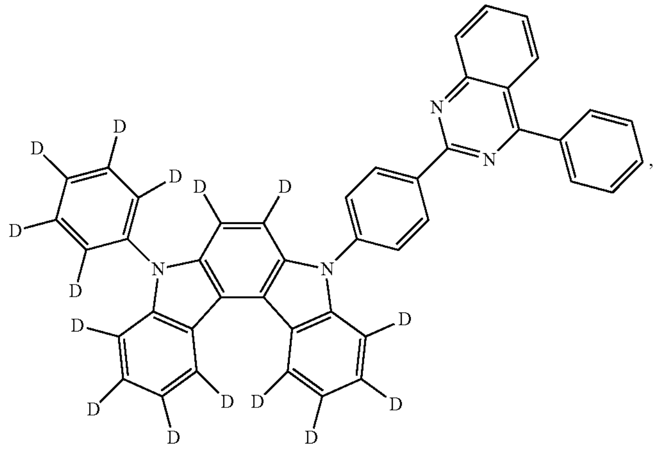
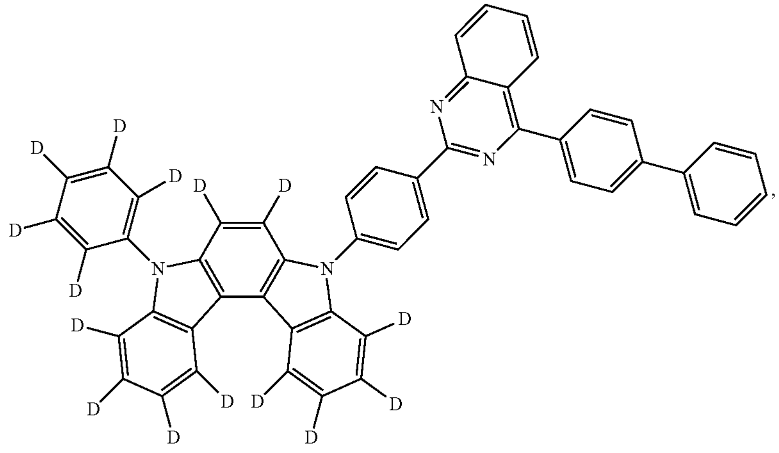

-continued
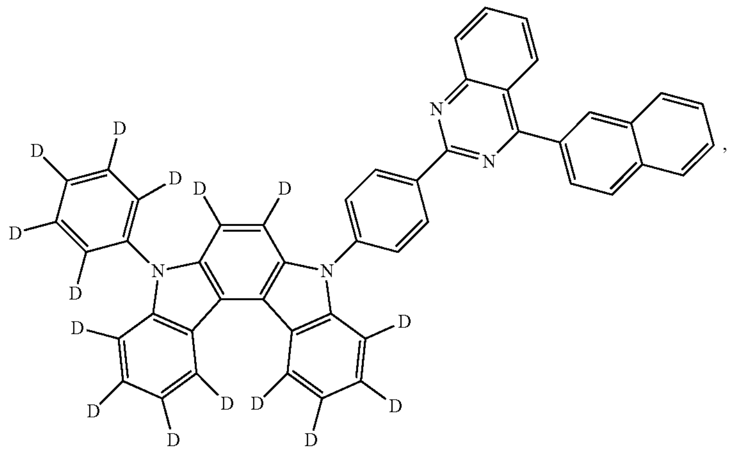
,
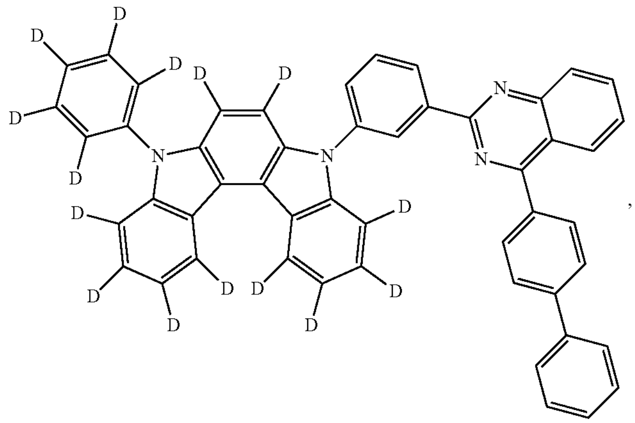
,
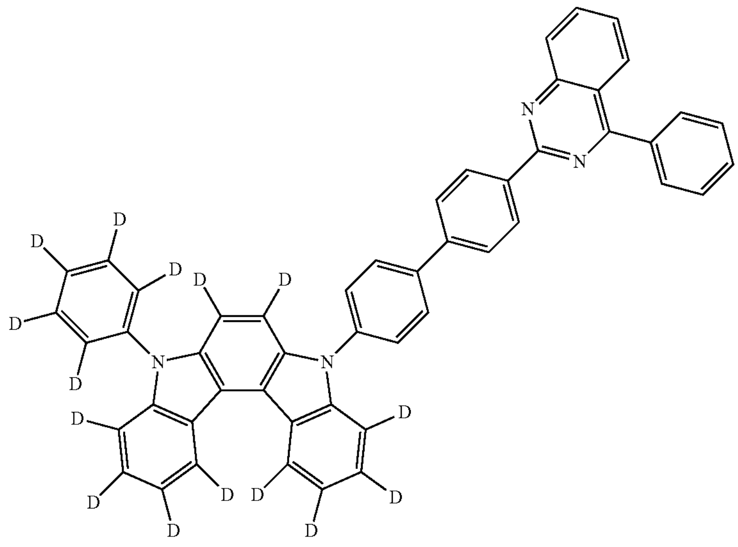
,

-continued
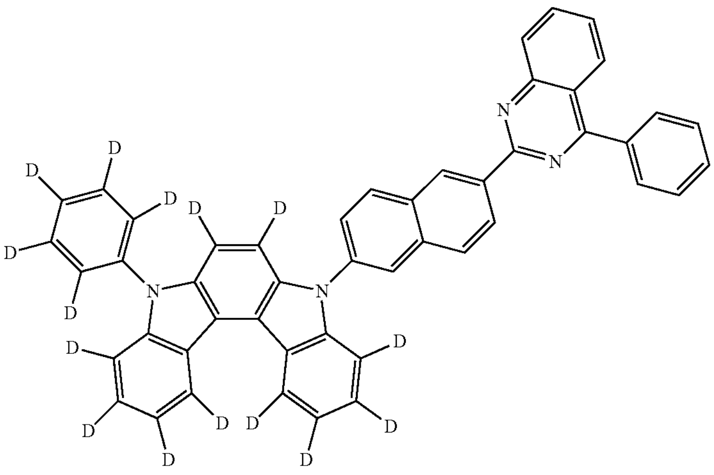
,
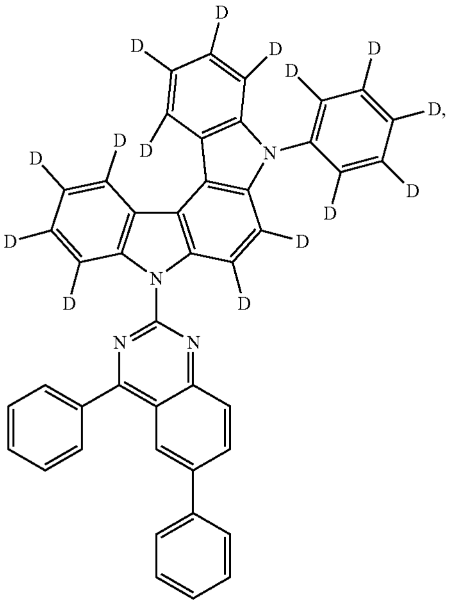
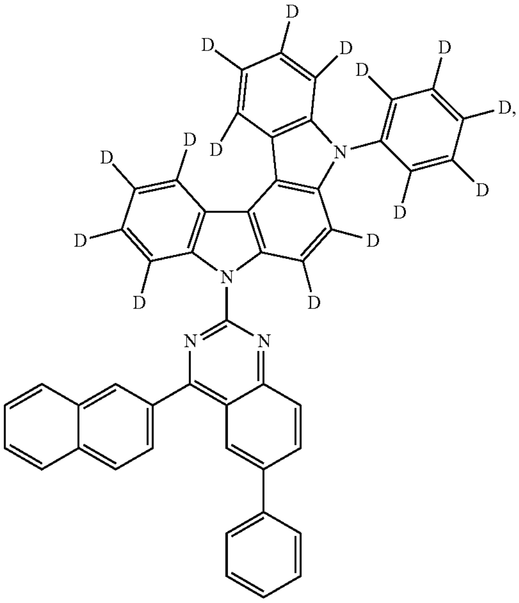
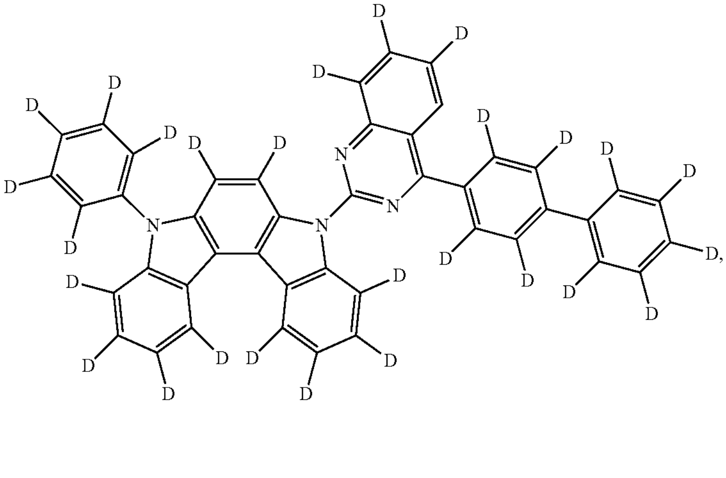

-continued
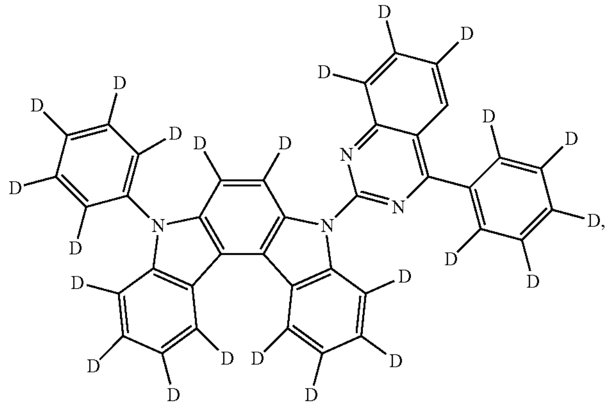
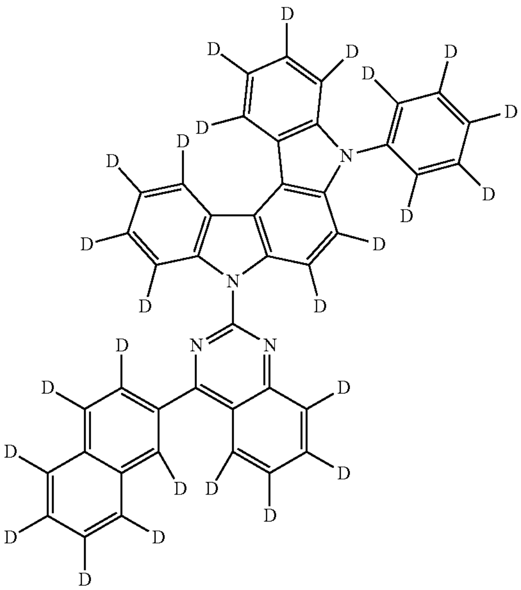
,
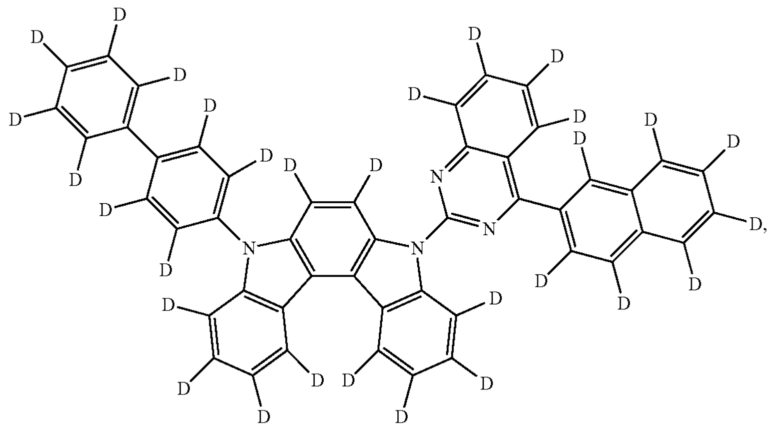
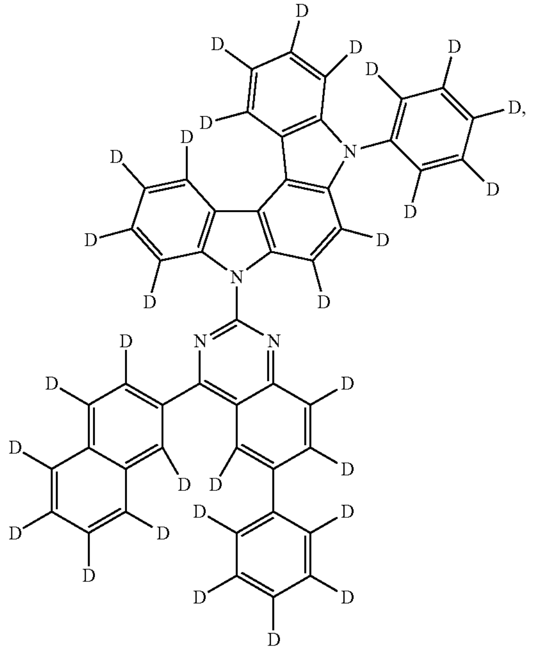
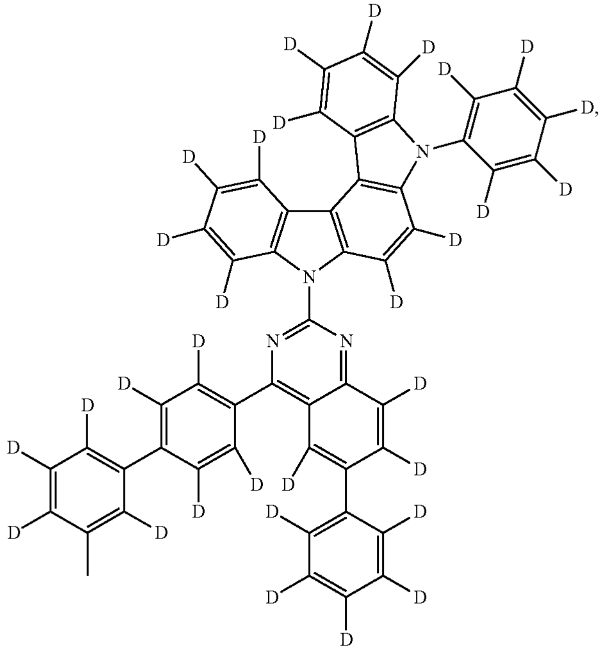

-continued
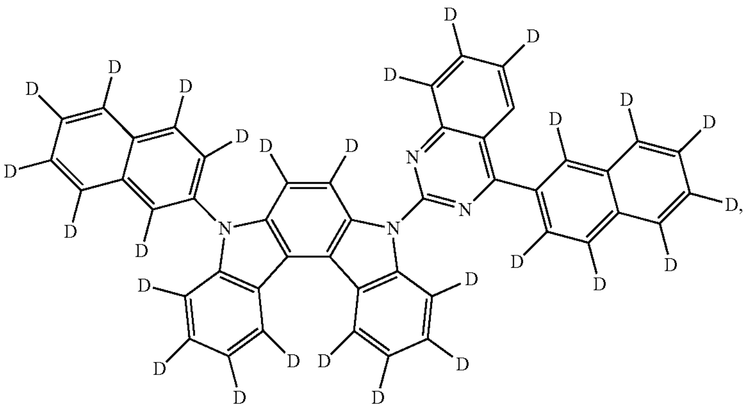
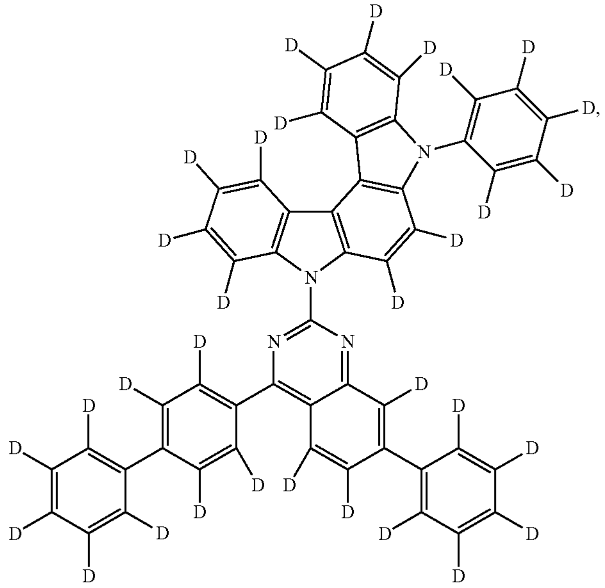
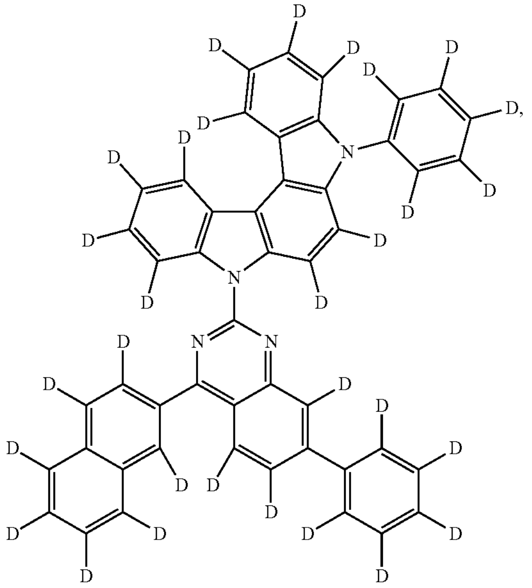
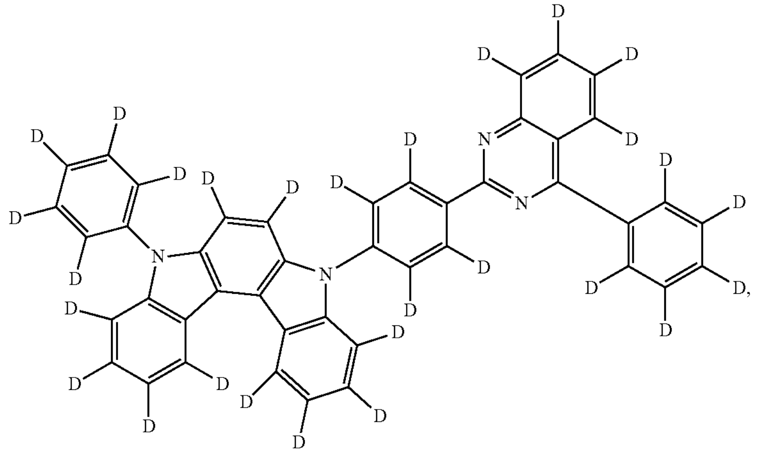

-continued
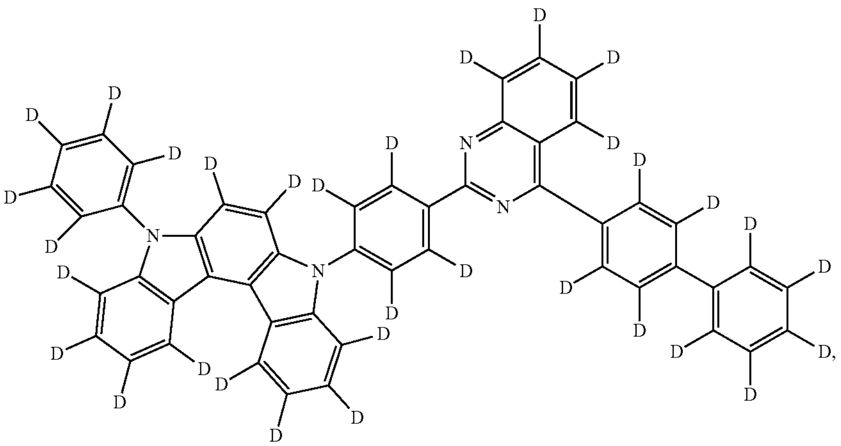
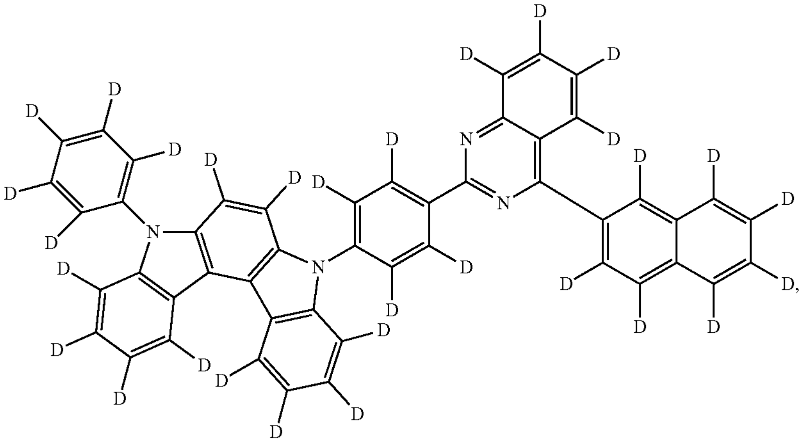
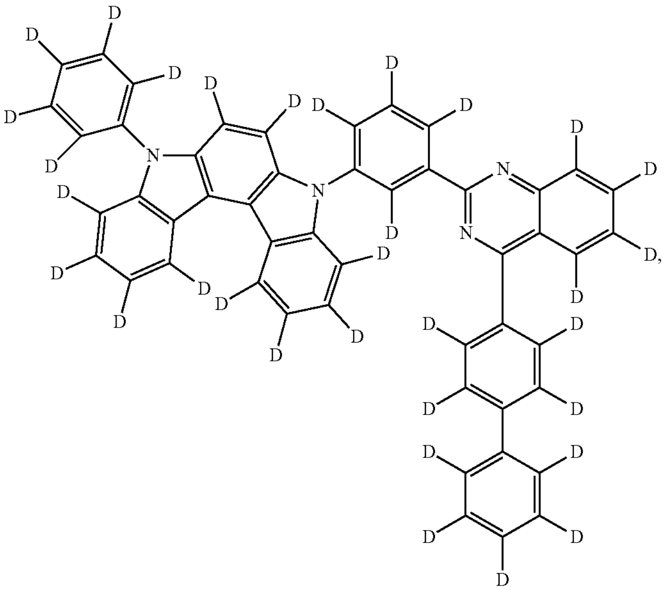

-continued
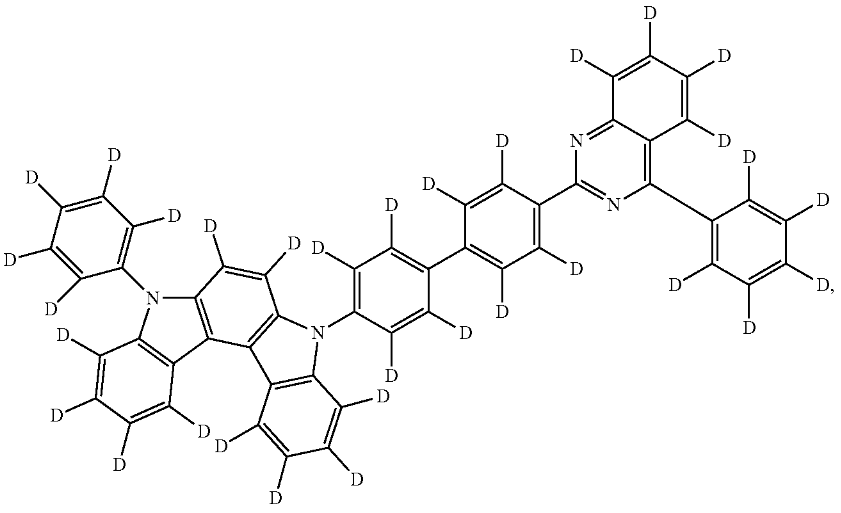
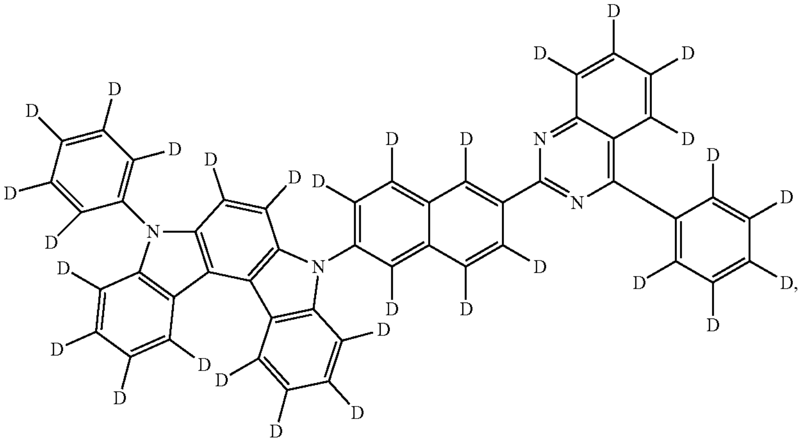
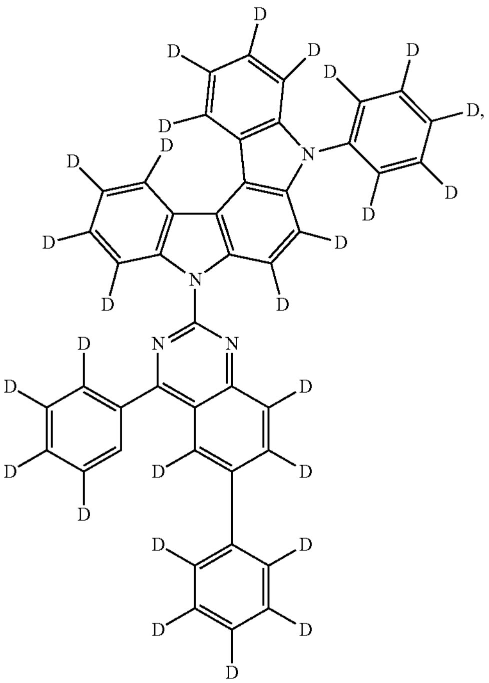
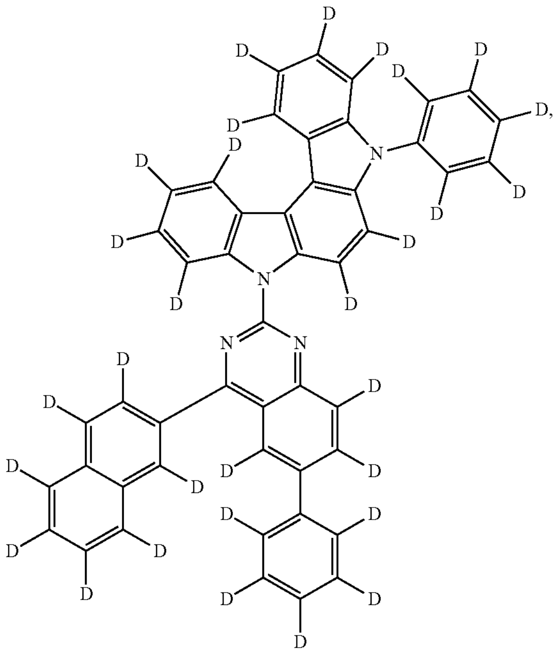

-continued
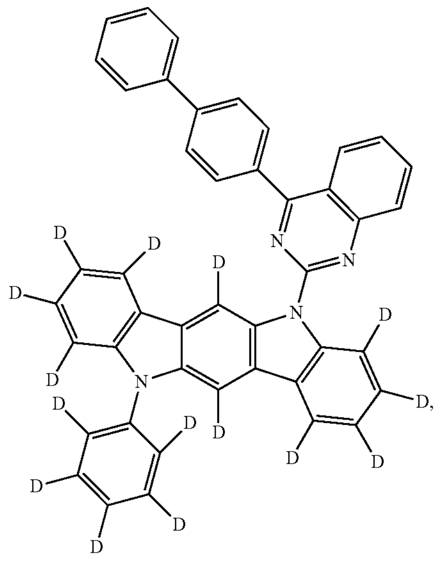,
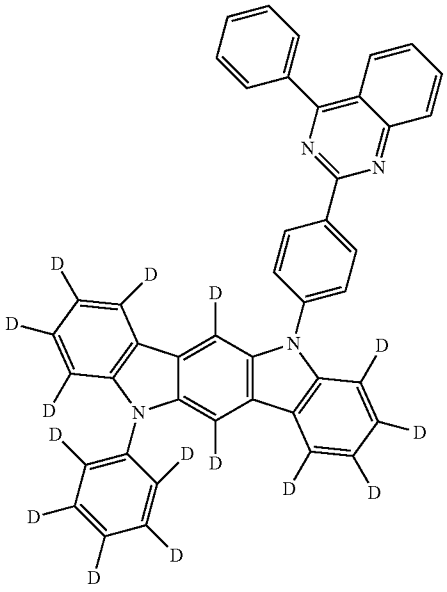,
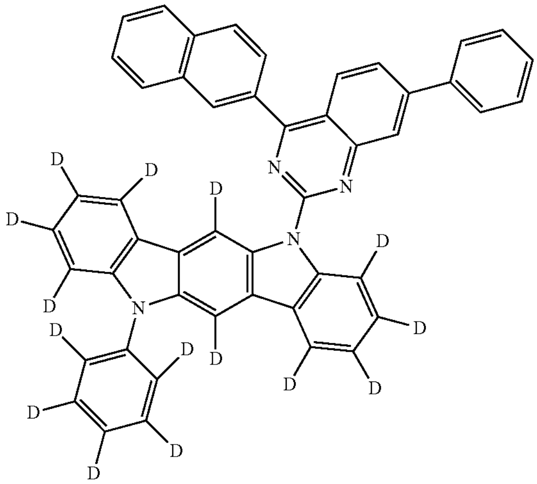,
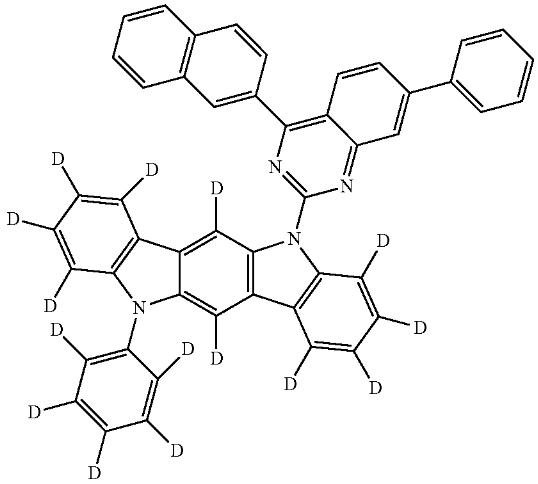,
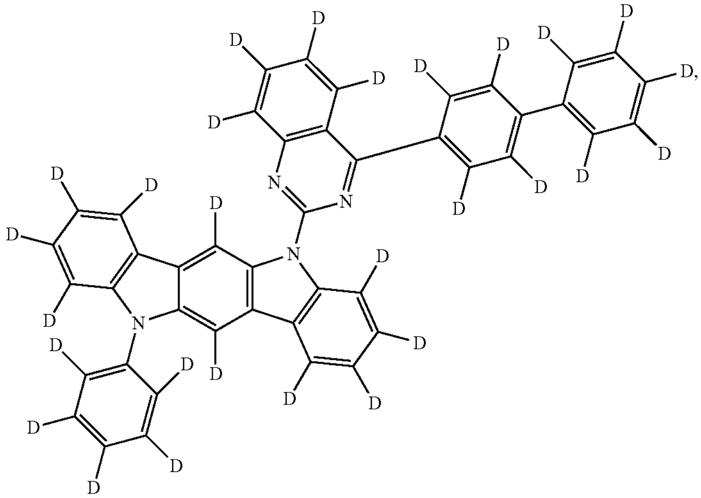,

-continued
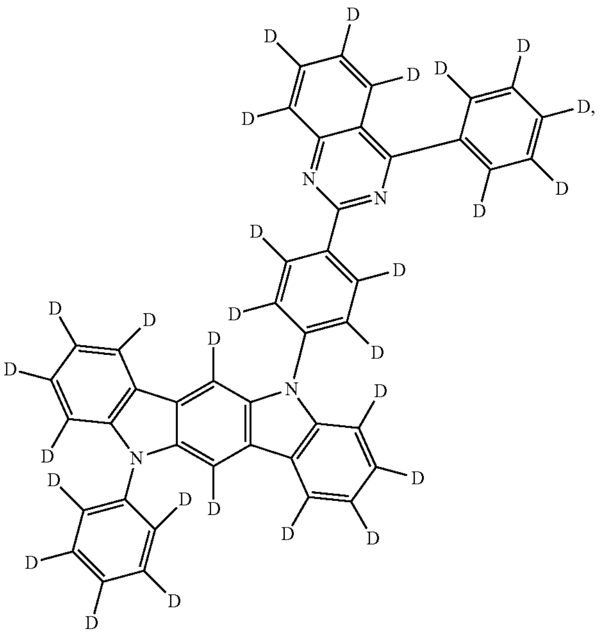
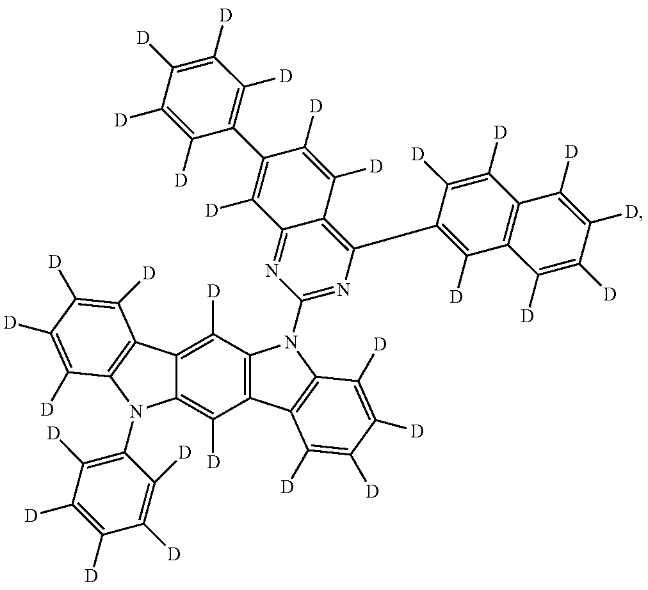

-continued
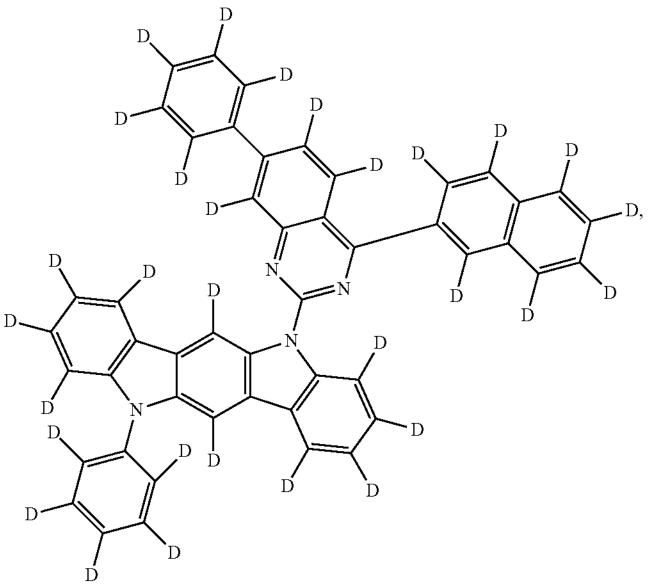
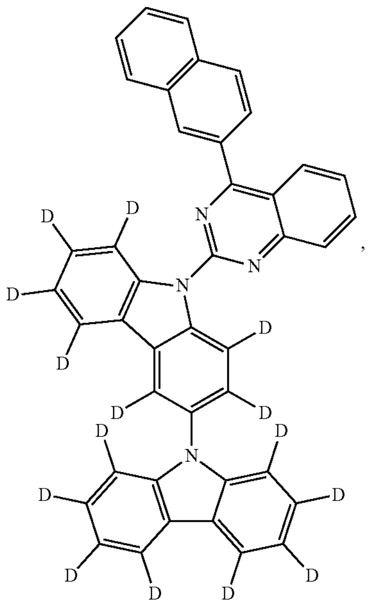
,
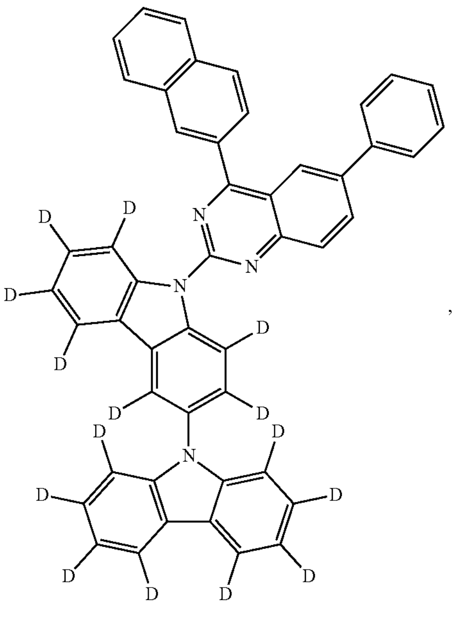
,
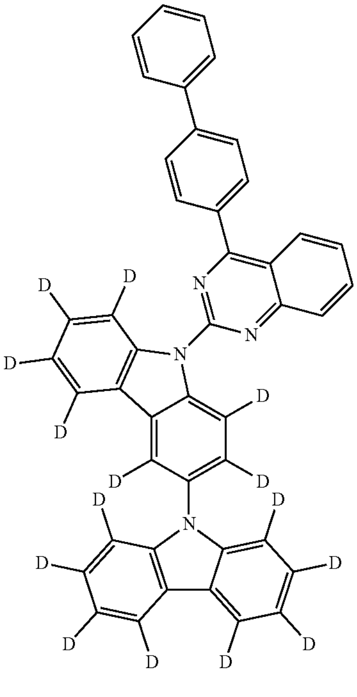
,

-continued
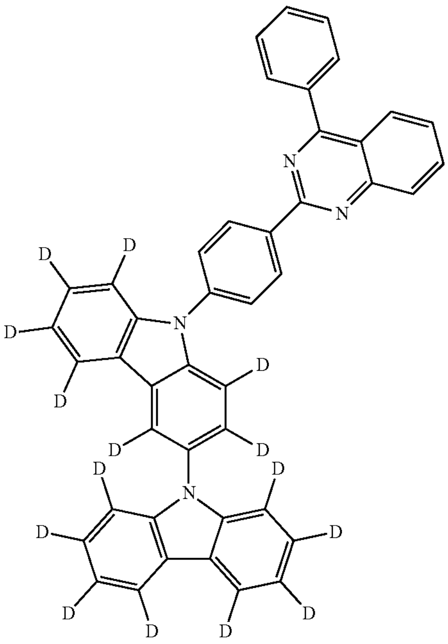
,
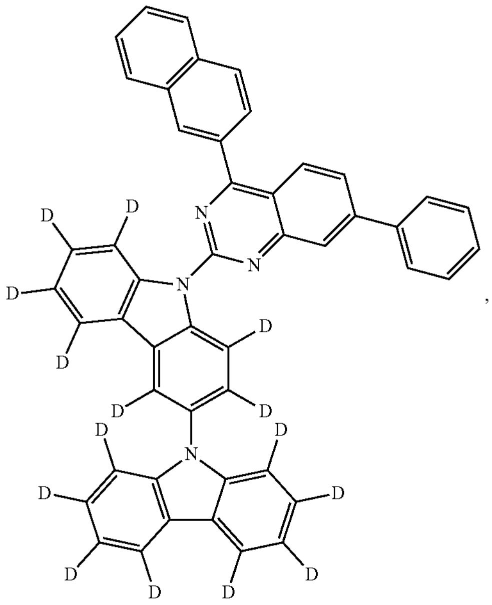
,
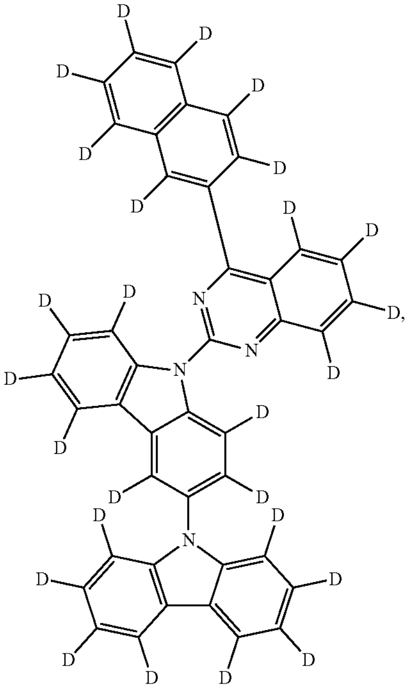
,
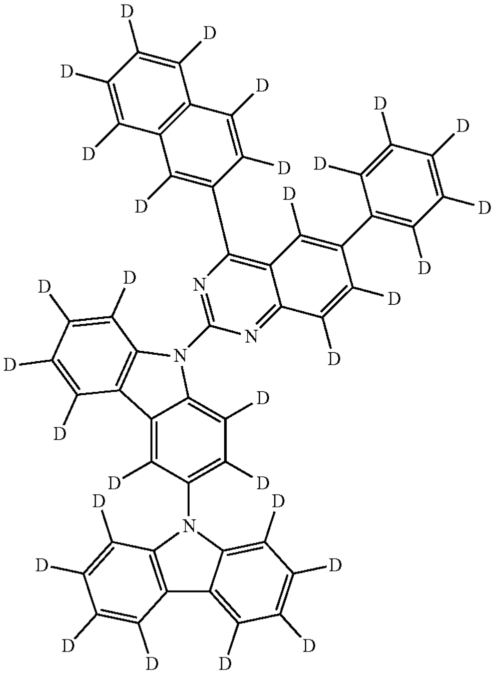
,

-continued
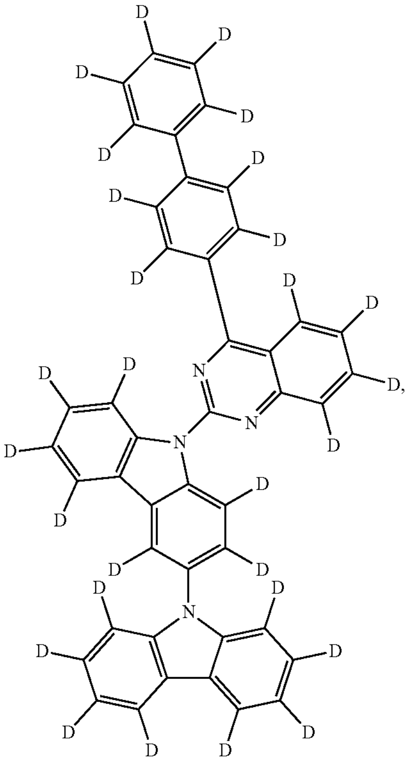
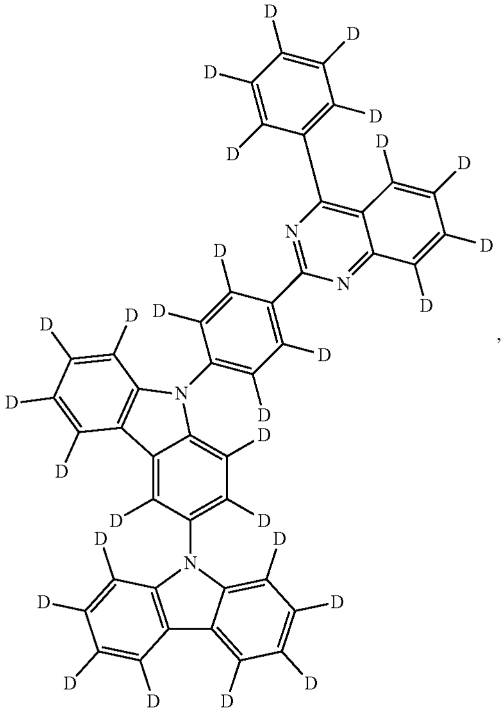
,
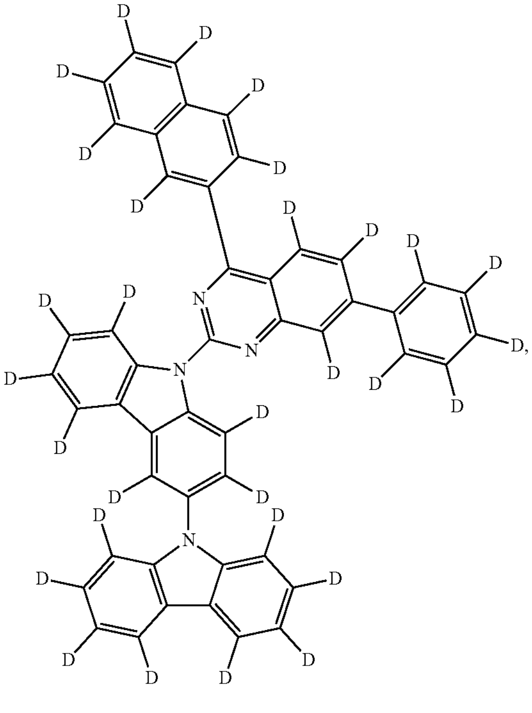
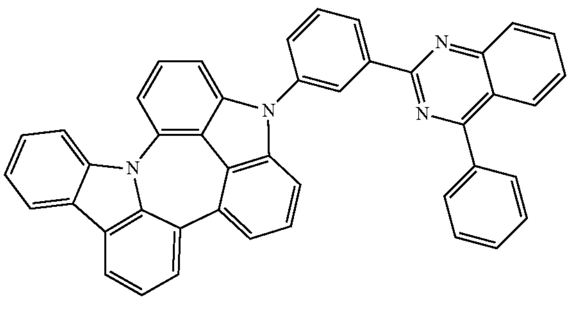
,

-continued
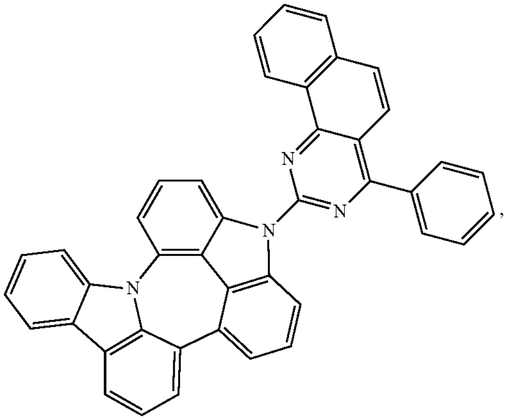
,
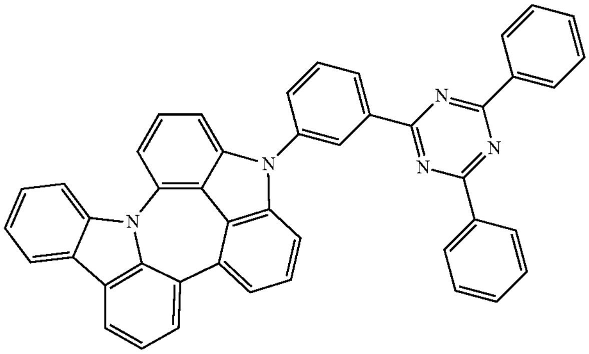
,
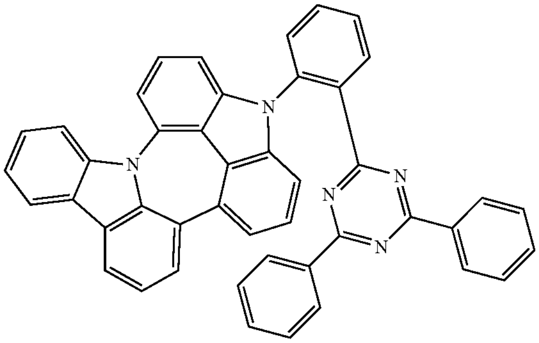
,
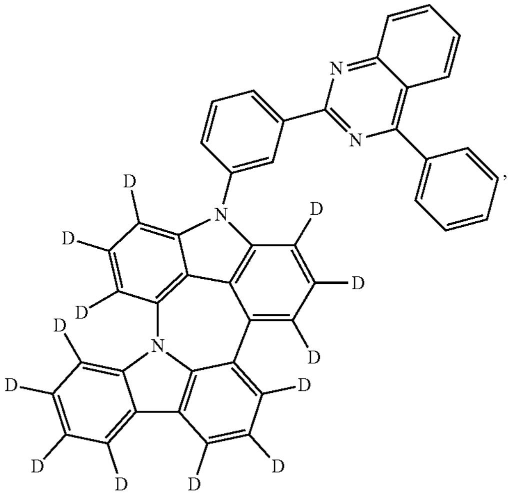
,
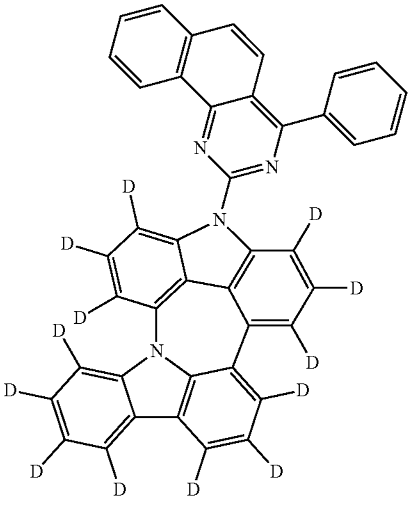

,
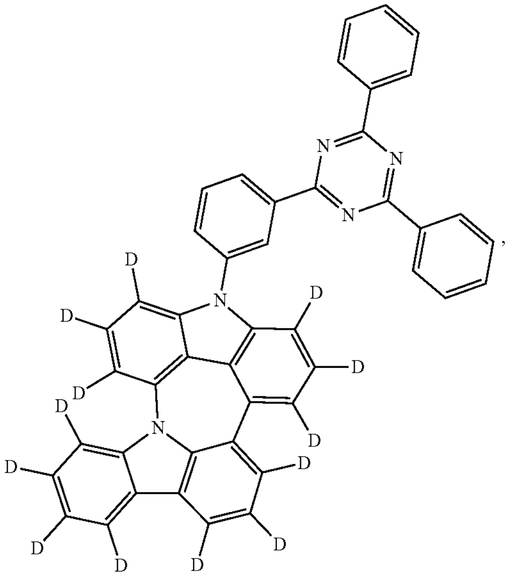
,
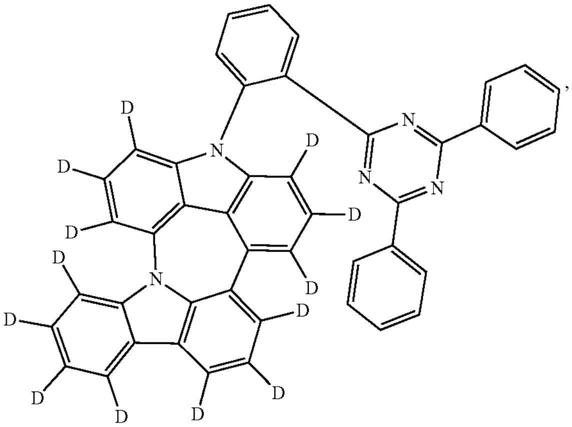
,
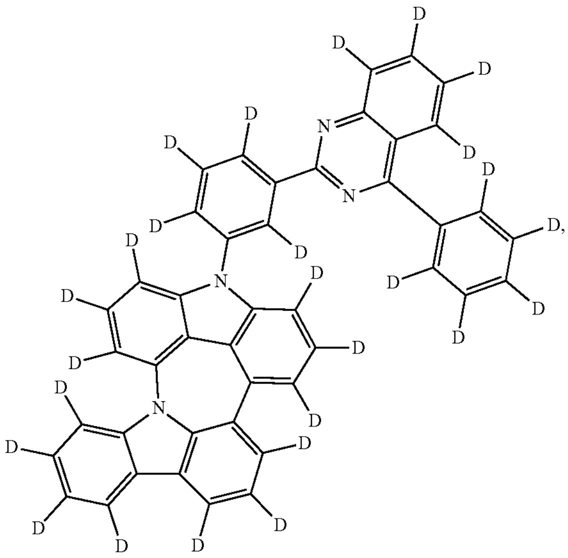
-continued
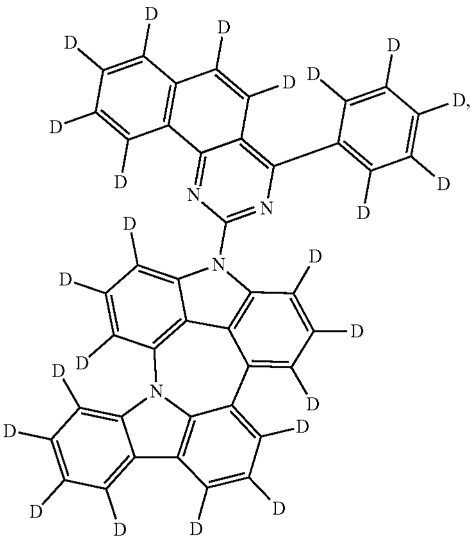
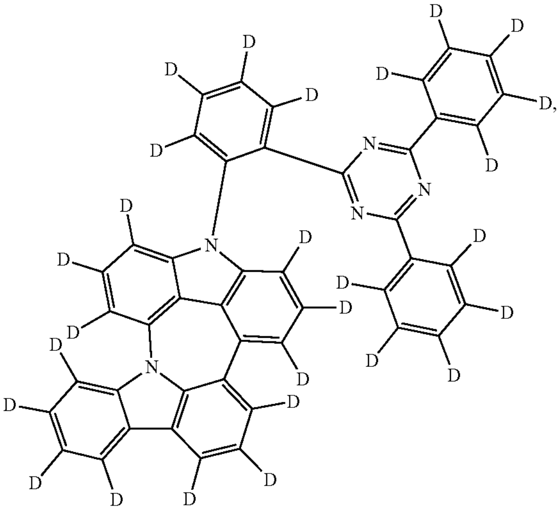
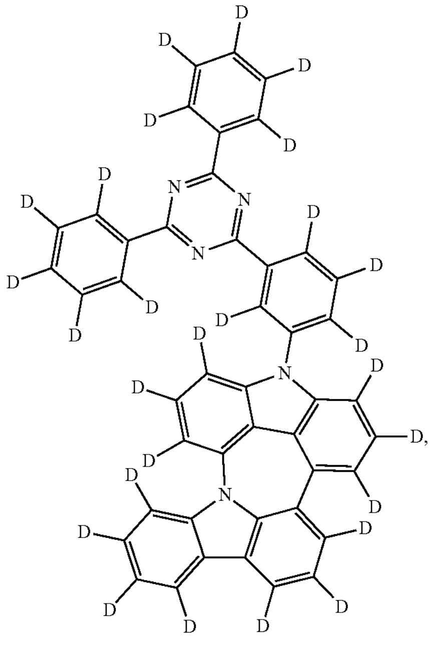
and -continued

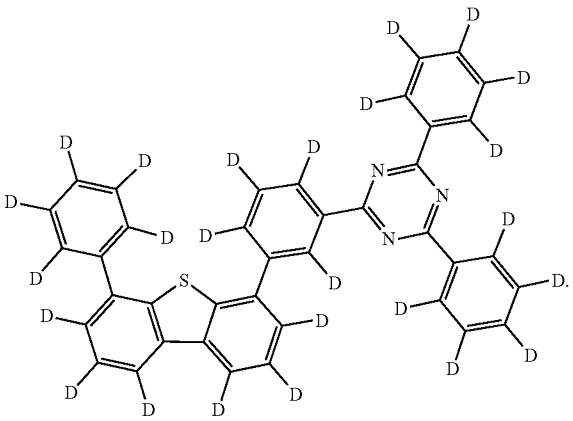

In some embodiments, the phosphorescent dopant has a formula of $M(L_A)_p(L_B)_q(L_C)_r$ wherein $L_B$ and $L_C$ are each a bidentate ligand; and wherein p is 1, 2, or 3; q is 0, 1, or 2; r is 0, 1, or 2; and p+q+r is the oxidation state of the metal M.

In some embodiments, the phosphorescent dopant has a formula selected from the group consisting of $Ir(L_A)_3$, $Ir(L_A)(L_B)_2$, $Ir(L_A)_2(L_B)$, $Ir(L_A)_2(L_C)$, and $Ir(L_A)(L_B)(L_C)$; and wherein $L_A$, $L_B$, and $L_C$ are different from each other.

In some embodiments, $L_B$ is a substituted or unsubstituted phenylpyridine, and $L_C$ is a substituted or unsubstituted acetylacetonate.

In some embodiments, the phosphorescent dopant has a formula of $Pt(L_A)(L_B)$; and $L_A$ and $L_B$ can be same or different. In some such embodiments, $L_A$ and $L_B$ are connected to form a tetradentate ligand.

In some embodiments, the phosphorescent dopant is a transition metal complex having at least one ligand or part of the ligand, if the ligand is more than bidentate, selected from the group consisting of the structures of following LIST 8:

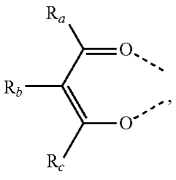

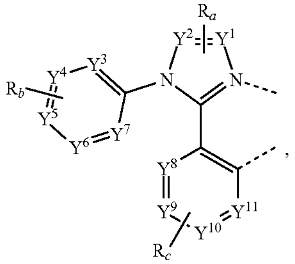

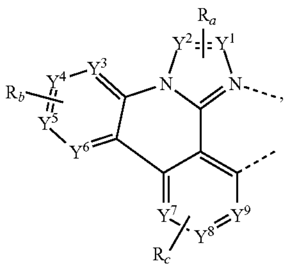

-continued

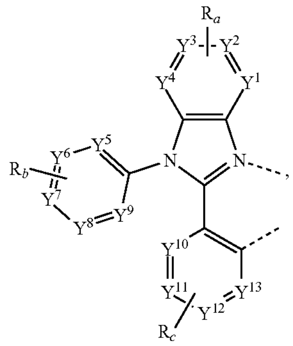

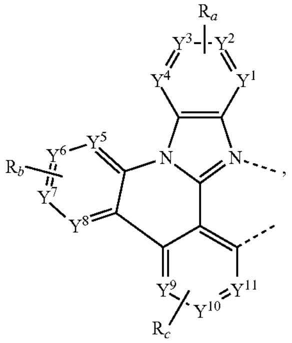

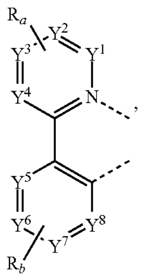

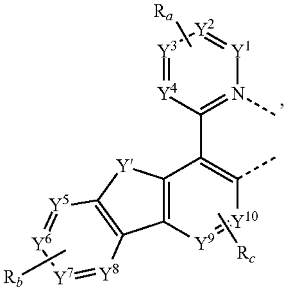

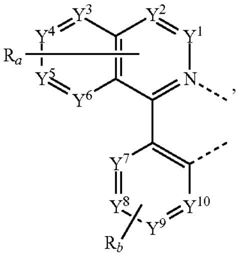

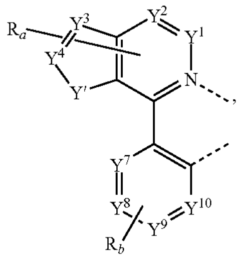

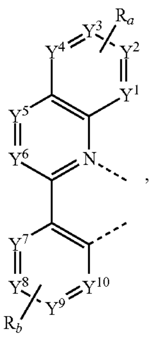

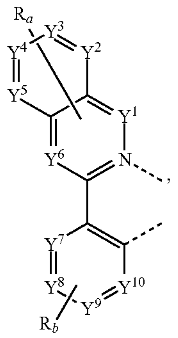

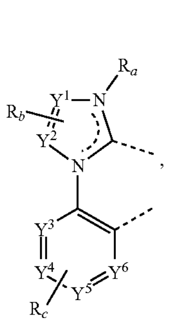

-continued

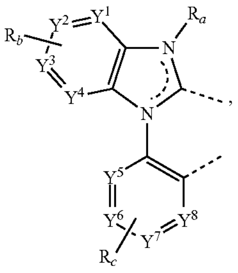

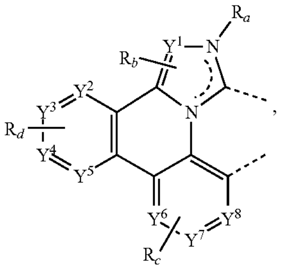

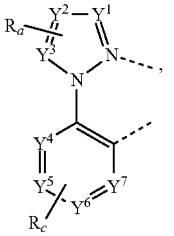

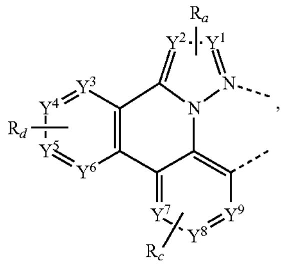

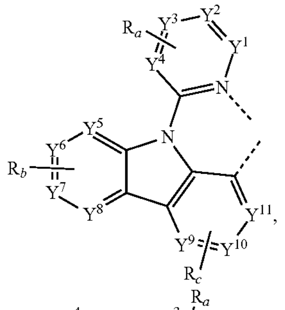

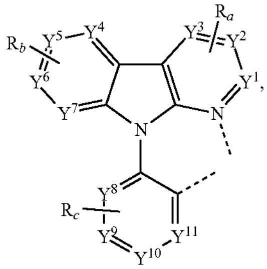

and

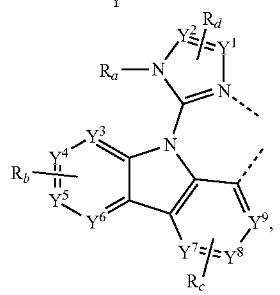

wherein:

each $Y^1$ to $Y^{13}$ are independently selected from the group consisting of carbon and nitrogen;

Y' is selected from the group consisting of $BR_e$, $BR_eR_f$, $NR_e$, $PR_e$, $P(O)R_e$, O, S, Se, C═O, C═S, C═Se, C═$NR_e$, C═$CR_eR_f$, S═O, $SO_2$, $CR_eR_f$, $SiR_eR_f$, and $GeR_eR_f$;

$R_e$ and $R_f$ can be fused or joined to form a ring;

each $R_a$, $R_b$, $R_c$, and $R_d$ independently represents zero, mono, or up to the maximum number of allowed substitutions to its associated ring;

each of $R_a$, $R_b$, $R_c$, $R_d$, $R_e$ and $R_f$ is independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof; and two adjacent substituents of $R_a$, $R_b$, $R_c$, and $R_d$ can be fused or joined to form a ring or form a multidentate ligand.

In some embodiments, the phosphorescent dopant is selected from the group consisting of the structures of the following LIST 9:

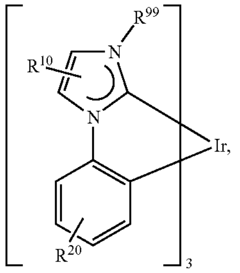

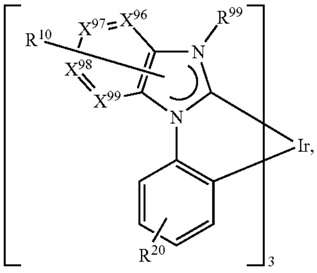

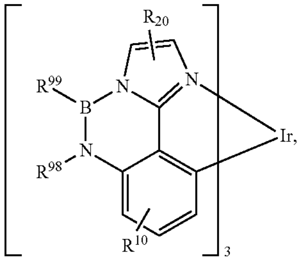

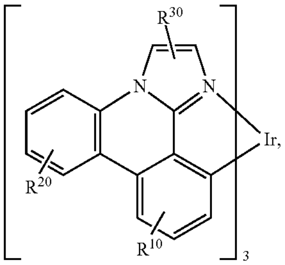

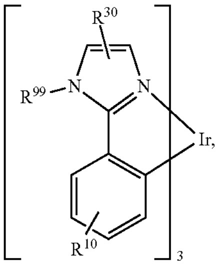

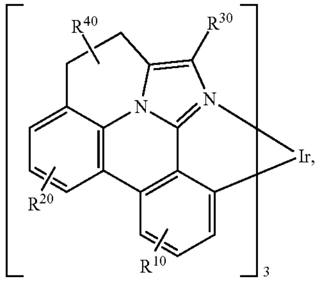

-continued
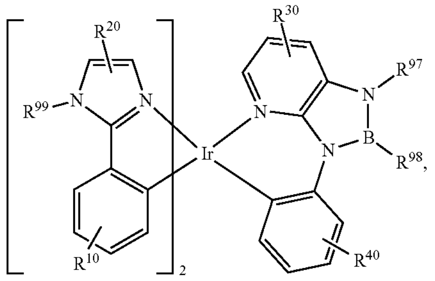
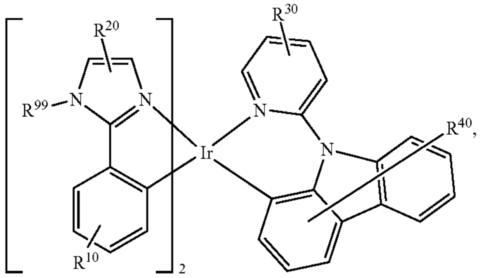
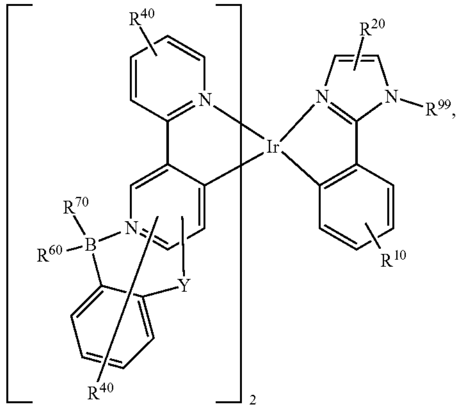
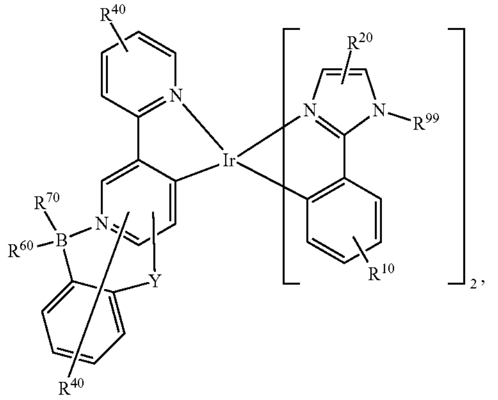
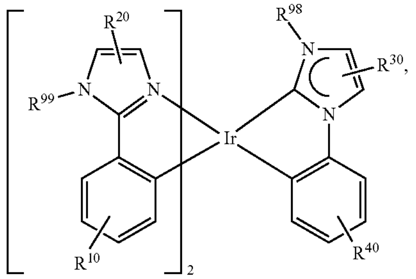
-continued
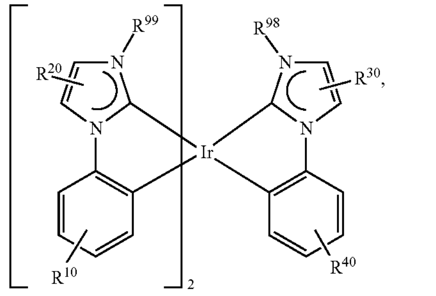
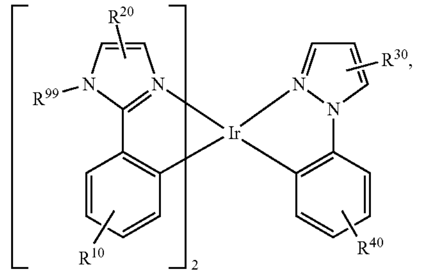
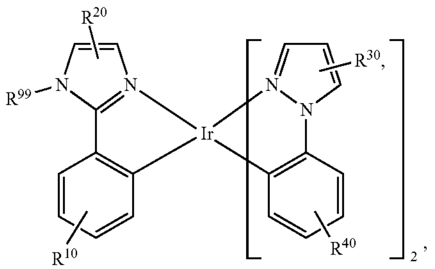
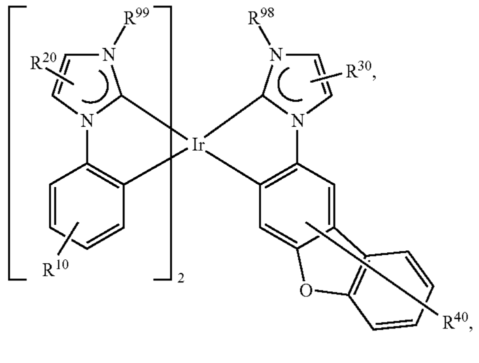
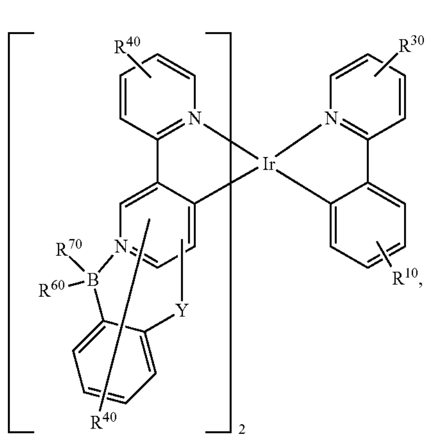

-continued
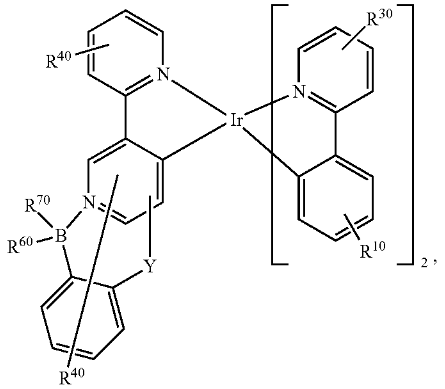
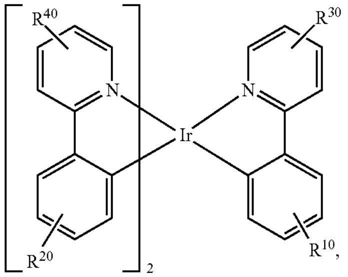
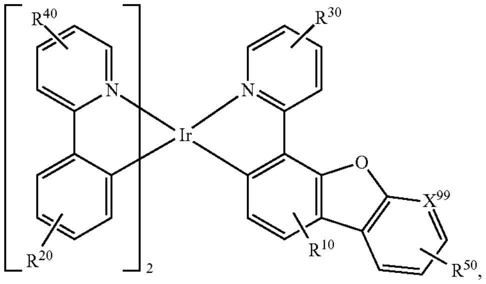
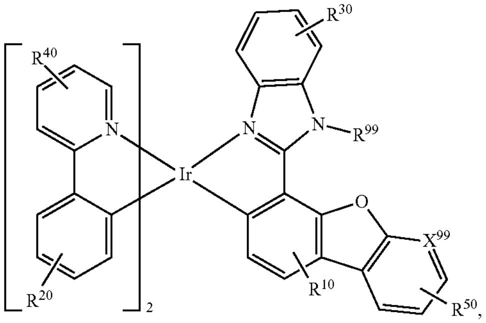
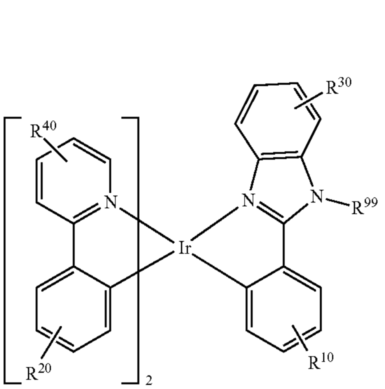
-continued
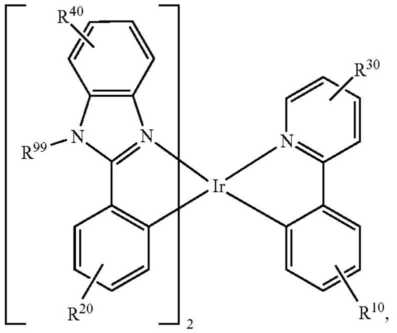
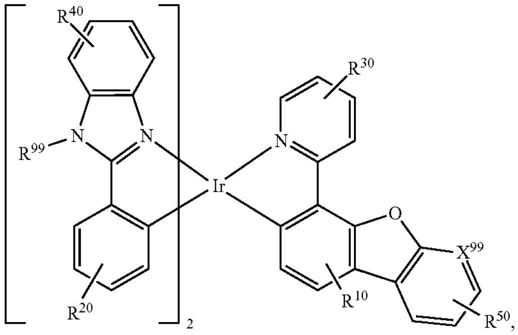
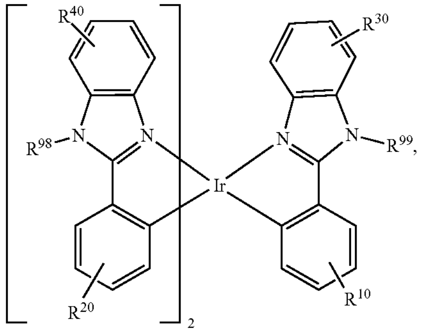
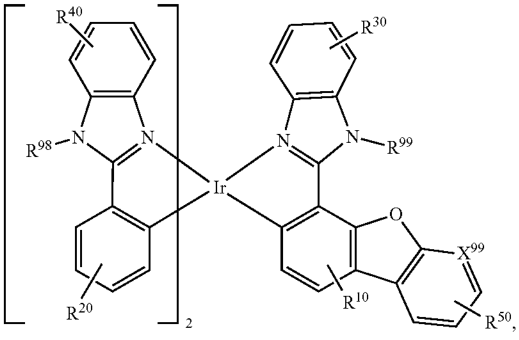
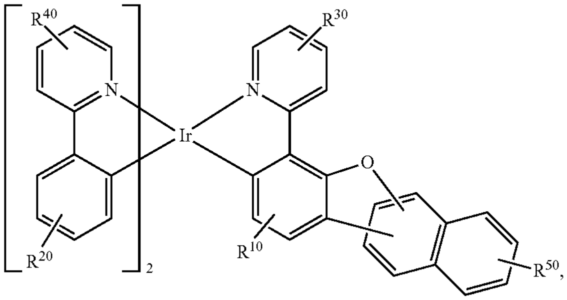

-continued
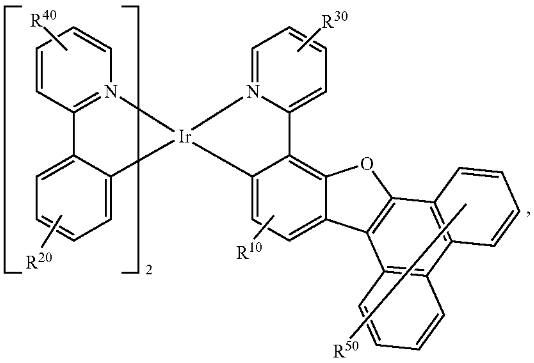
,
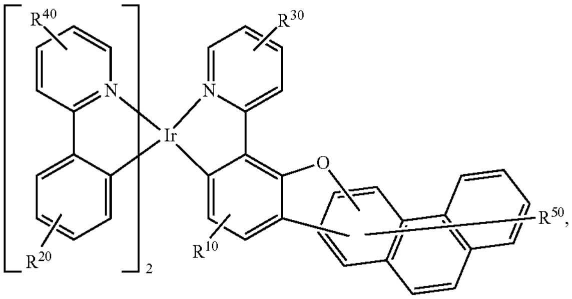
,
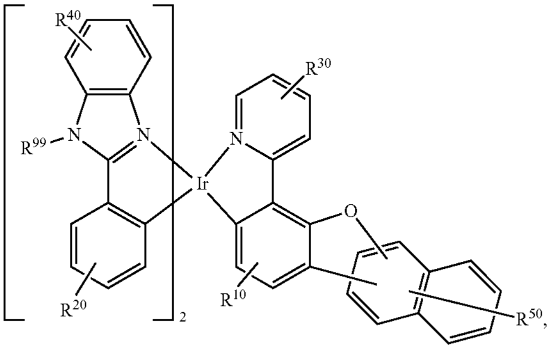
,
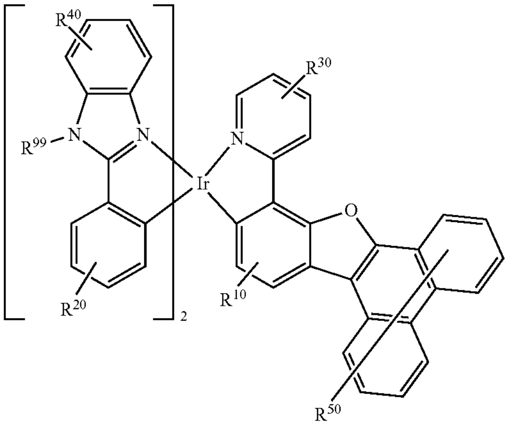
-continued
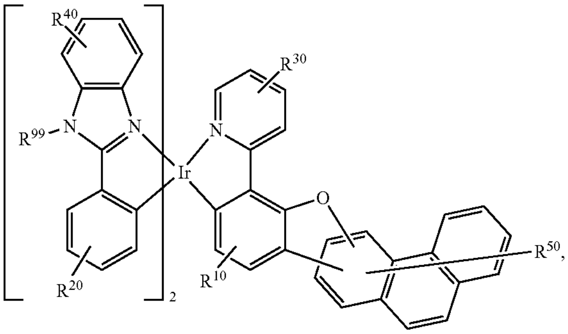
,
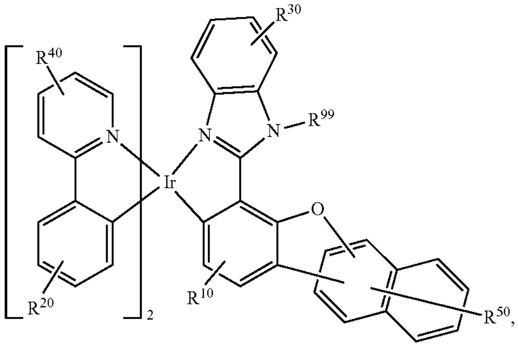
,
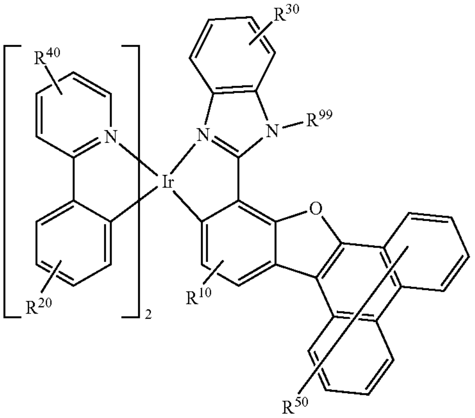
,
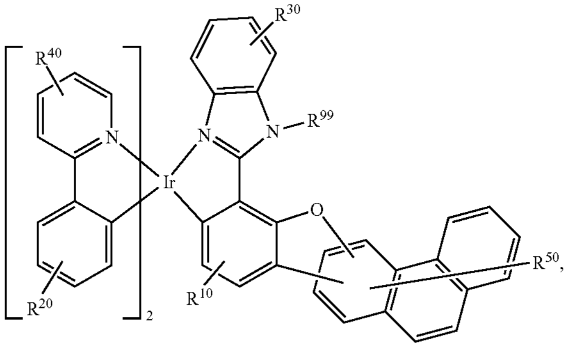
, -continued
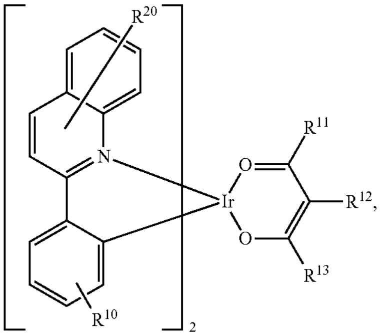
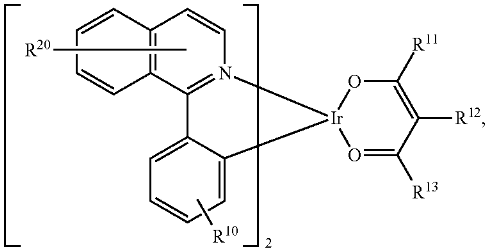
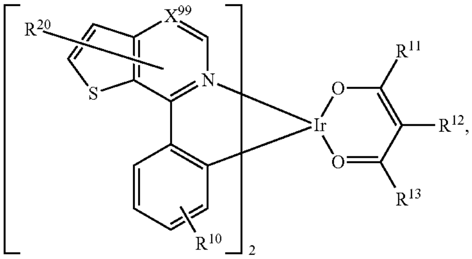
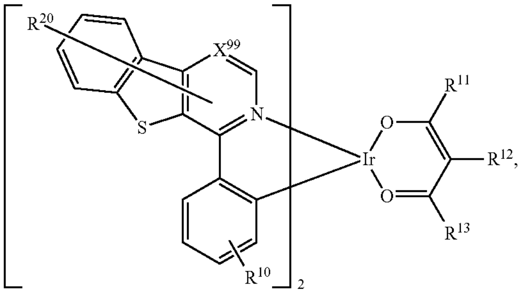
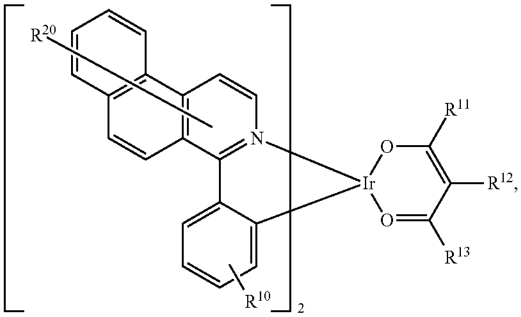
-continued
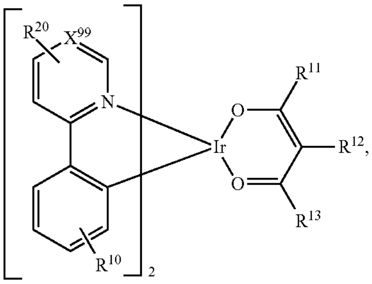
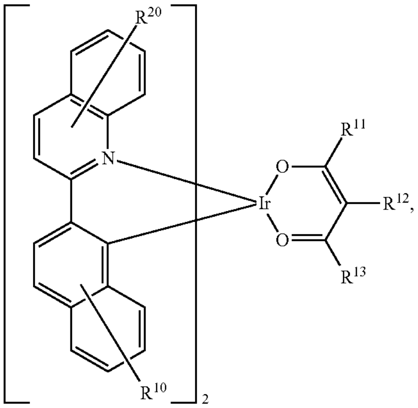
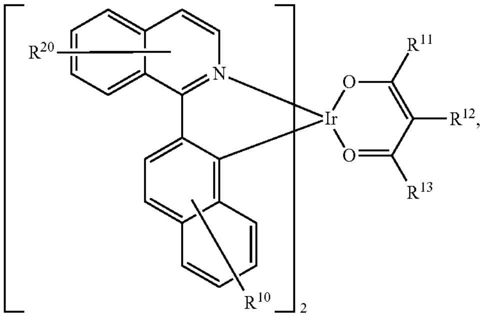
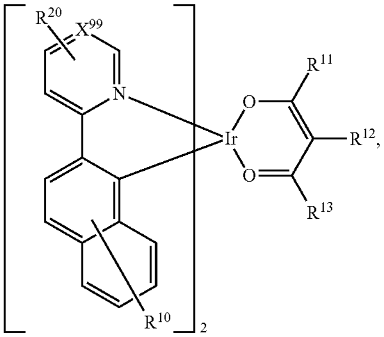
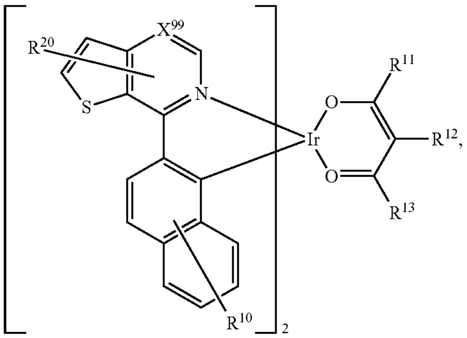

-continued

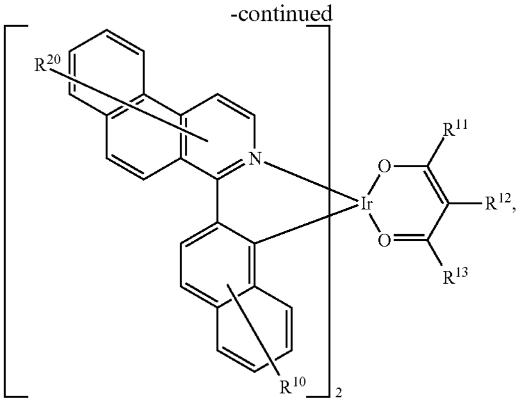

and

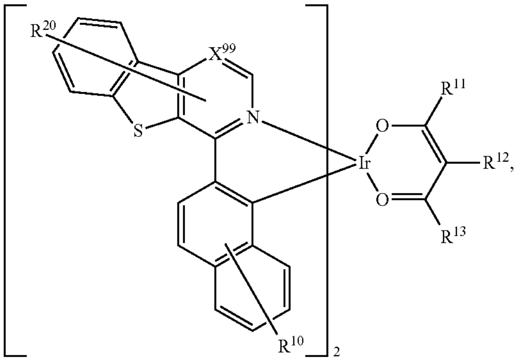

, wherein each of $X^{96}$ to $X^{99}$ is independently C or N;

each Y is independently selected from the group consisting of a NR, O, S, and Se;

each of $R^{10}$, $R^{20}$, $R^{30}$, $R^{40}$, and $R^{50}$ independently represents mono, up to the maximum number of allowed substitutions, or no substitution;

each of R, $R^{10}$, $R^{11}$, $R^{12}$, $R^{13}$, $R^{20}$, $R^{30}$, $R^{40}$, $R^{50}$, $R^{60}$, $R^{70}$, $R^{97}$, $R^{98}$, and $R^{99}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof; and two adjacent of $R^{10}$, $R^{11}$, $R^{12}$, $R^{13}$, $R^{20}$, $R^{30}$, $R^{40}$, $R^{50}$, $R^{60}$, $R^{70}$, $R^{97}$, $R^{98}$, and $R^{99}$ can be joined or fused to form a ring.

In some embodiments, the phosphorescent dopant is selected from the group consisting of the structures of the following LIST 10:

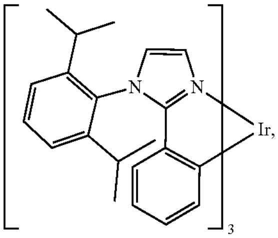

,

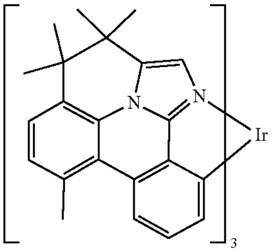

,

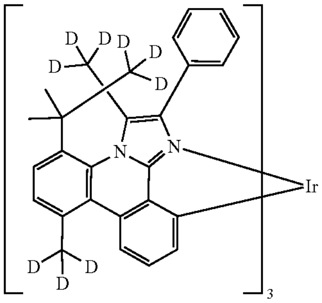

,

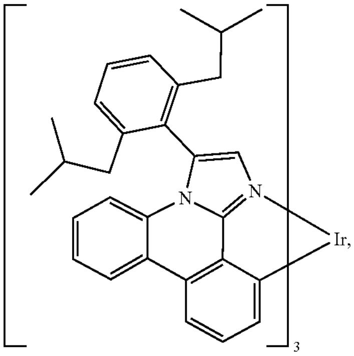

,

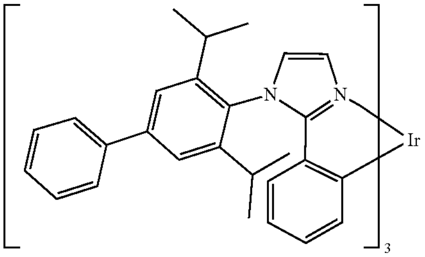

,

-continued
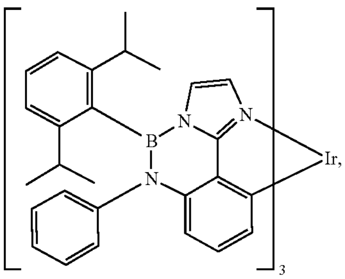
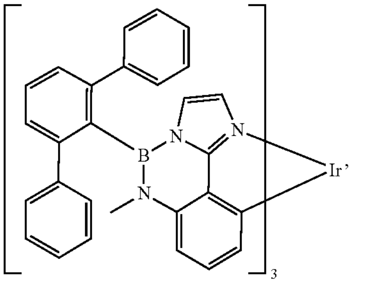
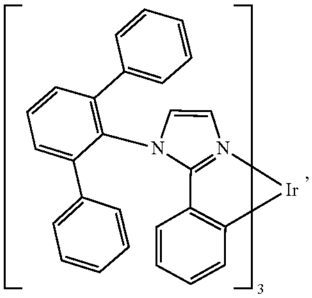
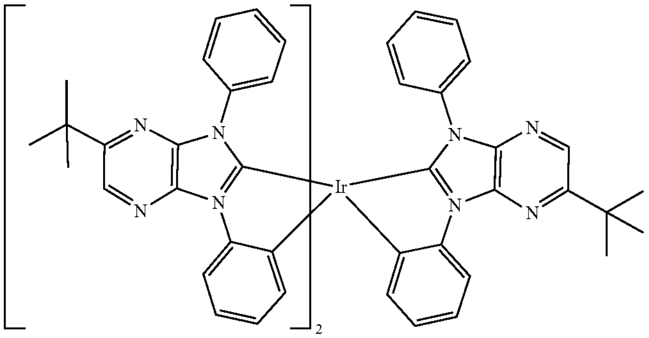
,
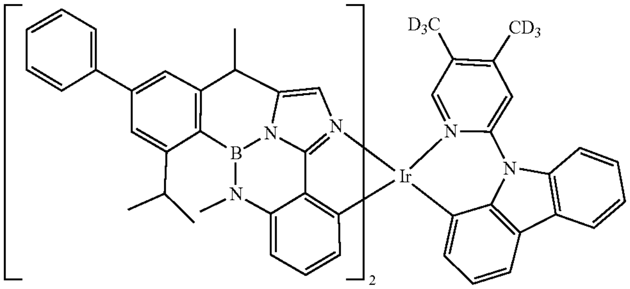
,
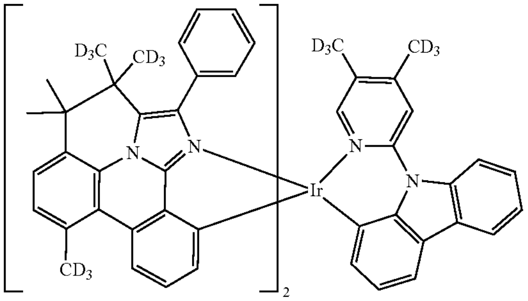
,
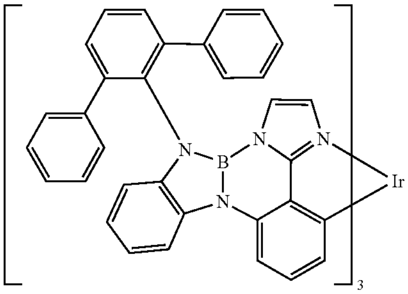
,
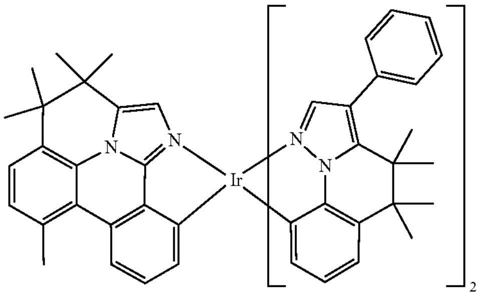
,
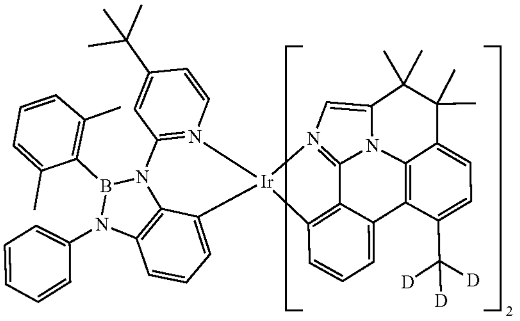
, -continued
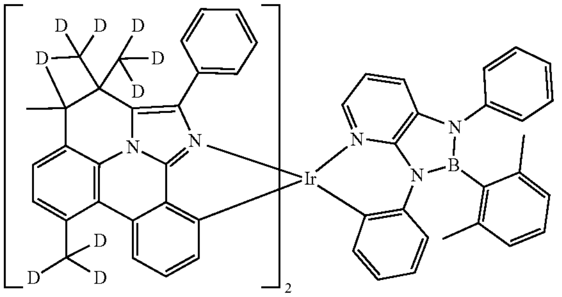
,
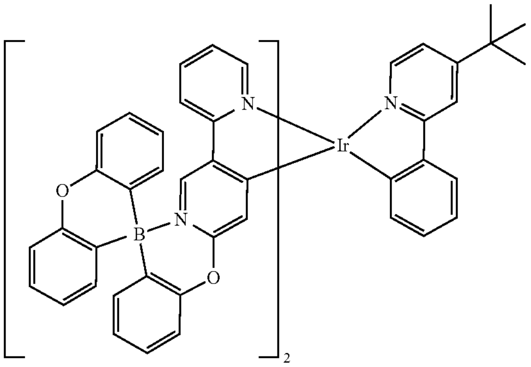
,
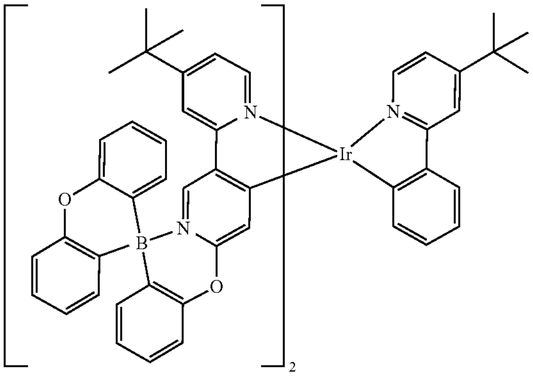
,
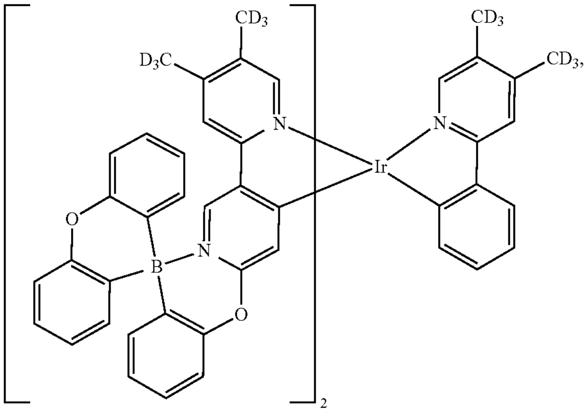
,
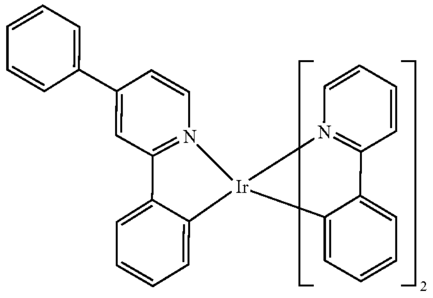
,
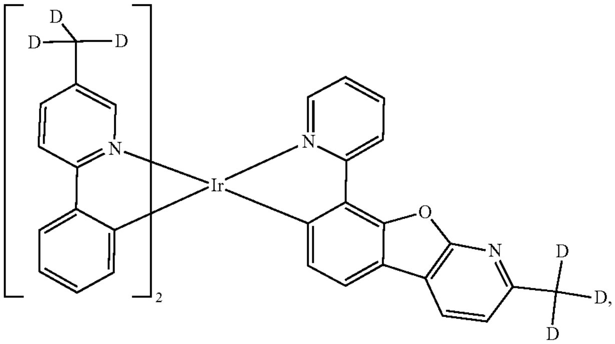
, -continued
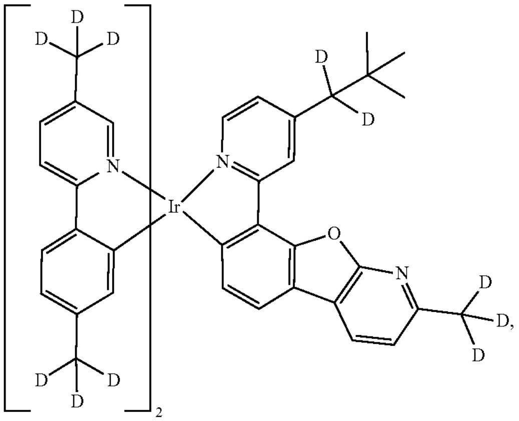
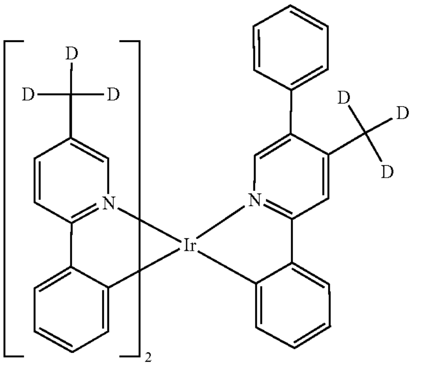
,
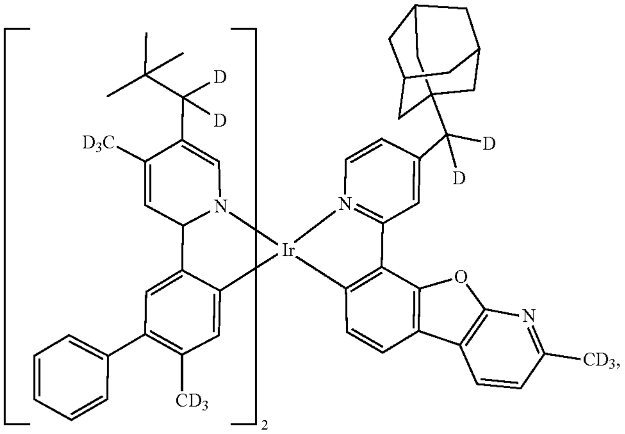
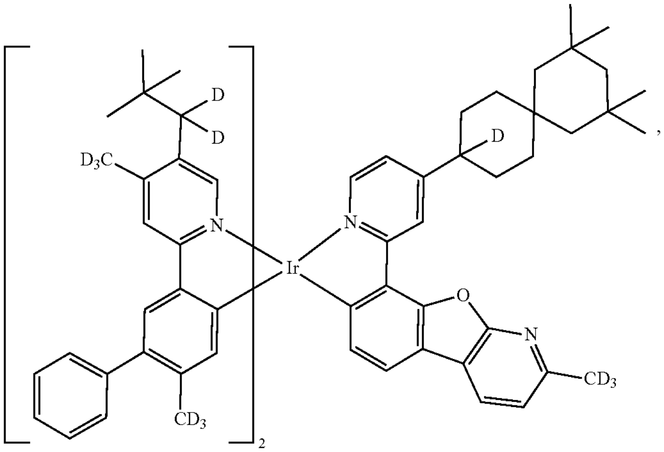
,
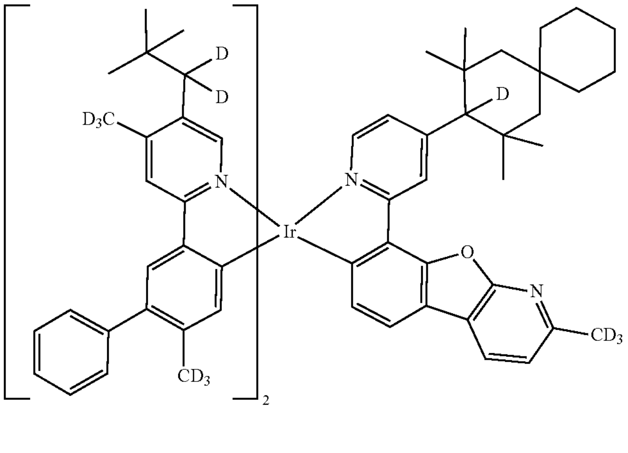
, -continued
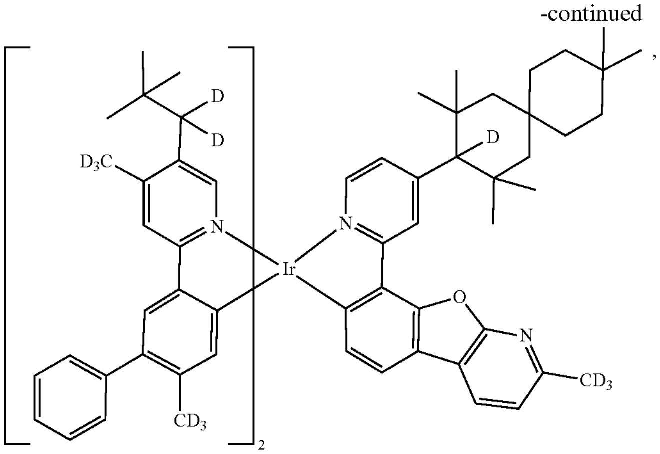
,
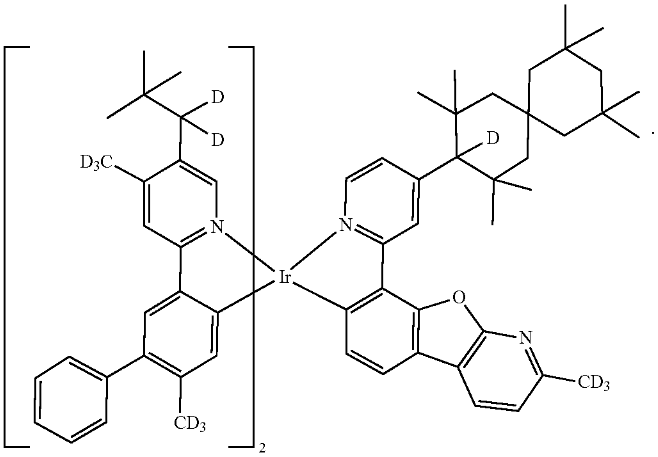
.
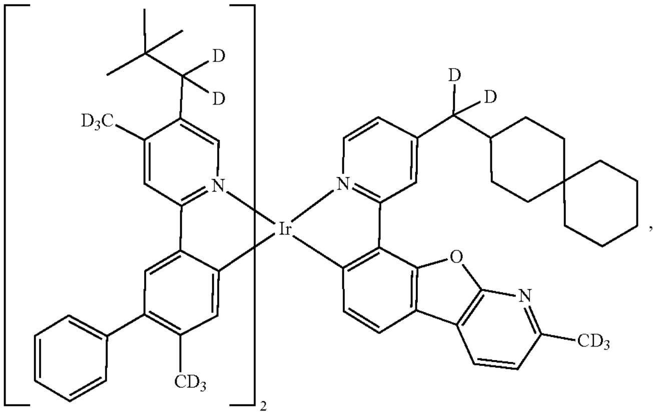
,
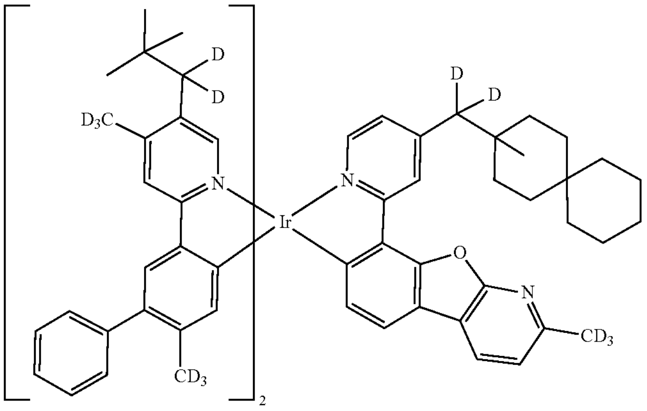
, -continued
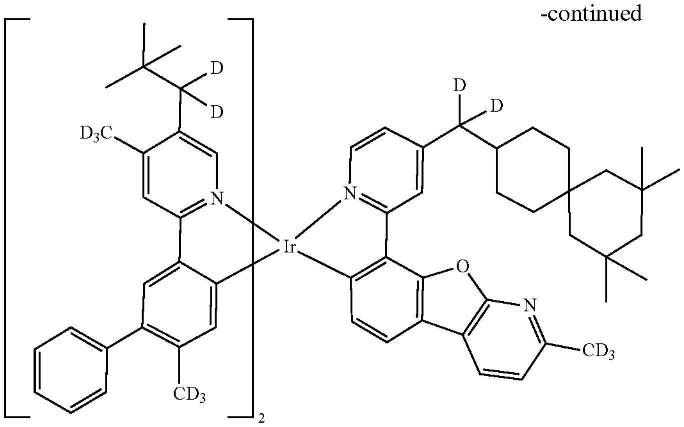
,
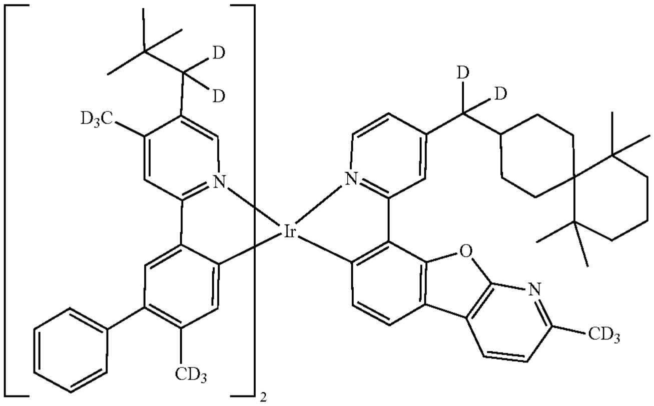
,
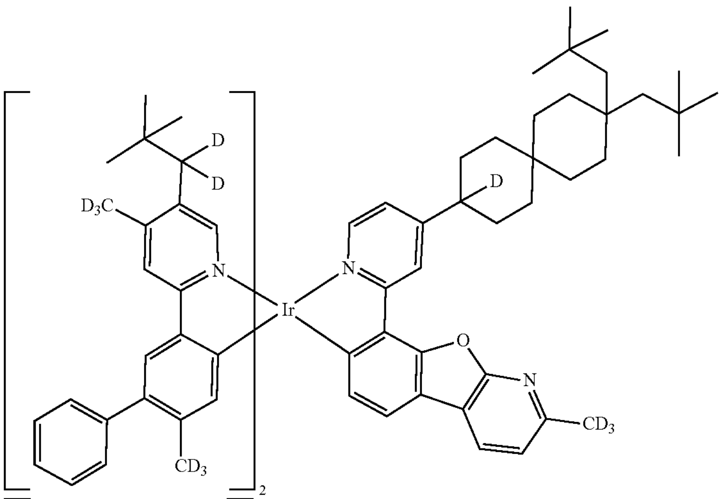
,
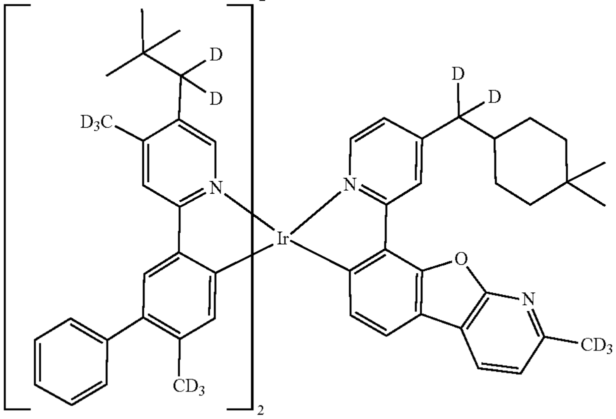
, -continued
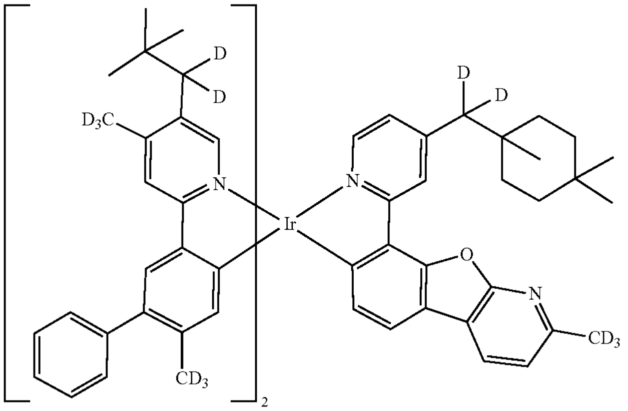
,
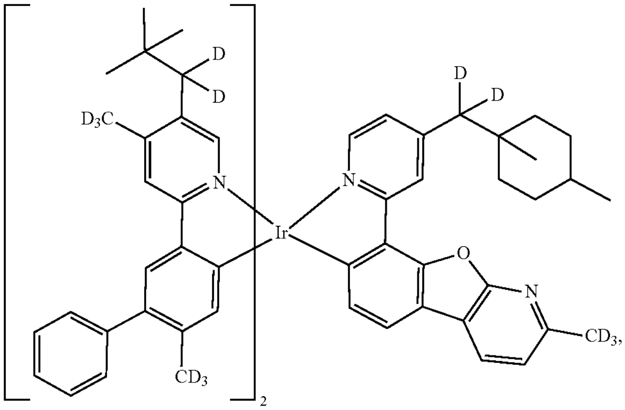
,
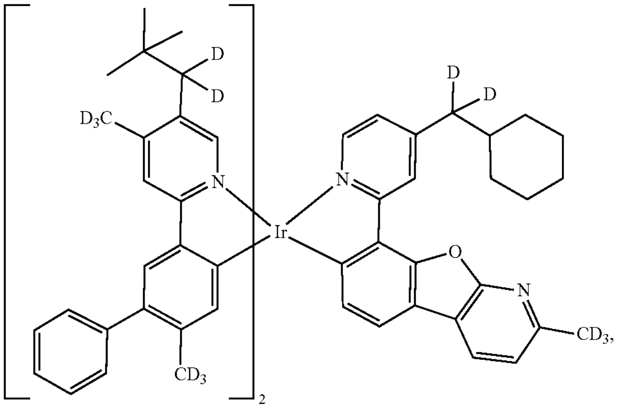
,
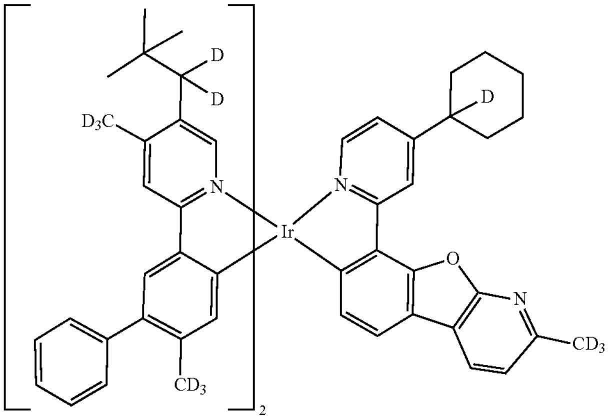

-continued
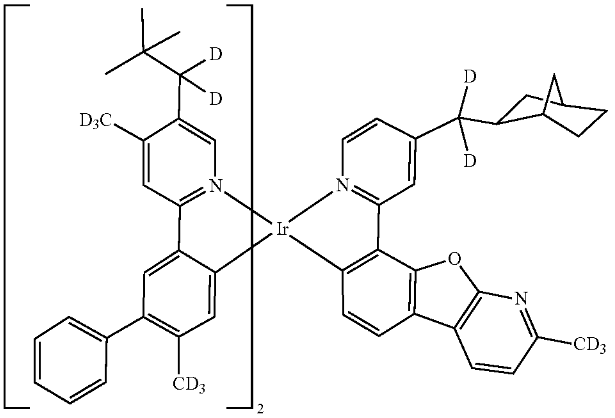
,
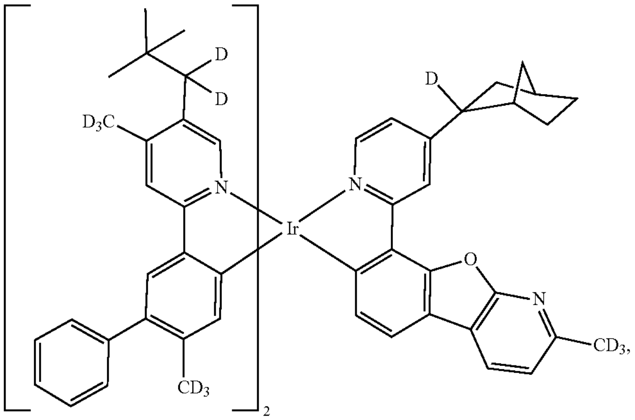
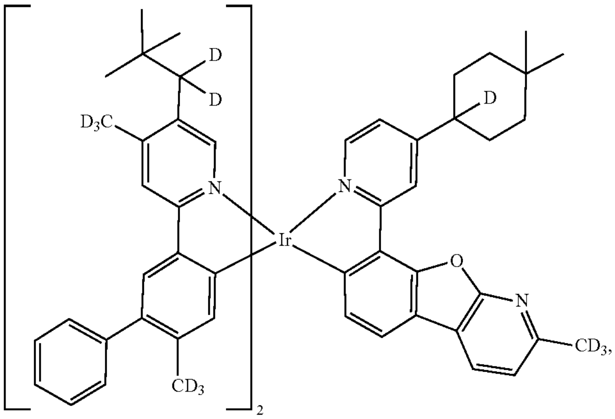
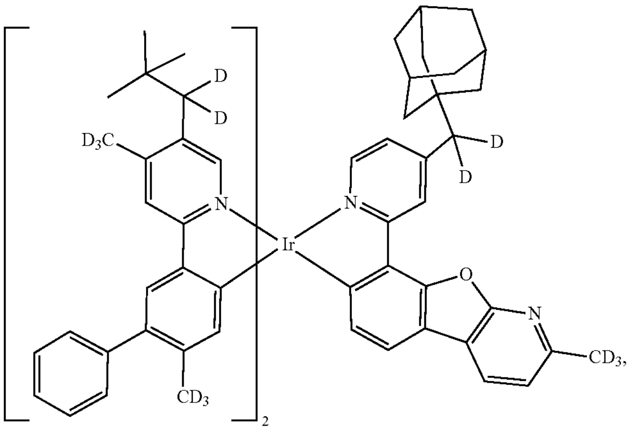

-continued
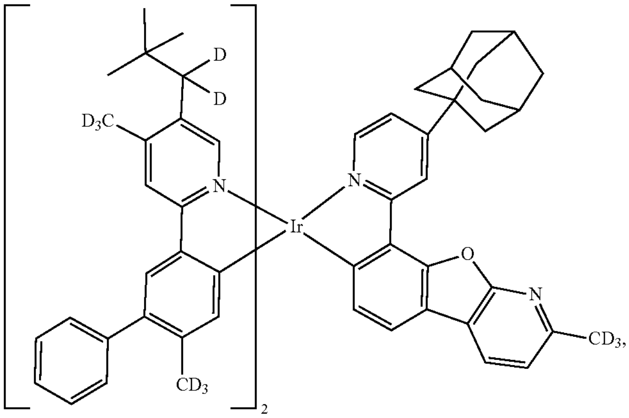
,
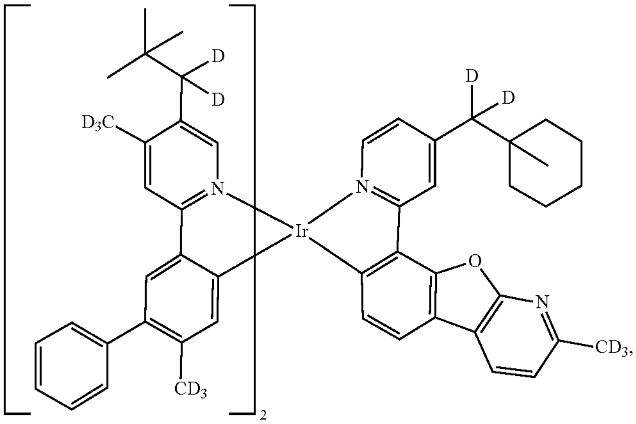
,
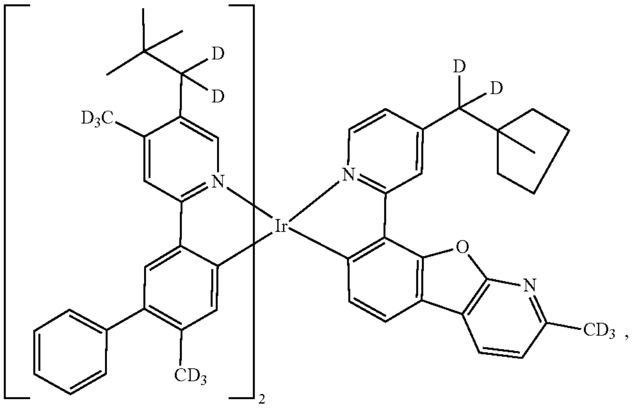
,
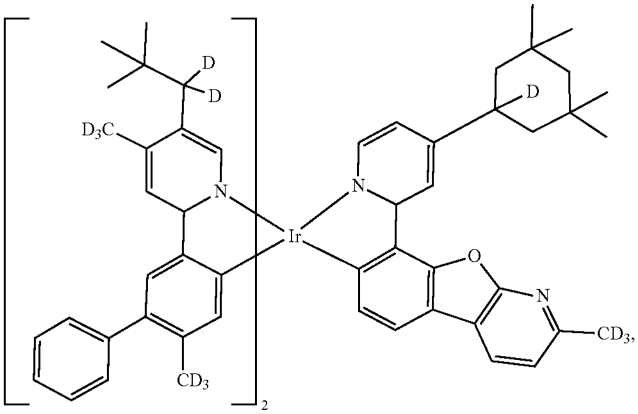
,

-continued
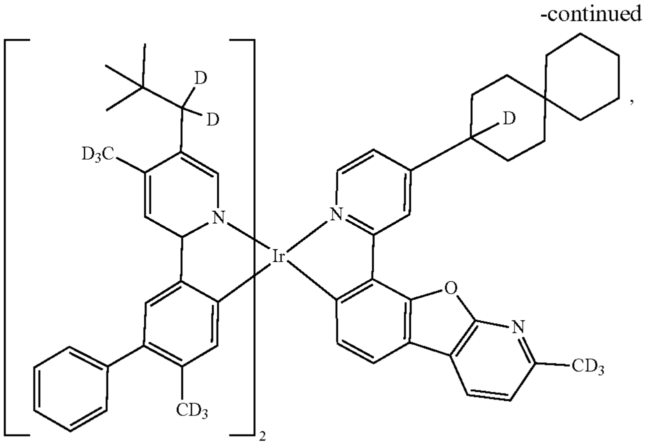
,
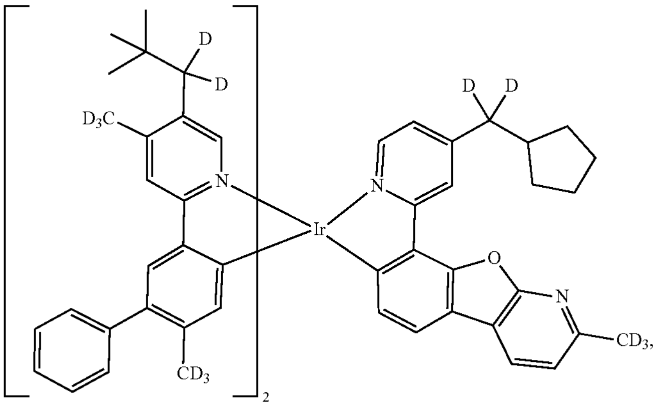
,
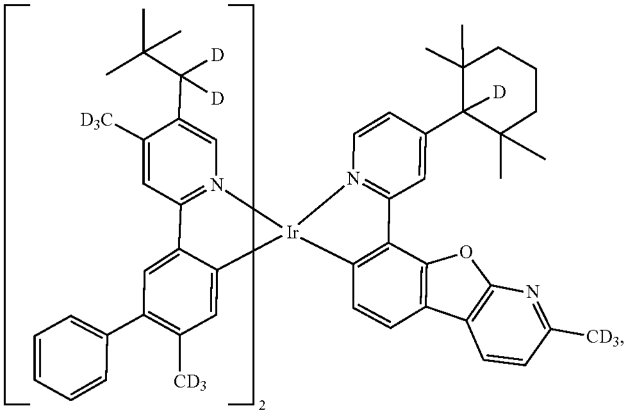
,
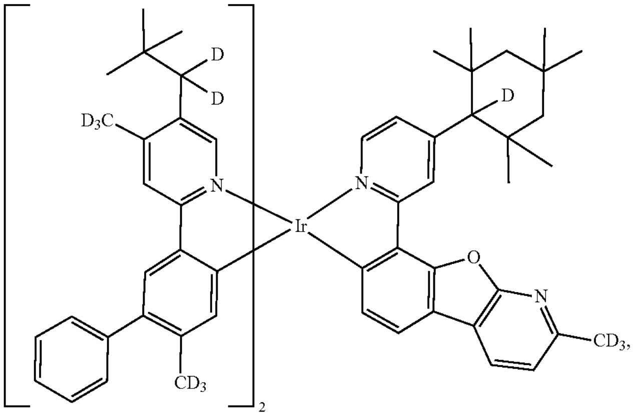
,

-continued
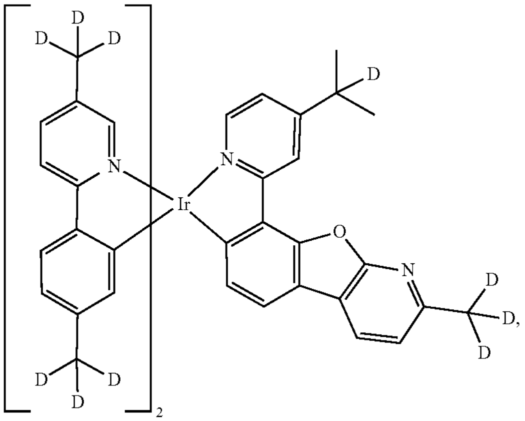
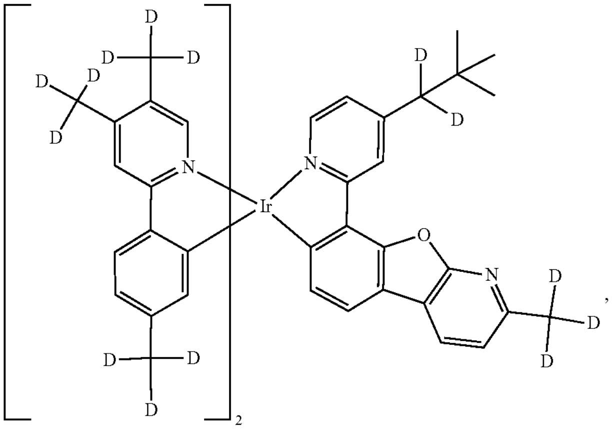
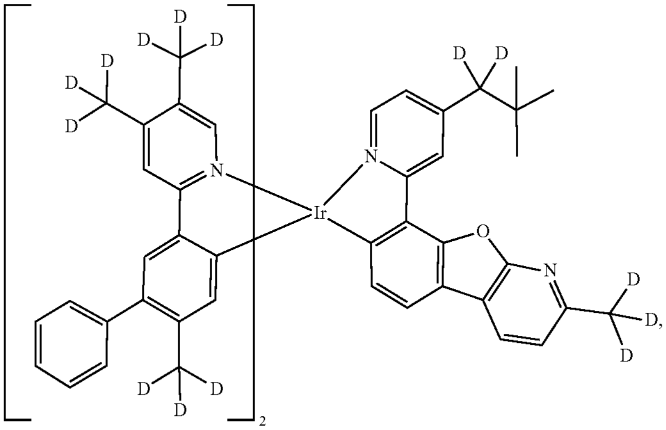
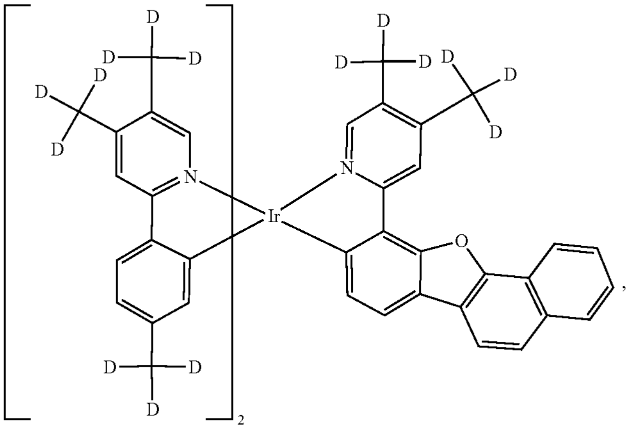

-continued
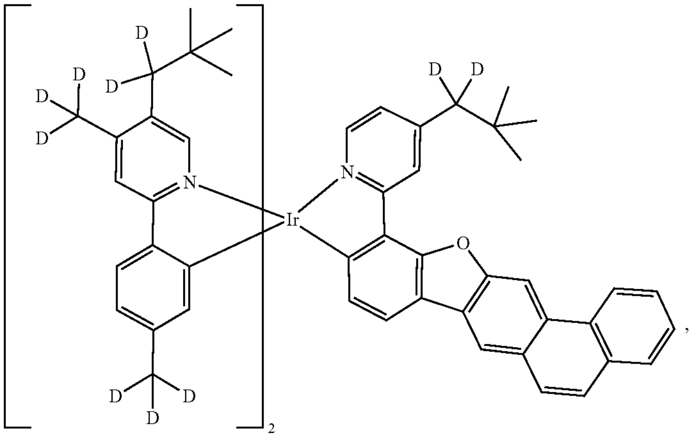
,
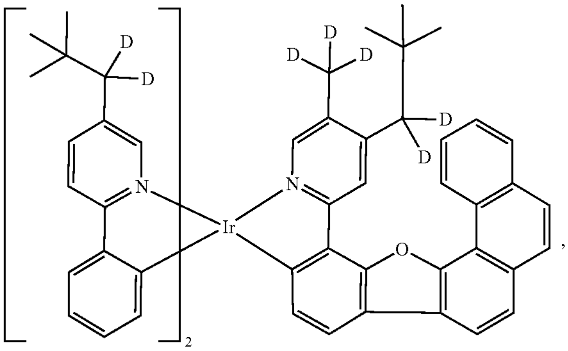
,
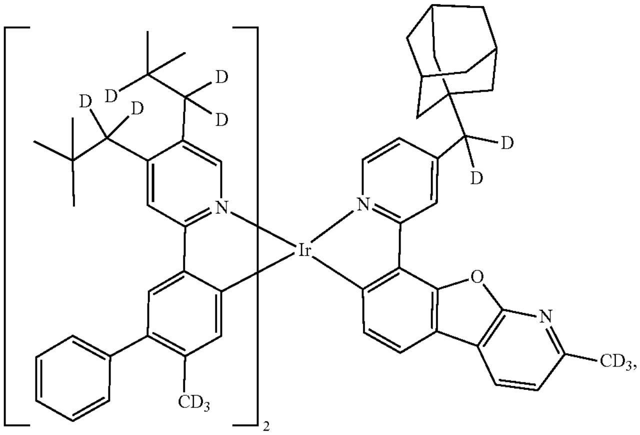
,
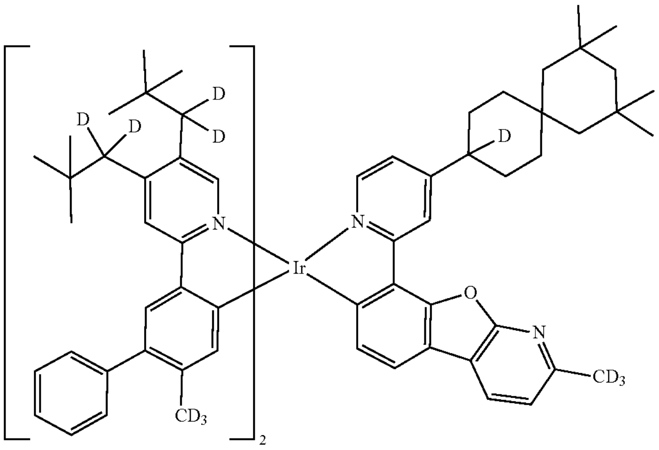
,

-continued
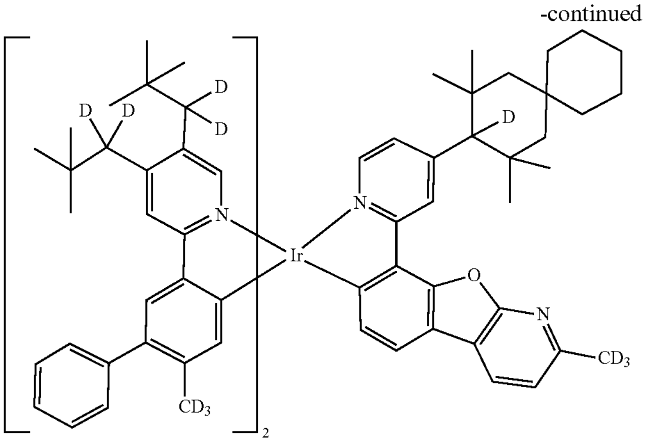
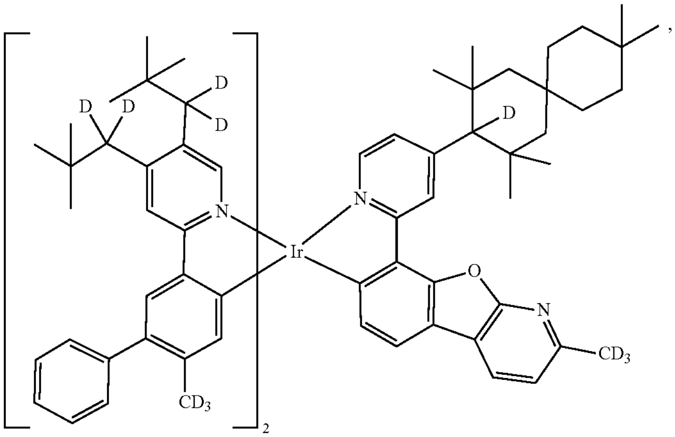
,
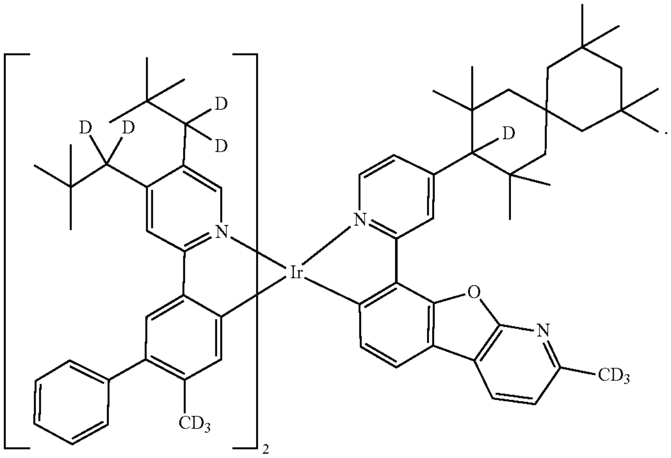
.
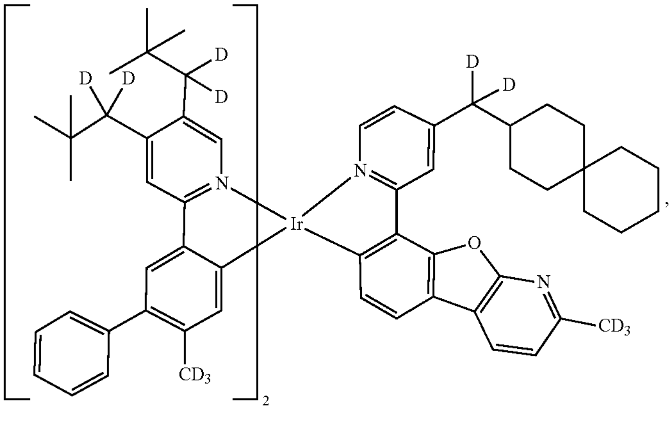
,

-continued
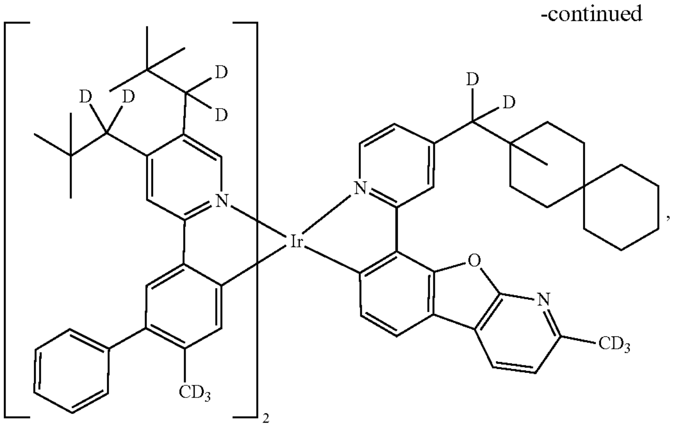
,
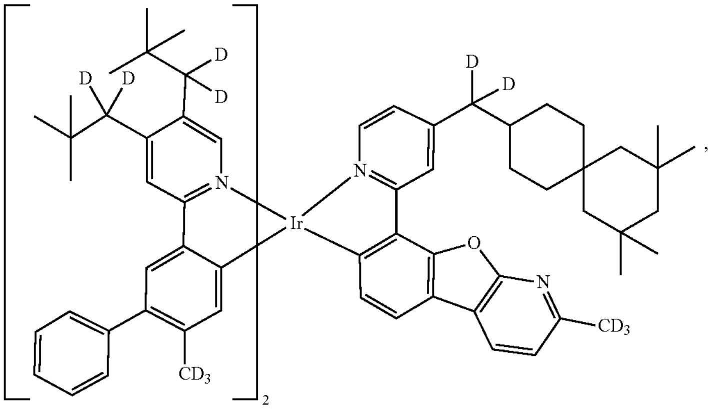
,
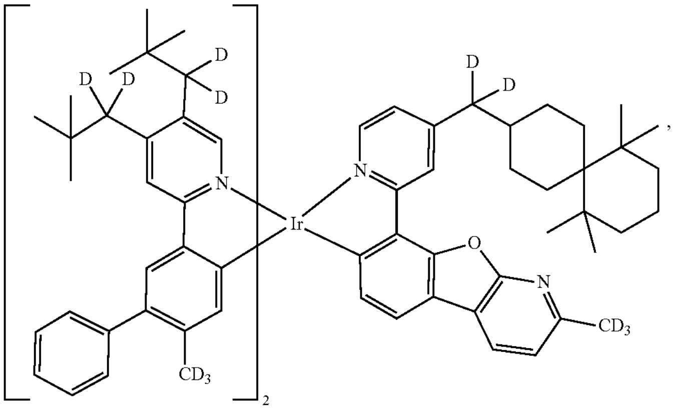
,
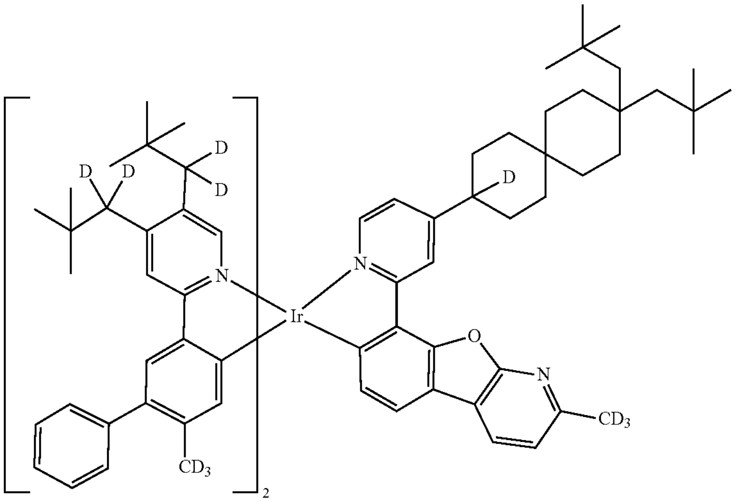
,

-continued
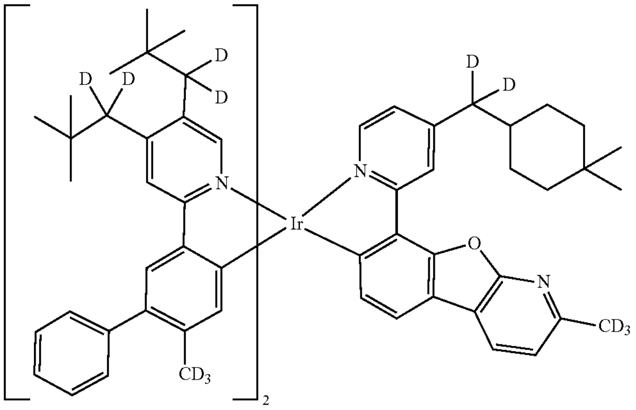
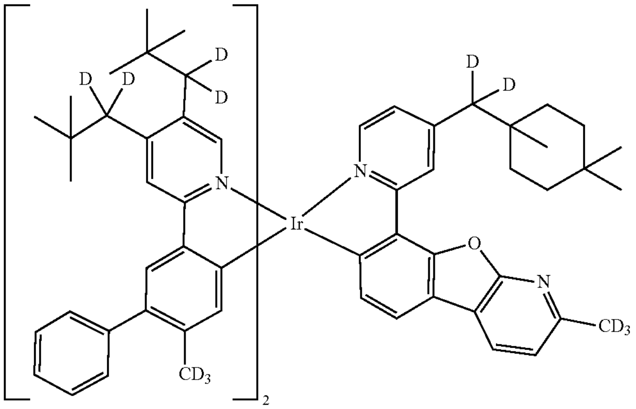
,
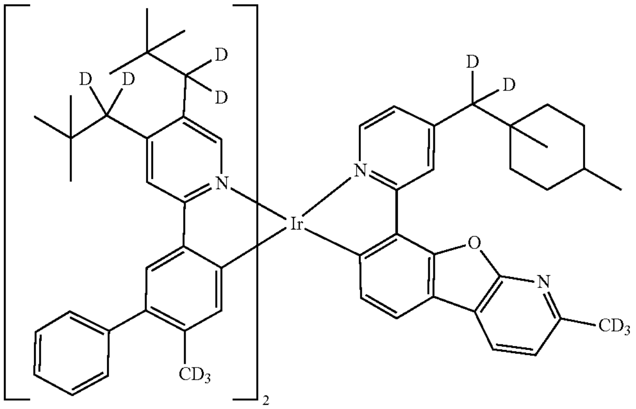
,
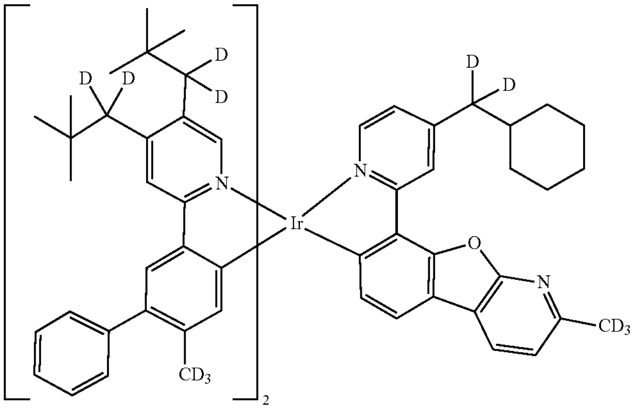
,

-continued
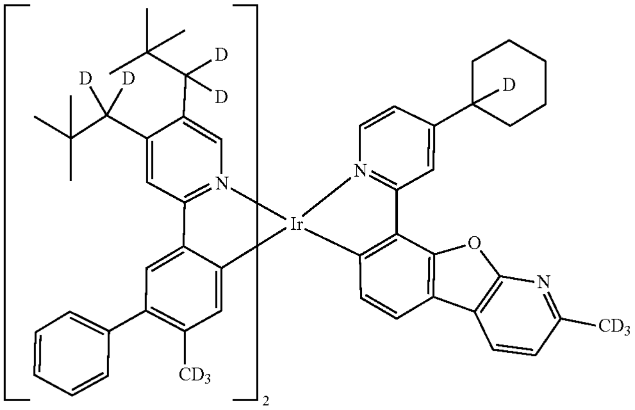
,
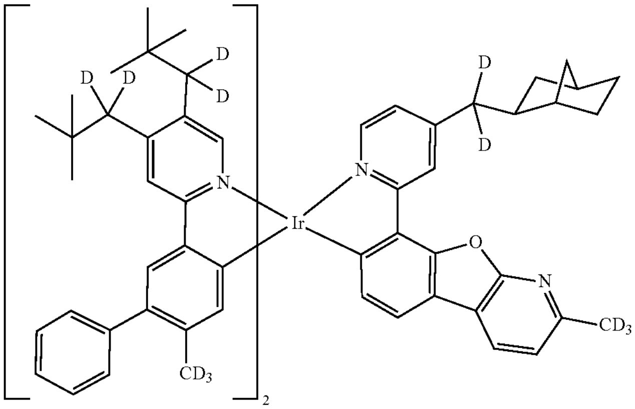
,
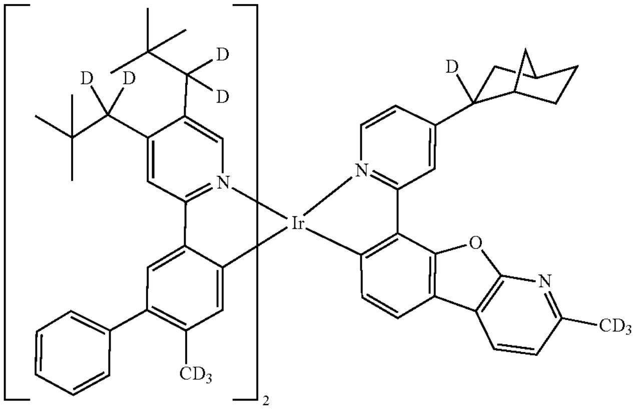
,
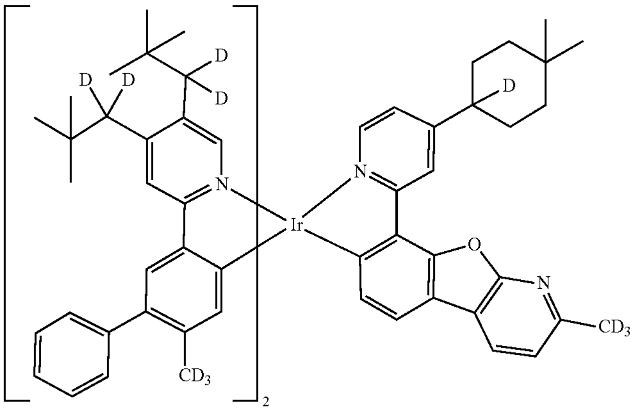
,

-continued
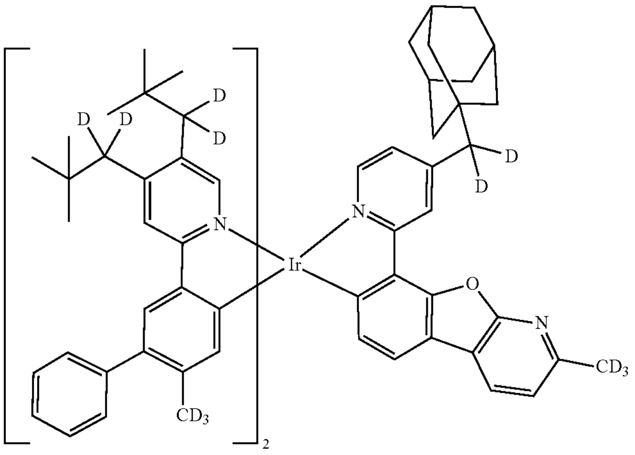
,
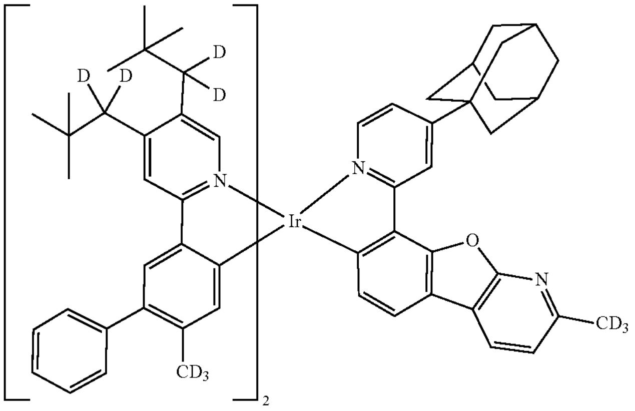
,
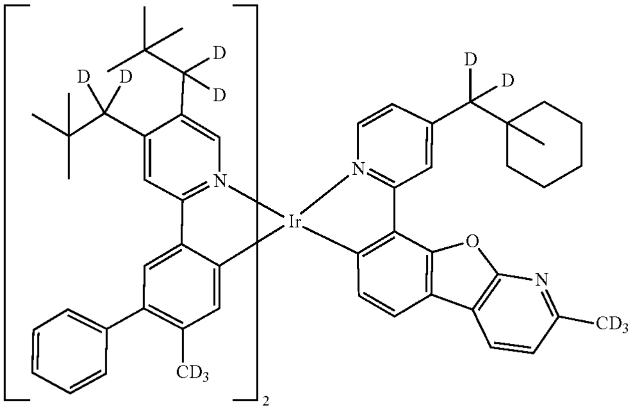
,
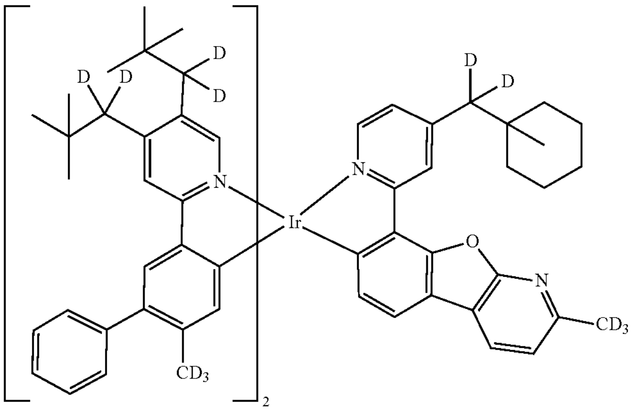
,

-continued
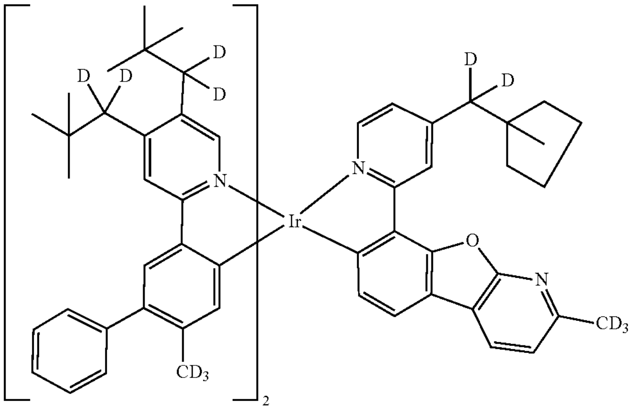
,
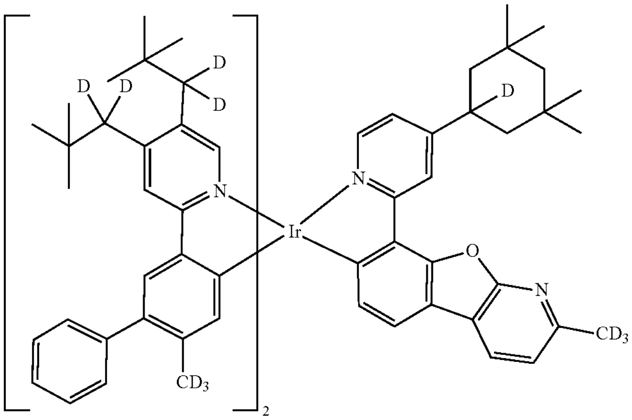
,
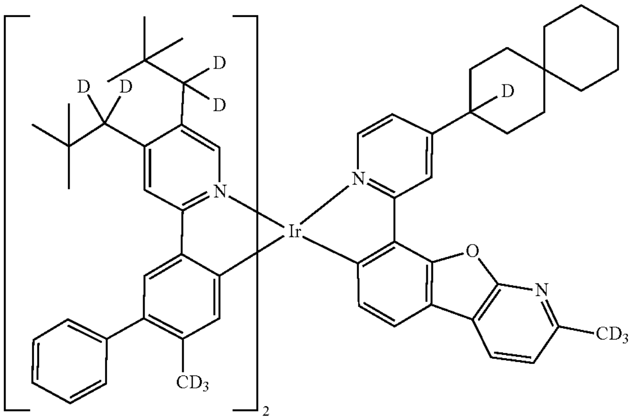
,
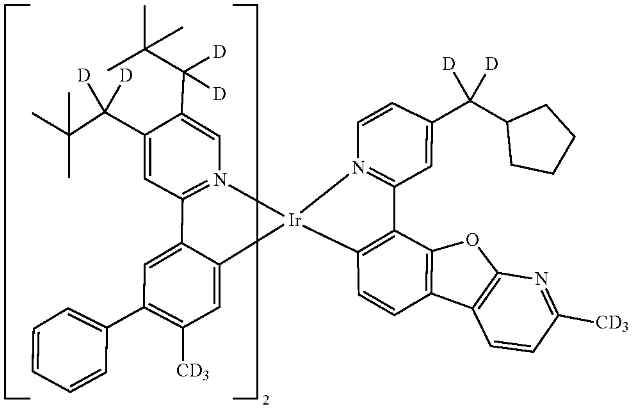
,

-continued
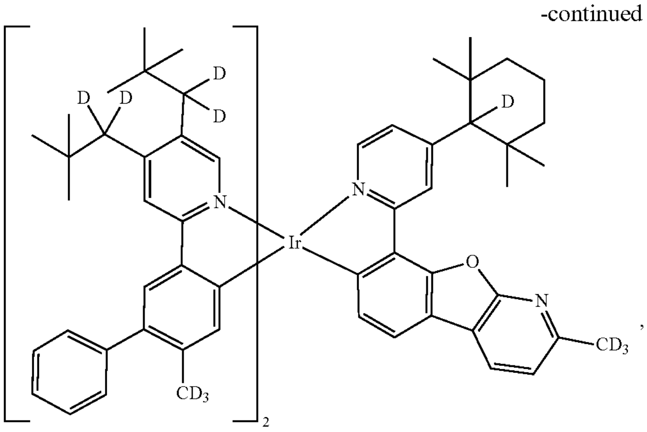
,
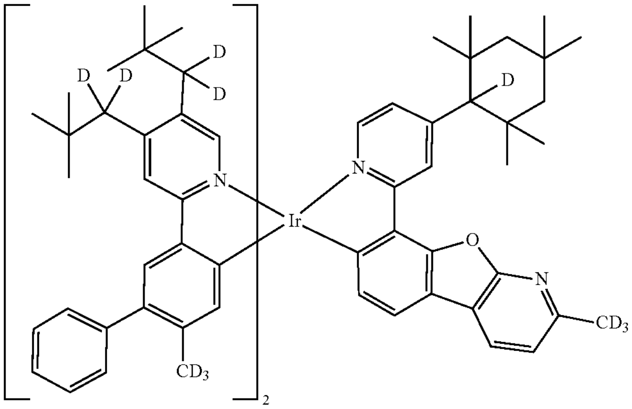
,
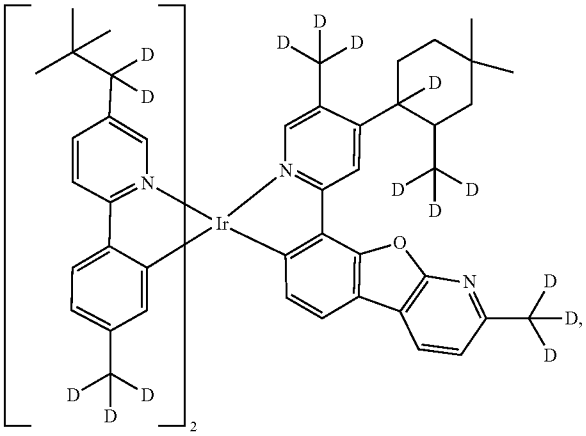
,
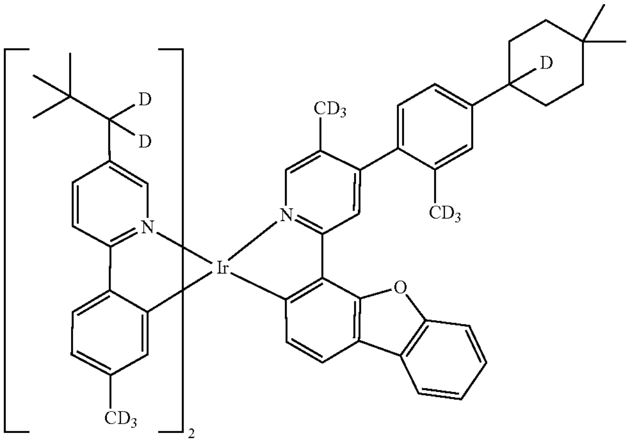
,

-continued
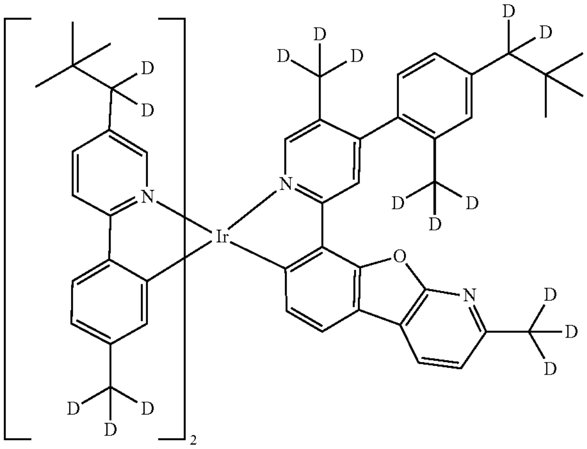
,
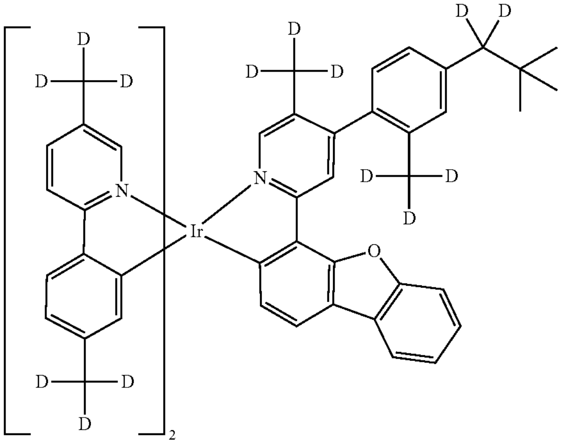
,
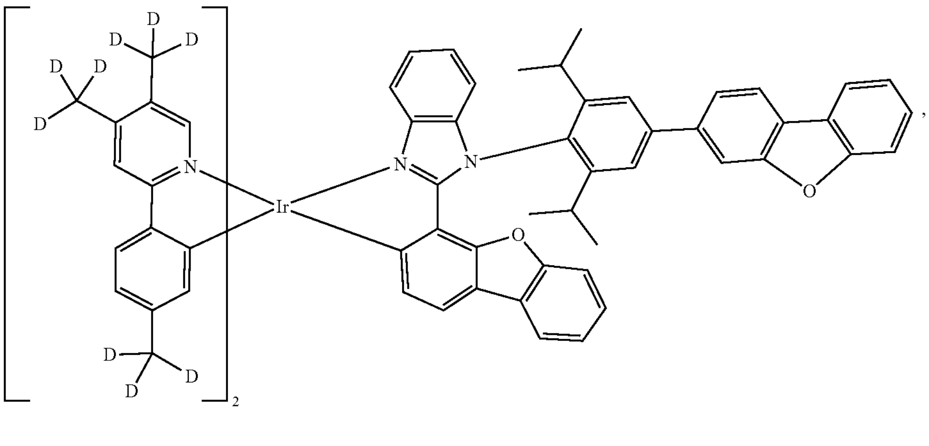
,

-continued
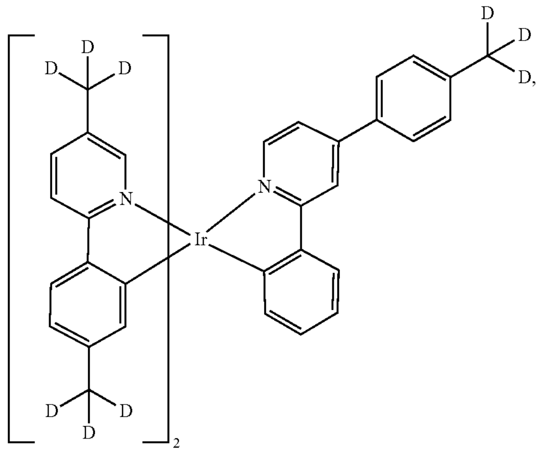
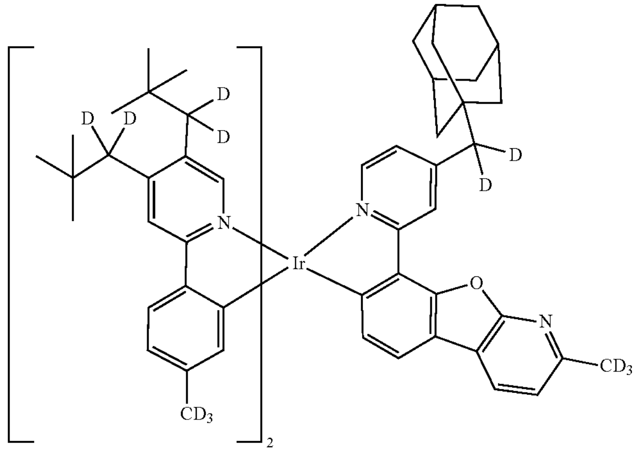
,
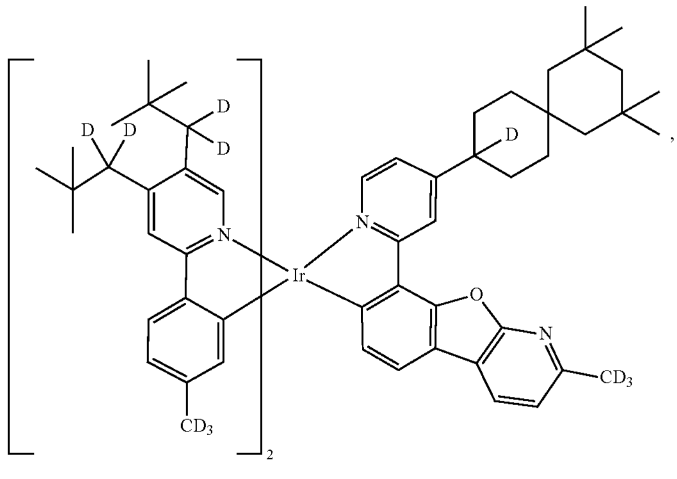
,

-continued
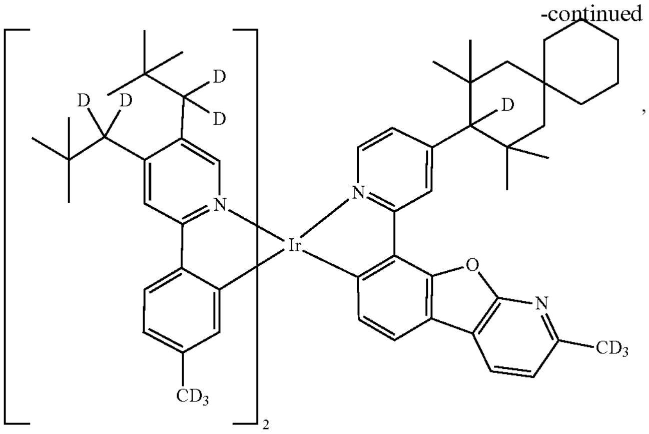
,
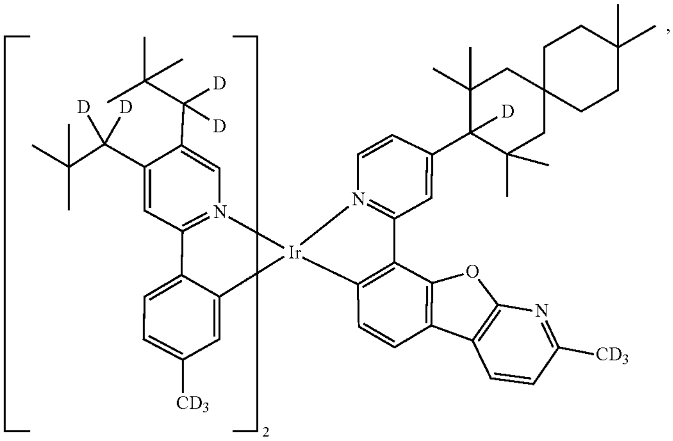
,
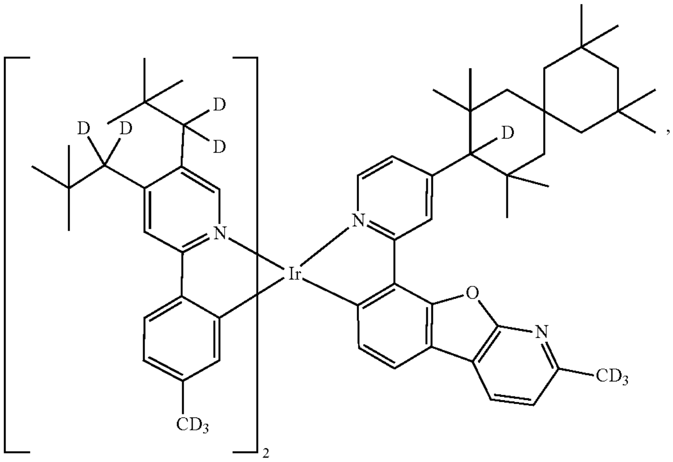
,
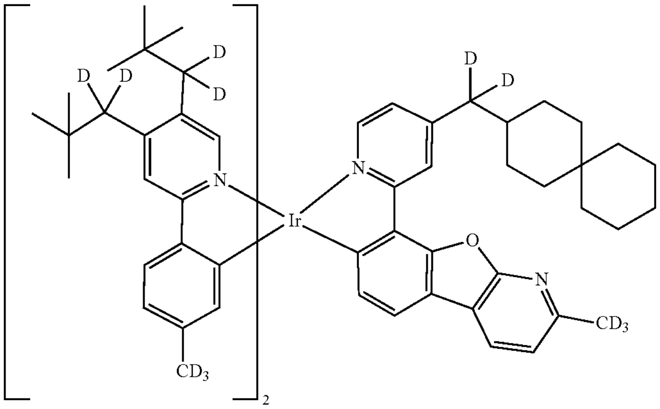
,

-continued
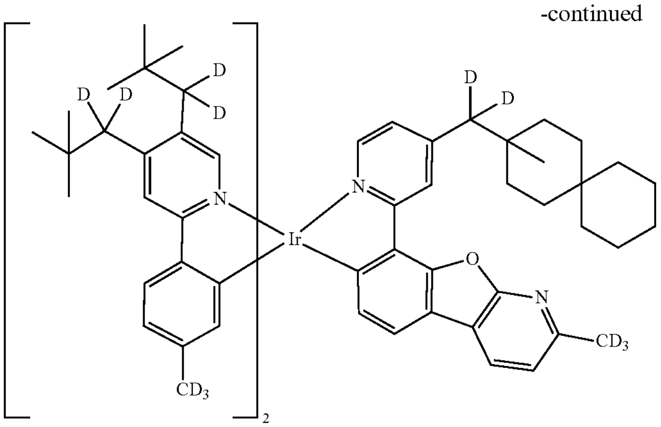
,
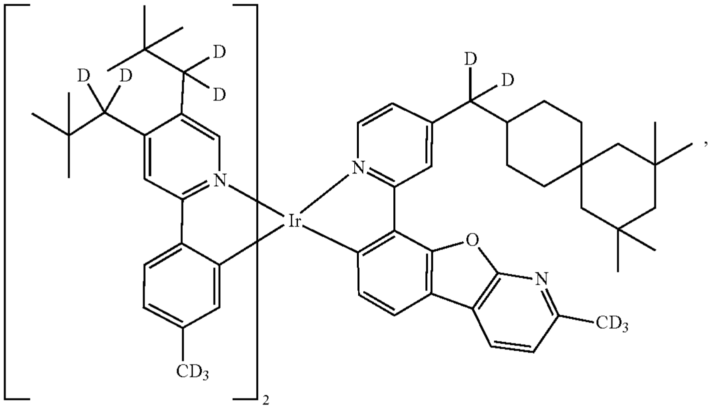
,
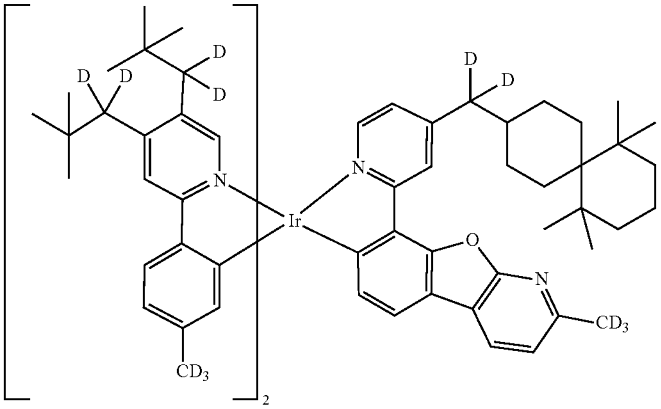
,
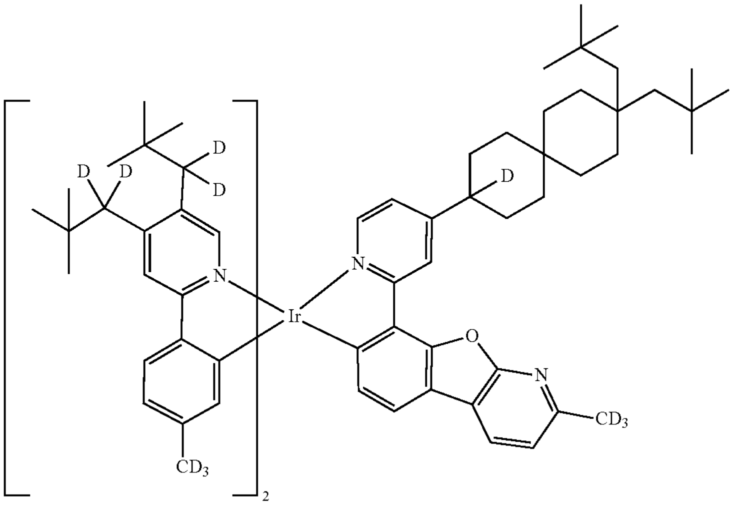
,

-continued
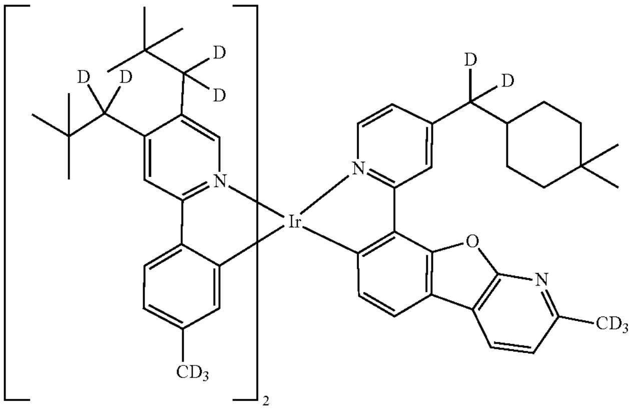
,
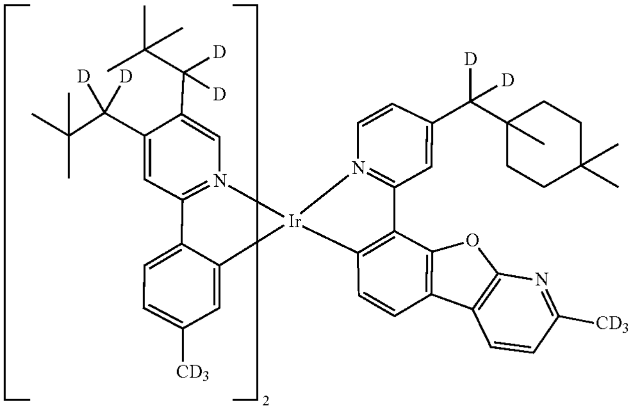
,
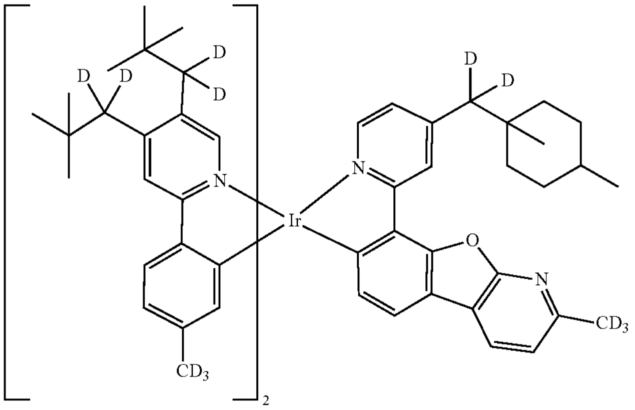
,
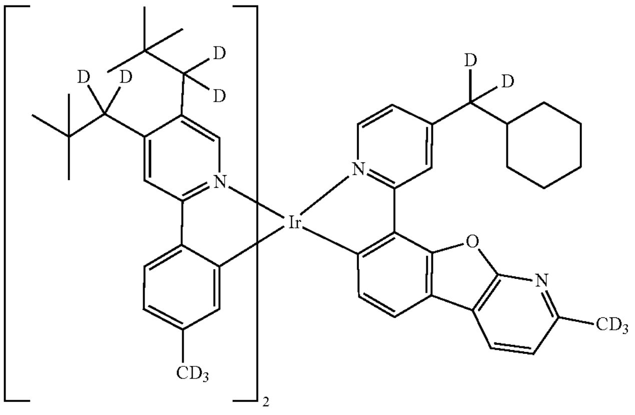
,

-continued
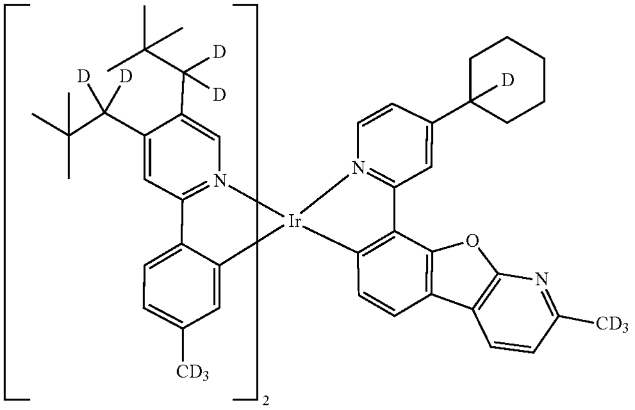
,
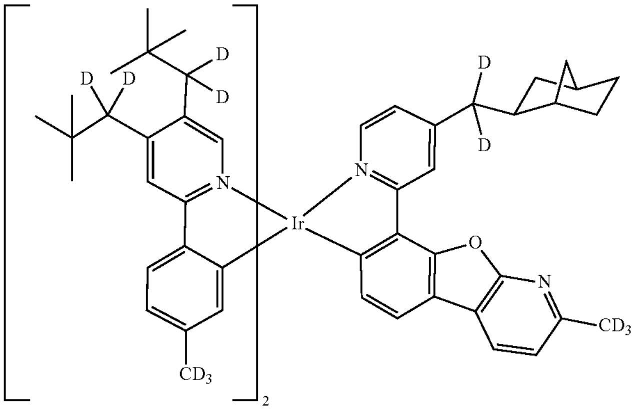
,
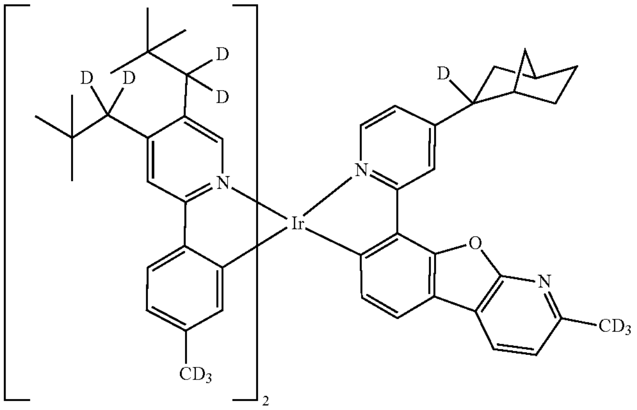
,
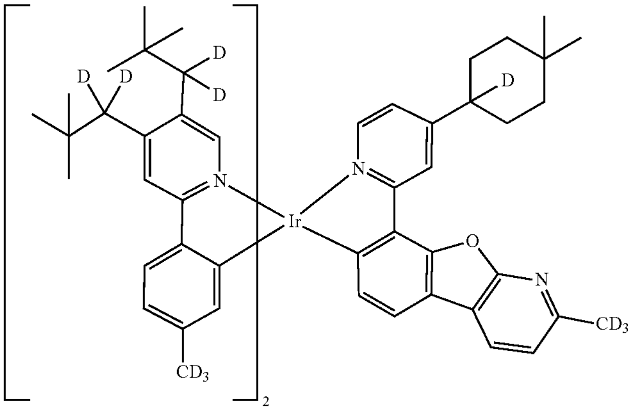
,

-continued
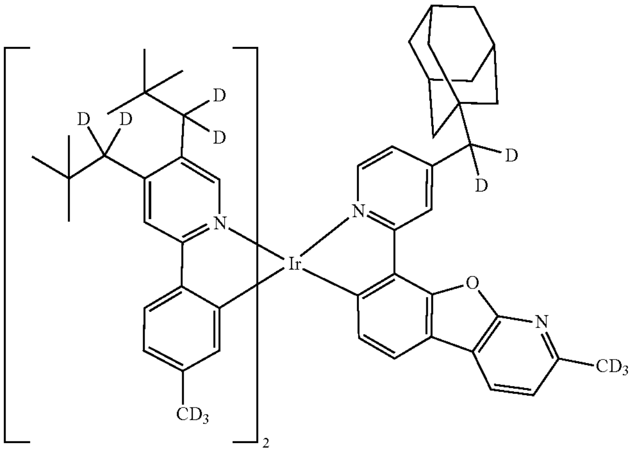
,
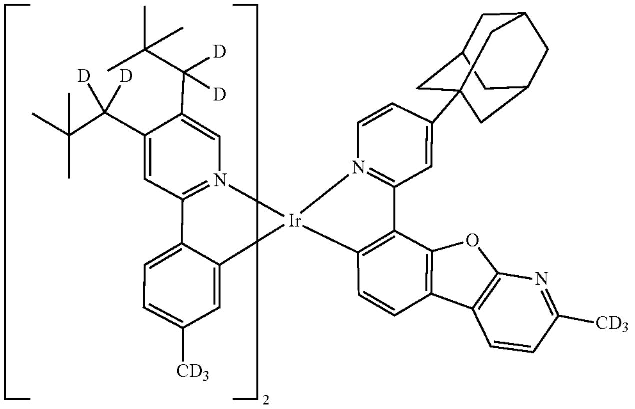
,
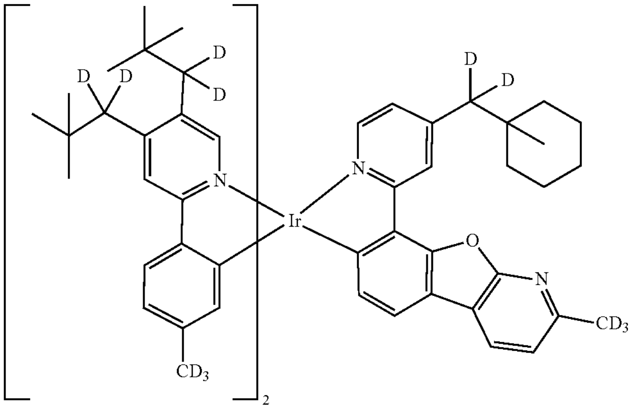
,
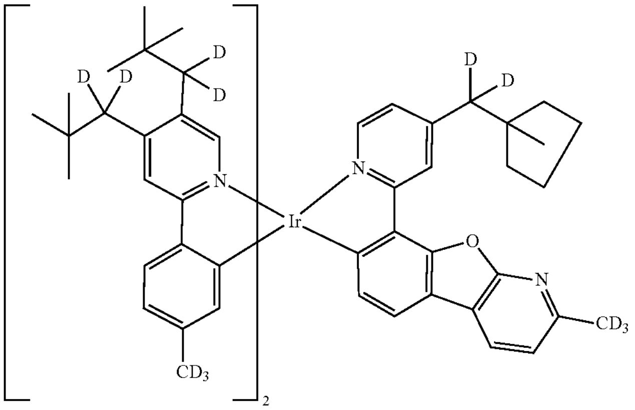
,

-continued
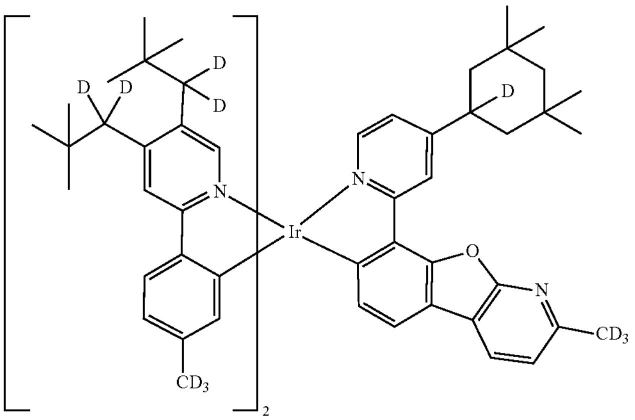
,
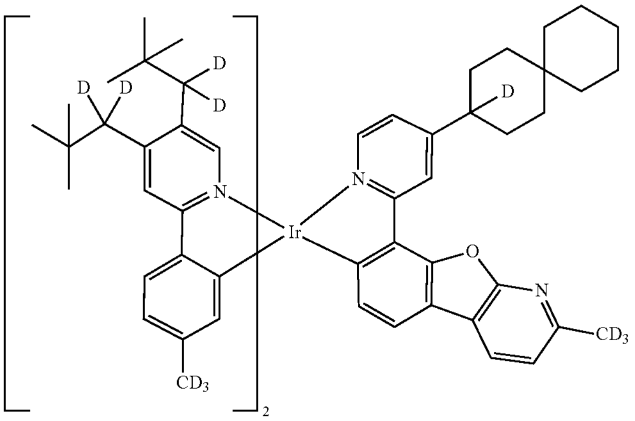
,
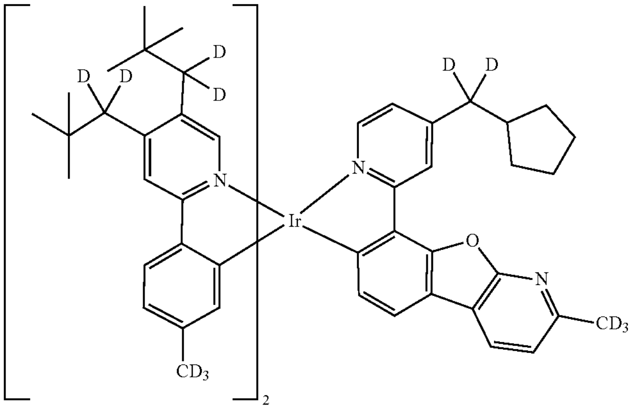
,
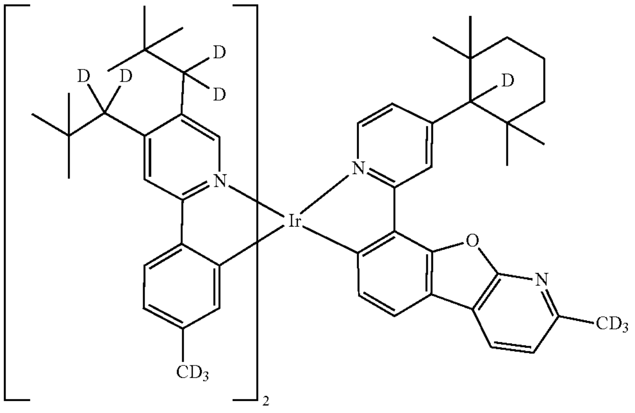
,

-continued
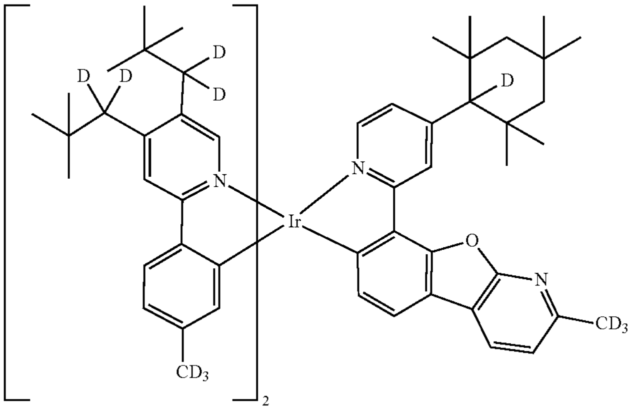
,
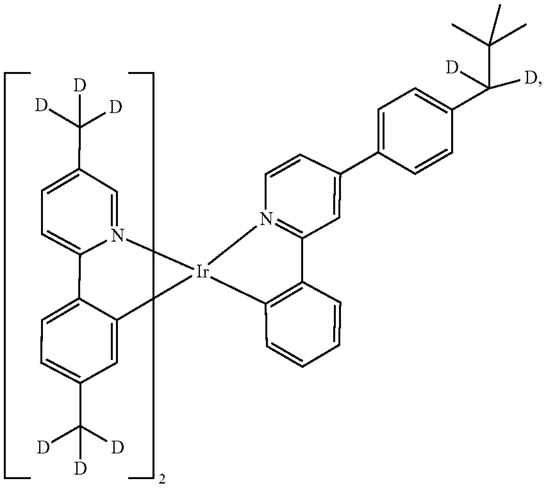
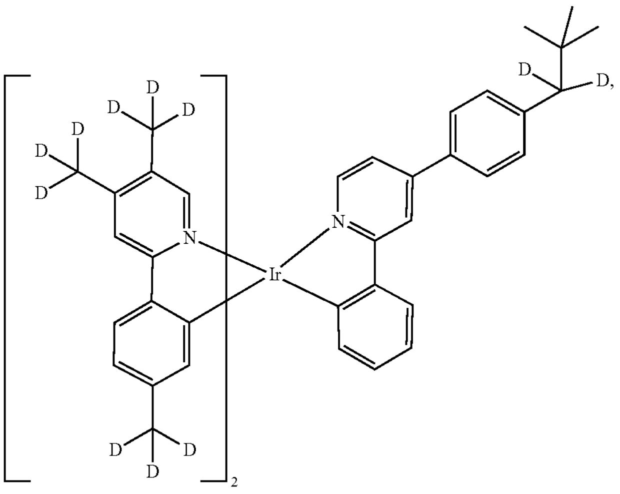

-continued
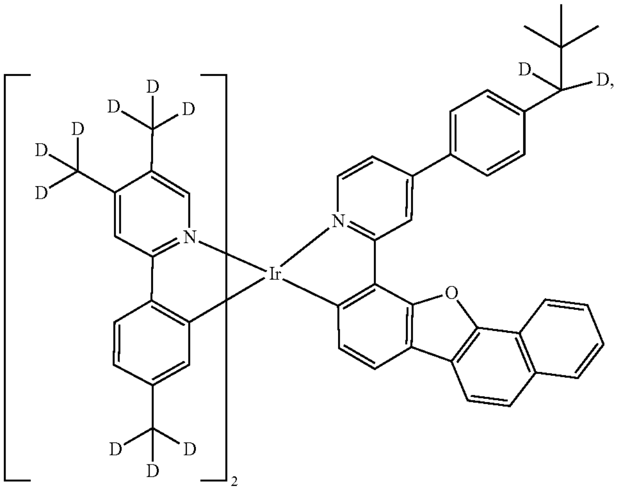
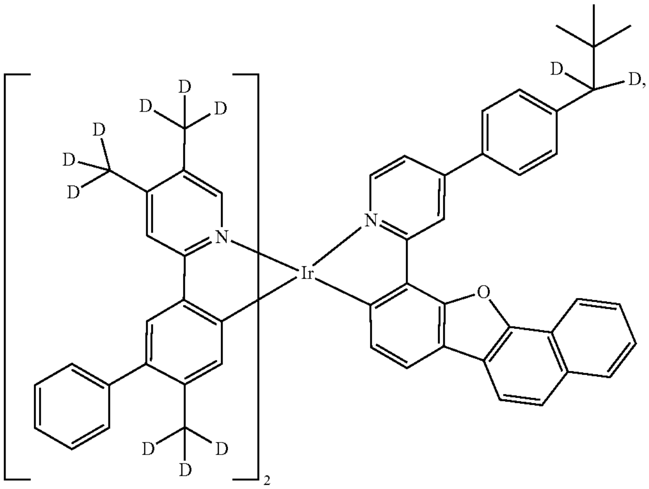
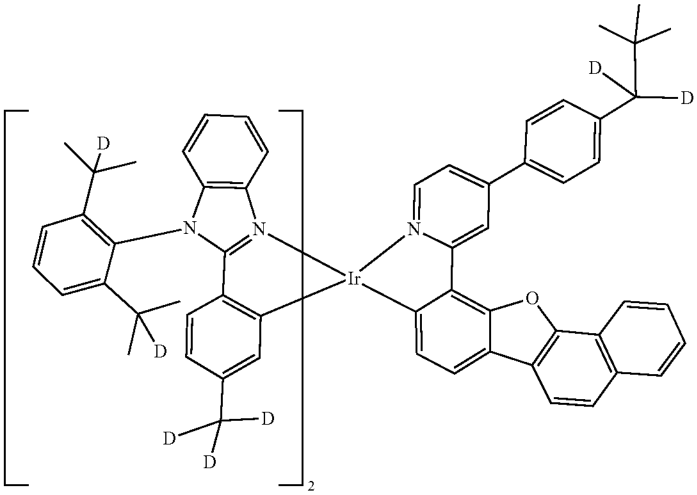
,

-continued
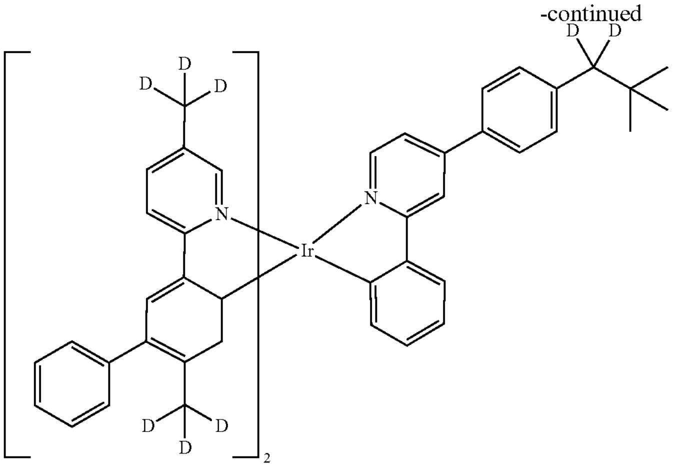
,
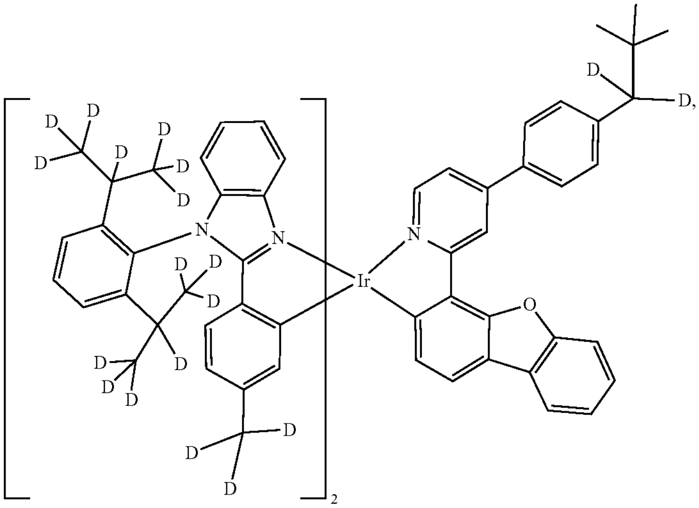
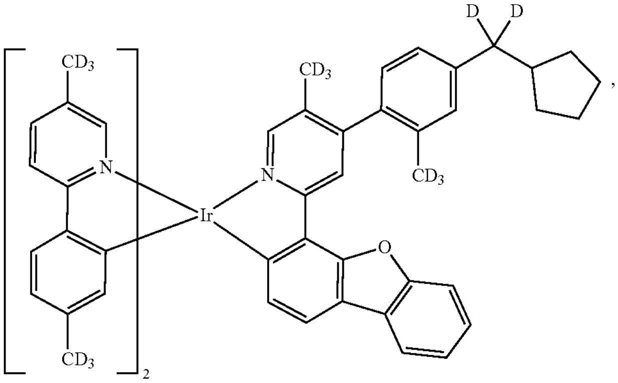
,
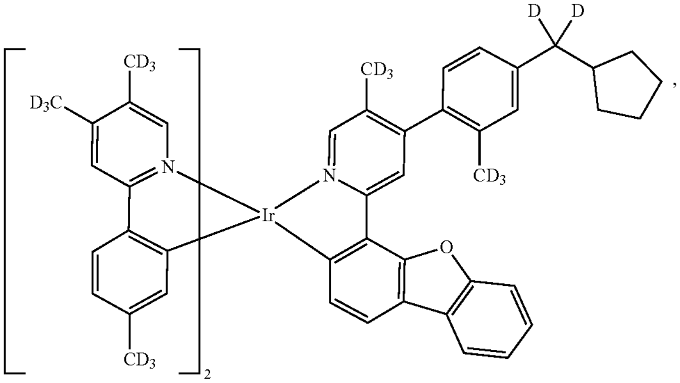
,

-continued
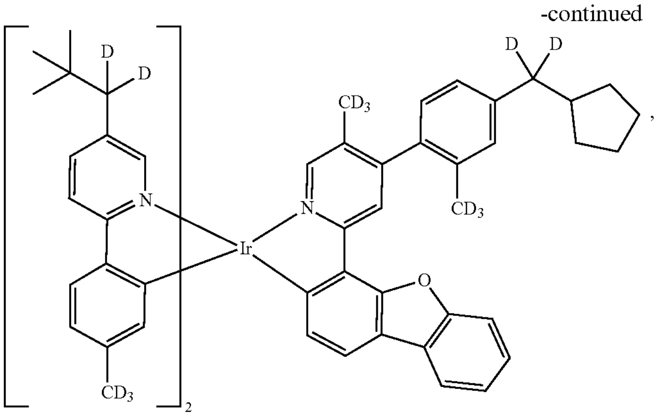
,
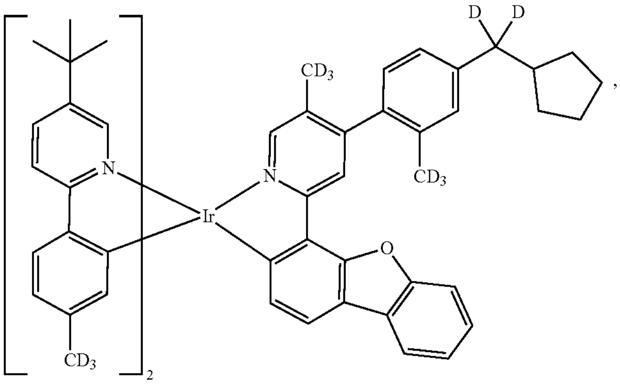
,
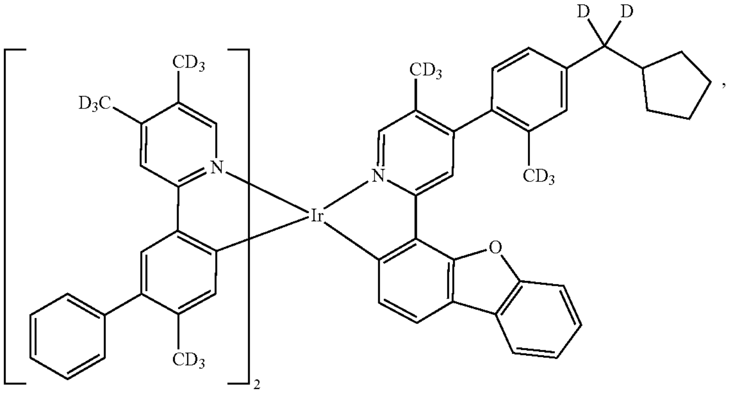
,
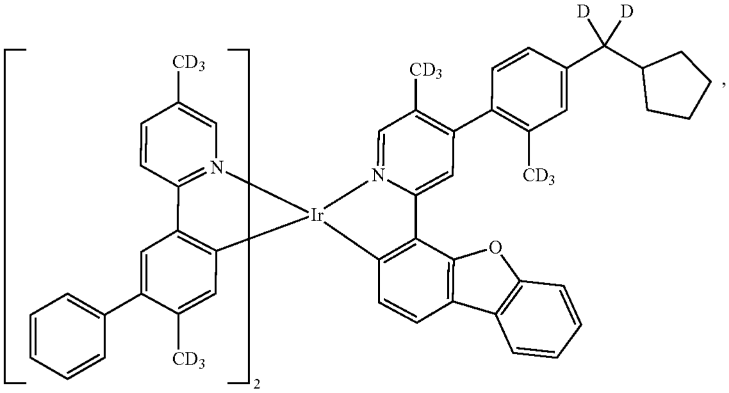
,

-continued
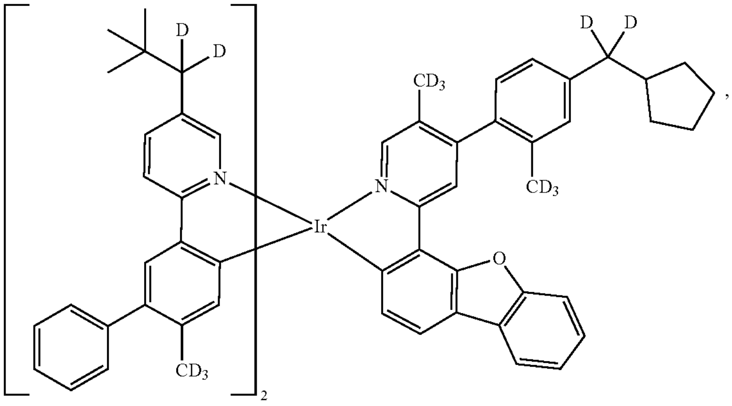
,
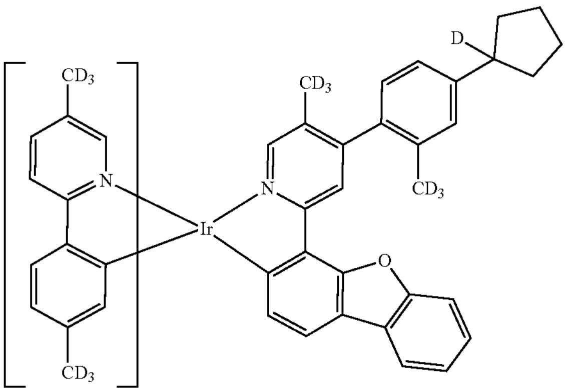
,
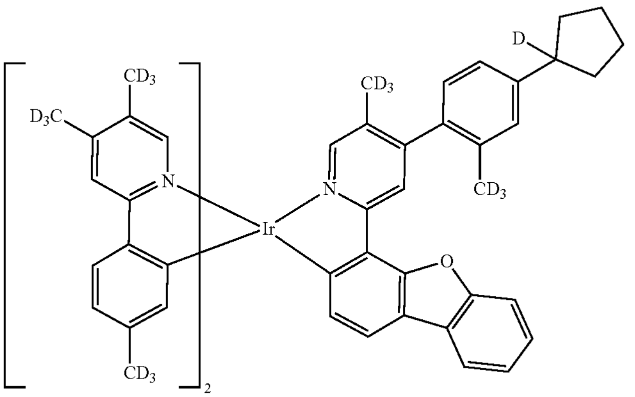
,
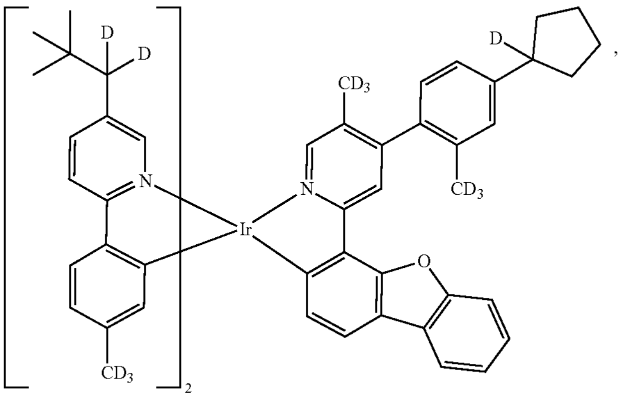
,

-continued
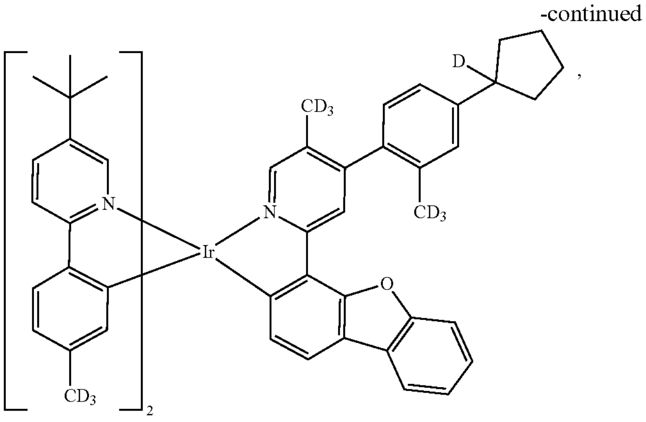
,
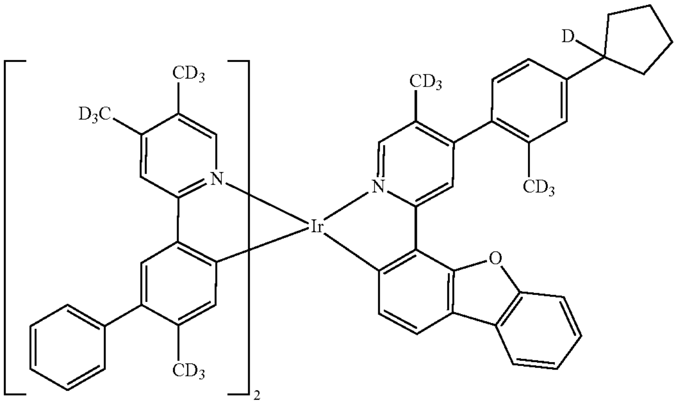
,
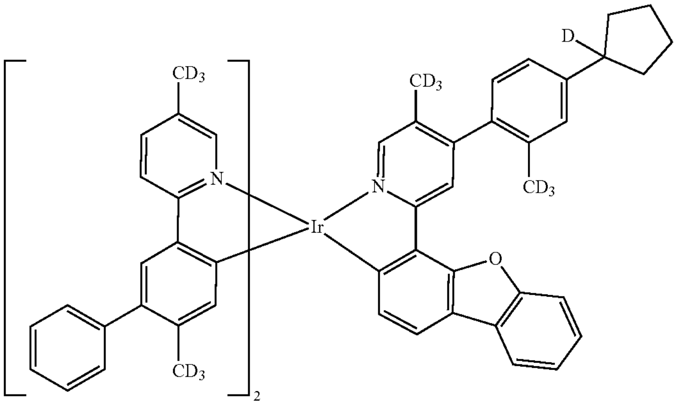
,
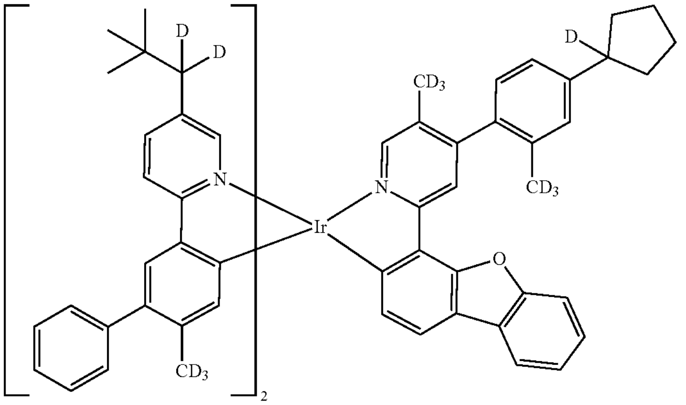
,

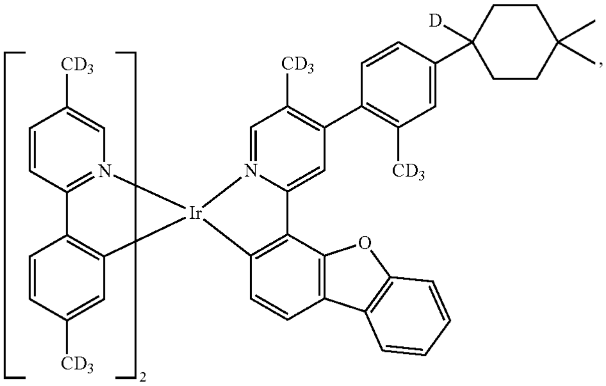,
,
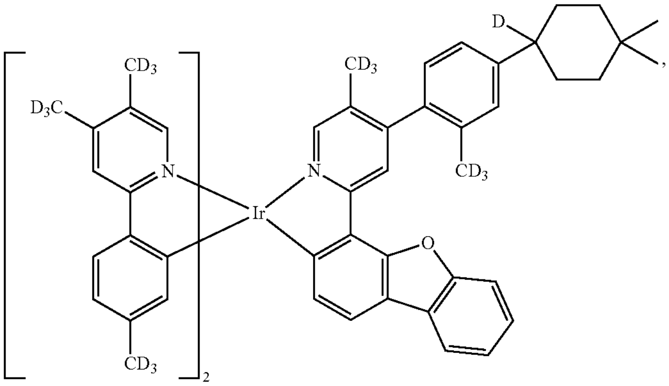,
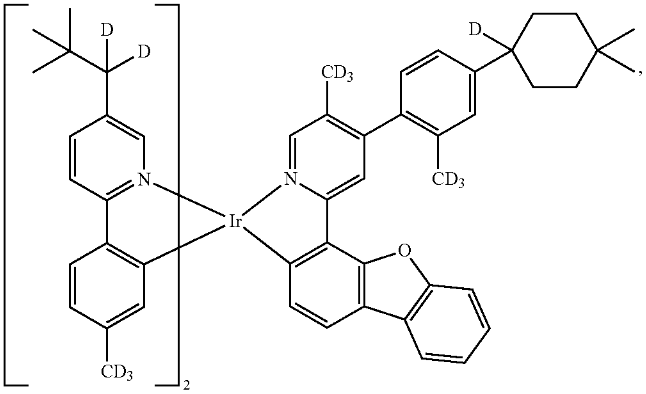,
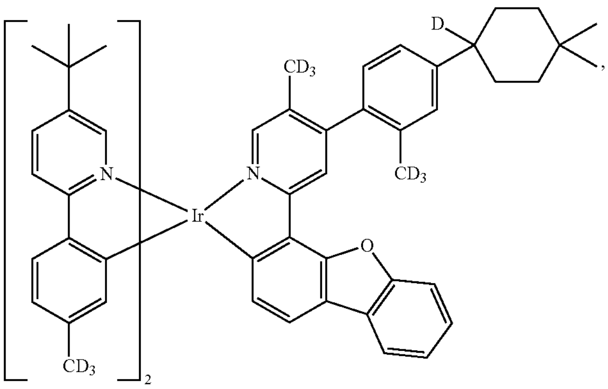,

-continued
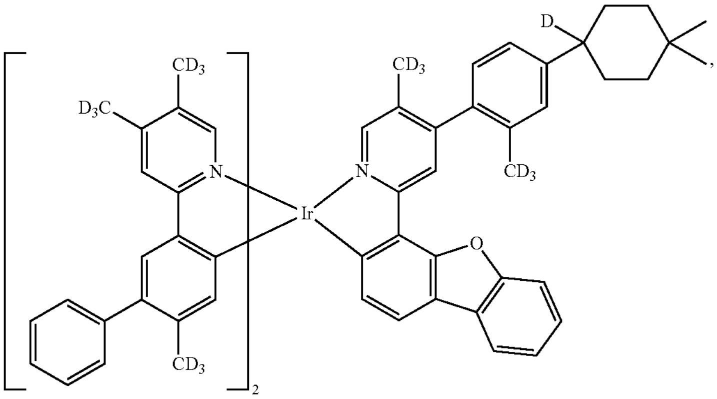
,
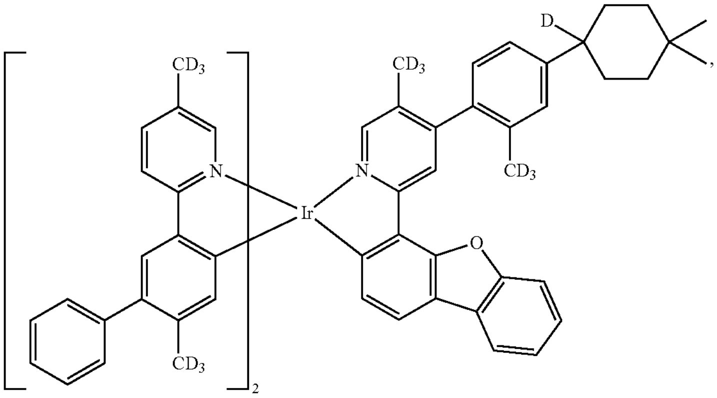
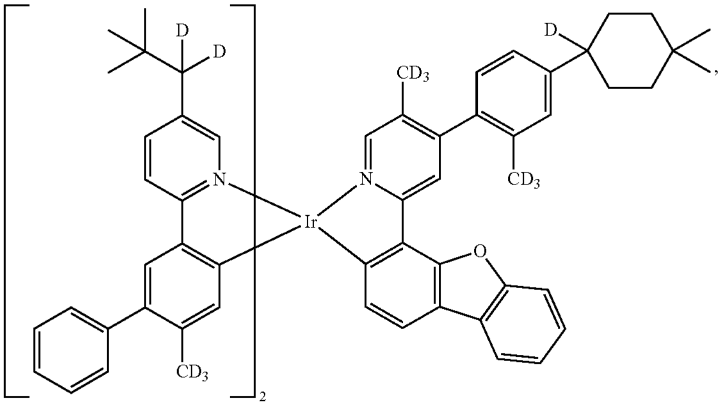
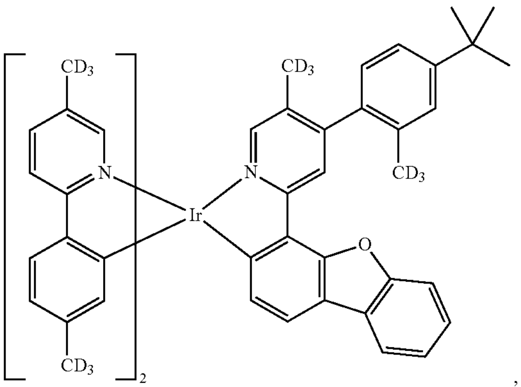
,
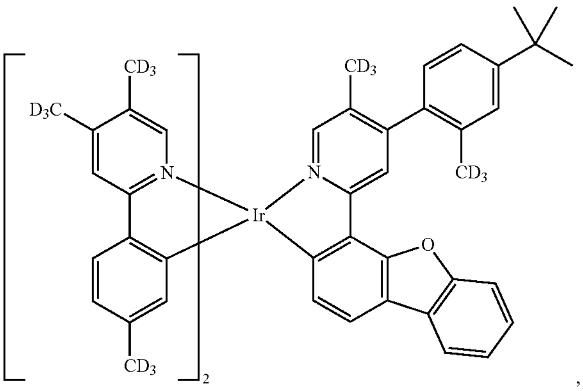
,

-continued
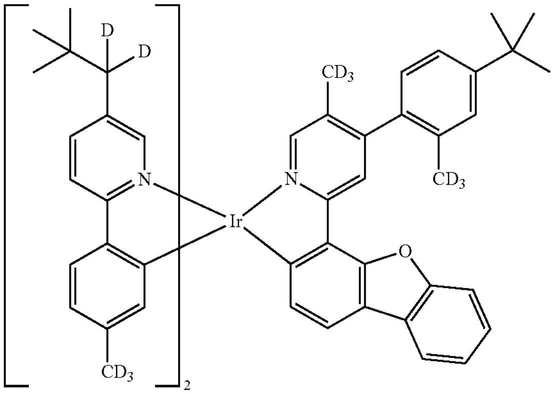
,
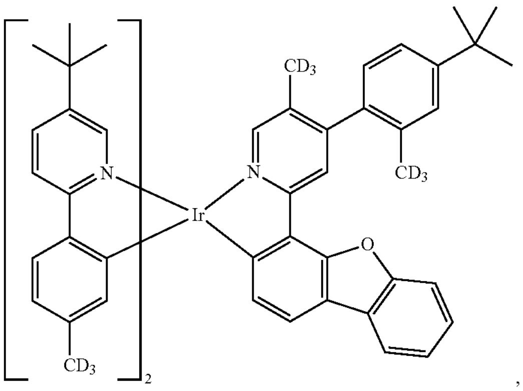
,
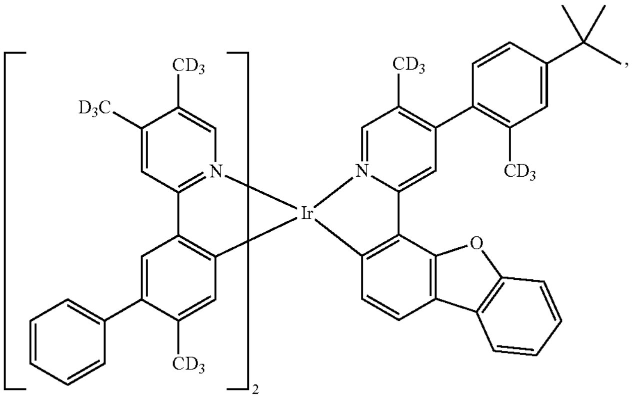
,
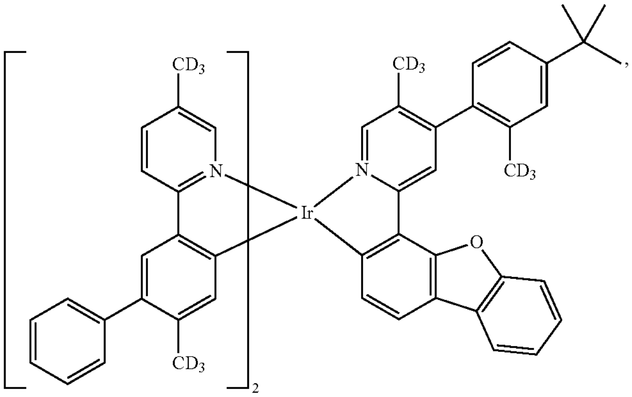
,
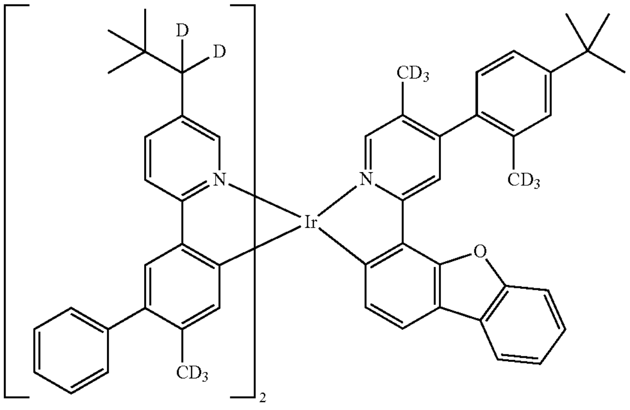

-continued
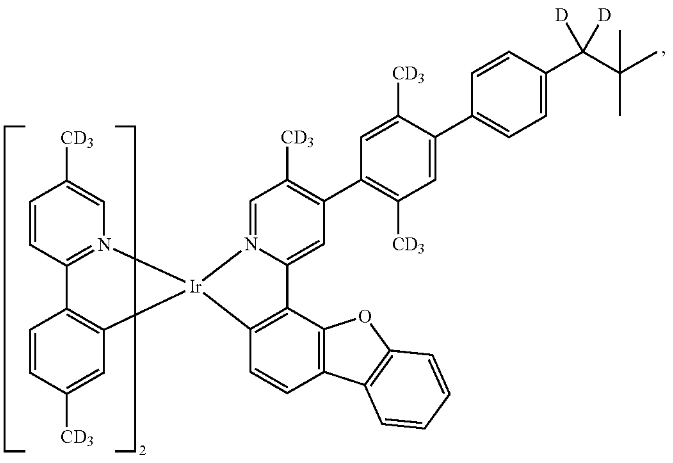
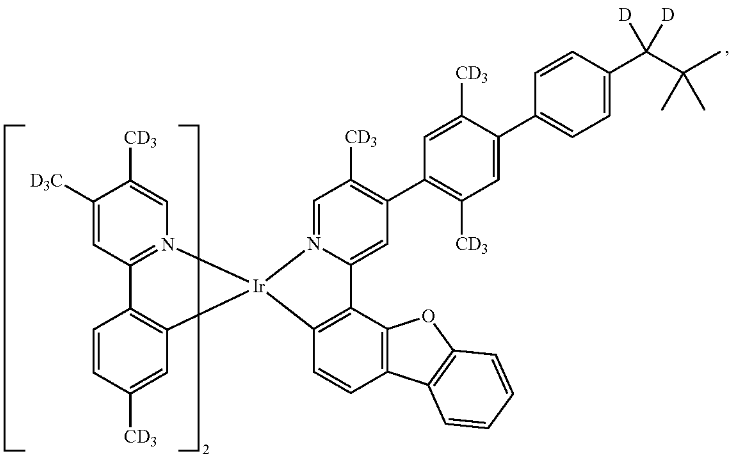
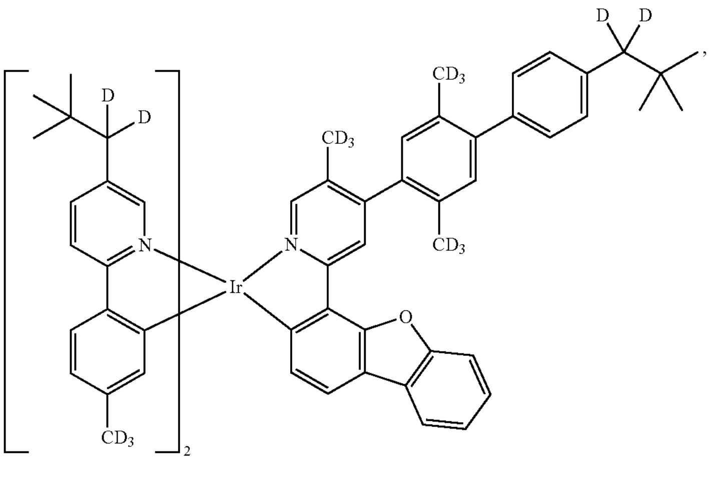

-continued
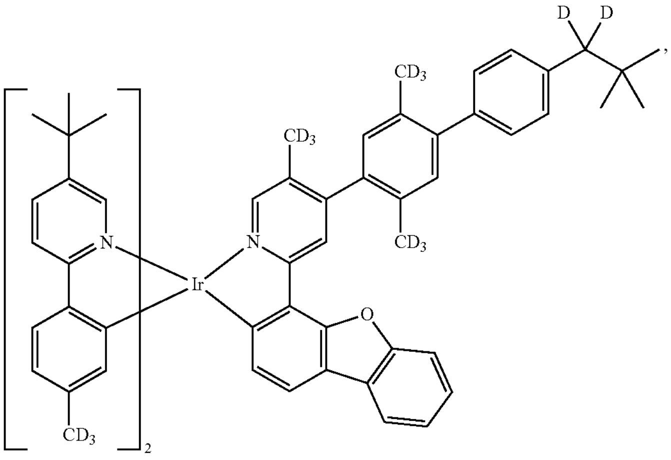
,
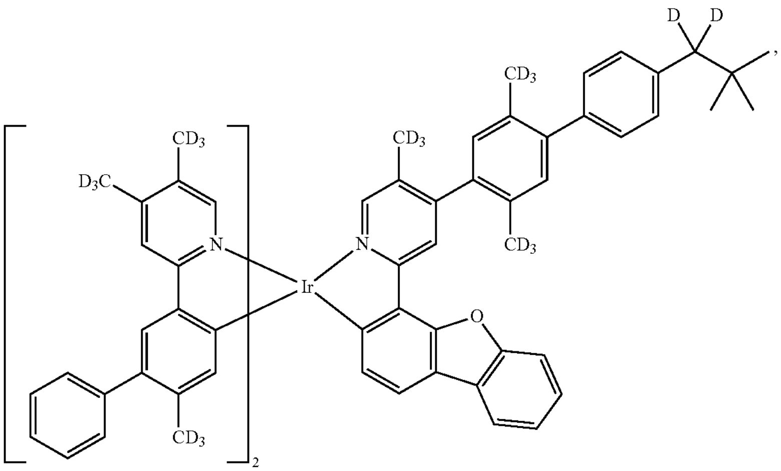
,
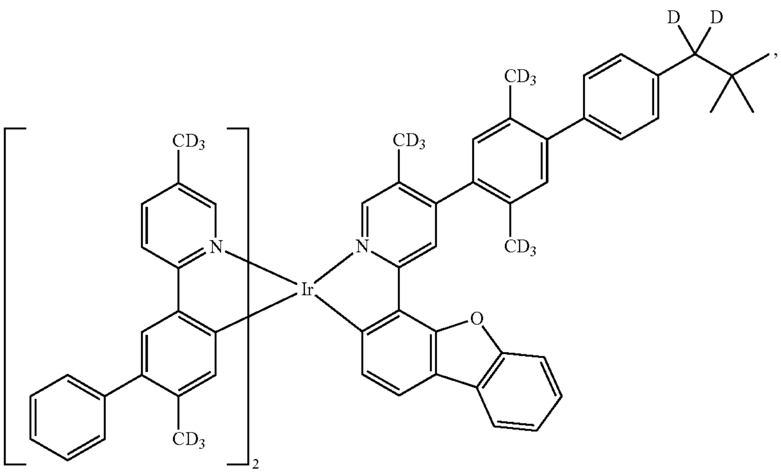
,

-continued
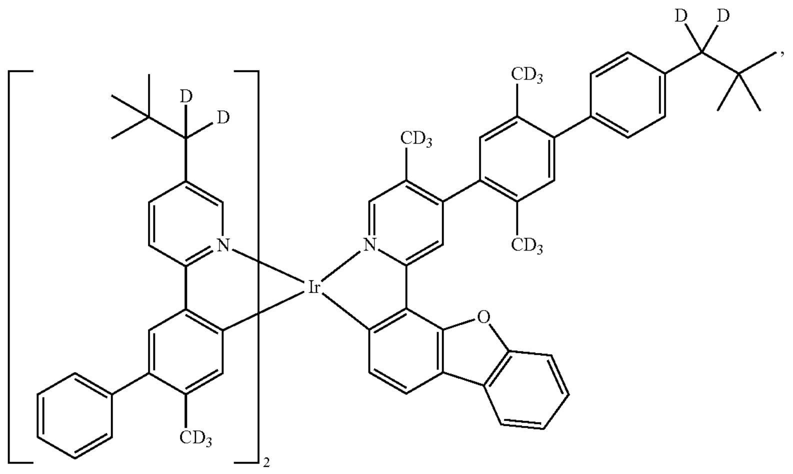
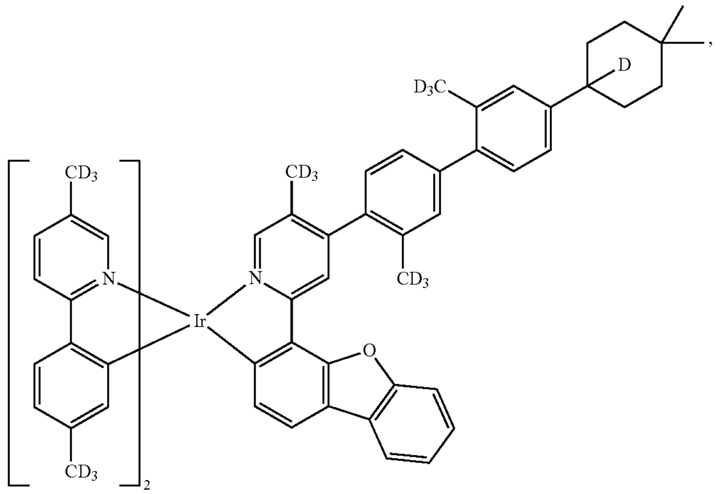
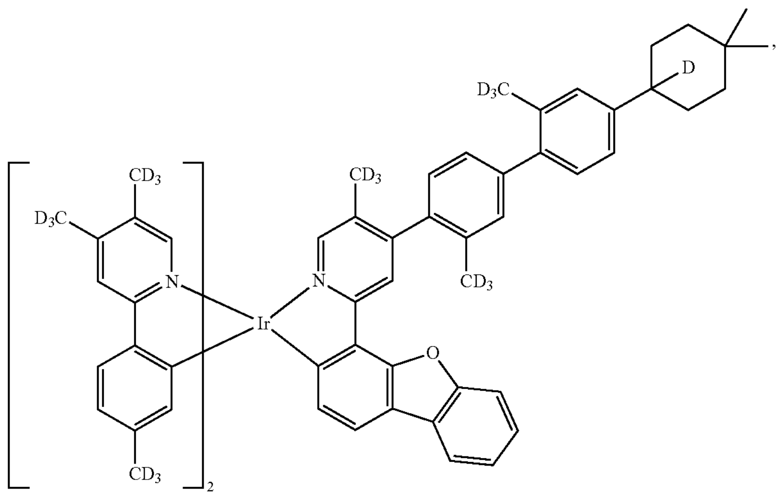

-continued
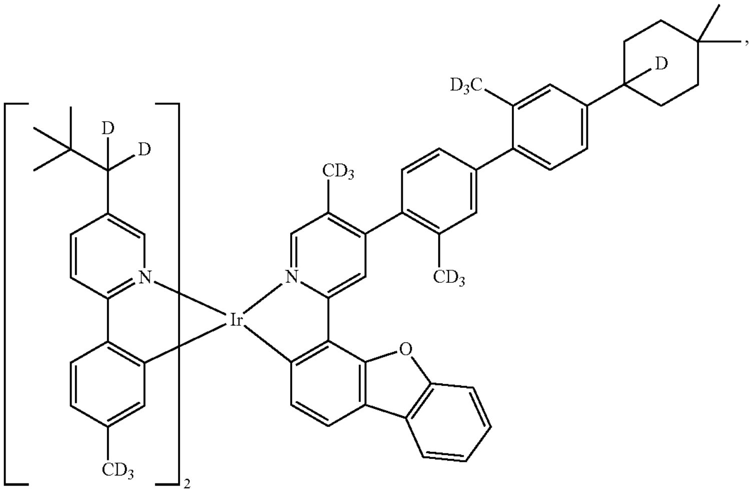
,
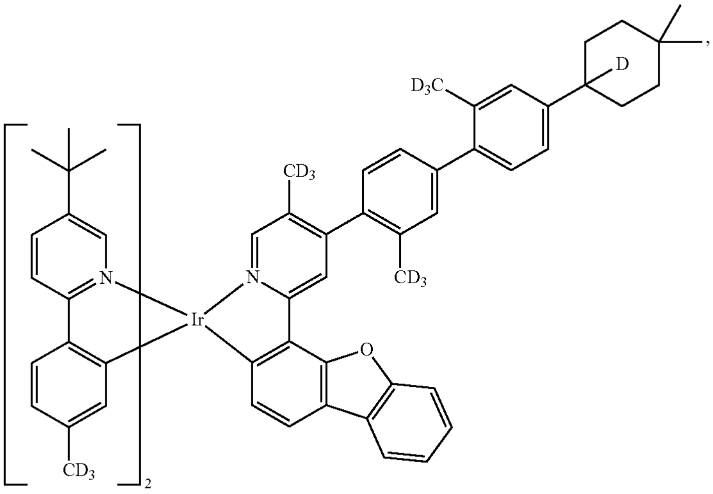
,
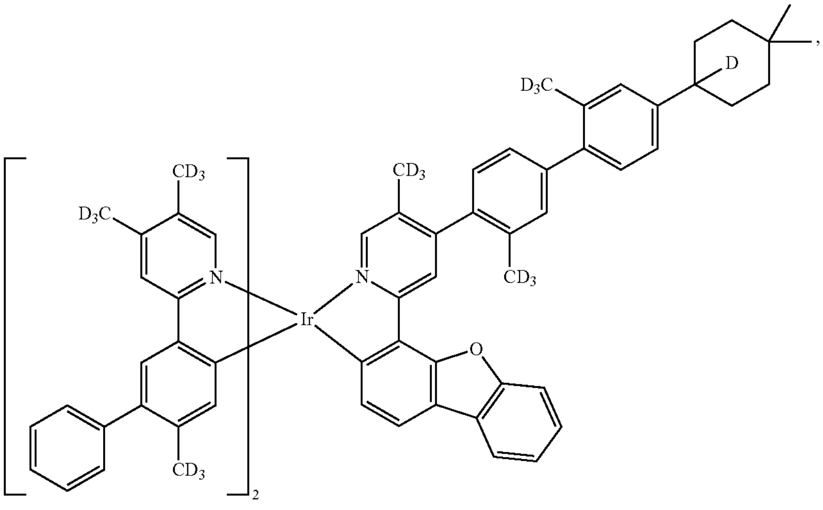
,

-continued
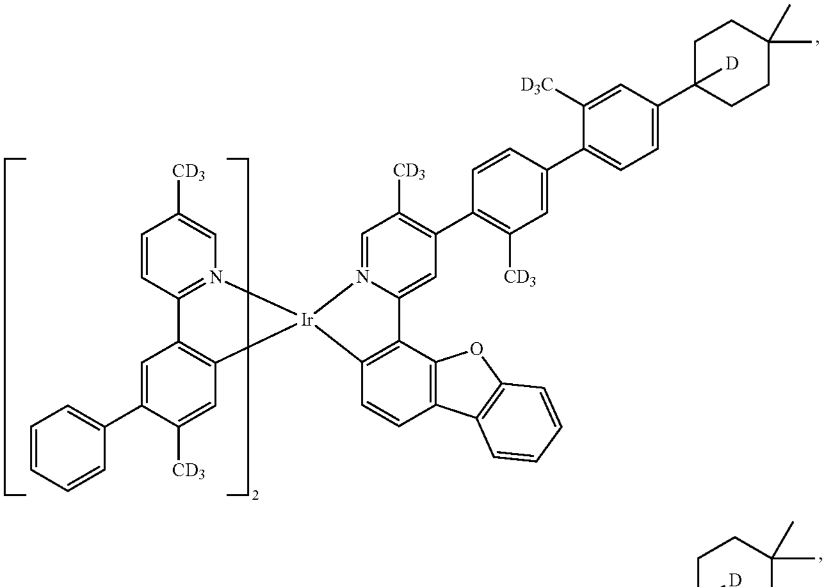
,
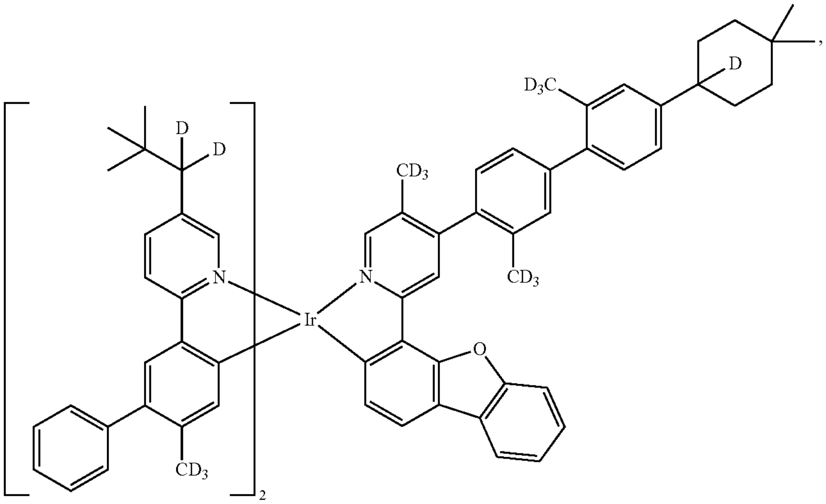
,
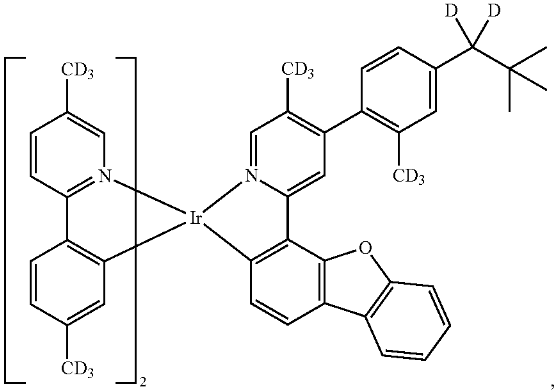
,
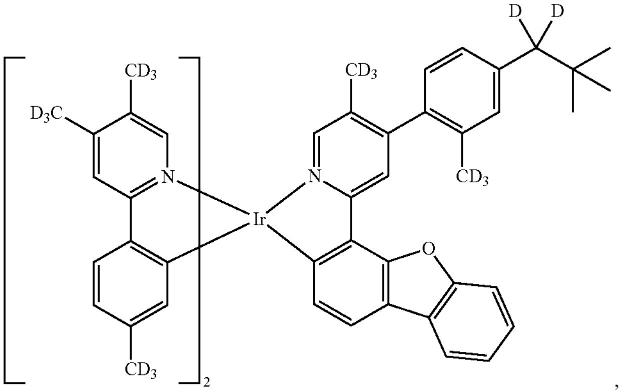
,

-continued
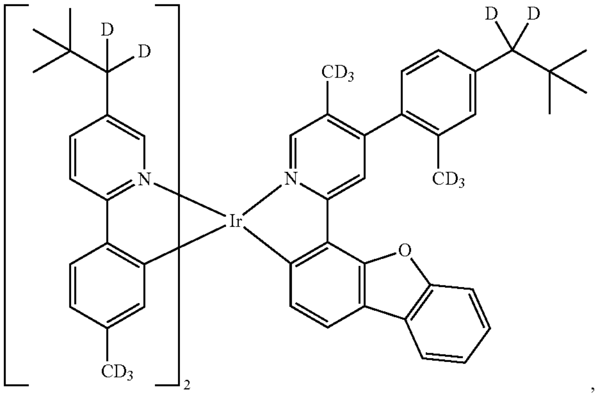
,
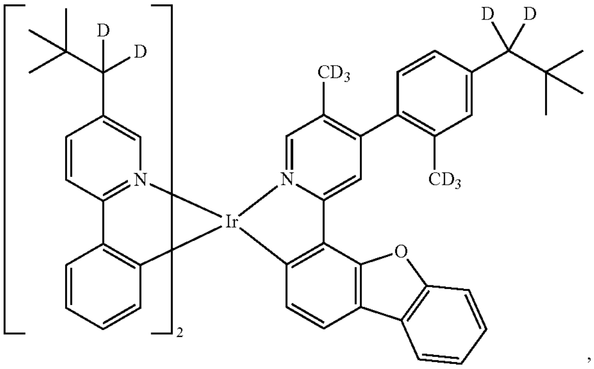
,
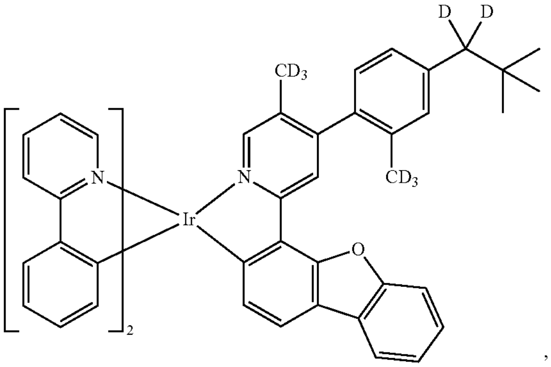
,
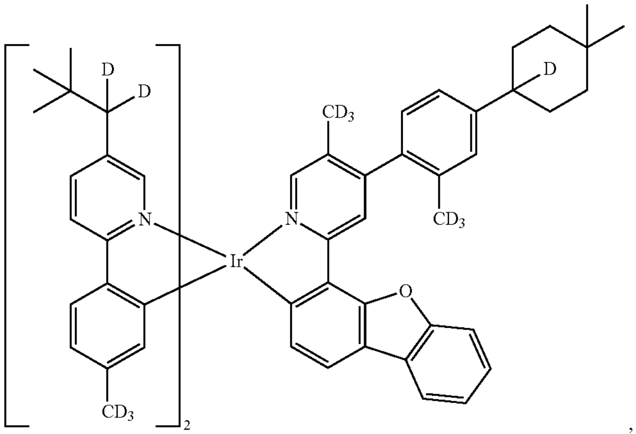
,
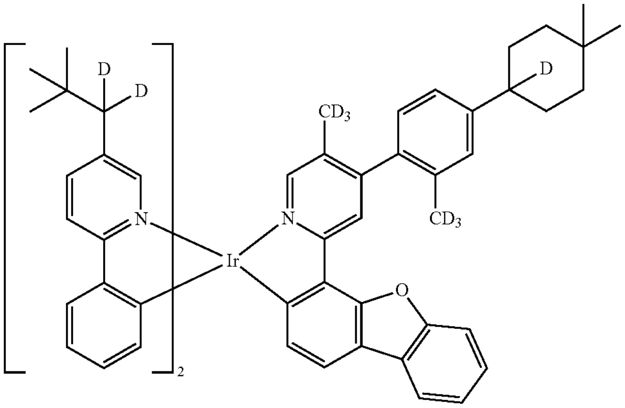
,
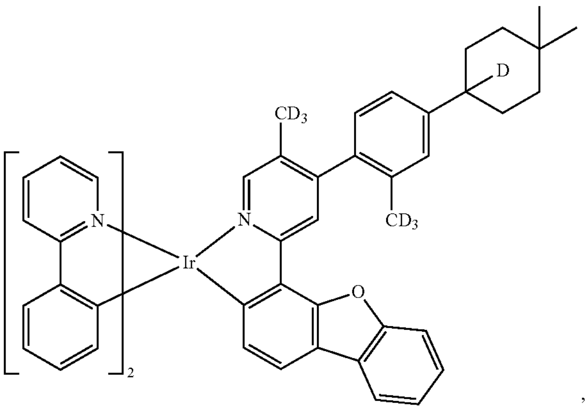
,
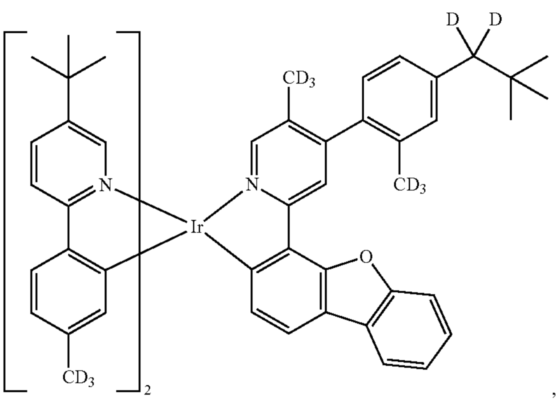
, -continued
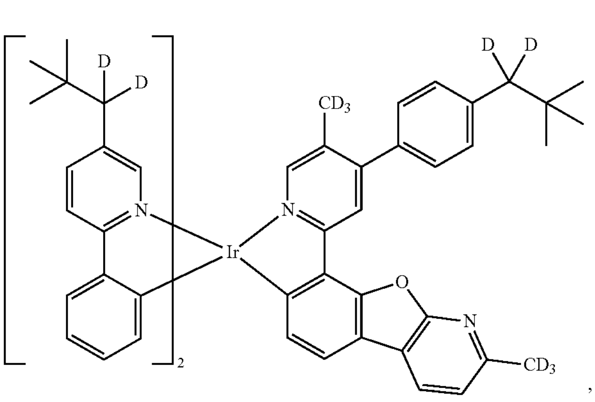
,
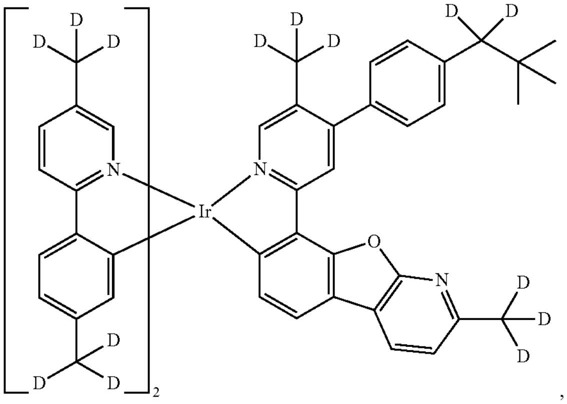
,
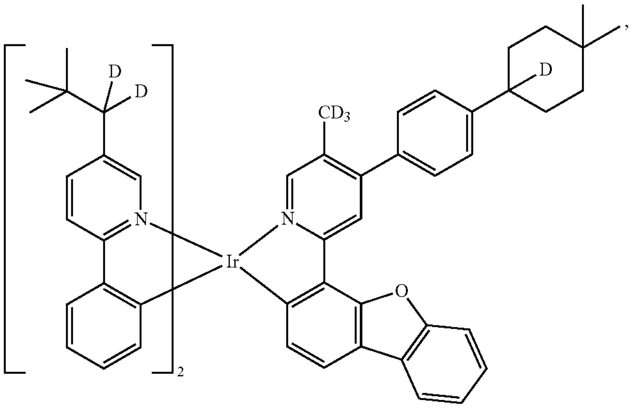
,
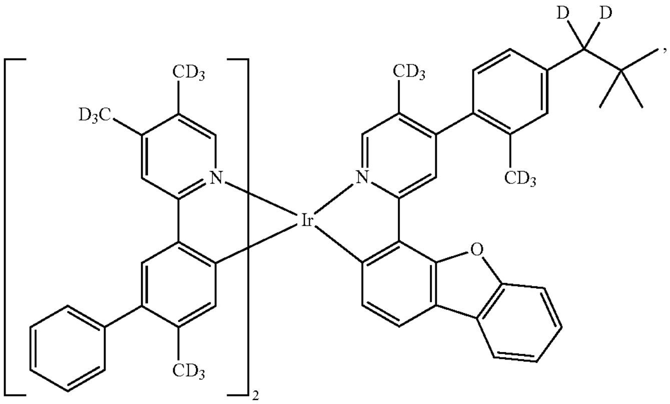
,
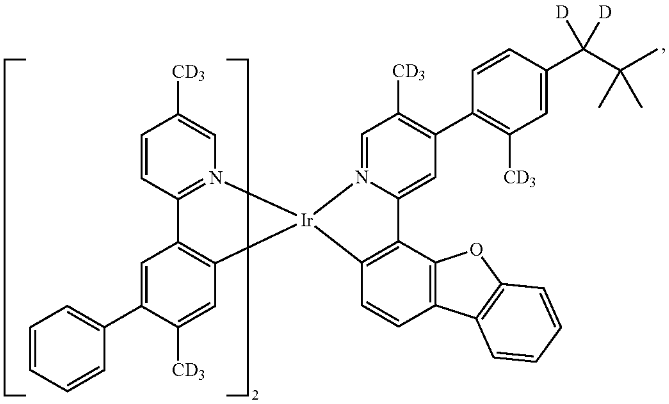
, -continued
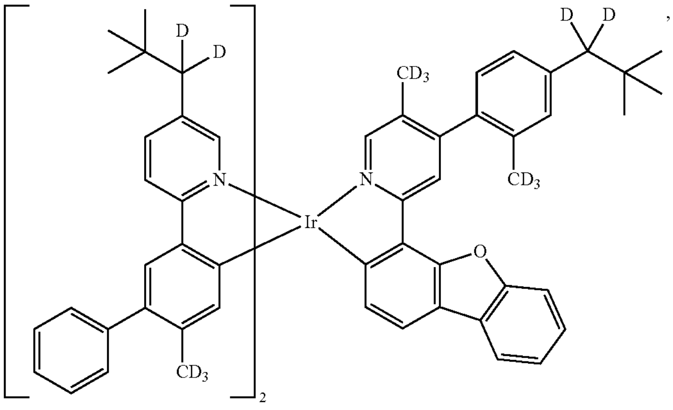
,
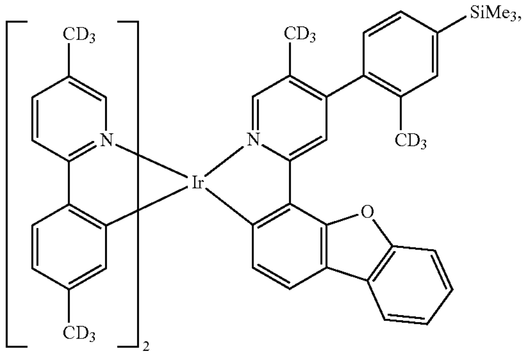
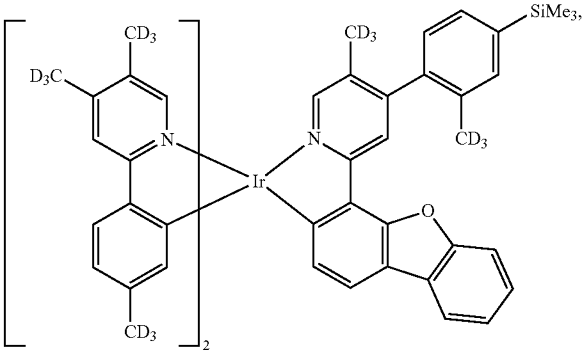
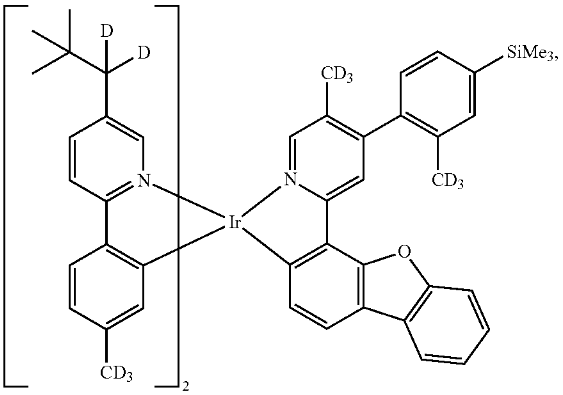
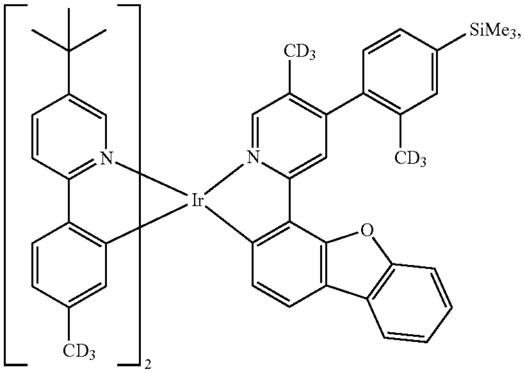
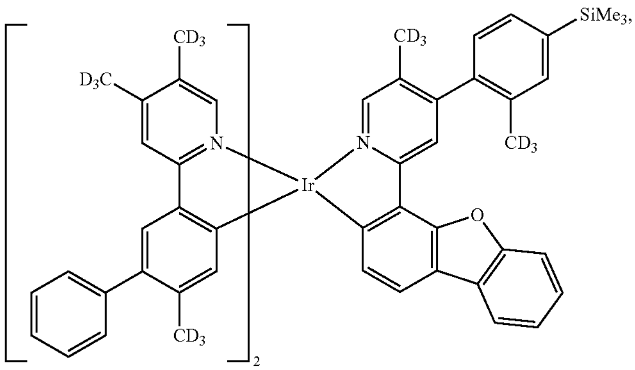
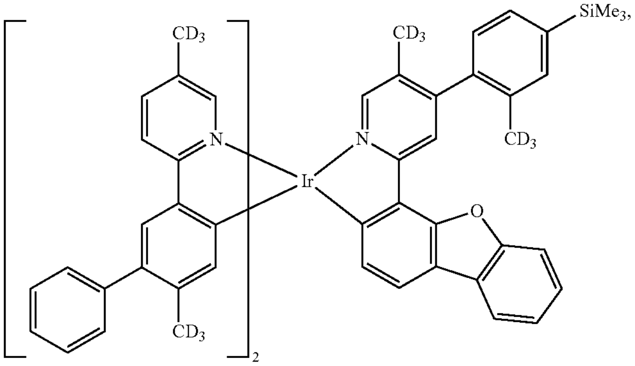

-continued
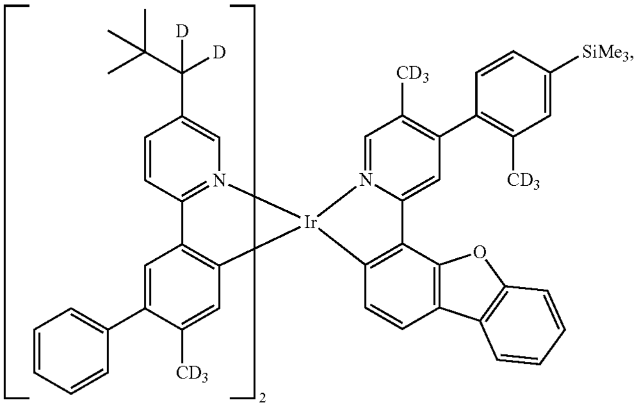,
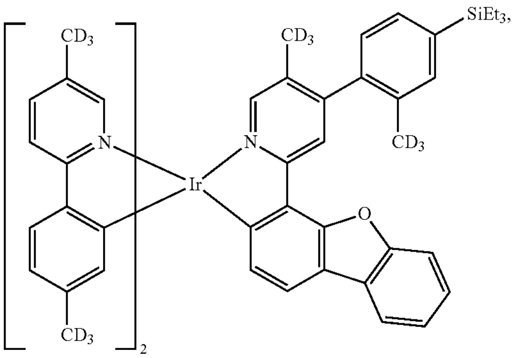,
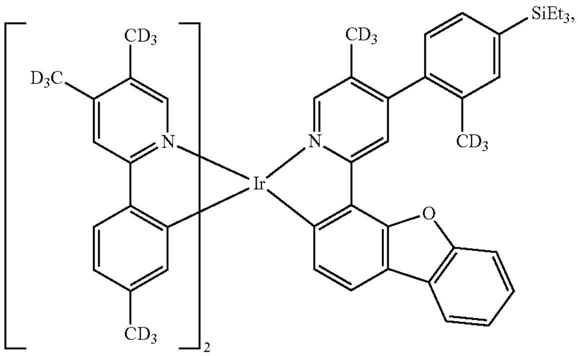,
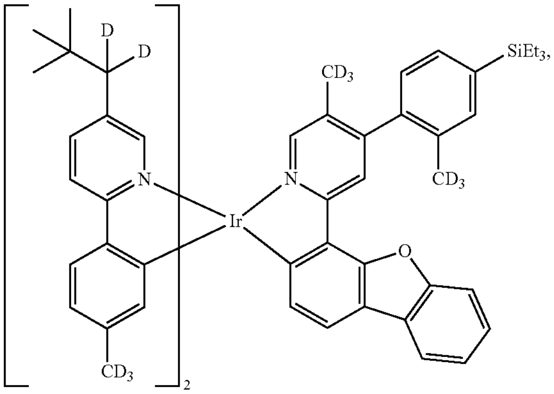,
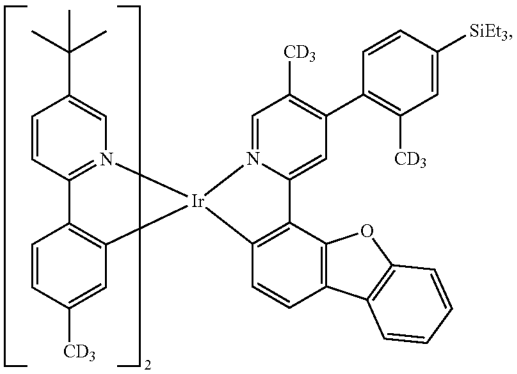,
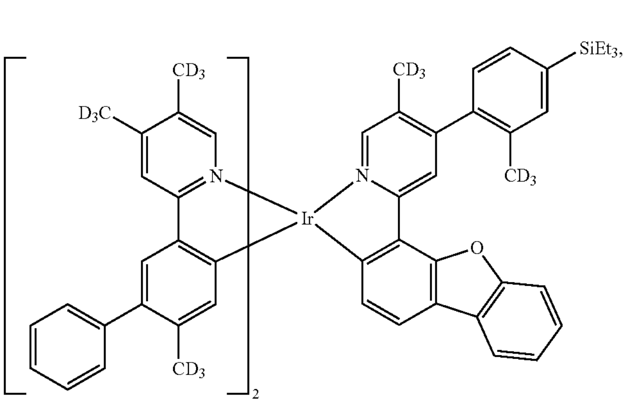, -continued
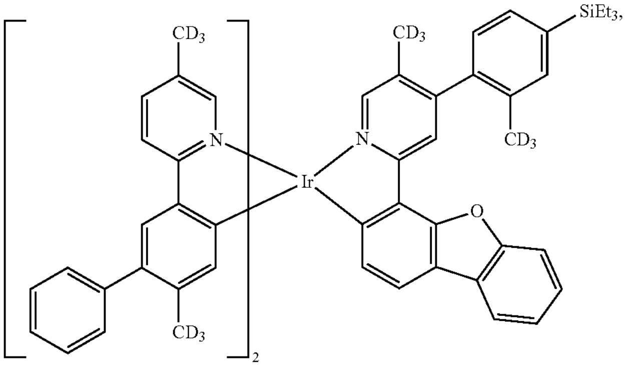
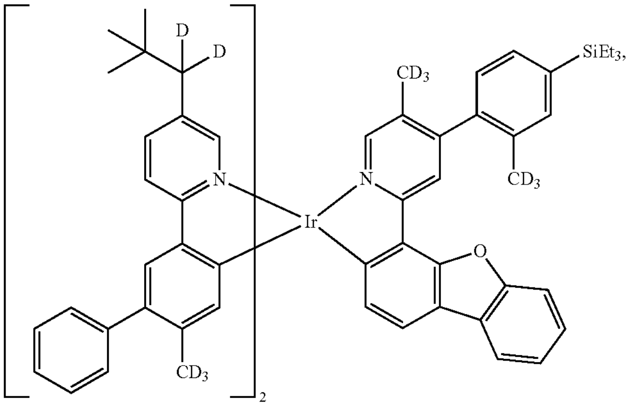
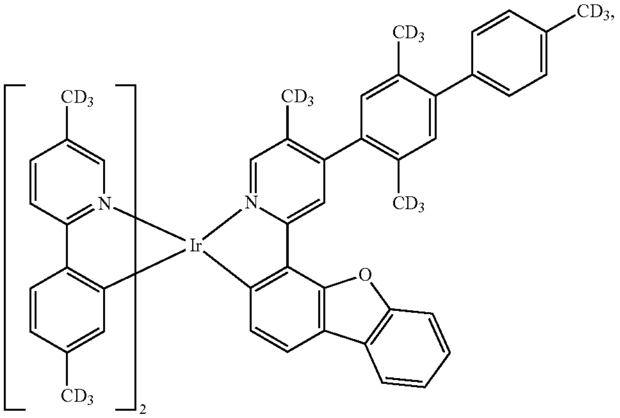
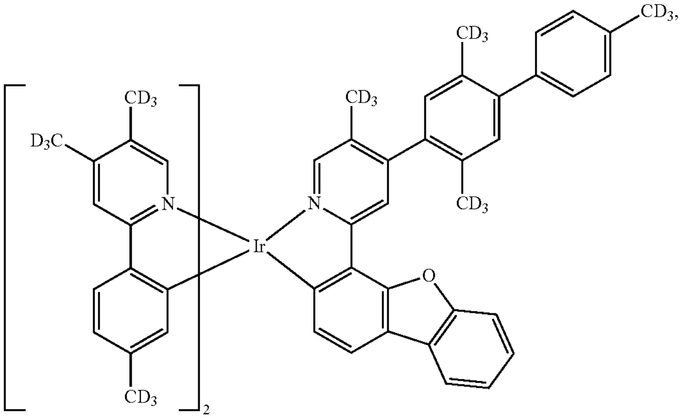

-continued
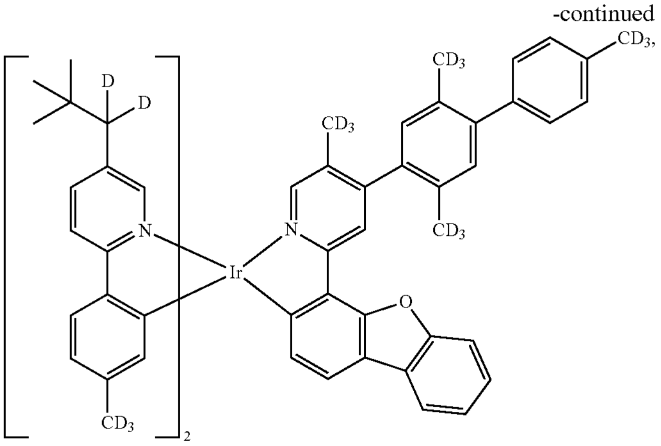
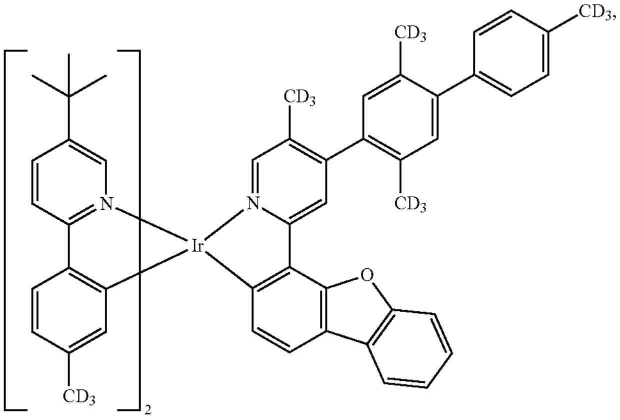
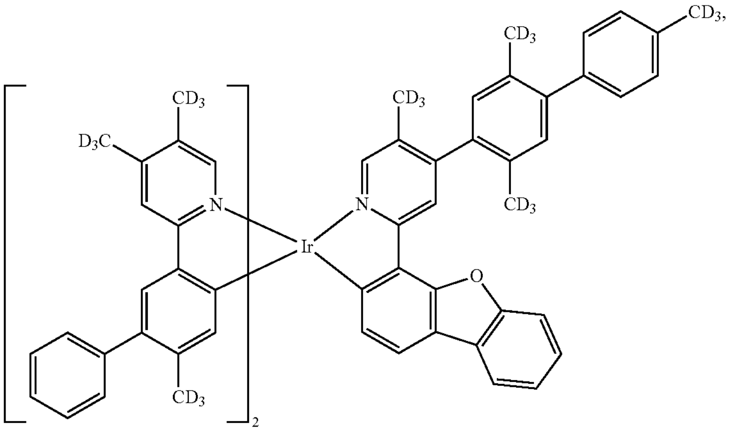
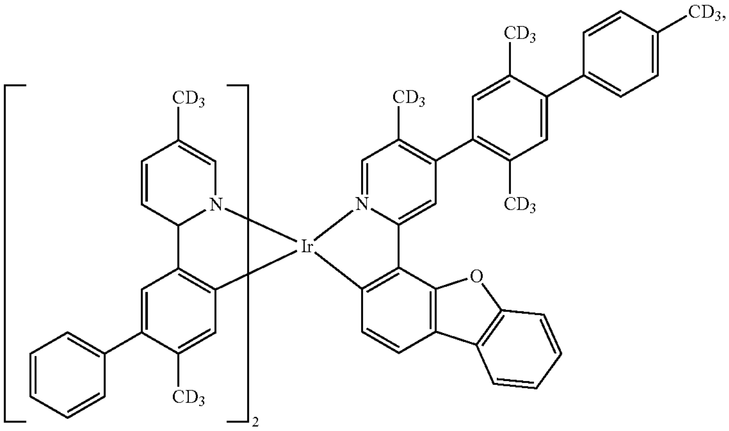

-continued
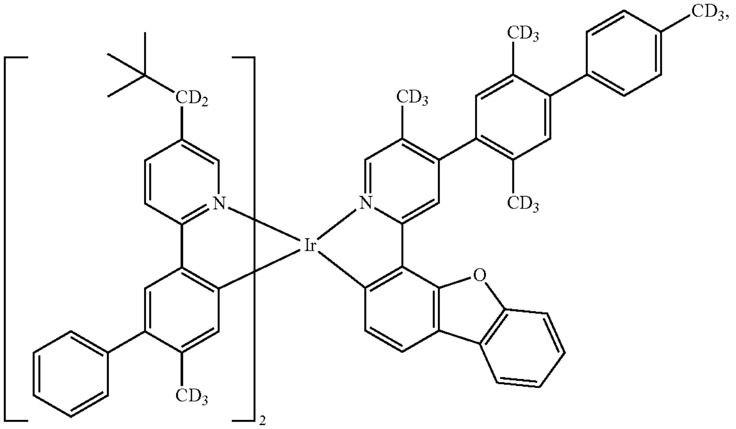
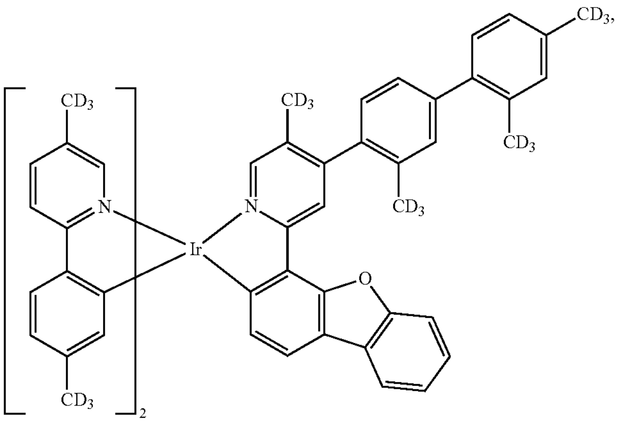
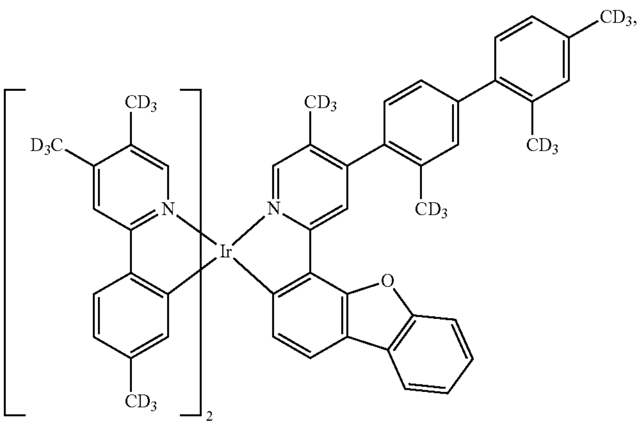

-continued
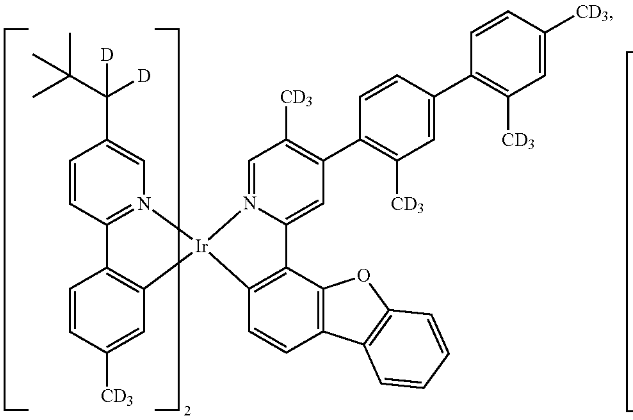
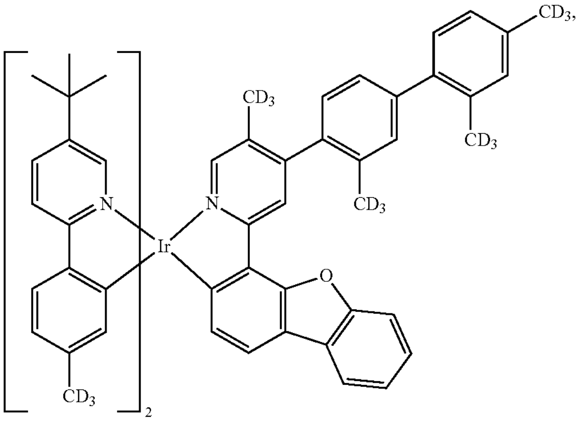
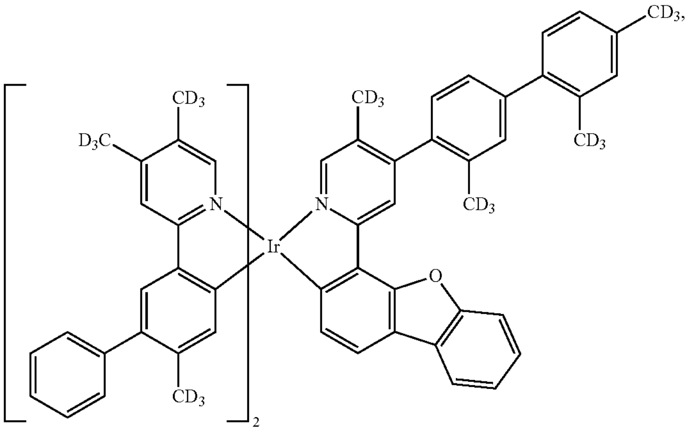
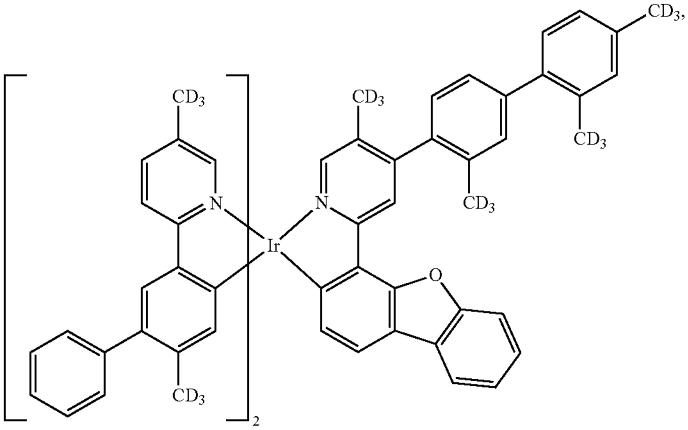
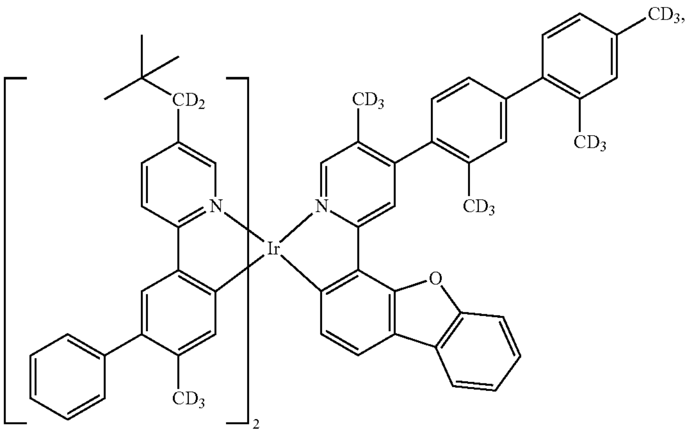

-continued
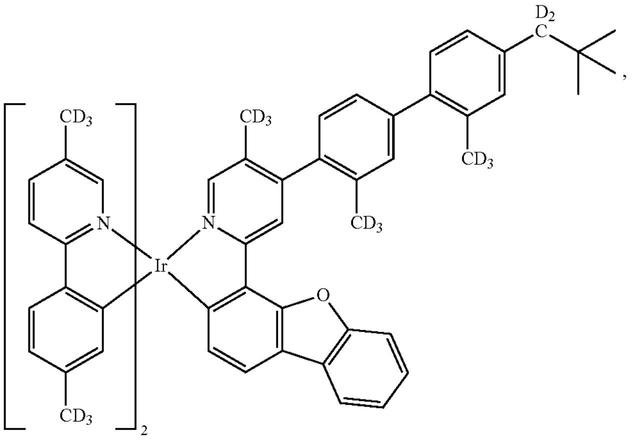
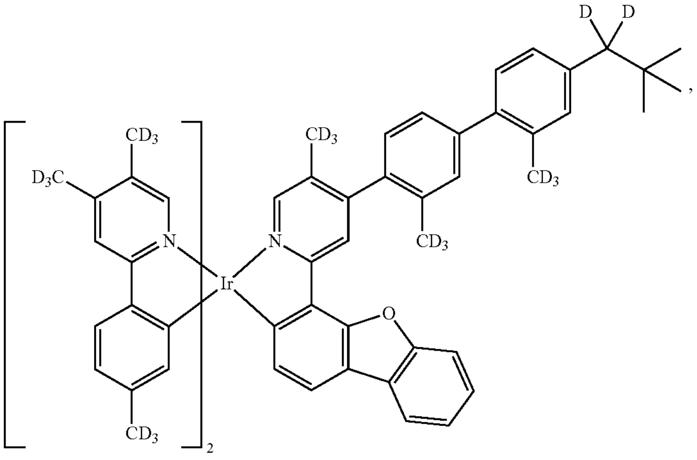
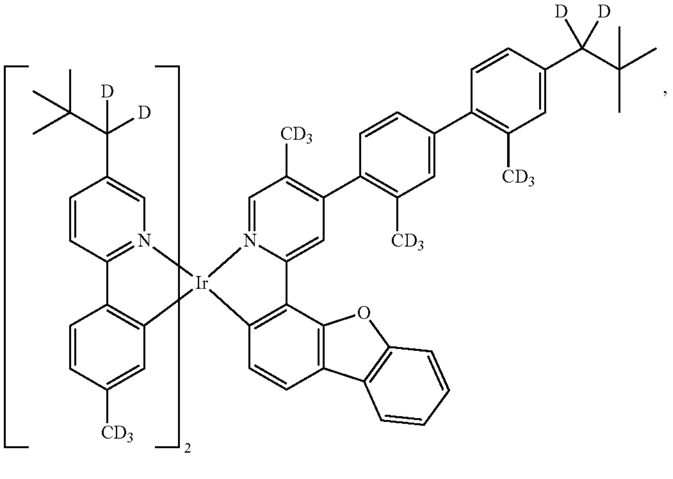

-continued
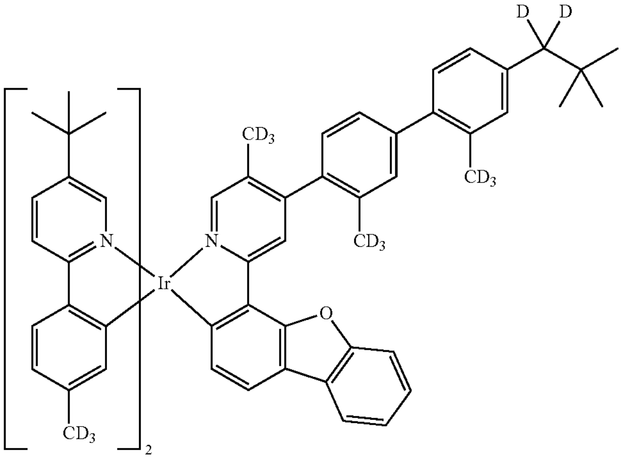
,
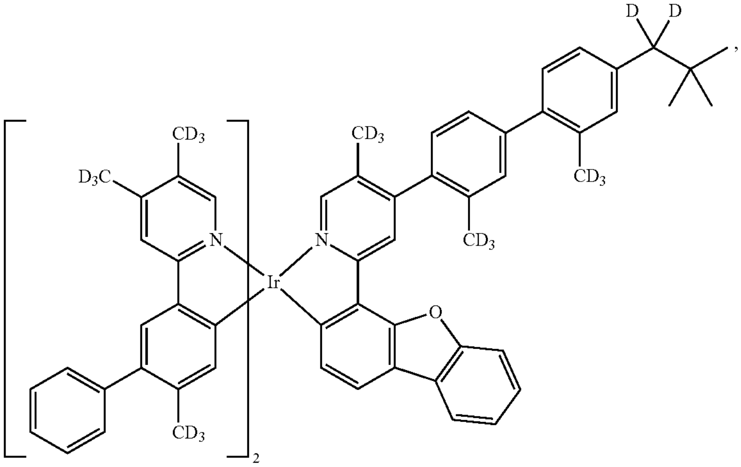
,
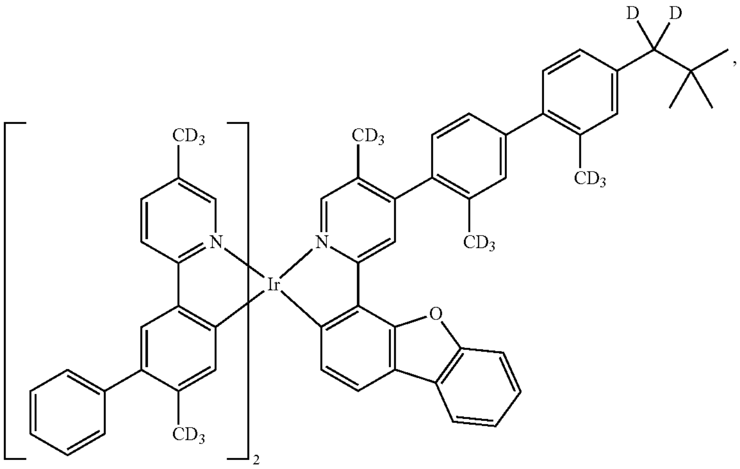
,

-continued
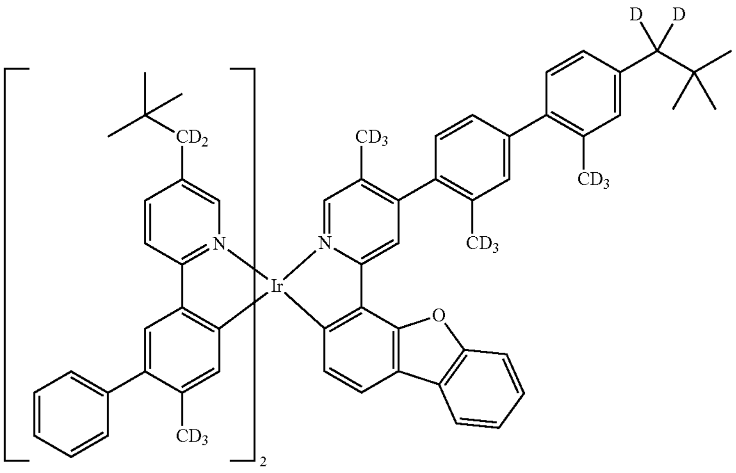
,
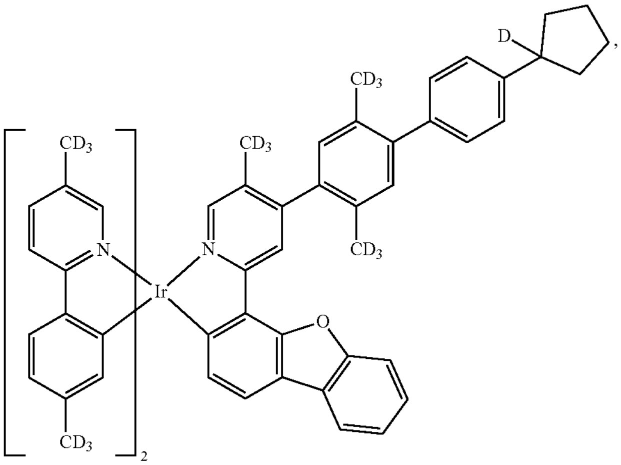
,
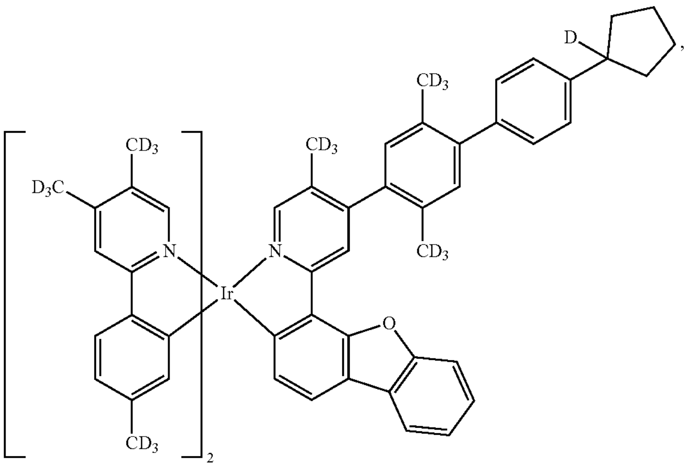
,

-continued
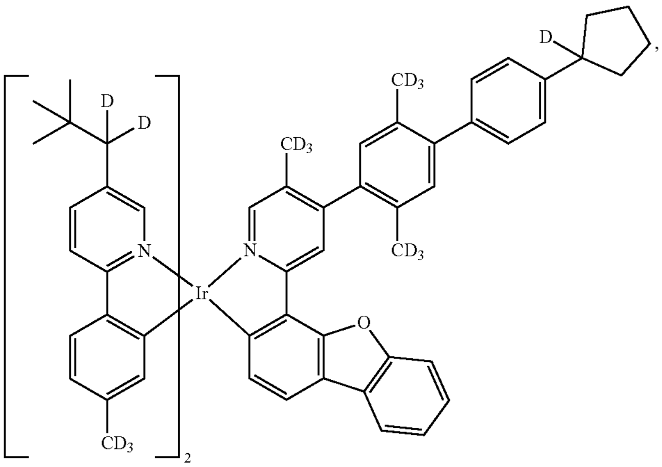
,
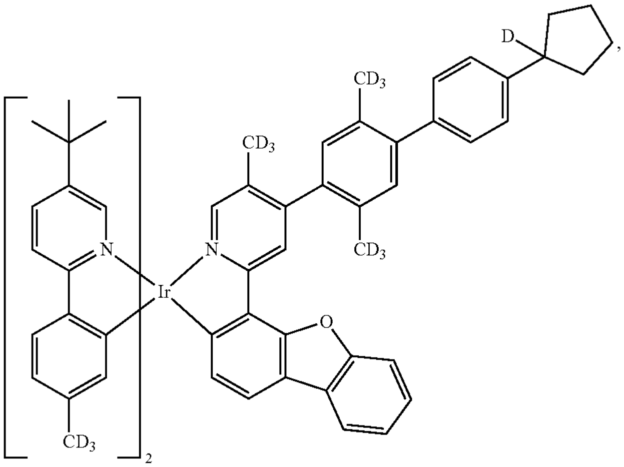
,
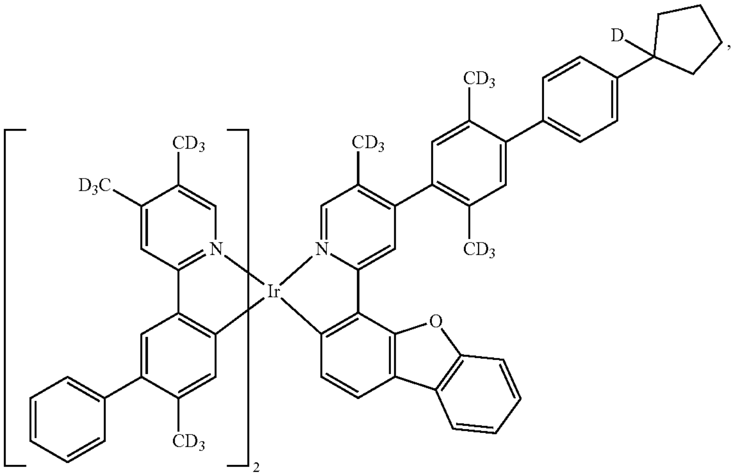
,

-continued
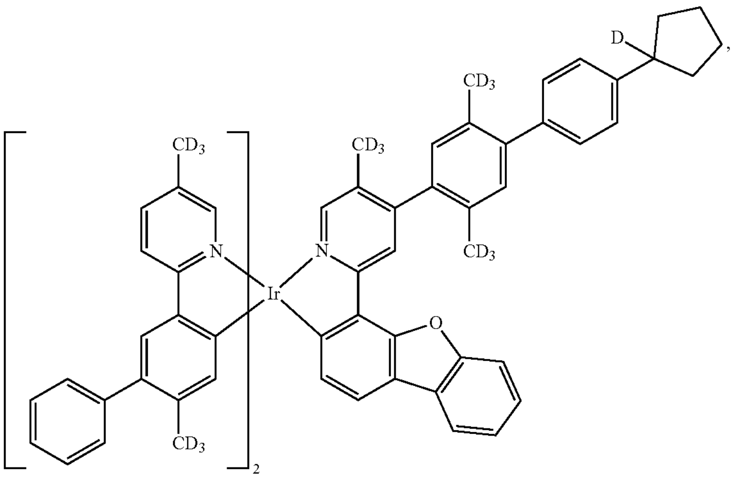
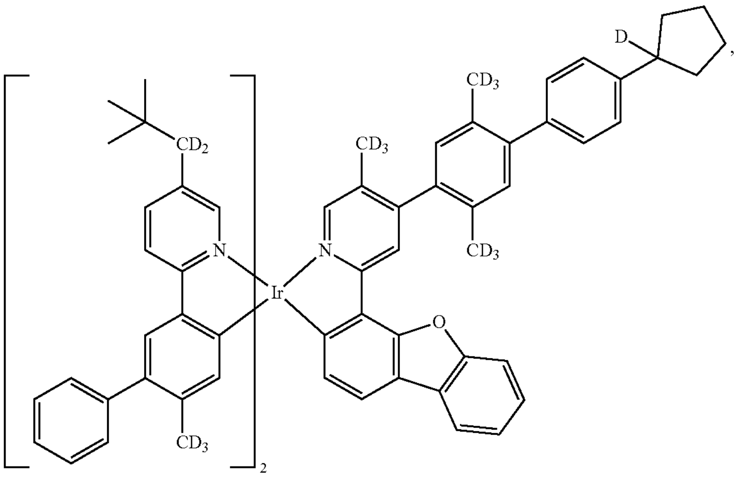
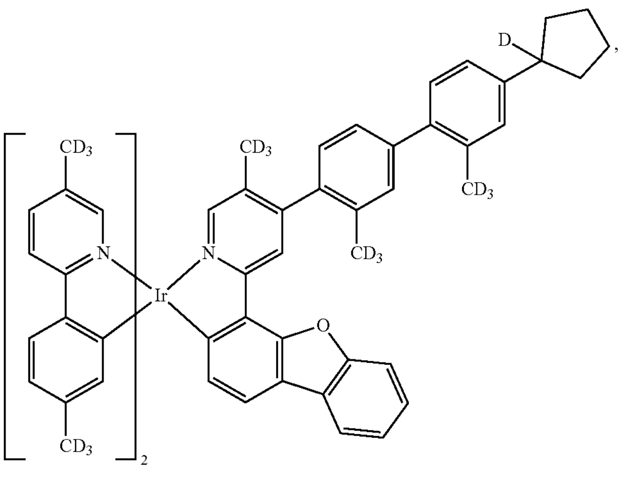

-continued
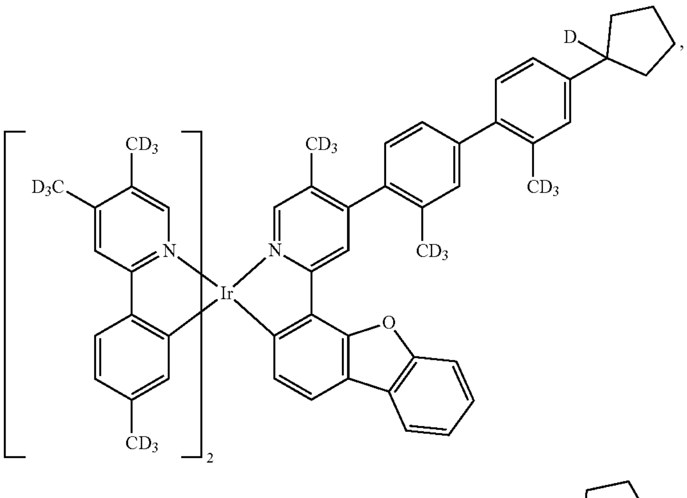
,
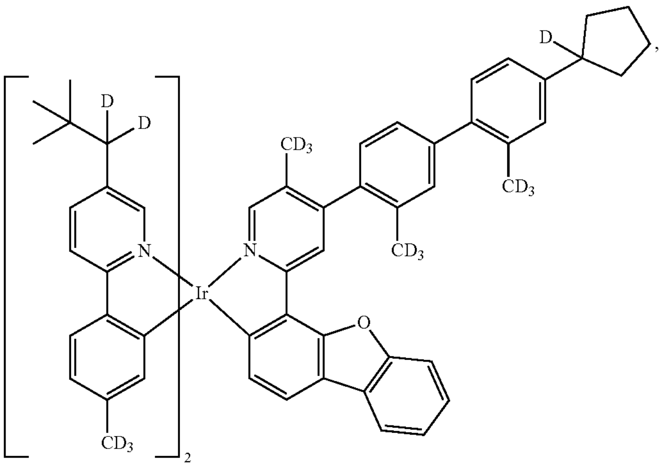
,
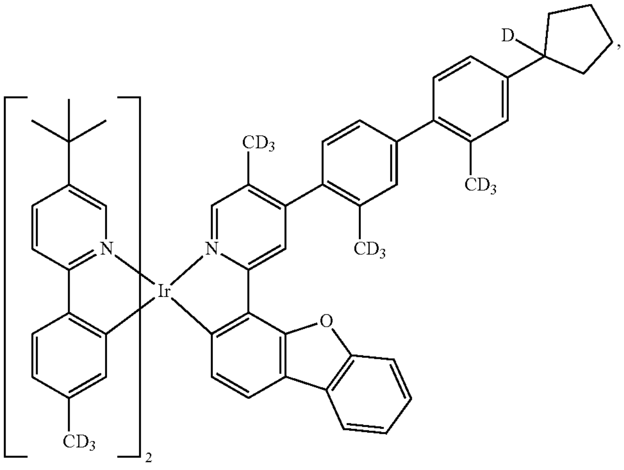
,

-continued
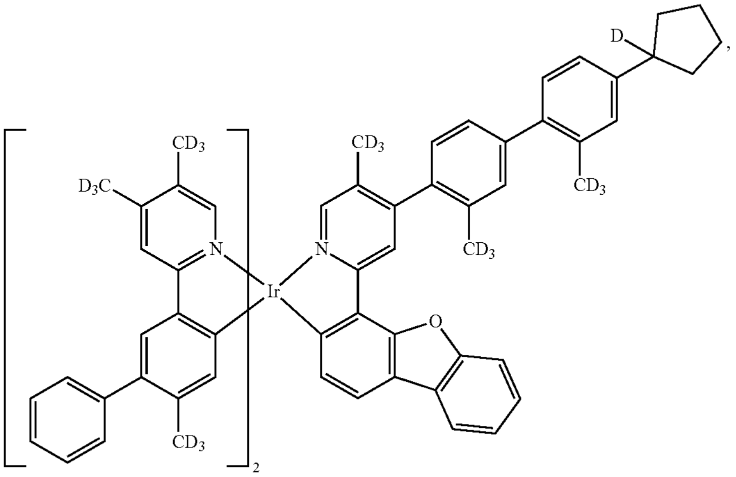
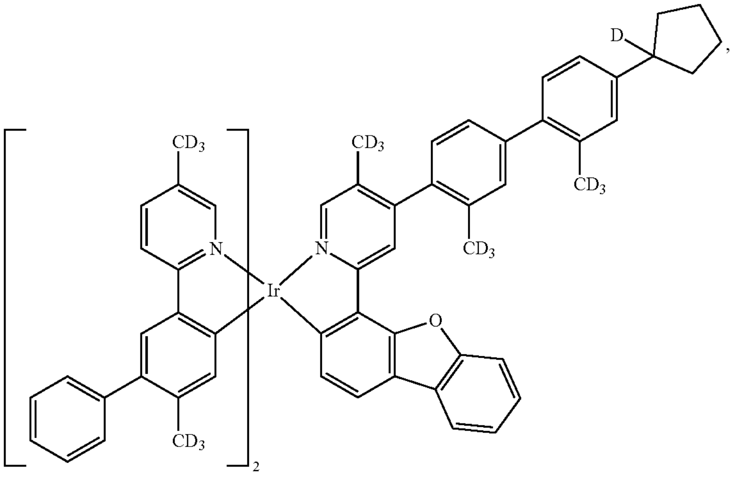
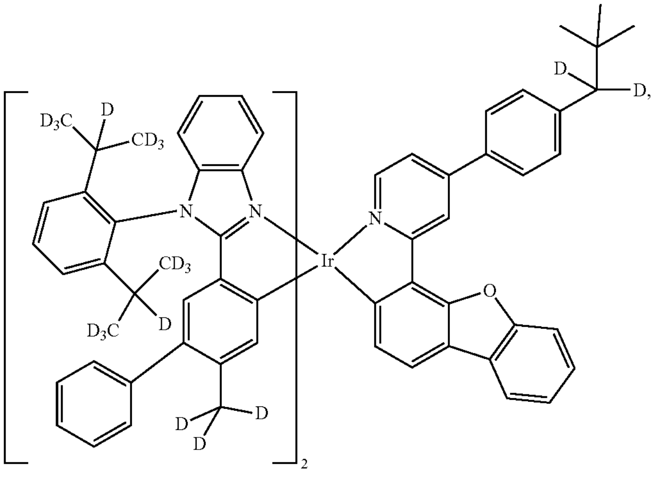

-continued
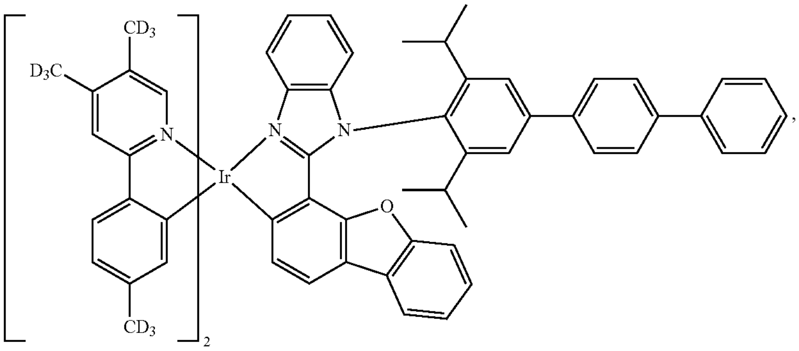
,
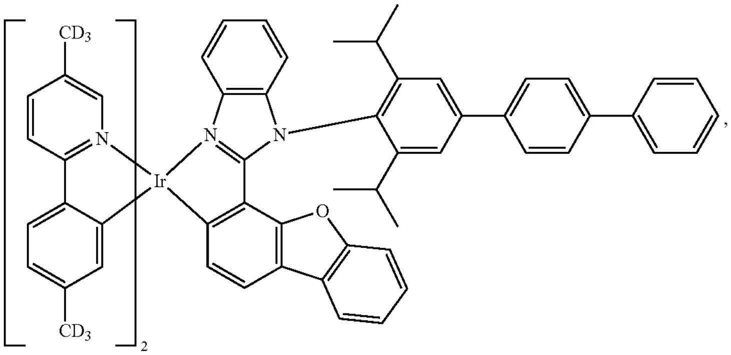
,
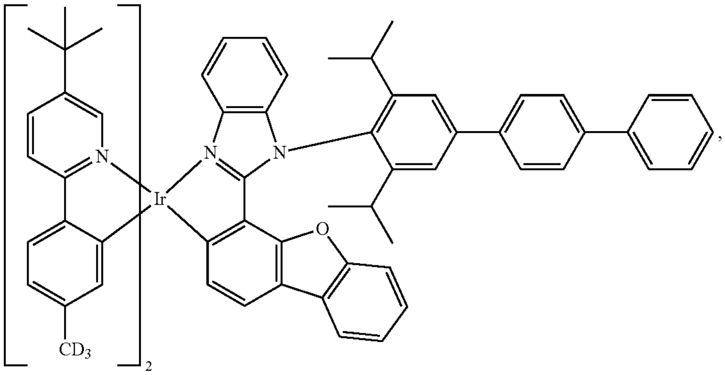
,
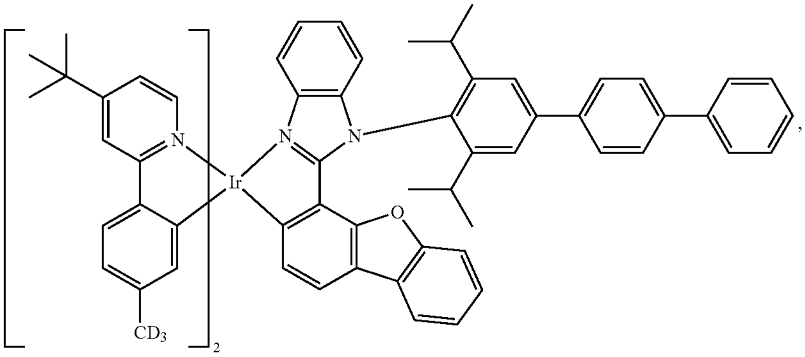
,

-continued
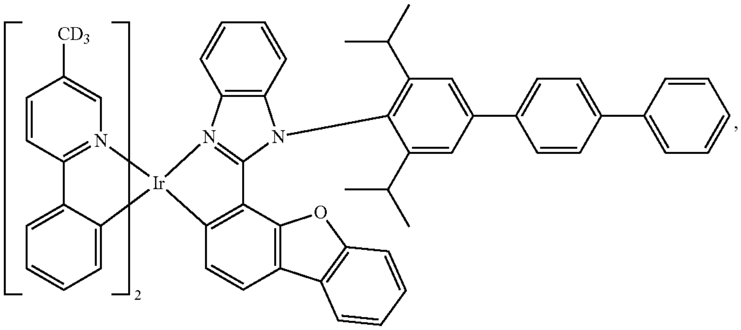
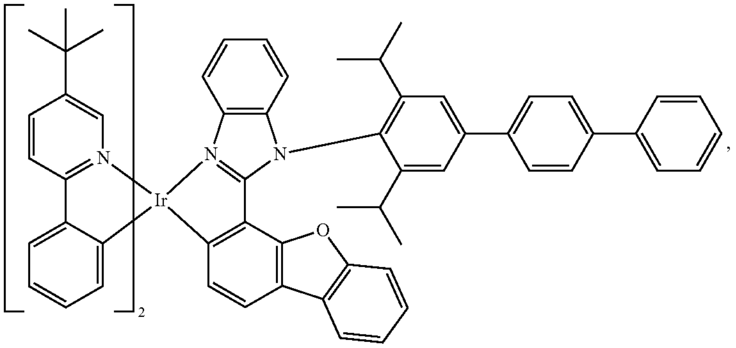
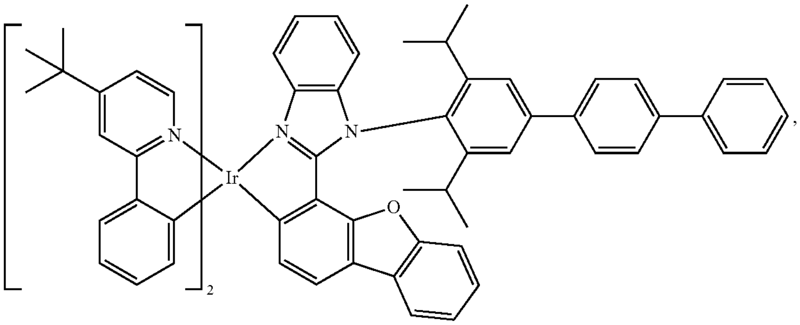
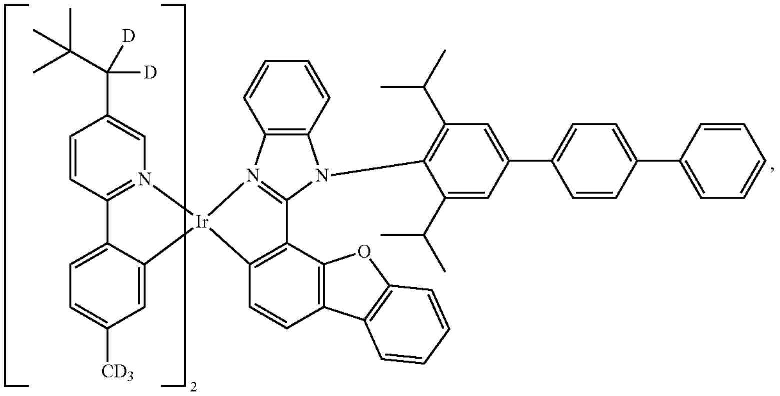

-continued
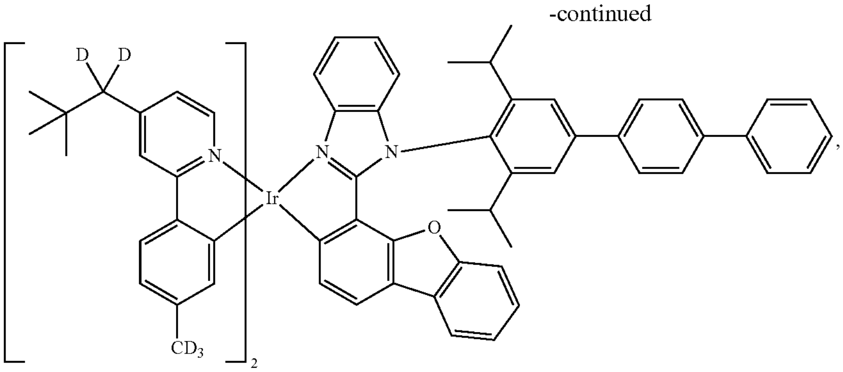
,
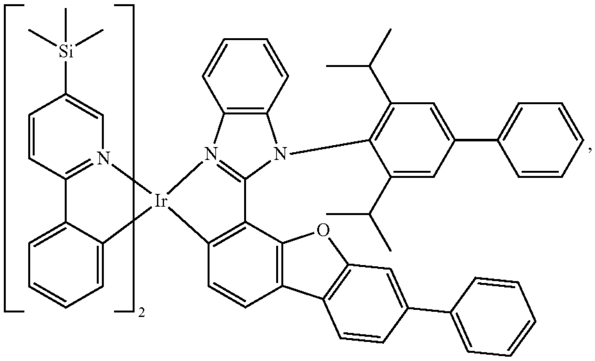
,
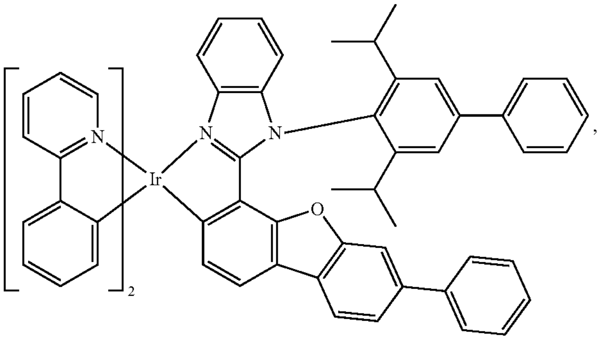
,
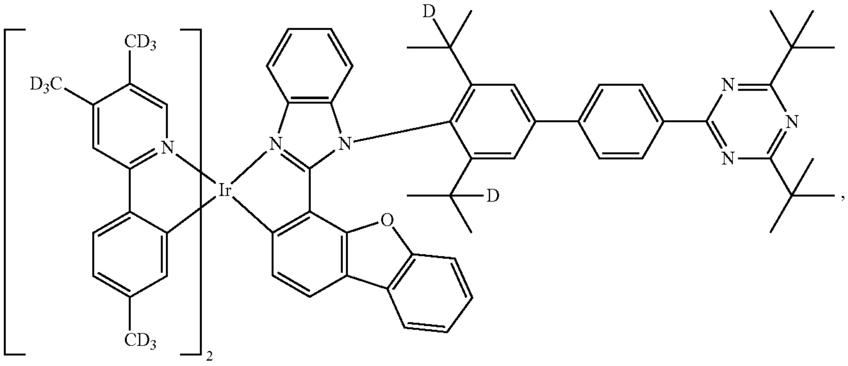
,
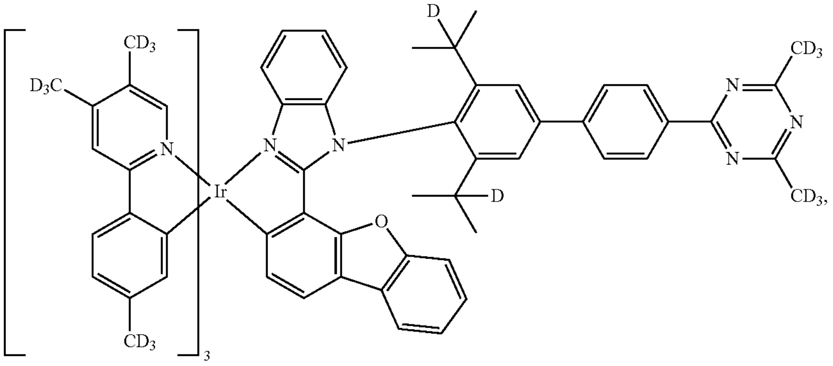

-continued
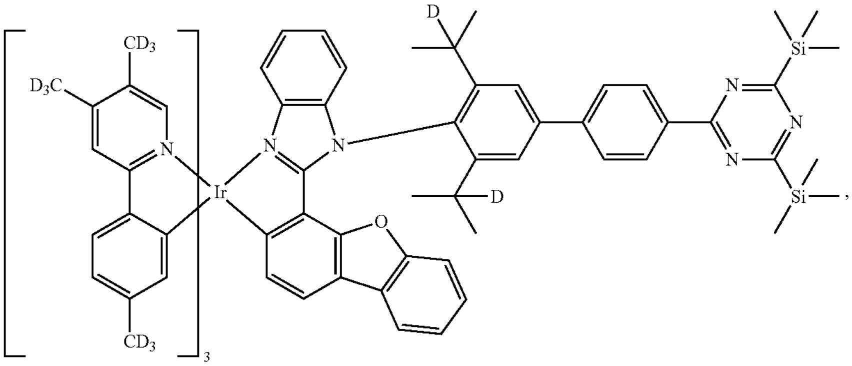
,
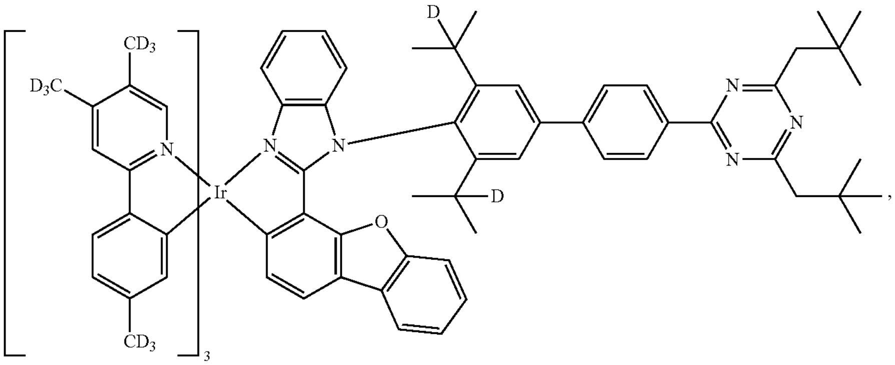
,
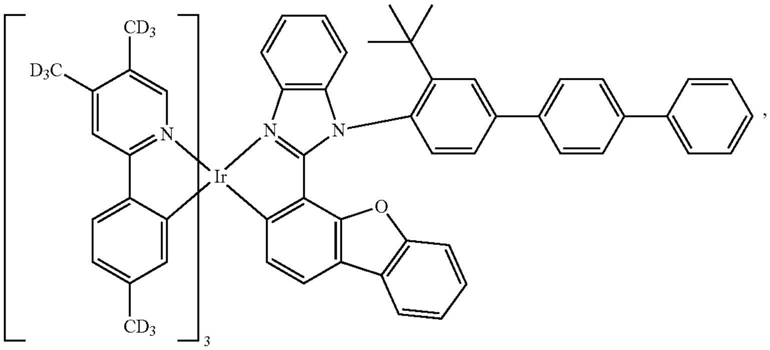
,
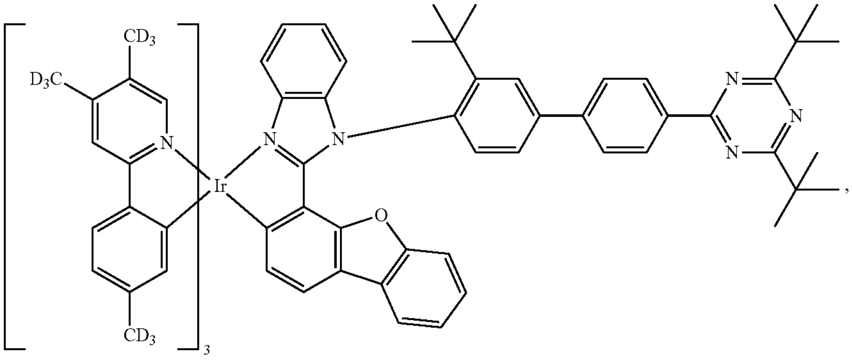
,

-continued
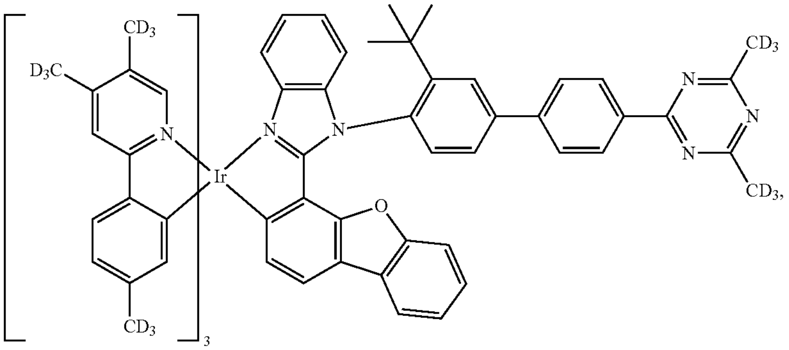
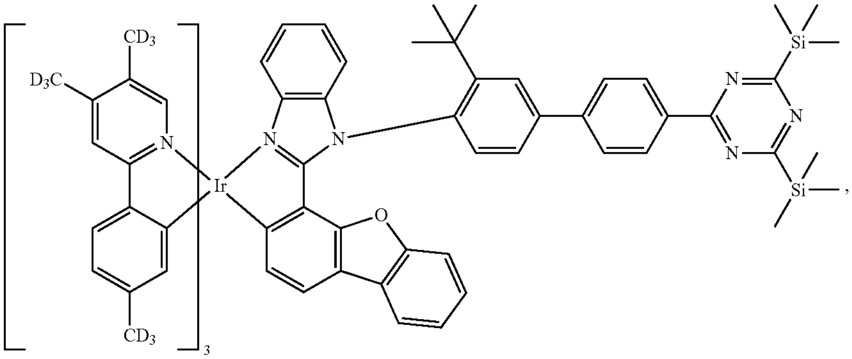
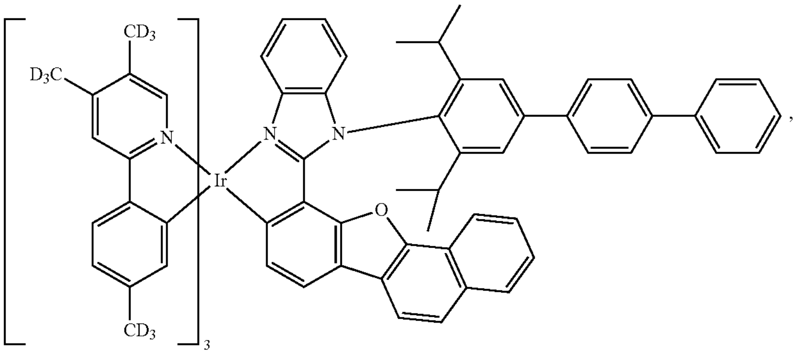
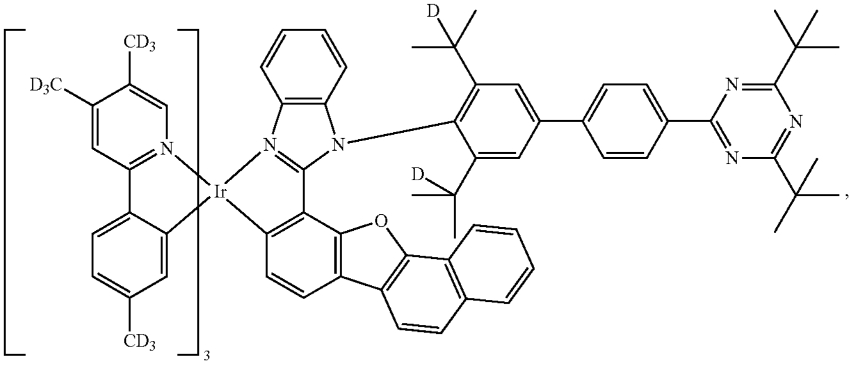

-continued
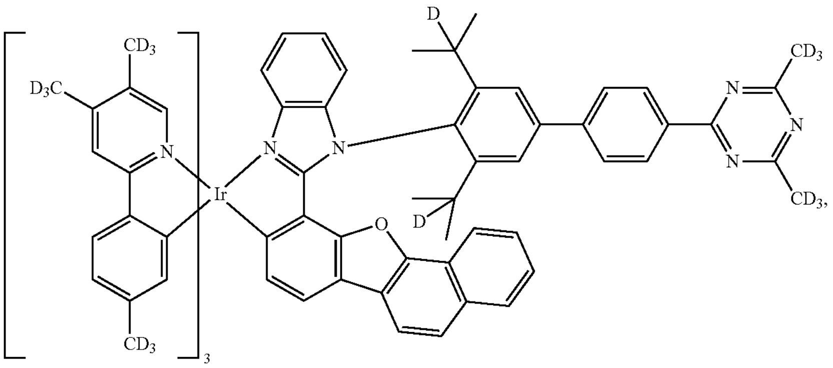
,
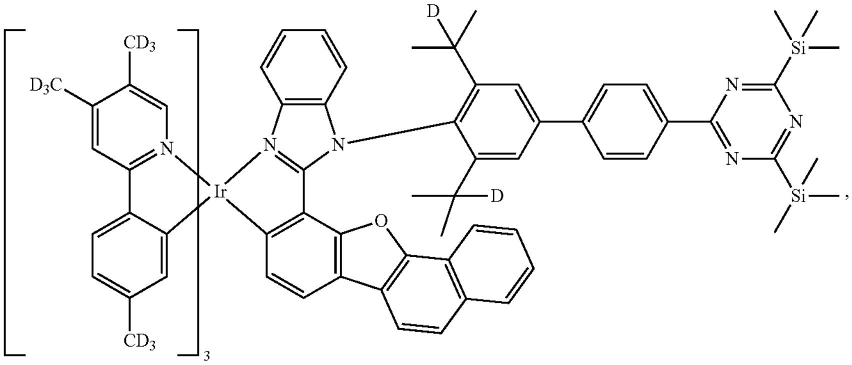
,
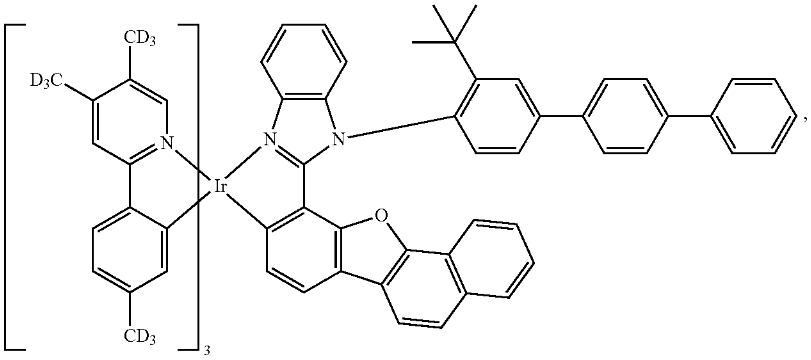
,
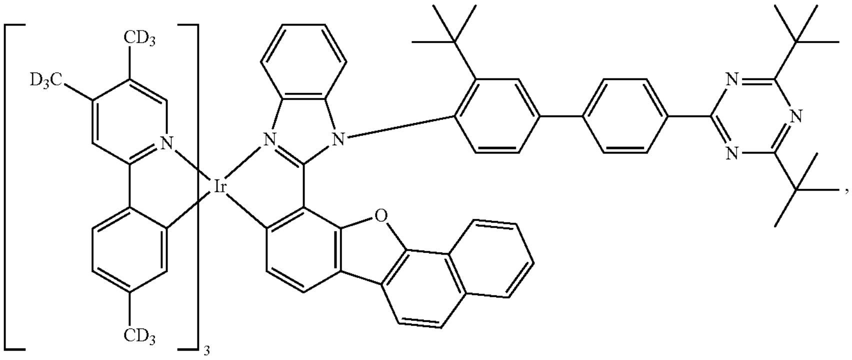
,

-continued
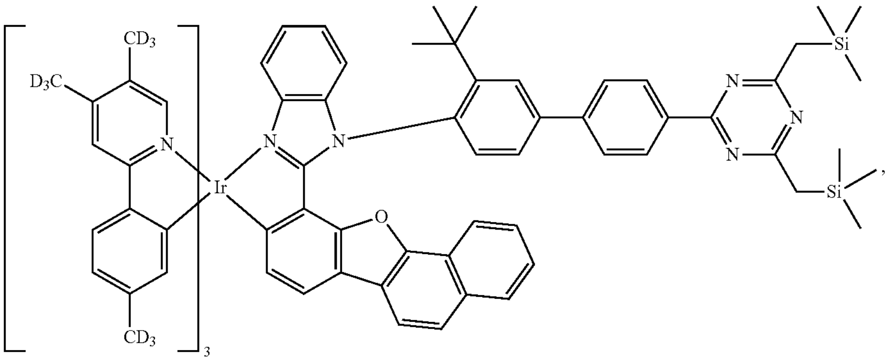
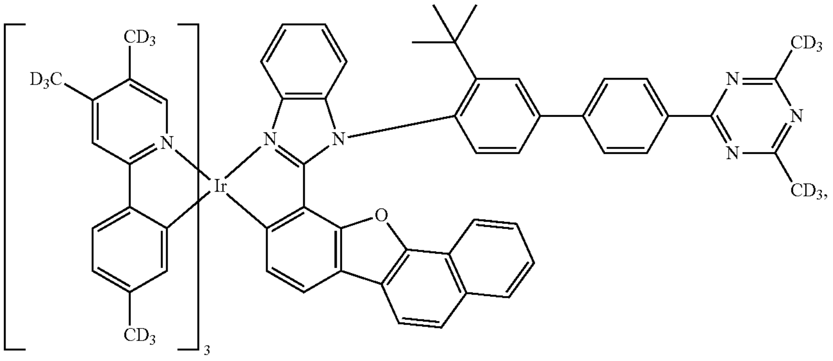
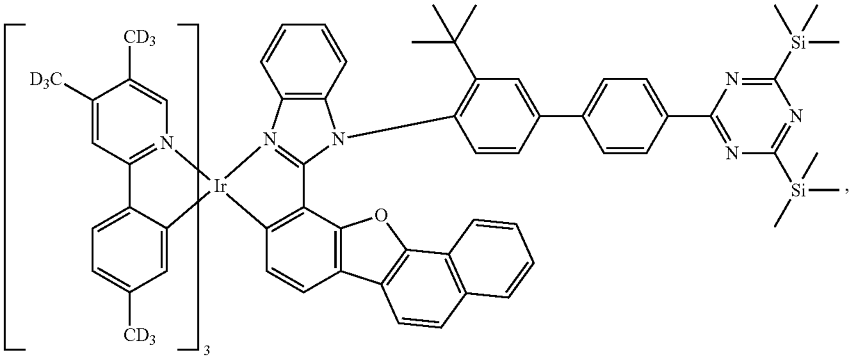
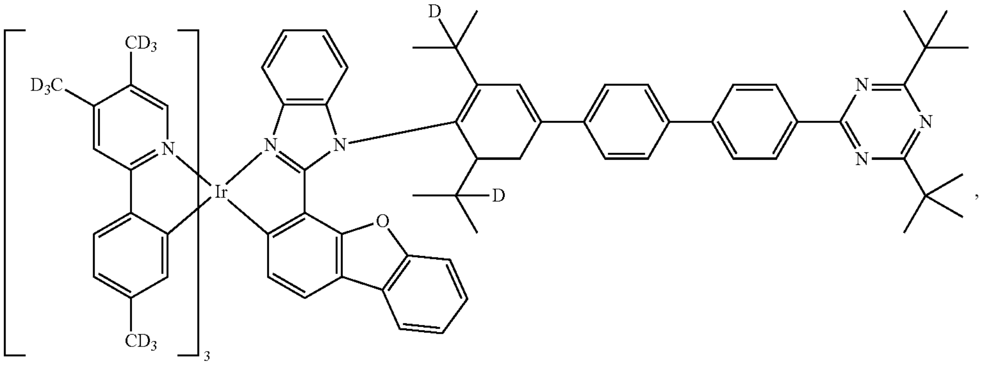

-continued
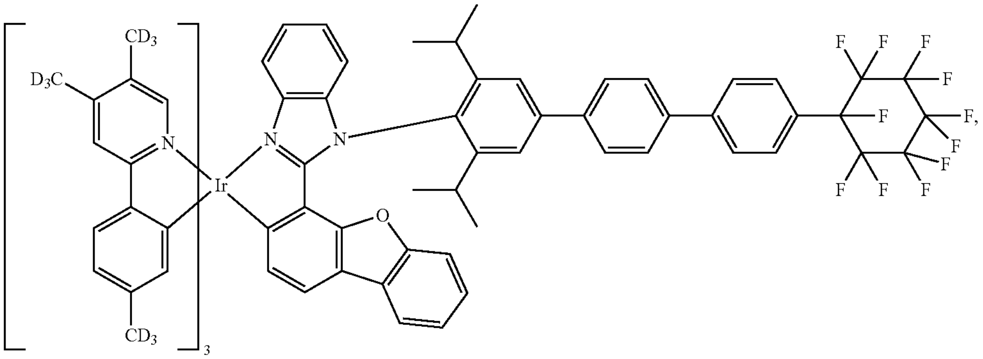
,
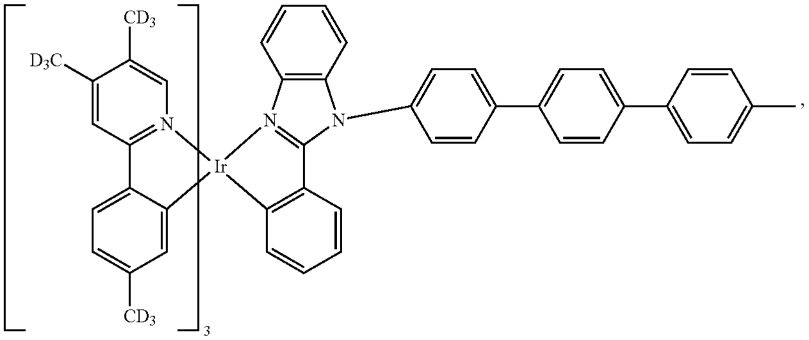
,
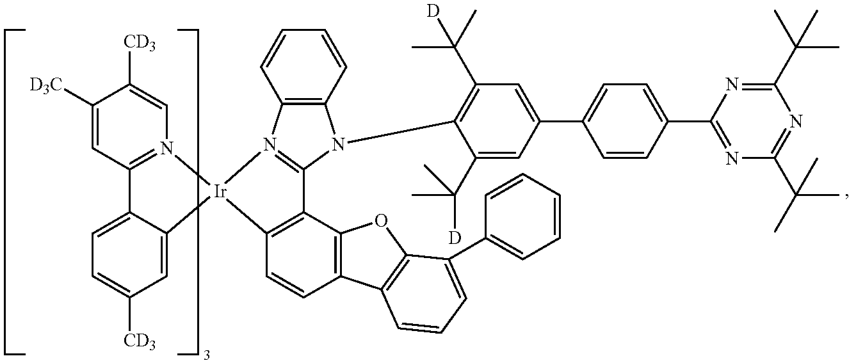
,
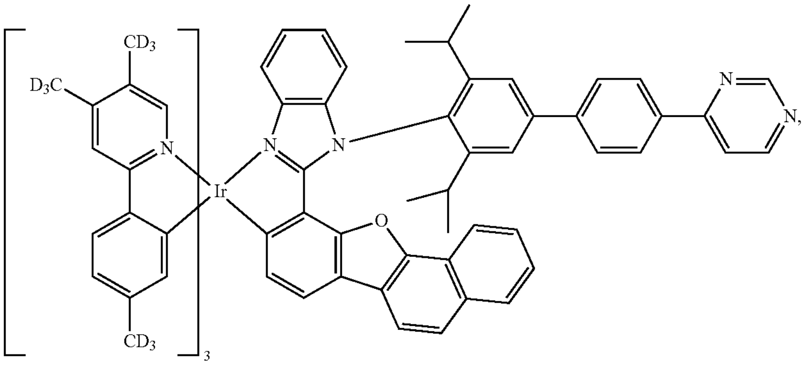
,

-continued
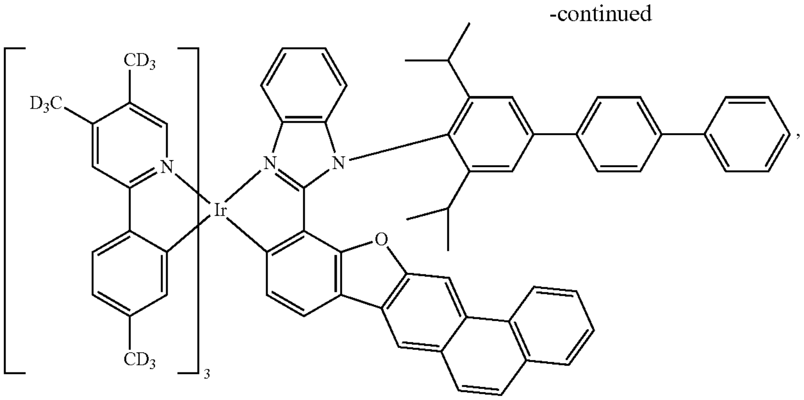
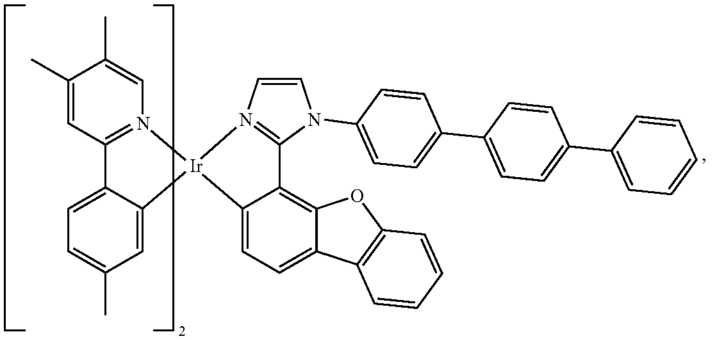
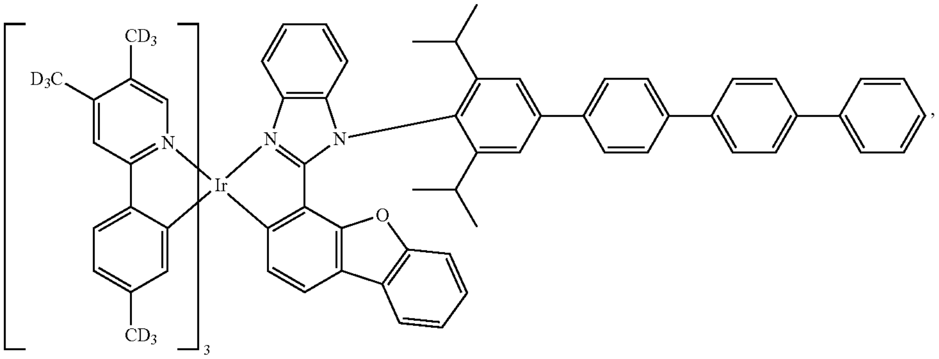
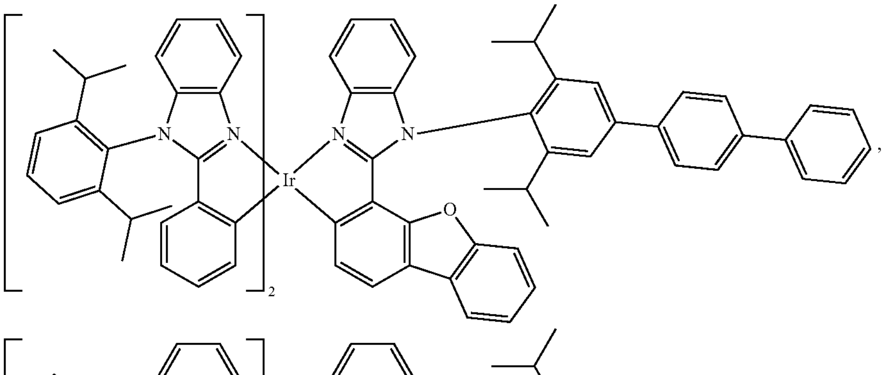
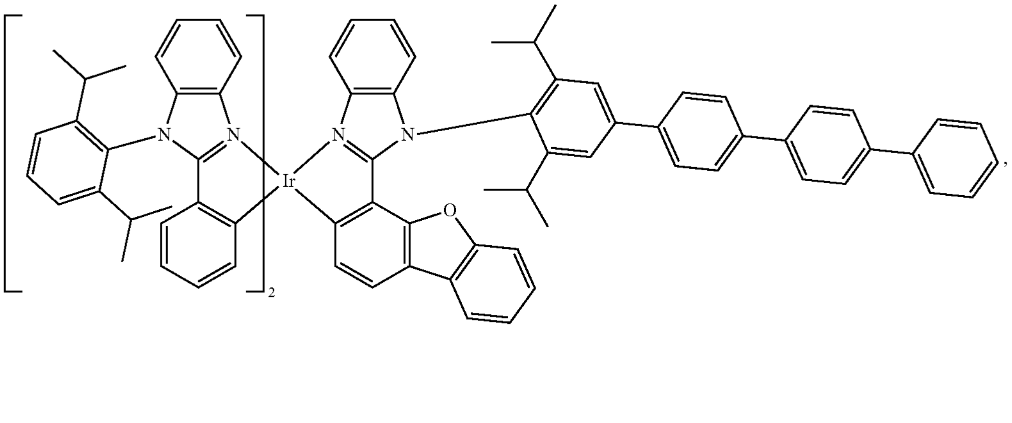

-continued
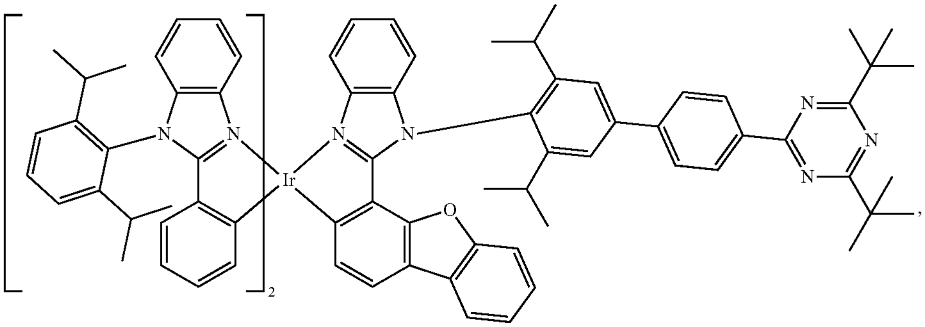
,
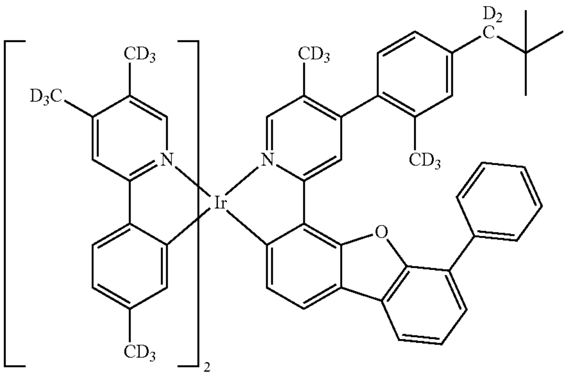
,
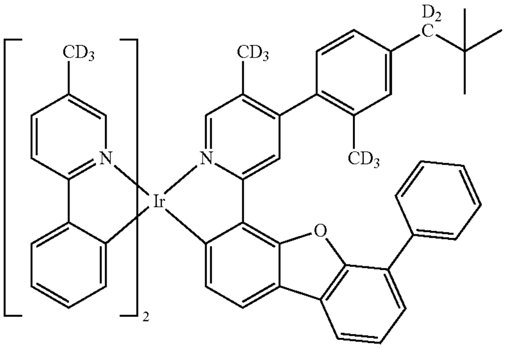
,
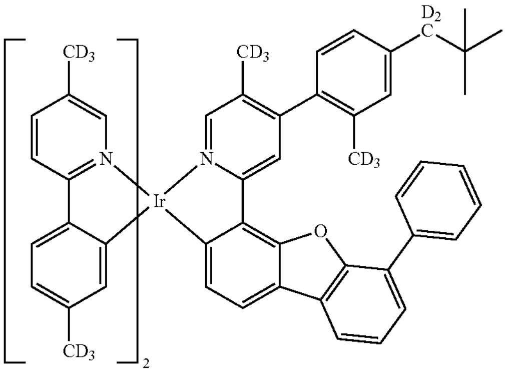
,
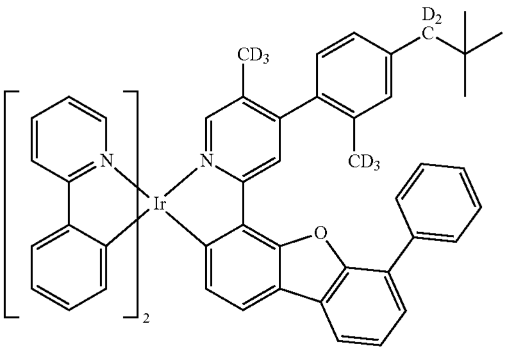
,
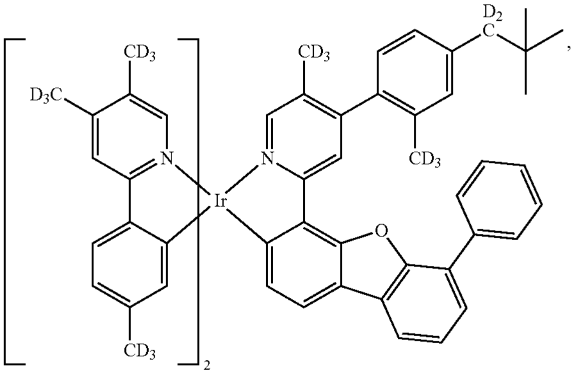
,
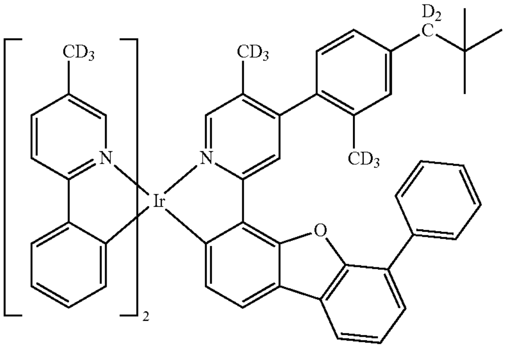
, -continued
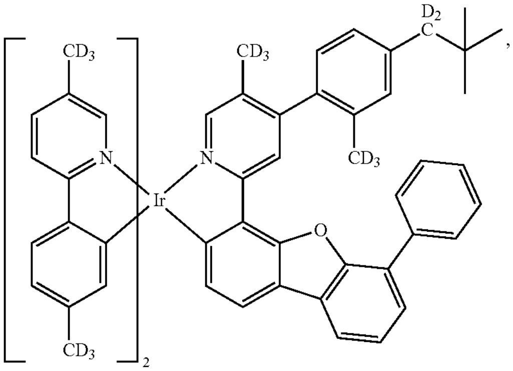
,
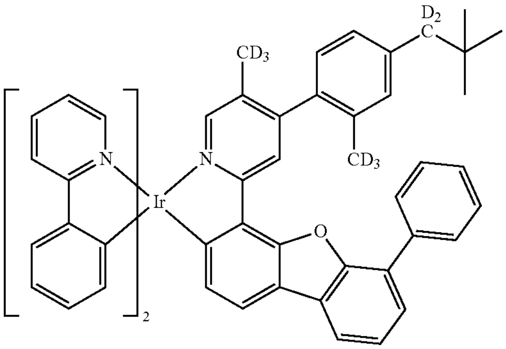
,
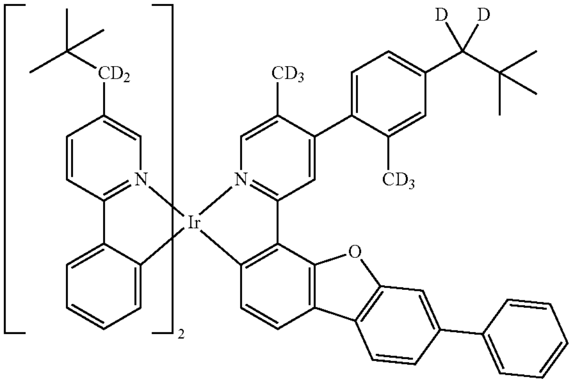
,
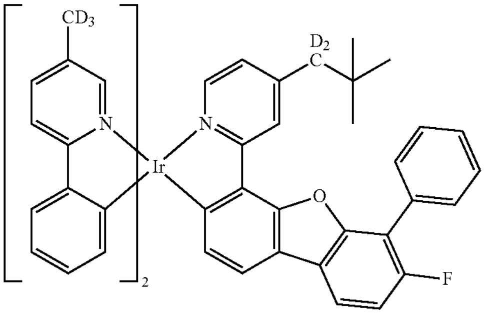
,
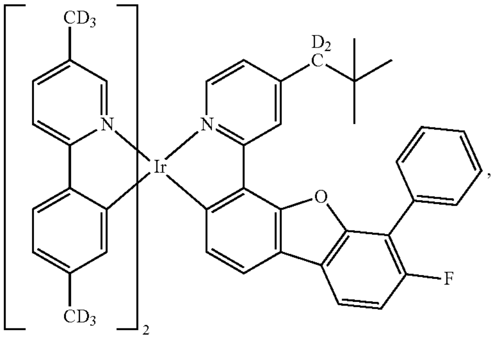
,
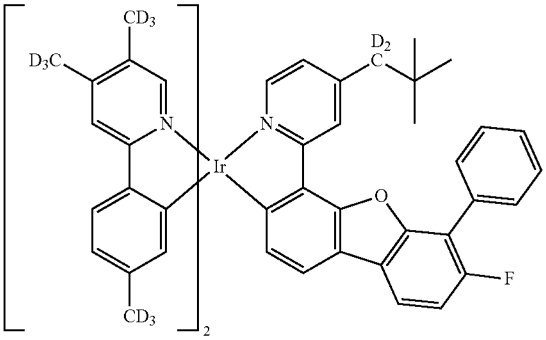
,
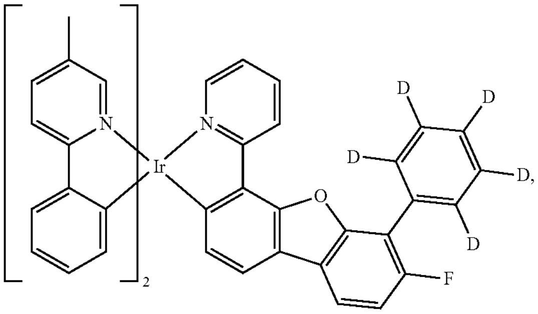
,
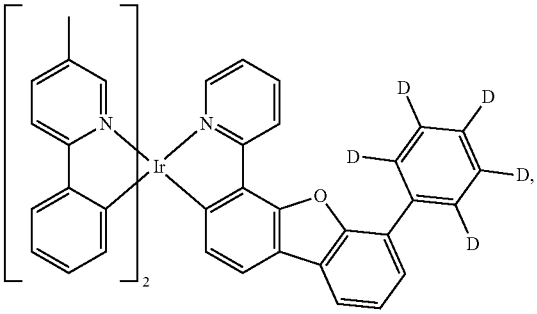
,
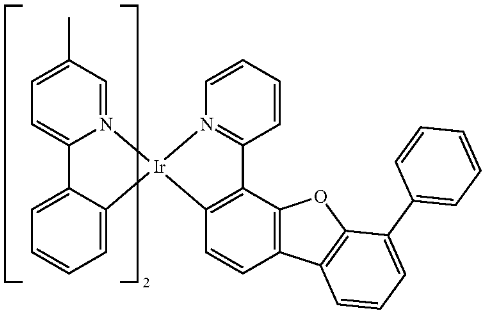
,
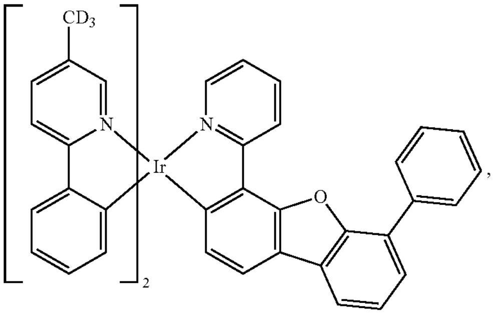
, -continued
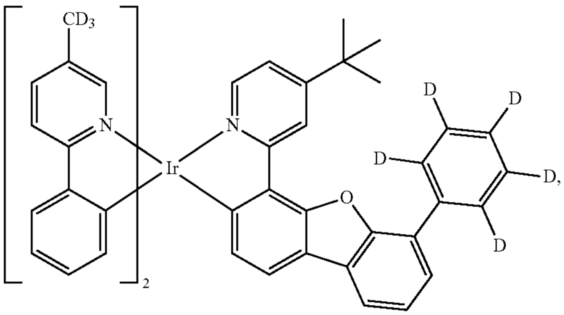,
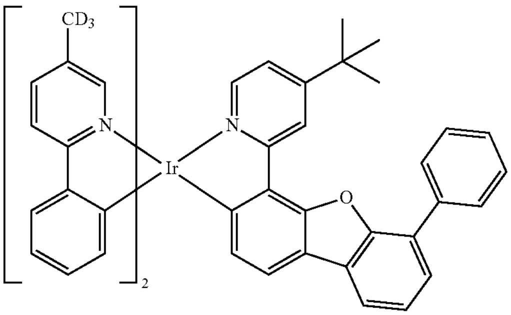,
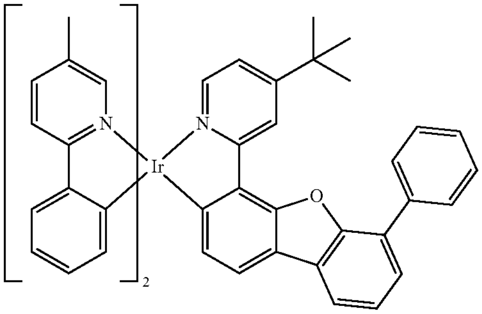,
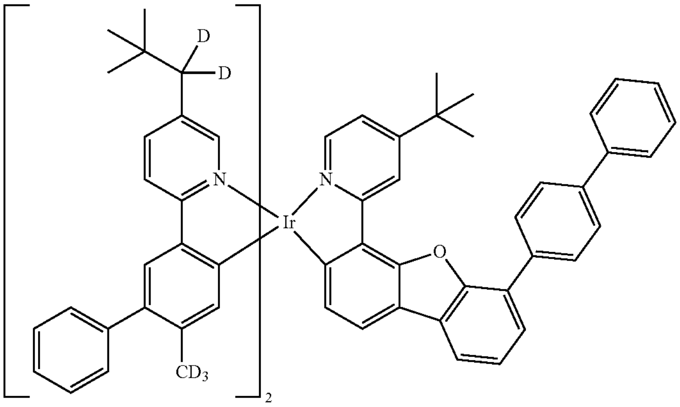,
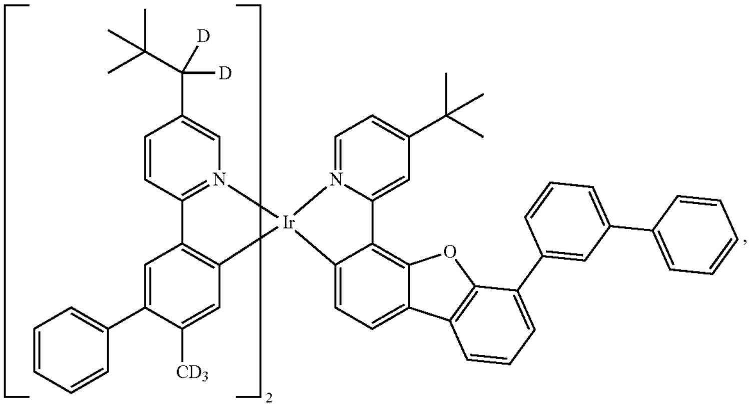,
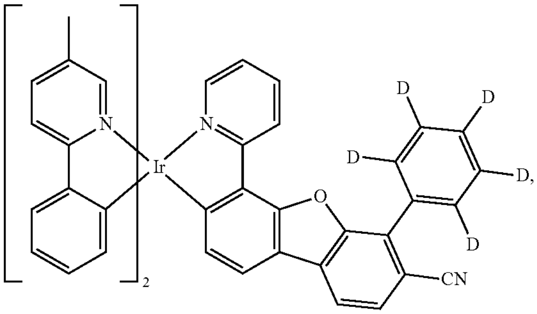,
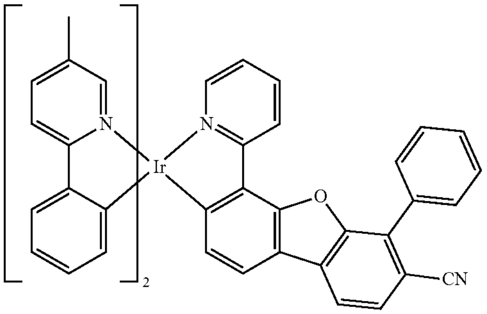, -continued
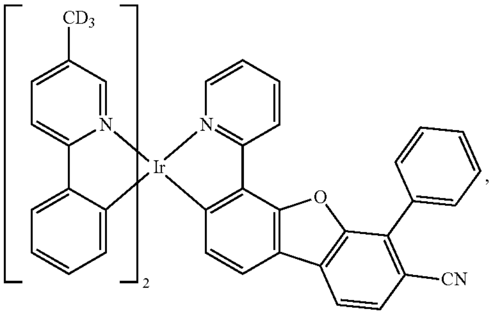
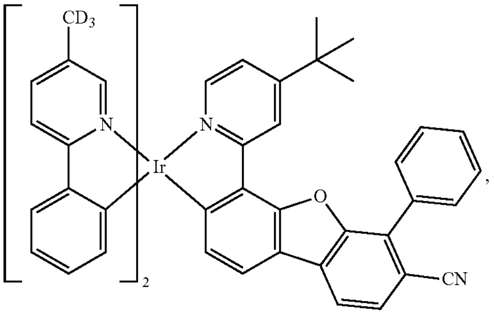
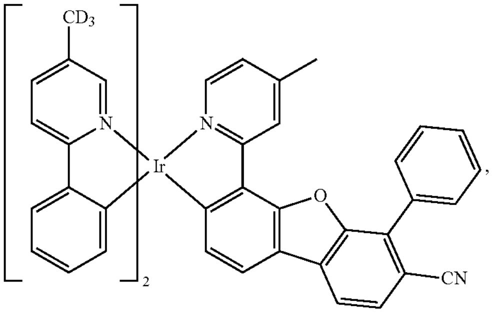
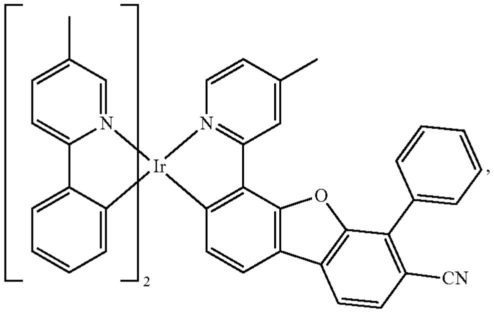
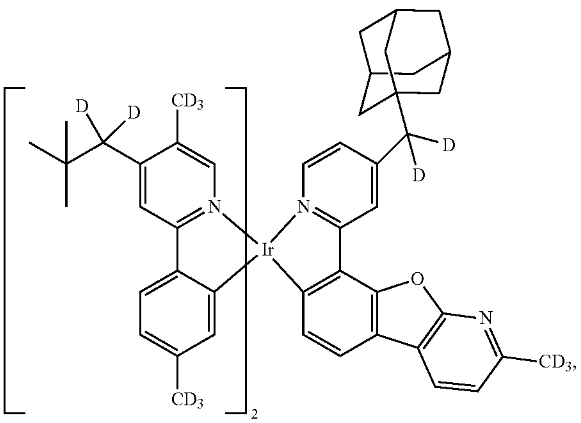
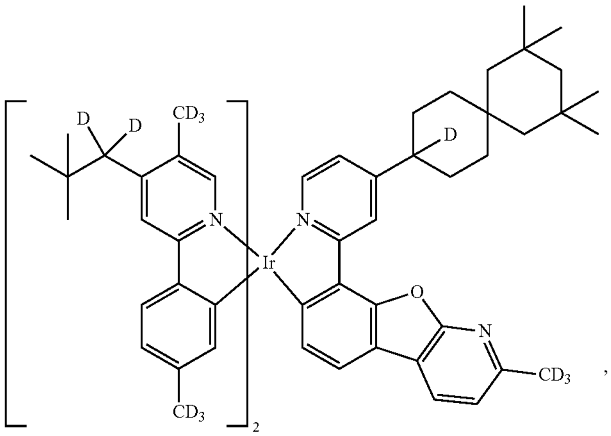
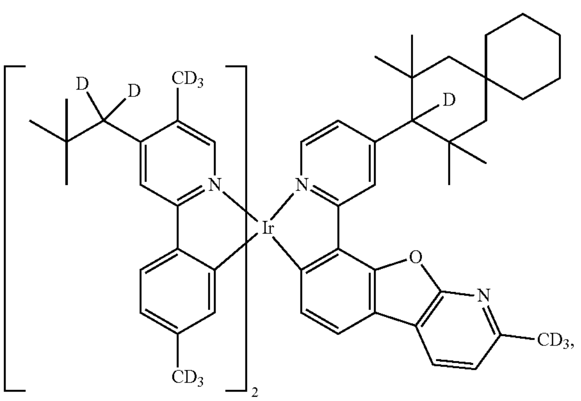
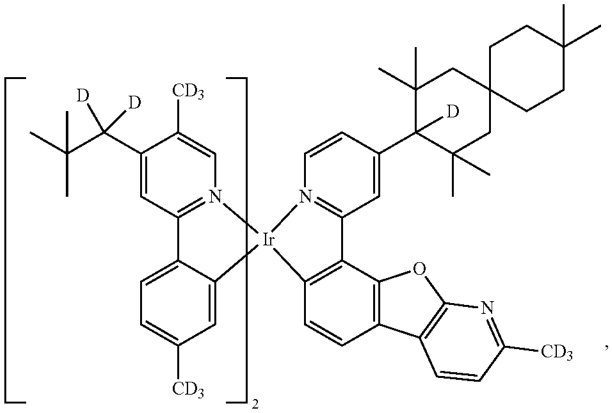

-continued
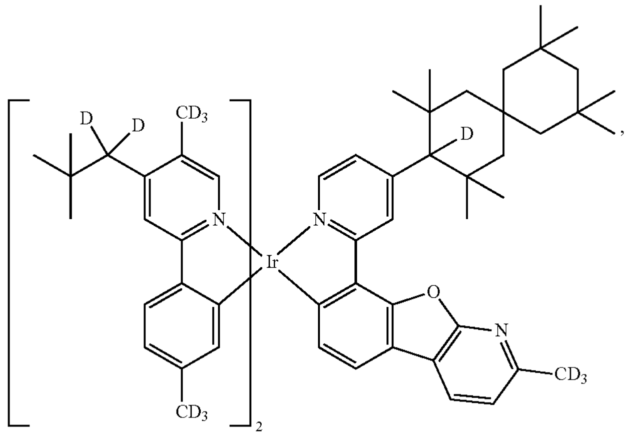
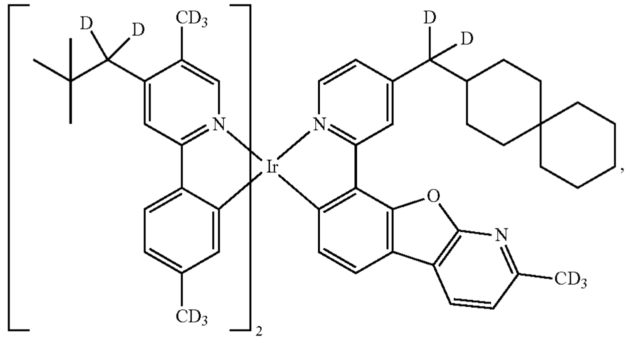
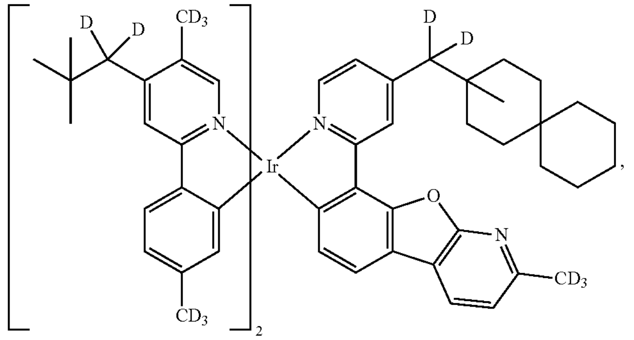
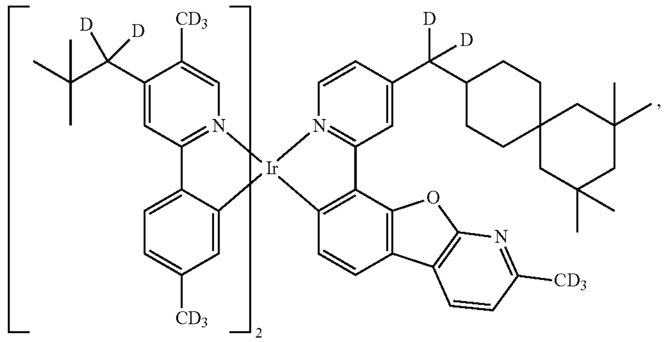

-continued
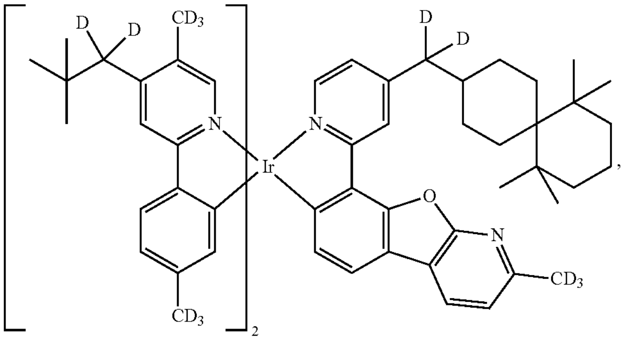
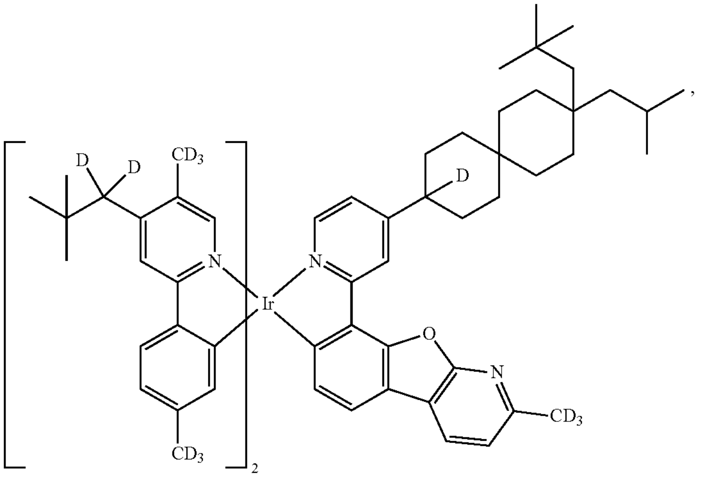
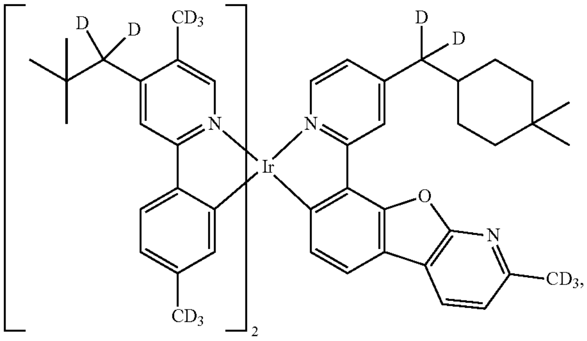
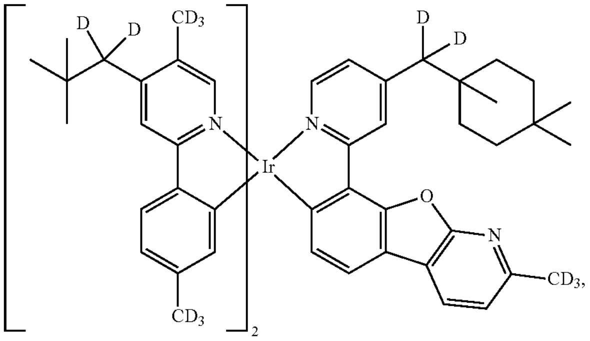
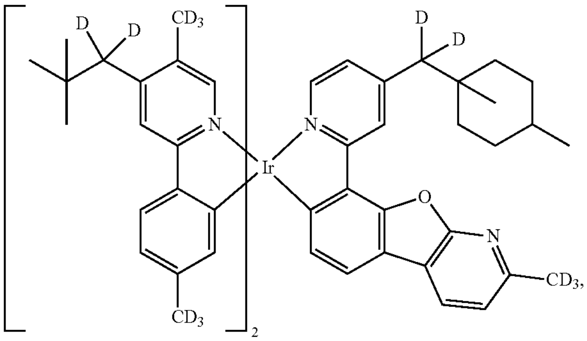
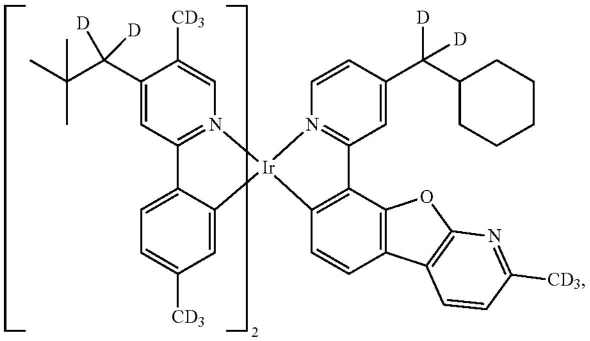

-continued
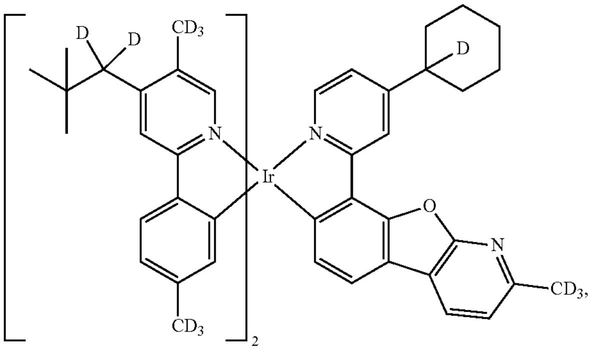
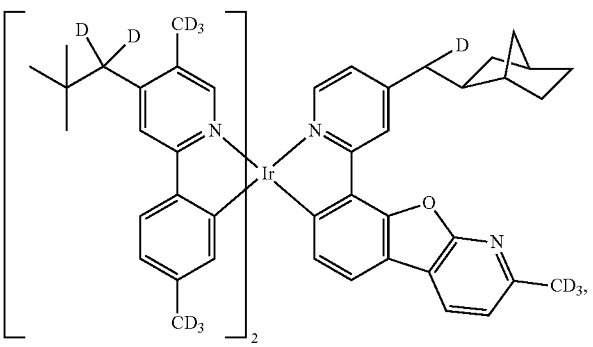
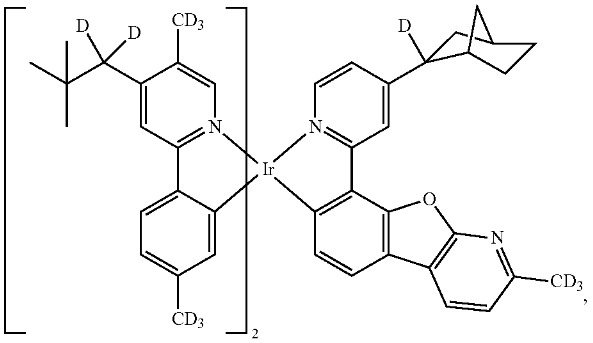
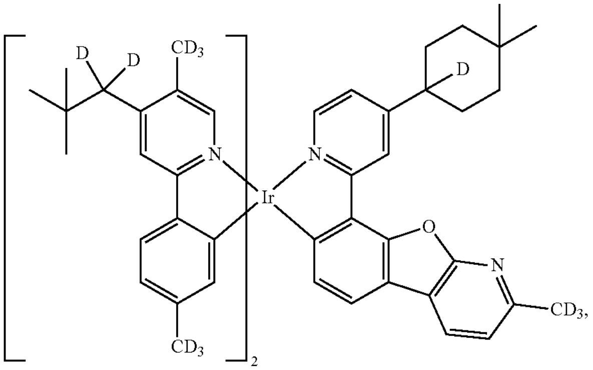
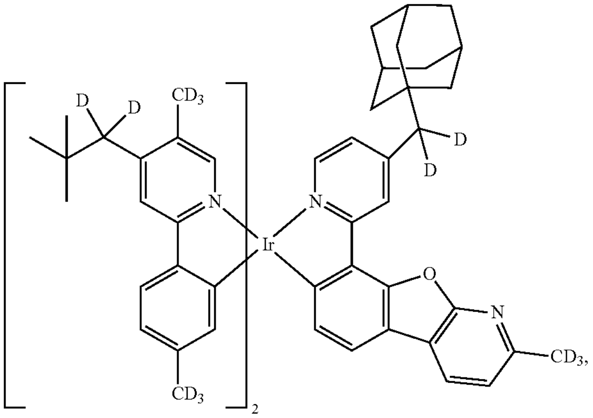
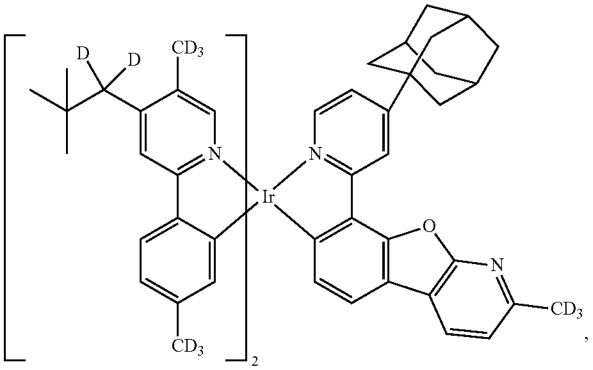
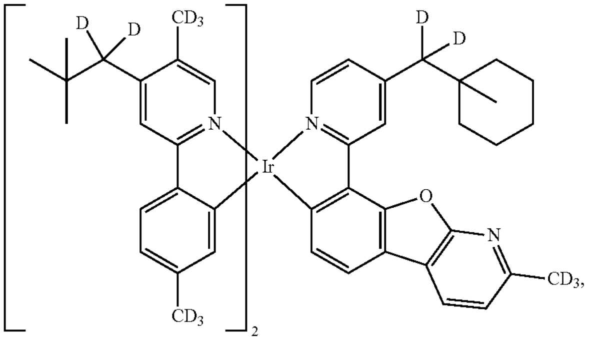
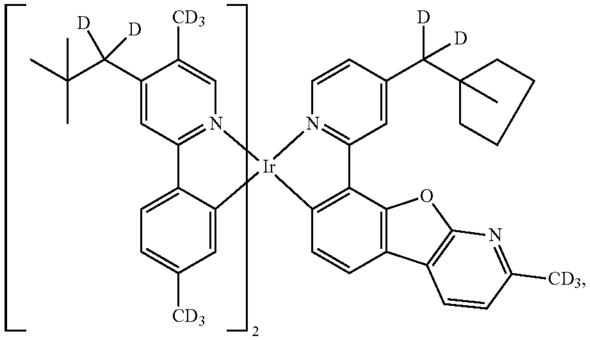

-continued
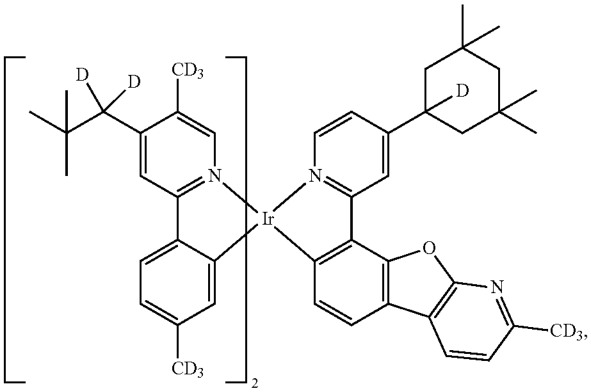
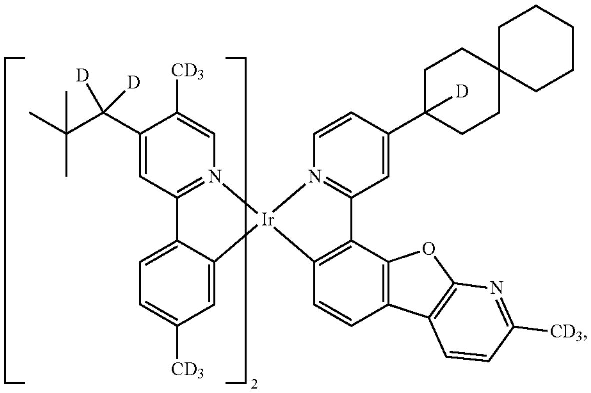
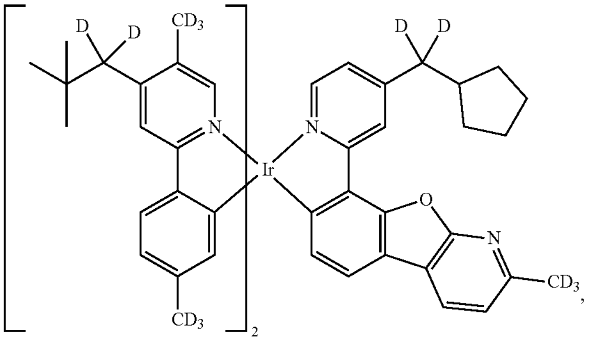
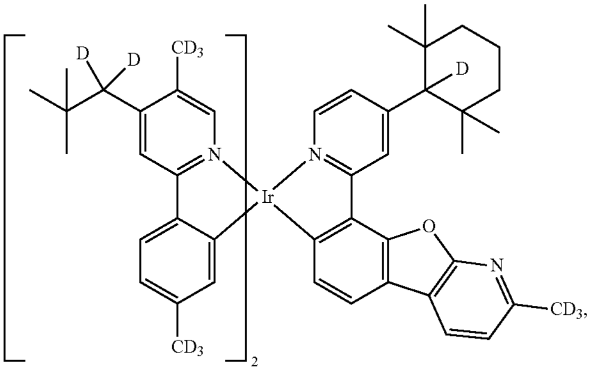
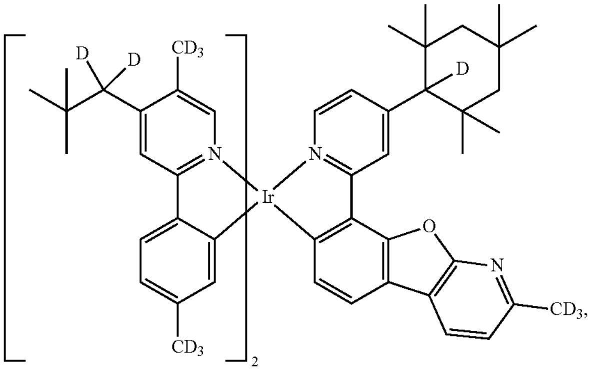
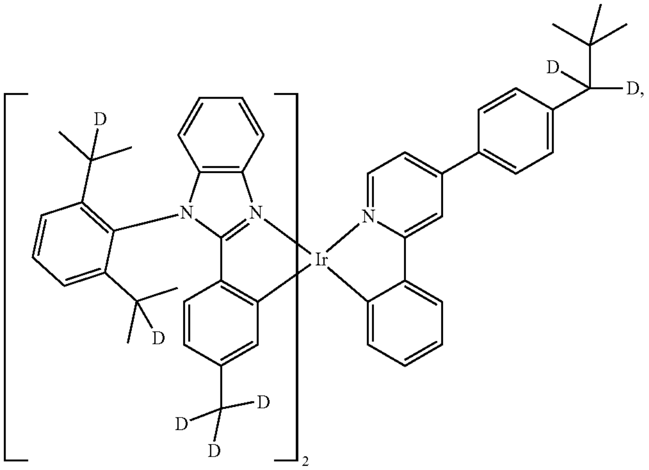

-continued
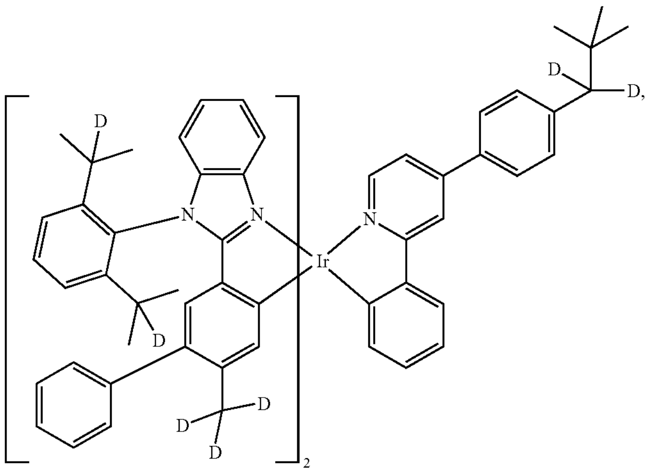
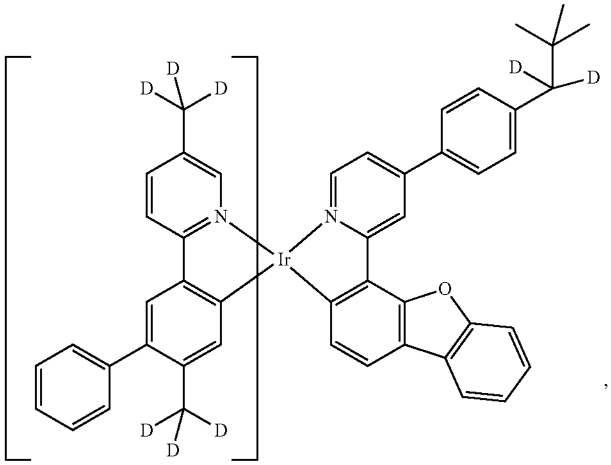
,
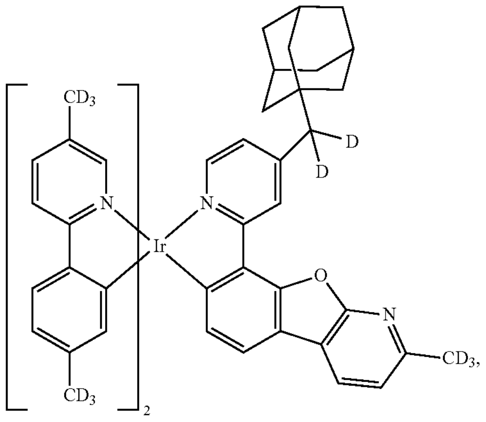
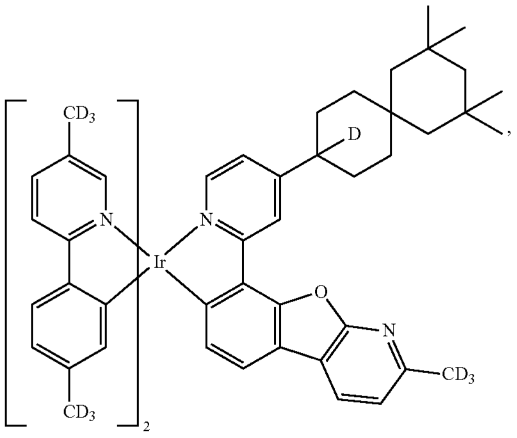

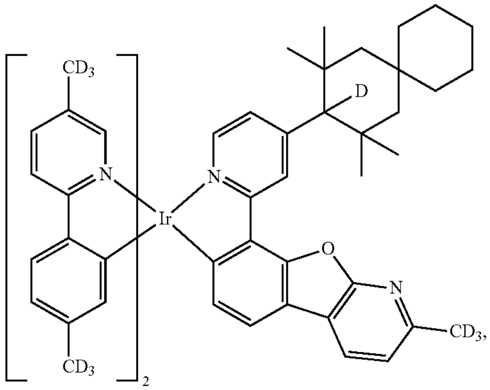
,
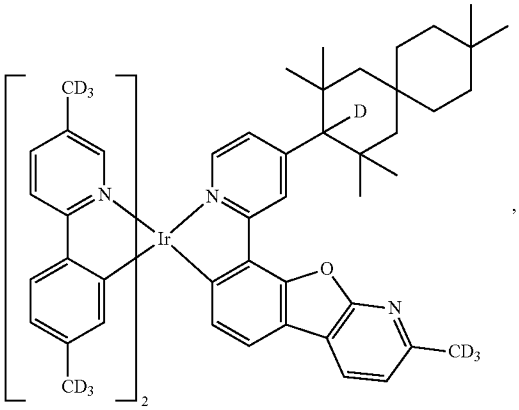
,
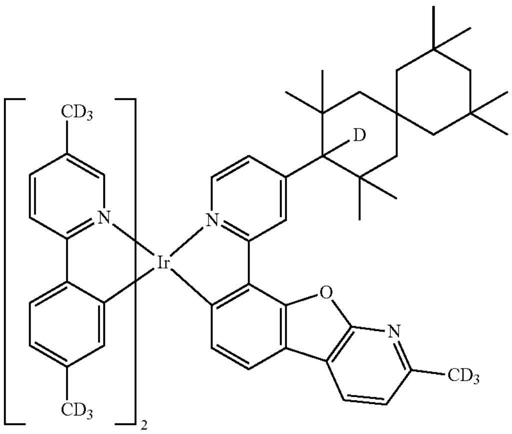
,
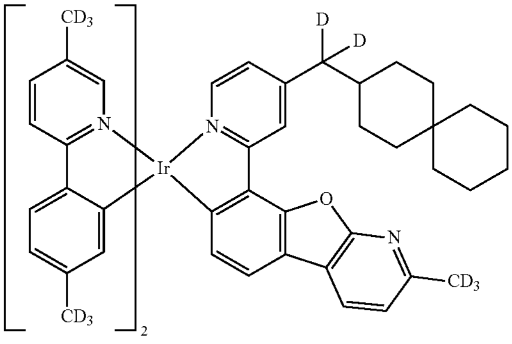
,
-continued
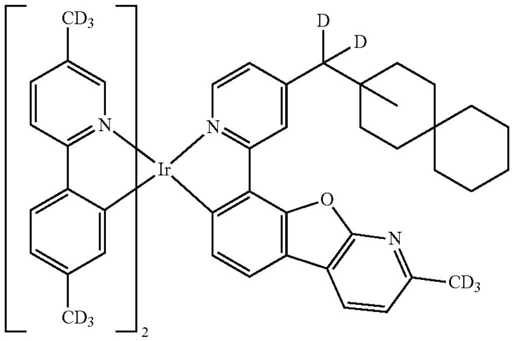
,
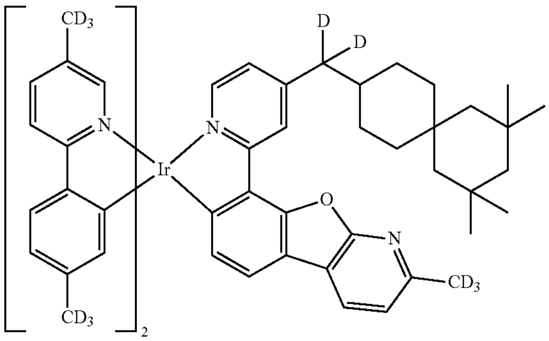
,
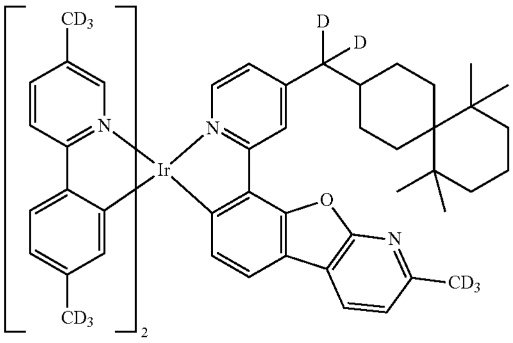
,
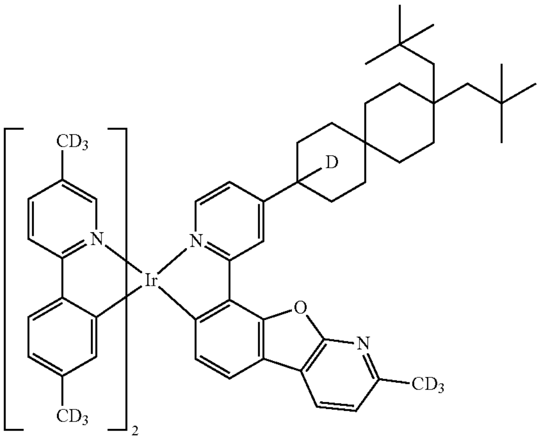
, -continued
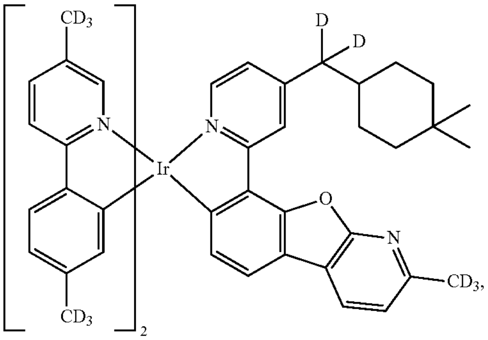
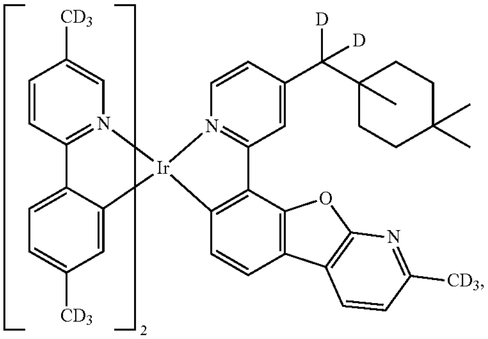
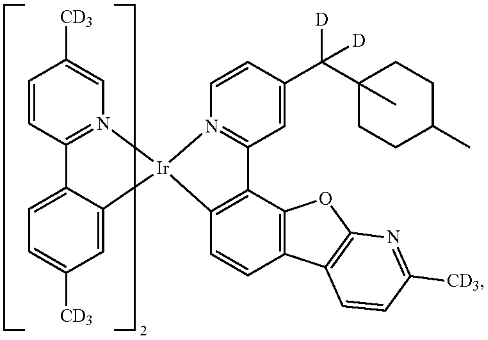
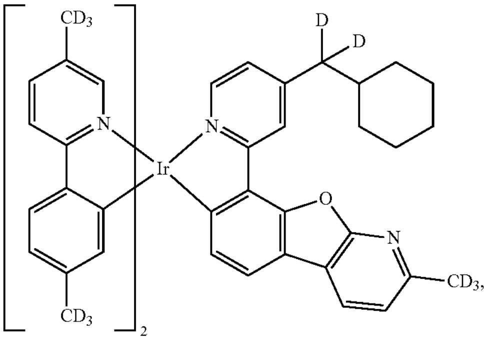
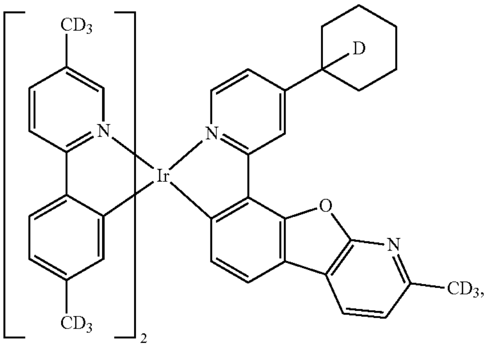
-continued
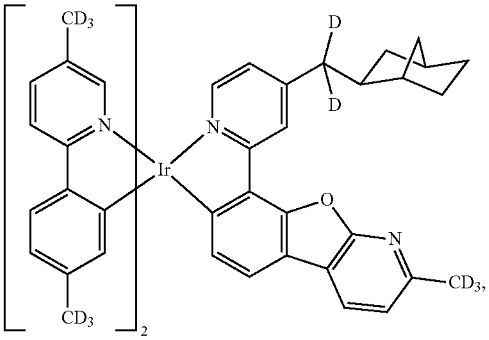
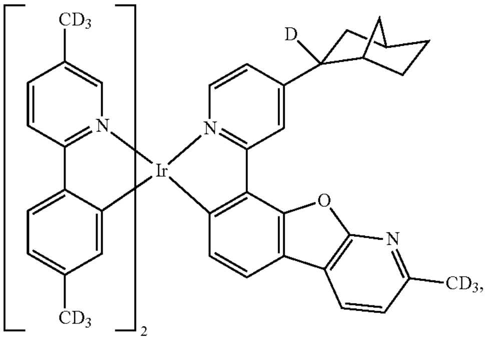
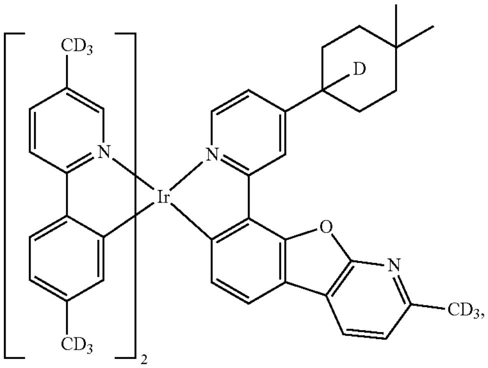
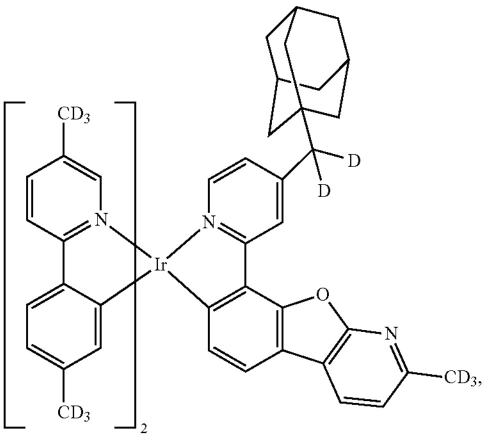

-continued
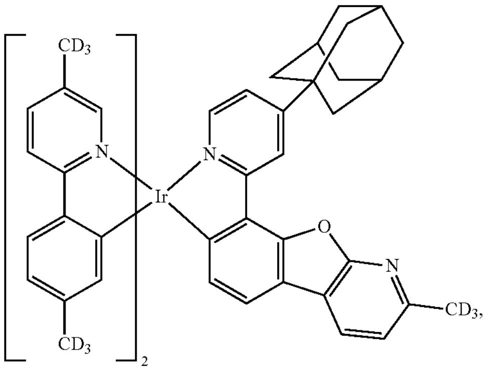
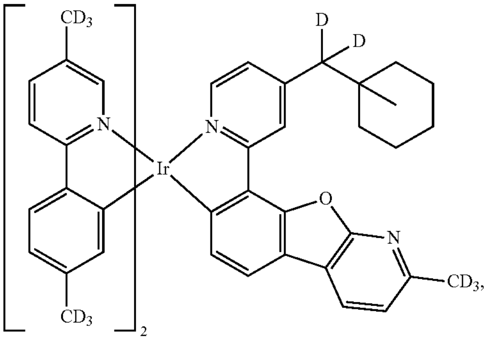
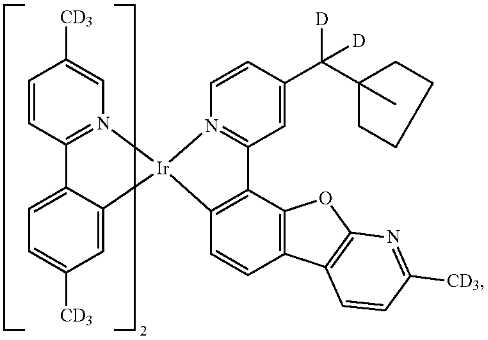
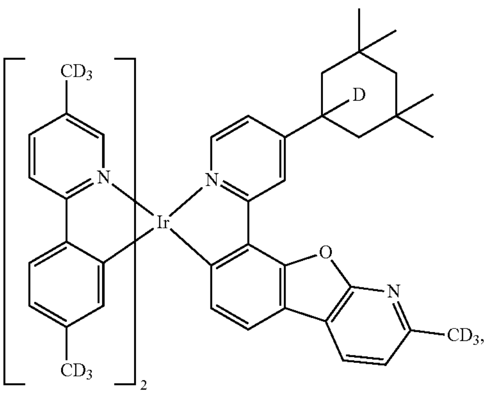
-continued
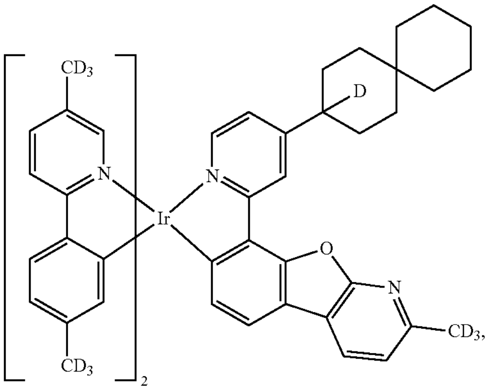
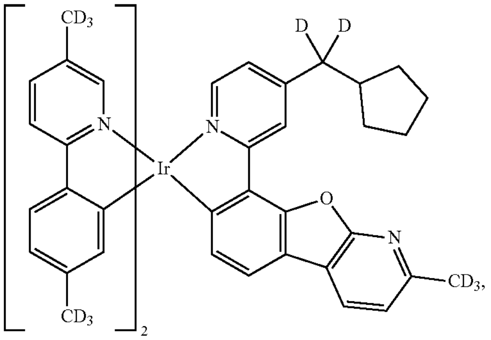
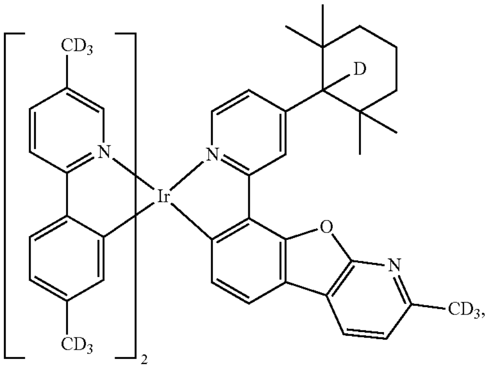
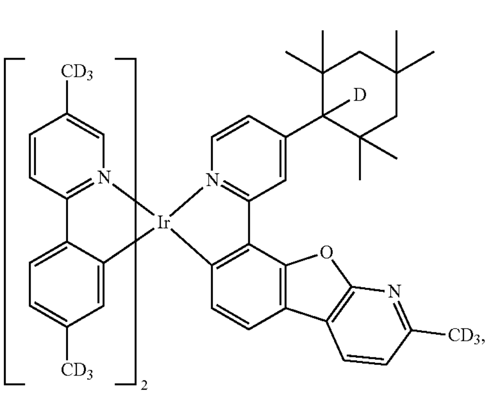

-continued
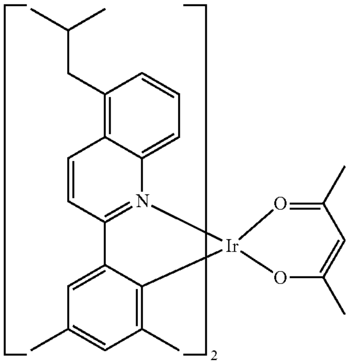
,
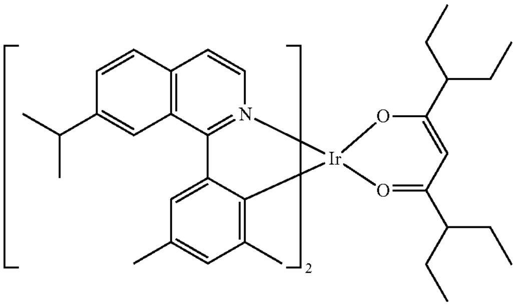
,
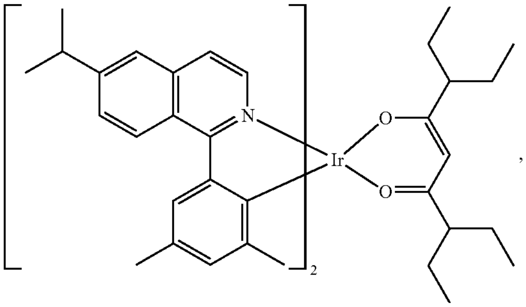
,
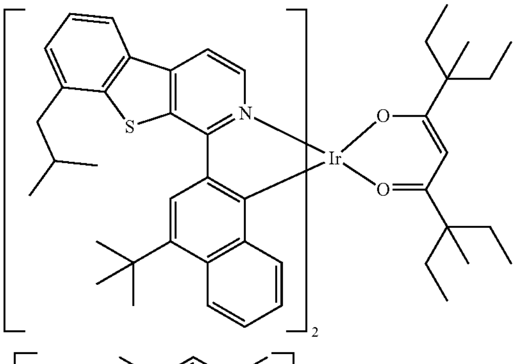
,
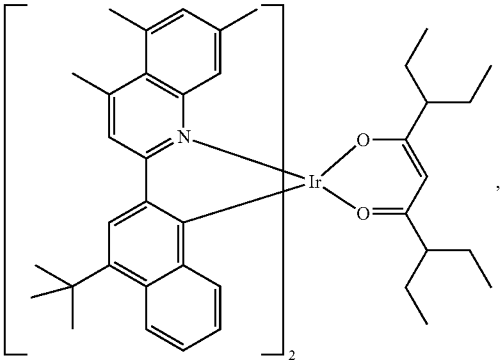
,
-continued
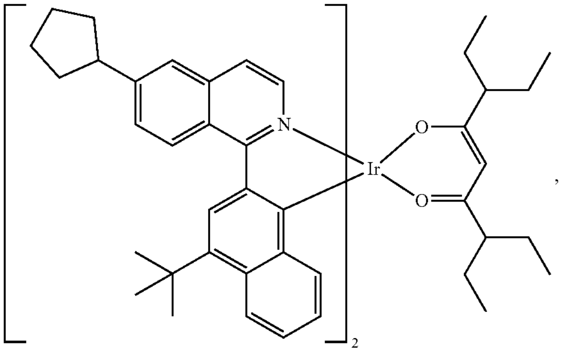
,
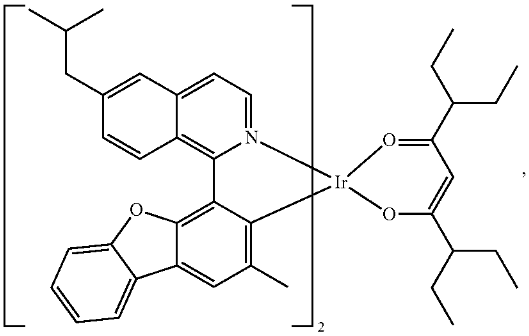
,
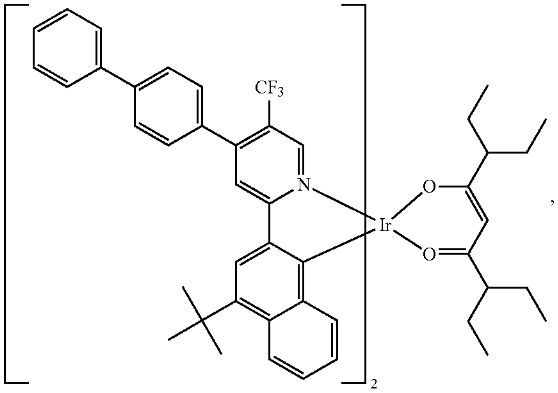
,
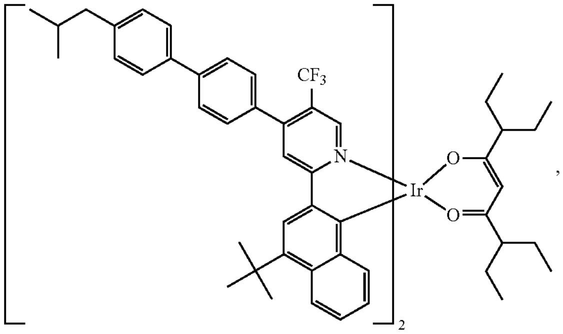
, -continued
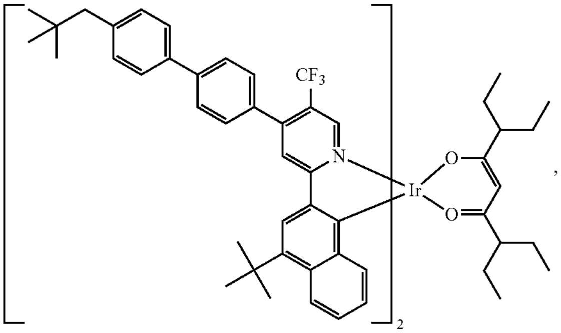
,
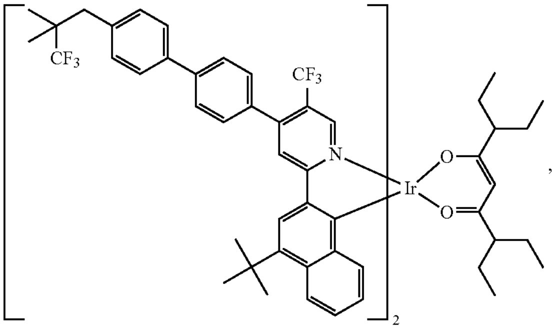
,
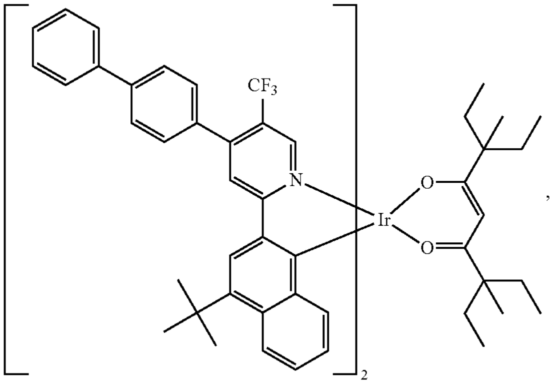
,
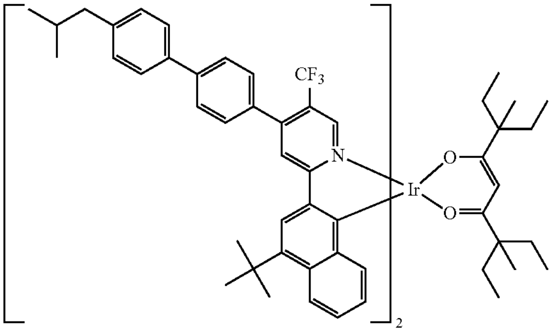
,
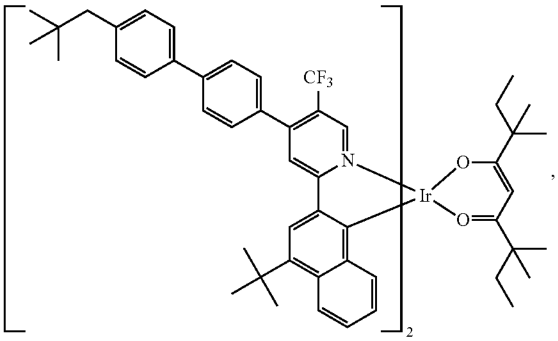
,
-continued
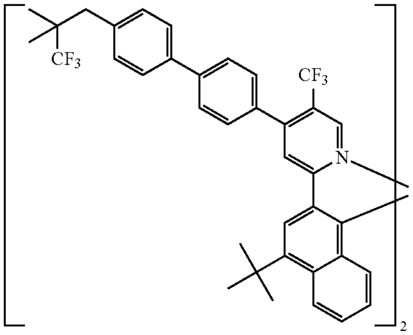
,
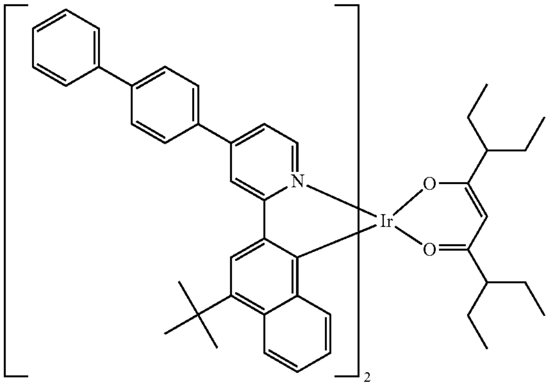
,
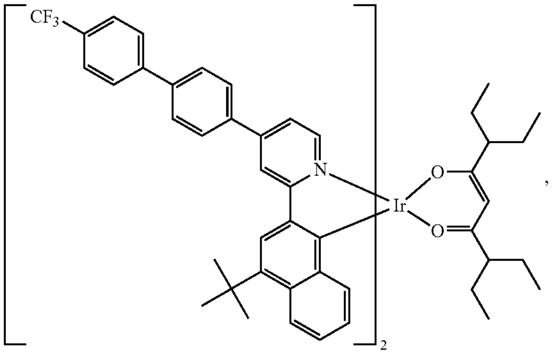
,
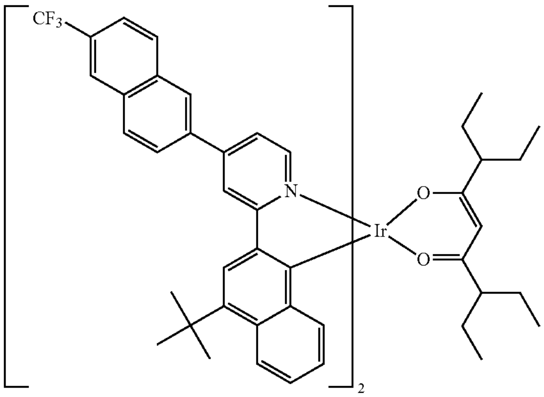
, -continued
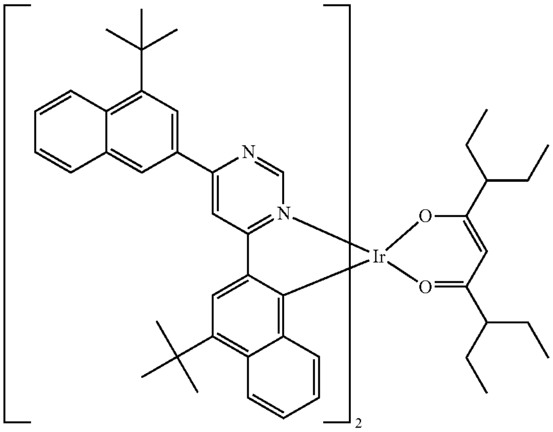
,
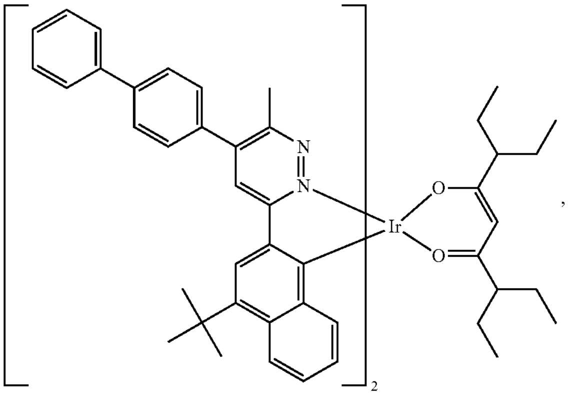
,
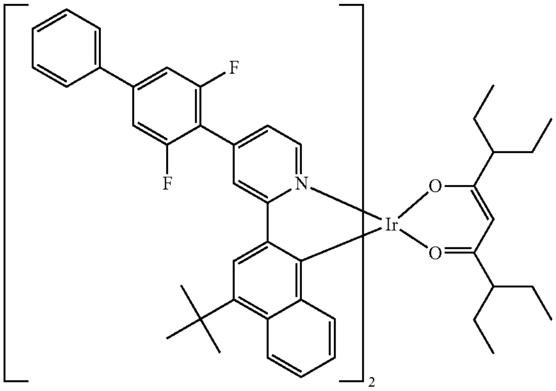
,
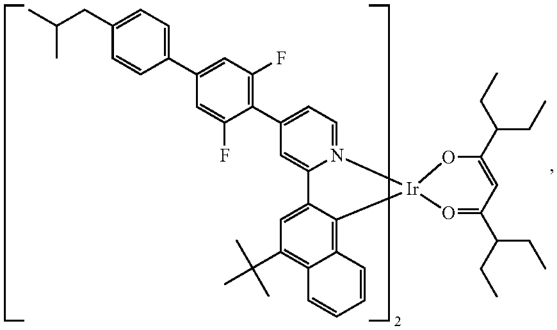
,
-continued
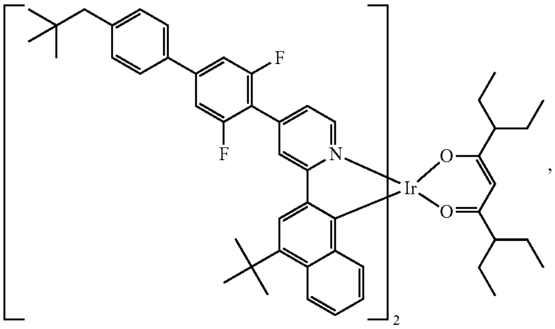
,
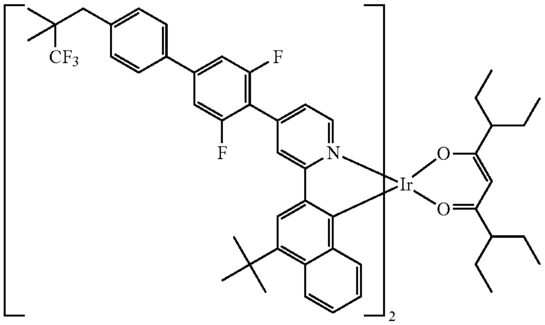
,
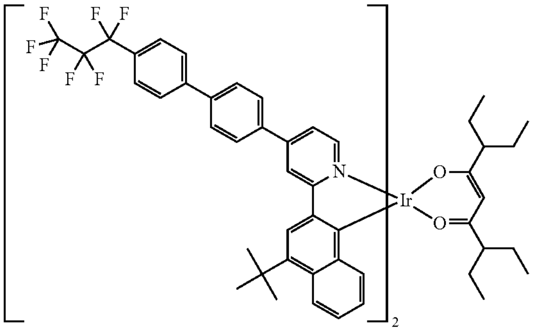
,
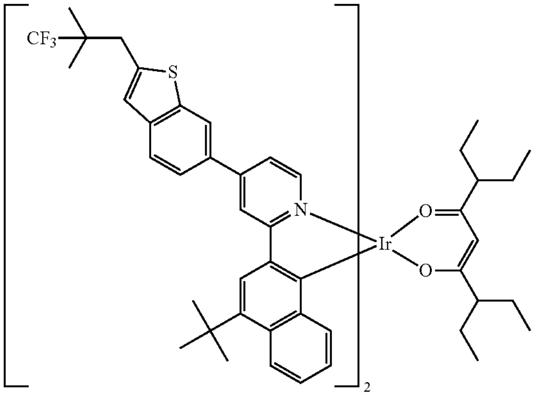
, -continued
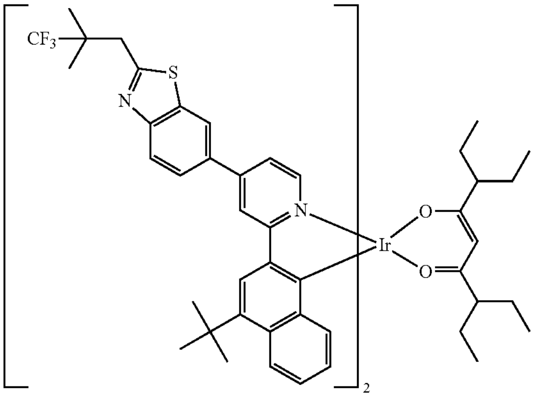
,
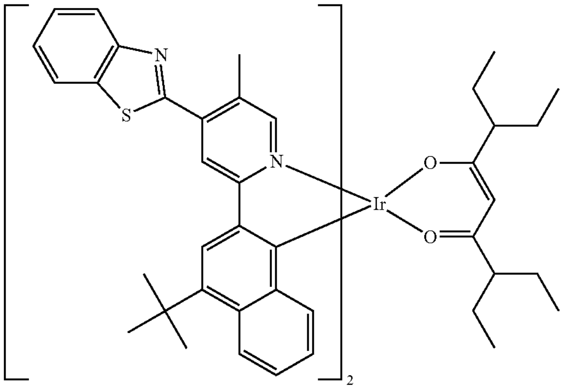
,
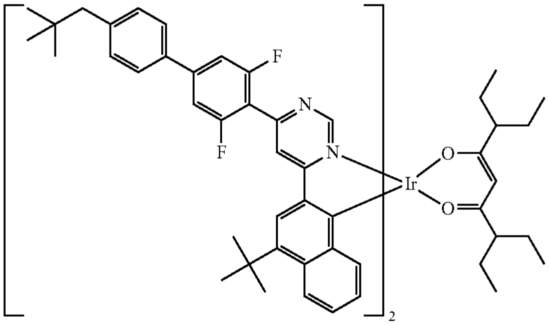
,
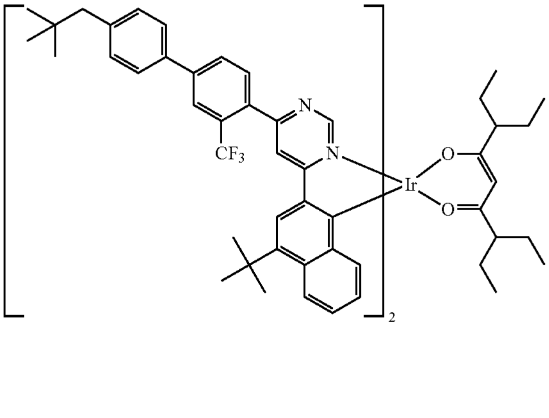
,
-continued
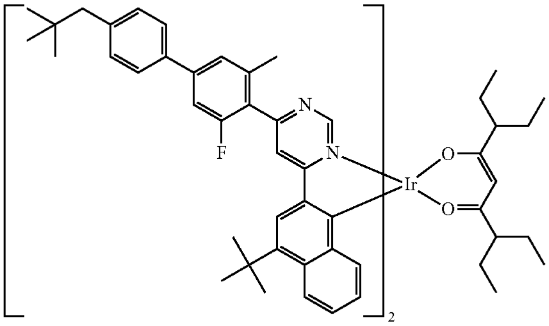
,
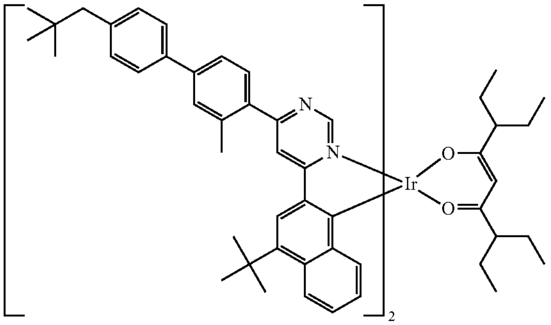
,
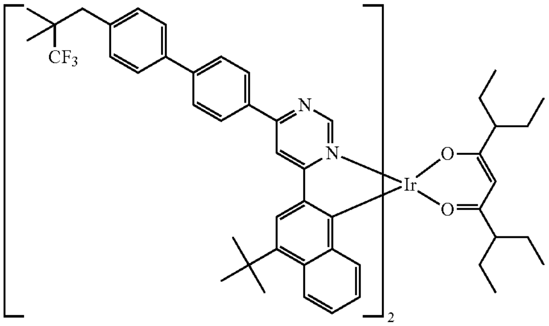
,
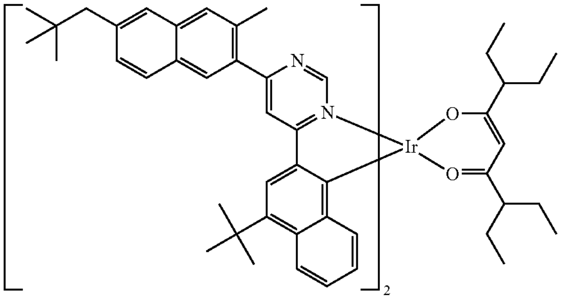
,
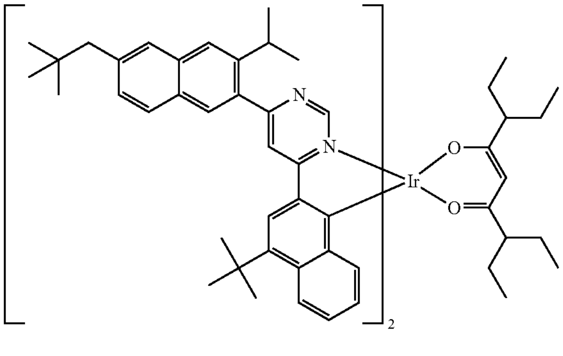
, -continued
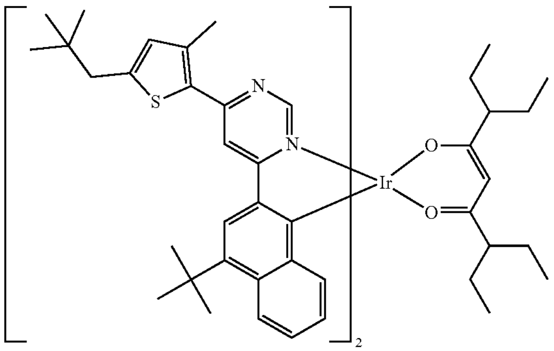
,
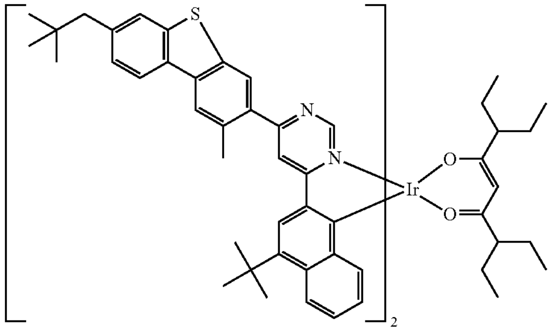
,
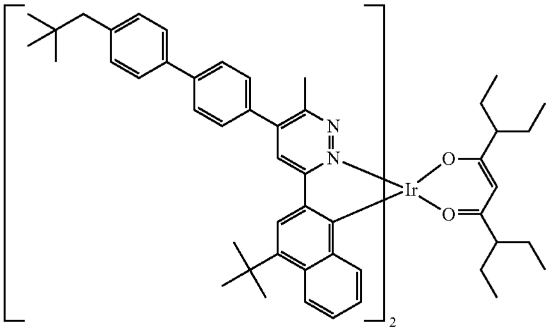
,
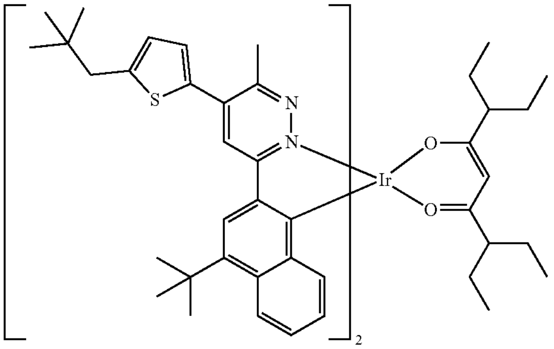
,
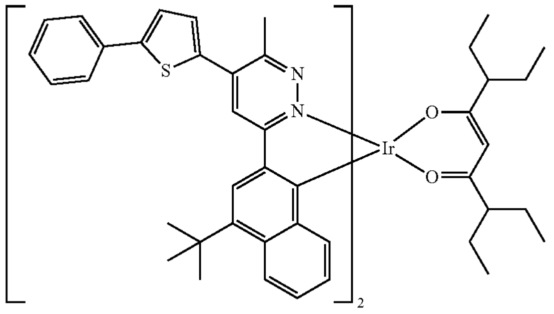
,
-continued
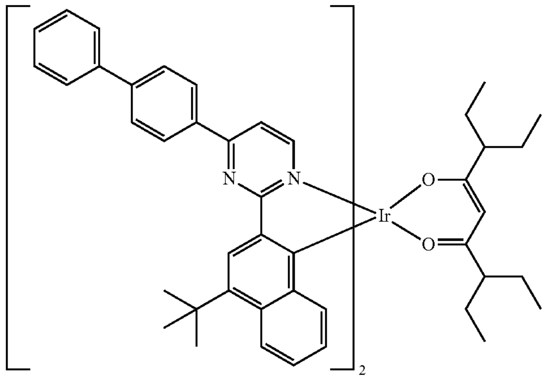
,
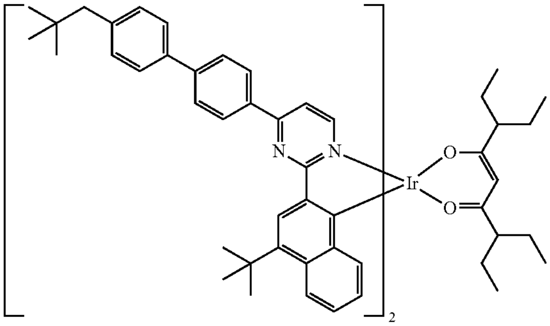
,
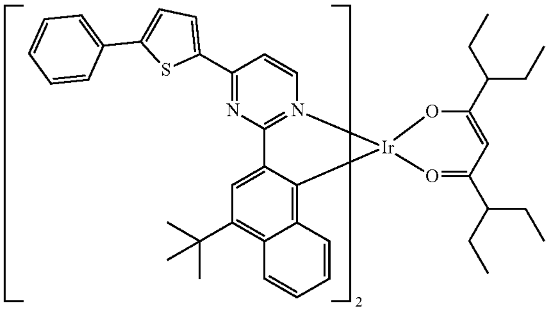
,
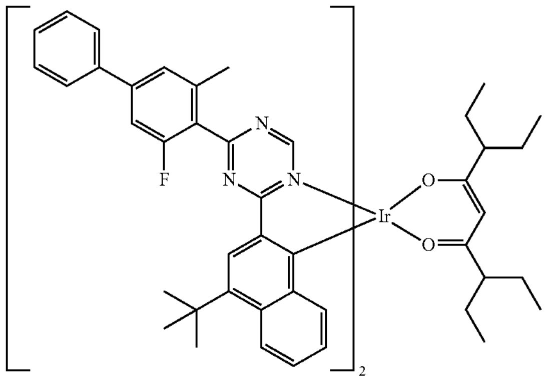
,
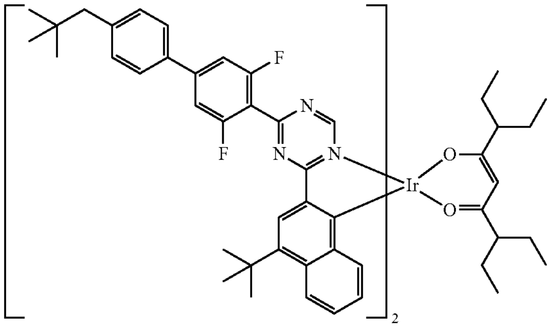
, -continued
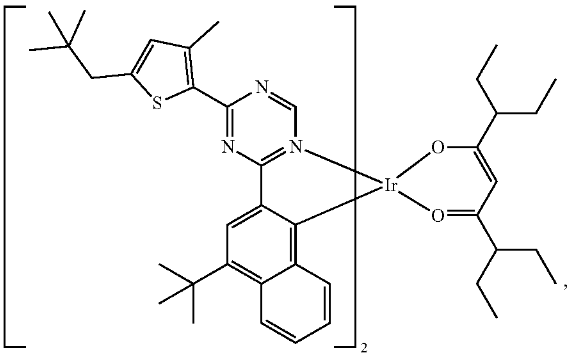
,
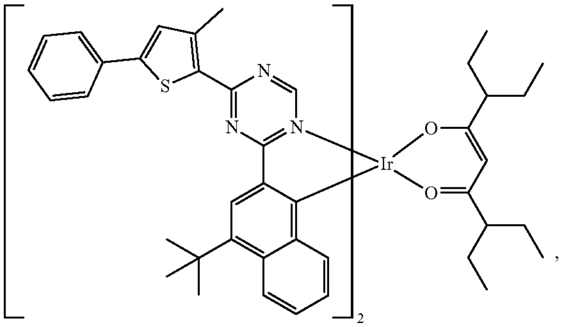
,
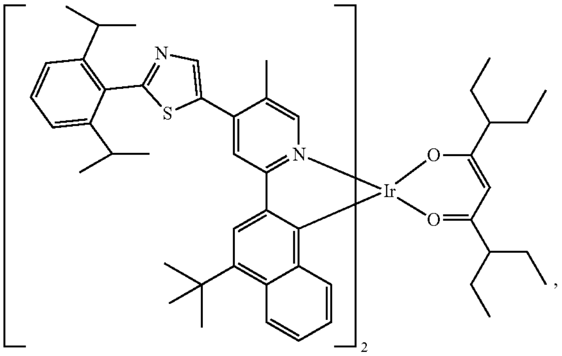
,
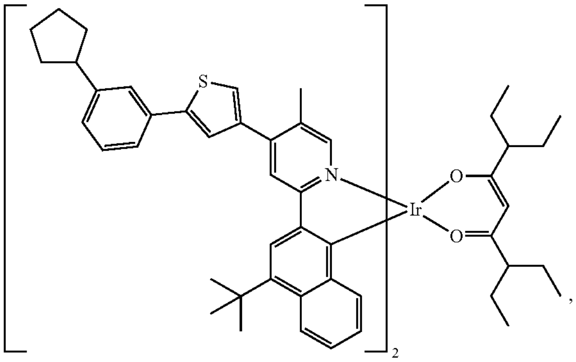
,
-continued
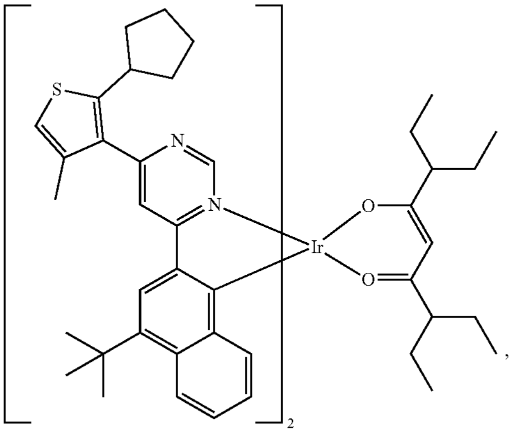
,
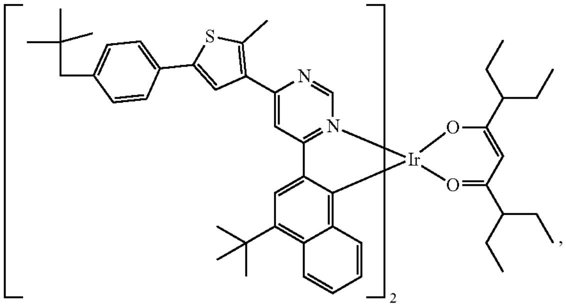
,
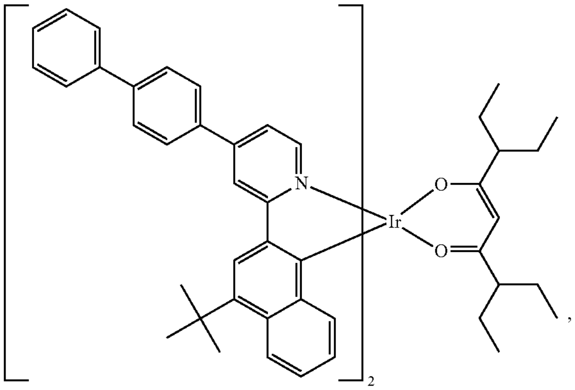
,
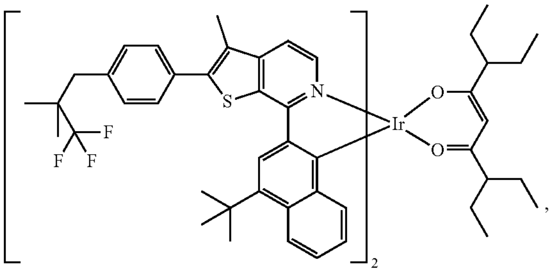
,
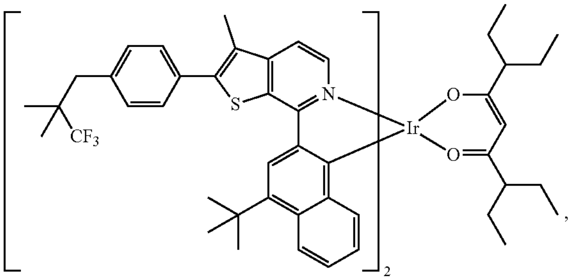
, -continued
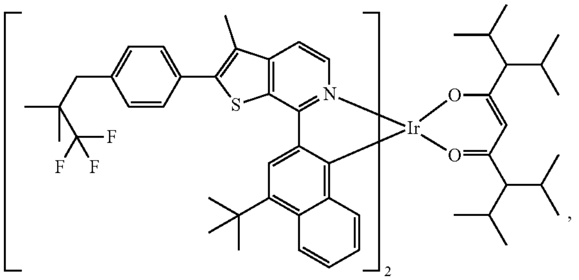
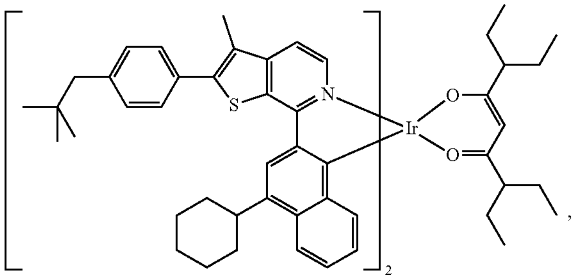
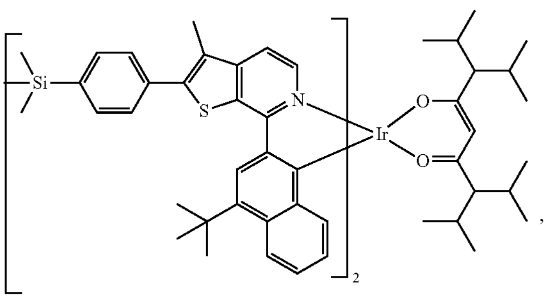
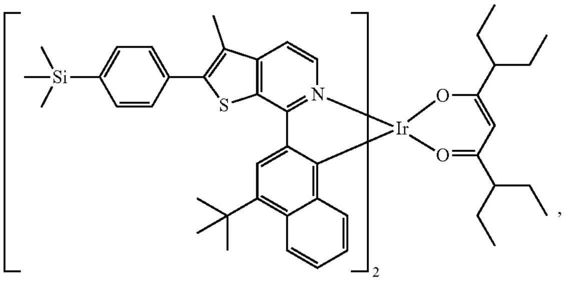
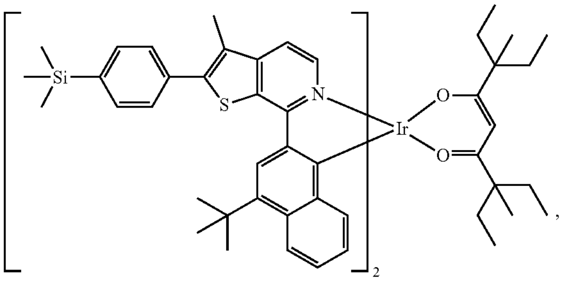
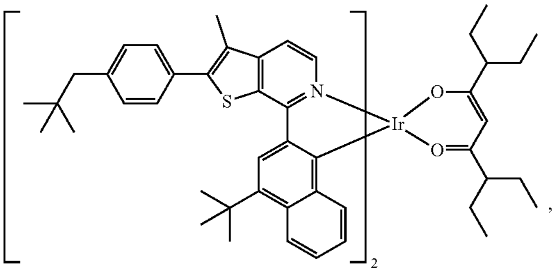
-continued
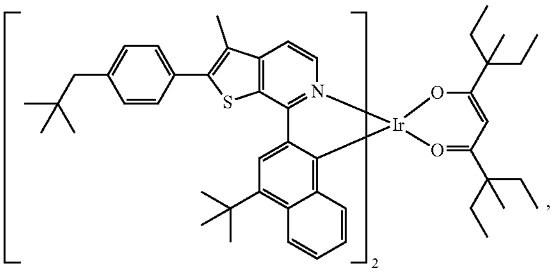
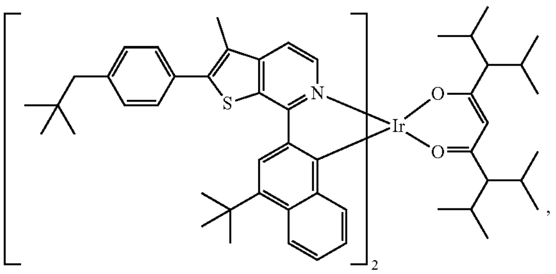
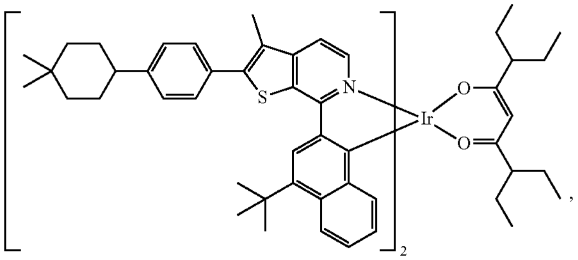
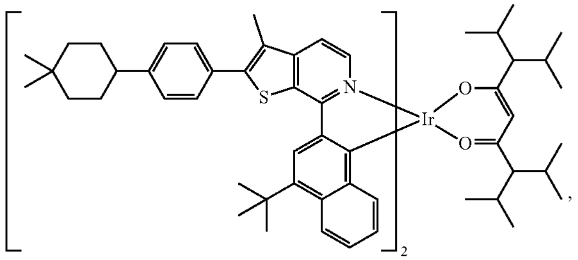
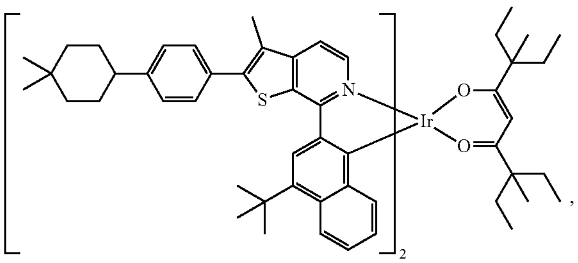
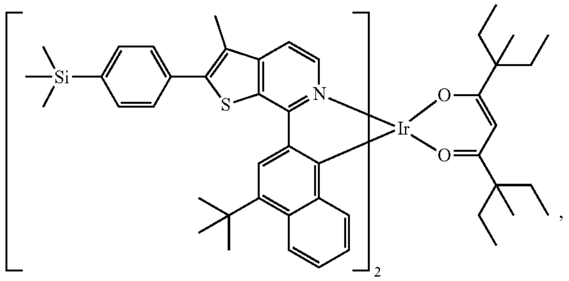

-continued
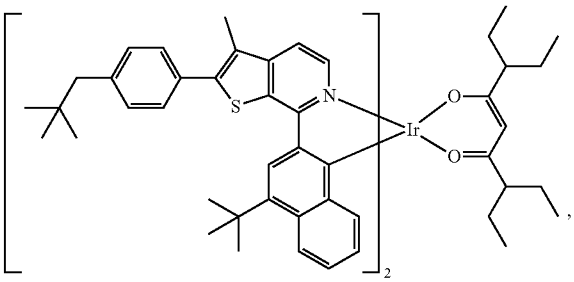
,
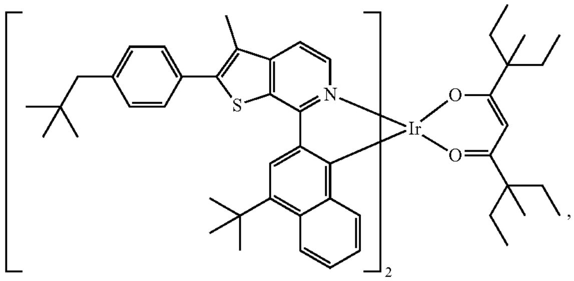
,
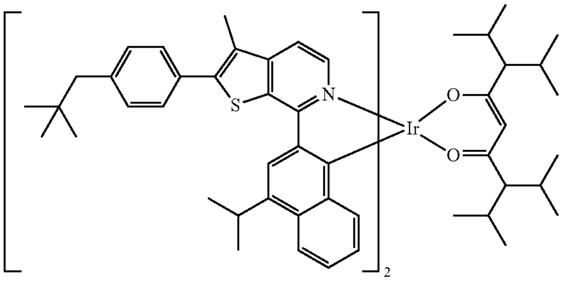
,
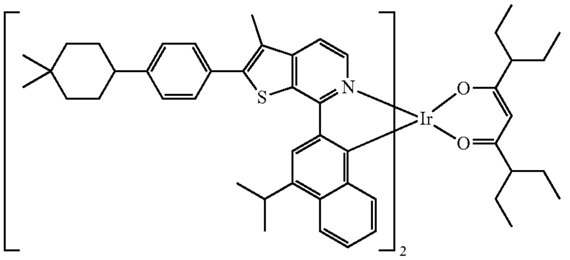
,
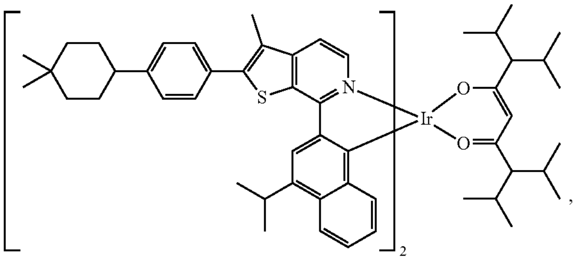
,
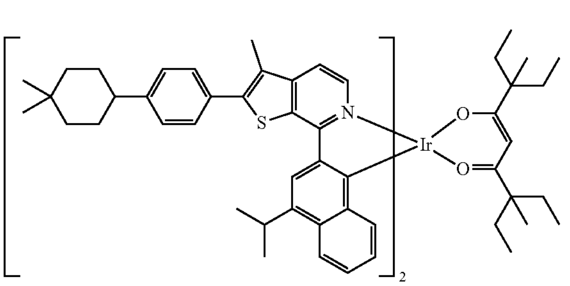
,
-continued
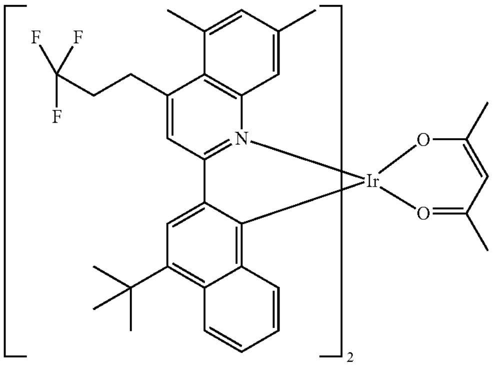
,
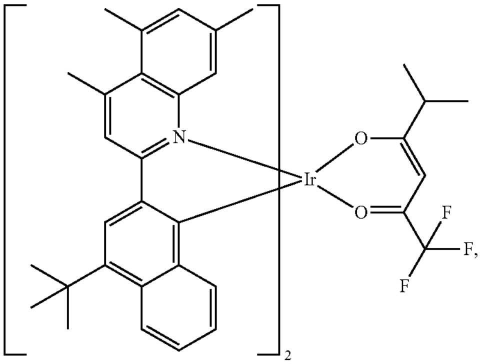
,
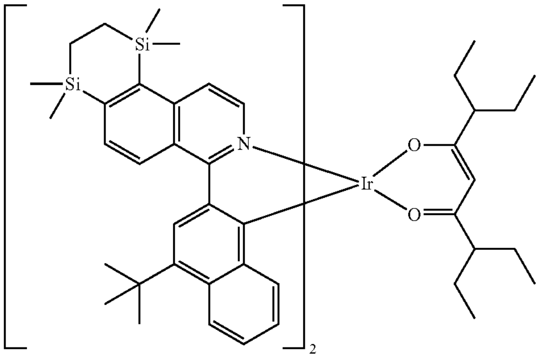
,
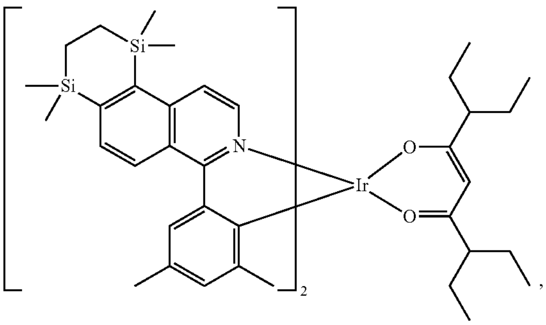
,
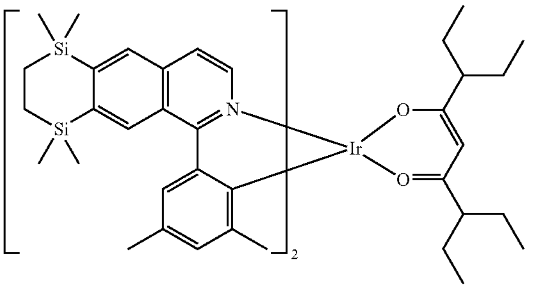
, -continued
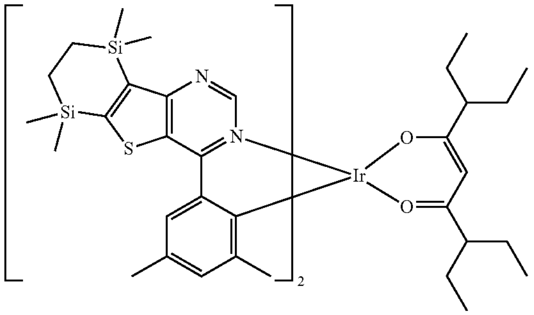
,
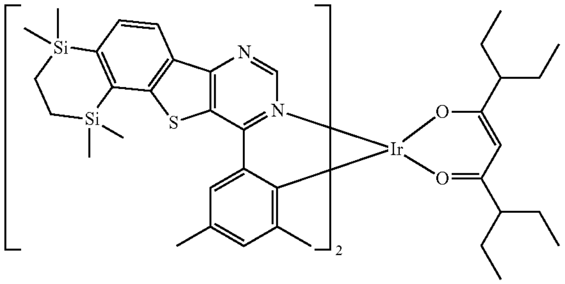
,
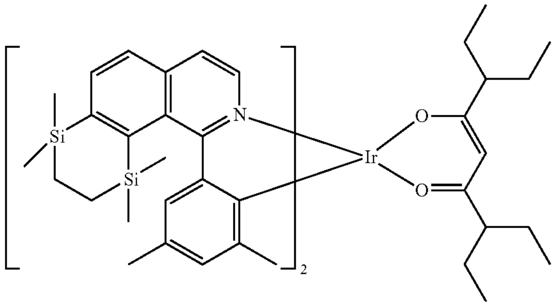
,
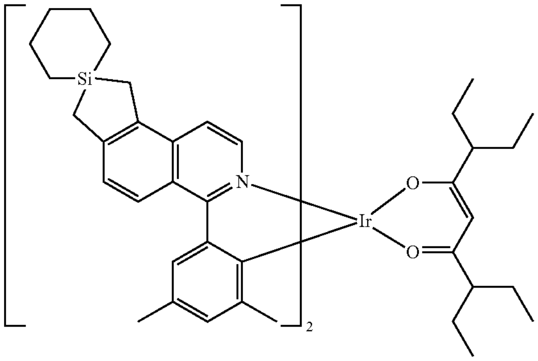
,
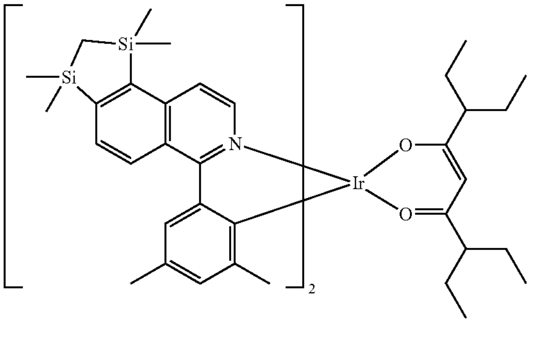
,
-continued
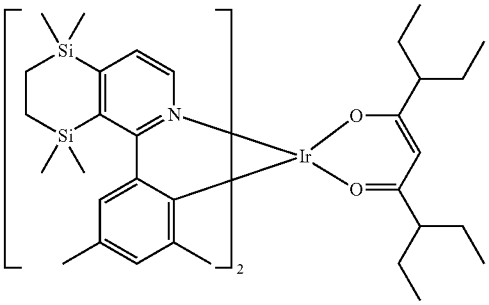
,
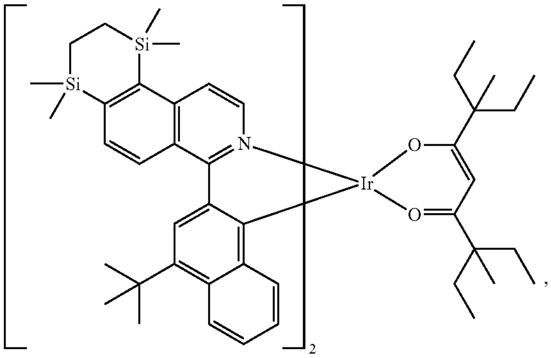
,
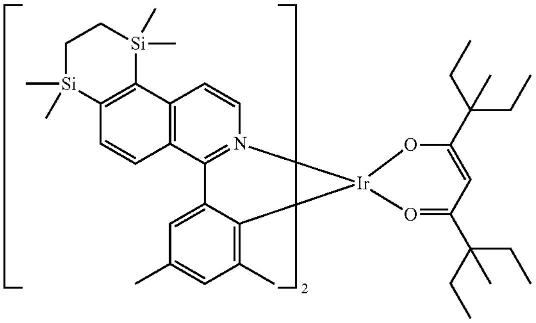
,
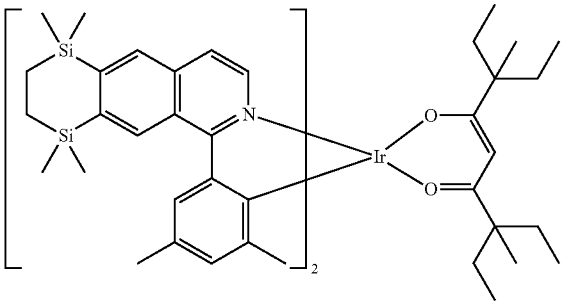
,
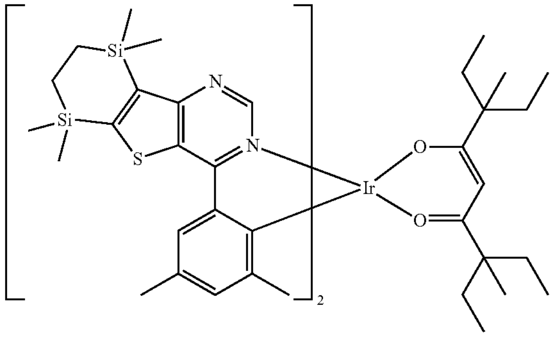
, -continued
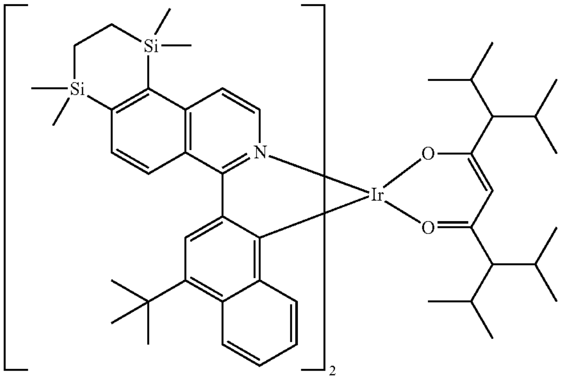
,
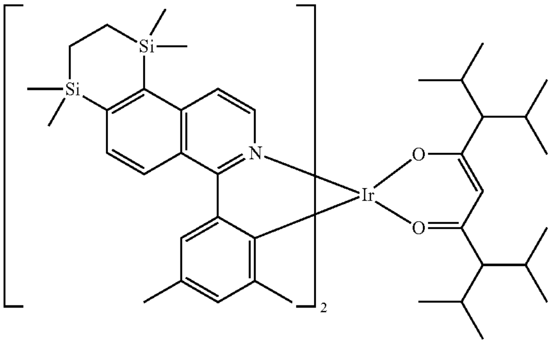
,
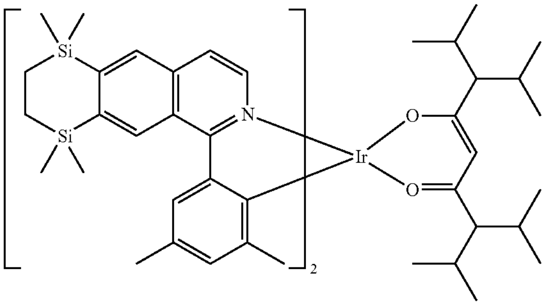
,
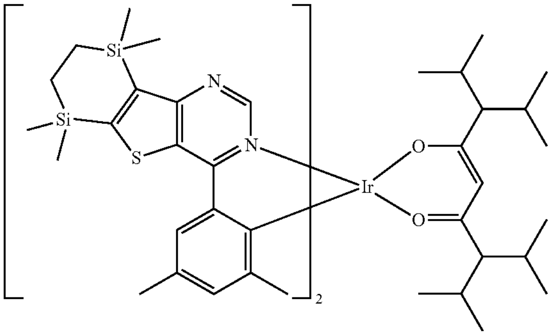
,
-continued
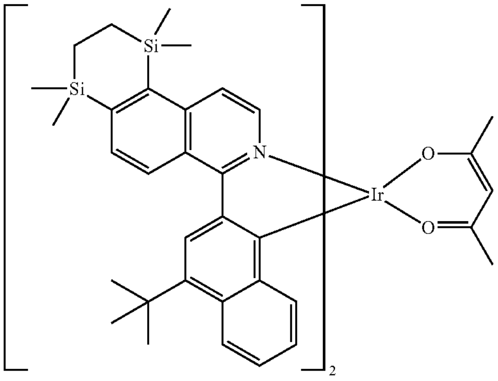
,
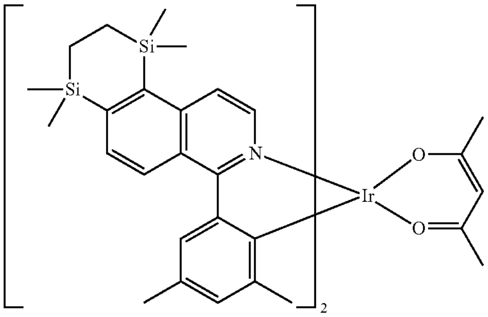
,
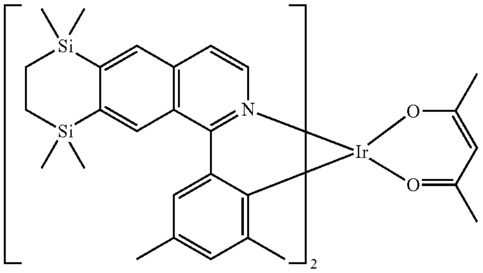
,
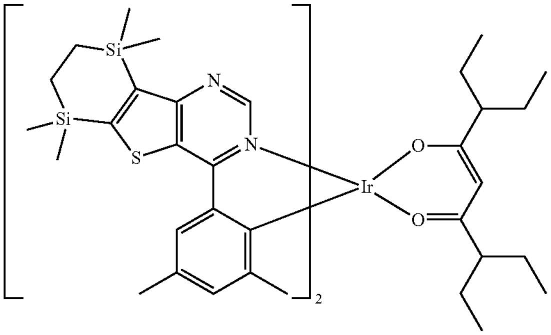
,
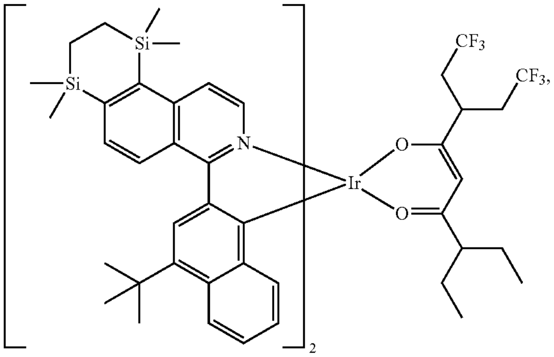

-continued
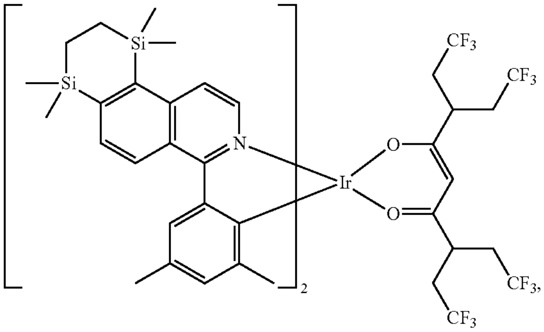
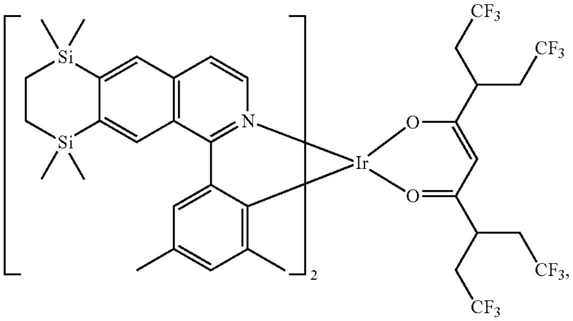
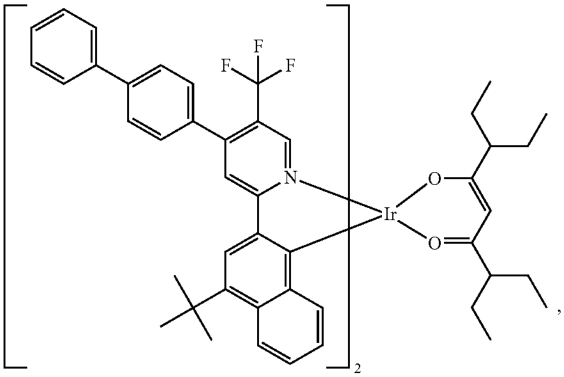
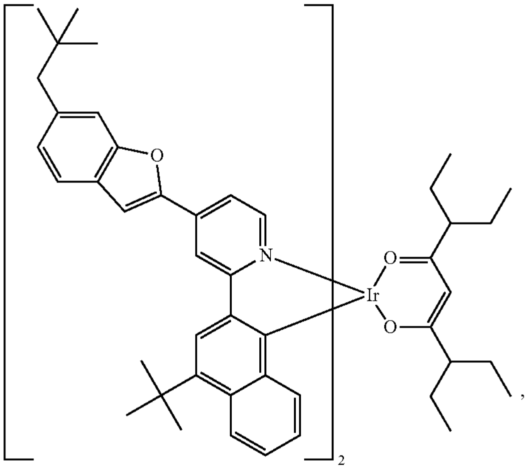
-continued
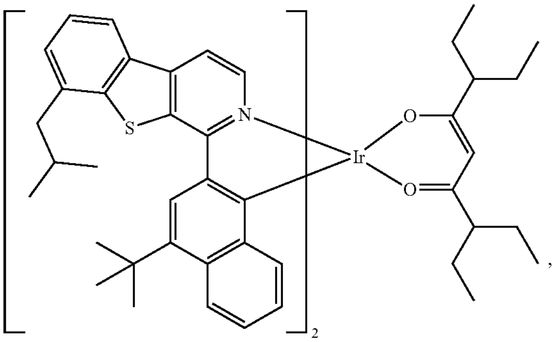
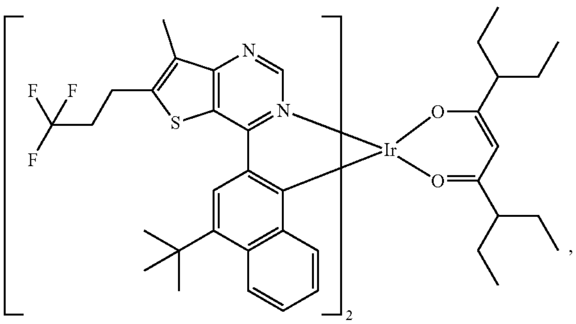
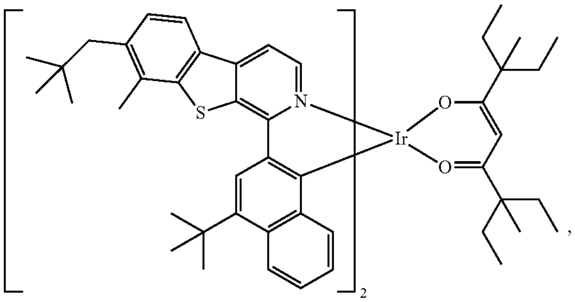
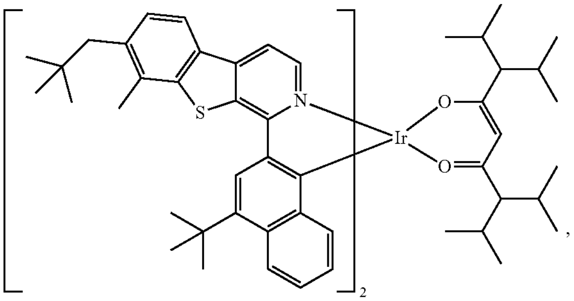
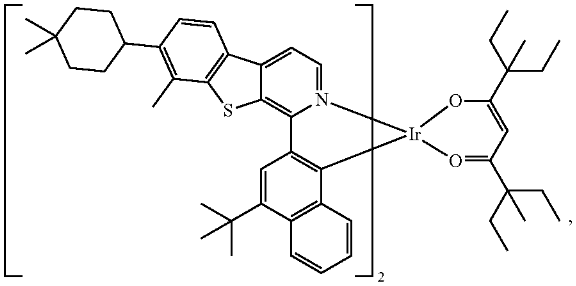

-continued
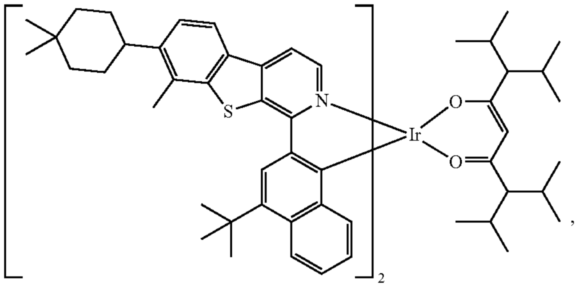
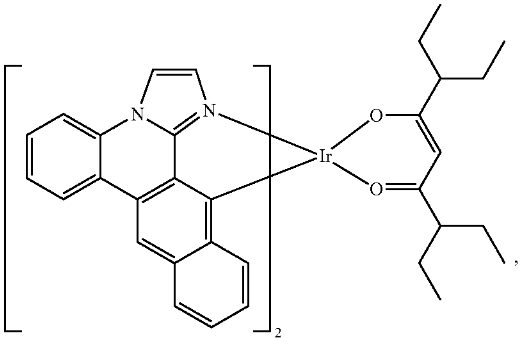
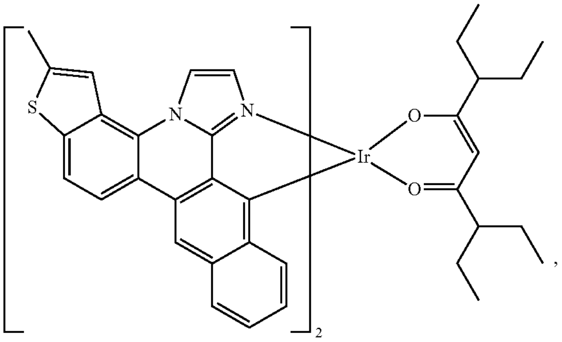
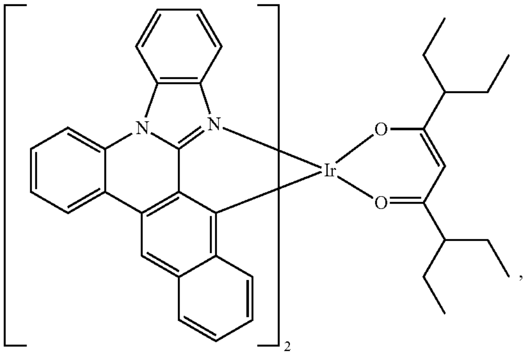
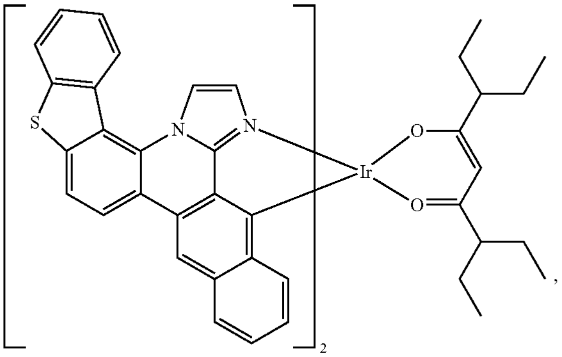
-continued
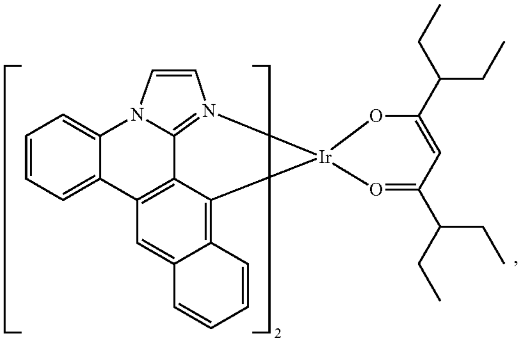
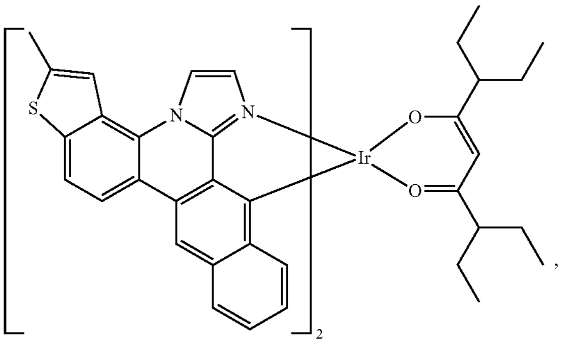
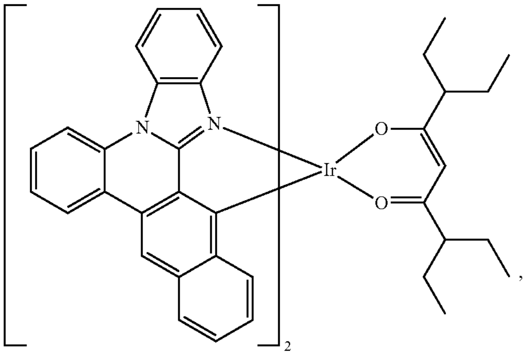
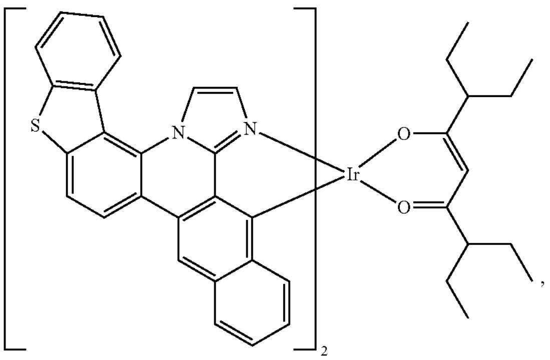

-continued
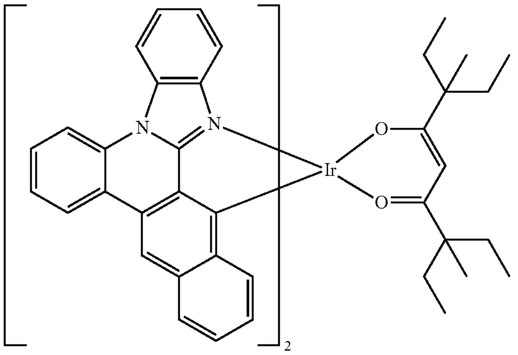
,
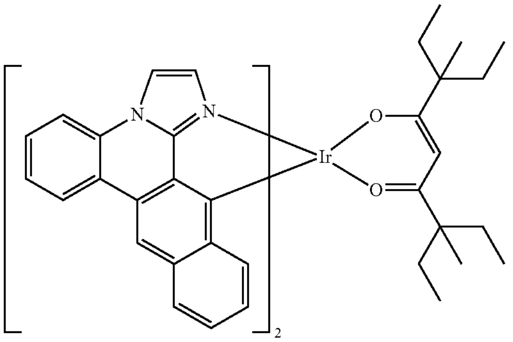
,
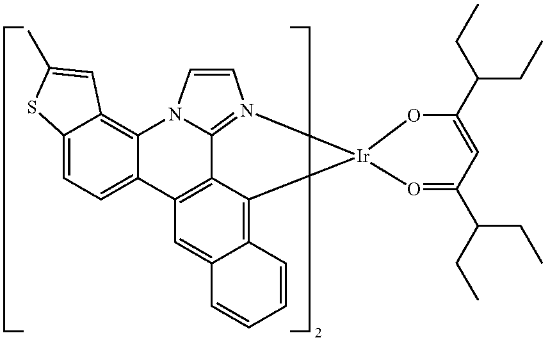
,
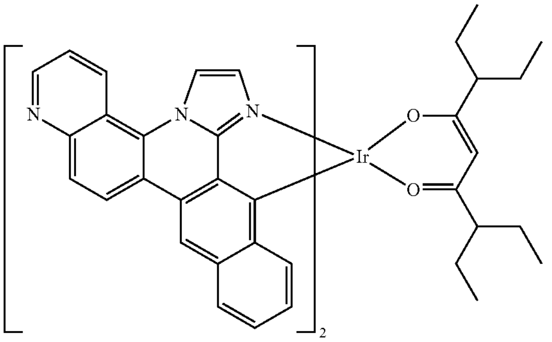
,
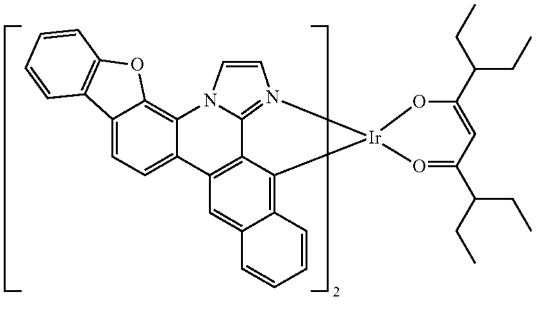
,
-continued
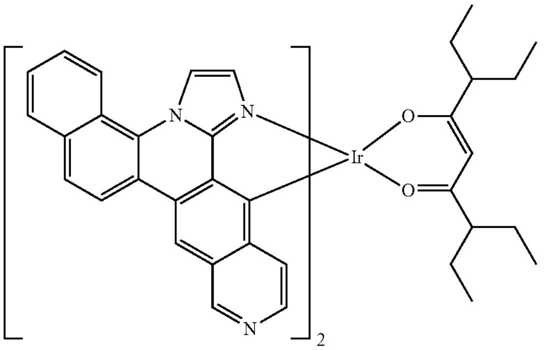
,
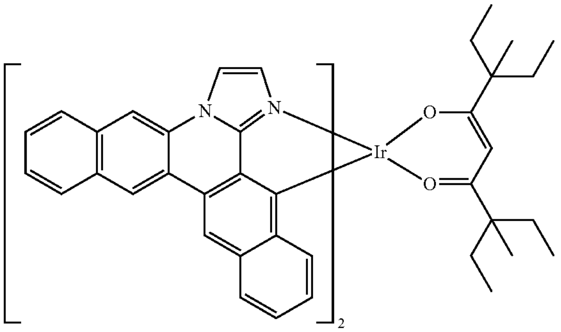
,
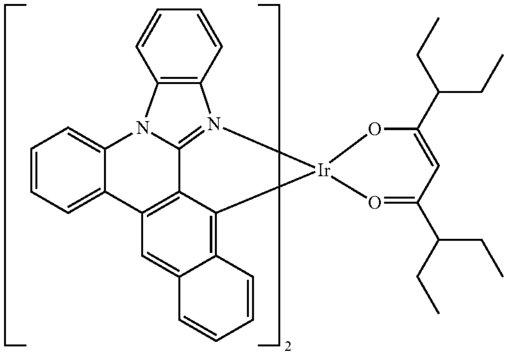
,
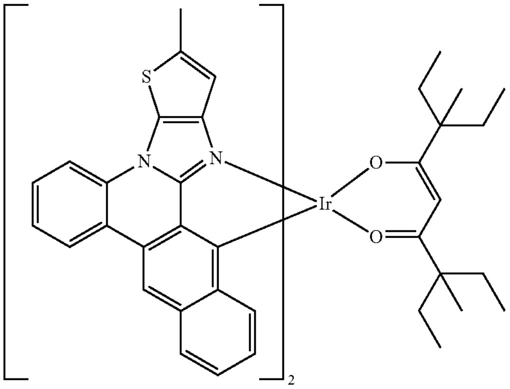
, -continued
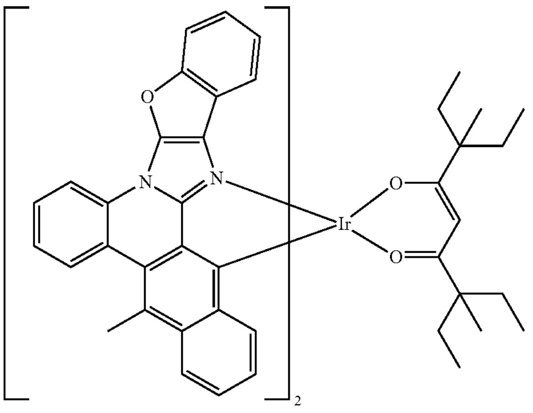
,
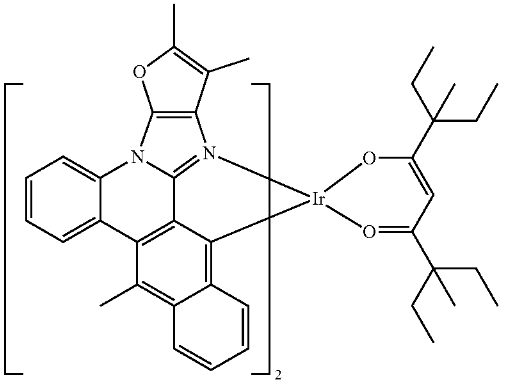
,
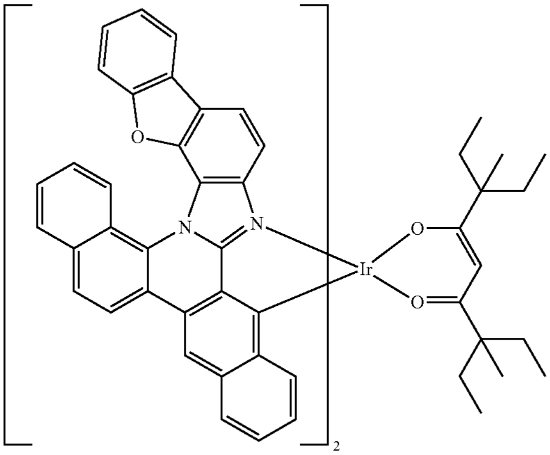
,
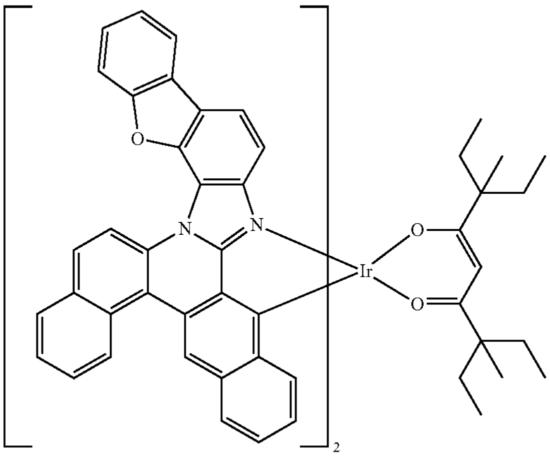
,
-continued
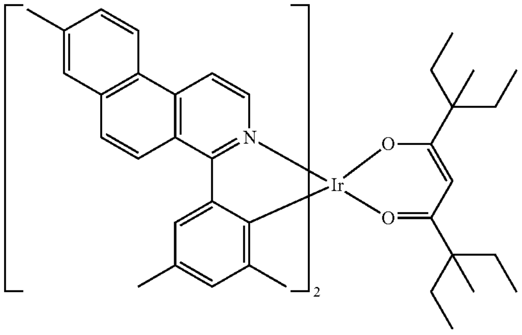
,
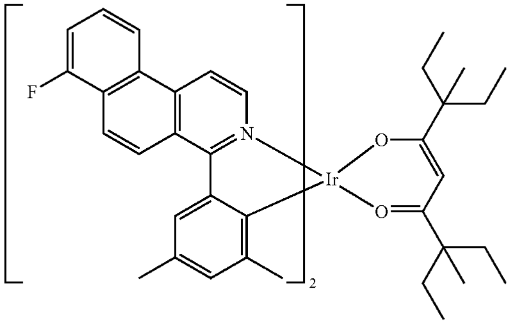
, and
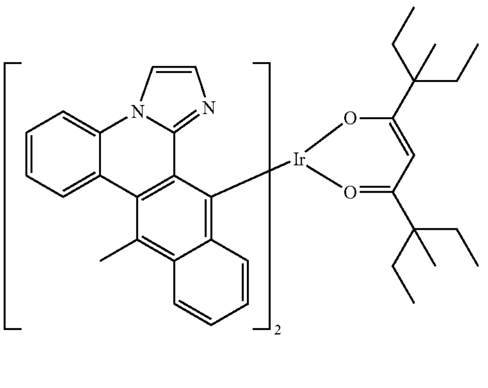
.
In some embodiments, the phosphorescent dopant is selected from the group consisting of the structures of the following LIST 11:
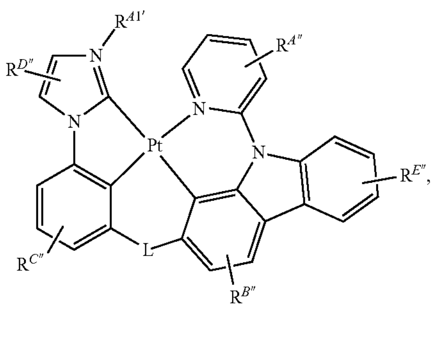

-continued
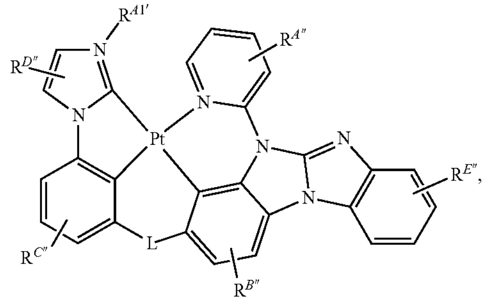
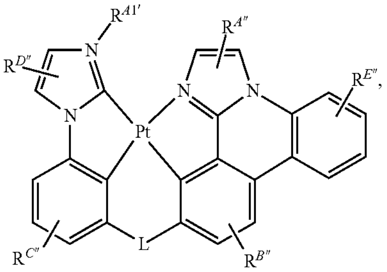
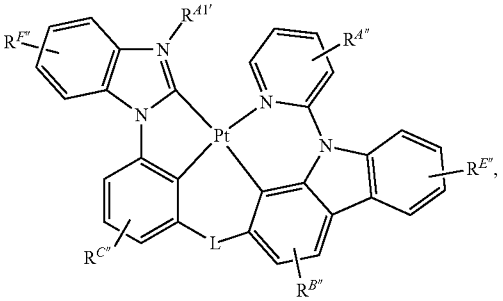
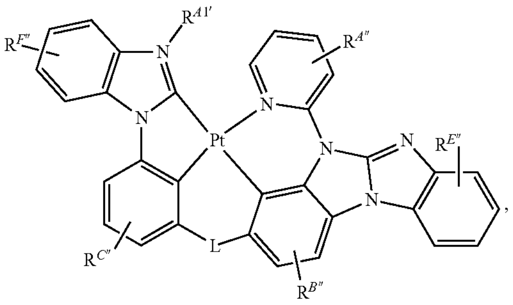
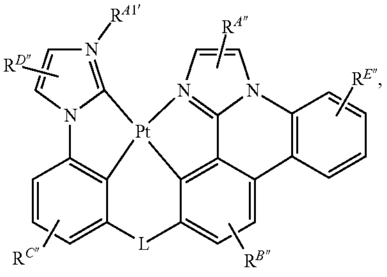
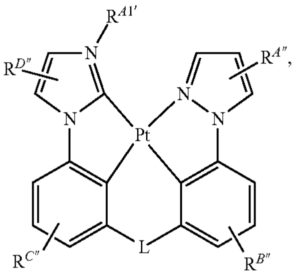
-continued
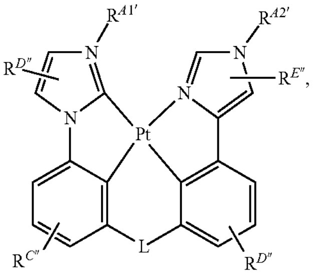
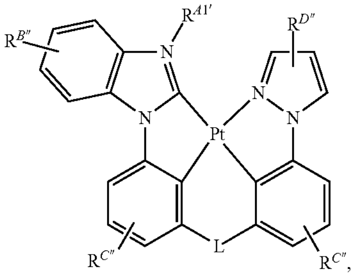
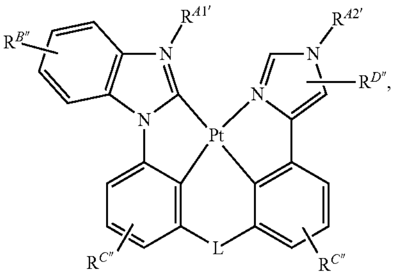
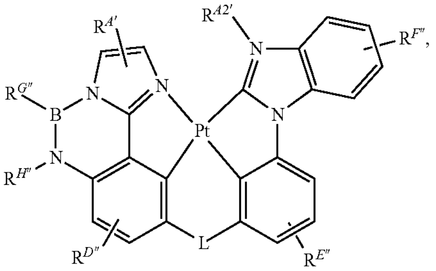
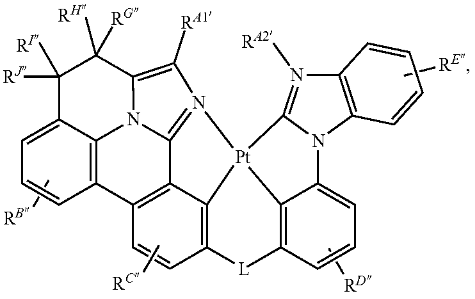
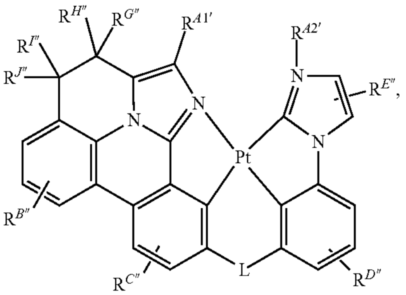

-continued
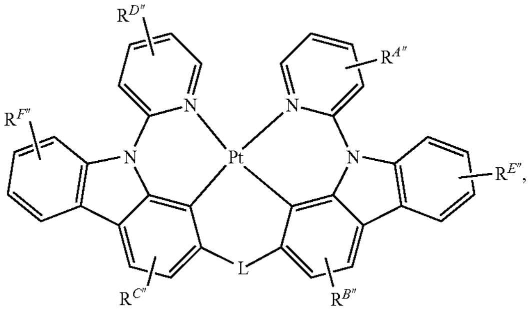
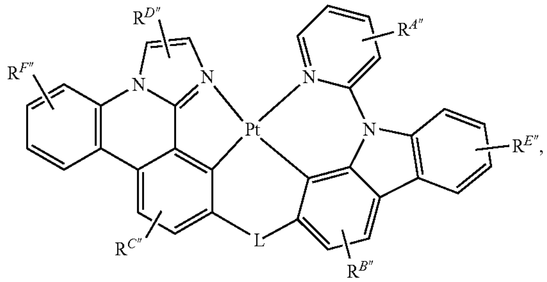
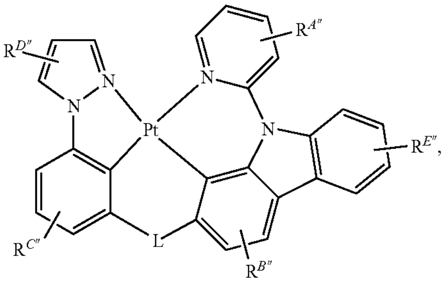
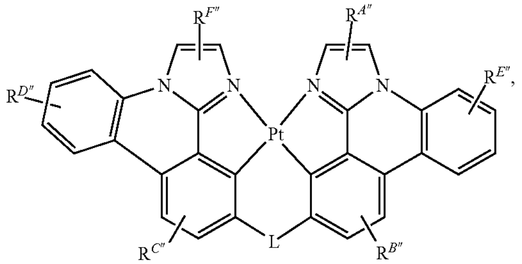
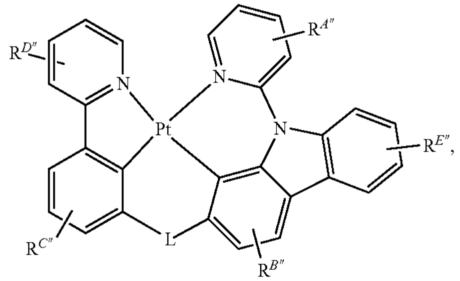
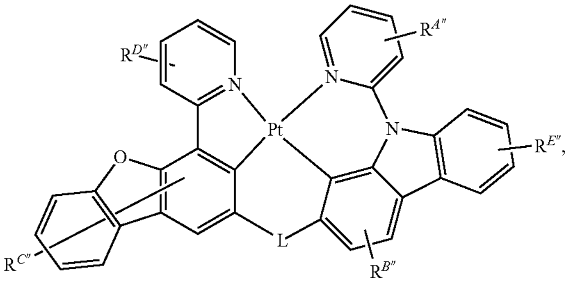
-continued
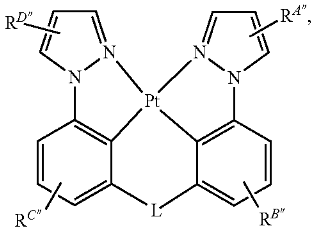
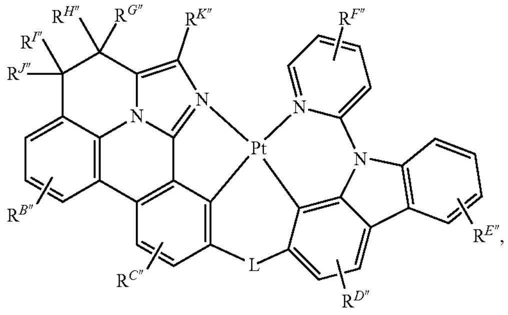
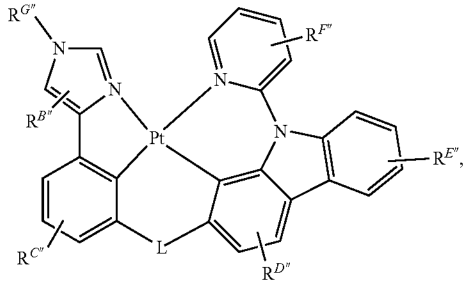
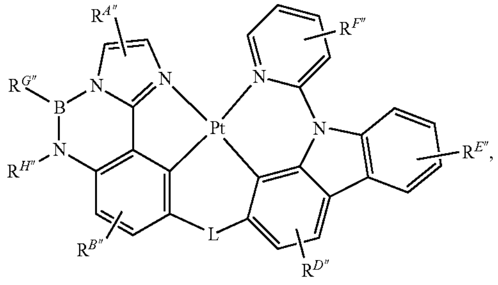
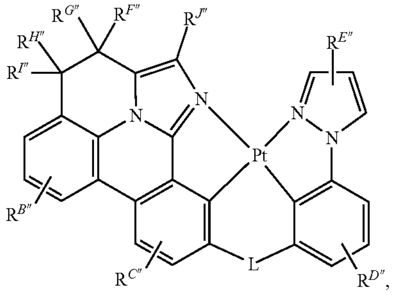
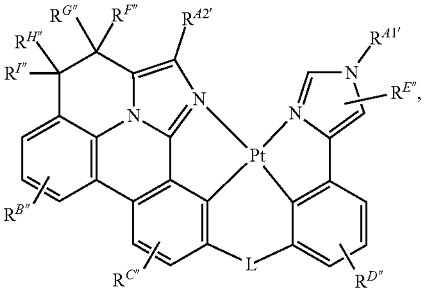

-continued
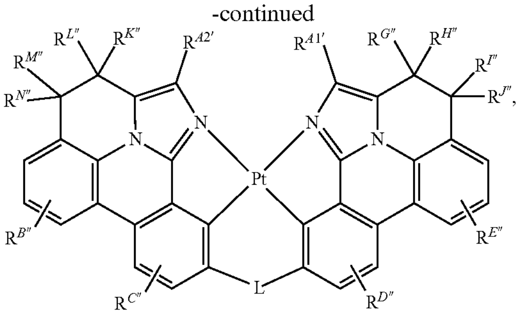
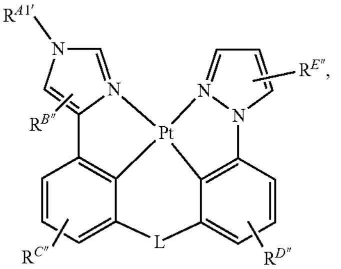
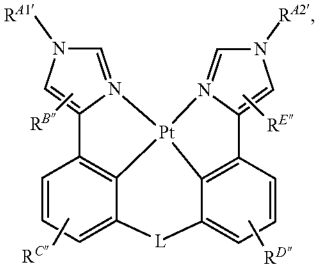
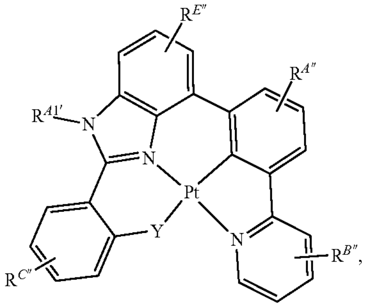
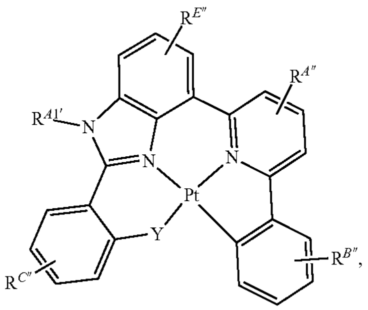
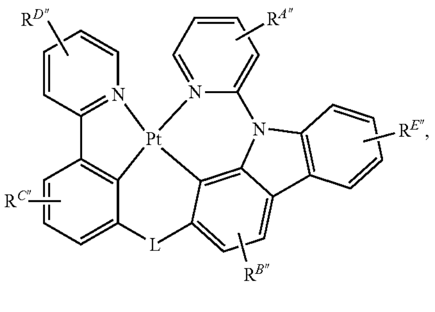
-continued
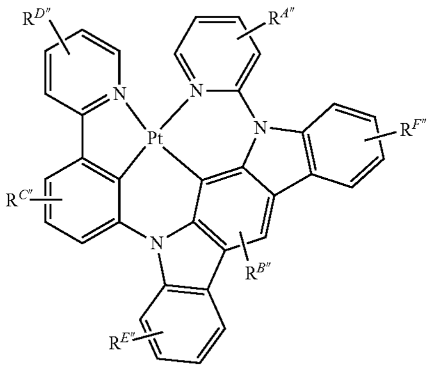
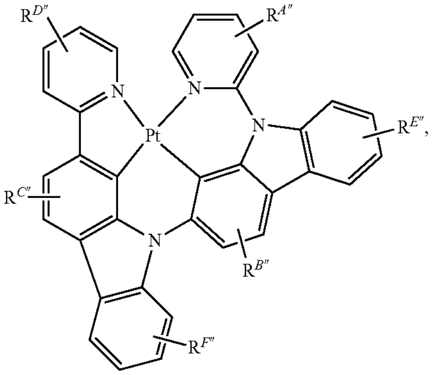
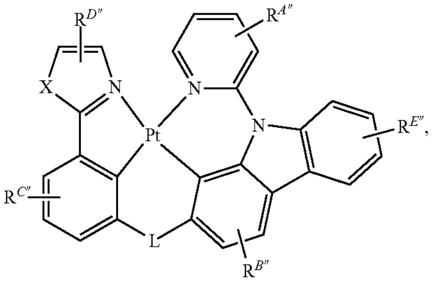
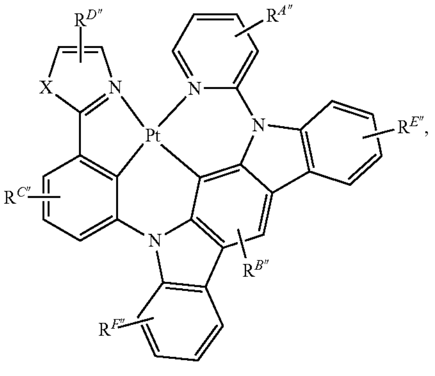

-continued
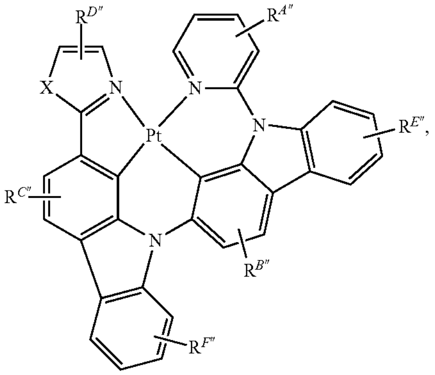
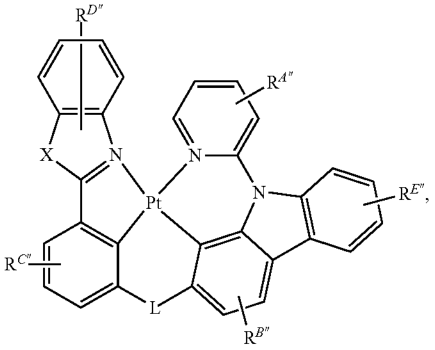
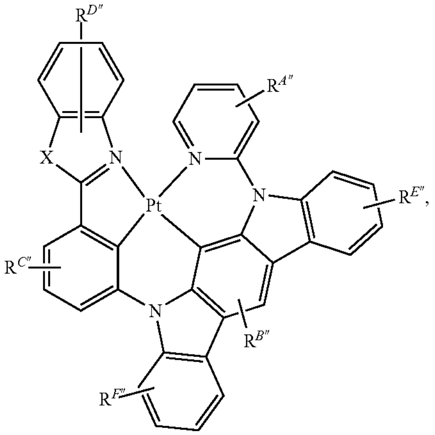
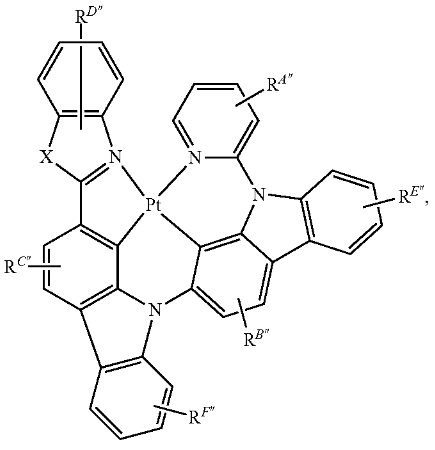
-continued
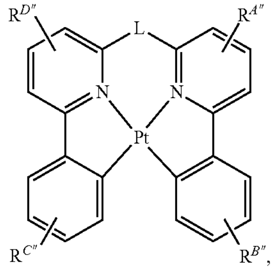
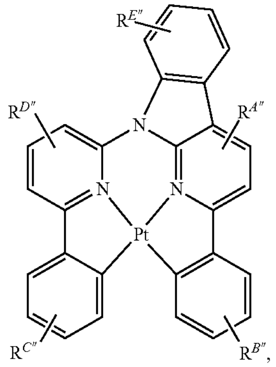
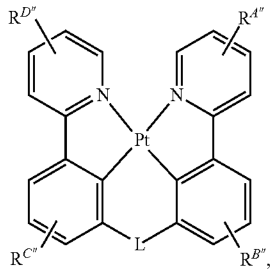
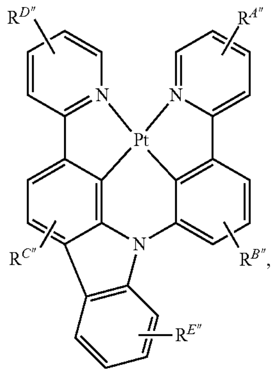
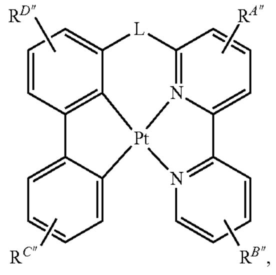
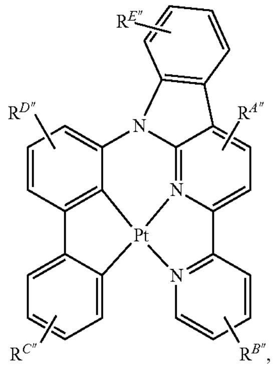
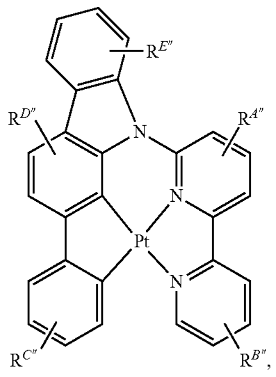

-continued
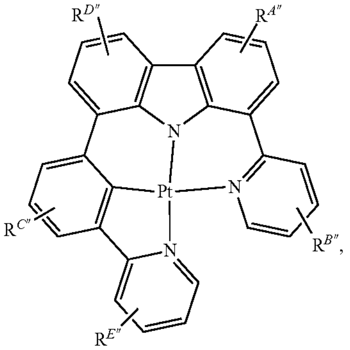
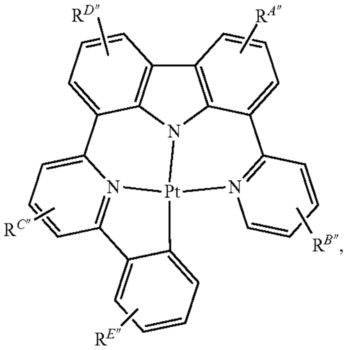
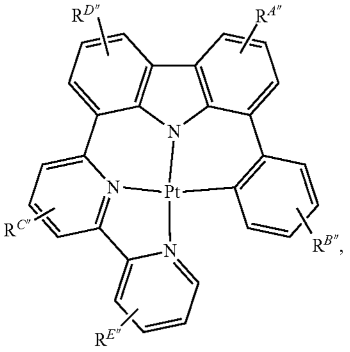
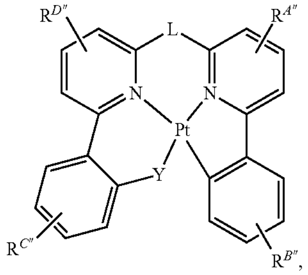
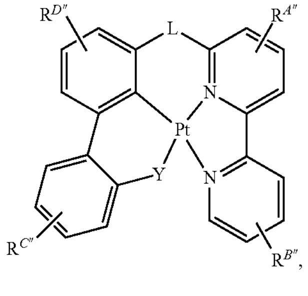
-continued
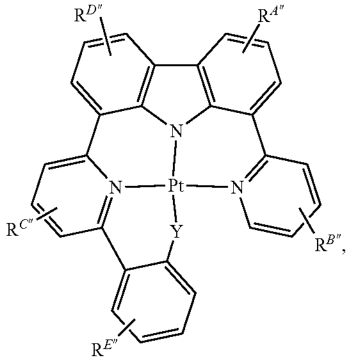
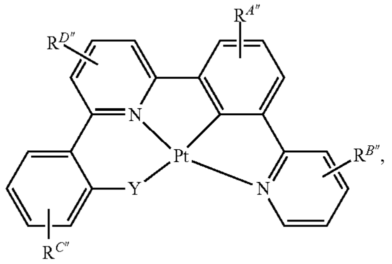
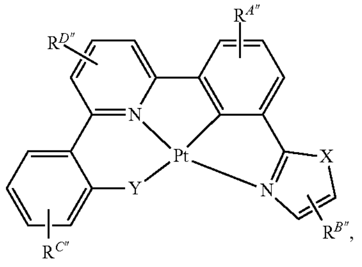
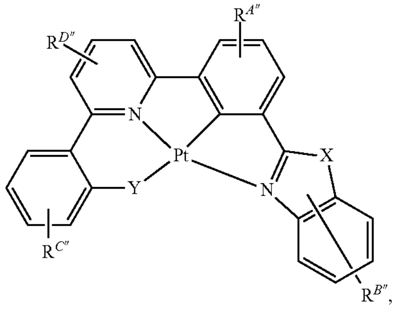
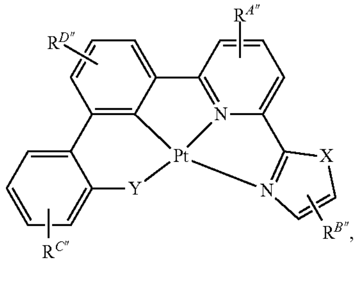

-continued

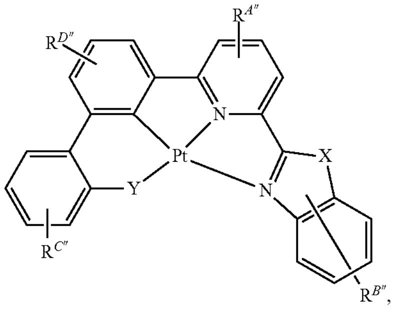

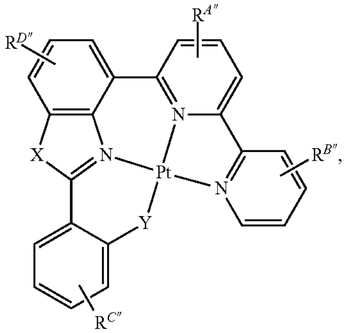

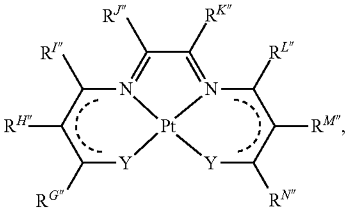

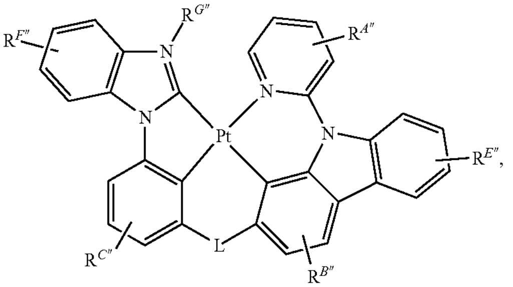

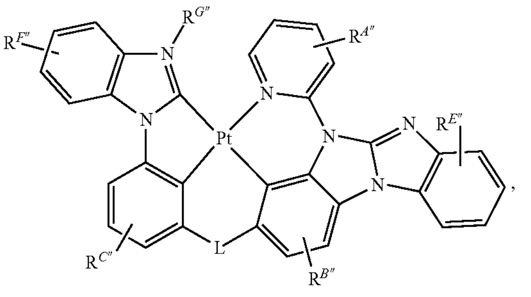

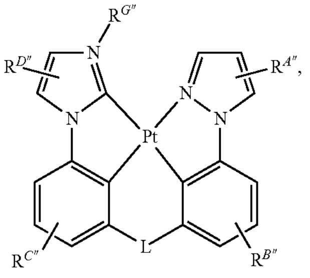

-continued

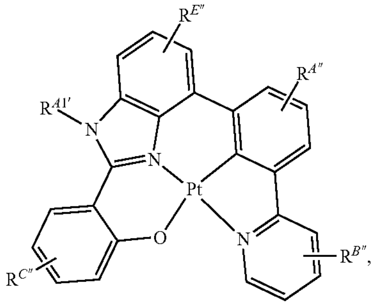

and

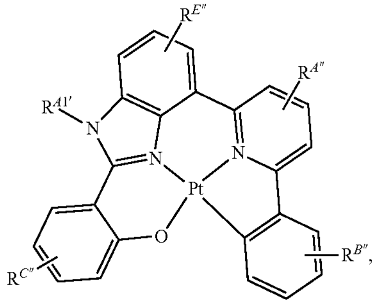

wherein:

each Y is independently selected from the group consisting of a NR, O, S, and Se;

L is independently selected from the group consisting of a direct bond, BR, BRR', NR, PR, O, S, Se, C=X', S=O, $SO_2$, CR, CRR', SiRR', GeRR', alkyl, cycloalkyl, aryl, heteroaryl, and combinations thereof;

each X and X' is independently selected from the group consisting of O, S, Se, NR'', and CR''R''';

each R, R', R'', R''', $R^{A''}$, $R^{B''}$, $R^{C''}$, $R^{D''}$, $R^{E''}$, and $R^{F''}$ independently represents mono, up to the maximum number of allowed substitutions, or no substitution;

each of R, R', $R^{A1'}$, $R^{A2'}$, $R^{A''}$, $R^{B''}$, $R^{C''}$, $R^{D''}$, $R^{E''}$, $R^{F''}$, $R^{G''}$, $R^{H''}$, $R^{I''}$, $R^{J''}$, $R^{K''}$, $R^{L''}$, $R^{M''}$, and $R^{N''}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof.

In some embodiments, the phosphorescent dopant is selected from the group consisting of the structures of the following LIST 12:

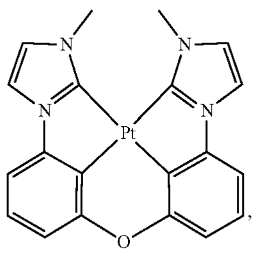

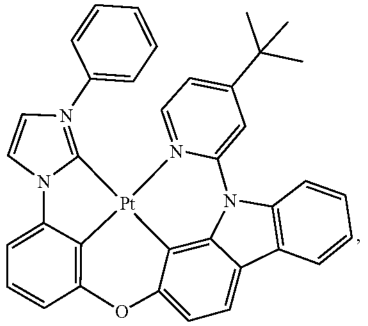
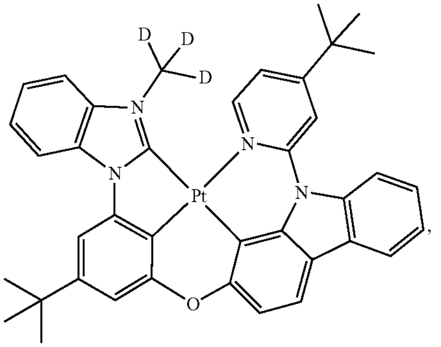
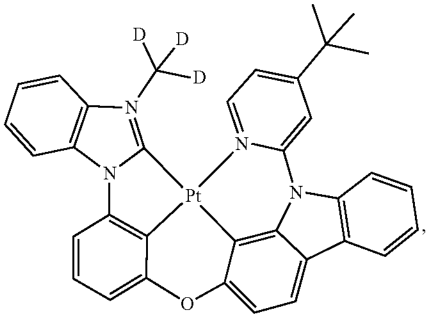
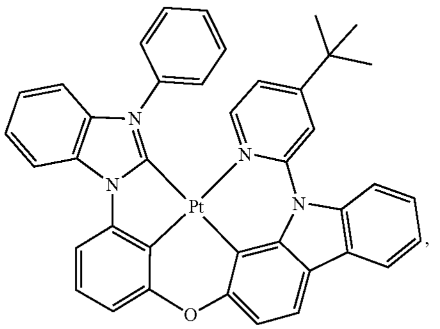
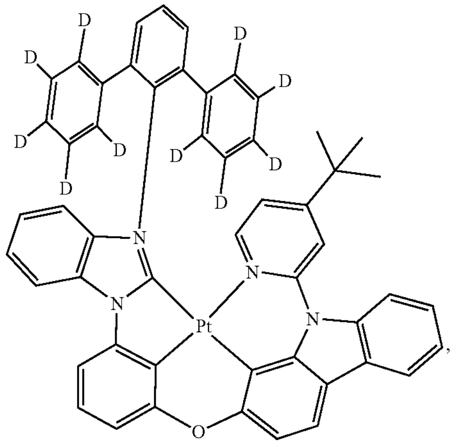
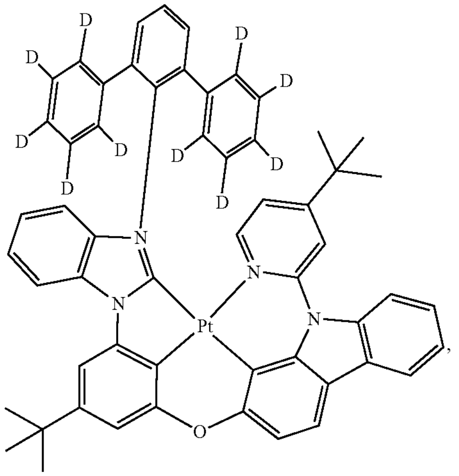
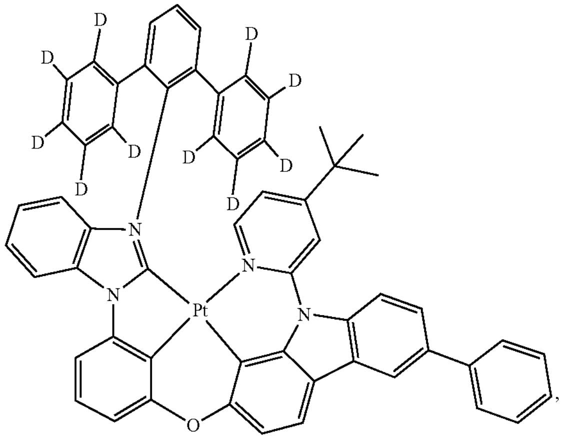

-continued
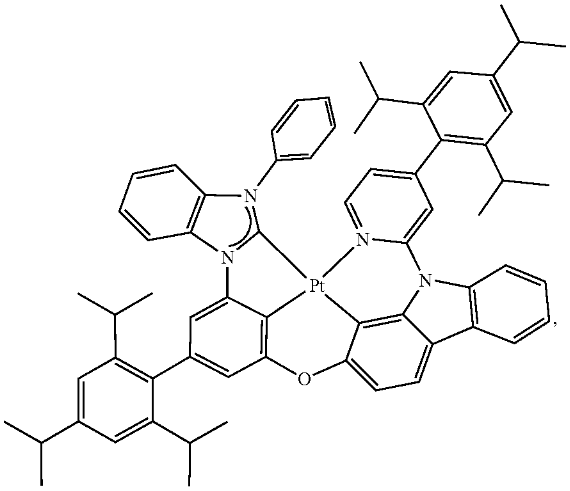
,
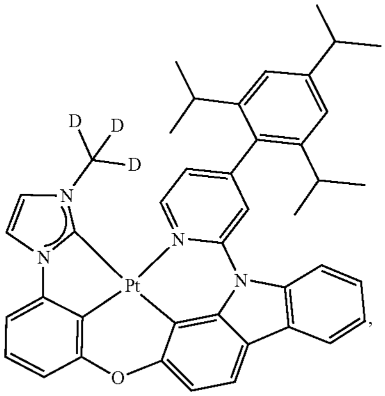
,
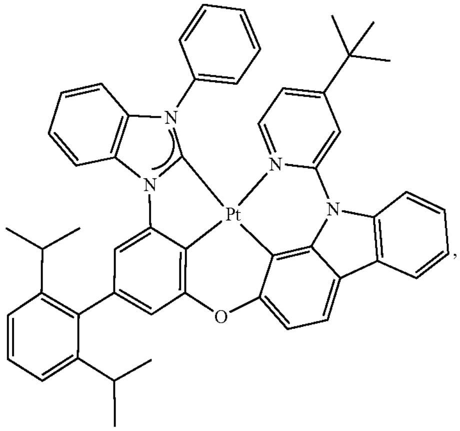
,
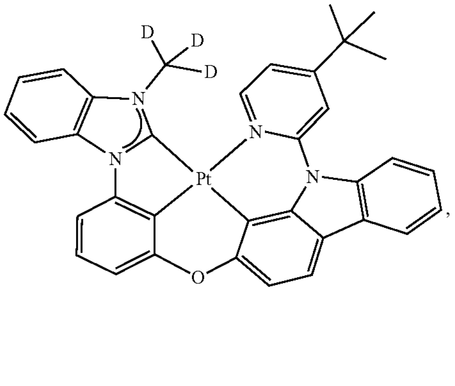
,
-continued
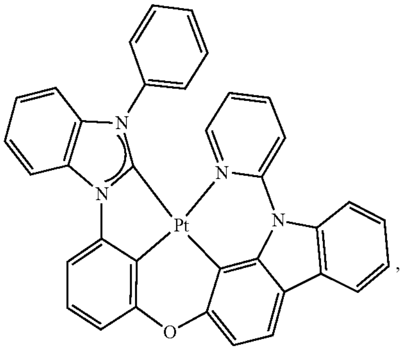
,
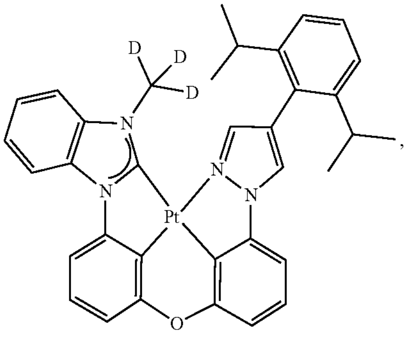
,
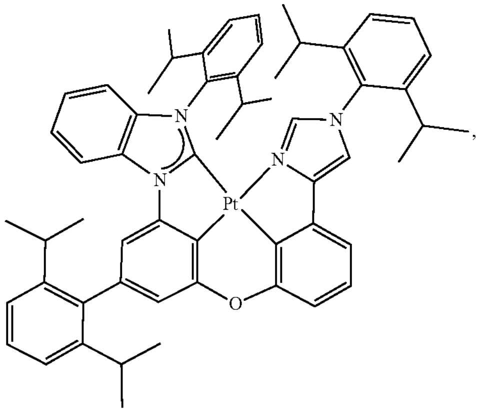
,
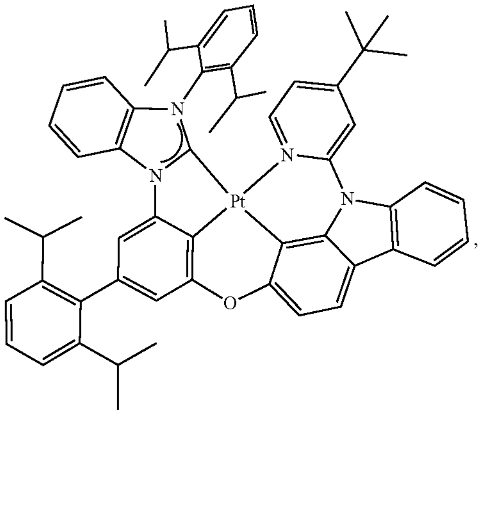
, -continued
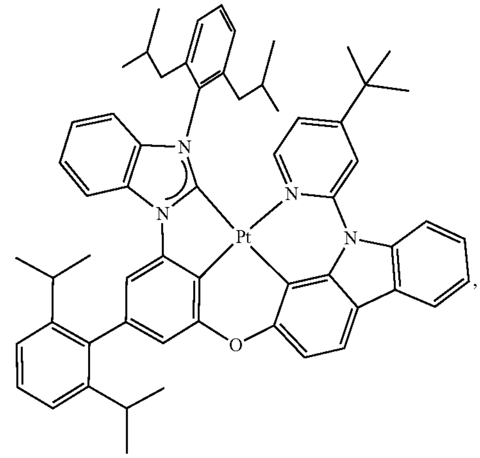
,
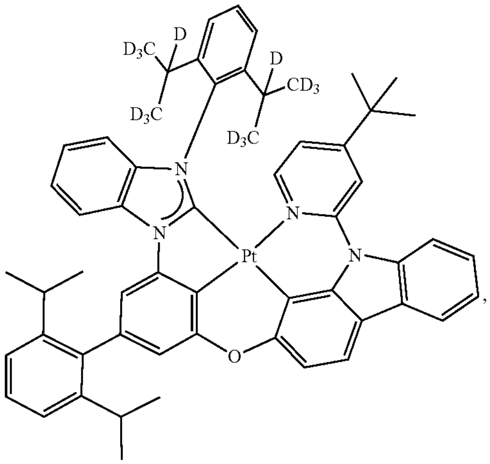
,
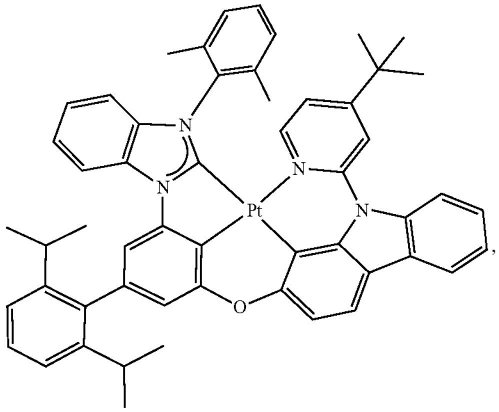
,
-continued
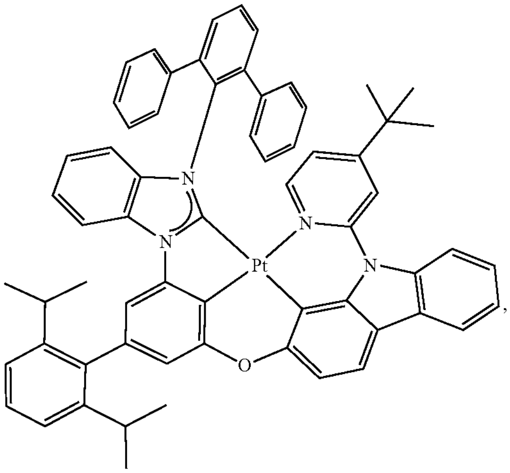
,
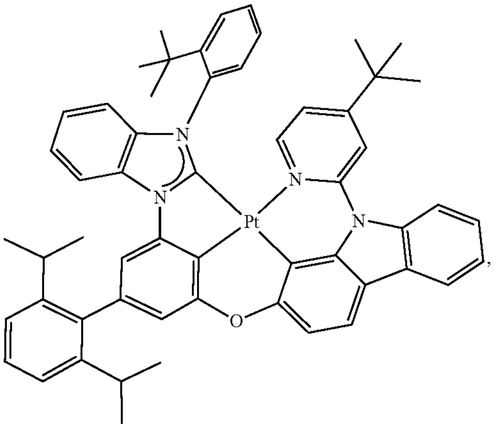
,
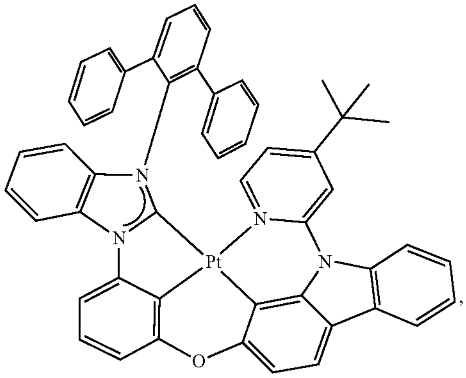
,
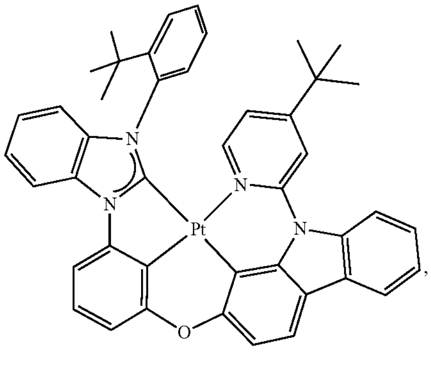
,

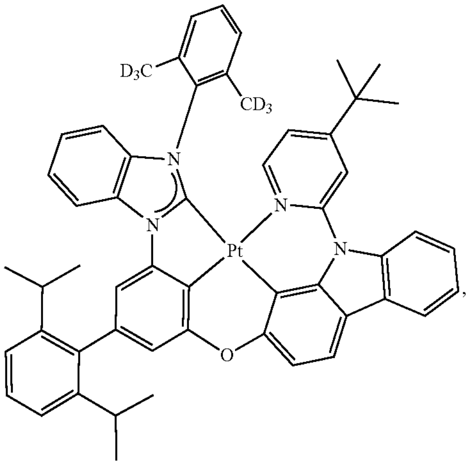
,
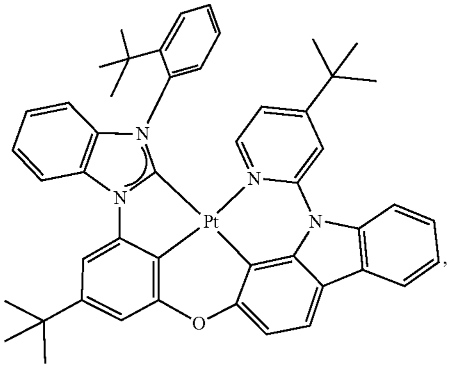
,
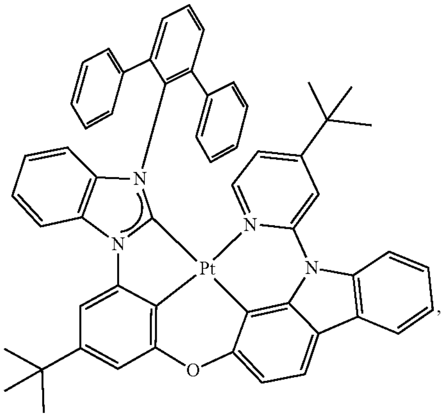
,
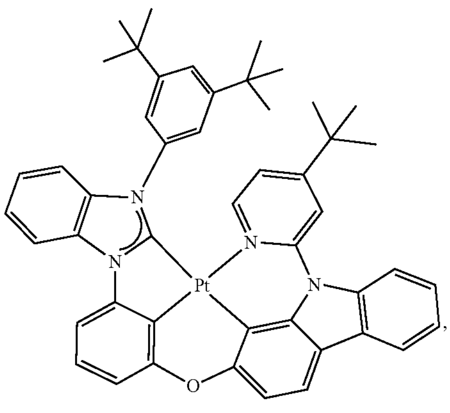
,
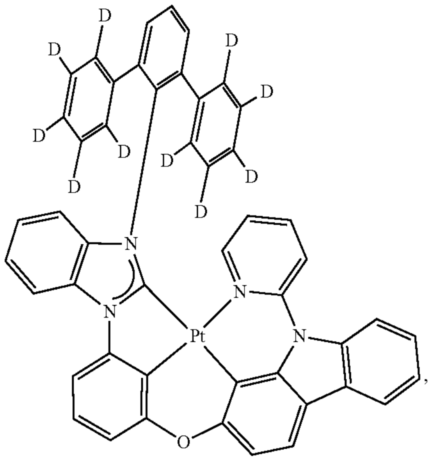
,
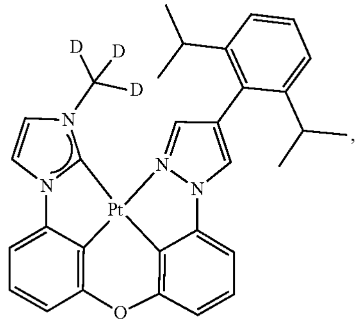
,
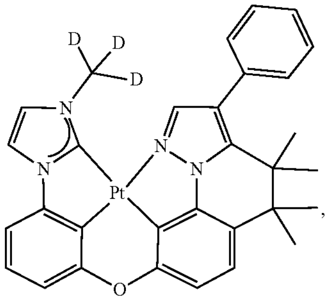
,
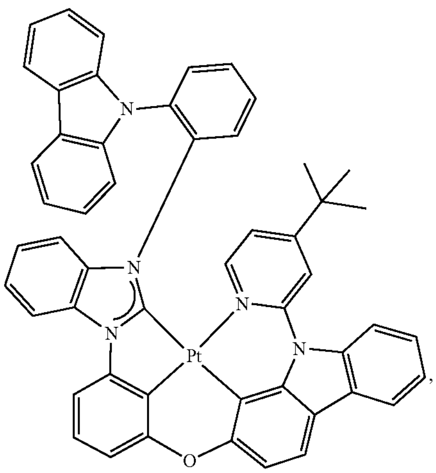
, -continued
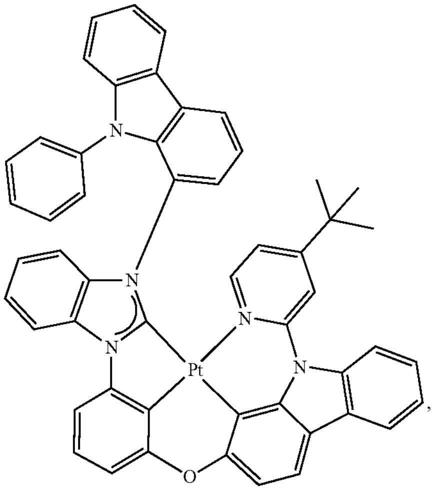
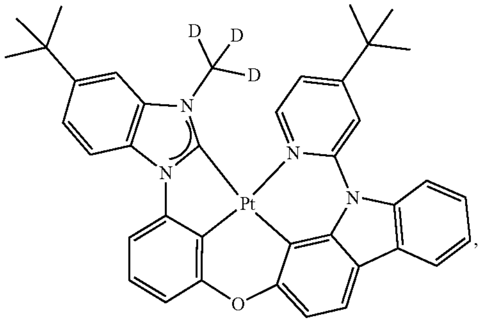
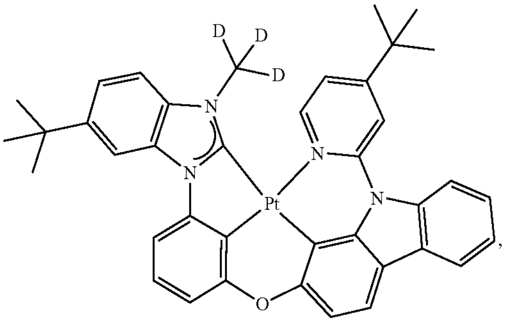
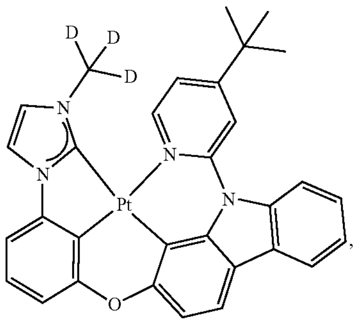
-continued
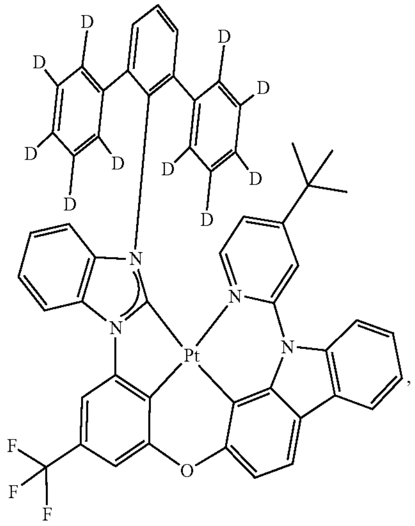
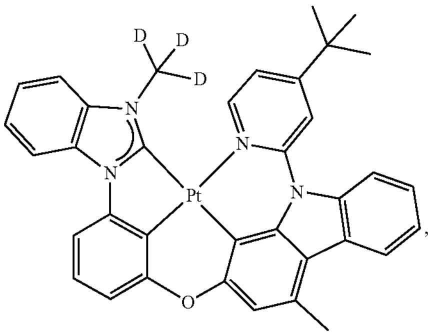
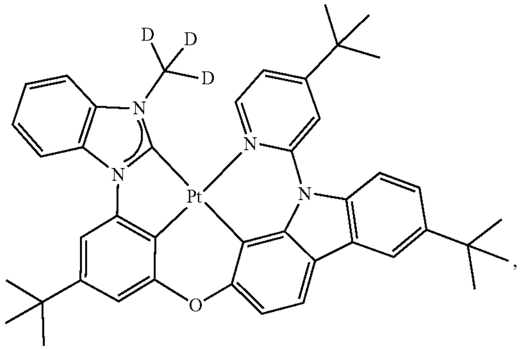
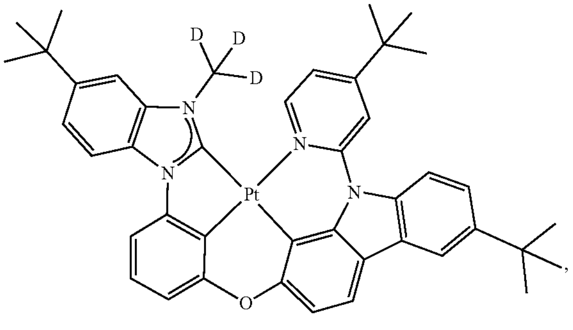

-continued
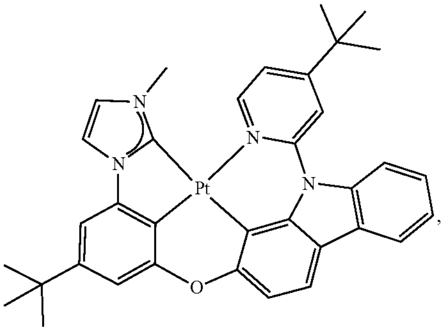
,
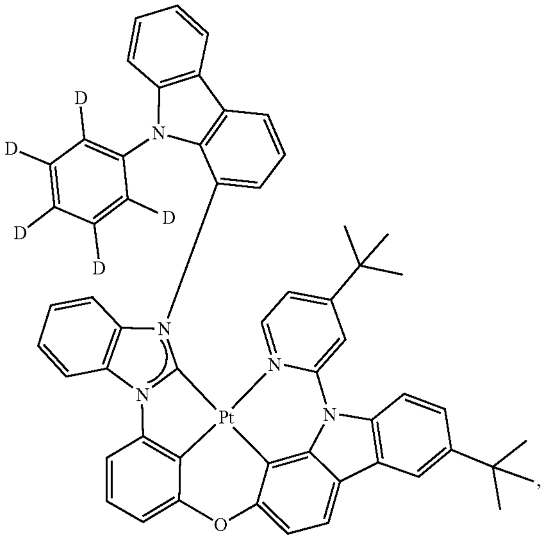
,
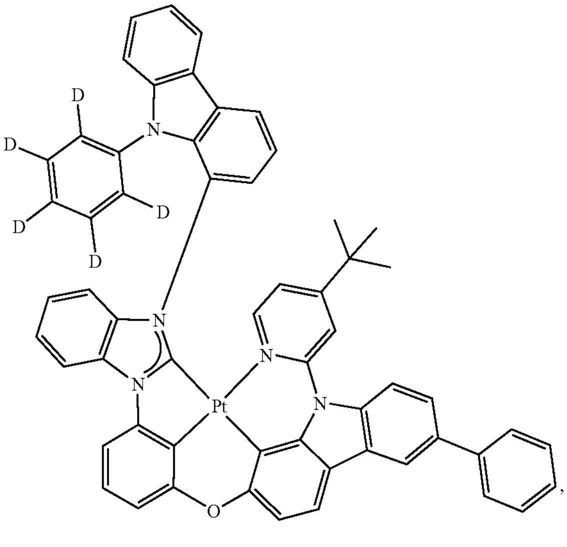
,
-continued
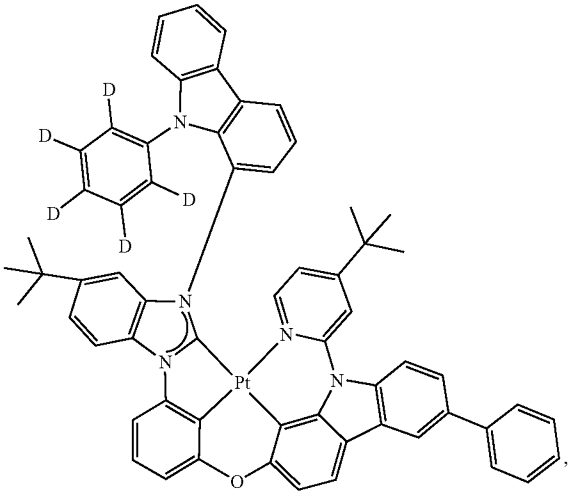
,
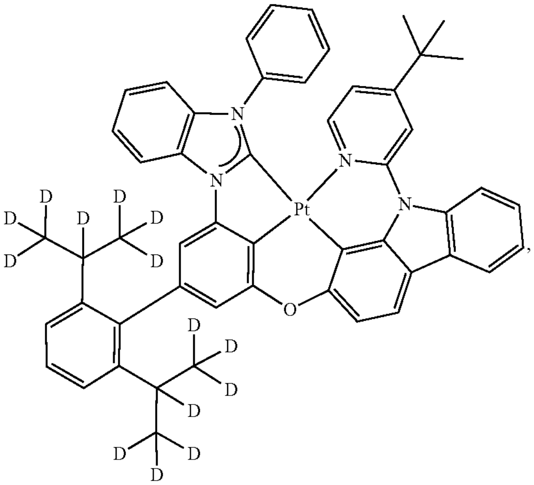
,
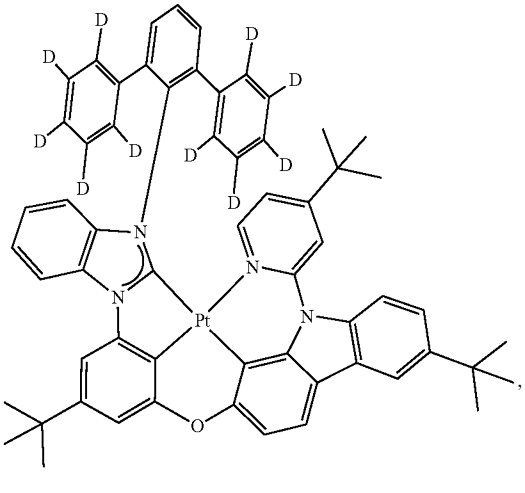
, -continued
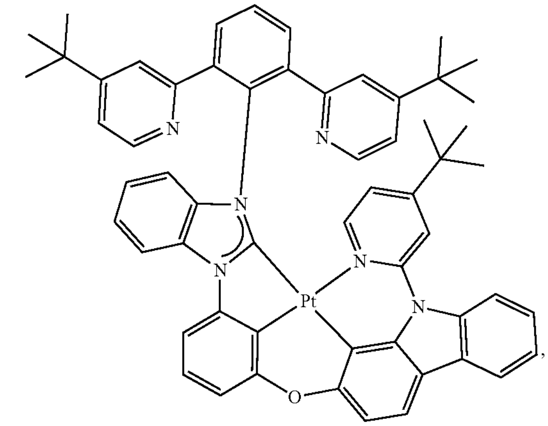
,
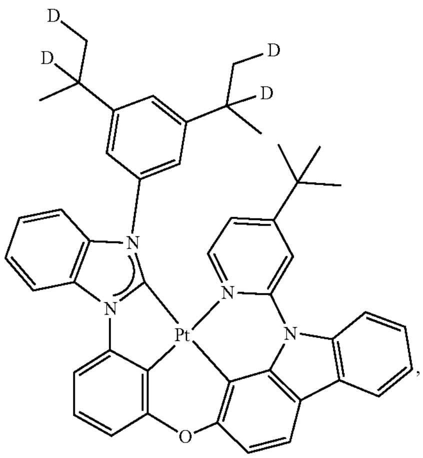
,
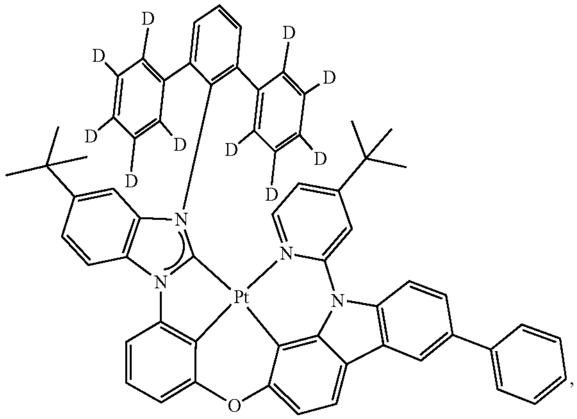
,
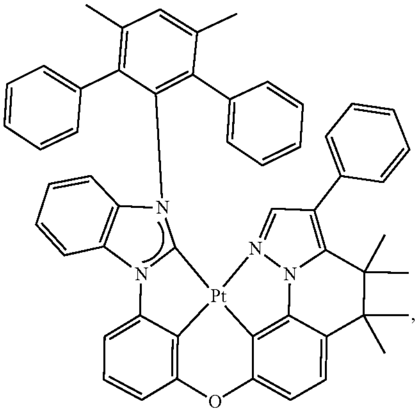
,
-continued
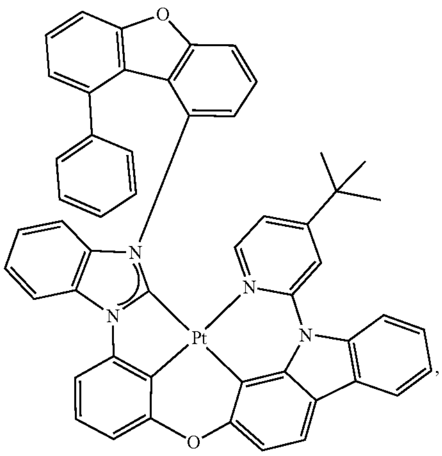
,
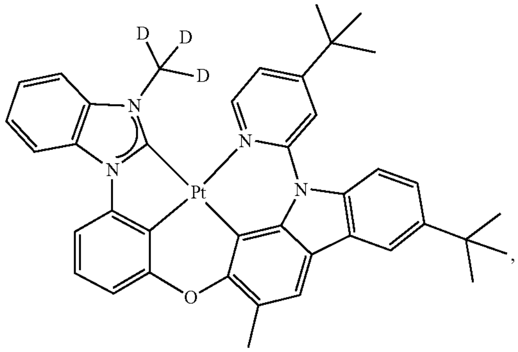
,
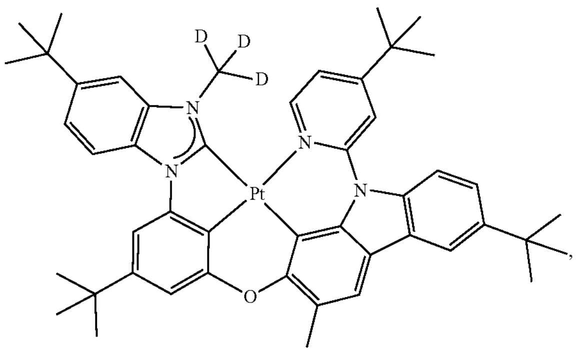
, -continued
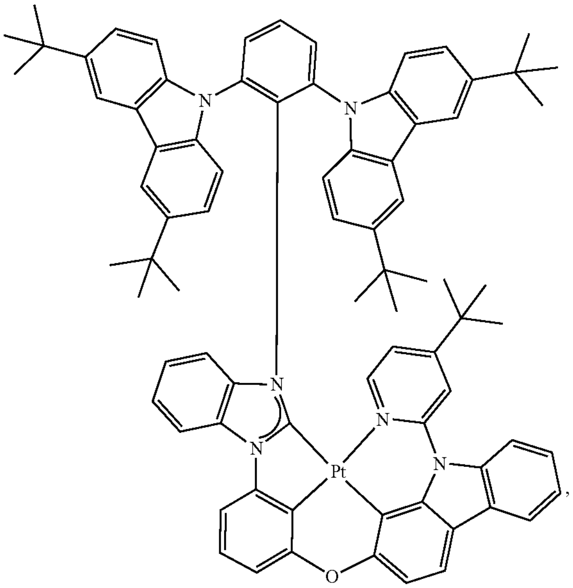
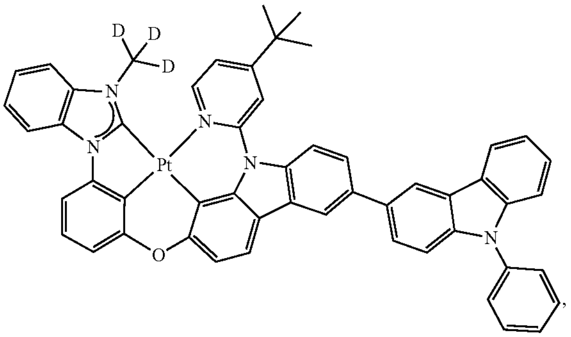
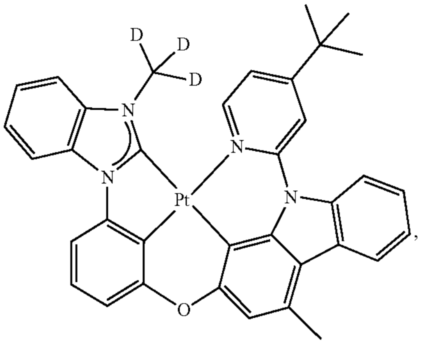
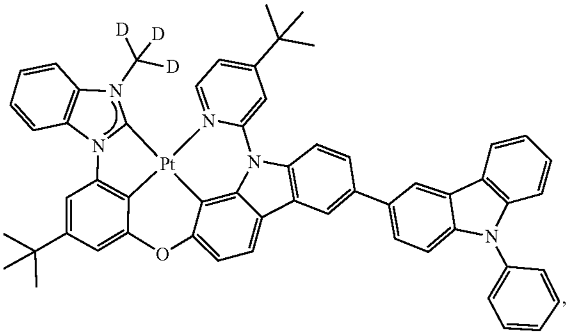
-continued
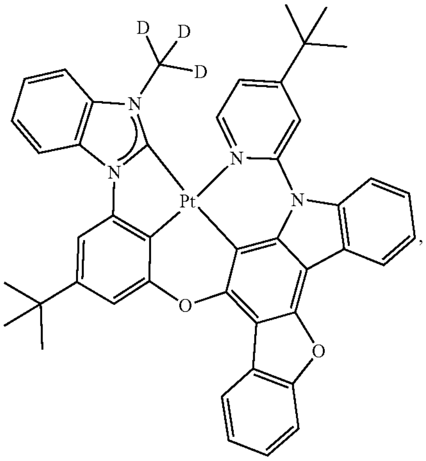
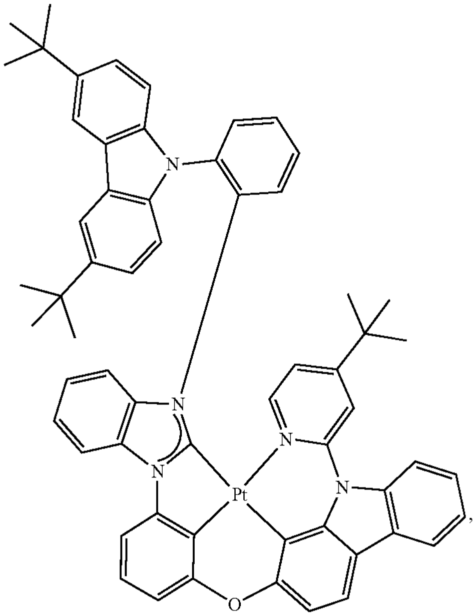
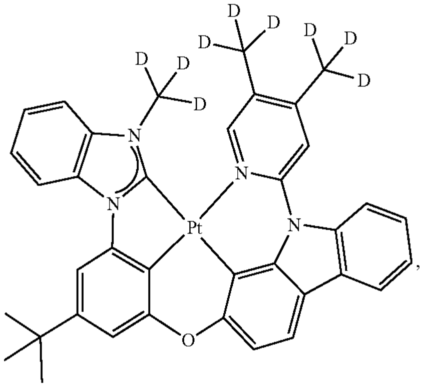

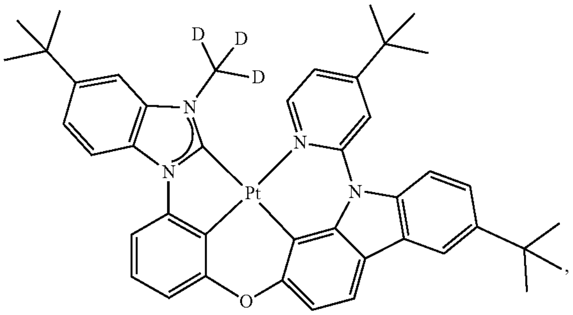
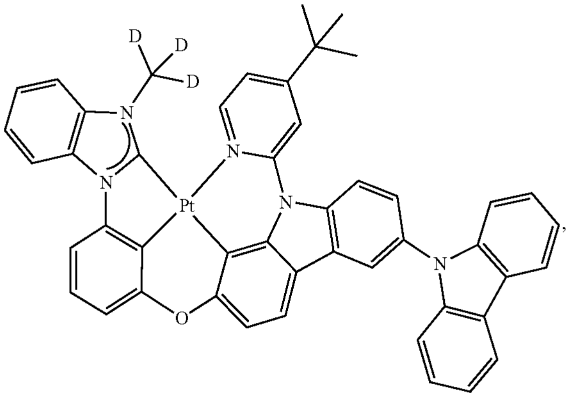
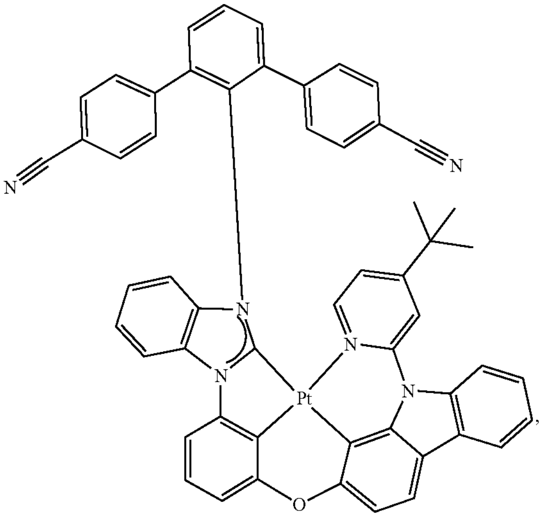
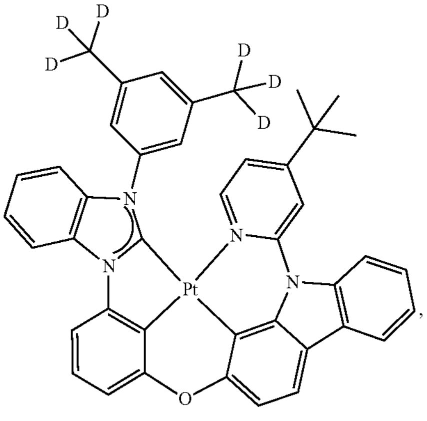
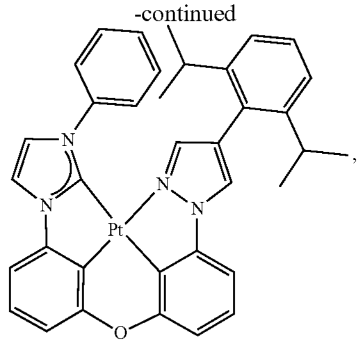
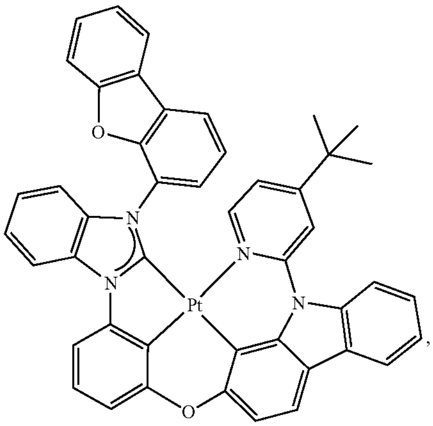
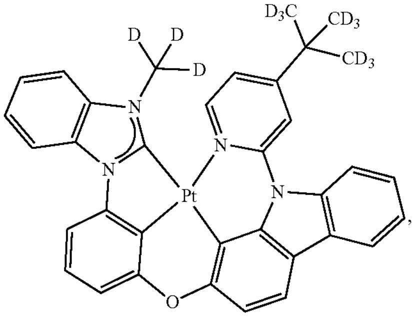
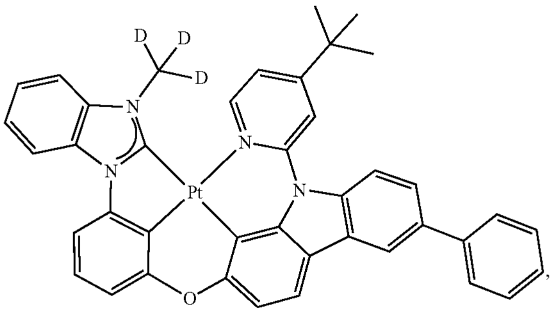
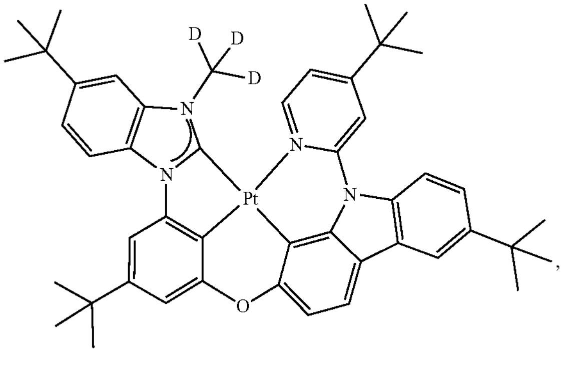

-continued
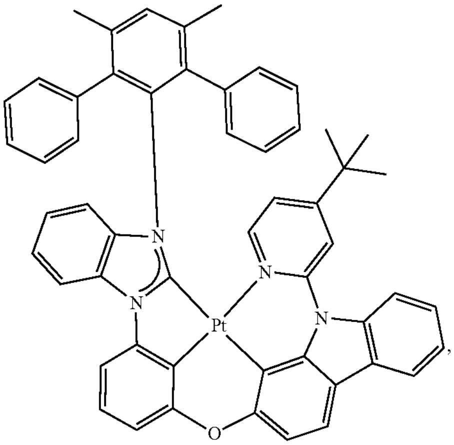
,
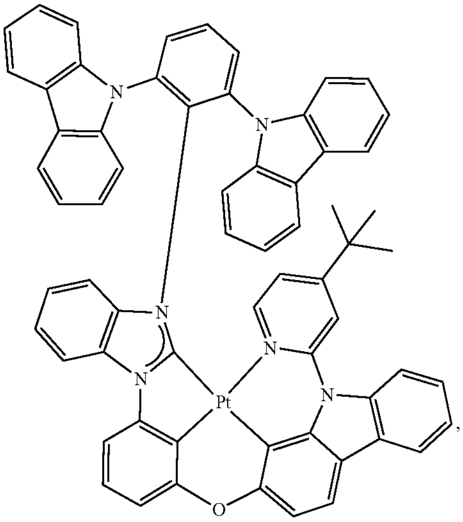
,
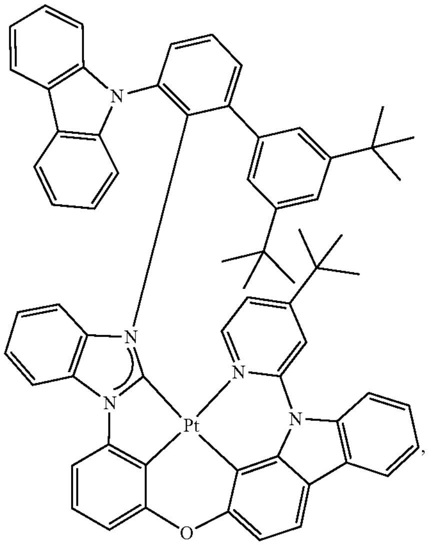
,
-continued
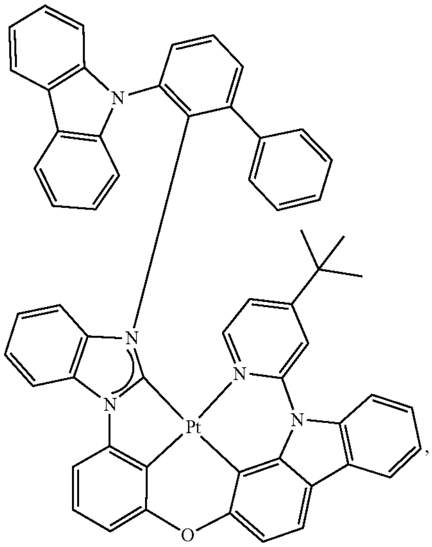
,
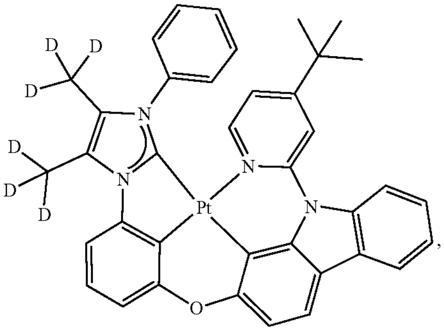
,
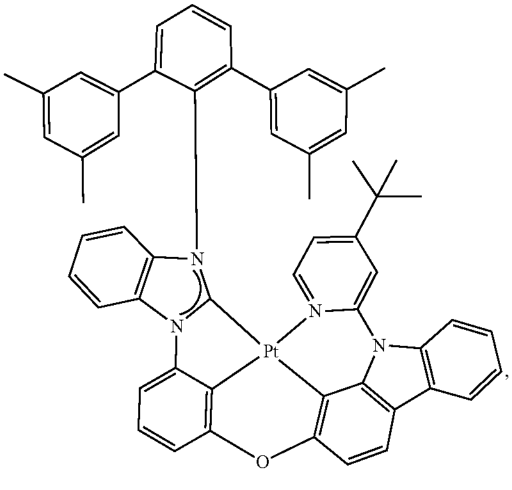
, -continued
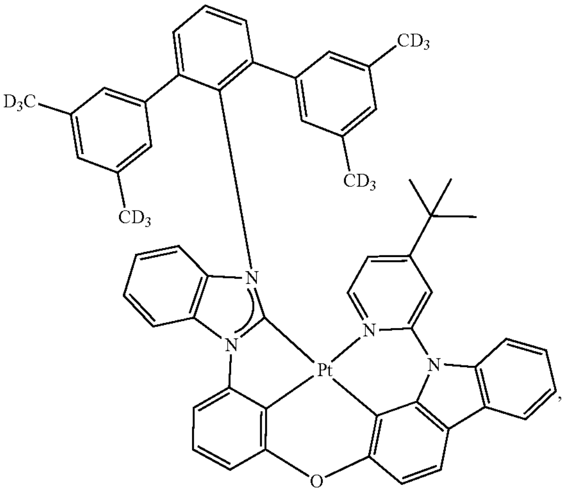
,
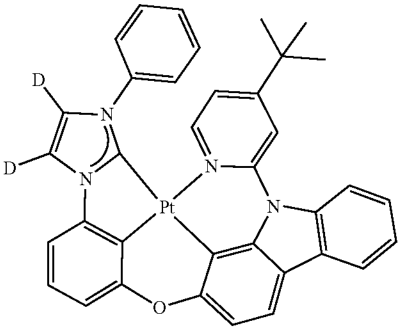
,
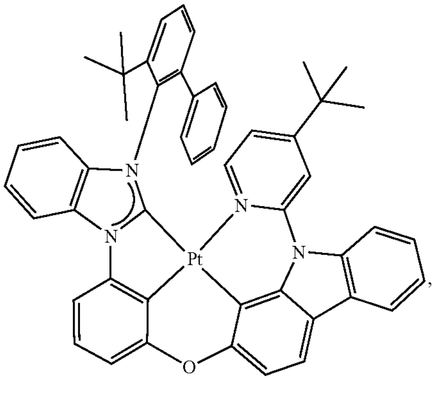
,
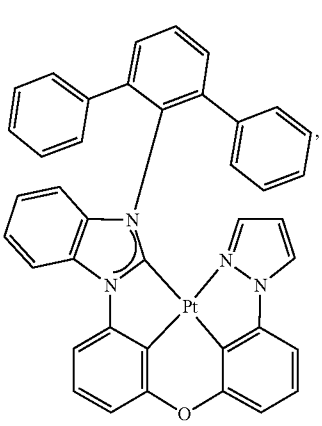
,
-continued
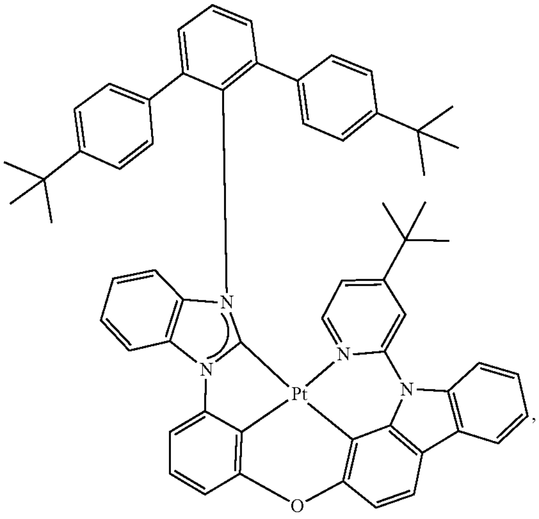
,
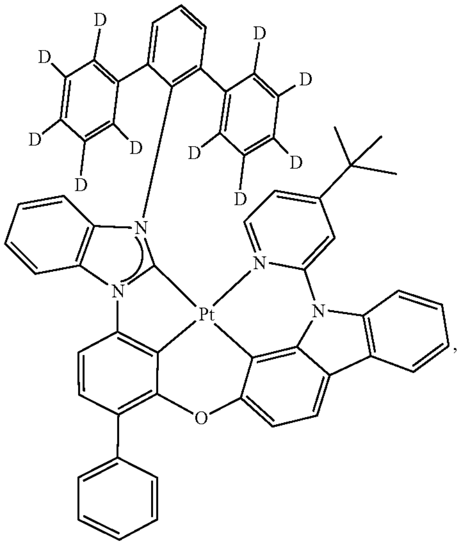
,
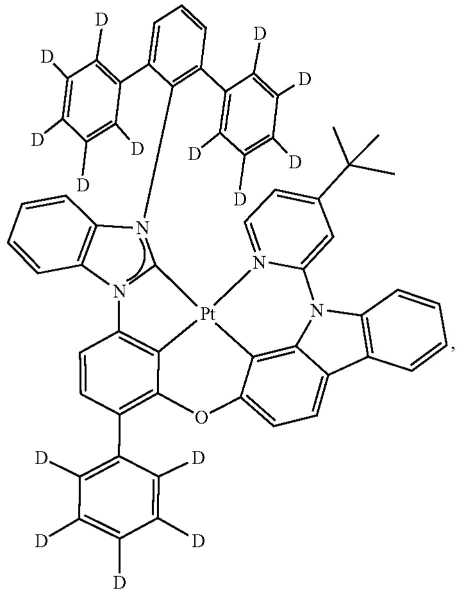
, -continued
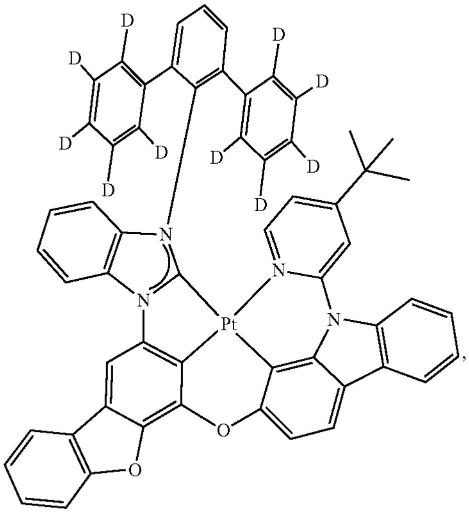
,
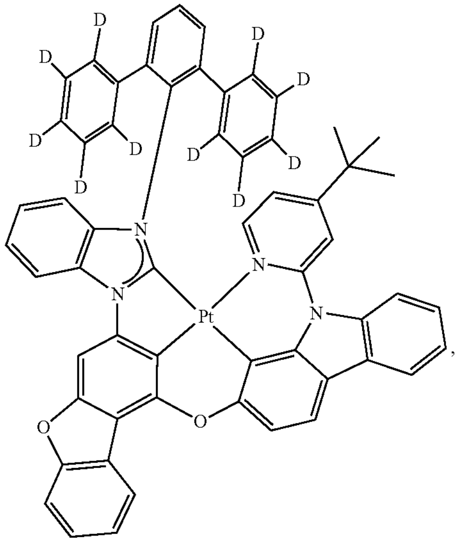
,
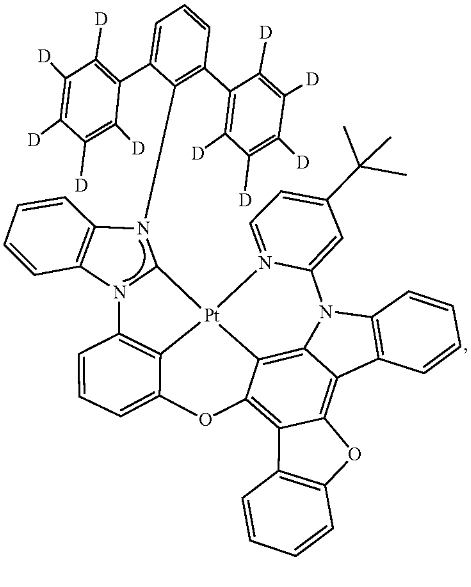
,
-continued
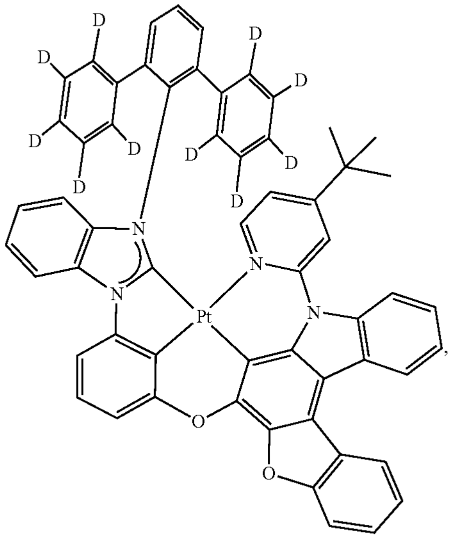
,
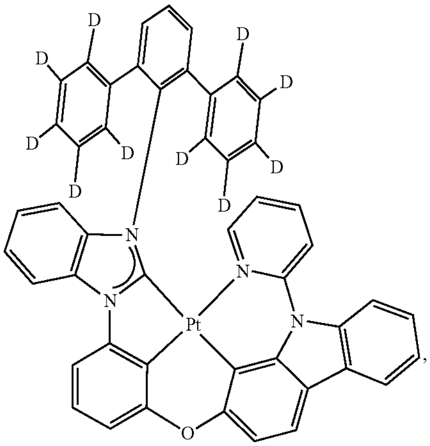
,
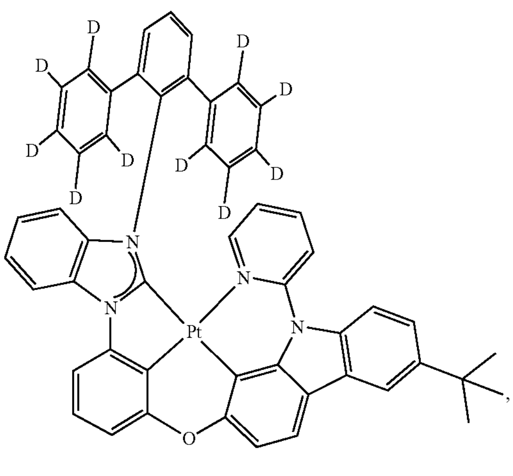
, -continued
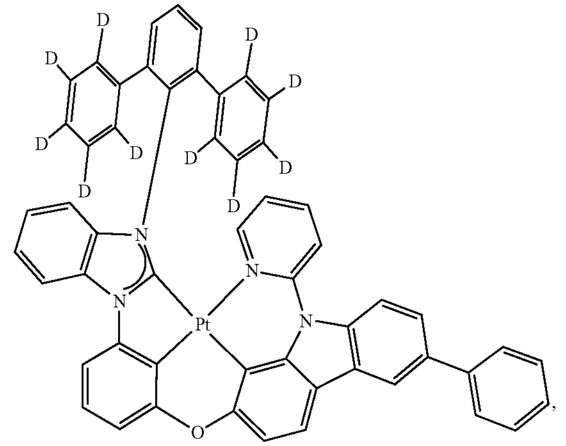
,
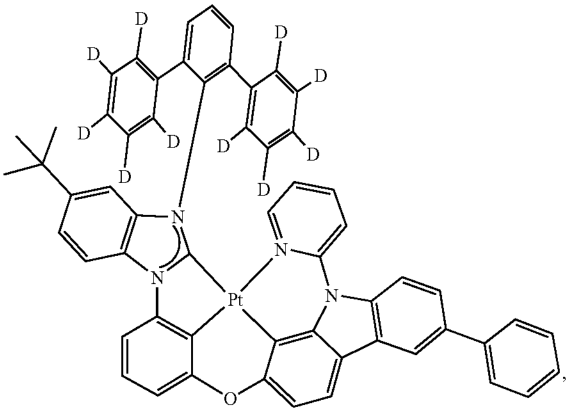
,
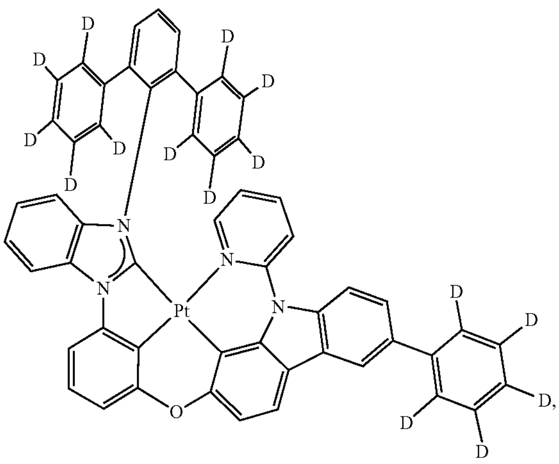
,
-continued
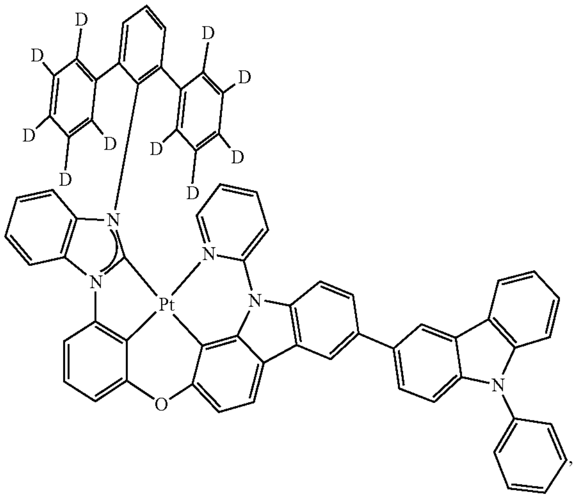
,
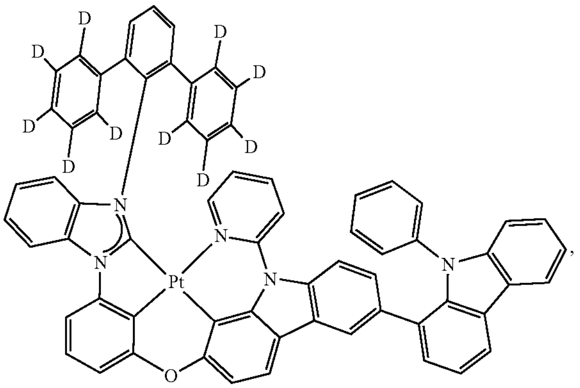
,
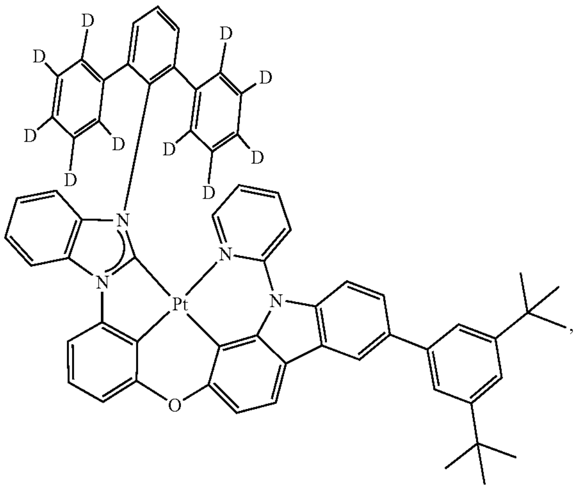
, -continued
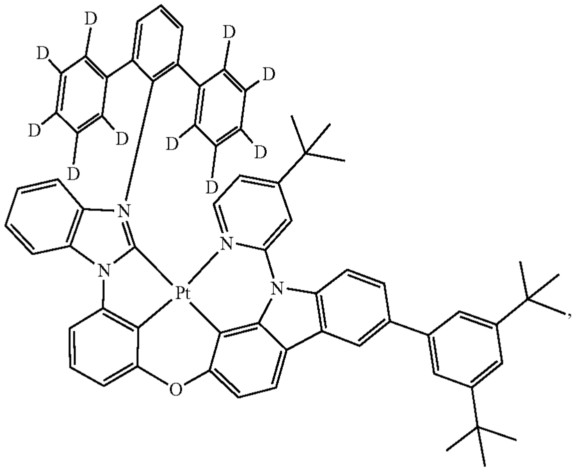
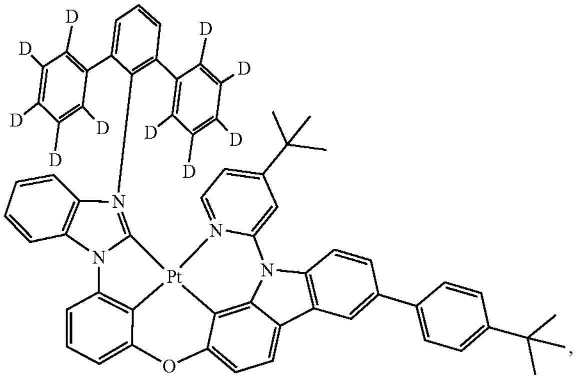
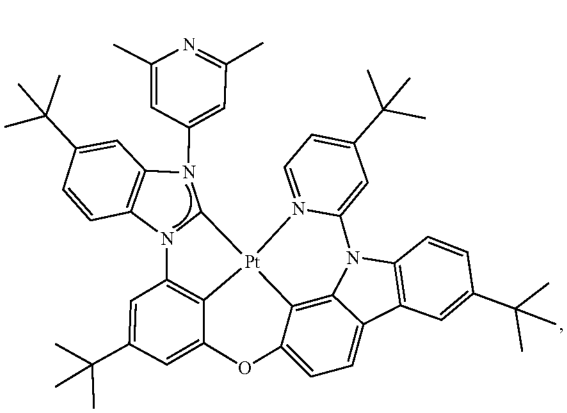
-continued
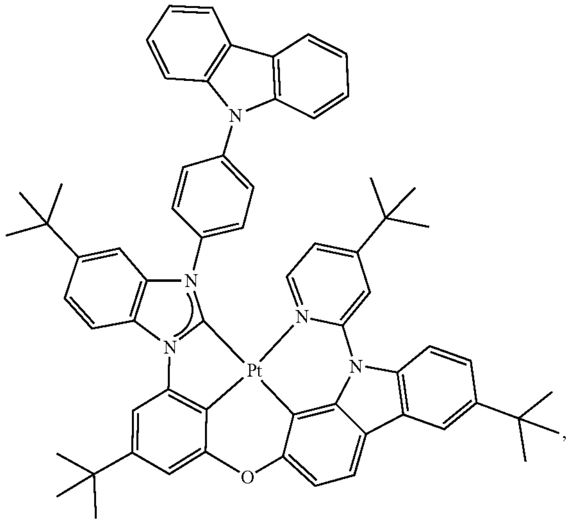
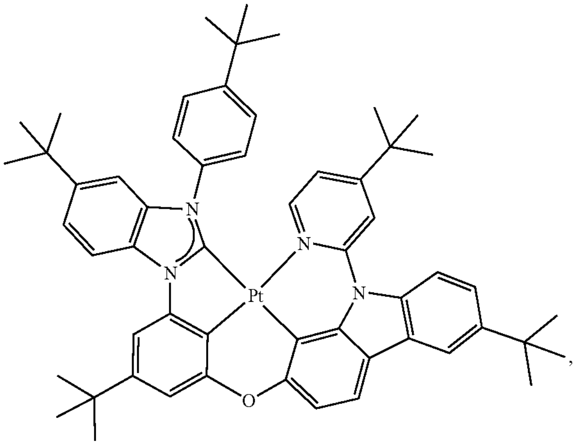
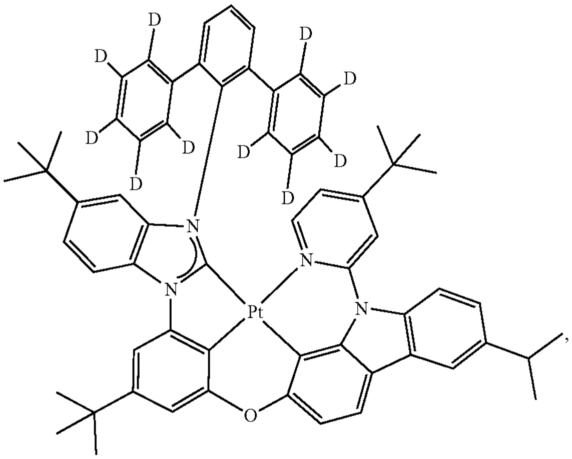

-continued
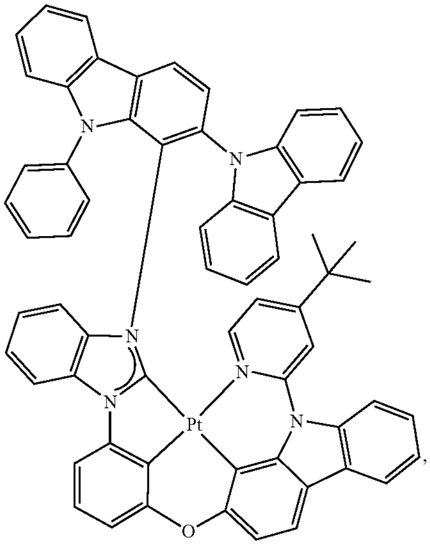
,
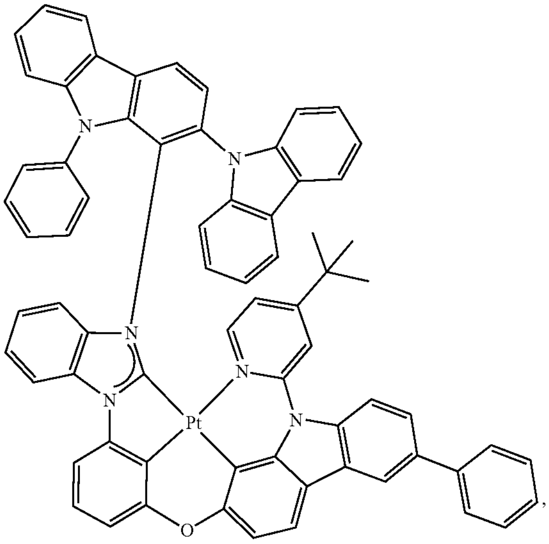
,
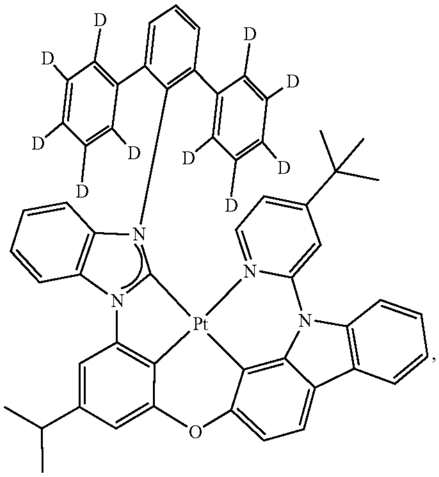
,
-continued
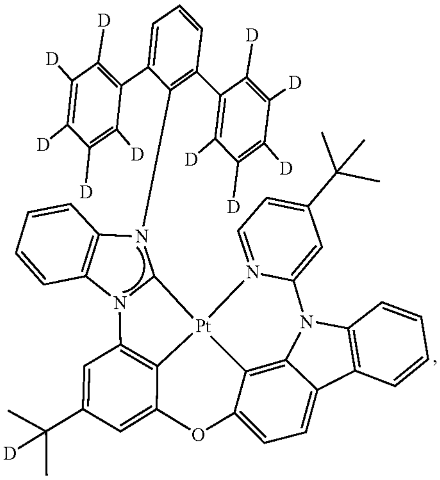
,
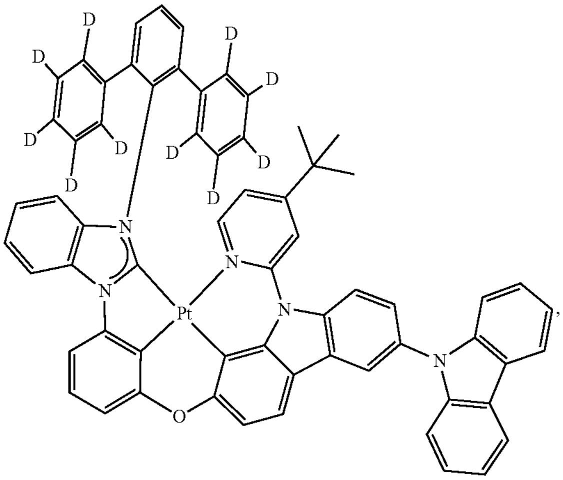
,
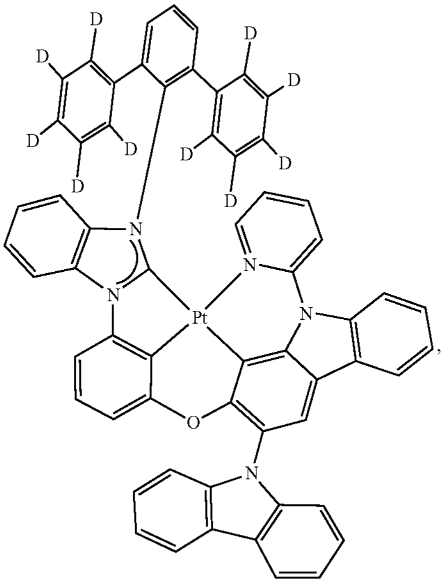
,

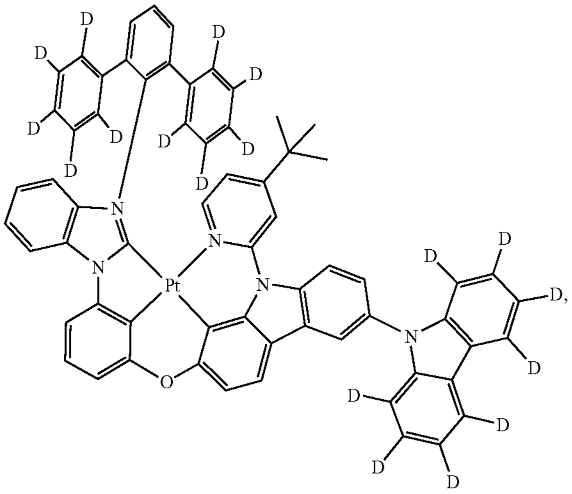
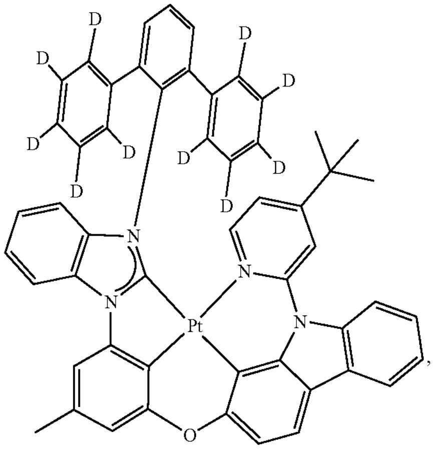
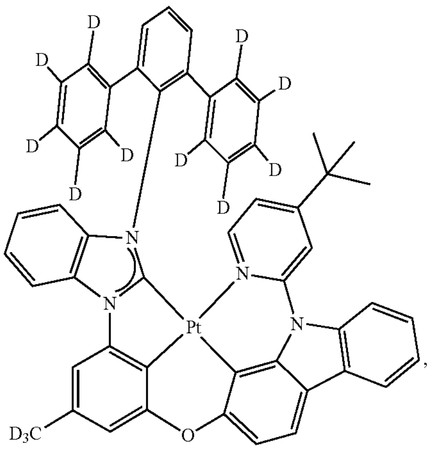
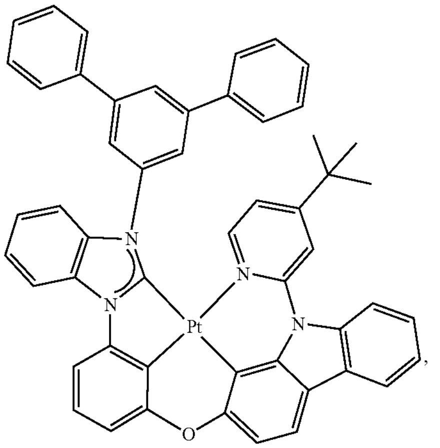
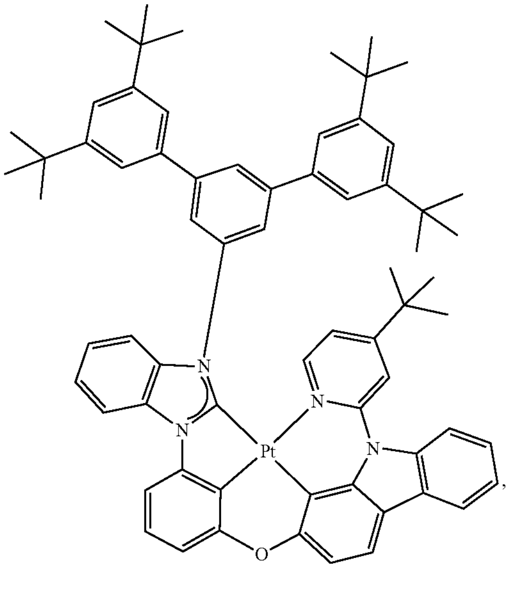

-continued
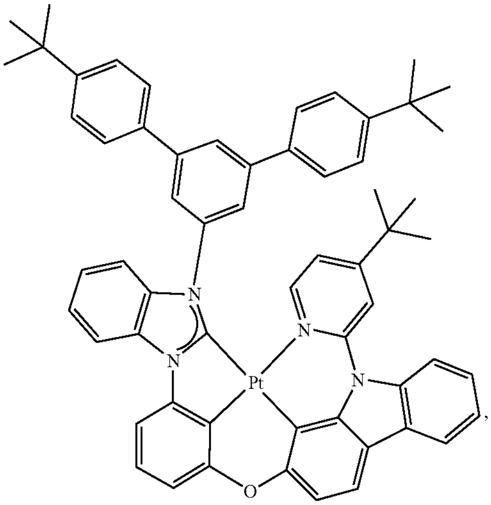
,
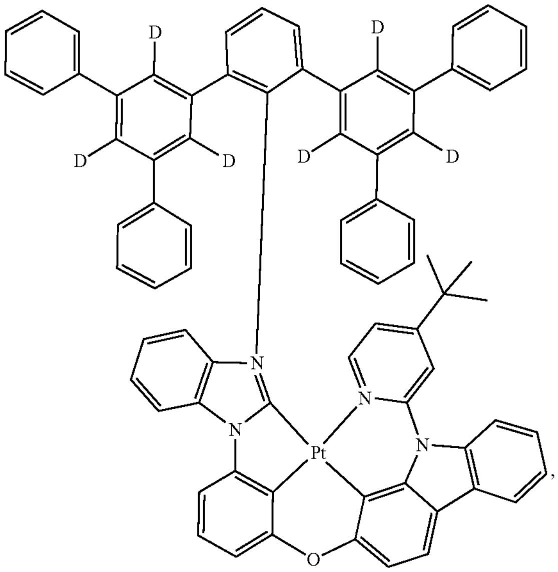
,
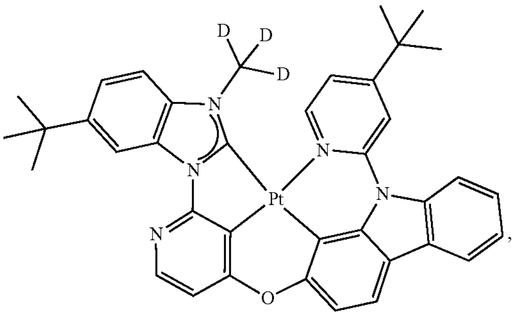
,
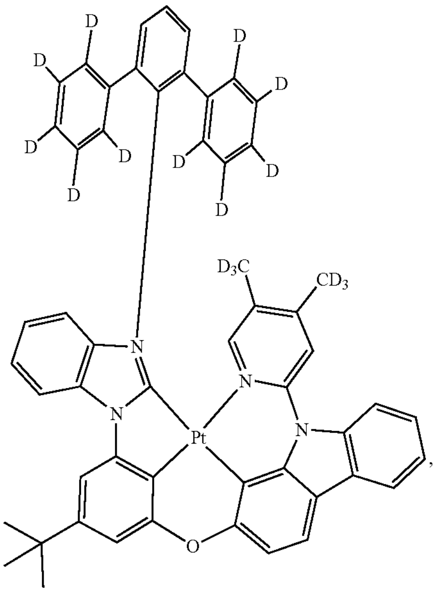
,

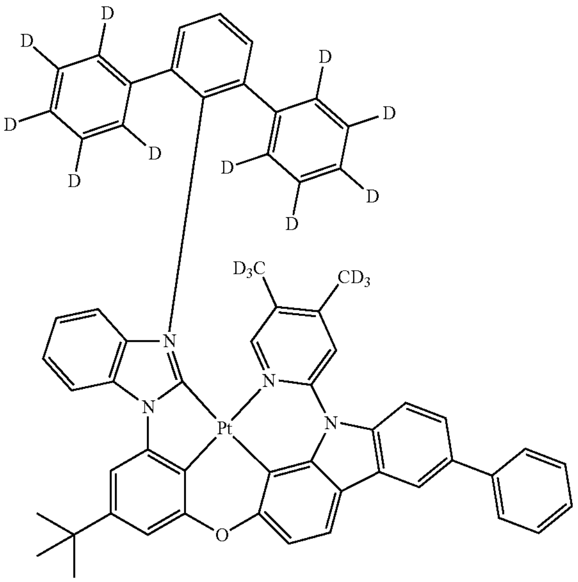,
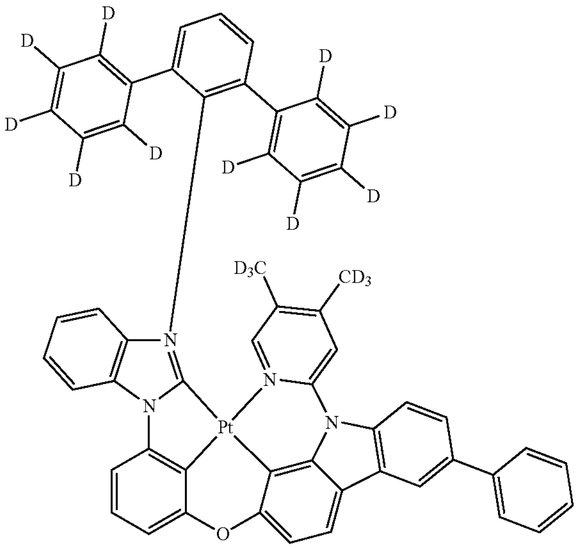,
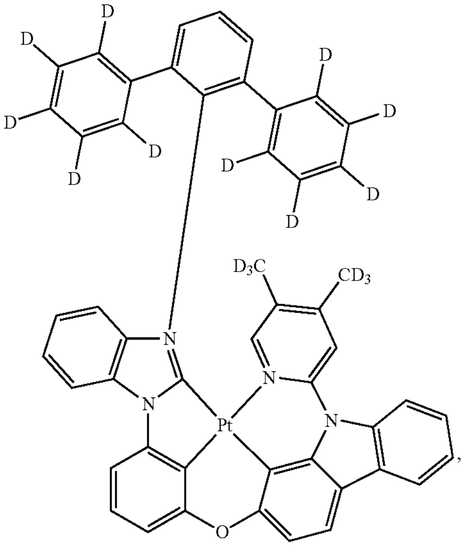,
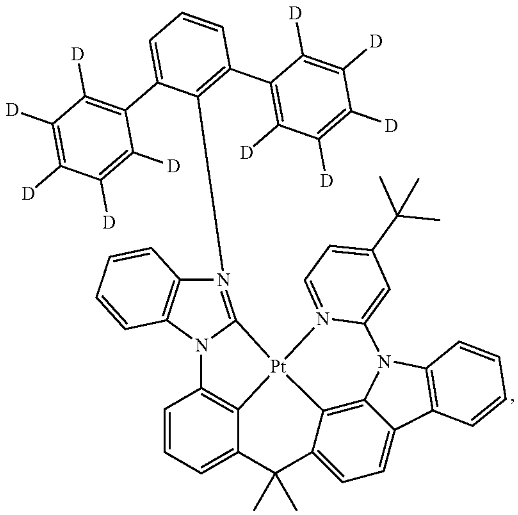,
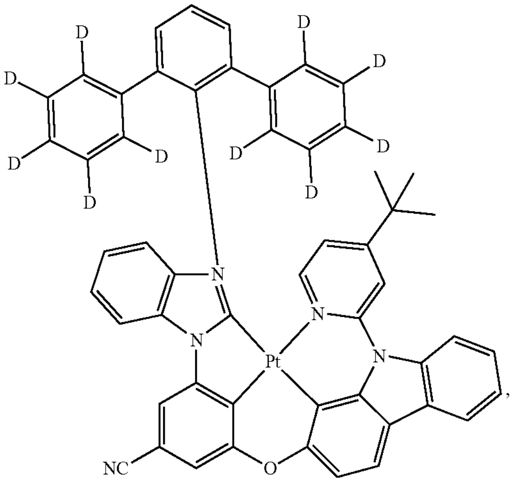,
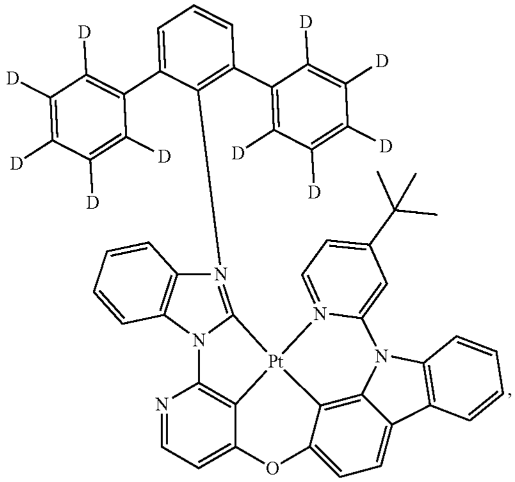, -continued
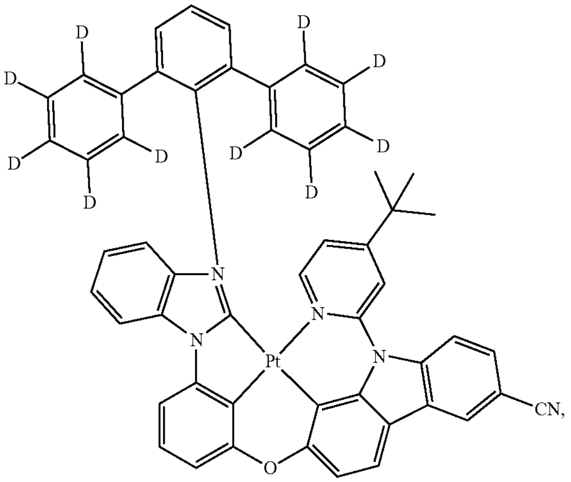
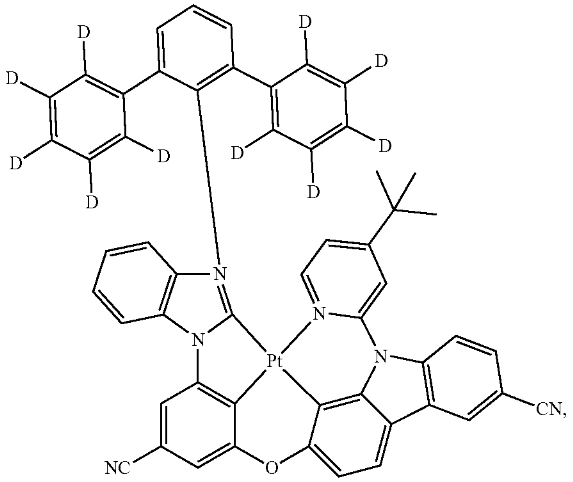
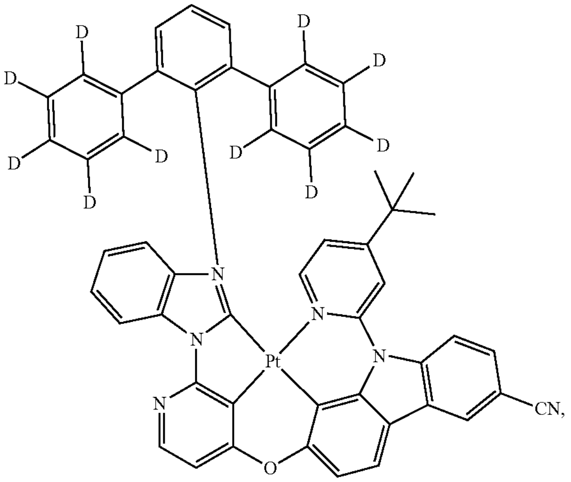
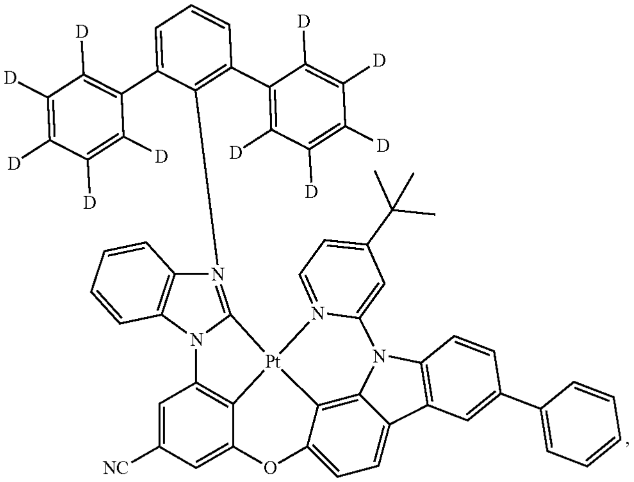

-continued
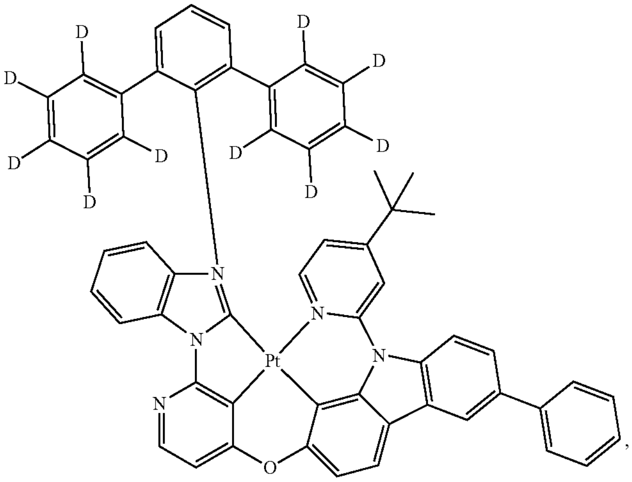
,
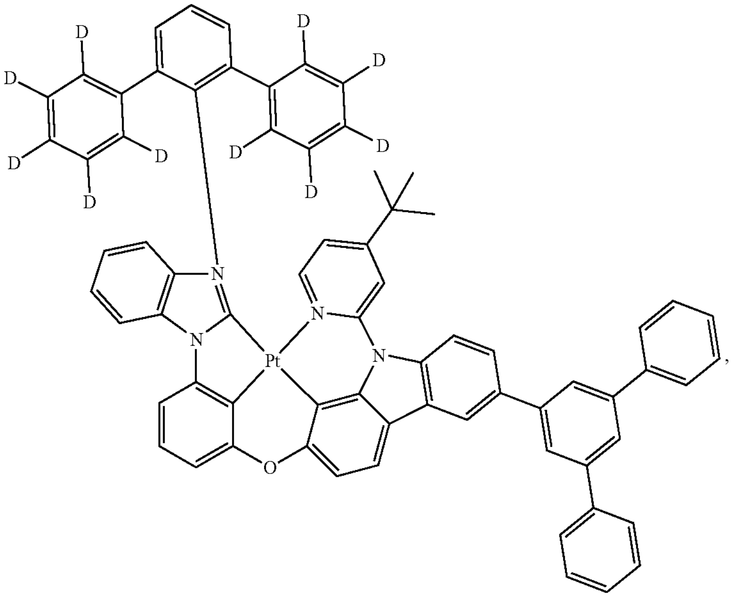
,
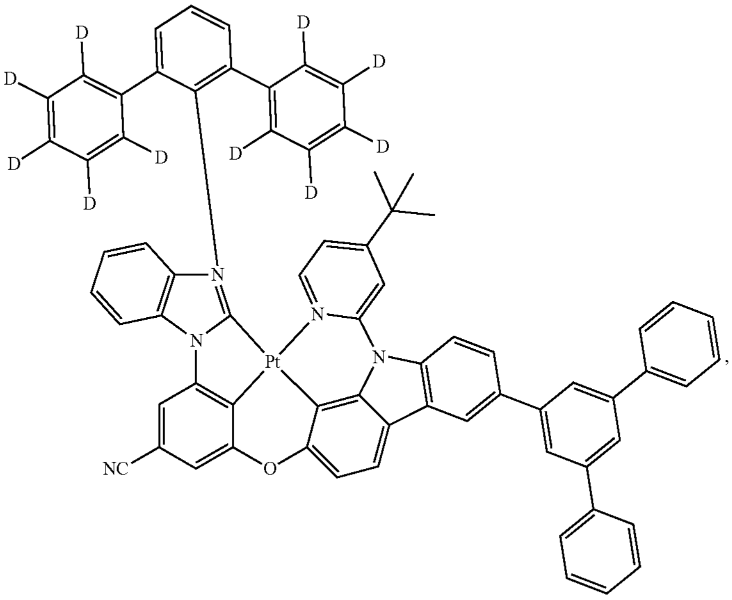
,

-continued
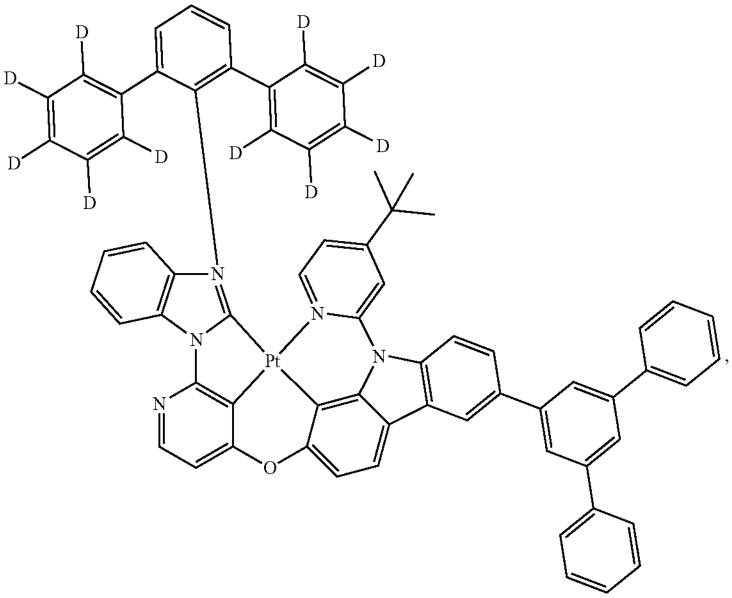
,
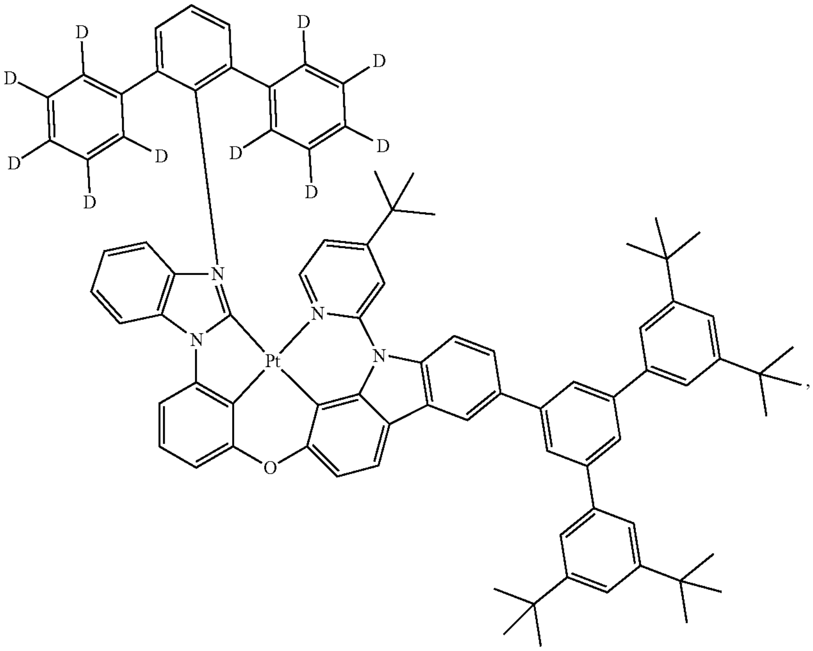
,

-continued
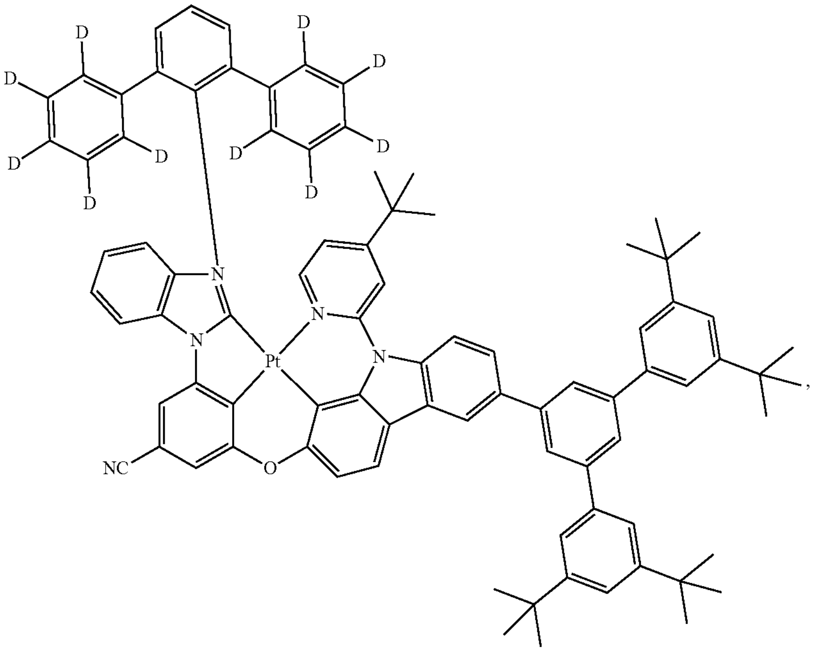
,
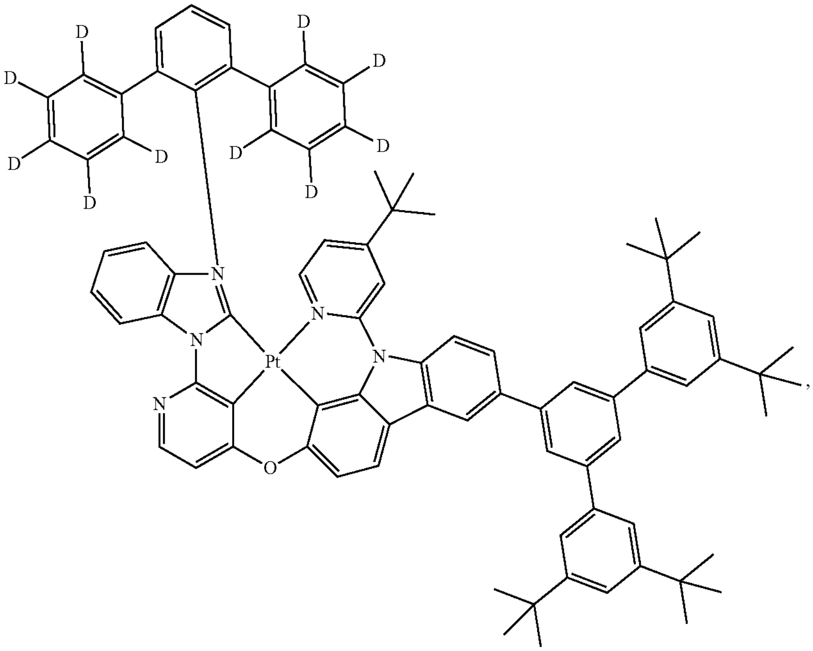
,

-continued
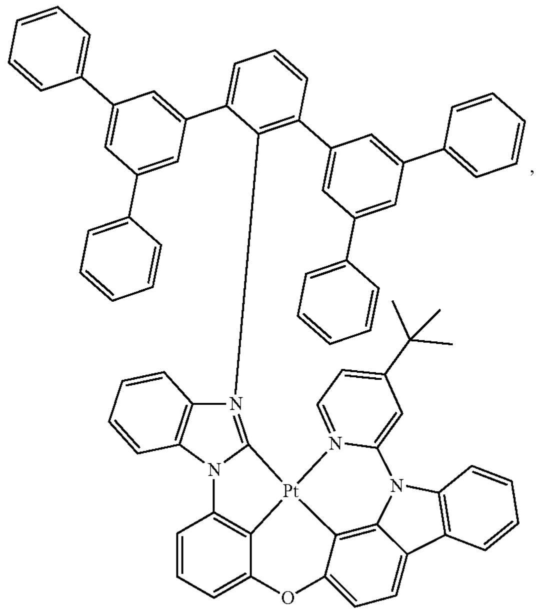
,
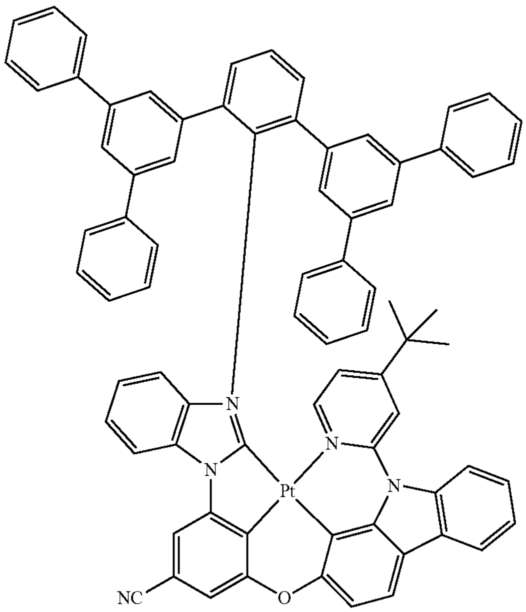
,
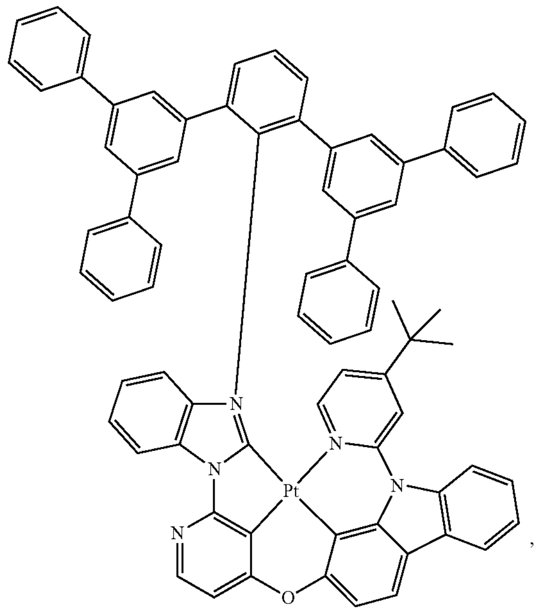
,
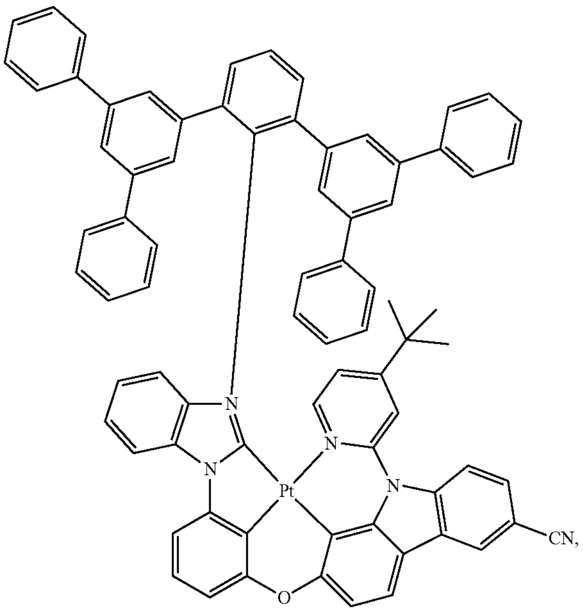
,

-continued
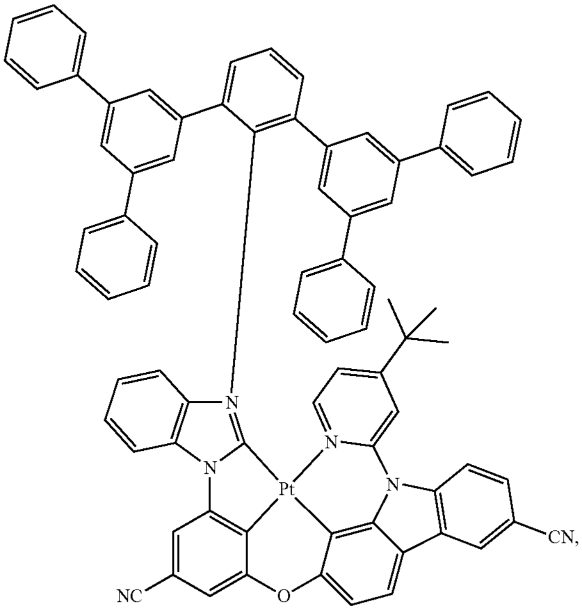
CN,
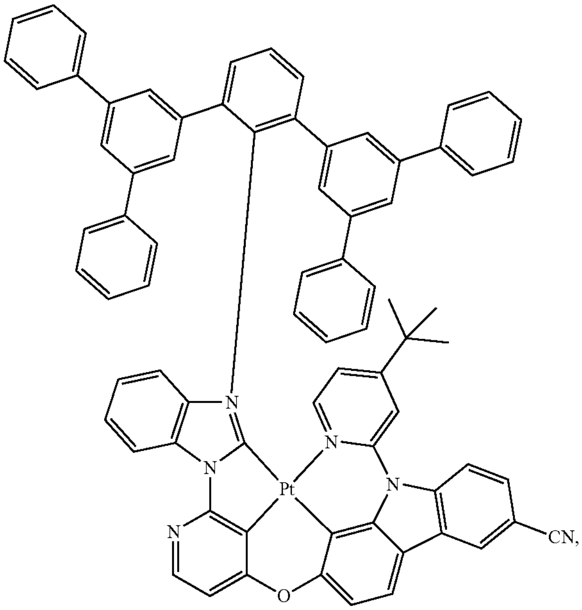
CN,
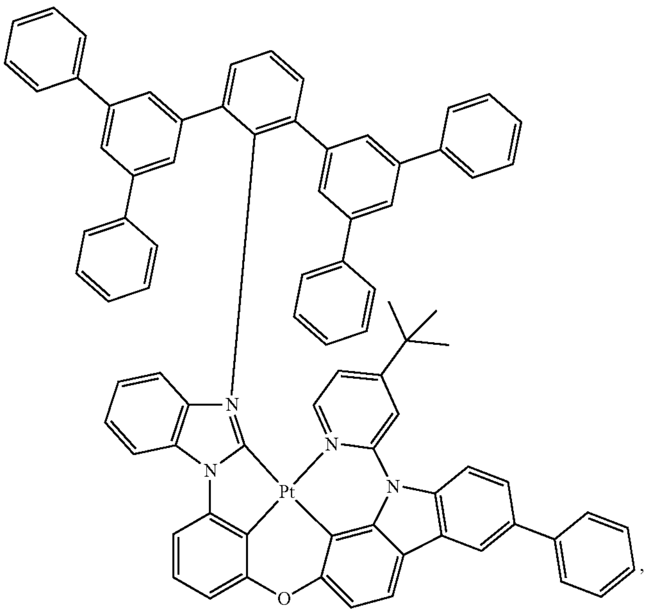
,

-continued
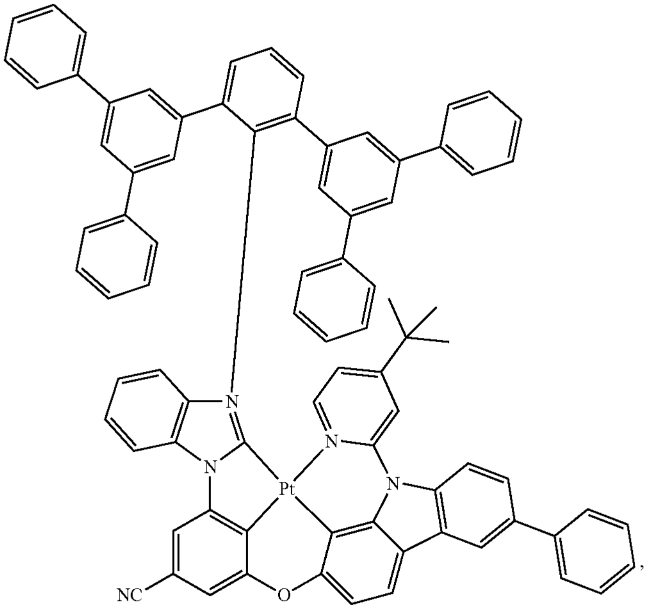
,
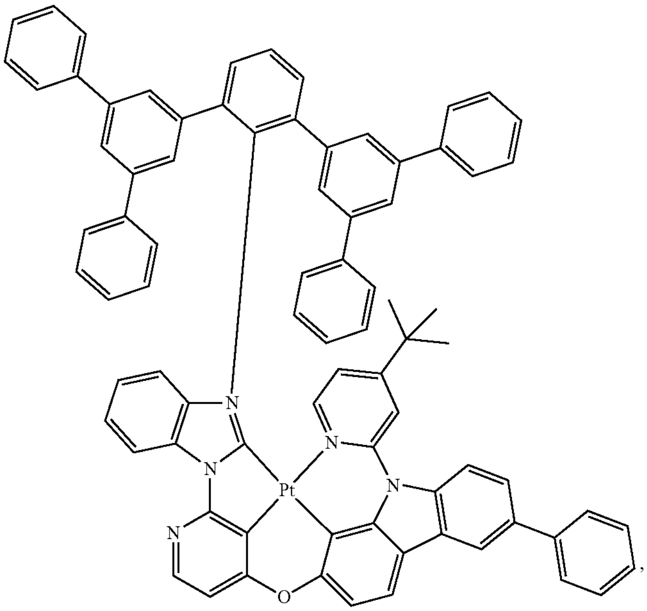
,

-continued
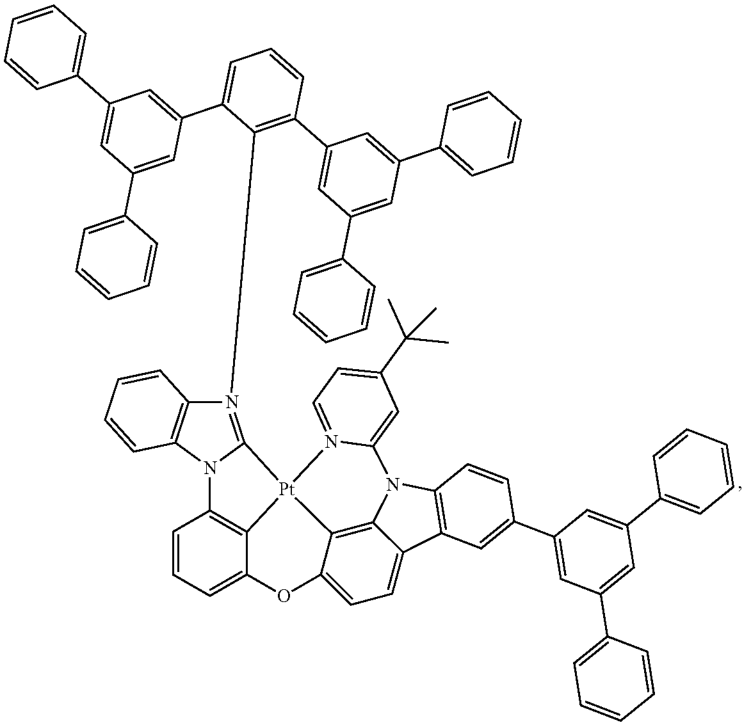
,
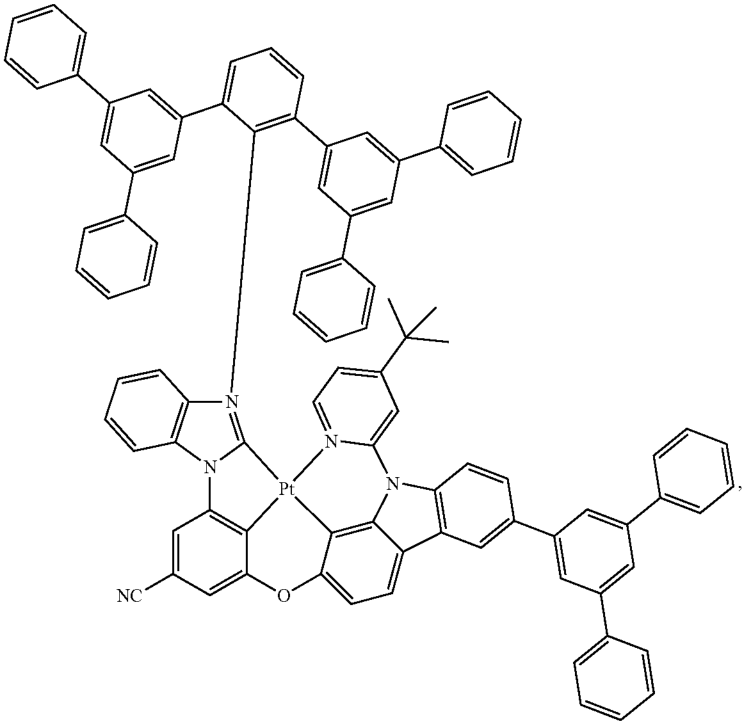
,

-continued
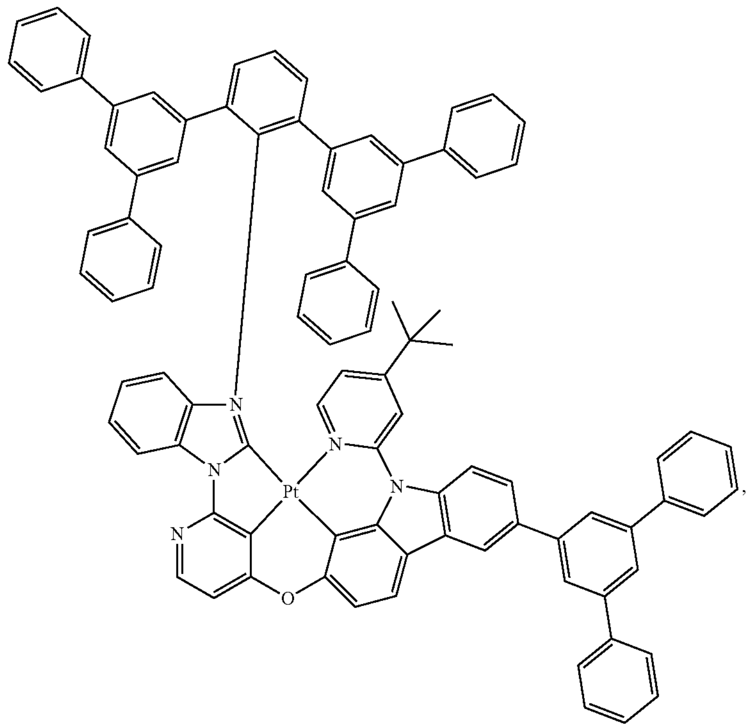
,
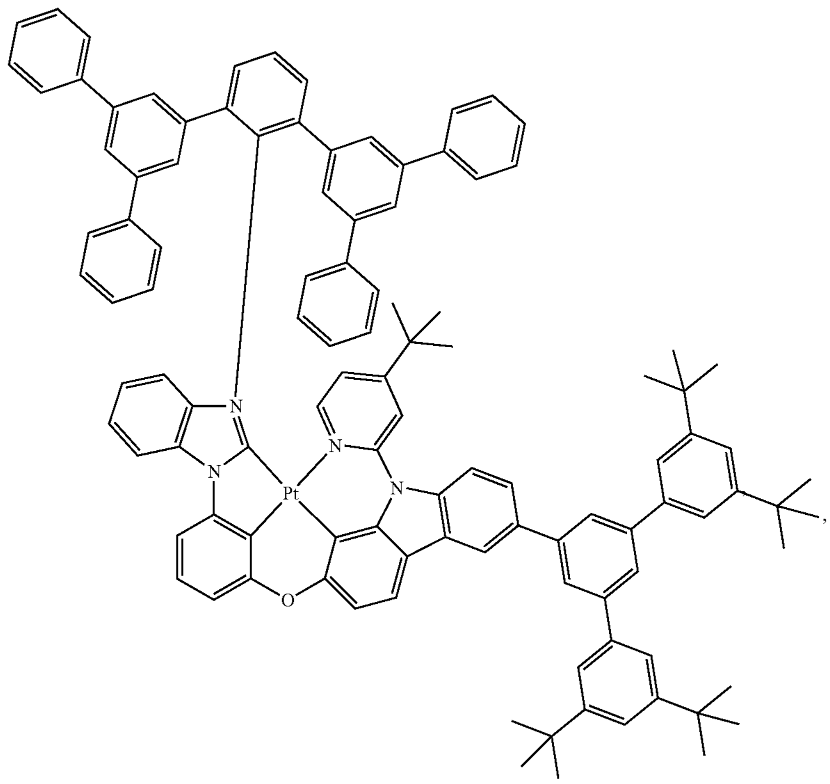
,

-continued
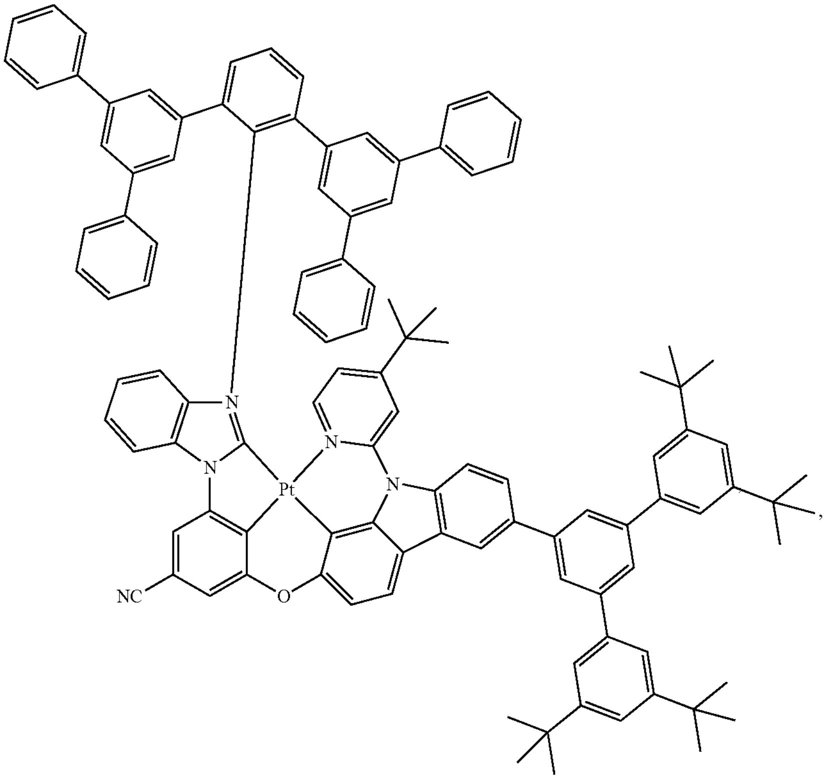
,
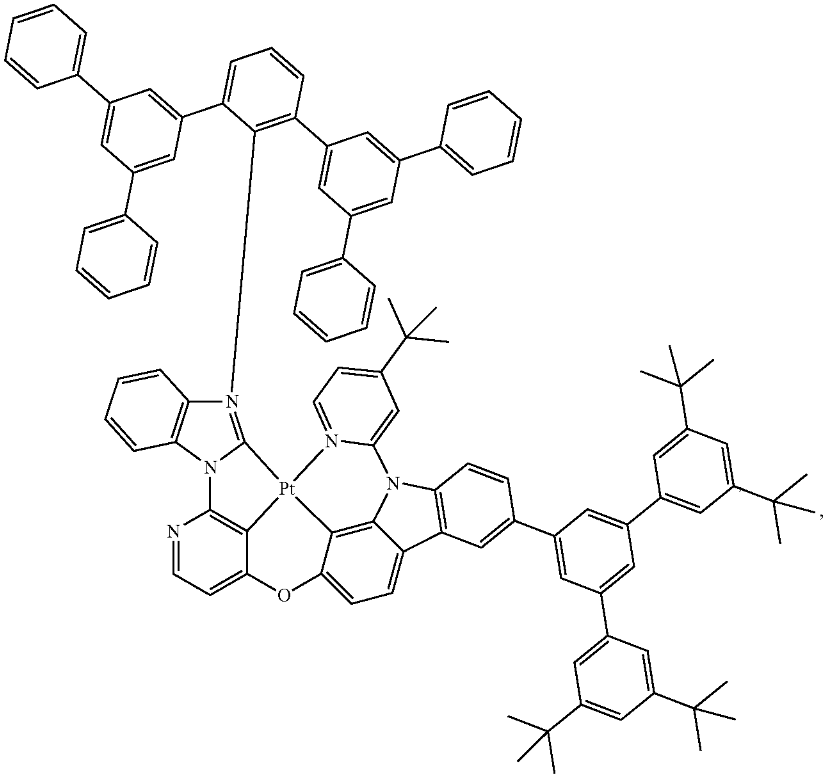
,

-continued
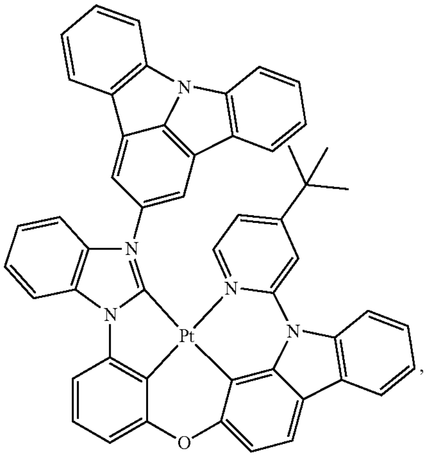
,
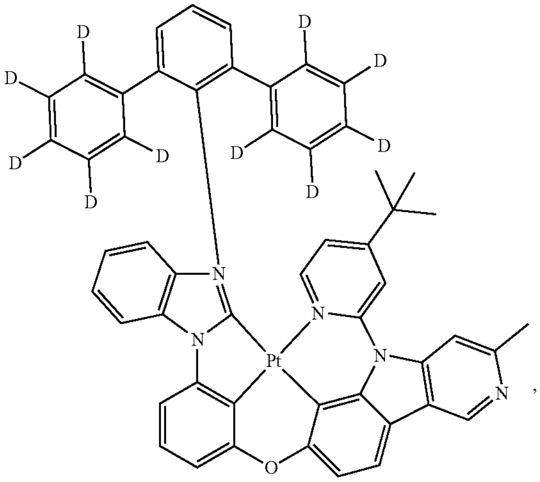
,
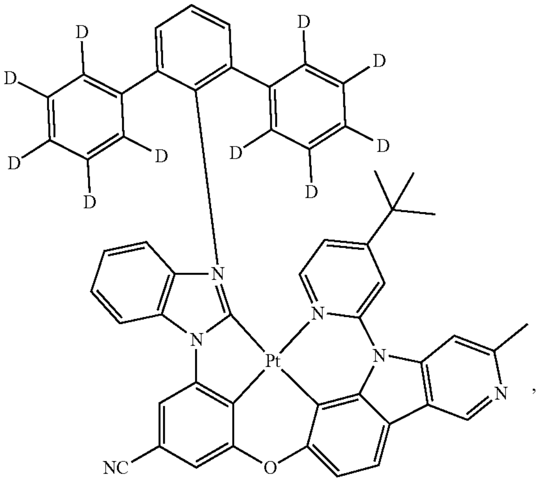
,
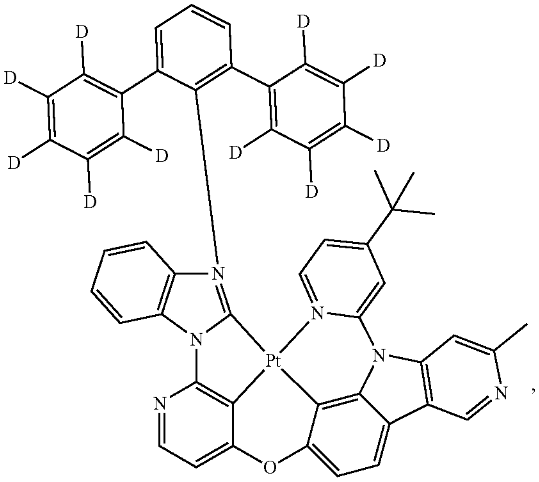
,
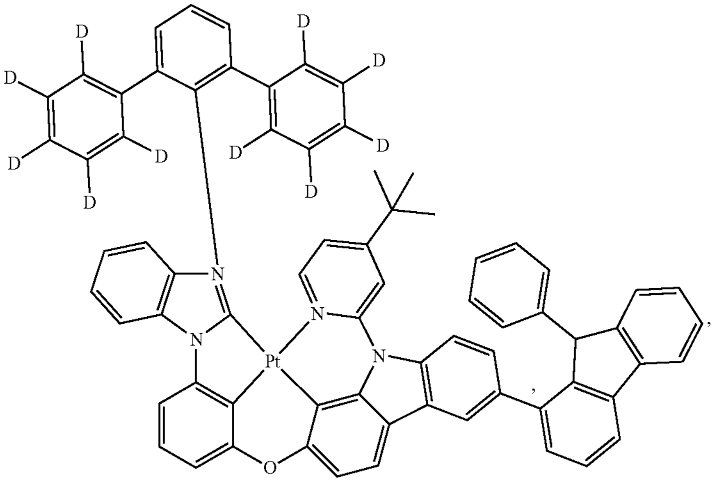
, -continued
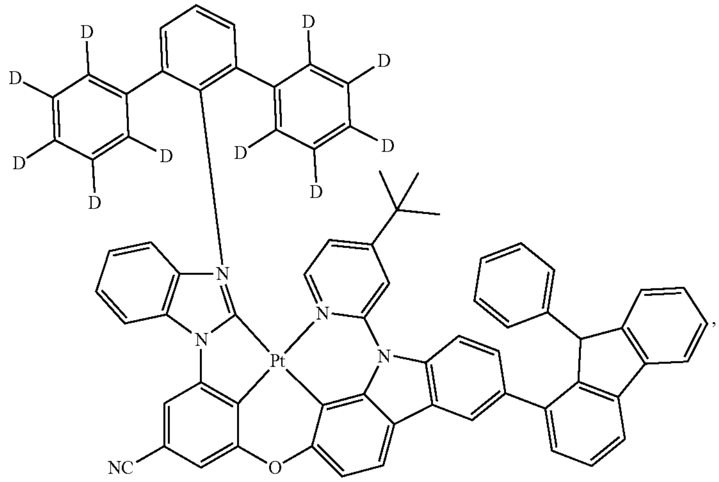
,
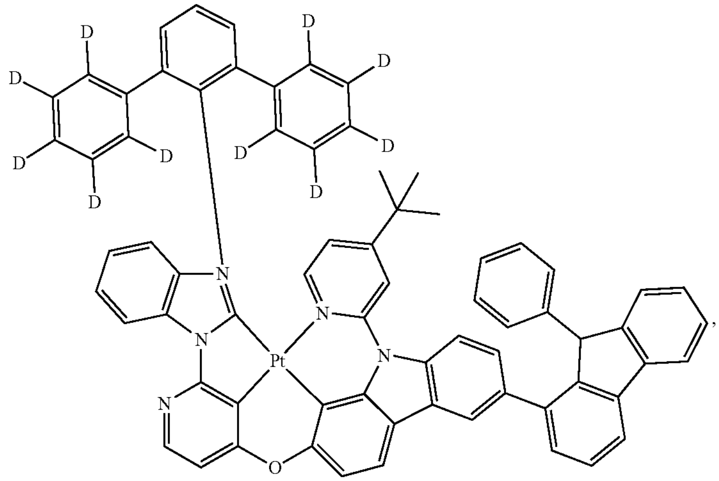
,
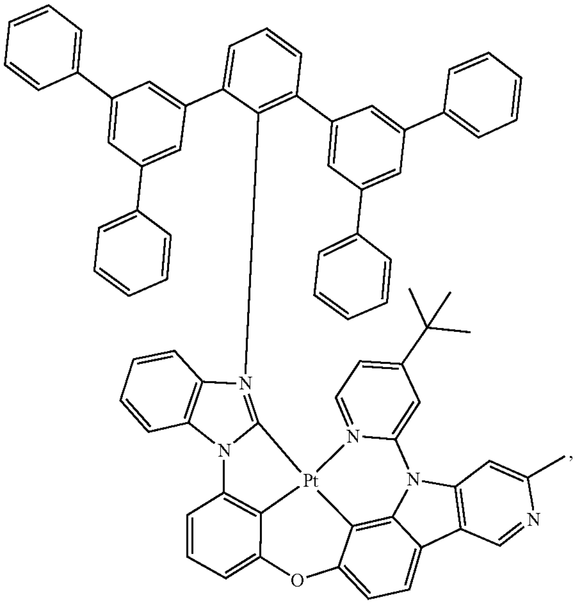
,
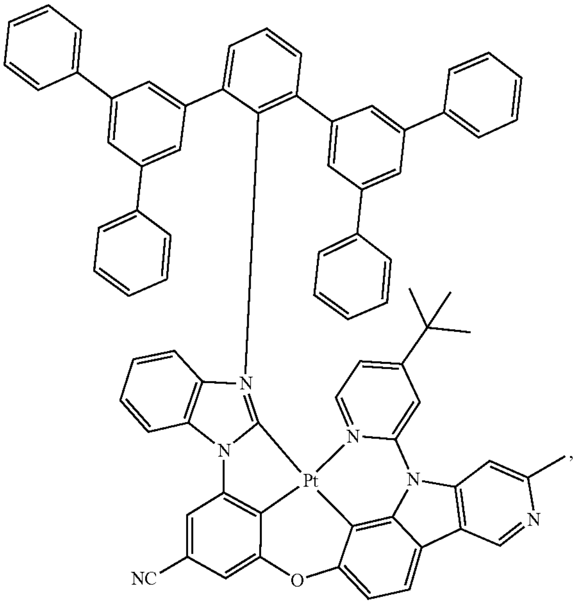
, -continued
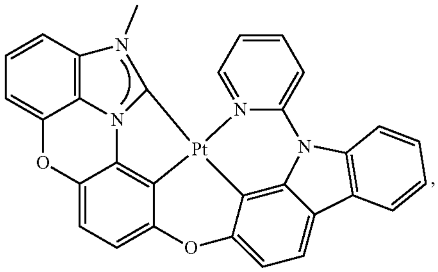
,
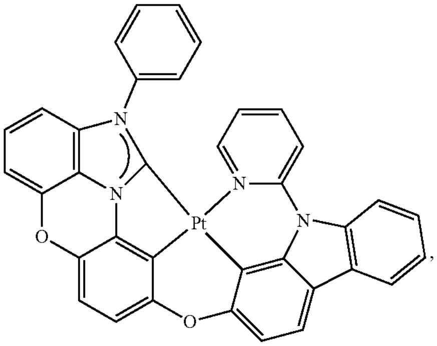
,
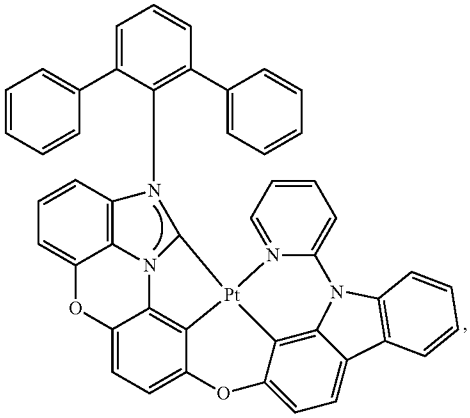
,
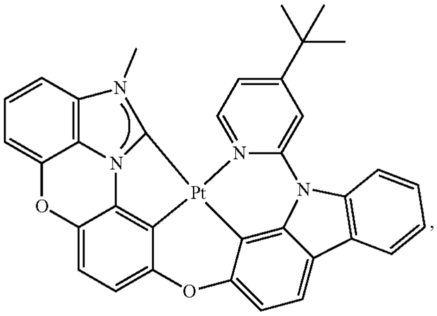
,
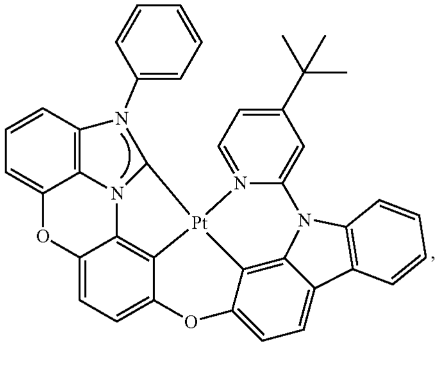
,
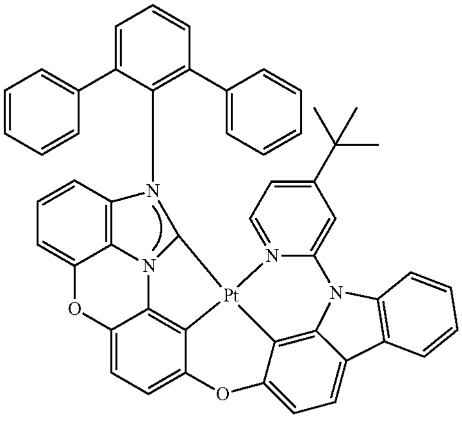
, -continued
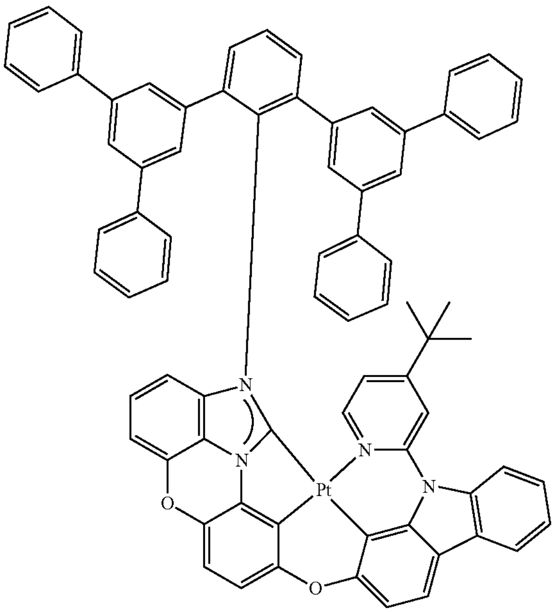
,
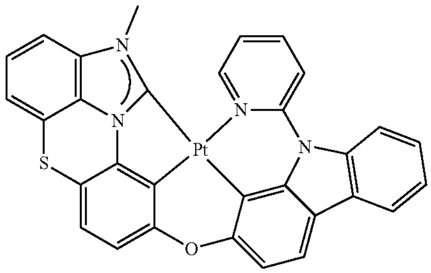
,
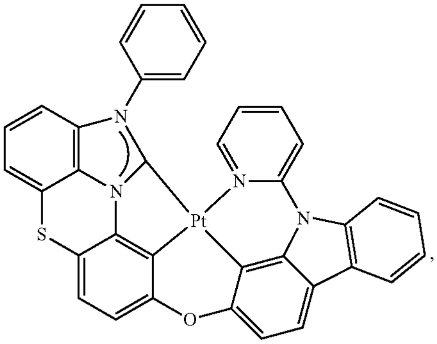
,
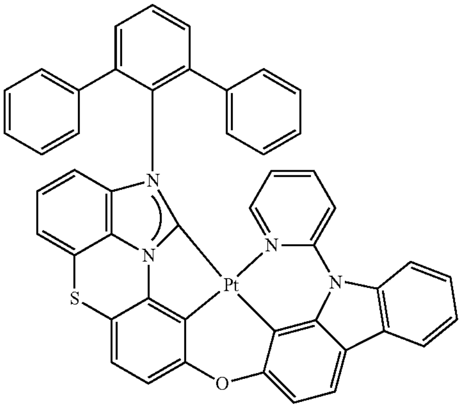
,
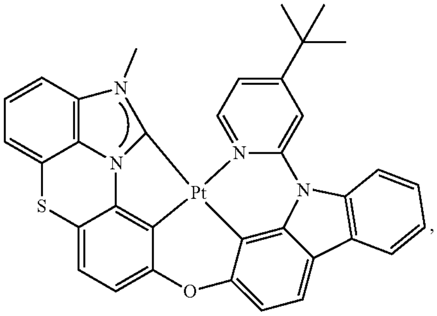
,
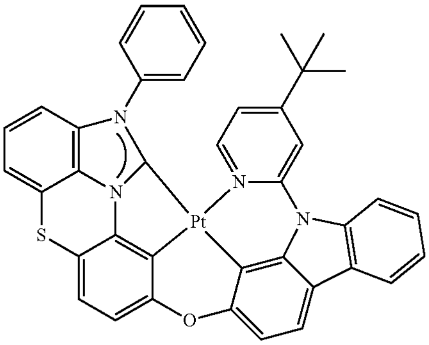
, -continued
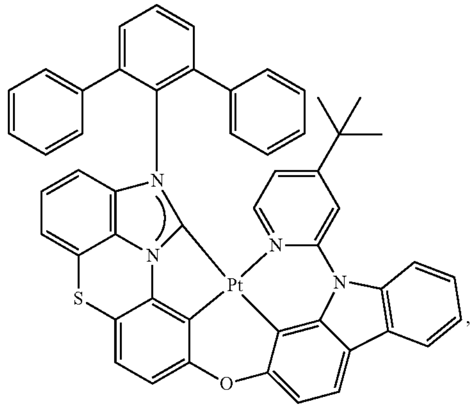,
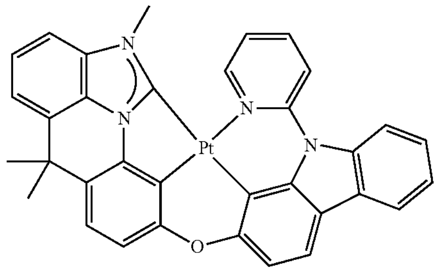,
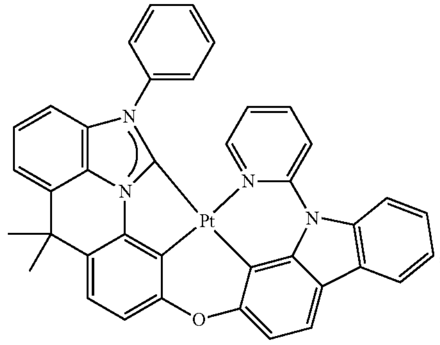,
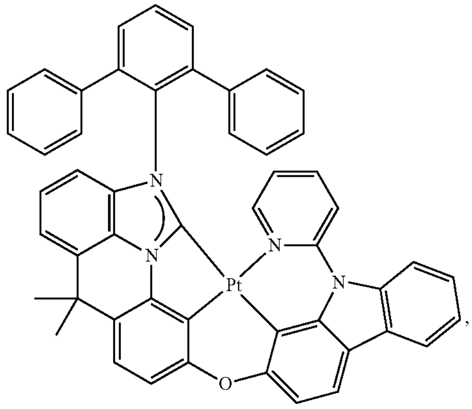,
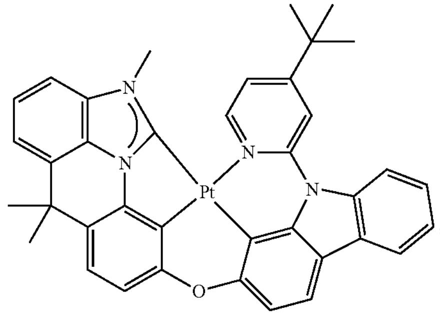,
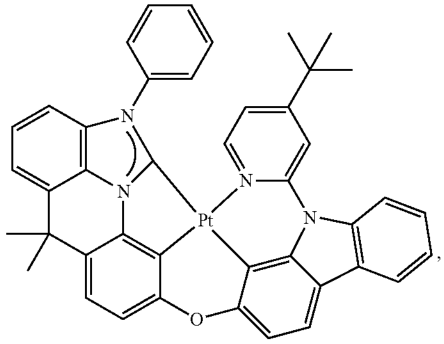, -continued
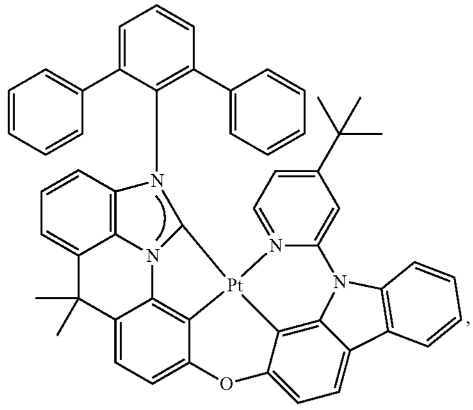,
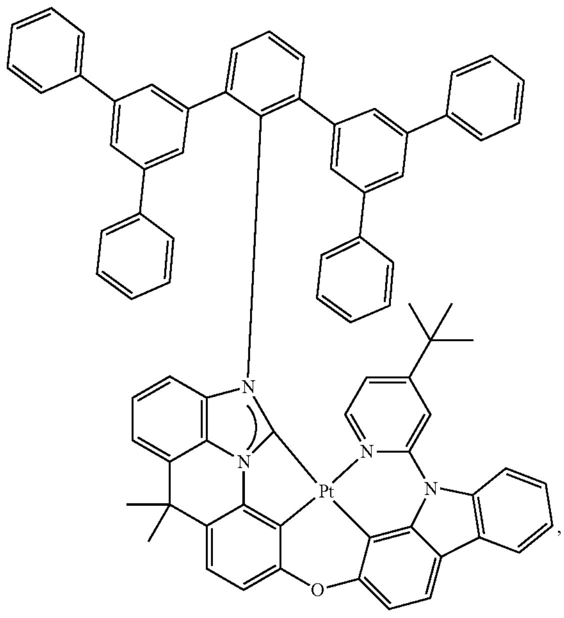,
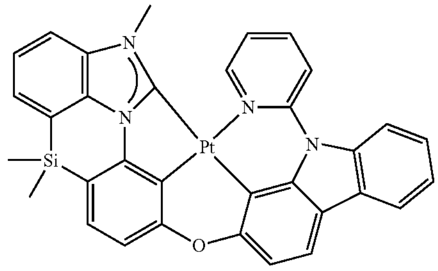,
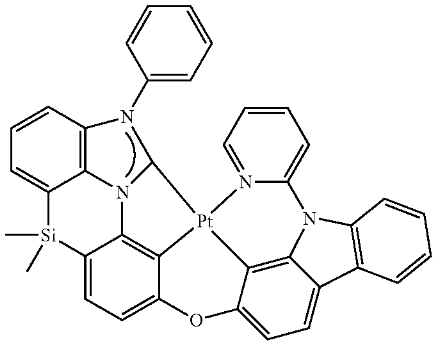,
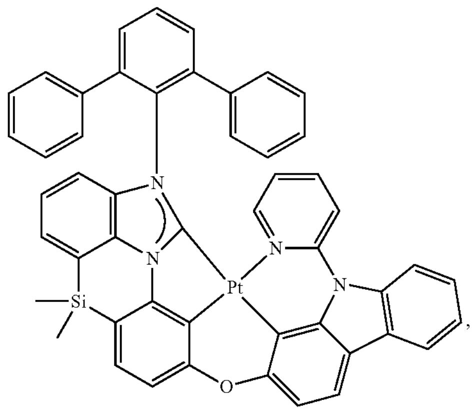,
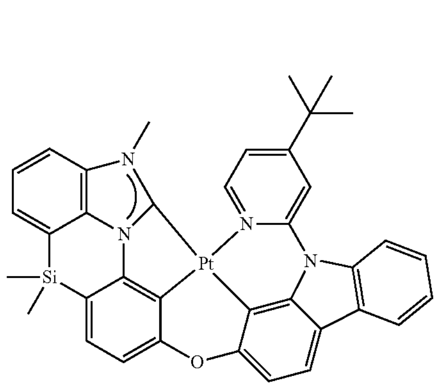, -continued
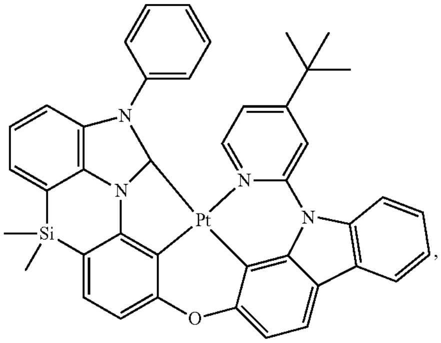,
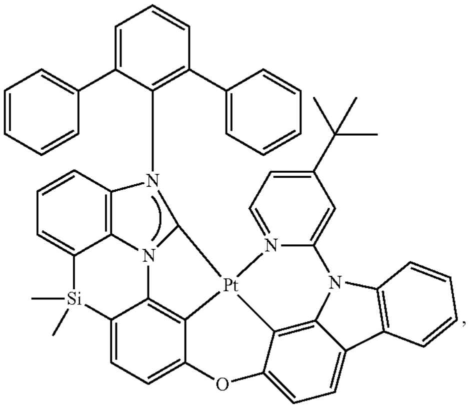,
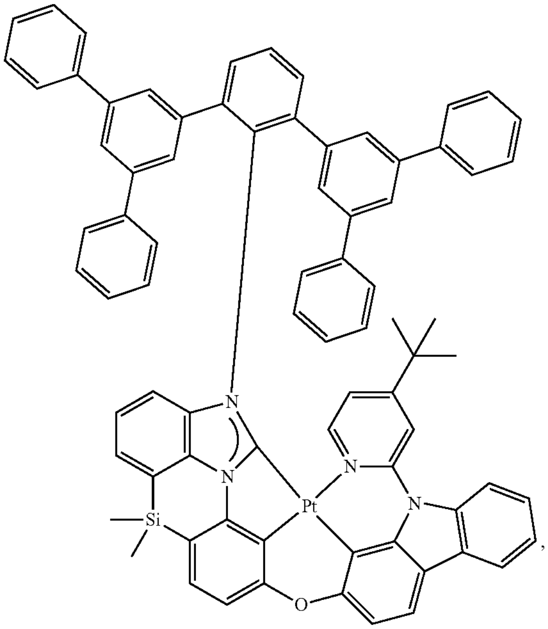,
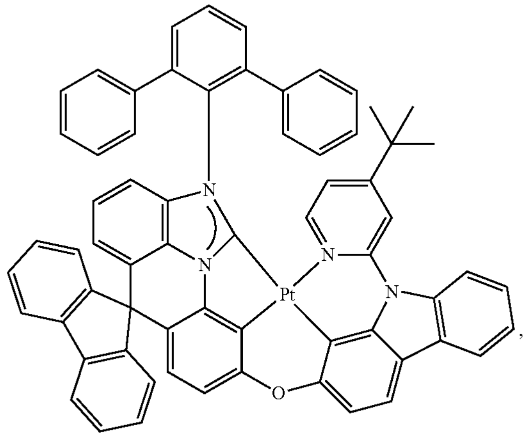,
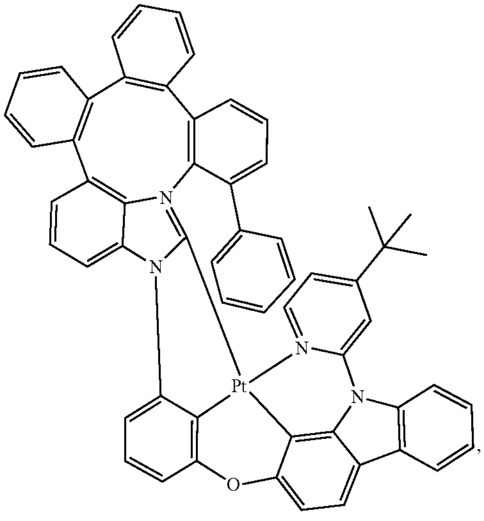,
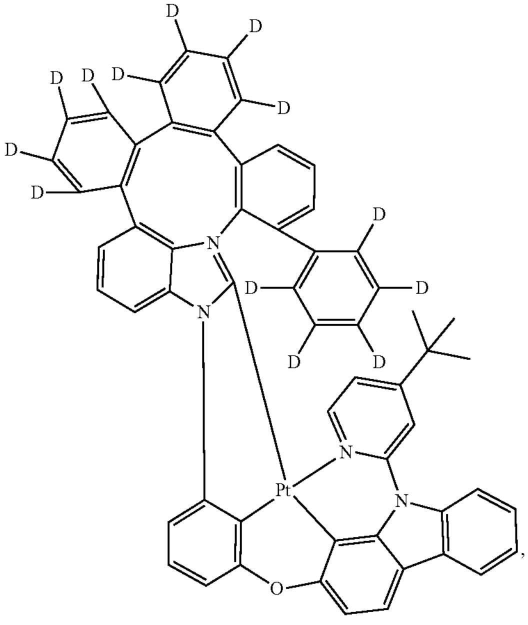, -continued
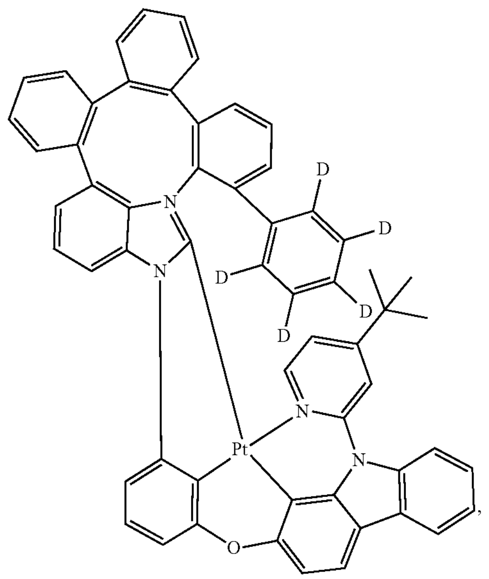
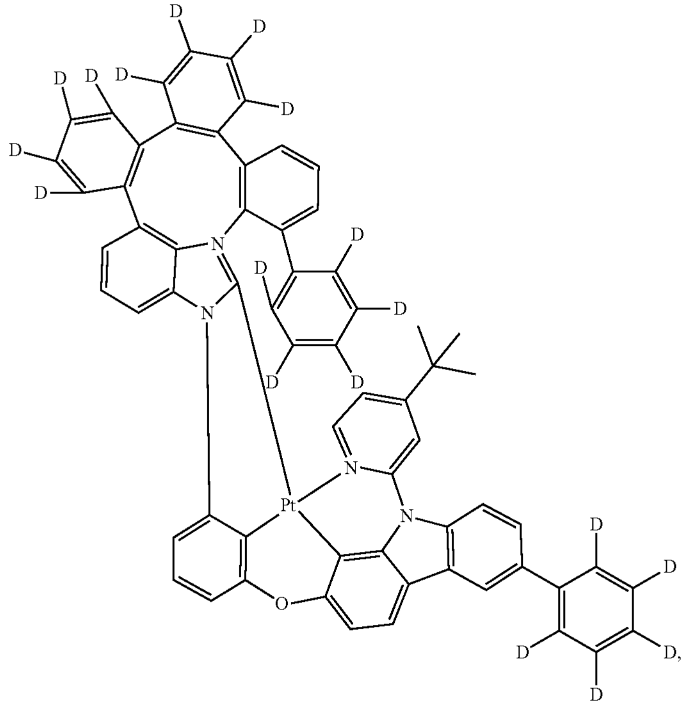

-continued
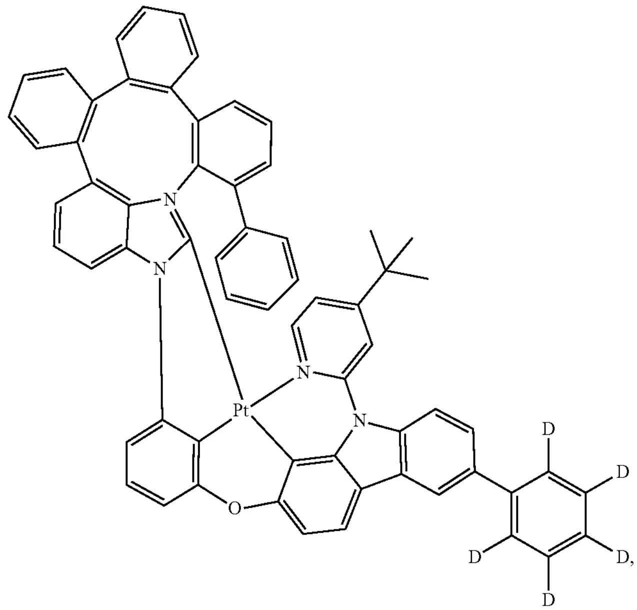
,
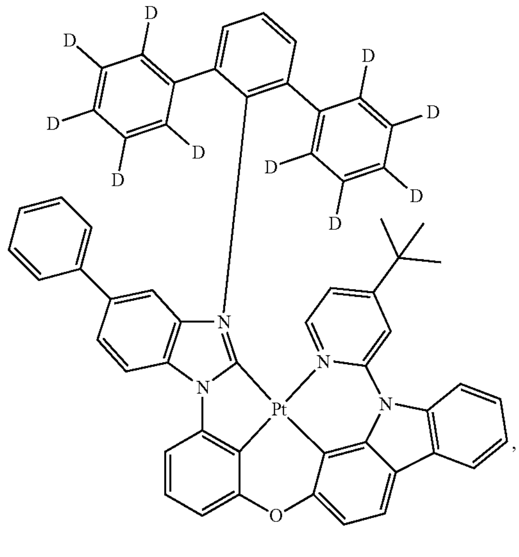
,

-continued
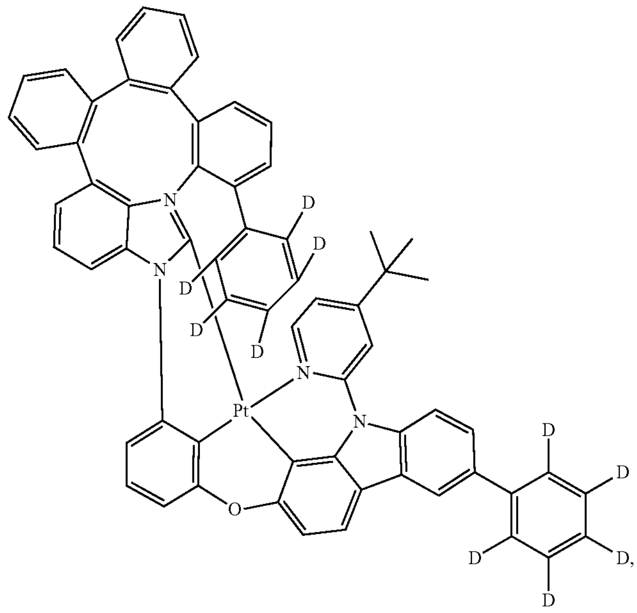,
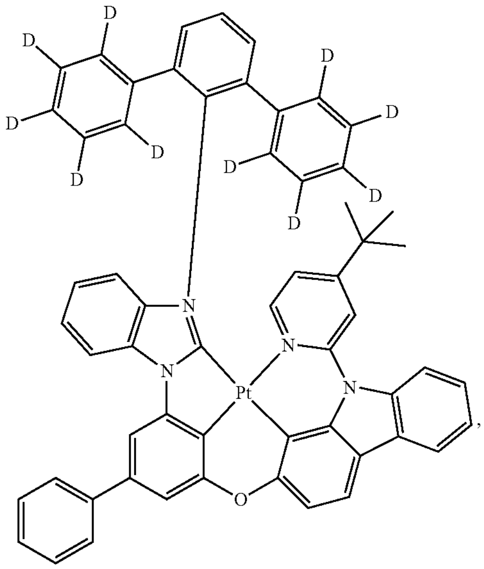,
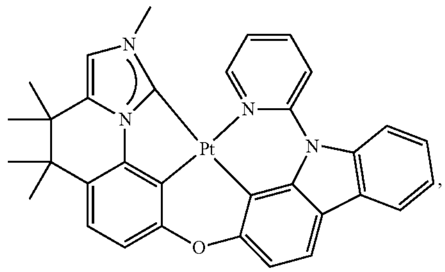,
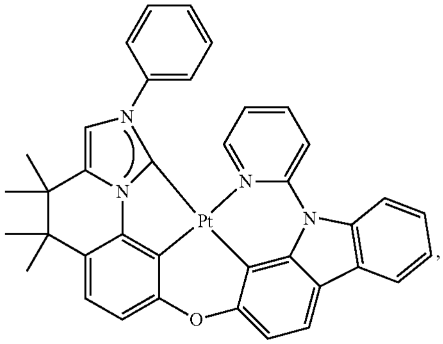,
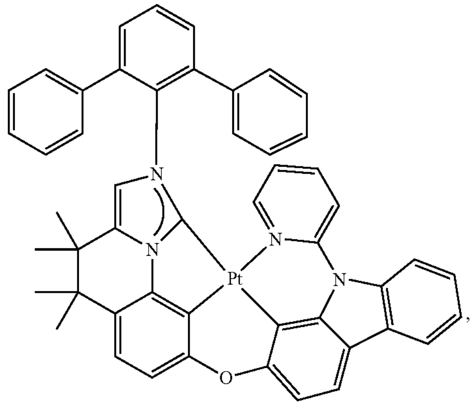,
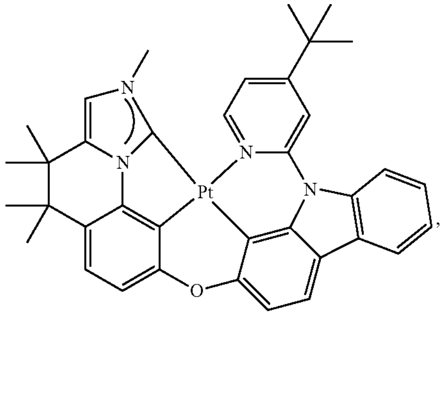, -continued
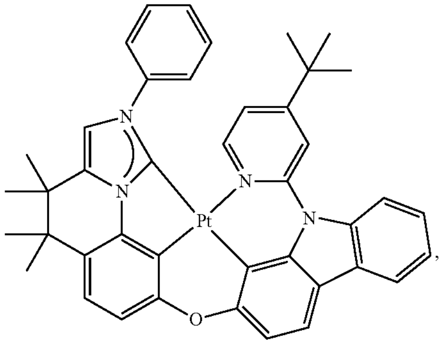
,
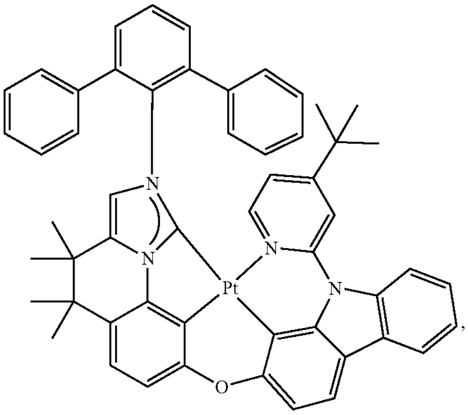
,
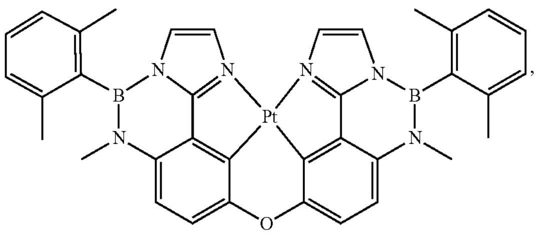
,
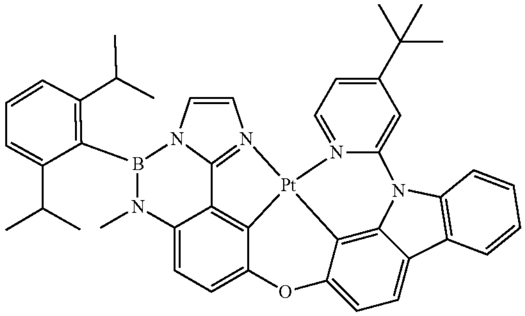
,
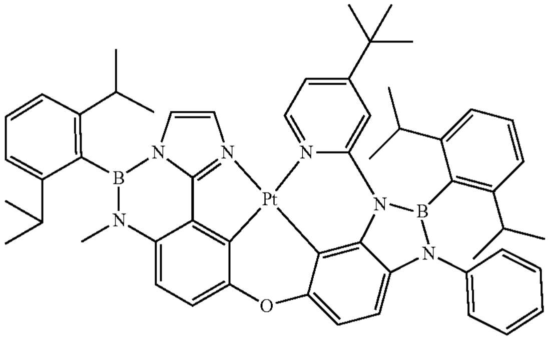
,
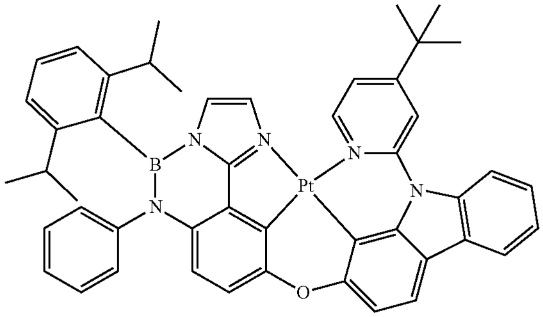
,
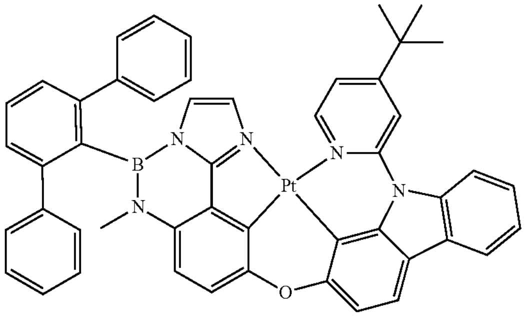
, -continued
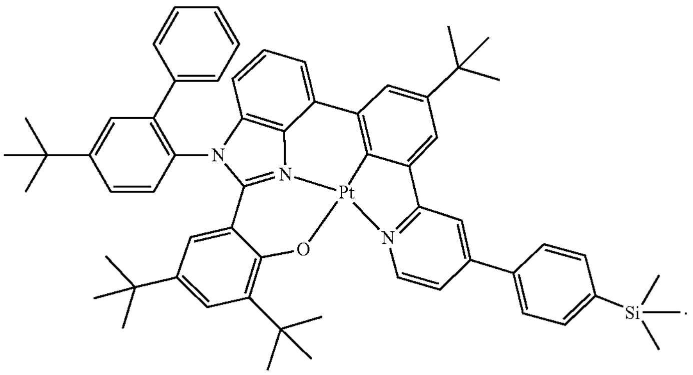
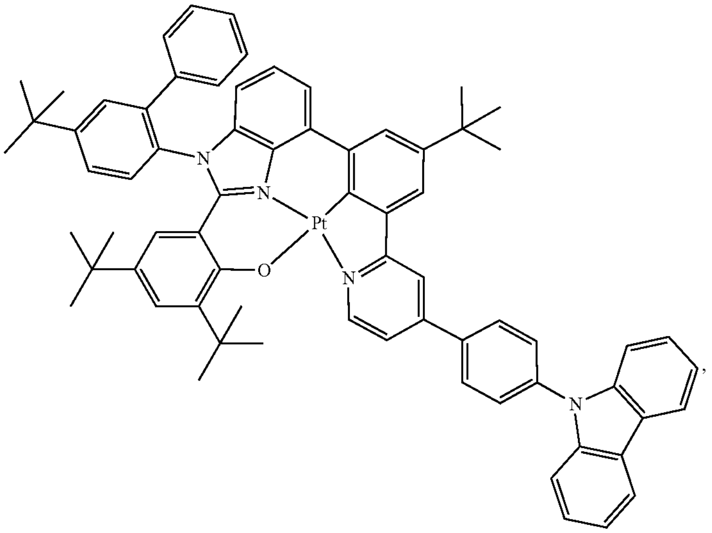
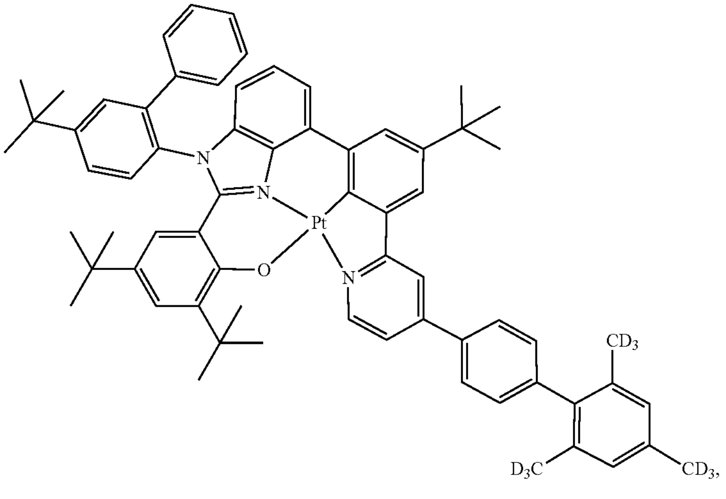

-continued
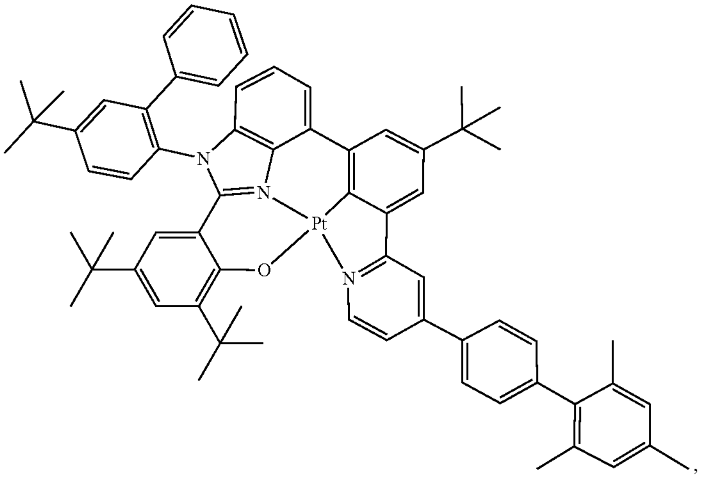
,
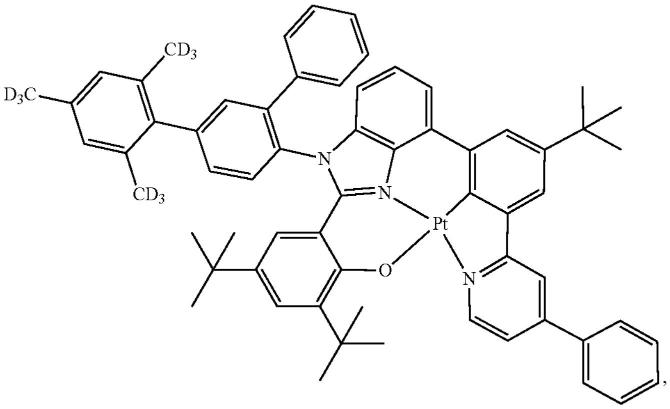
,
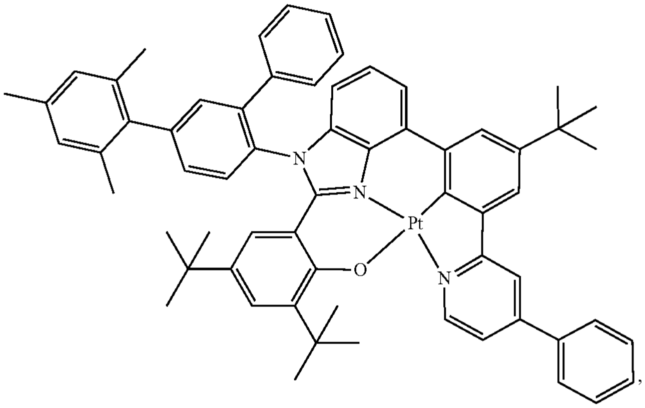
,
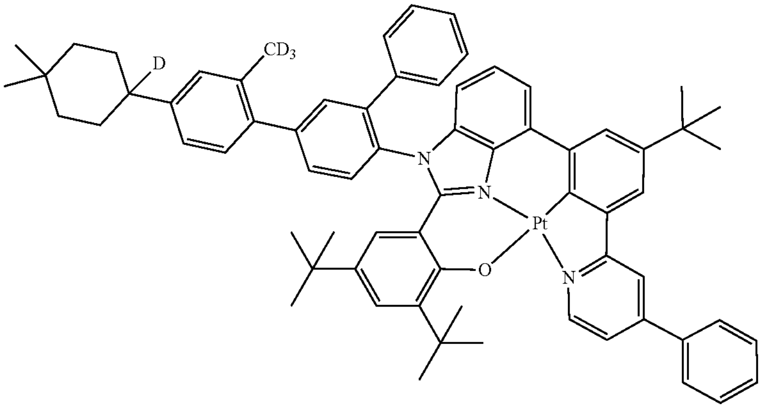
and

-continued

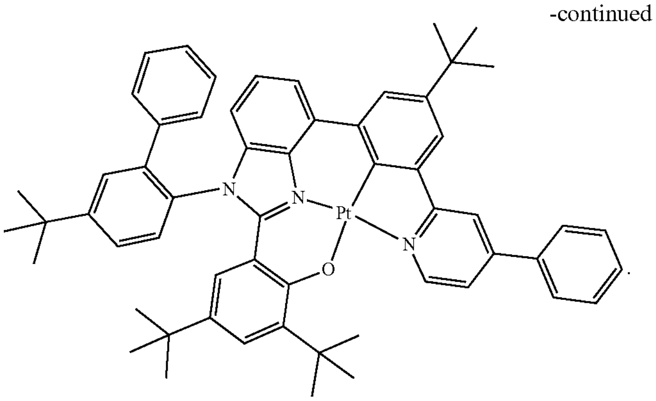

In some embodiments, at least one of the anode, the cathode, or a new layer disposed over the organic emissive layer functions as an enhancement layer. The enhancement layer comprises a plasmonic material exhibiting surface plasmon resonance that non-radiatively couples to the emitter material and transfers excited state energy from the emitter material to non-radiative mode of surface plasmon polariton. The enhancement layer is provided no more than a threshold distance away from the organic emissive layer, wherein the emitter material has a total non-radiative decay rate constant and a total radiative decay rate constant due to the presence of the enhancement layer and the threshold distance is where the total non-radiative decay rate constant is equal to the total radiative decay rate constant. In some embodiments, the OLED further comprises an outcoupling layer. In some embodiments, the outcoupling layer is disposed over the enhancement layer on the opposite side of the organic emissive layer. In some embodiments, the outcoupling layer is disposed on opposite side of the emissive layer from the enhancement layer but still outcouples energy from the surface plasmon mode of the enhancement layer. The outcoupling layer scatters the energy from the surface plasmon polaritons. In some embodiments this energy is scattered as photons to free space. In other embodiments, the energy is scattered from the surface plasmon mode into other modes of the device such as but not limited to the organic waveguide mode, the substrate mode, or another waveguiding mode. If energy is scattered to the non-free space mode of the OLED other outcoupling schemes could be incorporated to extract that energy to free space. In some embodiments, one or more intervening layer can be disposed between the enhancement layer and the outcoupling layer. The examples for intervening layer(s) can be dielectric materials, including organic, inorganic, perovskites, oxides, and may include stacks and/or mixtures of these materials.

The enhancement layer modifies the effective properties of the medium in which the emitter material resides resulting in any or all of the following: a decreased rate of emission, a modification of emission line-shape, a change in emission intensity with angle, a change in the stability of the emitter material, a change in the efficiency of the OLED, and reduced efficiency roll-off of the OLED device. Placement of the enhancement layer on the cathode side, anode side, or on both sides results in OLED devices which take advantage of any of the above-mentioned effects. In addition to the specific functional layers mentioned herein and illustrated in the various OLED examples shown in the figures, the OLEDs according to the present disclosure may include any of the other functional layers often found in OLEDs.

The enhancement layer can be comprised of plasmonic materials, optically active metamaterials, or hyperbolic metamaterials. As used herein, a plasmonic material is a material in which the real part of the dielectric constant crosses zero in the visible or ultraviolet region of the electromagnetic spectrum. In some embodiments, the plasmonic material includes at least one metal. In such embodiments the metal may include at least one of Ag, Al, Au, Ir, Pt, Ni, Cu, W, Ta, Fe, Cr, Mg, Ga, Rh, Ti, Ru, Pd, In, Bi, Ca alloys or mixtures of these materials, and stacks of these materials. In general, a metamaterial is a medium composed of different materials where the medium as a whole acts differently than the sum of its material parts. In particular, we define optically active metamaterials as materials which have both negative permittivity and negative permeability. Hyperbolic metamaterials, on the other hand, are anisotropic media in which the permittivity or permeability are of different sign for different spatial directions. Optically active metamaterials and hyperbolic metamaterials are strictly distinguished from many other photonic structures such as Distributed Bragg Reflectors ("DBRs") in that the medium should appear uniform in the direction of propagation on the length scale of the wavelength of light. Using terminology that one skilled in the art can understand: the dielectric constant of the metamaterials in the direction of propagation can be described with the effective medium approximation. Plasmonic materials and metamaterials provide methods for controlling the propagation of light that can enhance OLED performance in a number of ways.

In some embodiments, the enhancement layer is provided as a planar layer. In other embodiments, the enhancement layer has wavelength-sized features that are arranged periodically, quasi-periodically, or randomly, or sub-wavelength-sized features that are arranged periodically, quasi-periodically, or randomly. In some embodiments, the wavelength-sized features and the sub-wavelength-sized features have sharp edges.

In some embodiments, the outcoupling layer has wavelength-sized features that are arranged periodically, quasi-periodically, or randomly, or sub-wavelength-sized features that are arranged periodically, quasi-periodically, or randomly. In some embodiments, the outcoupling layer may be composed of a plurality of nanoparticles and in other embodiments the outcoupling layer is composed of a plurality of nanoparticles disposed over a material. In these embodiments the outcoupling may be tunable by at least one of varying a size of the plurality of nanoparticles, varying a shape of the plurality of nanoparticles, changing a material of the plurality of nanoparticles, adjusting a thickness of the material, changing the refractive index of the material or an additional layer disposed on the plurality of nanoparticles, varying a thickness of the enhancement layer, and/or varying the material of the enhancement layer. The plurality of nanoparticles of the device may be formed from at least one of metal, dielectric material, semiconductor materials, an alloy of metal, a mixture of dielectric materials, a stack or layering of one or more materials, and/or a core of one type of material and that is coated with a shell of a different type of material. In some embodiments, the outcoupling layer is composed of at least metal nanoparticles wherein the metal is selected from the group consisting of Ag, Al, Au, Ir, Pt, Ni, Cu, W, Ta, Fe, Cr, Mg, Ga, Rh, Ti, Ru, Pd, In, Bi, Ca, alloys or mixtures of these materials, and stacks of these materials. The plurality of nanoparticles may have additional layer disposed over them. In some embodiments, the polarization of the emission can be tuned using the outcoupling layer. Varying the dimensionality and periodicity of the outcoupling layer can select a type of polarization that is preferentially outcoupled to air. In some embodiments the outcoupling layer also acts as an electrode of the device.

In another aspect, the inventive OLED of the present disclosure can include an emissive region containing an emissive layer that comprises a phosphorescent dopant, a first host, and a second host, wherein the first host transports holes, the second host transports electrons, and the first host is fully or partially deuterated.

In another aspect, the present disclosure also provides a consumer product that comprises an inventive OLED of the present disclosure, where the inventive OLED includes an emissive layer that comprises a phosphorescent dopant, a first host, and a second host, wherein the first host transports holes, the second host transports electrons, and the first host is fully or partially deuterated.

In some embodiments, the consumer product can be one of a flat panel display, a computer monitor, a medical monitor, a television, a billboard, a light for interior or exterior illumination and/or signaling, a heads-up display, a fully or partially transparent display, a flexible display, a laser printer, a telephone, a cell phone, tablet, a phablet, a personal digital assistant (PDA), a wearable device, a laptop computer, a digital camera, a camcorder, a viewfinder, a micro-display that is less than 2 inches diagonal, a 3-D display, a virtual reality or augmented reality display, a vehicle, a video wall comprising multiple displays tiled together, a theater or stadium screen, a light therapy device, and a sign.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

Several OLED materials and configurations are described in U.S. Pat. Nos. 5,844,363, 6,303,238, and 5,707,745, which are incorporated herein by reference in their entirety.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
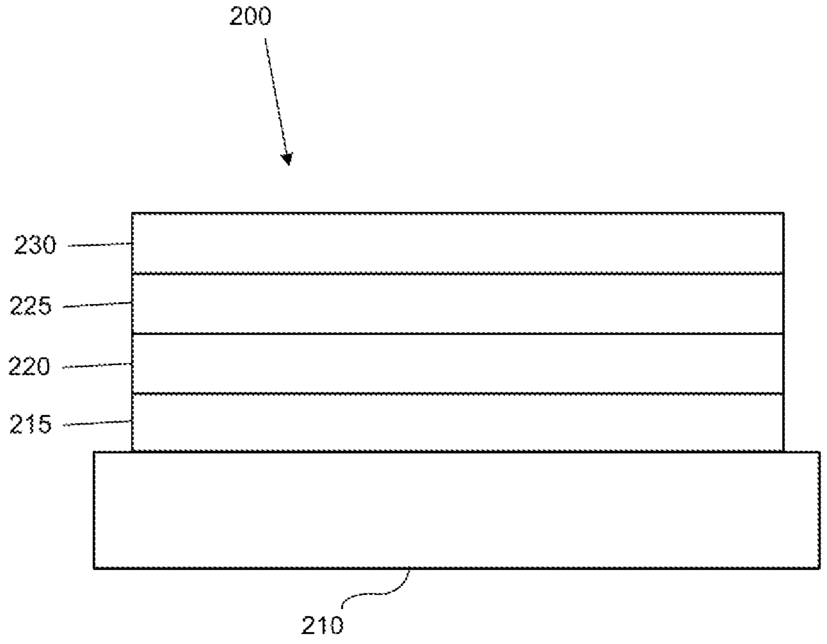
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the present disclosure may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP, also referred to as organic vapor jet deposition (OVJD)), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and organic vapor jet printing (OVJP). Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons are a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present disclosure may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the present disclosure can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the present disclosure can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, curved displays, computer monitors, medical monitors, televisions, billboards, lights for interior or exterior illumination and/or signaling, heads-up displays, fully or partially transparent displays, flexible displays, rollable displays, foldable displays, stretchable displays, laser printers, telephones, mobile phones, tablets, phablets, personal digital assistants (PDAs), wearable devices, laptop computers, digital cameras, camcorders, viewfinders, micro-displays (displays that are less than 2 inches diagonal), 3-D displays, virtual reality or augmented reality displays, vehicles, video walls comprising multiple displays tiled together, theater or stadium screen, a light therapy device, and a sign. Various control mechanisms may be used to control devices fabricated in accordance with the present disclosure, including passive matrix and active matrix. Many of the devices are intended for use in a temperature range comfortable to humans, such as 18 degrees C. to 30 degrees C., and more preferably at room temperature (20-25° C.), but could be used outside this temperature range, for example, from −40 degree C. to +80° C.

More details on OLEDs, and the definitions described above, can be found in U.S. Pat. No. 7,279,704, which is incorporated herein by reference in its entirety.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics selected from the group consisting of being flexible, being rollable, being foldable, being stretchable, and being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

a) Conductivity Dopants:

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

Non-limiting examples of the conductivity dopants that may be used in an OLED in combination with materials disclosed herein are exemplified below together with references that disclose those materials: EP01617493, EP01968131, EP2020694, EP2684932, US20050139810, US20070160905, US20090167167, US2010288362, WO06081780, WO2009003455, WO2009008277, WO2009011327, WO2014009310, US2007252140, US2015060804, US20150123047, and US2012146012.

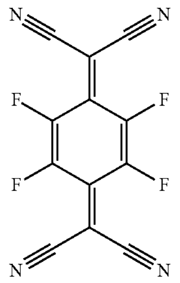

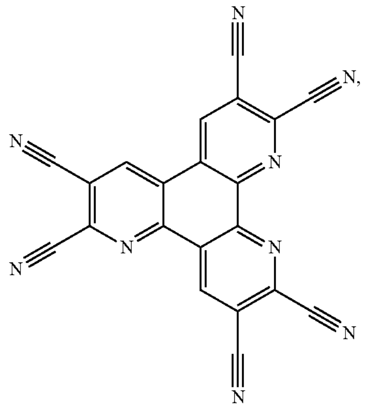

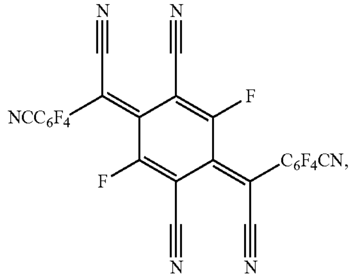

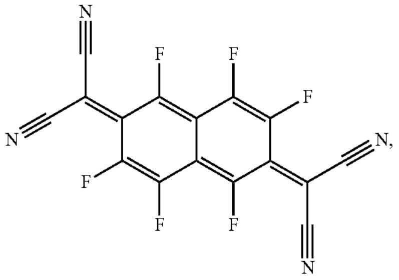

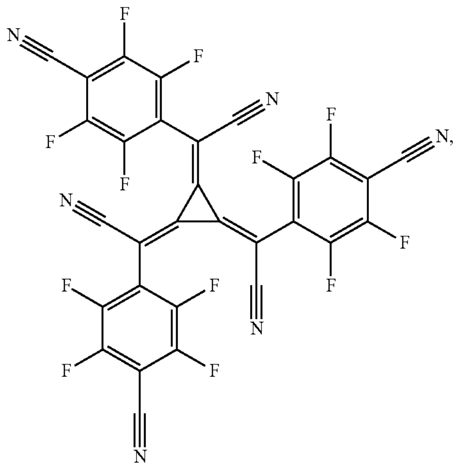

-continued

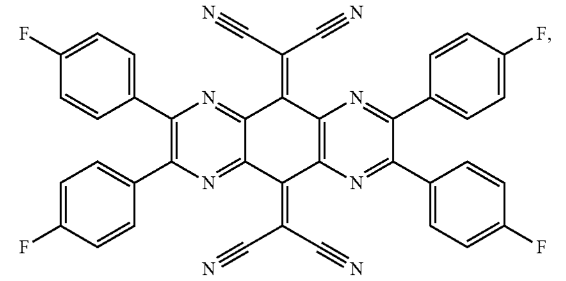

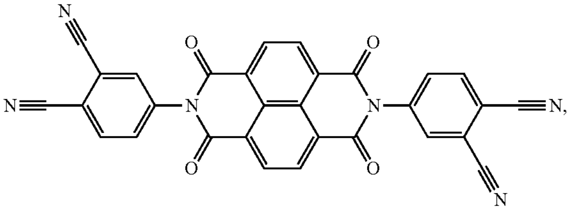

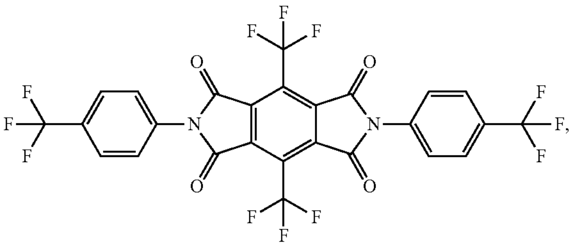

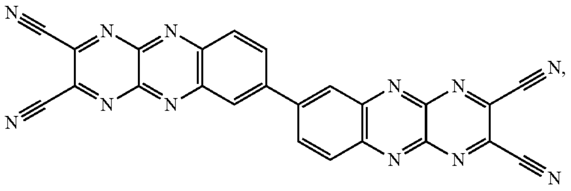

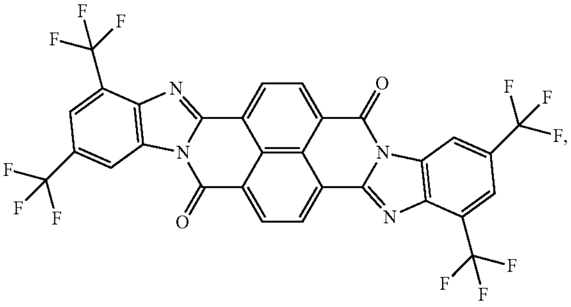

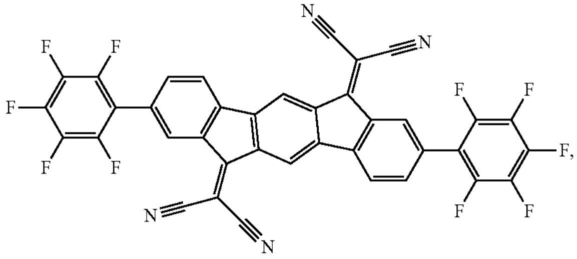

-continued

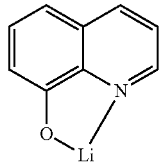,

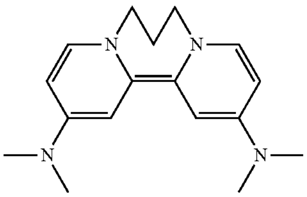

and

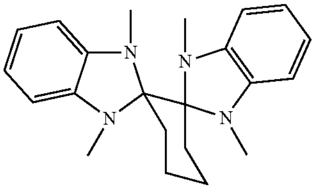.

b) HIL/HTL:

A hole injecting/transporting material to be used in the present disclosure is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but not limit to the following general structures:

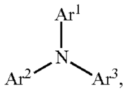

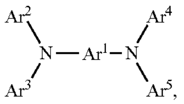

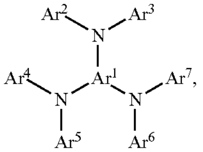

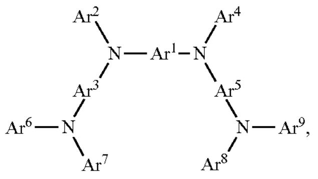

and

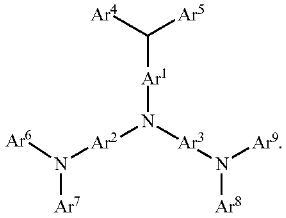

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Each Ar may be unsubstituted or may be substituted by a substituent selected from the group consisting of deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof.

In one aspect, $Ar^1$ to $Ar^9$ is independently selected from the group consisting of:

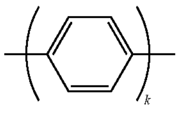,
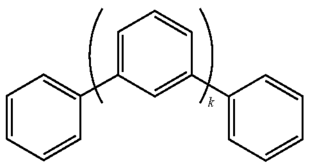,

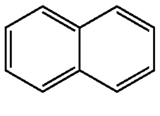,
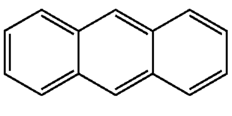,

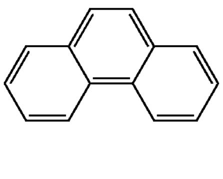,
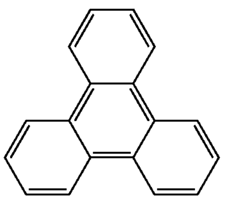,

-continued

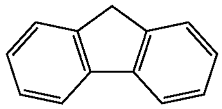, and
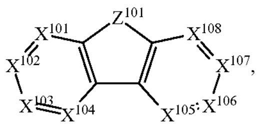, wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to the following general formula:

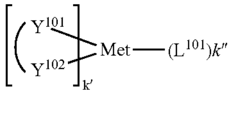

wherein Met is a metal, which can have an atomic weight greater than 40; ($Y^{101}$-$Y^{102}$) is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, ($Y^{101}$-$Y^{102}$) is a 2-phenylpyridine derivative. In another aspect, ($Y^{101}$-$Y^{102}$) is a carbene ligand. In another aspect, Met is selected from Ir, Pt, Os, and Zn. In a further aspect, the metal complex has a smallest oxidation potential in solution vs. Fc*/Fc couple less than about 0.6 V.

Non-limiting examples of the HIL and HTL materials that may be used in an OLED in combination with materials disclosed herein are exemplified below together with references that disclose those materials: CN102702075, DE102012005215, EP01624500, EP01698613, EP01806334, EP01930964, EP01972613, EP01997799, EP02011790, EP02055700, EP02055701, EP1725079, EP2085382, EP2660300, EP650955, JP07-073529, JP2005112765, JP2007091719, JP2008021687, JP2014-009196, KR20110088898, KR20130077473, TW201139402, U.S. Ser. No. 06/517,957, US20020158242, US20030162053, US20050123751, US20060182993, US20060240279, US20070145888, US20070181874, US20070278938, US20080014464, US20080091025, US20080106190, US20080124572, US20080145707, US20080220265, US20080233434, US20080303417, US2008107919, US20090115320, US20090167161, US2009066235, US2011007385, US20110163302, US2011240968, US2011278551, US2012205642, US2013241401, US20140117329, US2014183517, U.S. Pat. Nos. 5,061,569, 5,639,914, WO05075451, WO07125714, WO08023550, WO08023759, WO2009145016, WO2010061824, WO2011075644, WO2012177006, WO2013018530, WO2013039073, WO2013087142, WO2013118812, WO2013120577, WO2013157367, WO2013175747, WO2014002873, WO2014015935, WO2014015937, WO2014030872, WO2014030921, WO2014034791, WO2014104514, WO2014157018.

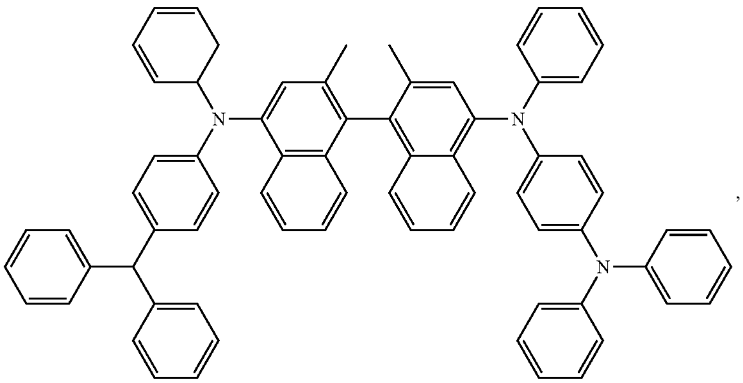
,
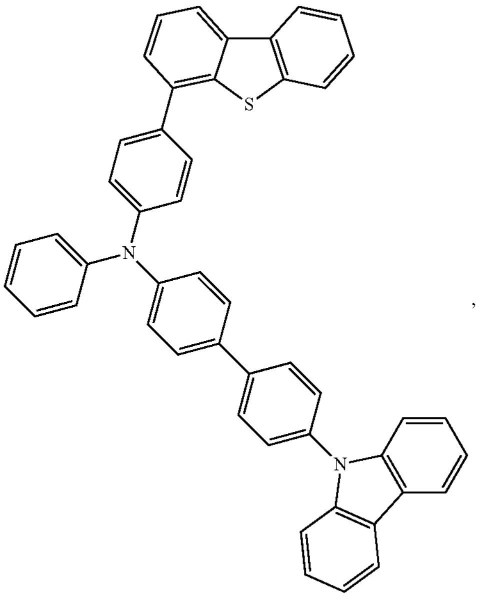
,
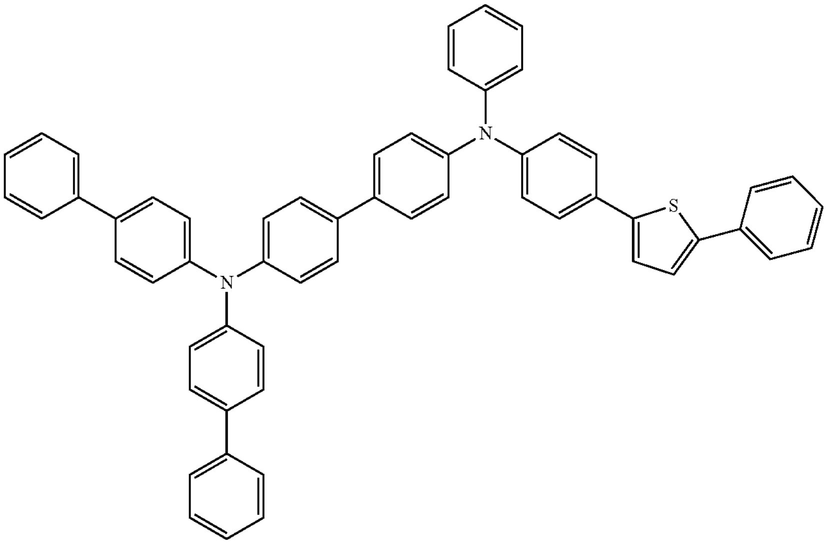
,

-continued
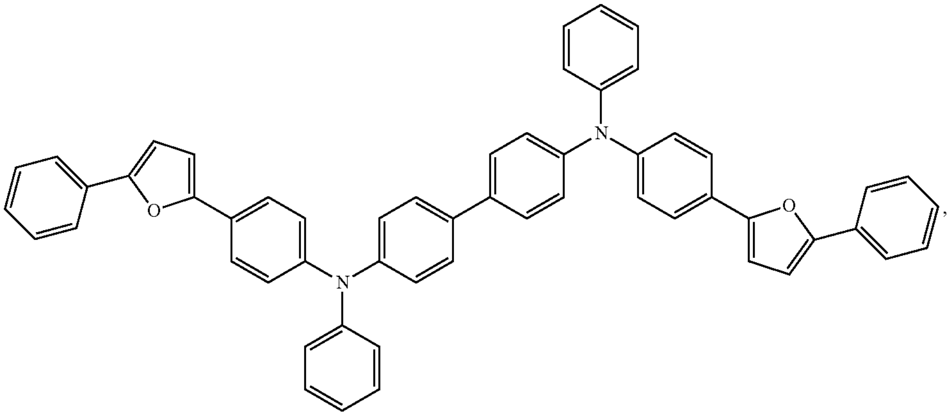,
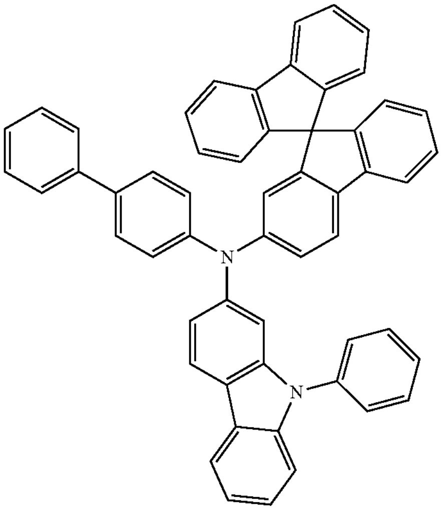,
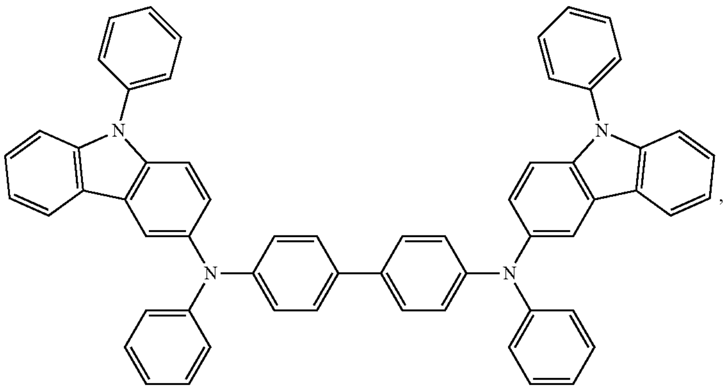,
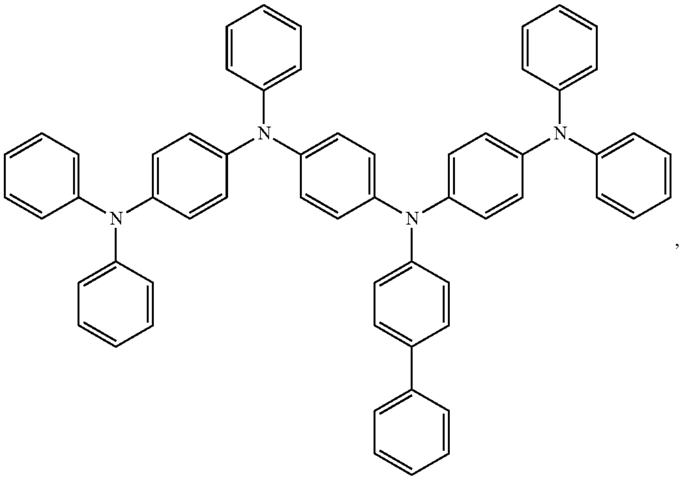,

-continued
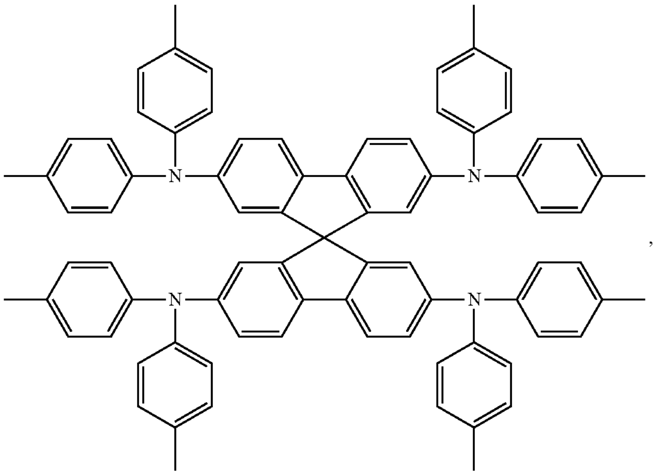
,
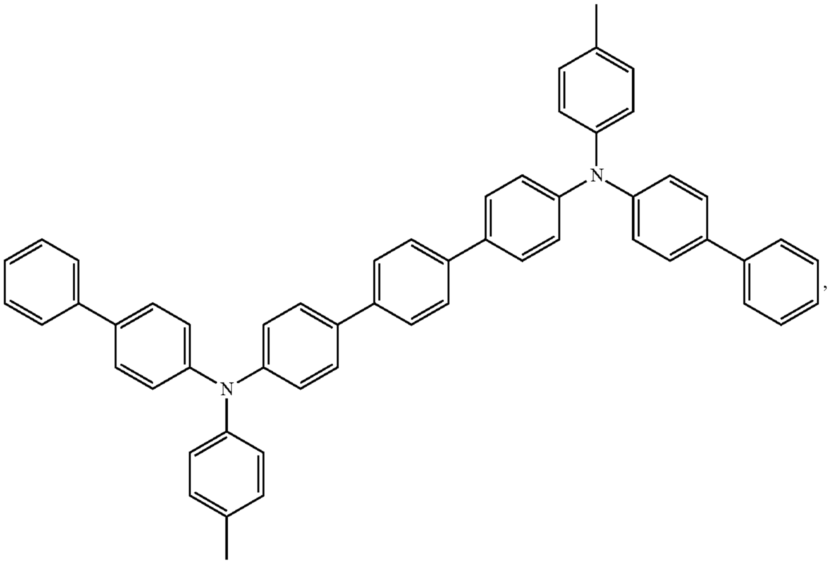
,

-continued
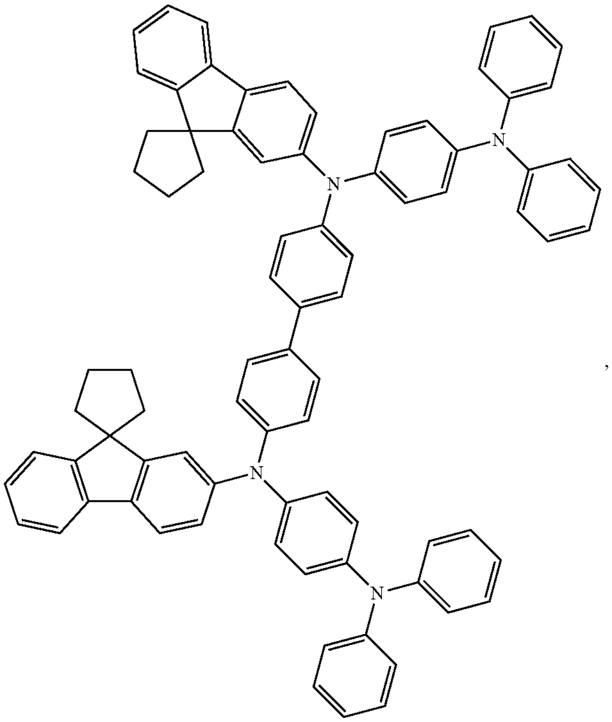
,
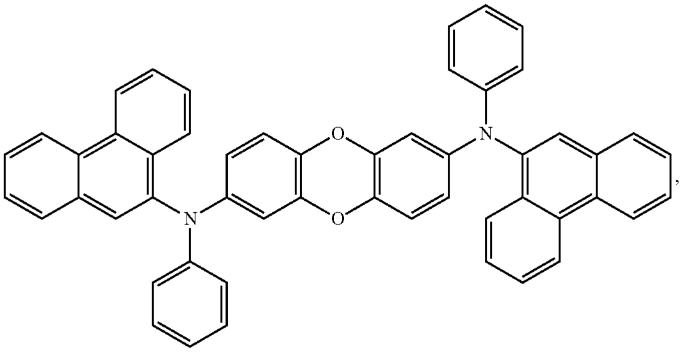
,
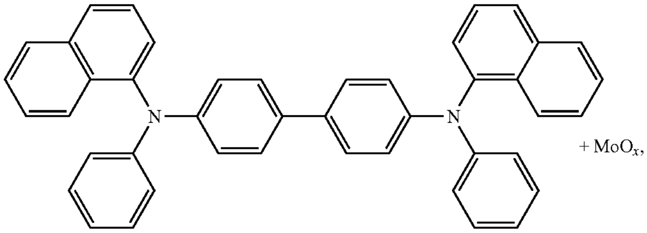
+ $MoO_x$,

-continued
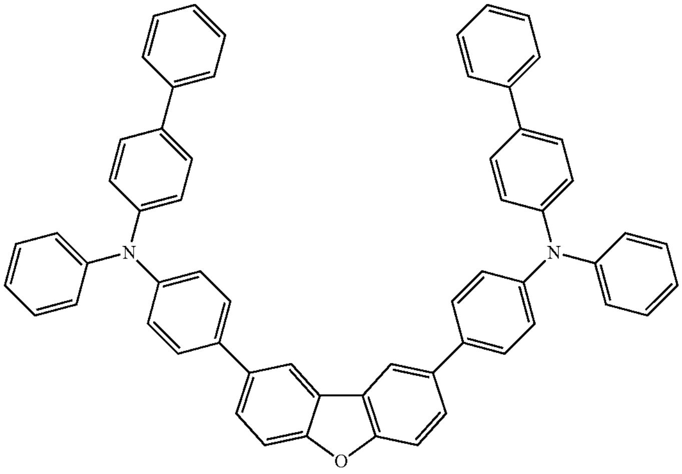
,
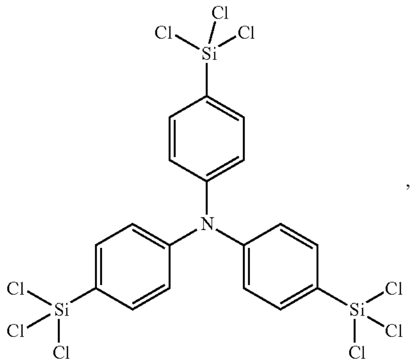
,
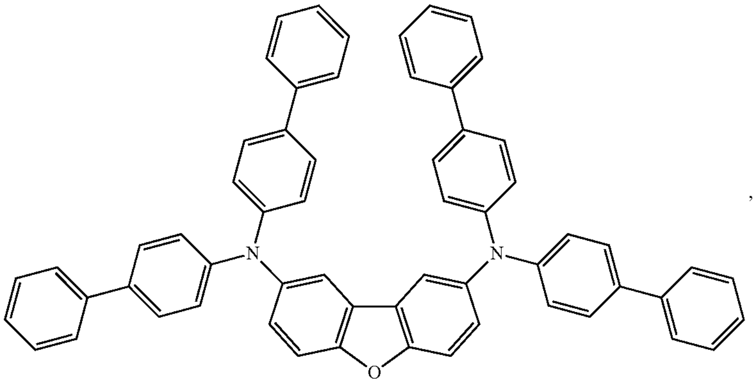
,
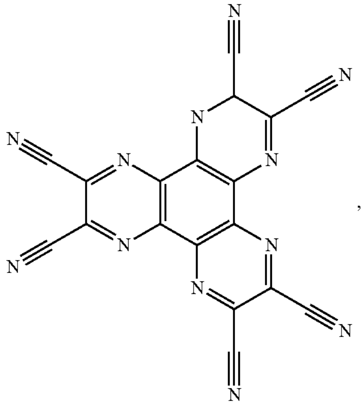
,
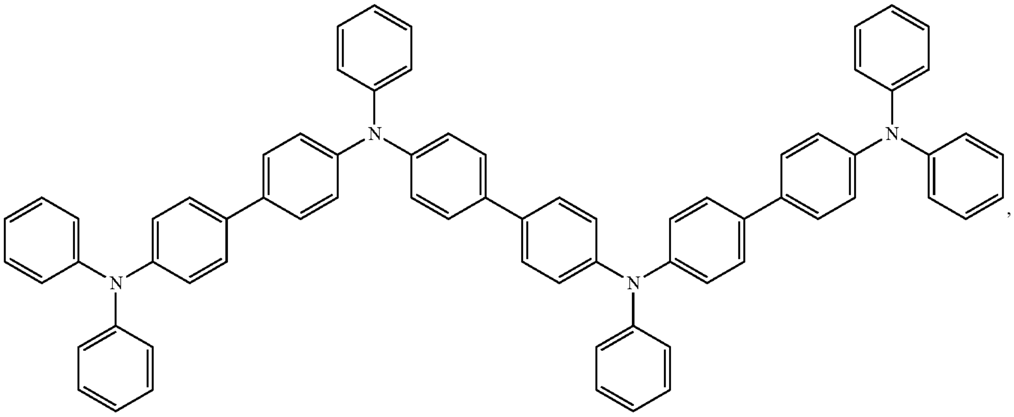
, -continued
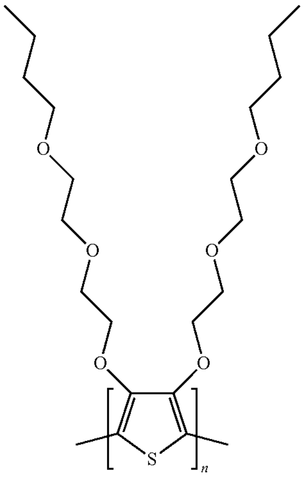
,
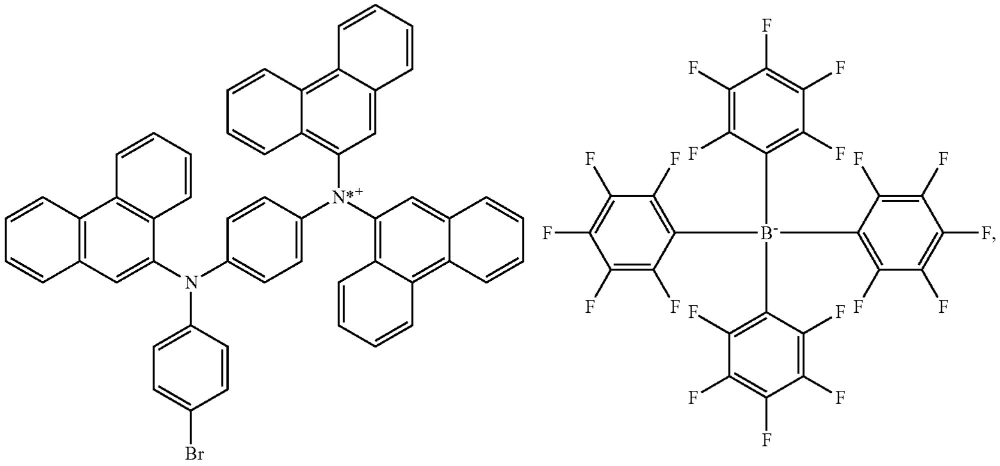
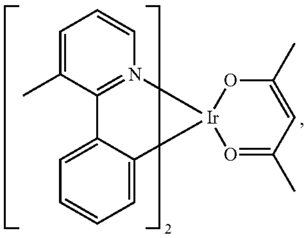
,
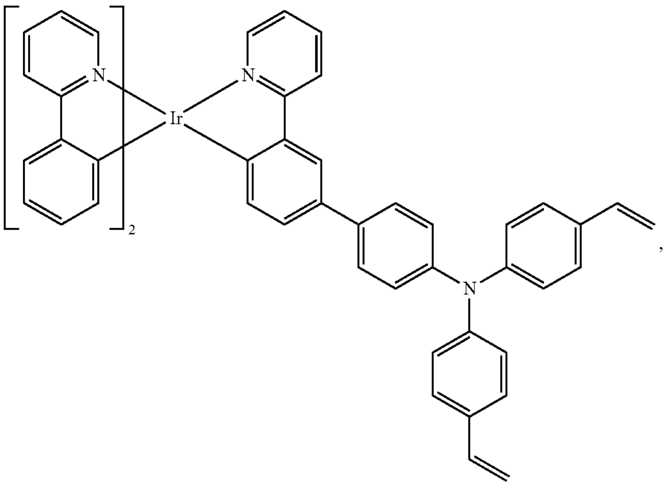
, -continued
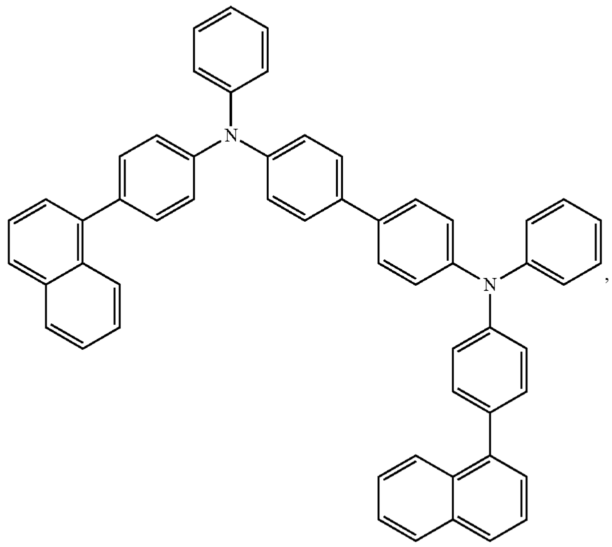
,
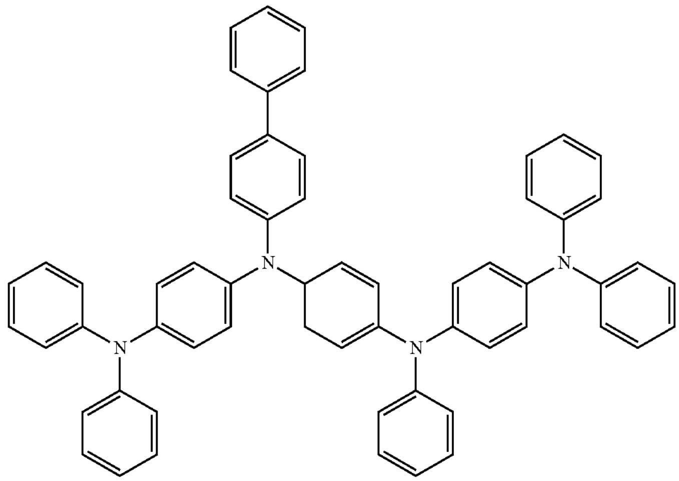
,
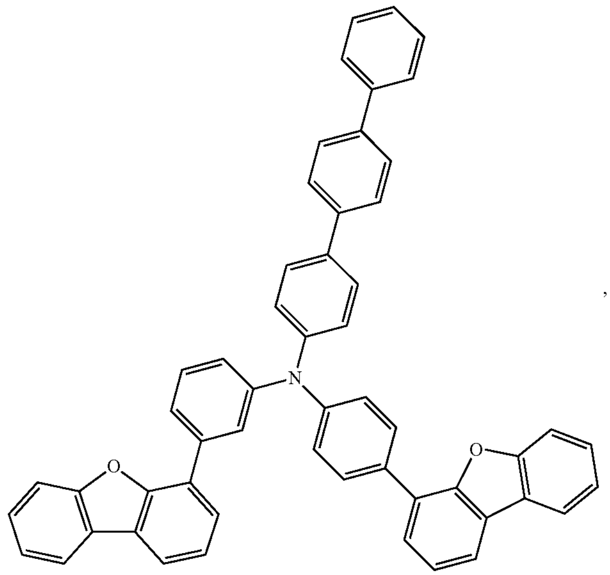
, -continued
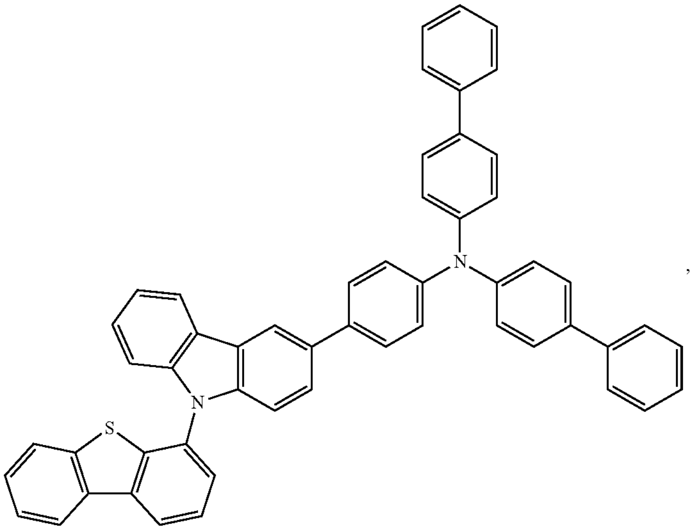
,
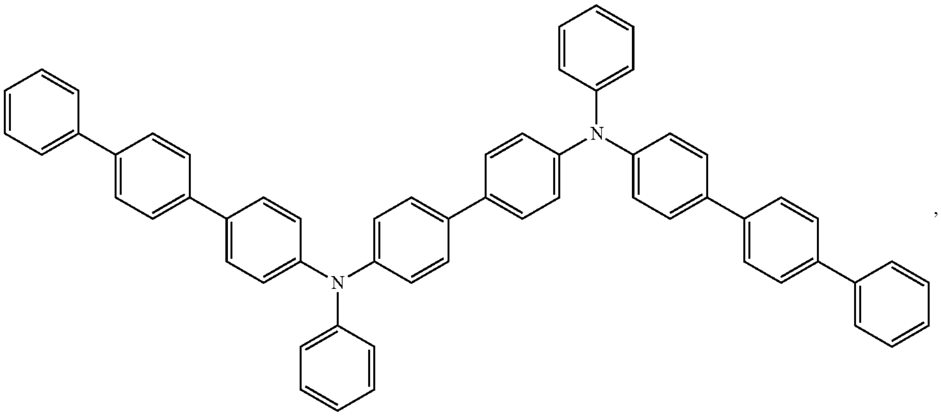
,
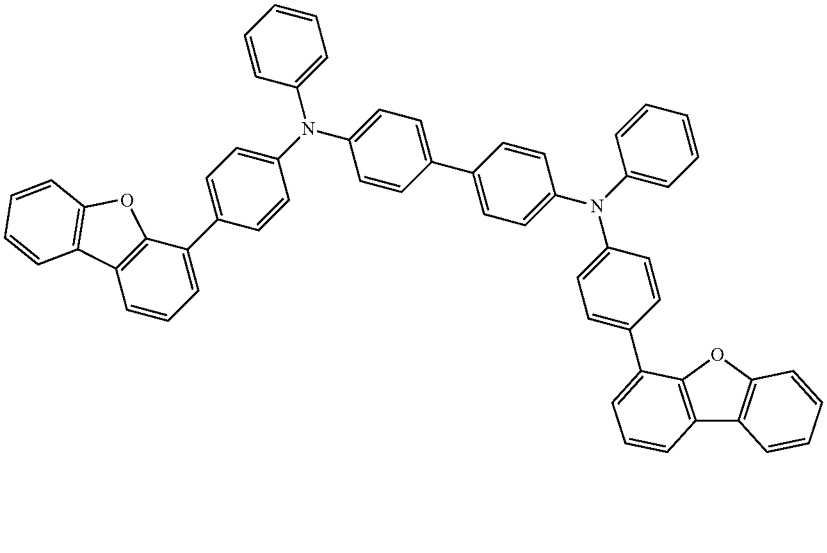
, -continued
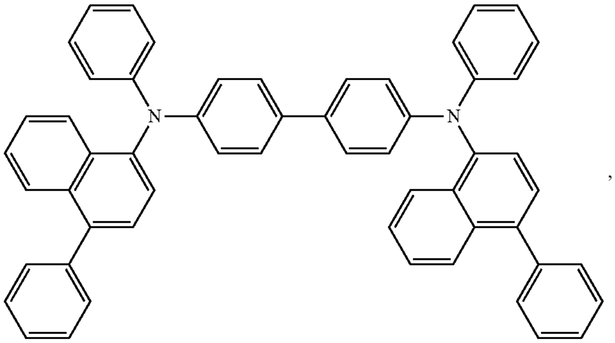
,
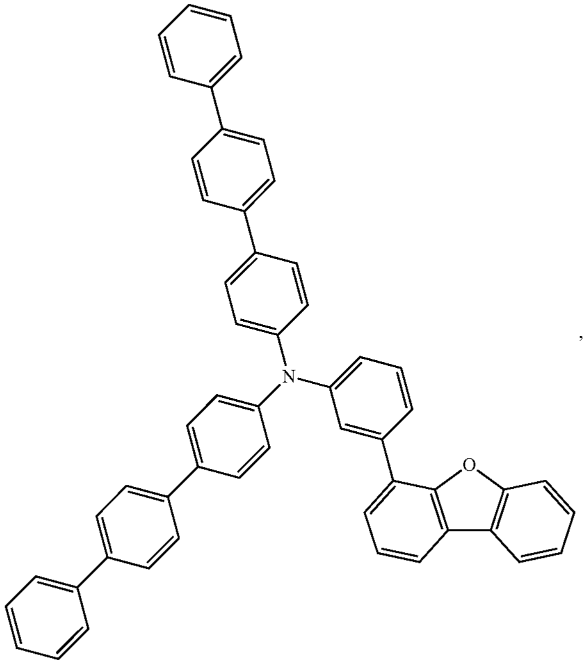
,
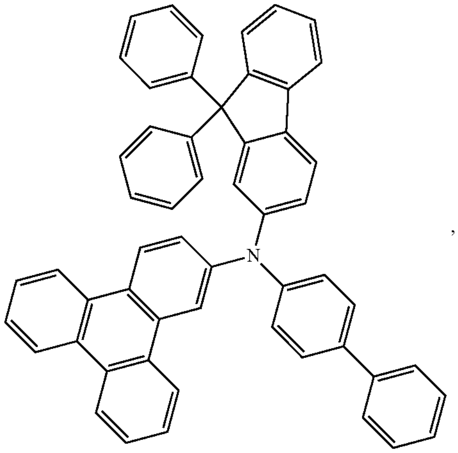
,
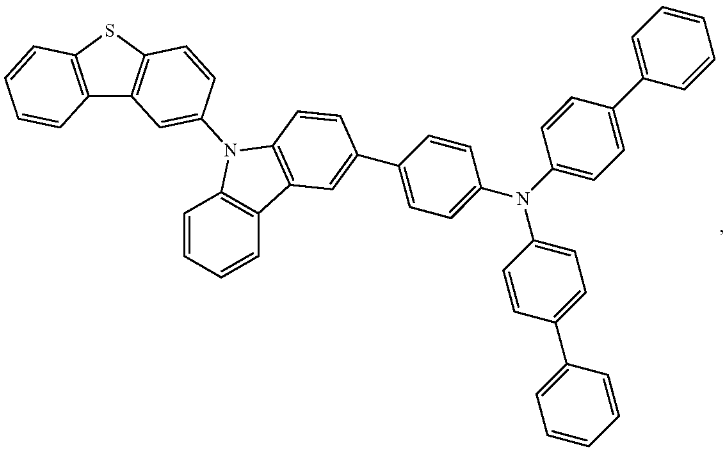
, -continued
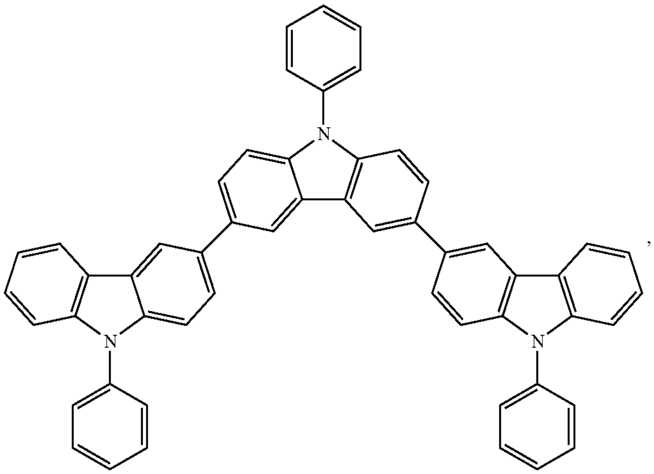
,
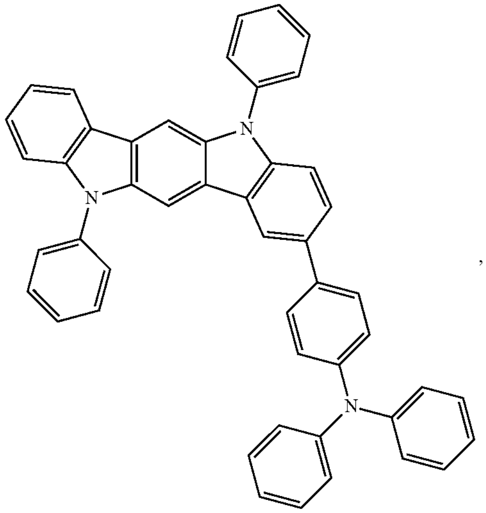
,
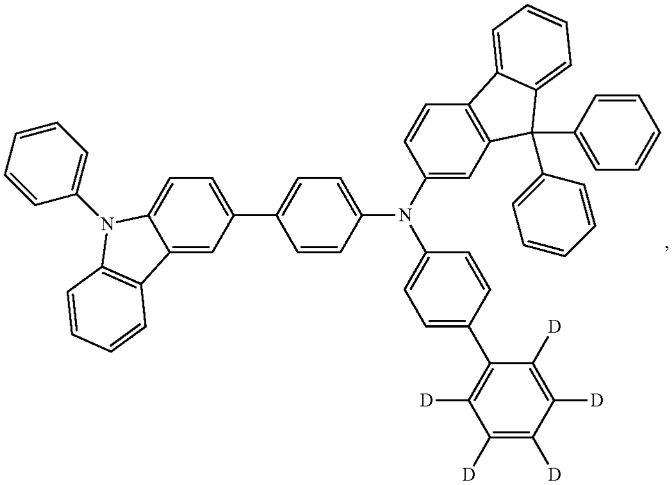
,
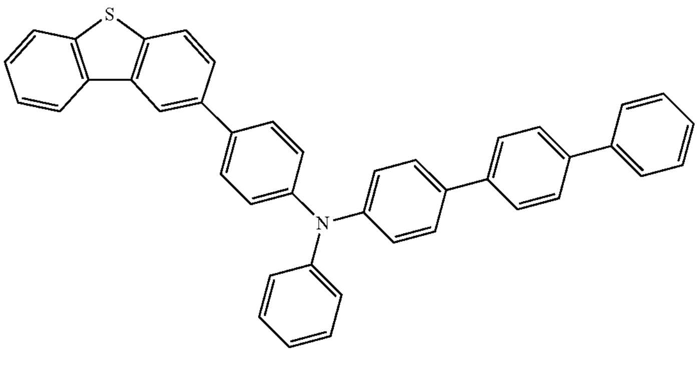
, -continued
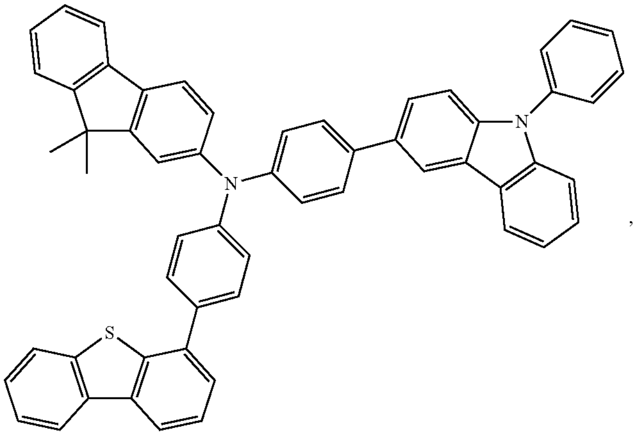
,
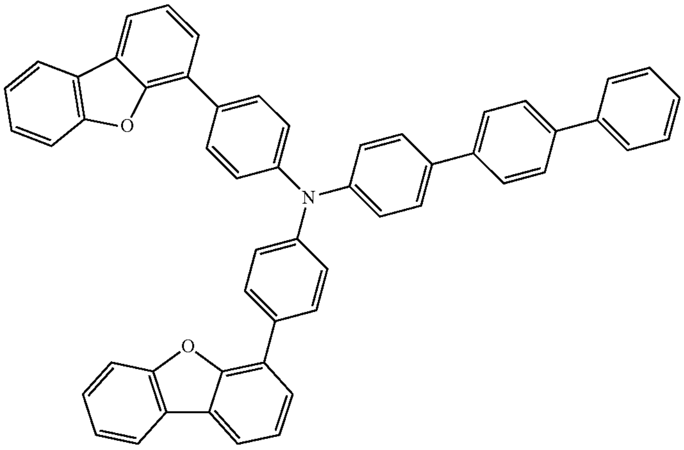
,
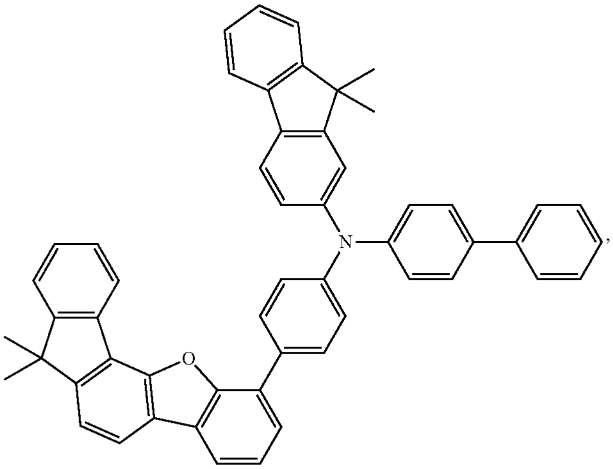
,
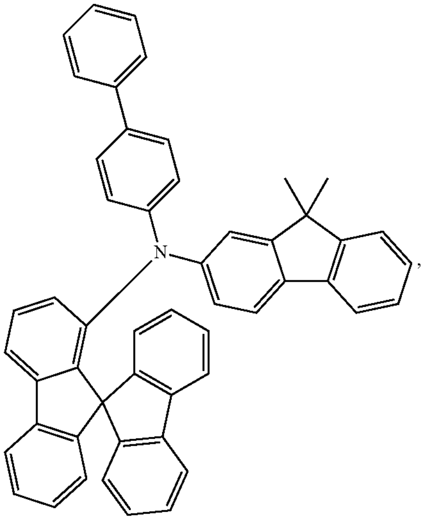
, -continued
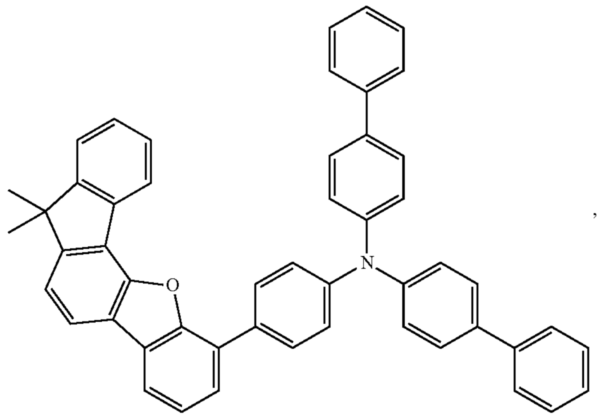
,
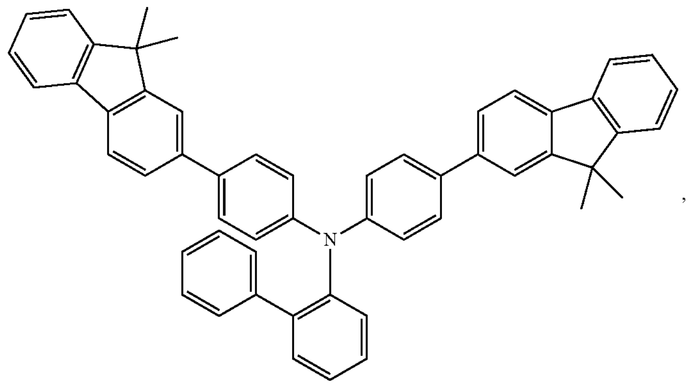
,
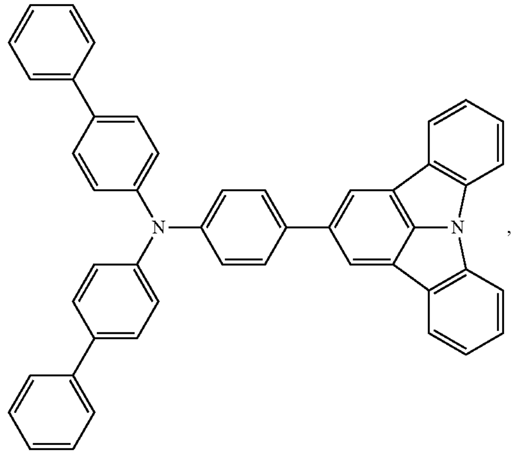
, -continued
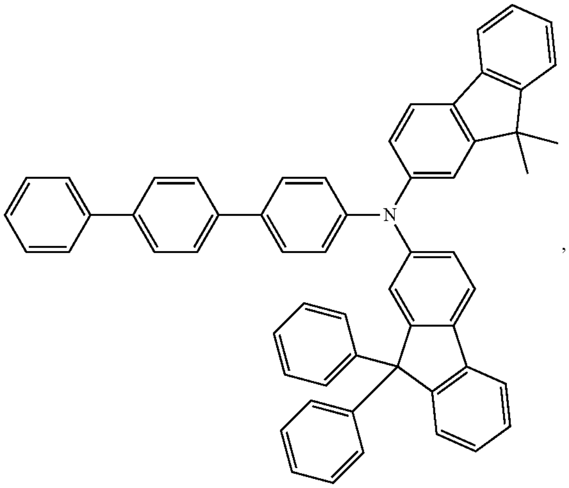
,
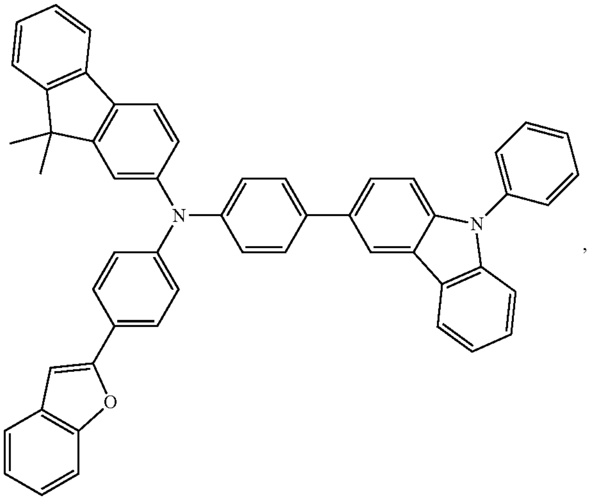
,
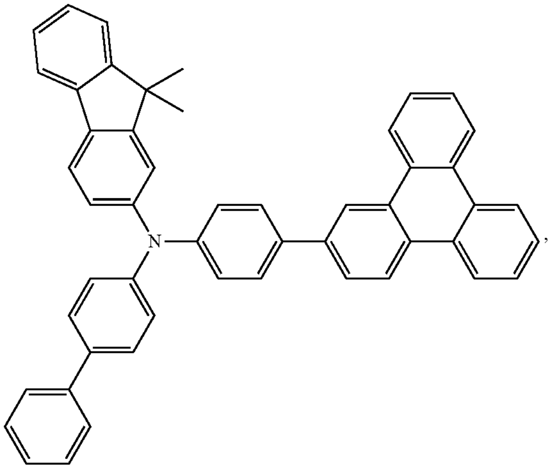
,
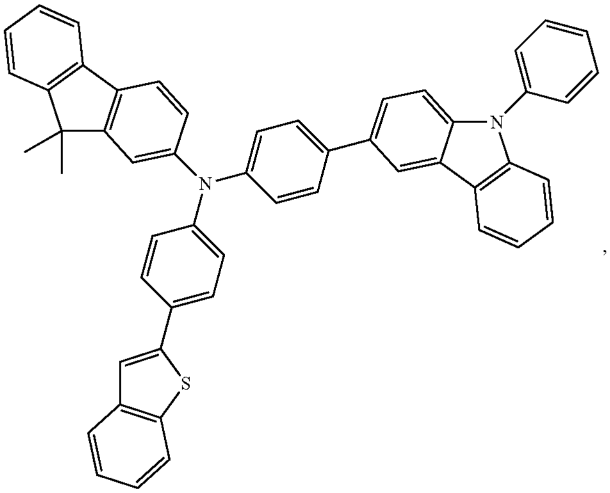
, -continued
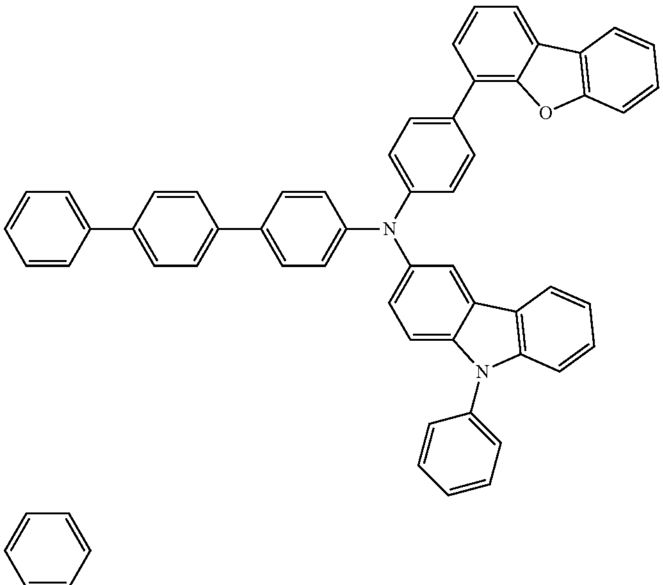
,
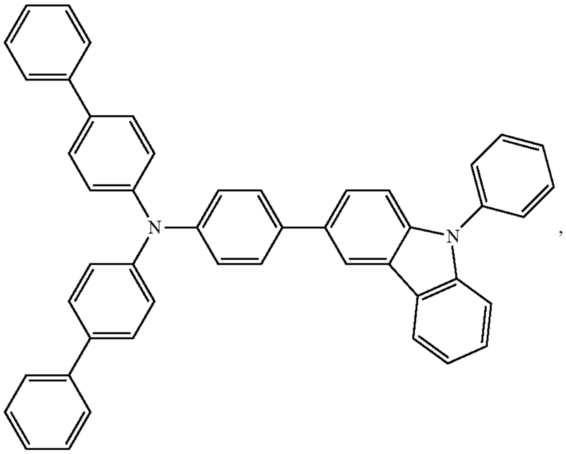
,
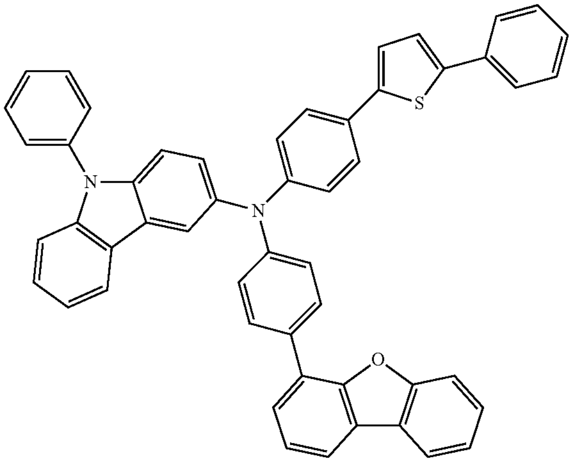
,
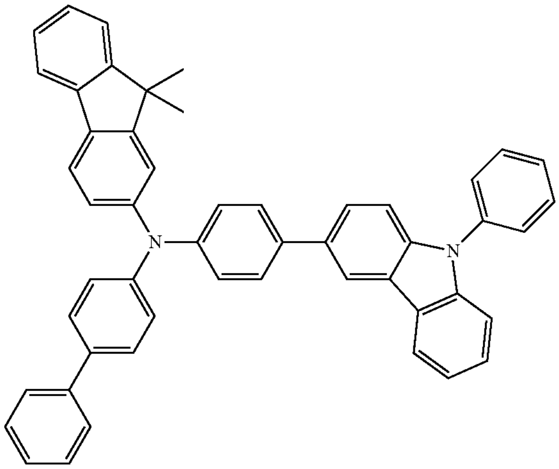
, -continued
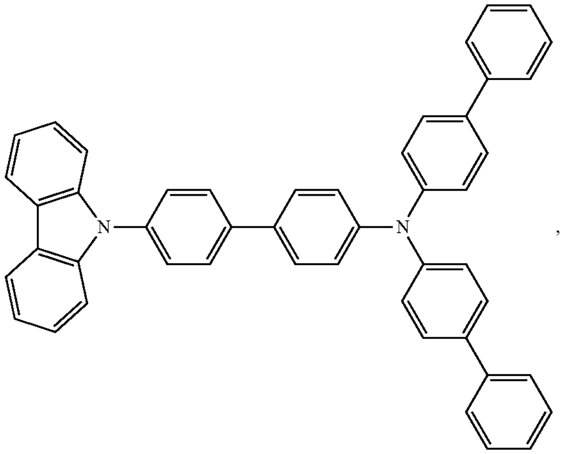
,
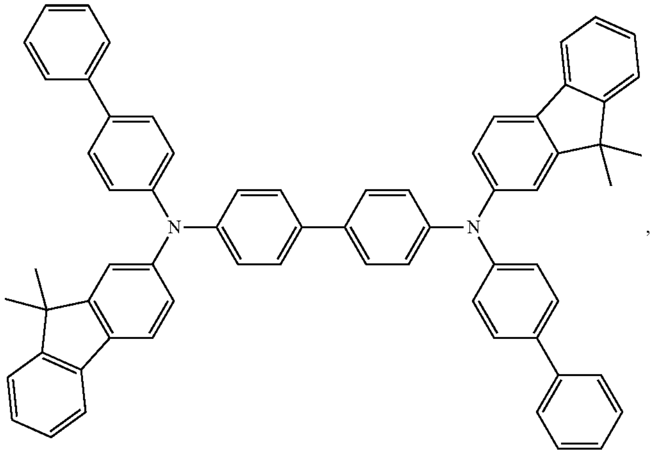
,
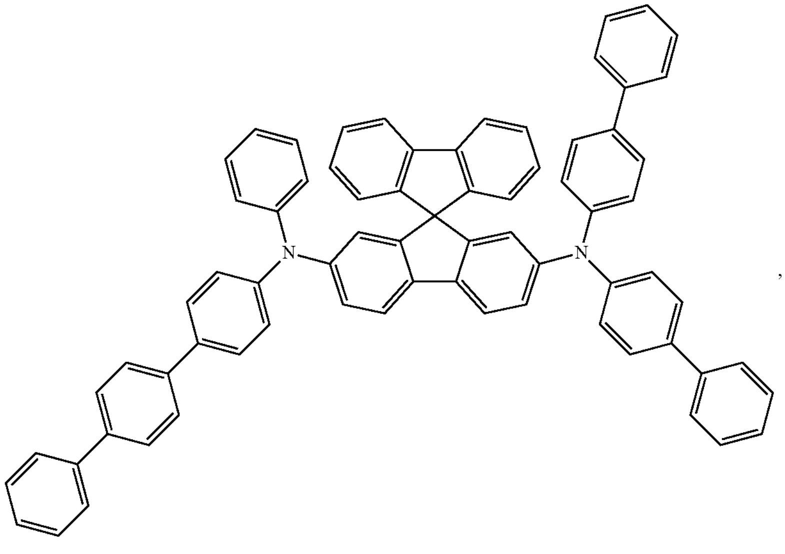
, -continued
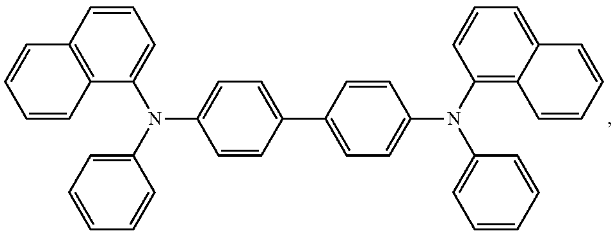
,
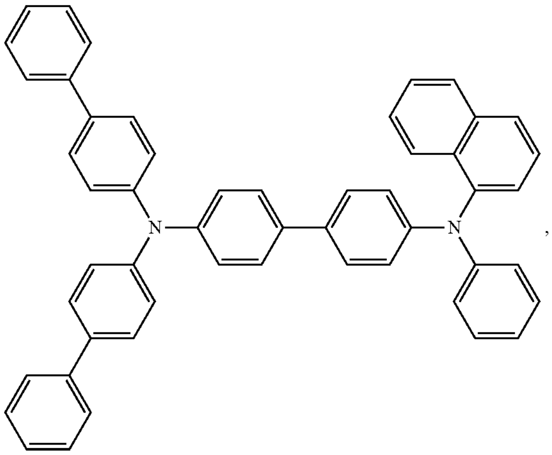
,
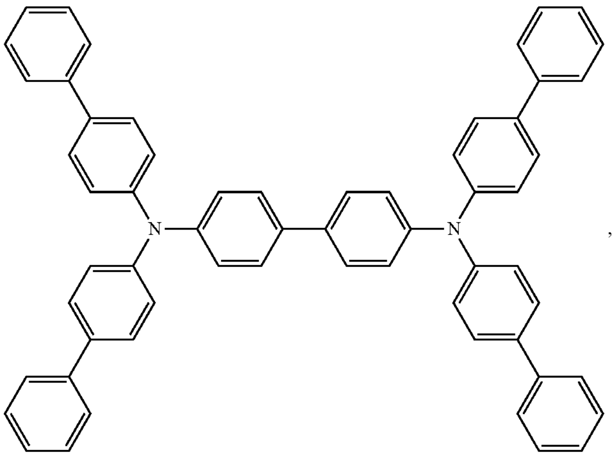
,
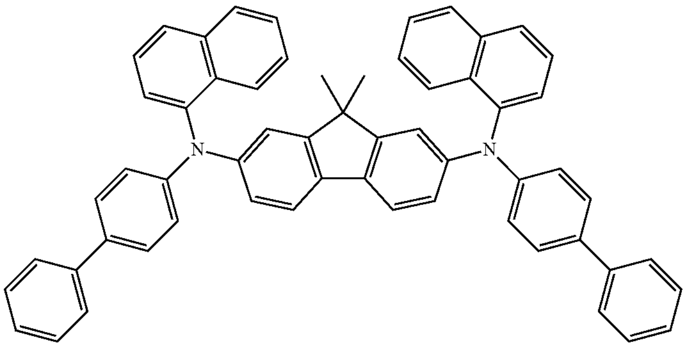
, -continued
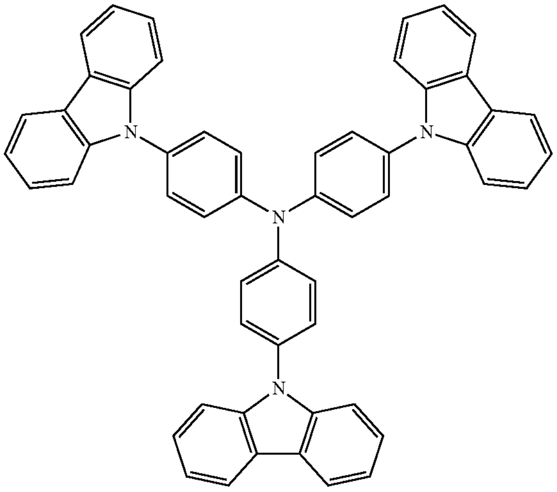
,
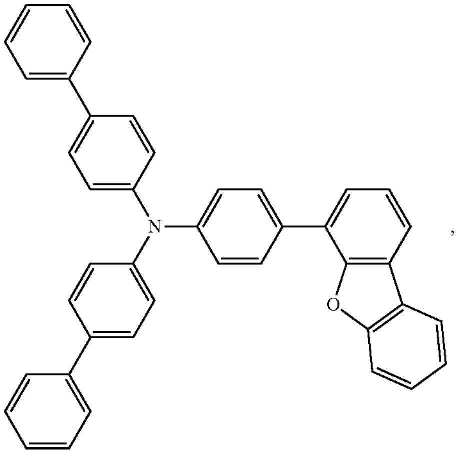
,
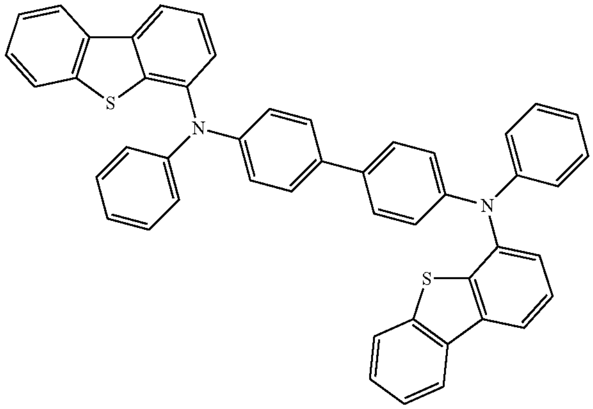
,
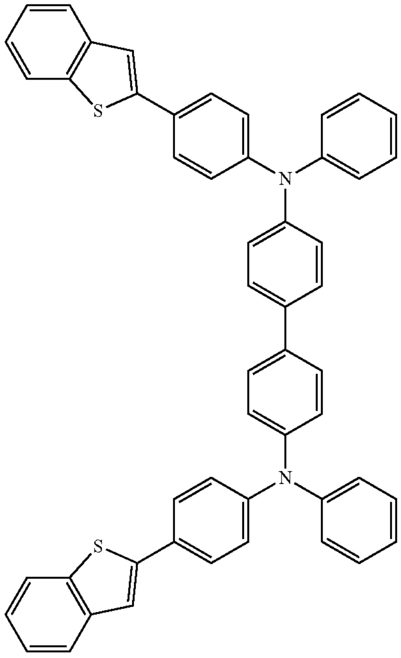
, and
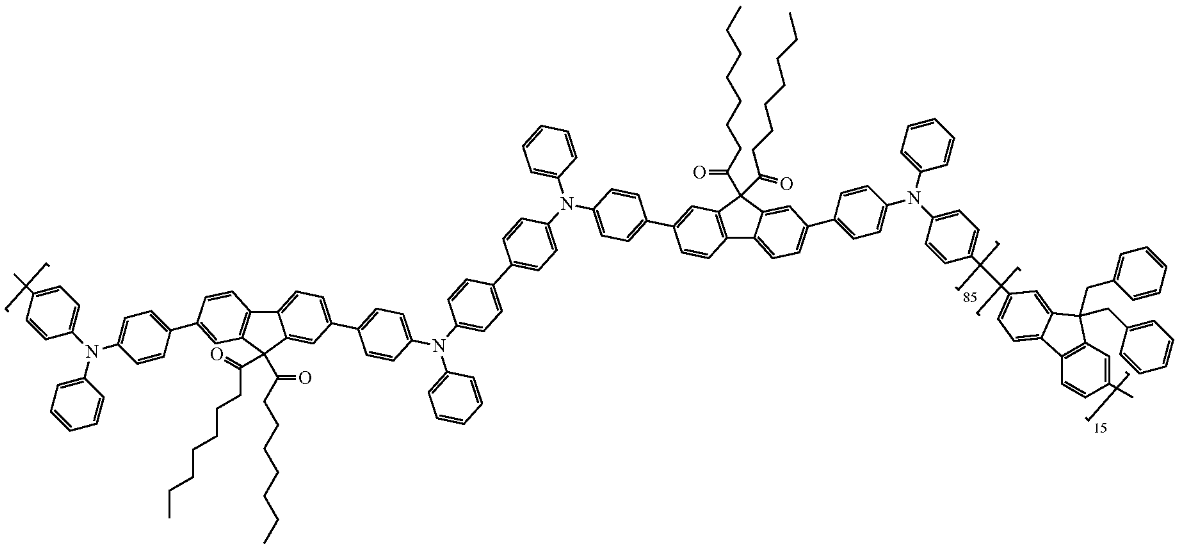
.

c) EBL:

An electron blocking layer (EBL) may be used to reduce the number of electrons and/or excitons that leave the emissive layer. The presence of such a blocking layer in a device may result in substantially higher efficiencies, and/or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and/or higher triplet energy than one or more of the hosts closest to the EBL interface. In one aspect, the compound used in EBL contains the same molecule or the same functional groups used as one of the hosts described below.

d) Additional Emitters:

One or more additional emitter dopants may be used in the OLED of the present disclosure. Examples of the additional emitter dopants are not particularly limited, and any compounds may be used as long as the compounds are typically used as emitter materials. Examples of suitable emitter materials include, but are not limited to, compounds which can produce emissions via phosphorescence, fluorescence, thermally activated delayed fluorescence, i.e., TADF (also referred to as E-type delayed fluorescence), triplet-triplet annihilation, or combinations of these processes.

Non-limiting examples of the emitter materials that may be used in an OLED in combination with materials disclosed herein are exemplified below together with references that disclose those materials: CN103694277, CN1696137, EB01238981, EP01239526, EP01961743, EP1239526, EP1244155, EP1642951, EP1647554, EP1841834, EP1841834B, EP2062907, EP2730583, JP2012074444, JP2013110263, JP4478555, KR1020090133652, KR20120032054, KR20130043460, TW201332980, U.S. Ser. Nos. 06/699,599, 06/916,554, US20010019782, US20020034656, US20030068526, US20030072964, US20030138657, US20050123788, US20050244673, US2005123791, US2005260449, US20060008670, US20060065890, US20060127696, US20060134459, US20060134462, US20060202194, US20060251923, US20070034863, US20070087321, US20070103060, US20070111026, US20070190359, US20070231600, US2007034863, US2007104979, US2007104980, US2007138437, US2007224450, US2007278936, US20080020237, US20080233410, US20080261076, US20080297033, US200805851, US2008161567, US2008210930, US20090039776, US20090108737, US20090115322, US20090179555, US2009085476, US2009104472, US20100090591, US20100148663, US20100244004, US20100295032, US2010102716, US2010105902, US2010244004, US2010270916, US20110057559, US20110108822, US20110204333, US2011215710, US2011227049, US2011285275, US2012292601, US20130146848, US2013033172, US2013165653, US2013181190, US2013334521, US20140246656, US2014103305, U.S. Pat. Nos. 6,303,238, 6,413,656, 6,653,654, 6,670,645, 6,687,266, 6,835,469, 6,921,915, 7,279,704, 7,332,232, 7,378,162, 7,534,505, 7,675,228, 7,728,137, 7,740,957, 7,759,489, 7,951,947, 8,067,099, 8,592,586, 8,871,361, WO06081973, WO06121811, WO07018067, WO07108362, WO07115970, WO07115981, WO08035571, WO2002015645, WO2003040257, WO2005019373, WO2006056418, WO2008054584, WO2008078800, WO2008096609, WO2008101842, WO2009000673, WO2009050281, WO2009100991, WO2010028151, WO2010054731, WO2010086089, WO2010118029, WO2011044988, WO2011051404, WO2011107491, WO2012020327, WO2012163471, WO2013094620, WO2013107487, WO2013174471, WO2014007565, WO2014008982, WO2014023377, WO2014024131, WO2014031977, WO2014038456, WO2014112450.

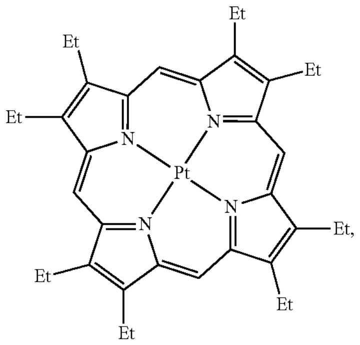

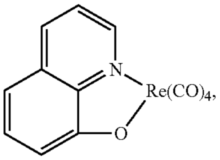,

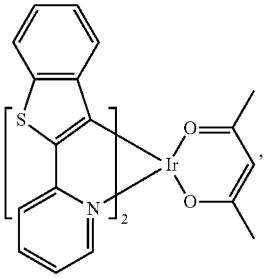,

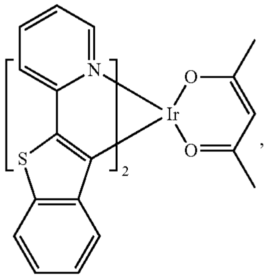,

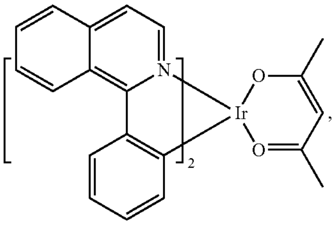,

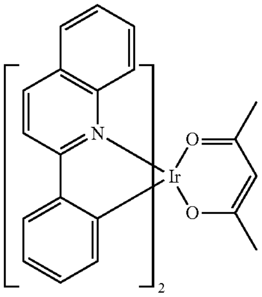,

-continued
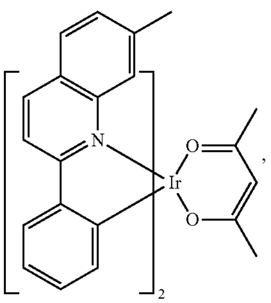
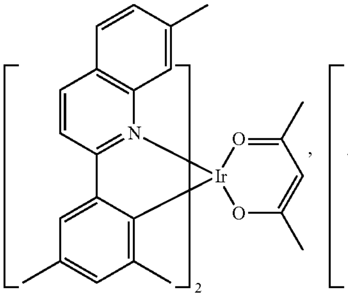
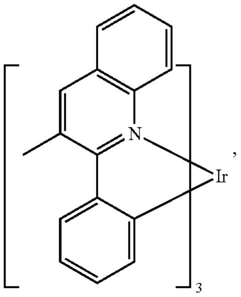
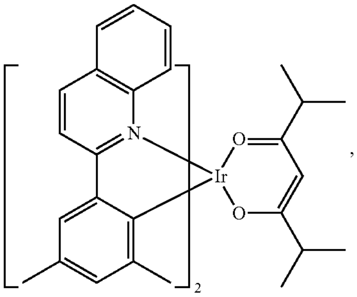
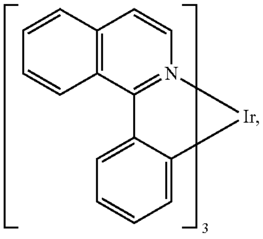
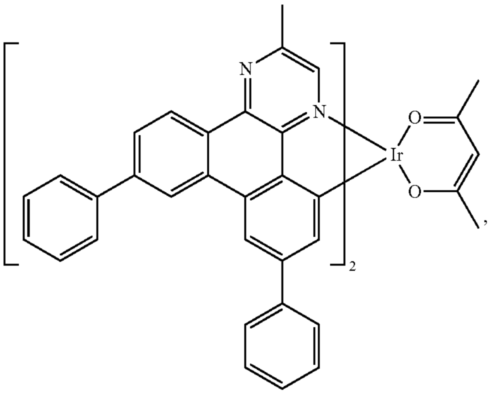
-continued
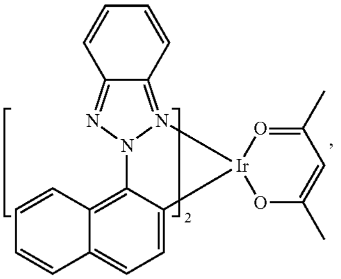
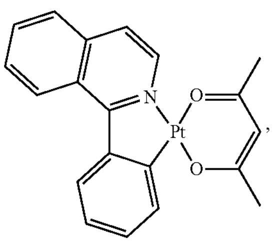
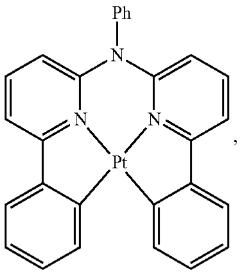
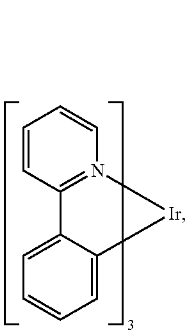
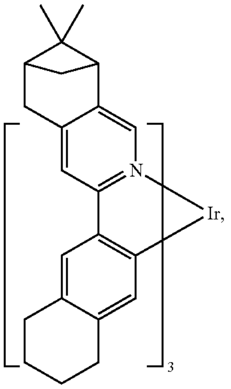
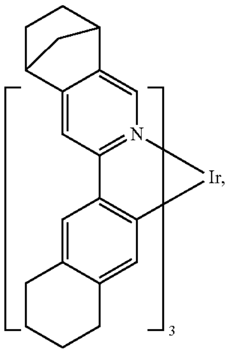
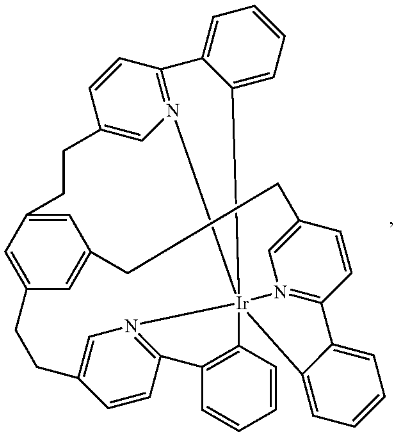

-continued
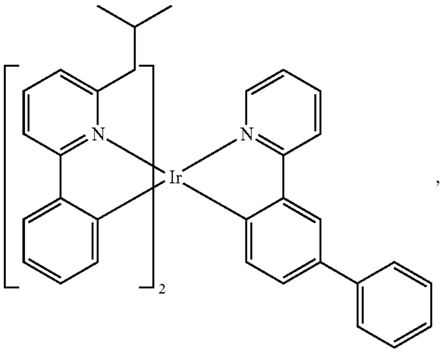
,
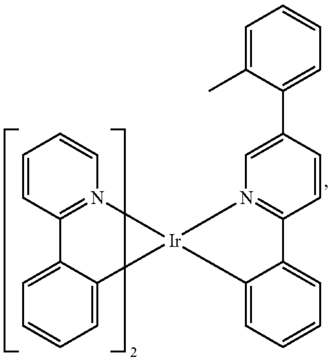
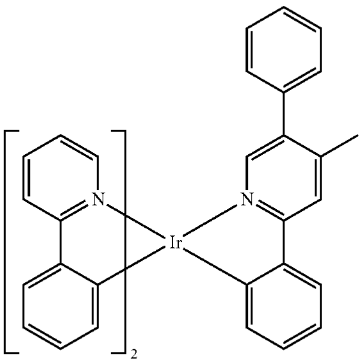
,
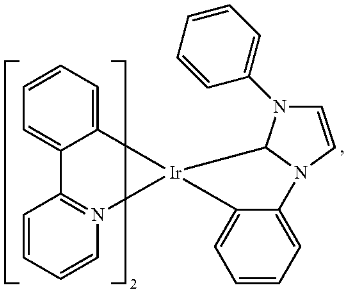
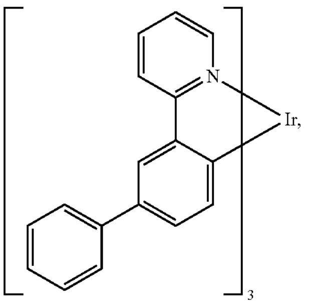
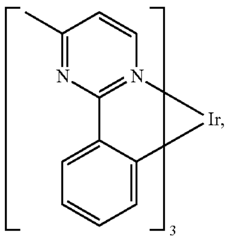
-continued
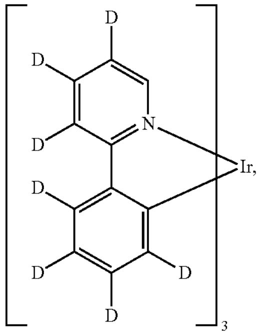
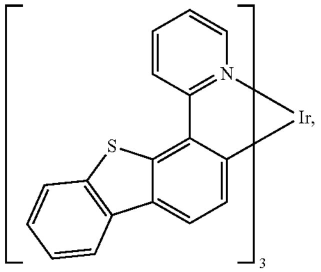
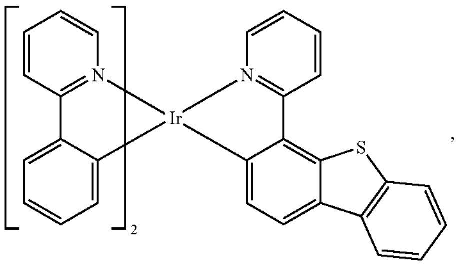
,
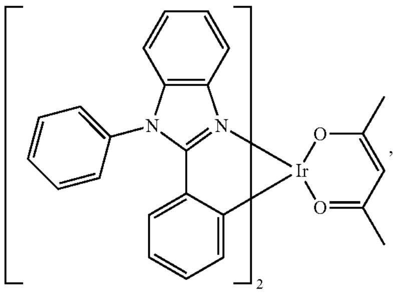
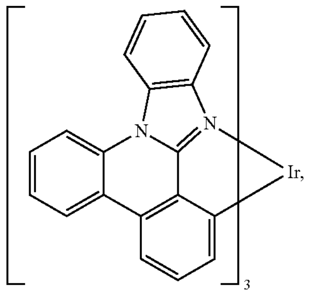

-continued
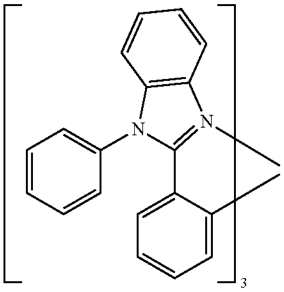
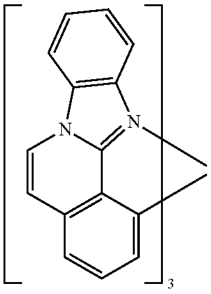
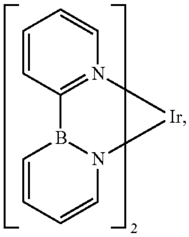
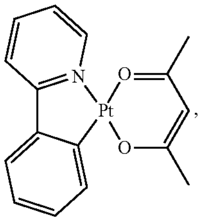
,
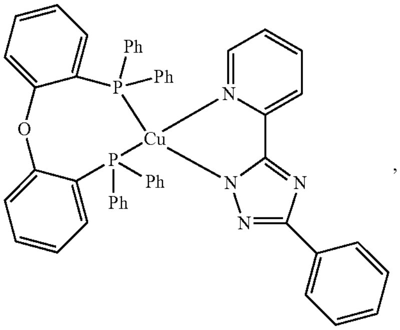
,
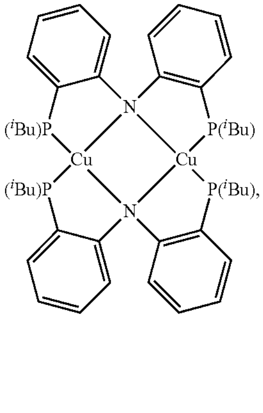
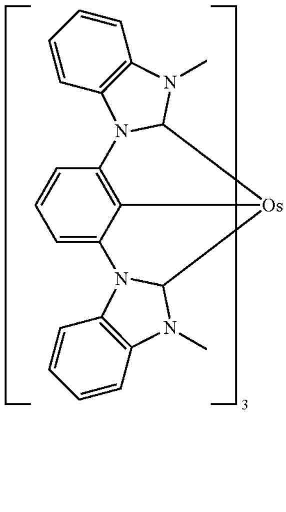
,
-continued
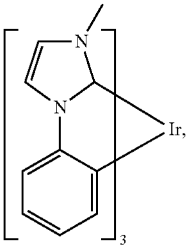
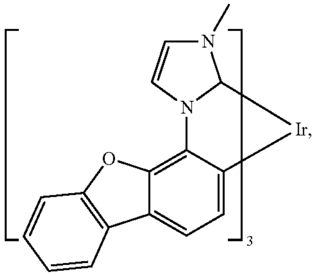
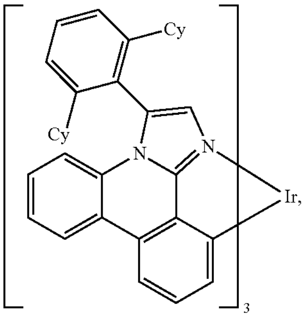
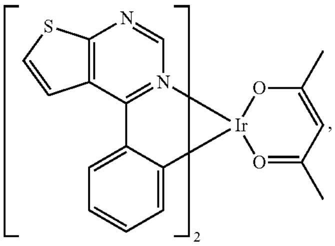
,
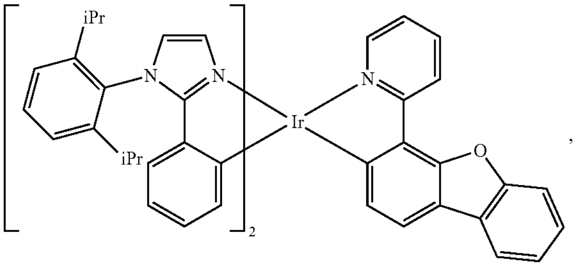
,
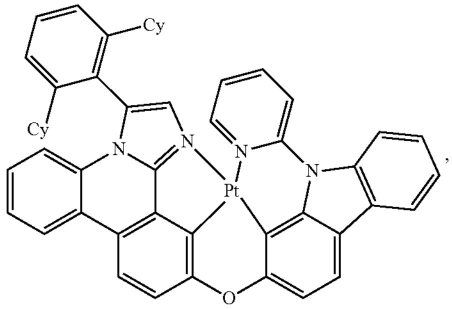
, -continued
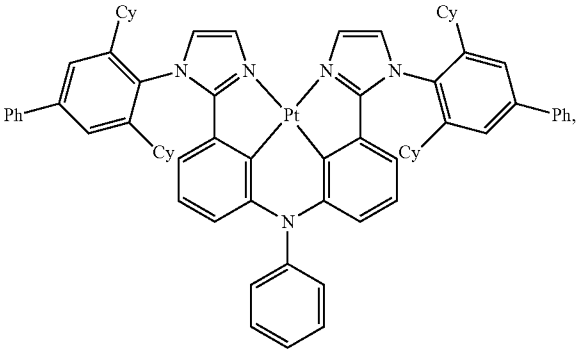
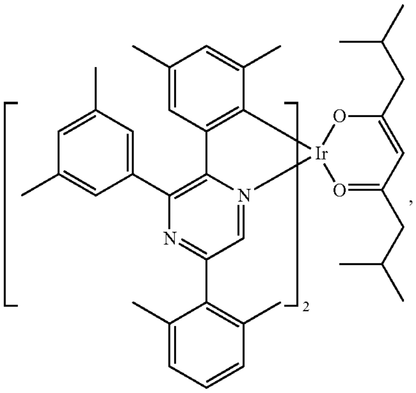
,
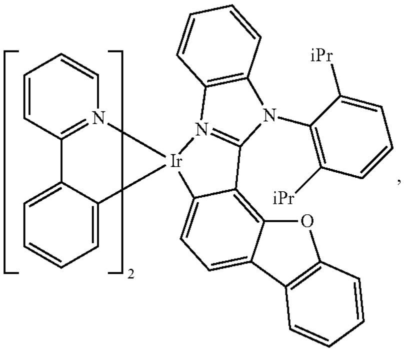
,
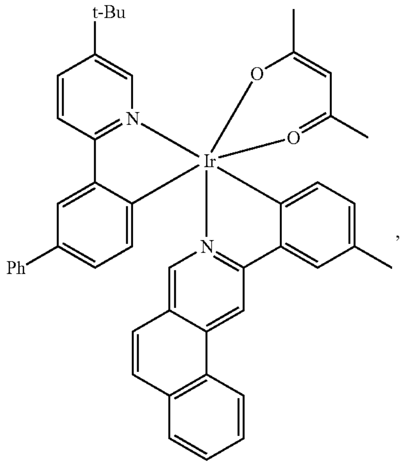
,
-continued
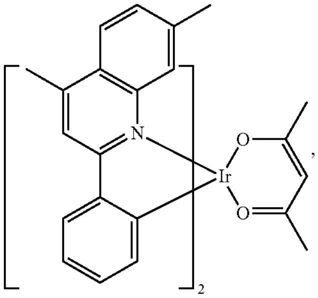
,
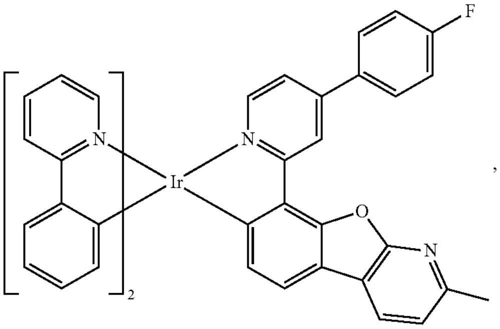
,
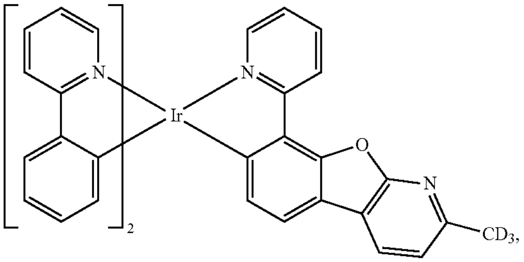
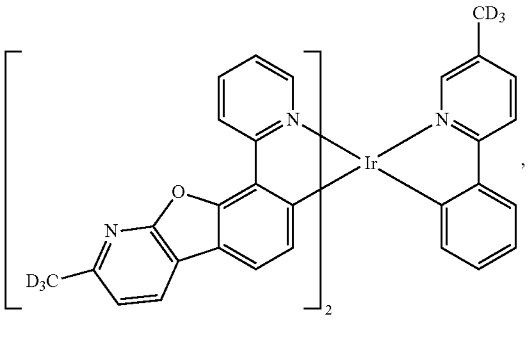
,
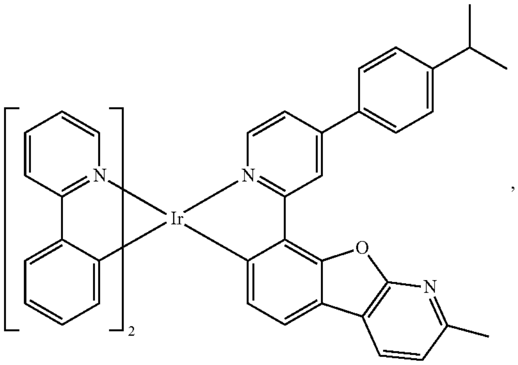
, -continued
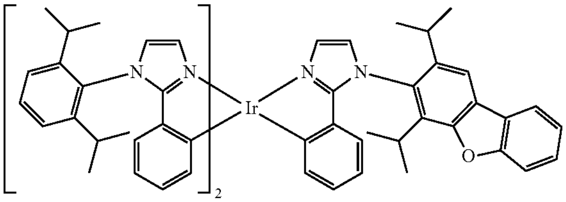
,
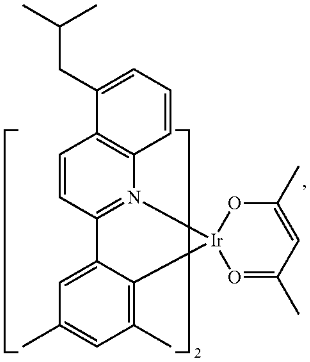
,
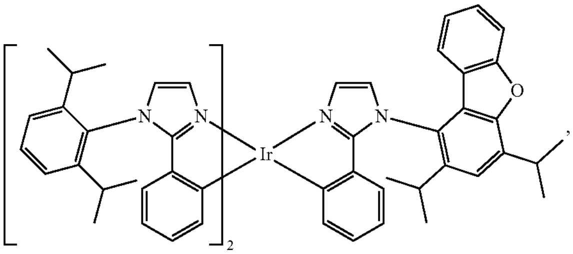
,
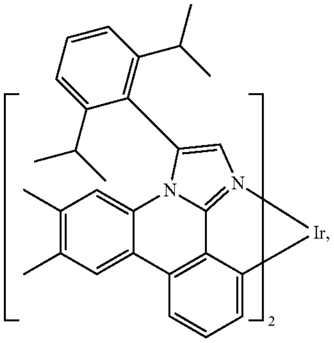
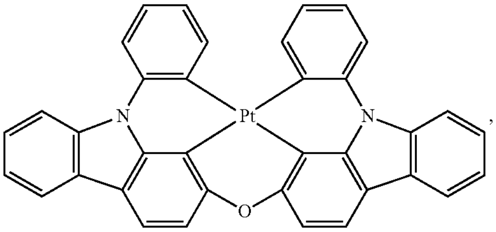
,
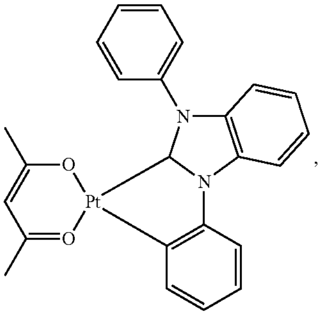
,
-continued
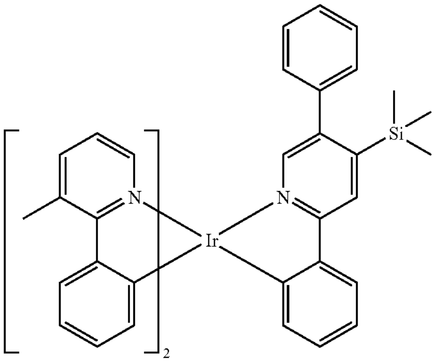
,
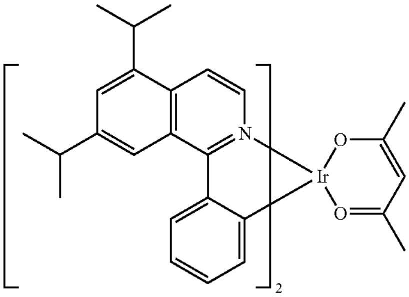
,
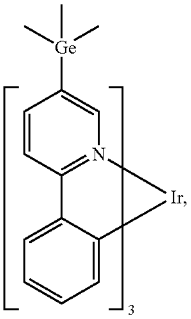
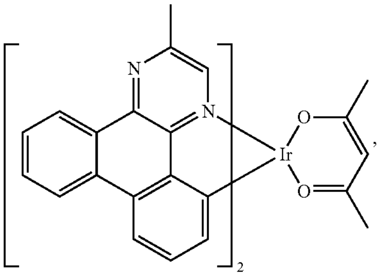
,
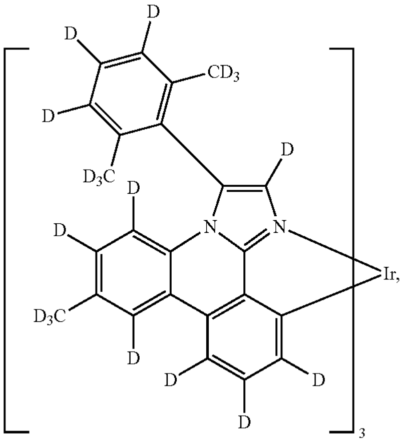

-continued
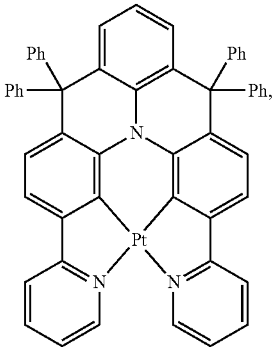
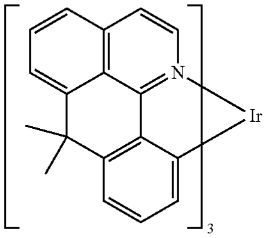
,
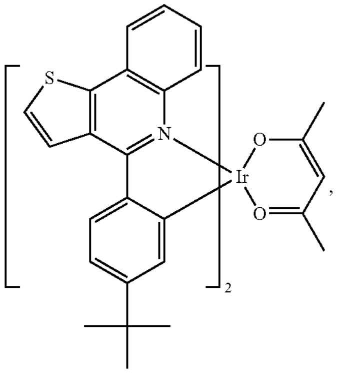
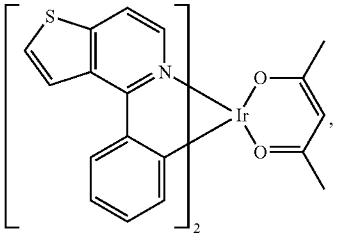
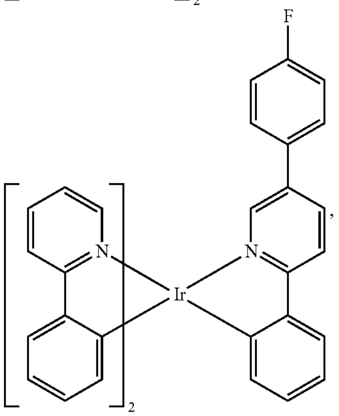
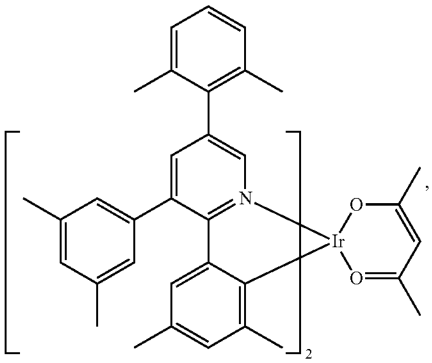
-continued
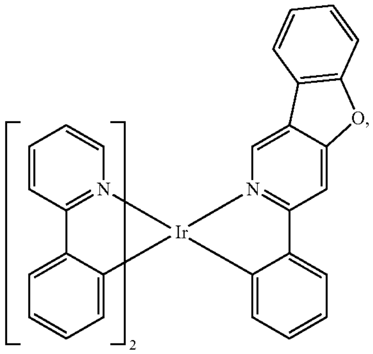
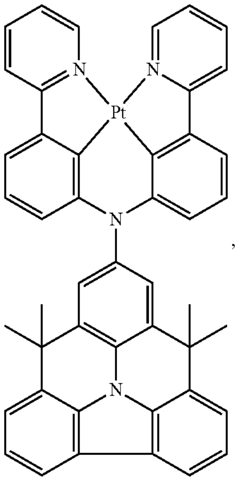
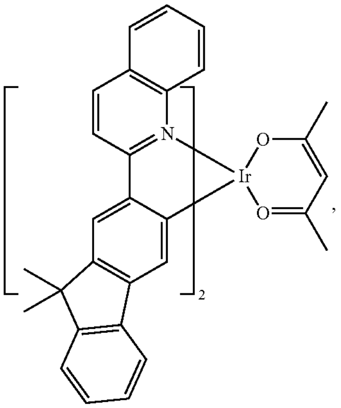
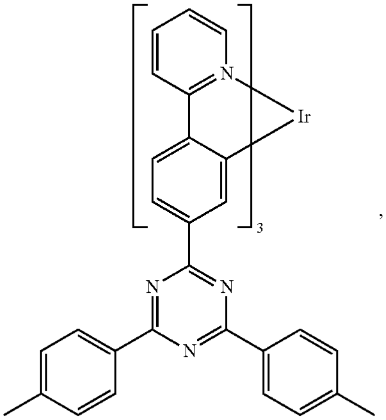

-continued
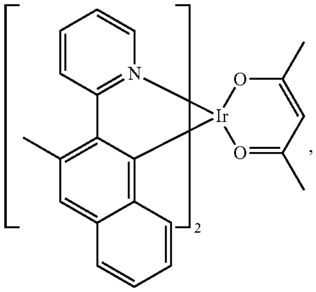
,
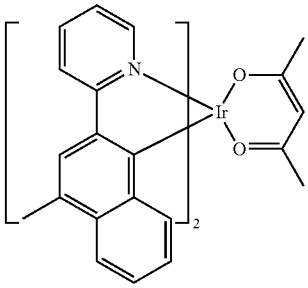
,
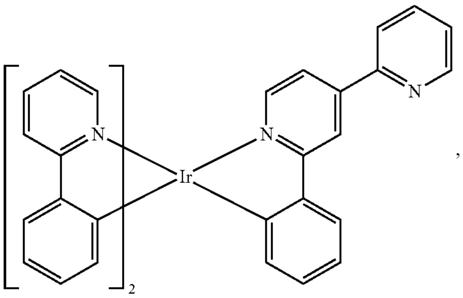
,
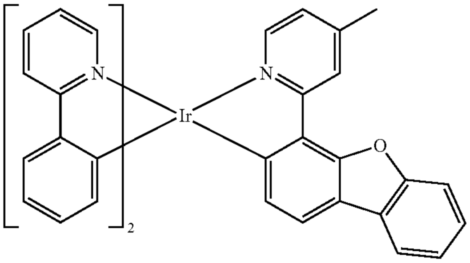
,
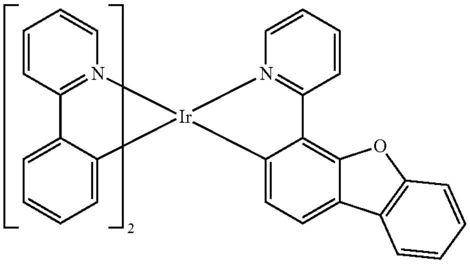
,
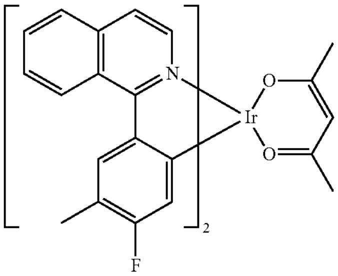
,
-continued
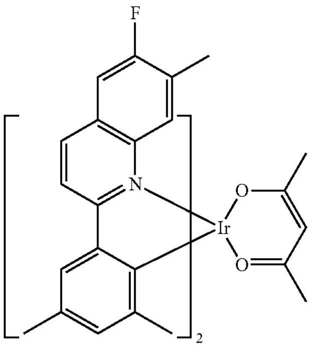
,
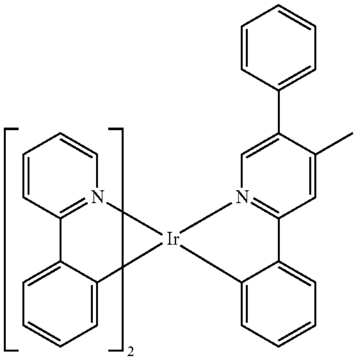
,
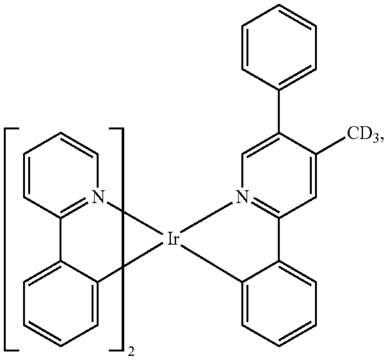
,
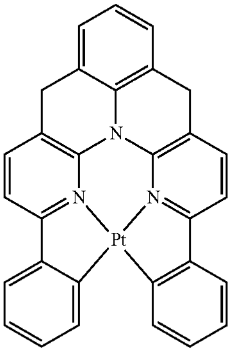
, -continued
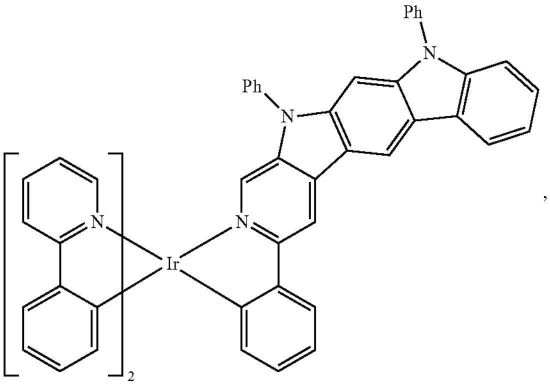
,
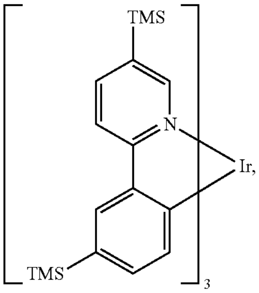
,
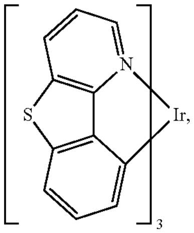
,
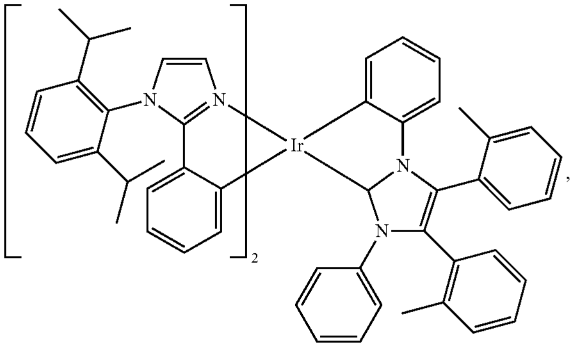
,
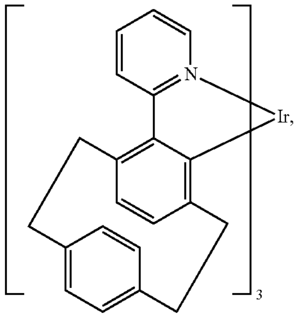
,
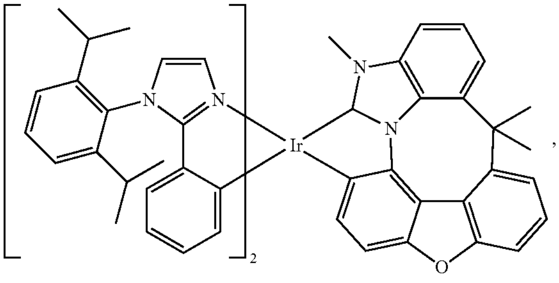
,
-continued
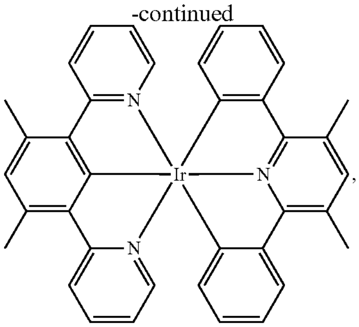
,
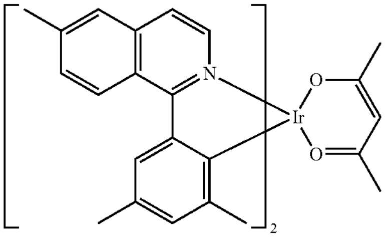
,
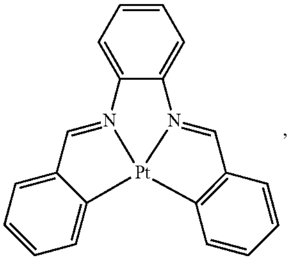
,
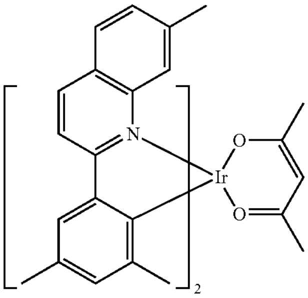
,
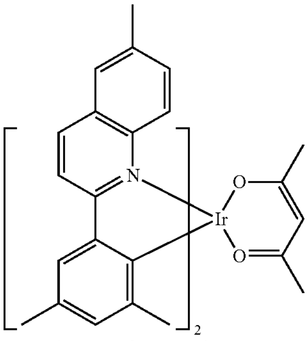
,
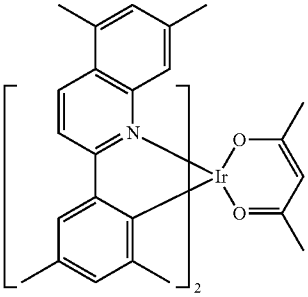
, -continued
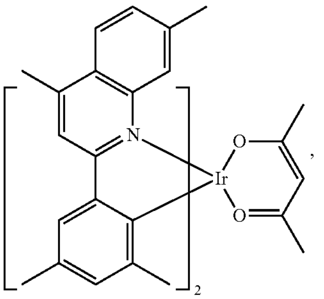
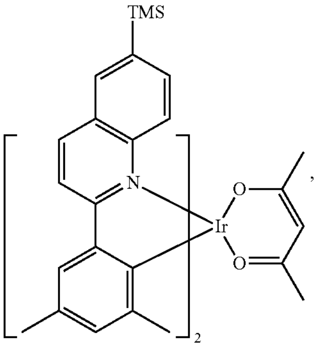
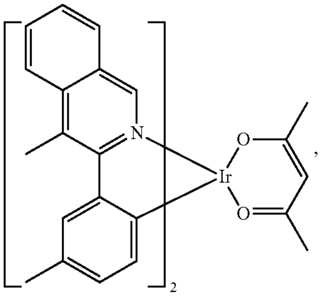
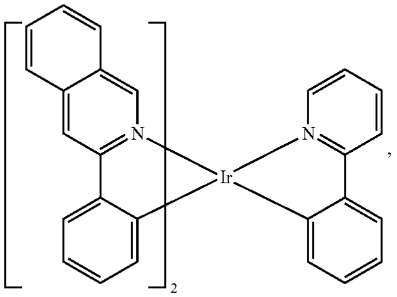
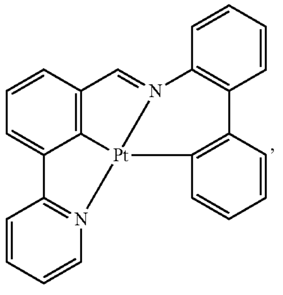
-continued
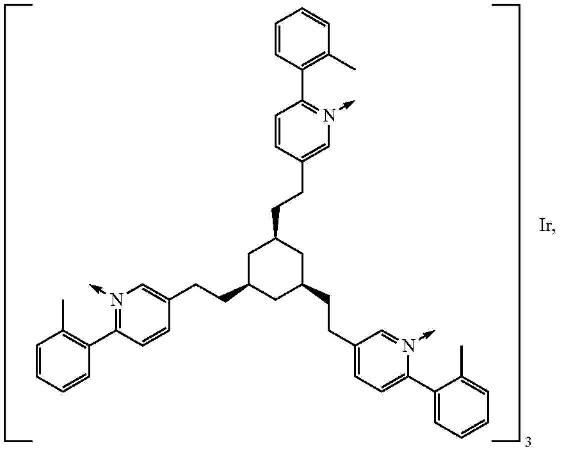
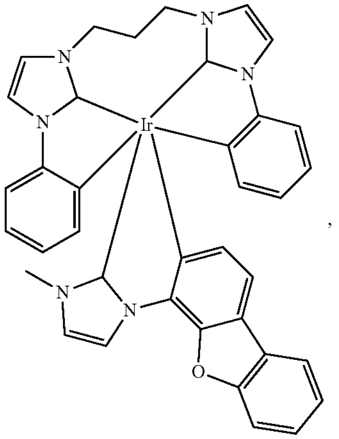
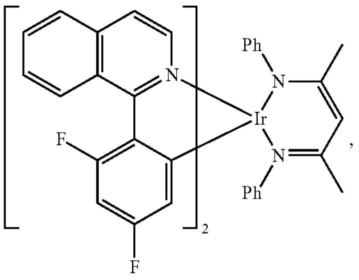
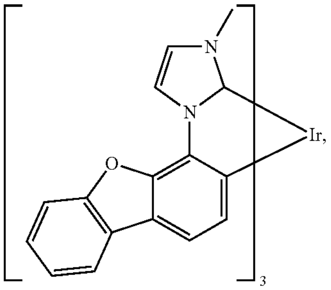

-continued
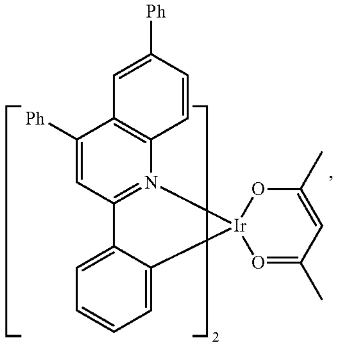
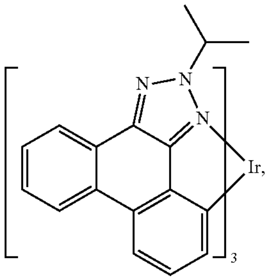
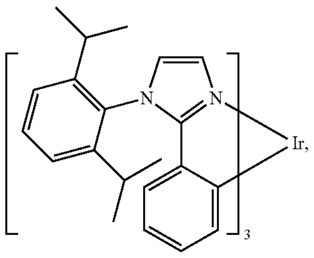
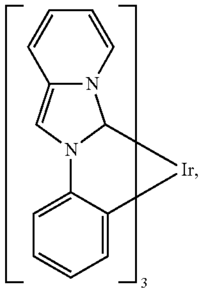
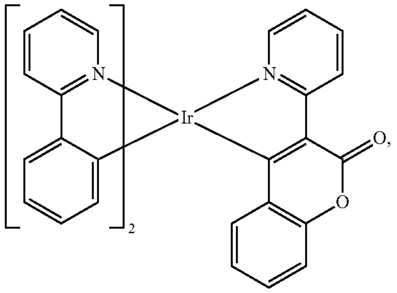
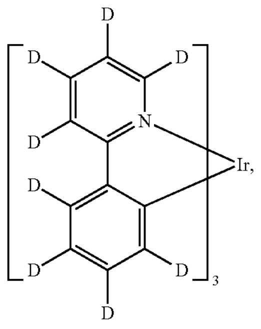
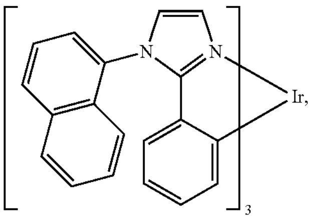
-continued
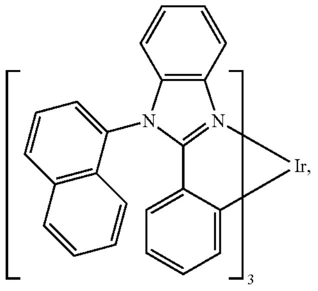
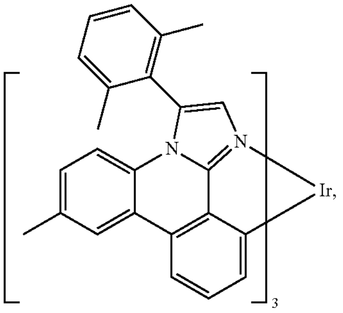
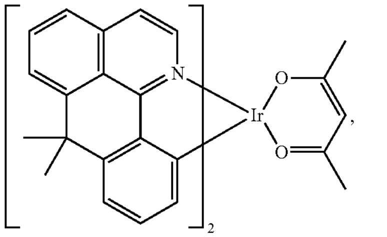
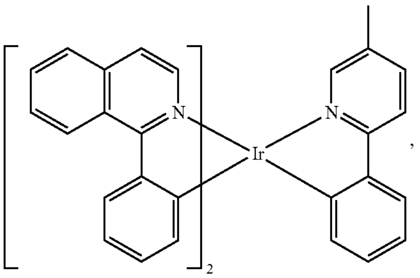
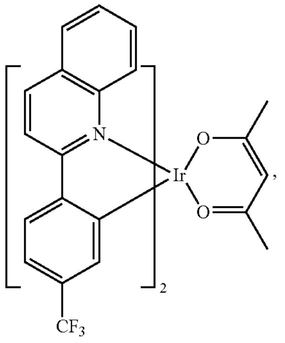

-continued

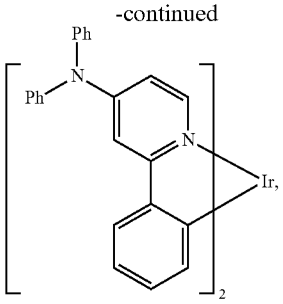

, and

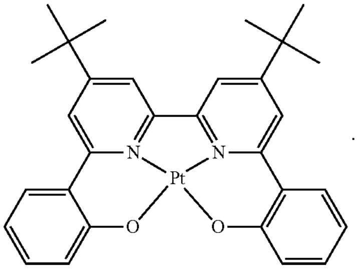

.

e) HBL:

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and/or higher triplet energy than the emitter closest to the HBL interface. In some embodiments, the HBL material has a lower HOMO (further from the vacuum level) and/or higher triplet energy than one or more of the hosts closest to the HBL interface.

In one aspect, compound used in HBL contains the same molecule or the same functional groups used as host described above.

In another aspect, compound used in HBL contains at least one of the following groups in the molecule:

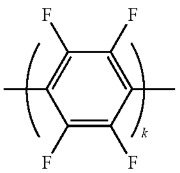

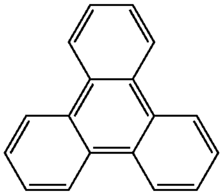

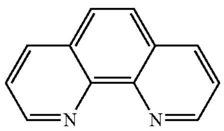

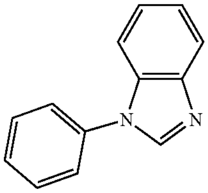

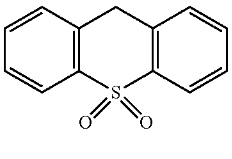

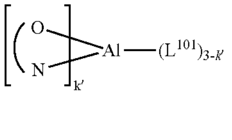

wherein k is an integer from 1 to 20; $L^{101}$ is another ligand, k' is an integer from 1 to 3.

e) ETL:

Electron transport layer (ETHL) may include a material capable of transporting electrons. Electron transport layer may be intrinsic (undoped), or doped. Doping may be used to enhance conductivity. Examples of the ET material are not particularly limited, and any metal complexes or organic compounds may be used as long as they are typically used to transport electrons.

In one aspect, compound used in ETL contains at least one of the following groups in the molecule:

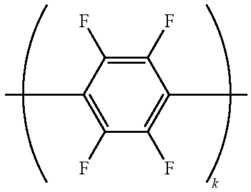

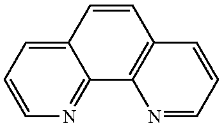

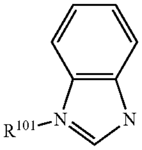

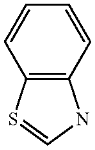

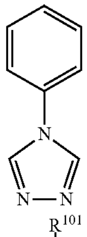

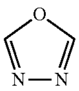

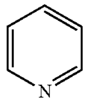

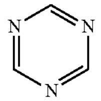

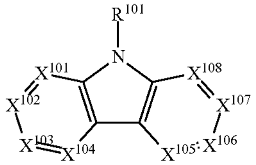

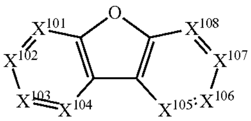

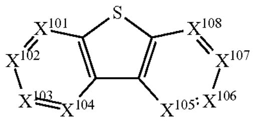

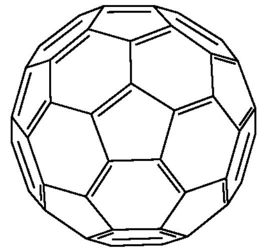

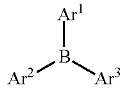

wherein $R^{101}$ is selected from the group consisting of hydrogen, deuterium, halogen, alkyl, cycloalkyl, heteroalkyl, heterocycloalkyl, arylalkyl, alkoxy, aryloxy, amino, silyl, alkenyl, cycloalkenyl, heteroalkenyl, alkynyl, aryl, heteroaryl, acyl, carboxylic acids, ether, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but not limit to the following general formula:

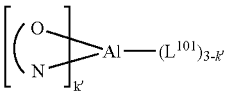

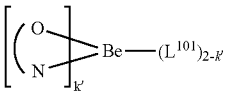

-continued

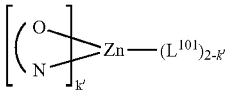

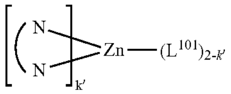

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

Non-limiting examples of the ETL materials that may be used in an OLED in combination with materials disclosed herein are exemplified below together with references that disclose those materials: CN103508940, EP01602648, EP01734038, EP01956007, JP2004-022334, JP2005149918, JP2005-268199, KR0117693, KR20130108183, US20040036077, US20070104977, US2007018155, US20090101870, US20090115316, US20090140637, US20090179554, US2009218940, US2010108990, US2011156017, US2011210320, US2012193612, US2012214993, US2014014925, US2014014927, US20140284580, U.S. Pat. Nos. 6,656,612, 8,415,031, WO2003060956, WO2007111263, WO2009148269, WO2010067894, WO2010072300, WO2011074770, WO2011105373, WO2013079217, WO2013145667, WO2013180376, WO2014104499, WO2014104535,

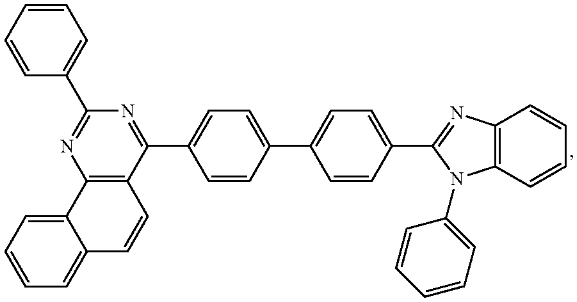

,

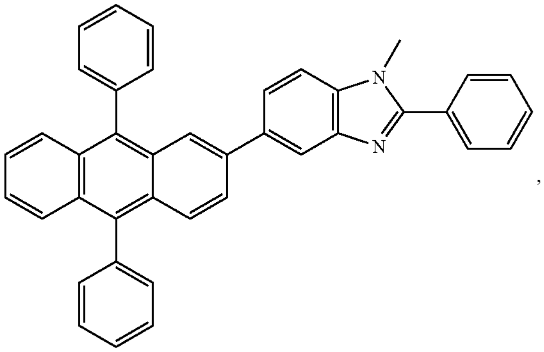

,

-continued

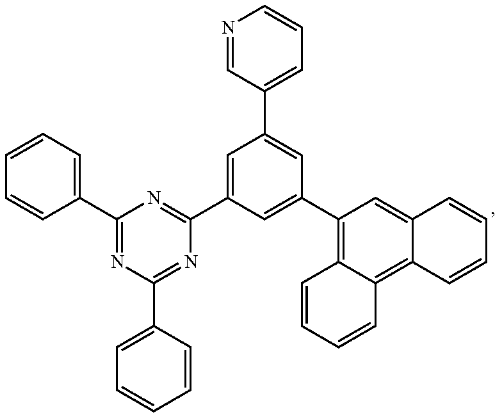

,

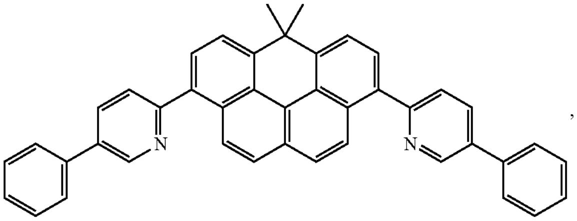

,

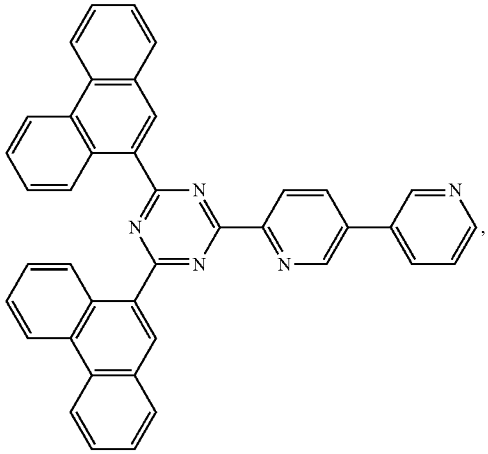

,

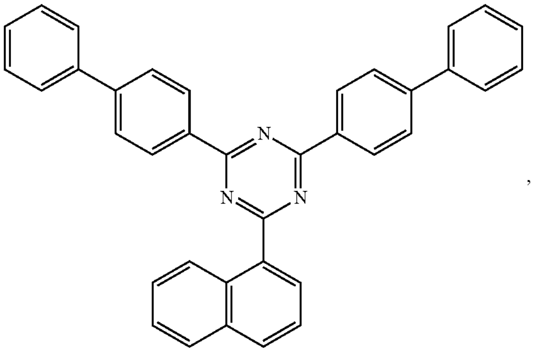

,

-continued
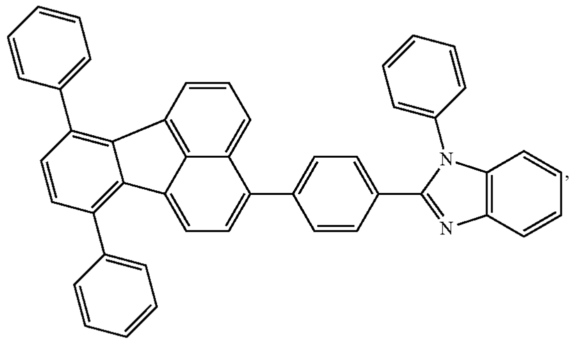
,
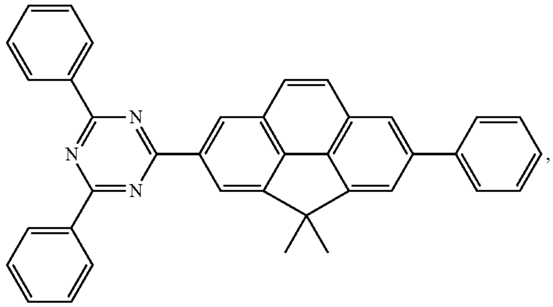
,
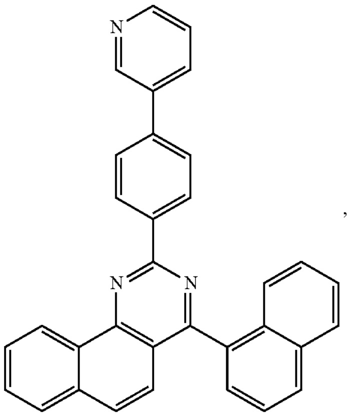
,
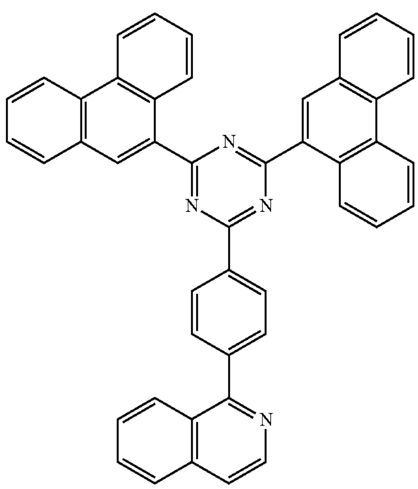
,
-continued
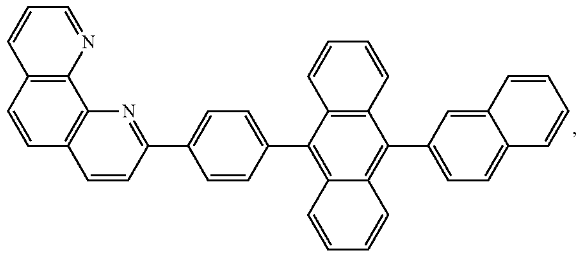
,
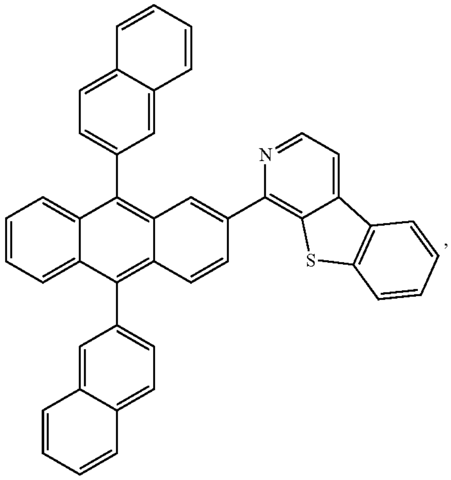
,
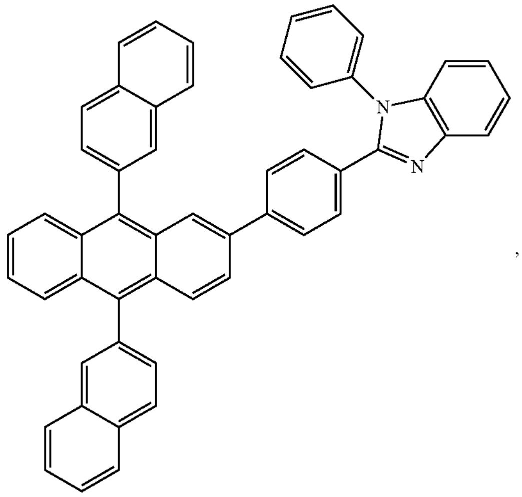
,
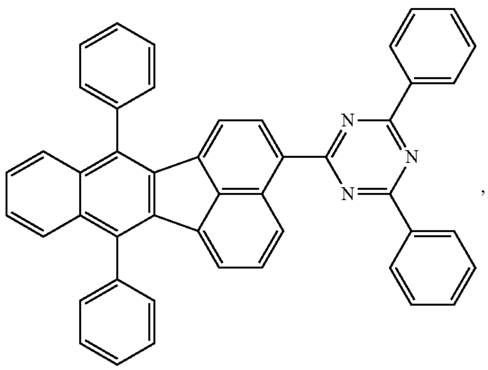
, -continued
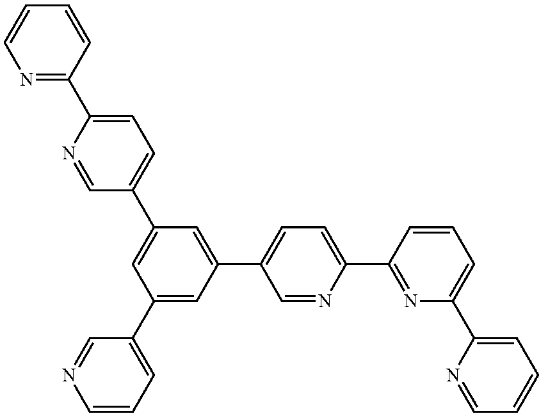
,
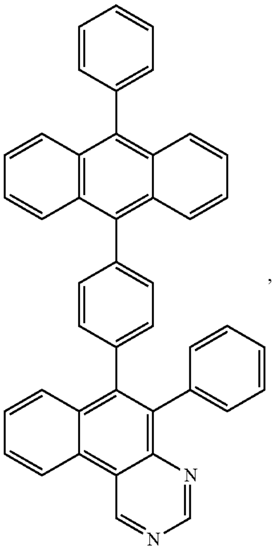
,
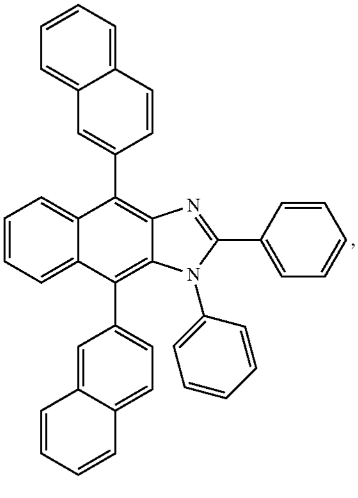
,
-continued
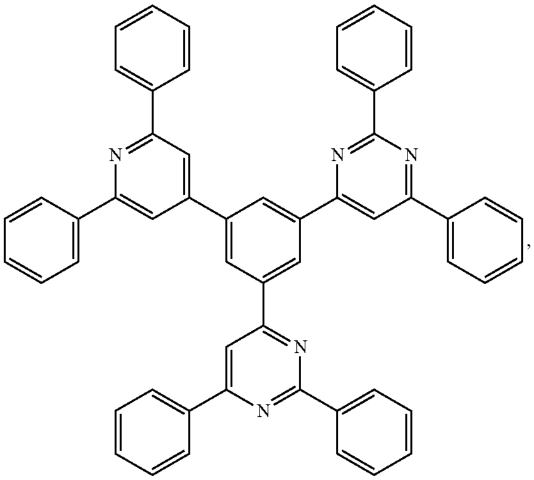
,
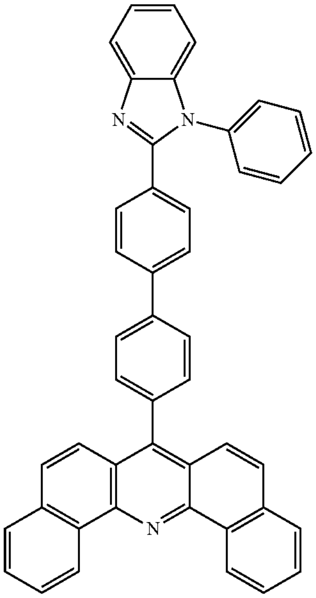
,
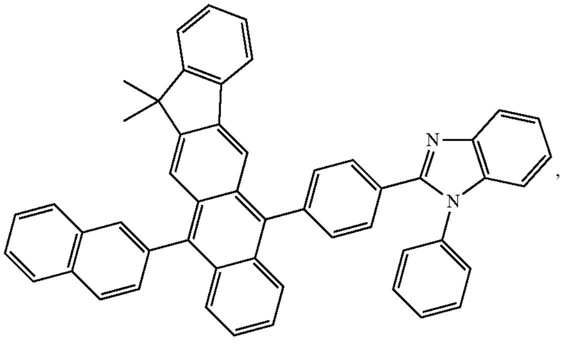
, -continued
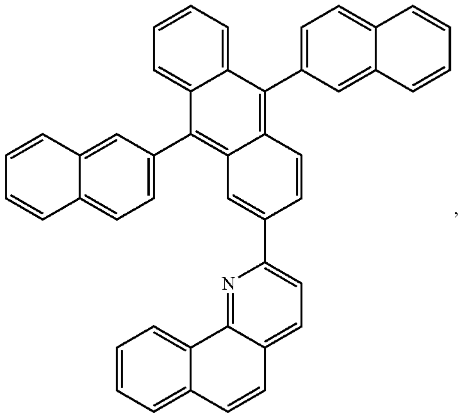
,
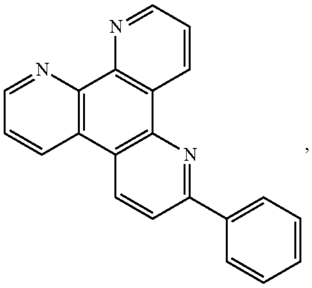
,
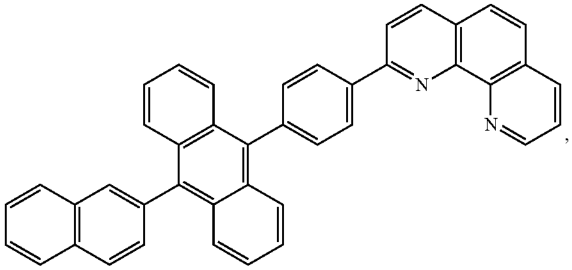
,
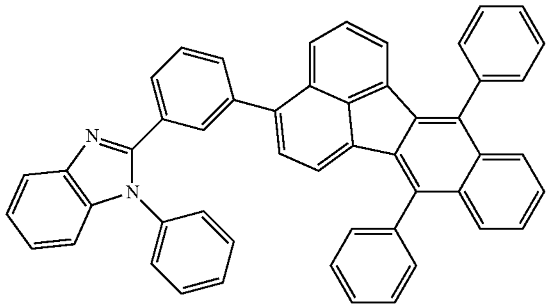
,
-continued
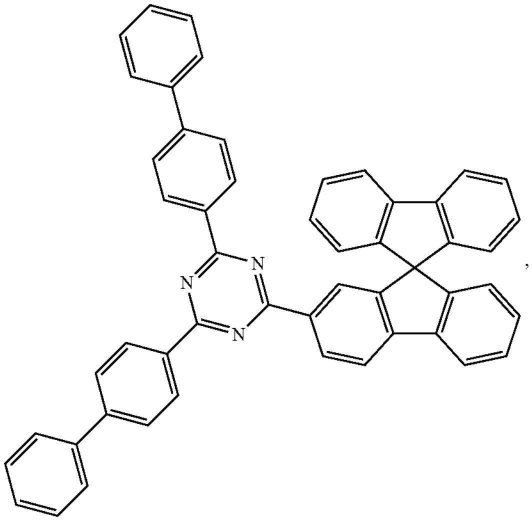
,
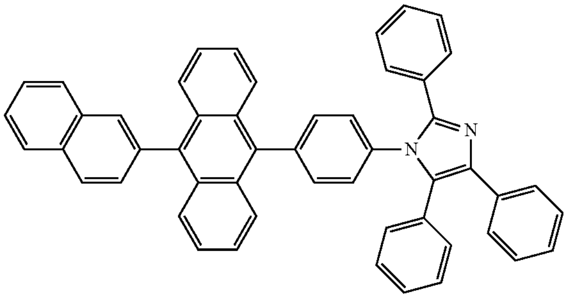
,
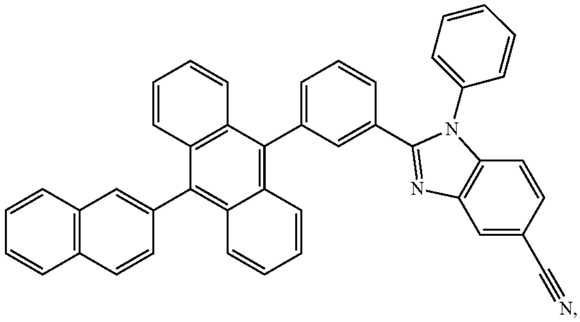
,
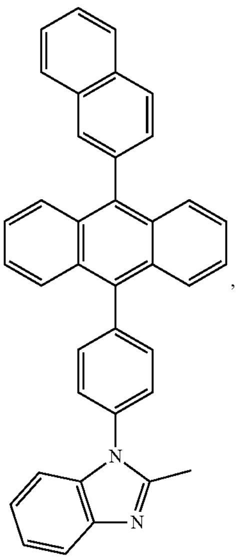
, -continued

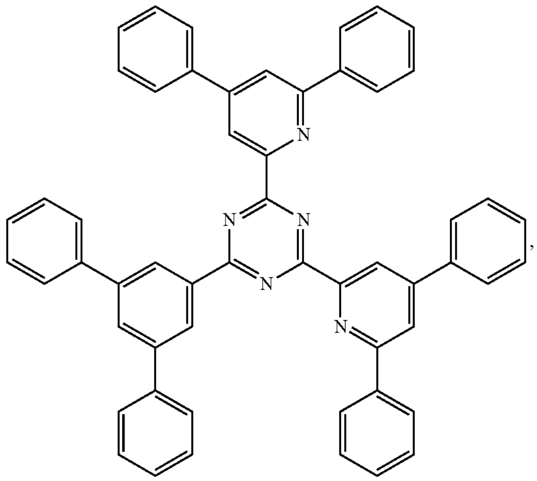

,

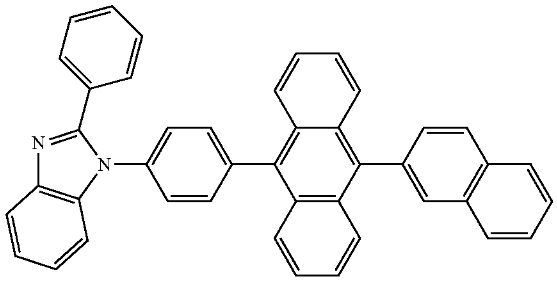

,

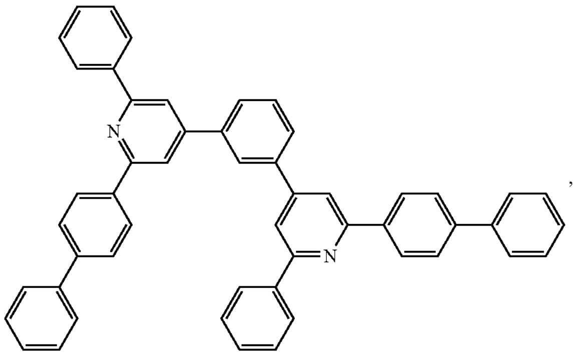

,

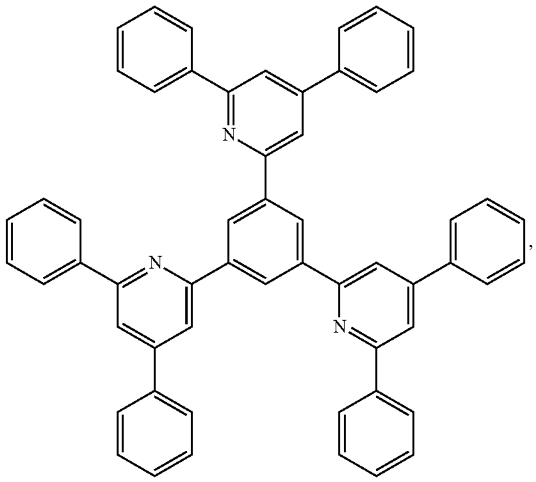

,

-continued

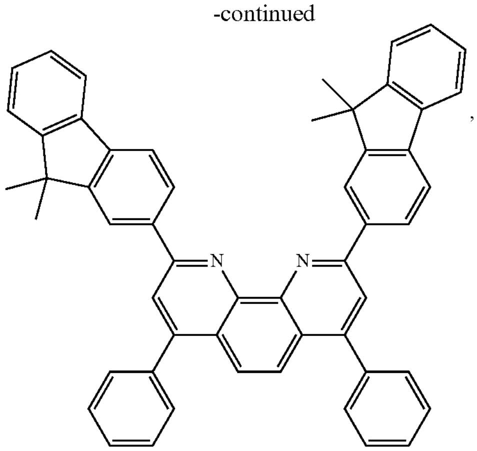

, and

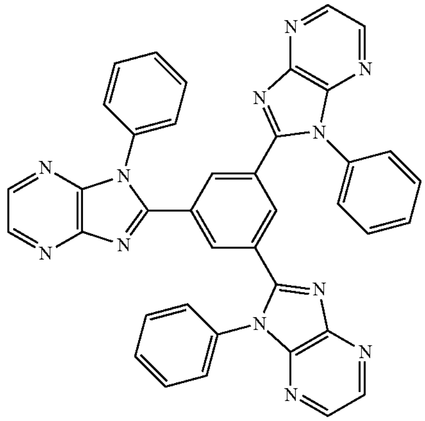

.

g) Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

In any above-mentioned compounds used in each layer of the OLED device, the hydrogen atoms can be partially or fully deuterated. The minimum amount of hydrogen of the compound being deuterated is selected from the group consisting of 30%, 40%, 50%, 60%, 70%, 80%, 90%, 95%, 99%, and 100%. Thus, any specifically listed substituent, such as, without limitation, methyl, phenyl, pyridyl, etc. may be undeuterated, partially deuterated, and fully deuterated versions thereof. Similarly, classes of substituents such as, without limitation, alkyl, aryl, cycloalkyl, heteroaryl, etc. also may be undeuterated, partially deuterated, and fully deuterated versions thereof.

It is understood that the various embodiments described herein are by way of example only and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

EXPERIMENTAL SECTION

All experimental devices tested were fabricated by high vacuum (<10-7 Torr) thermal evaporation (VTE). The anode electrode was 800 Å of indium tin oxide (ITO). The cathode consisted of 10 Å of LiQ followed by 1000 Å of Al. All devices were encapsulated with a glass lid sealed with an epoxy resin in a nitrogen glove box (<1 ppm of $H_2O$ and $O_2$) immediately after fabrication, and a moisture getter was incorporated inside the package.

The organic stack of the device examples consisted of sequentially, from the ITO surface, 100 Å of HATCN as the hole injection layer (HIL), 400 Å of hole transport material HTM as the hole transport layer (HTL), 50 Å of EBL as an electron blocking layer (EBL), 400 Å of the first host doped with 30 wt % of a second host and 10 wt % emitter (see table) as the emissive layer (EML), 50 Å of the second host as a blocking layer (BL), and 300 Å of 35% ETM in LiQ as the electron transport layer (ETL). As used herein, HATCN, HTM, ETM, EBL, H1, H2, DH1, DH2, GD1, GD2, GD3, and GD4 have the following structures:

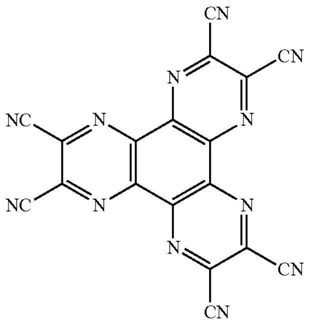

HATCN

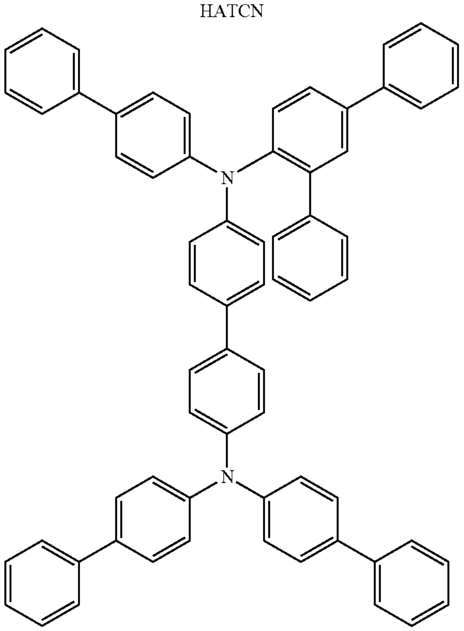

HTM

-continued

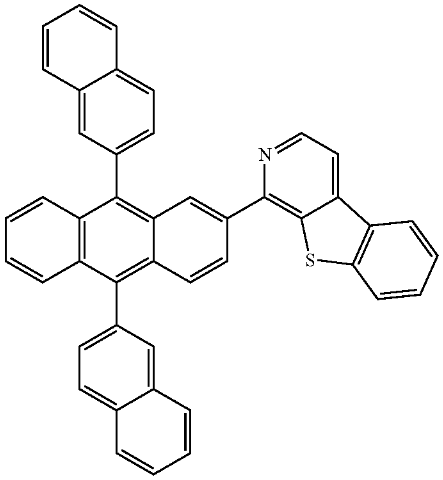

ETM

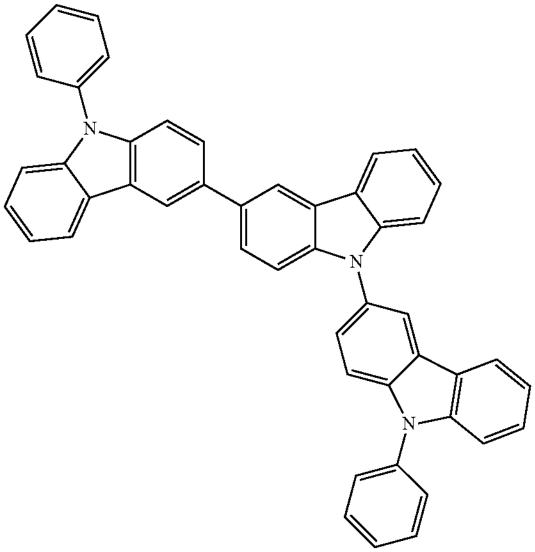

EBL

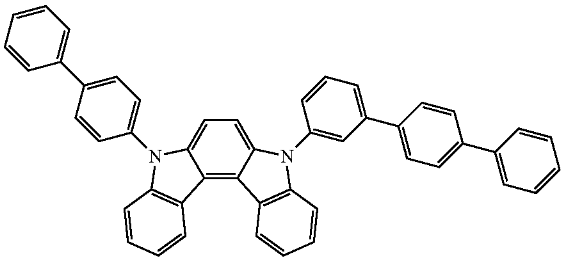

H1

-continued

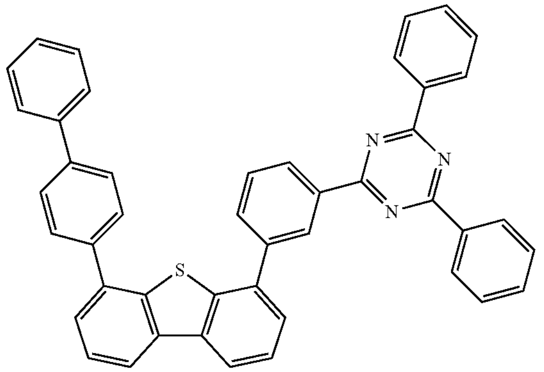

H2

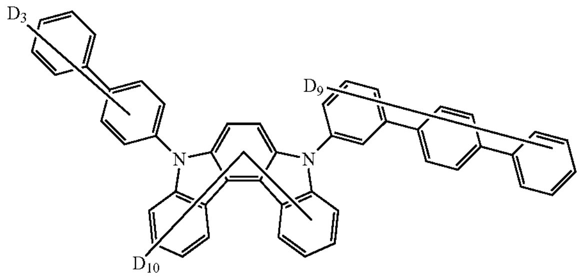

DH1

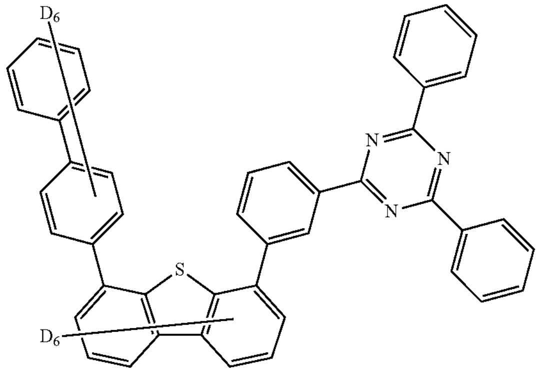

DH2

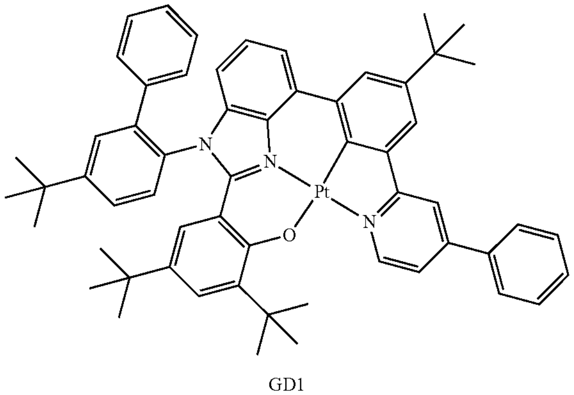

GD1

-continued

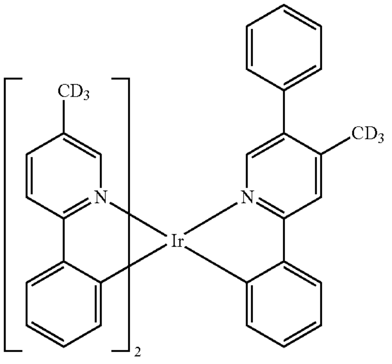

GD2

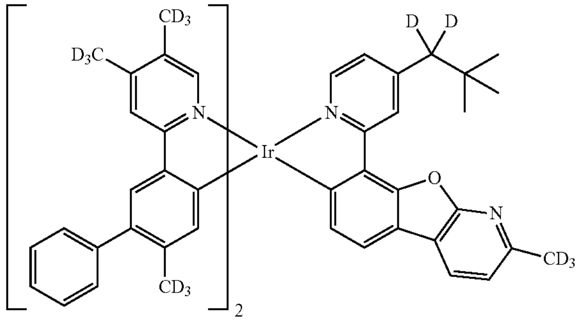

GD3

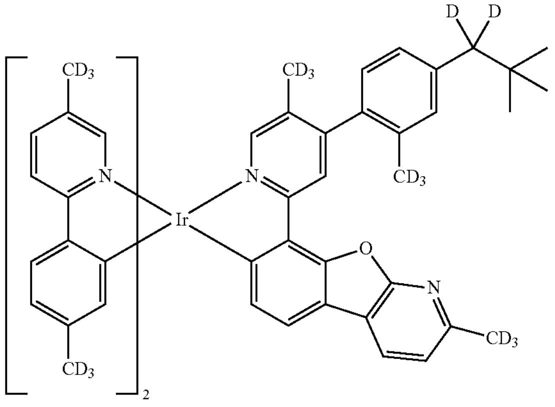

GD4

DH1 and DH2 were synthesized by subjecting H1 and H2, respectively, to H/D exchange conditions as described by WO2011053334A1. The inventive devices, Example 1 through Example 8, were fabricated with deuterated first host DH1 according to the present disclosure. The comparative devices, Comparison 1 through Comparison 8, were fabricated with the non-deuterated first host H1. The measured lifetime ($LT_{95}$) for Example 1-8 and Comparison 1-8 are reported in Table 1 below where $LT_{95}$ is the time to reduction of brightness to 95% of the initial luminance at a constant current density of 80 $mA/cm^2$. $LT_{95}$ reported for Comparison 1, Comparison 2, Example 1, and Example 2 are normalized relative to the $LT_{95}$ for Comparison 1. $LT_{95}$ reported for Comparison 3, Comparison 4, Example 3, and Example 4 are normalized relative to the $LT_{95}$ for Comparison 3. $LT_{95}$ reported for Comparison 5, Comparison 6, Example 5, and Example 6 are normalized relative to the $LT_{95}$ for Comparison 5. $LT_{95}$ reported for Comparison 7, Comparison 8, Example 7, and Example 8 are normalized relative to the $LT_{95}$ for Comparison 7.

TABLE 1

| | First Host | Second Host | Emitter | $LT_{95}$ @ 80 mA/cm$^2$ |
|---|---|---|---|---|
| Comparison 1 | H1 | H2 | GD1 | 1.0 |
| Comparison 2 | H1 | DH2 | GD1 | 1.2 |
| Example 1 | DH1 | H2 | GD1 | 2.1 |
| Example 2 | DH1 | DH2 | GD1 | 2.3 |
| Comparison 3 | H1 | H2 | GD2 | 1.0 |
| Comparison 4 | H1 | DH2 | GD2 | 1.0 |
| Example 3 | DH1 | H2 | GD2 | 2.2 |
| Example 4 | DH1 | DH2 | GD2 | 2.2 |
| Comparison 5 | H1 | H2 | GD3 | 1.0 |
| Comparison 6 | H1 | DH2 | GD3 | 1.0 |
| Example 5 | DH1 | H2 | GD3 | 1.7 |
| Example 6 | DH1 | DH2 | GD3 | 1.8 |
| Comparison 7 | H1 | H2 | GD4 | 1.0 |
| Comparison 8 | H1 | DH2 | GD4 | 1.0 |
| Example 7 | DH1 | H2 | GD4 | 1.5 |
| Example 8 | DH1 | DH2 | GD4 | 1.7 |

The above data shows that the inventive device Examples 1-2 each exhibited a substantially higher lifetime than the comparative devices Comparison 1 and Comparison 2. The 100%-130% lifetime enhancement is beyond any value that could be attributed to experimental error and the observed improvement is statistically significant. Furthermore, enhancement from deuteration of the first host is greater than 90% larger than the enhancement from deuteration of the second host in Comparison 2. Based on the fact that the devices have the same structure with the only difference being the deuteration of the first host, the significant performance improvement observed in the above data was unexpected. Similarly, the inventive devices Examples 3-8 each exhibited 50-120% longer lifetimes than their respective comparative devices Comparison 3-8. This is in contrast to Comparison 4, Comparison 6, and Comparison 8 in which deuteration of the second host gave significantly smaller enhancement compared to the non-deuterated host system. Without being bound by any theories, this improvement may be attributed to the suppression of intermolecular decomposition reactions between deuterated hosts and dopants involving hosts in their cationic state.

What is claimed is:

1. An organic electroluminescent device (OLED) comprising:

an anode;

a cathode; and an emissive layer, disposed between the anode and the cathode, wherein the emissive layer comprises a phosphorescent dopant, a first host, and a second host, wherein the first host transports holes, the second host transports electrons, wherein the first host is fully or partially deuterated; and at least one of the following conditions is true:

(i) the second host does not comprise a carbazole or an indolocarbazole;

(ii) the second host has a HOMO level <–5.75 eV;

(iii) the second host has a HOMO level >–5.5 eV and is at least 25% deuterated;

(iv) the second host comprises biscarbazole or indolocarbazole moiety that is at least 60% deuterated;

(v) the first host comprises a hole transporting moiety that is at least 50% deuterated and the second host comprises an electron transporting moiety that is at least 50% deuterated; and (vi) the OLED has a lifetime represented by LT95, that is at least 75% higher than the lifetime LT95 of a comparative OLED, wherein the comparative OLED is constructed so that the only difference between the OLED and the comparative OLED is that the comparative OLED has a first host that is not deuterated, and wherein LT95 of a device is measured as a time to reduction of luminance of said device to 95% of its initial luminance at a constant current density of 80 mA/cm$^2$.

2. The OLED of claim 1, wherein the first host comprises at least one moiety selected from the group consisting of naphthalene, biphenyl, triphenylene, dibenzothiophene, dibenzofuran, silyl, boryl, phenanthrene, phenanthridine, arylamine, and fluorene.

3. The OLED of claim 1, wherein the second host comprises at least one moiety selected from the group consisting of benzene, pyridine, pyrimidine, pyridazine, pyrazine, triazine, imidazole, aza-dibenzothiophene, aza-dibenzofuran, and aza-carbazole, boryl, thiazole, naphthalene, quinoline, isoquinoline, quinazoline, benzoquinazoline, benzofuran, benzoxazole, benzothiophene, benzothiazole, benzoselenophene benzimidazole, carbazole, dibenzofuran, dibenzothiophene, quinoxaline, phthalazine, phenanthrene, phenanthridine, triphenylene, and fluorene.

4. The OLED of claim 1, wherein the first host is at least 10% deuterated.

5. The OLED of claim 1, wherein the first host comprises a carbazole or indolocarbazole moiety.

6. The OLED of claim 1, wherein the hole transporting moiety of the first host is selected from the group consisting of:

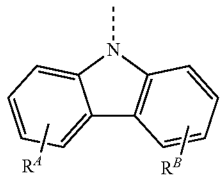
,
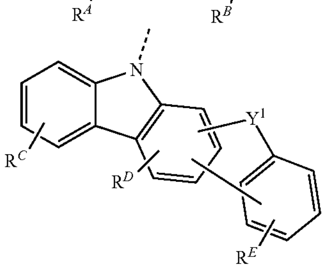
,
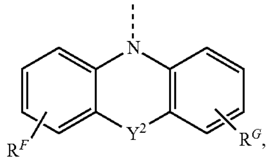
,
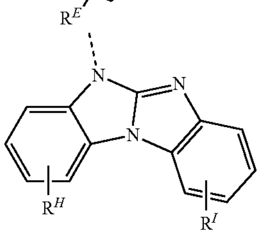
,
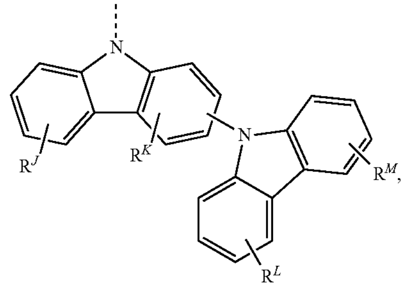
,

-continued

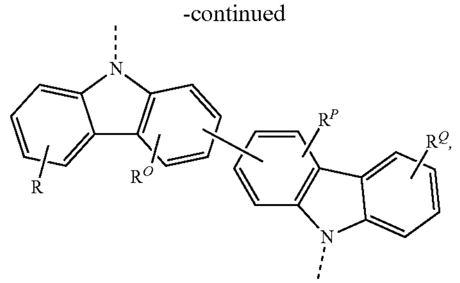

,

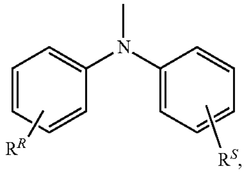

, and

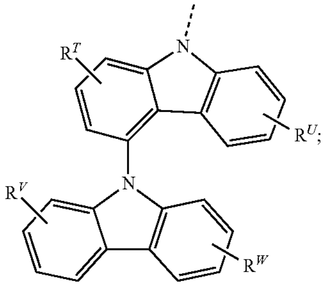

;

wherein:

each of $Y^1$ and $Y^2$ is independently selected from the group consisting of BR, BRR', NR, PR, P (O)R, O, S, Se, C═O, C═S, C═Se, C═NR, C═CRR', S═O, $SO_2$, CRR', SiRR', and GeRR';

each of $R^A$ to $R^W$ independently represents mono up to the maximum number of allowable substitutions, or no substitution;

each R, R', and $R^A$ to $R^W$ is independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

two adjacent of R, R', or $R^A$ to $R^W$ can be joined or fused to form a ring; and when present, at least 4 of $R^A$ and $R^B$ are D; at least 5 of $R^C$, $R^D$, and $R^E$ are D; at least 4 of $R^F$ and $R^G$ are D; at least 4 of $R^H$ and $R^I$ are D; at least 8 of $R^J$, $R^K$, $R^L$, $R^M$ are D; at least 7 of $R^N$, $R^O$, $R^P$, and $R^Q$ are D; at least 4 of $R^R$ and $R^S$ are D; and at least 7 of $R^T$, $R^U$, $R^V$, and $R^W$ are D.

7. The OLED of claim 6, wherein the electron transporting moiety of the second host is selected from the group consisting of the structures of:

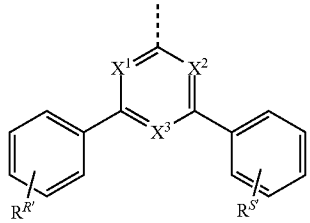

,

-continued

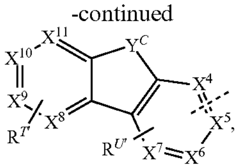

,

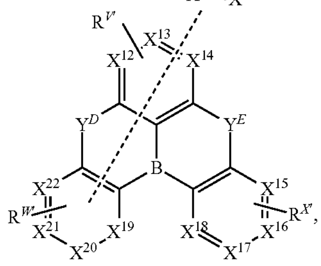

,

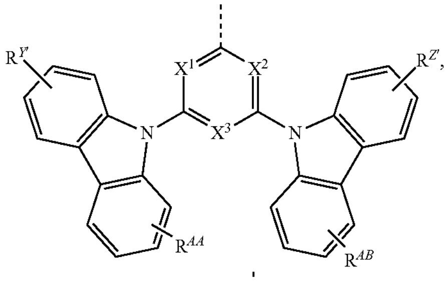

,

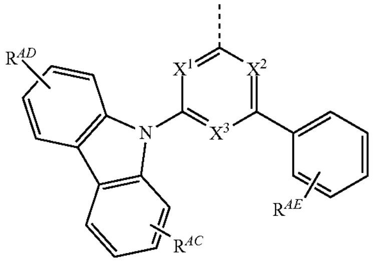

,

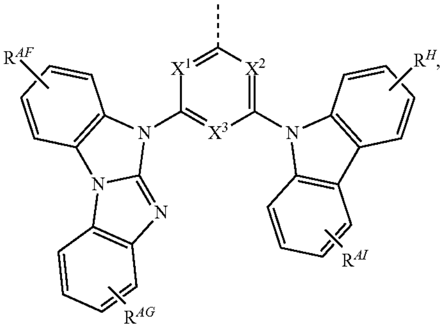

, and

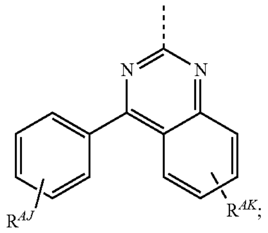

;

wherein:

each of $X^1$ to $X^{22}$ is independently C or N;

at least one of $X^1$ to $X^3$ is N;

at least one of $X^4$ to $X^{11}$ is N;

each of YC, YD, and YE is independently selected from the group consisting of BR, BRR', NR, PR, P (O)R, O, S, Se, C═O, C═S, C═Se, C═NR, C═CRR', S═O, $SO_2$, CRR', SiRR', and GeRR';

each of $R^{R'}$ to $R^{Z'}$ and $R^{AA}$ to $R^{AK}$ independently represents mono, up to the maximum number of allowable substitutions, or no substitution;

each R, R', $R^{R'}$ to $R^{Z'}$, and $R^{AA}$ to $R^{AK}$ is independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

two adjacent of R, R', $R^{R'}$ to $R^{Z'}$, or $R^{AA}$ to $R^{AK}$ can be joined or fused to form a ring; and when present, at least 5 of $R^{R'}$ and $R^{S'}$ are D; at least 4 of $R^{T'}$ and $R^{U'}$ are D; at least 6 of $R^{V'}$, $R^{W'}$, and $R^{X'}$ are D; at least 9 of $R^{Y'}$, $R^{Z'}$, $R^{AA}$, and $R^{AB}$ are D; at least 7 of $R^{AC}$, $R^{AD}$, and $R^{AE}$ are D; at least 9 of $R^{AF}$, $R^{AG}$, $R^{AH}$, and $R^{AI}$ are D; and at least 5 of $R^{AJ}$ and $R^{AK}$ are D.

8. The OLED of claim 1, wherein the first host is selected from the group consisting of:

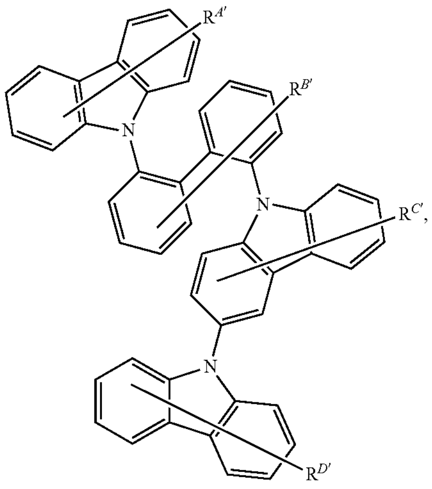

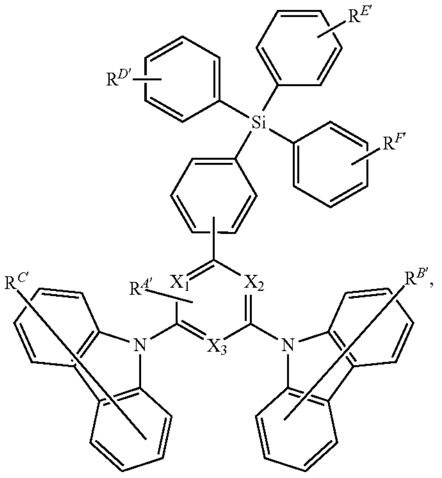

-continued

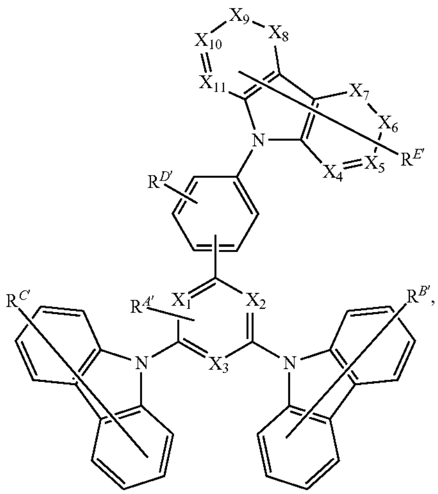

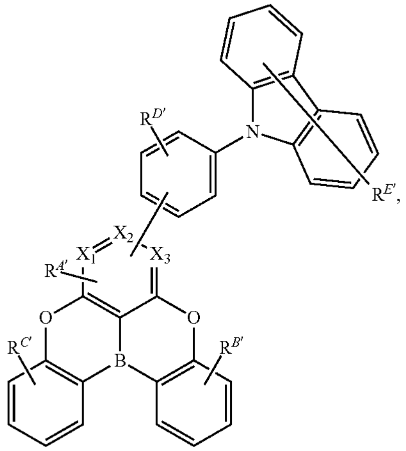

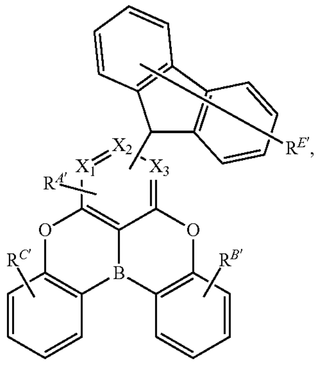

-continued
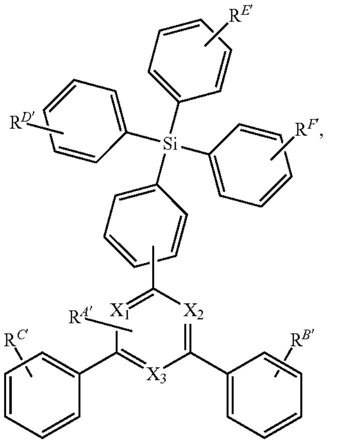
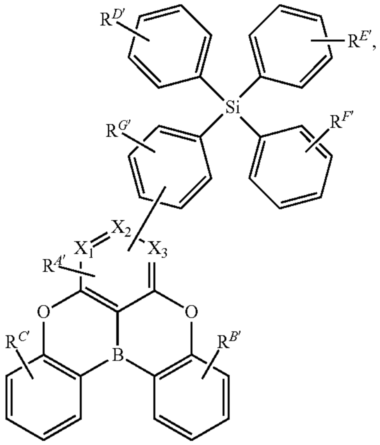
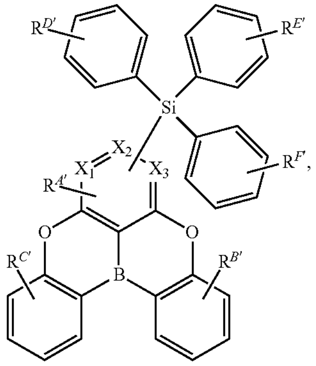
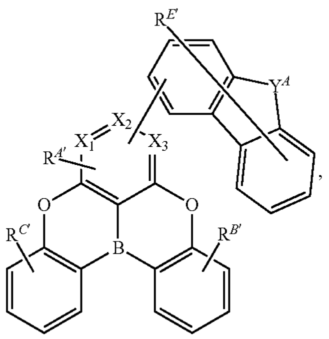
-continued
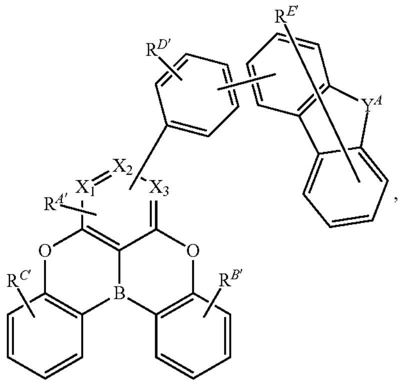
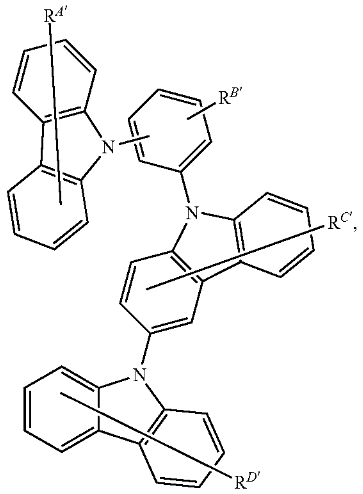
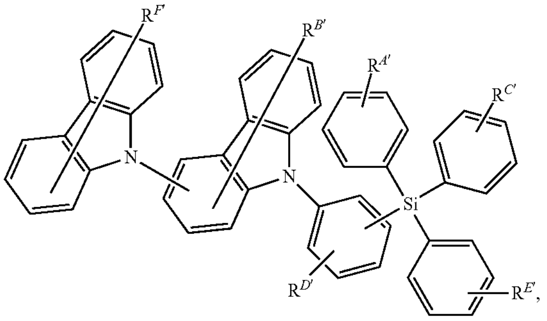
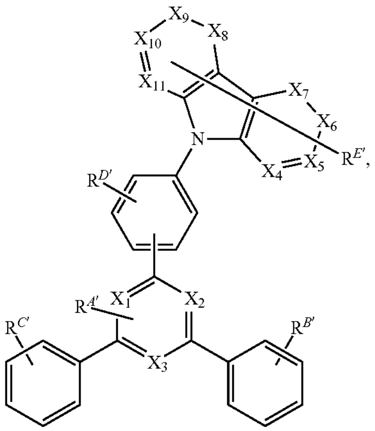

-continued
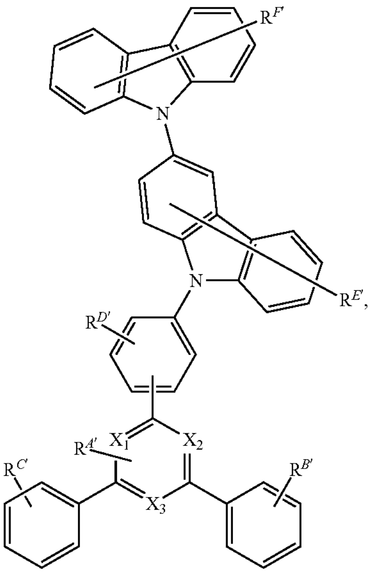
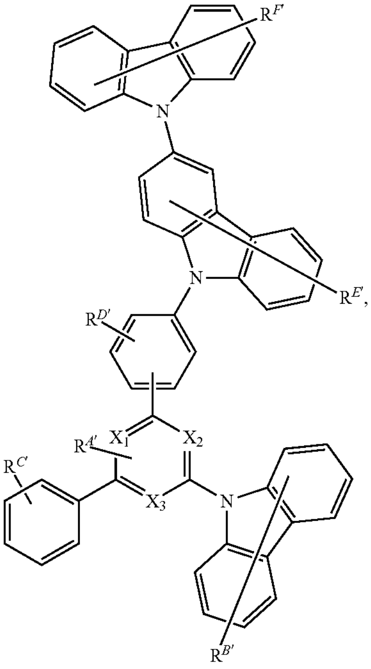
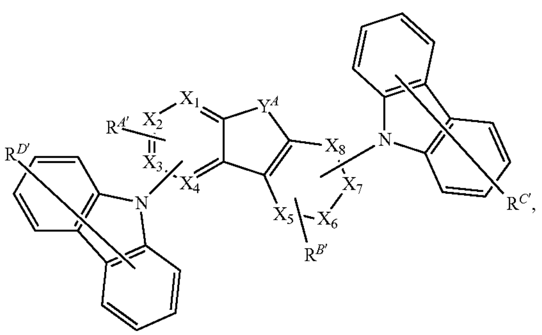
-continued
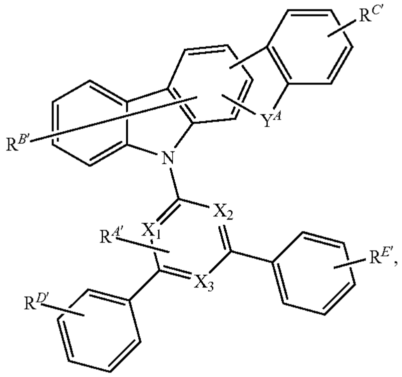
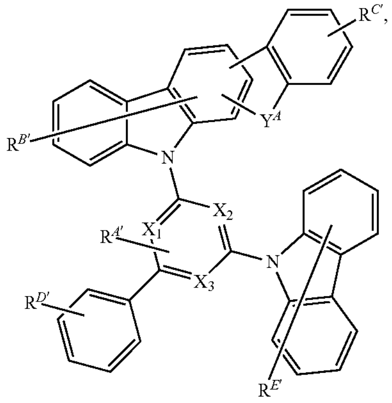
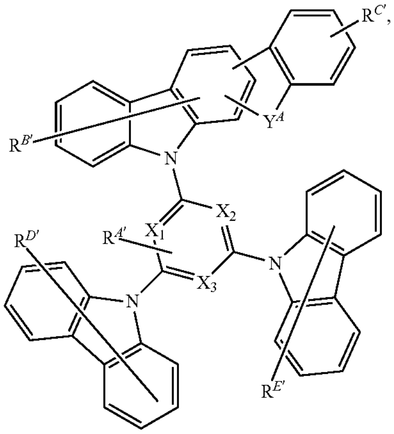
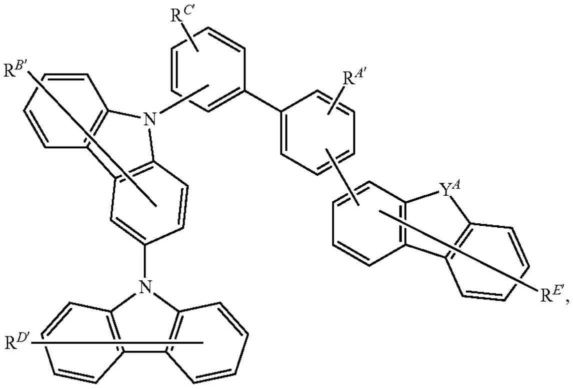

-continued
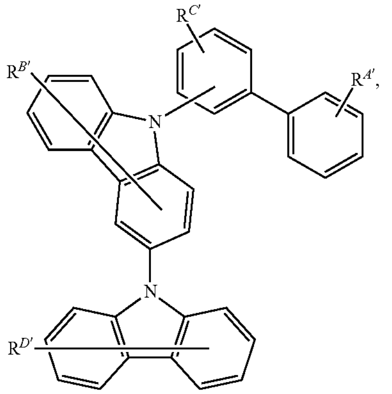
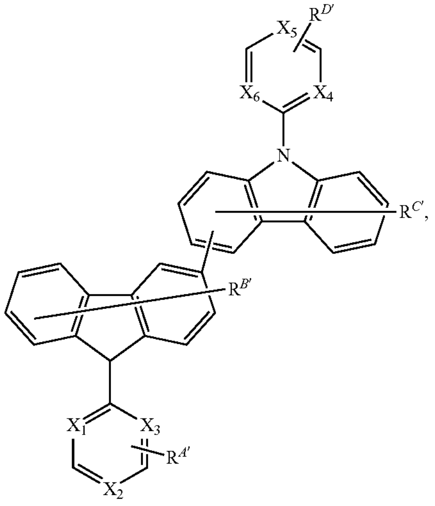
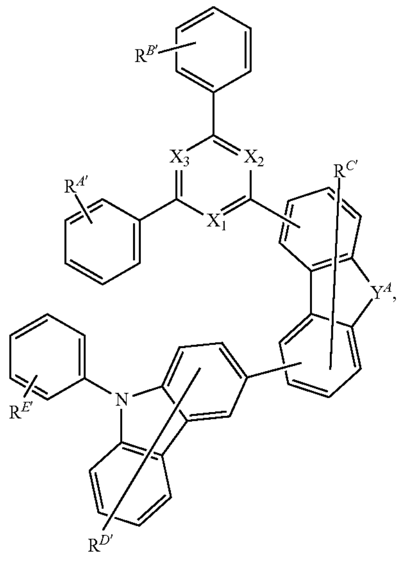
-continued
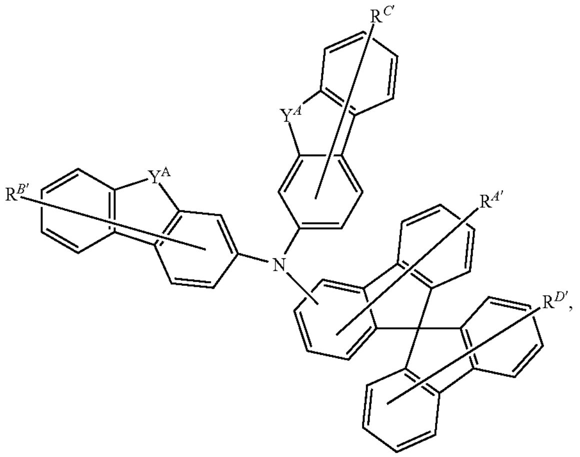
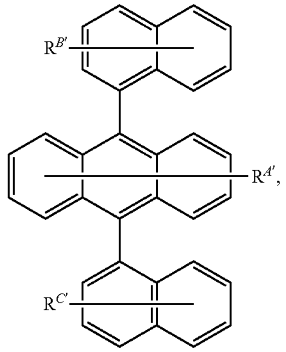
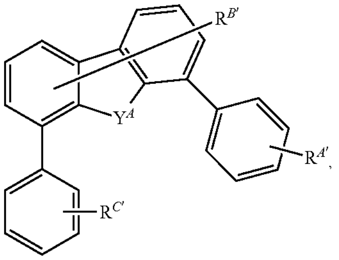
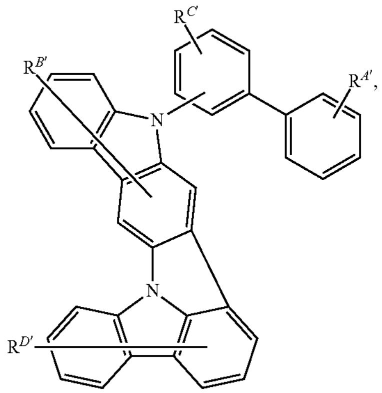

-continued
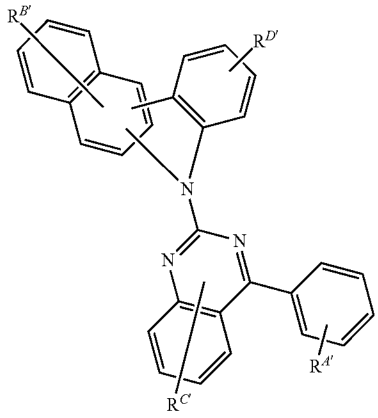
,
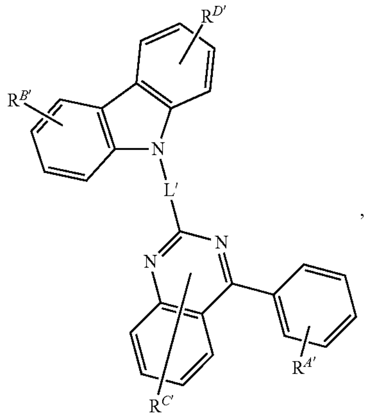
,
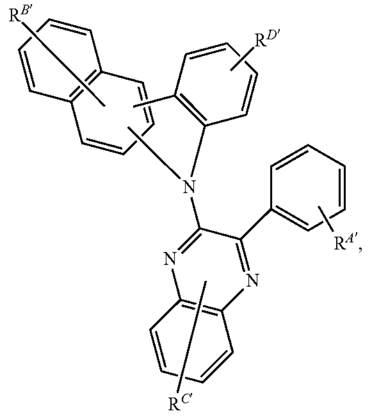
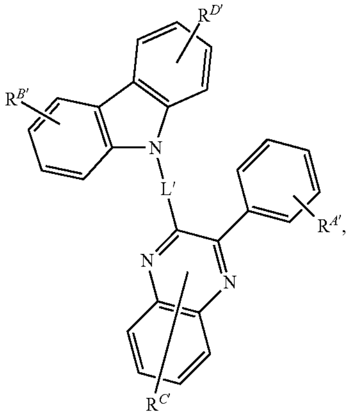
-continued
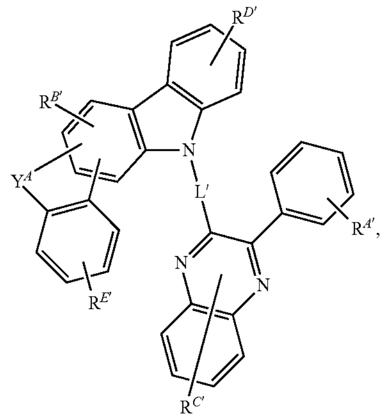
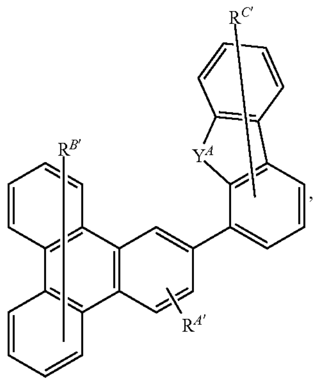
,
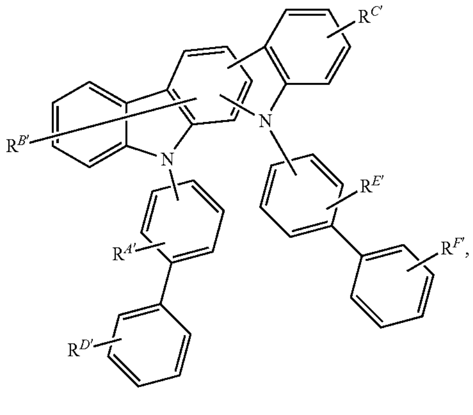
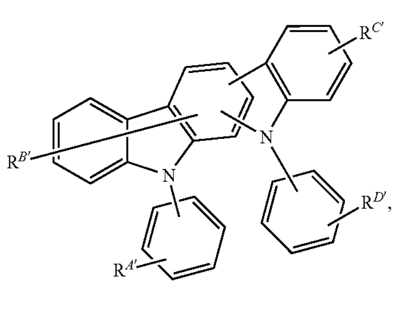

-continued
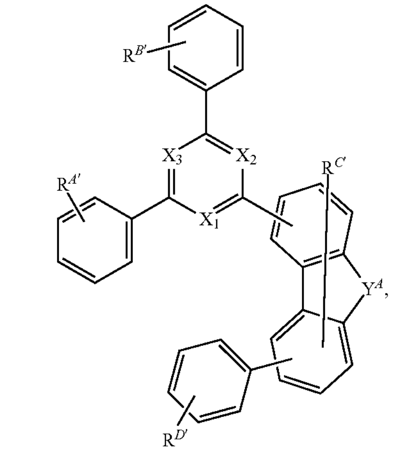
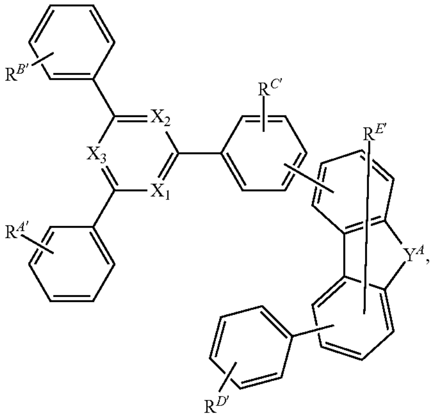
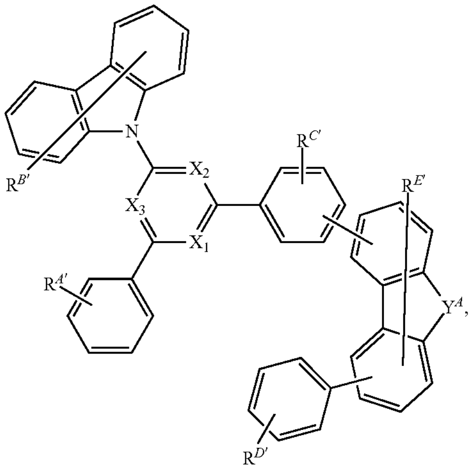
-continued
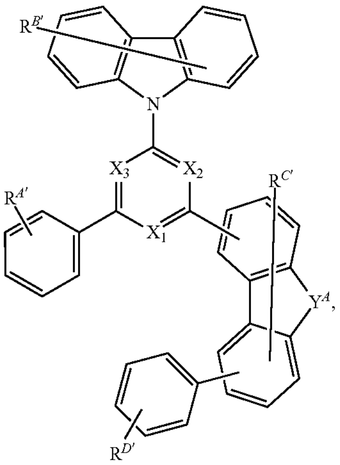
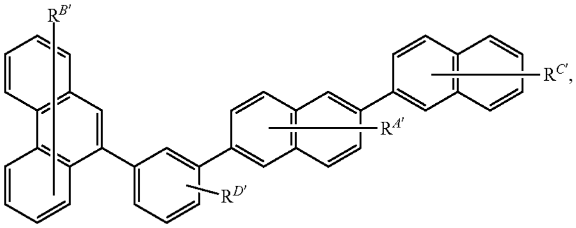
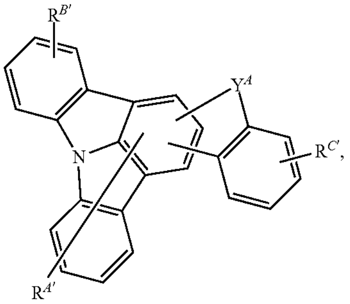
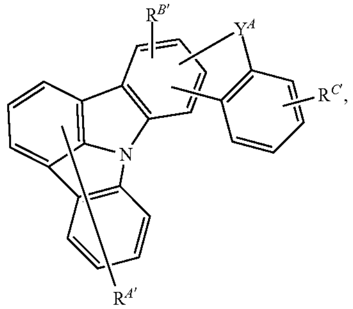
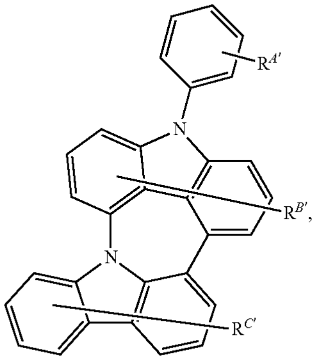

-continued
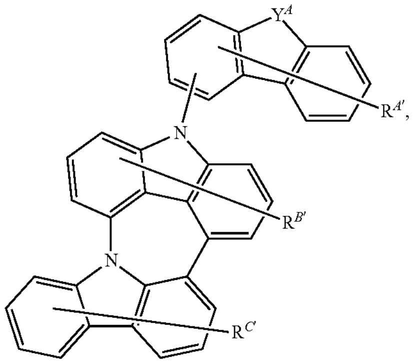
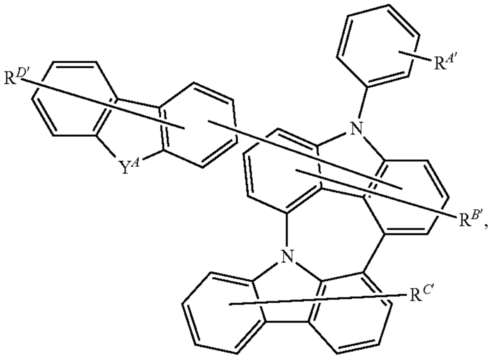
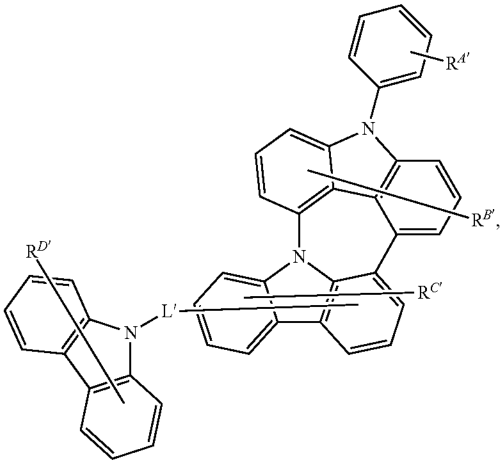
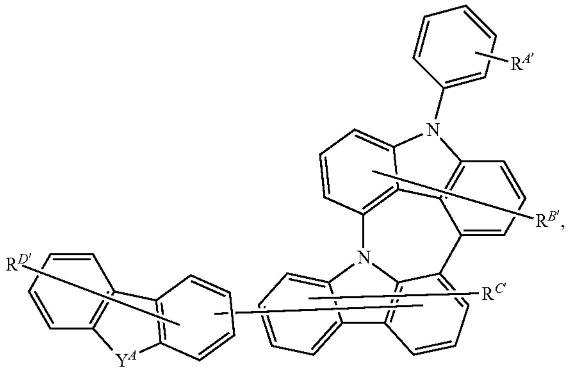
-continued
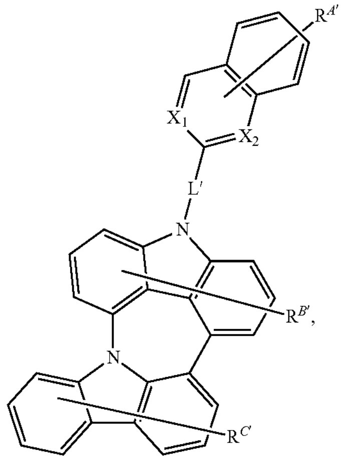
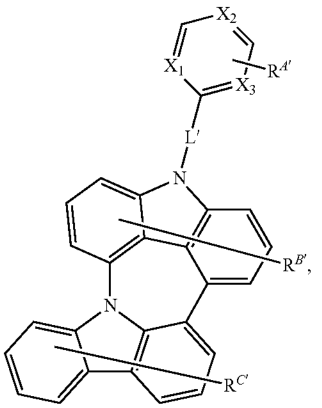
and
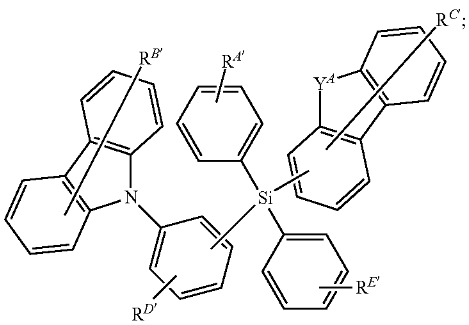

wherein:

each of $X_1$ to $X_{11}$ is independently C or N;

L' is a direct bond or an organic linker;

each $Y^A$ is independently selected from the group consisting of absent a bond, O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono, up to the maximum number of substitutions, or no substitution;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

two adjacent of $R^{A'}$, $R^{B'}$, $R^{C'}$, $R^{D'}$, $R^{E'}$, $R^{F'}$, and $R^{G'}$ can be joined or fused to form a ring; and at least one R, R', $R^{A'}$, $R^{B'}$, $R^{C'}$, $R^{D'}$, $R^{E'}$, $R^{F'}$, or $R^G$ comprises deuterium.

9. The OLED of claim 1, wherein the first host is selected from the group consisting of:

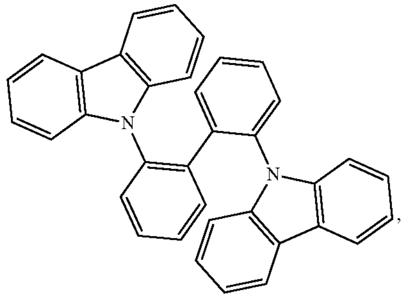
,
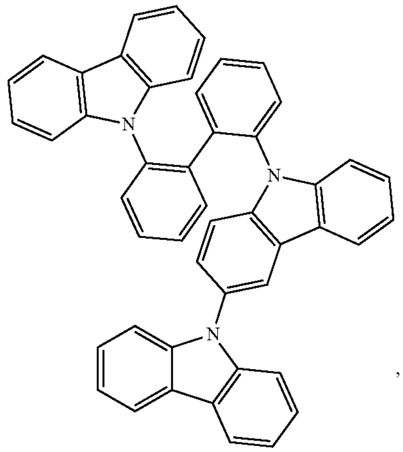
,
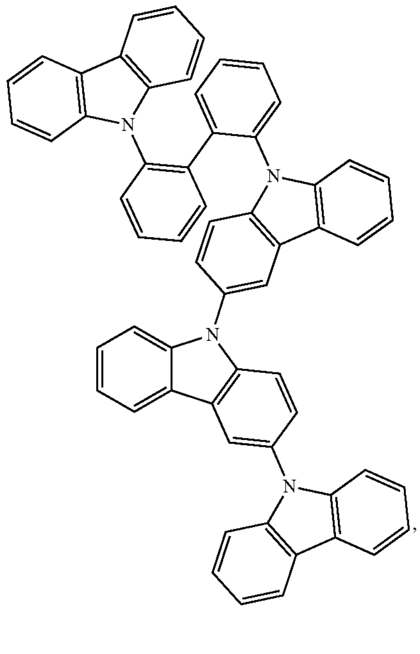
,
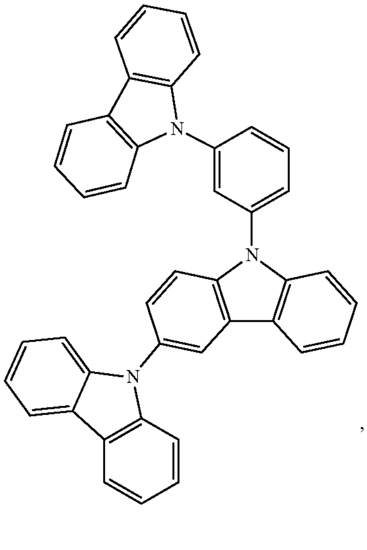
,

-continued
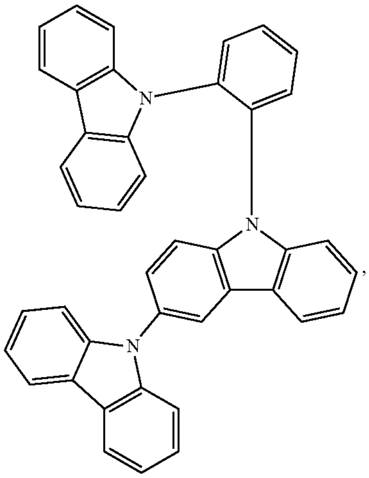,
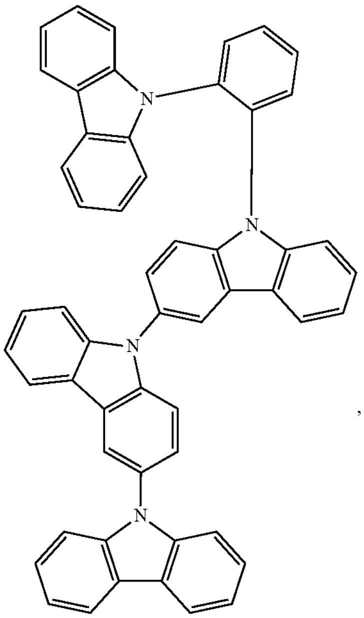,
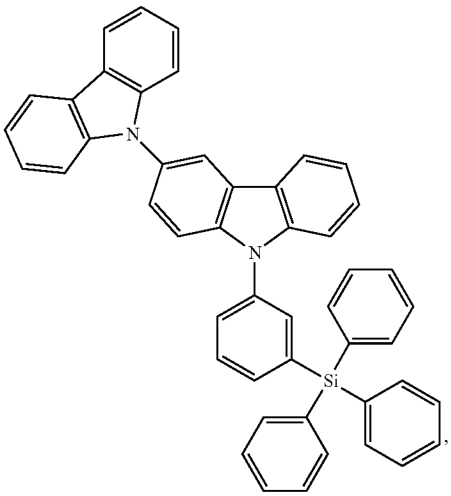,
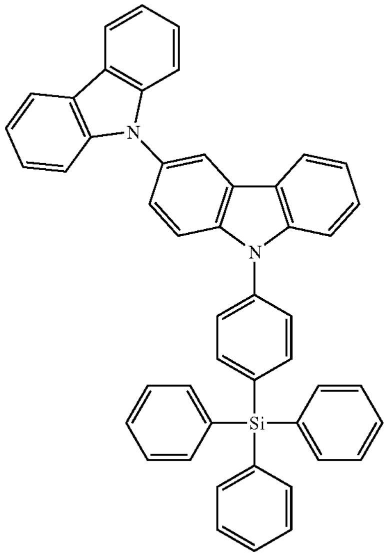,

-continued
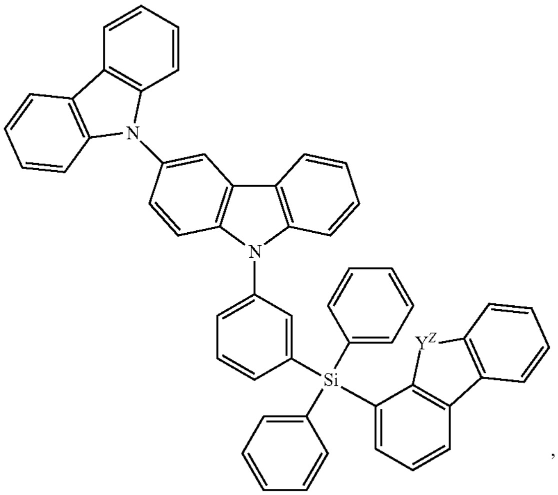
,
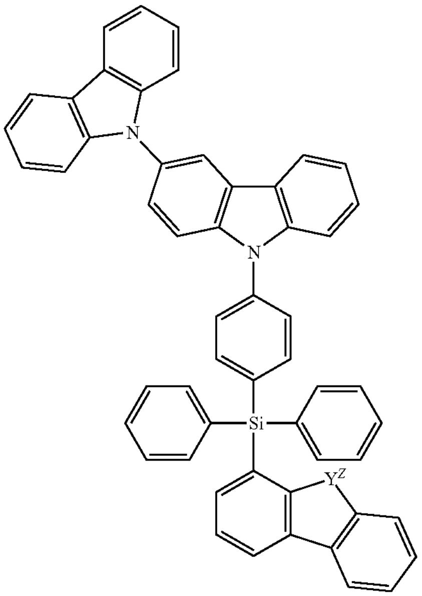
,
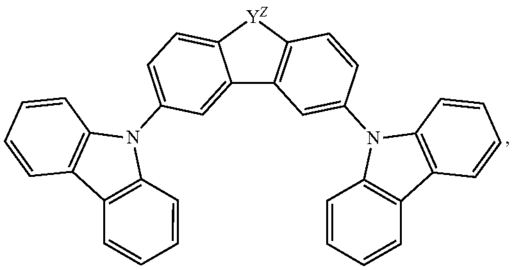
,
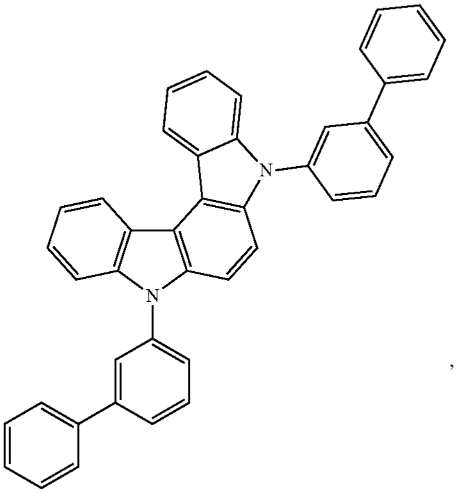
,
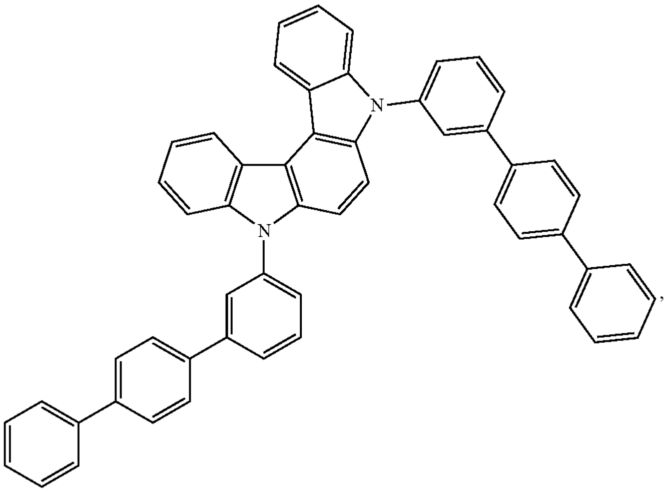
,
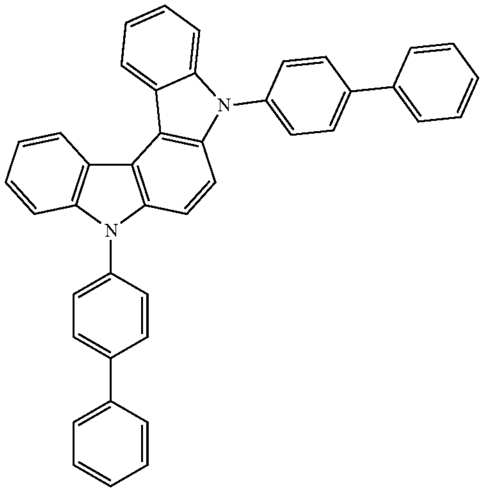
, -continued
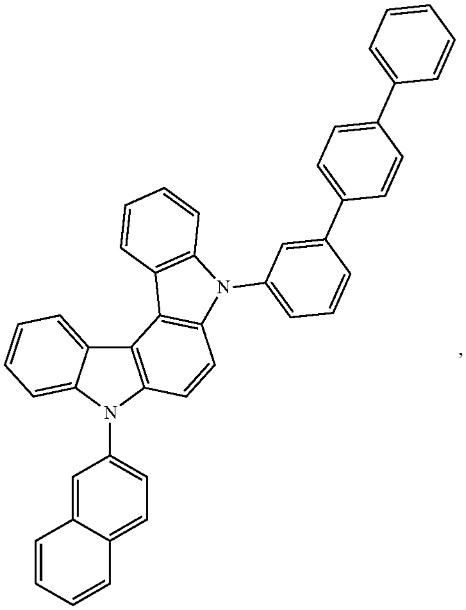
,
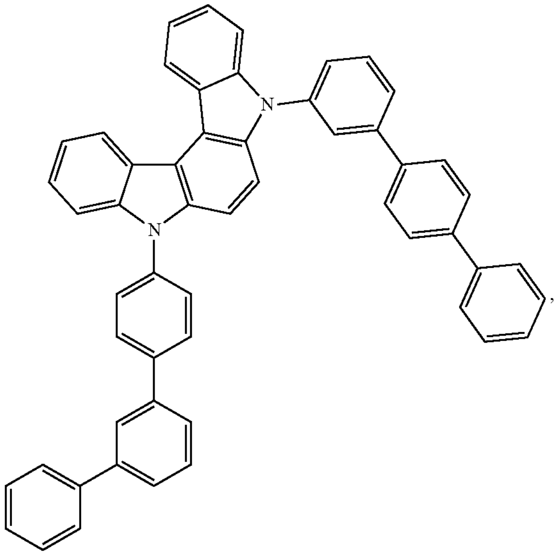
,
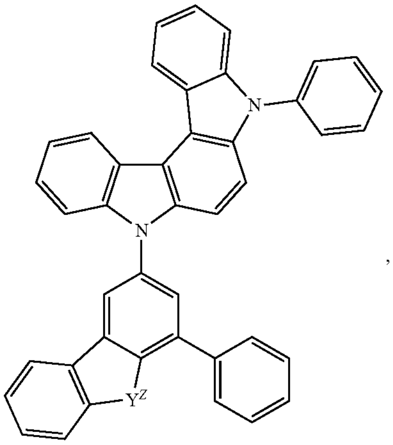
,
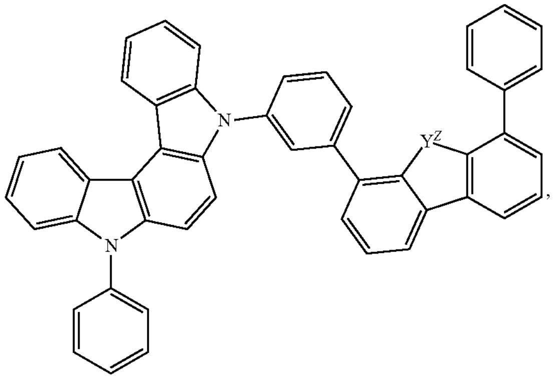
,
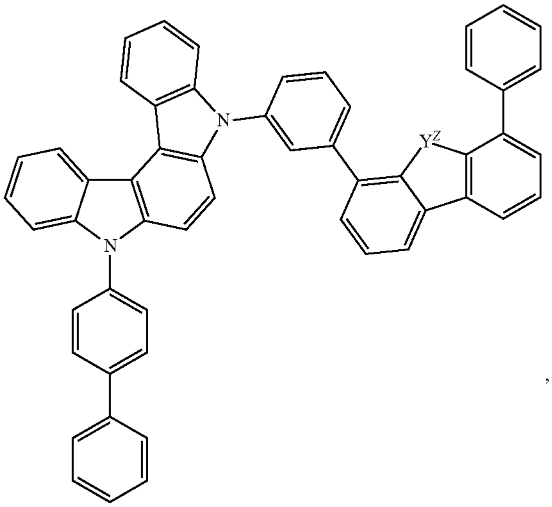
,
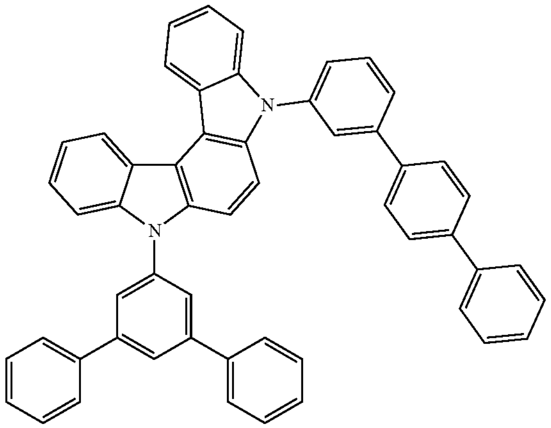
, -continued
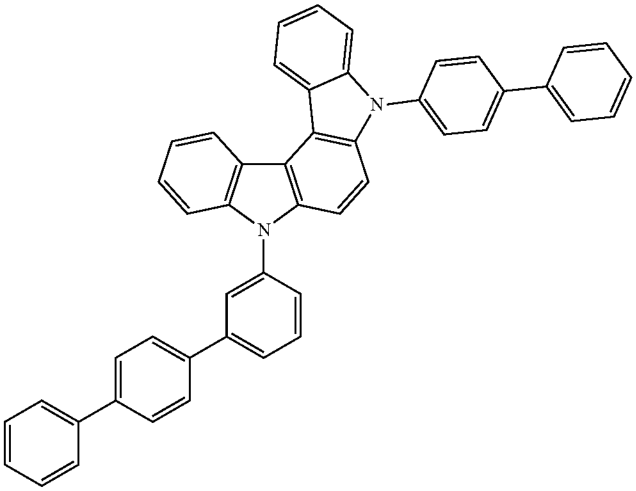
,
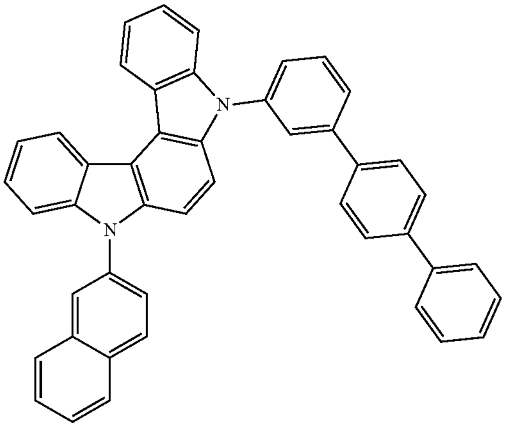
,
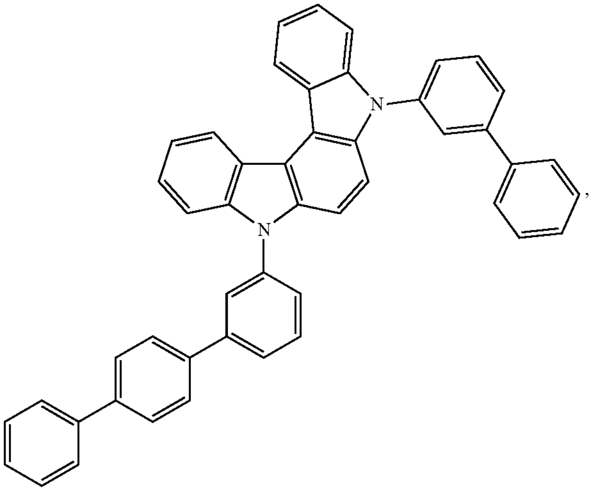
,
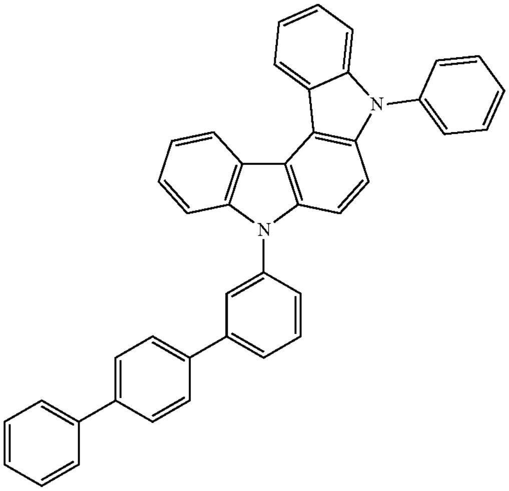
,
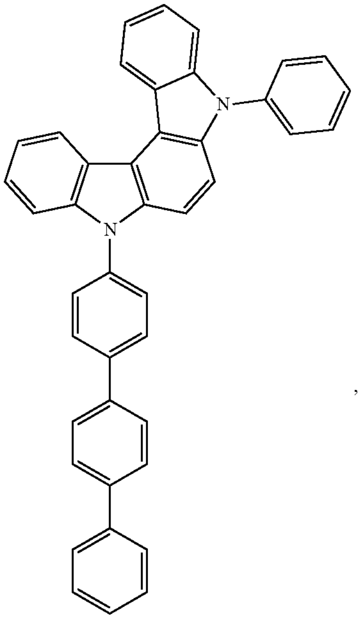
,
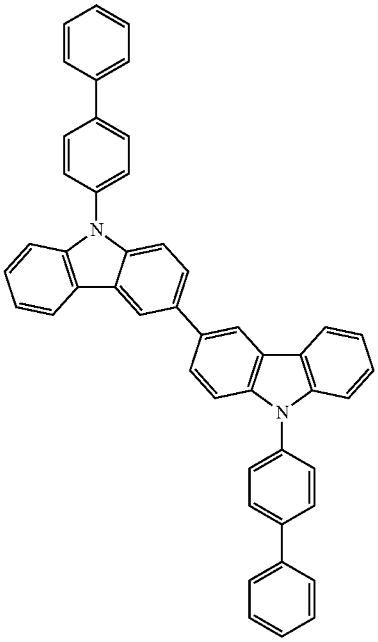
,
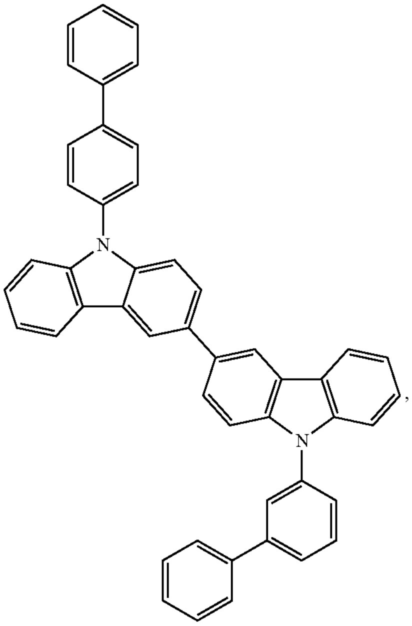
, -continued
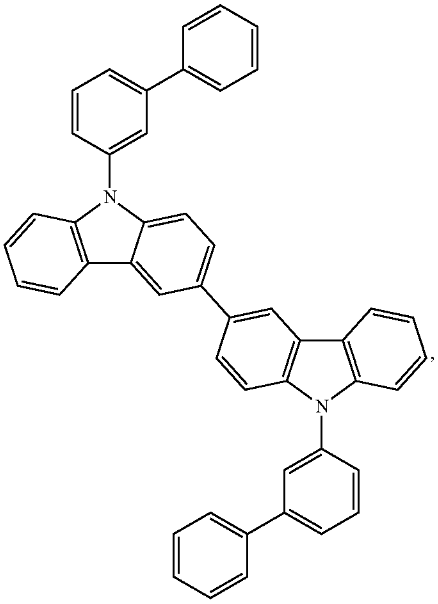
,
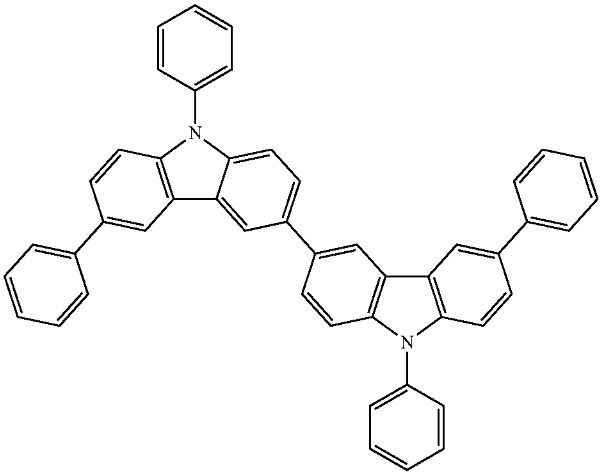
,
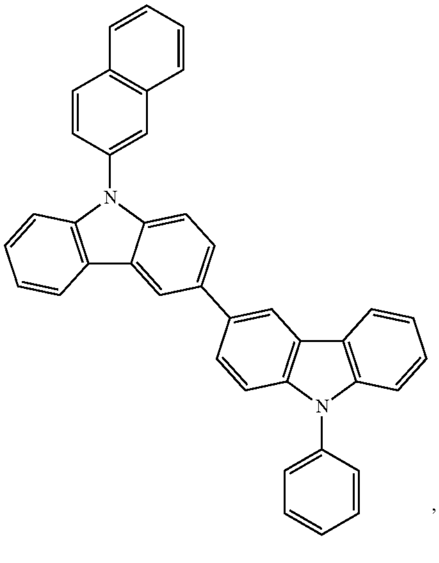
,
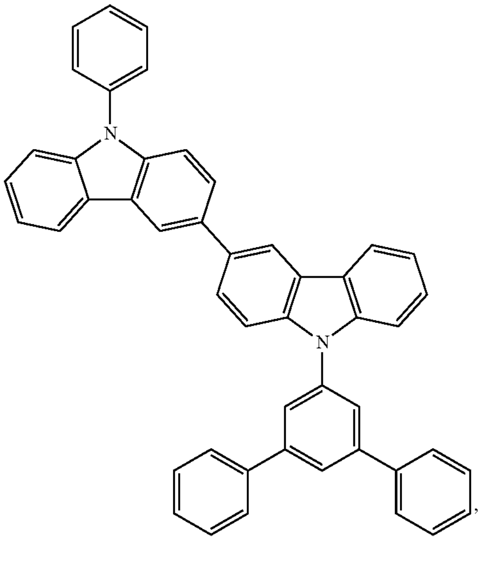
, -continued
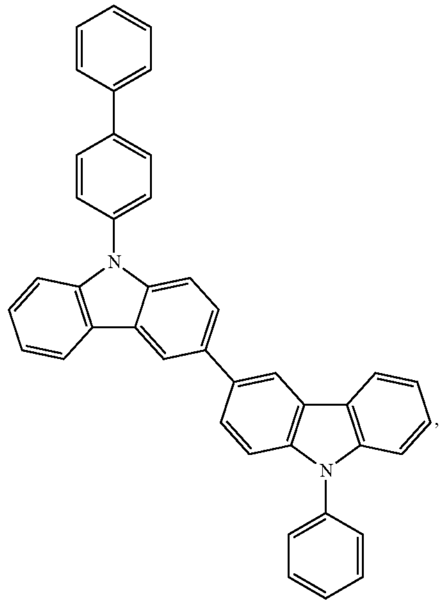
,
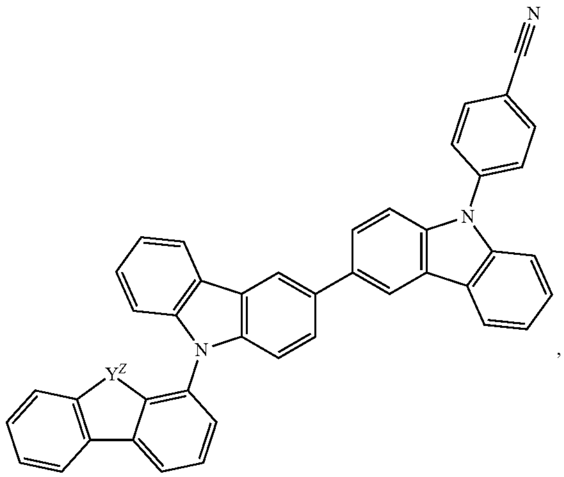
,
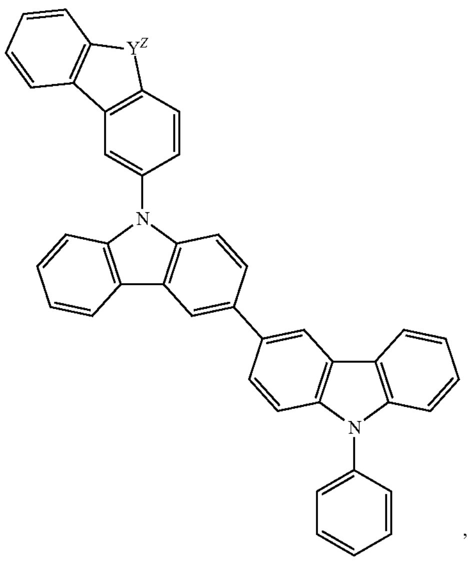
,
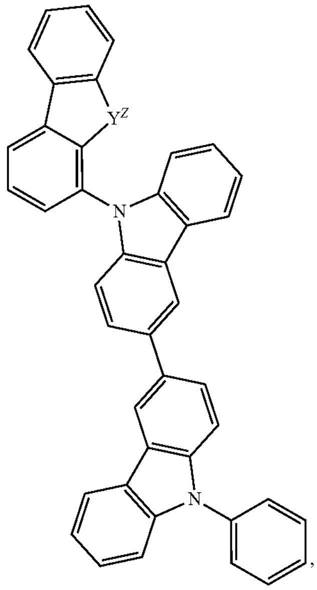
,
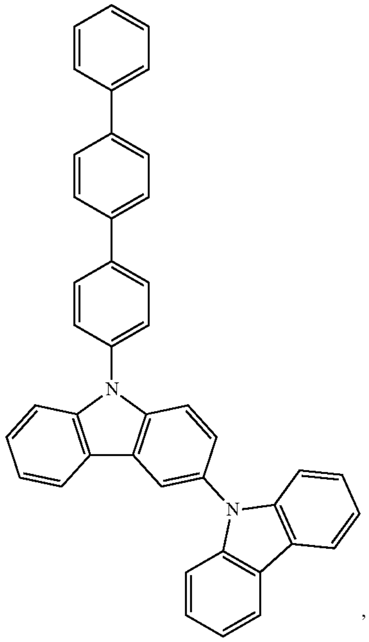
, -continued
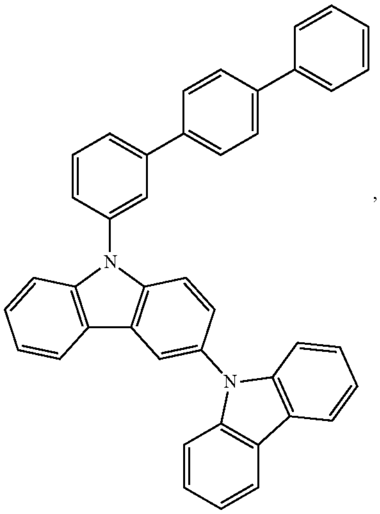
,
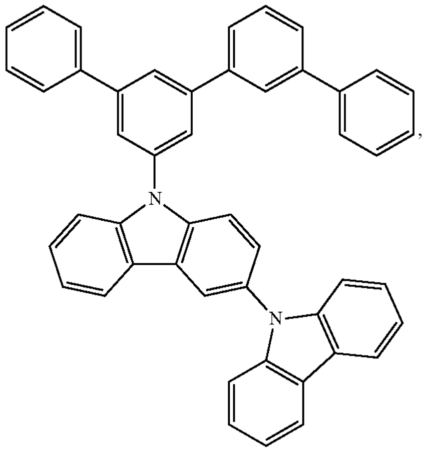
,
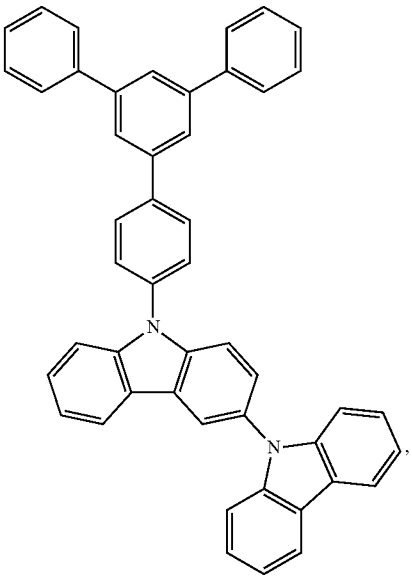
,
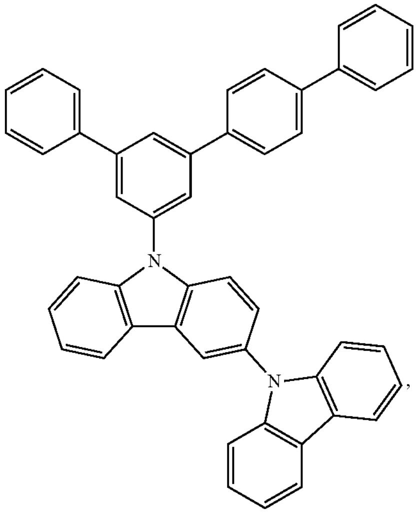
,
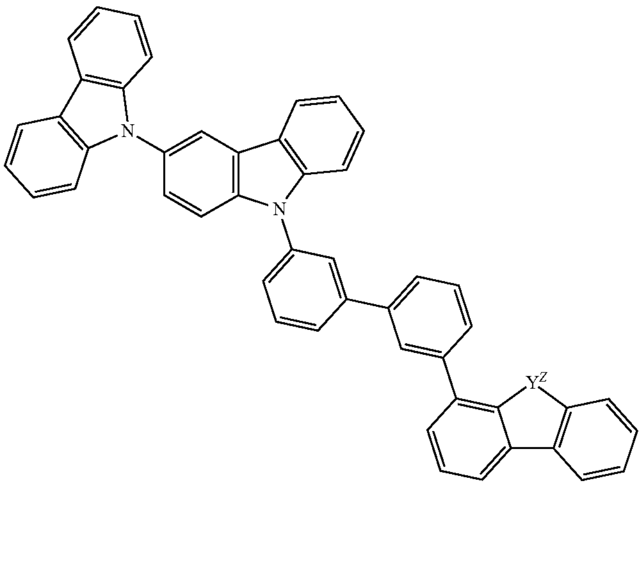
,
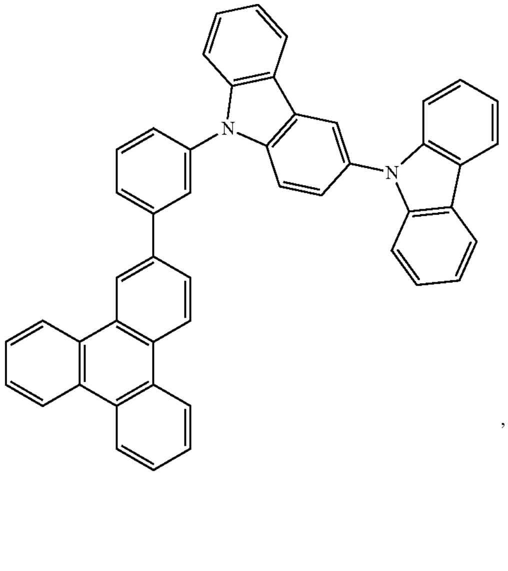
, -continued
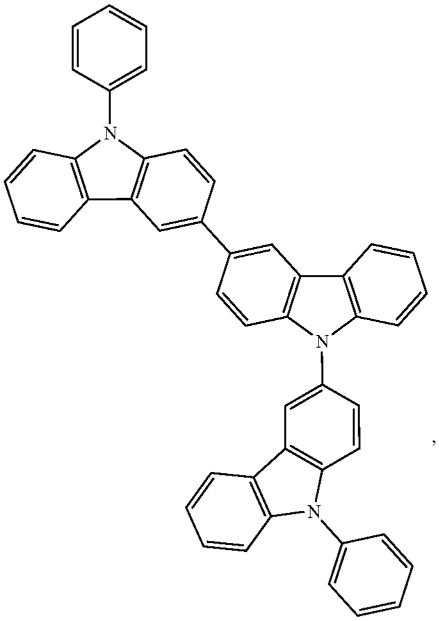
,
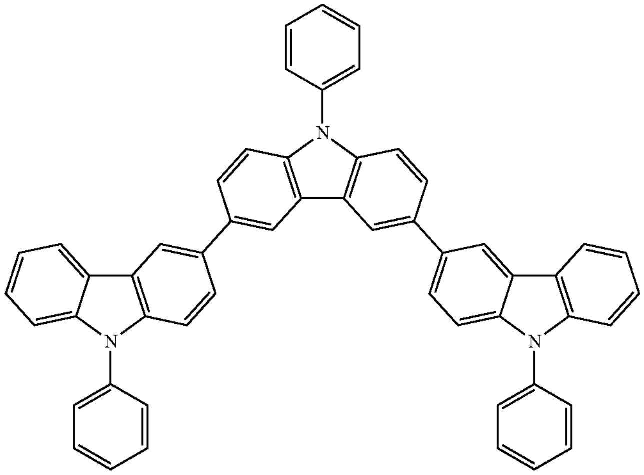
,
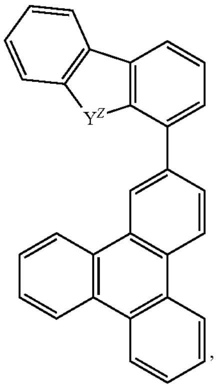
,
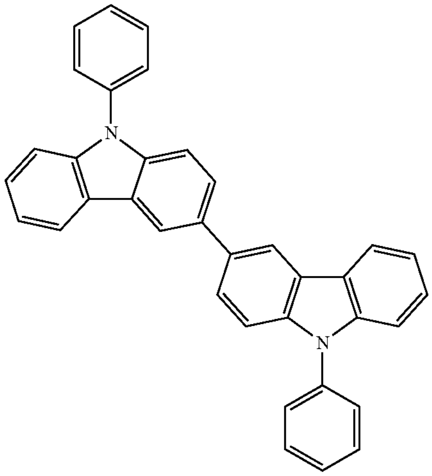
,
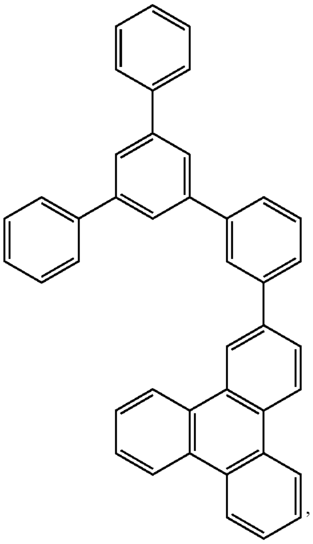
,
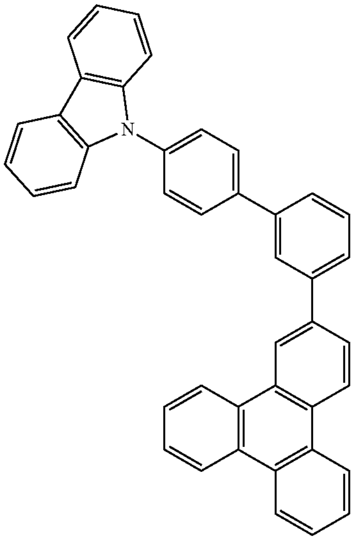
,
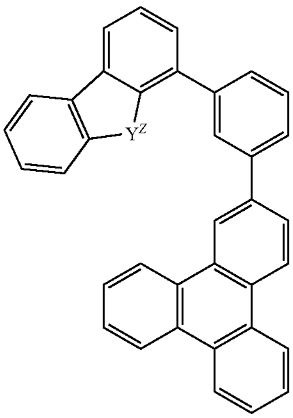
,
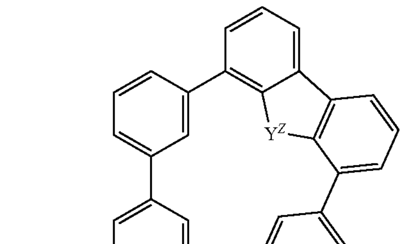
, -continued
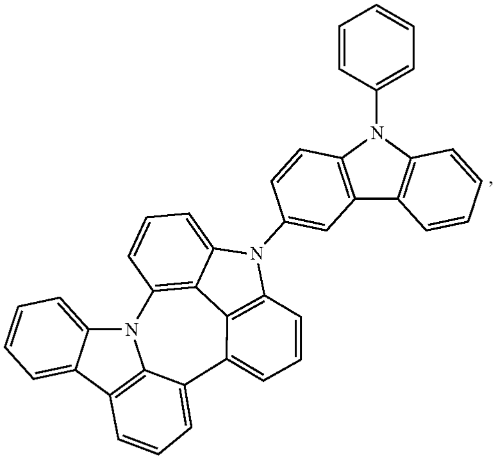,
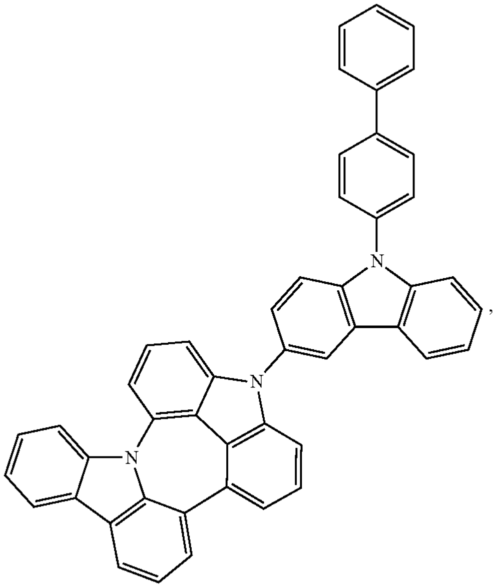,
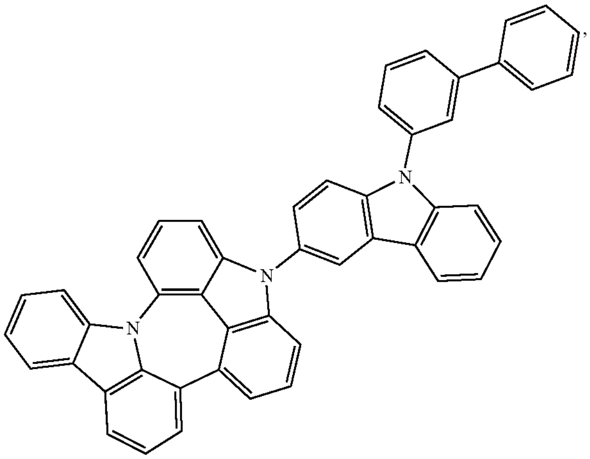,
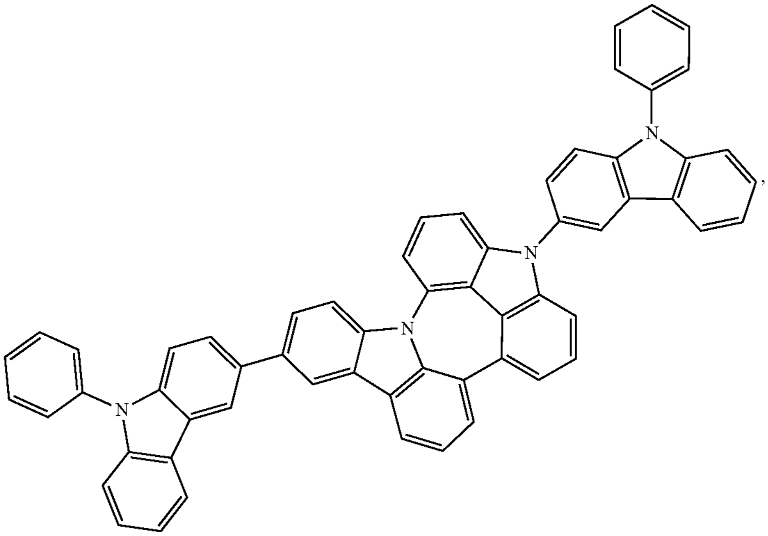, -continued
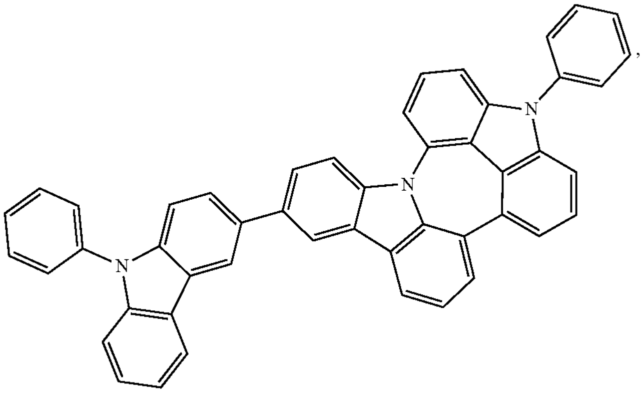
,
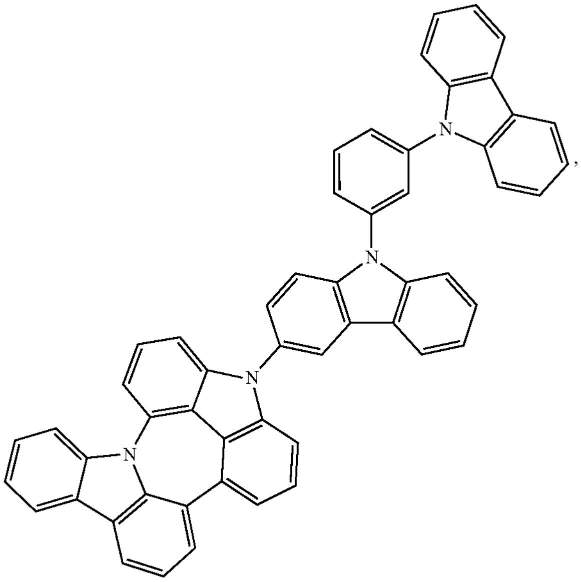
,
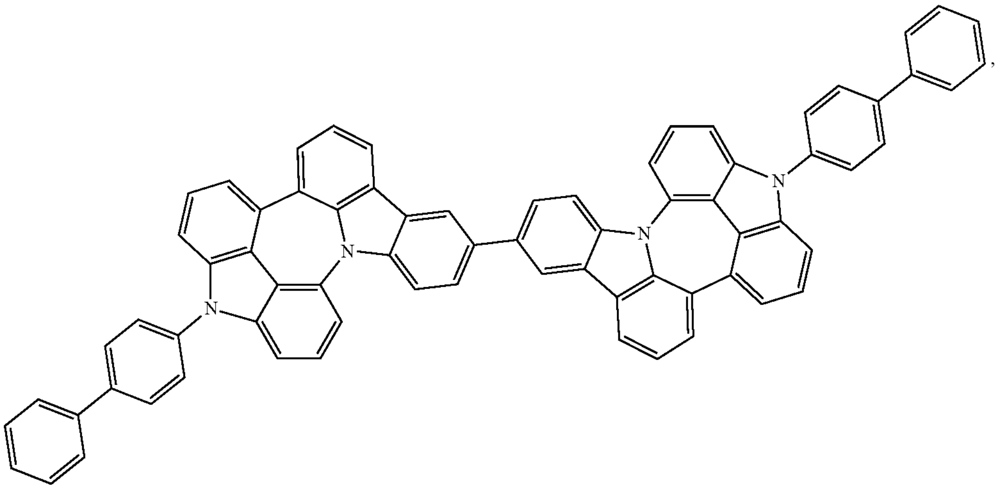
, -continued
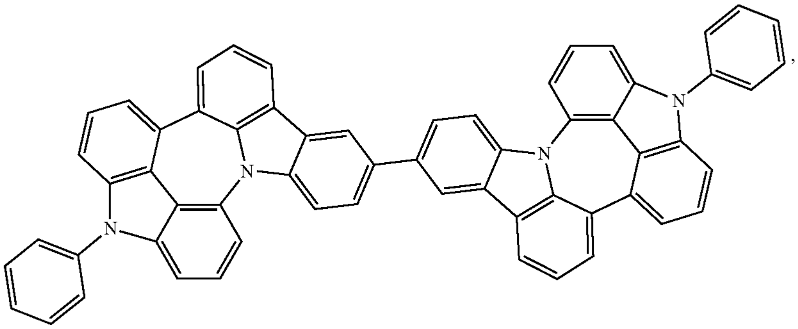
,
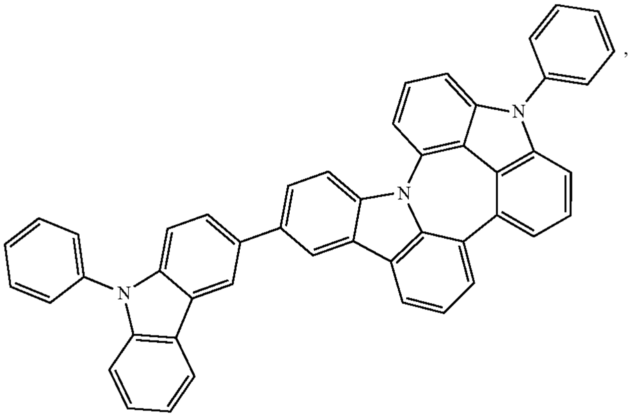
,
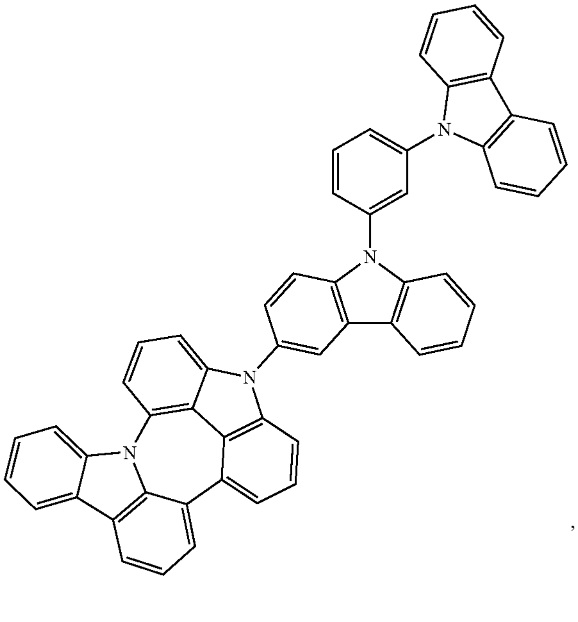
, and
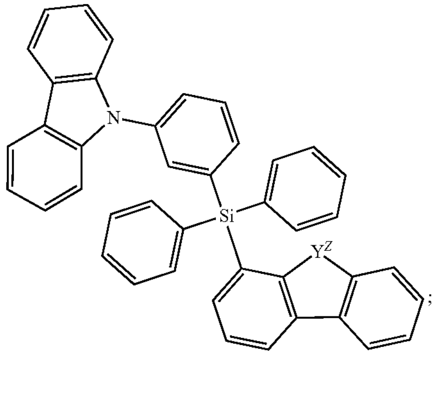
;

wherein:
$Y^Z$ is selected from the group consisting of O, S, and N-phenyl; and
the first host is at least partially deuterated.
10. The OLED of claim 9, wherein at least 50% of the hydrogen atoms are replaced with deuterium.
11. The OLED of claim 1, wherein the first host is selected from the group consisting of:
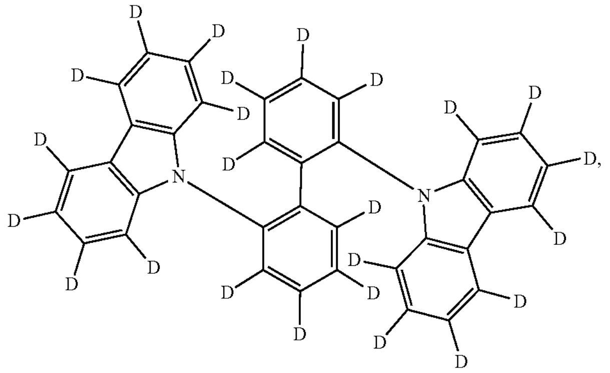
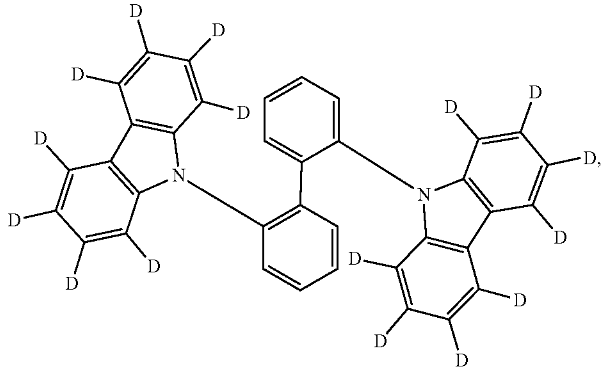
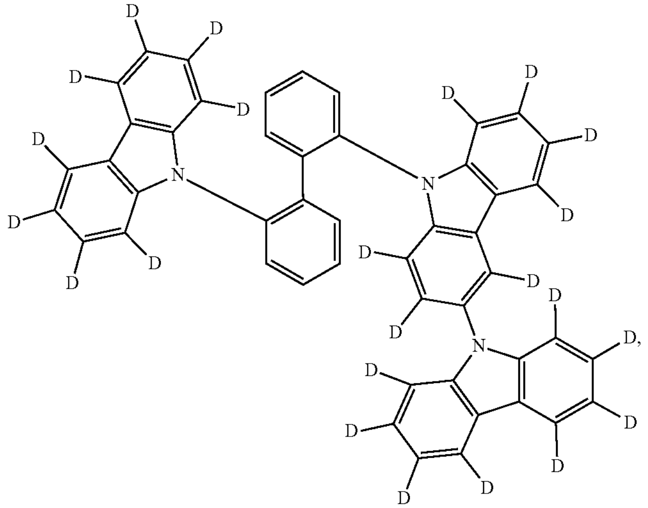

-continued
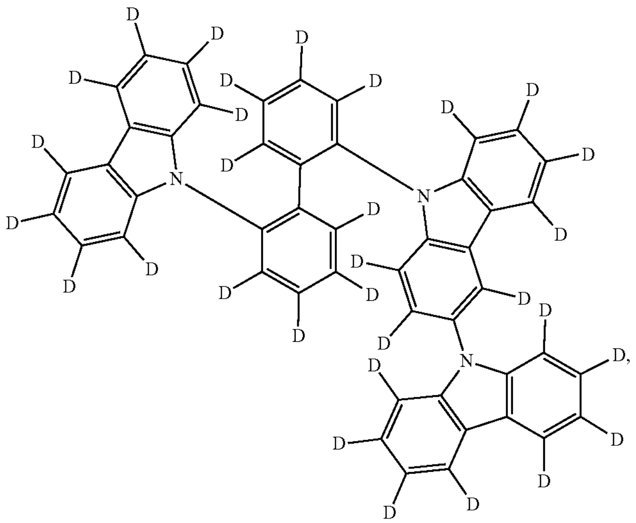
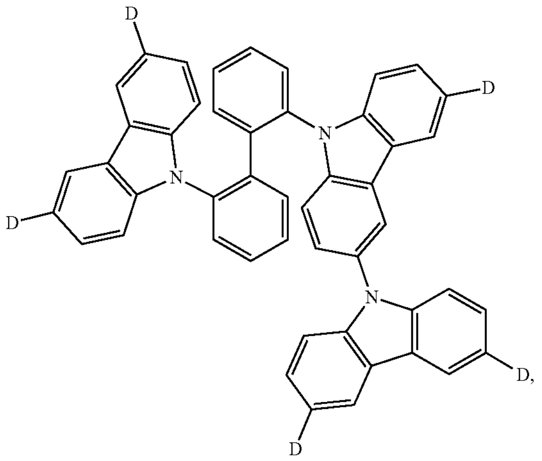
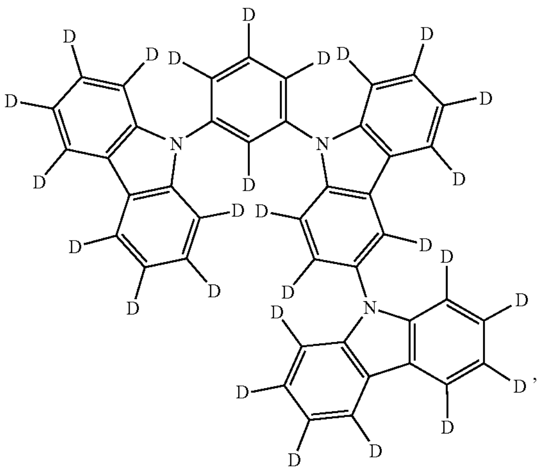
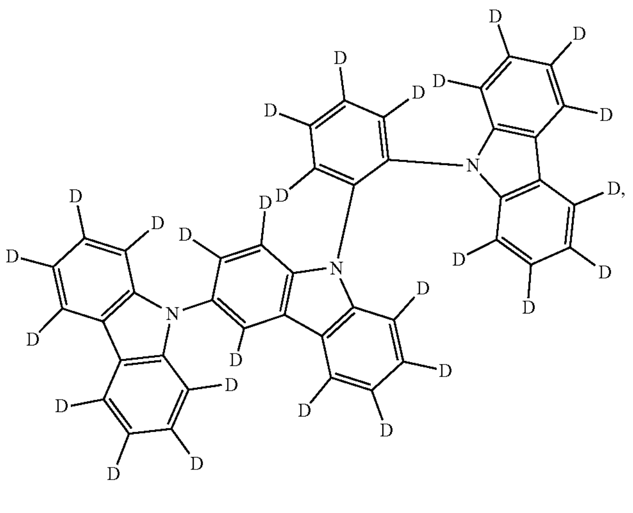

-continued
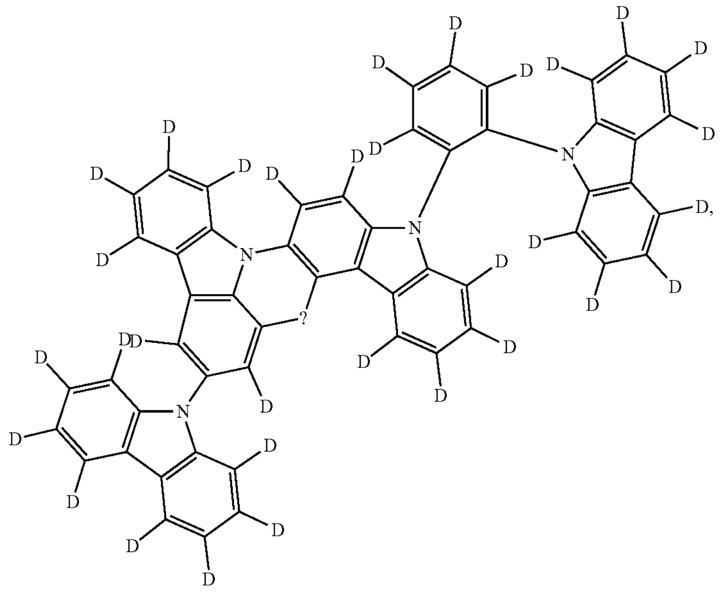
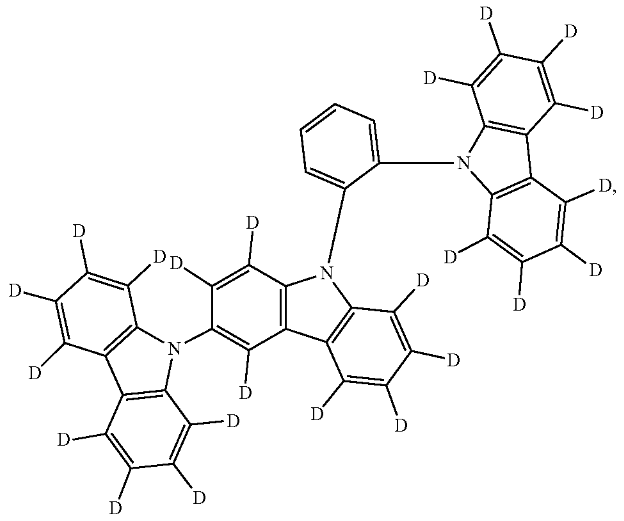
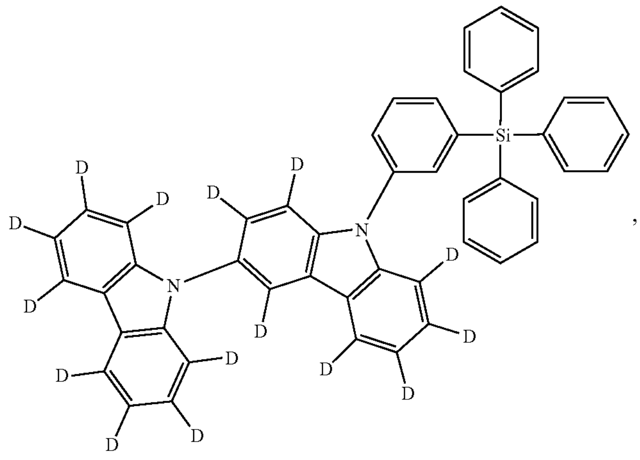
,

-continued
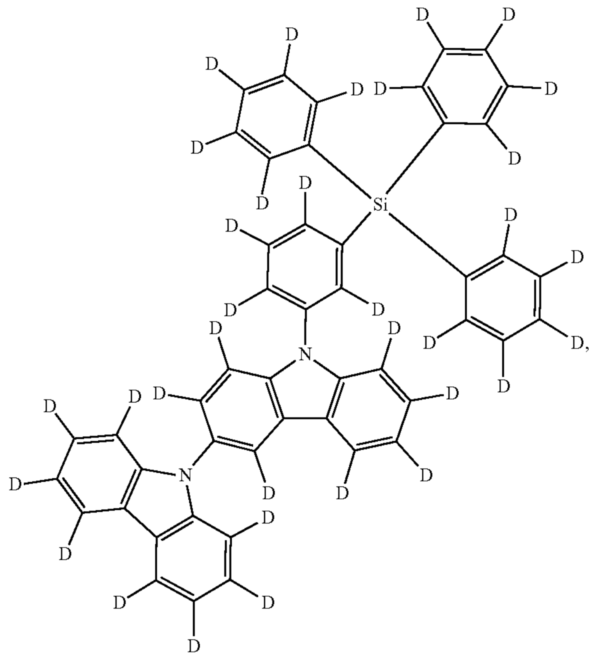
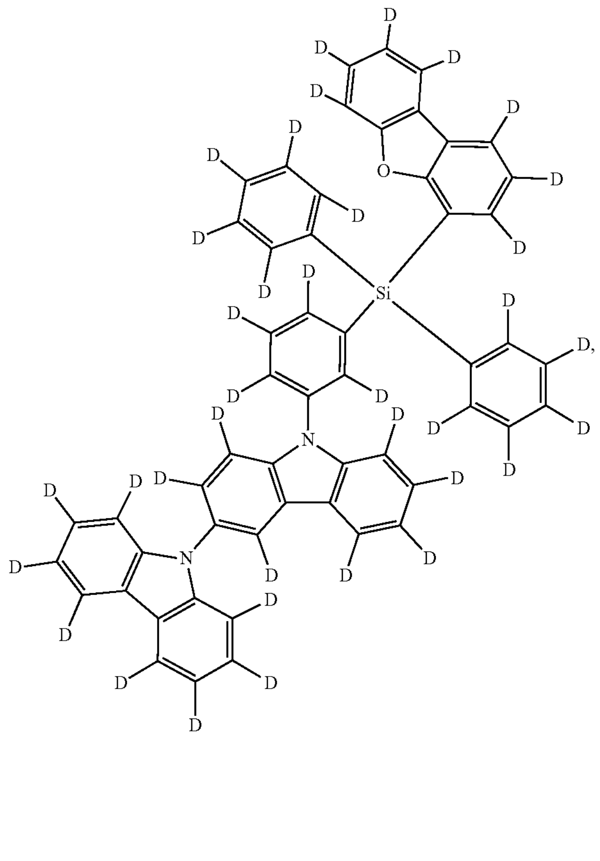
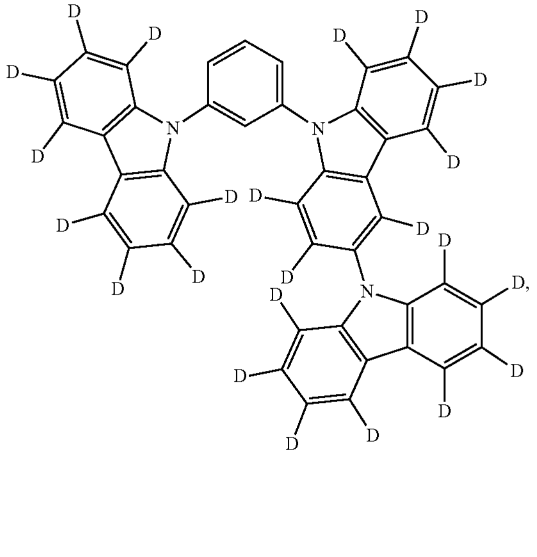

-continued
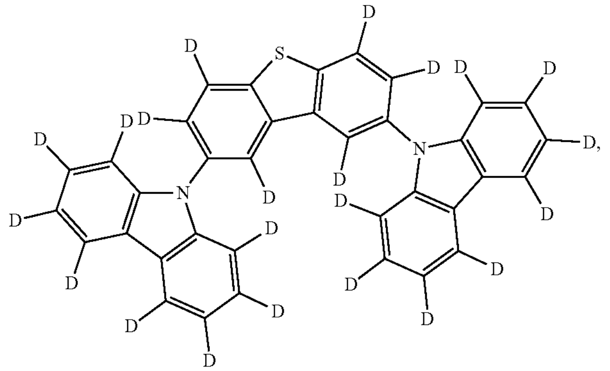
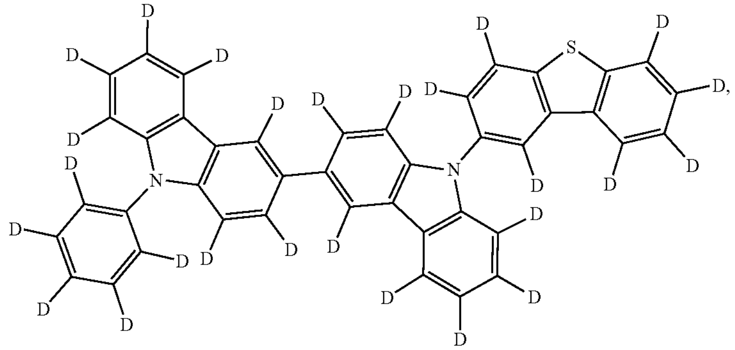
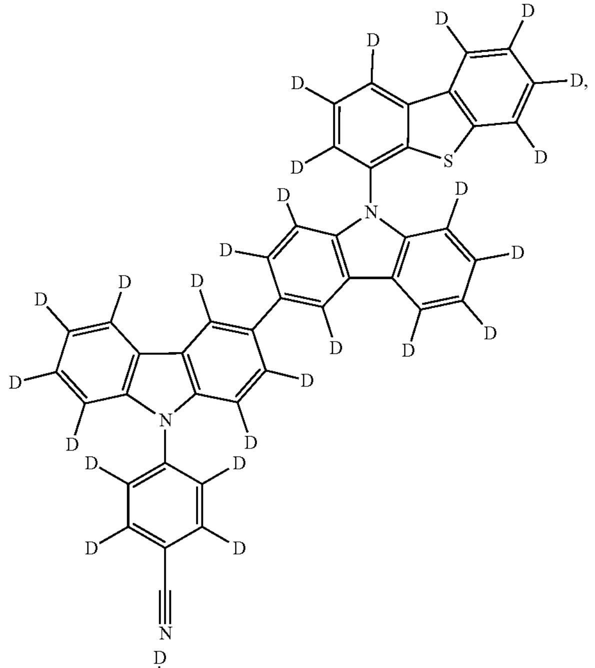
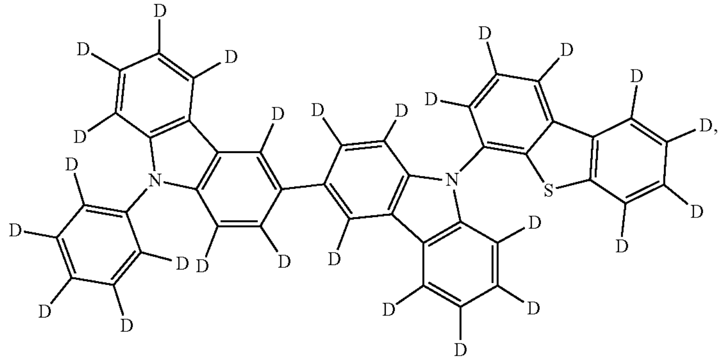

-continued
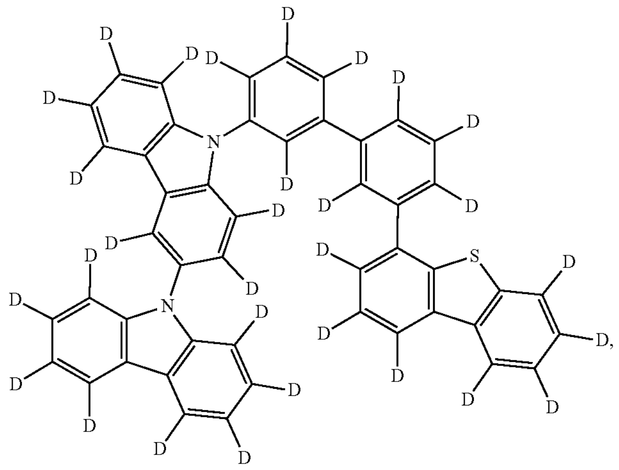
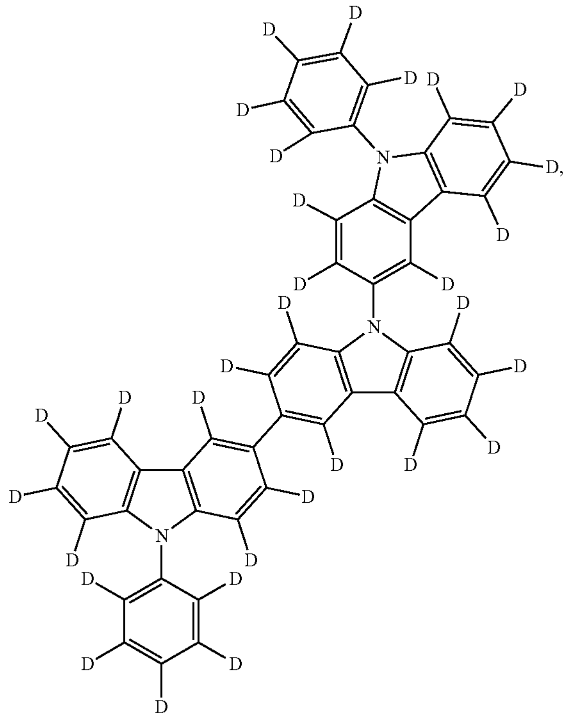

-continued
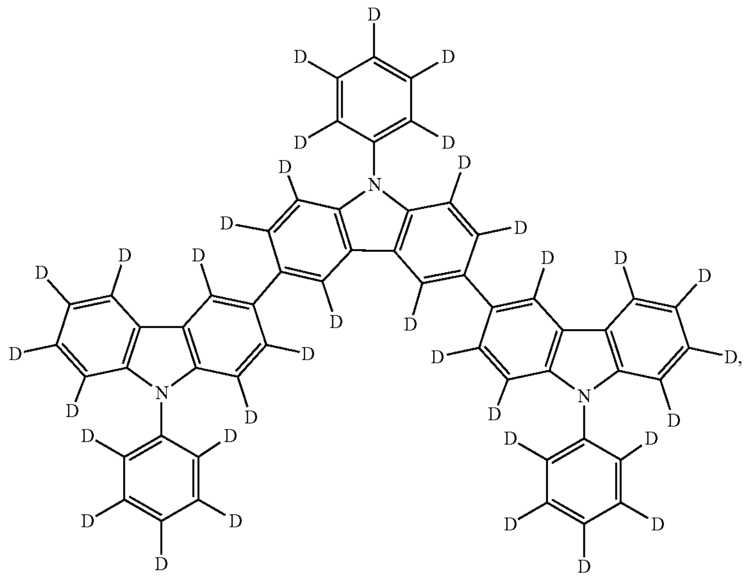
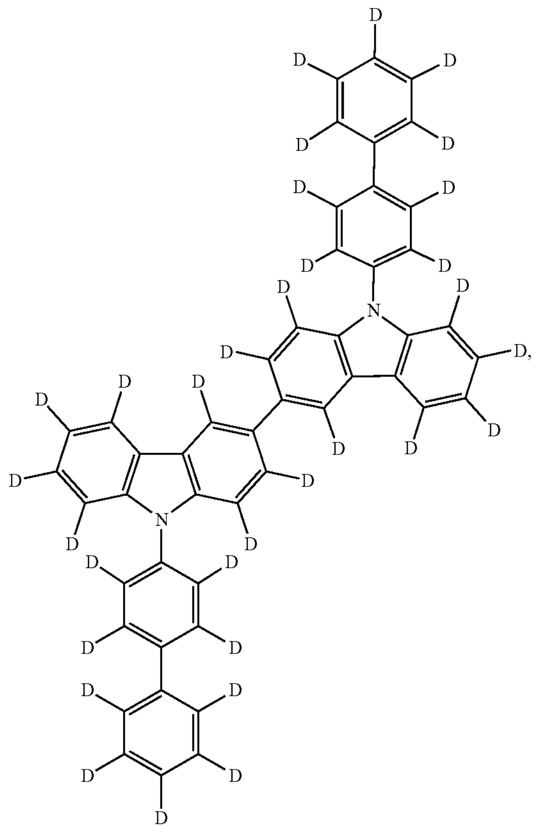
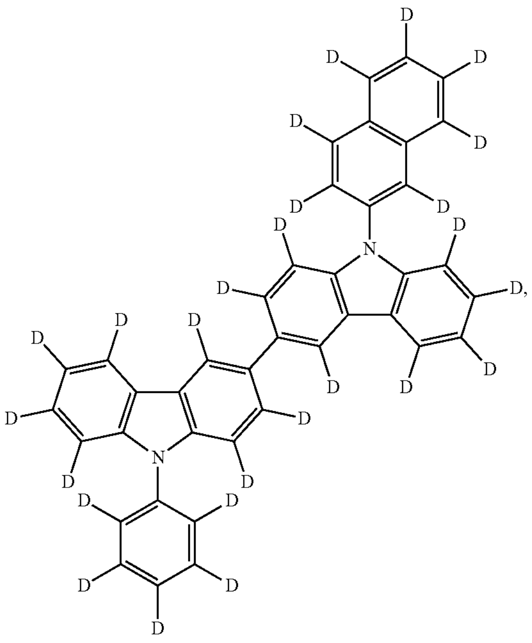

-continued
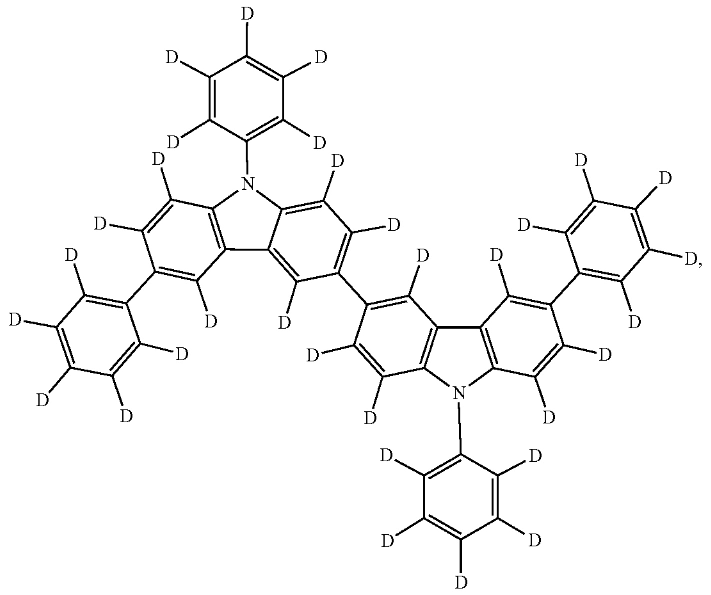
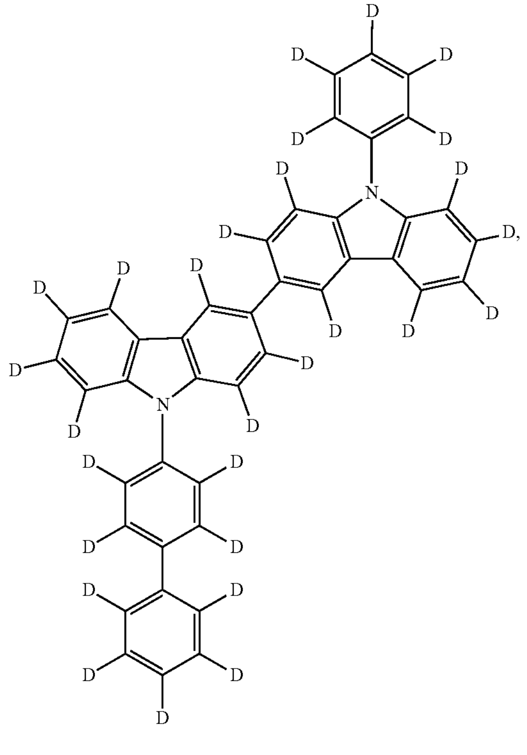
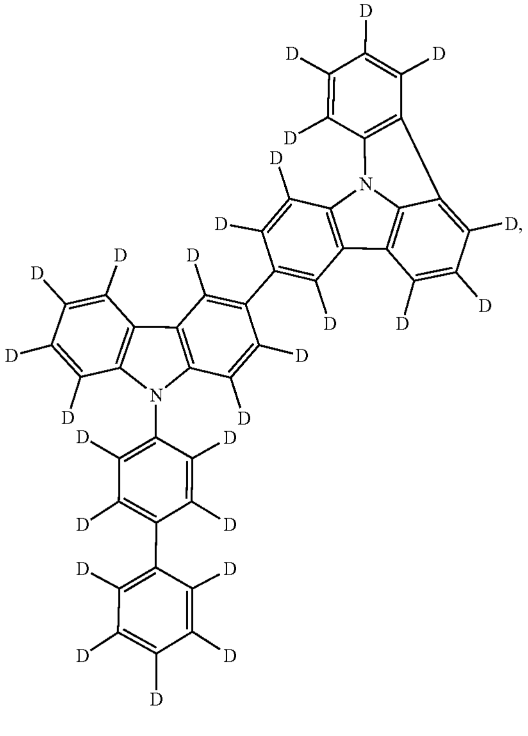

-continued
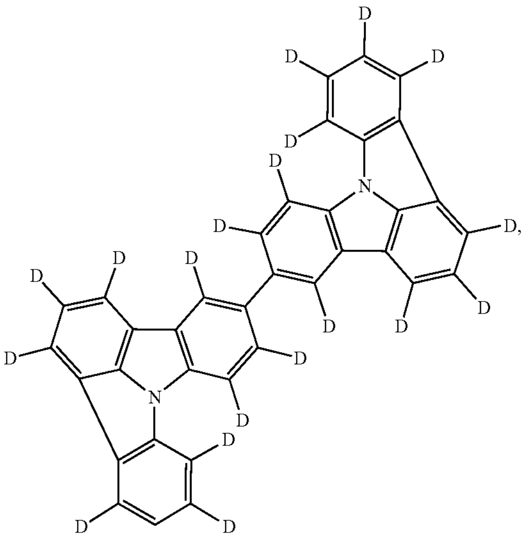
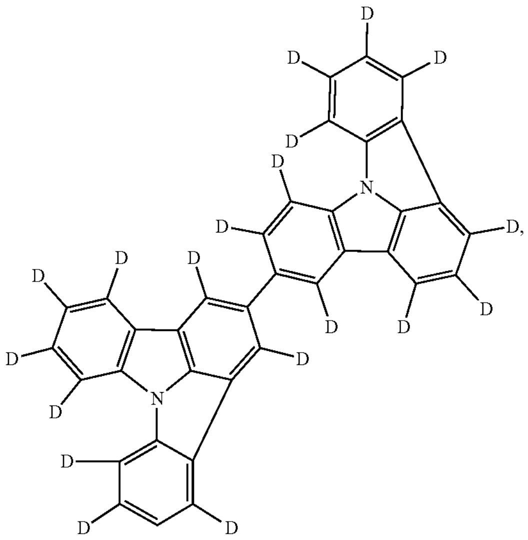
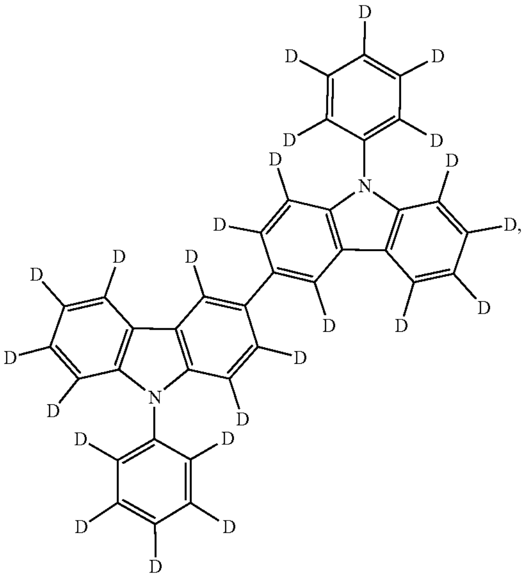
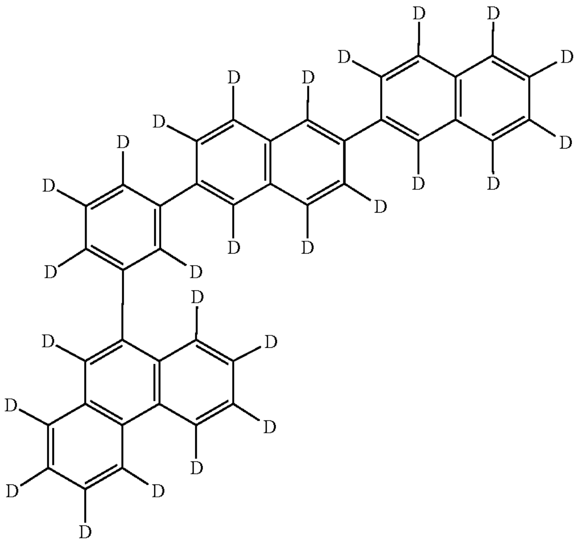
,
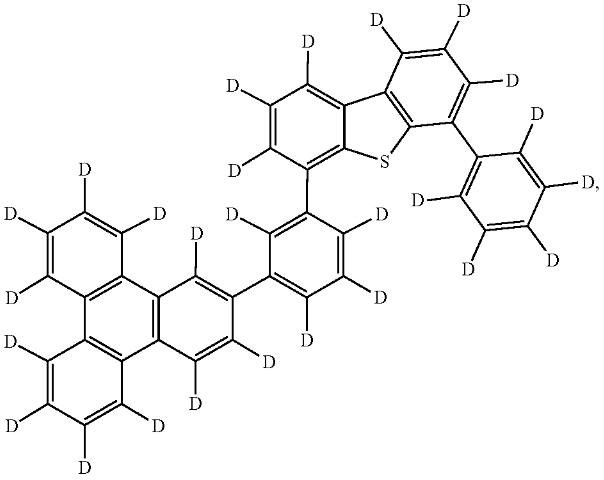

-continued
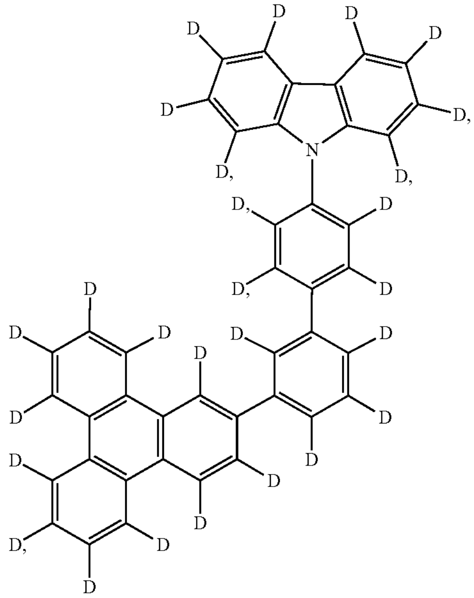
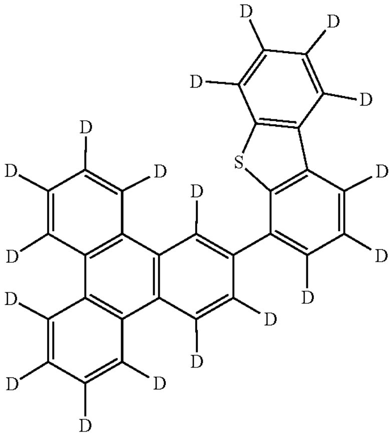
,
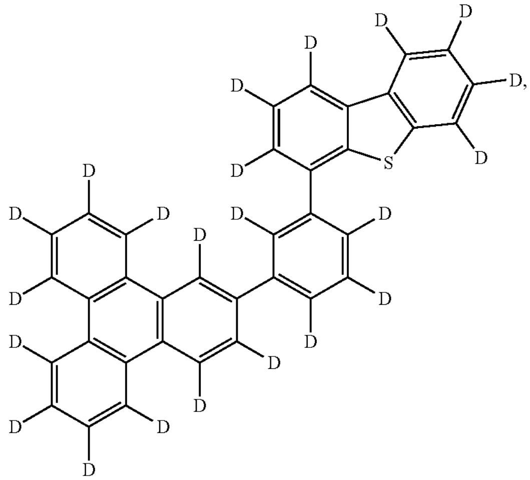
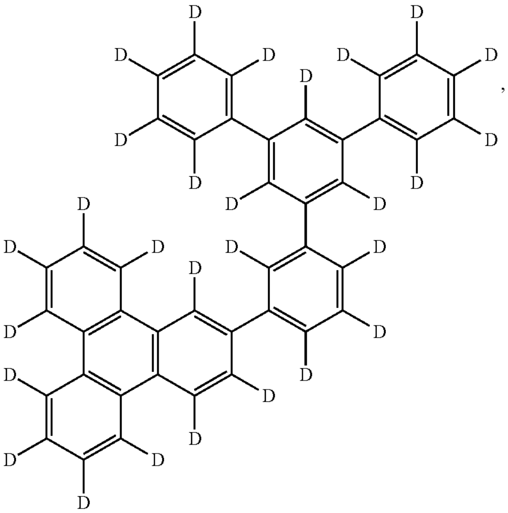
,
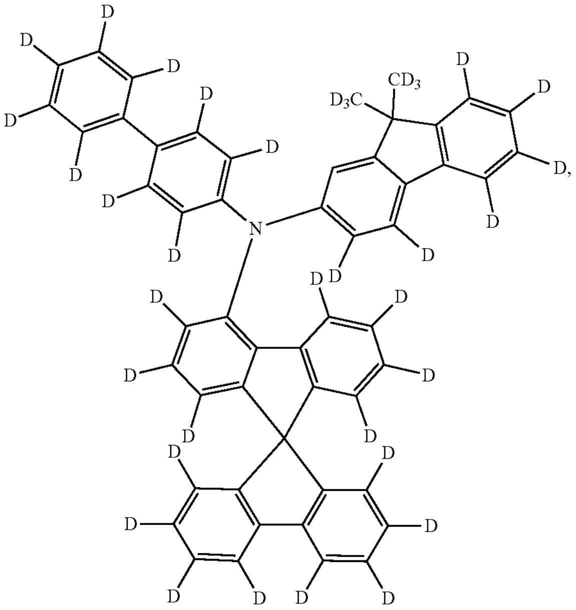
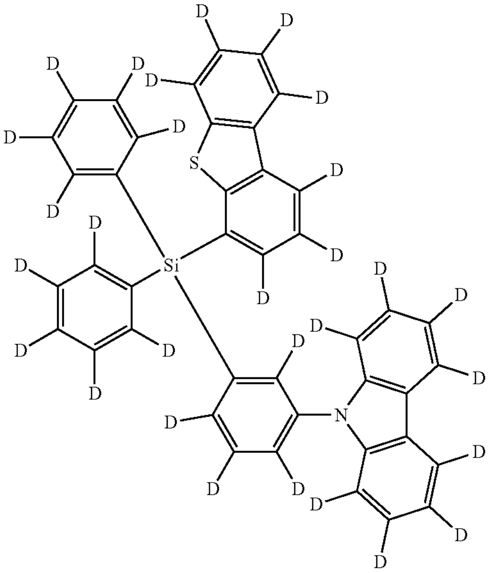
, -continued
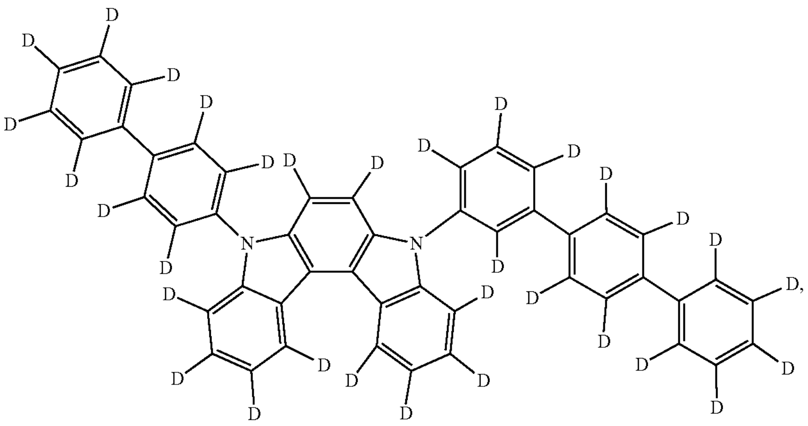
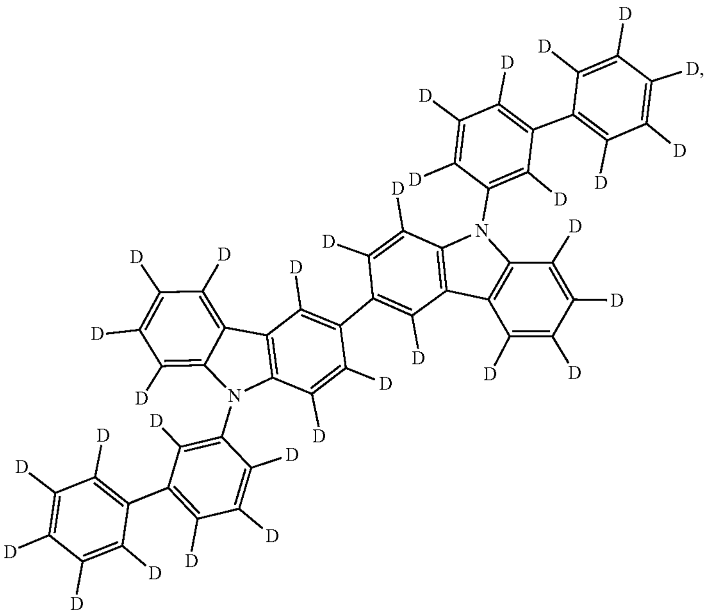

-continued
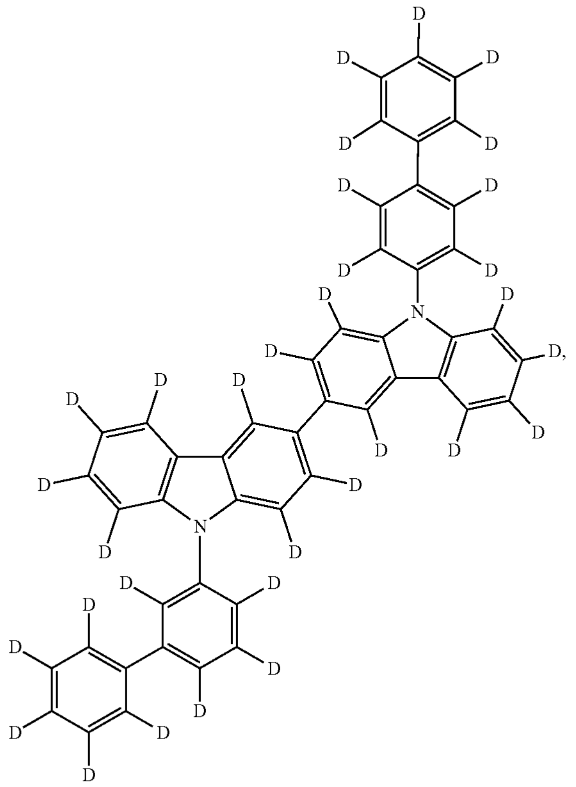
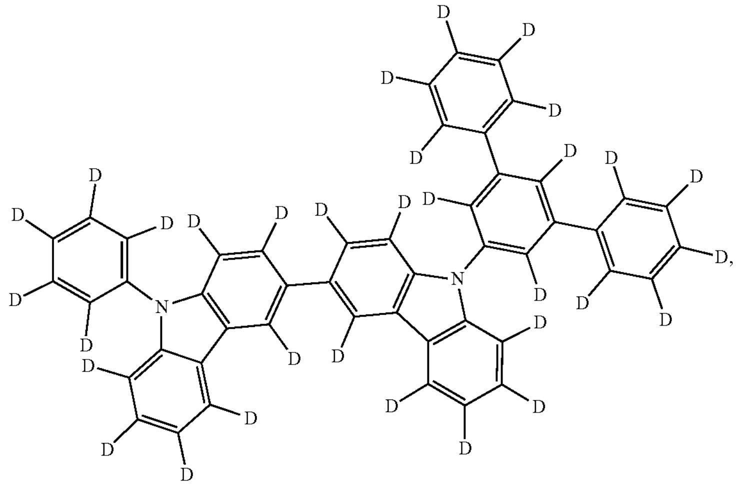

-continued
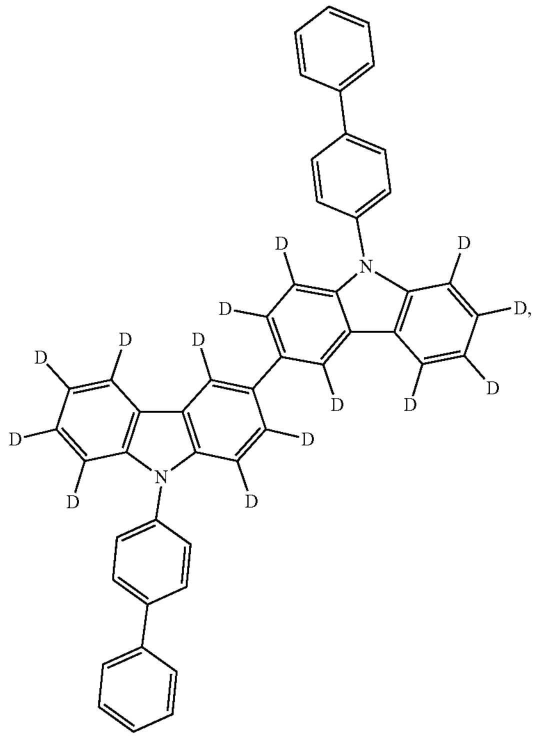
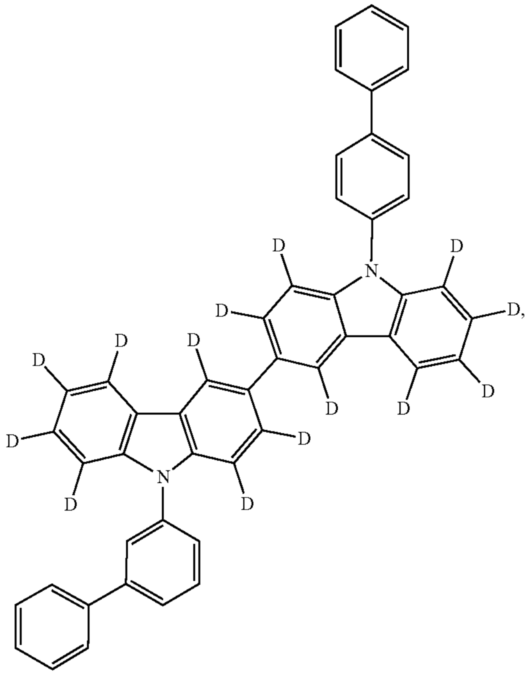
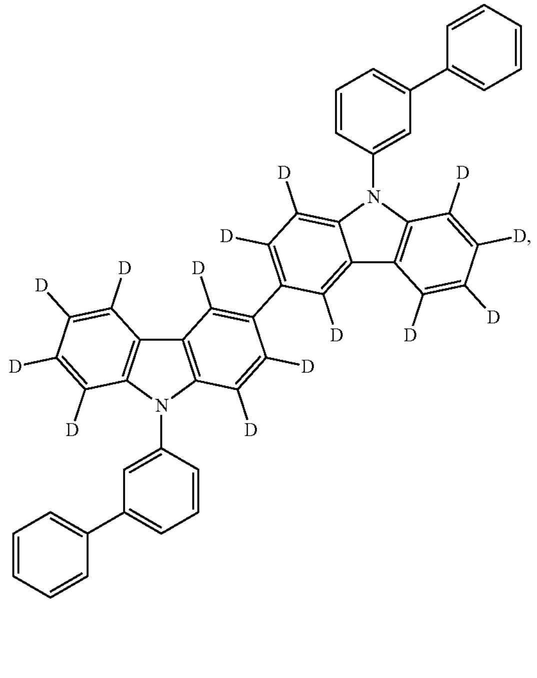
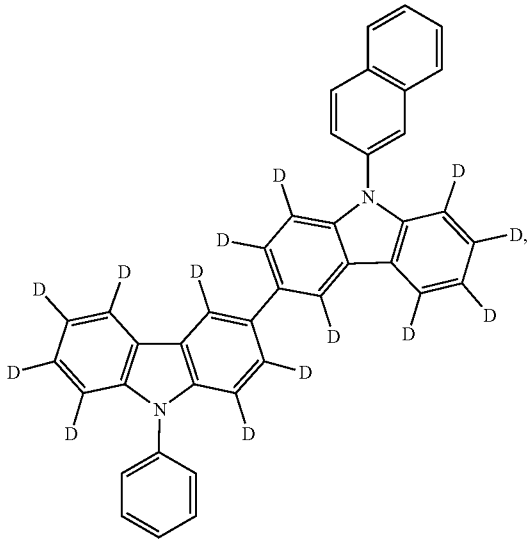

-continued
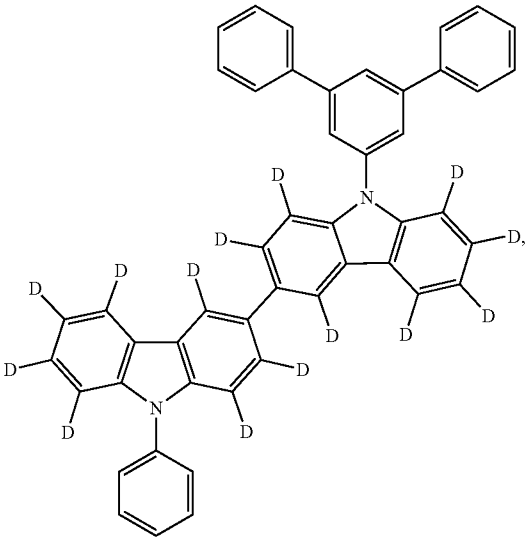
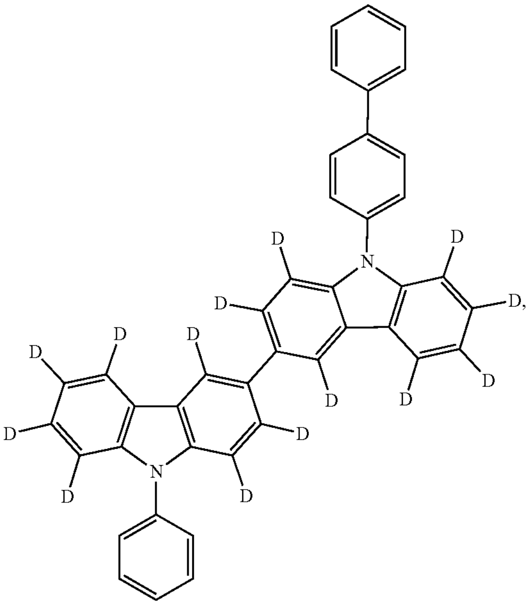
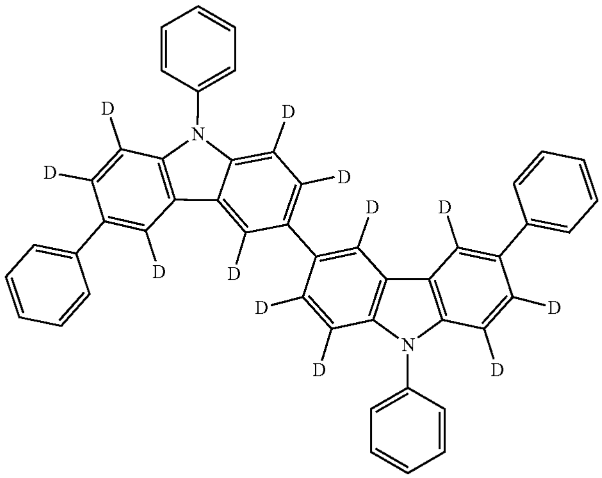
,
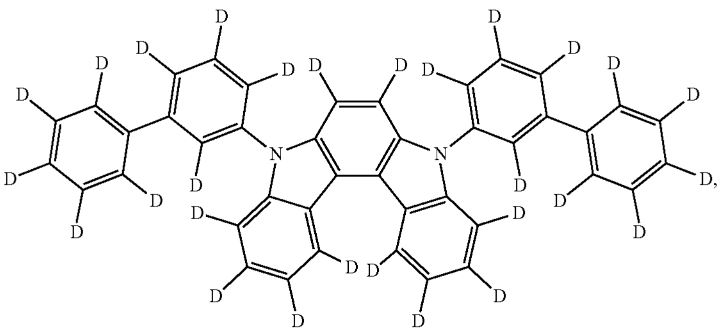

-continued
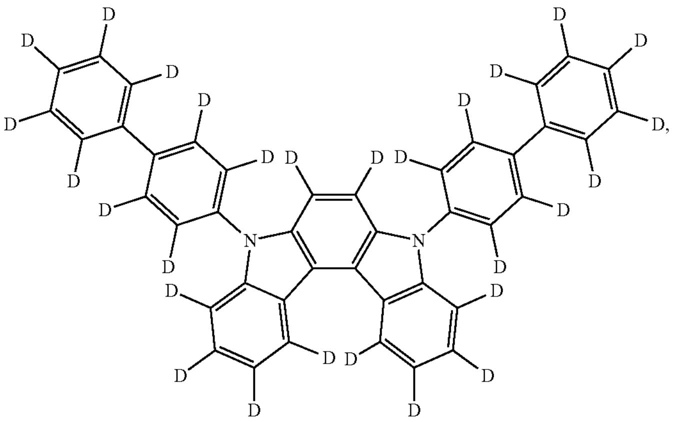
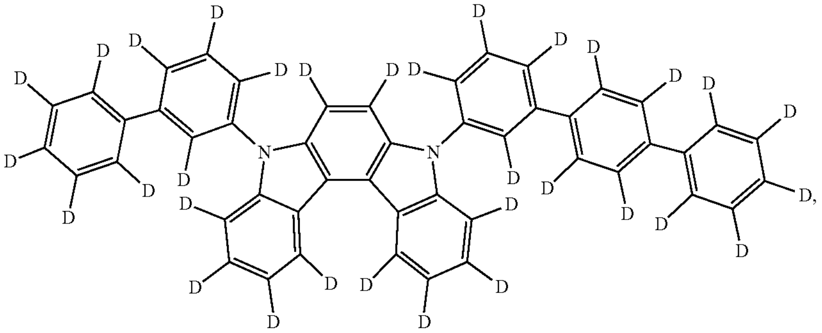
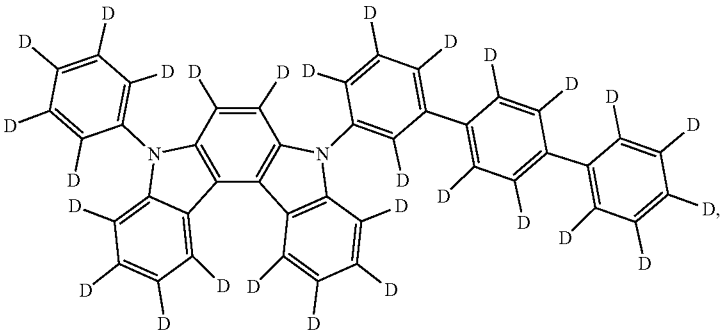
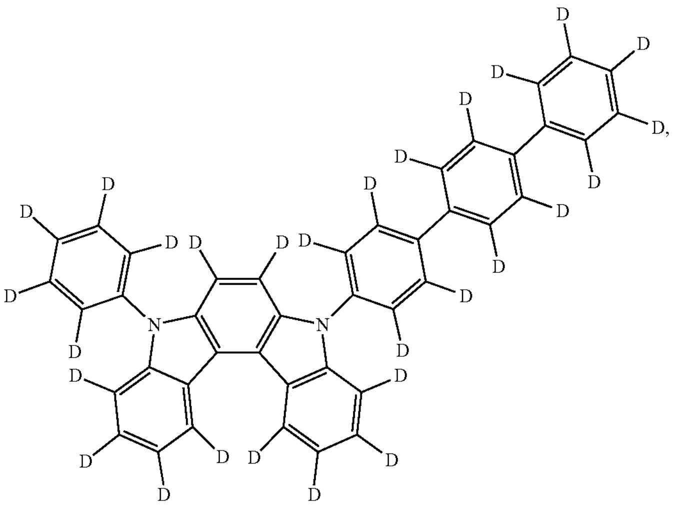

-continued
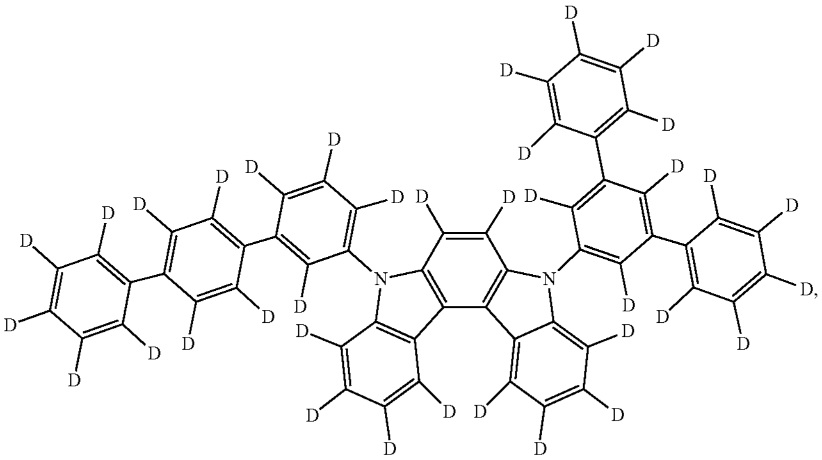
,
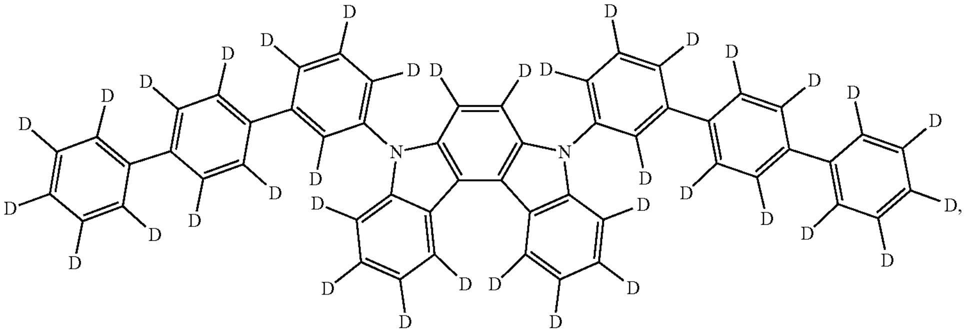
,
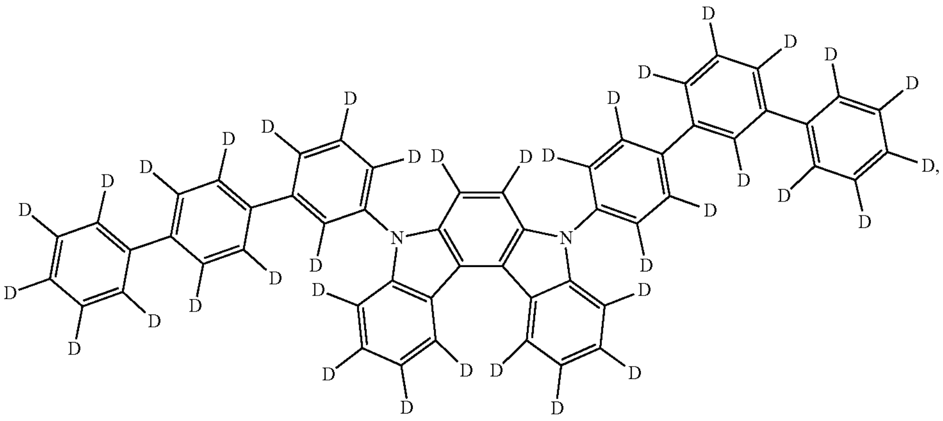
,
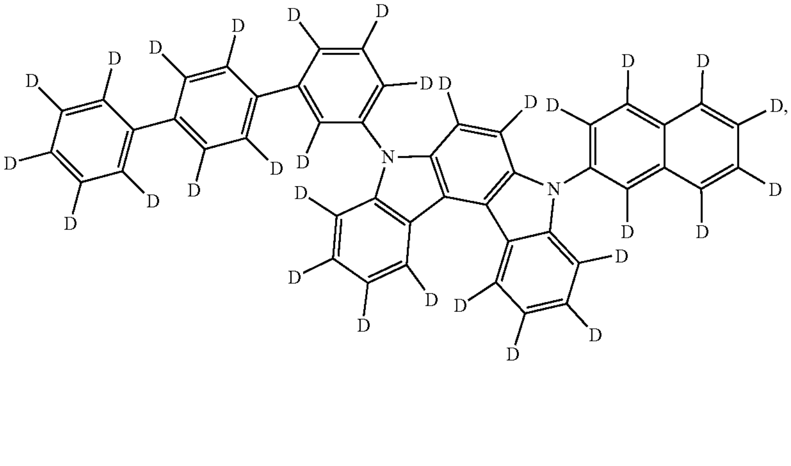
,

-continued
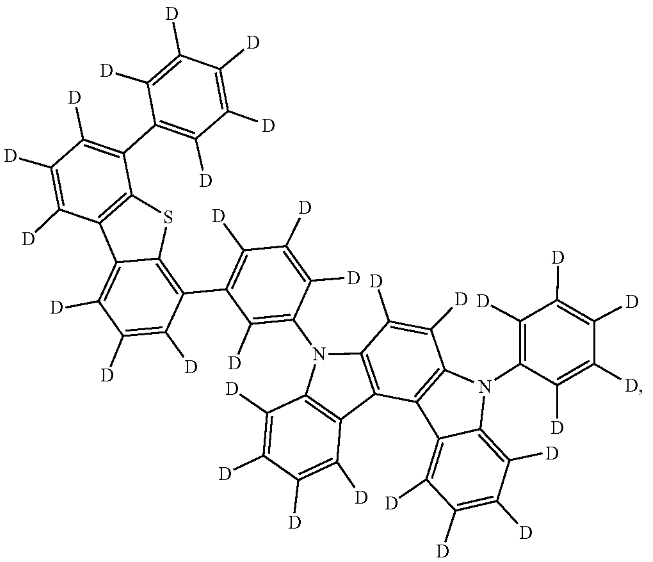
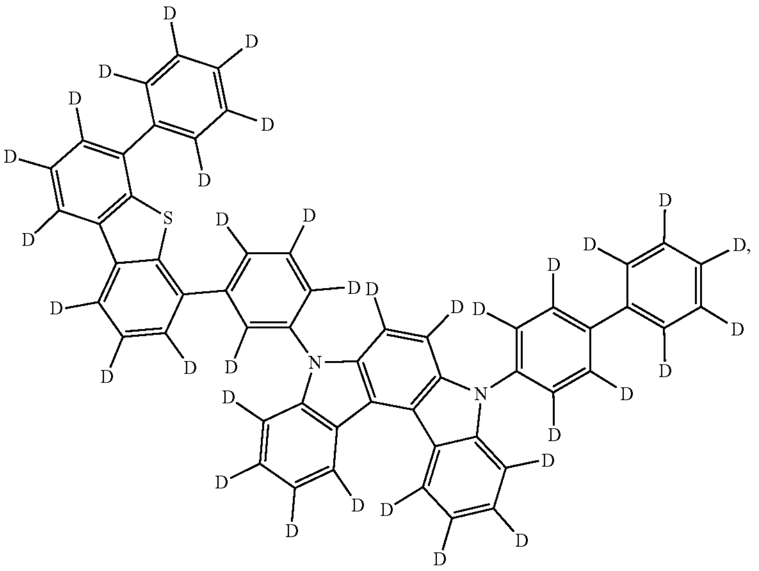

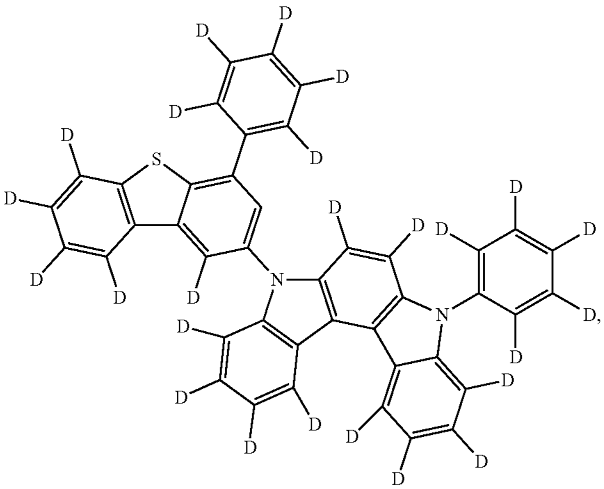
,
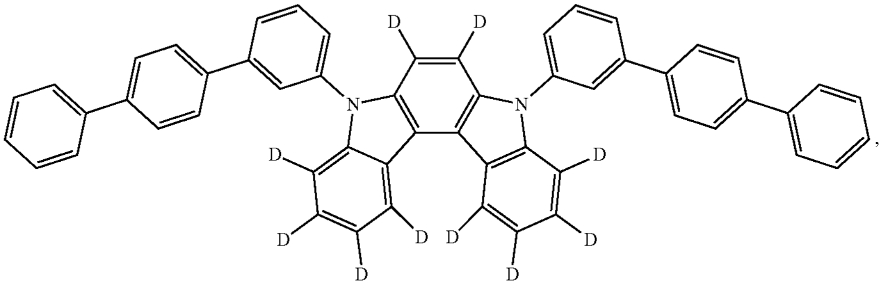
,
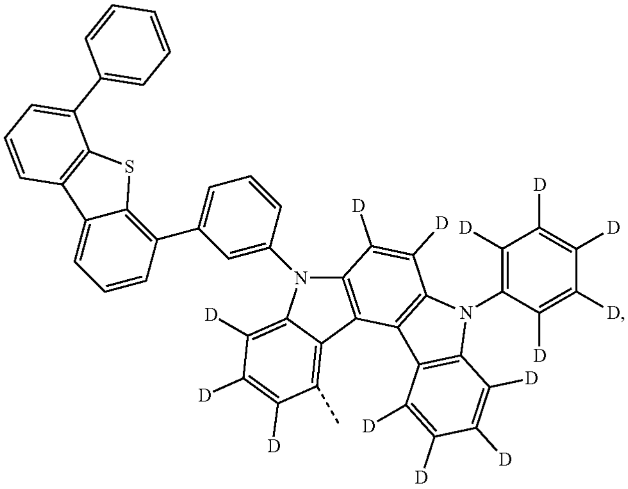
,
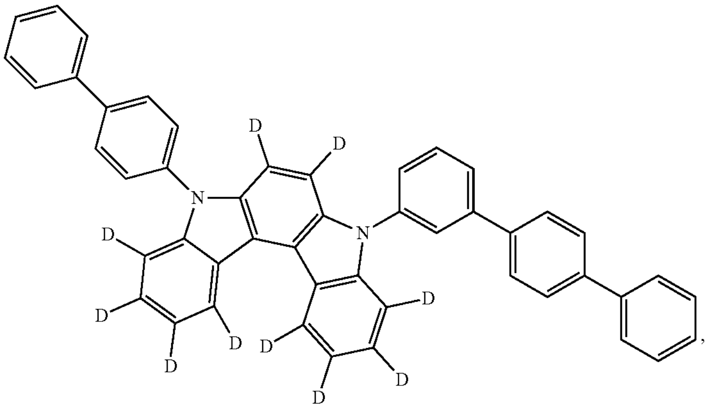
,

-continued
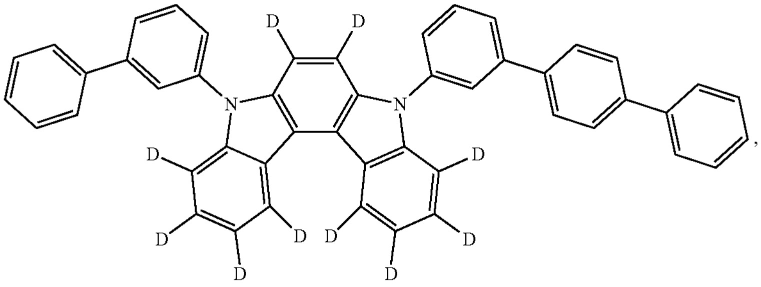
,
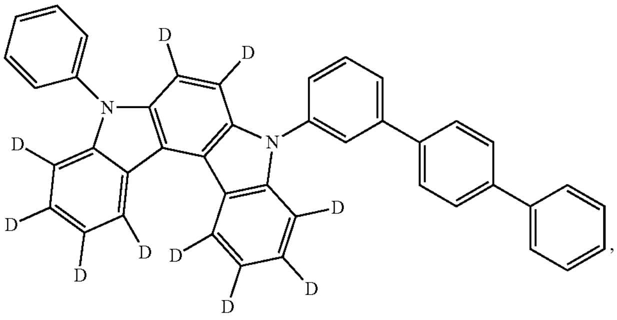
,
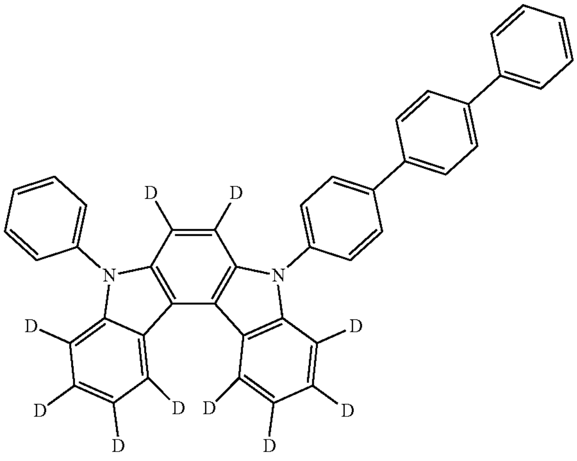
,
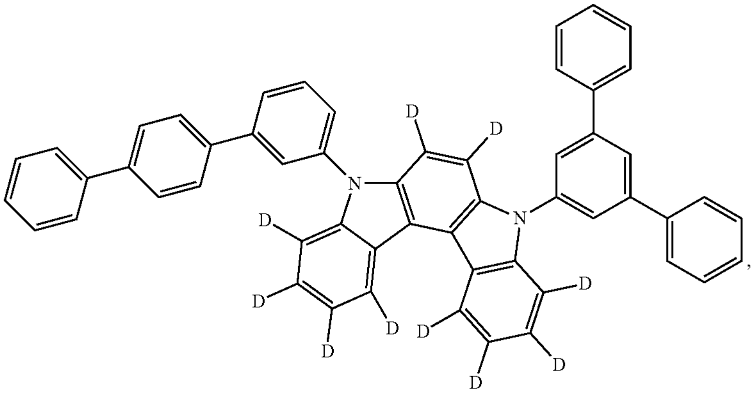
,

-continued
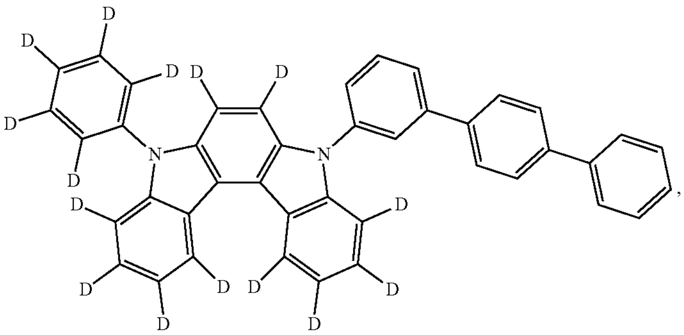
,
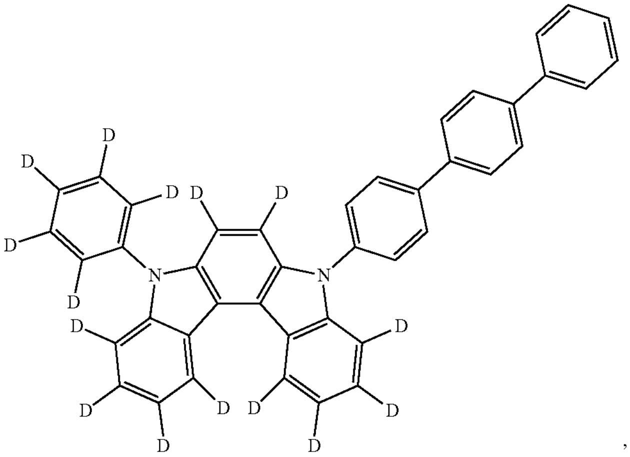
,
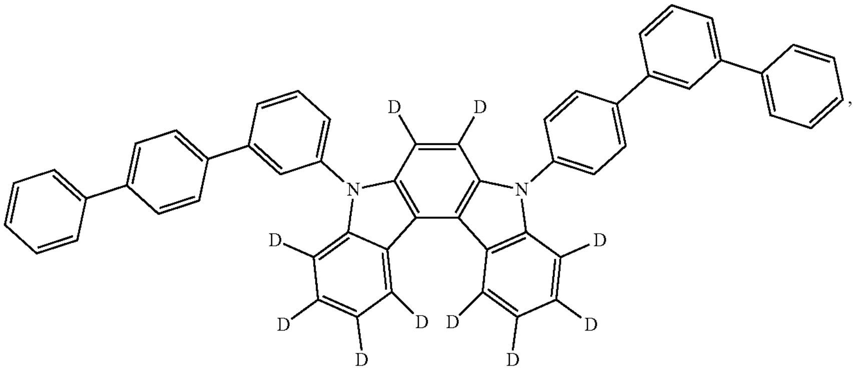
,
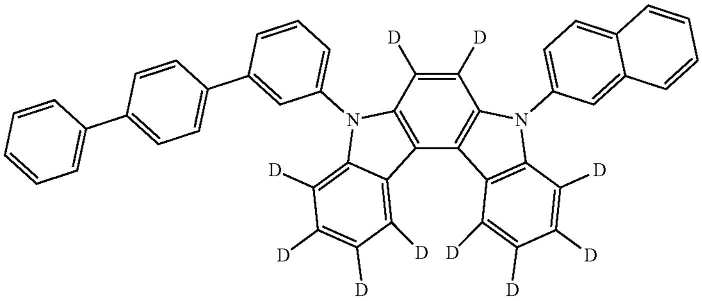
,

-continued
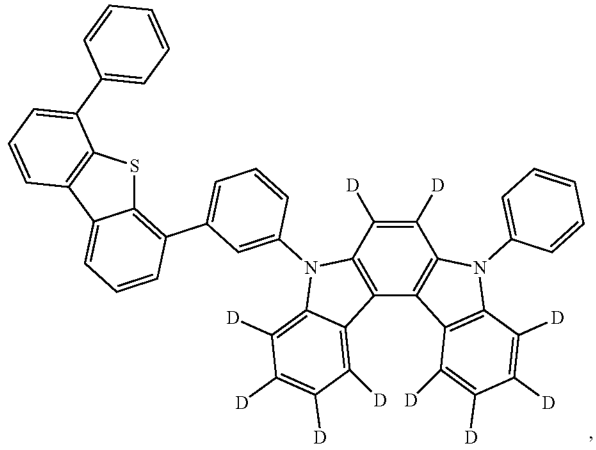
,
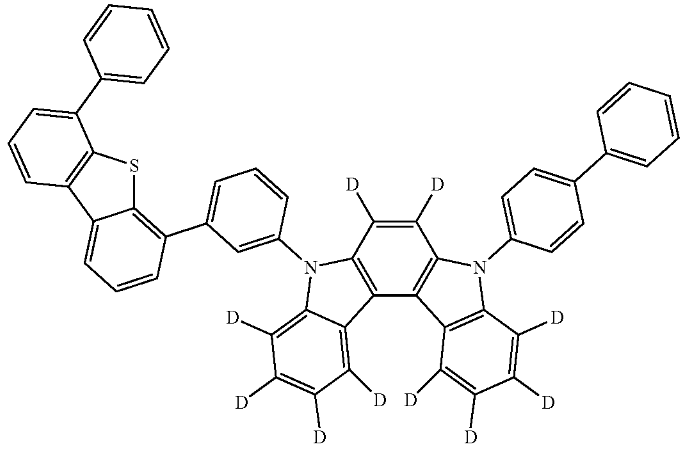
,
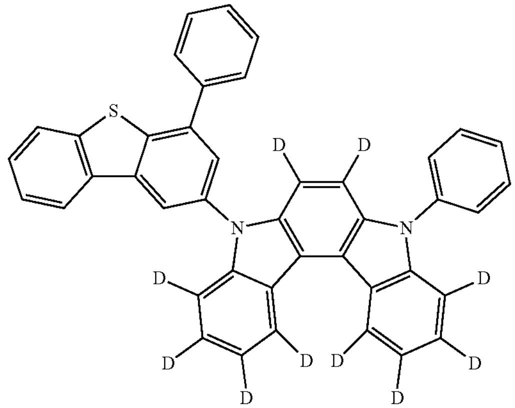
,
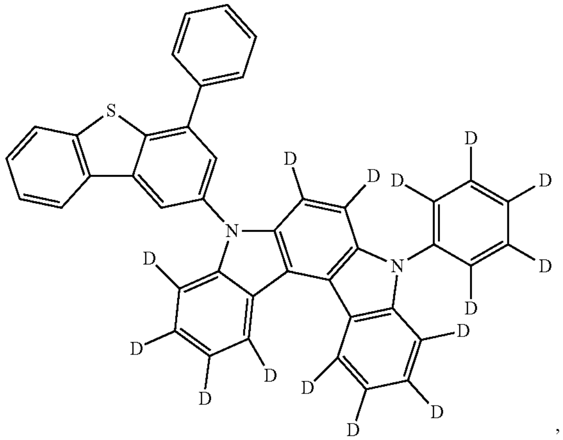
,

-continued
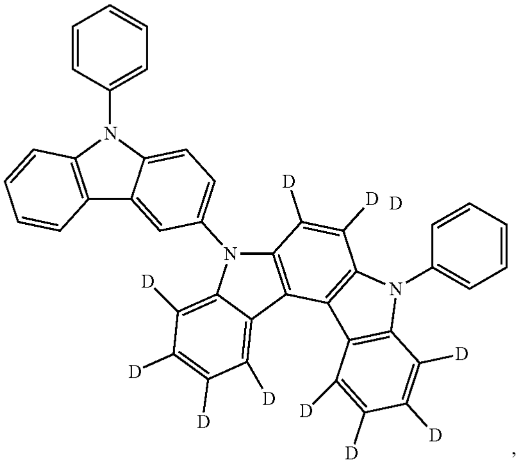
,
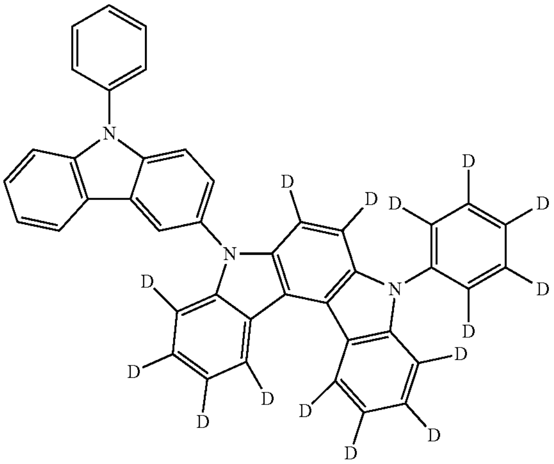
,
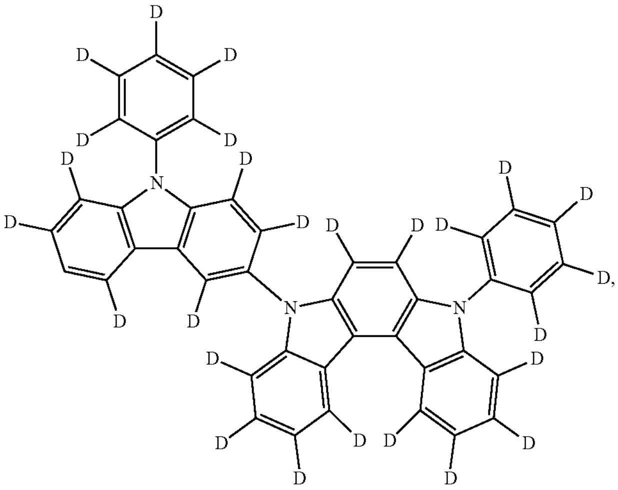
D,
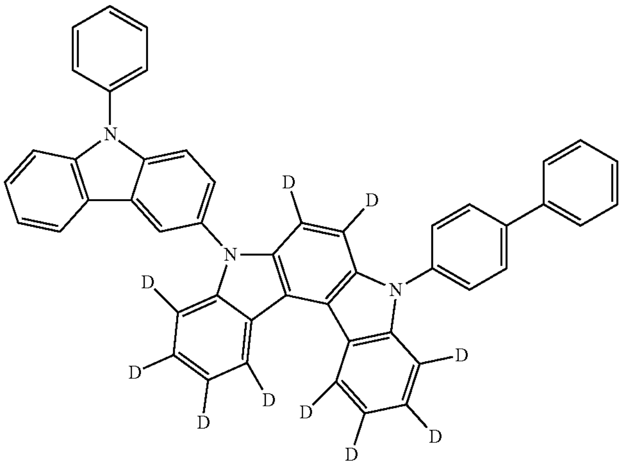
,

-continued
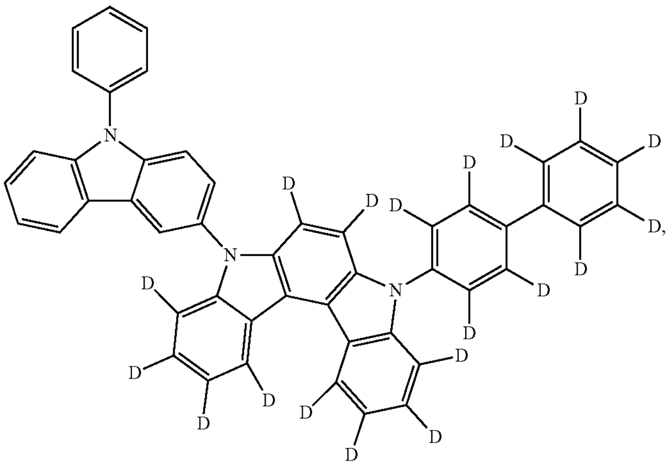
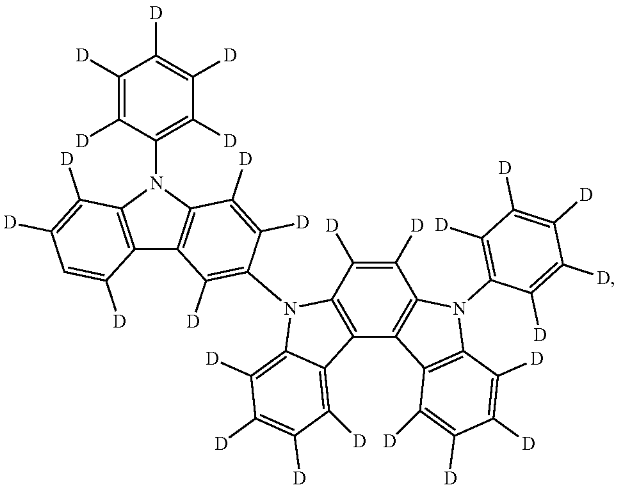
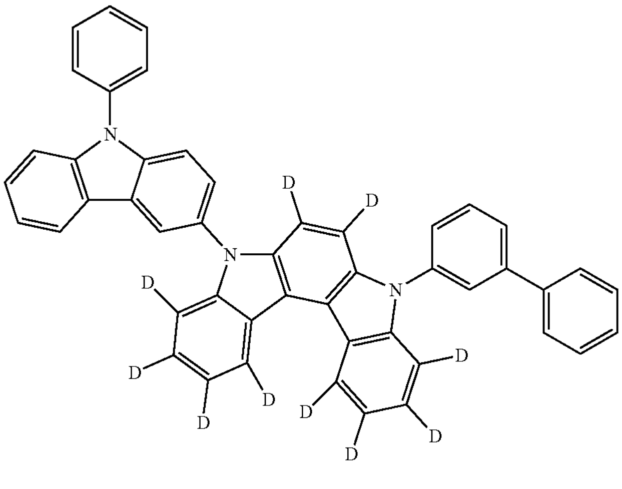
,

-continued
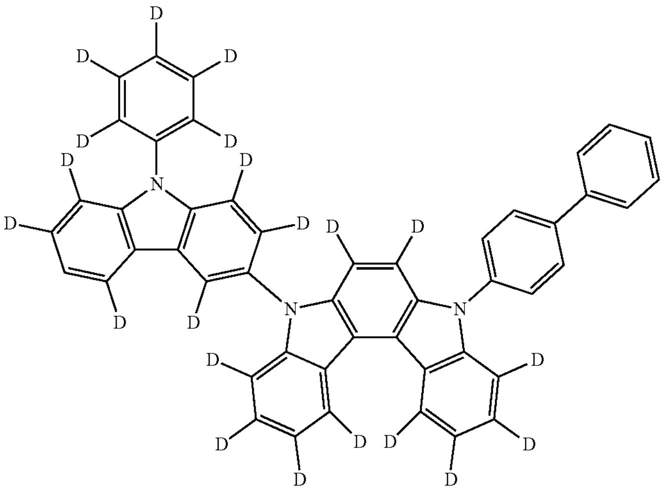
,
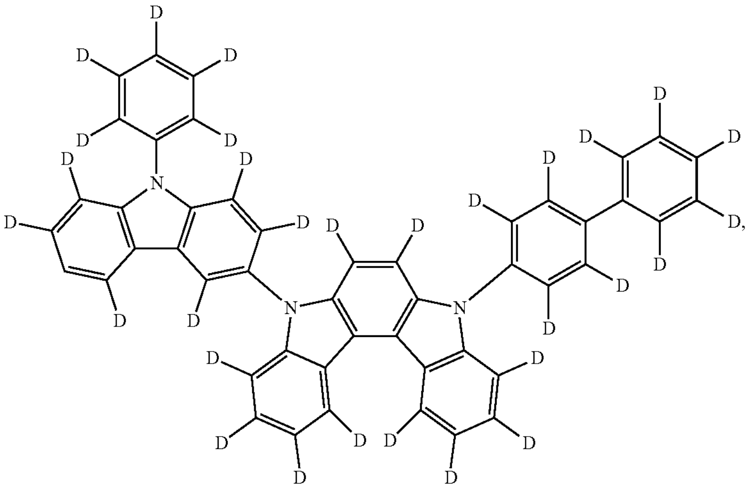
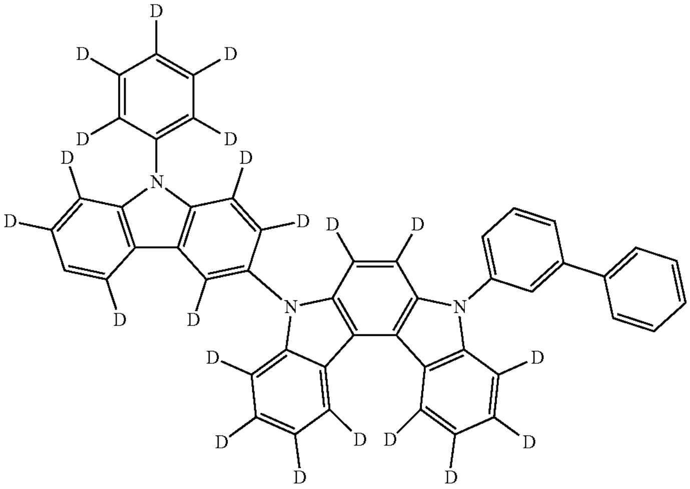
,

-continued
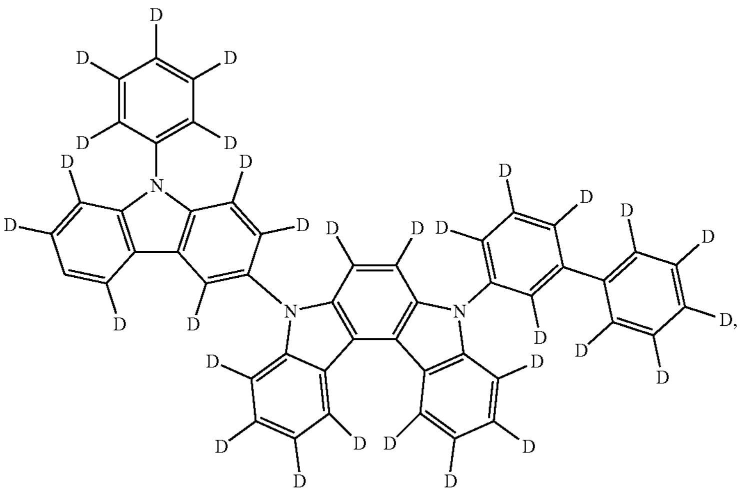
,
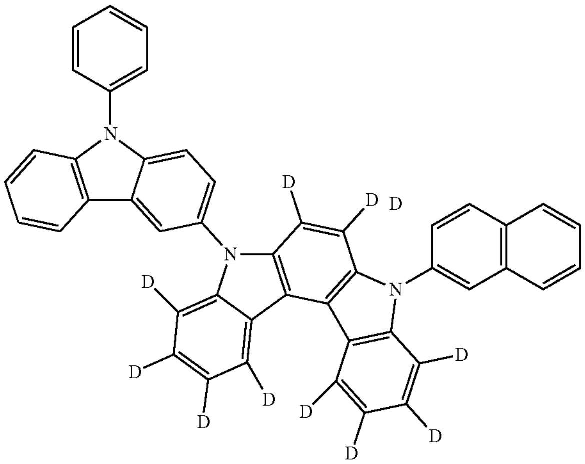
,
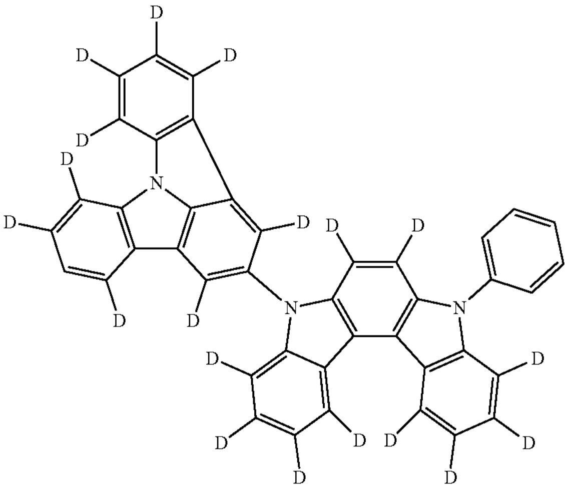
,
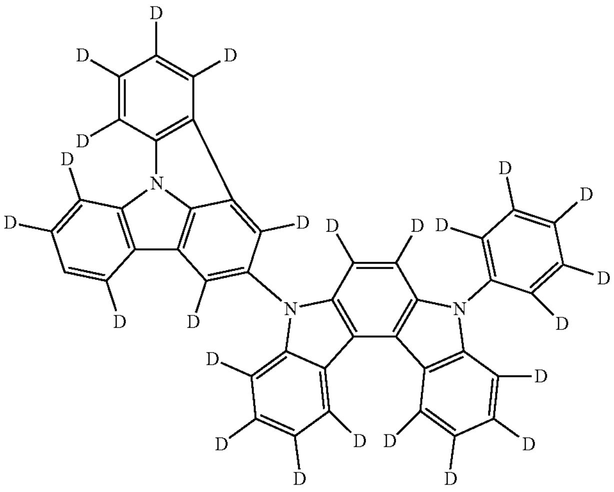
,
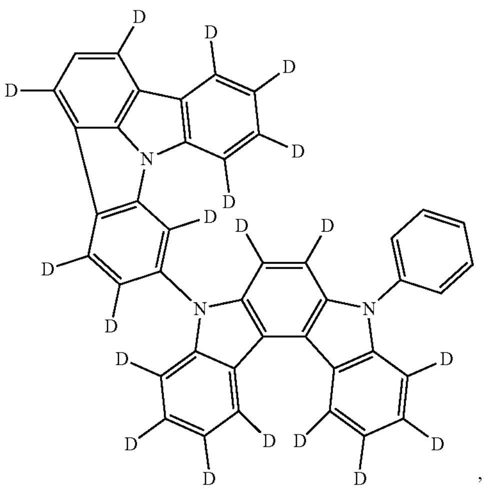
, -continued
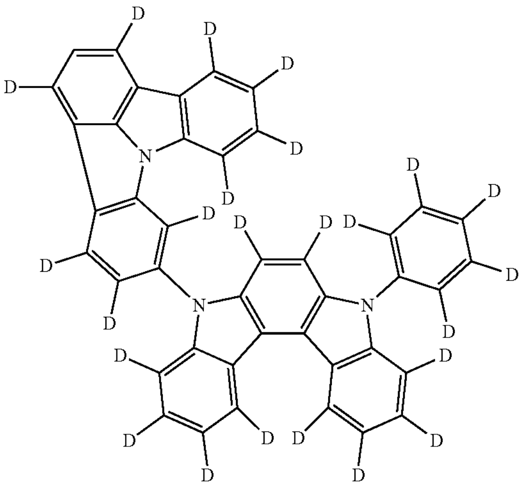
,
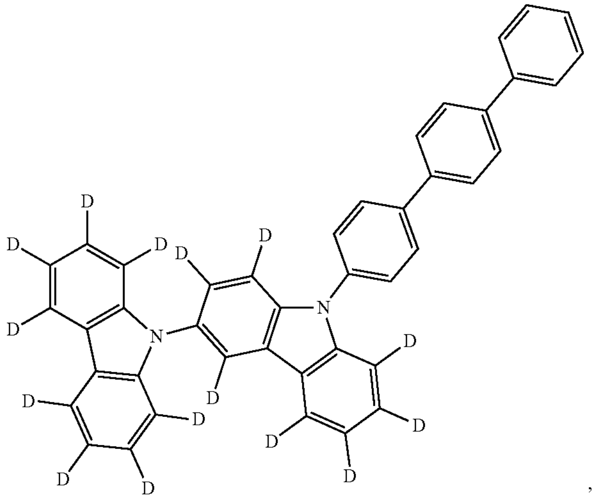
,
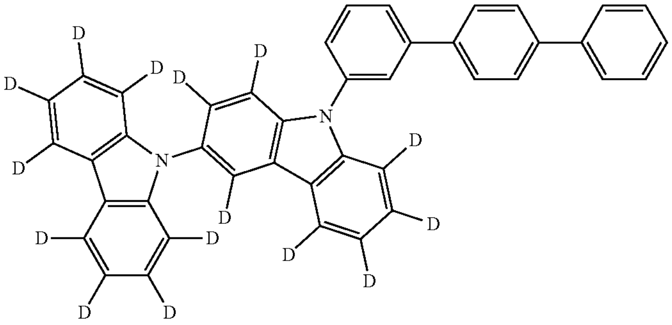
,
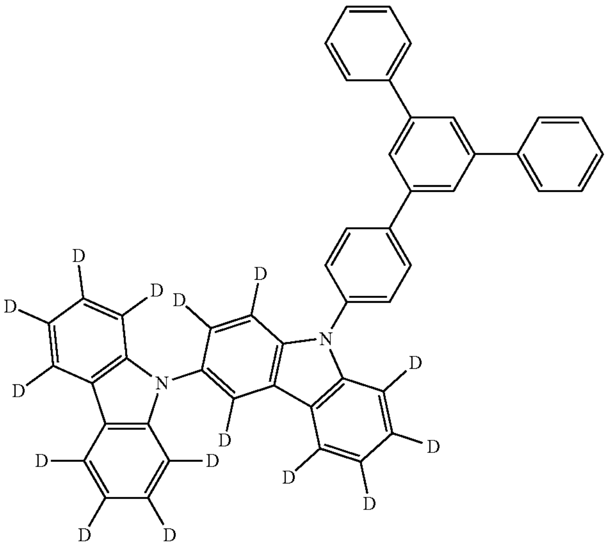
, -continued
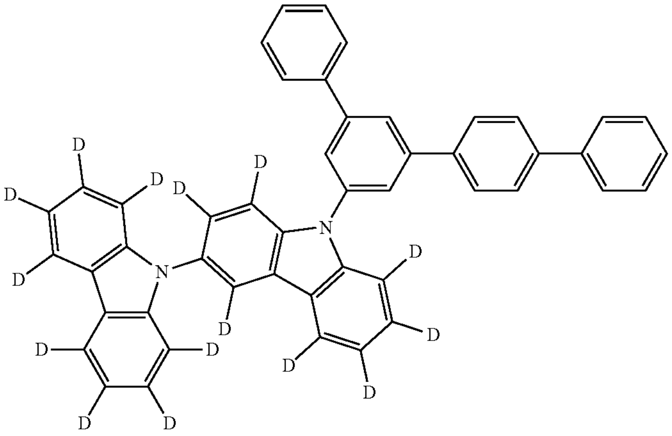
,
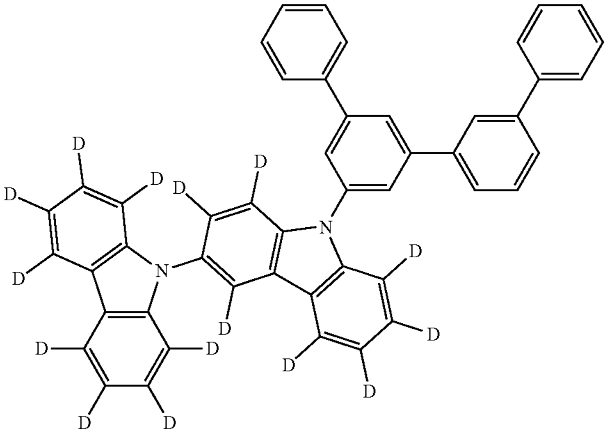
,
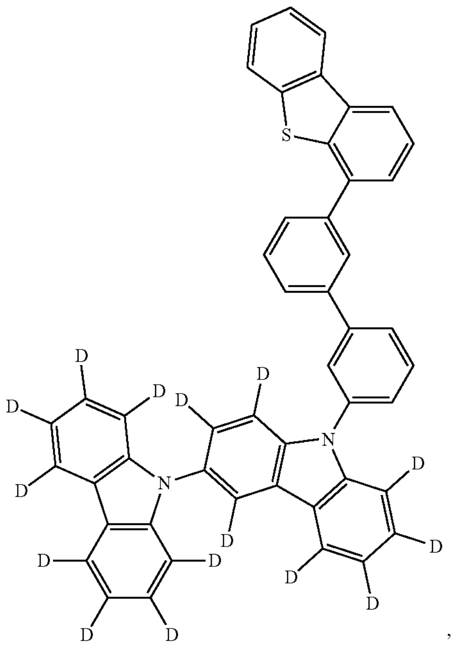
,
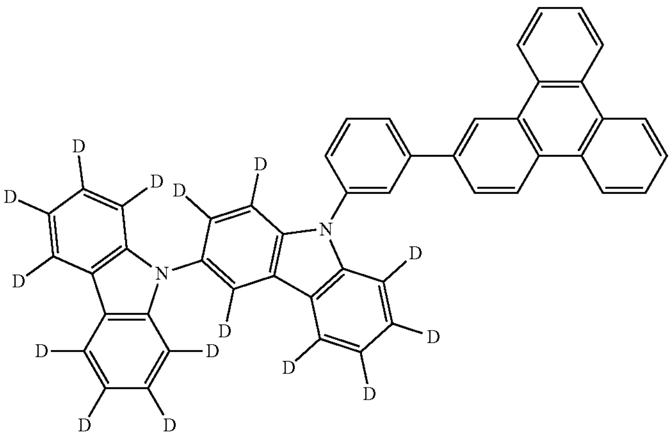
, -continued
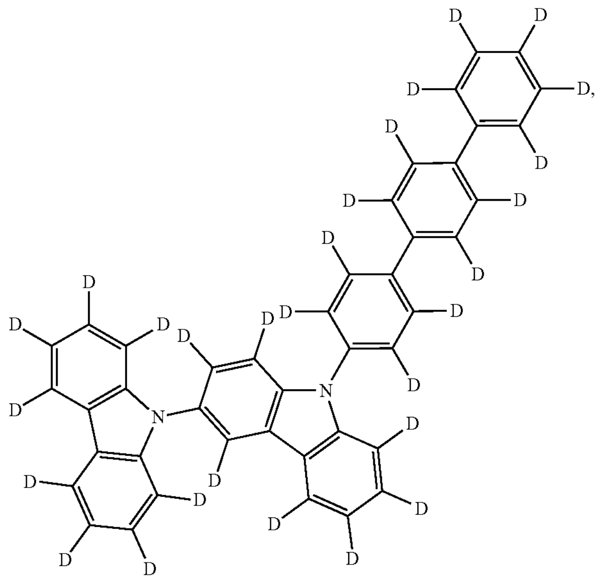
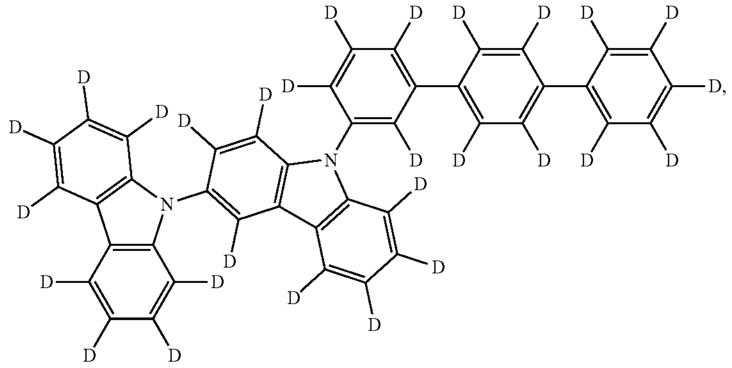
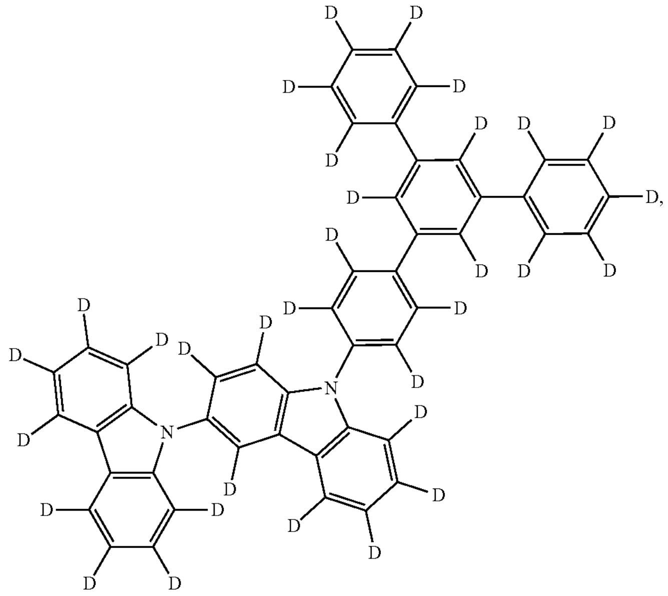

-continued
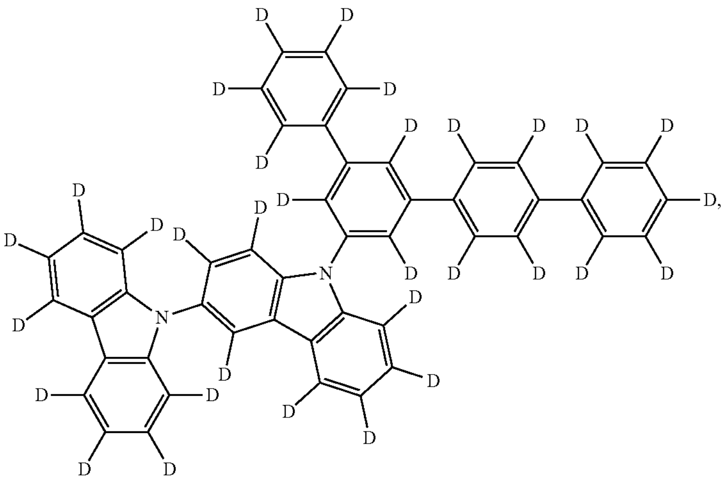
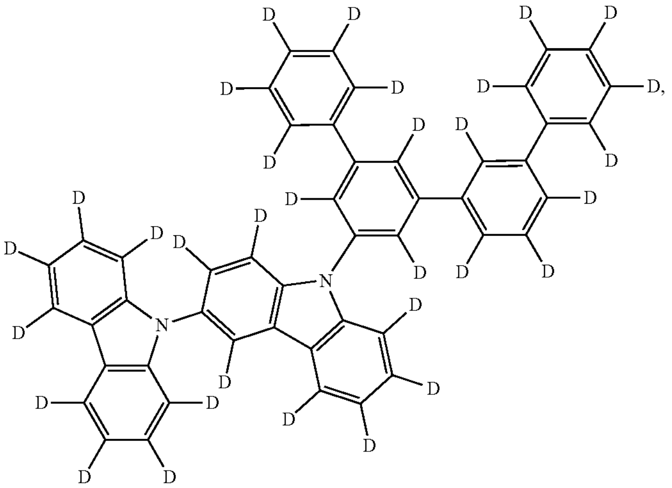
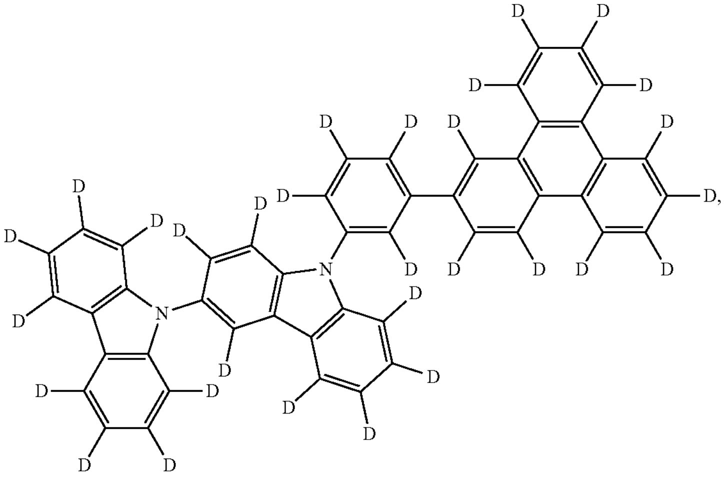

-continued
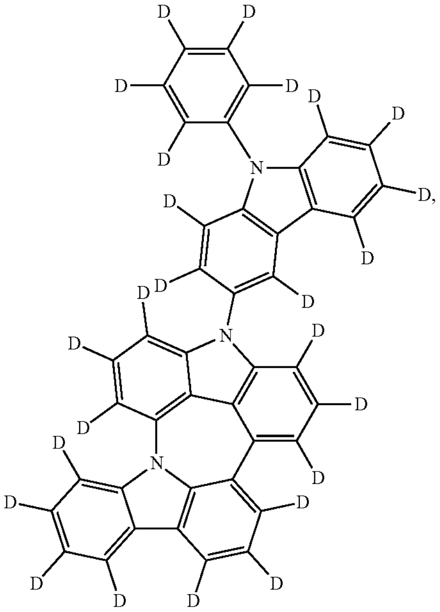
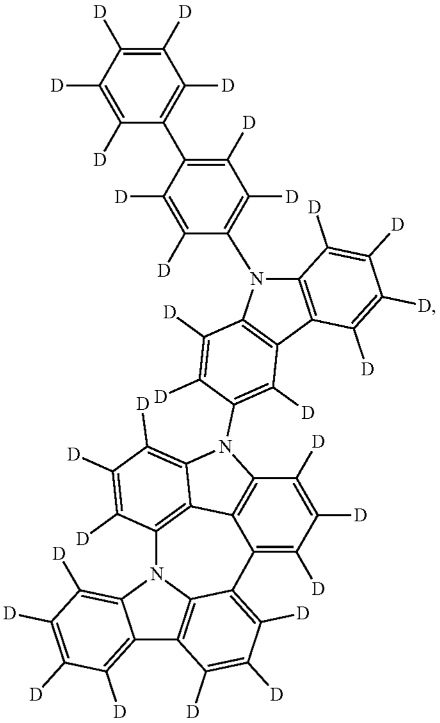
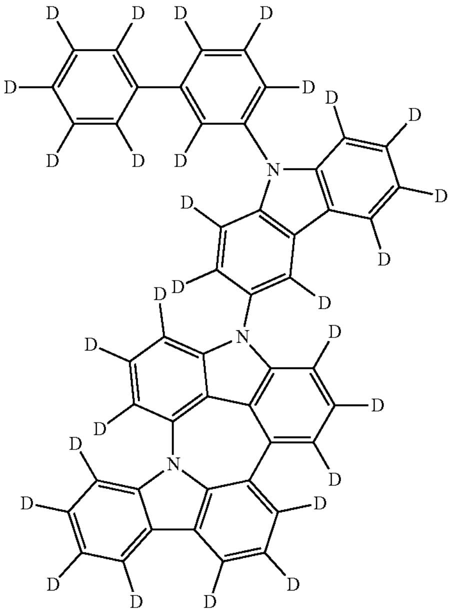
,
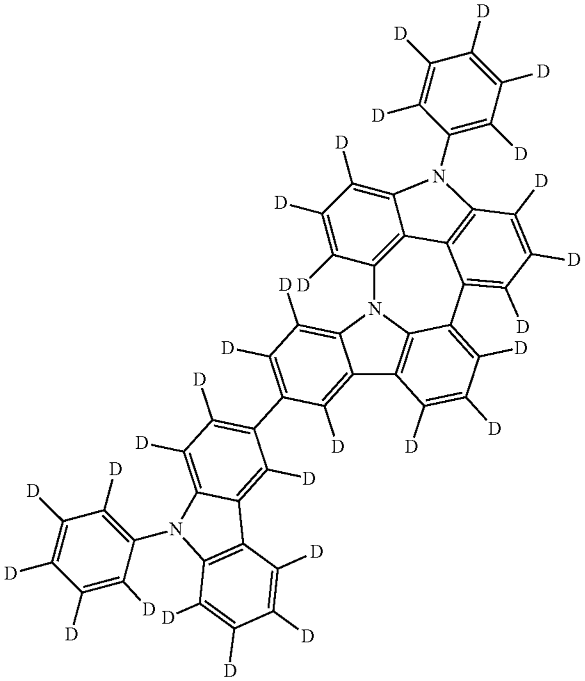
,

-continued
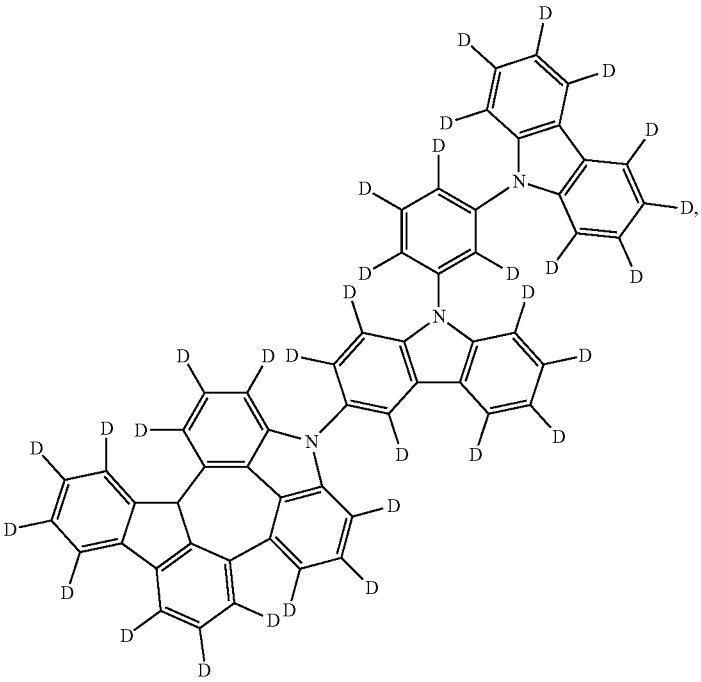
,
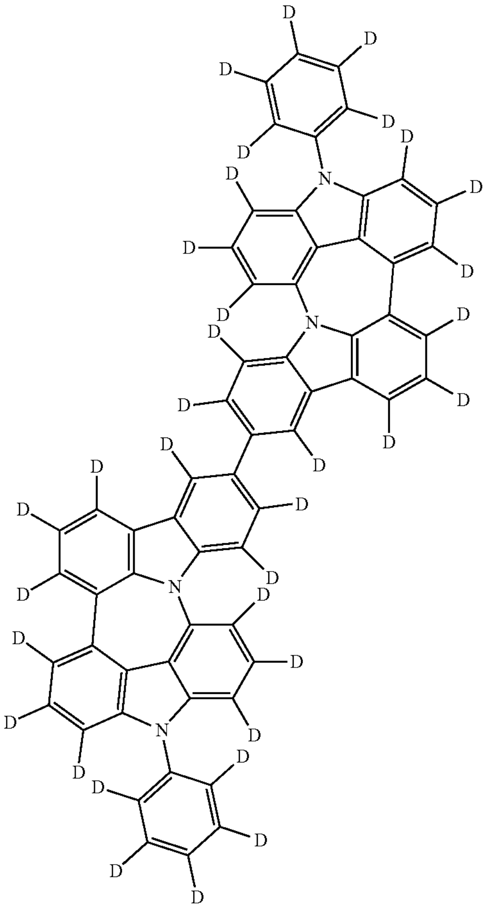
,
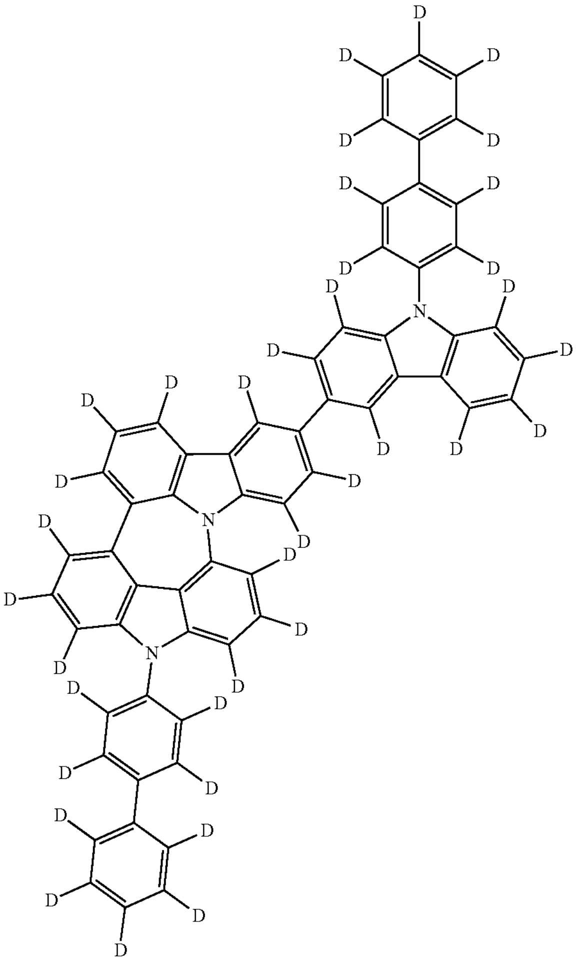
,

-continued
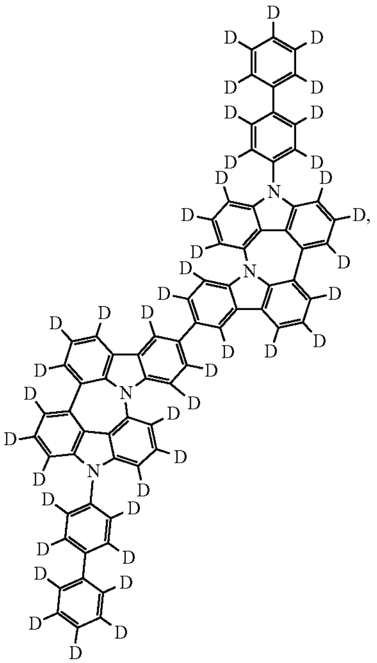
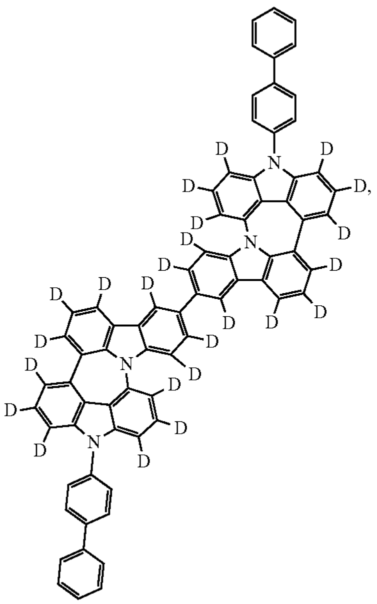
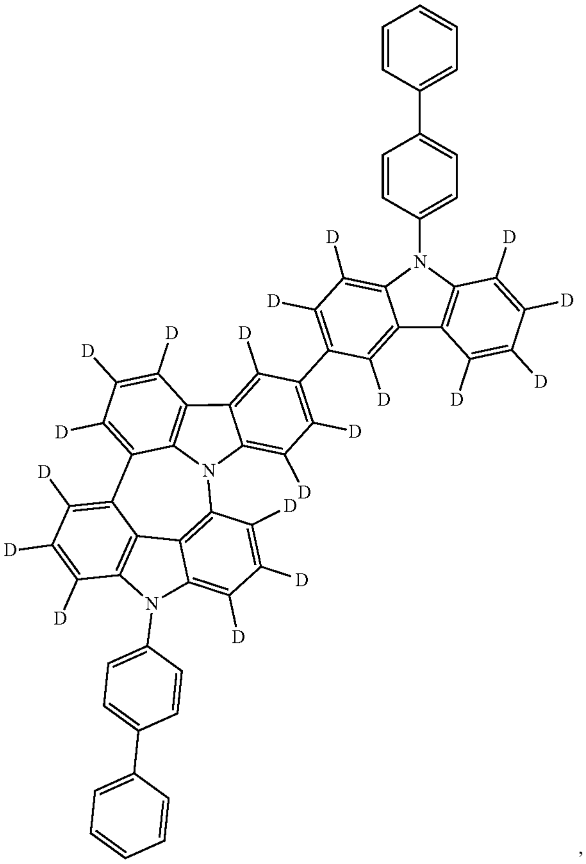
,
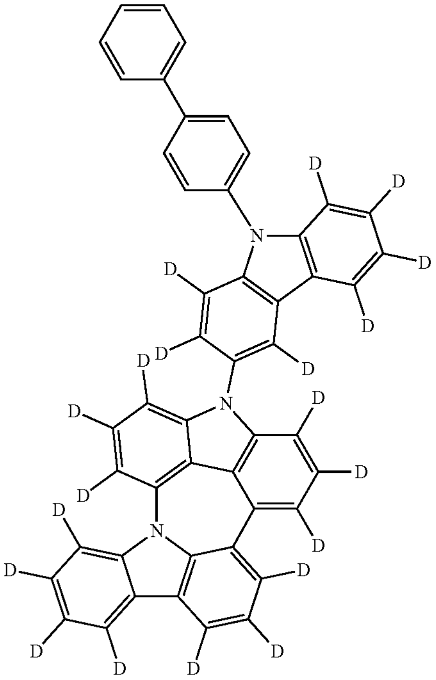
,

-continued
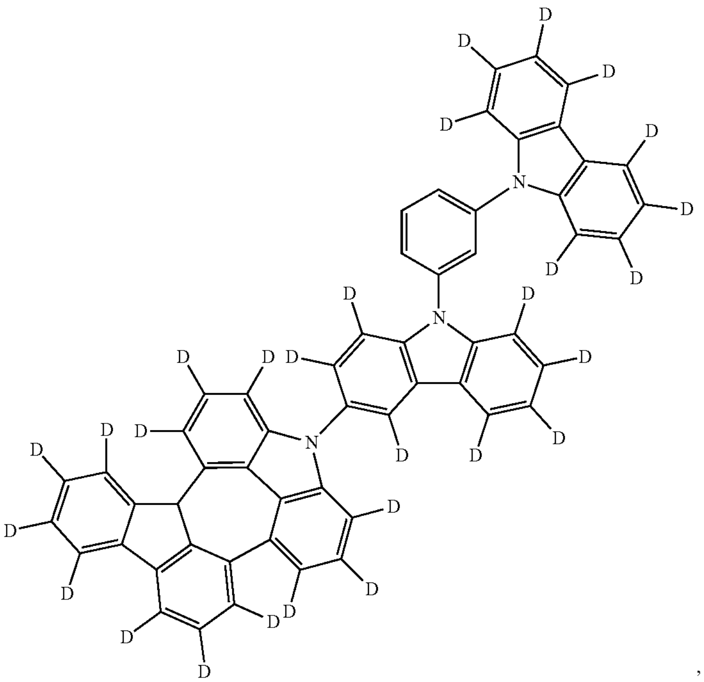
, and
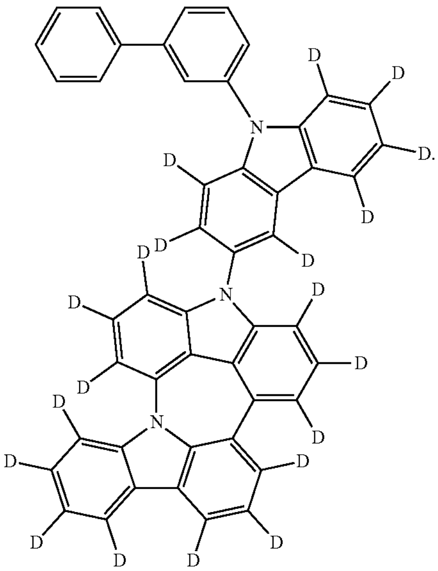
.

12. The OLED of claim 1, wherein the second host is selected from the group consisting of:
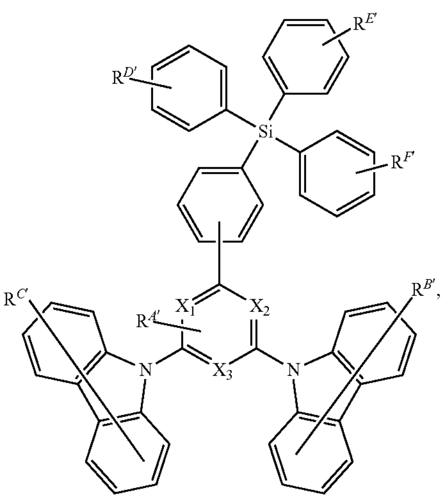
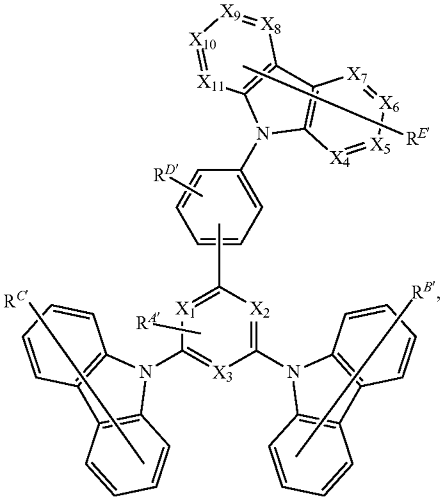
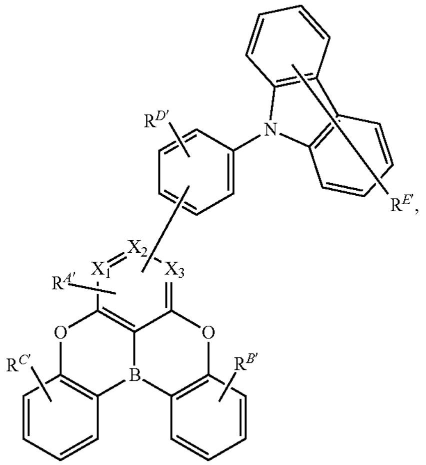
-continued
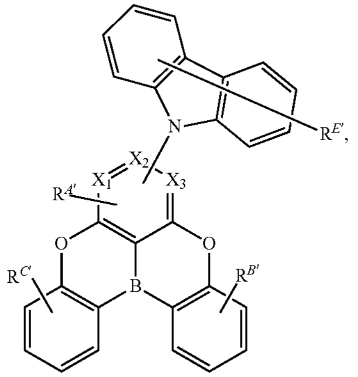
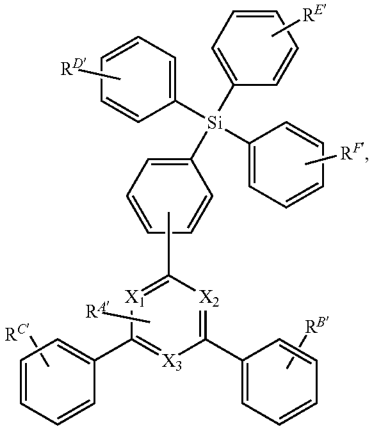
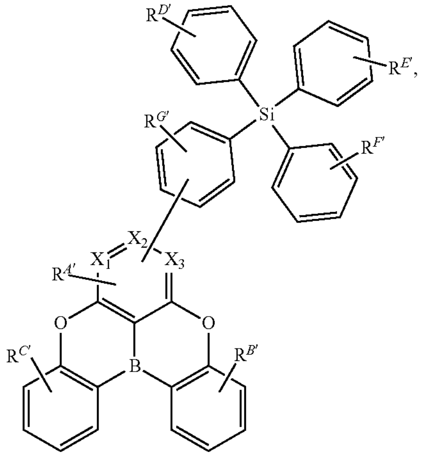
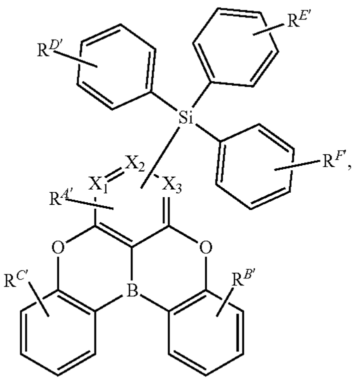

-continued
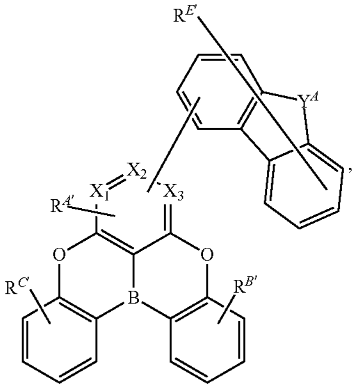
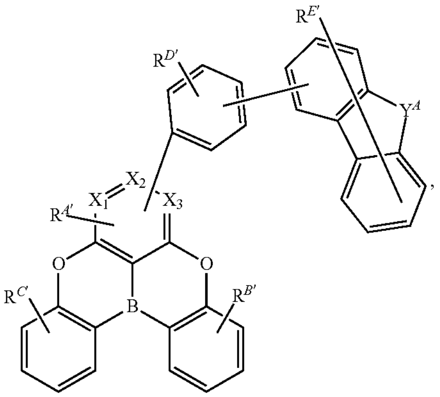
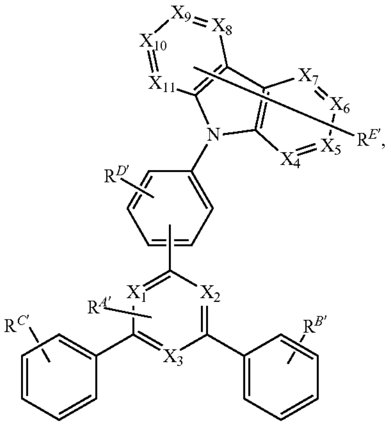
-continued
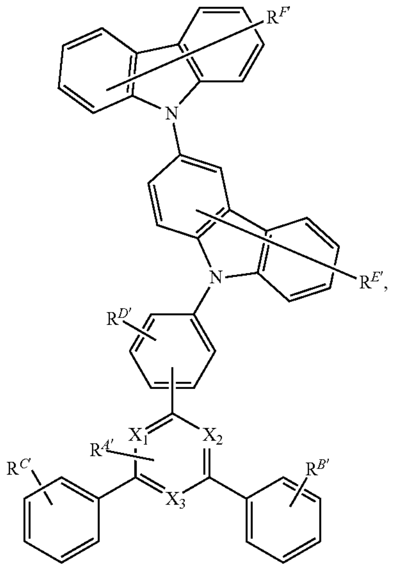
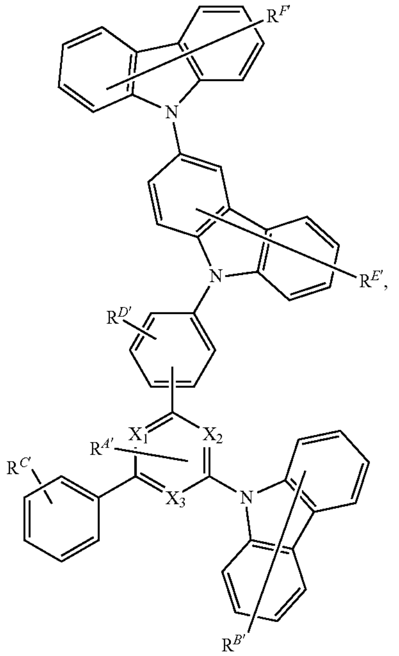
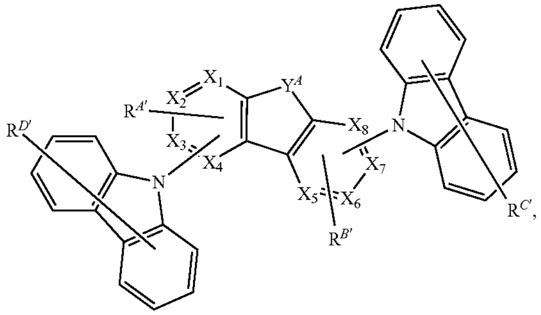

-continued
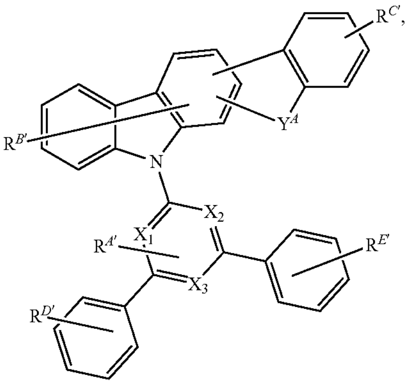
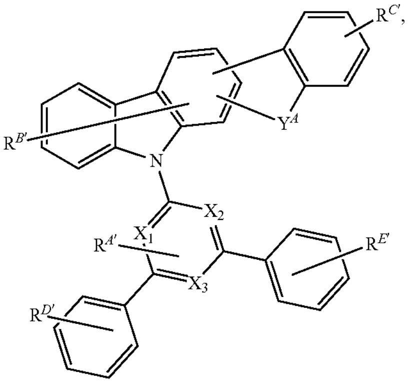
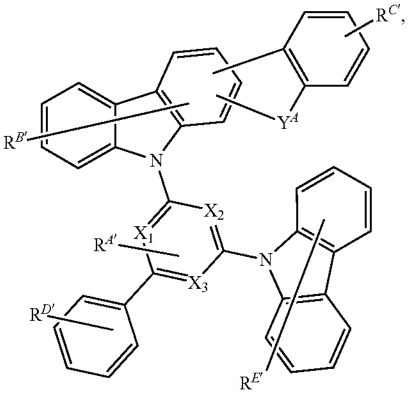
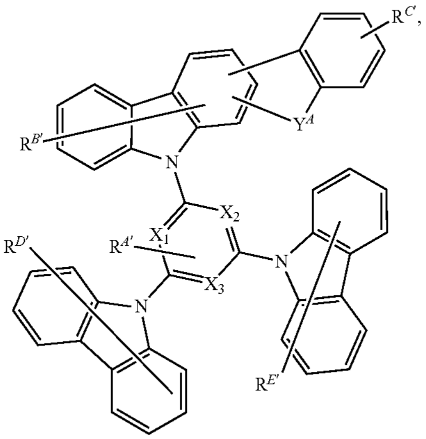
-continued
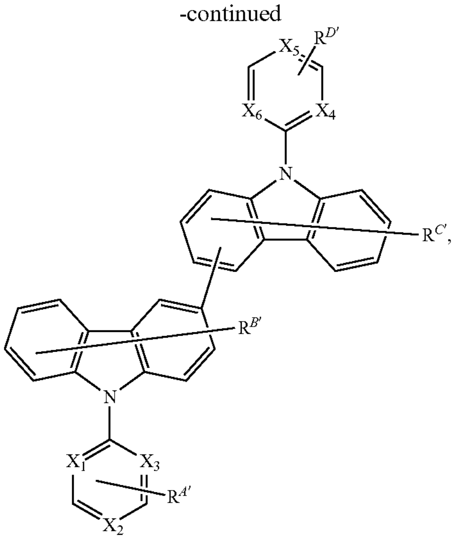
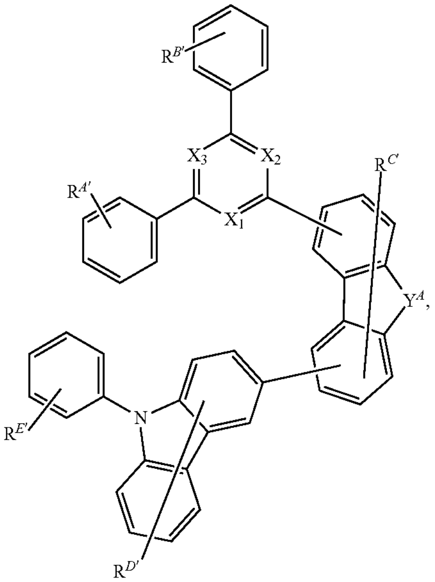
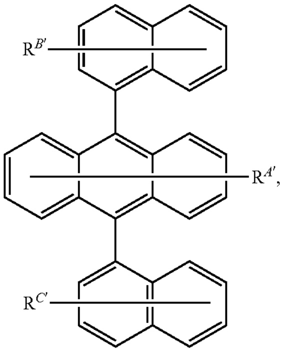
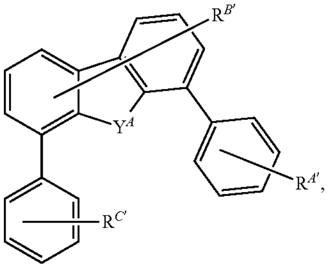

-continued
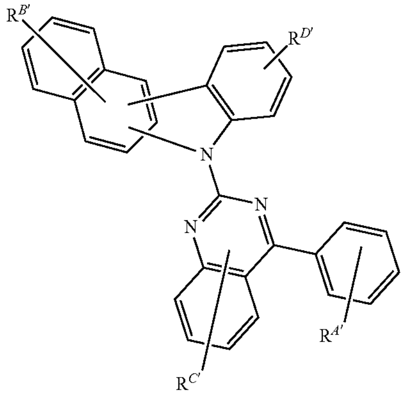
,
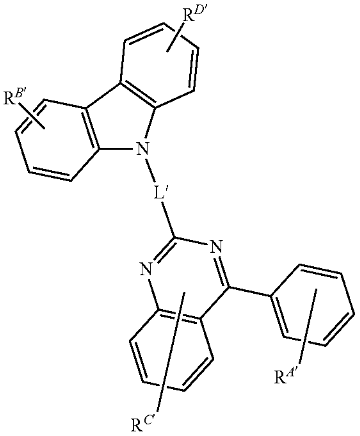
,
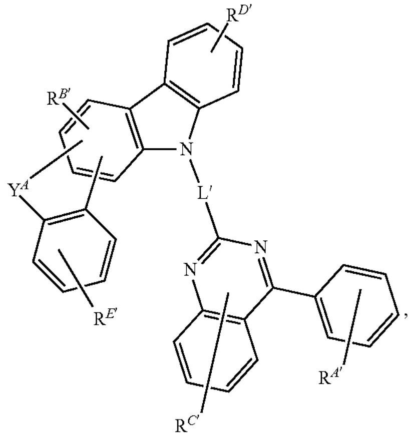
,
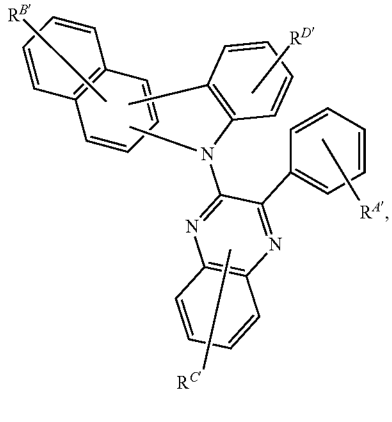
,
-continued
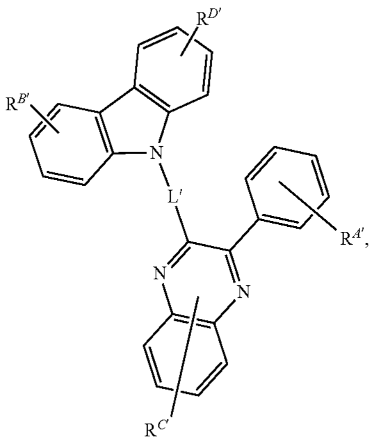
,
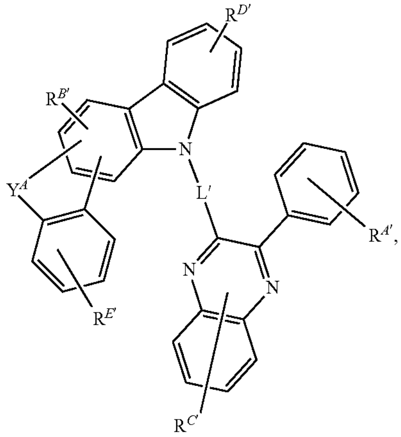
,
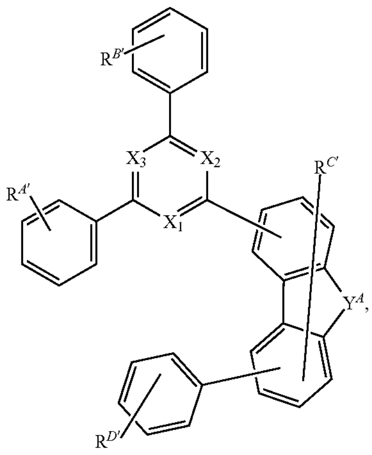
, -continued

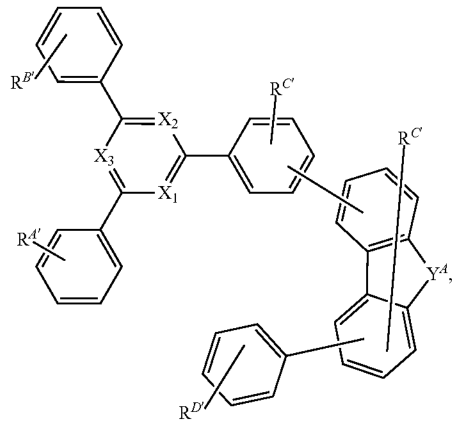

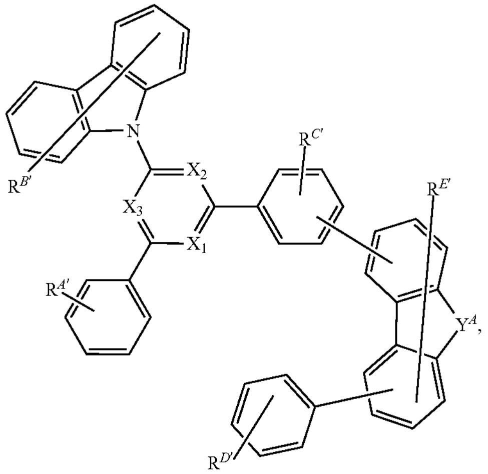

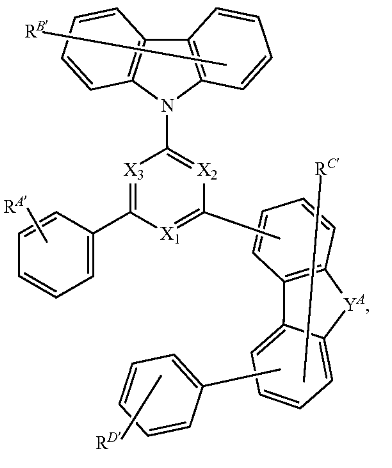

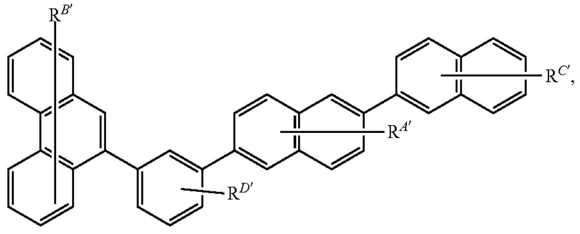

-continued

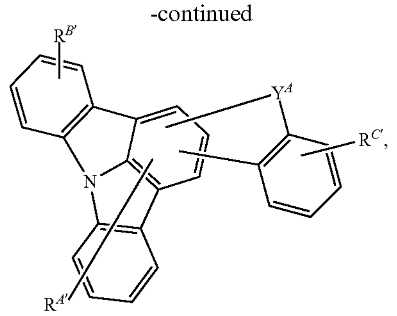

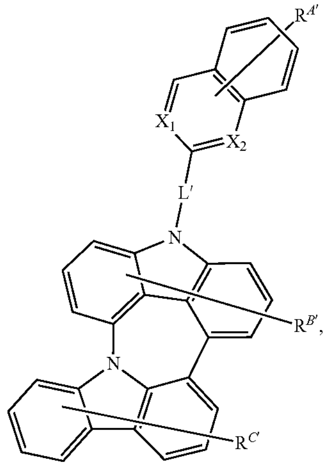

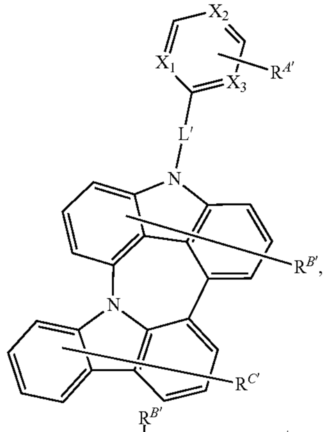

and

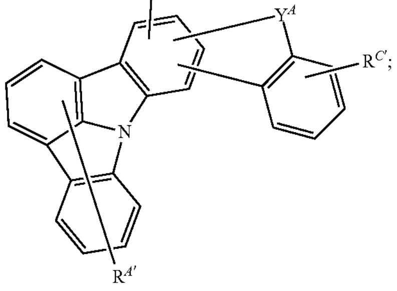

wherein:

each of $X_1$ to $X_{11}$ is independently C or N;

L' is a direct bond or an organic linker;

each $Y^A$ is independently selected from the group consisting of absent a bond, O, S, Se, CRR', SiRR', NR, BR, BRR';

each of $R^{A'}$, $R^{B'}$, $R^{C'}$, $R^{D'}$, $R^{E'}$, $R^{F'}$, and $R^{G'}$ independently represents mono, up to the maximum number of substitutions, or no substitution;

each of R, R', $R^{A'}$, $R^{B'}$, $R^{C'}$, $R^{D'}$, $R^{E'}$, $R^{F'}$, and $R^{G'}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof;

two adjacent of $R^{A'}$, $R^{B'}$, $R^{C'}$, $R^{D'}$, $R^{E'}$, $R^{F'}$, and $R^{G'}$ can be joined or fused to form a ring.

13. The OLED of claim 1, wherein the second host is selected from the group consisting of:

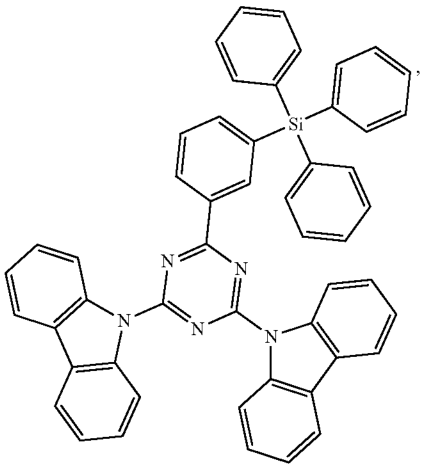

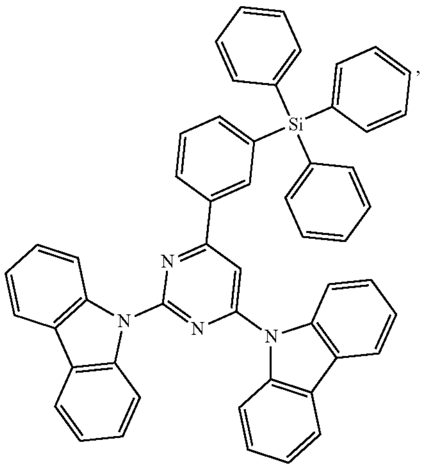

-continued

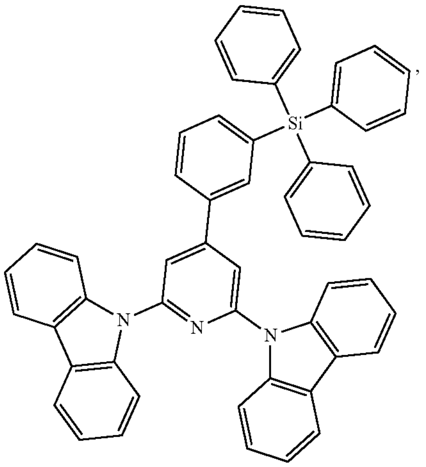

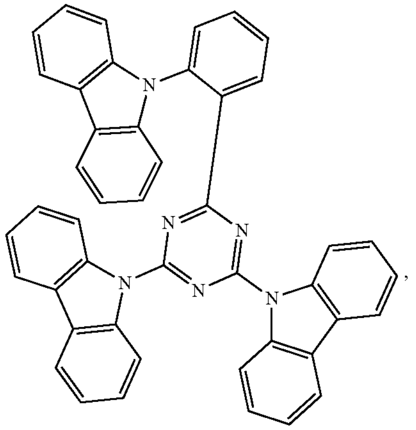

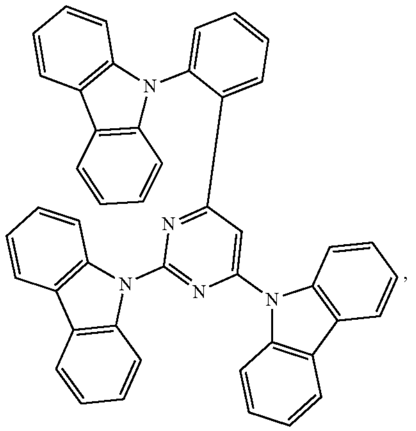

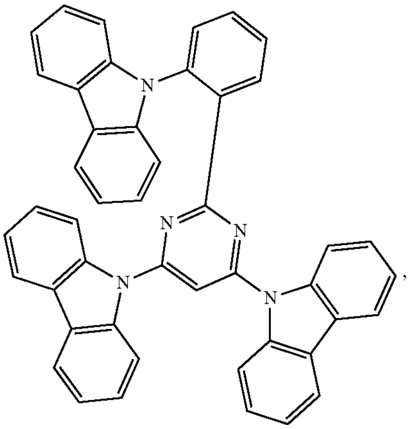
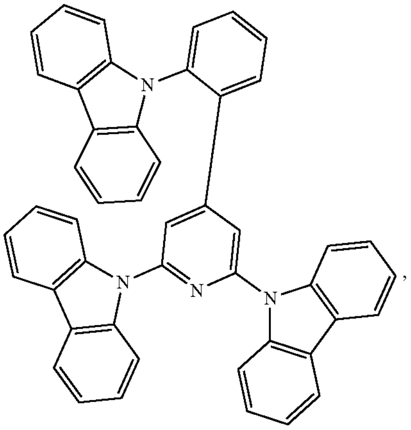
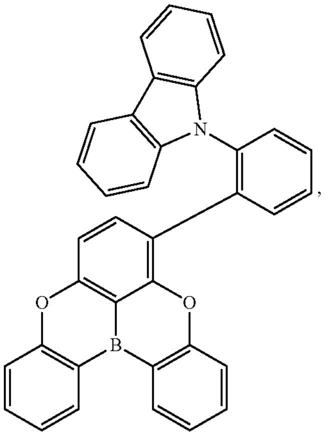
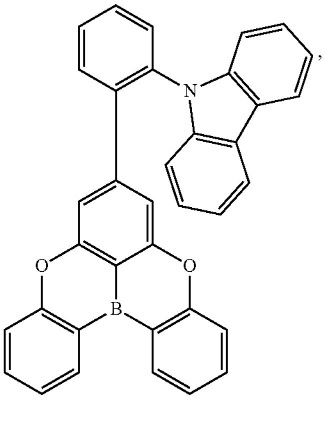
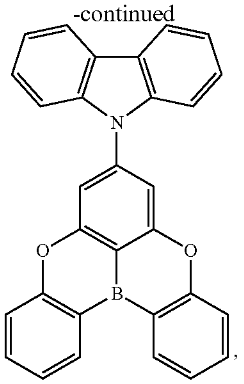
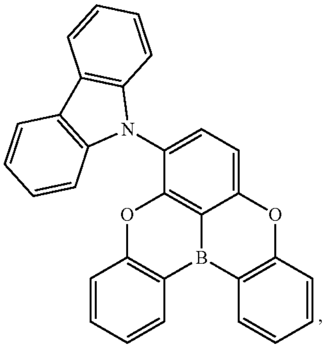
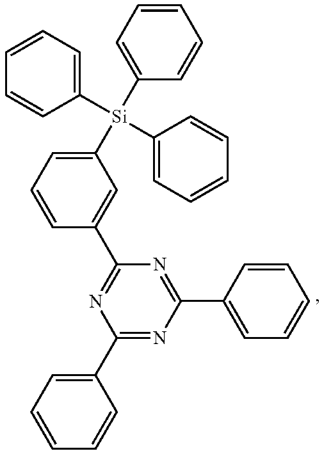
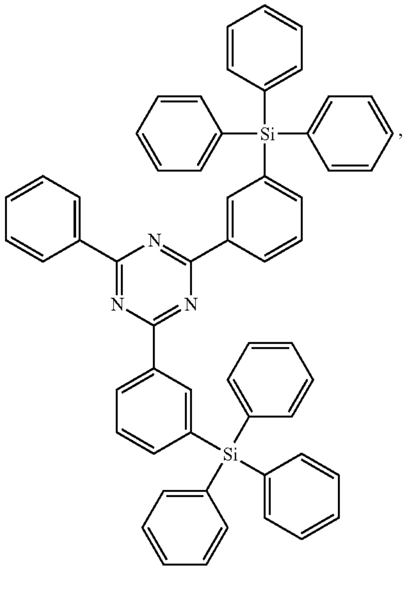

-continued
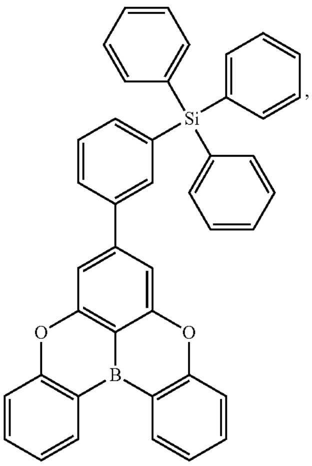
,
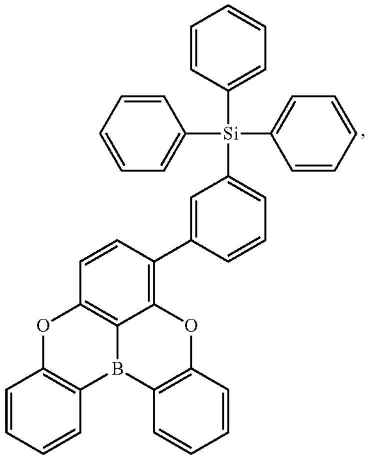
,
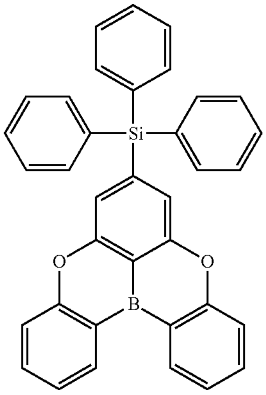
,
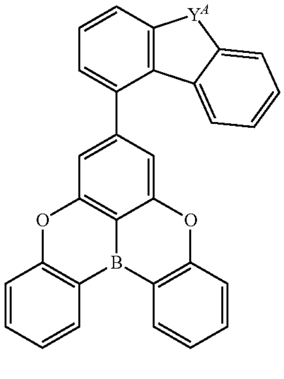
,
-continued
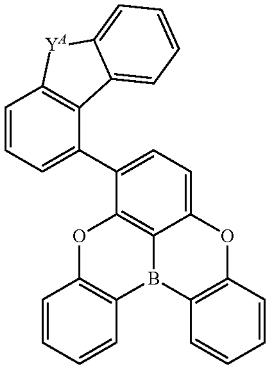
,
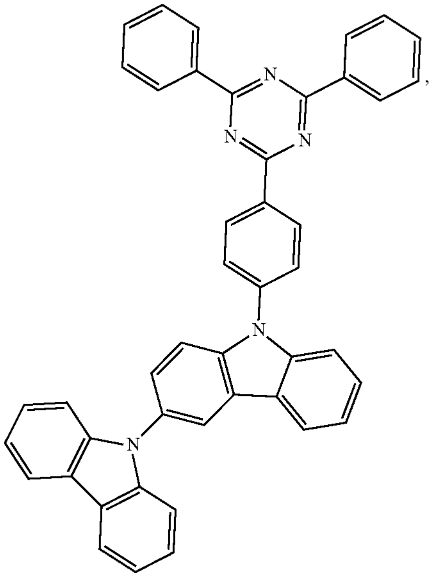
,
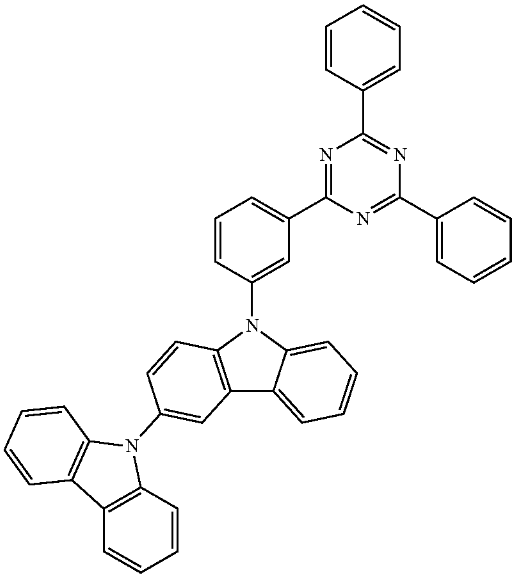
, -continued
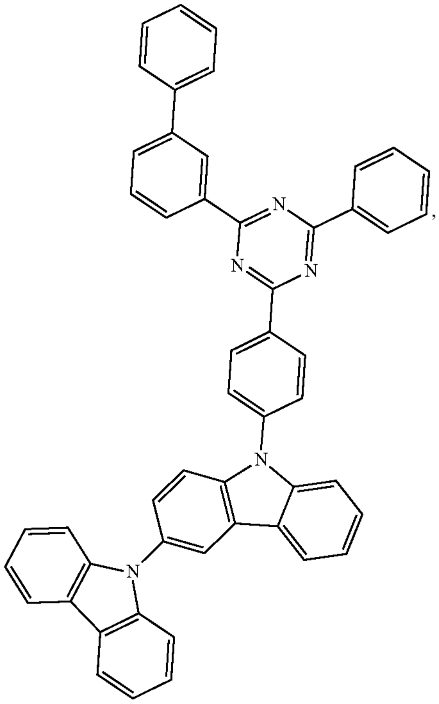
,
-continued
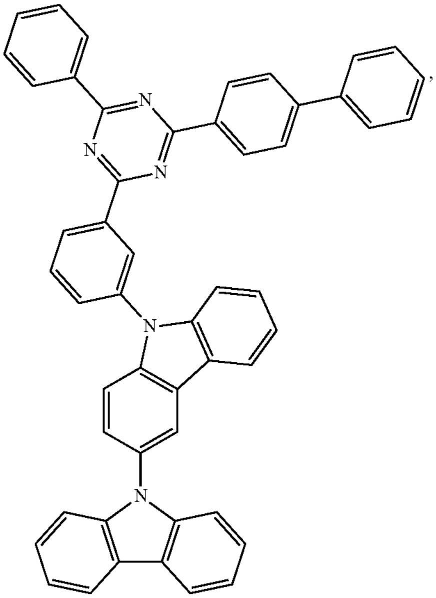
,
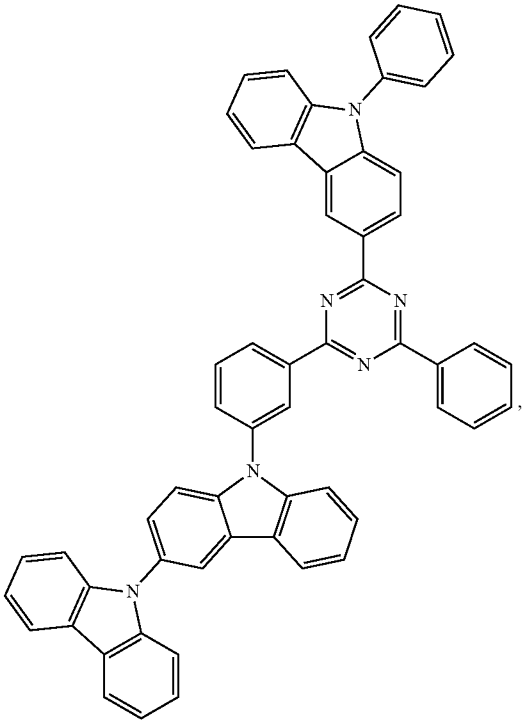
,
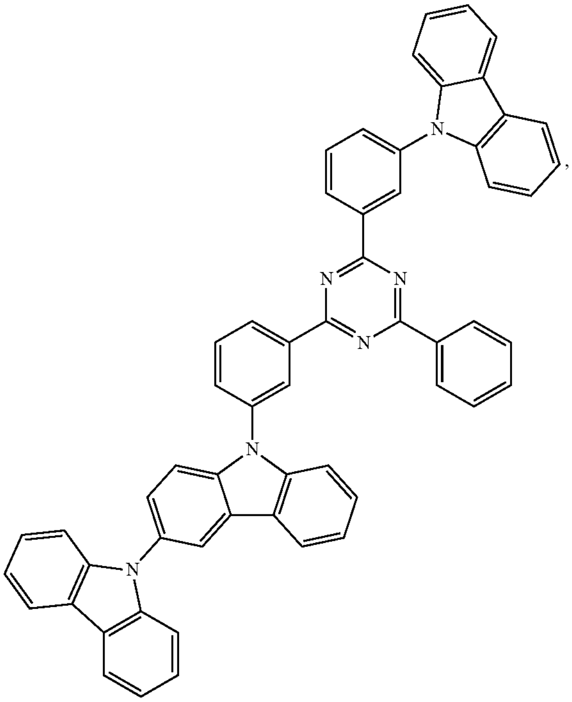
, -continued
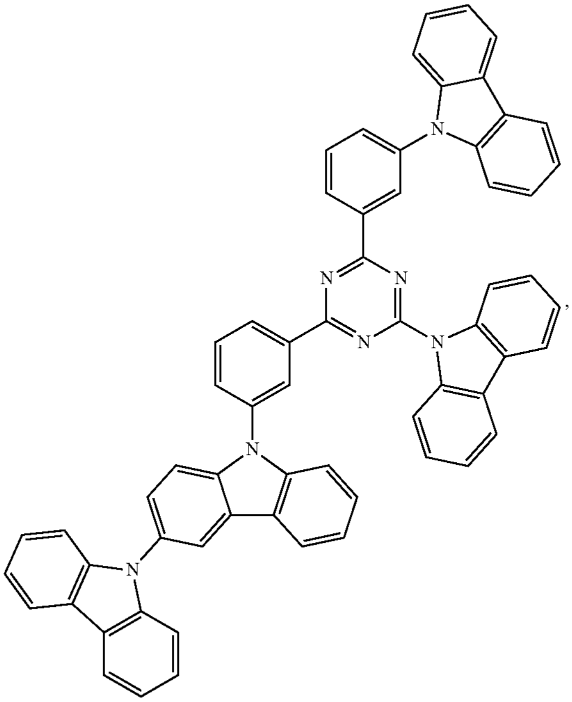
,
-continued
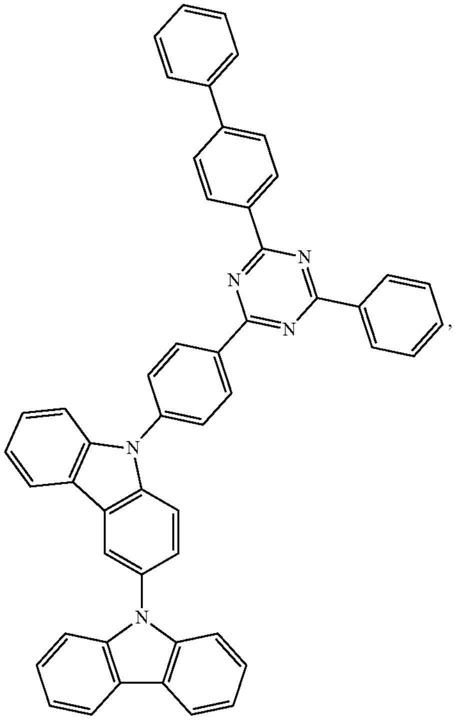
,
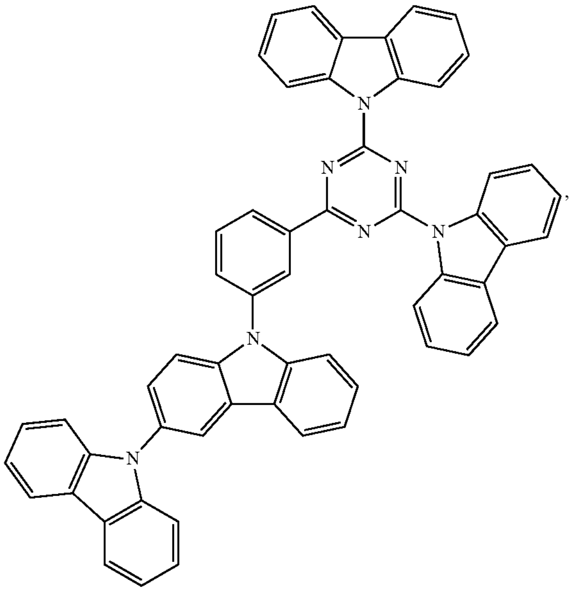
,
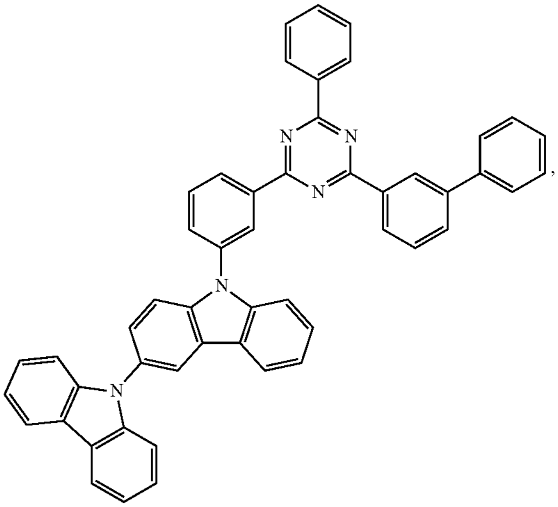
, -continued
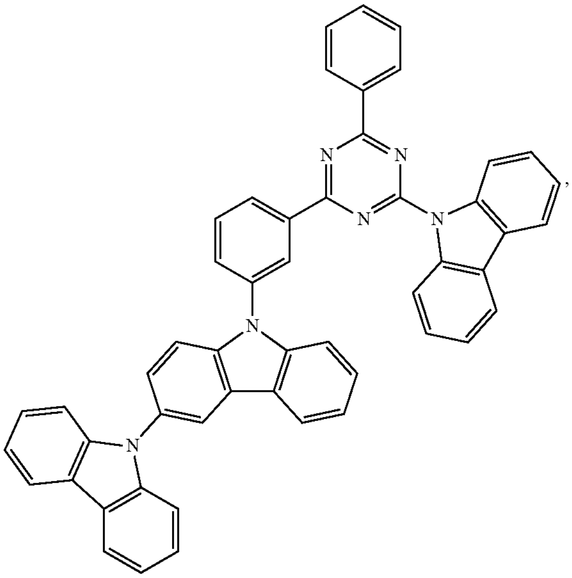
,
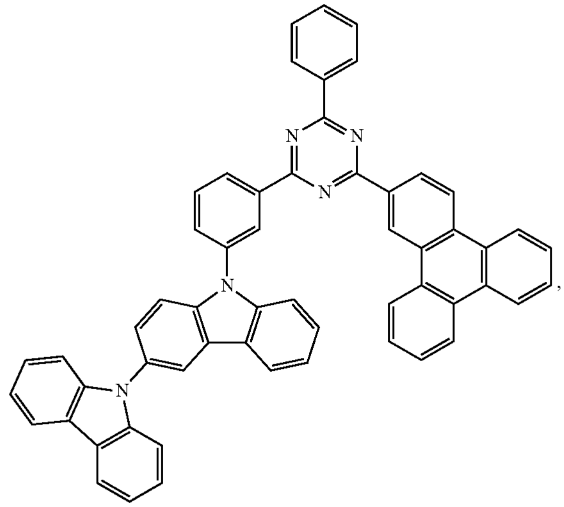
,
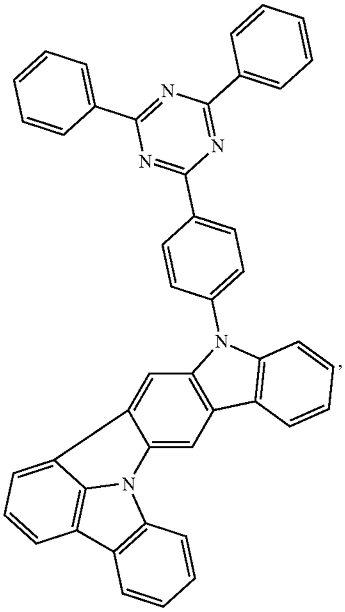
,
-continued
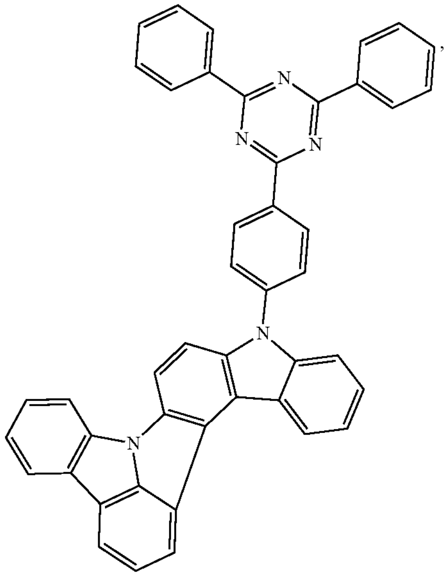
,
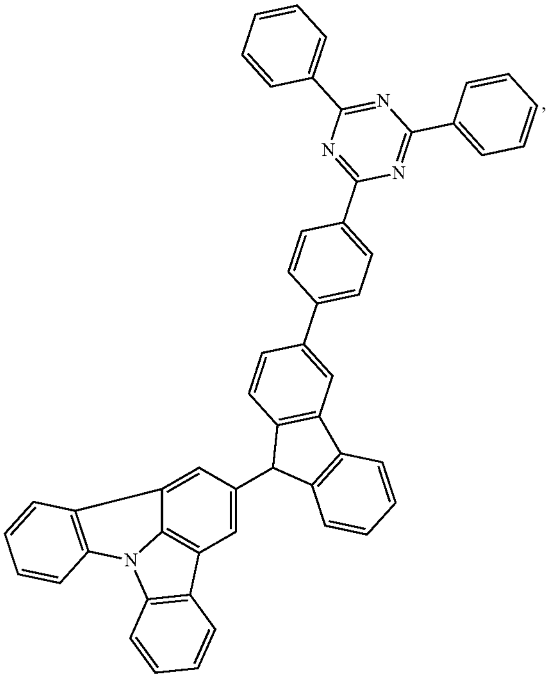
, -continued
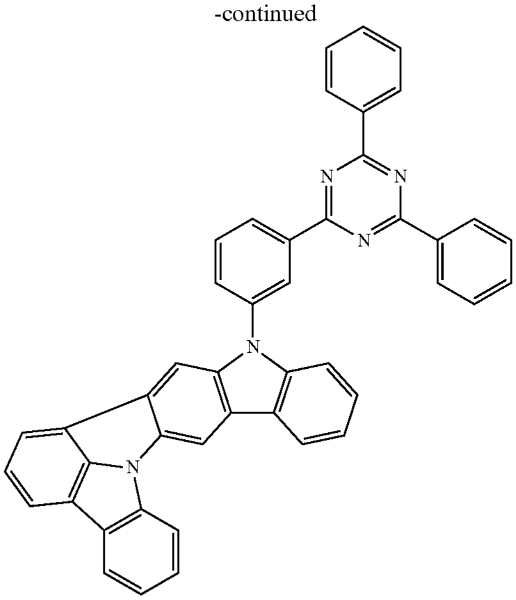
,
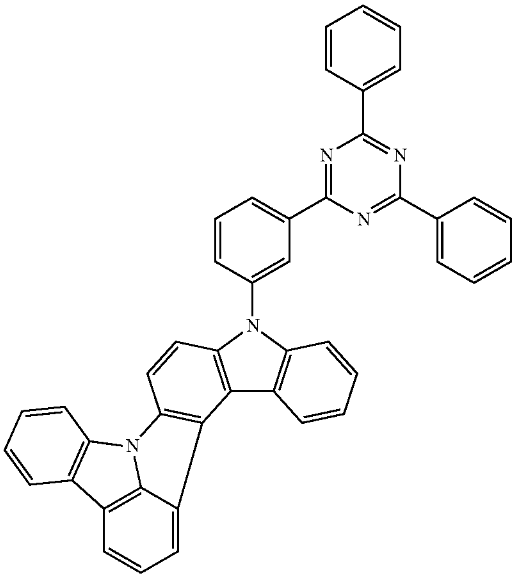
,
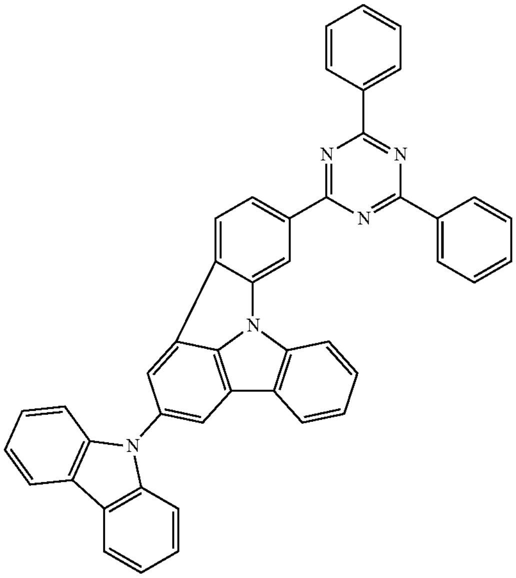
,
-continued
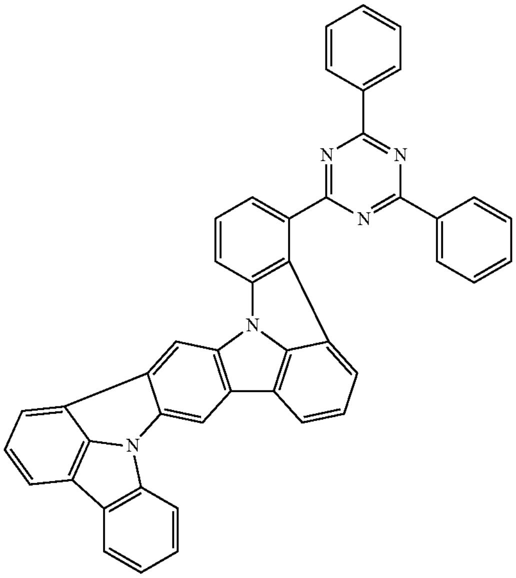
,
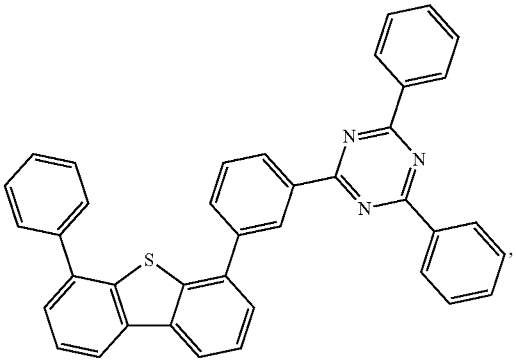
,
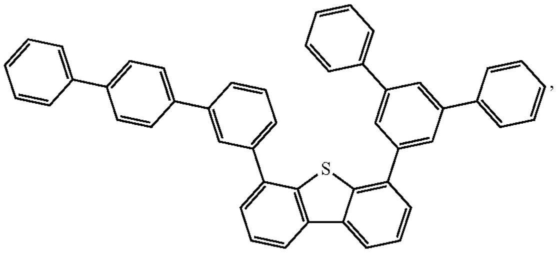
,
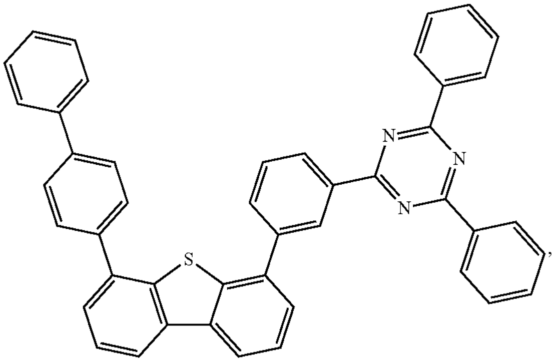
, -continued
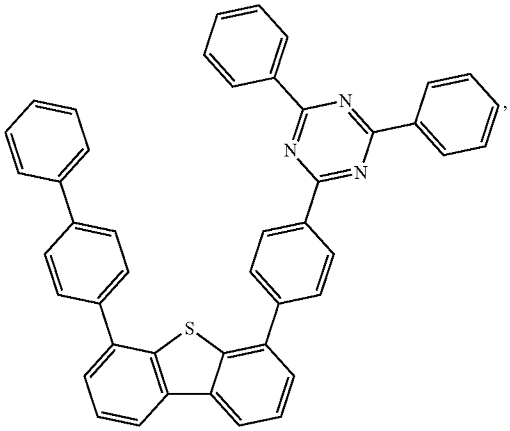
,
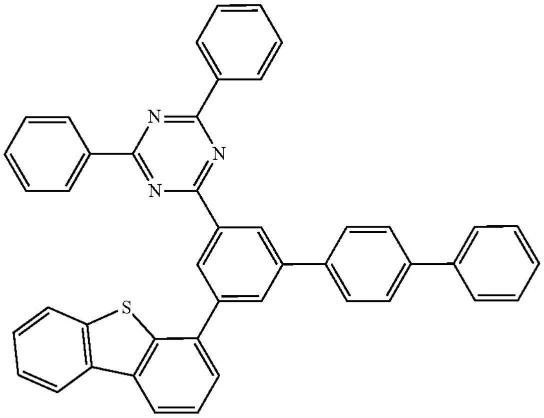
,
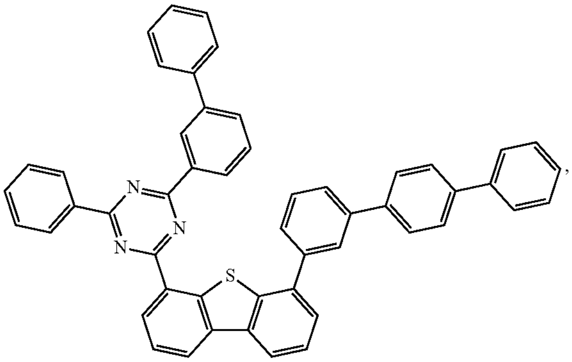
,
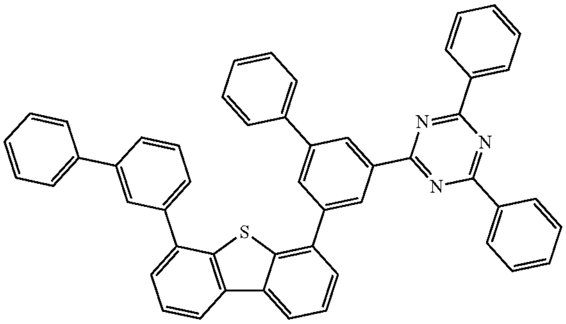
,
-continued
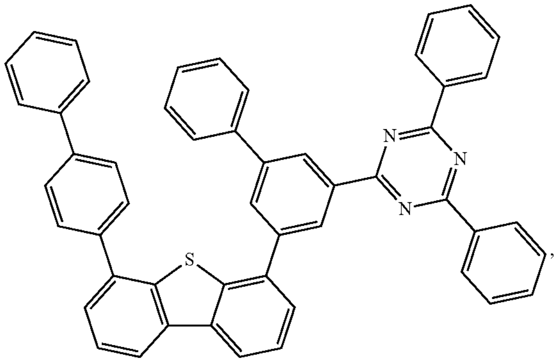
,
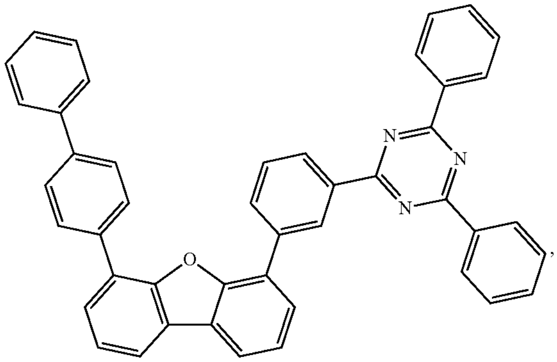
,
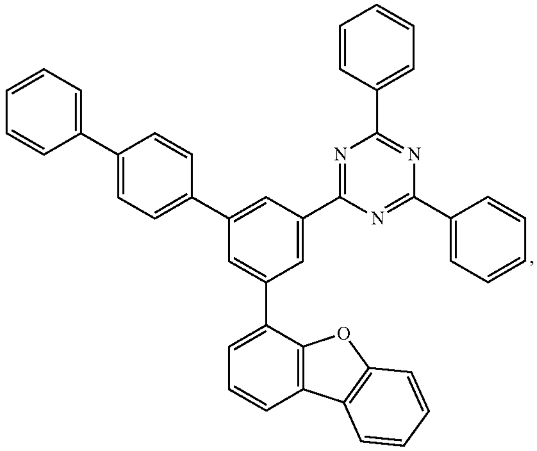
,
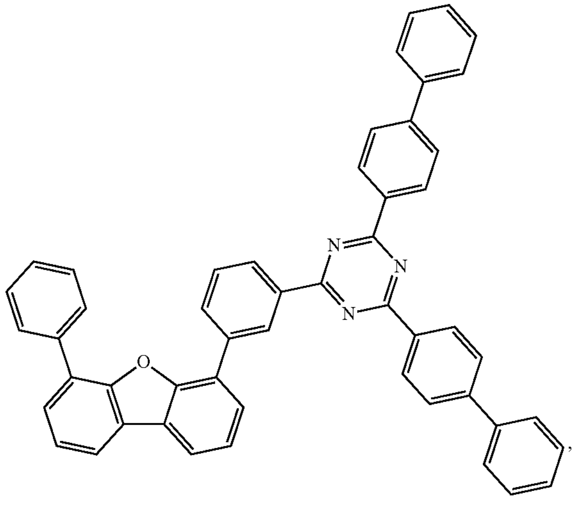
, -continued
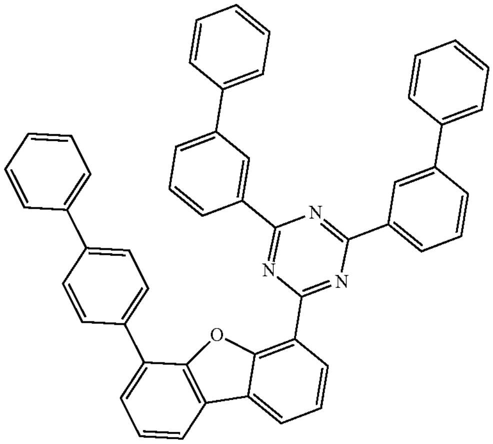
,
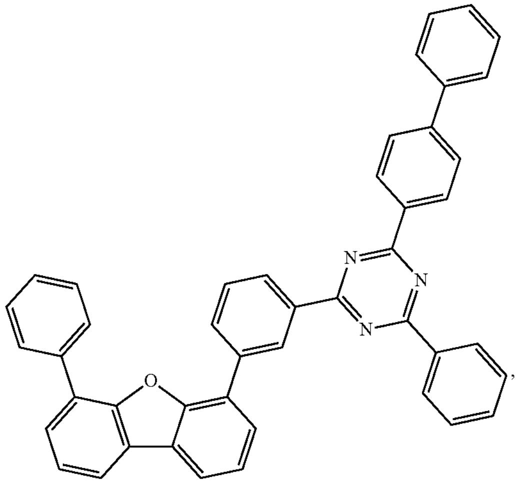
,
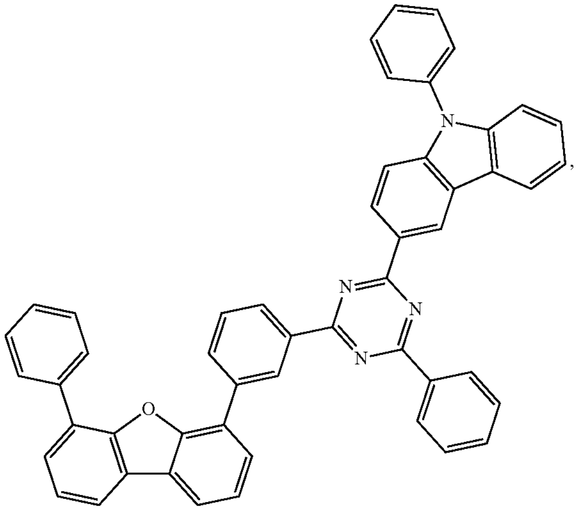
,
-continued
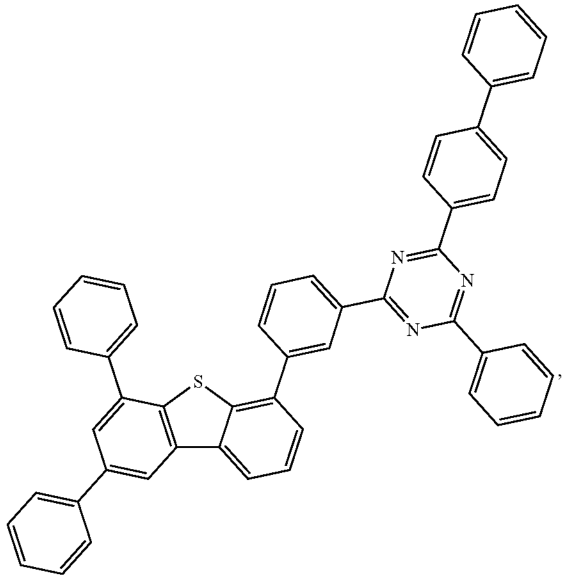
,
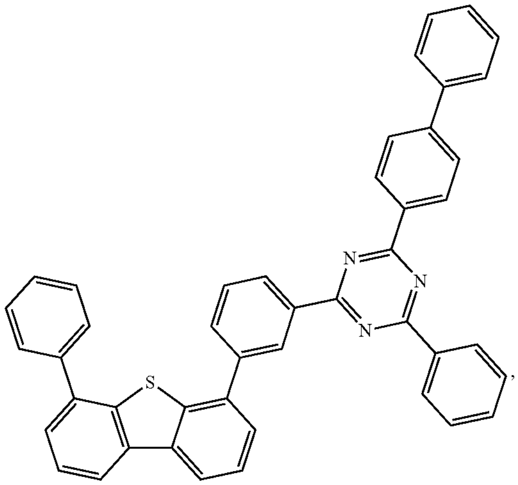
,
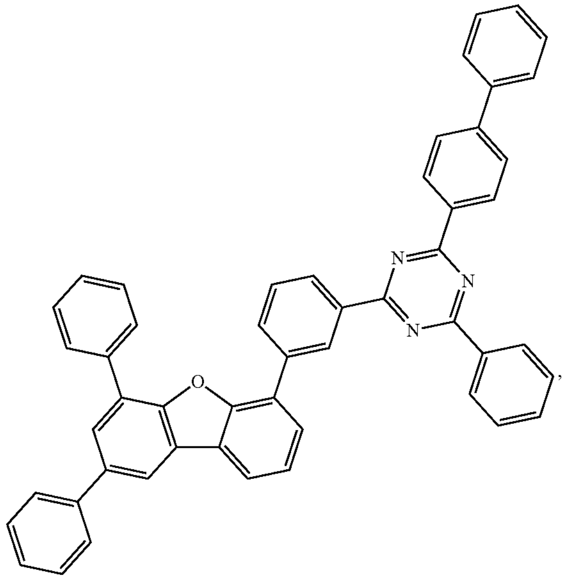
, -continued
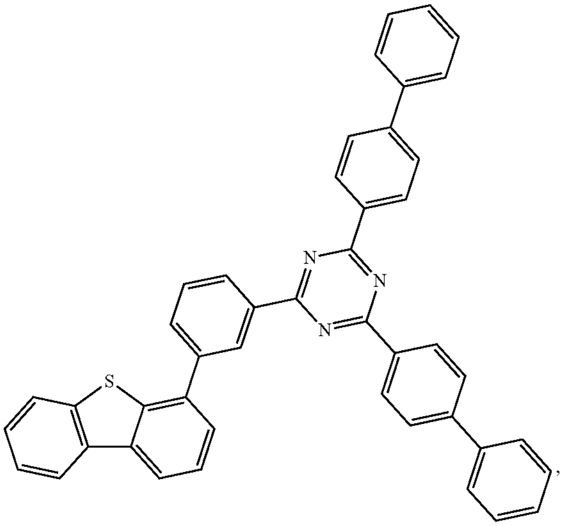
,
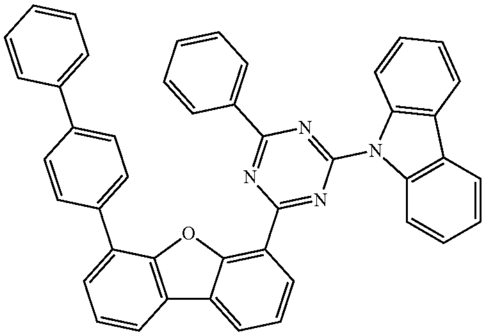
,
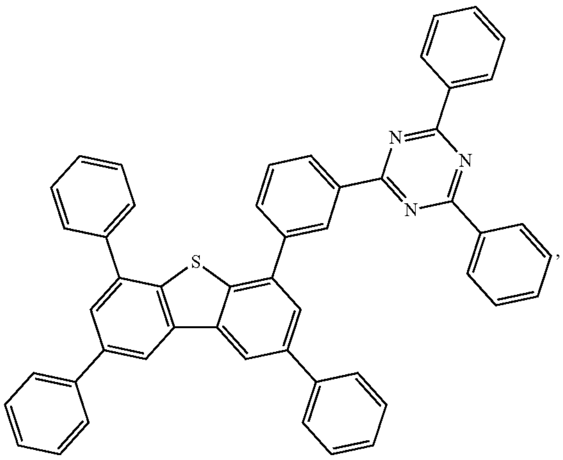
,
-continued
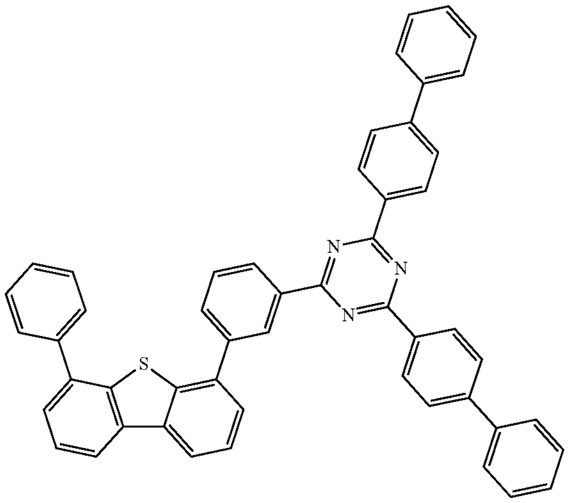
,
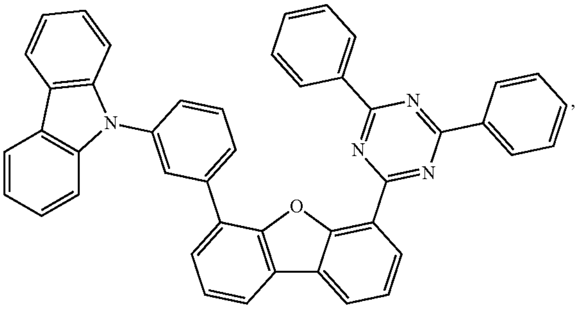
,
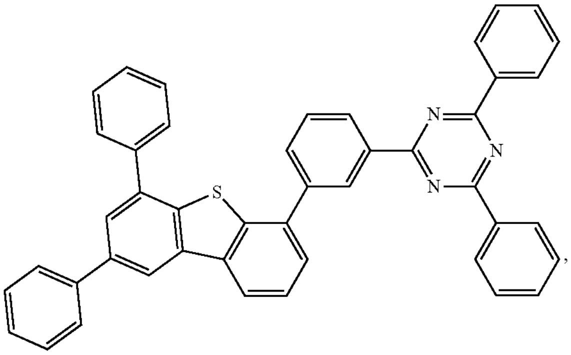
,
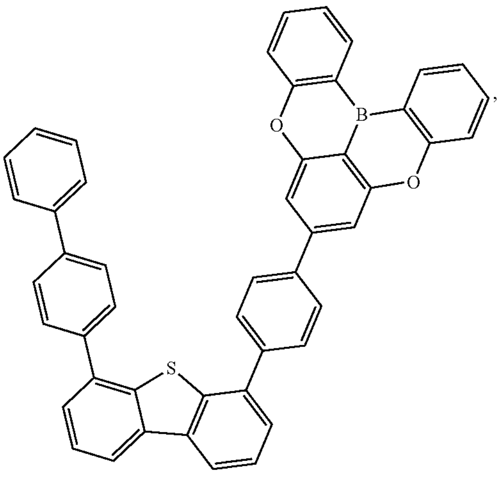
, -continued
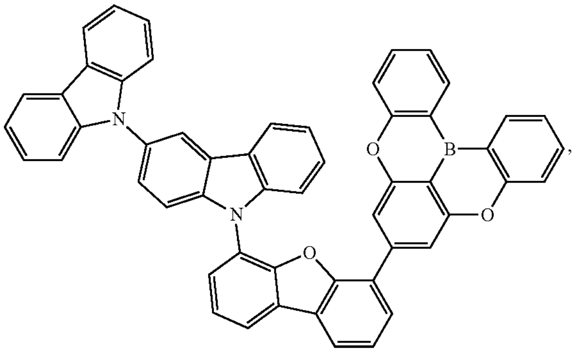
,
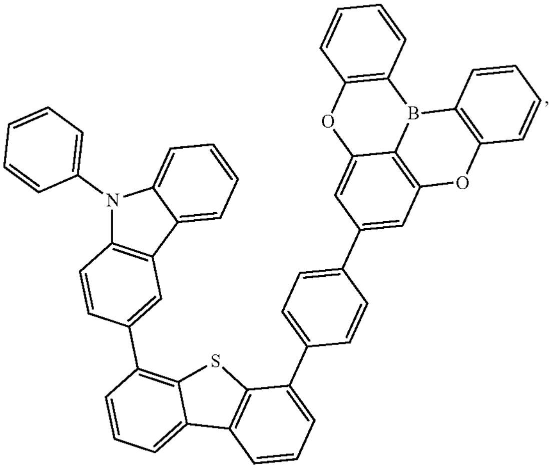
,
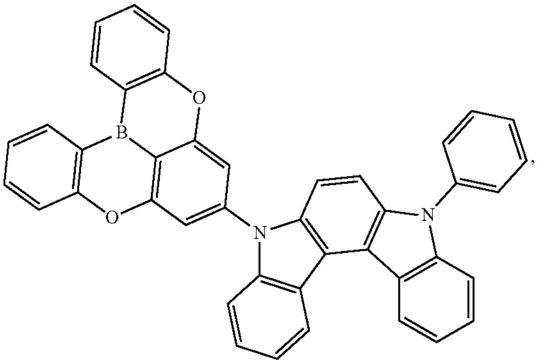
,
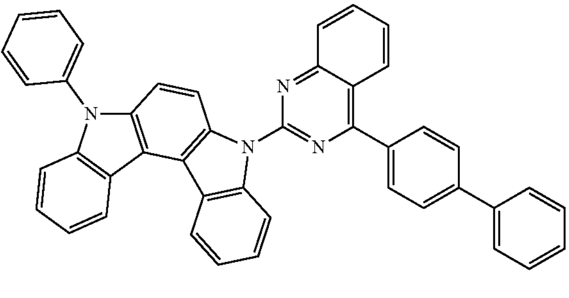
,
-continued
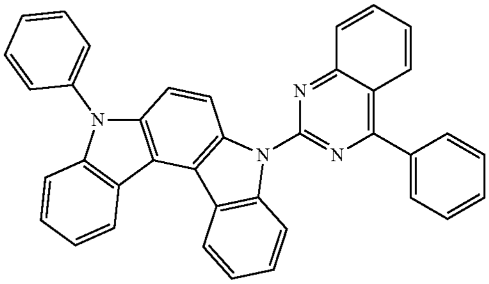
,
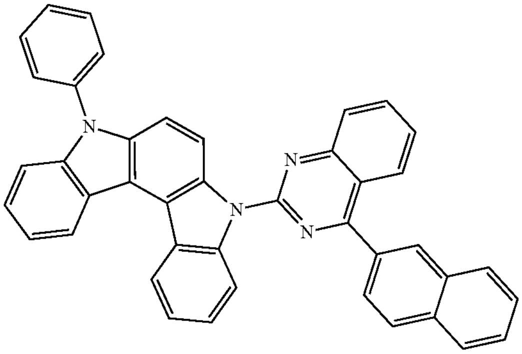
,
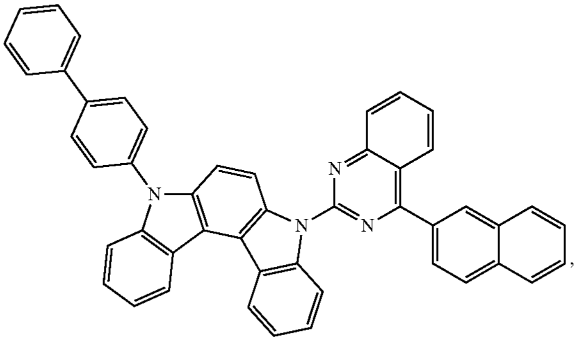
,
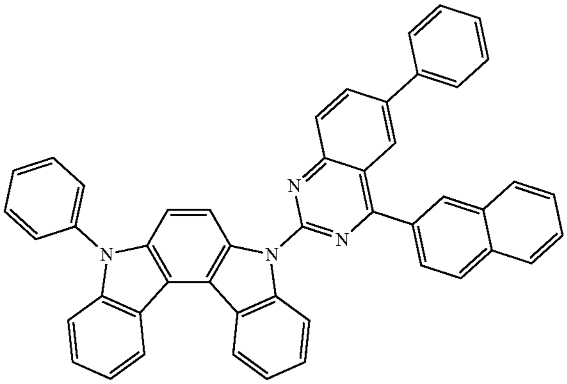
,

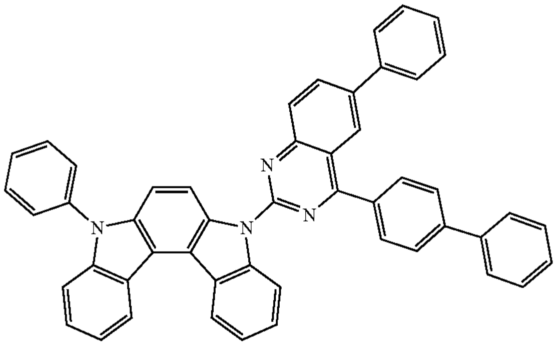
,
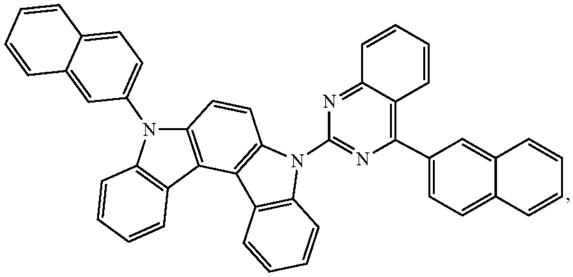
,
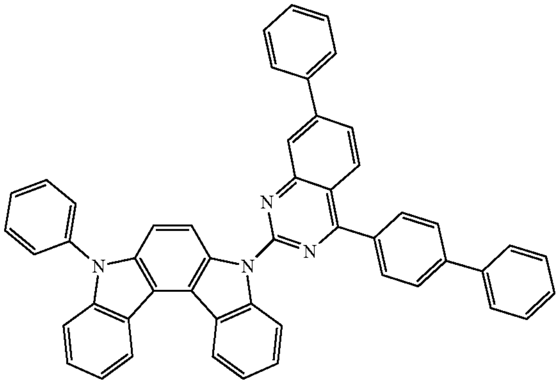
,
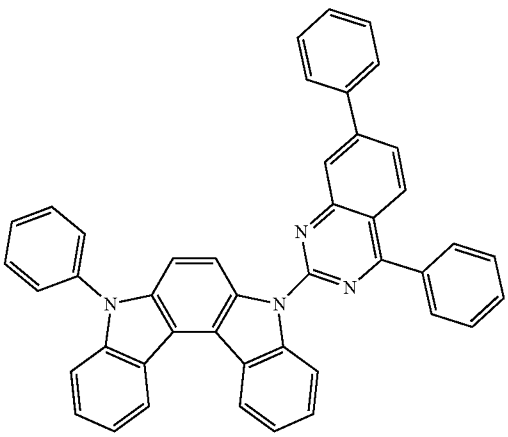
,
-continued
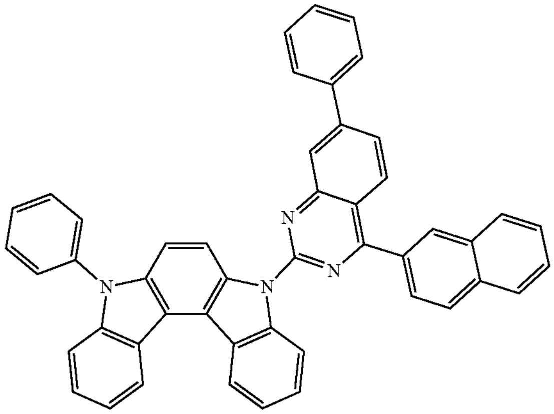
,
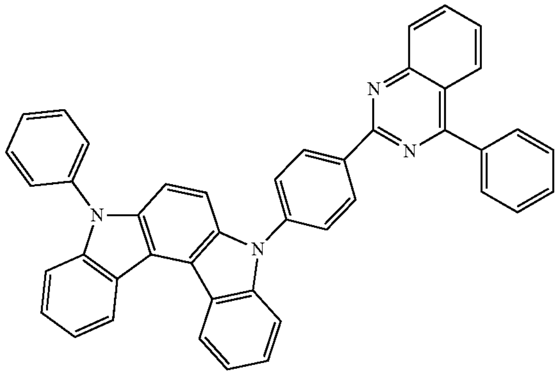
,
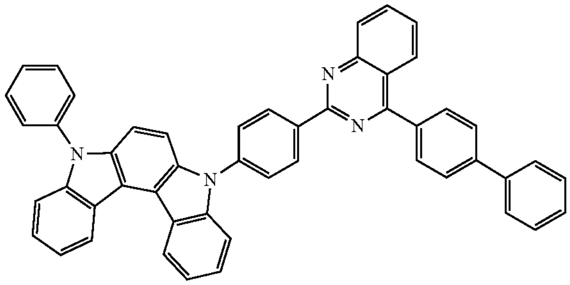
,
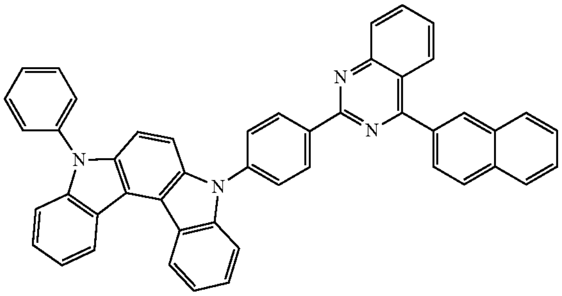
,
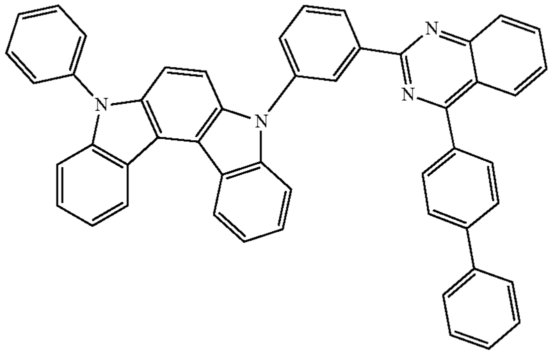
, -continued
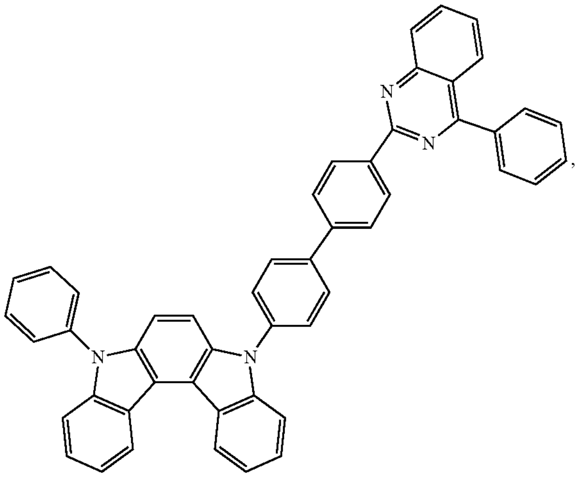
,
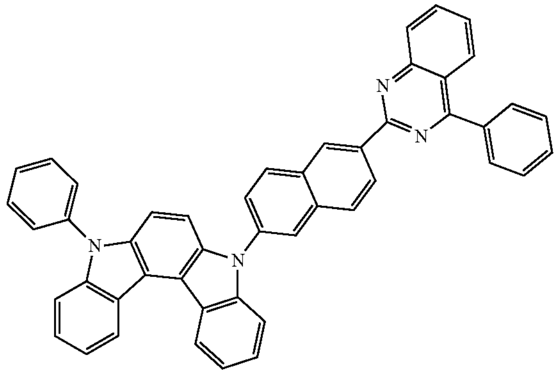
,
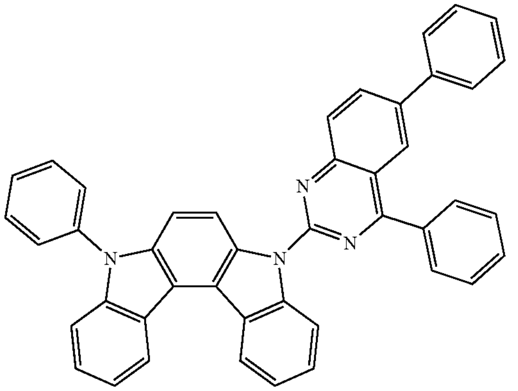
,
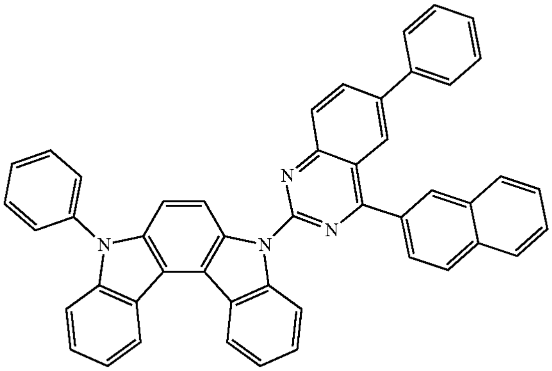
,
-continued
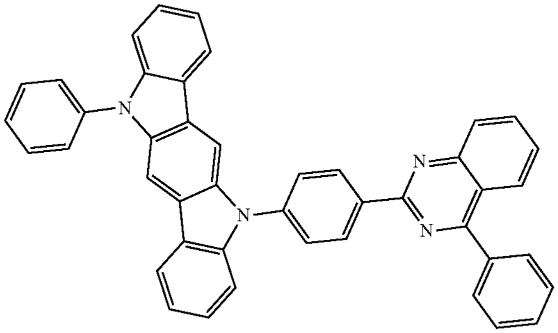
,
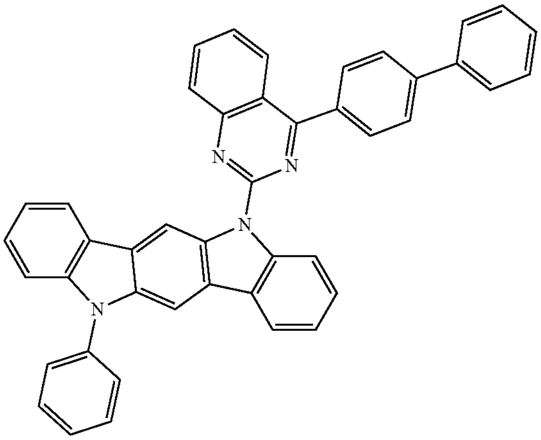
,
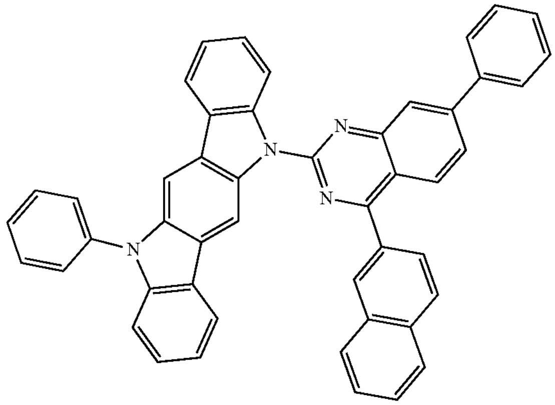
,
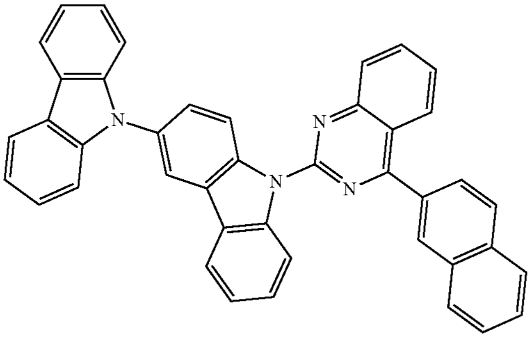
, -continued
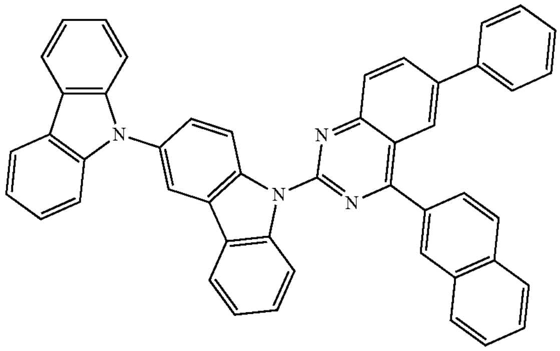
,
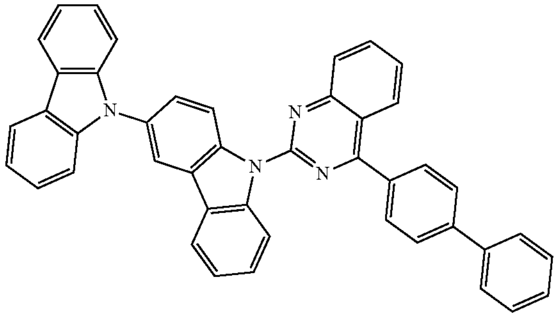
,
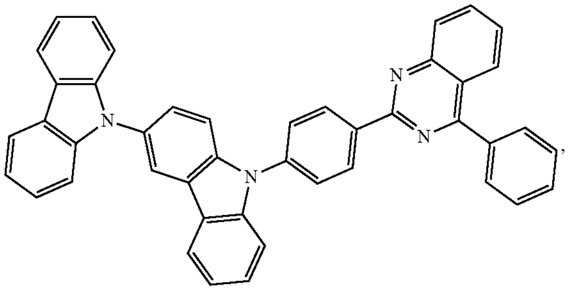
,
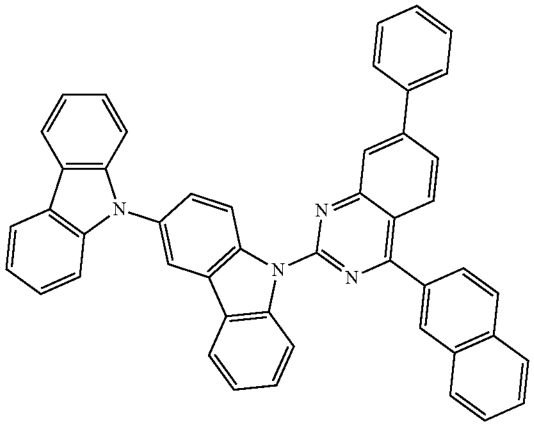
,
-continued
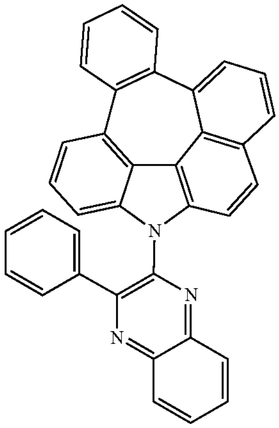
,
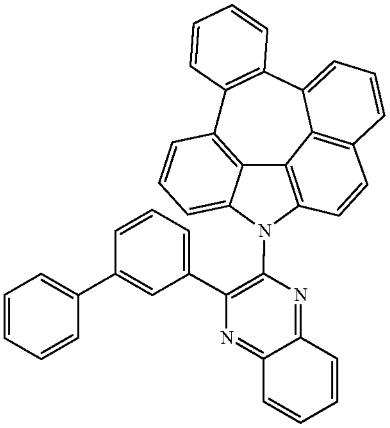
,
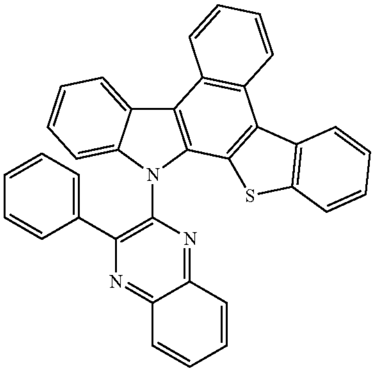
,
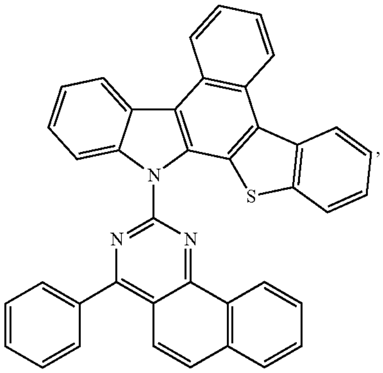
, -continued
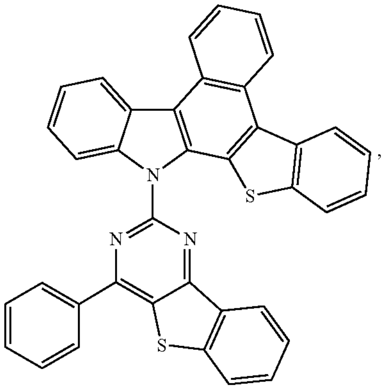
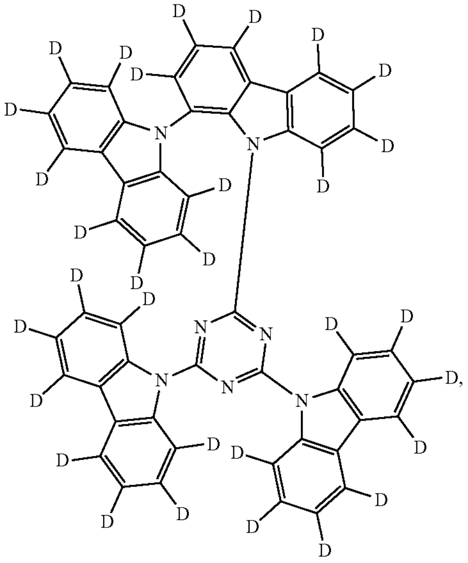
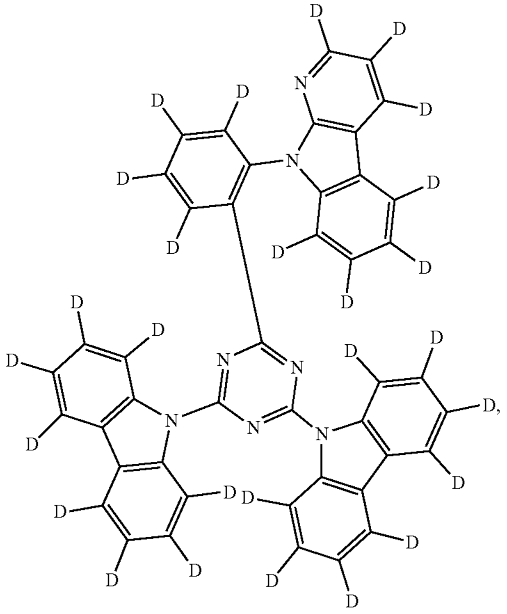
-continued
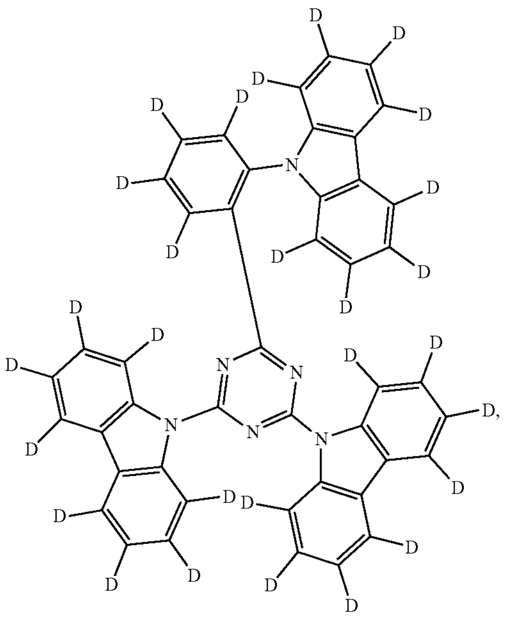
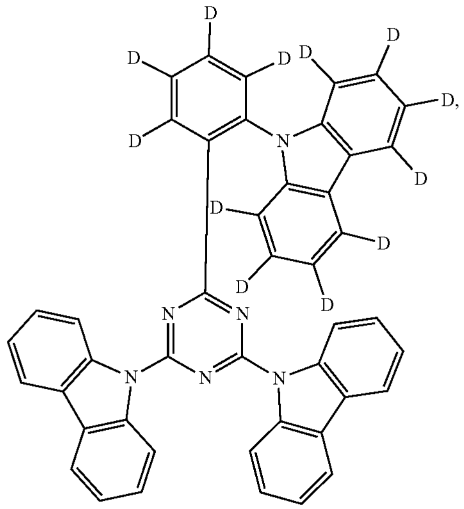
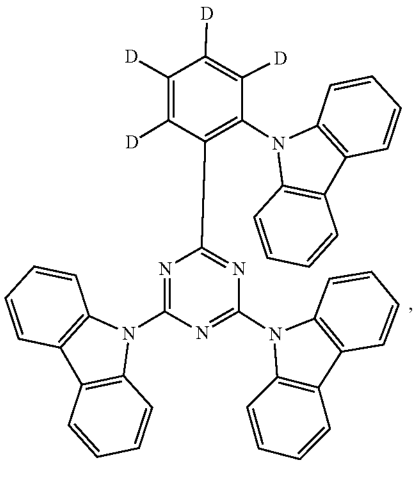

-continued
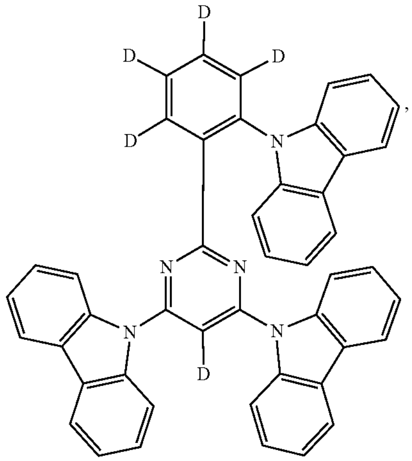
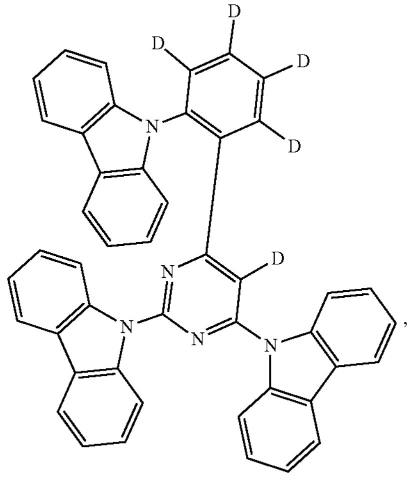
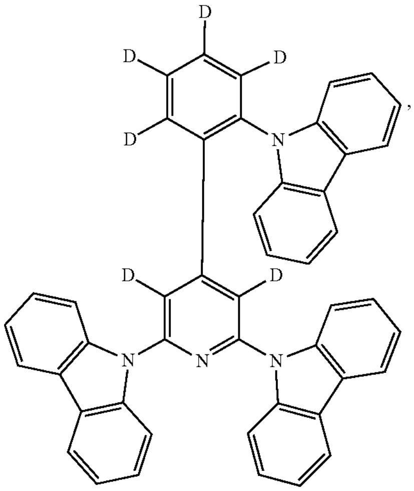
-continued
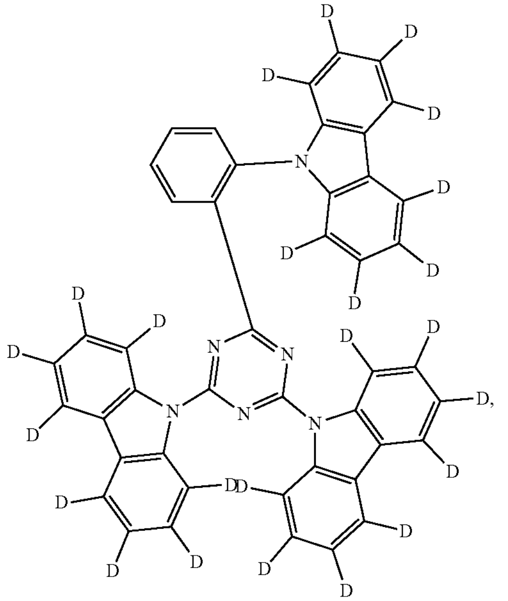
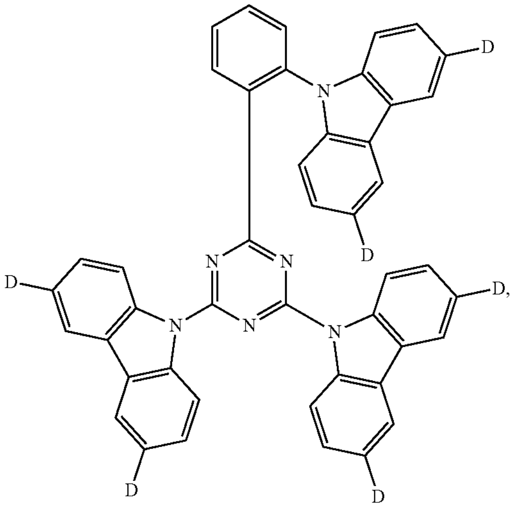
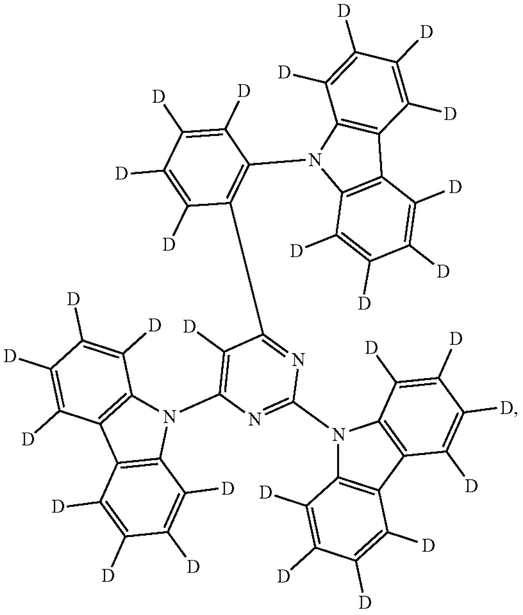

-continued
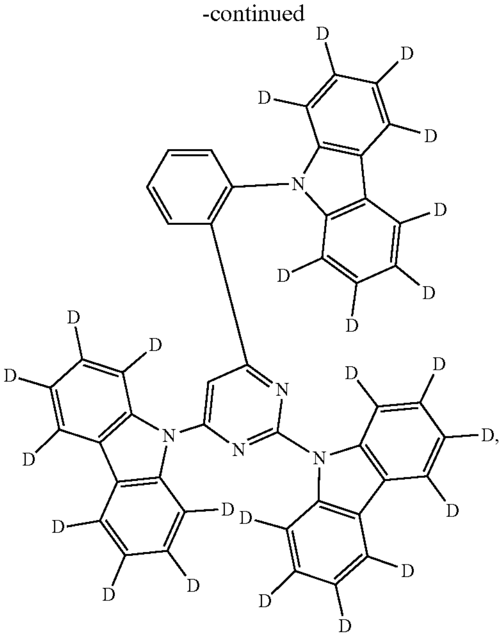
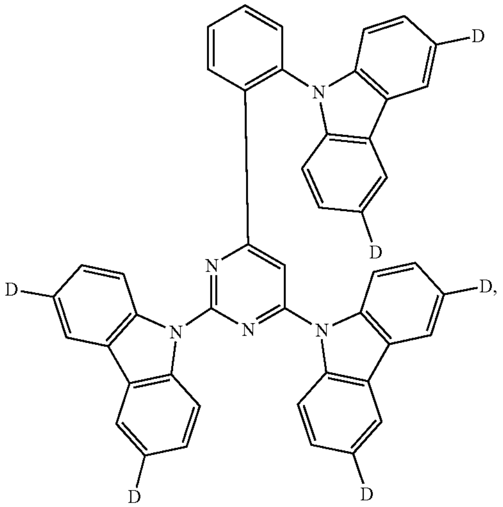
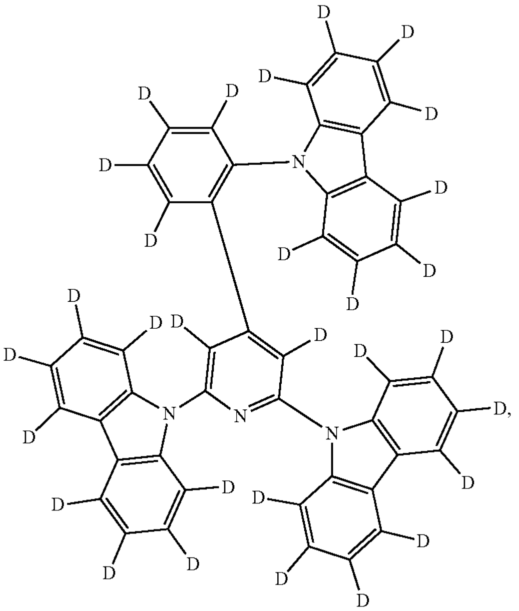
-continued
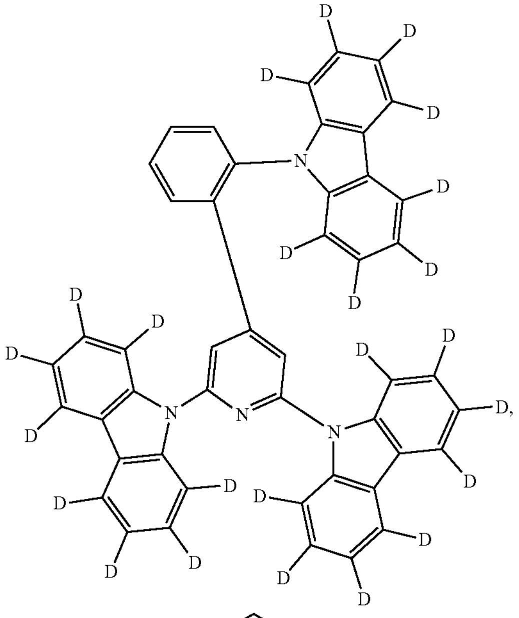
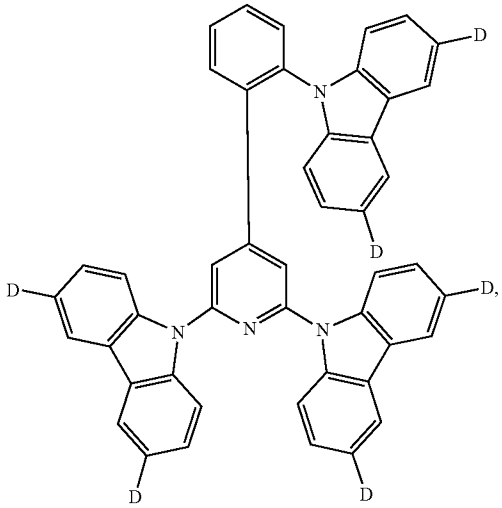
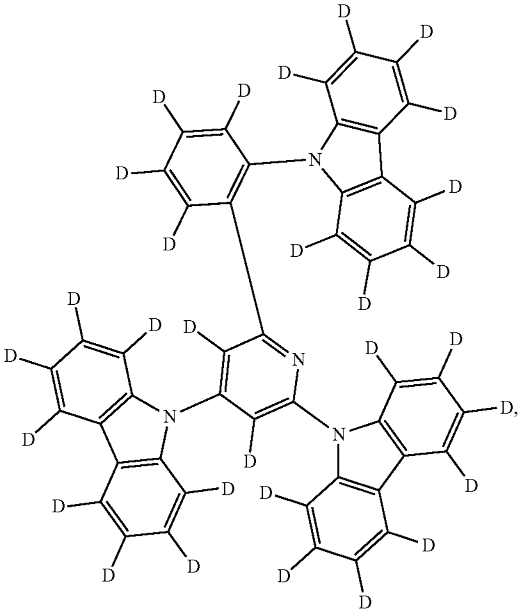

-continued
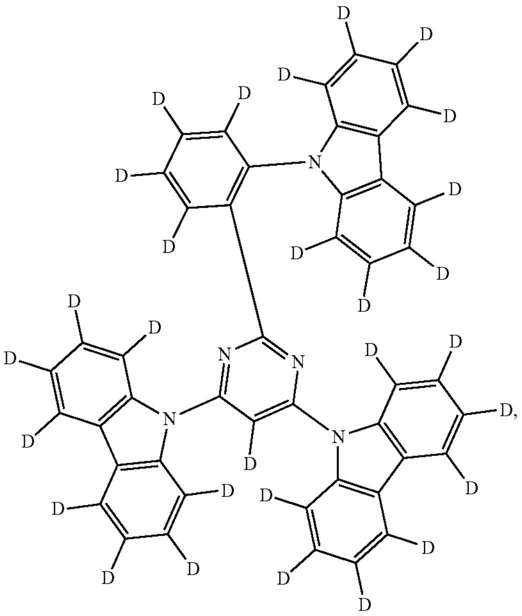
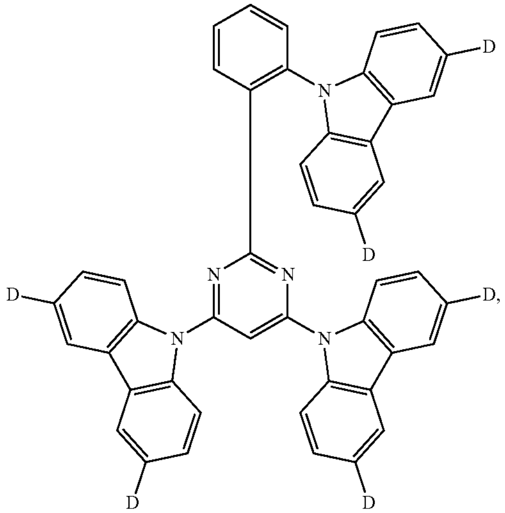
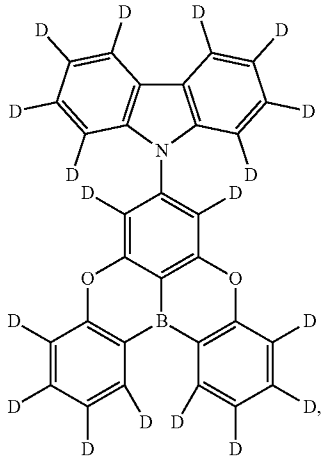
-continued
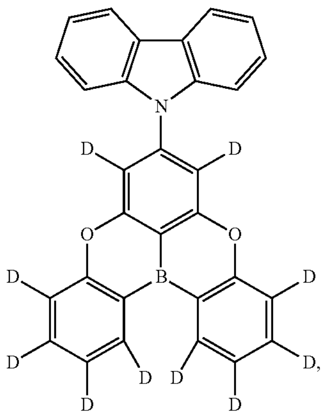
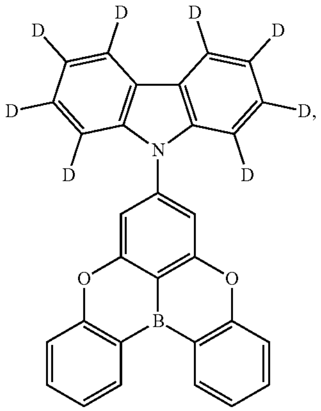
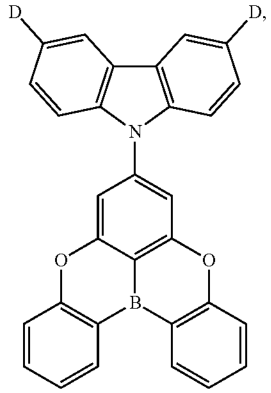
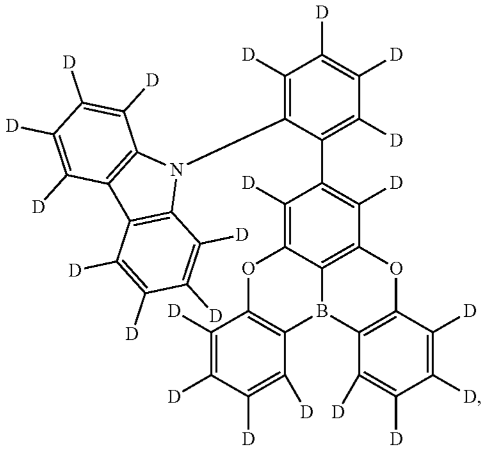

-continued
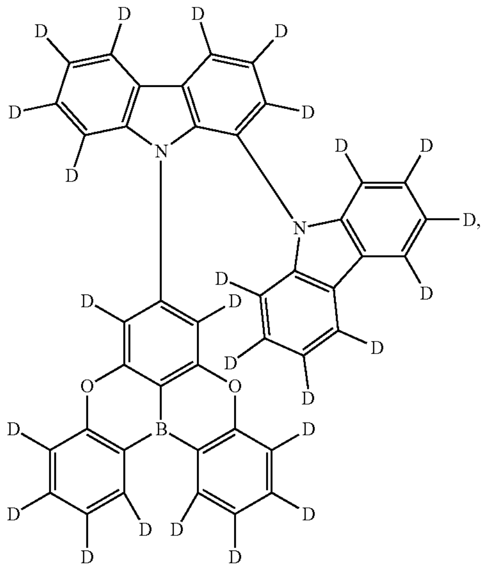
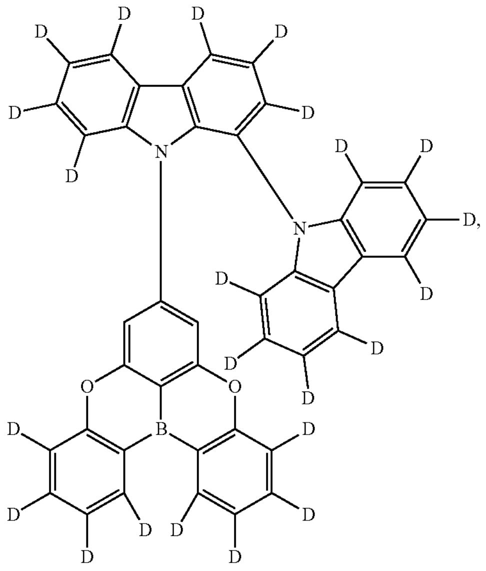
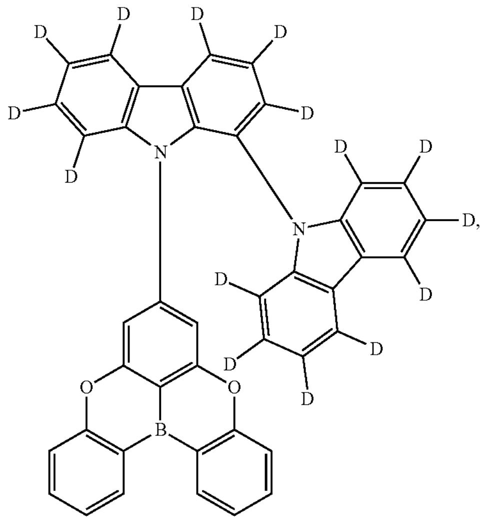
-continued
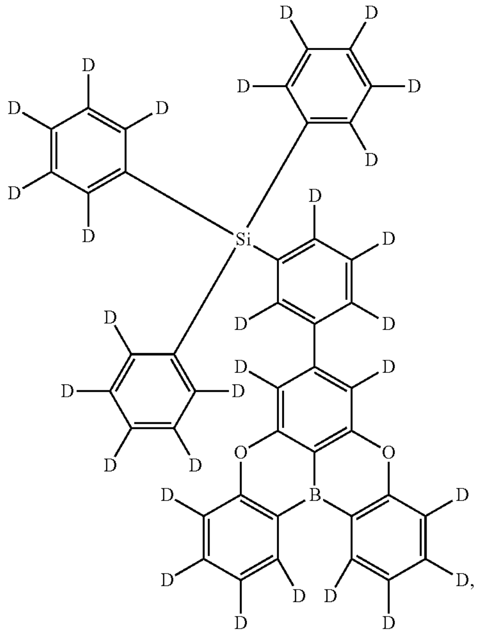
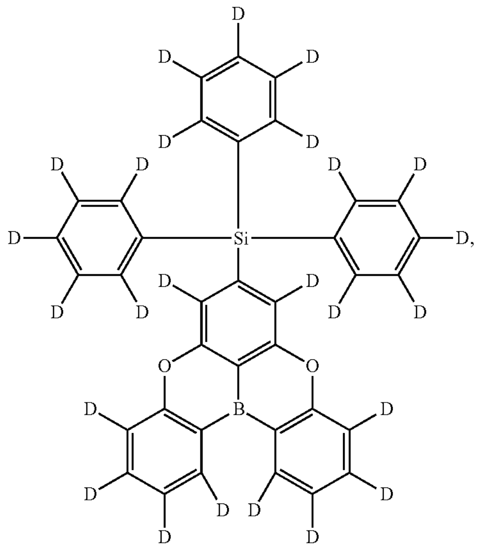

-continued
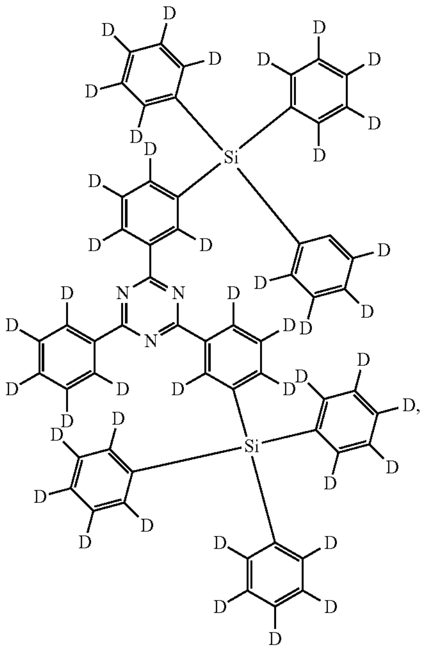
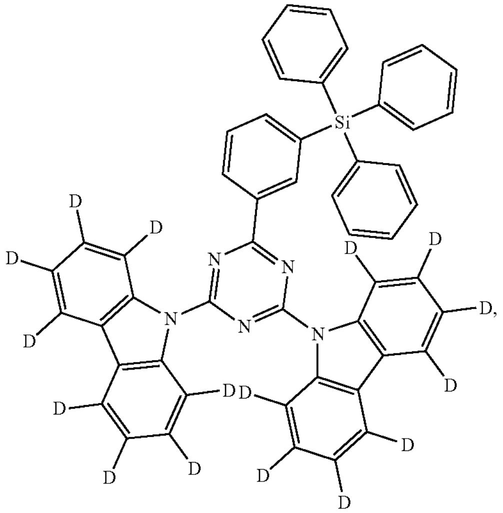
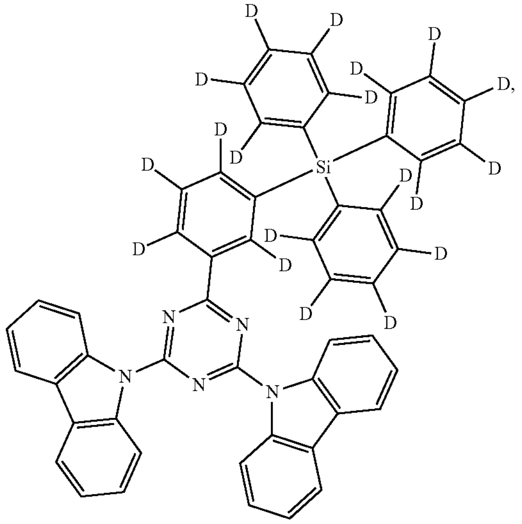
-continued
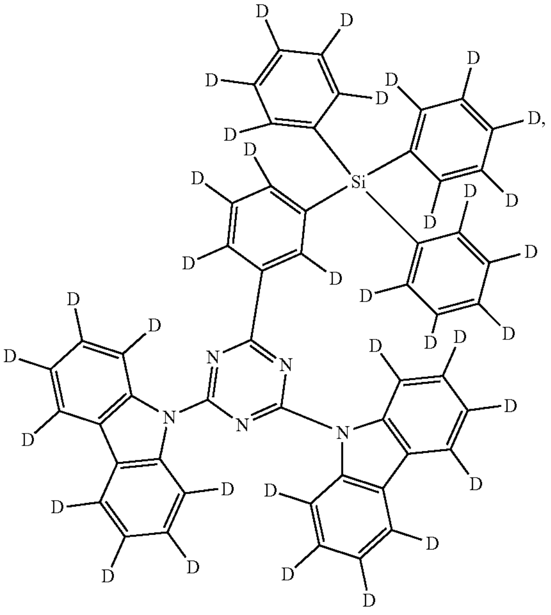
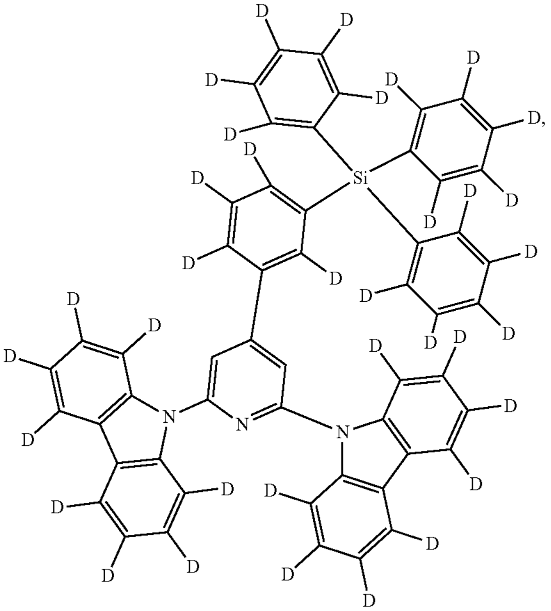

-continued
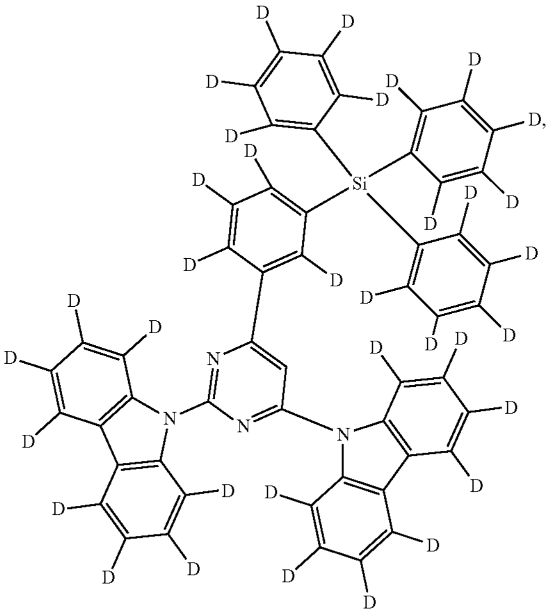
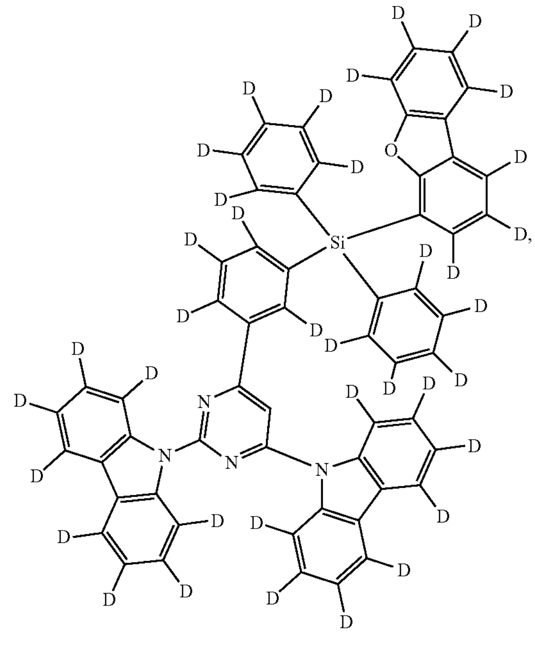
-continued
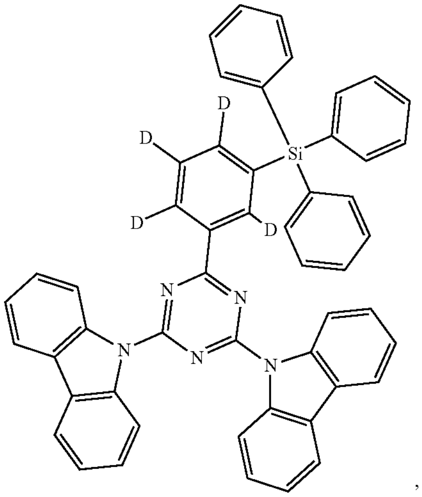
,
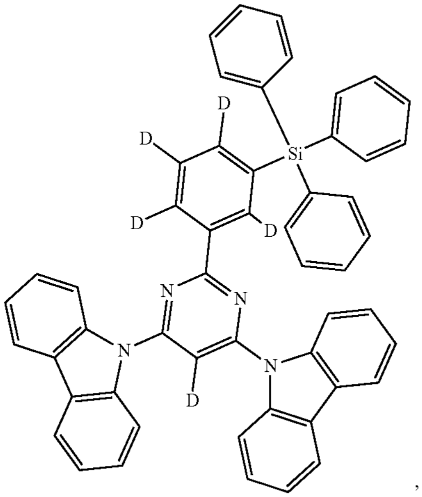
,
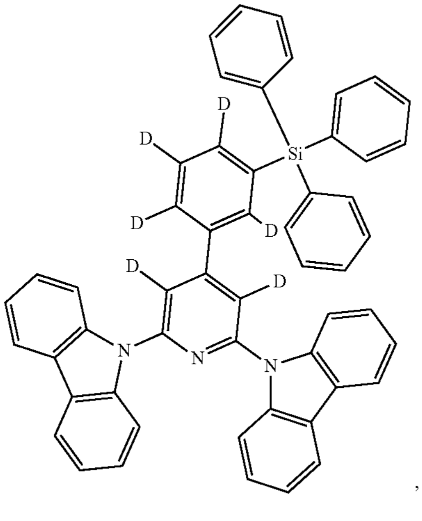
, -continued
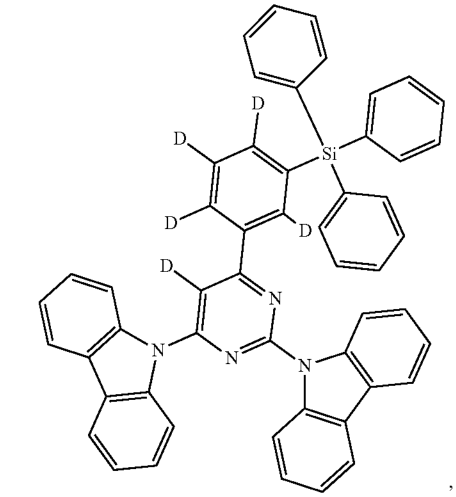
,
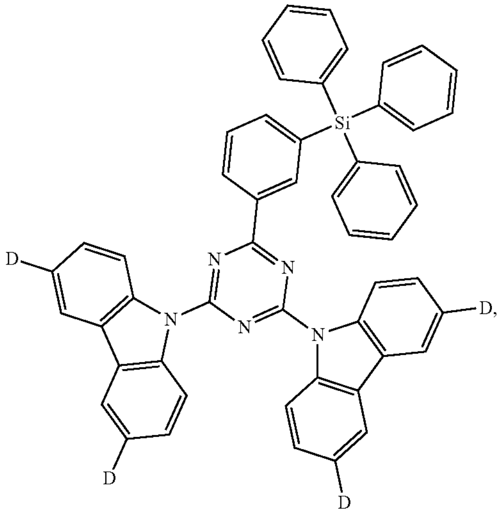
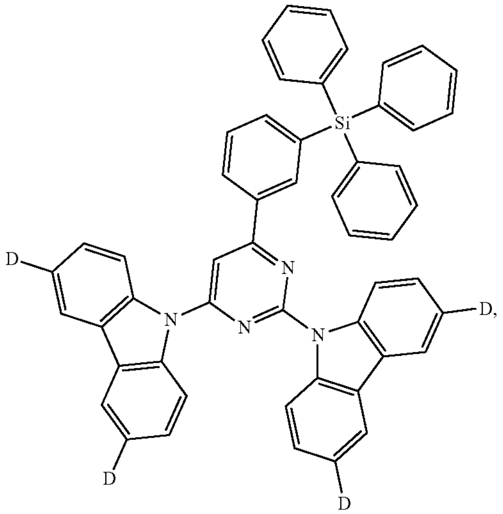
-continued
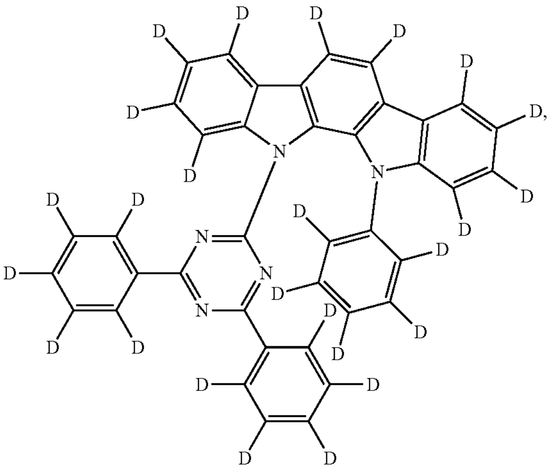
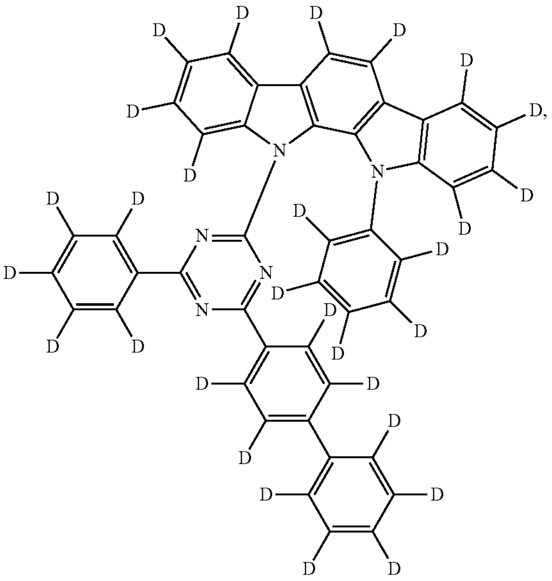
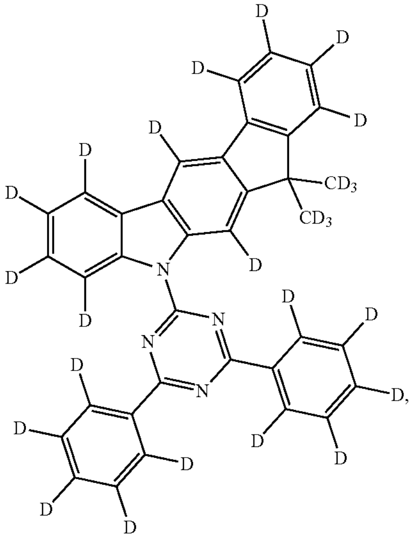

-continued
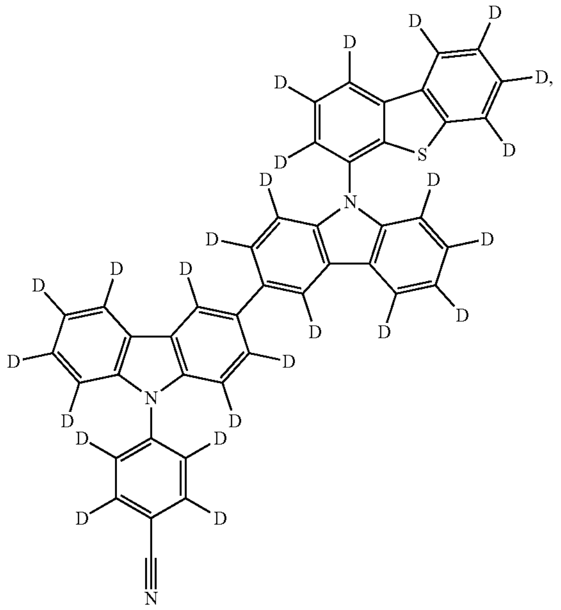
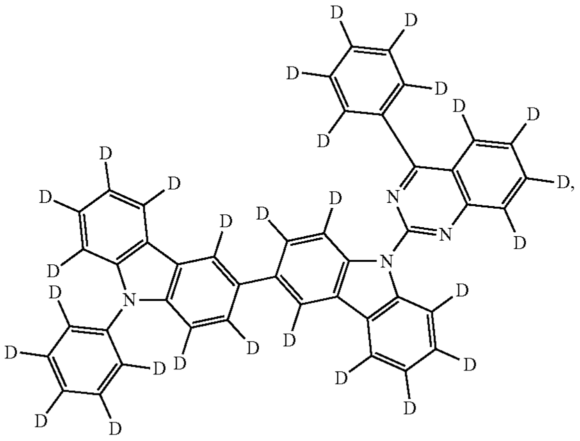
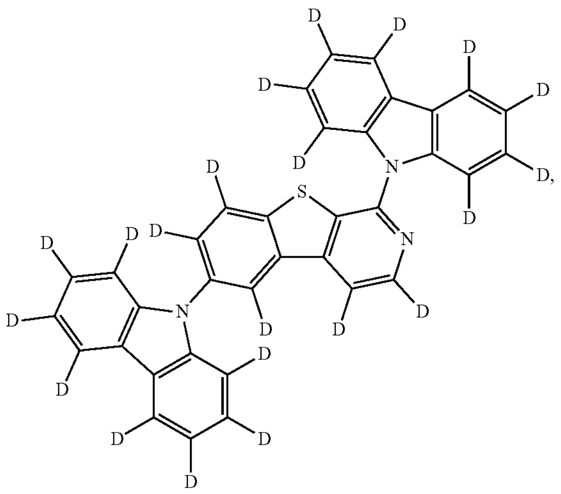
-continued
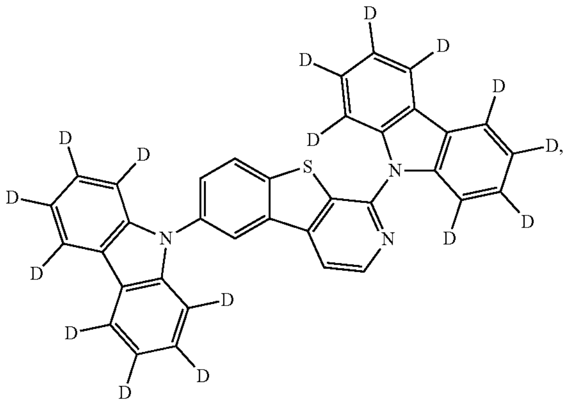
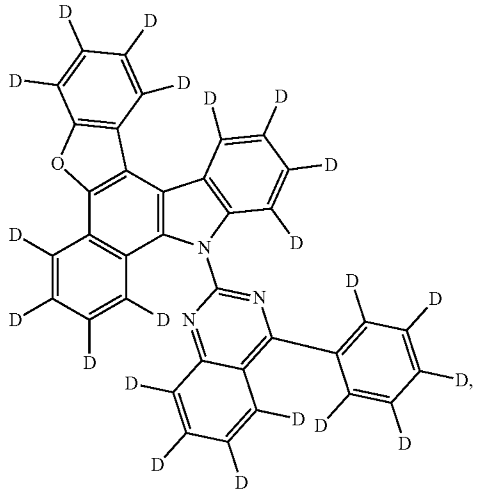
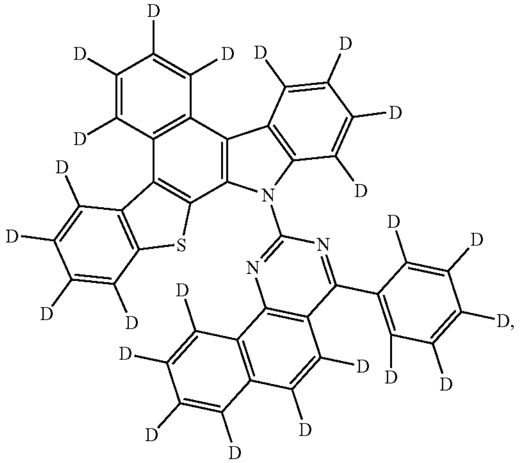

-continued
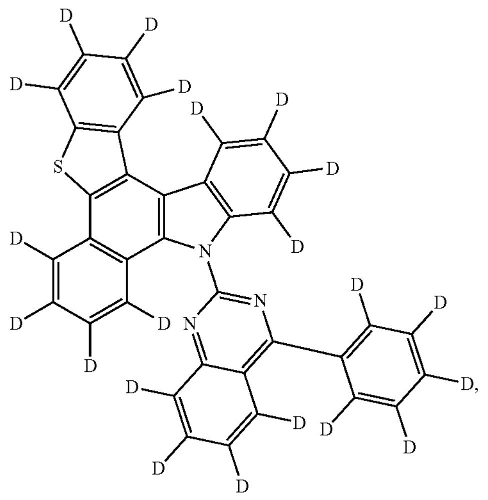
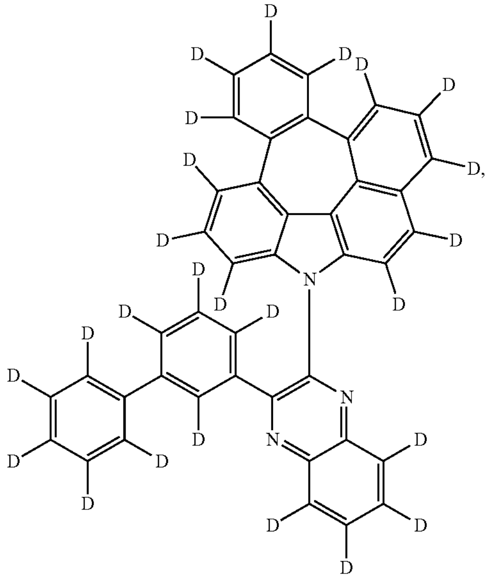
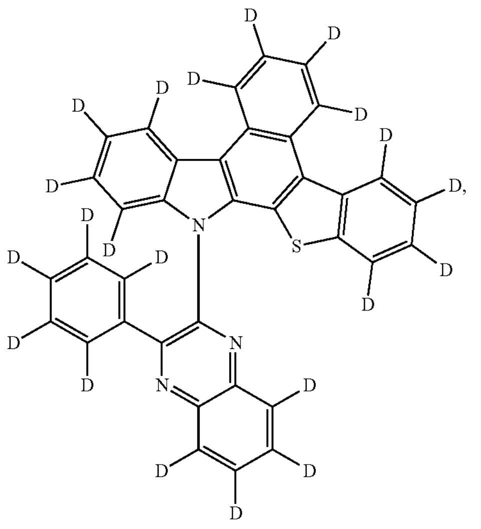
-continued
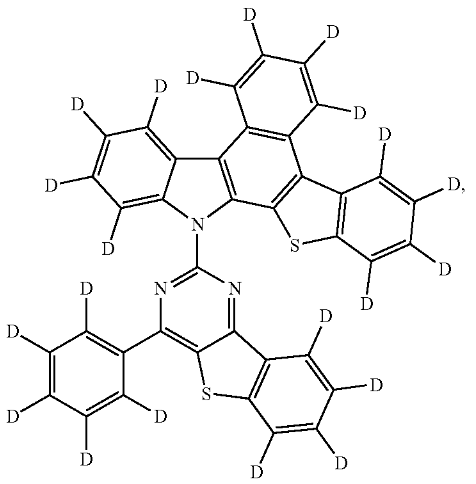
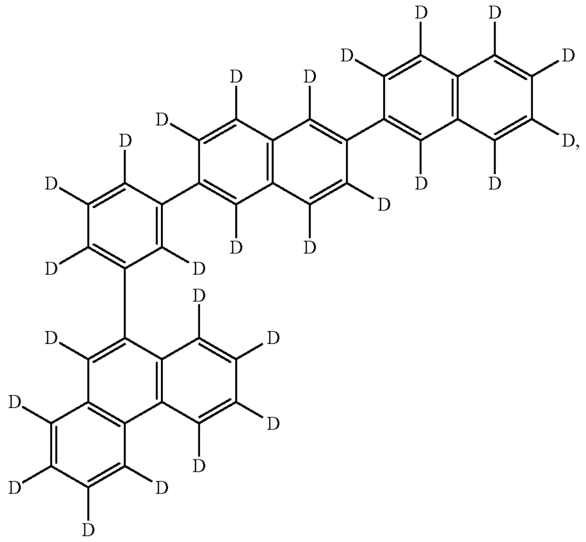
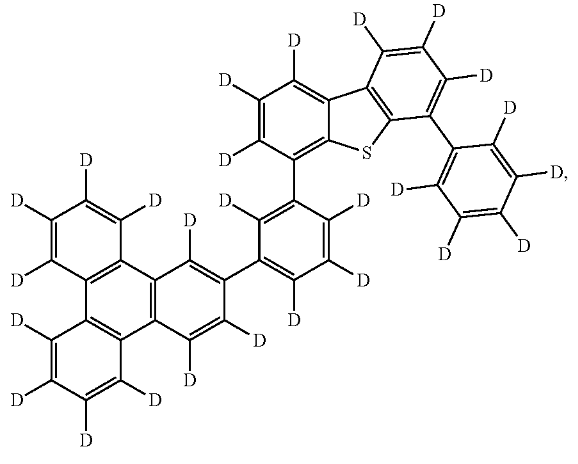

-continued
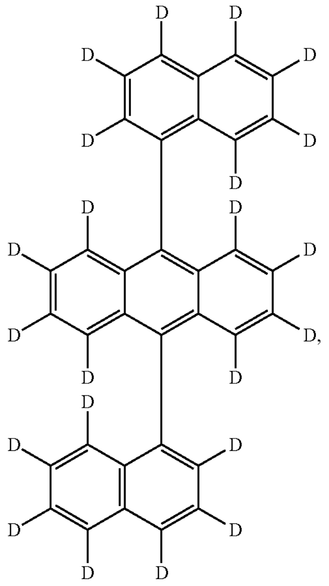
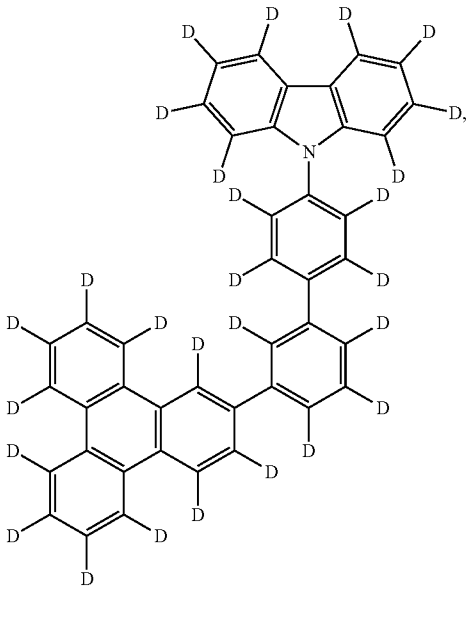
-continued
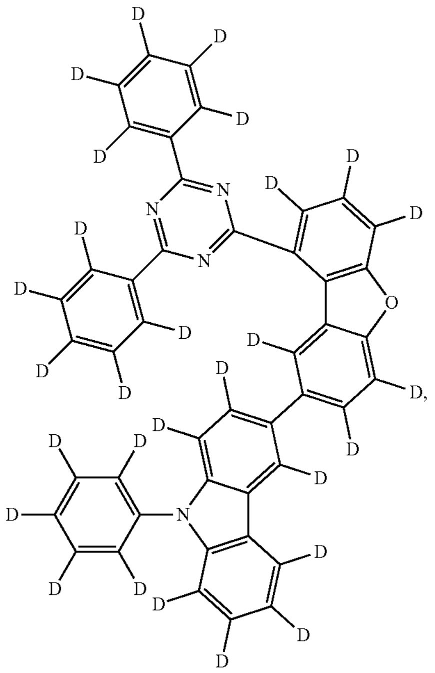
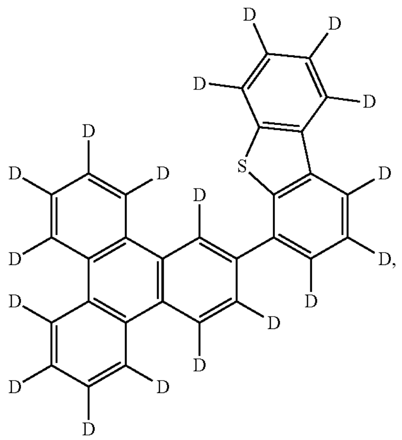
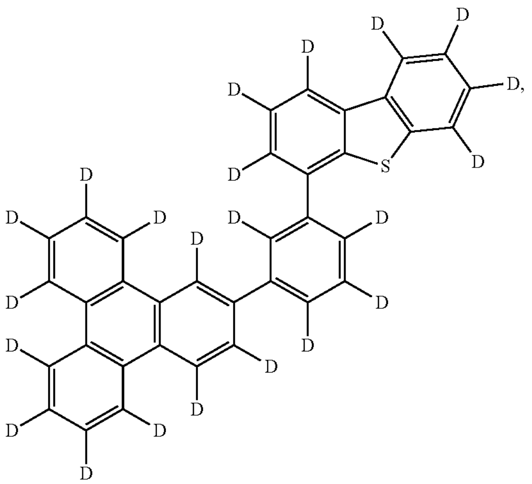

-continued
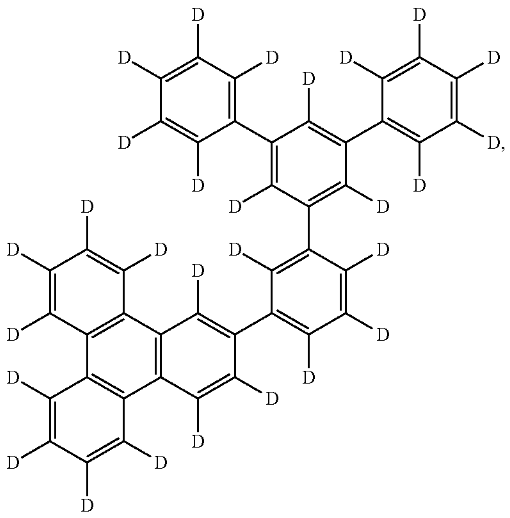
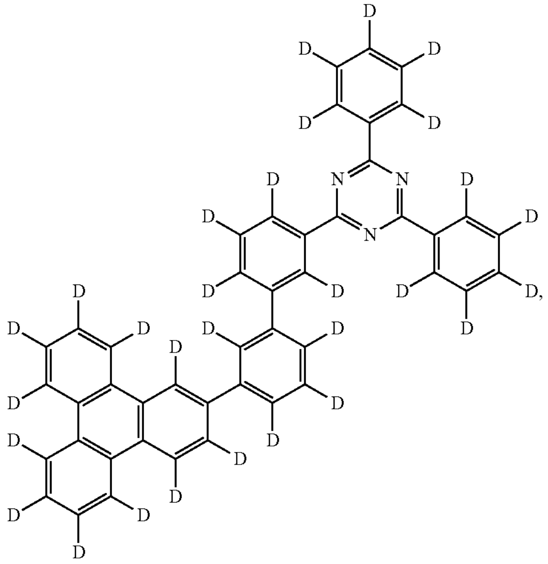
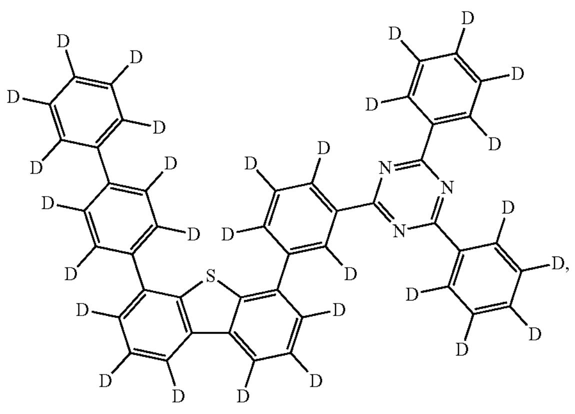
-continued
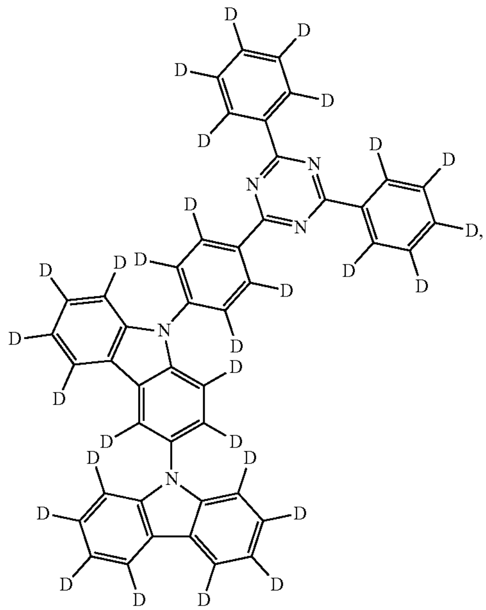
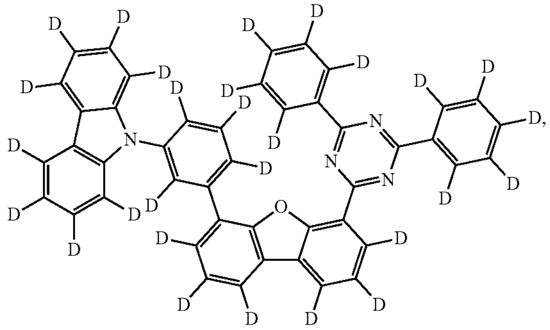
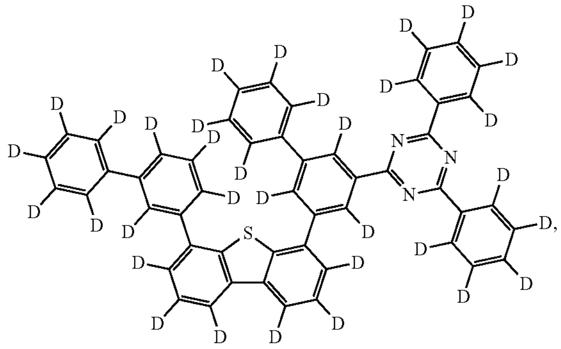

-continued
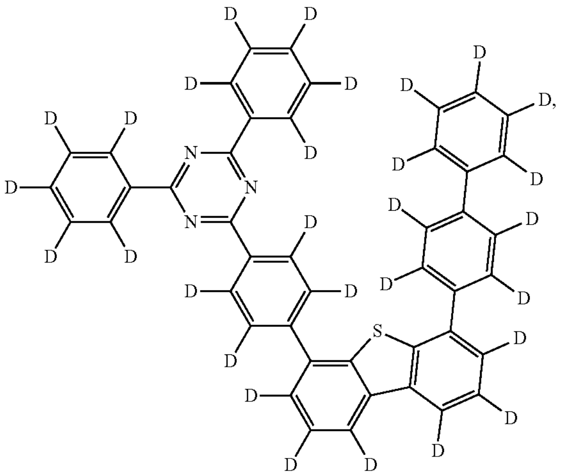
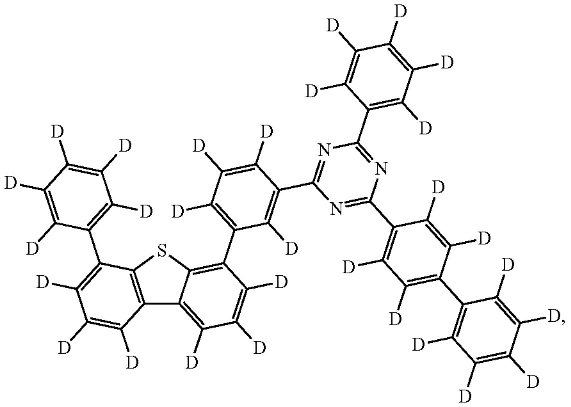
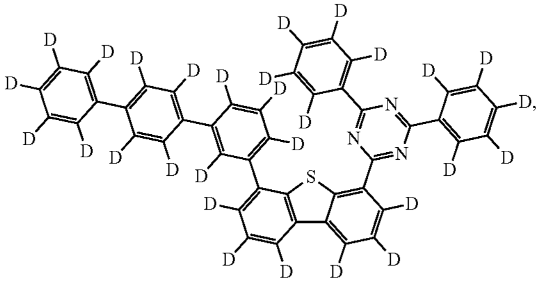
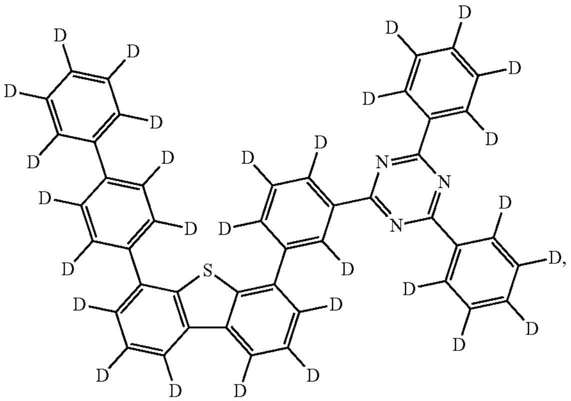
-continued
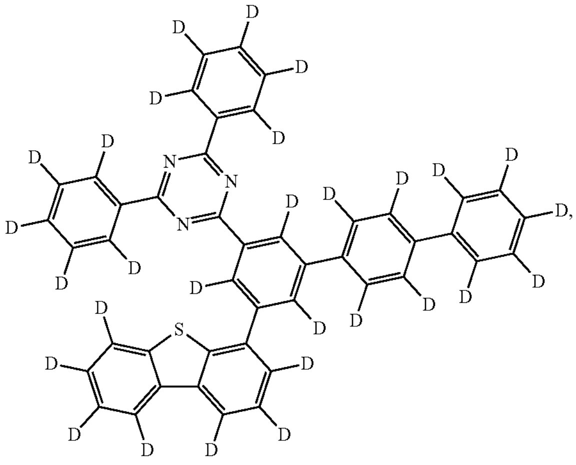
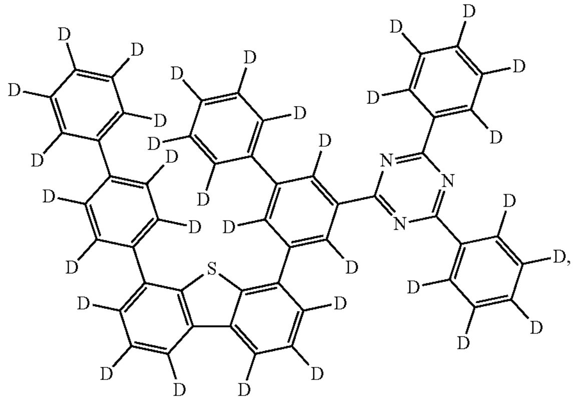
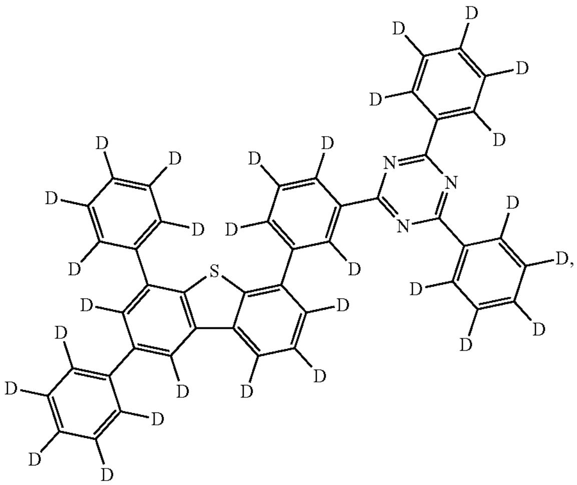
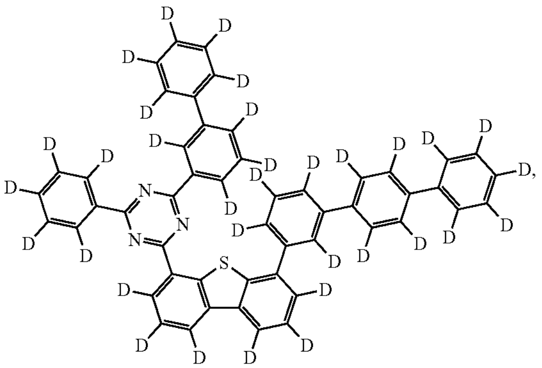

-continued
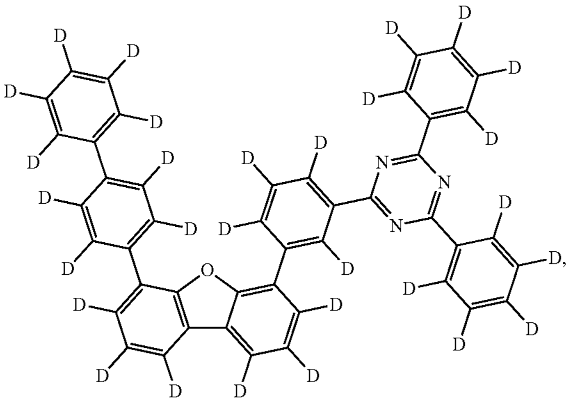
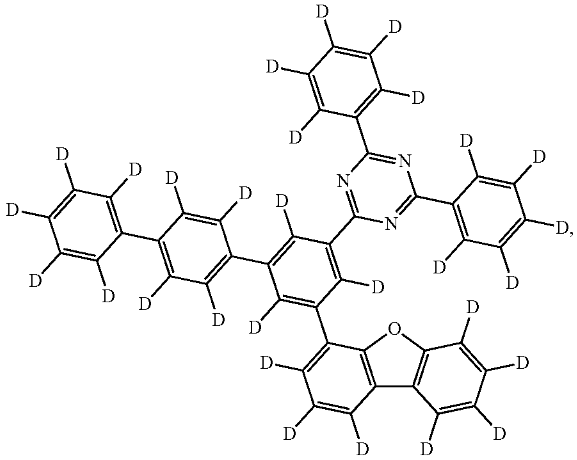
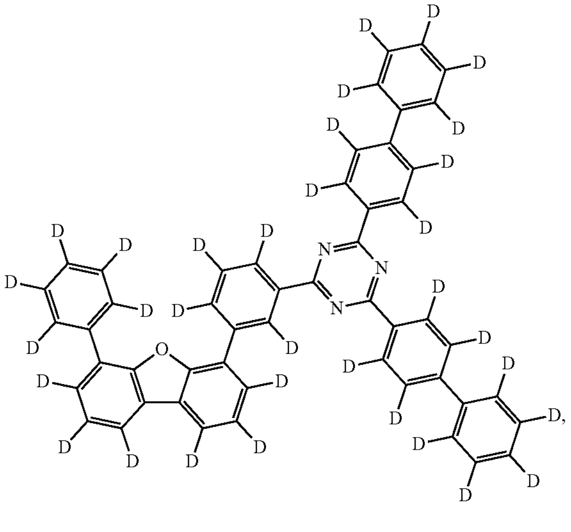
-continued
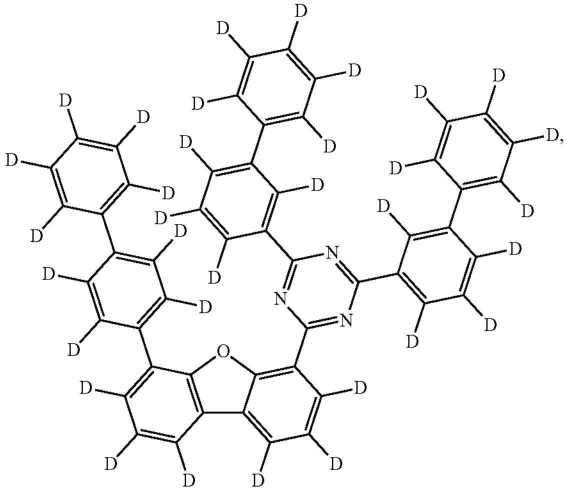
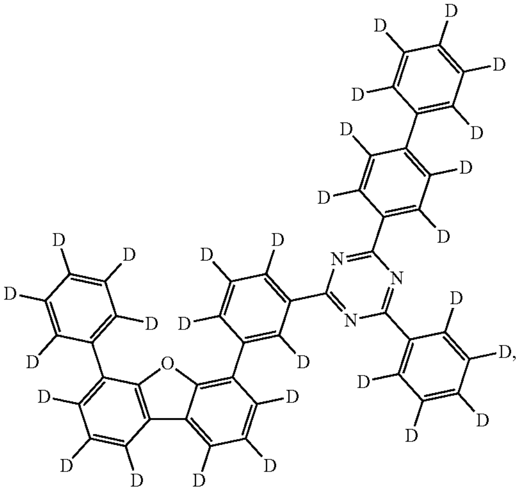
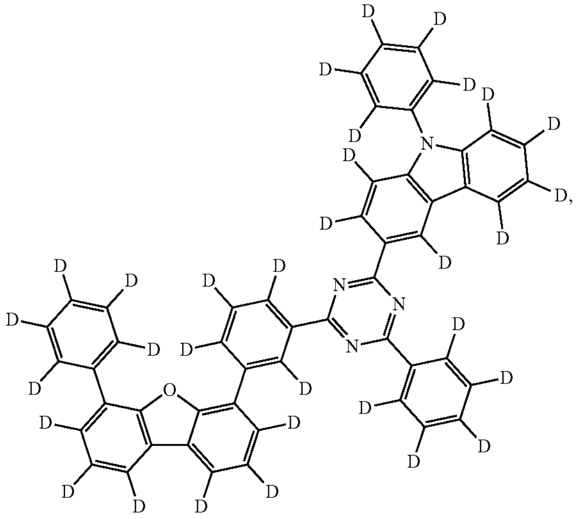

-continued
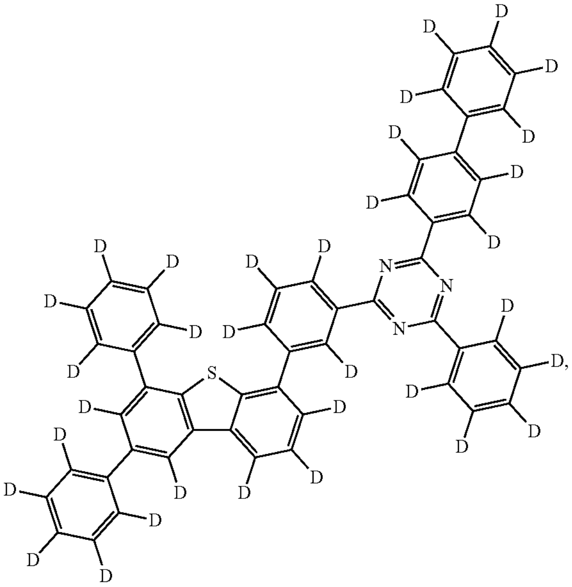
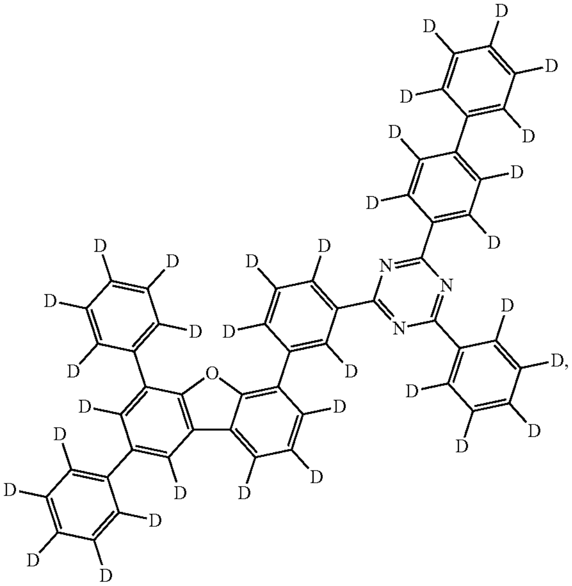
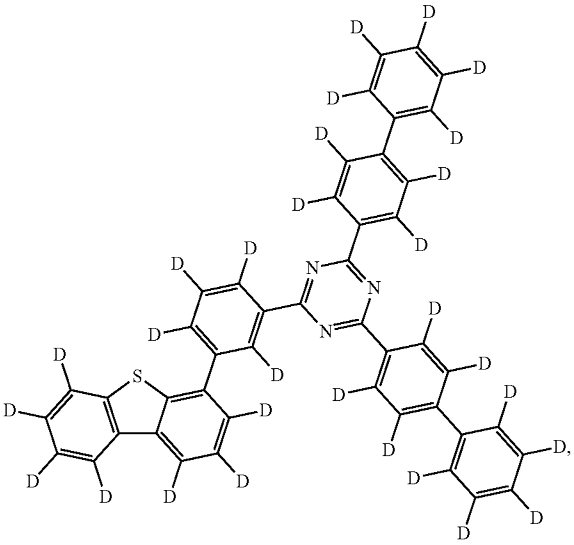
-continued
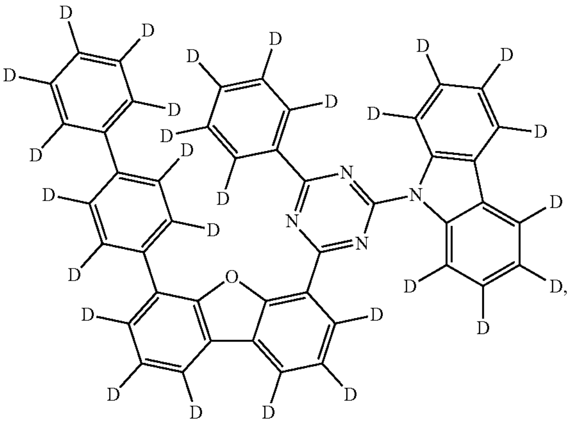
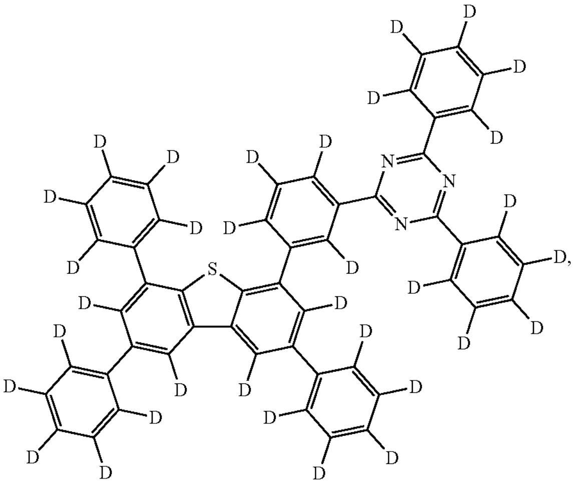
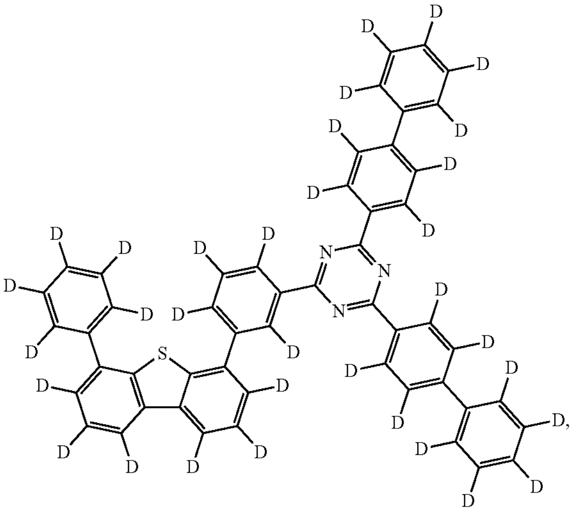

-continued
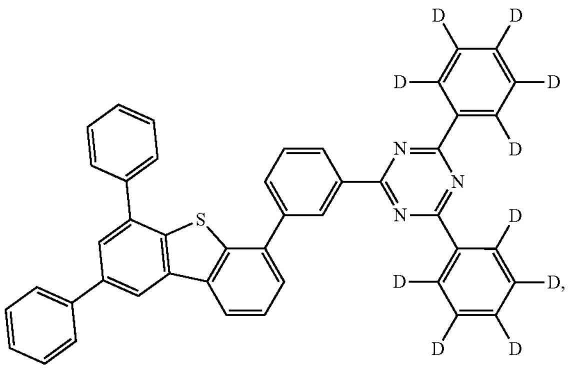
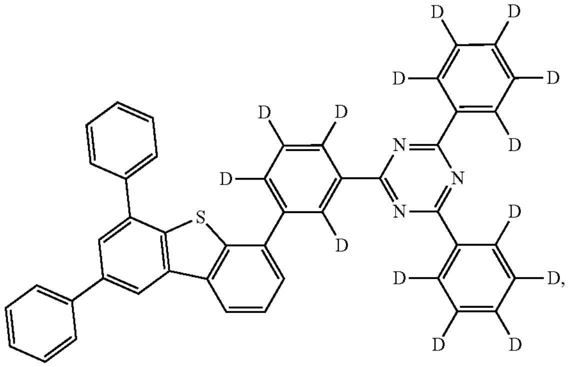
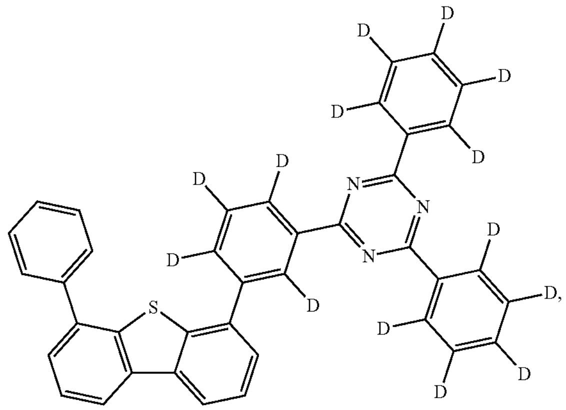
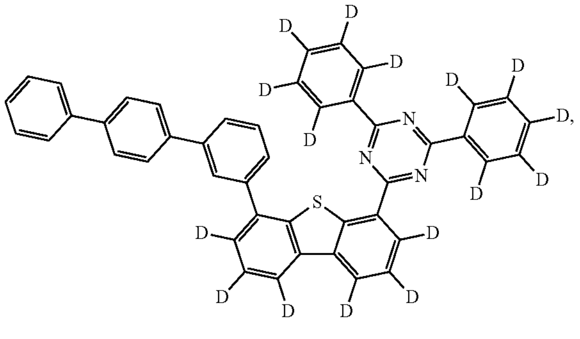
-continued
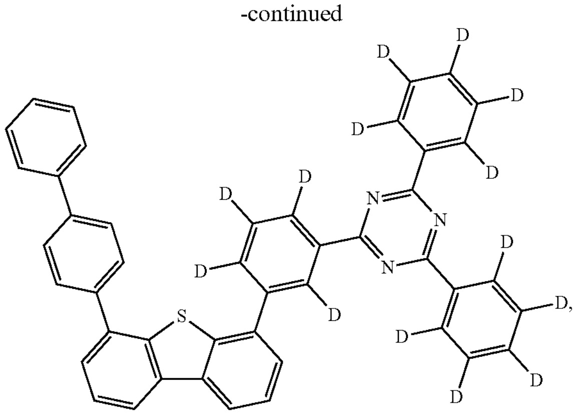
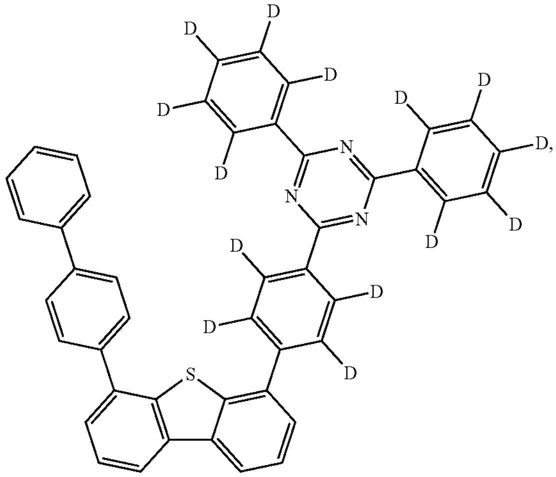
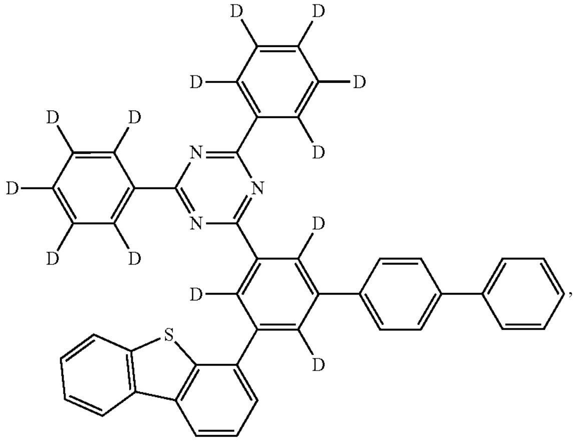
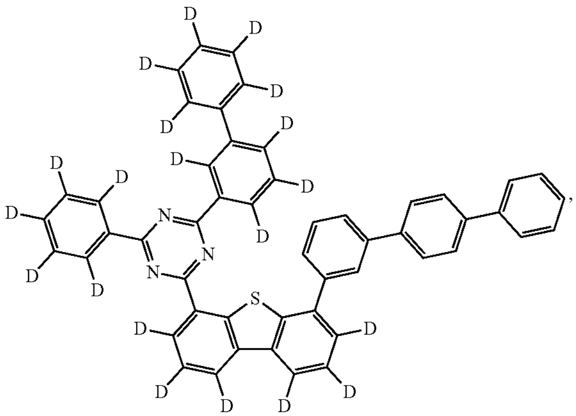

-continued
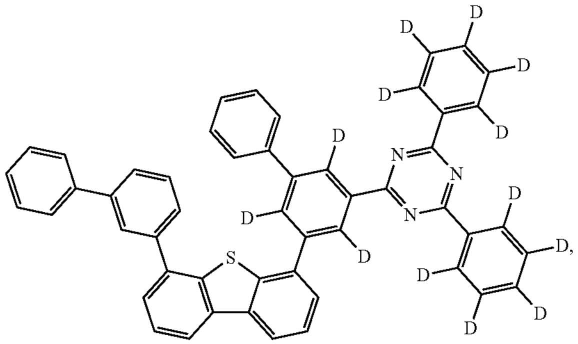
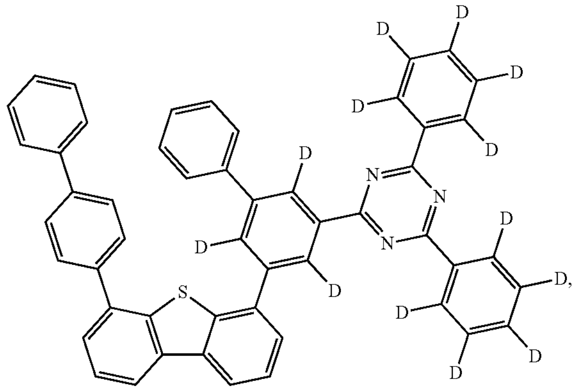
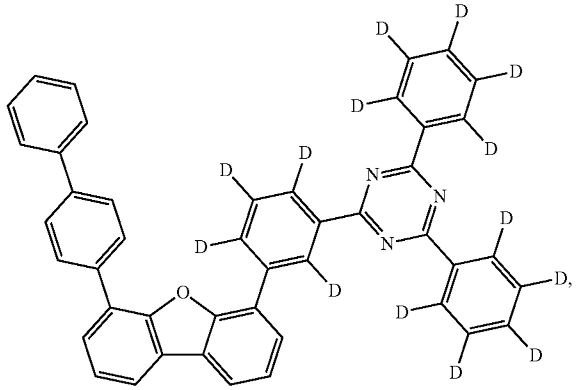
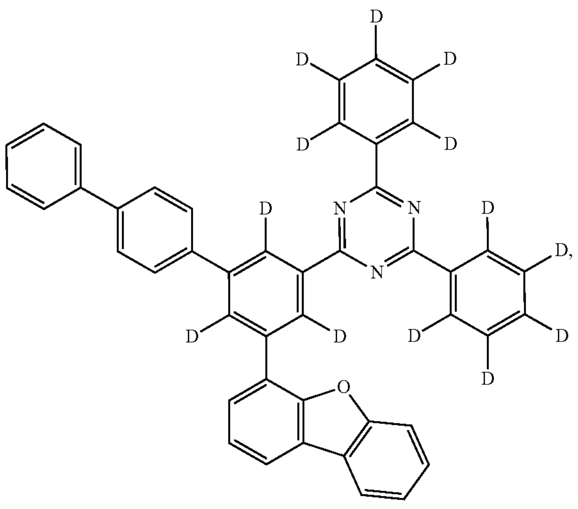
-continued
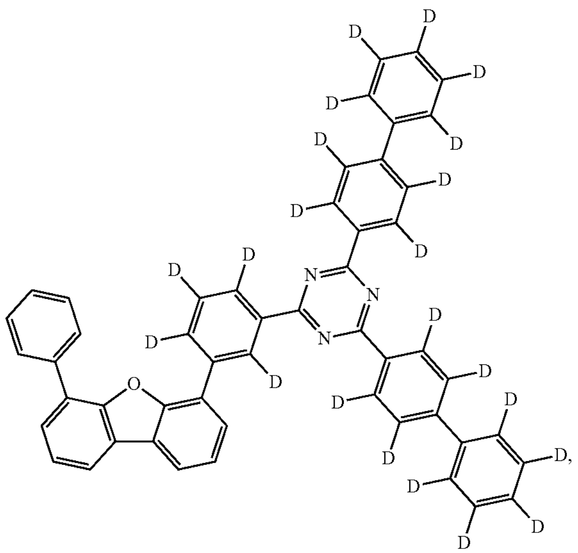
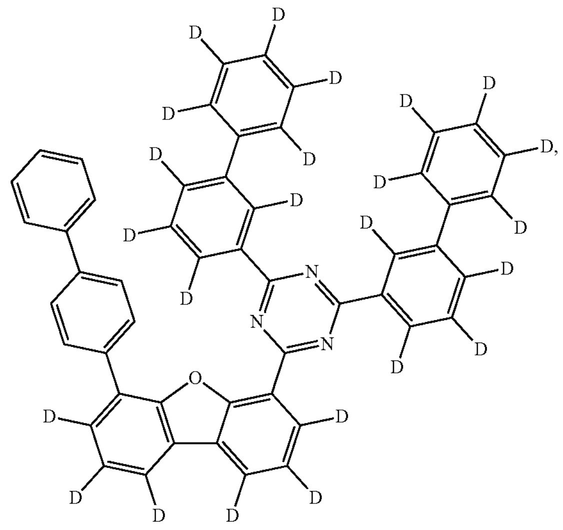
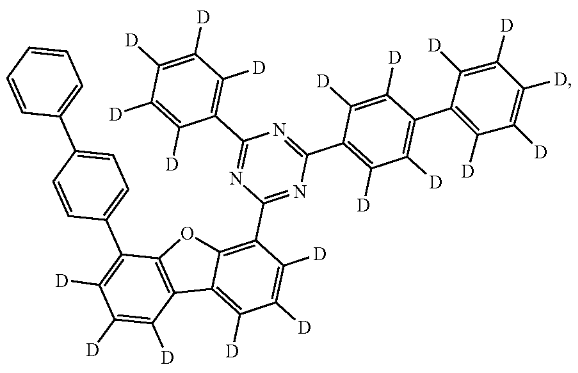

-continued
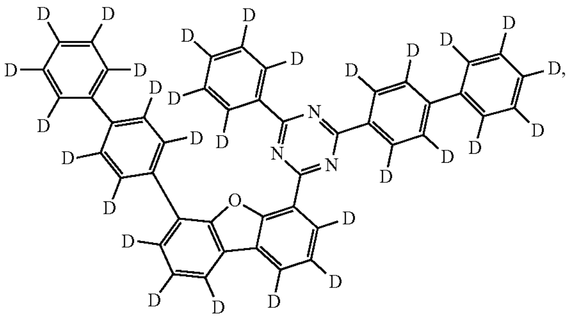
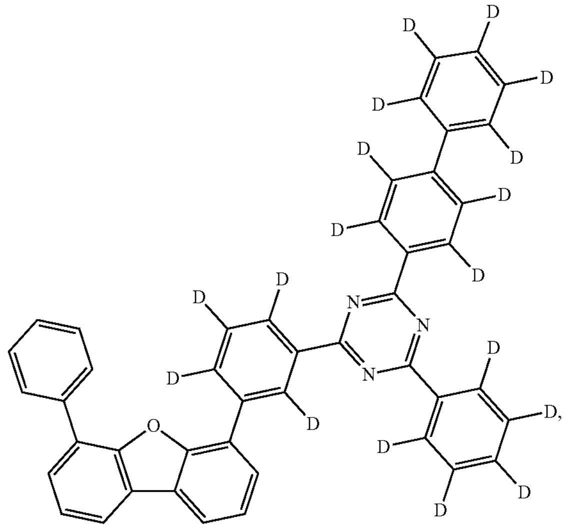
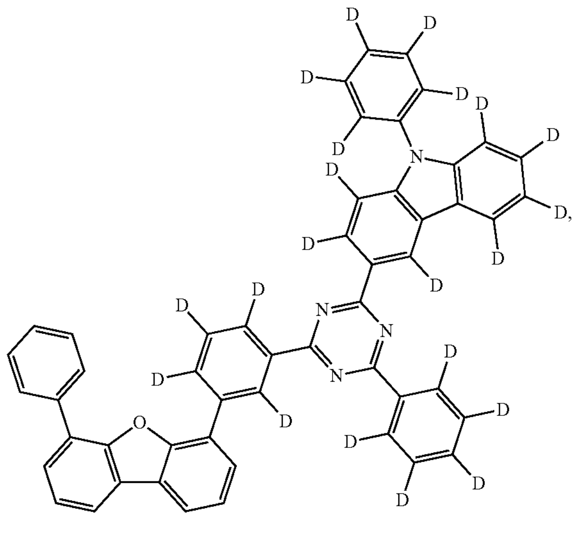
-continued
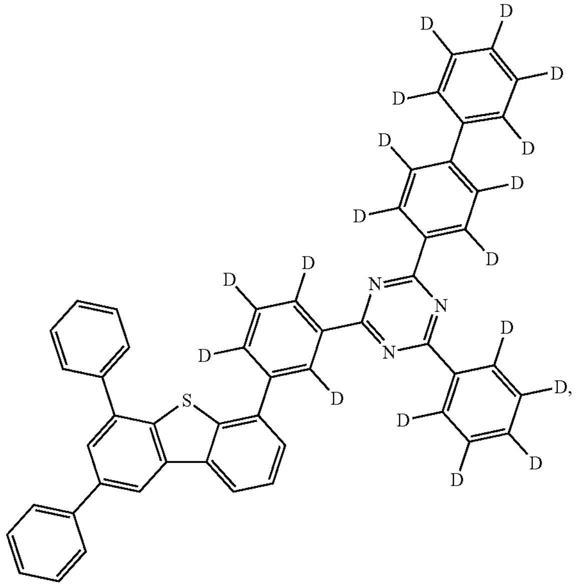
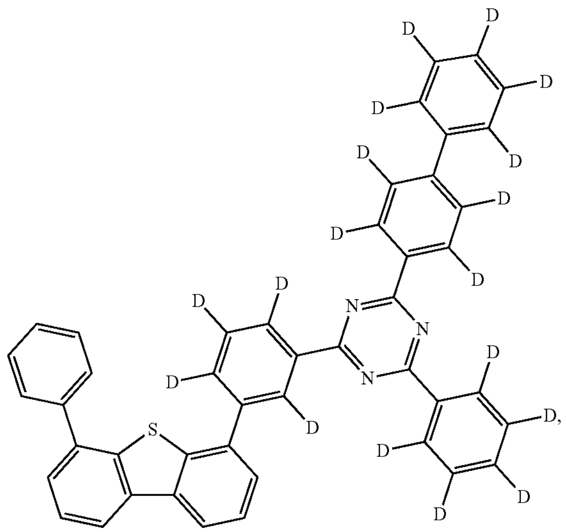
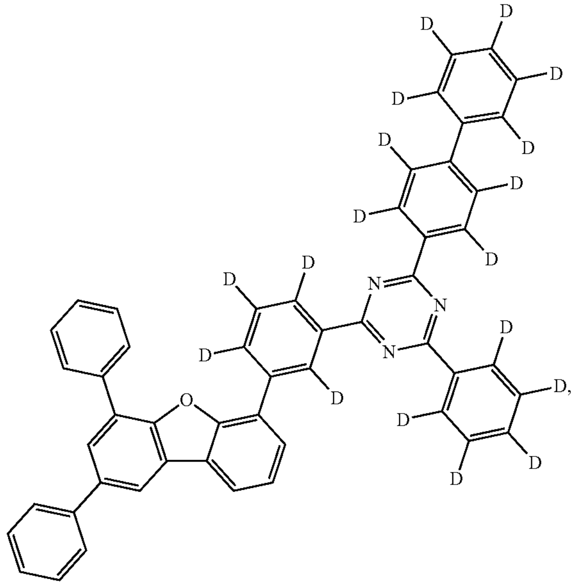

-continued
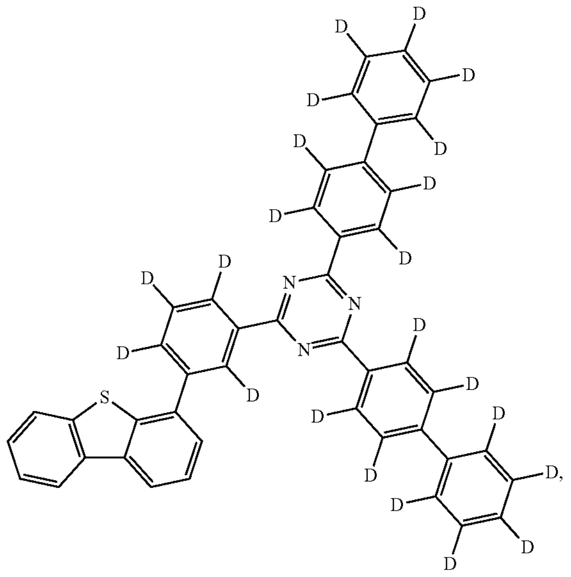
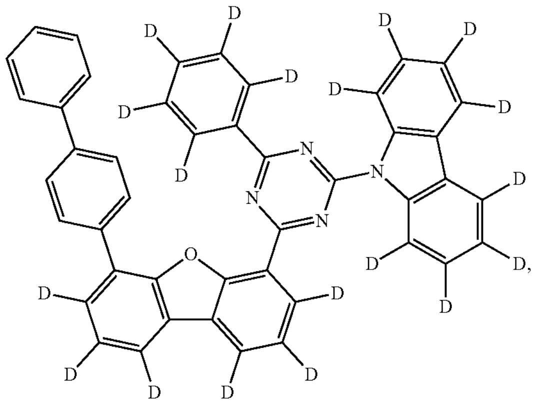
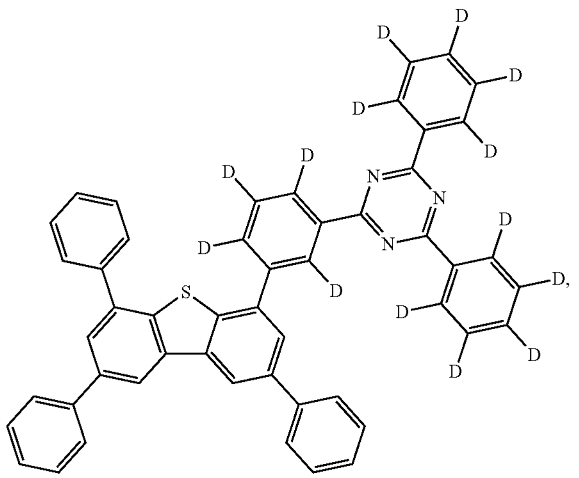
-continued
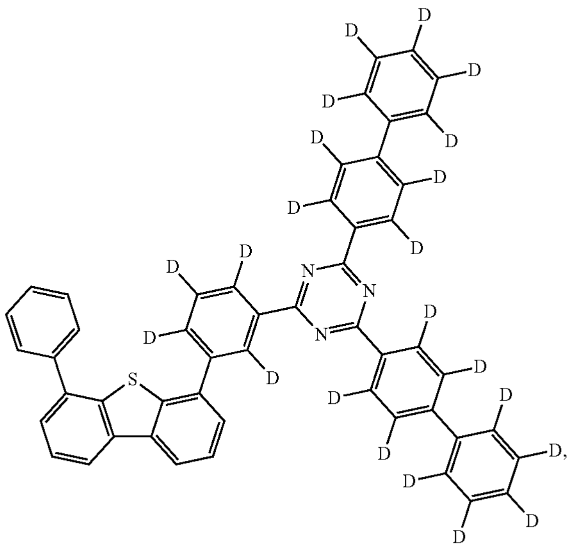
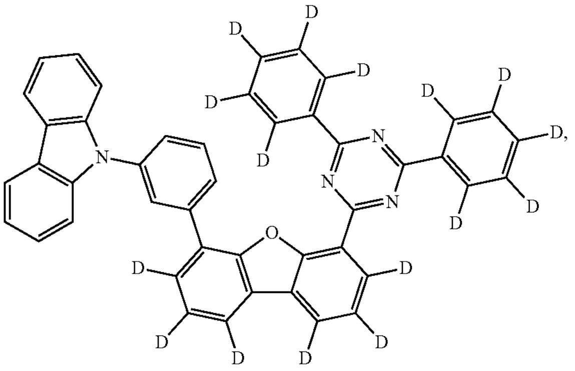
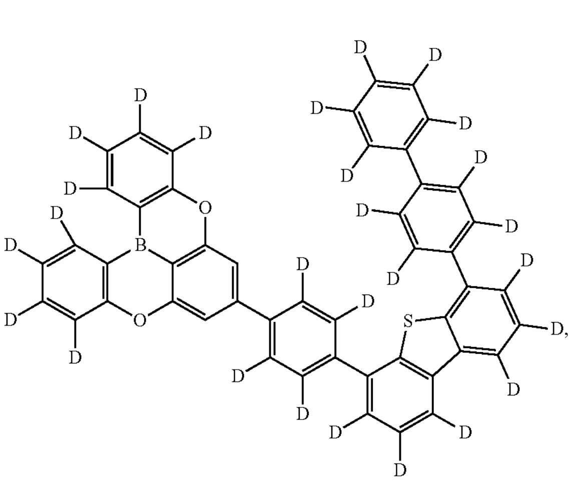

-continued
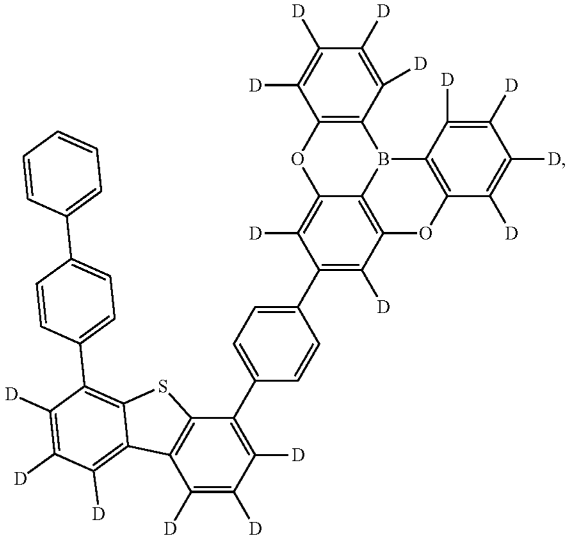
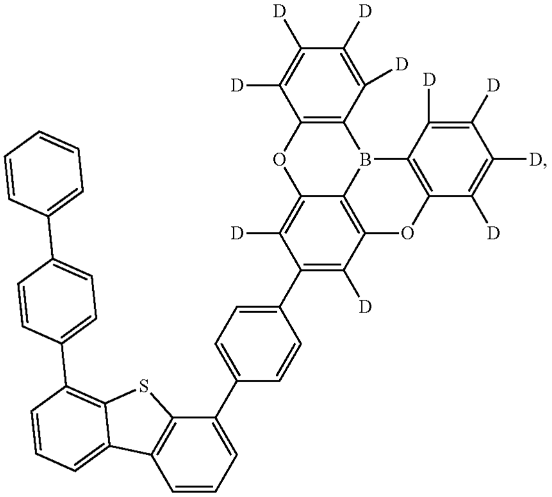
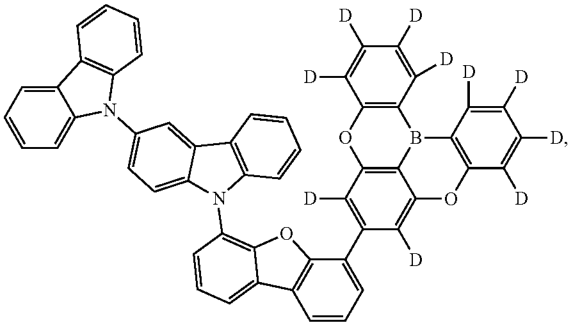
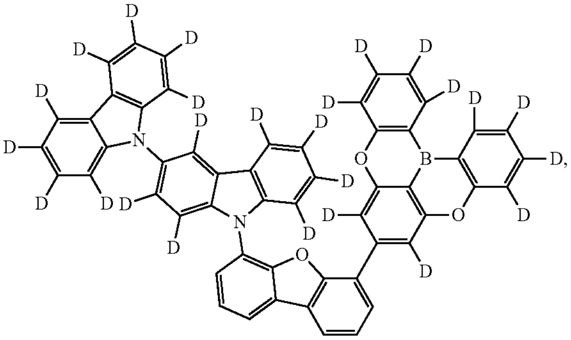
-continued
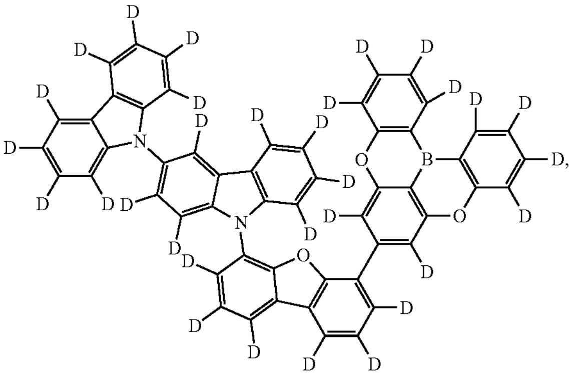
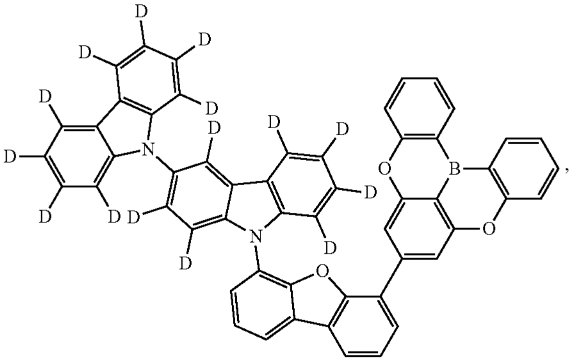
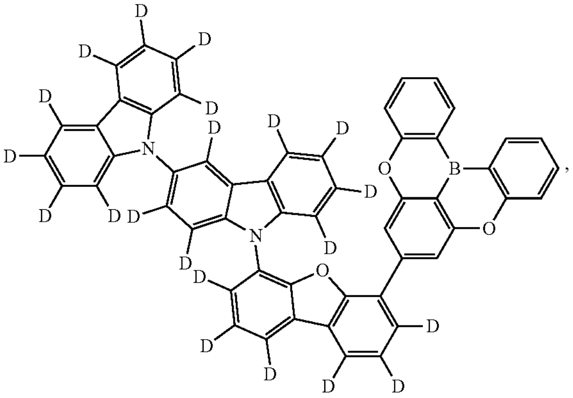
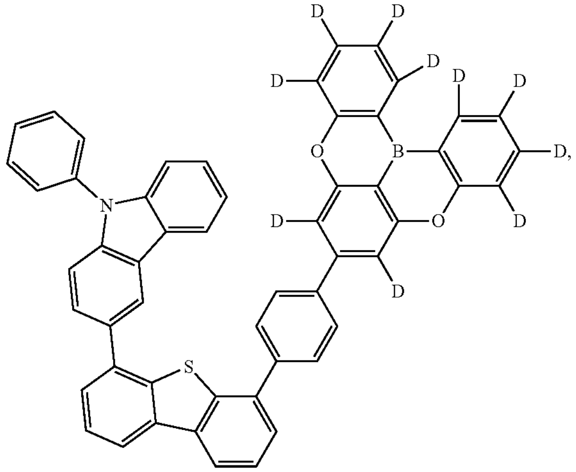

-continued
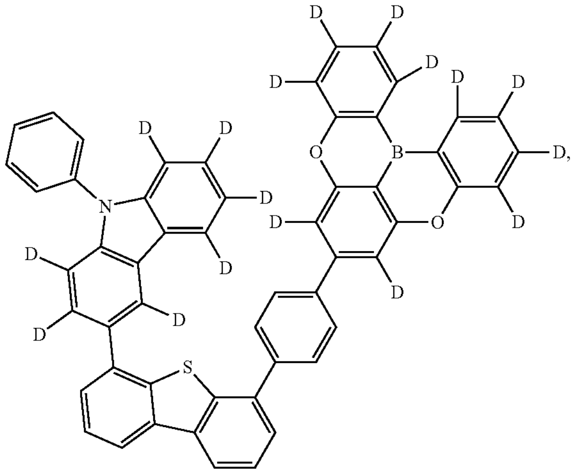
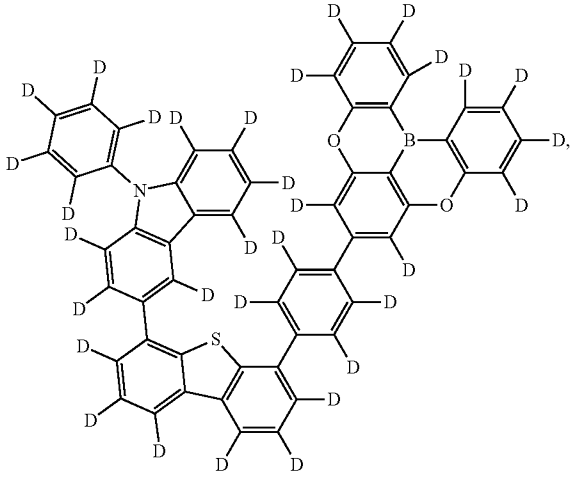
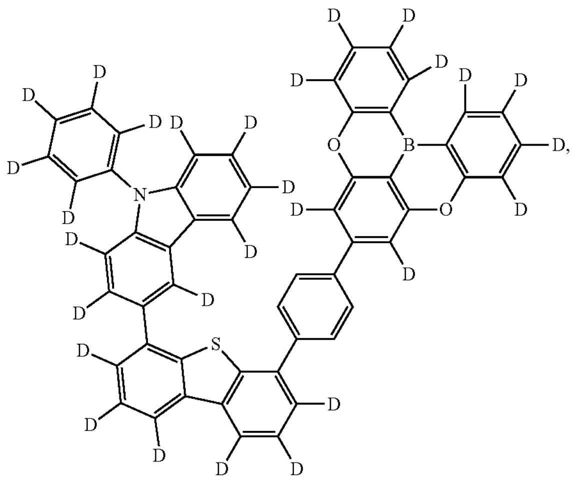
-continued
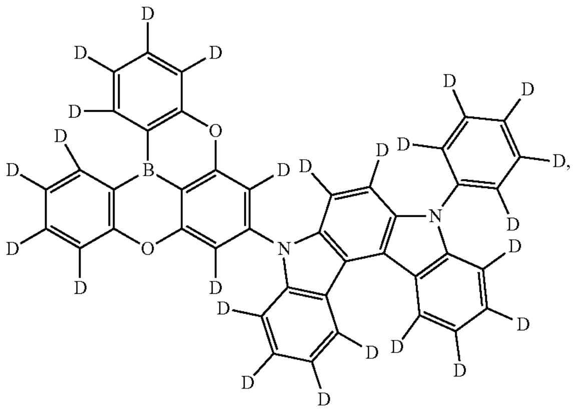
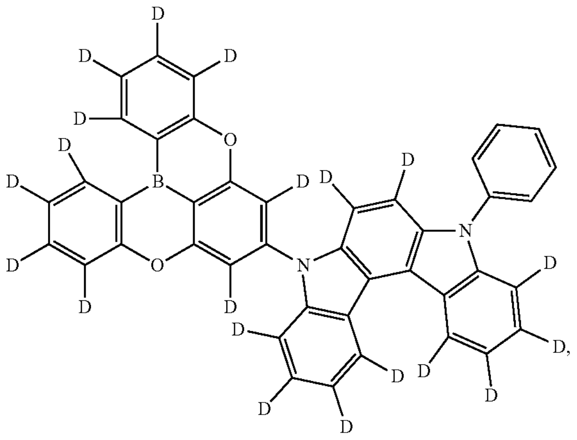
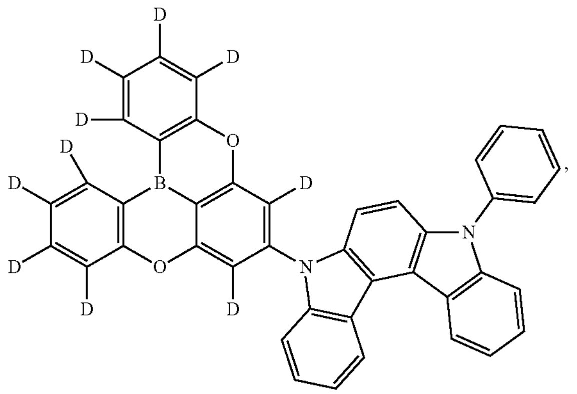

-continued
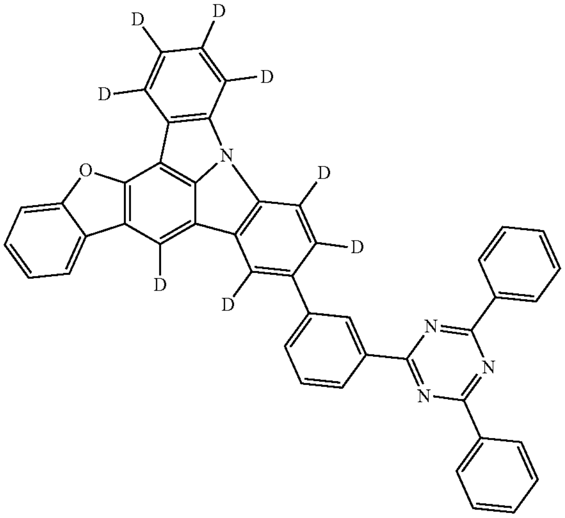
,
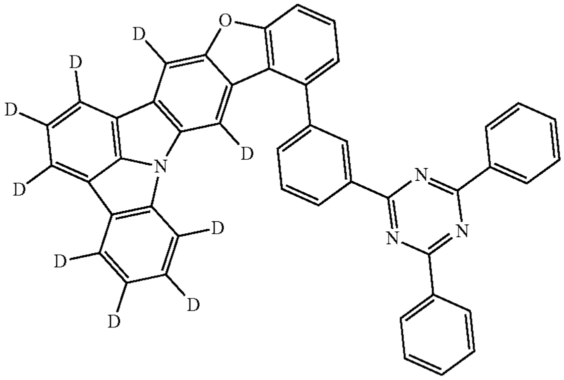
,
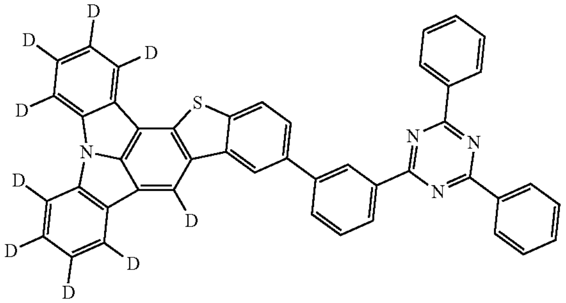
,
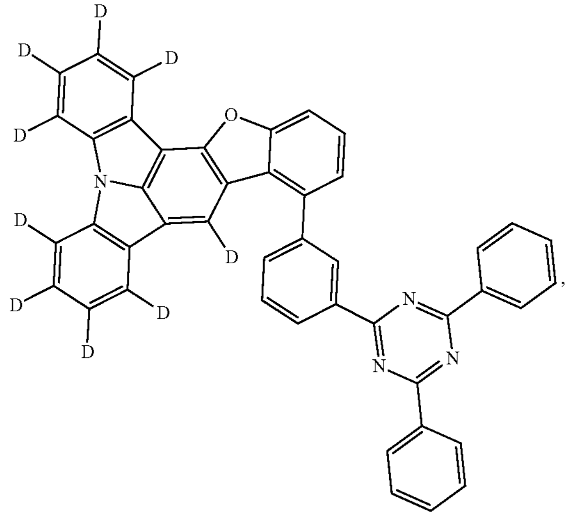
,
-continued
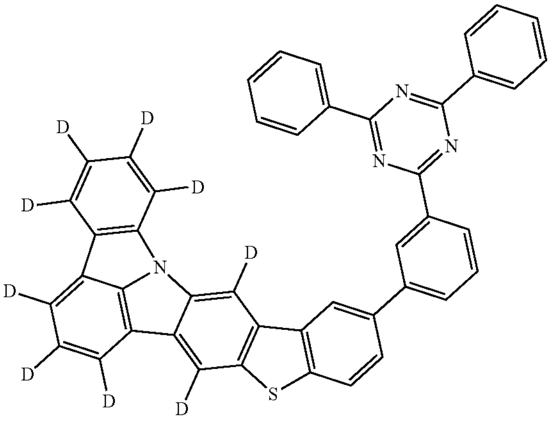
,
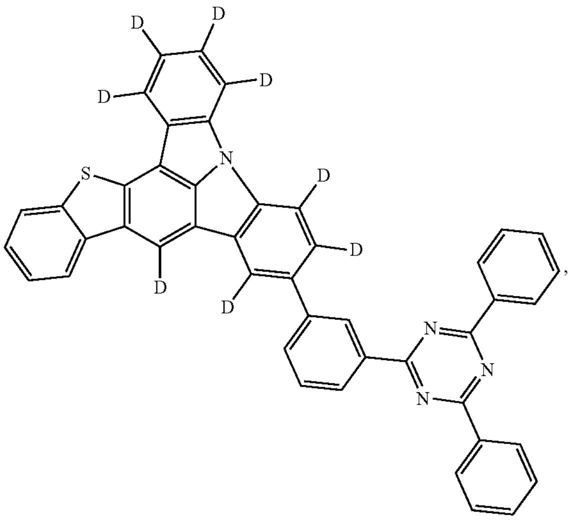
,
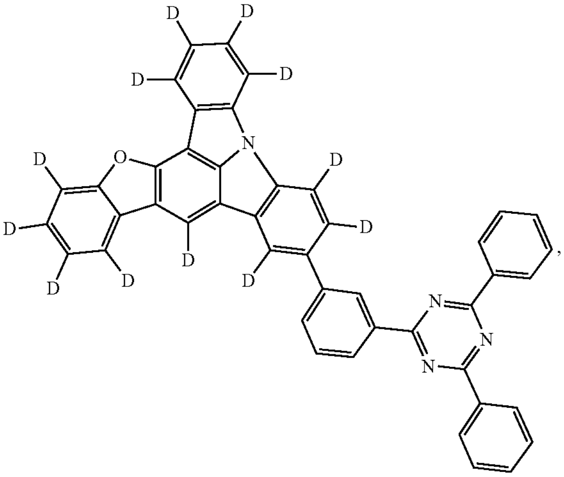
,

801
-continued
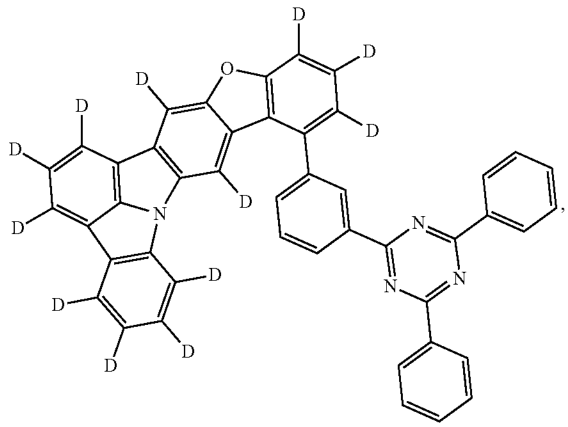
,
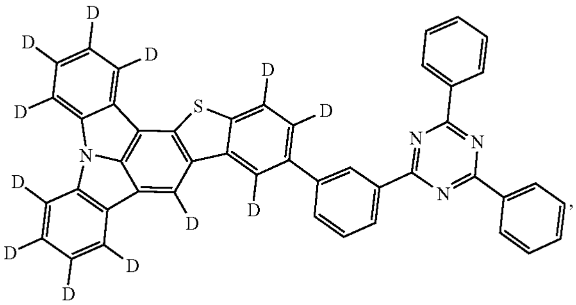
,
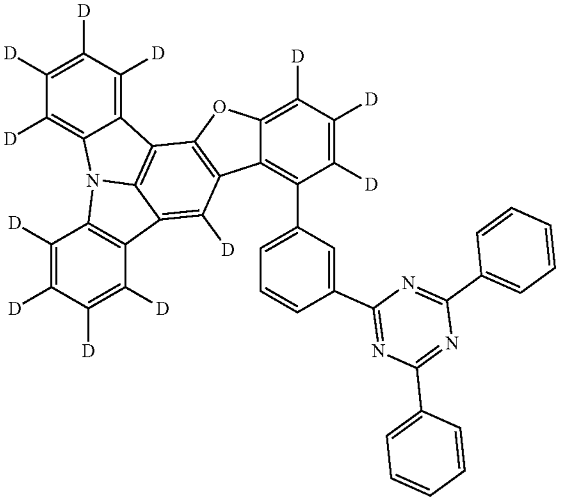
,
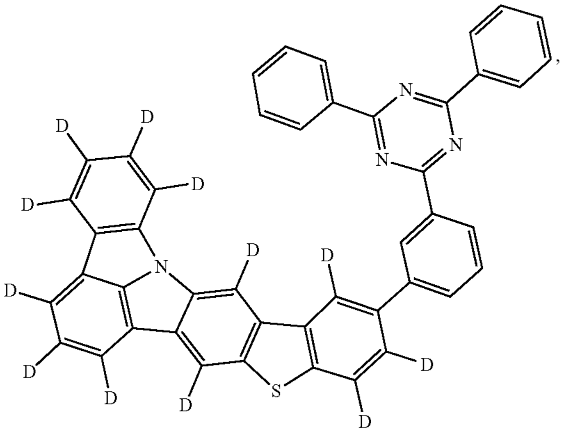
,
802
-continued
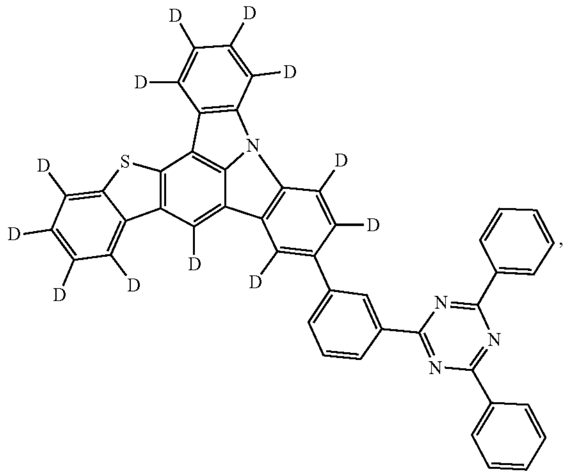
,
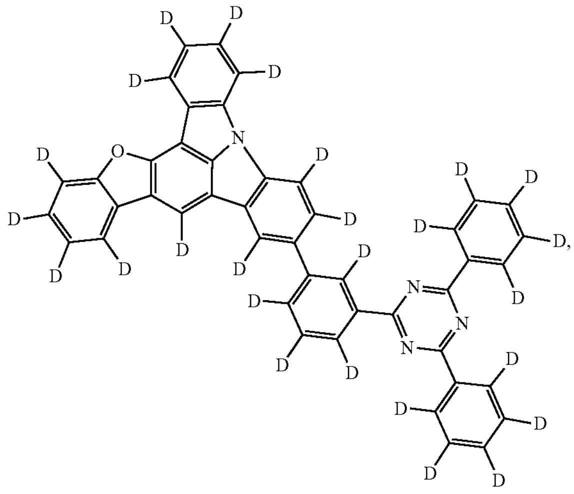
,
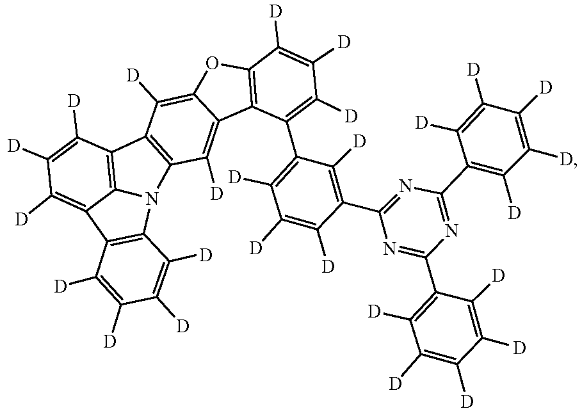
,
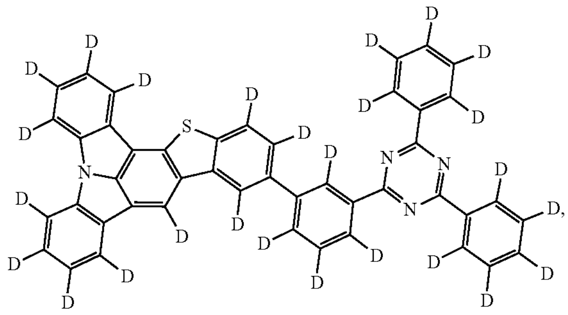
, -continued
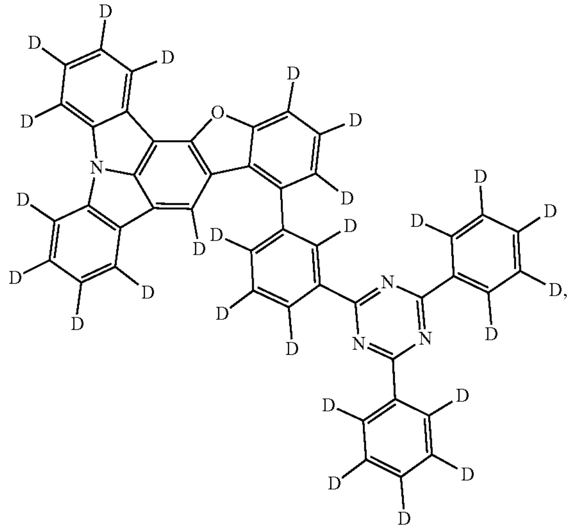
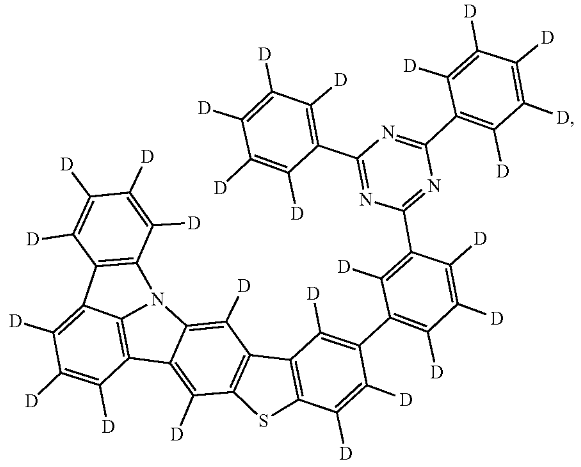
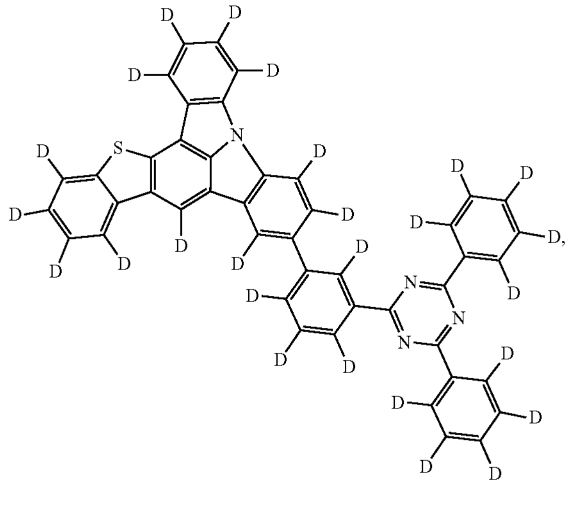
-continued
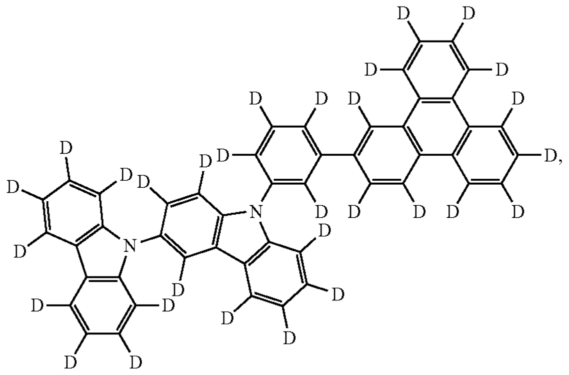
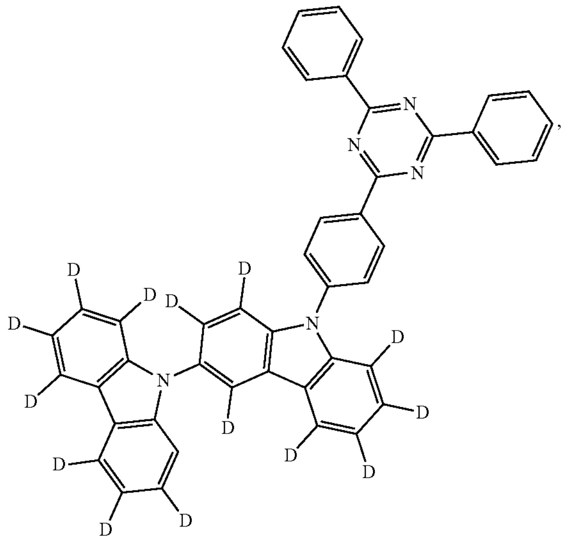
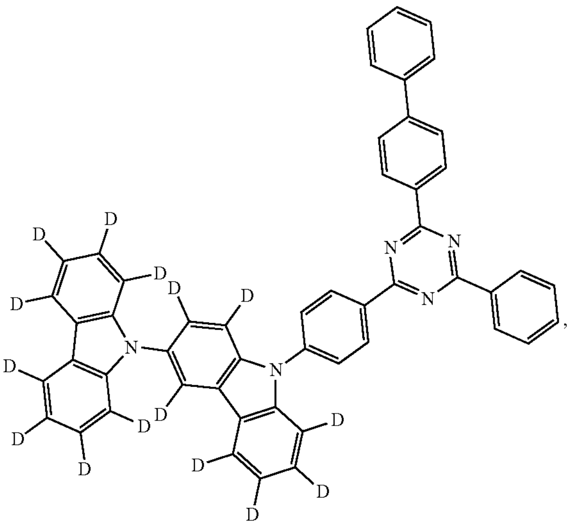

-continued
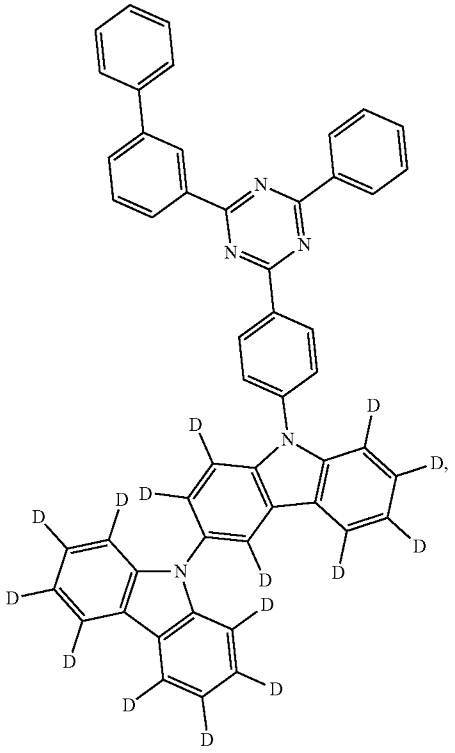
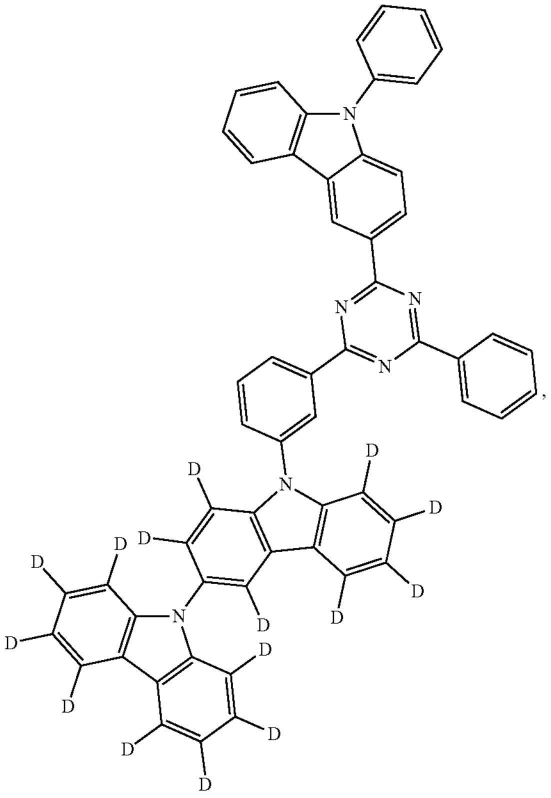
-continued
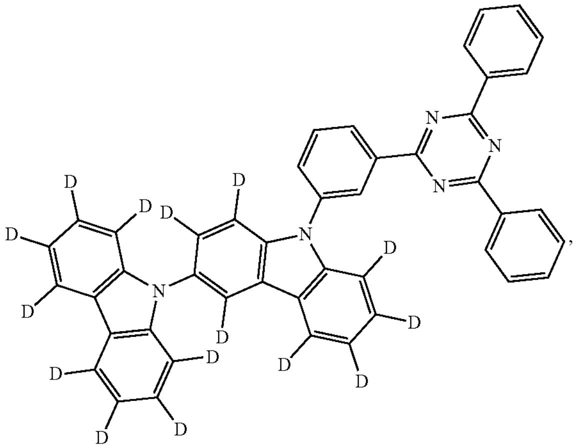
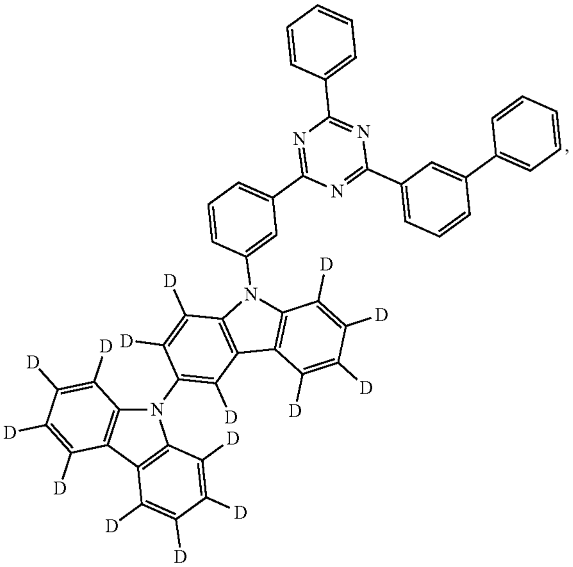
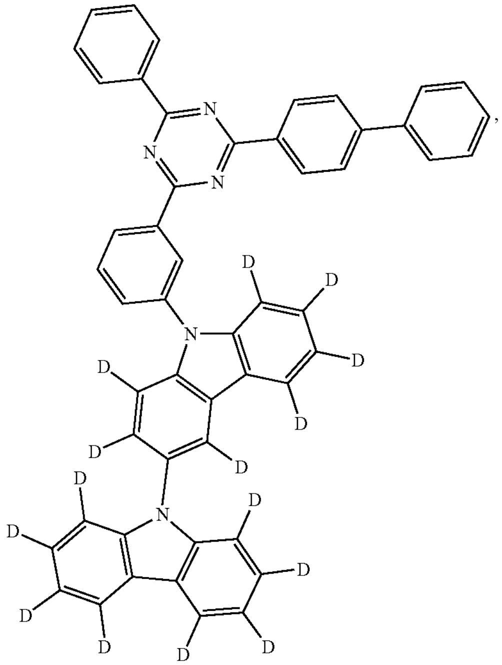

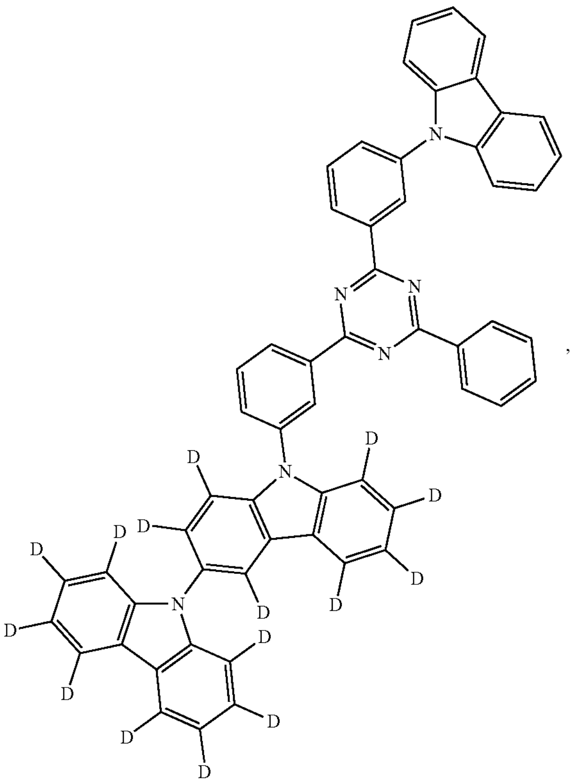
,
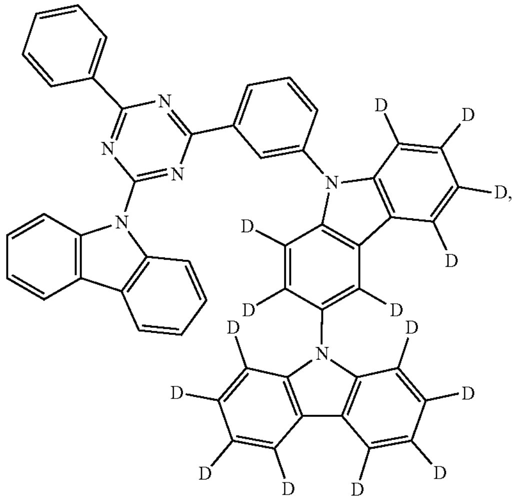
,
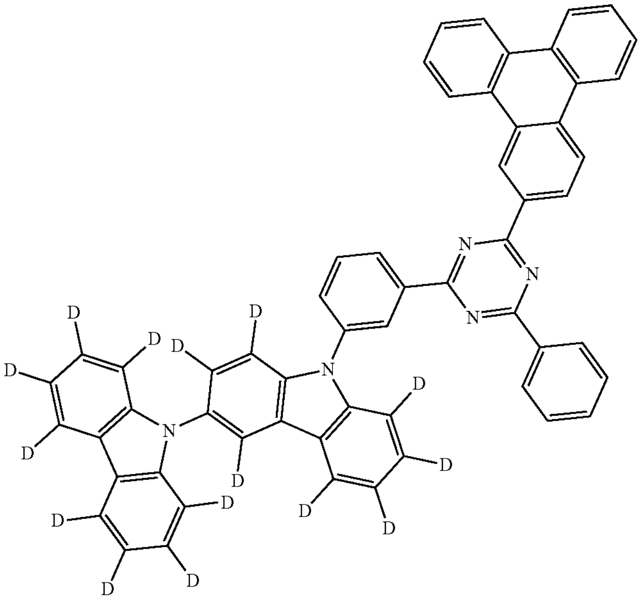
,

-continued
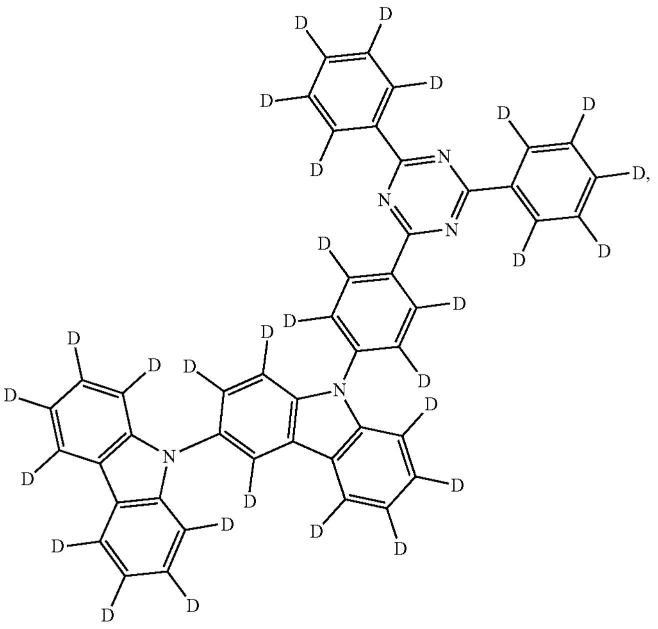
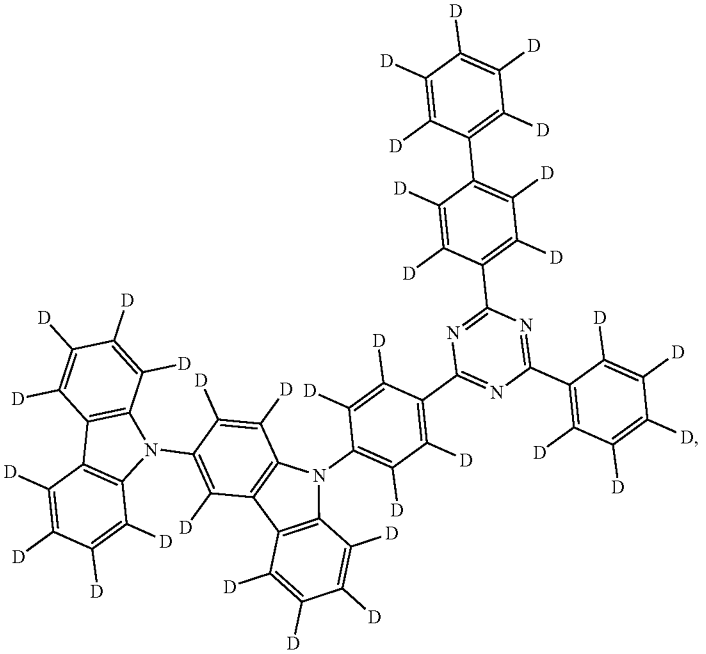

-continued
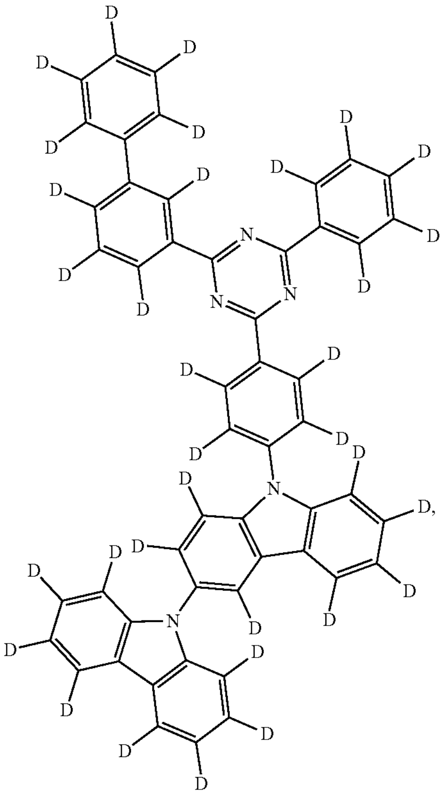
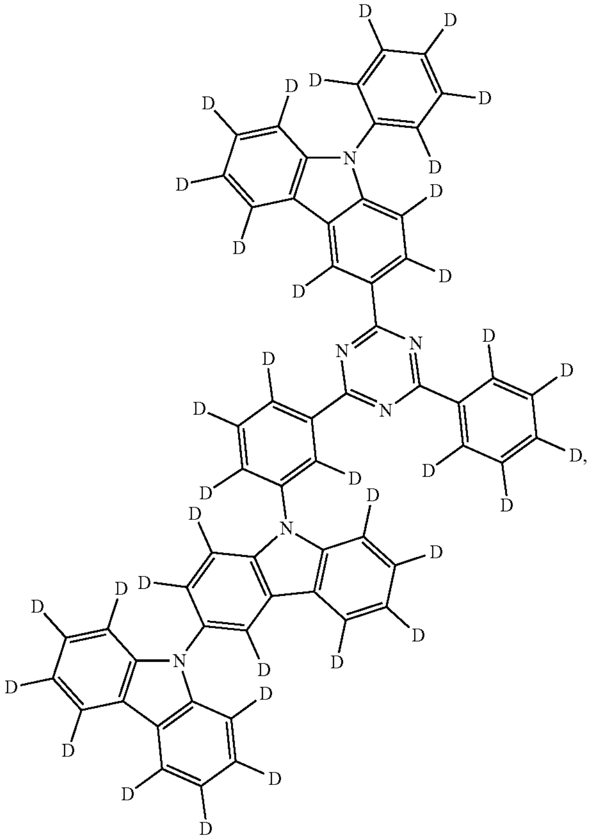
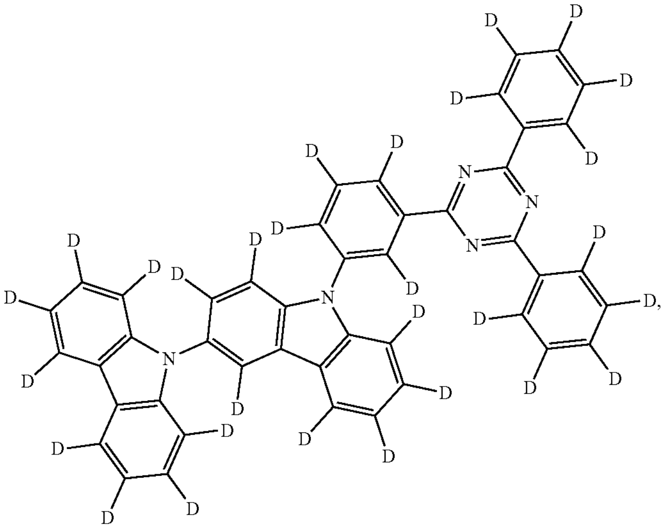

-continued
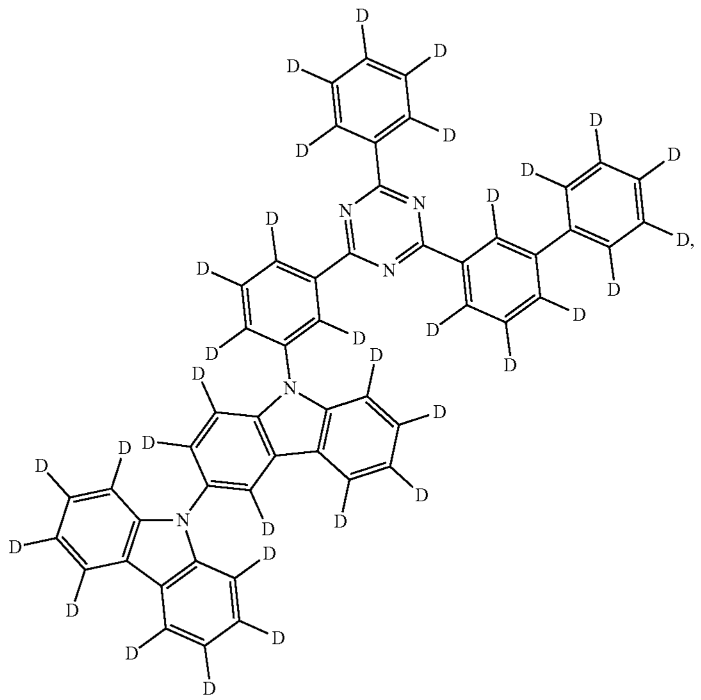
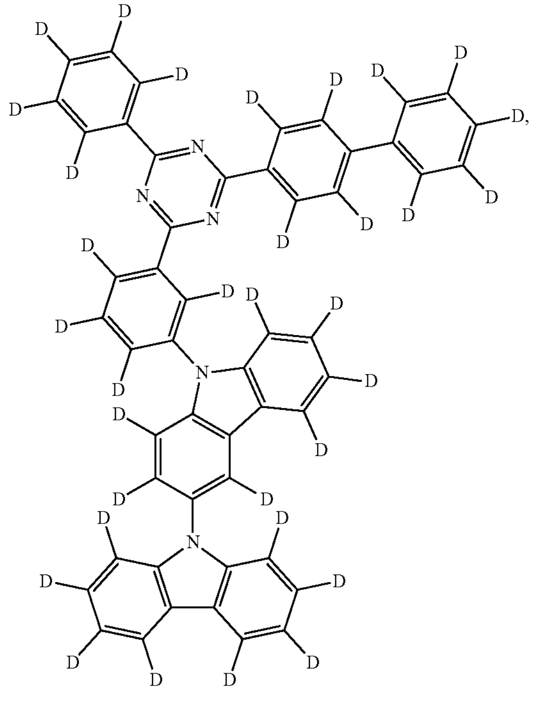

-continued
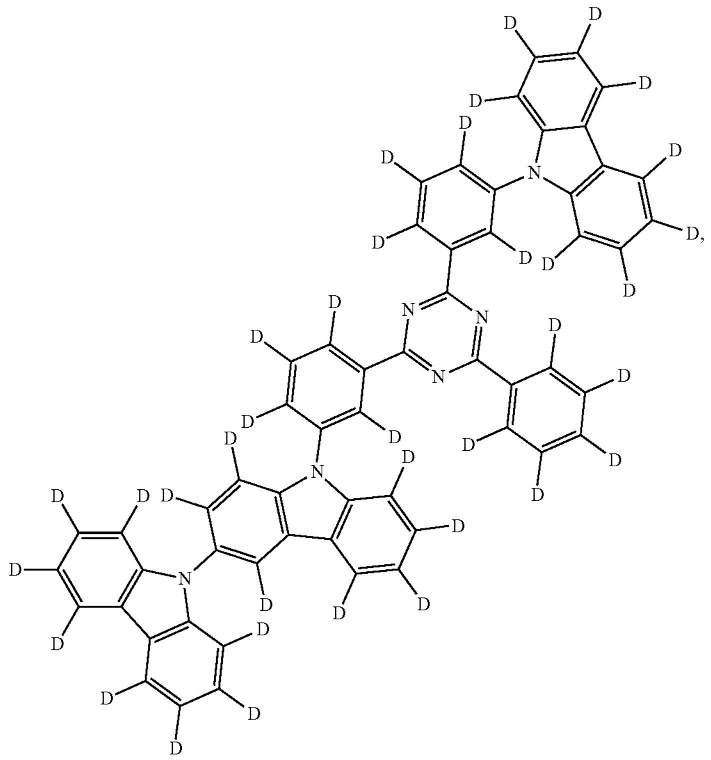
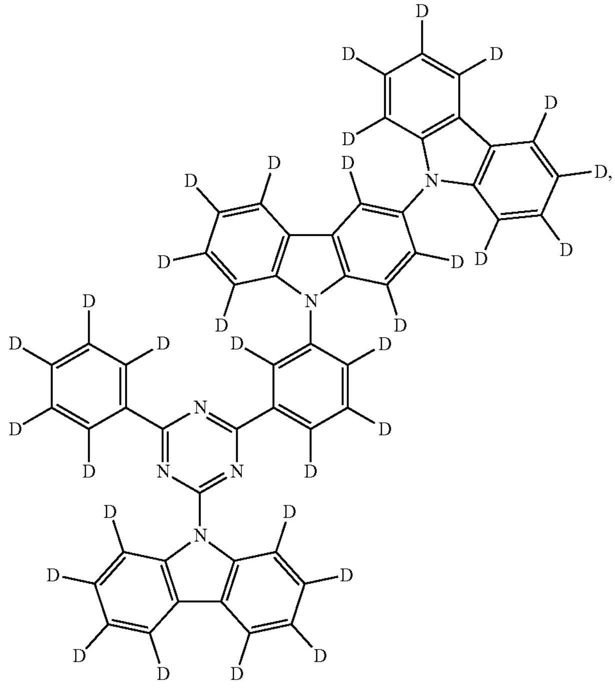

-continued
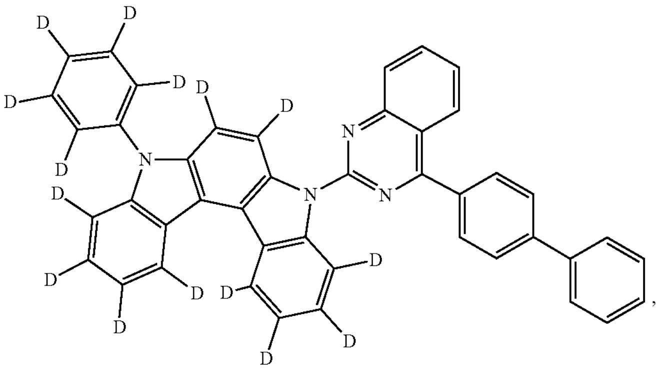
,
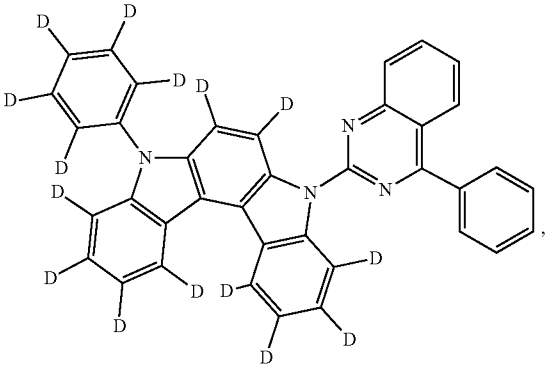
,
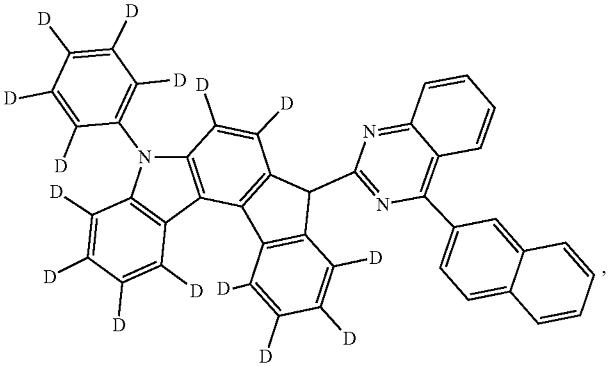
,
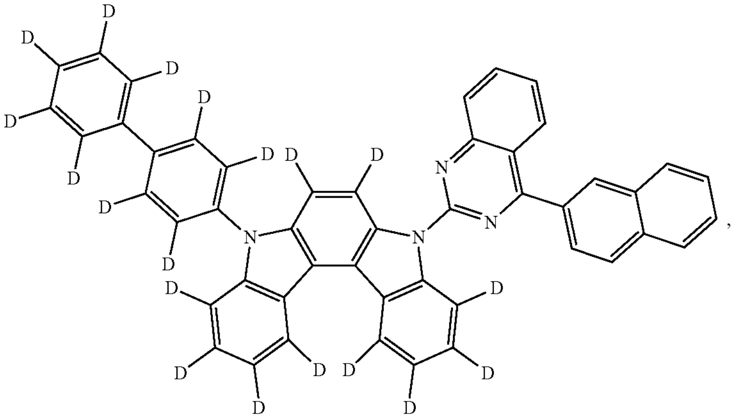
,

-continued
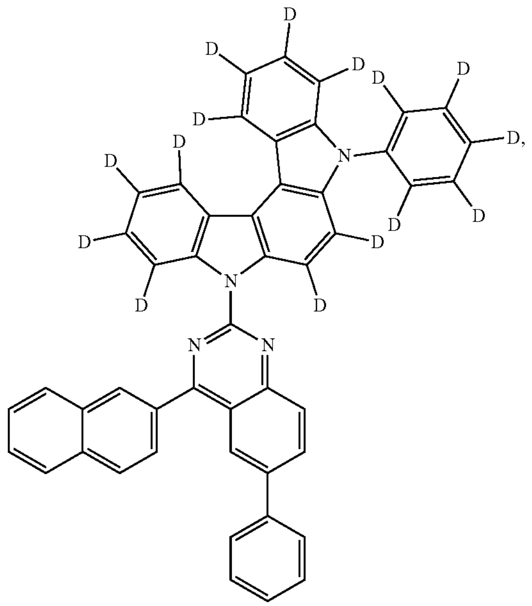
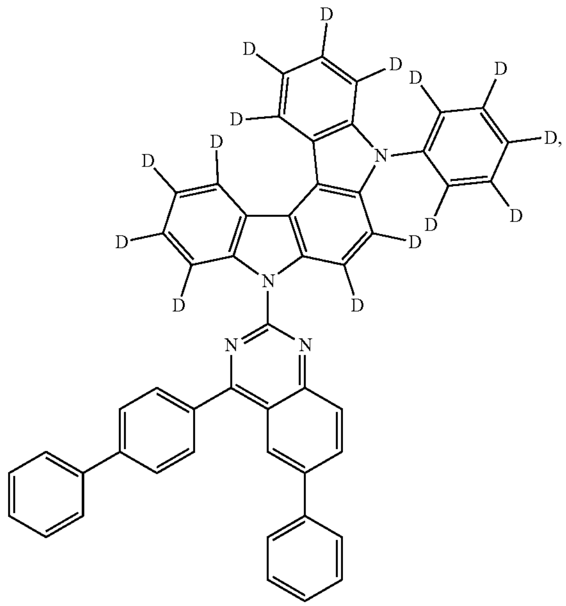
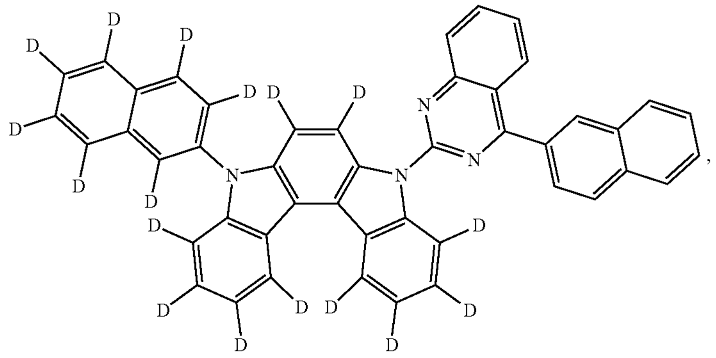
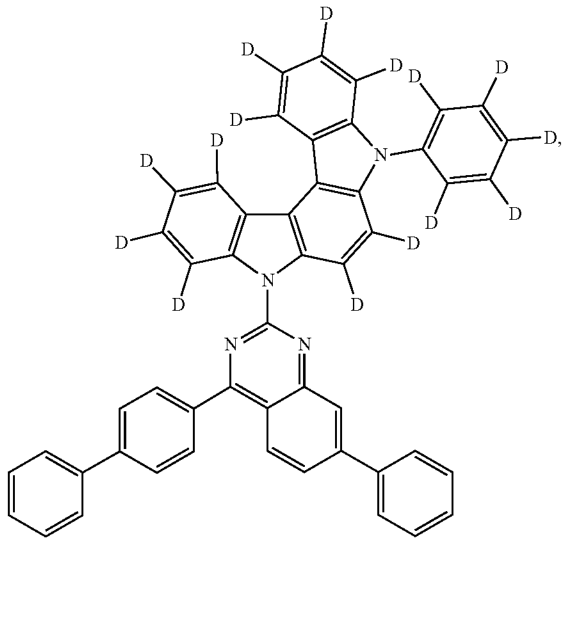
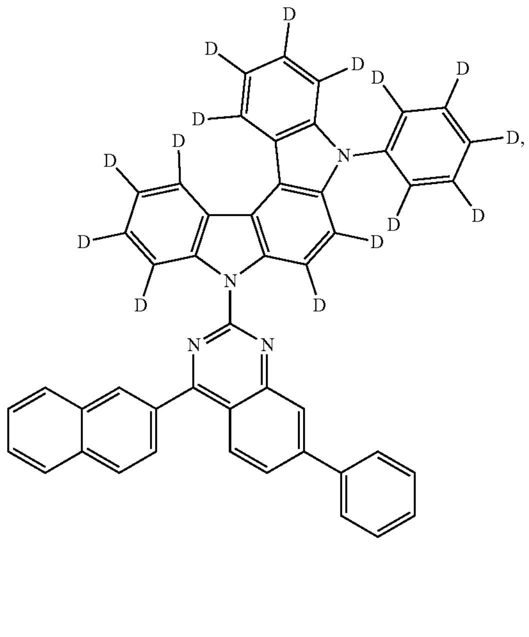

-continued
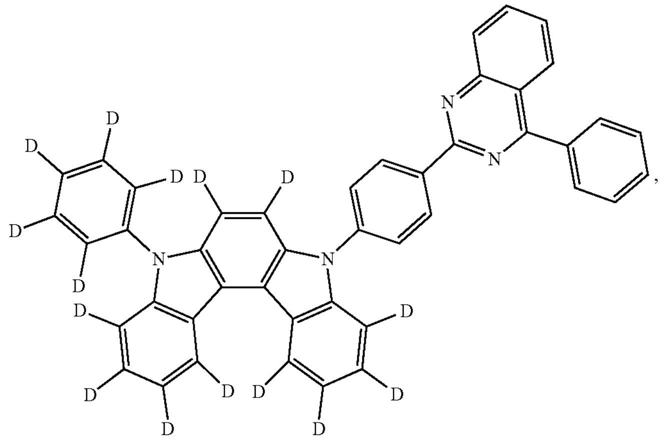
,
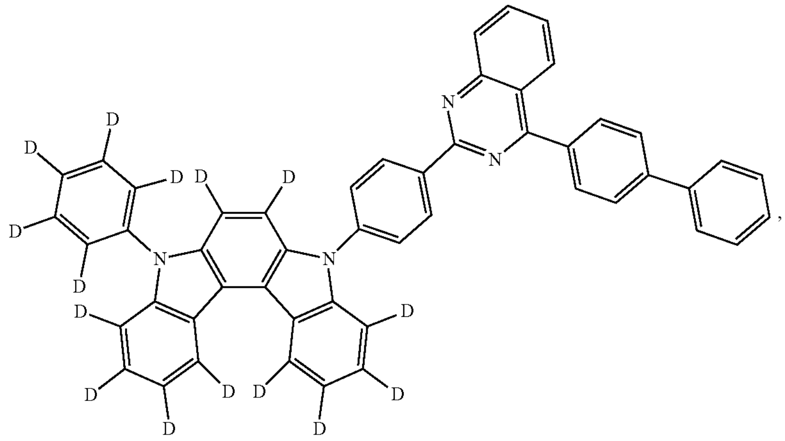
,
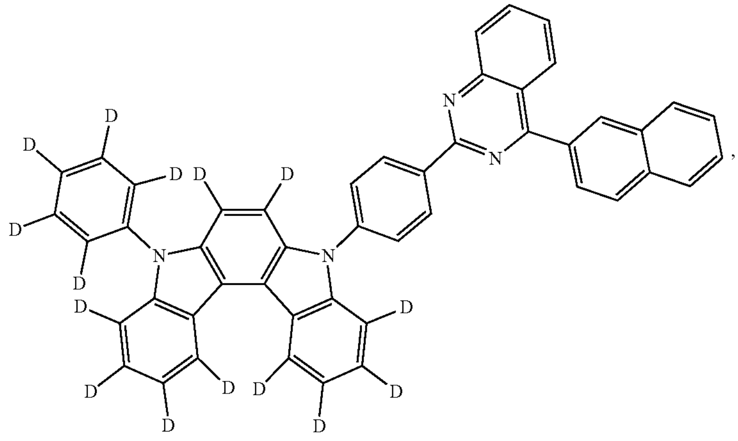
,

-continued
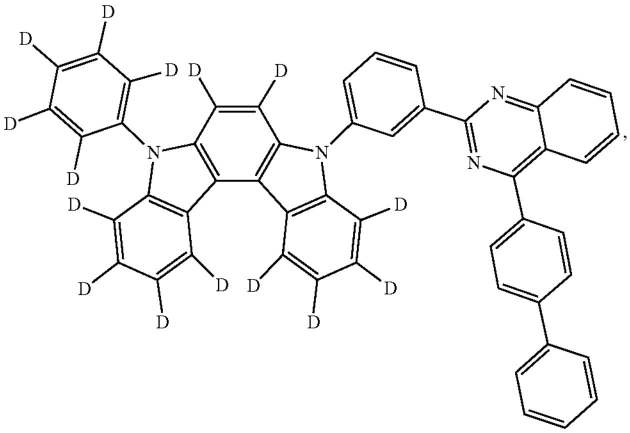
,
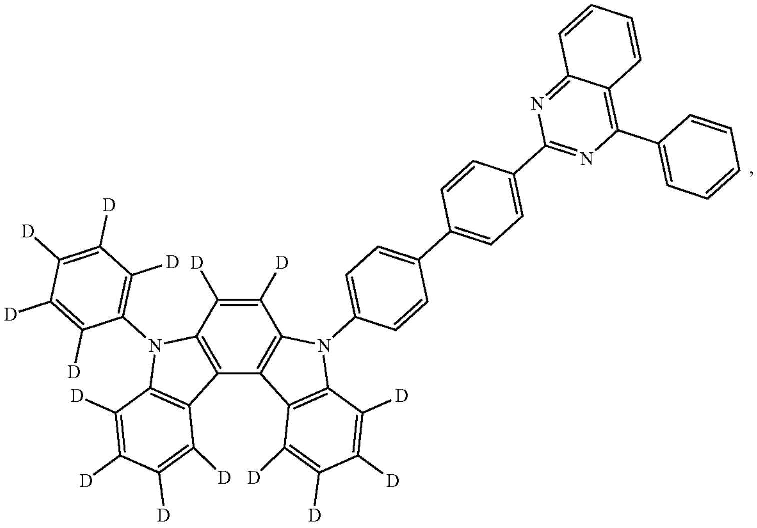
,
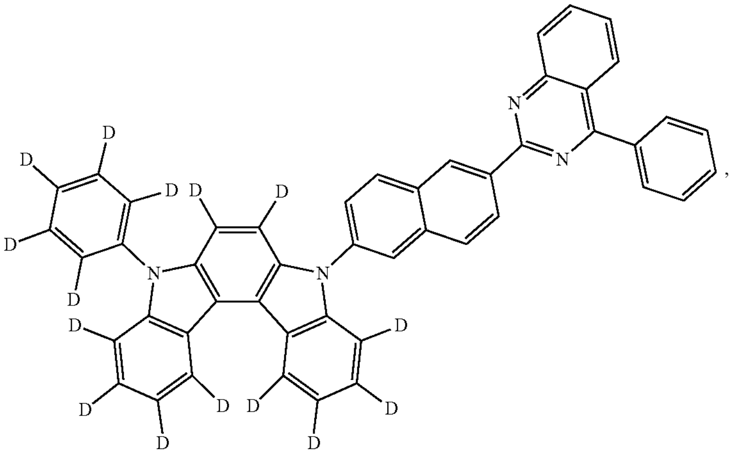
,
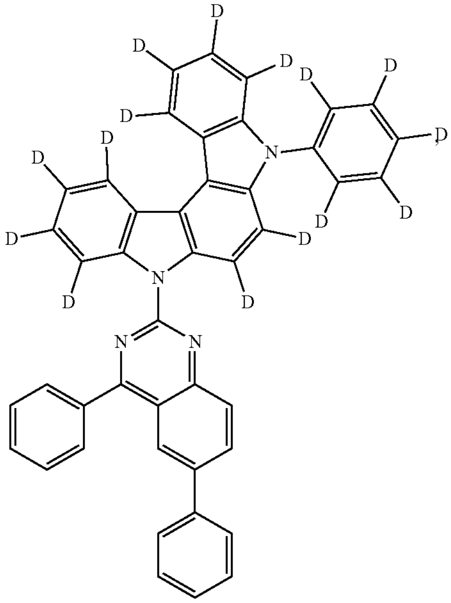
,

-continued
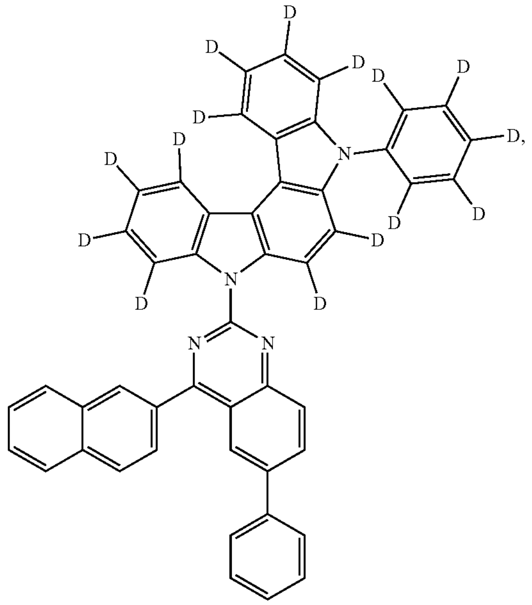
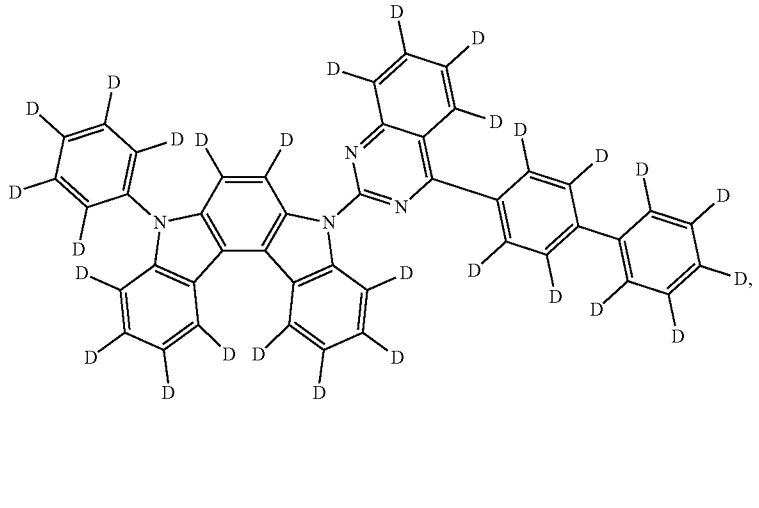

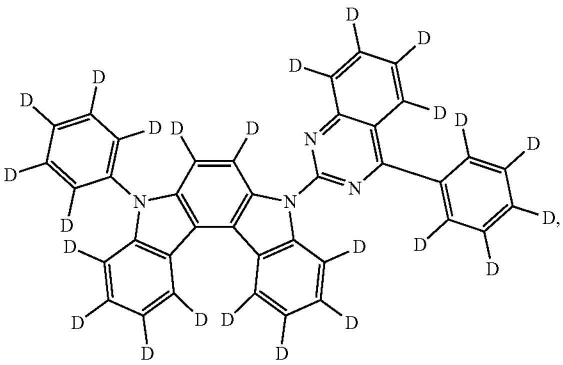
,
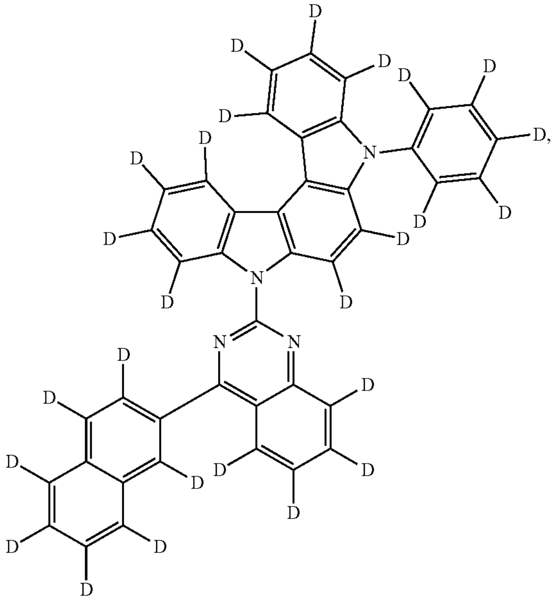
,
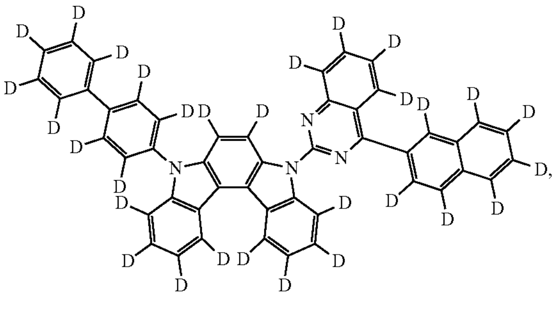
,
-continued
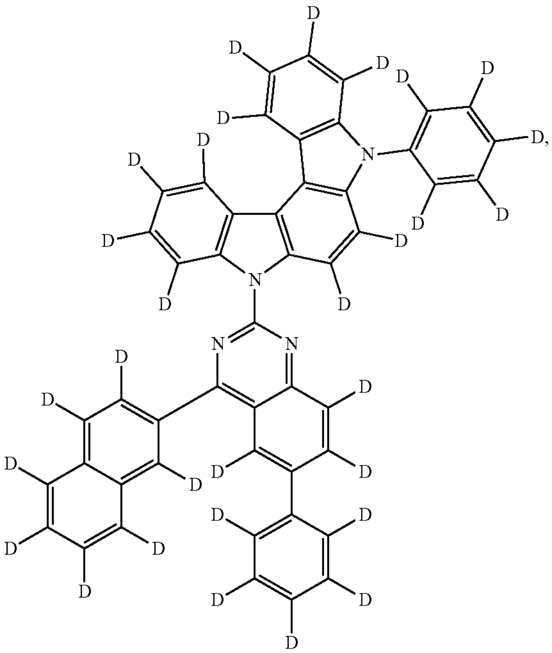
,
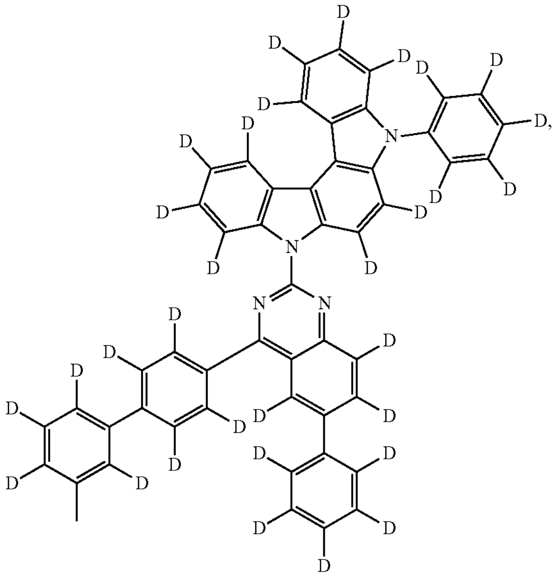
,
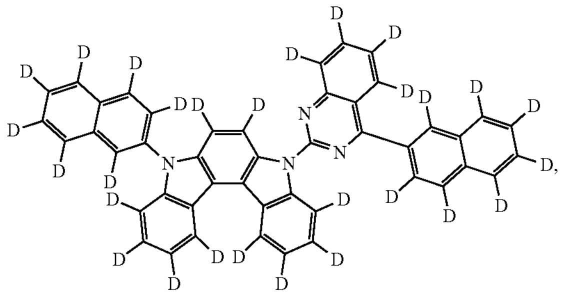
, -continued
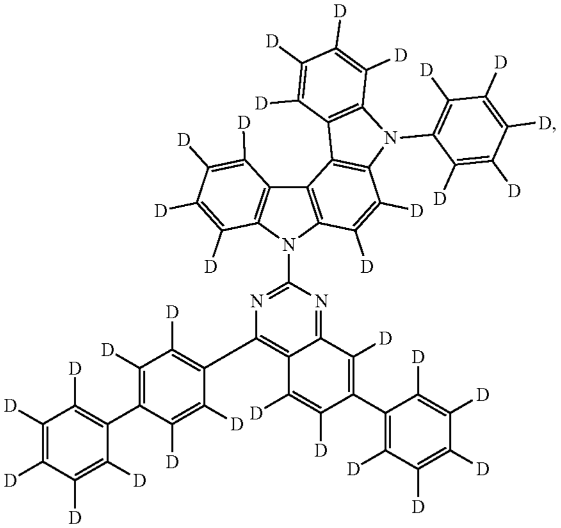
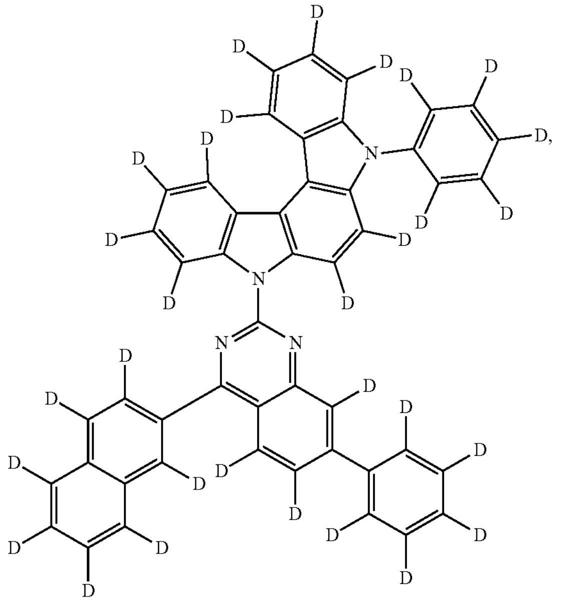
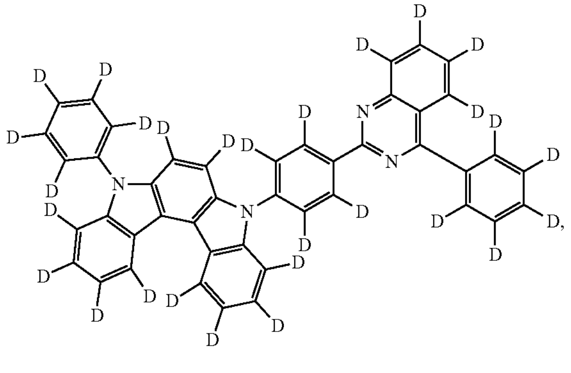
-continued
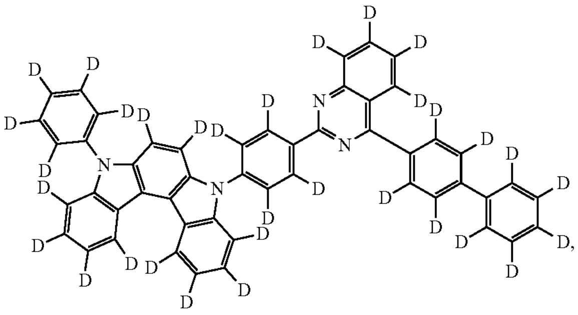
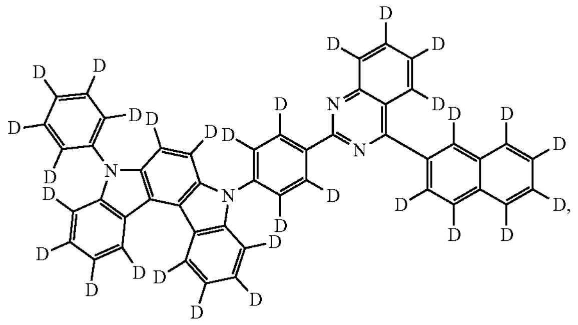
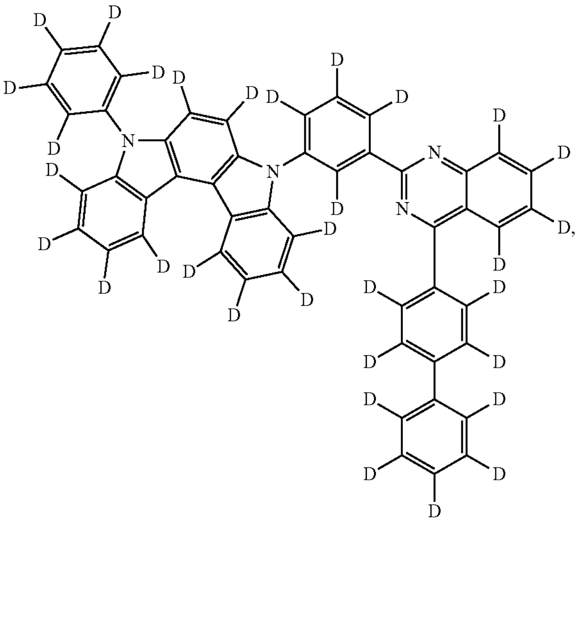

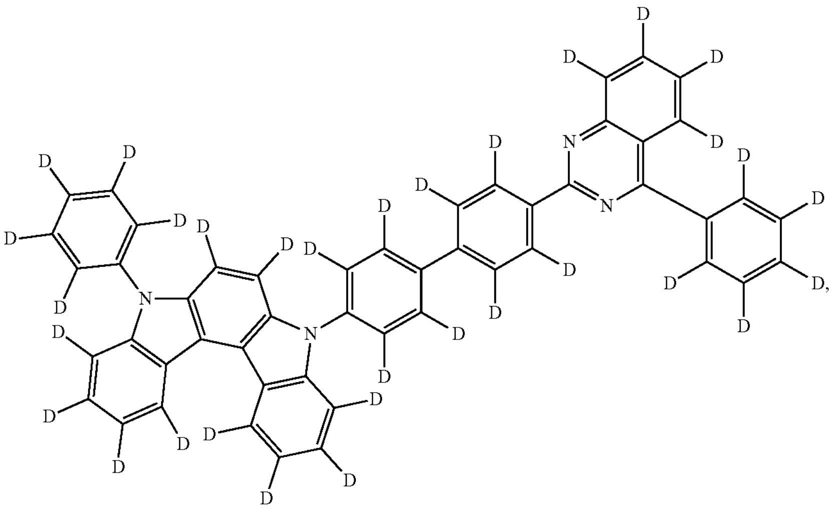
,
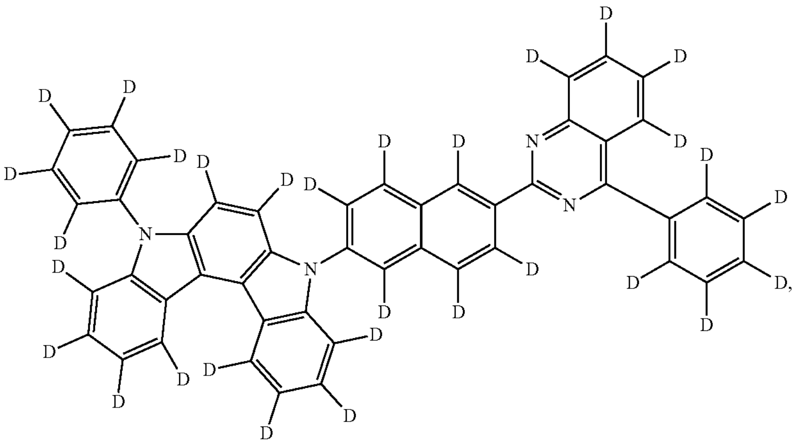
,
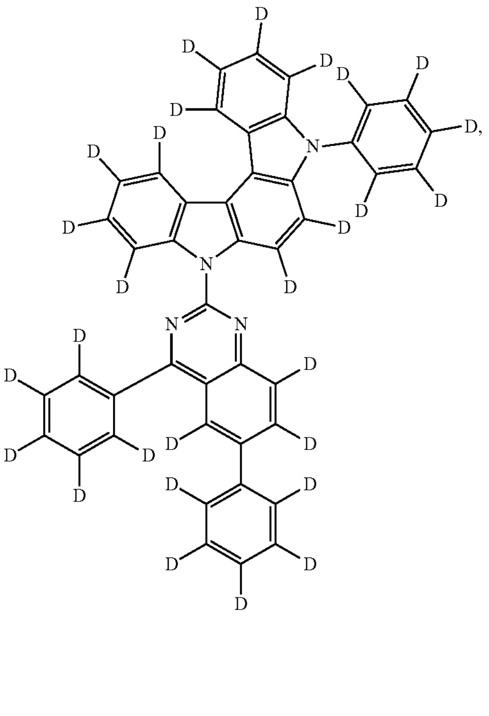
,
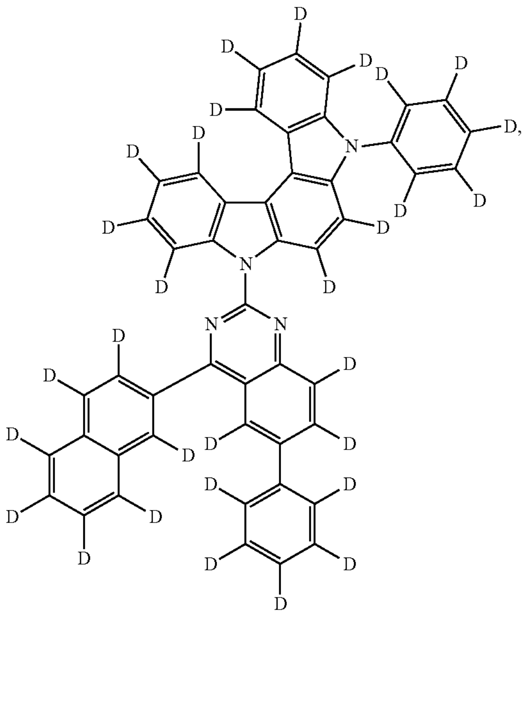

-continued
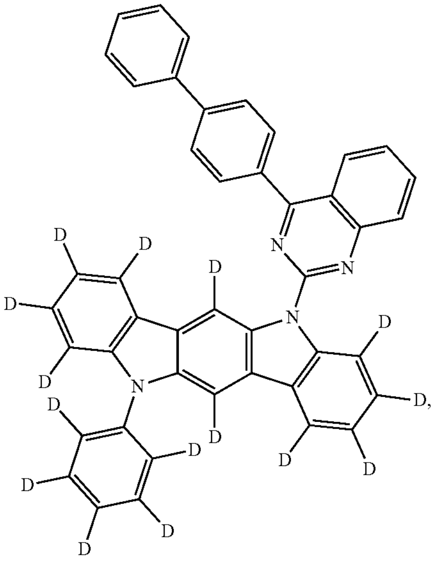
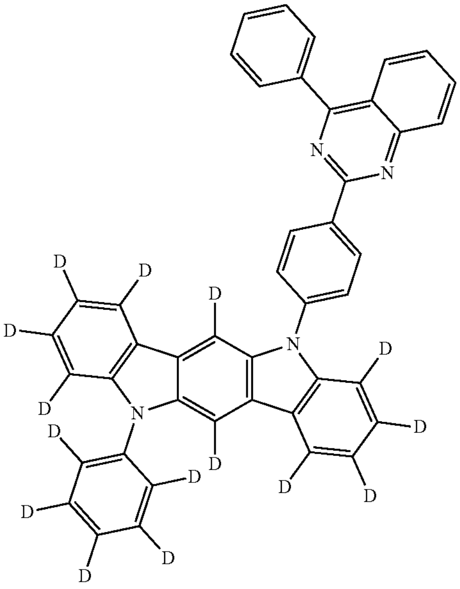
,
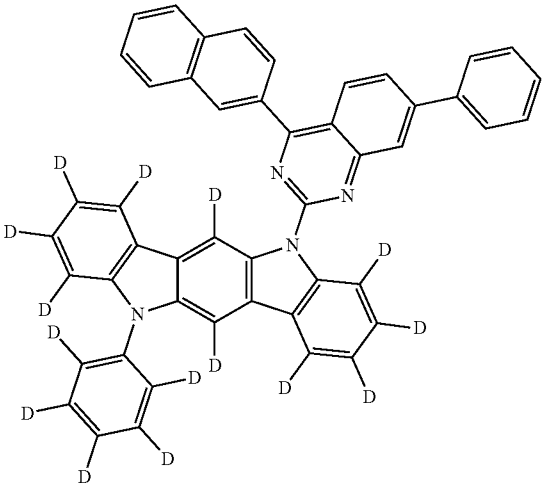
,
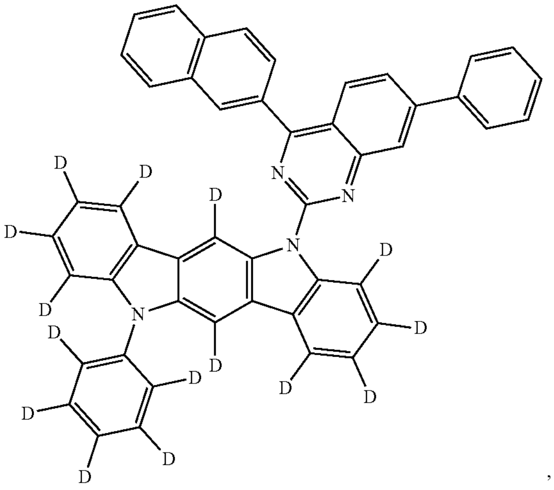
,
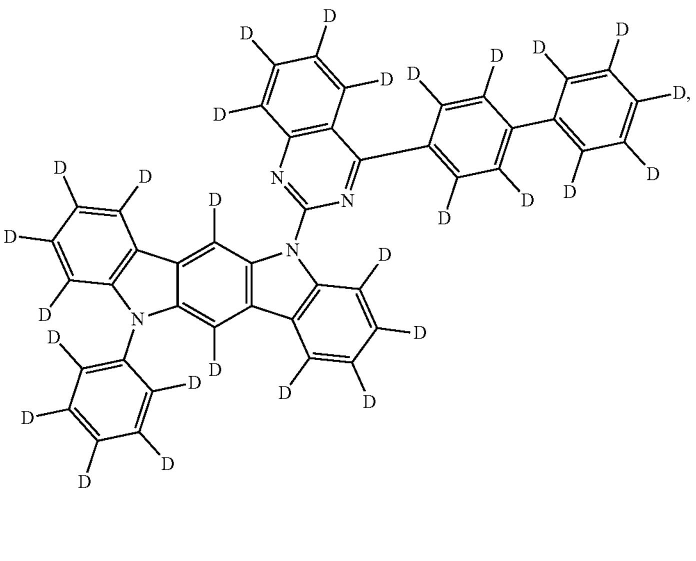

-continued
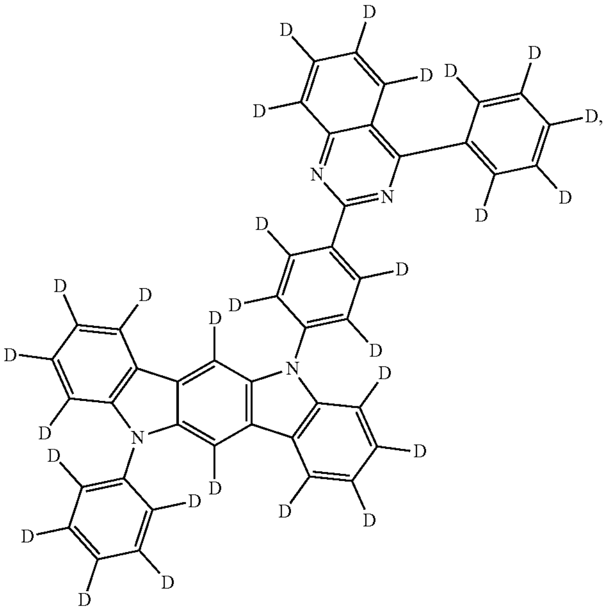
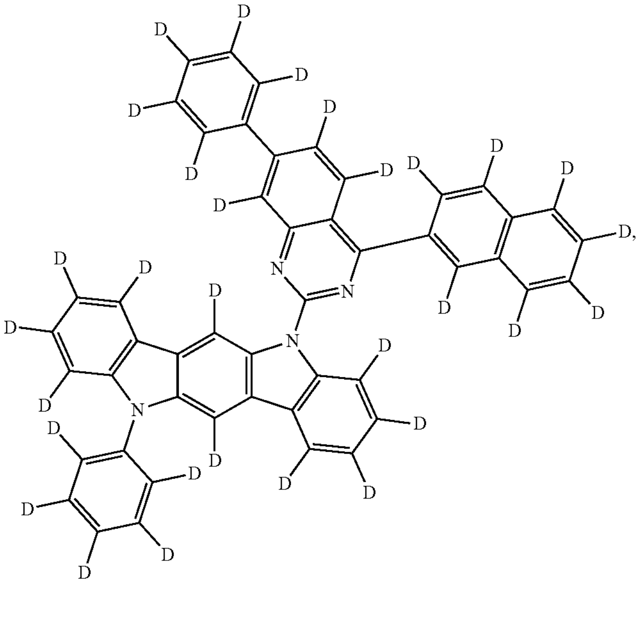

-continued
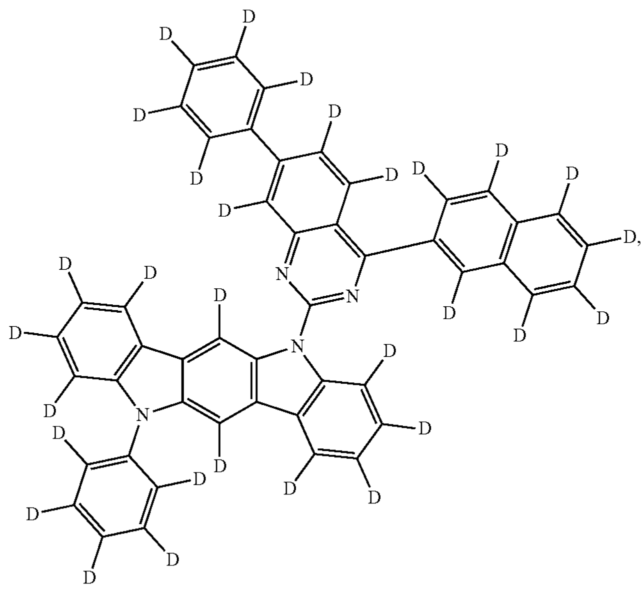
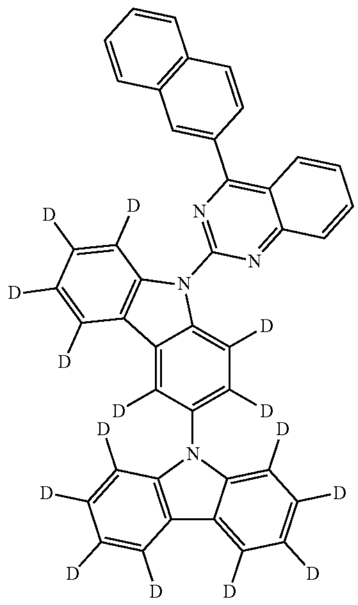
,
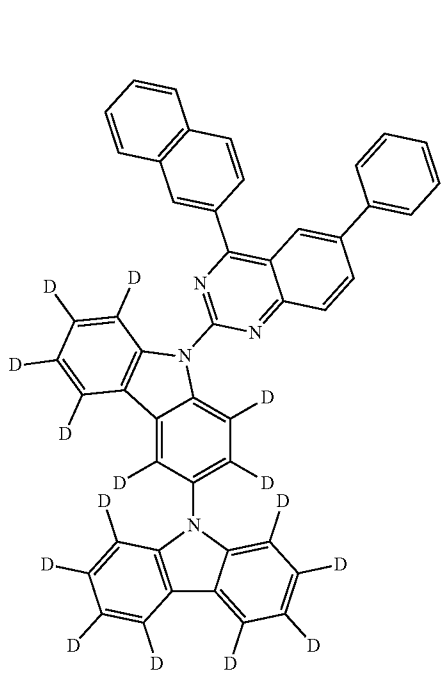
,
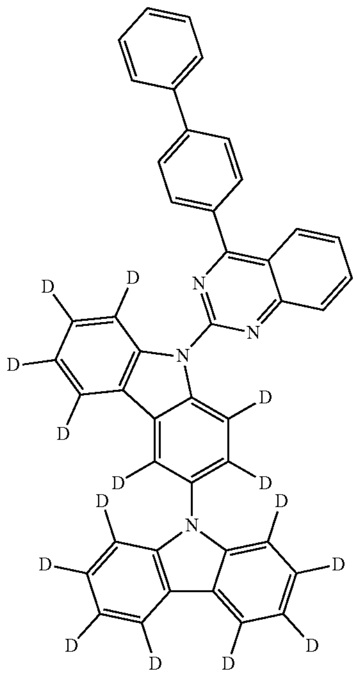
,

-continued
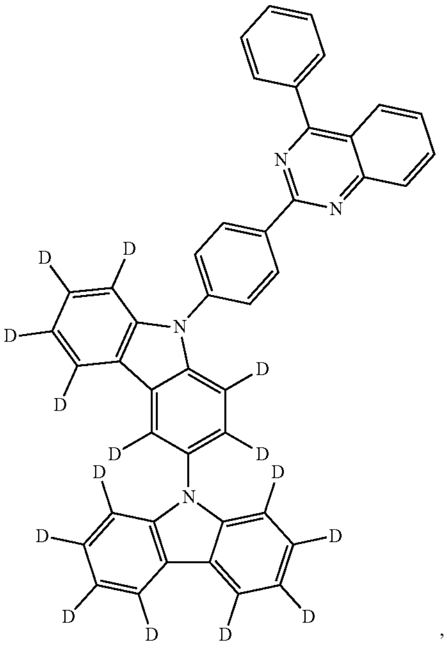
,
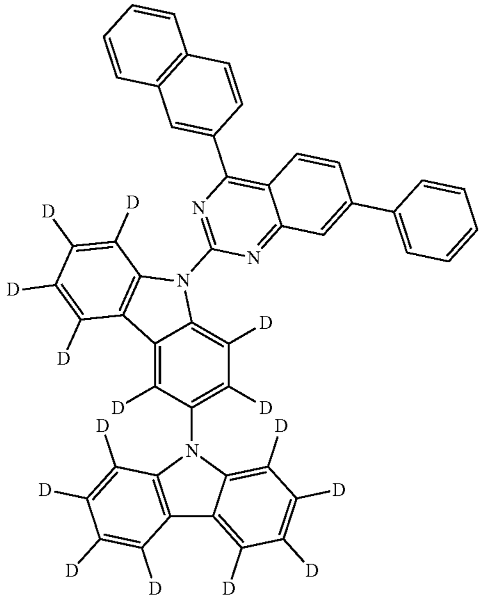
,
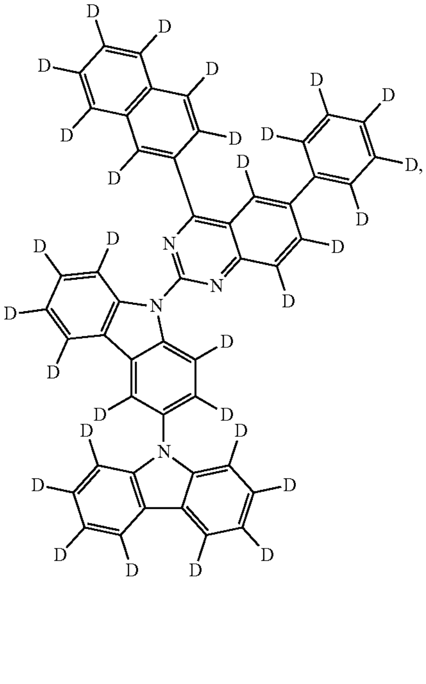
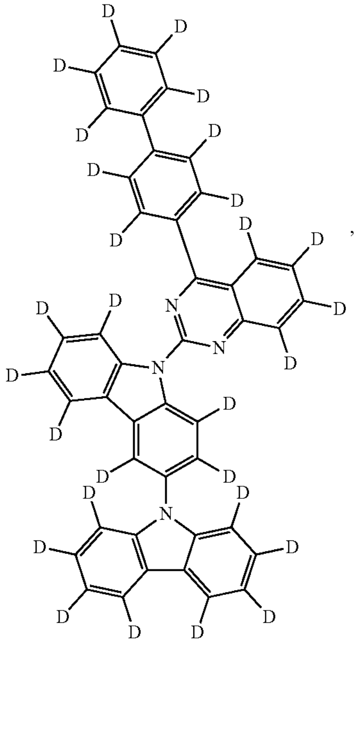
,

-continued
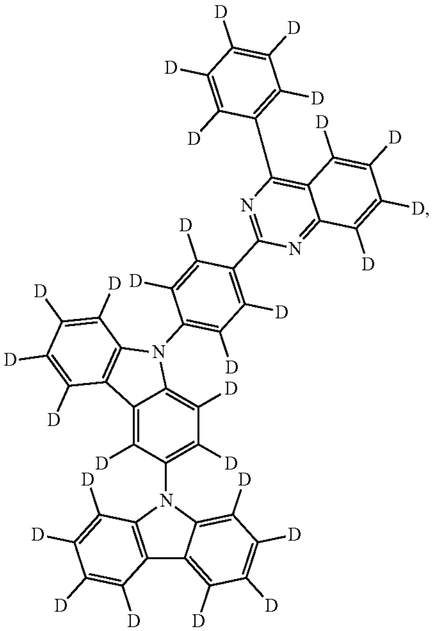
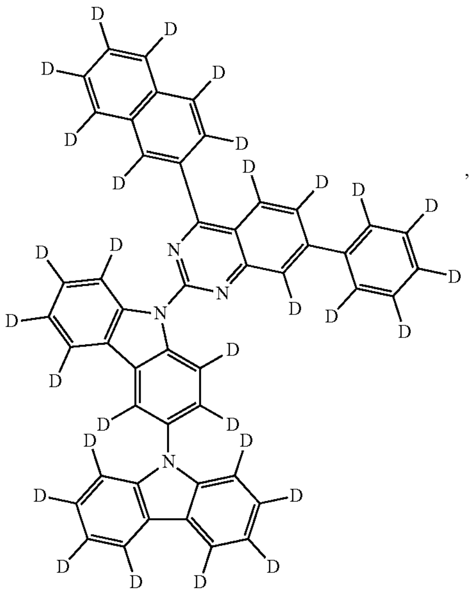
,
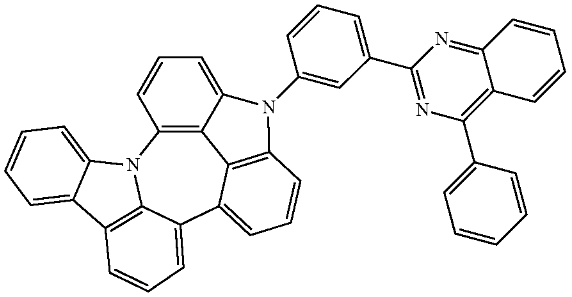
,
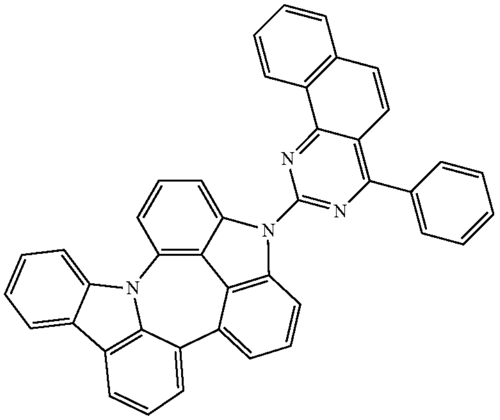
,
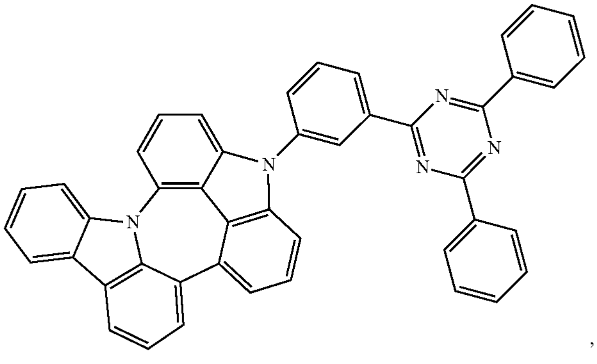
,
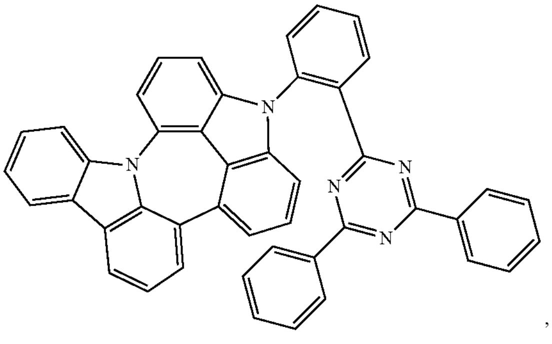
, -continued
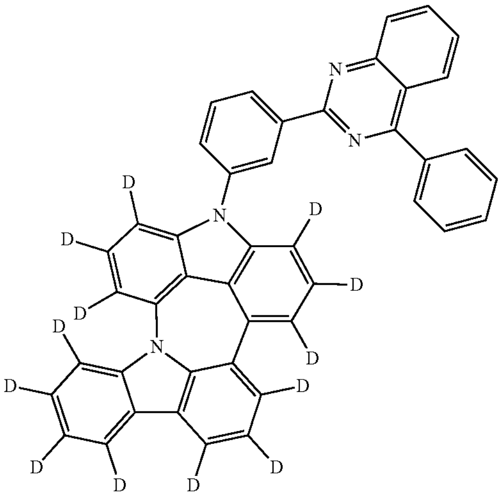
,
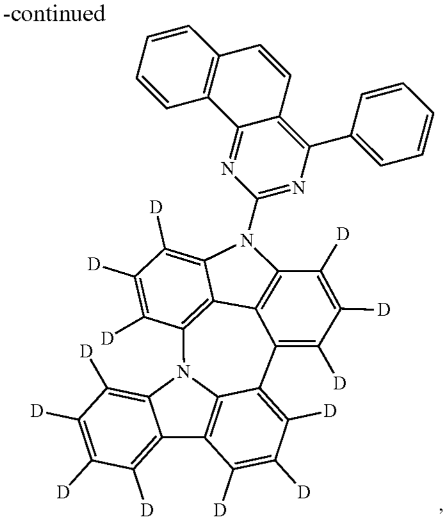
,
-continued
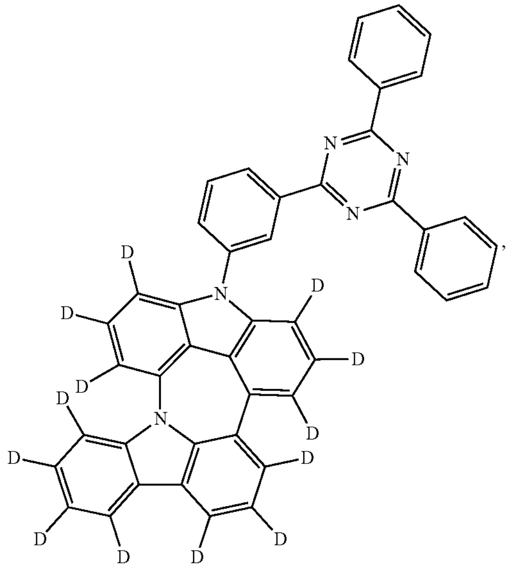
,
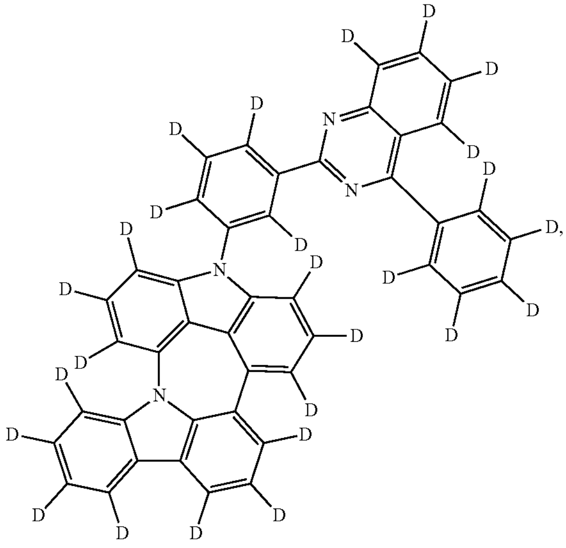
,
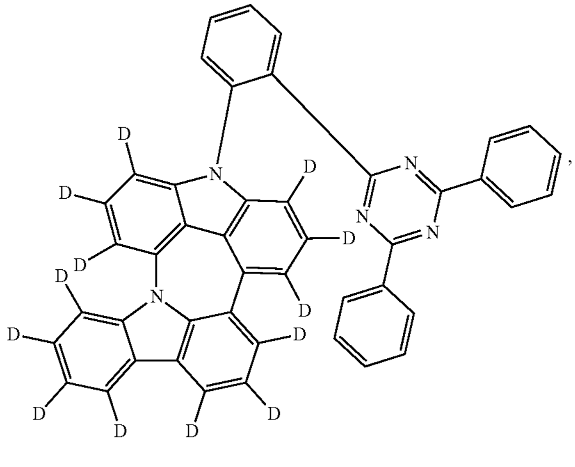
,
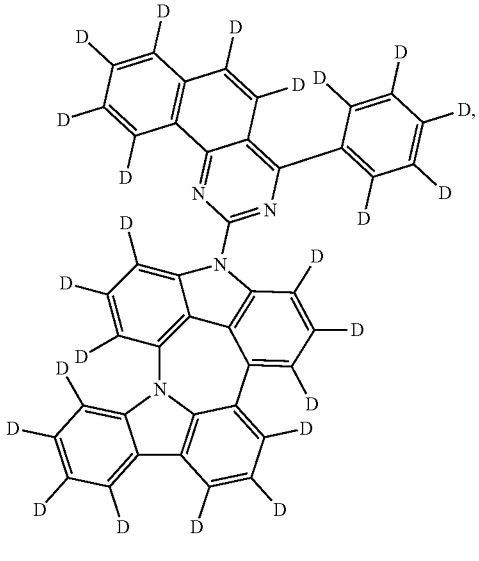
, -continued

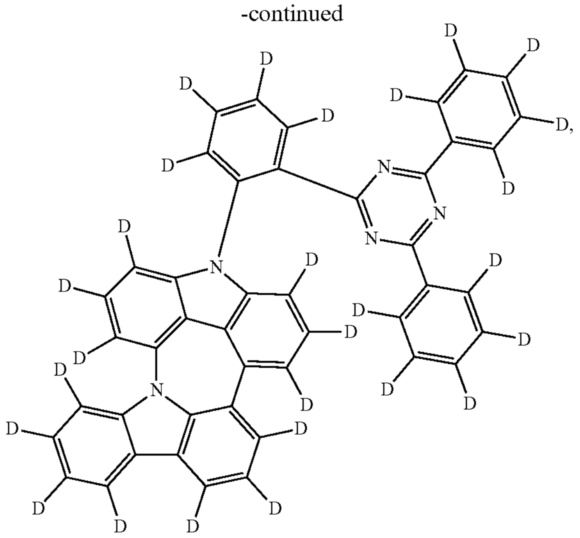

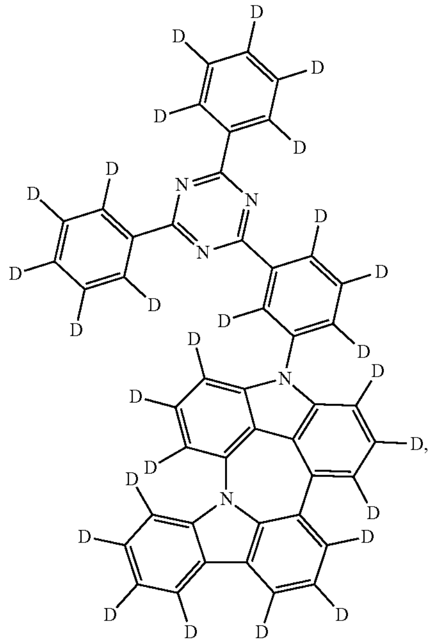

and

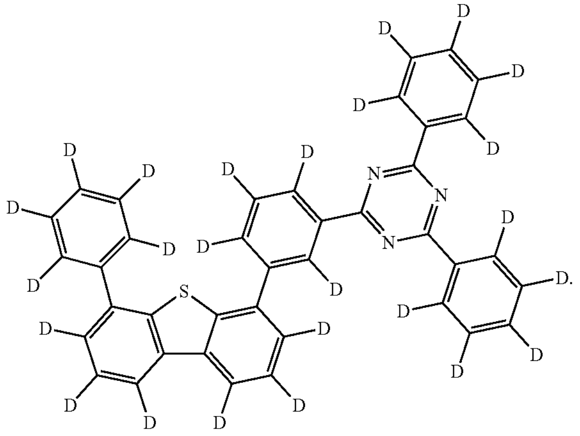

14. The OLED of claim 1, wherein the phosphorescent dopant has a formula of $M(L_A)_p(L_B)_q(L_C)$, wherein $L_B$ and $L_C$ are each a bidentate ligand; and wherein p is 1, 2, or 3; q is 0, 1, or 2; r is 0, 1, or 2; and p+q+r is the oxidation state of the metal M.

15. The OLED of claim 14, wherein the phosphorescent dopant is a transition metal complex having at least one ligand or part of the ligand if the ligand is more than bidentate selected from the group consisting of:

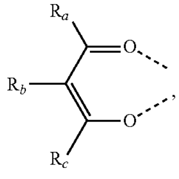

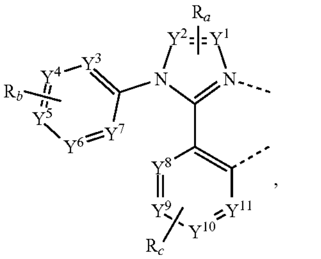

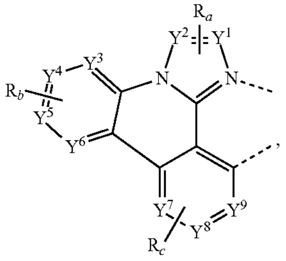

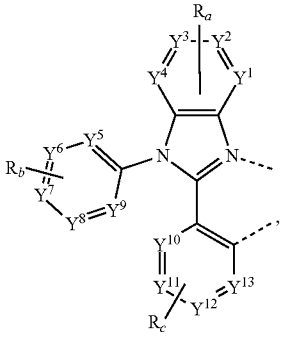

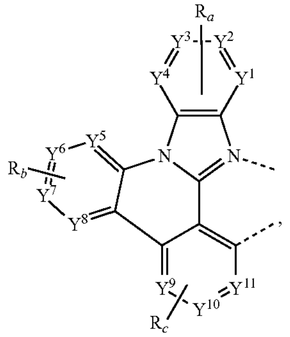

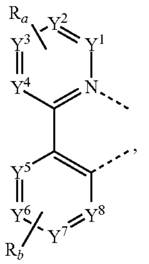

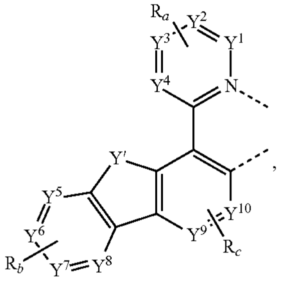

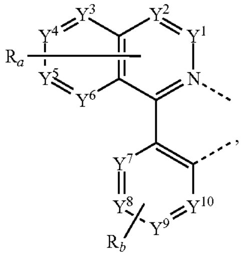

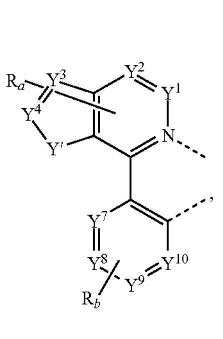

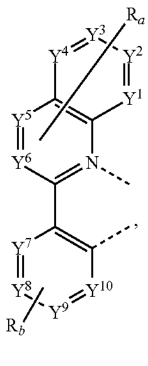

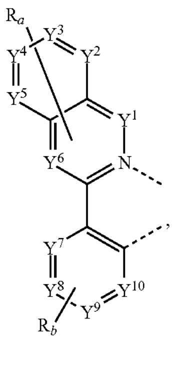

-continued

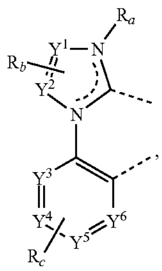

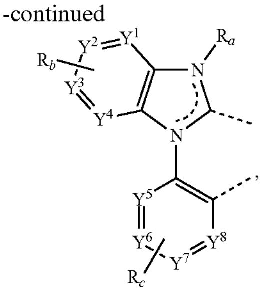

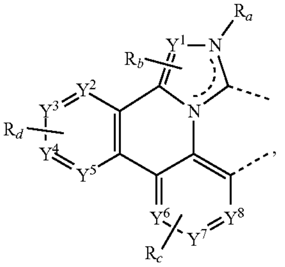

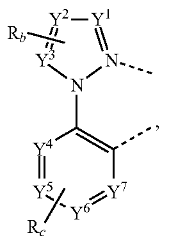

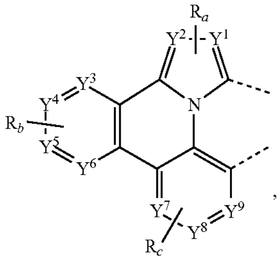

,

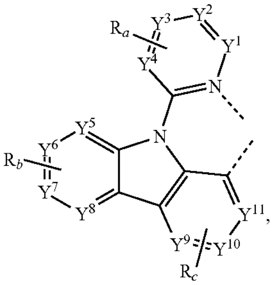

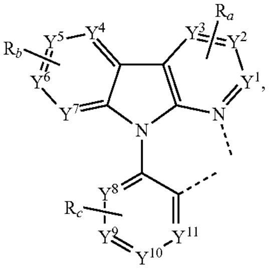

and

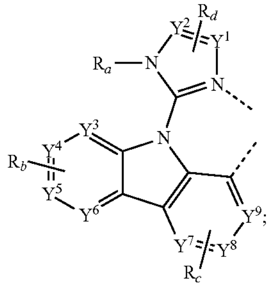

wherein:

each $Y^1$ to $Y^{13}$ is independently selected from the group consisting of carbon and nitrogen;

Y' is selected from the group consisting of $BR_e$, $BR_eR_f$, $NR_e$, $PR_e$, $P(O)R_e$, O, S, Se, C═O, C═S, C═Se, C═$NR_e$, C═$CR_eR_f$, S═O, $SO_2$, $CR_eR_f$, $SiR_eR_f$, and $GeR_eR^f$;

$R_e$ and $R_f$ are optionally fused or joined to form a ring;

each $R_a$, $R_b$, $R_c$, and $R_d$ independently represents mono, up to a maximum number of allowed substitutions, or no substitution to its associated ring;

each of $R_a$, $R_b$, $R_c$, $R_d$, $R_e$ and $R_f$ is independently hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof; and two adjacent substituents of $R_a$, $R_b$, $R_c$, and $R_a$ are optionally fused or joined to form a ring or form a multidentate ligand.

16. The OLED of claim 14, wherein the phosphorescent dopant is selected from the group consisting of:

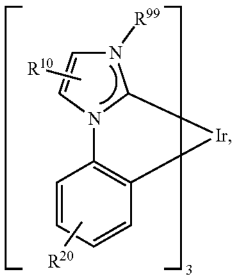

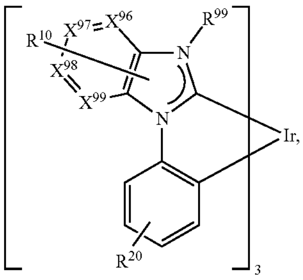

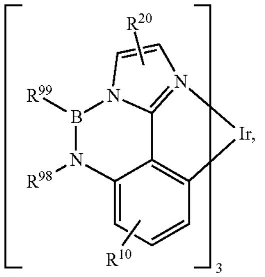

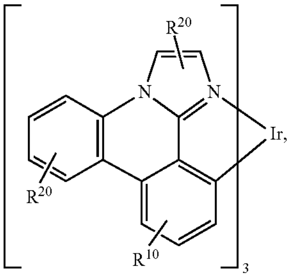

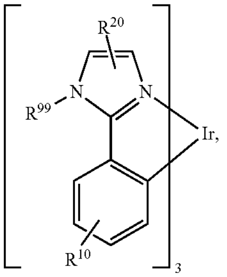

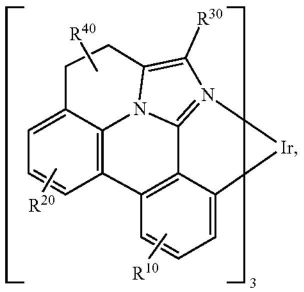

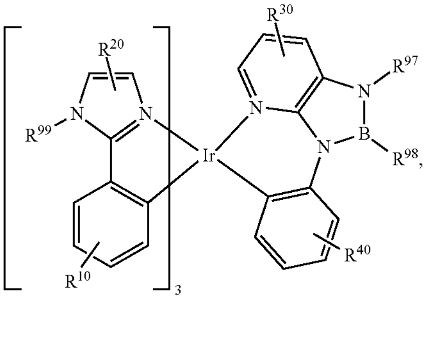

-continued
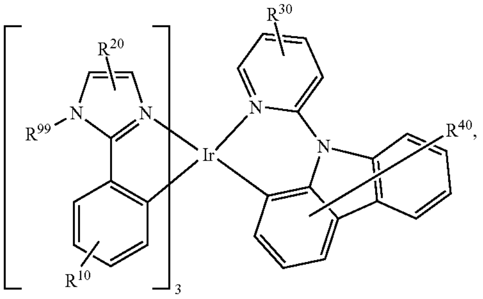
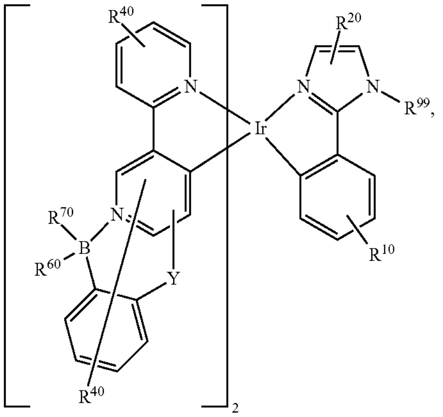
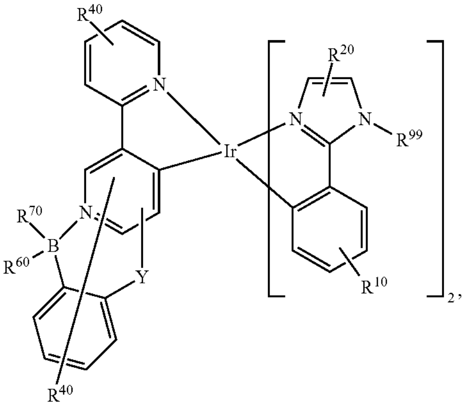
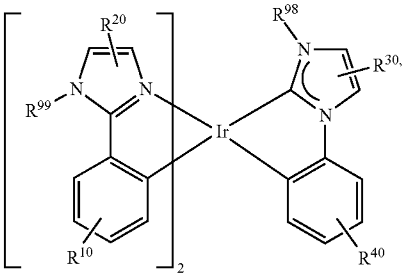
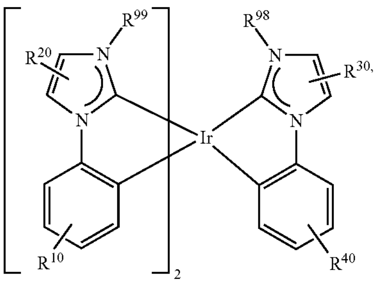
-continued
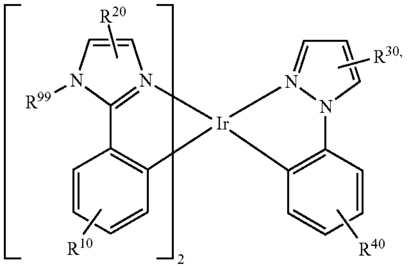
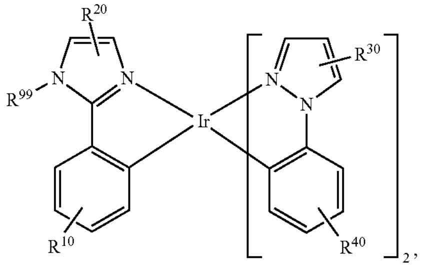
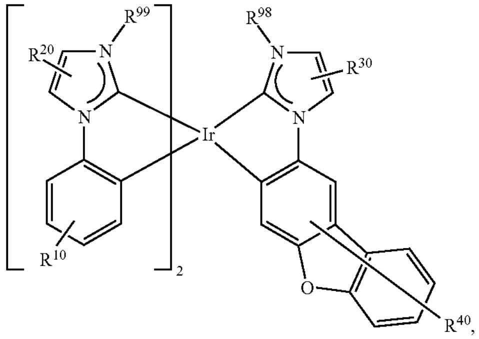
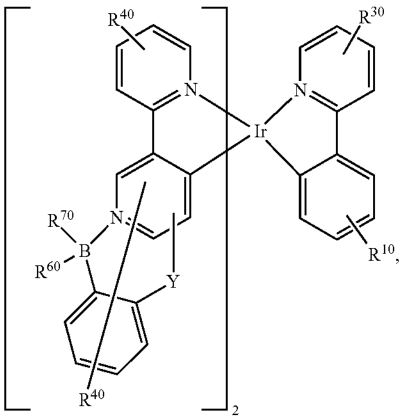
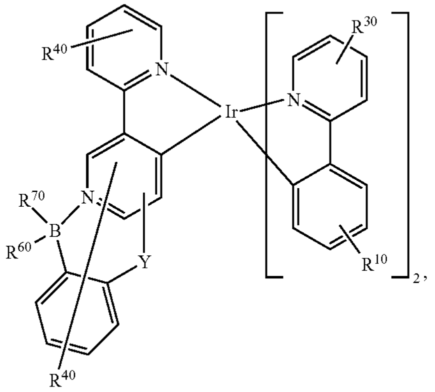

-continued
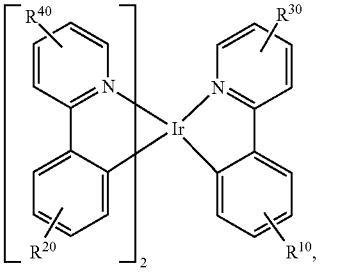
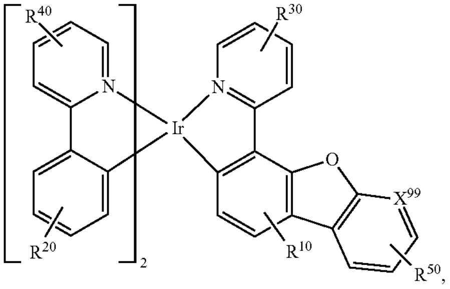
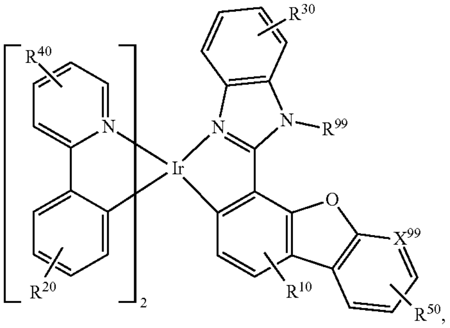
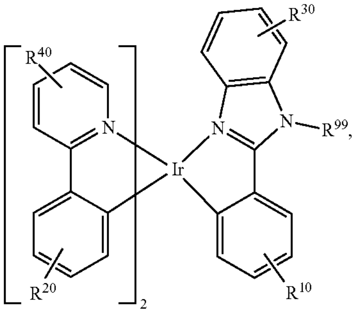
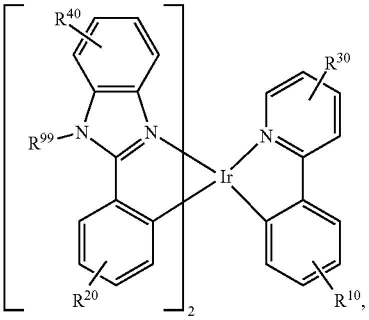
-continued
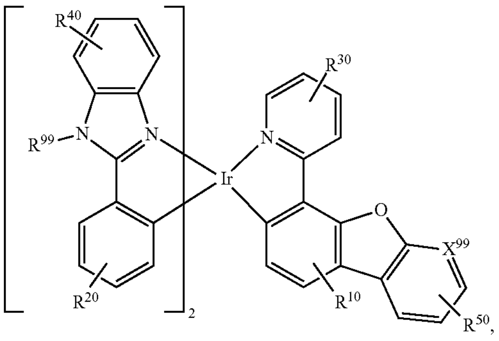
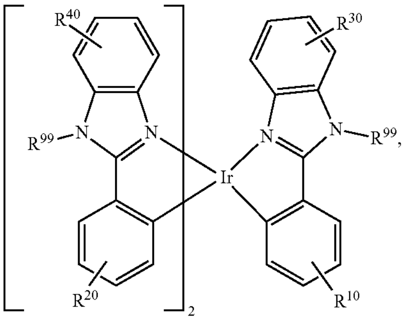
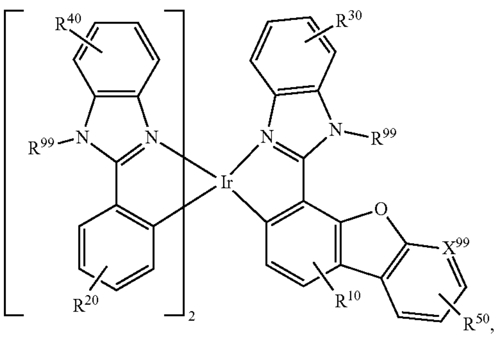
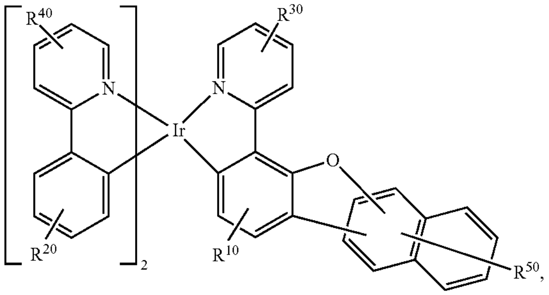
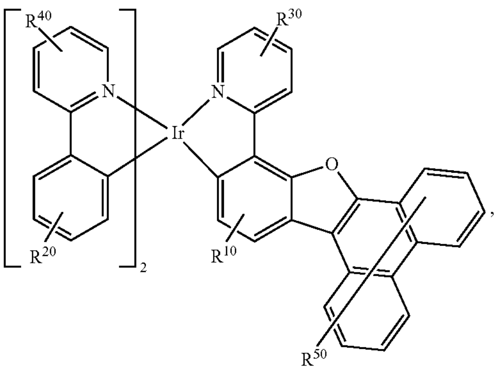

-continued
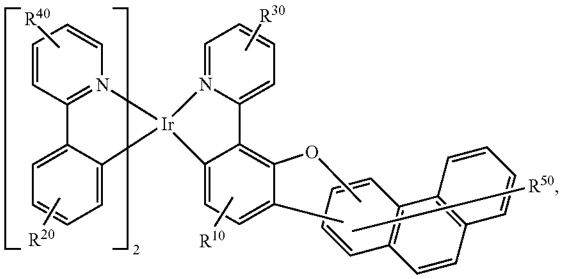
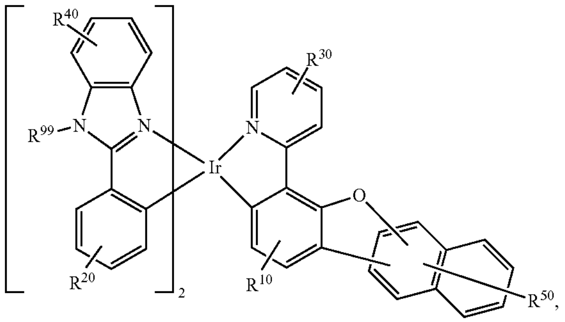
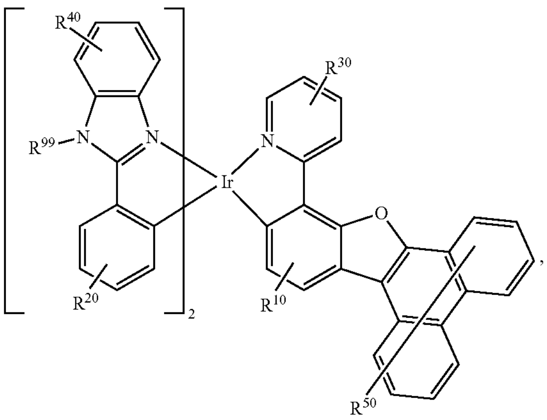
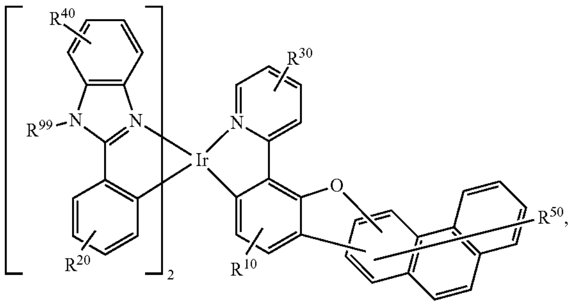
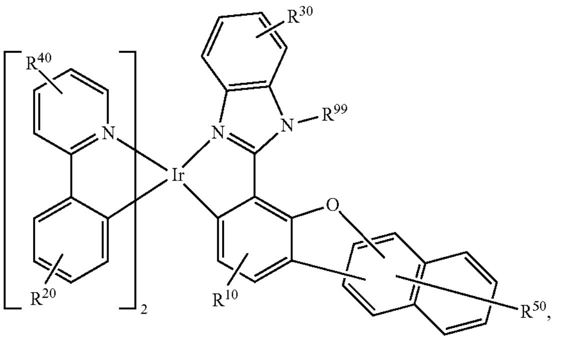
-continued
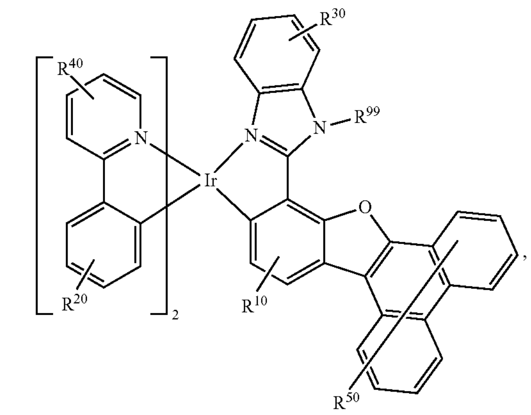
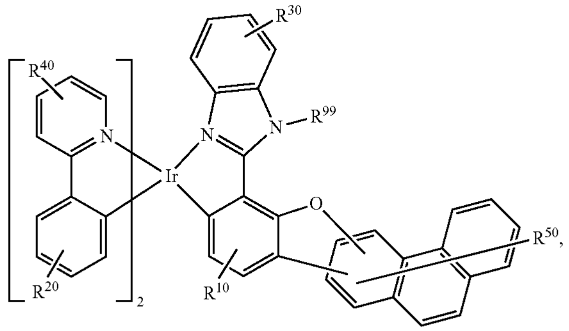
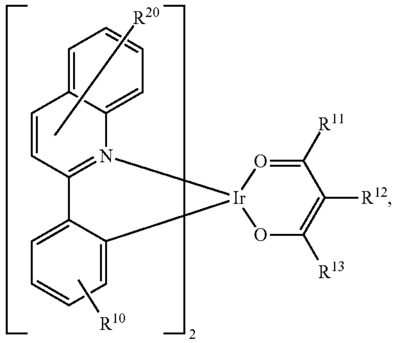
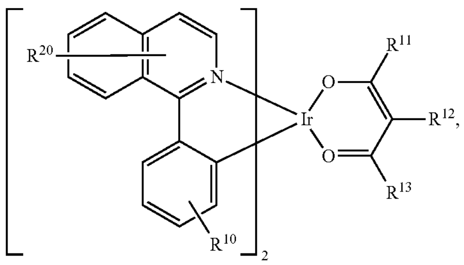
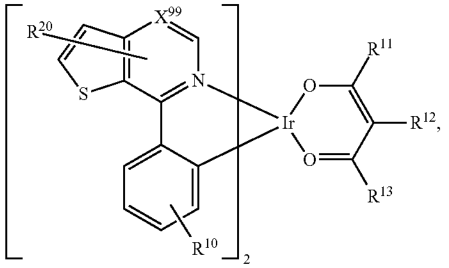

-continued

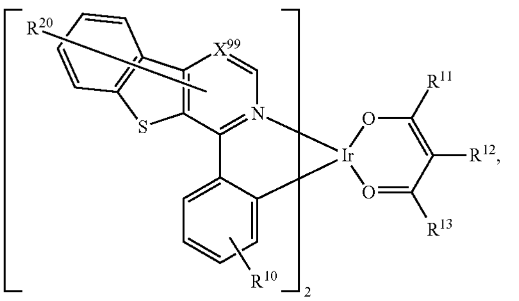

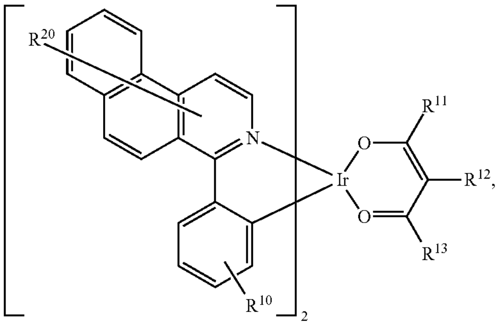

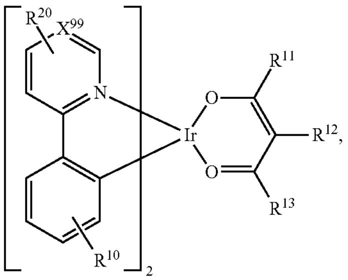

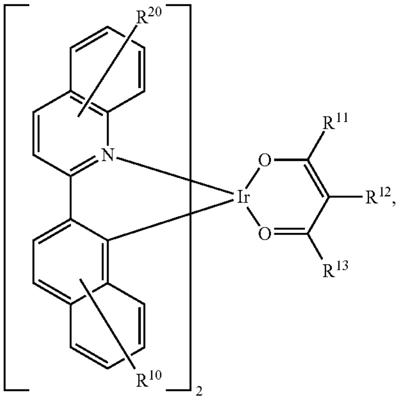

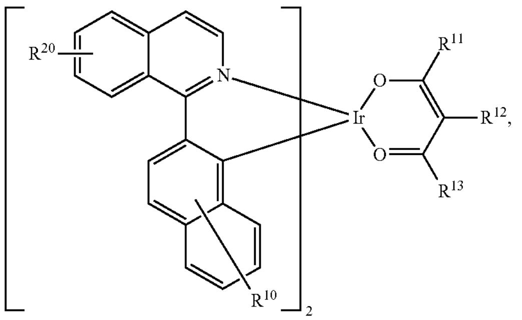

-continued

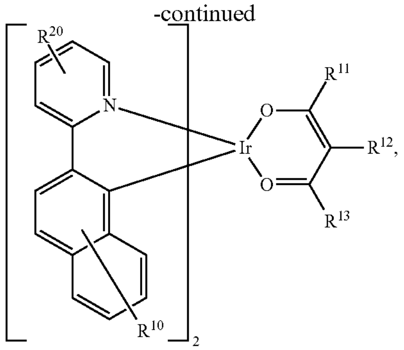

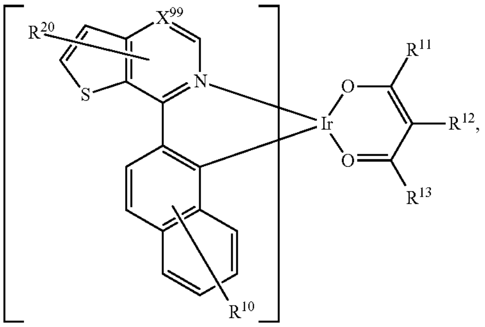

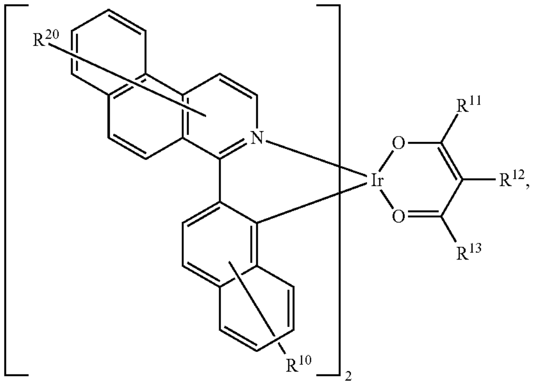

and

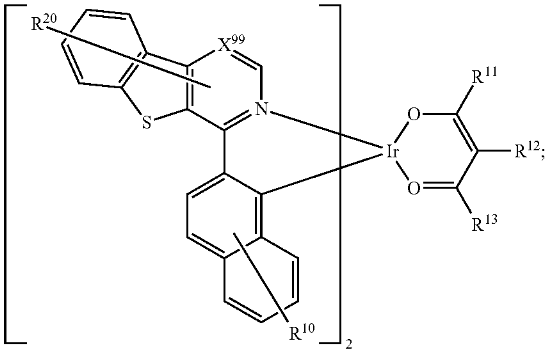

wherein:

each of $X^{96}$ to $X^{99}$ is independently C or N;

each Y is independently selected from the group consisting of a NR, O, S, and Se;

each of $R^{10}$, $R^{20}$, $R^{30}$, $R^{40}$, and $R^{50}$ independently represents mono, up to the maximum number of allowed substitutions, or no substitution;

each of R, $R^{10}$, $R^{11}$, $R^{12}$, $R^{13}$, $R^{20}$, $R^{30}$, $R^{40}$, $R^{50}$, $R^{60}$, $R^{70}$, $R^{97}$, $R^{98}$, and $R^{99}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof; and two adjacent of $R^{10}$, $R^{11}$, $R^{12}$, $R^{13}$, $R^{20}$, $R^{30}$, $R^{40}$, $R^{50}$, $R^{60}$, $R^{70}$, $R^{97}$, $R^{98}$, and $R^{99}$ can be joined or fused to form a ring.

17. The OLED of claim 14, wherein the phosphorescent dopant is selected from the group consisting of:

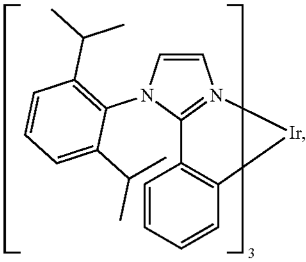

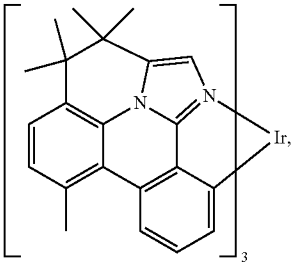

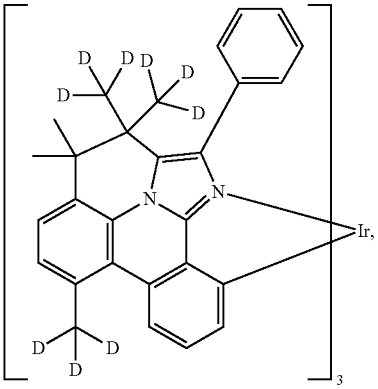

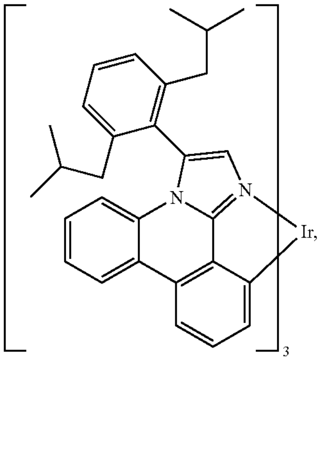

-continued

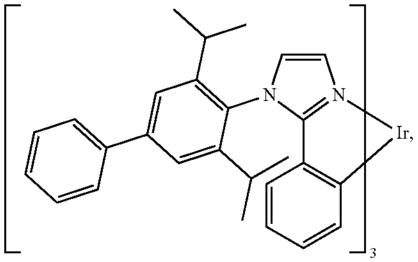

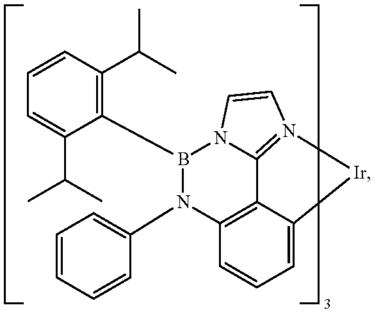

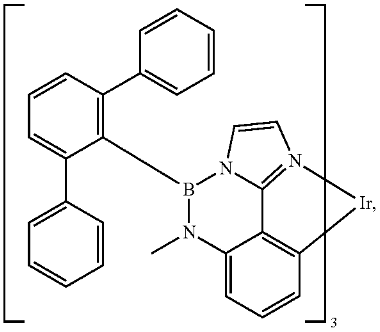

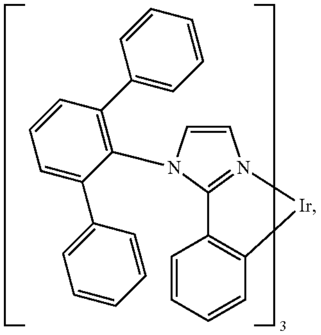

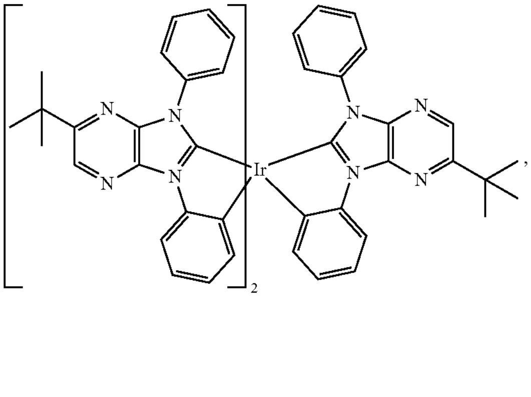

-continued
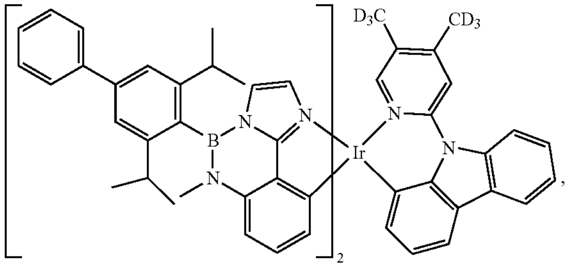
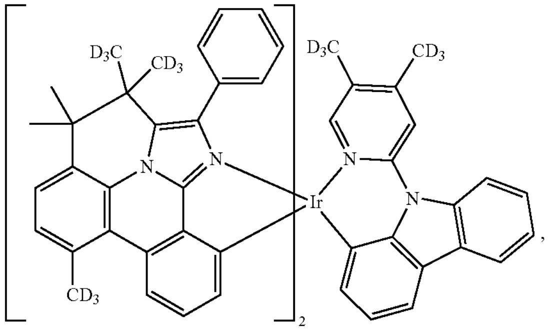
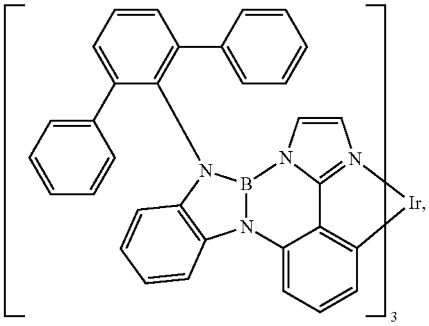
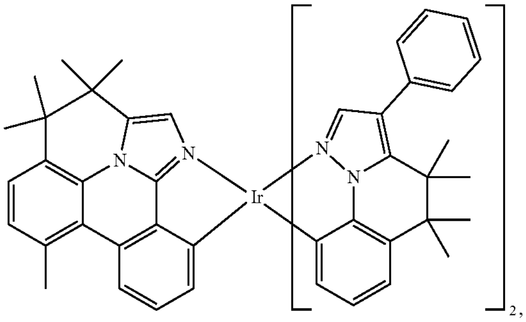
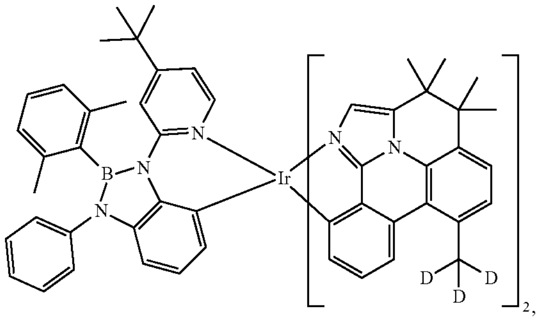
-continued
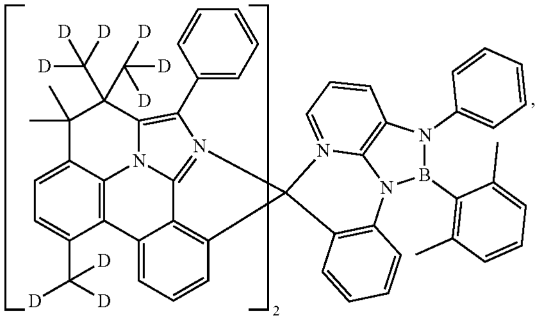
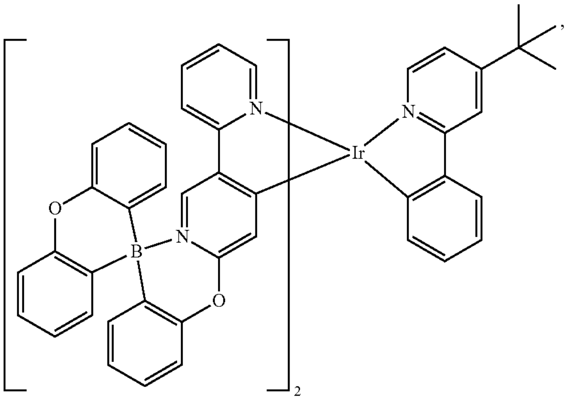
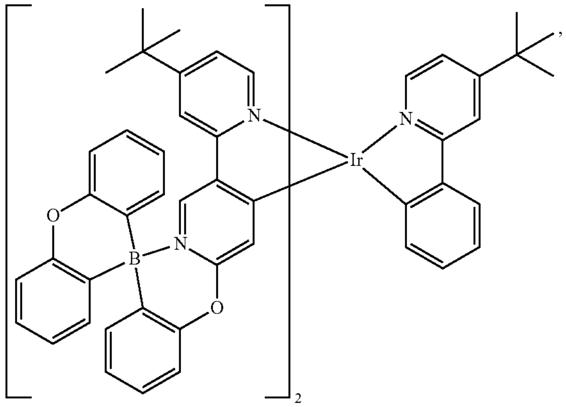
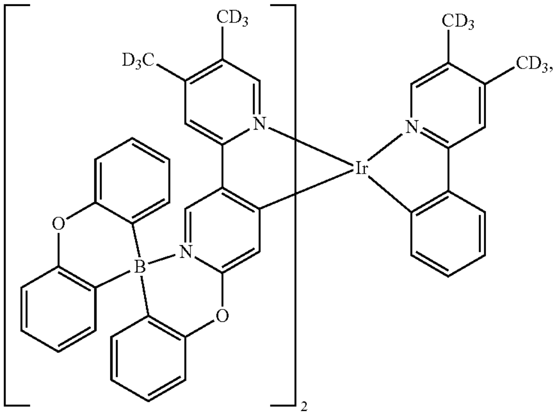

-continued
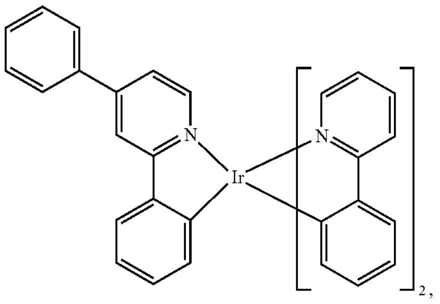
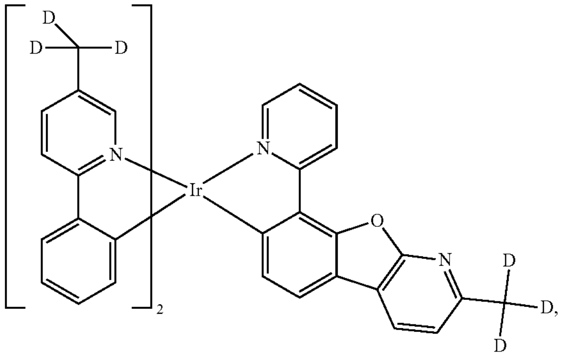
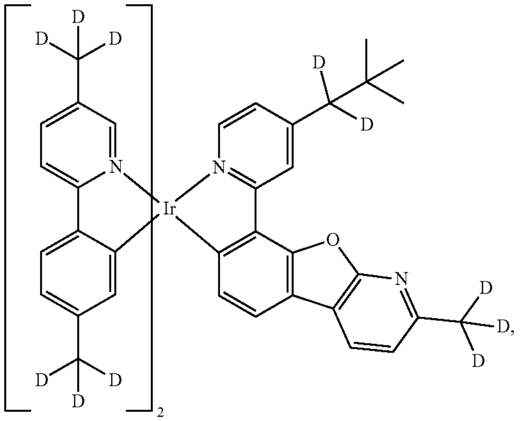
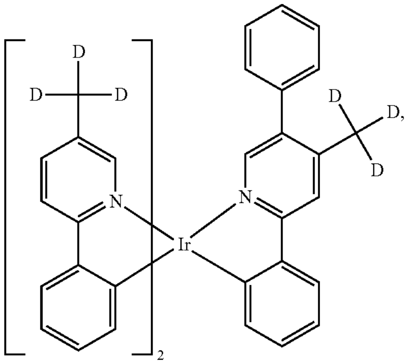
-continued
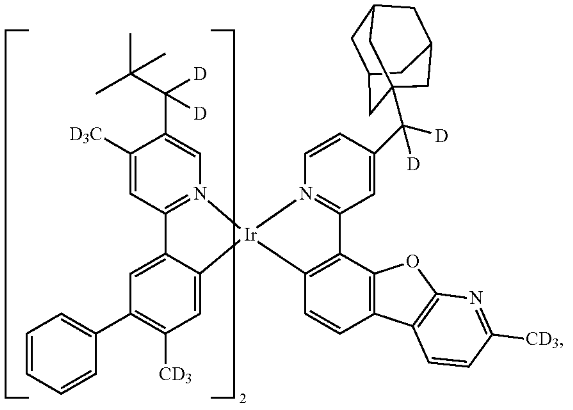
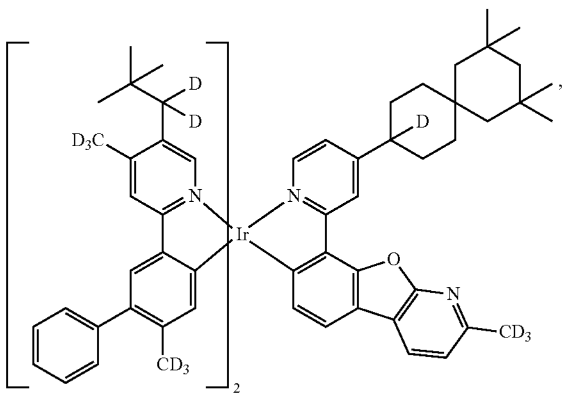
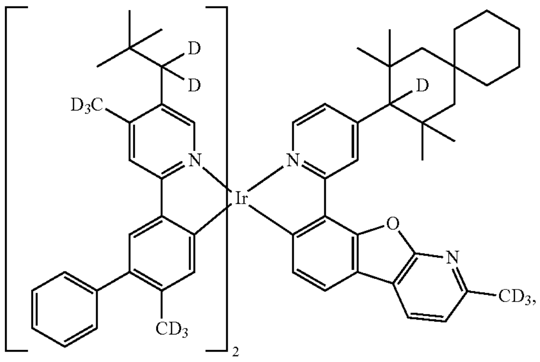
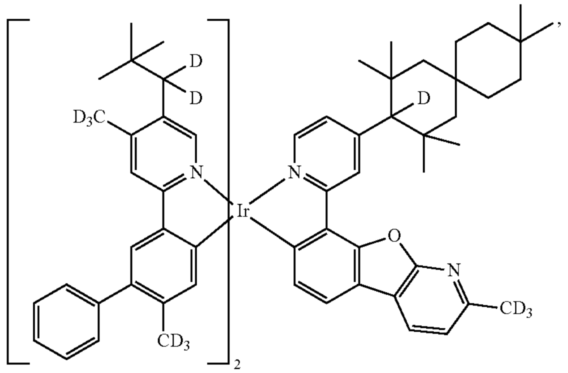

-continued
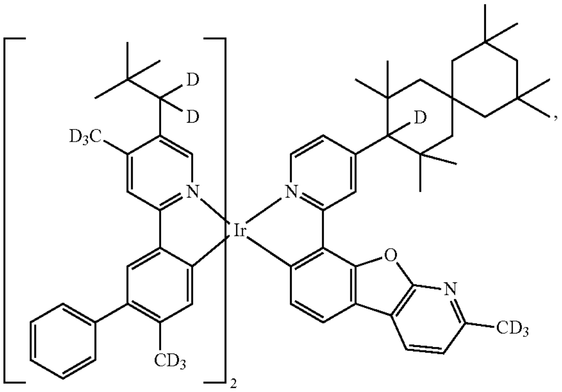
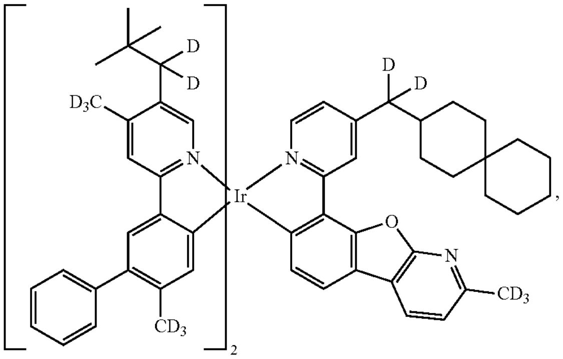
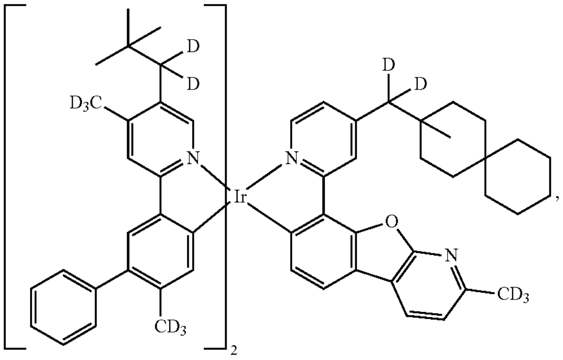
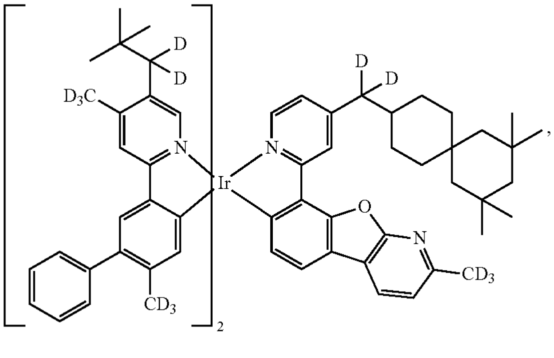
-continued
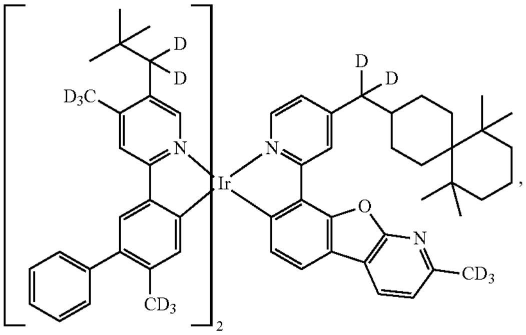
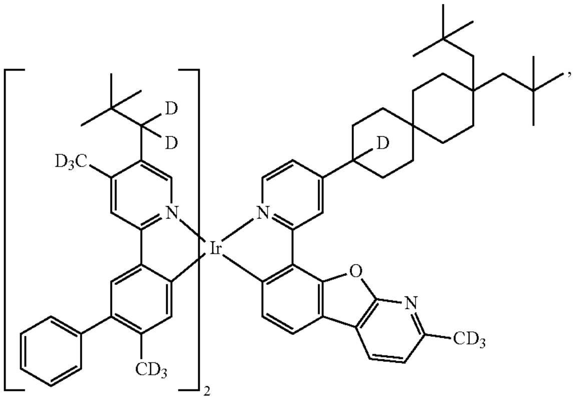
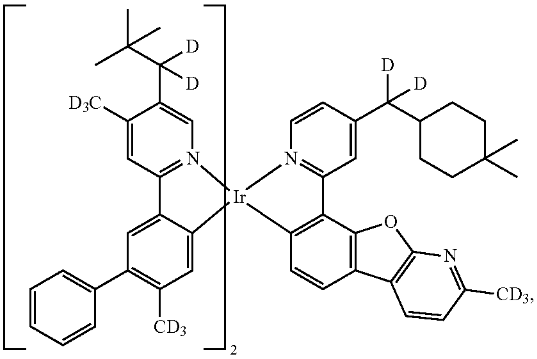
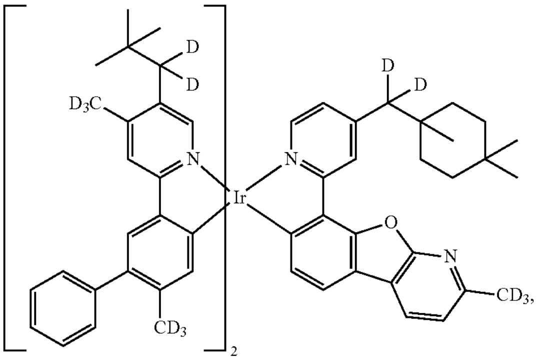

-continued
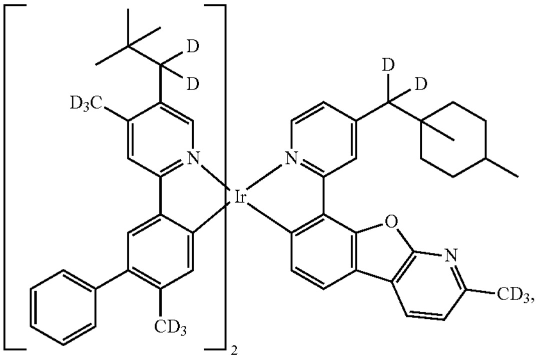
,
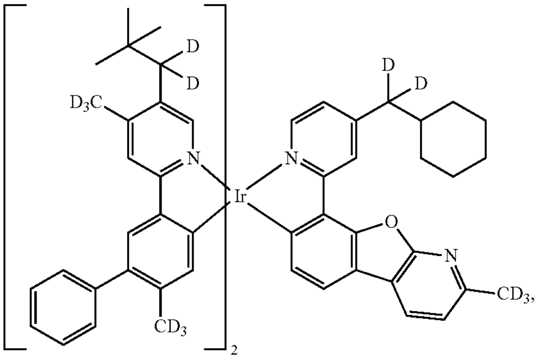
,
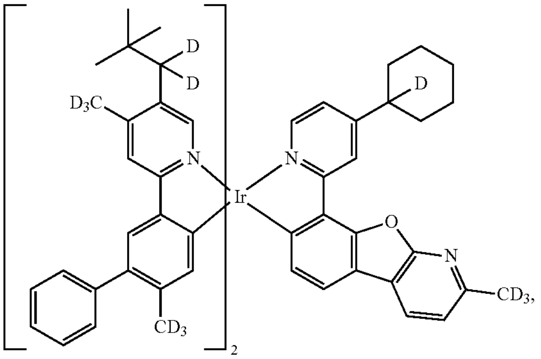
,
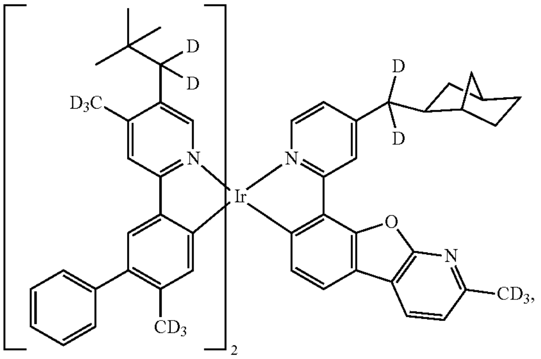
,
-continued
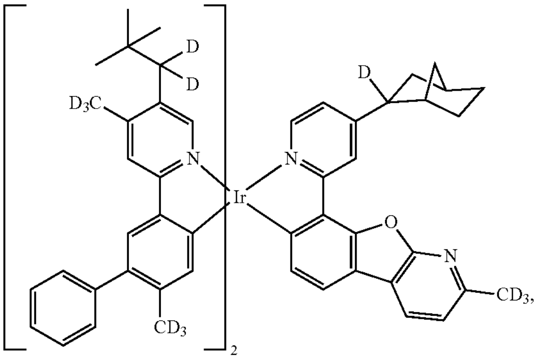
,
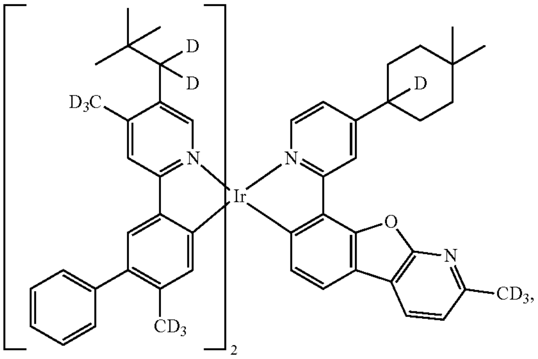
,
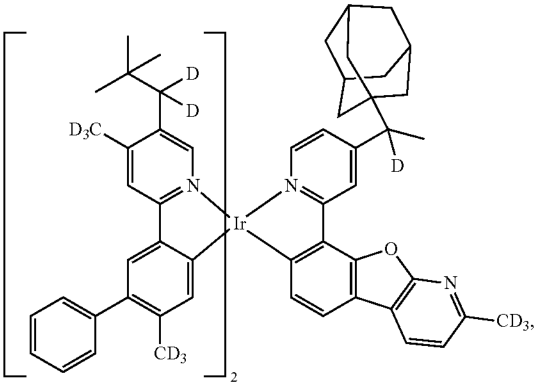
,
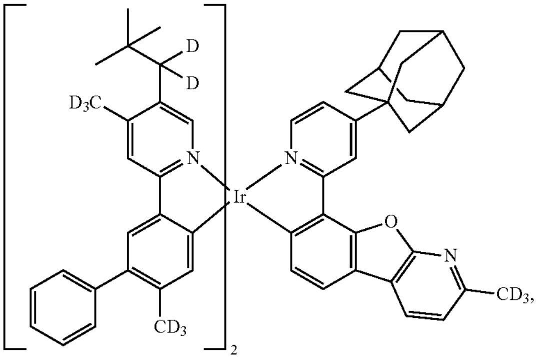
, -continued
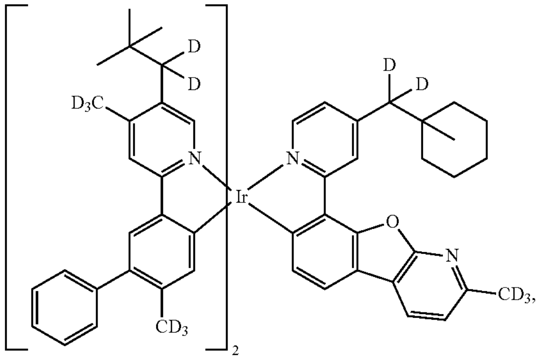
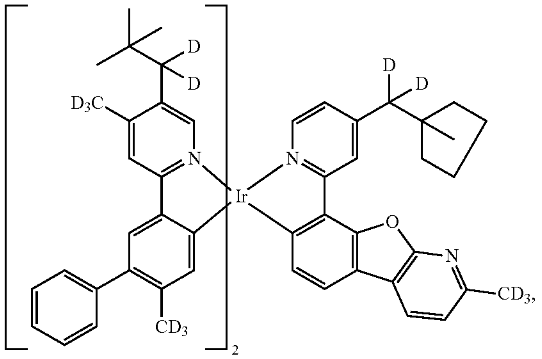
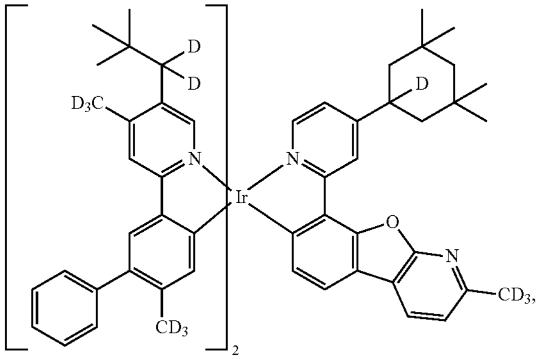
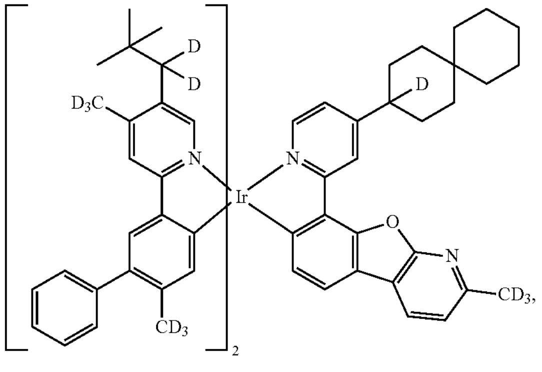
-continued
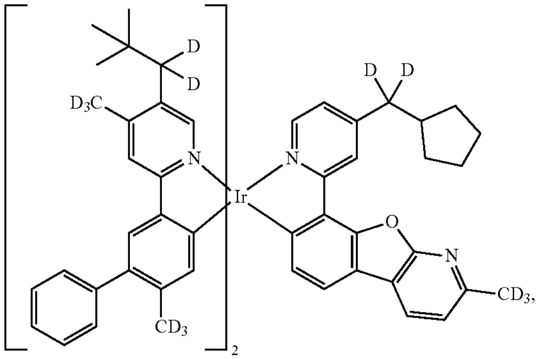
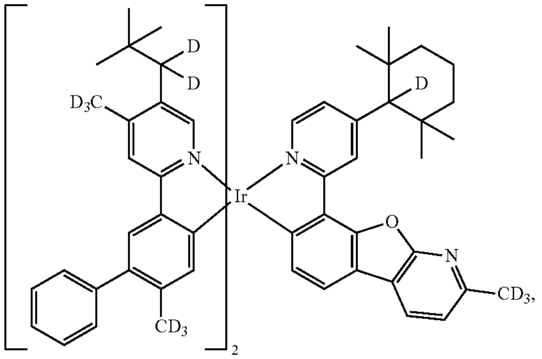
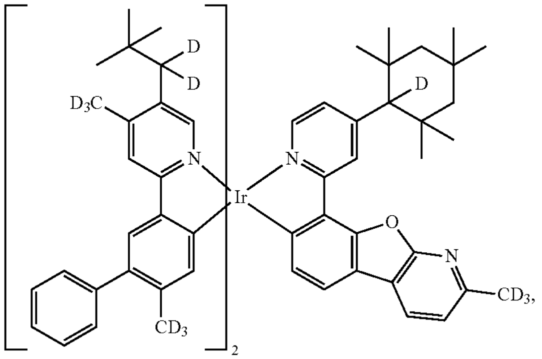
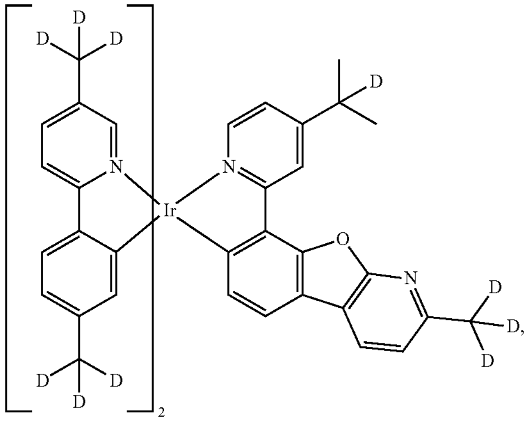

-continued
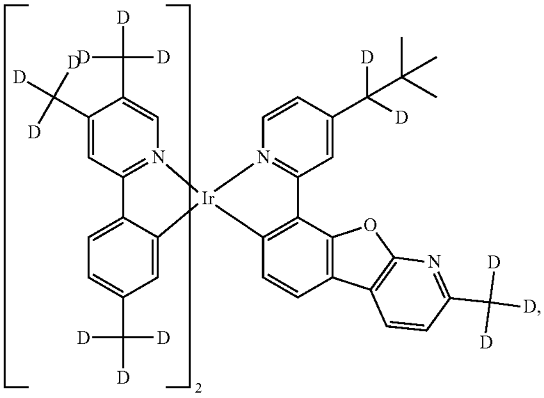
,
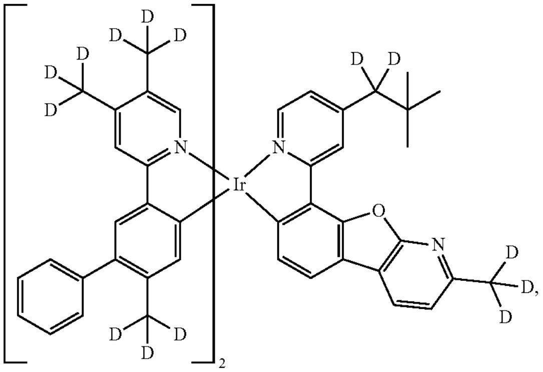
,
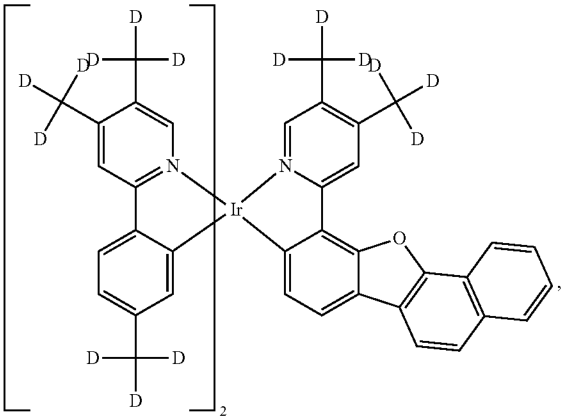
,
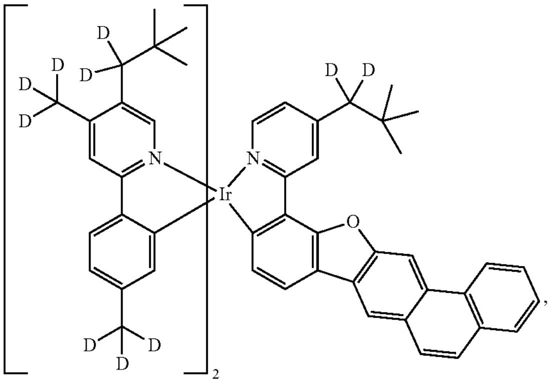
,
-continued
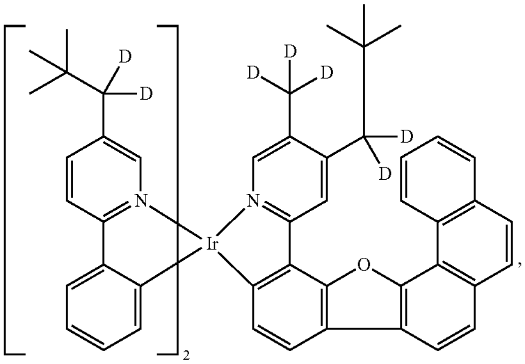
,
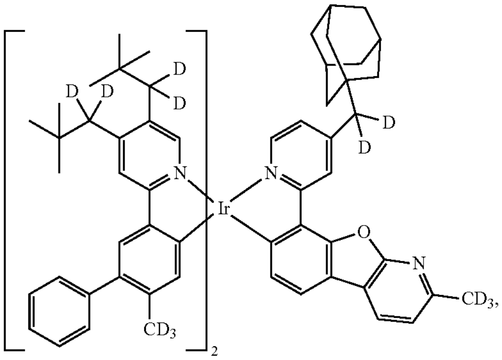
,
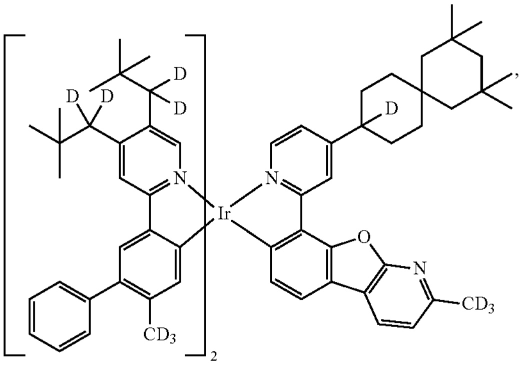
,
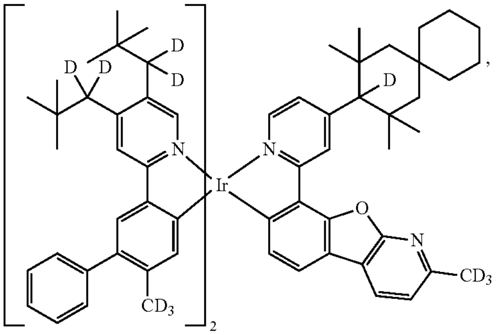
, -continued
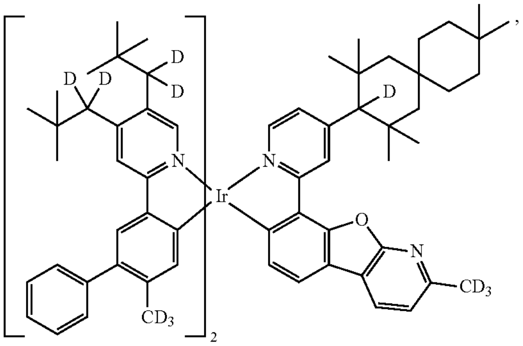
,
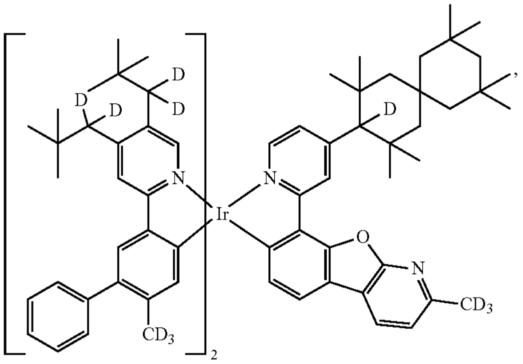
,
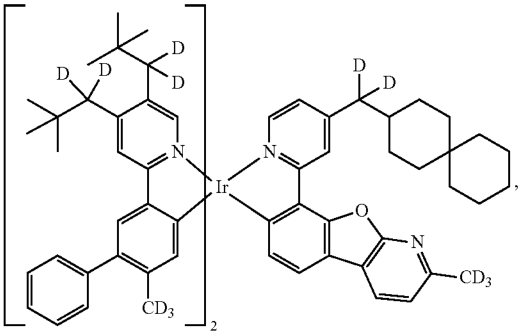
,
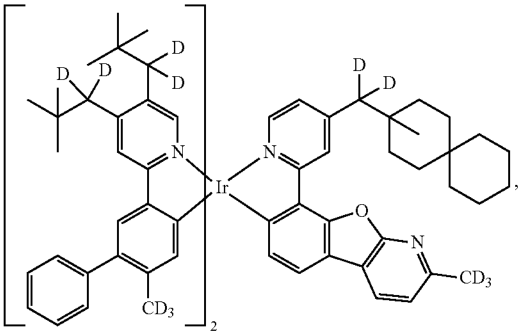
,
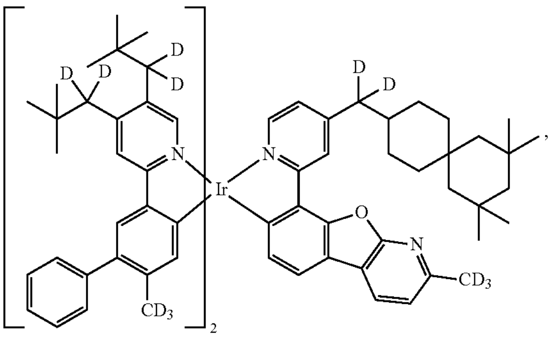
,
-continued
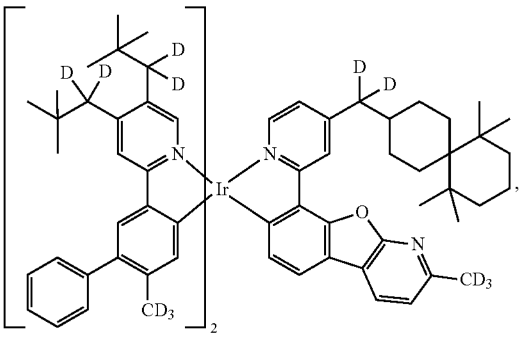
,
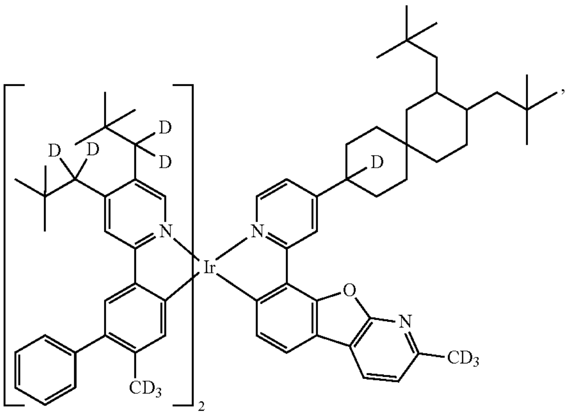
,
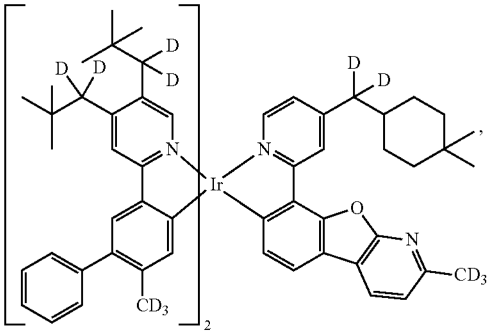
,
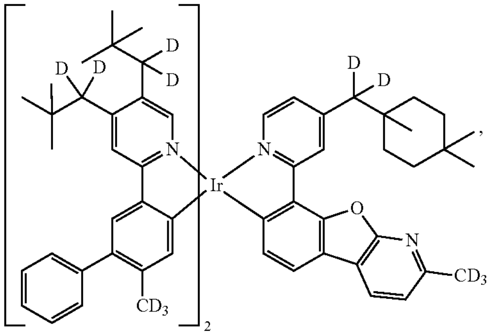
,

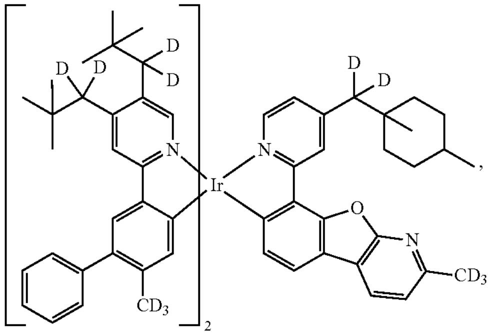
,
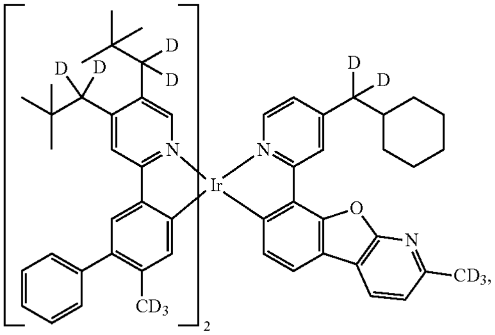
,
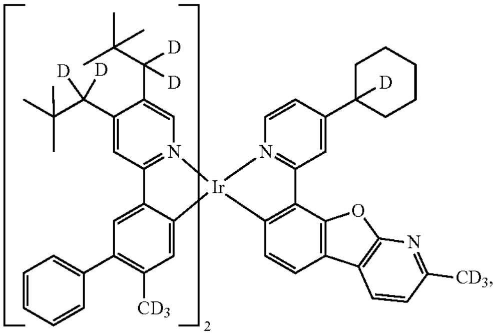
,
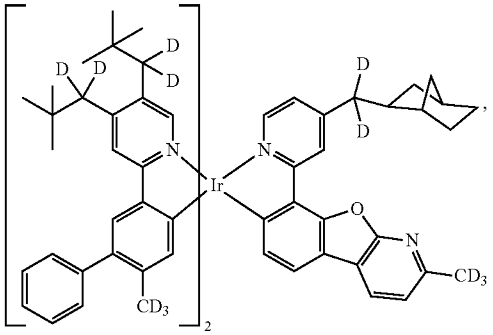
,
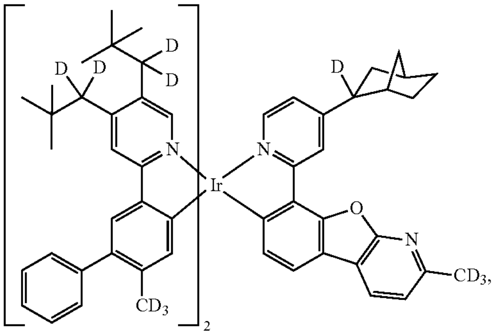
,
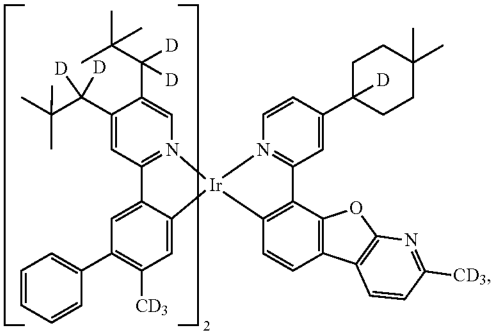
,
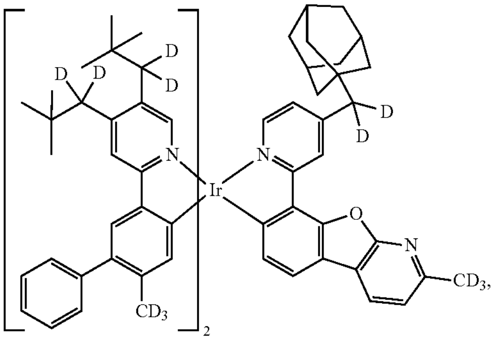
,
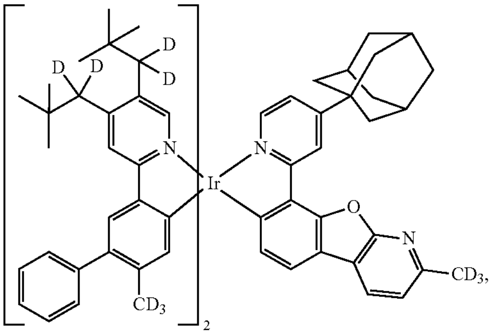
,
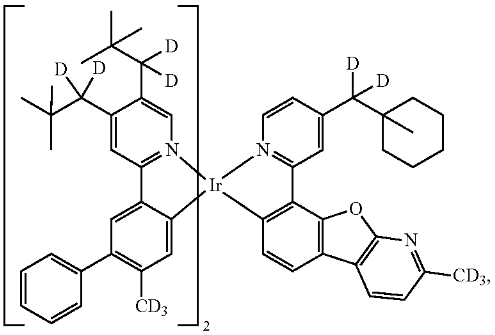
, -continued
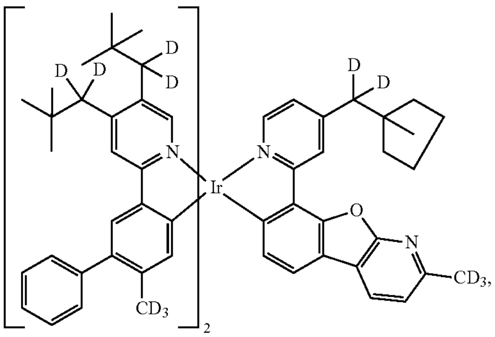
,
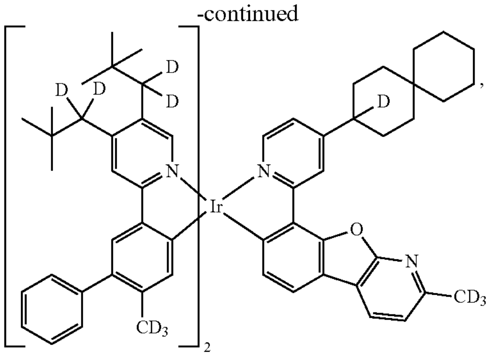
,
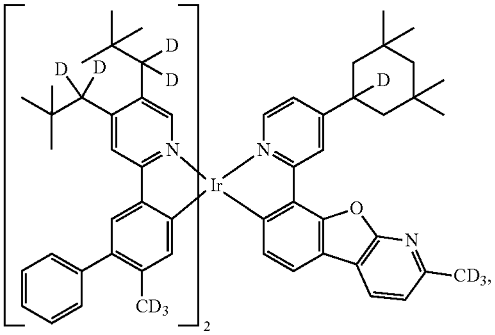
,
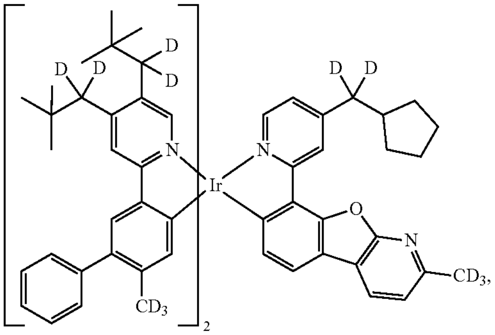
,
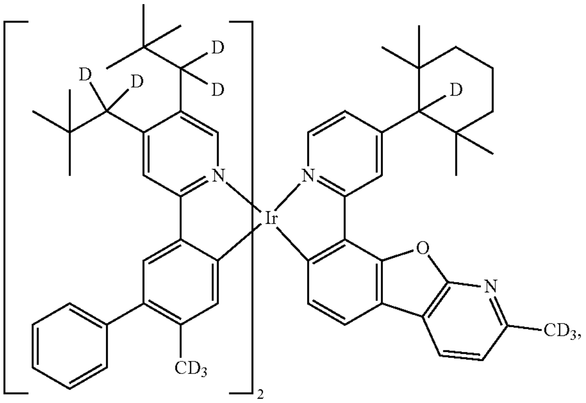
,
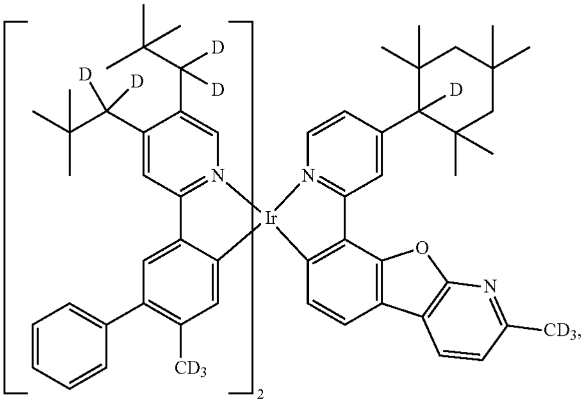
,
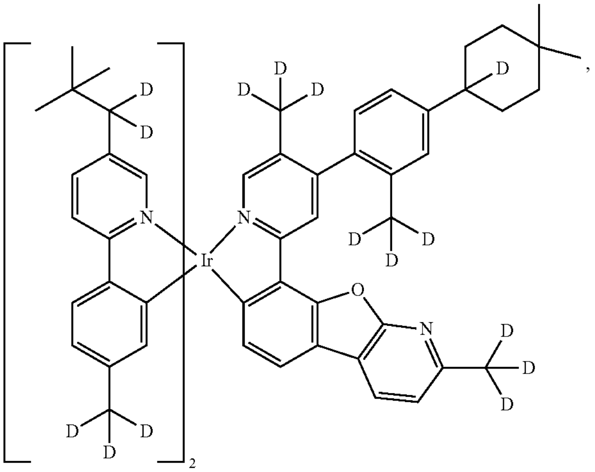
,
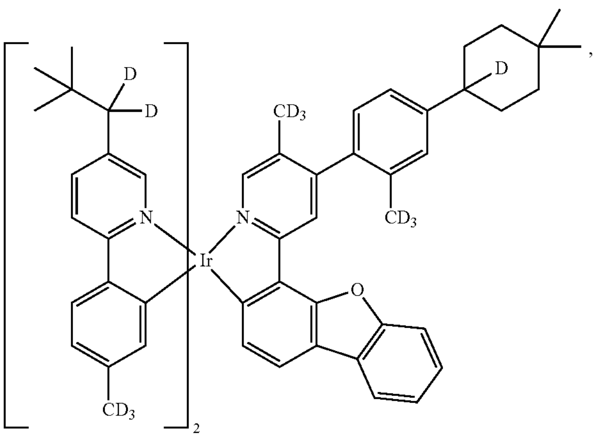
, -continued
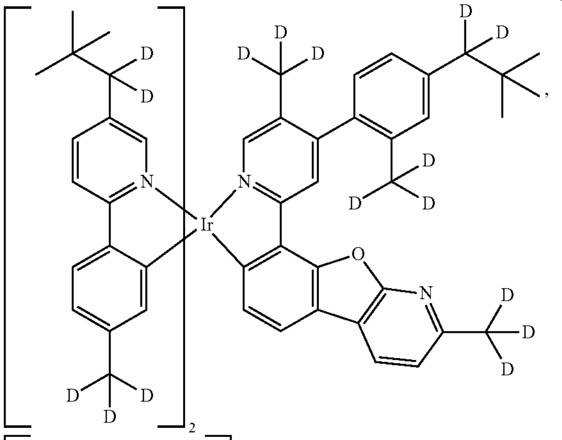
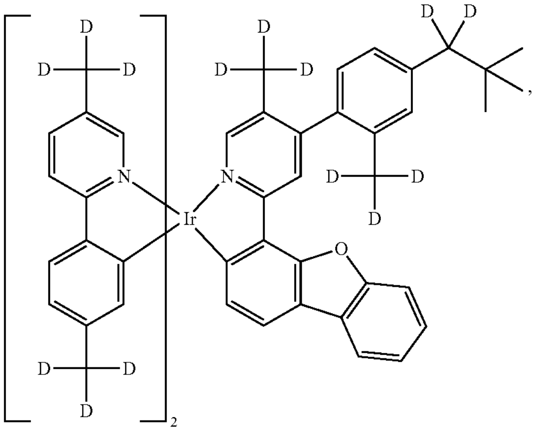
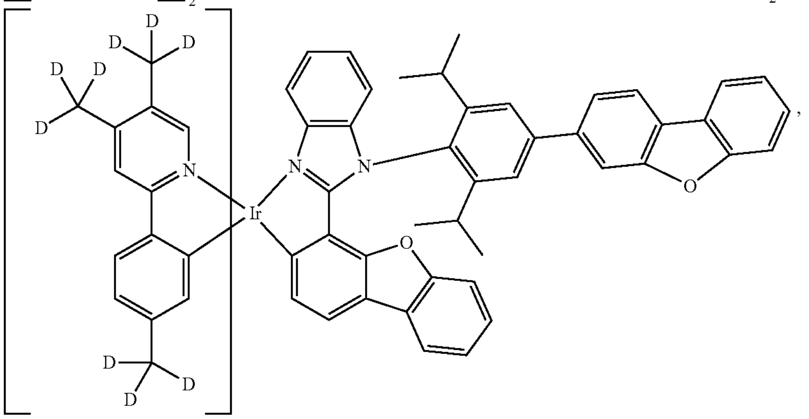
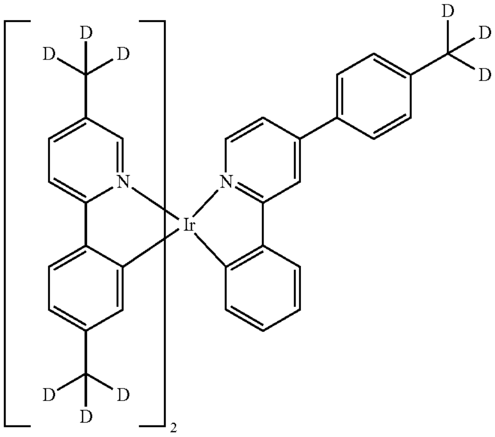
,
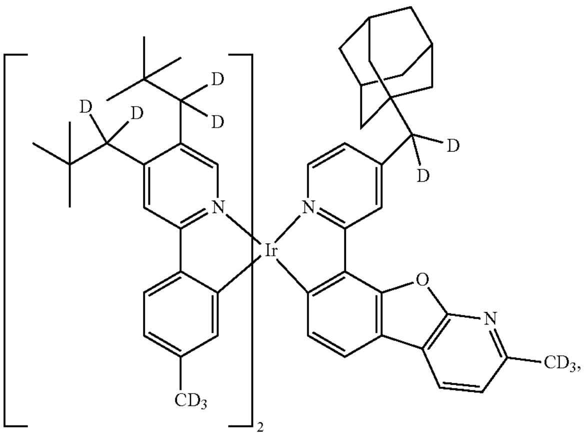
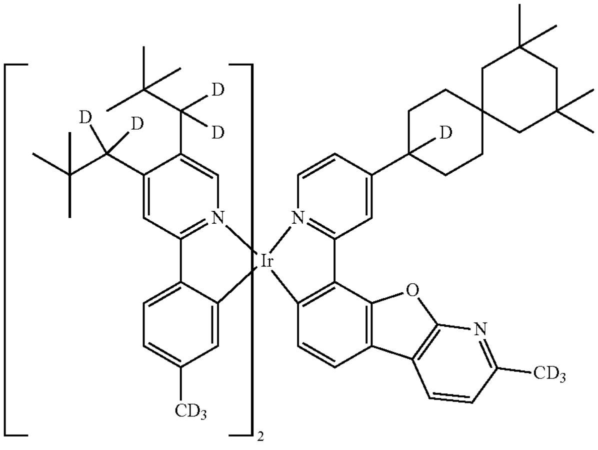
,
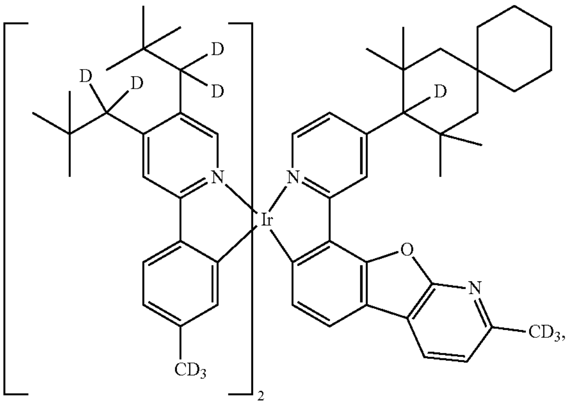

-continued
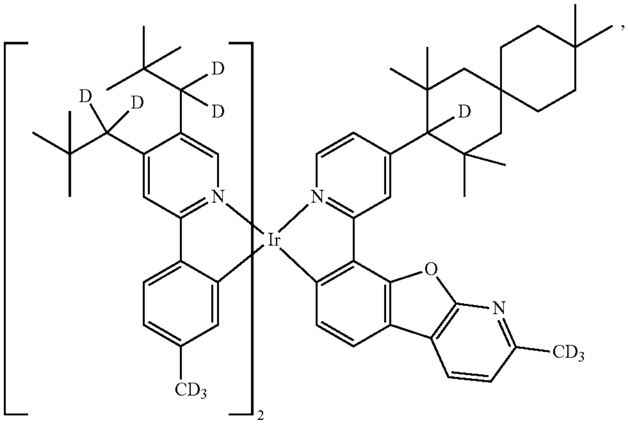
,
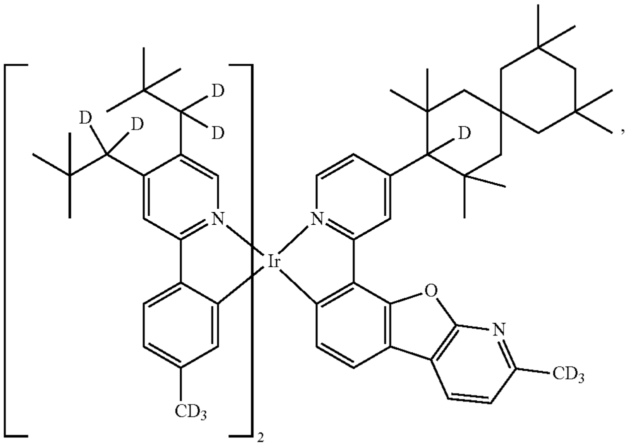
,
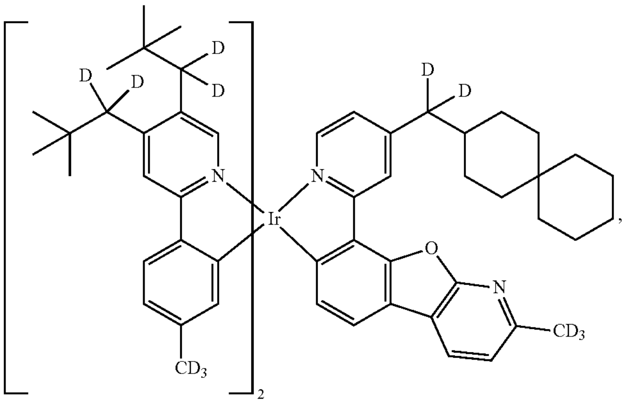
,
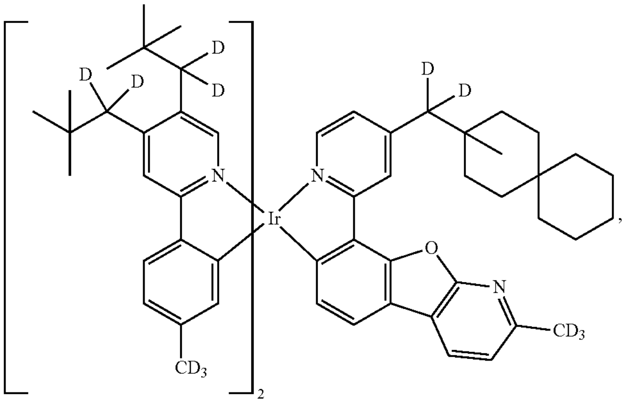
,

-continued
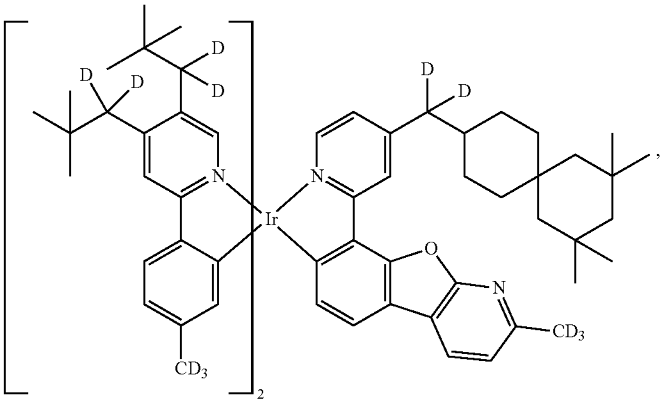
,
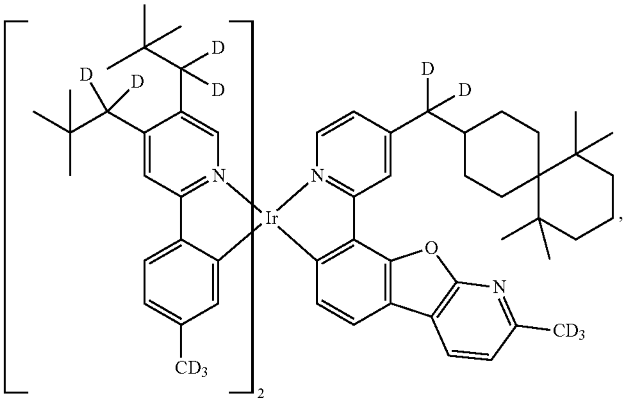
,
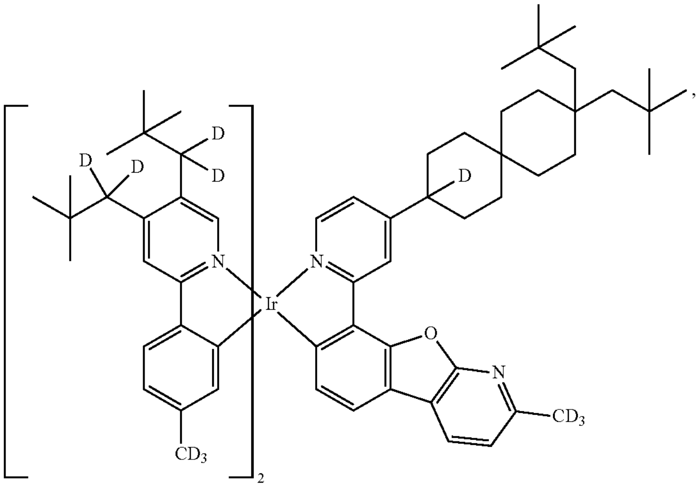
,
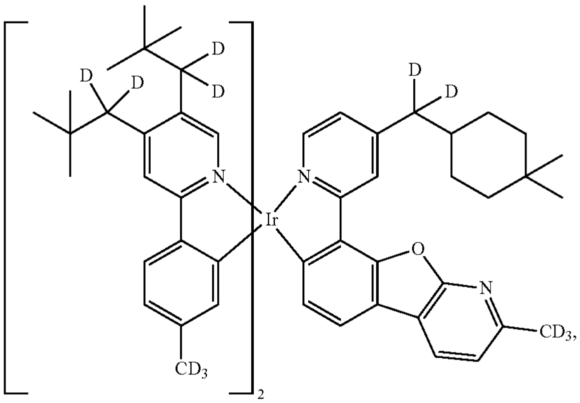
,
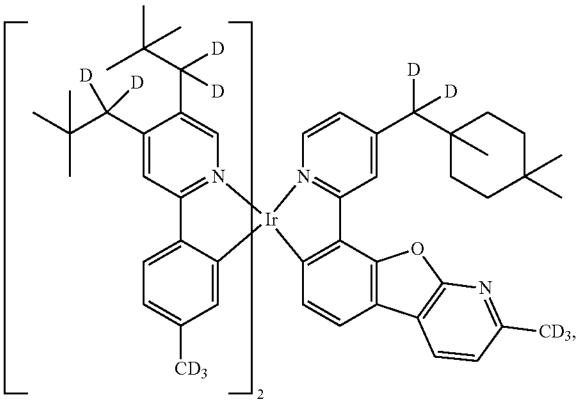
, -continued
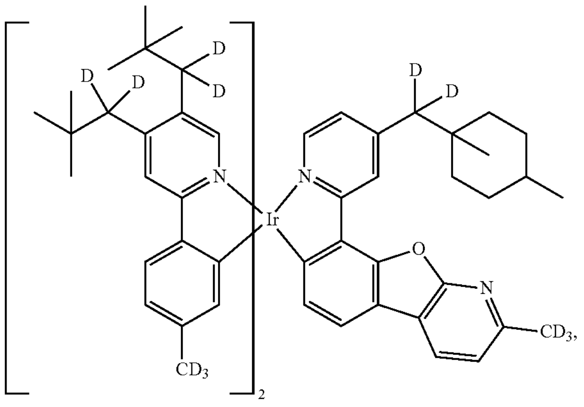
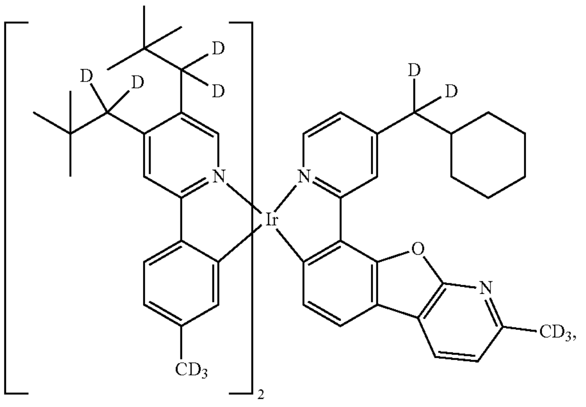
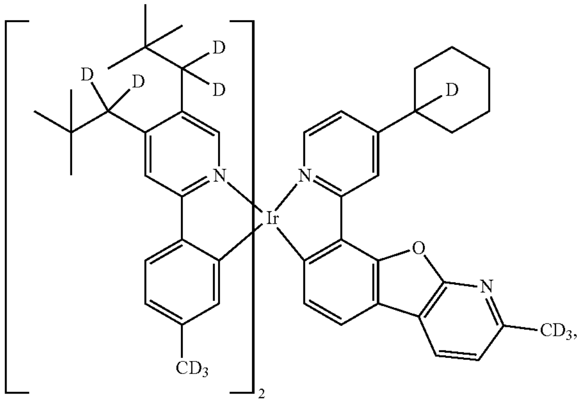
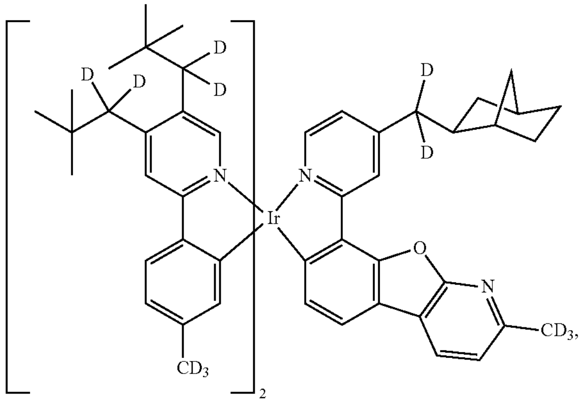
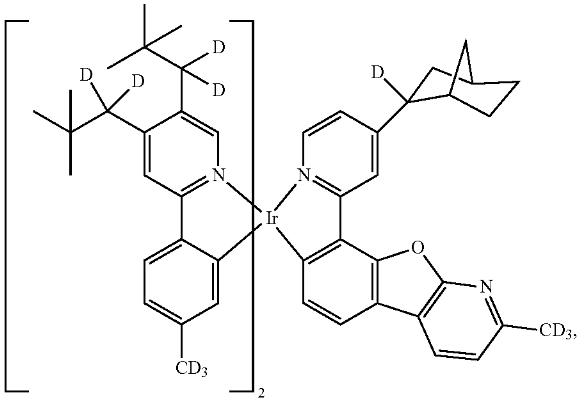
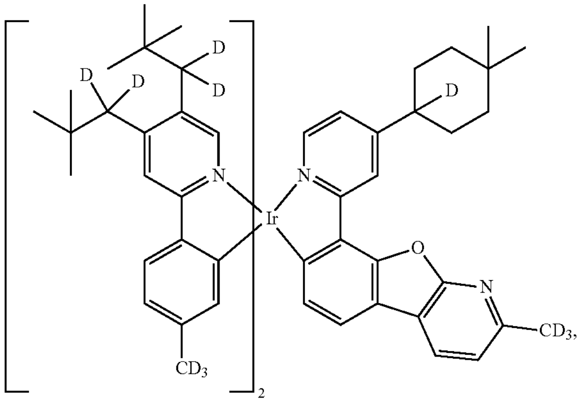
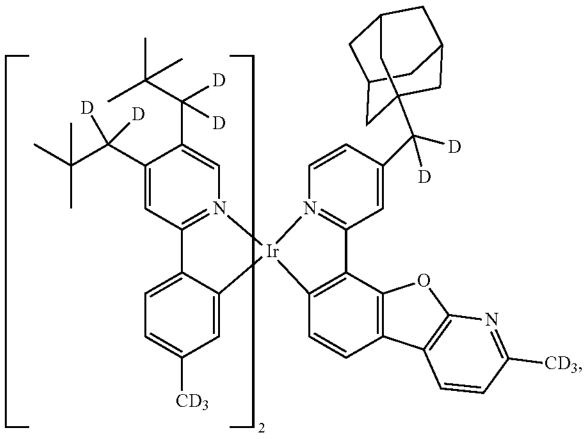
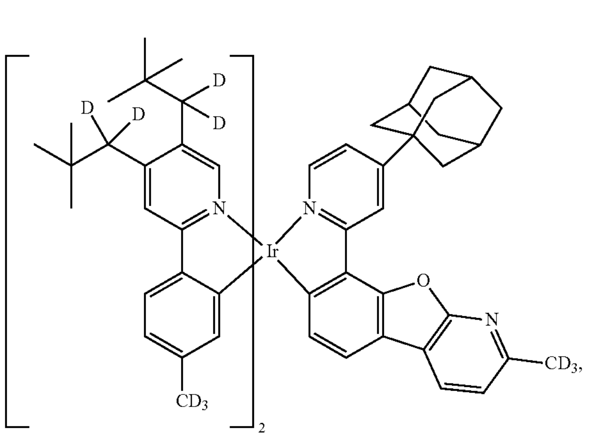

-continued
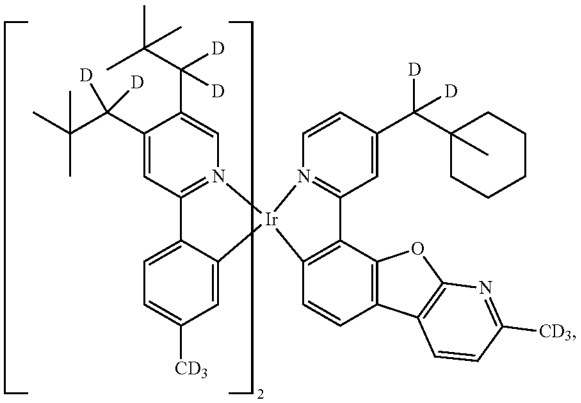
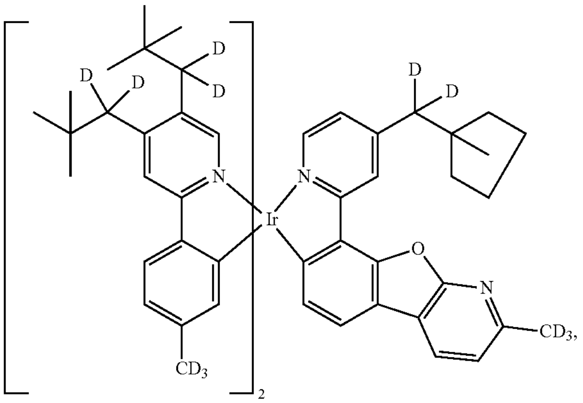
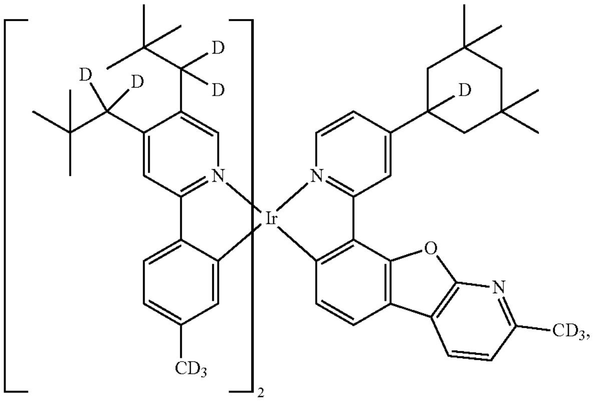
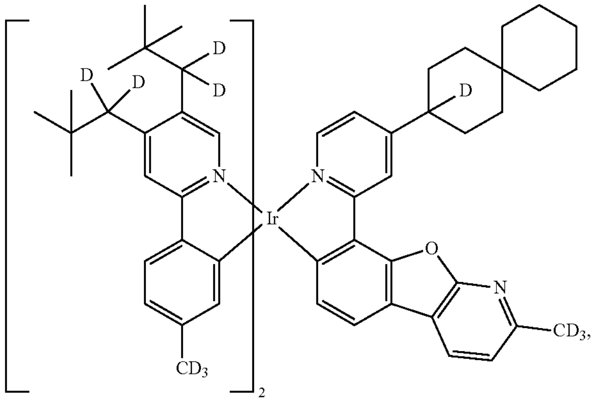
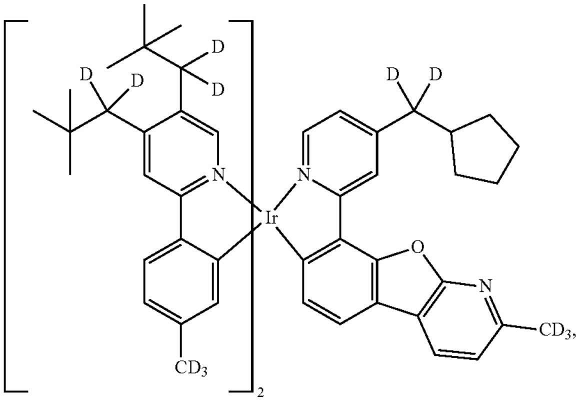
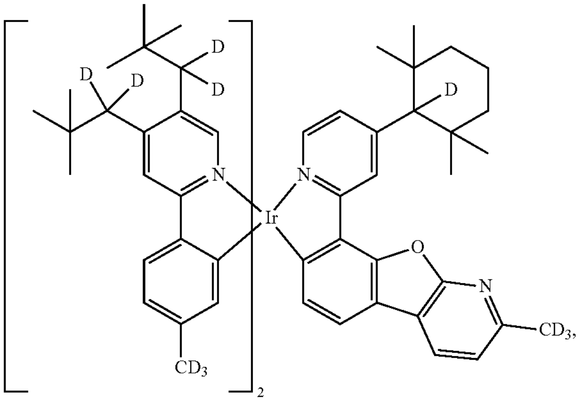
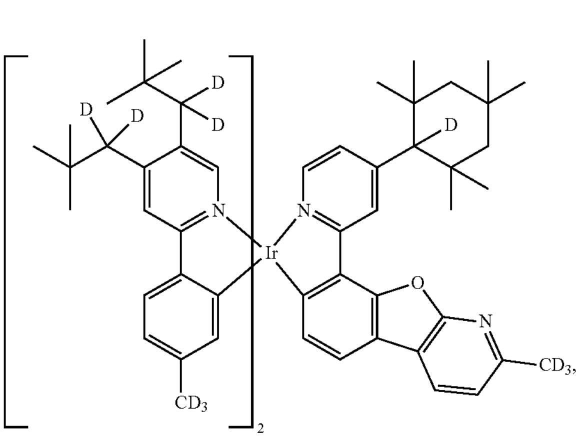
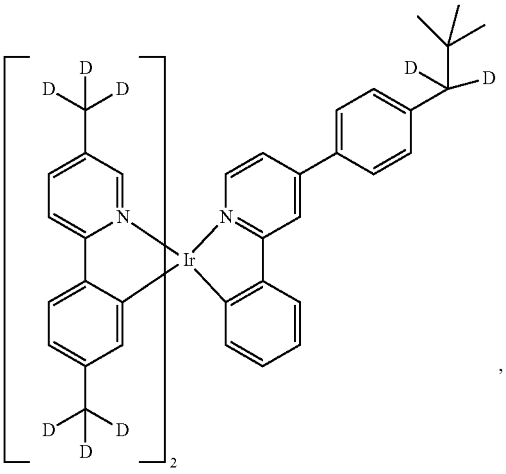
, -continued
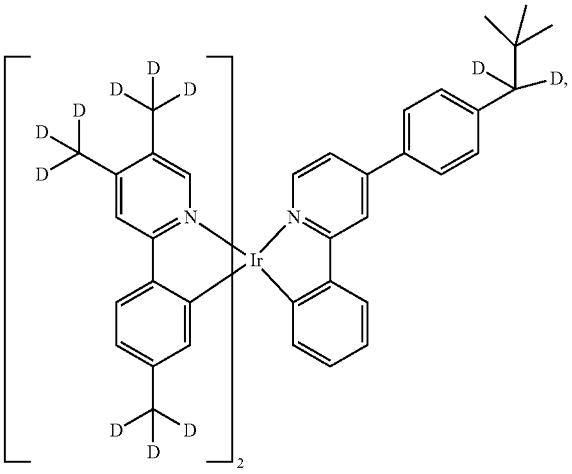
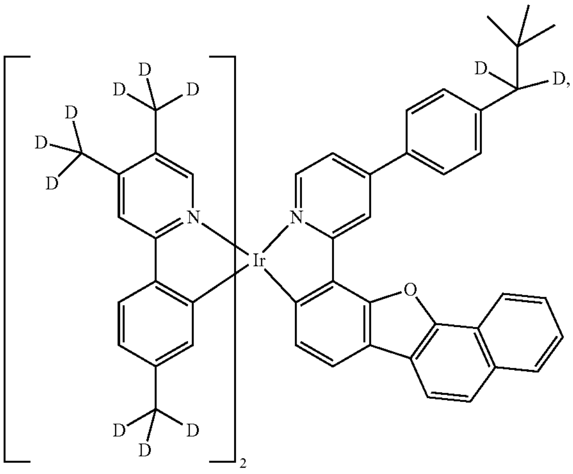
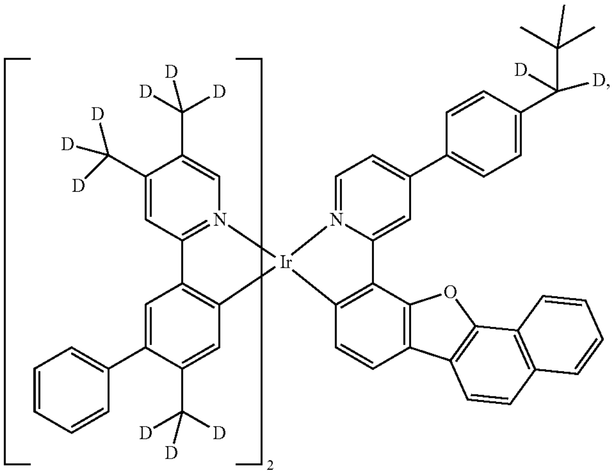
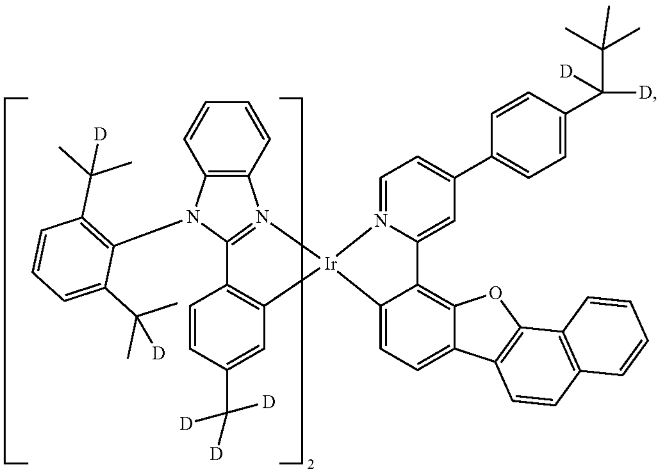

-continued
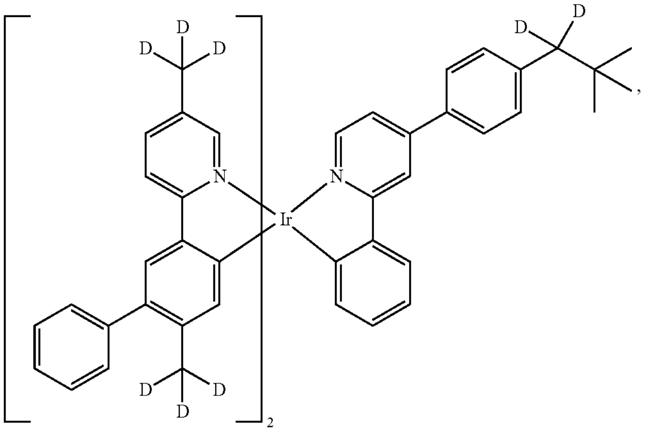
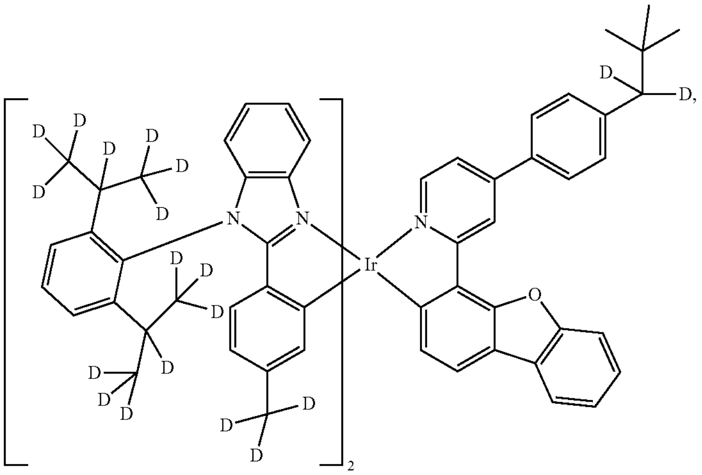
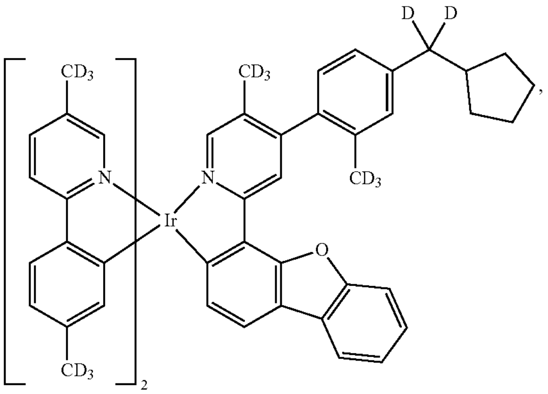
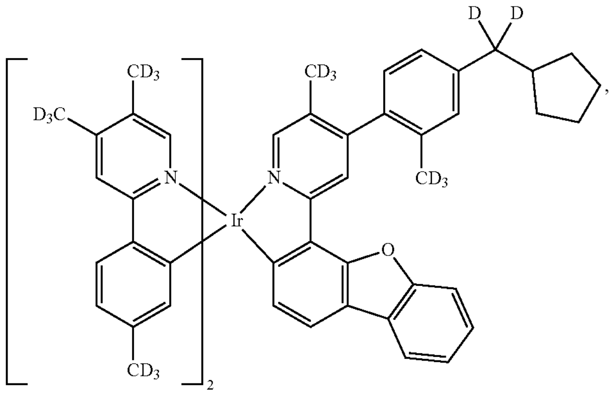
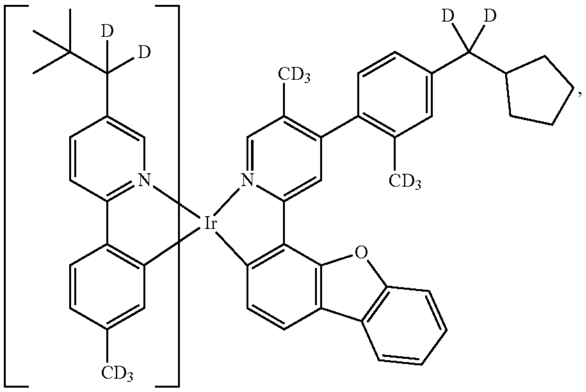
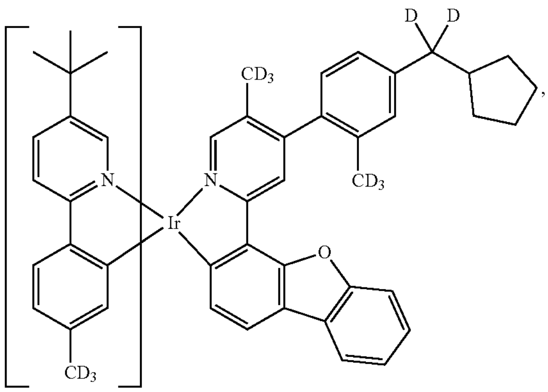

-continued
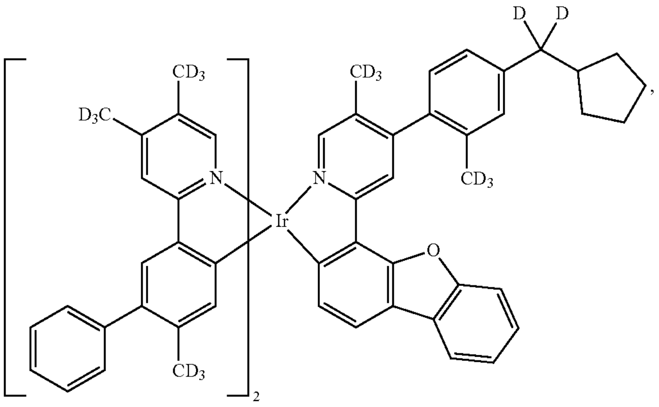
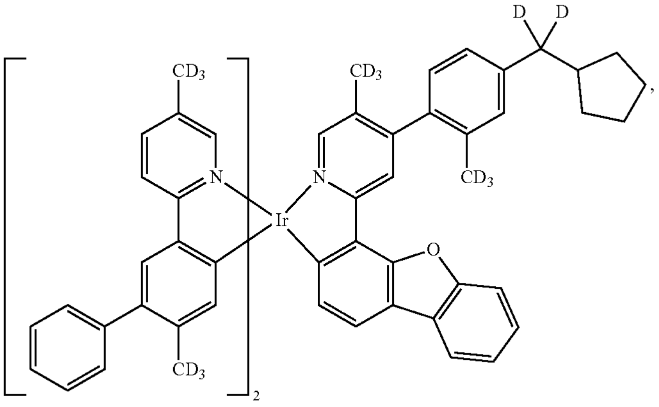
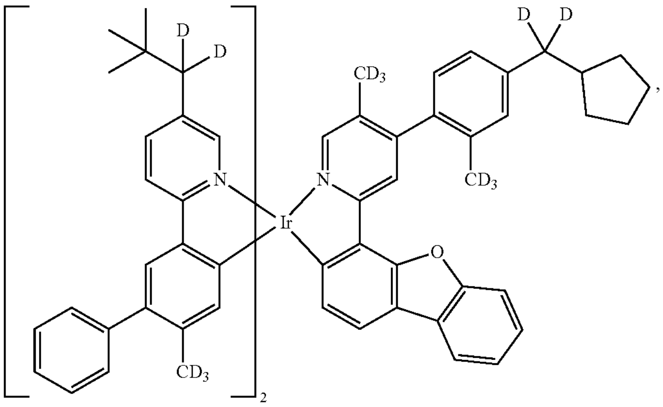
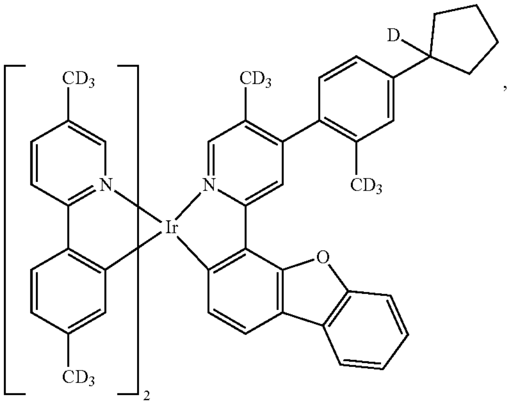
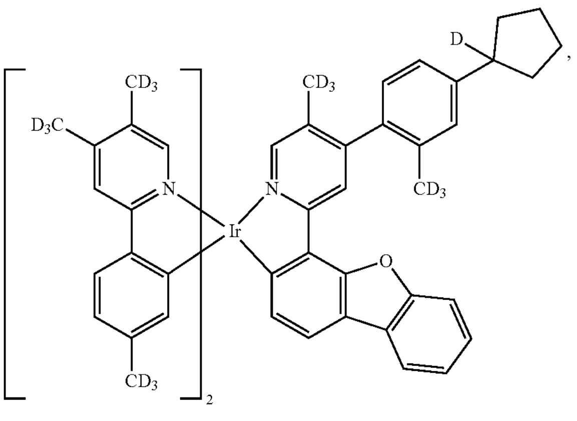
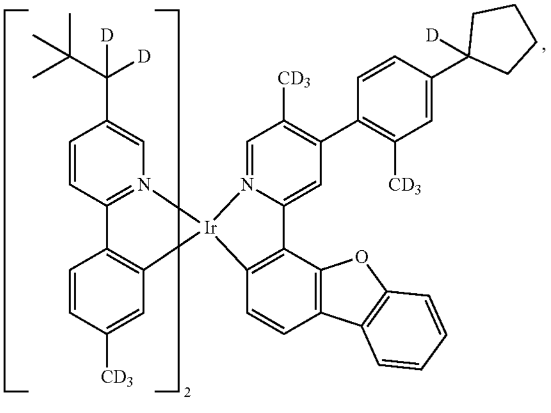

-continued
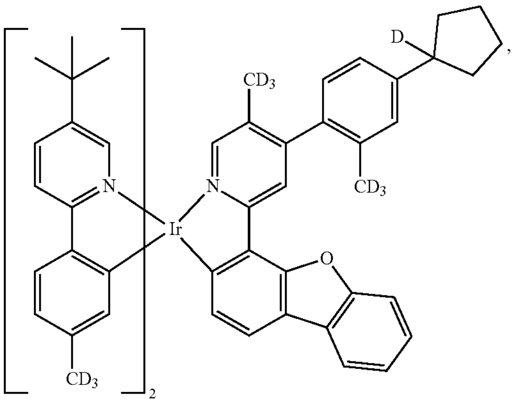
,
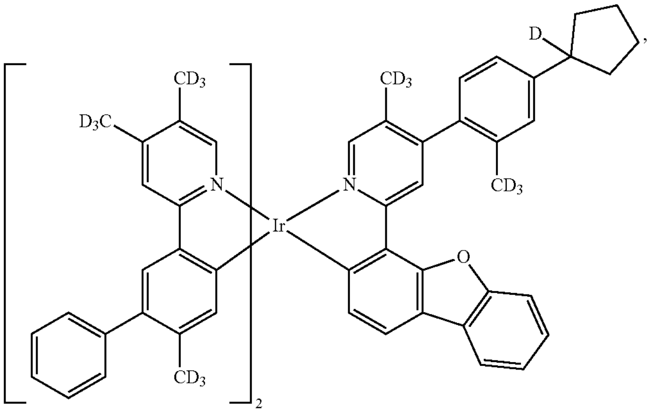
,
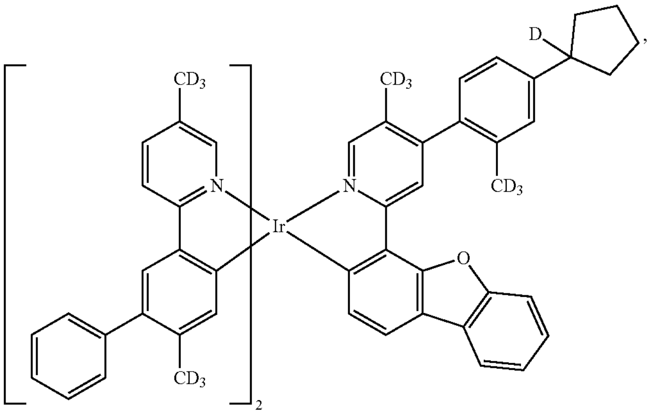
,

-continued
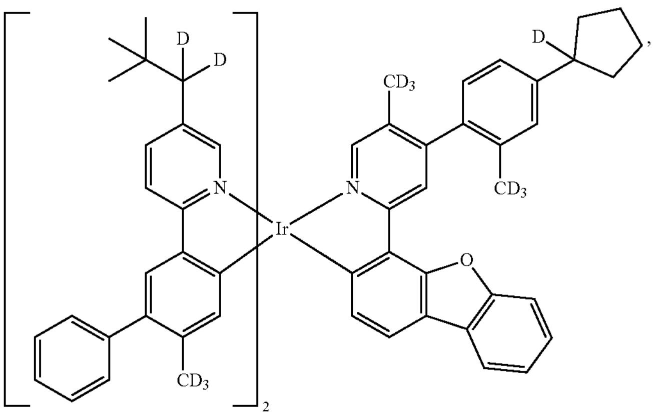
,
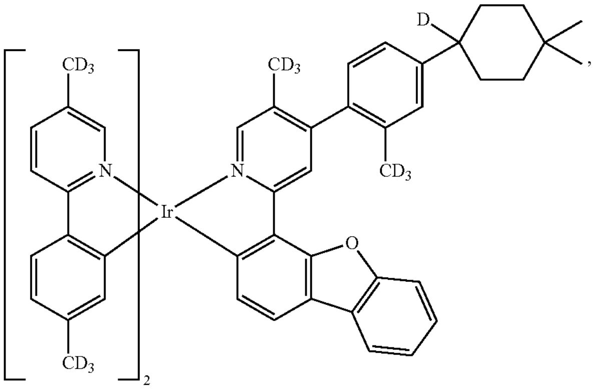
,
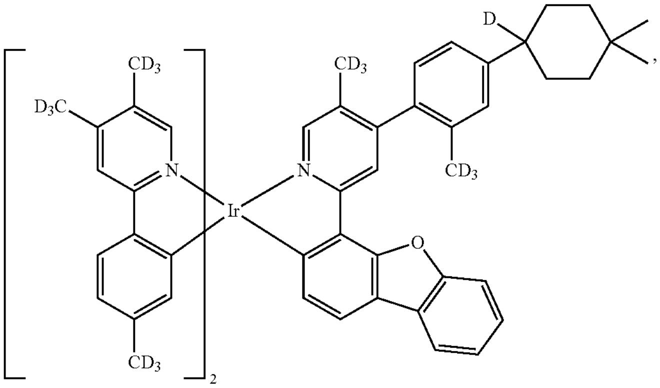
,
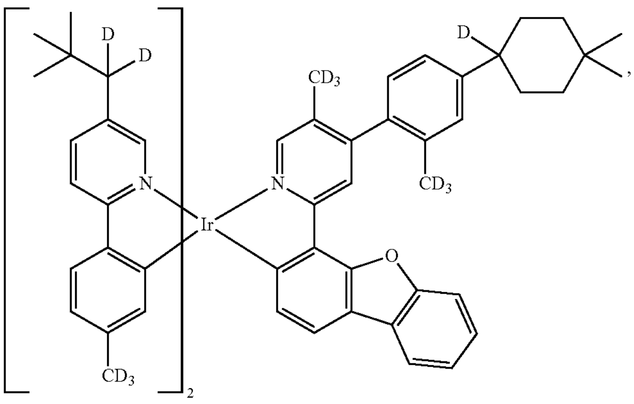
,

-continued
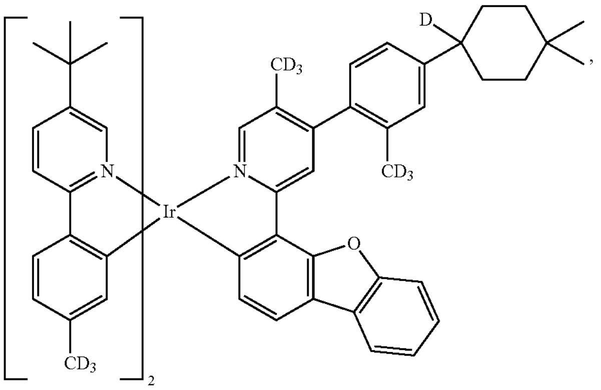
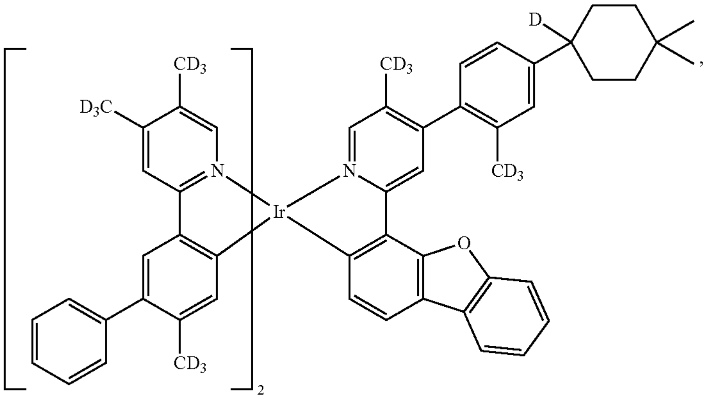
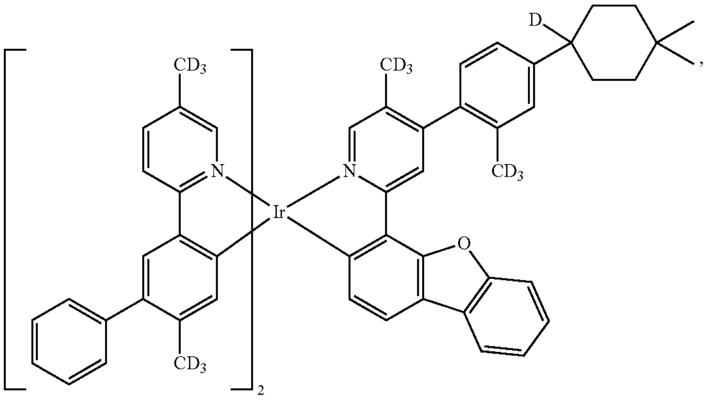
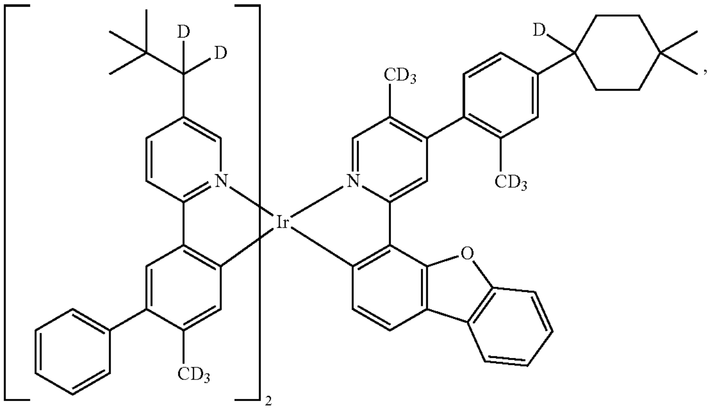

-continued
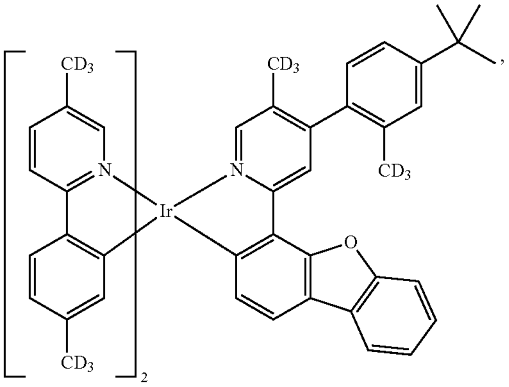
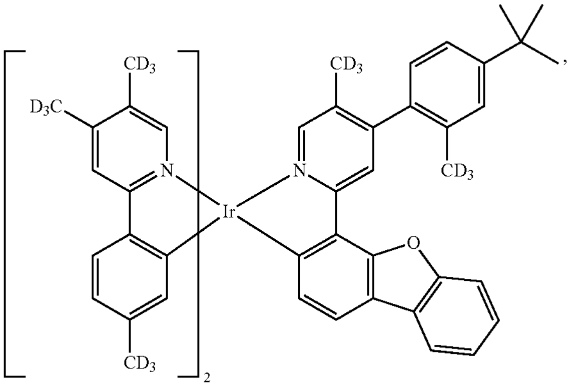
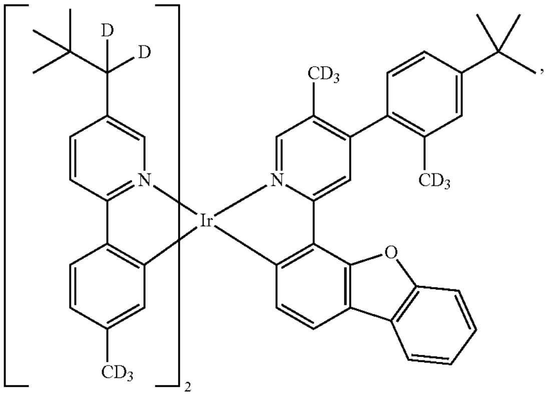
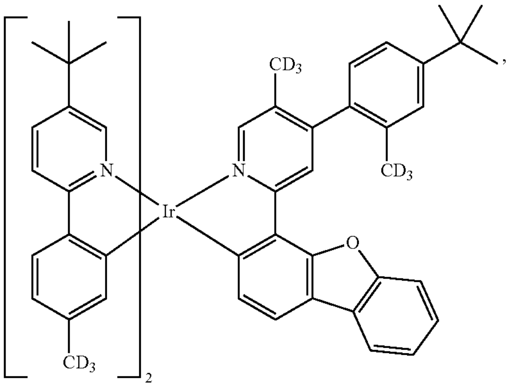

-continued
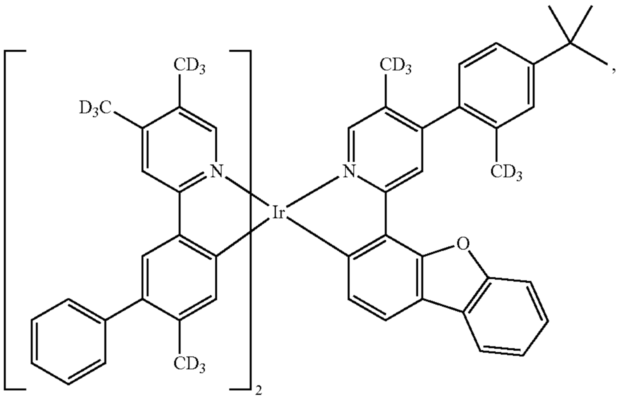
,
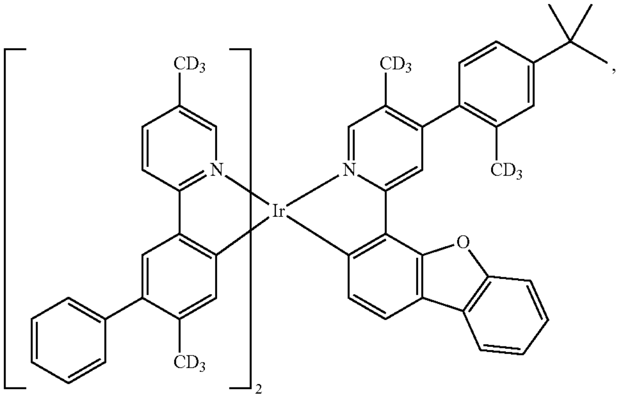
,
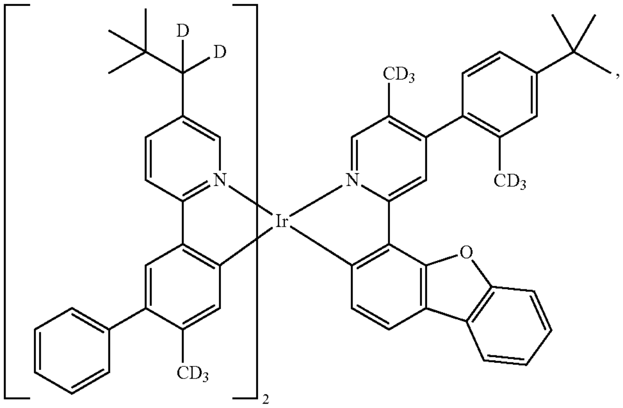
,
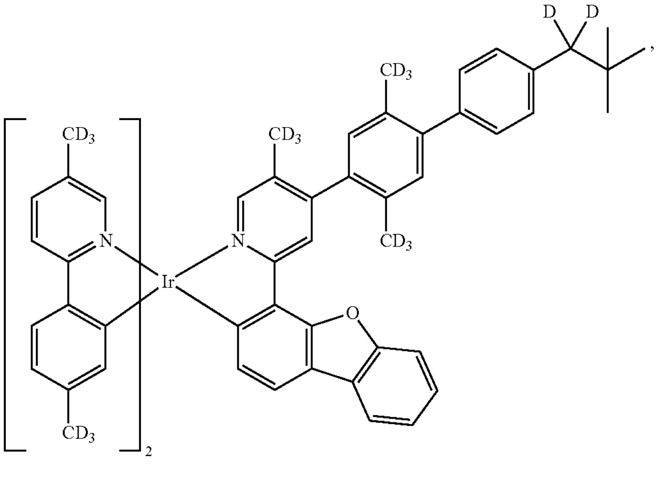
,

-continued
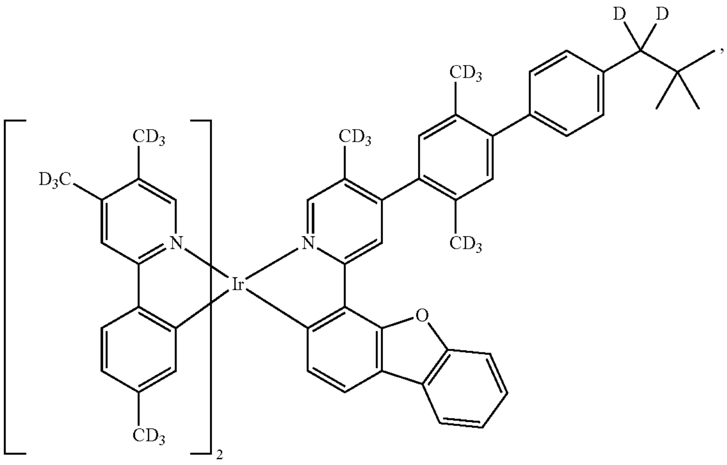
,
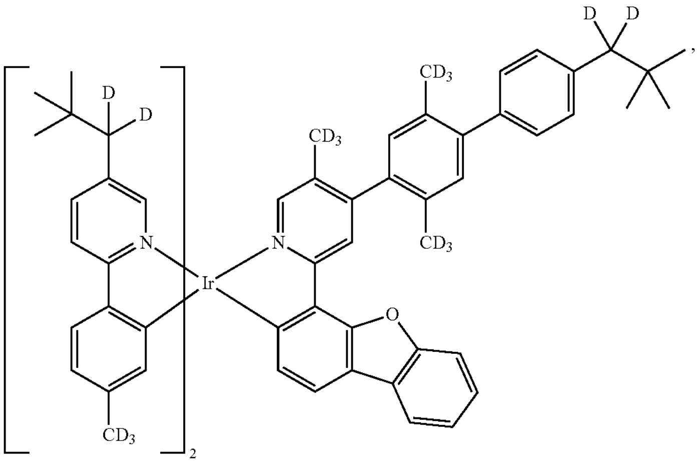
,
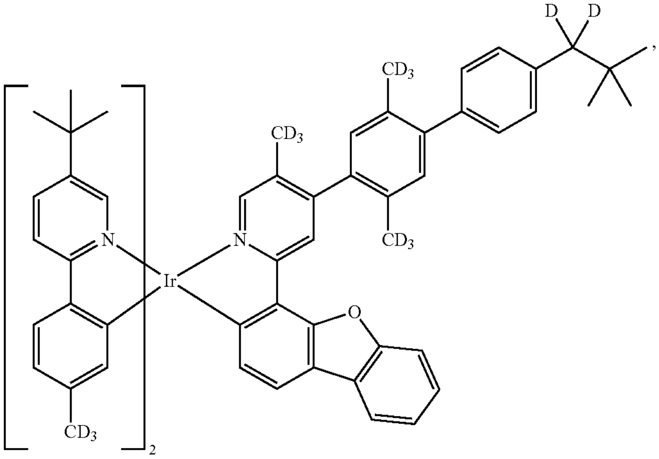
,

-continued
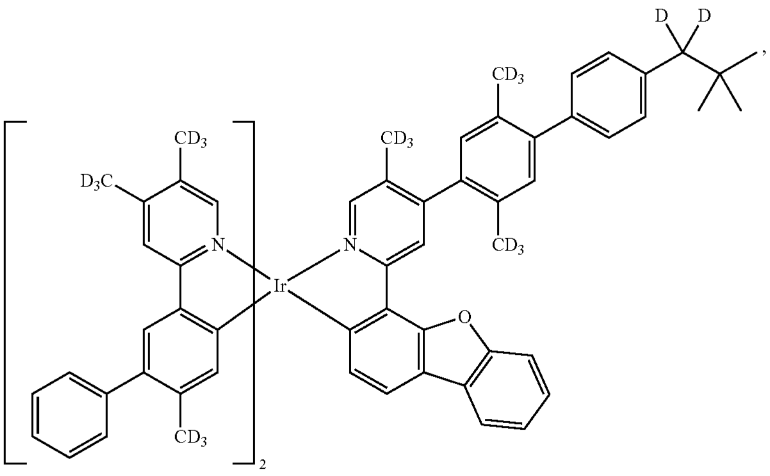
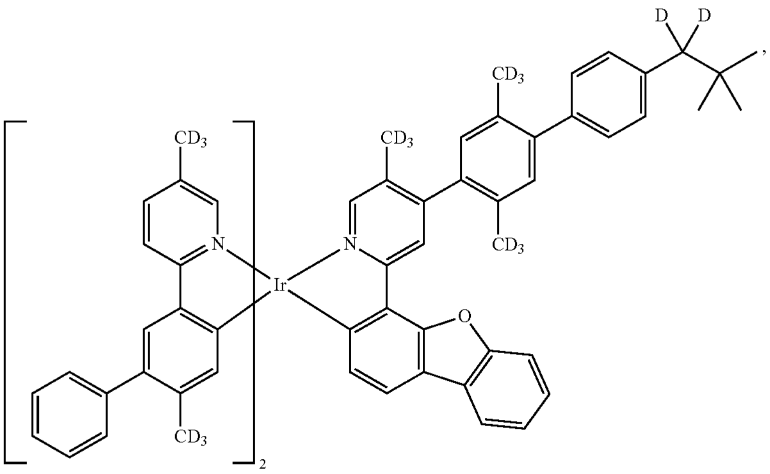
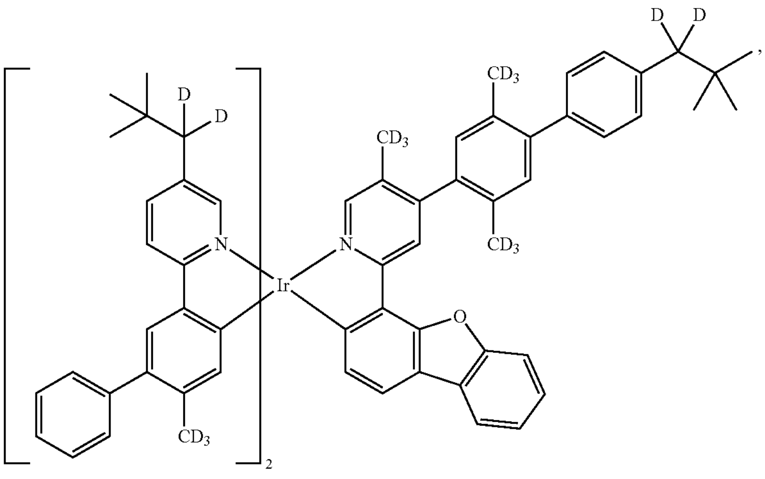

-continued
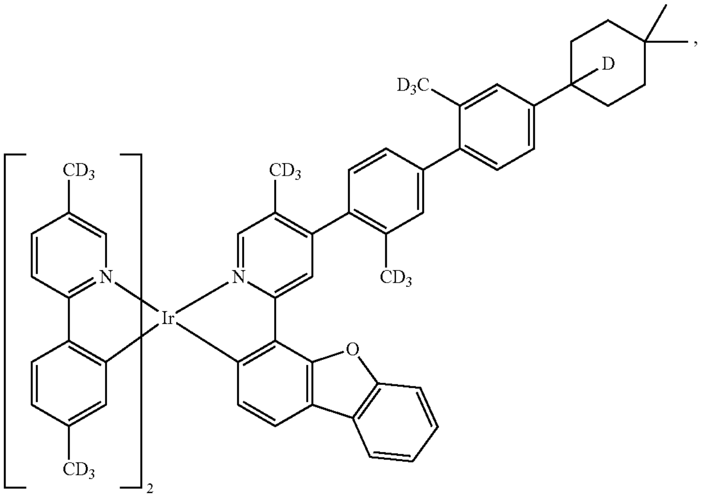
,
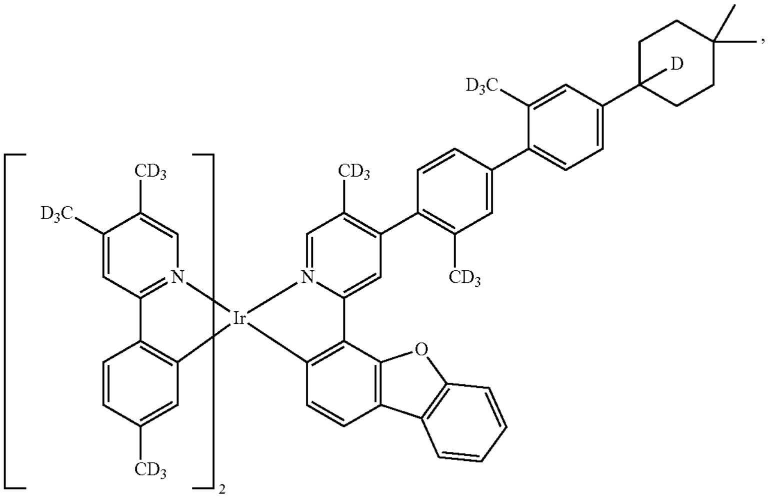
,
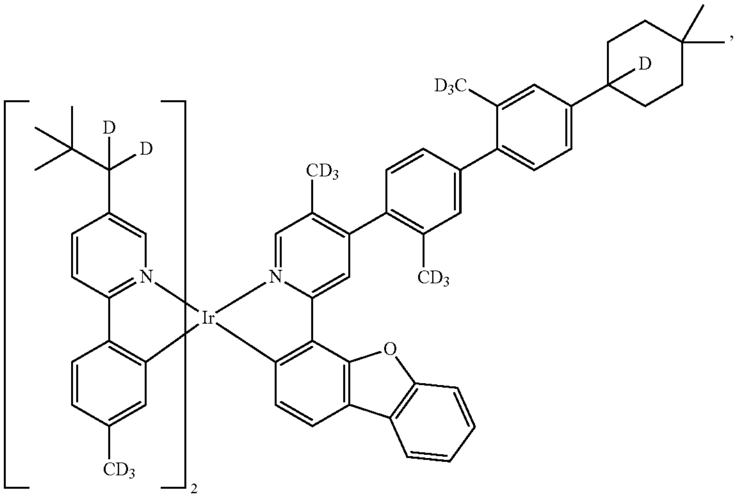
,

-continued
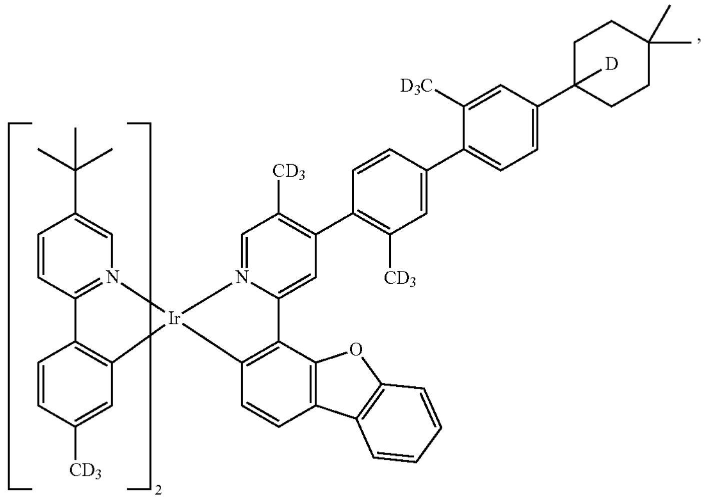
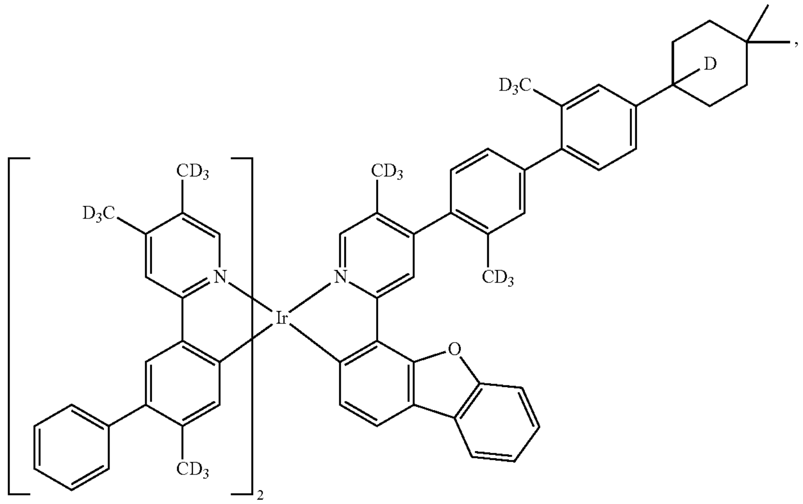
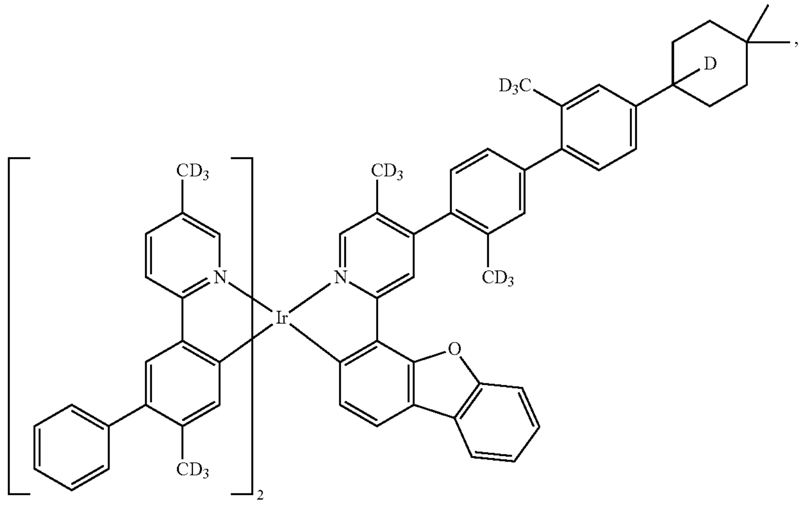

-continued
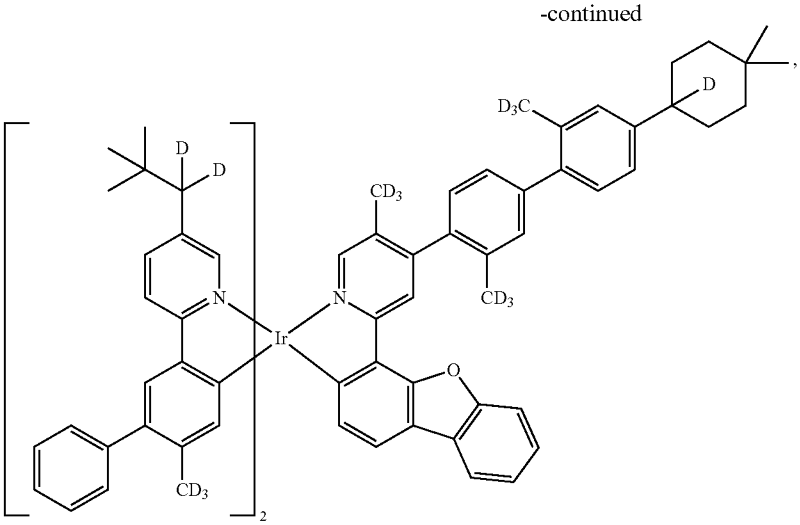
,
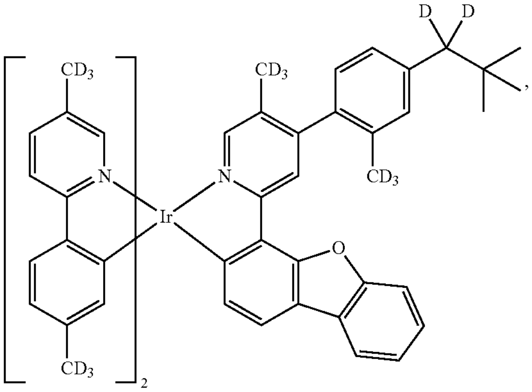
,
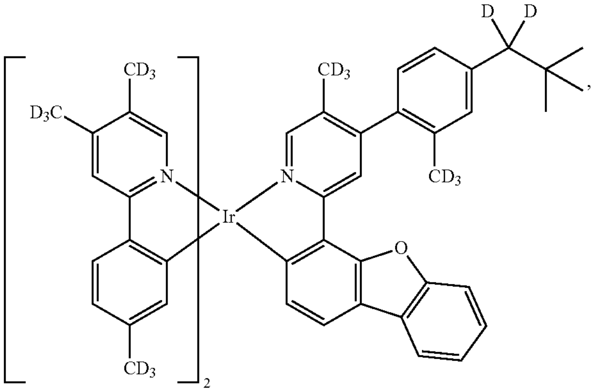
,
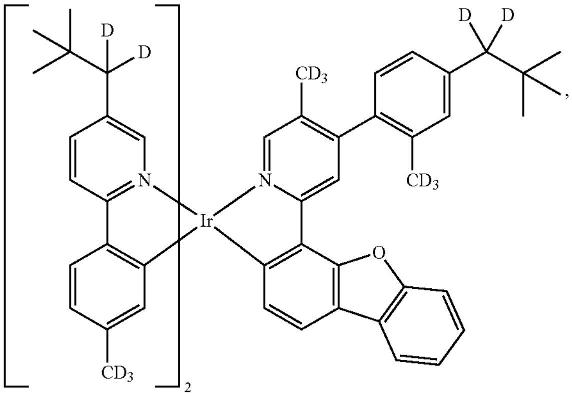
,
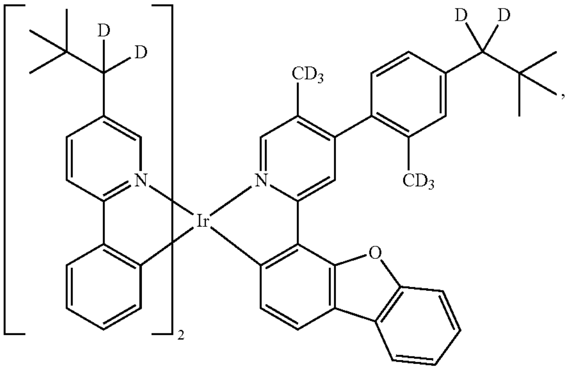
,
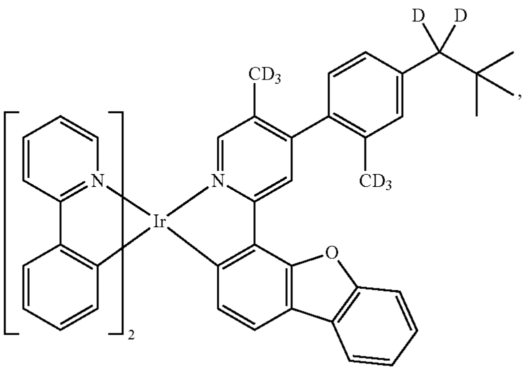
,
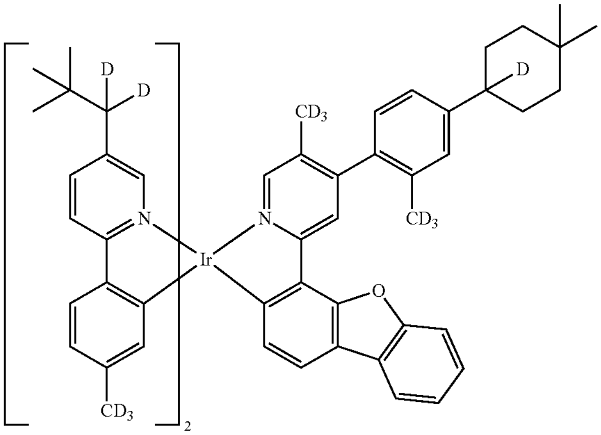
, -continued
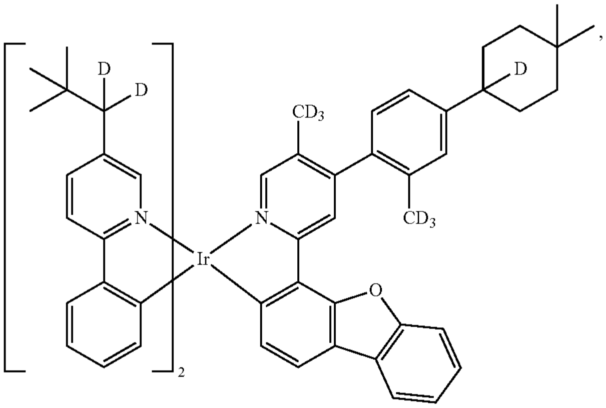
,
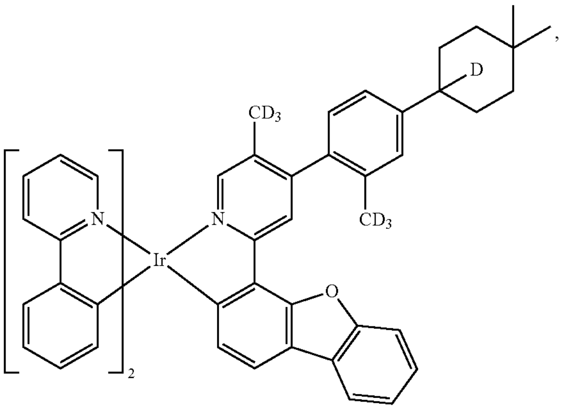
,
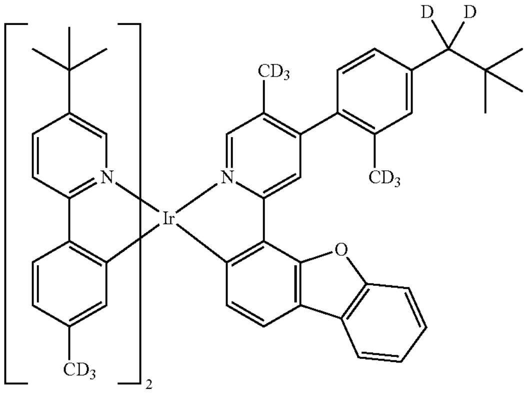
,
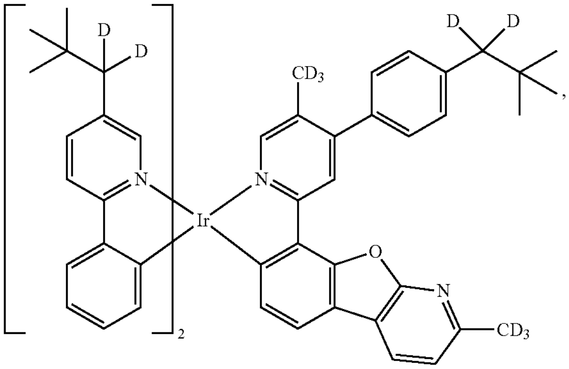
,
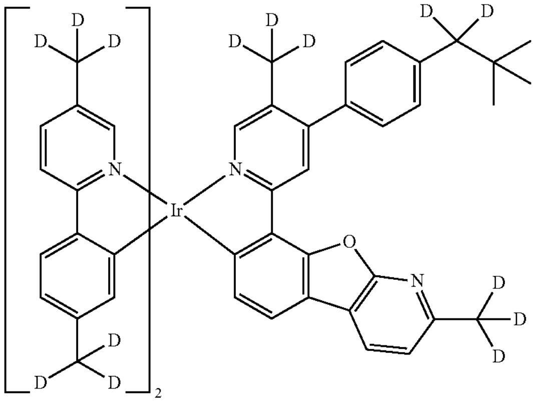
,
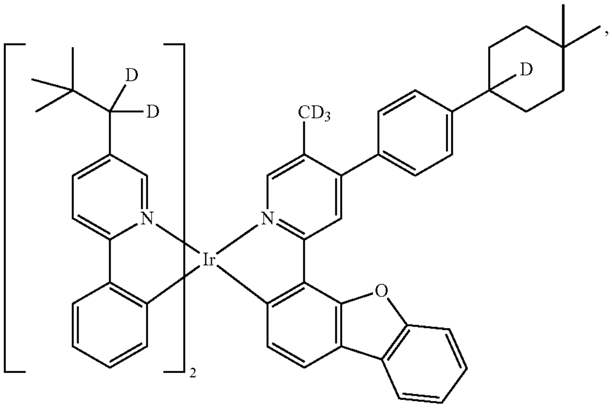
, -continued
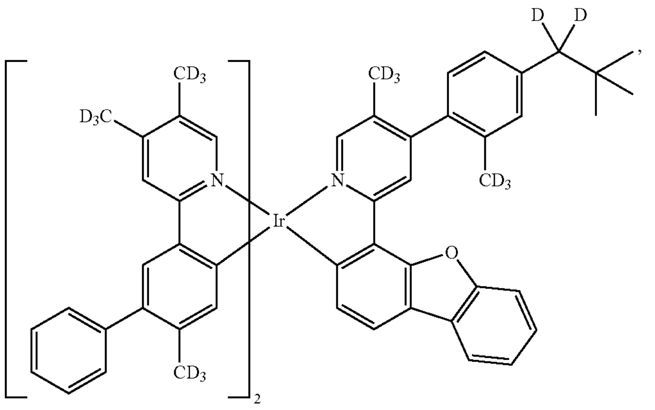
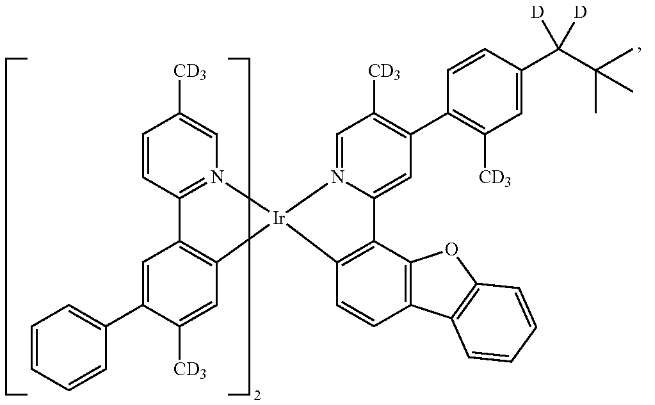
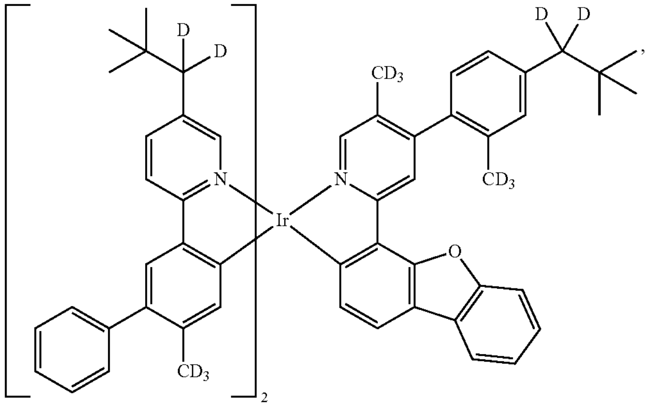
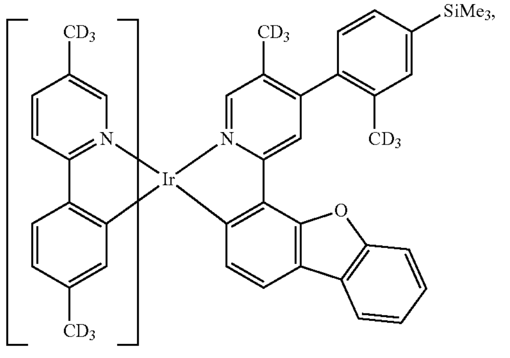
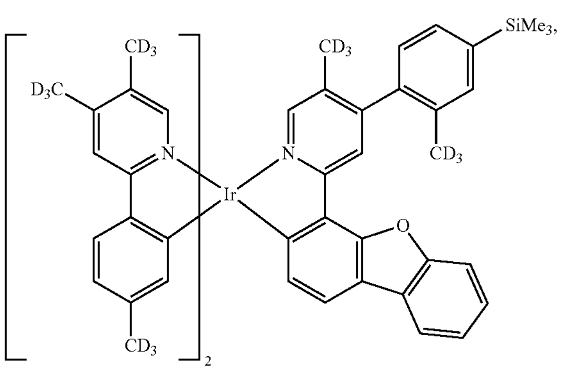
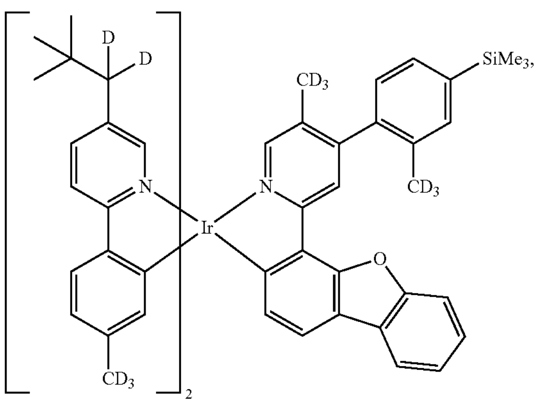

-continued
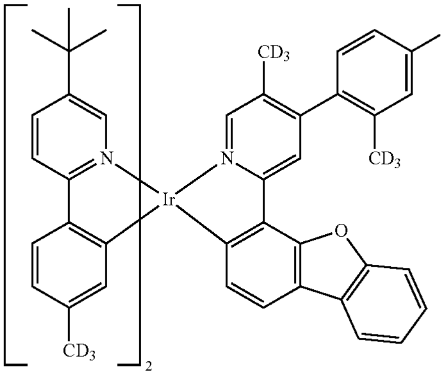
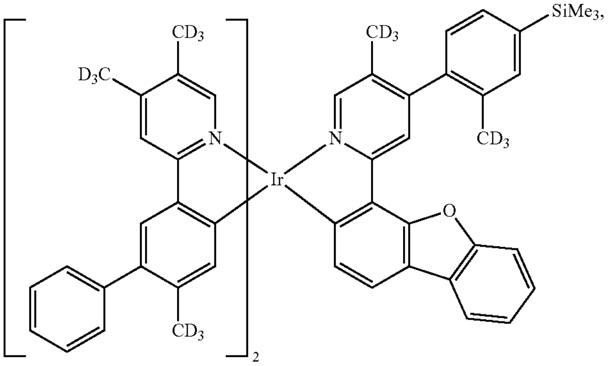
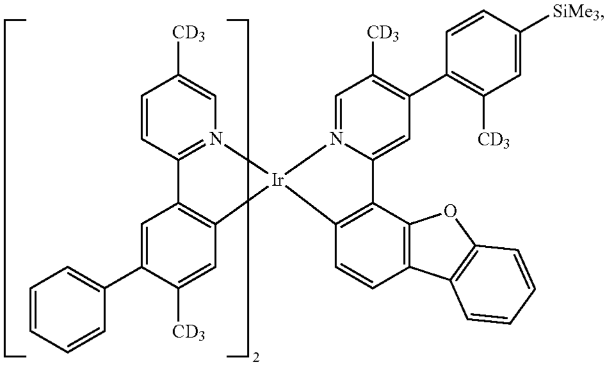
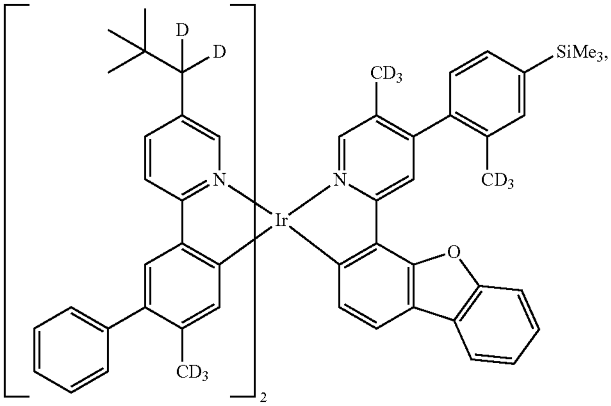
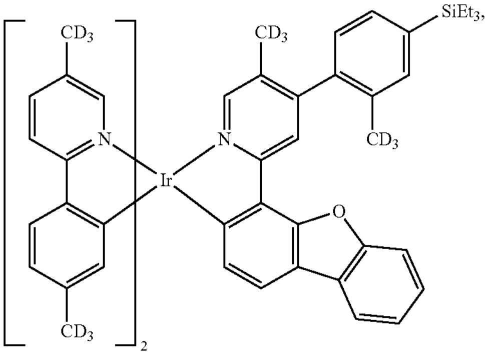
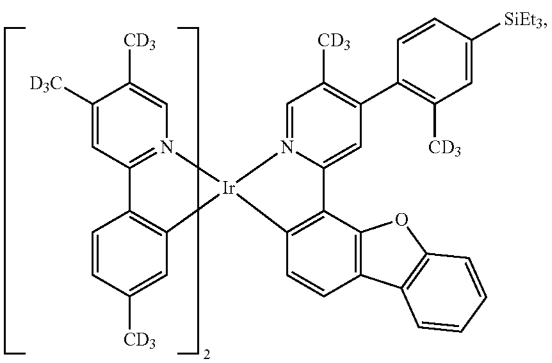
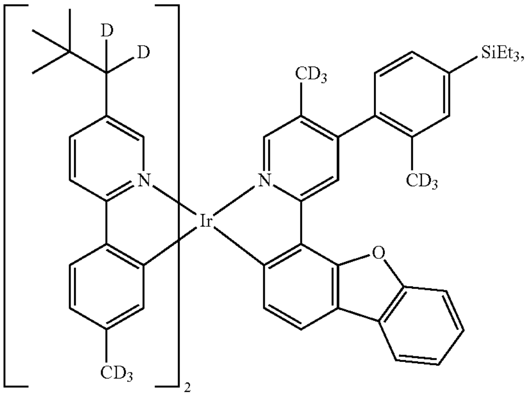

-continued
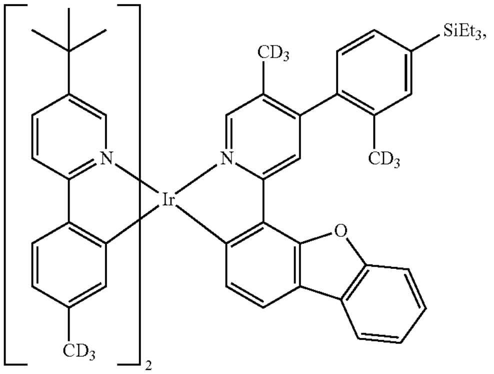
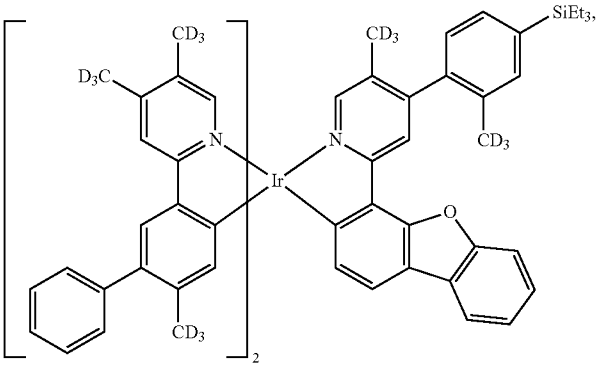
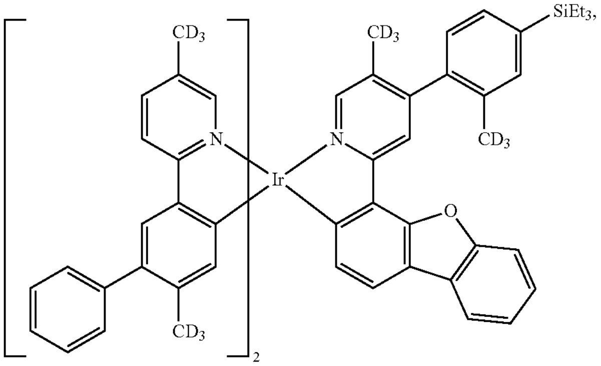
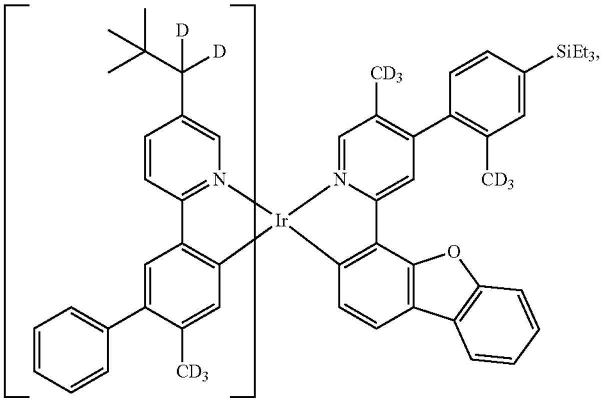
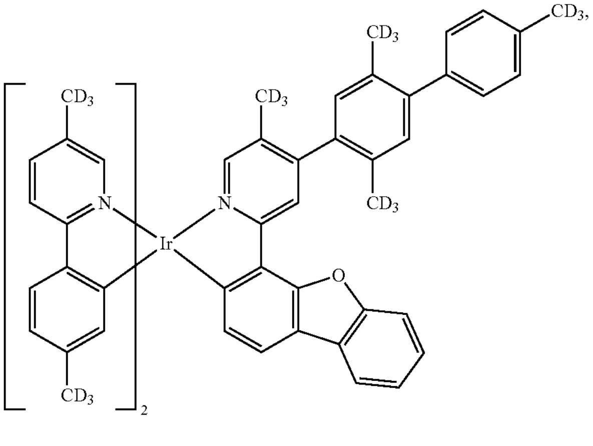

-continued
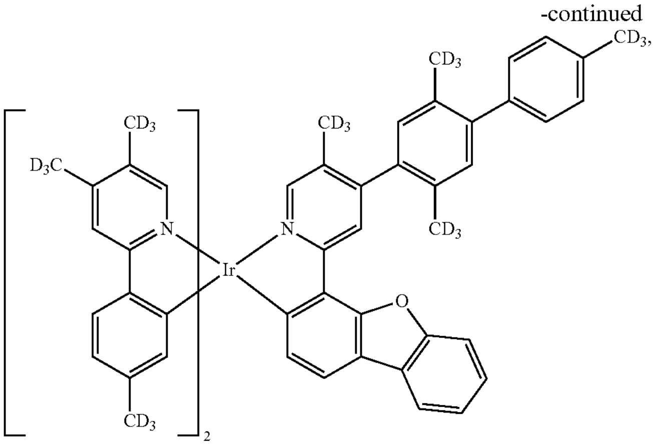
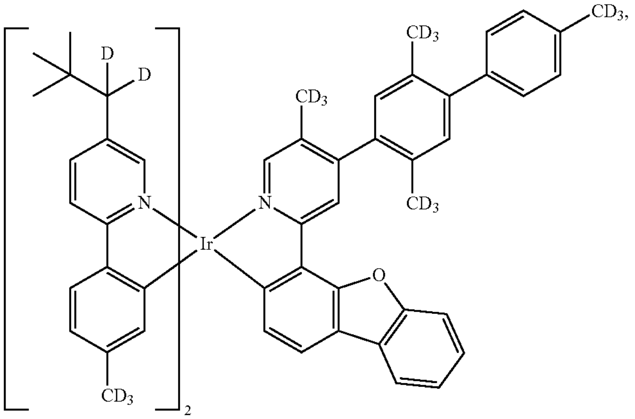
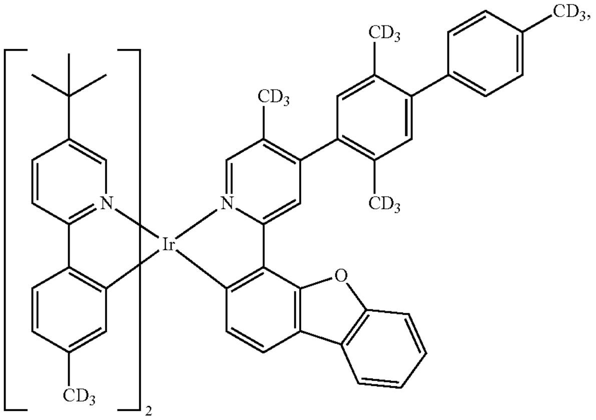
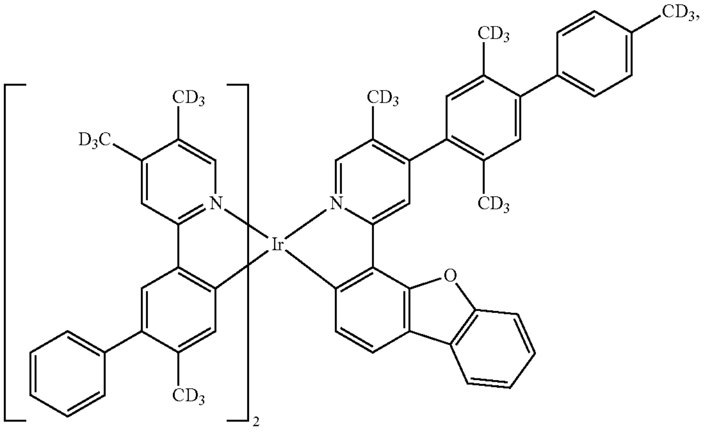

-continued
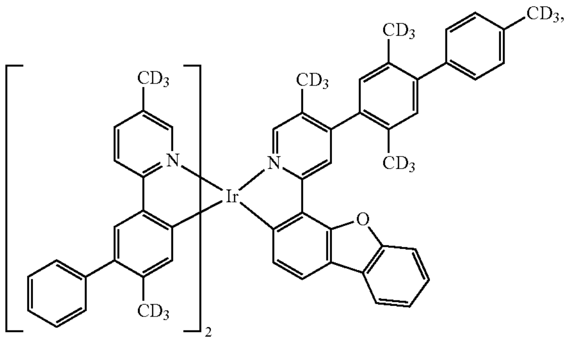
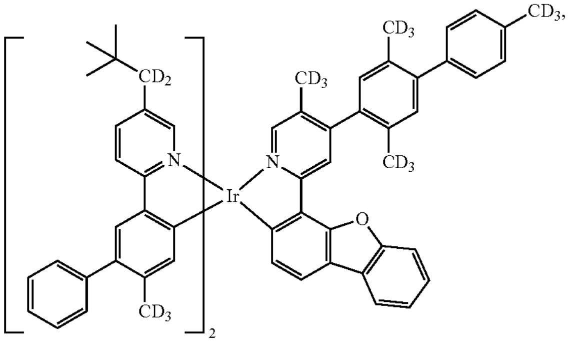
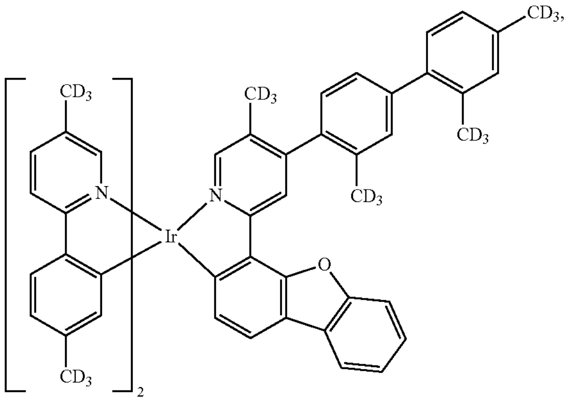
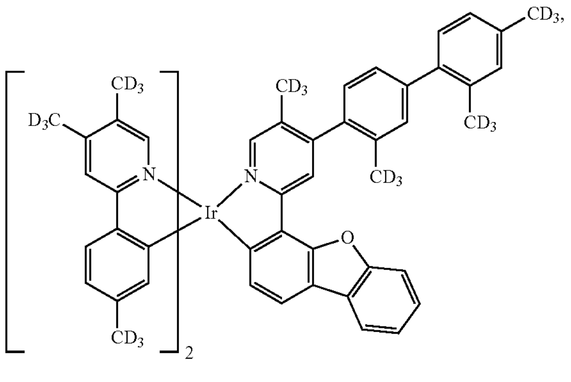
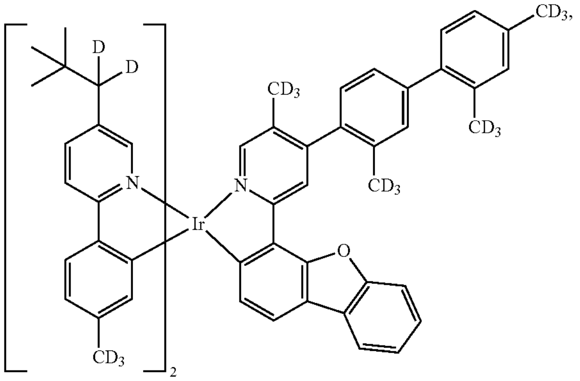
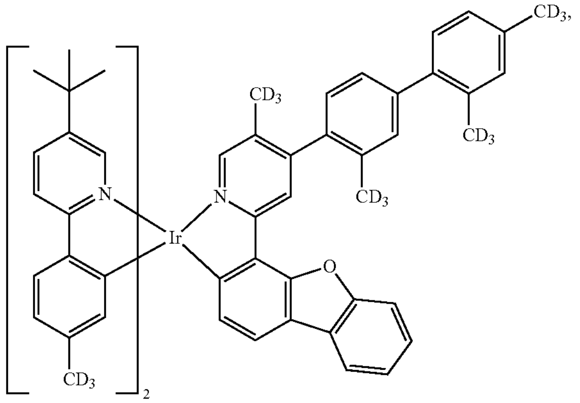
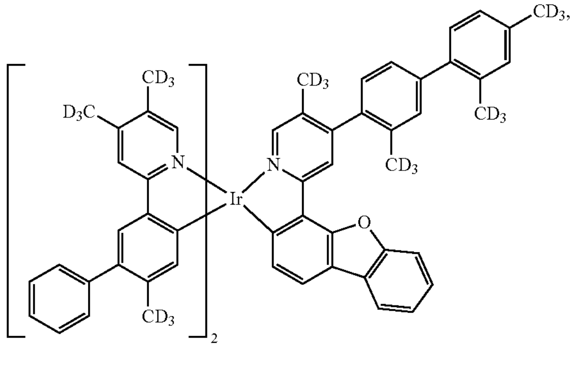
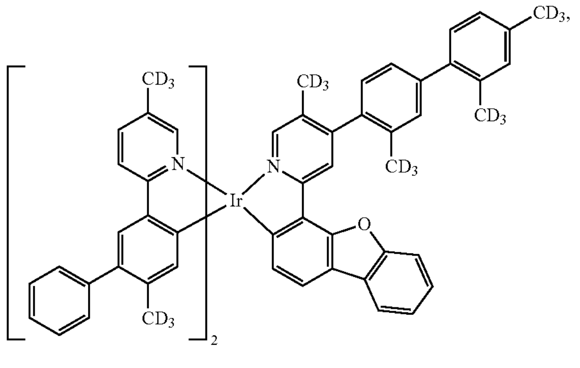

-continued
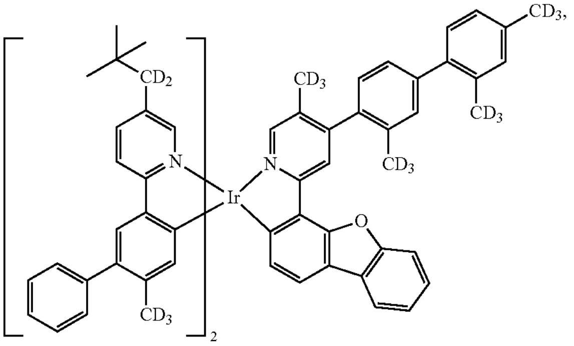
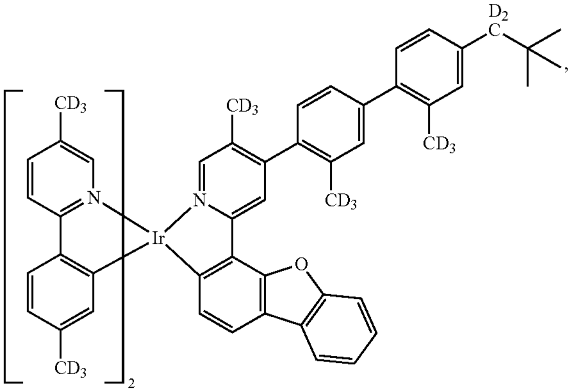
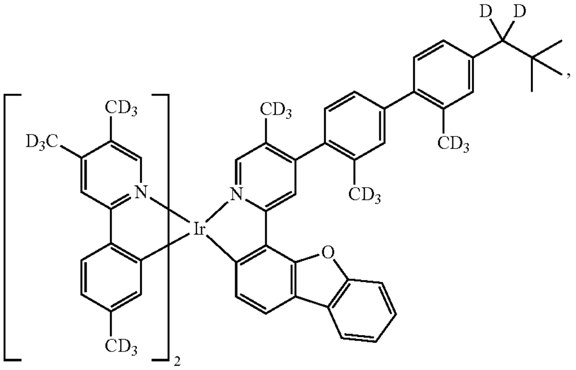
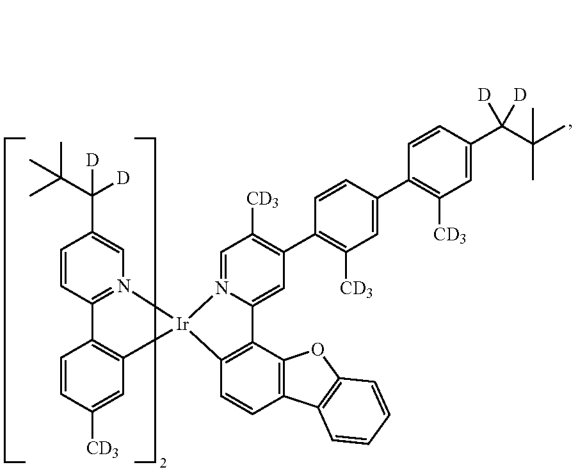
-continued
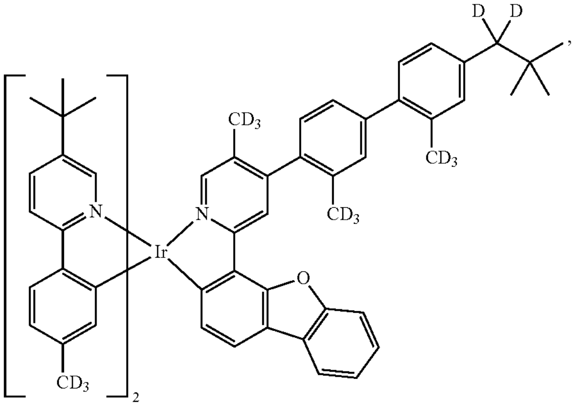
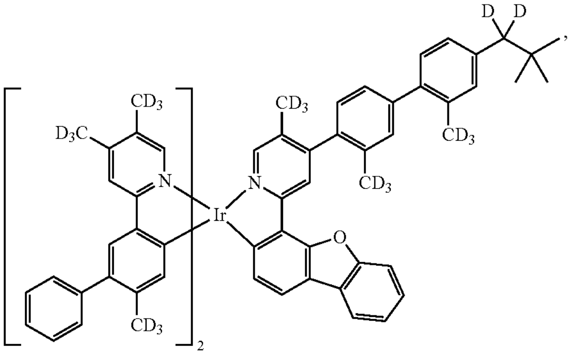
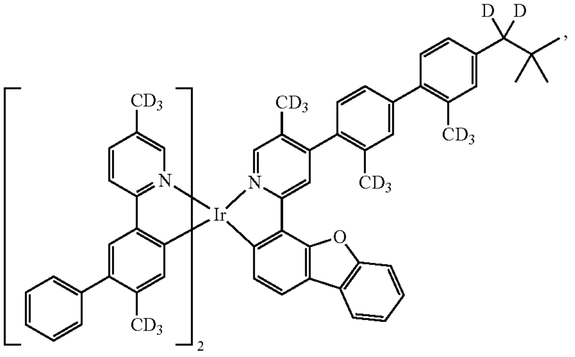
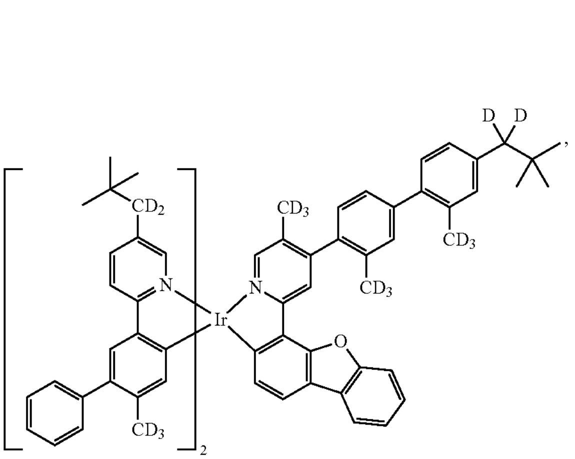

-continued
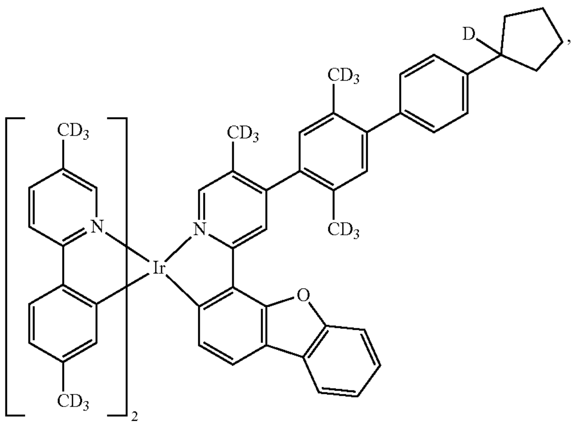
,
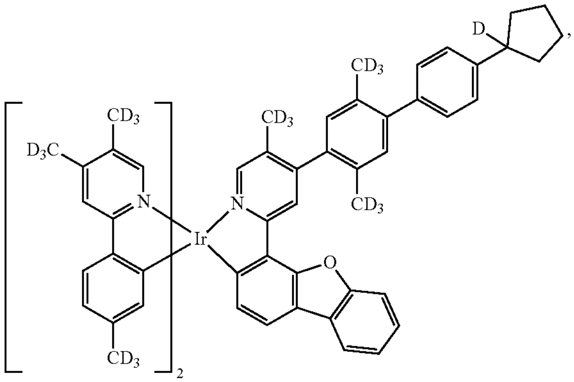
,
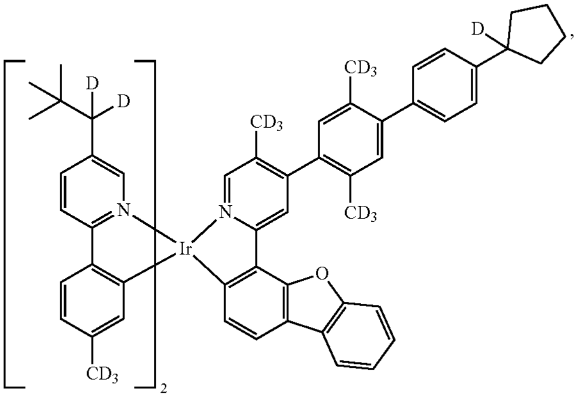
,
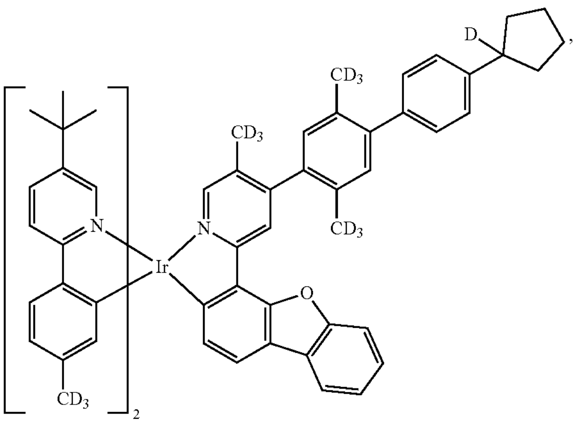
,
-continued
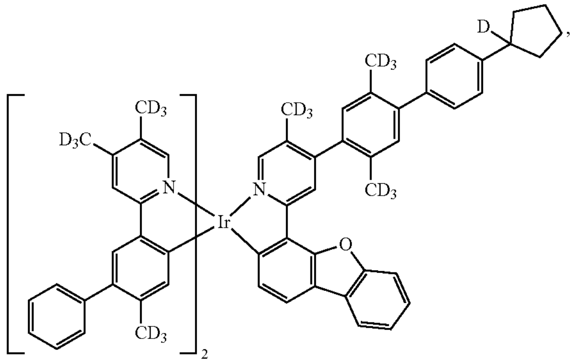
,
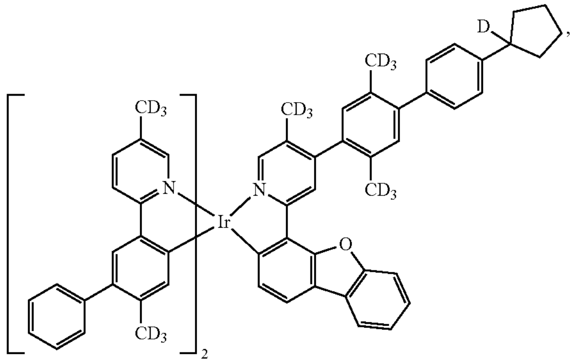
,
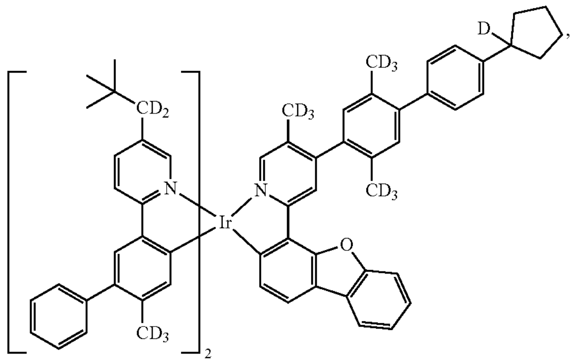
,
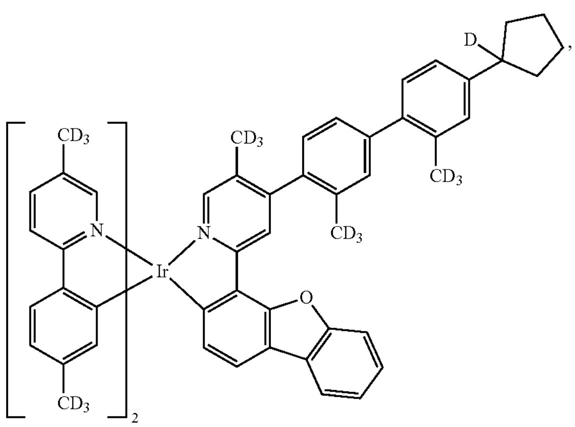
, -continued
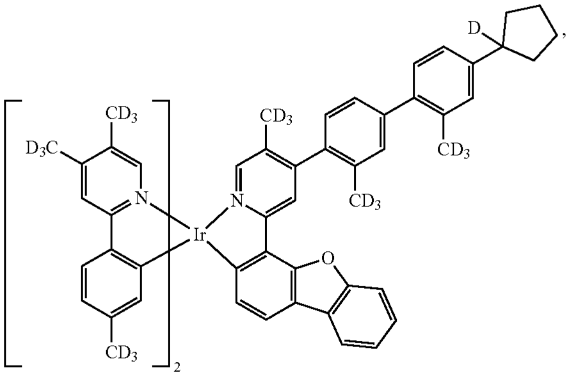
,
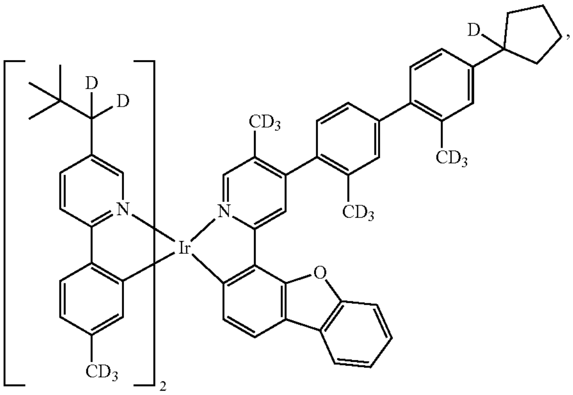
,
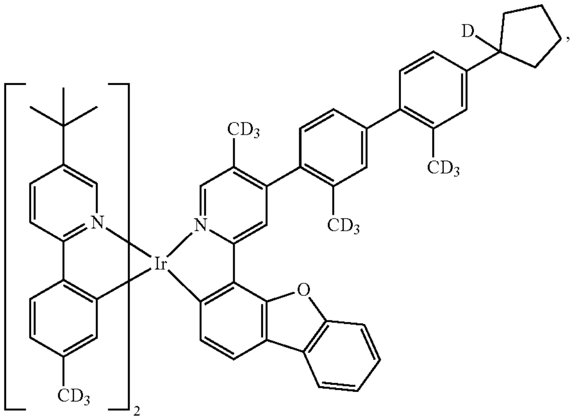
,
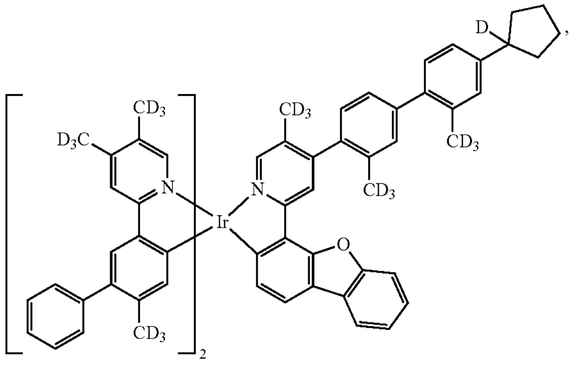
,
-continued
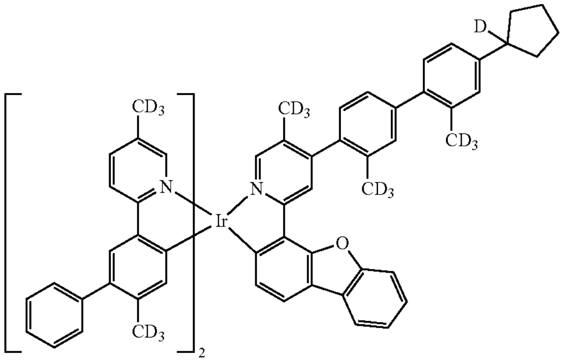
,
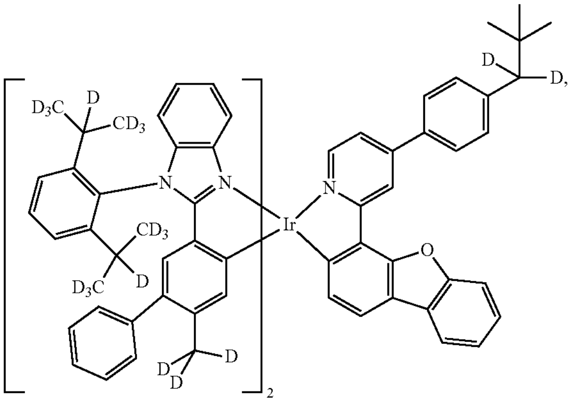
,
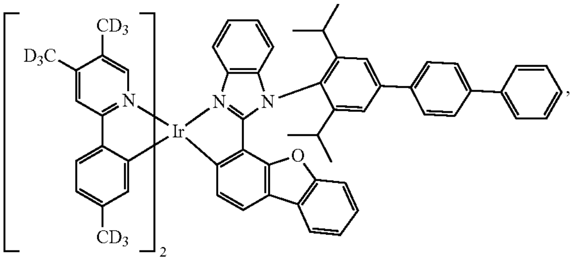
,
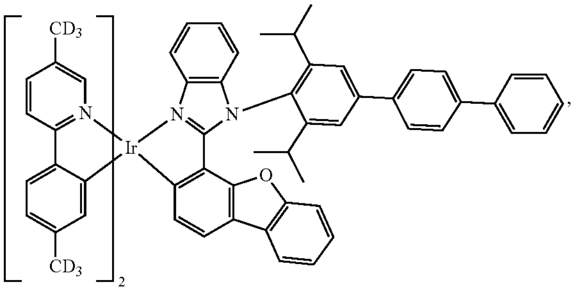
, -continued
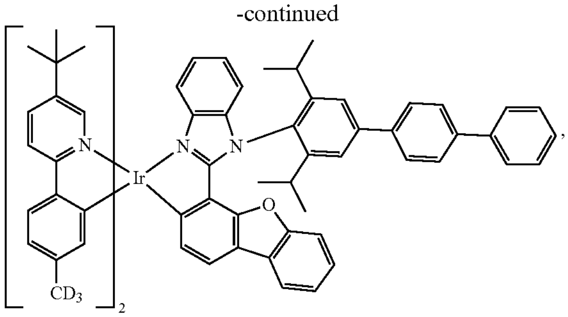
,
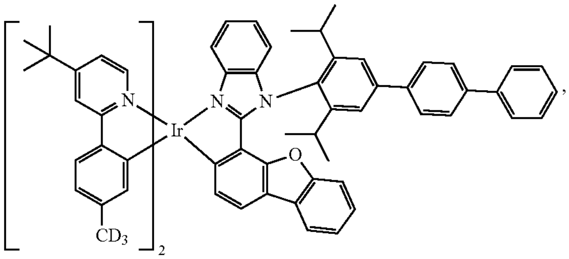
,
-continued
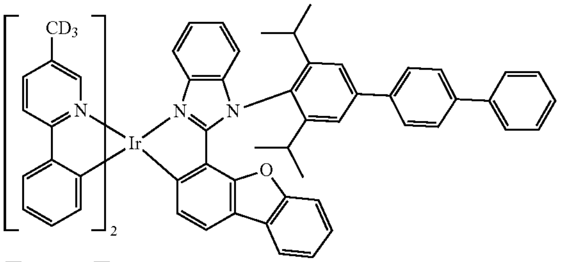
,
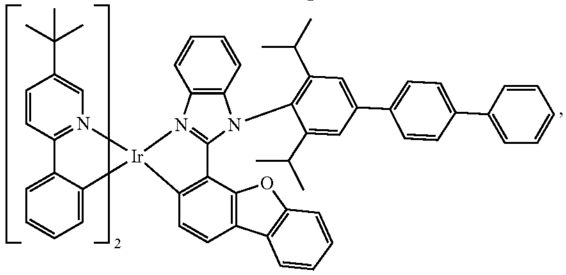
,
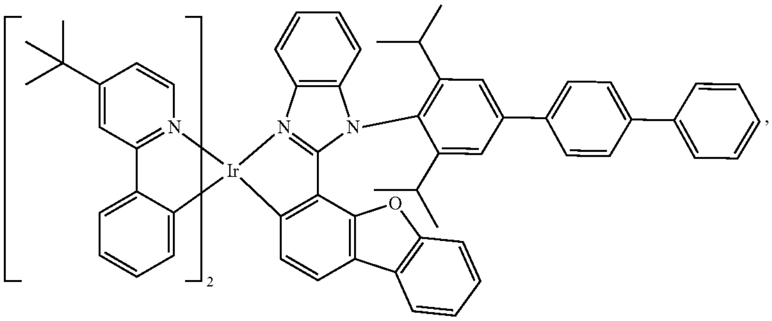
,
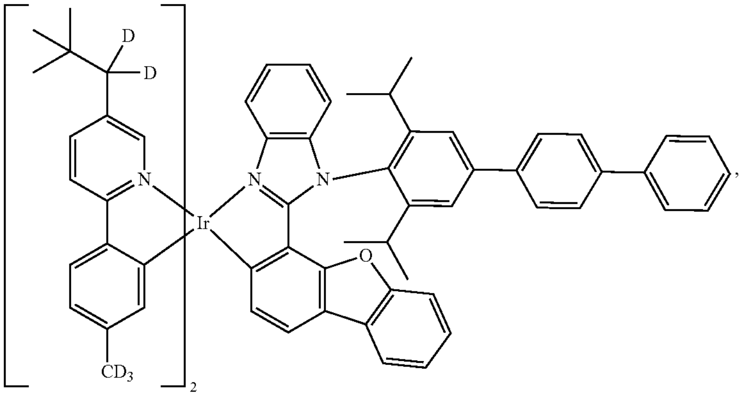
,
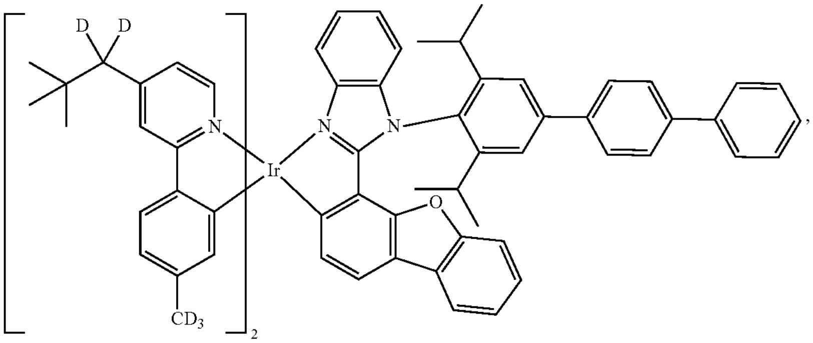
, -continued
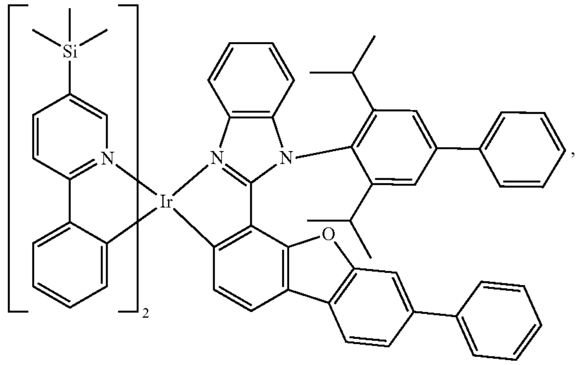
,
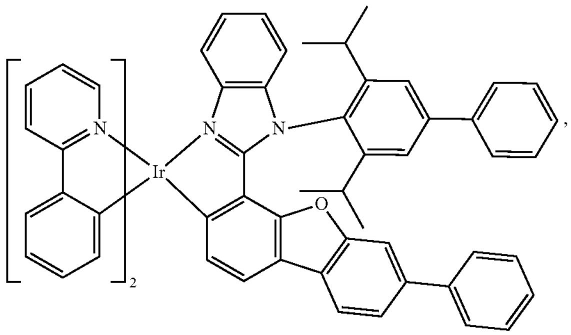
,
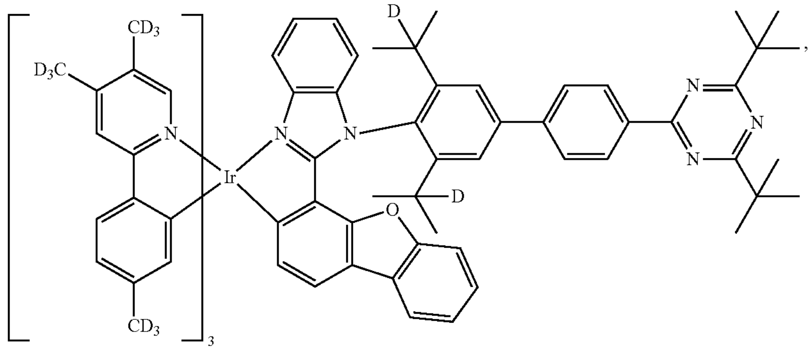
,
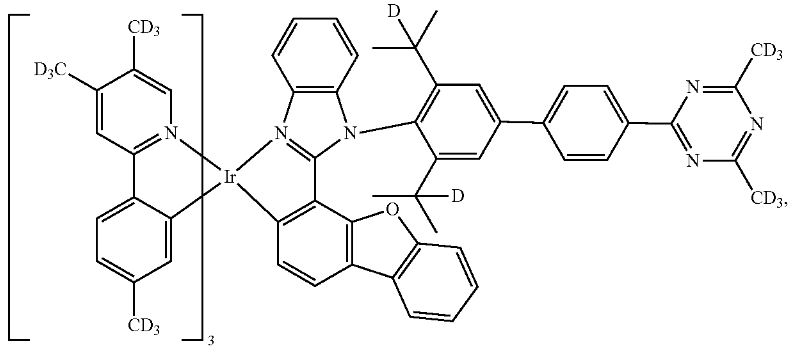
,
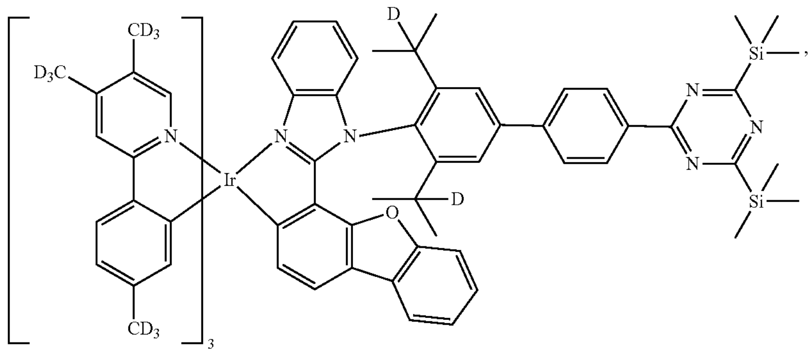
, -continued
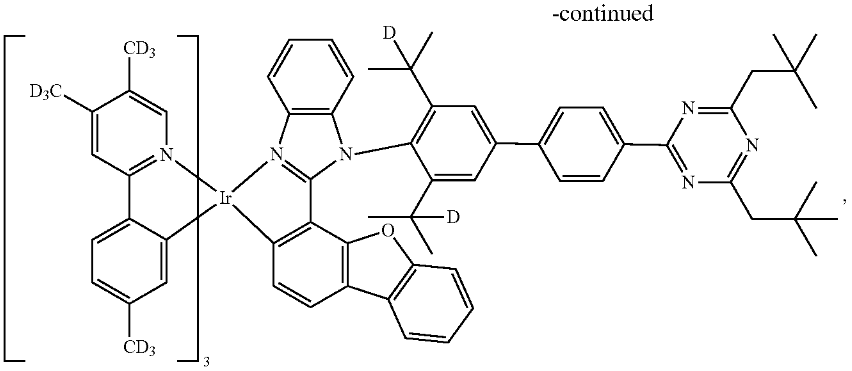
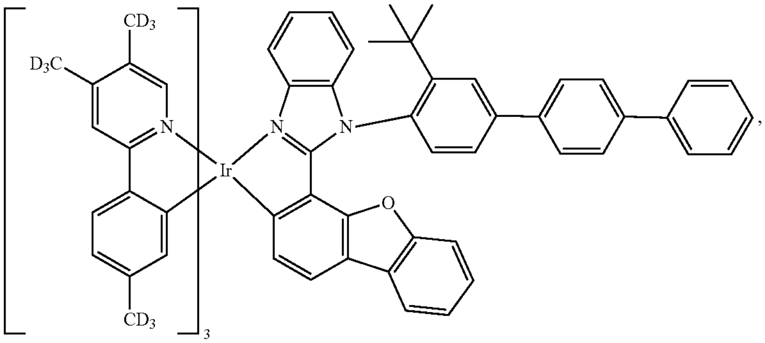
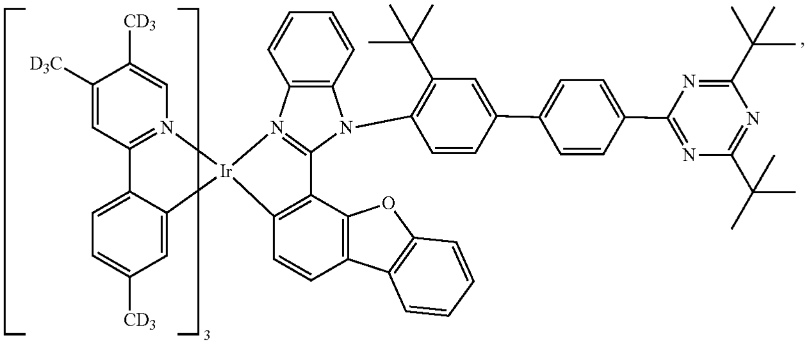
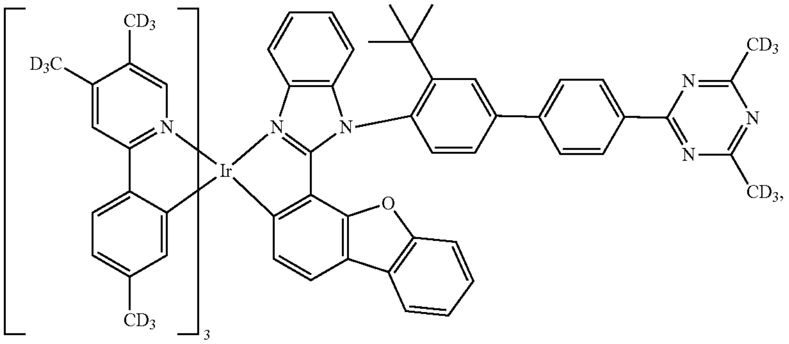
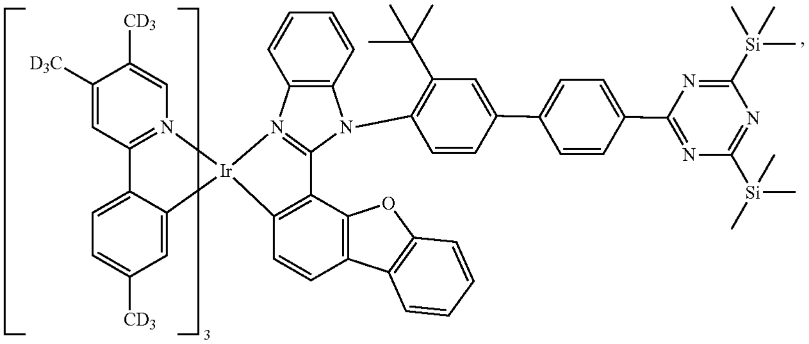

-continued
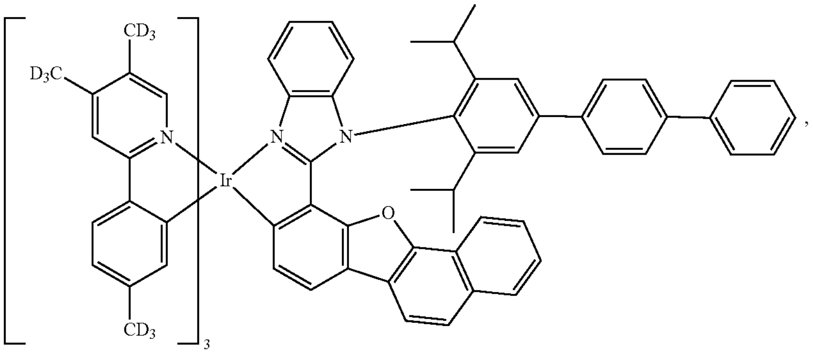
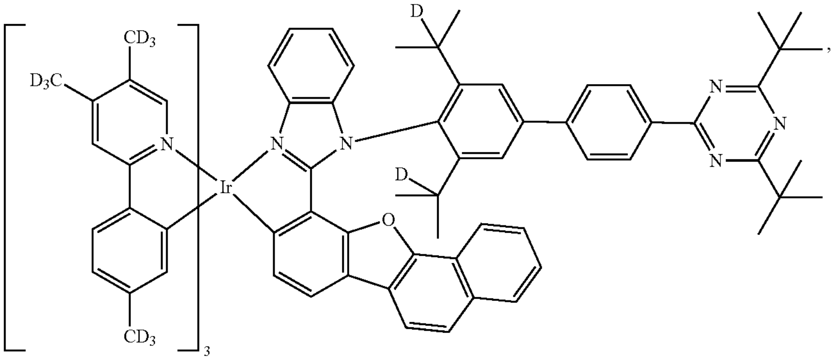
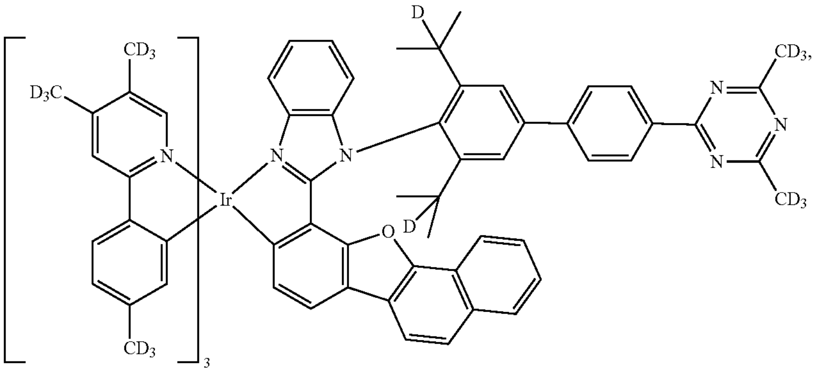
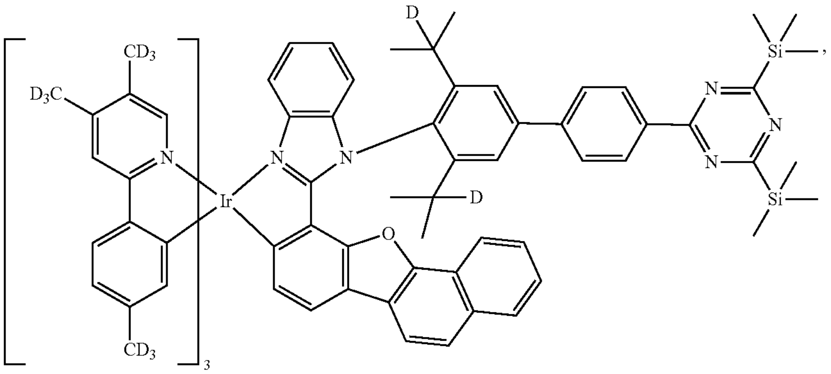

-continued
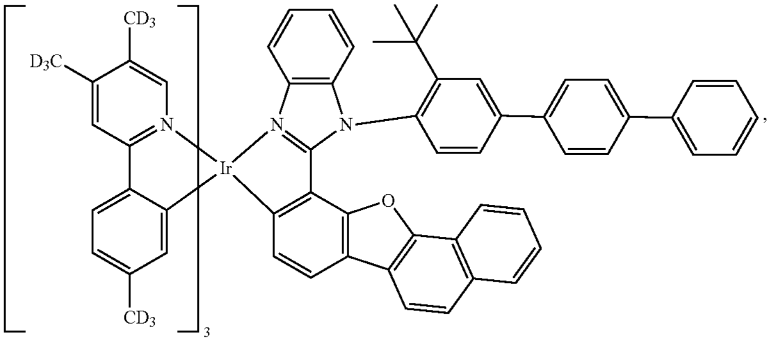
,
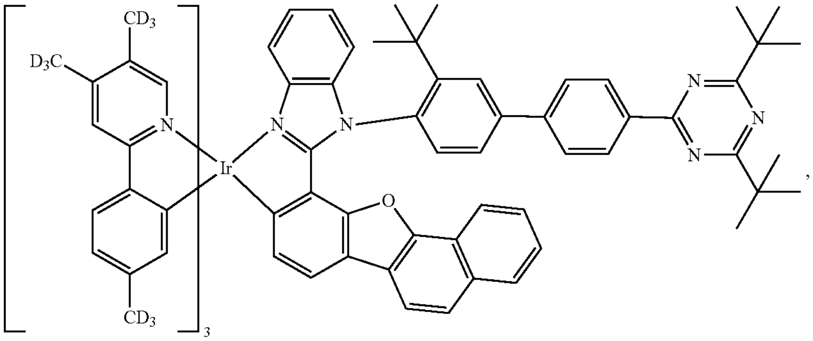
,
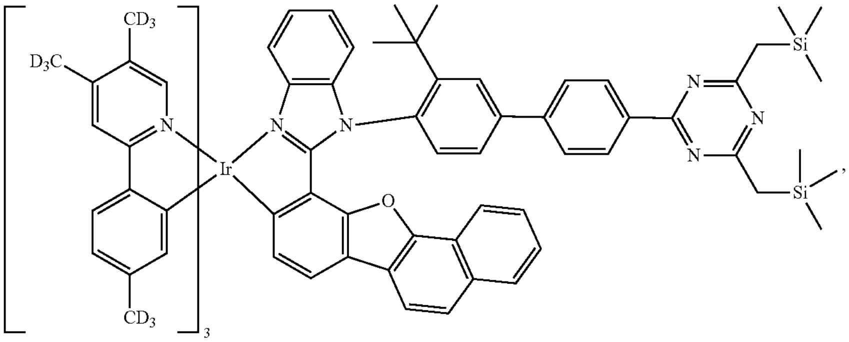
,
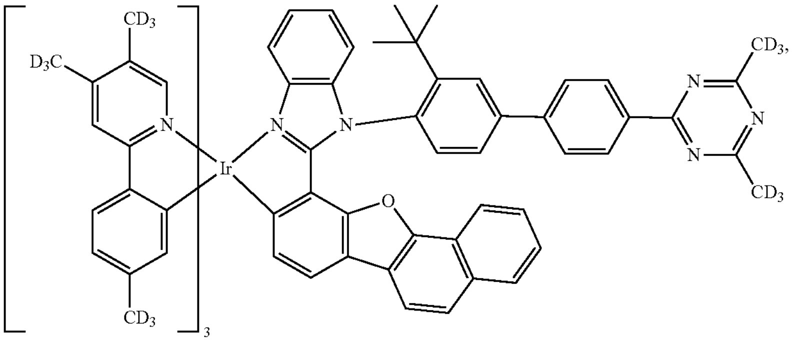
,
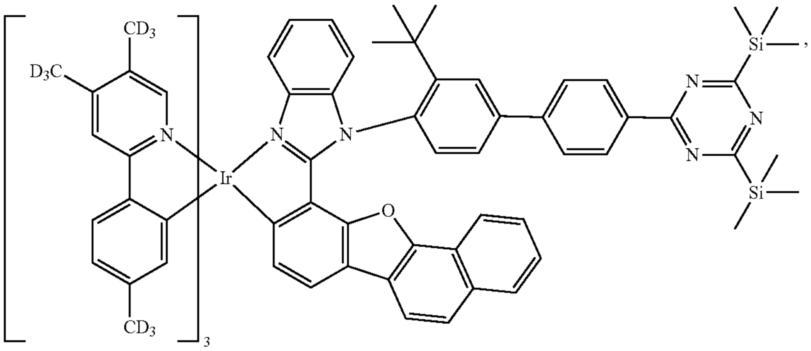
, -continued
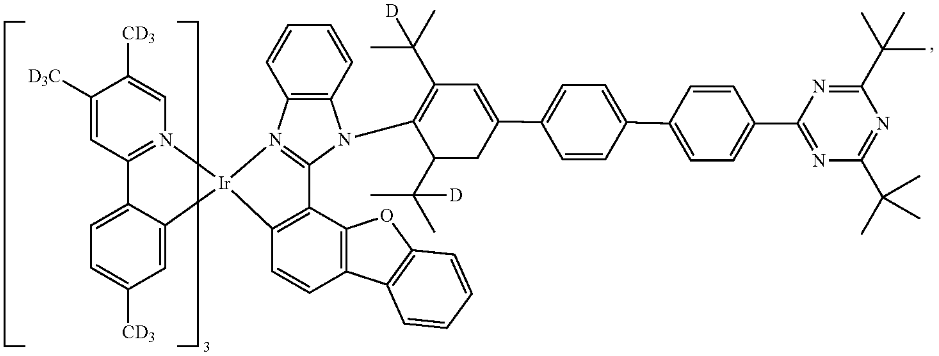
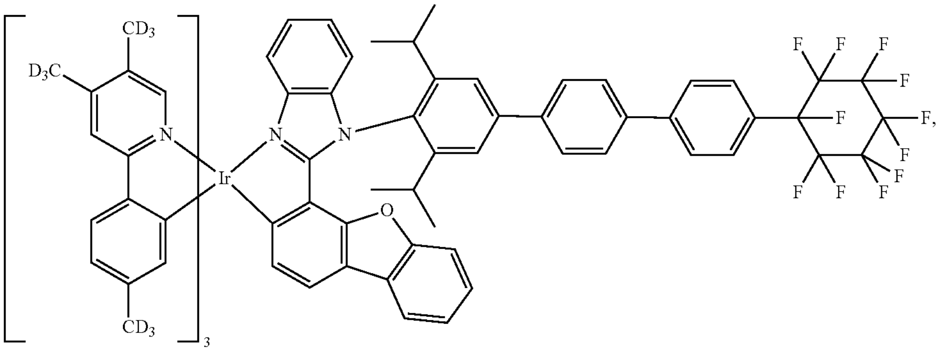
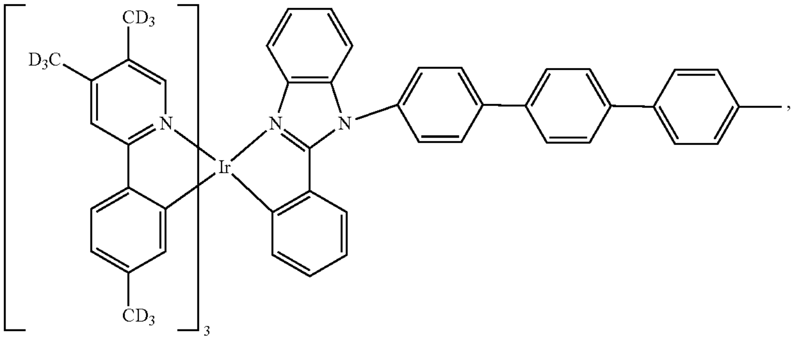
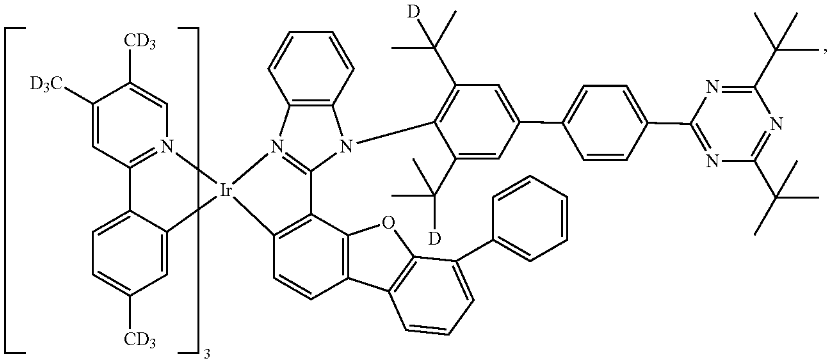

-continued
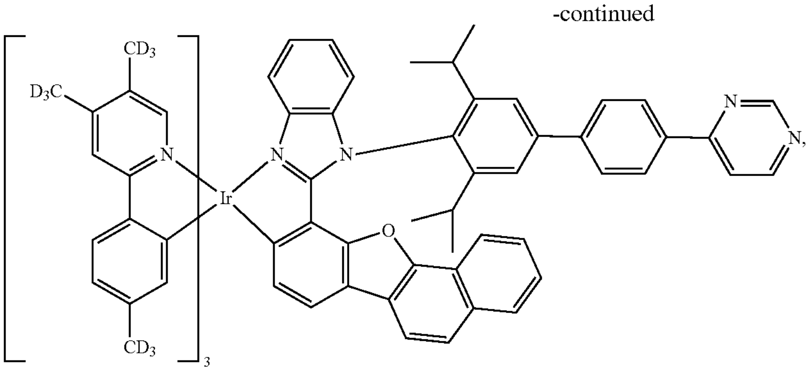
,
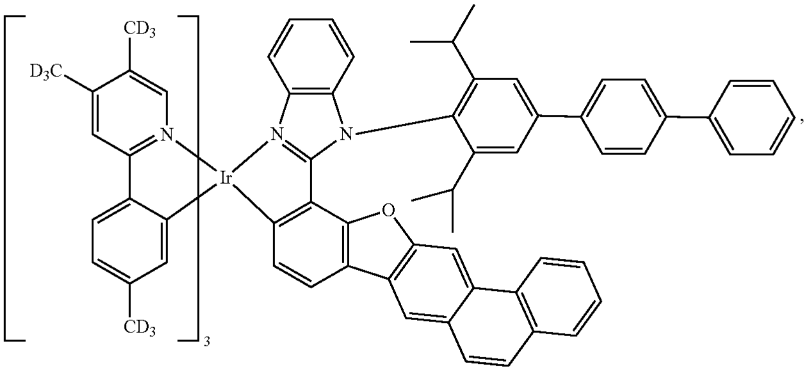
,
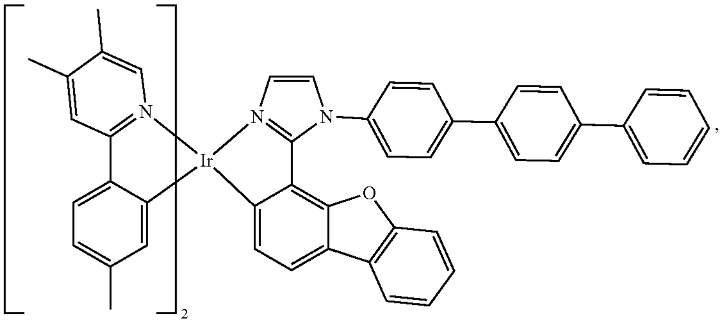
,
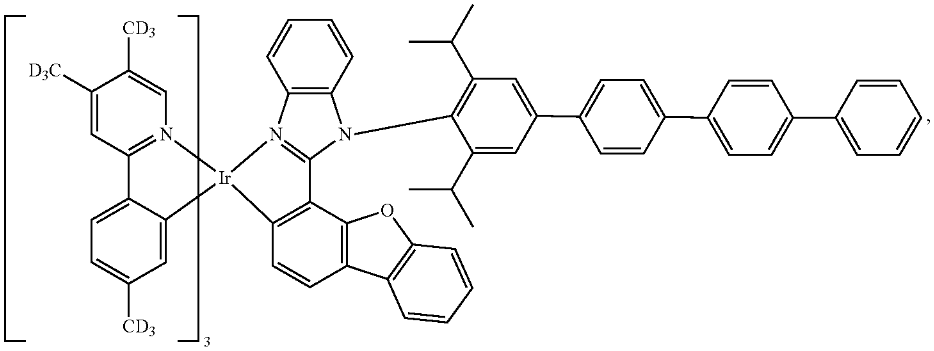
,
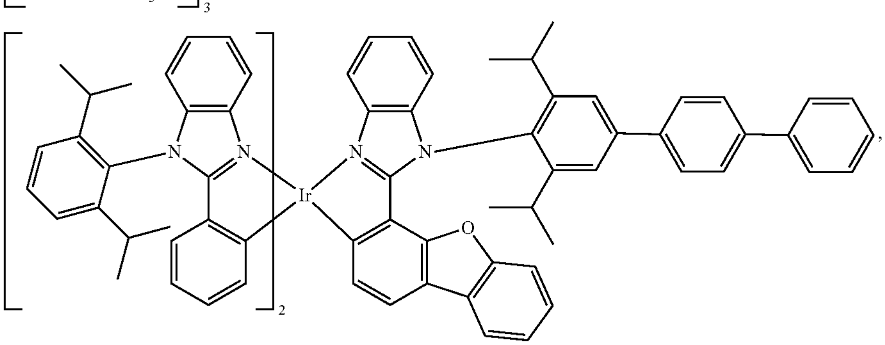
, -continued
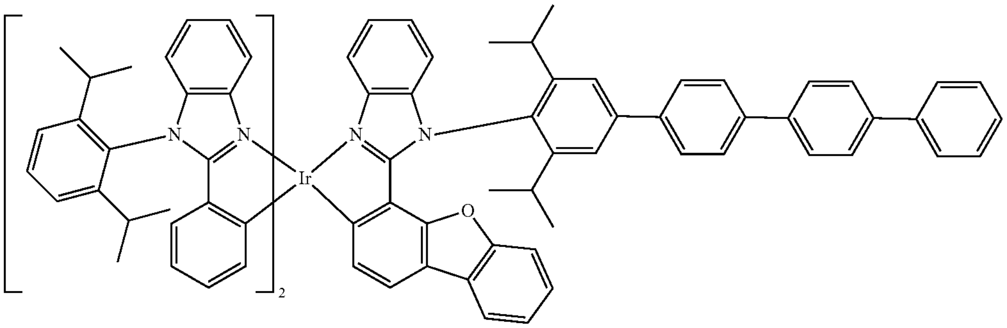
,
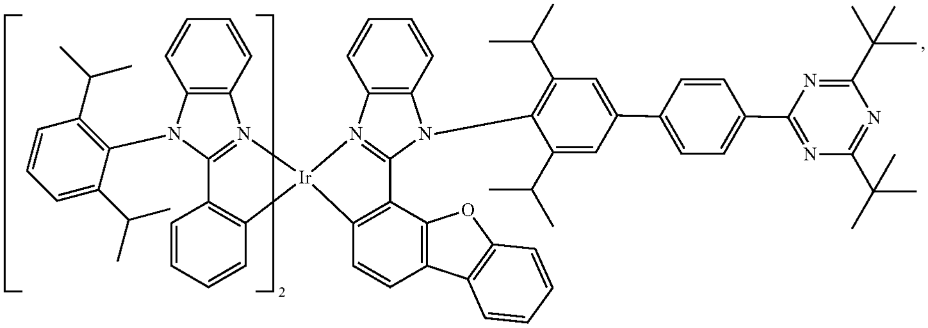
,
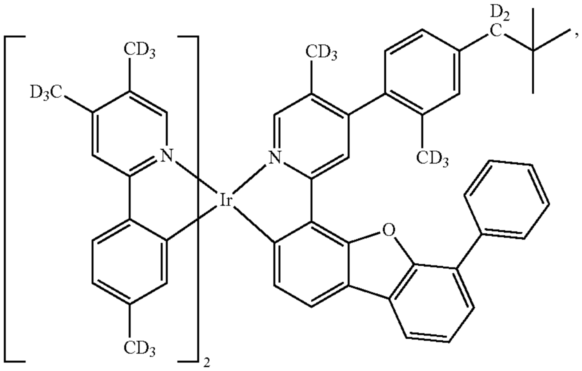
,
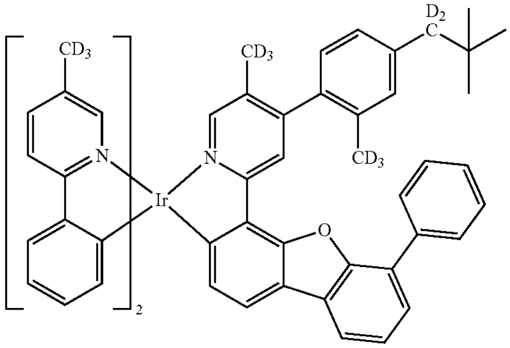
,
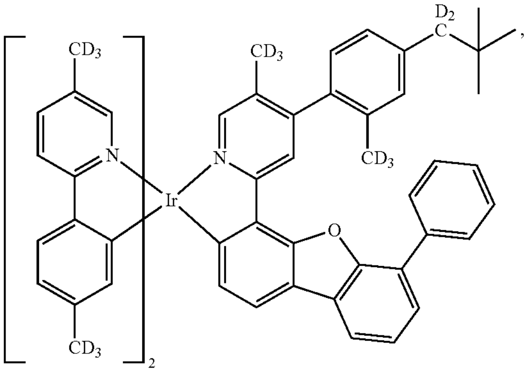
,
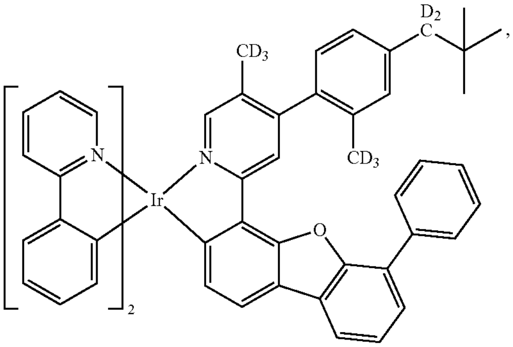
, -continued
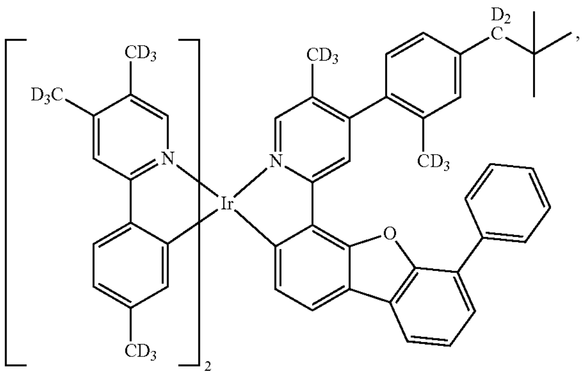
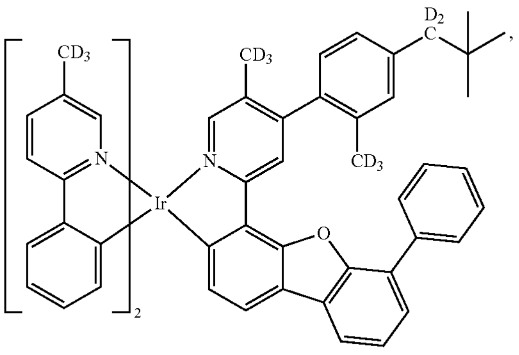
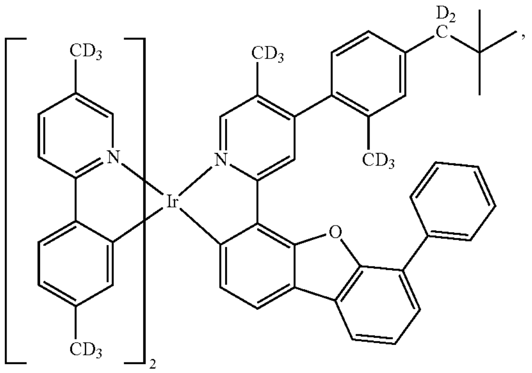
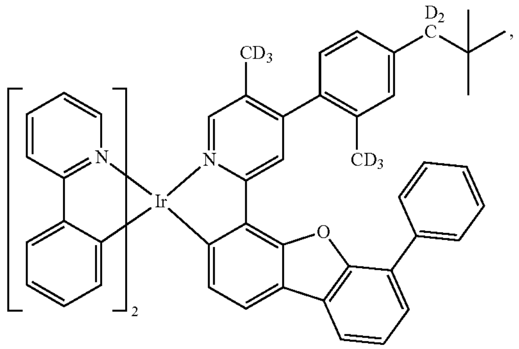
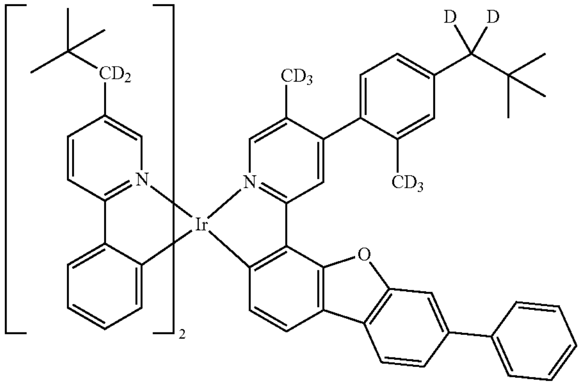
,
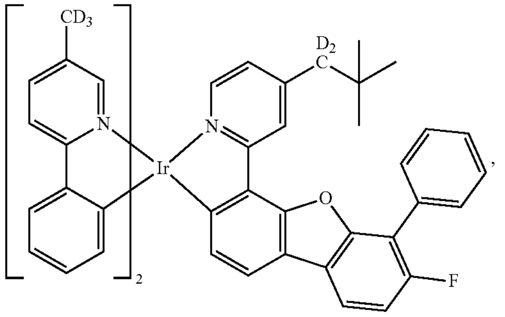
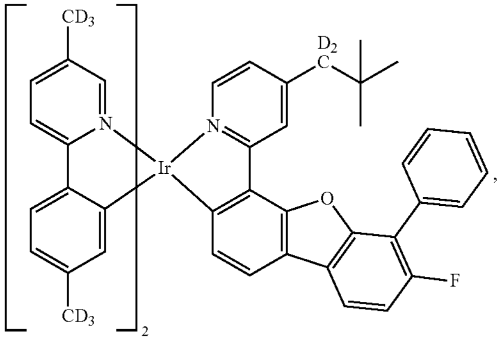
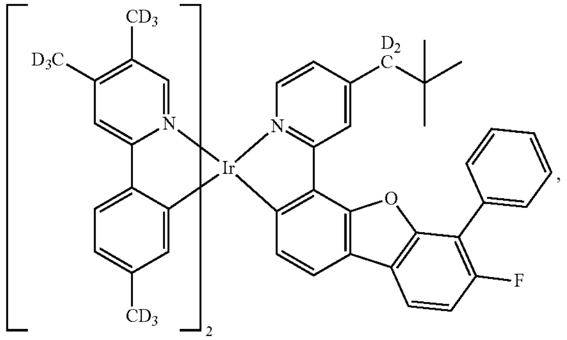

-continued
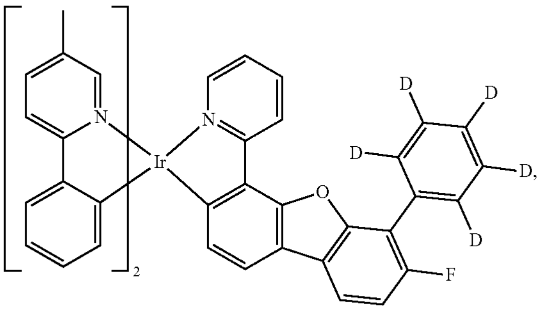,
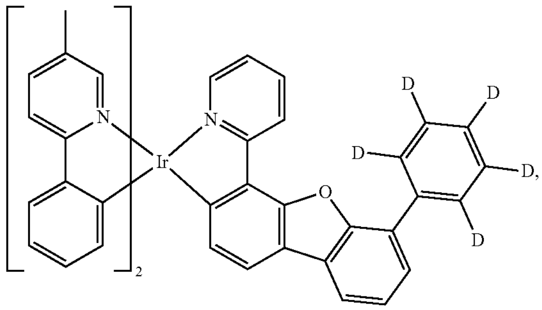,
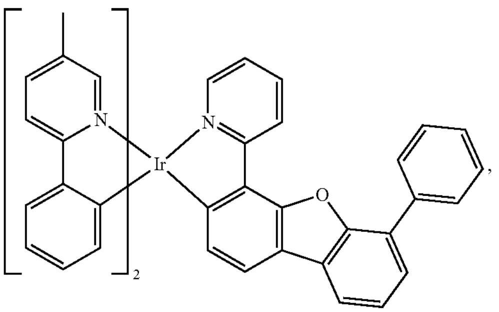,
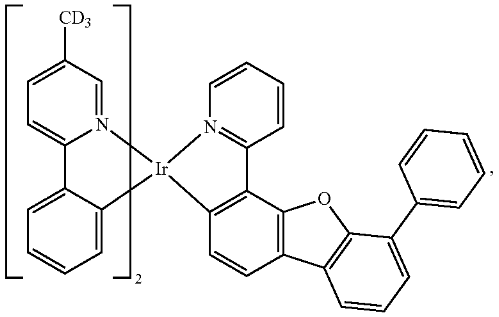,
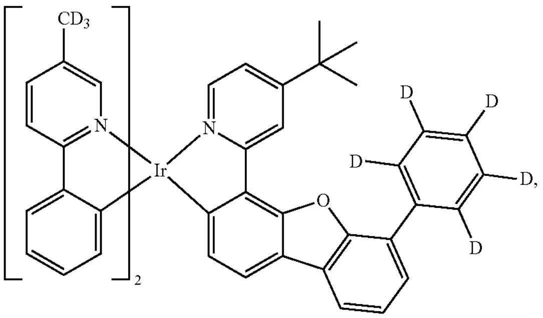,
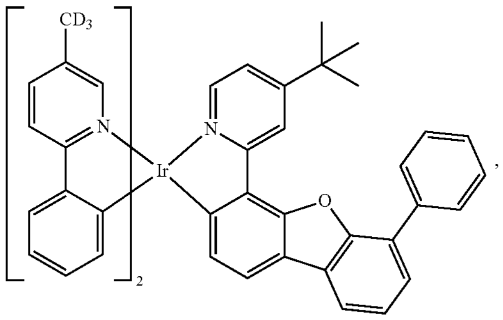,
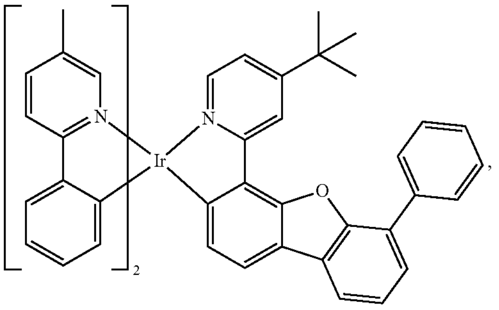,
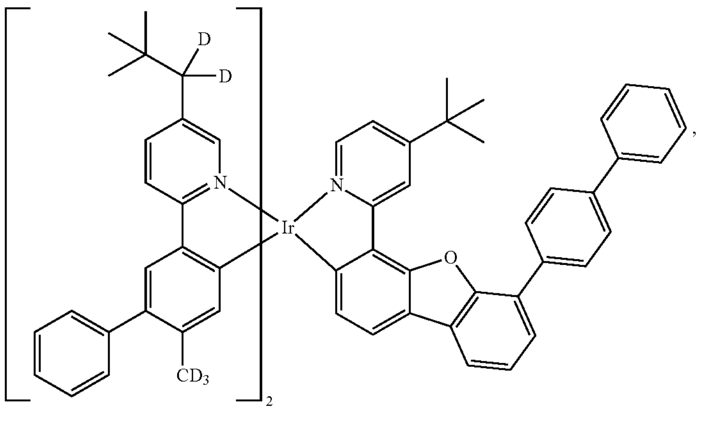, -continued
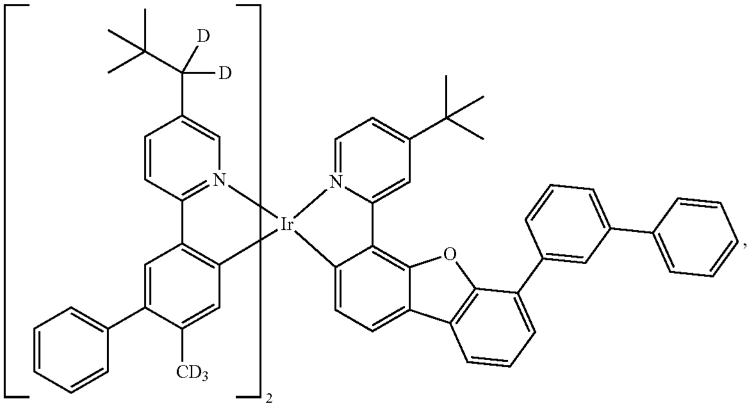,
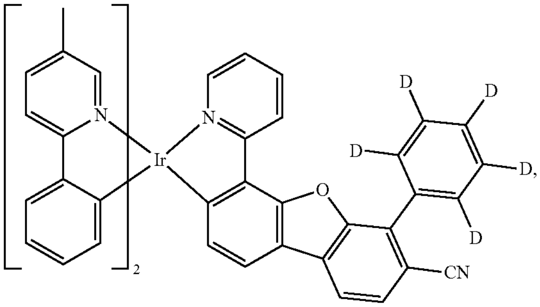, 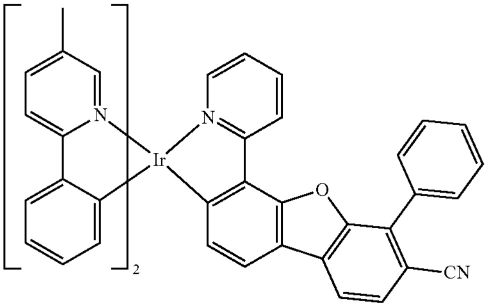,
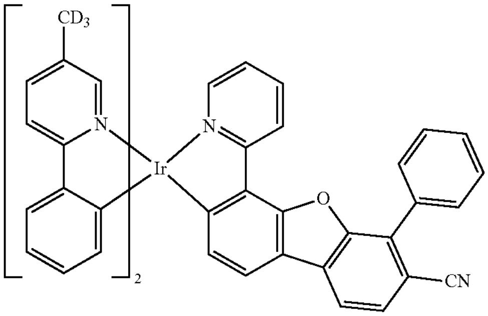, 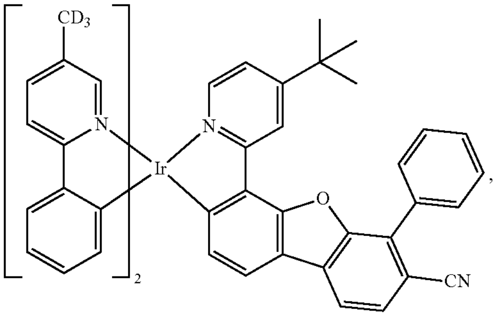,
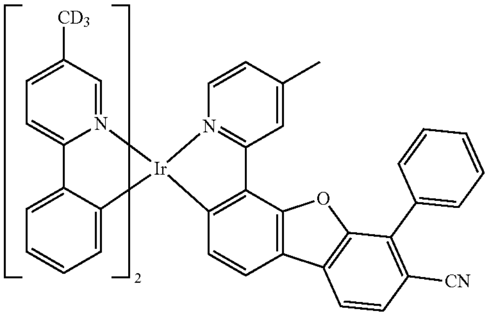, 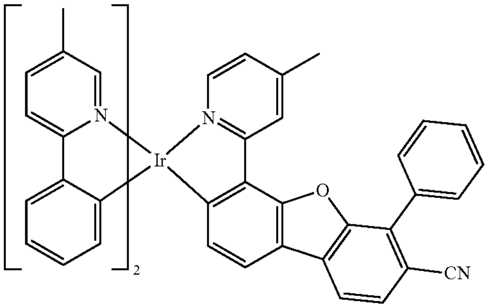, -continued
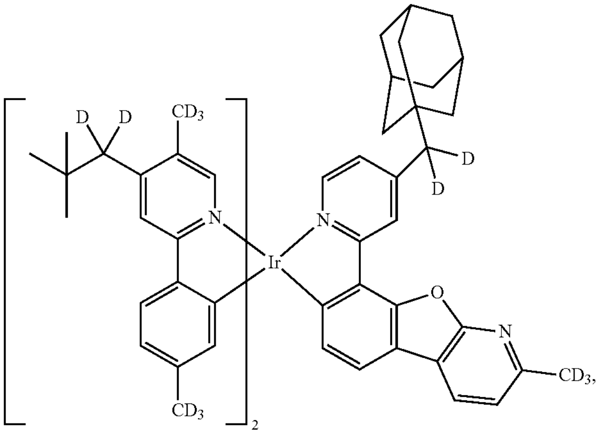
,
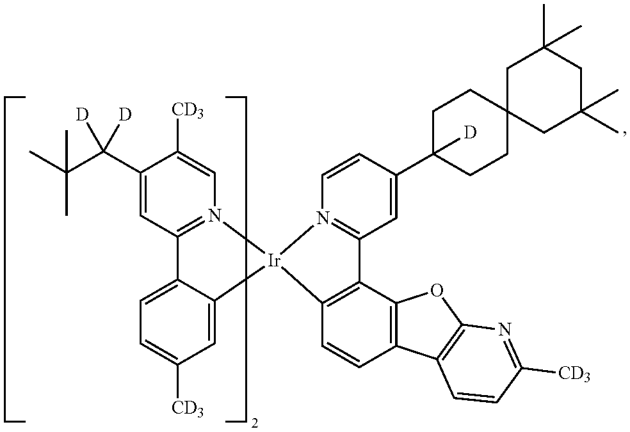
,
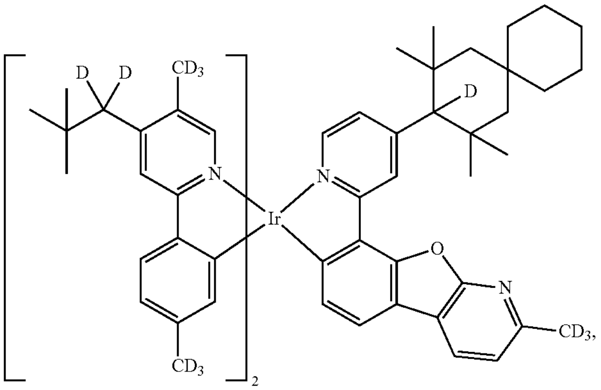
,
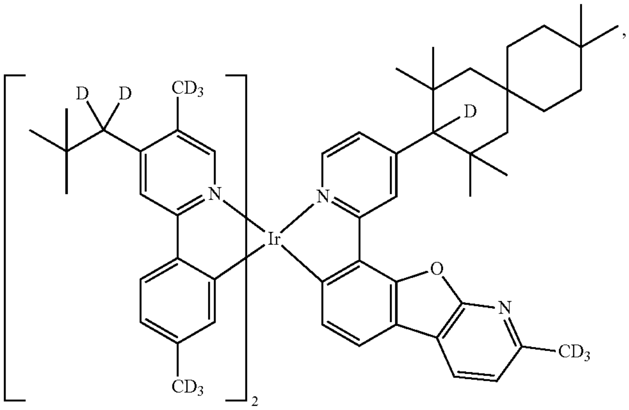
, -continued
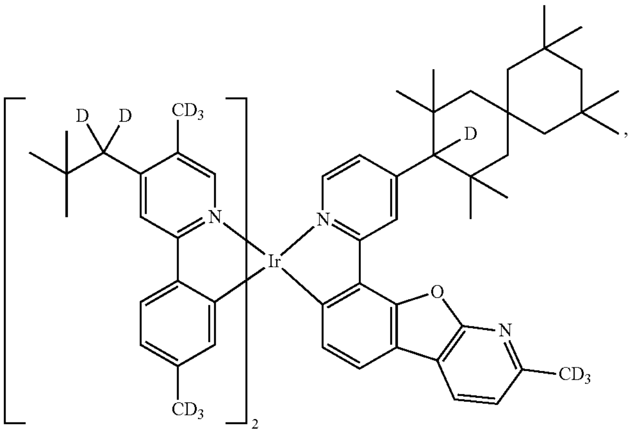
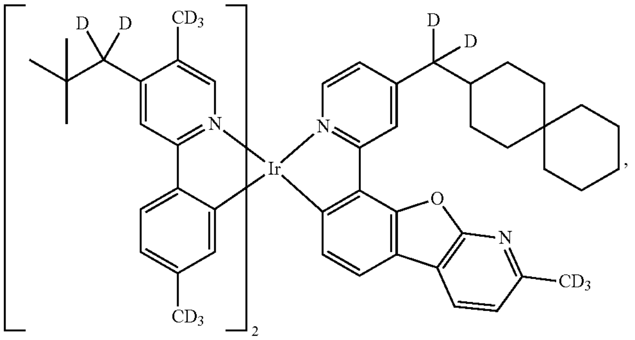
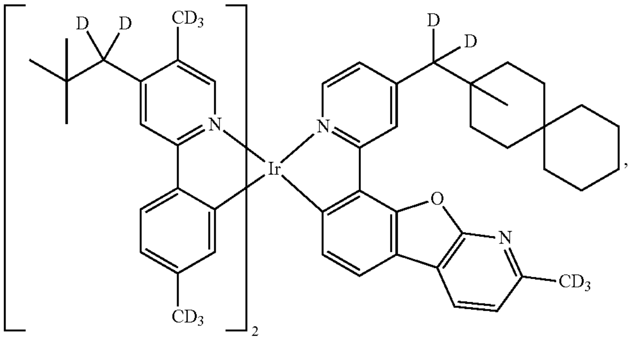
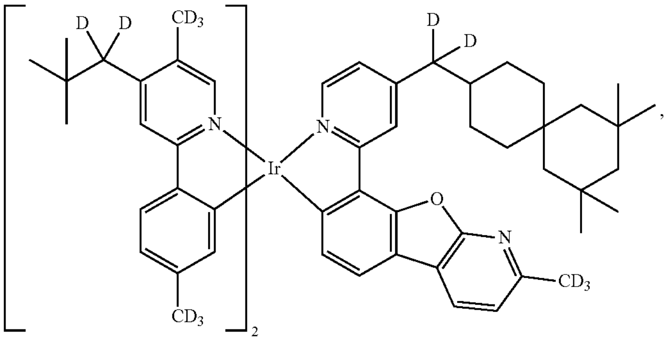

-continued
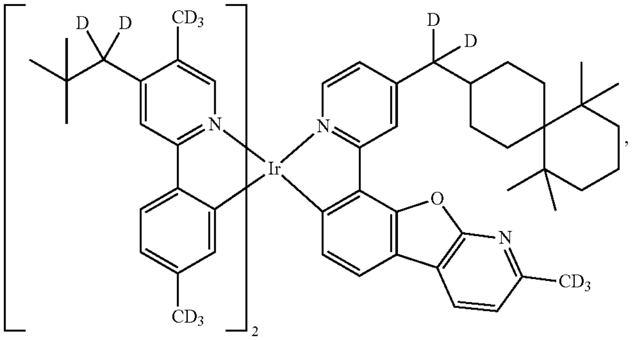
,
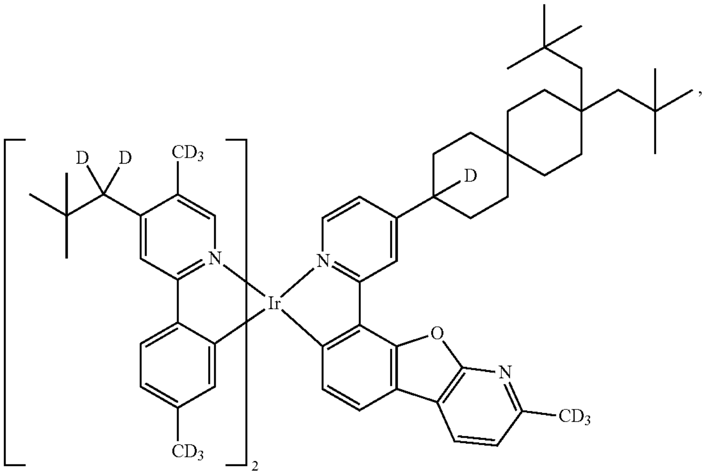
,
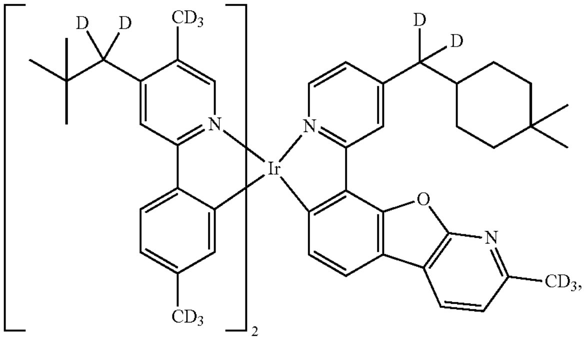
,
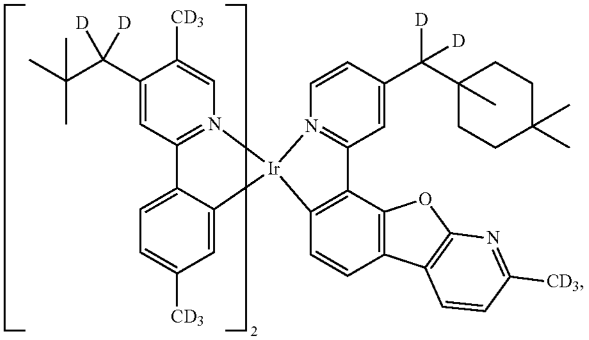
,
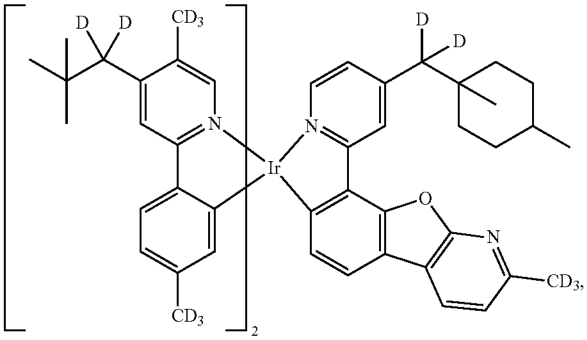
,
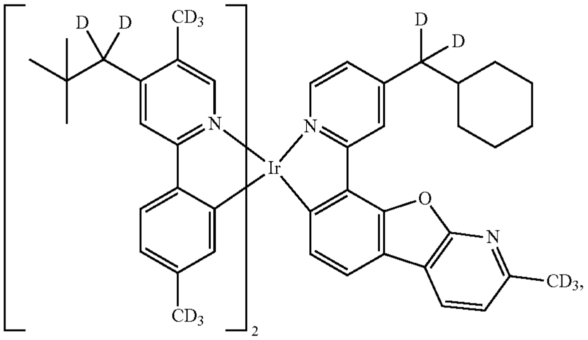
, -continued
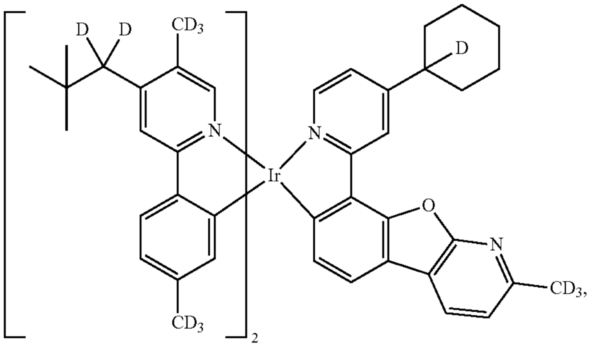
,
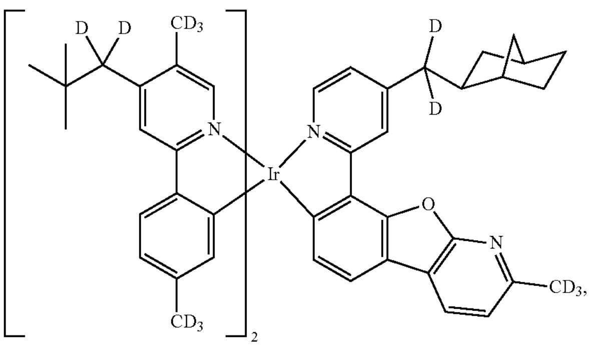
,
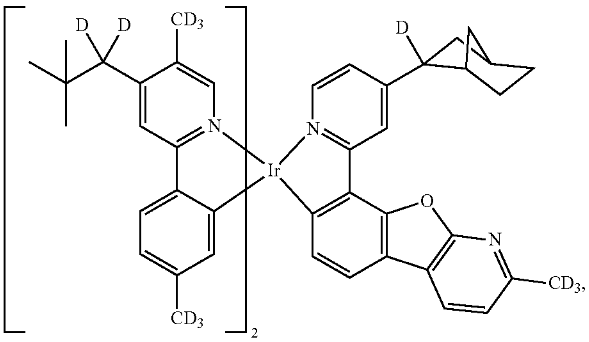
,
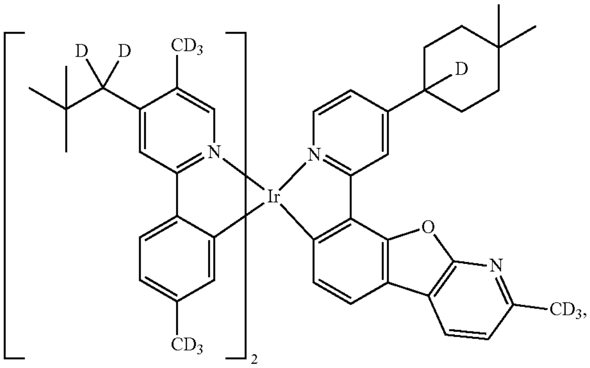
,
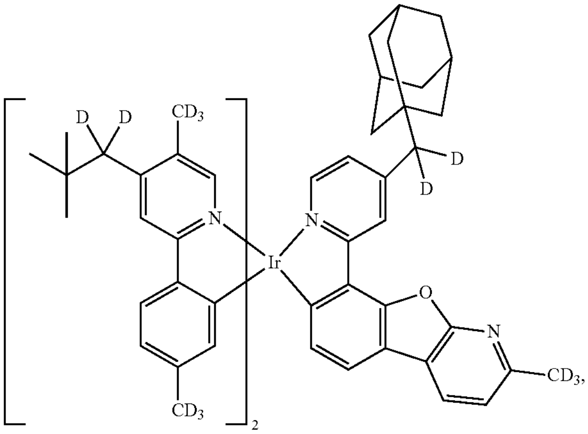
,
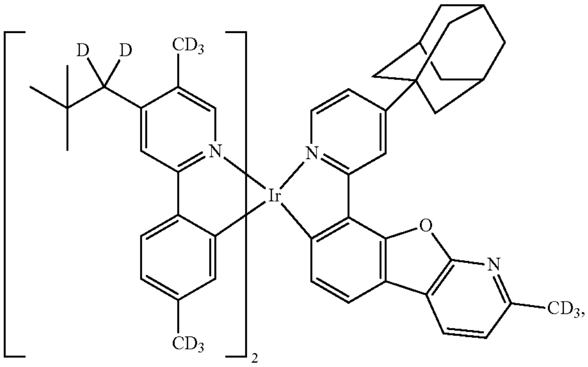
,
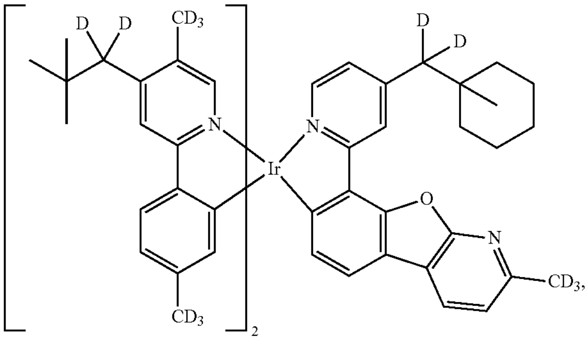
,
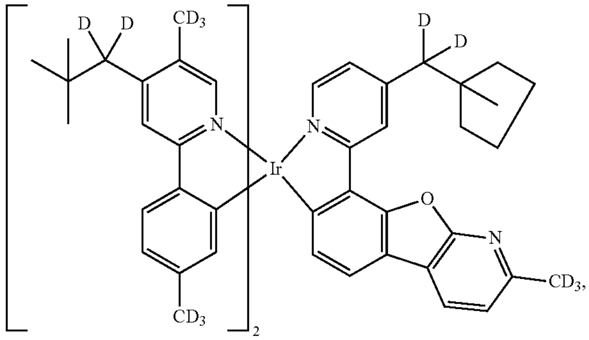
,

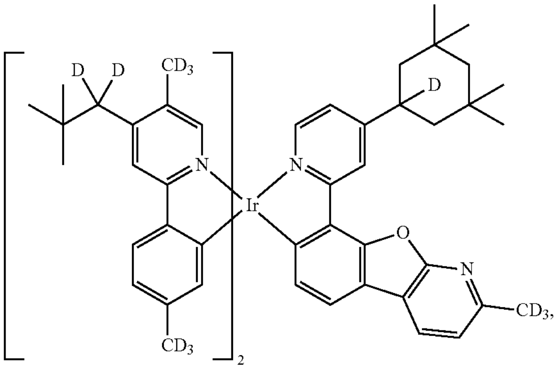
,
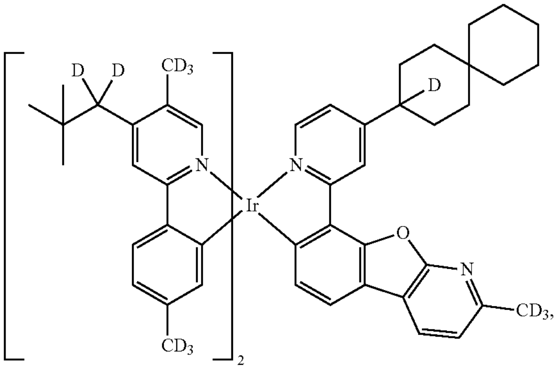
,
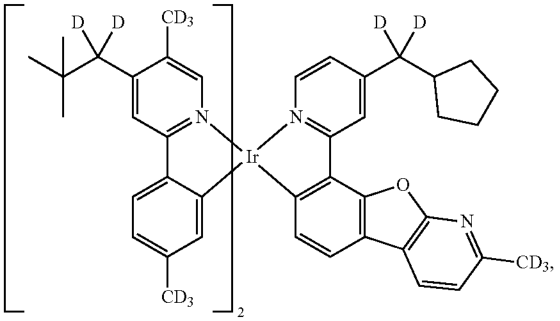
,
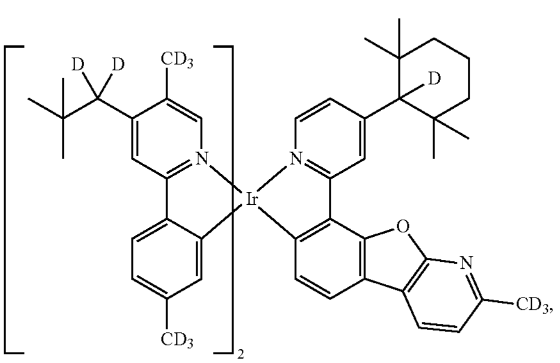
,
-continued
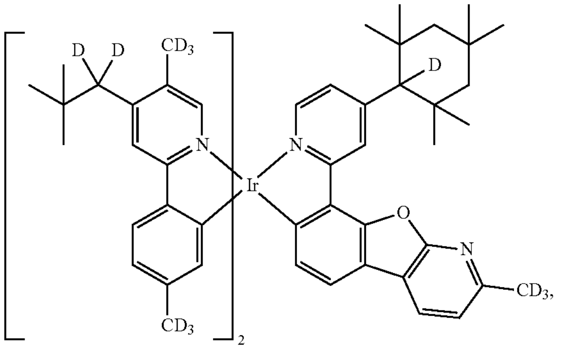
,
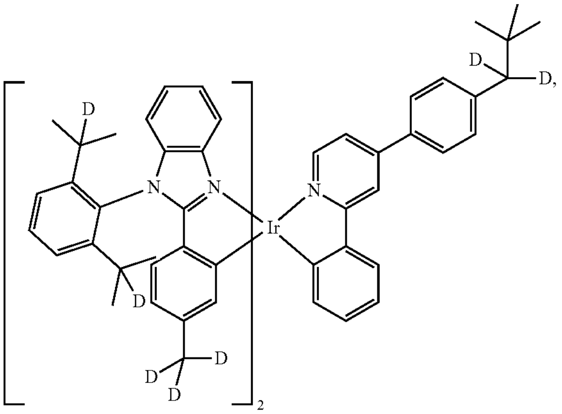
,
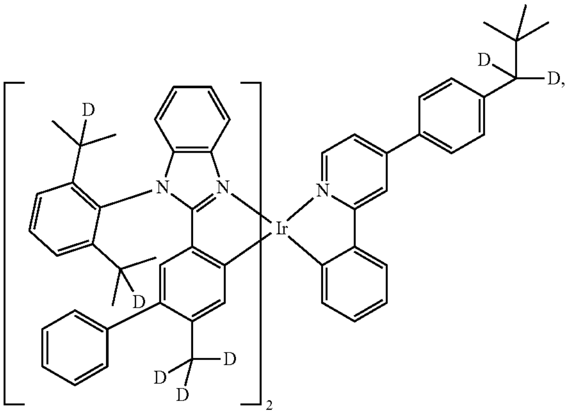
,
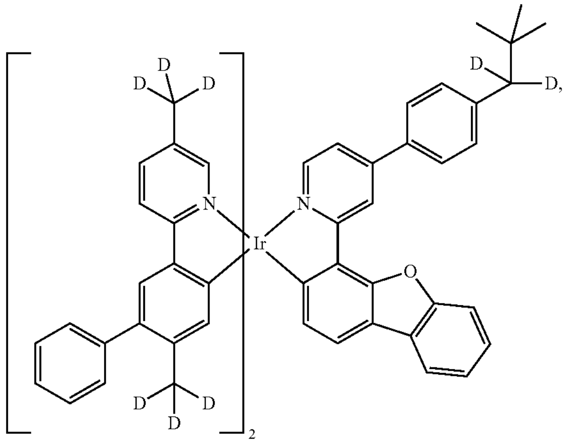
, -continued
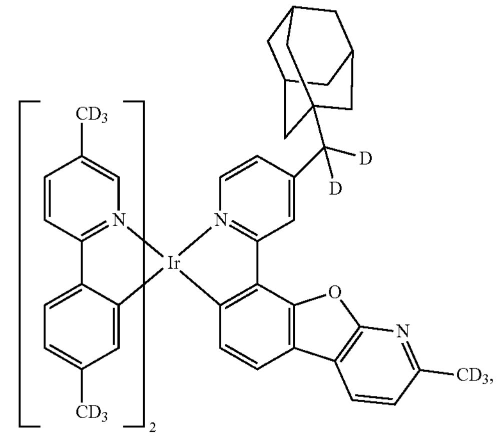
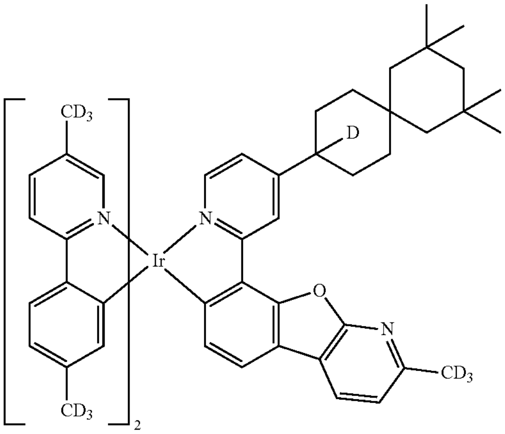
,
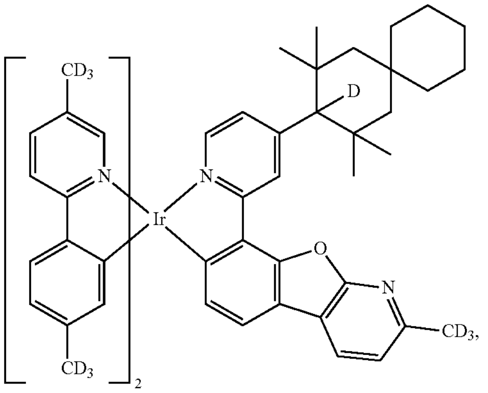
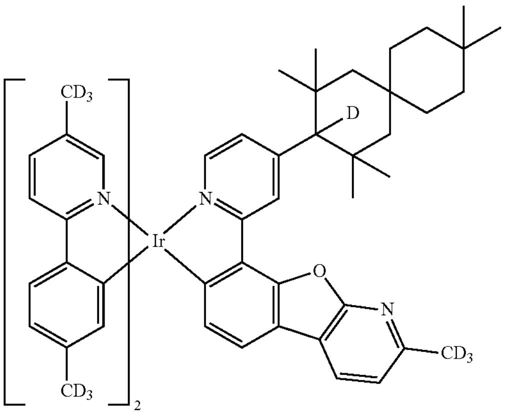
,
-continued
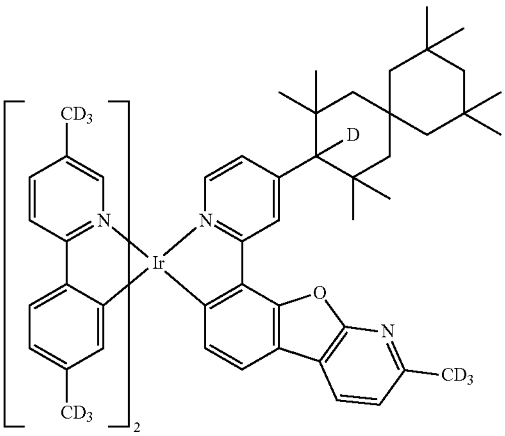
,
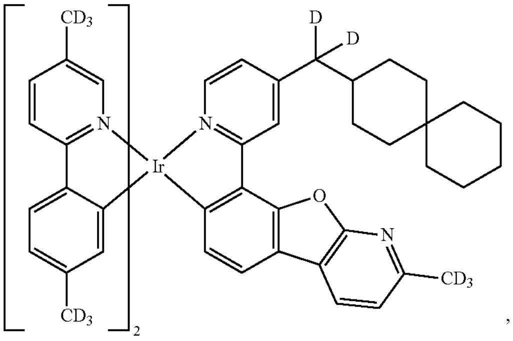
,
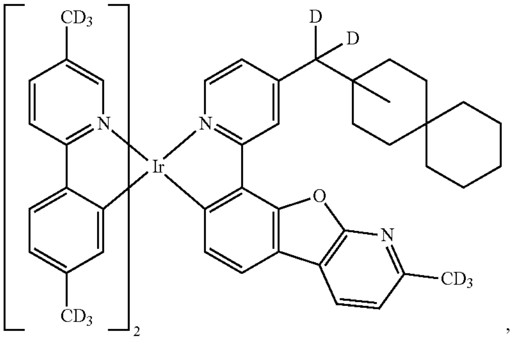
,
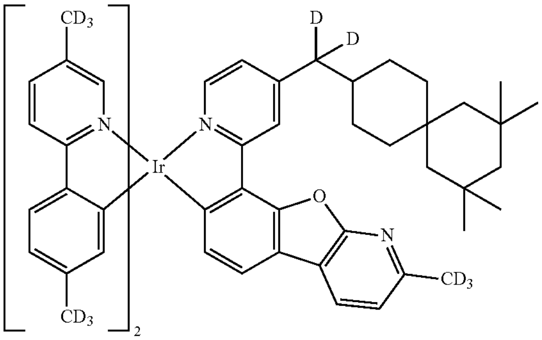
, -continued
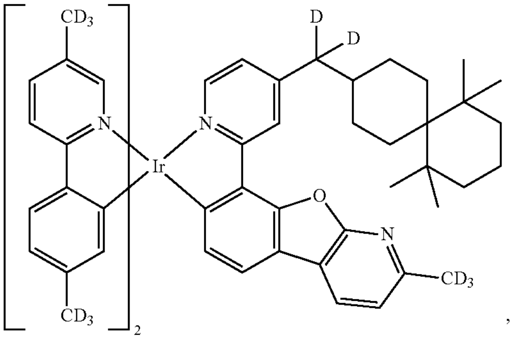
,
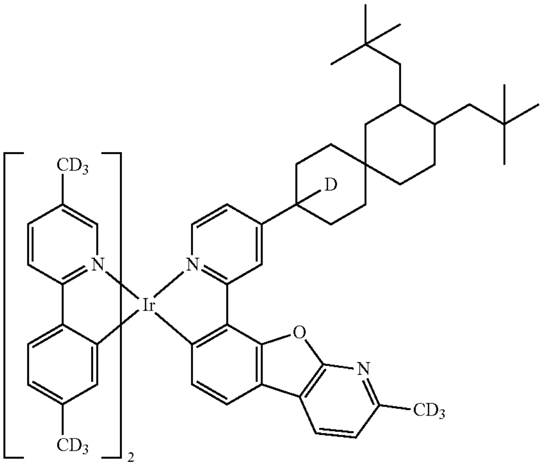
,
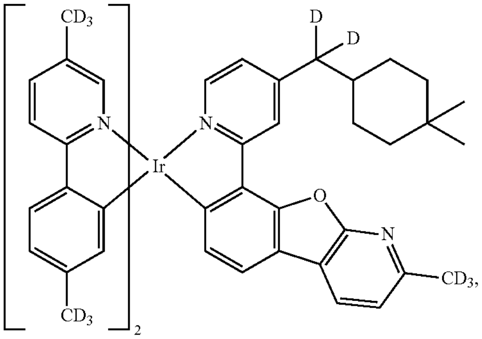
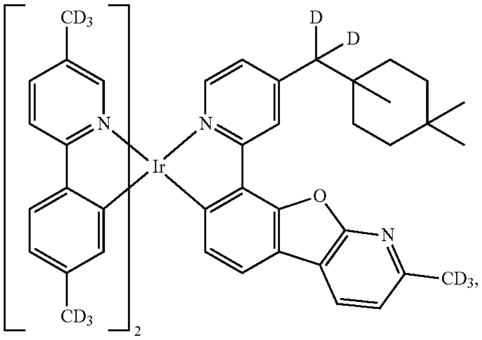
-continued
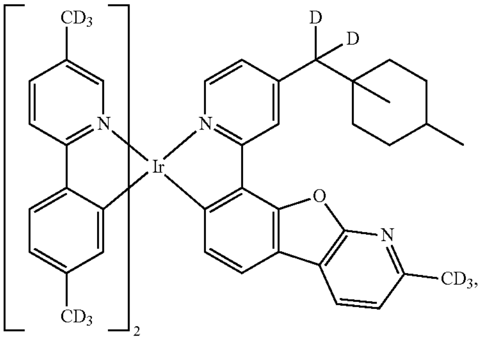
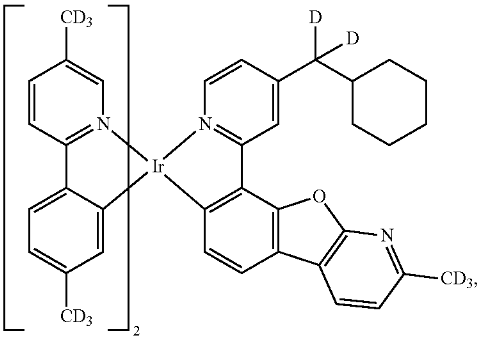
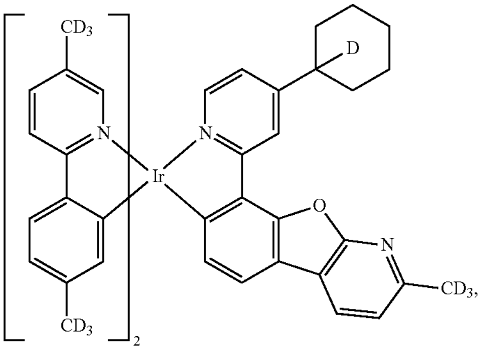
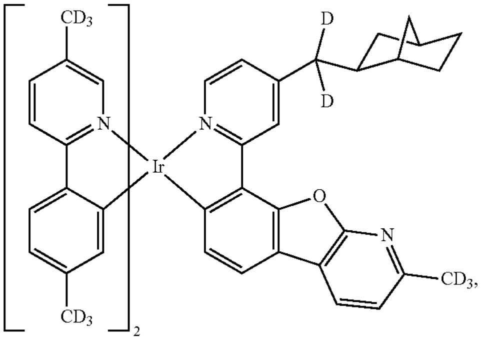
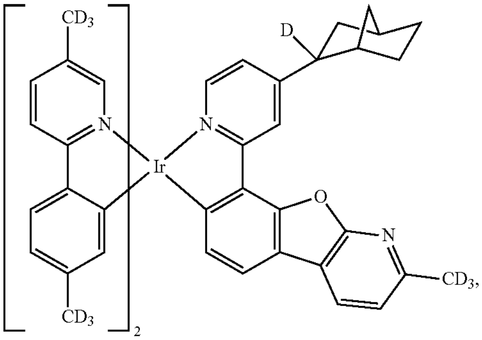

-continued
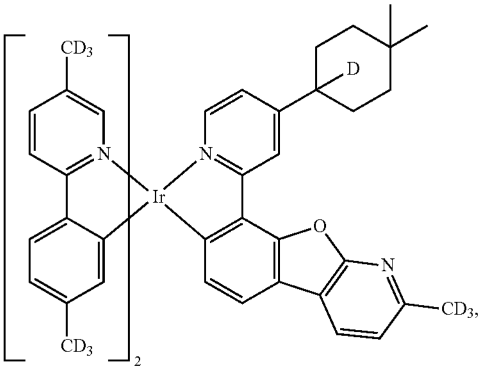
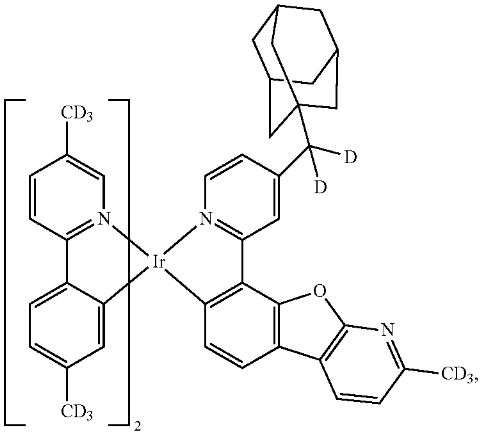
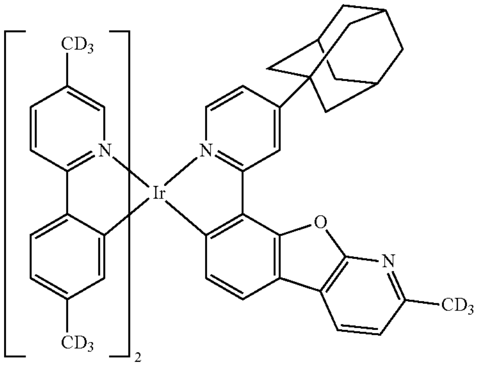
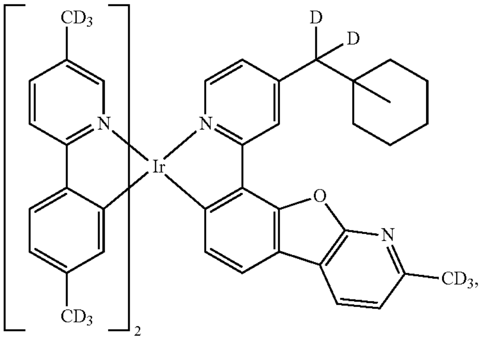
-continued
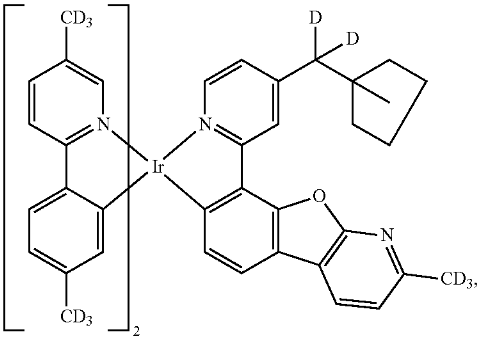
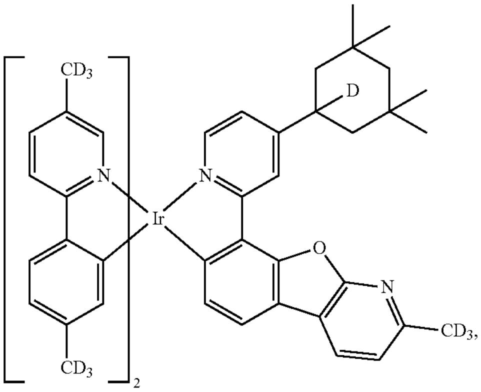
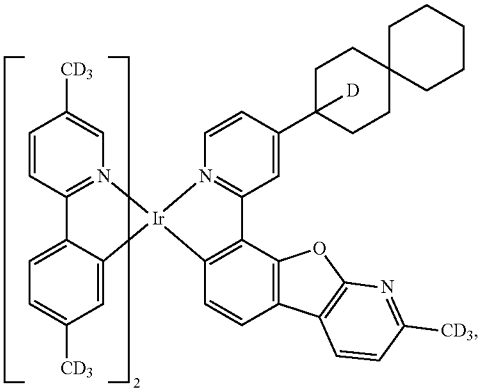
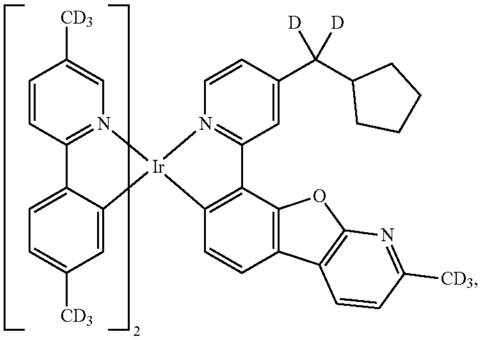

-continued
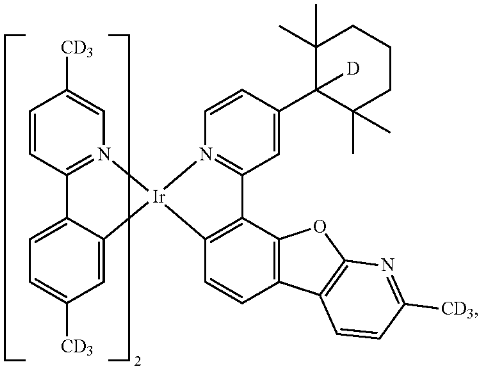
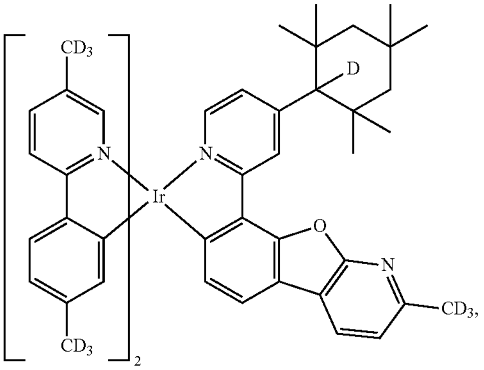
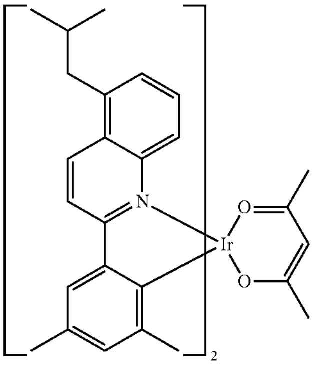
,
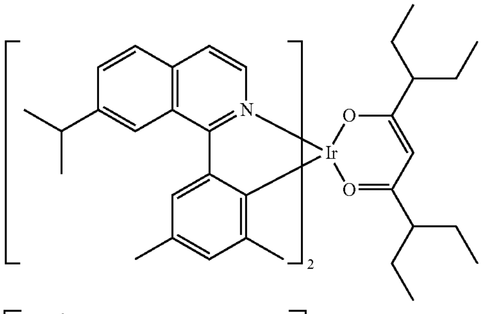
,
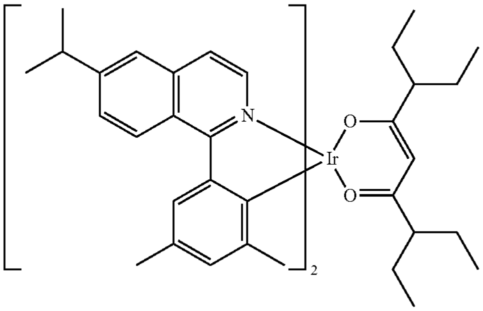
,
-continued
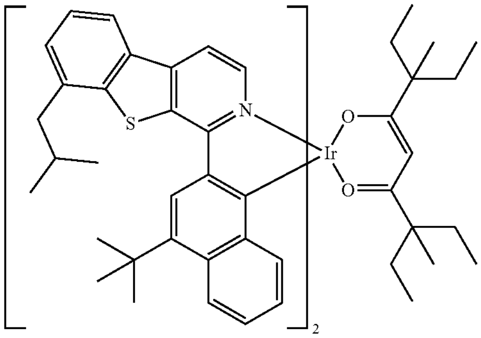
,
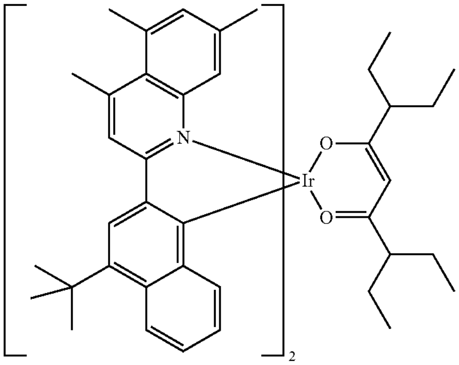
,
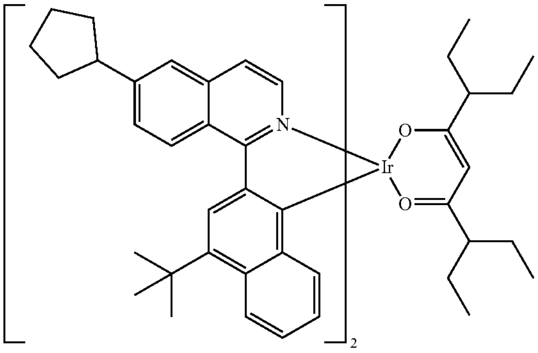
,
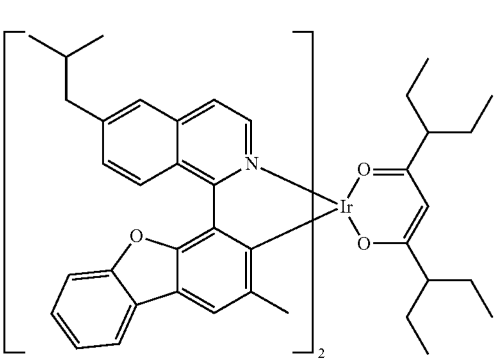
, -continued
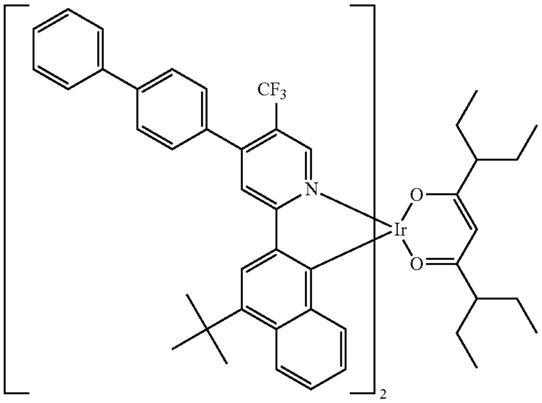
,
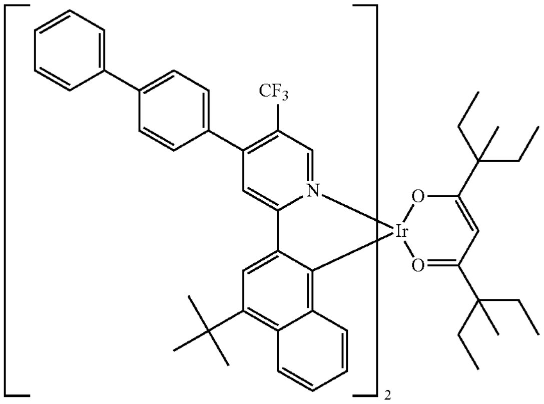
,
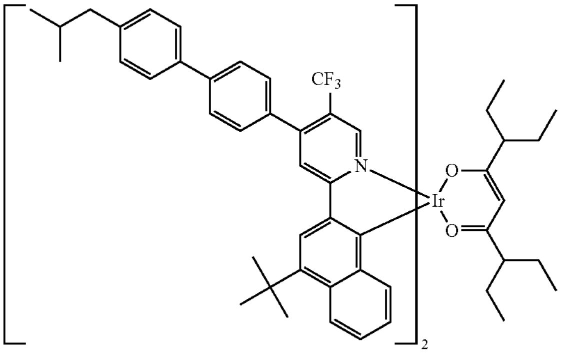
,
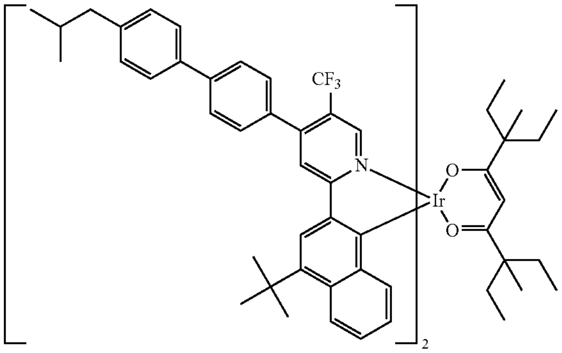
,
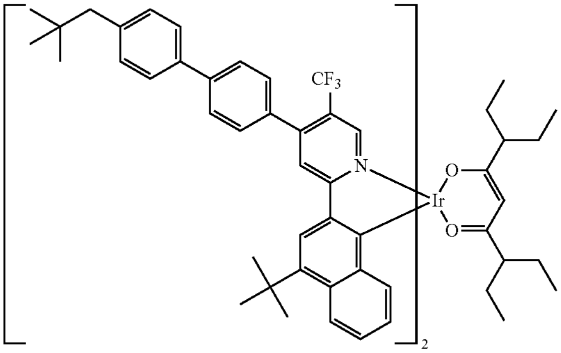
,
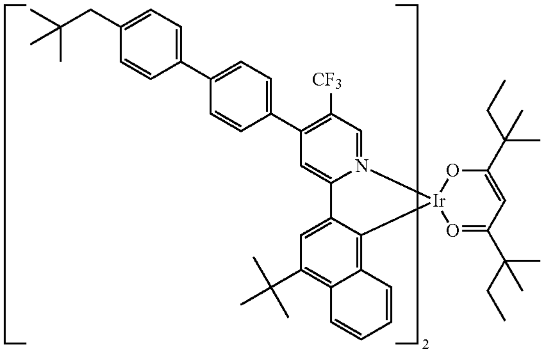
,
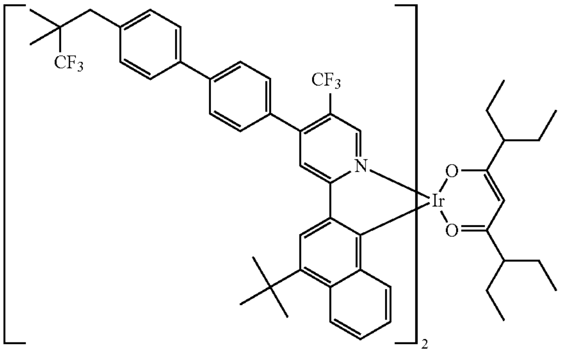
,
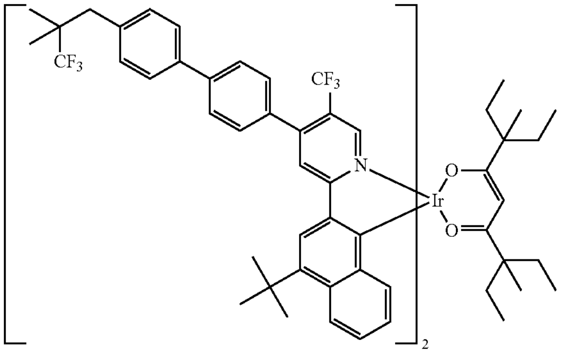
, -continued
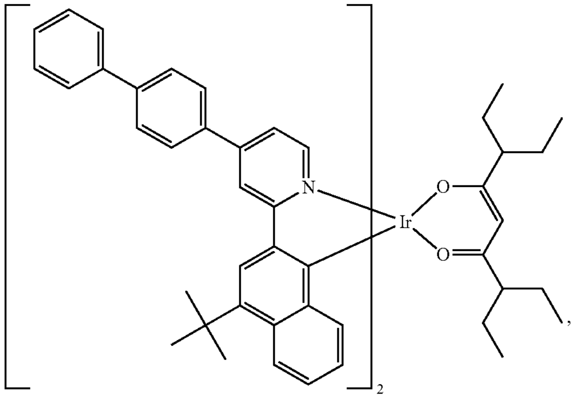
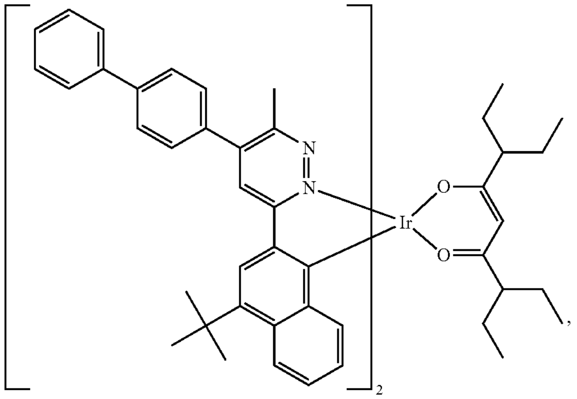
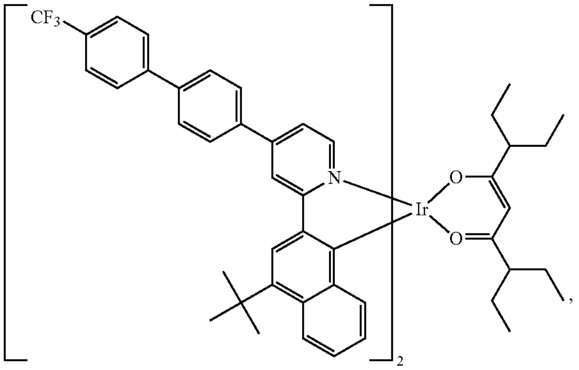
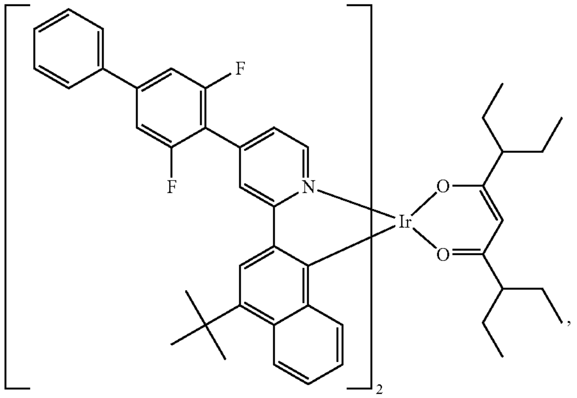
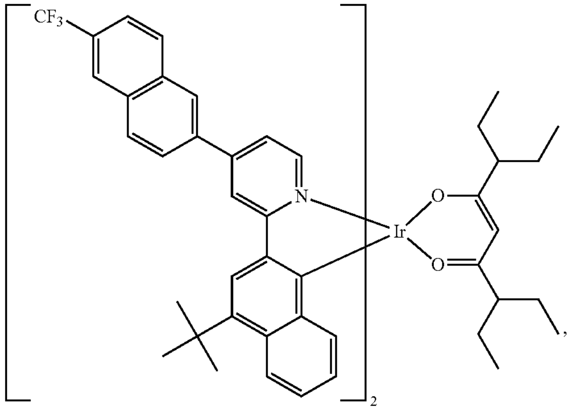
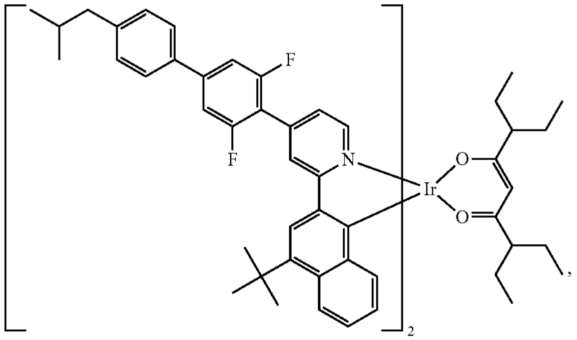
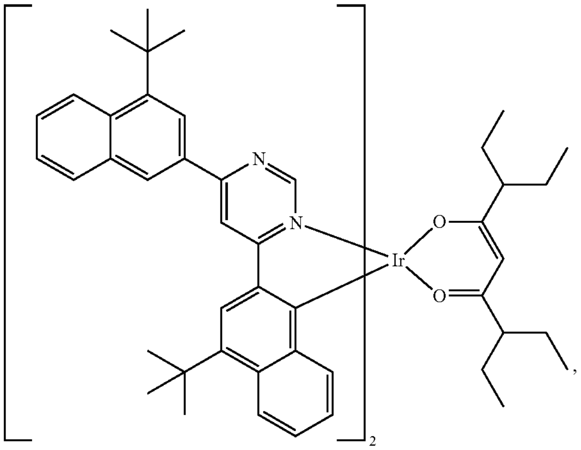
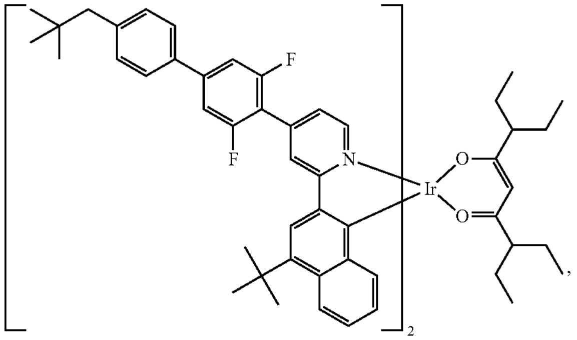

-continued
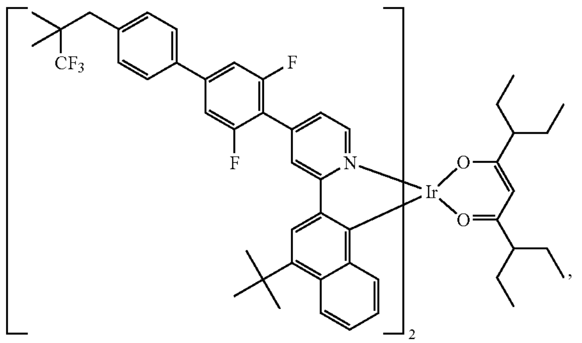
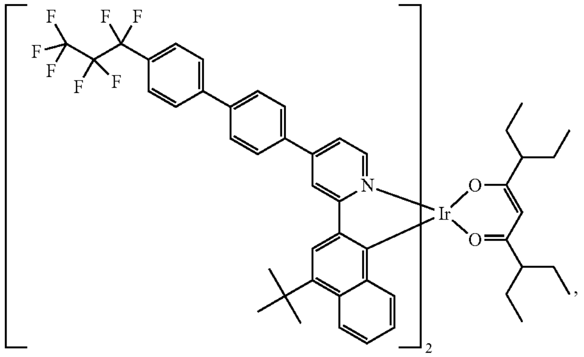
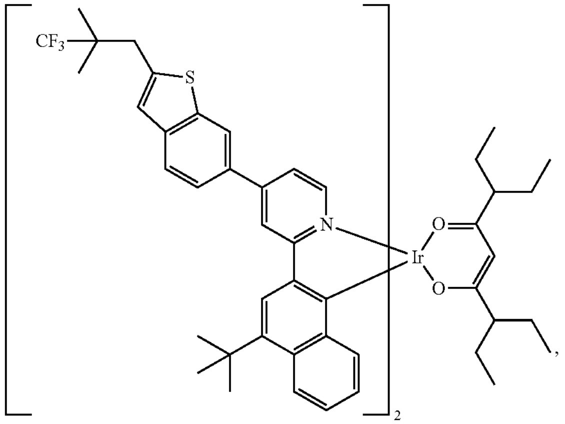
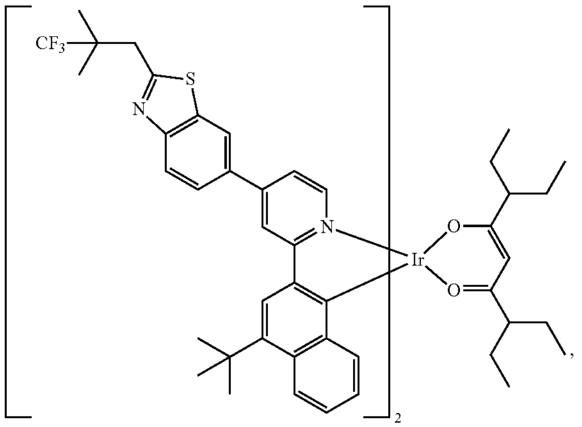
-continued
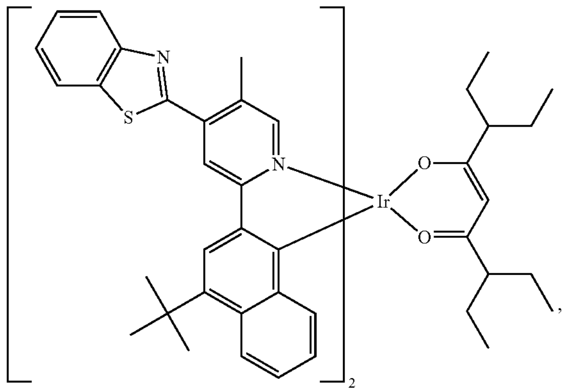
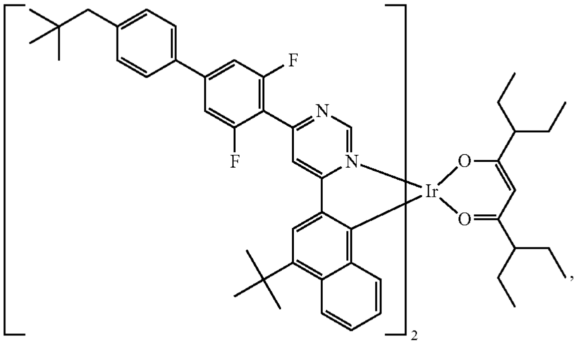
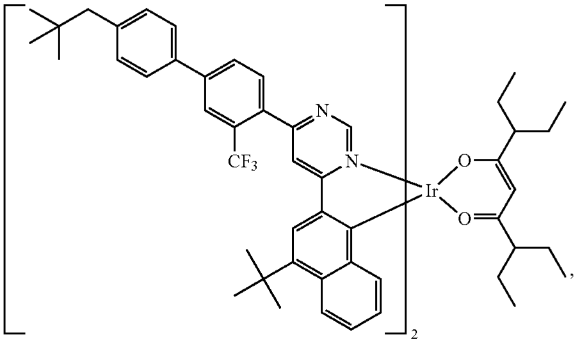
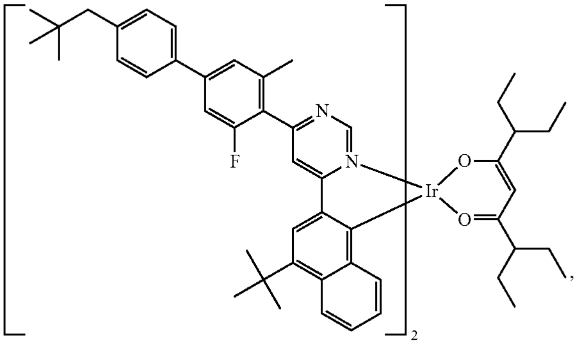

-continued
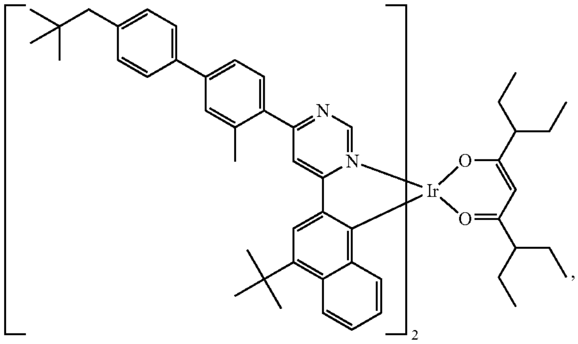
,
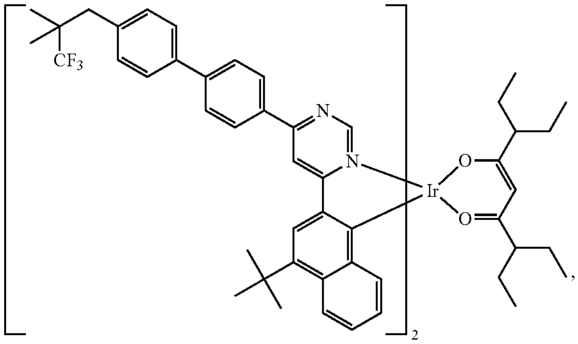
,
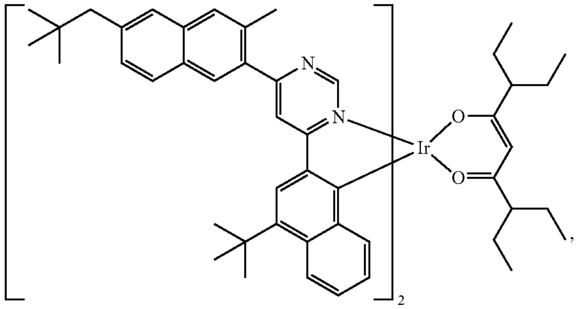
,
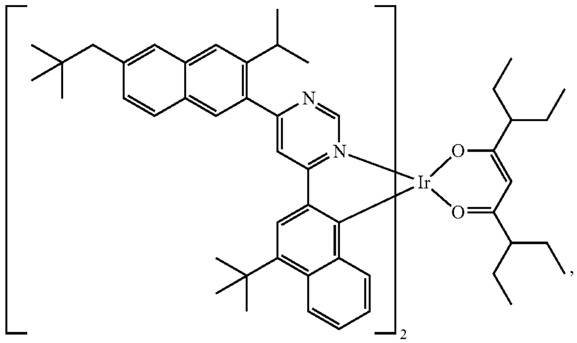
,
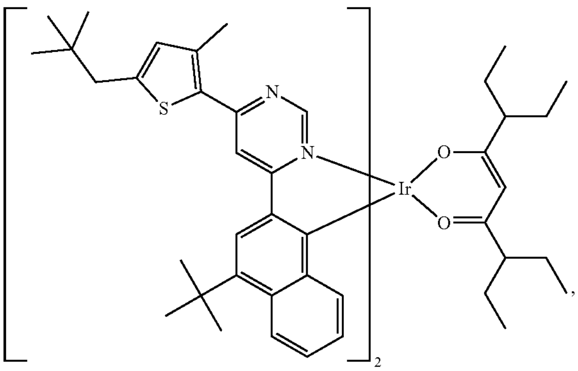
,
-continued
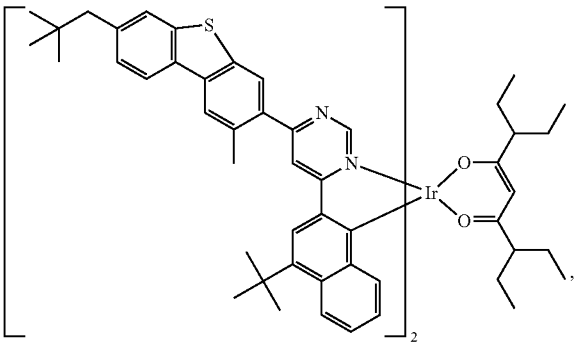
,
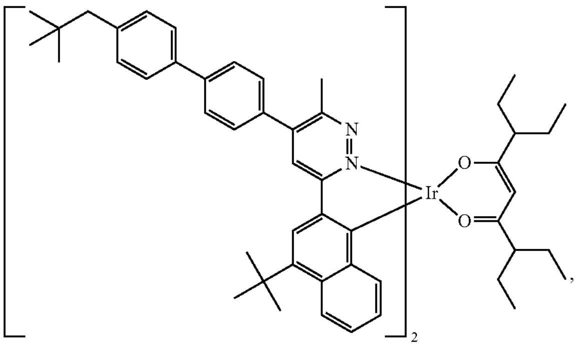
,
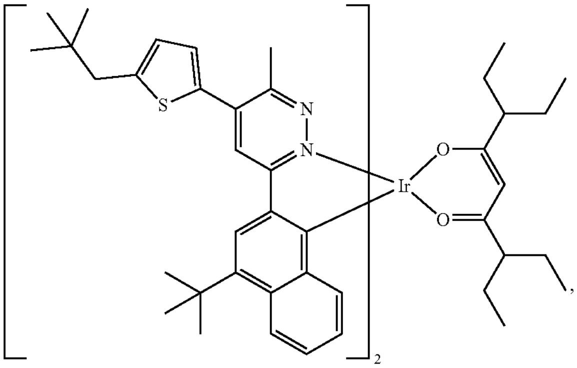
,
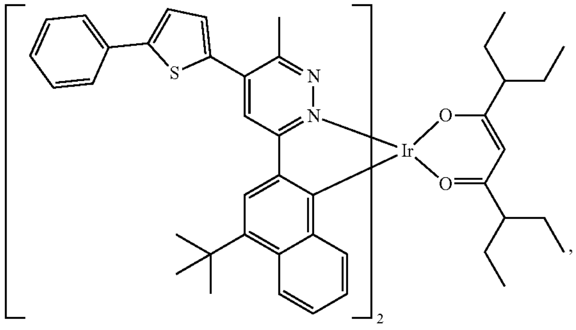
, -continued
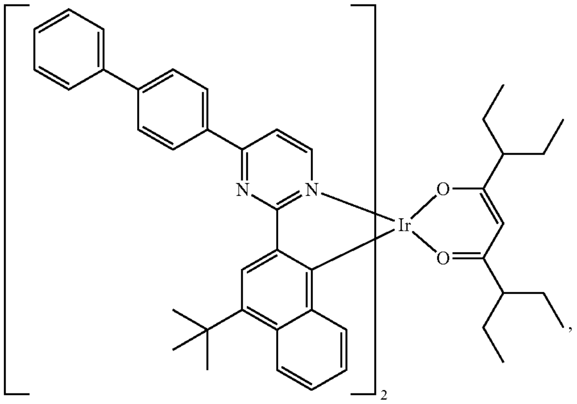
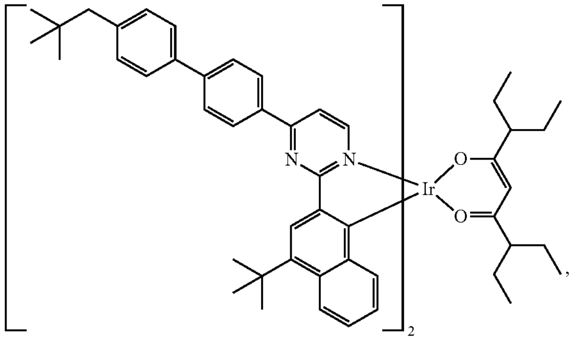
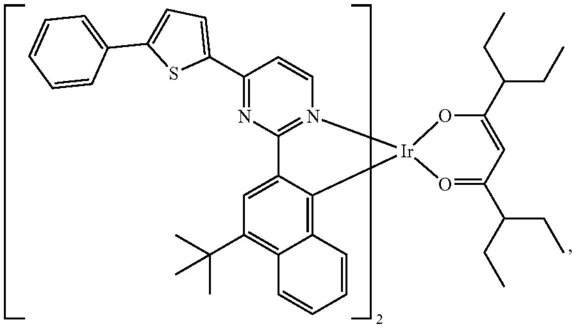
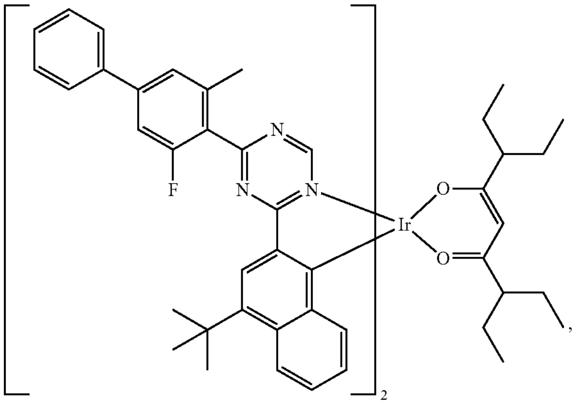
-continued
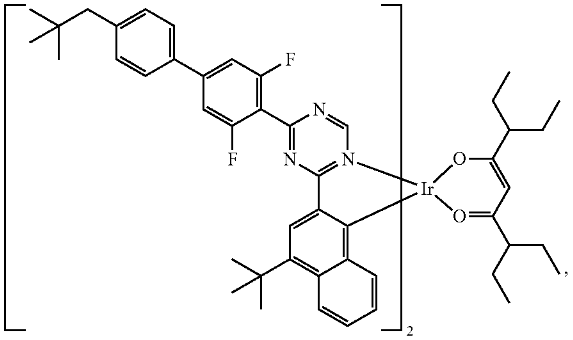
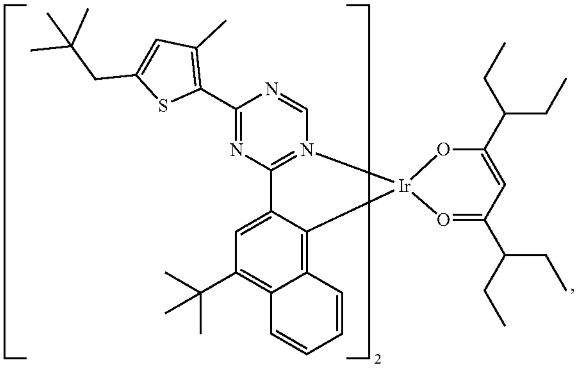
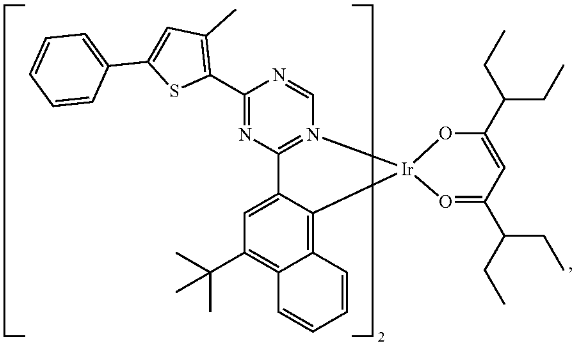
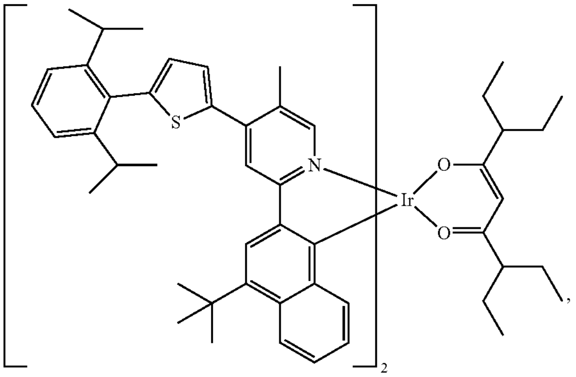

-continued
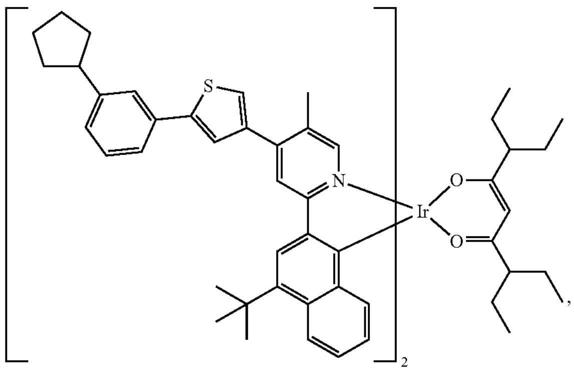
,
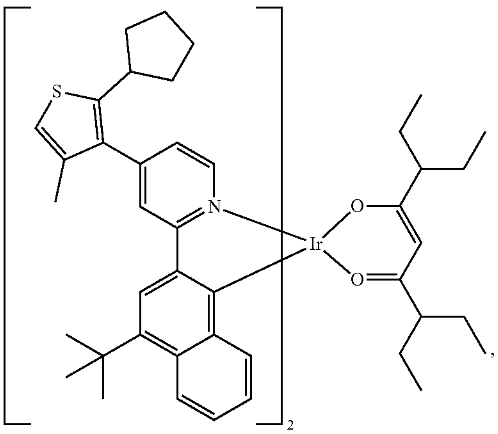
,
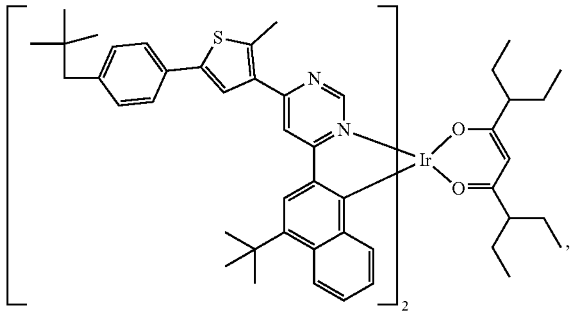
,
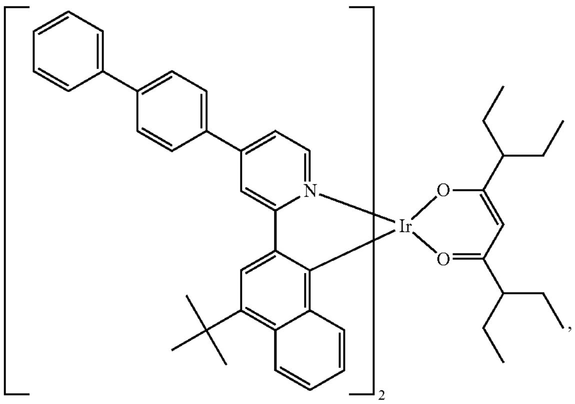
,
-continued
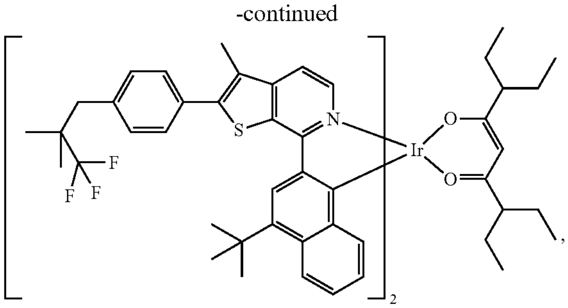
,
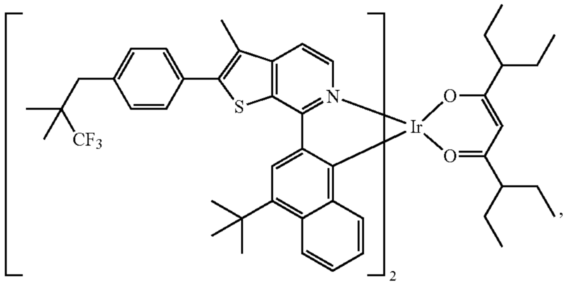
,
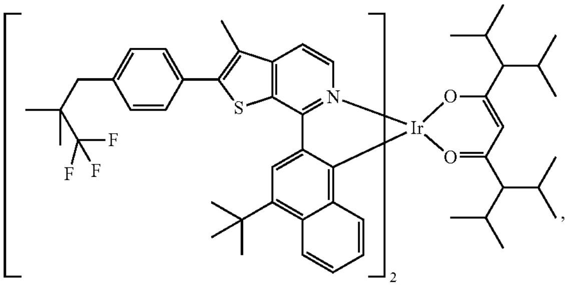
,
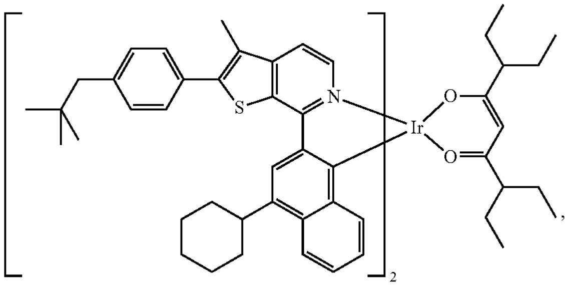
,
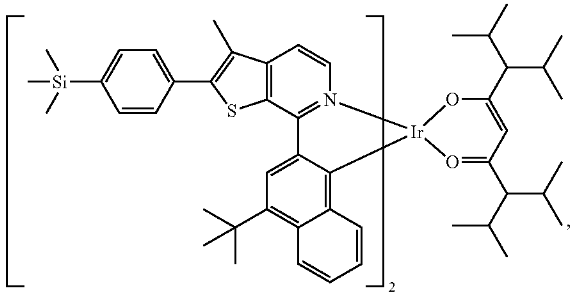
,
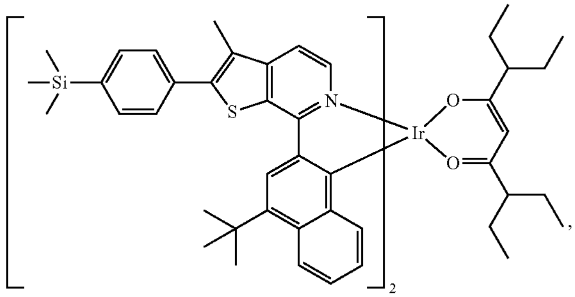
, -continued
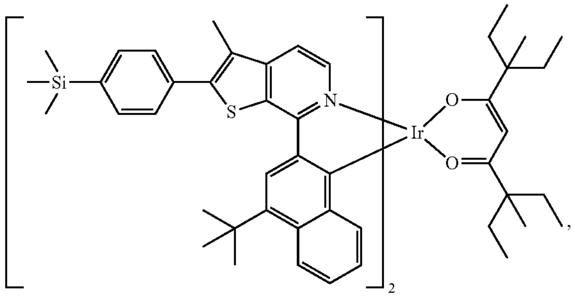,
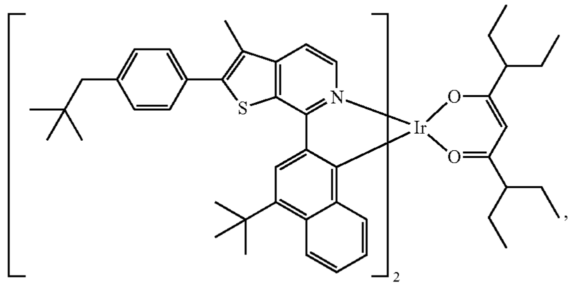,
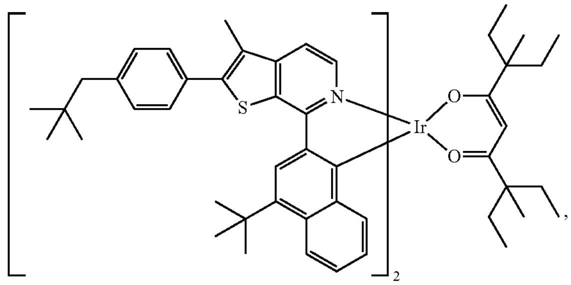,
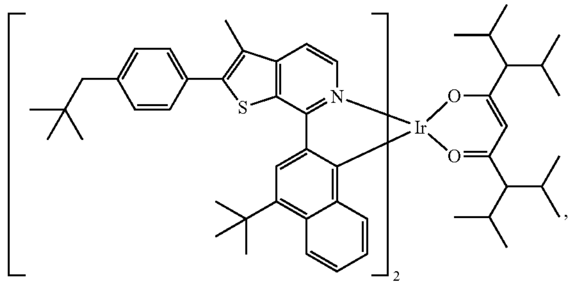,
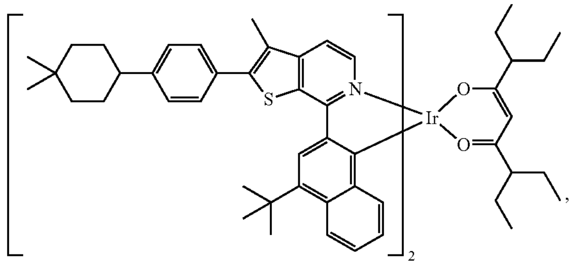,
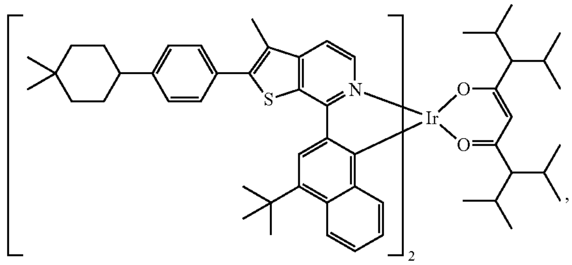,
-continued
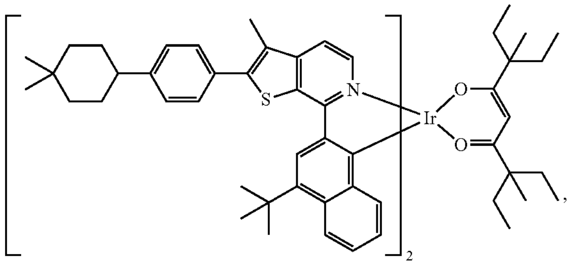,
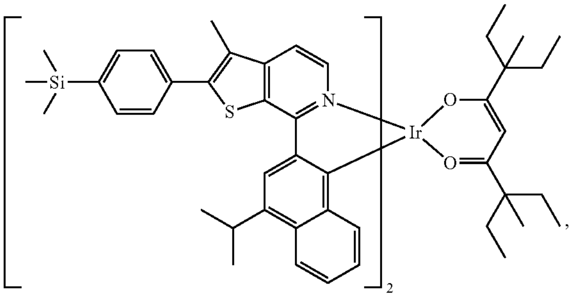,
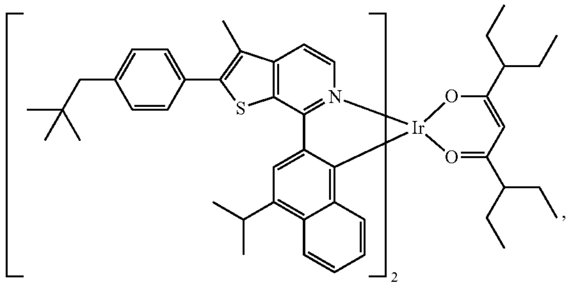,
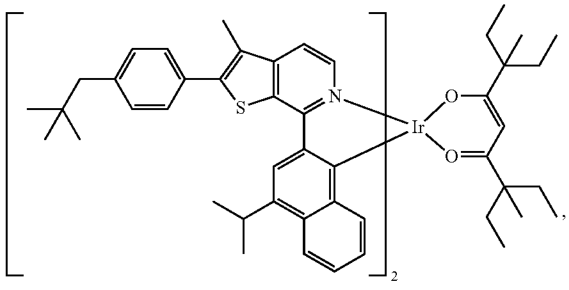,
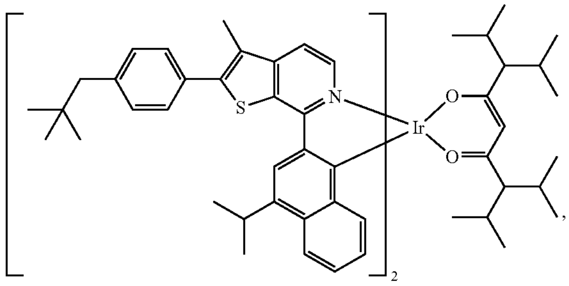,

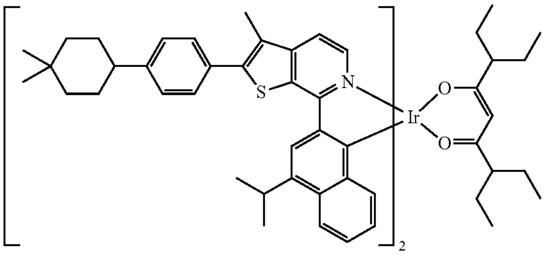
,
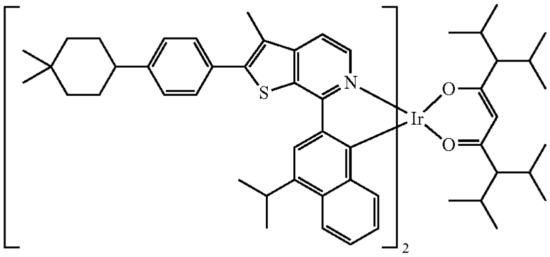
,
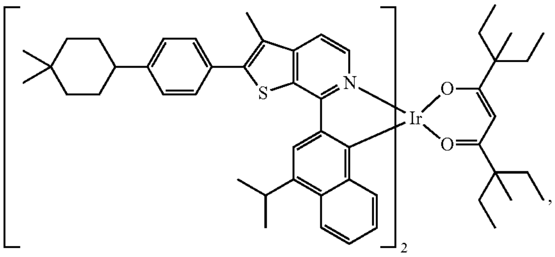
,
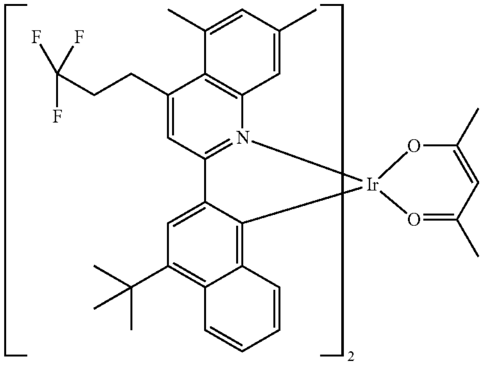
,
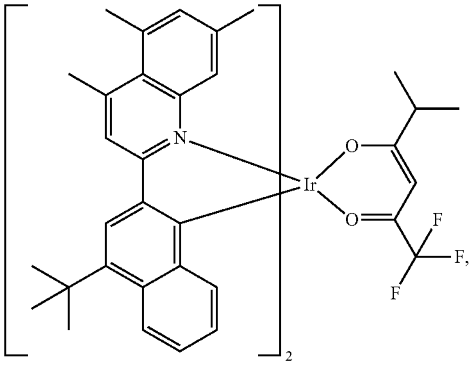
,
-continued
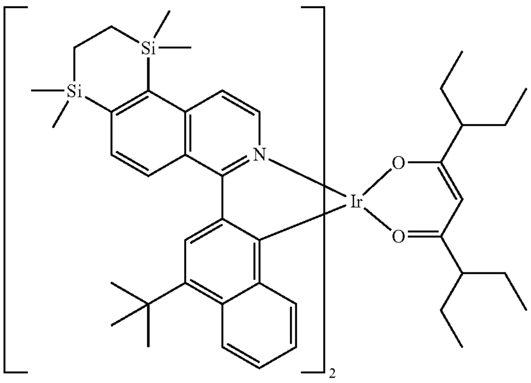
,
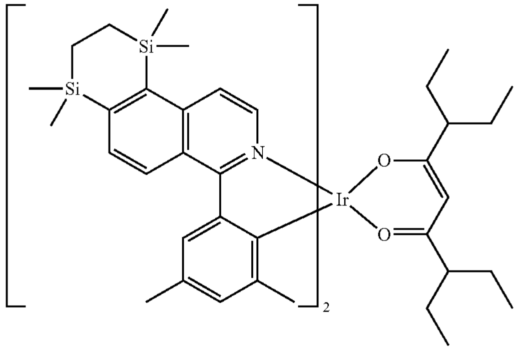
,
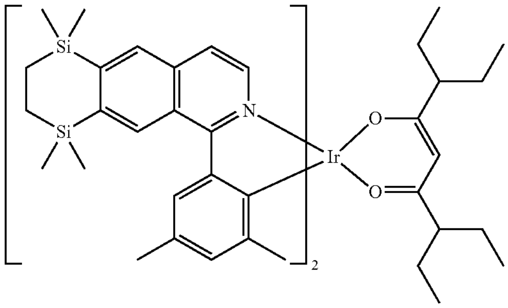
,
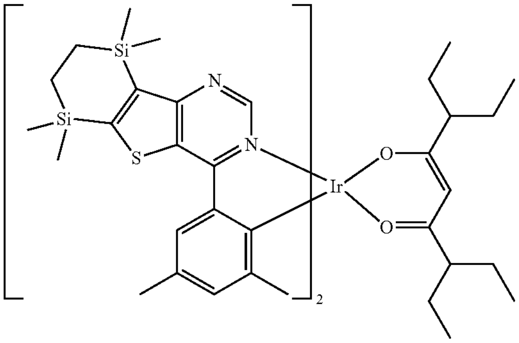
, -continued
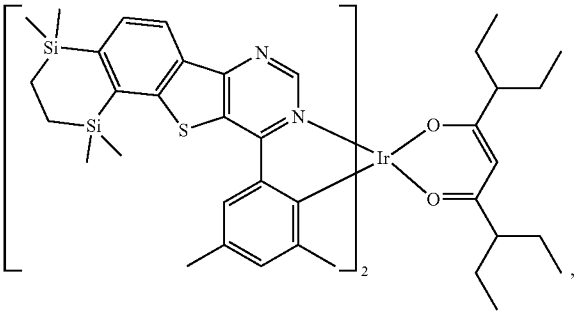
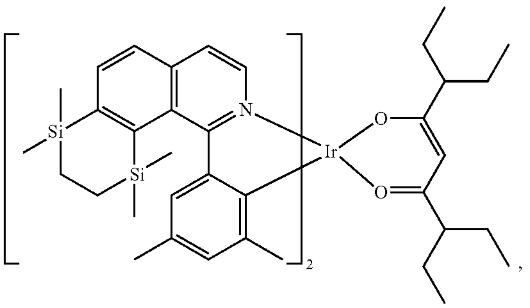
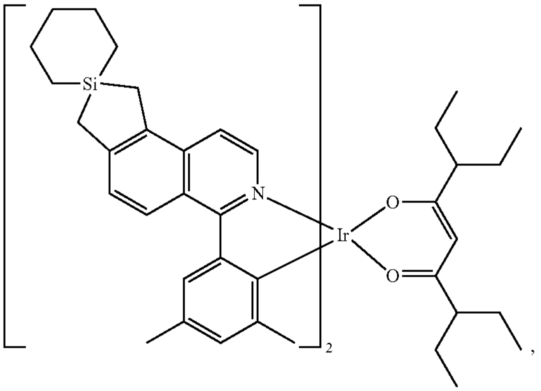
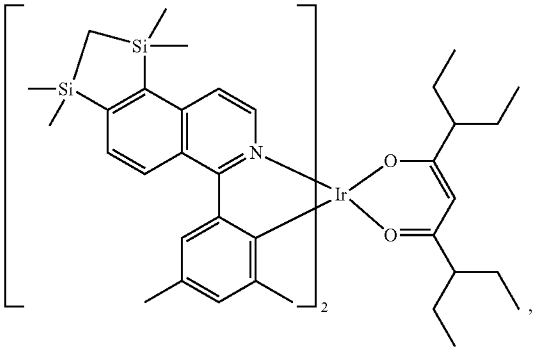
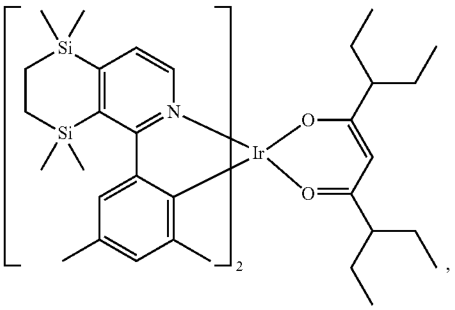
-continued
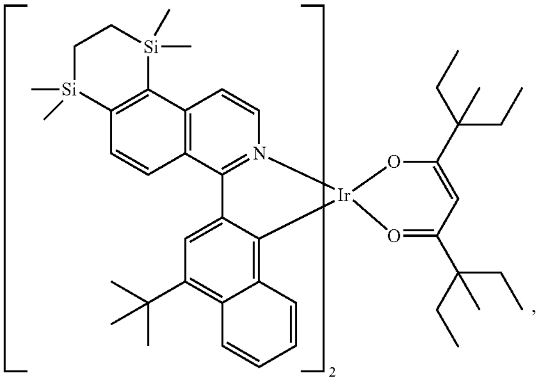
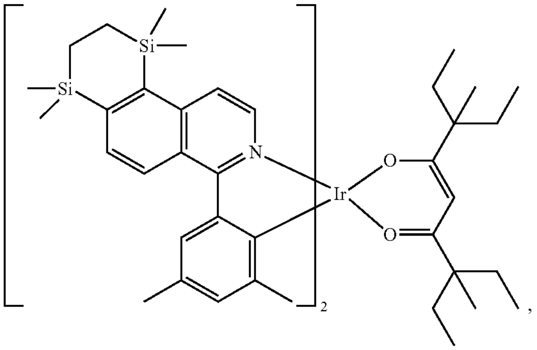
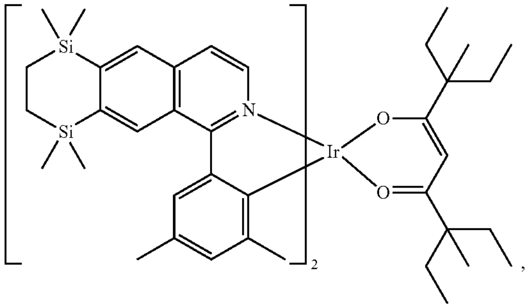
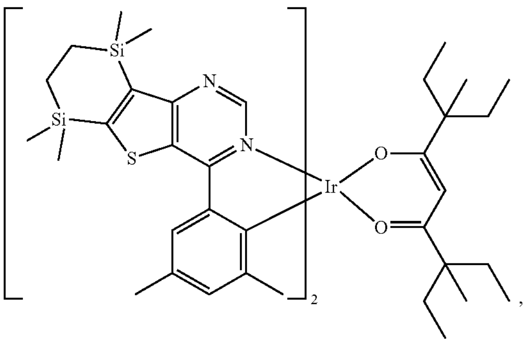

-continued
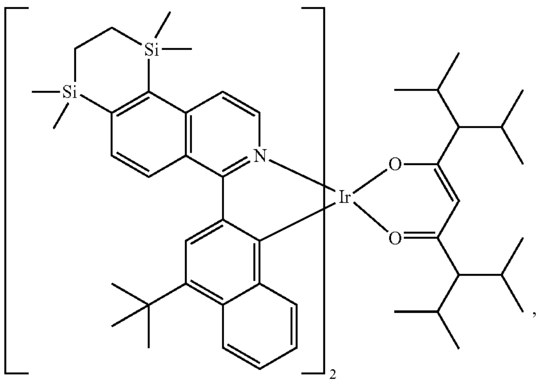
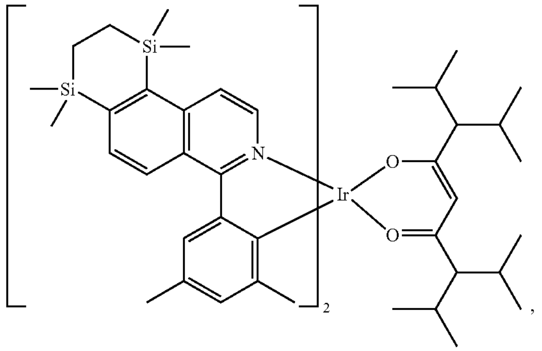
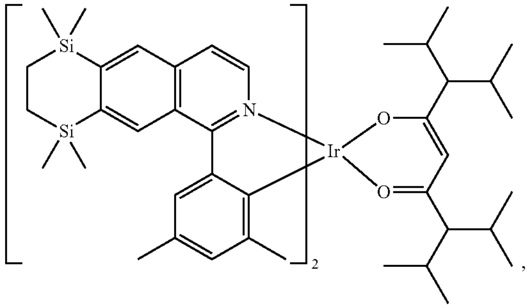
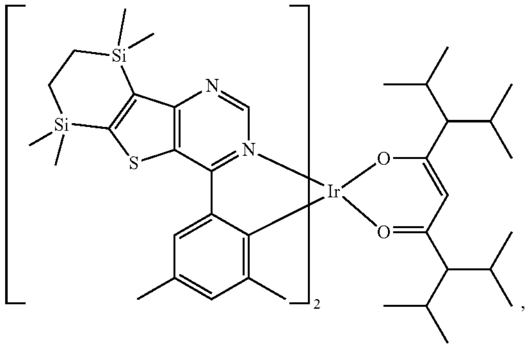
-continued
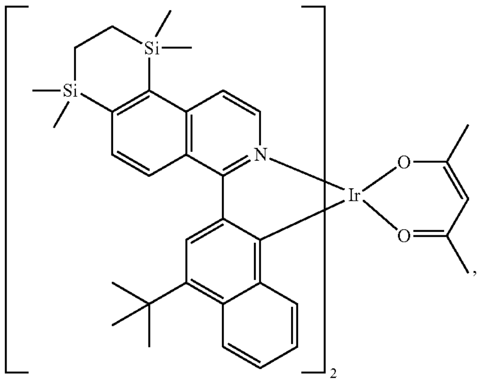
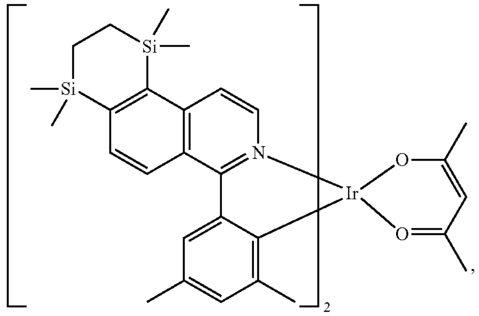
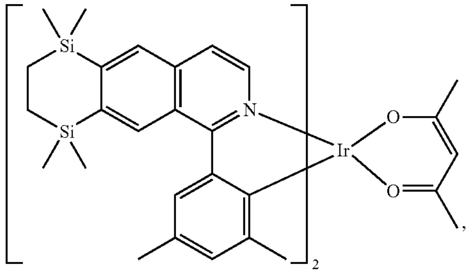
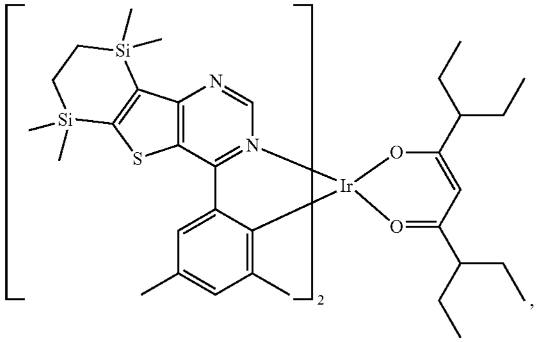
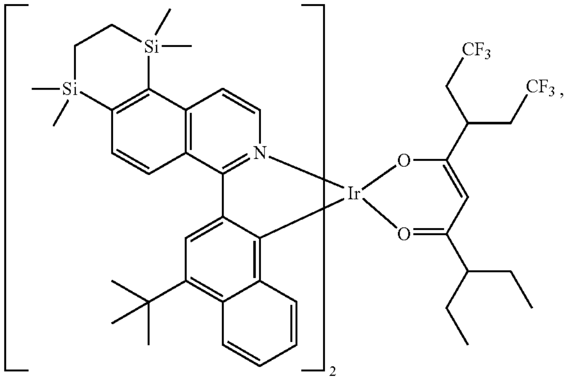

-continued
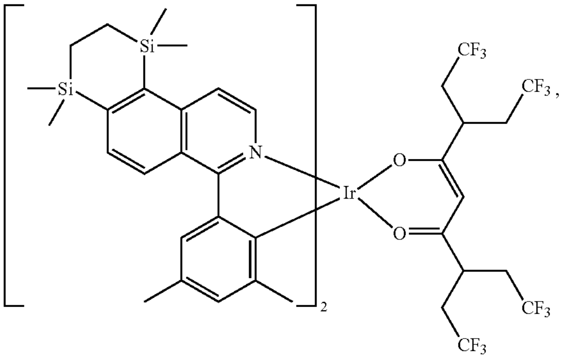
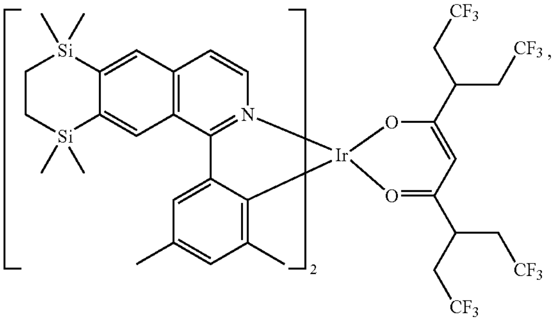
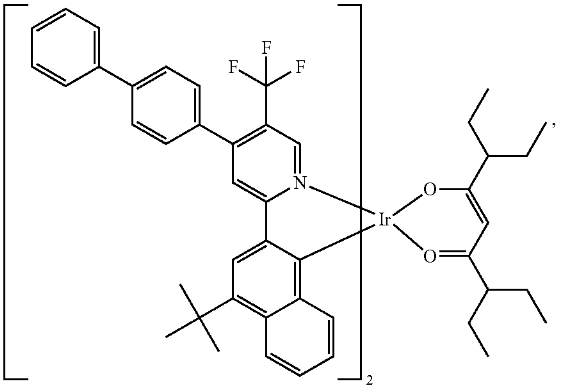
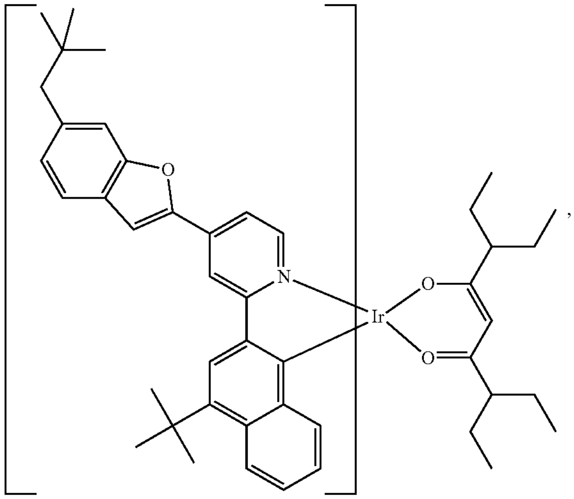
-continued
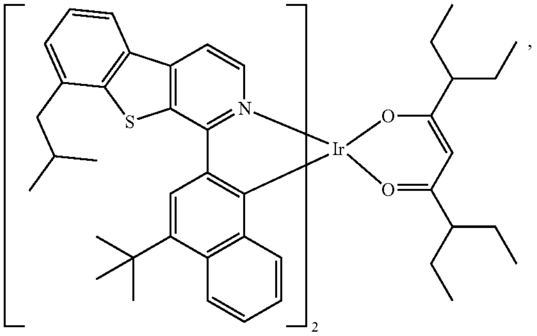
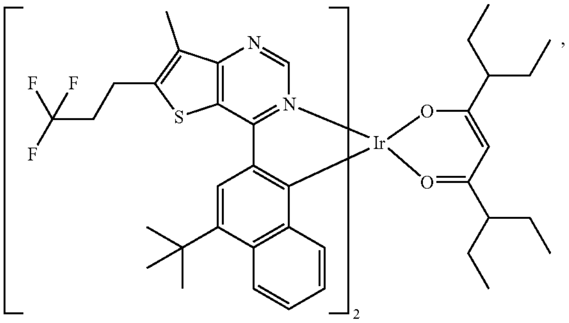
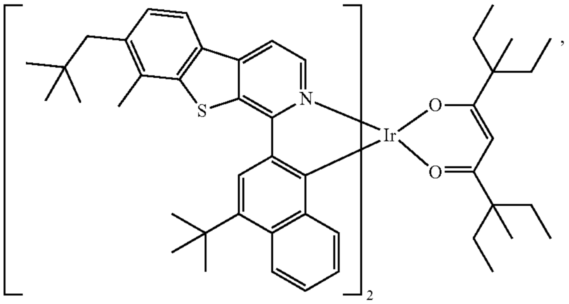
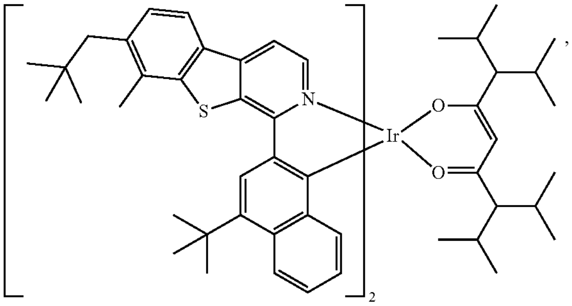
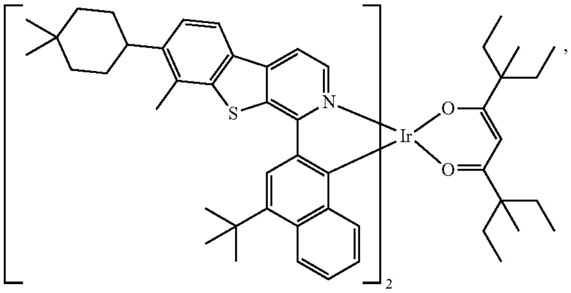

-continued
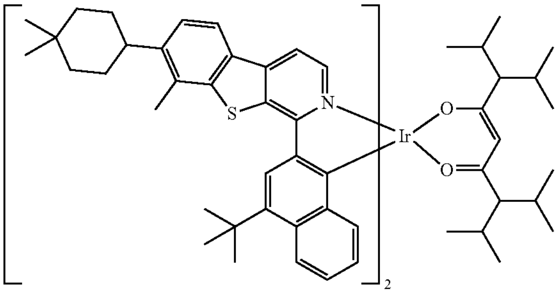
,
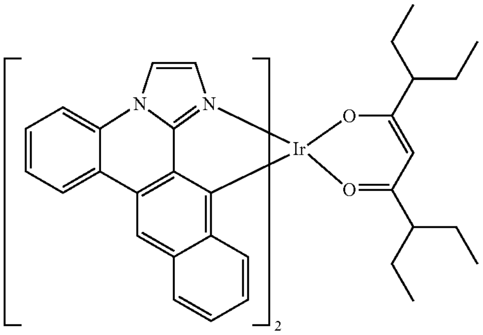
,
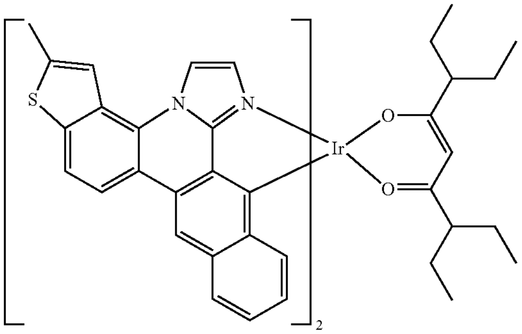
,
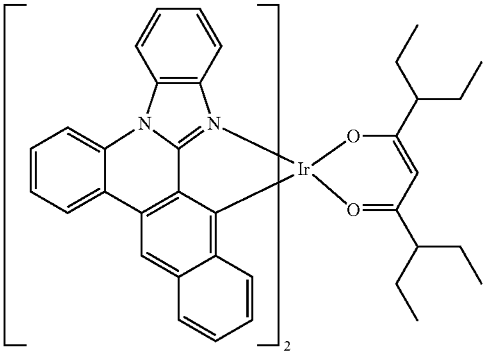
,
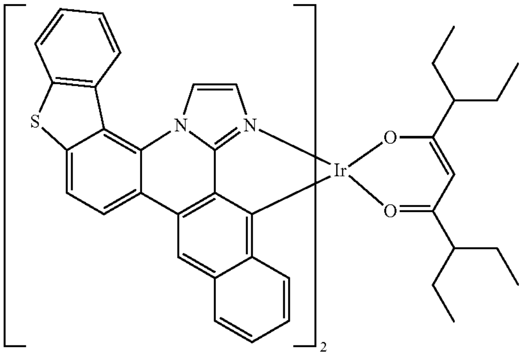
,
-continued
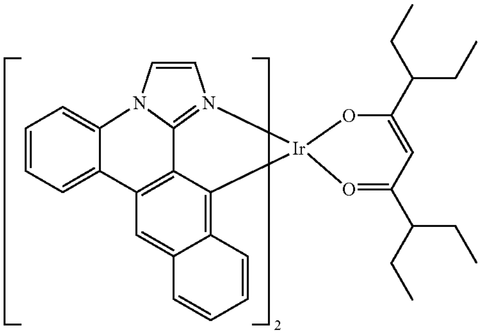
,
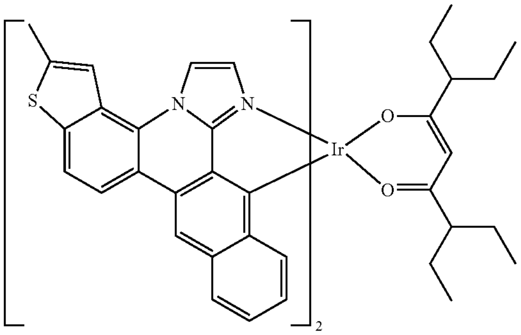
,
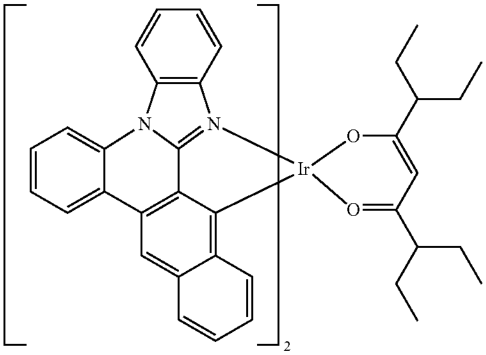
,
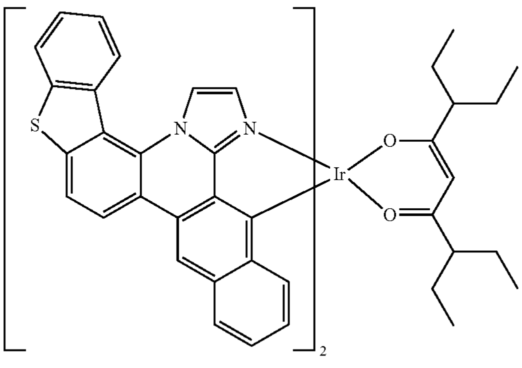
, -continued
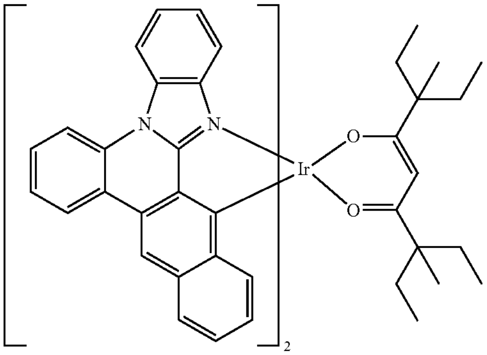
,
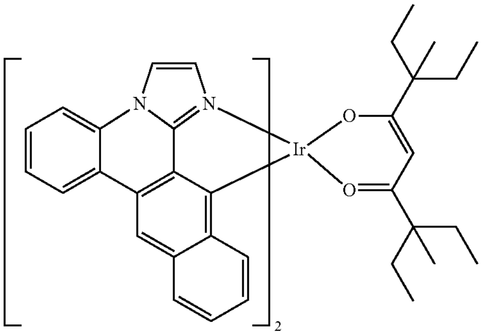
,
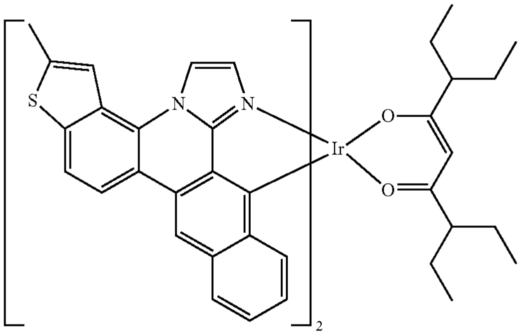
,
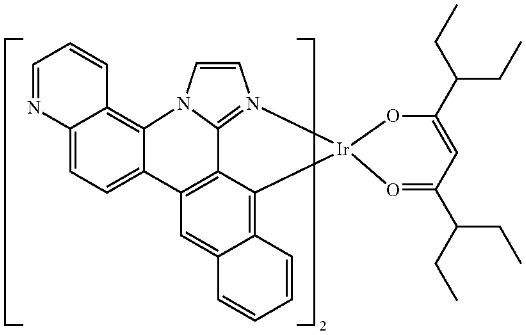
,
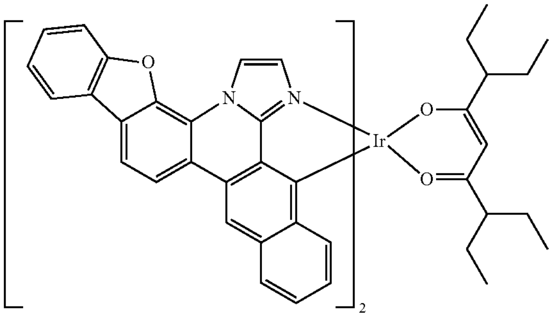
,
-continued
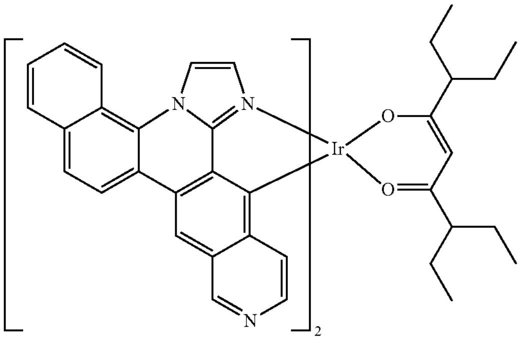
,
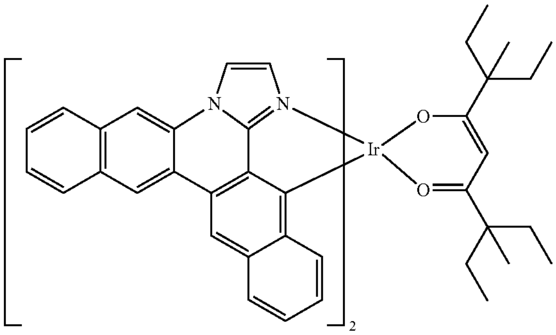
,
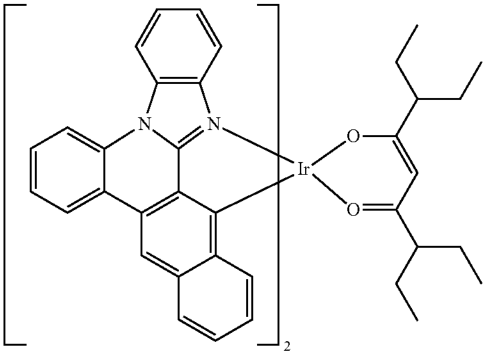
,
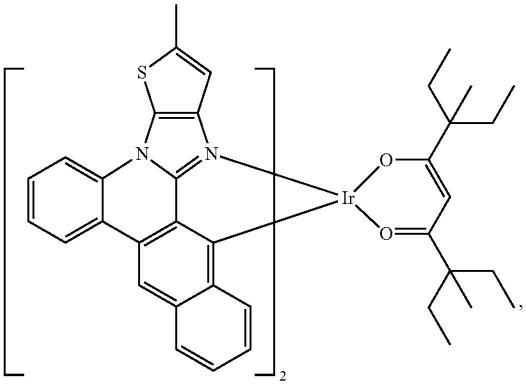
, -continued
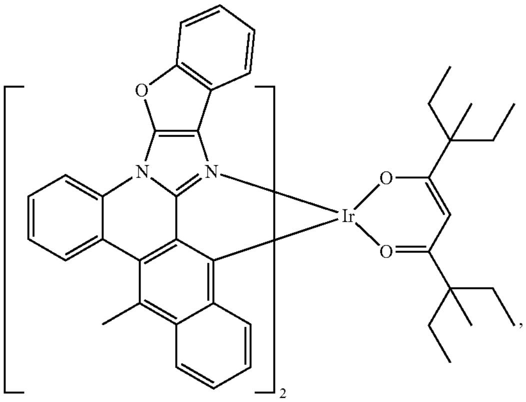
,
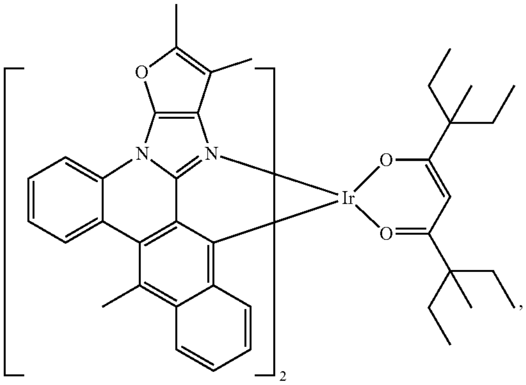
,
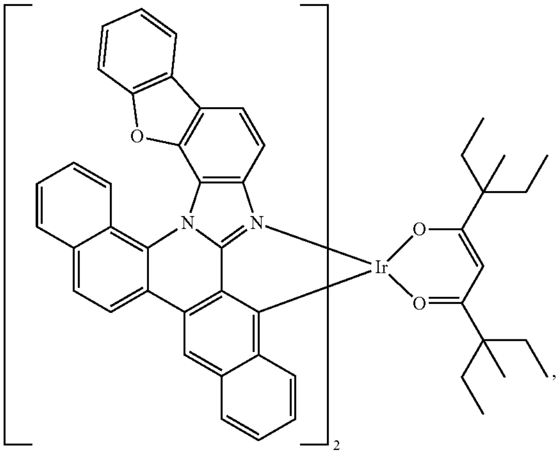
,
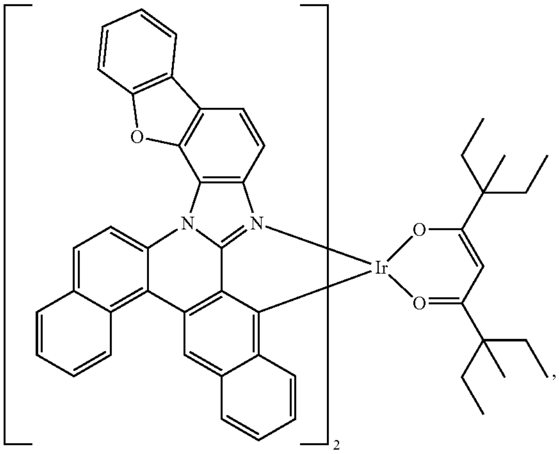
,
-continued
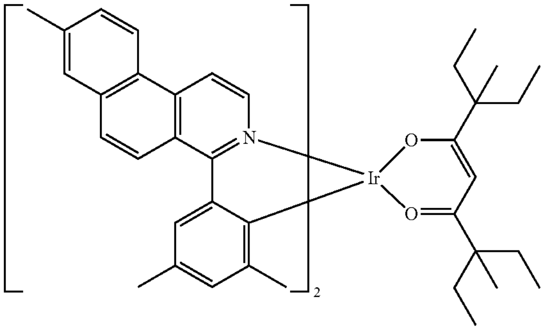
,
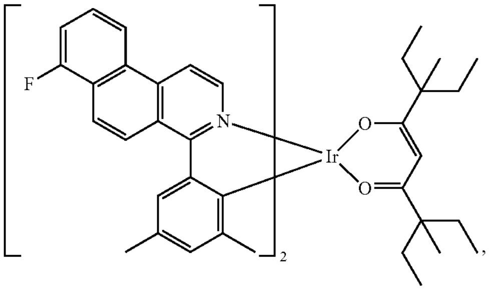
, and
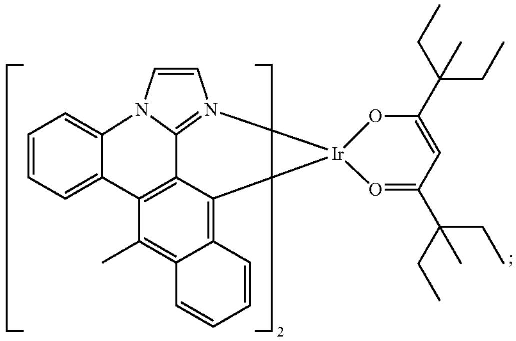
;
or
wherein the phosphorescent dopant is selected from the group consisting of:
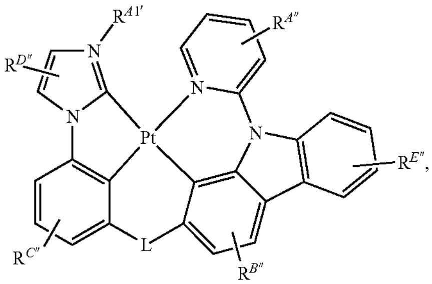
,
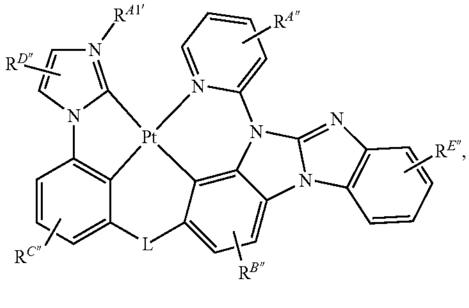
, -continued
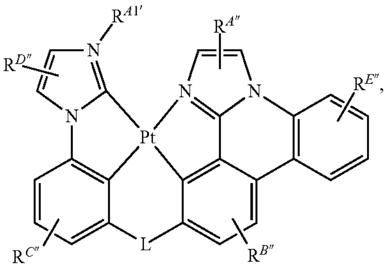
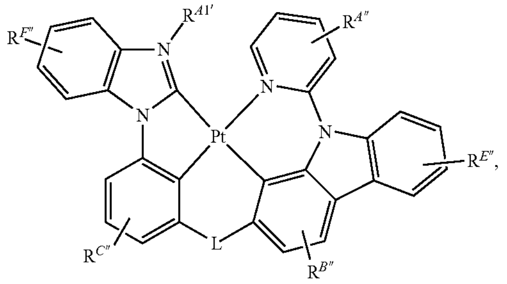
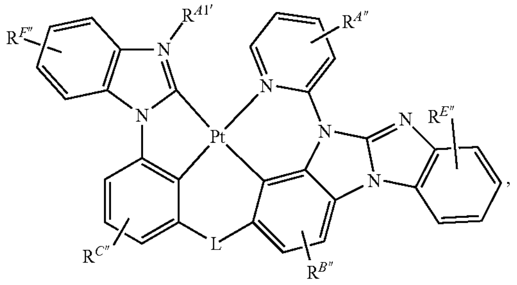
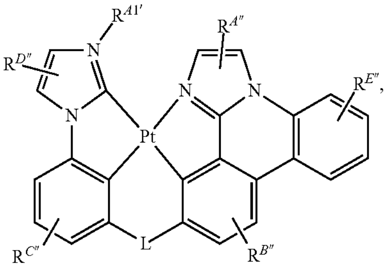
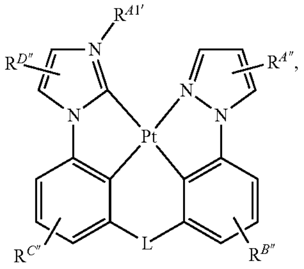
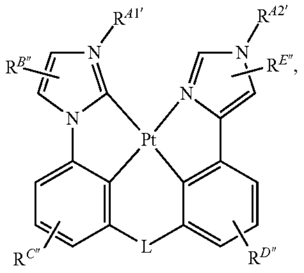
-continued
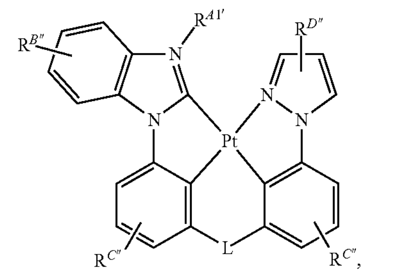
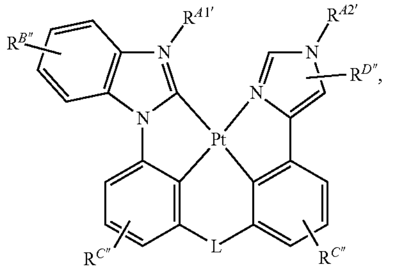
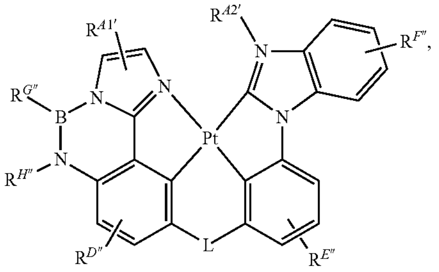
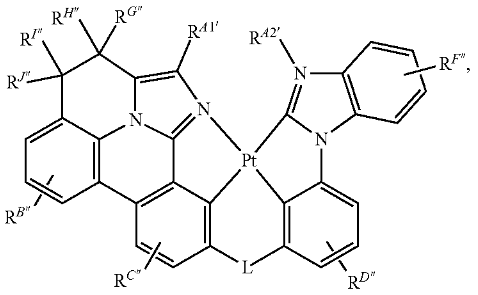
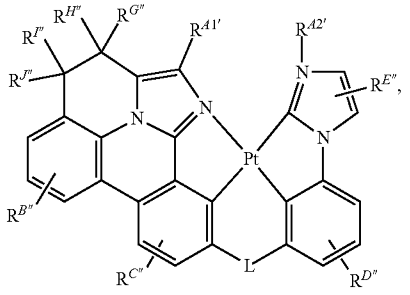
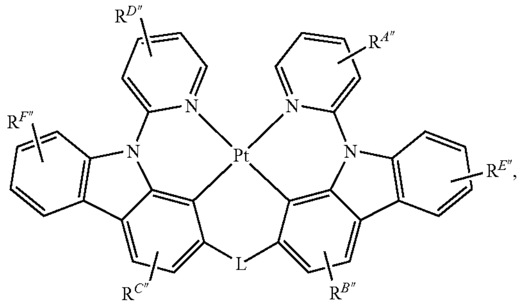

-continued
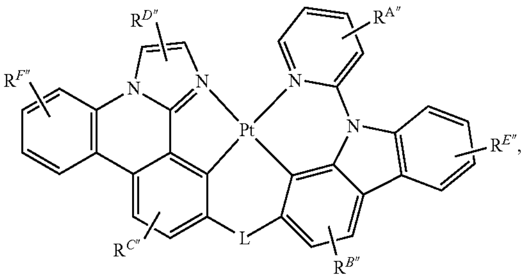
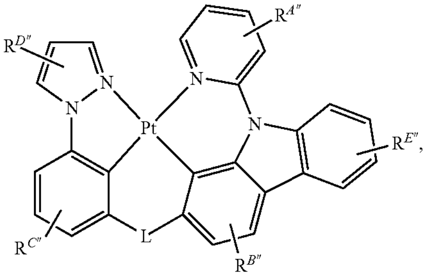
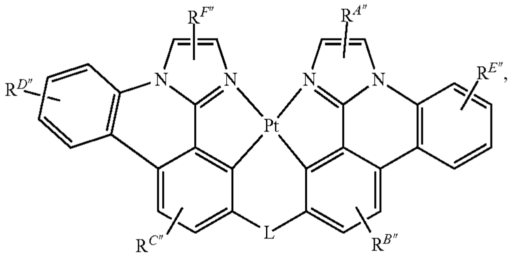
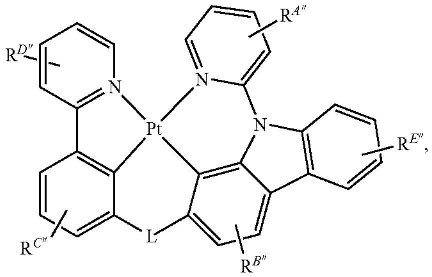
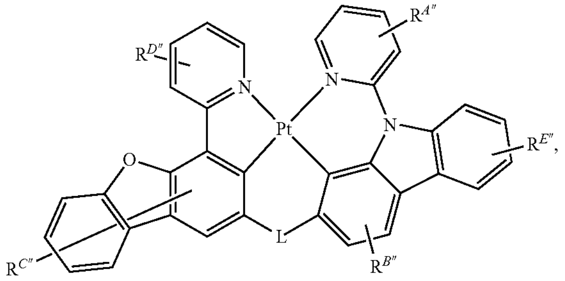
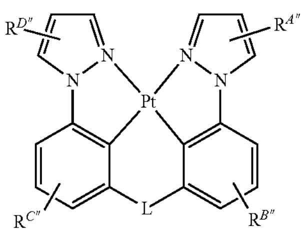
-continued
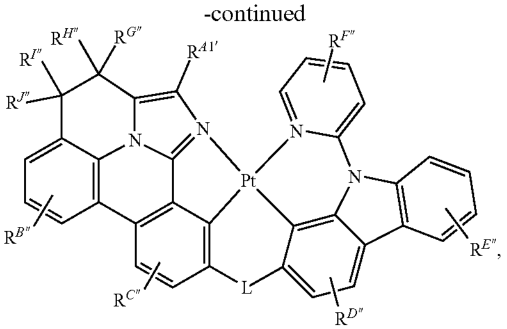
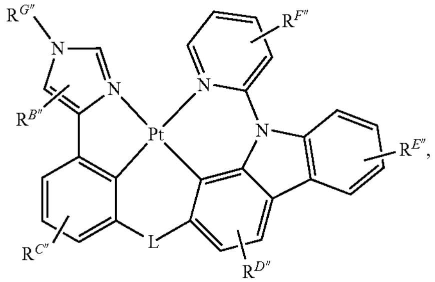
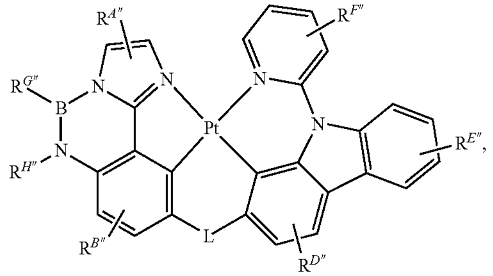
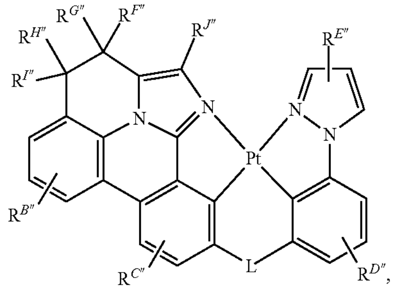
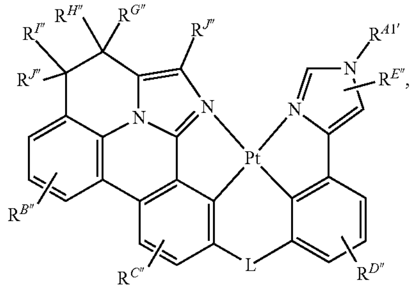
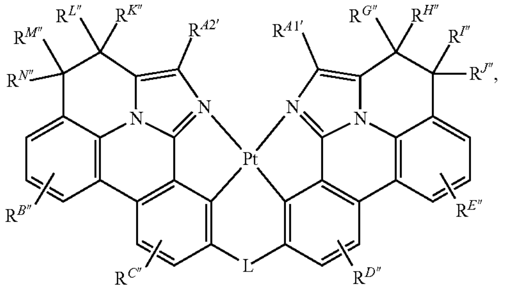

-continued
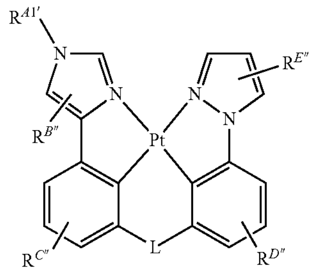
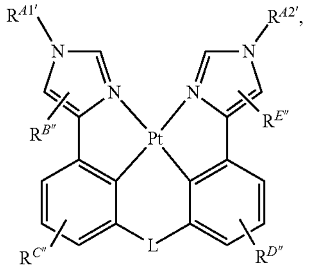
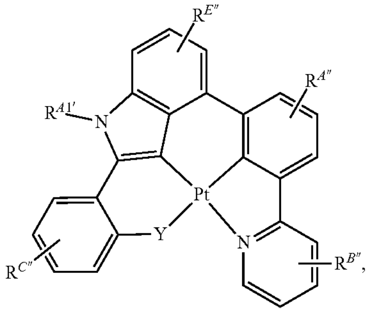
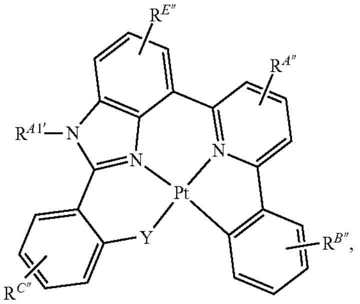
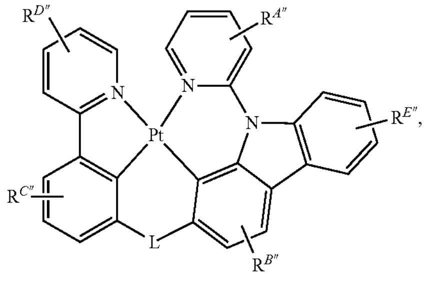
-continued
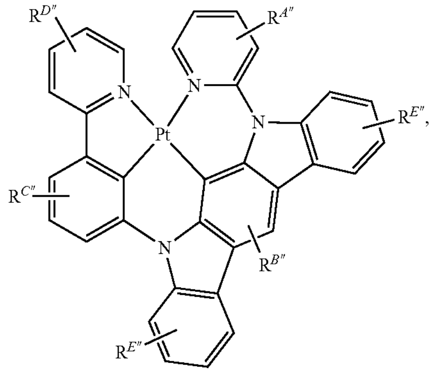
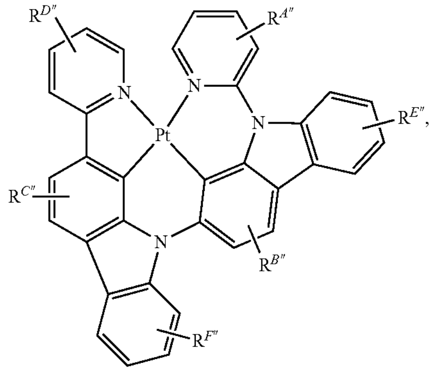
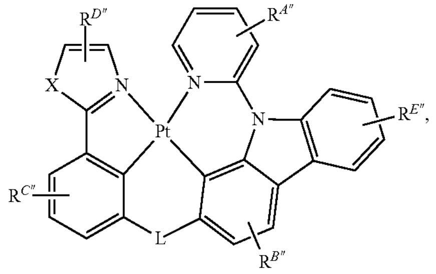
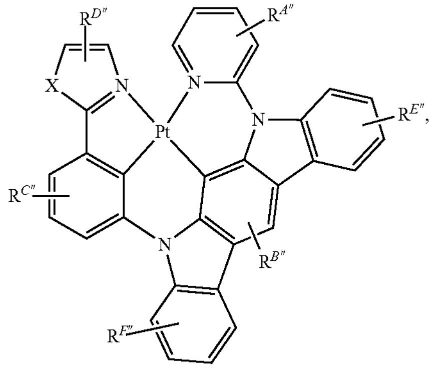

-continued
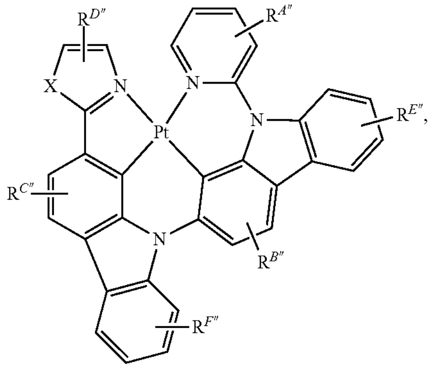
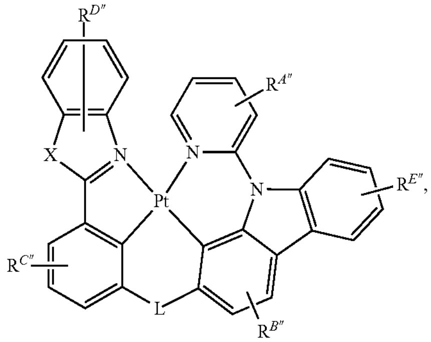
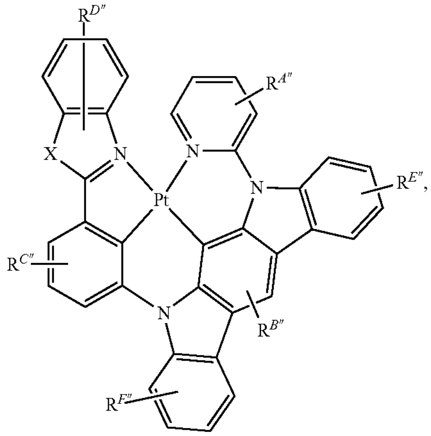
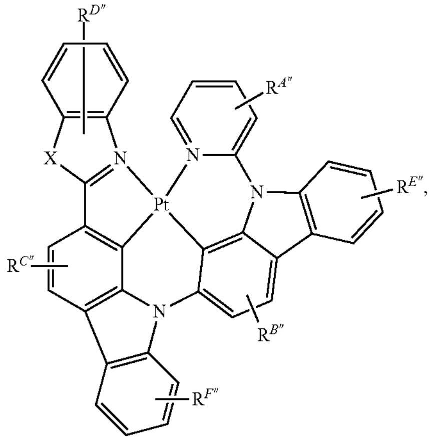
-continued
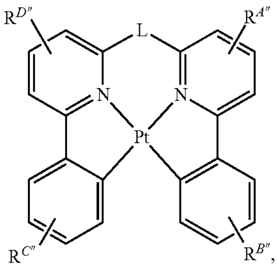
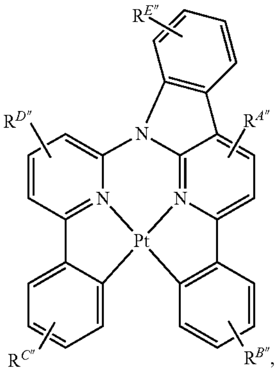
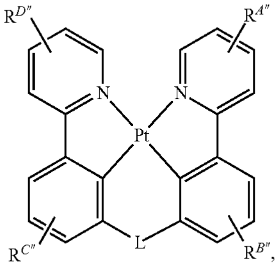
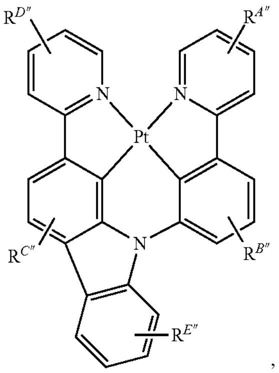
,
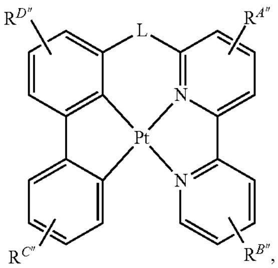
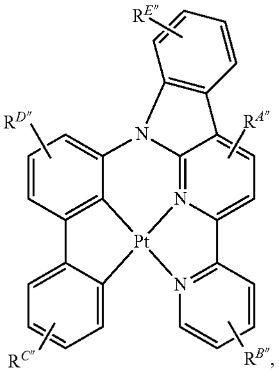
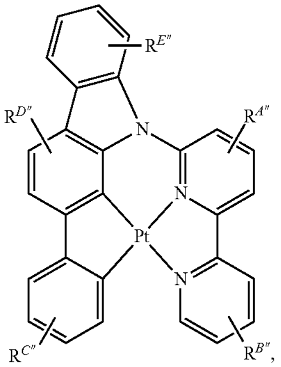

-continued
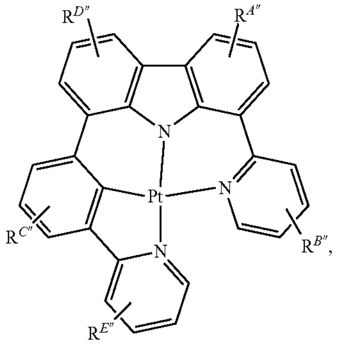
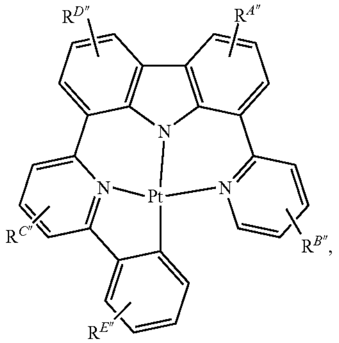
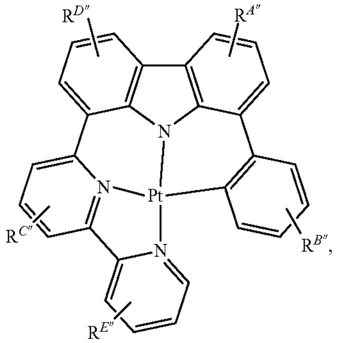
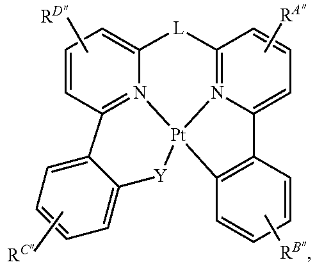
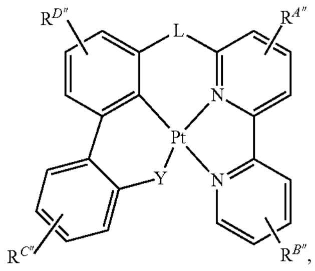
-continued
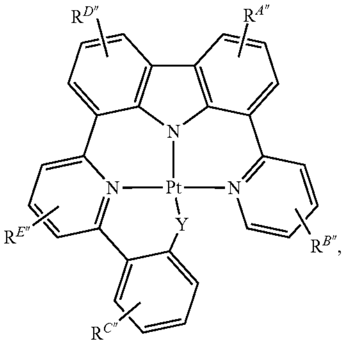
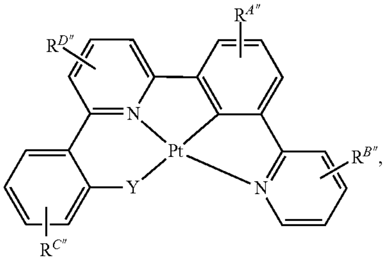
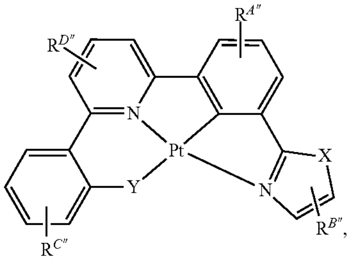
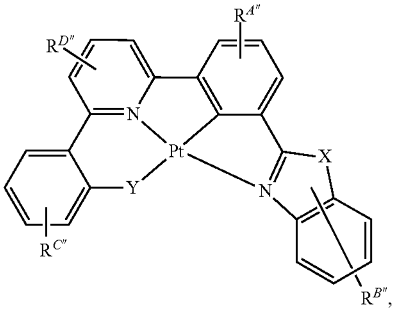
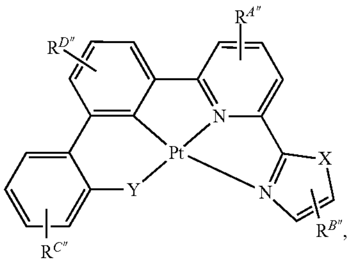

-continued

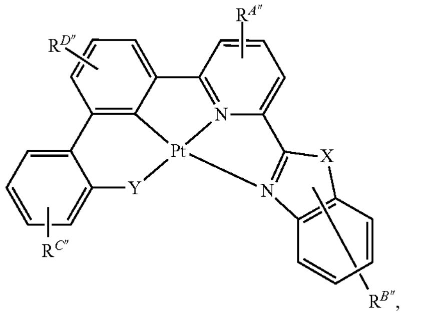

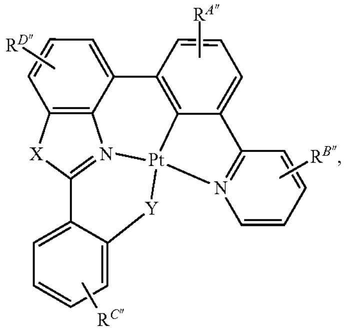

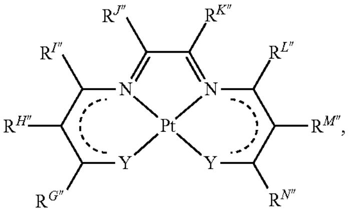

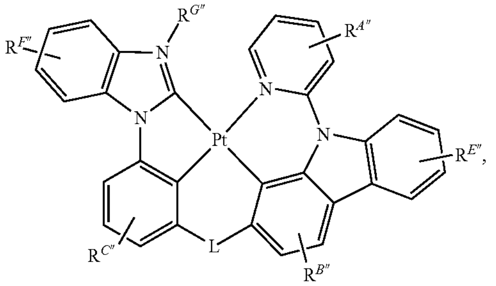

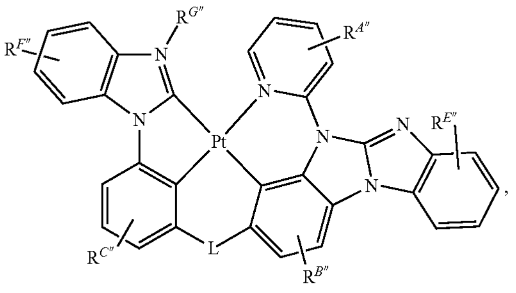

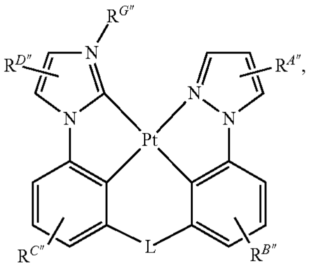

-continued

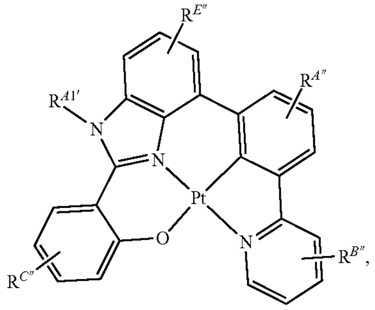

and

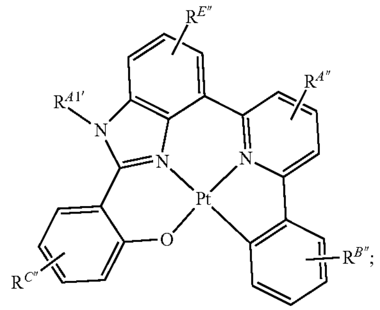

wherein:

each Y is independently selected from the group consisting of a NR, O, S, and Se;

L is independently selected from the group consisting of a direct bond, BR, BRR', NR, PR, O, S, Se, C═X', S═O, $SO_2$, CR, CRR', SiRR', GeRR', alkyl, cycloalkyl, aryl, heteroaryl, and combinations thereof;

each X and X' is independently selected from the group consisting of O, S, Se, NR", and CR"R";

each R, R', R", R"', $R^{A''}$, $R^{B''}$, $R^{C''}$, $R^{D''}$, $R^{E''}$, and $R^{F''}$ independently represents mono-, up to the maximum substitutions, or no substitutions;

each of R, R', $R^{A1'}$, $R^{A2'}$, $R^{A''}$, $R^{B''}$, $R^{C''}$, $R^{D''}$, $R^{E''}$, $R^{F''}$, $R^{G''}$, $R^{H''}$, R", R", $R^{K''}$, $R^{L''}$, $R^{M''}$, and $R^{N''}$ is independently a hydrogen or a substituent selected from the group consisting of deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, germyl, selenyl, and combinations thereof.

18. The OLED of claim 14, wherein the phosphorescent dopant is selected from the group consisting of:

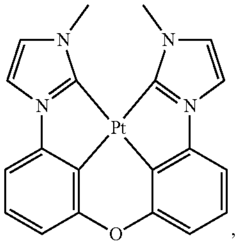

-continued
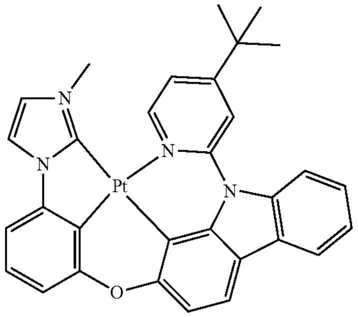
,
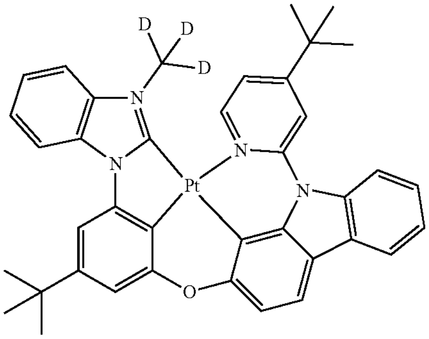
,
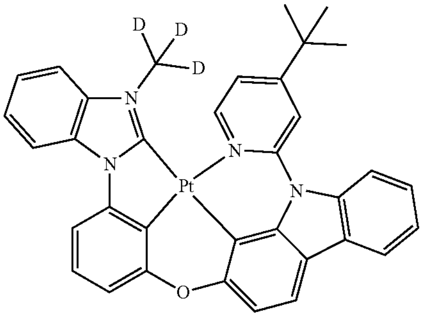
,
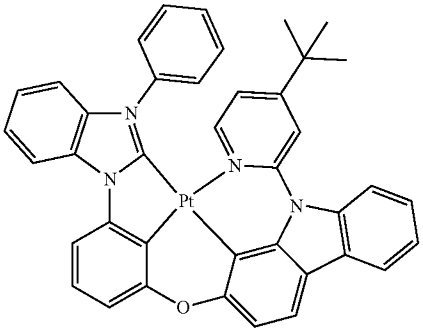
,
-continued
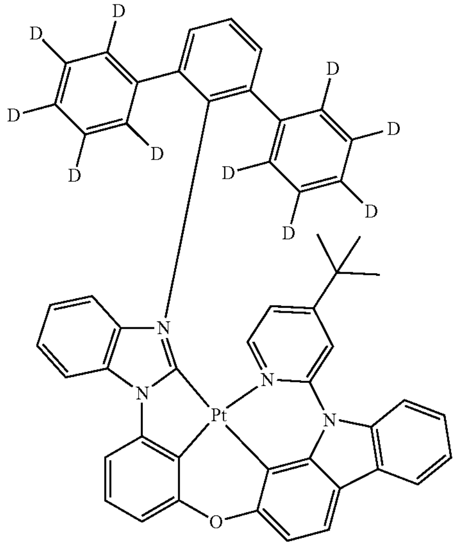
,
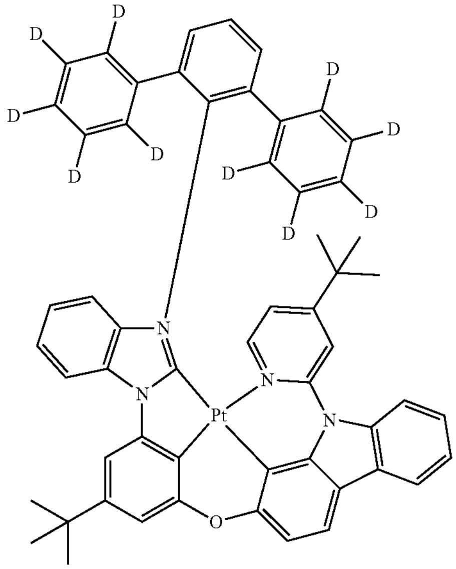
,
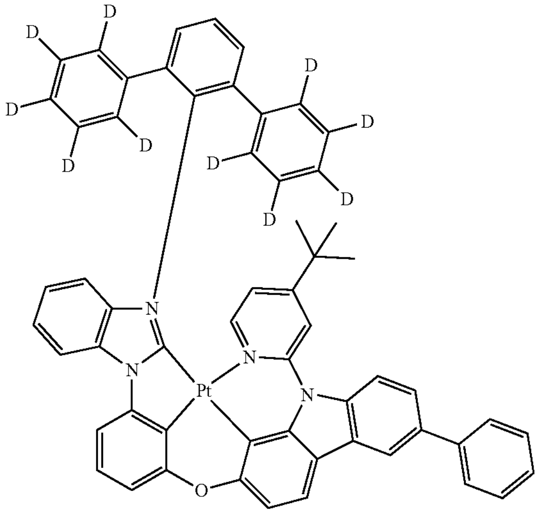
, -continued
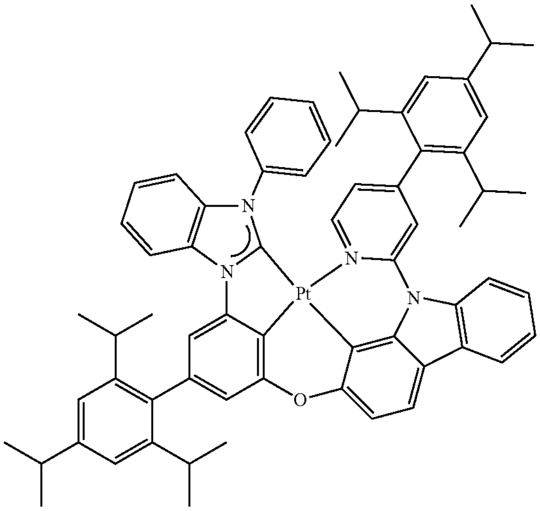
,
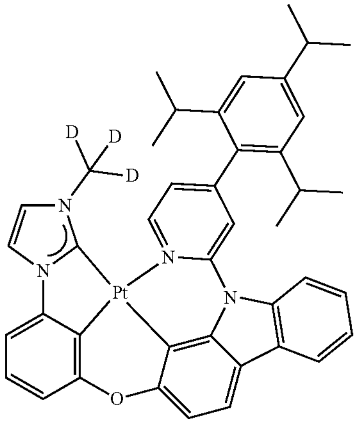
,
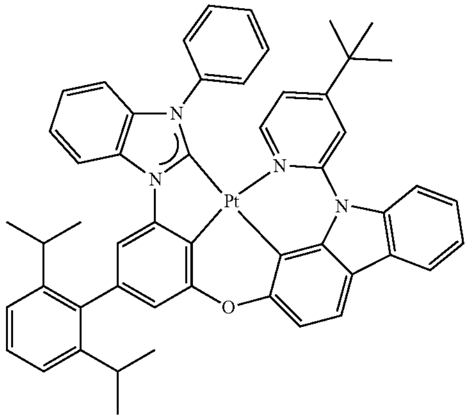
,
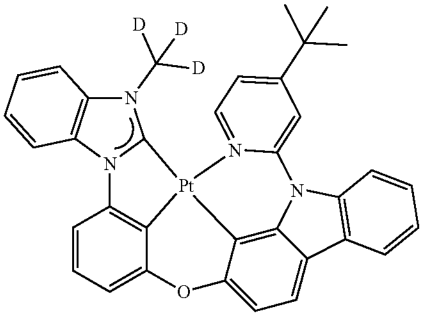
,
-continued
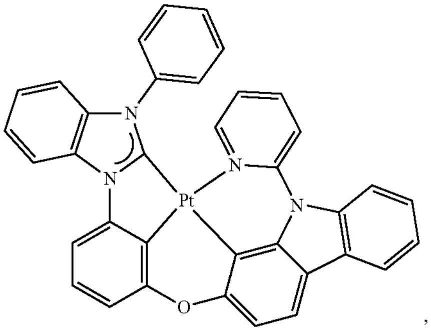
,
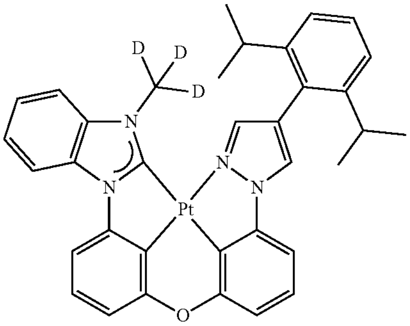
,
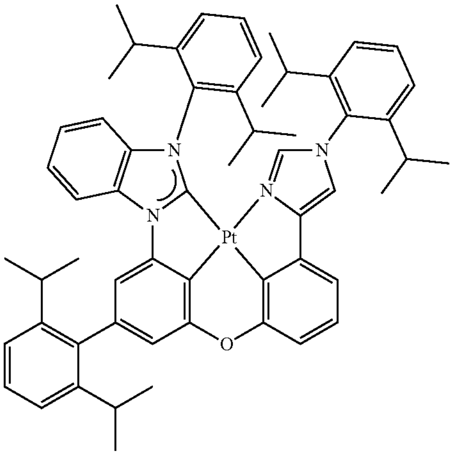
,
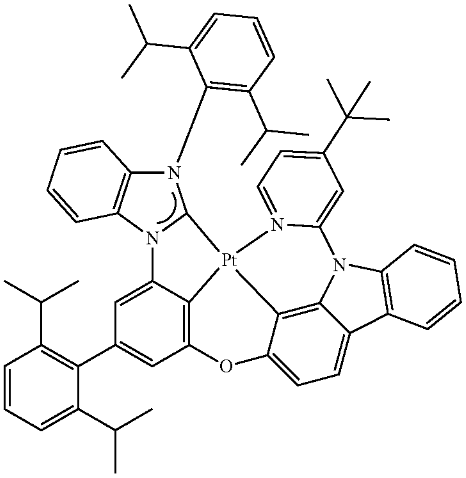
, -continued
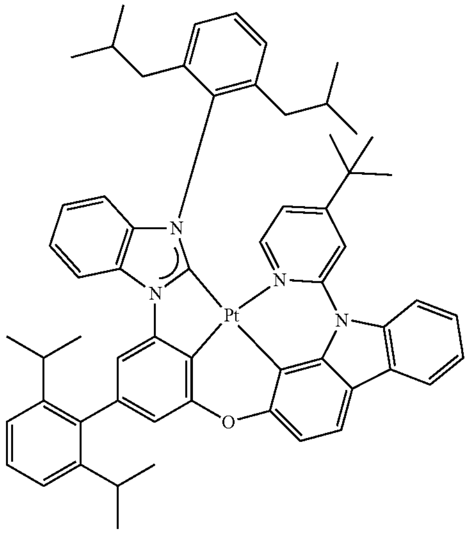
,
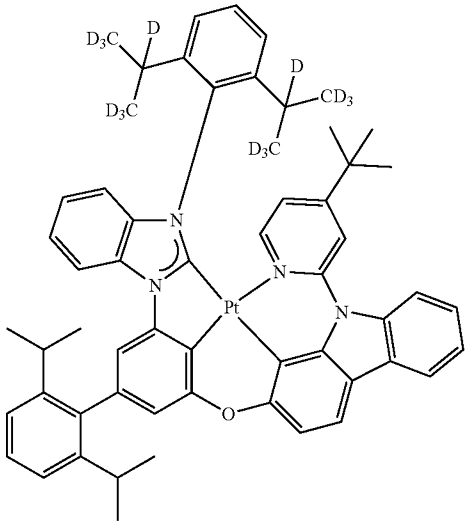
,
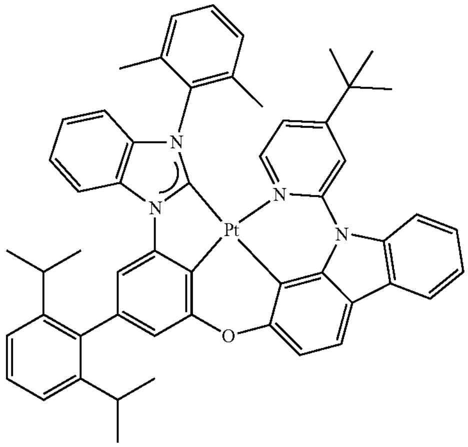
,
-continued
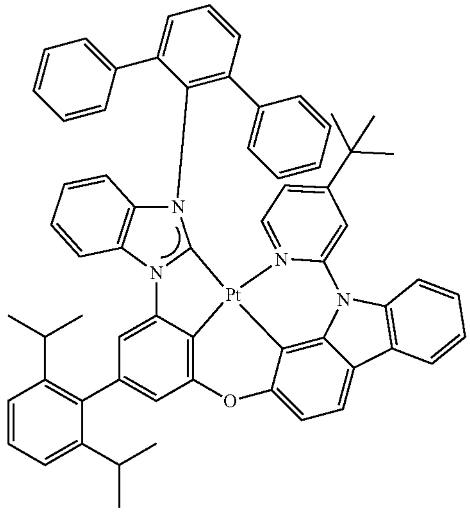
,
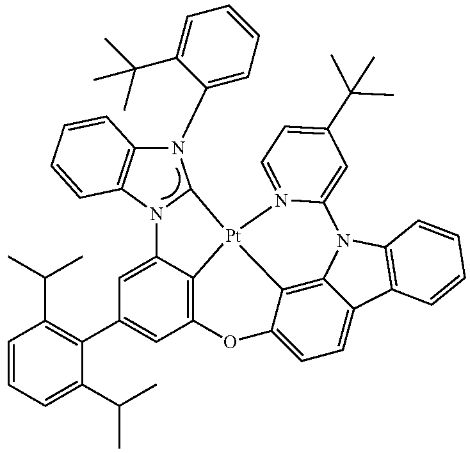
,
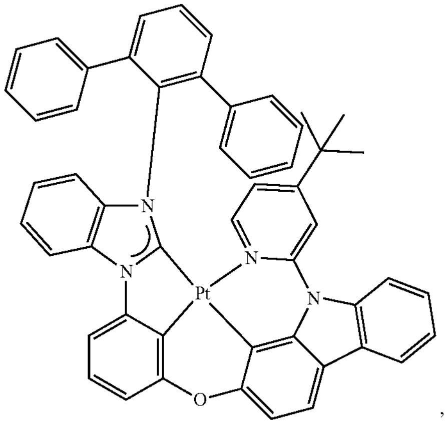
, -continued
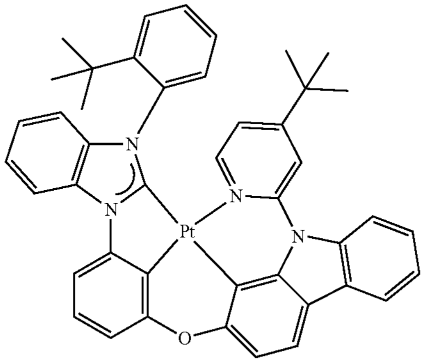
,
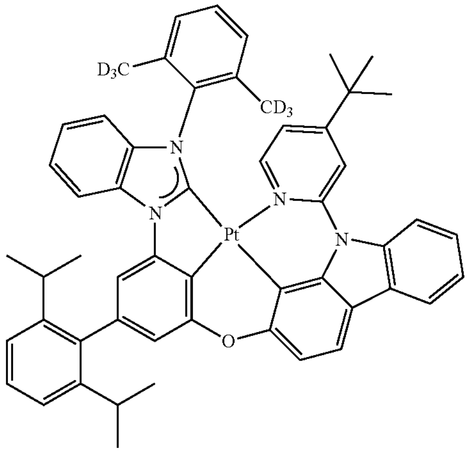
,
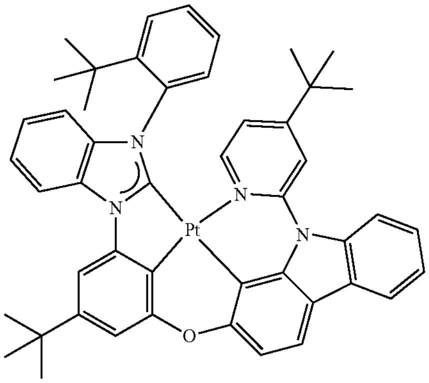
,
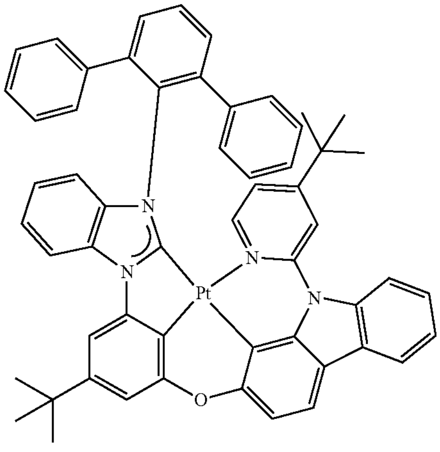
,
-continued
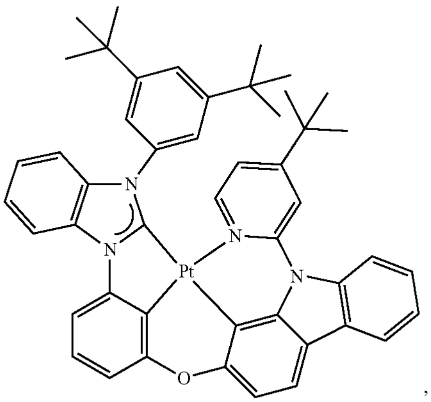
,
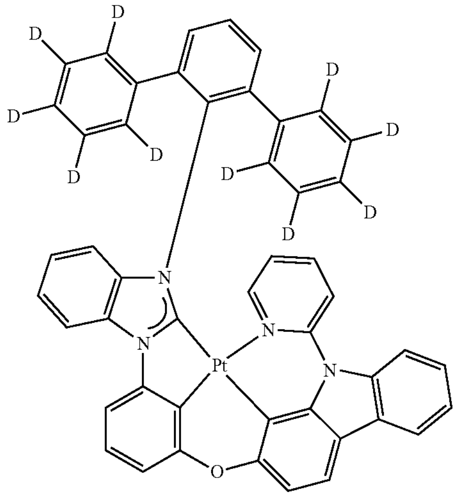
,
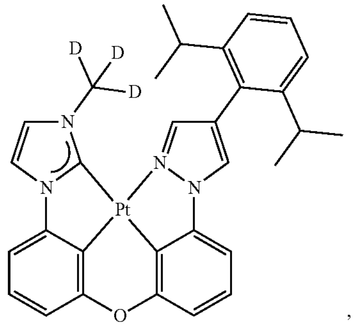
,
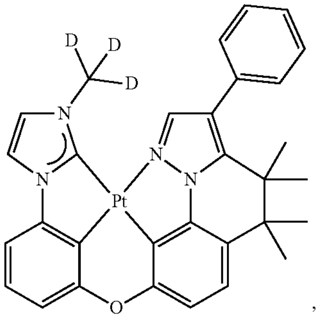
, -continued
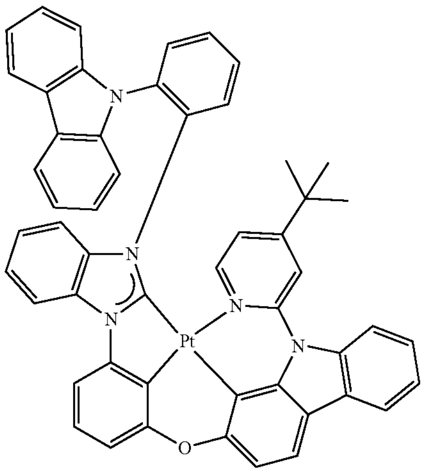
,
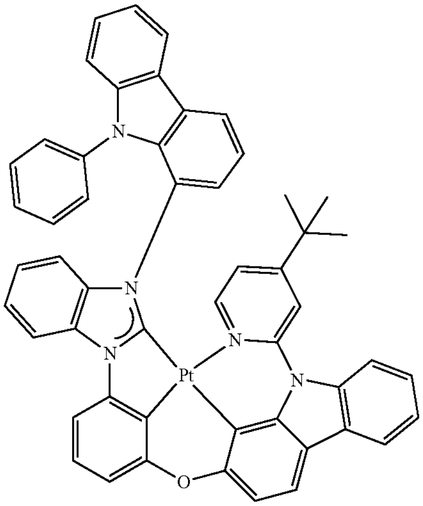
,
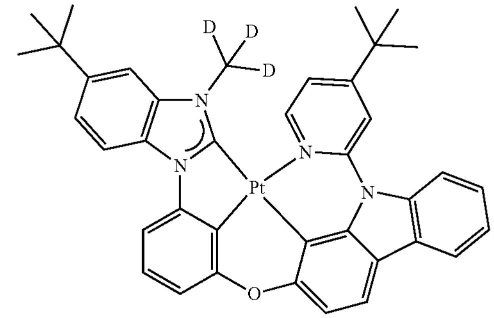
,
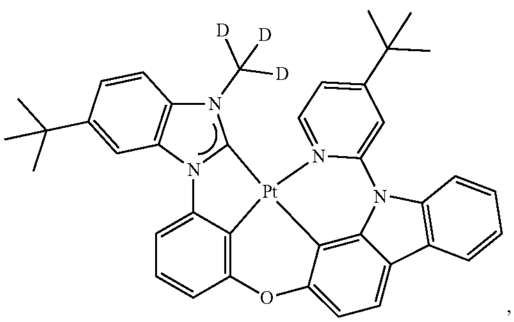
,
-continued
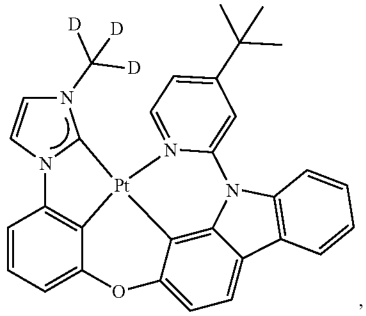
,
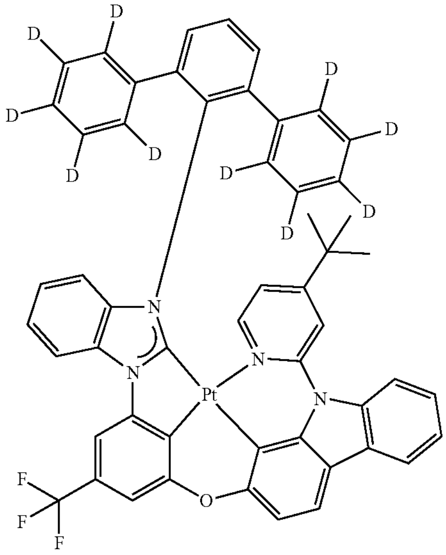
,
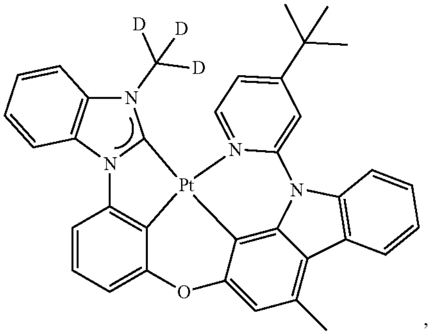
,
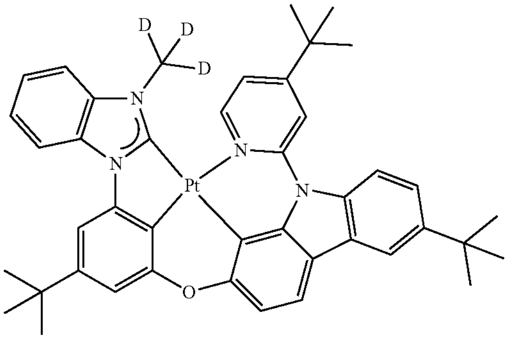
, -continued
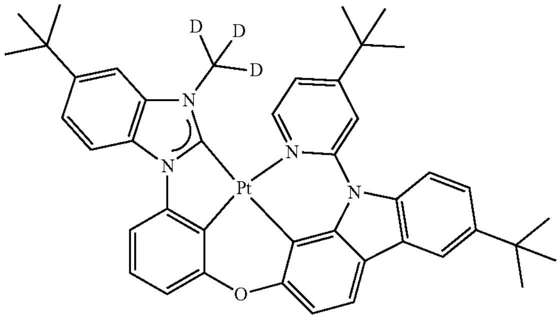
,
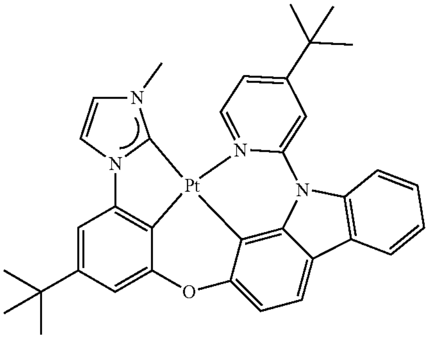
,
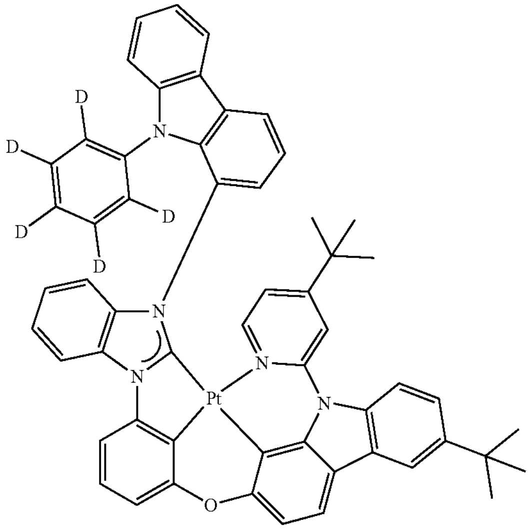
,
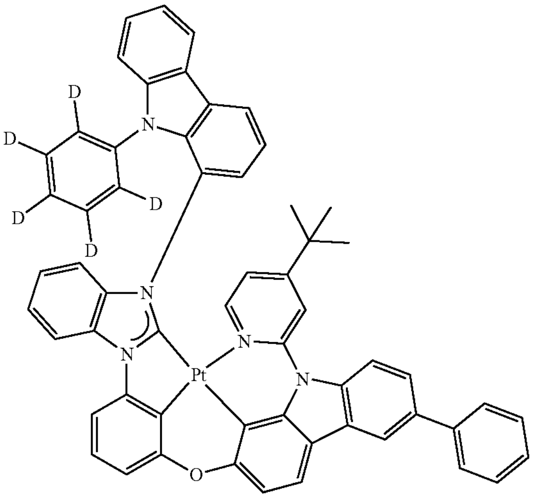
,
-continued
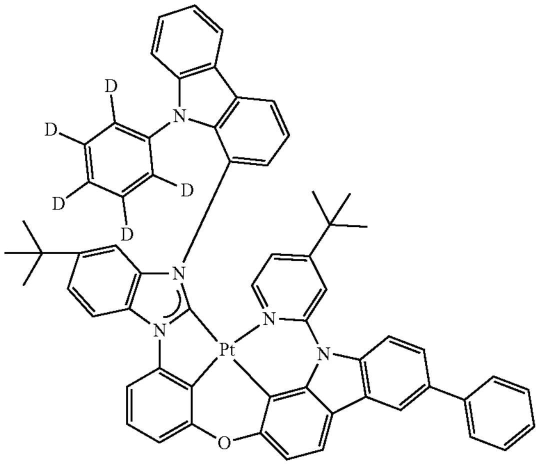
,
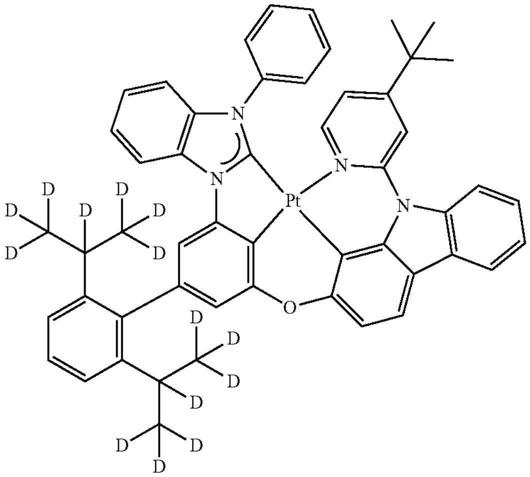
,
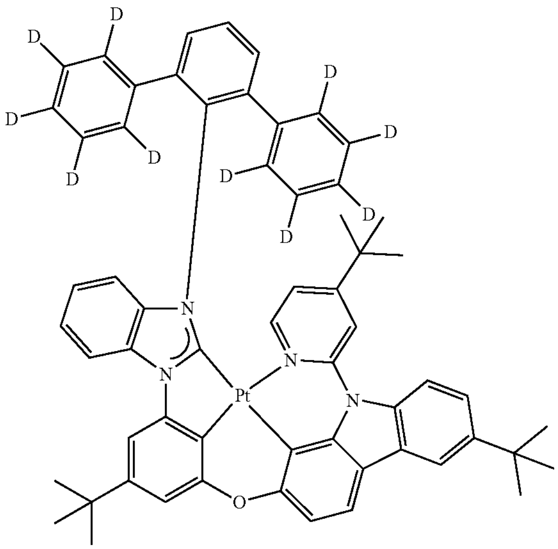
, -continued
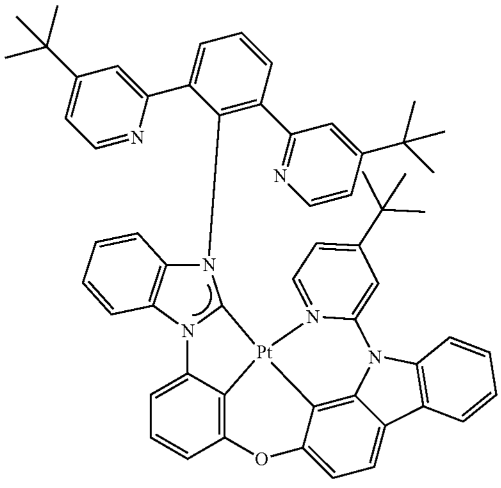
,
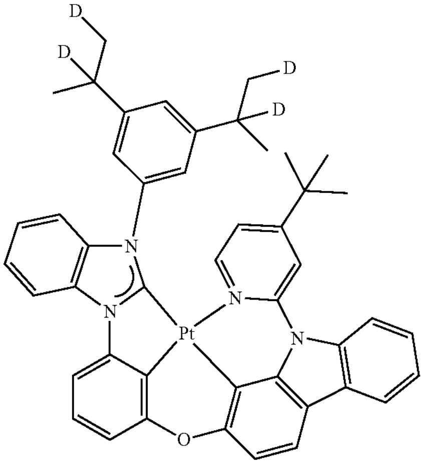
,
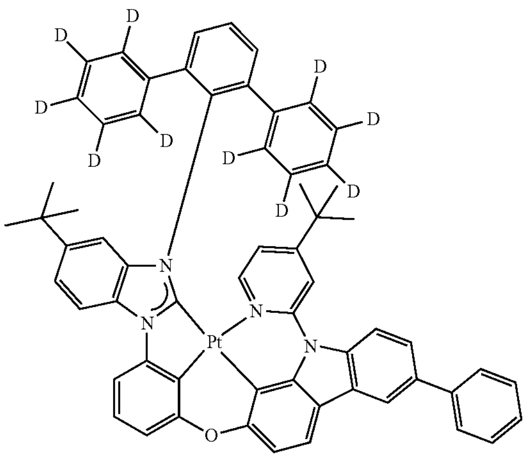
,
-continued
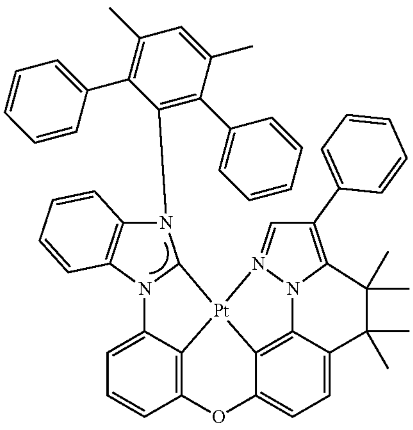
,
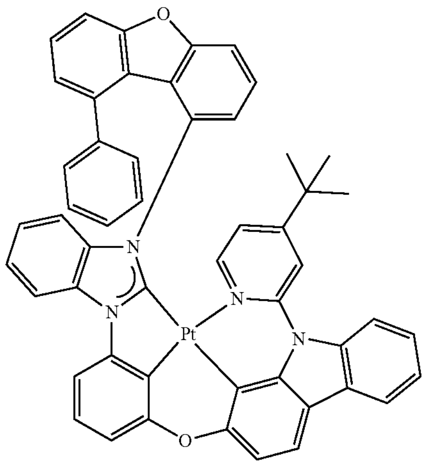
,
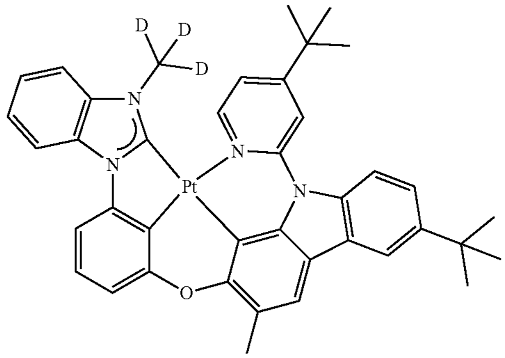
,
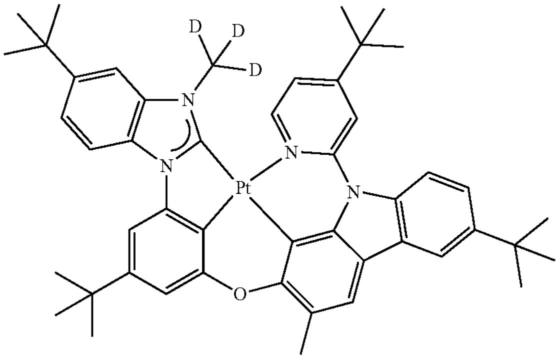
, -continued
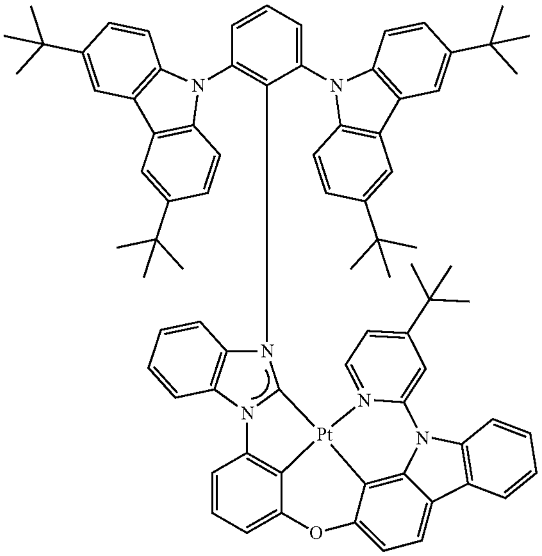
,
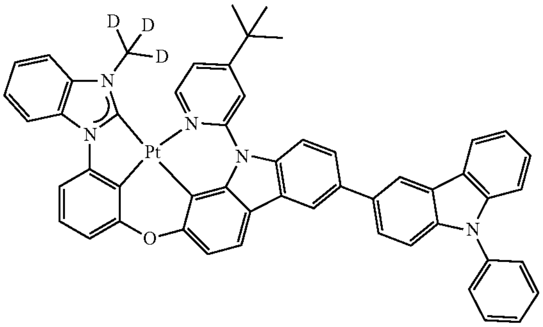
,
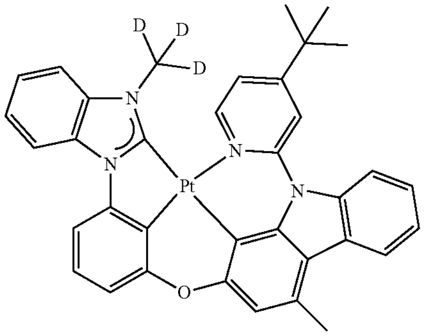
,
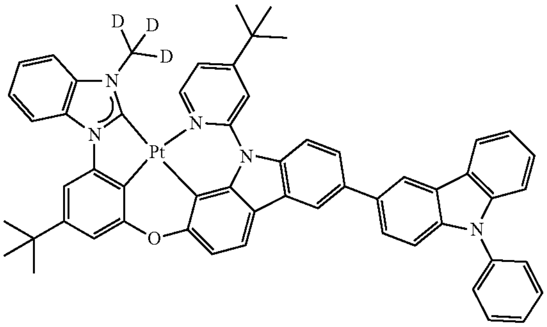
,
-continued
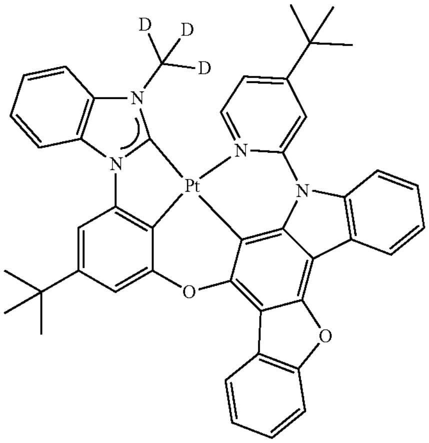
,
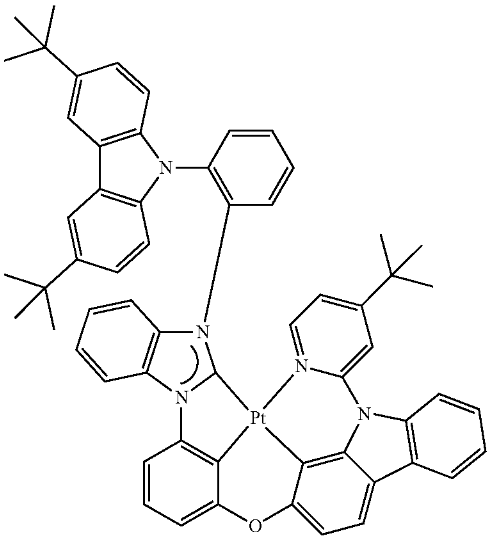
,
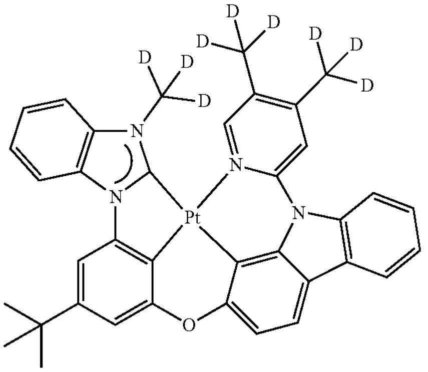
, -continued
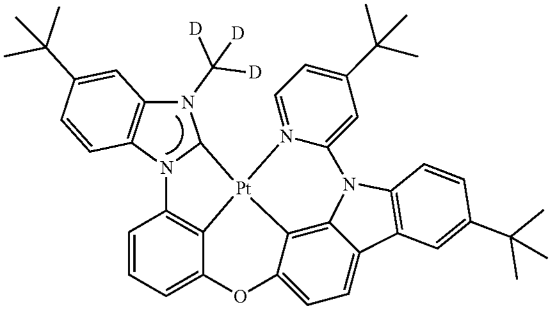
,
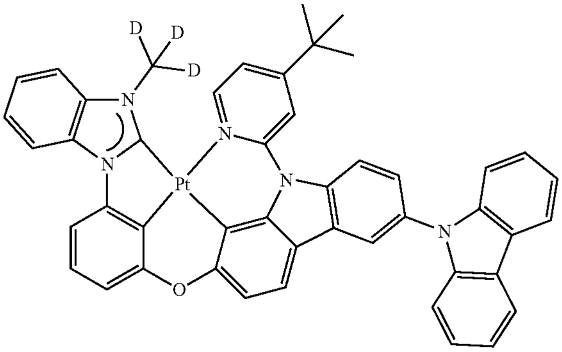
,
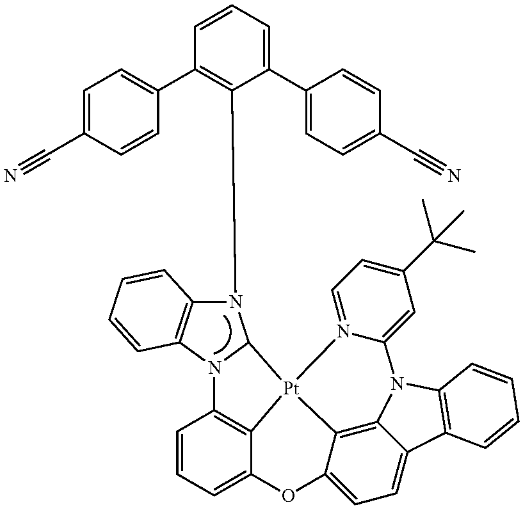
,
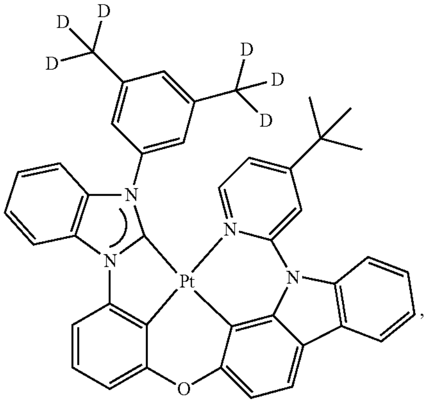
,
-continued
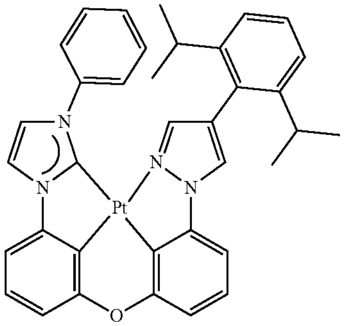
,
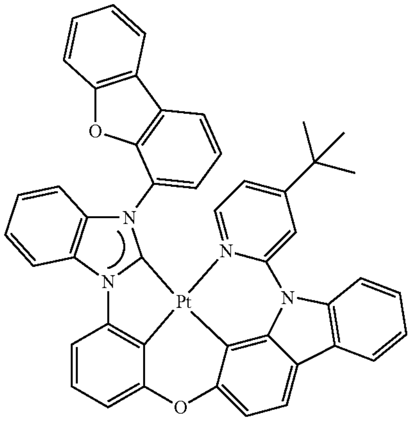
,
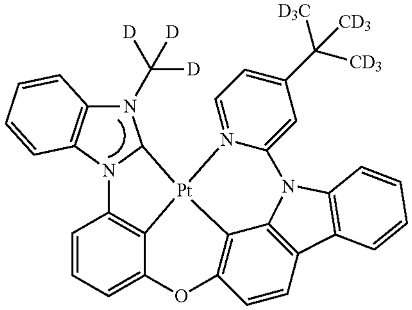
,
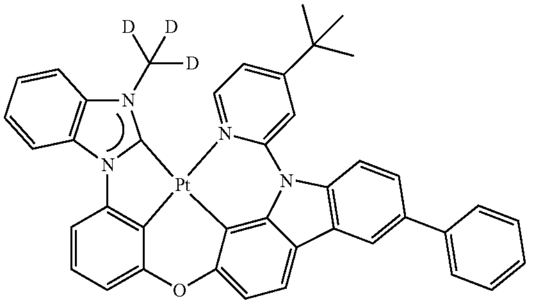
,
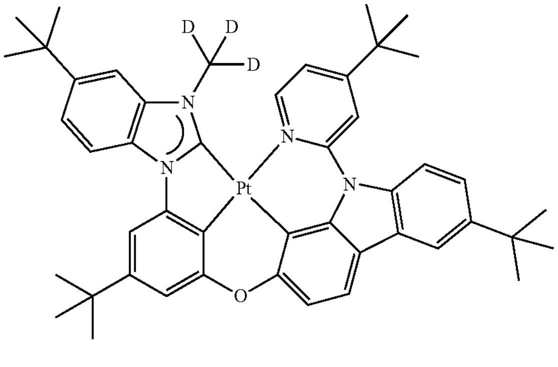
, -continued
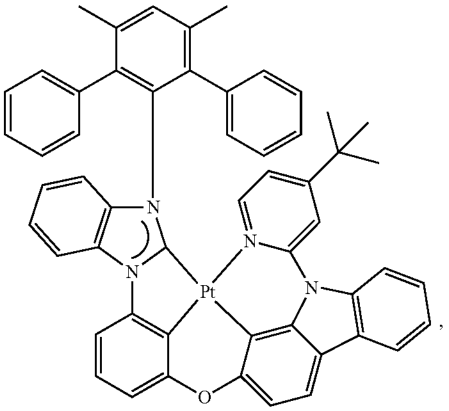
,
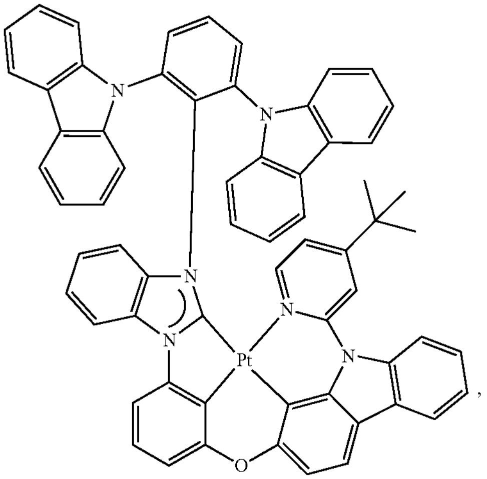
,
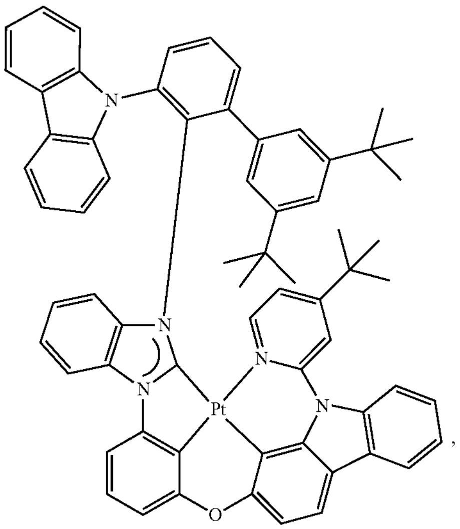
,
-continued
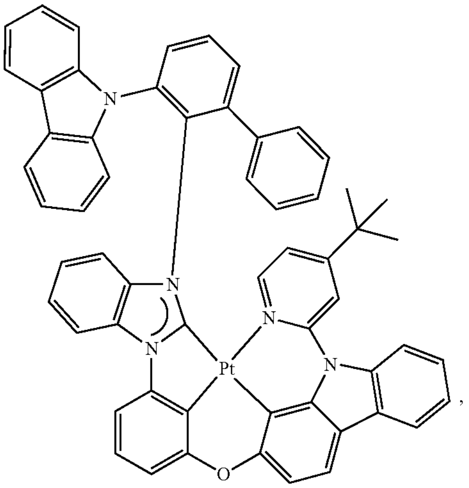
,
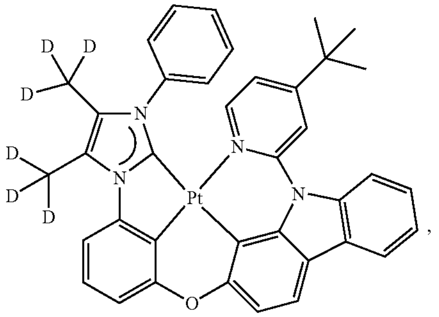
,
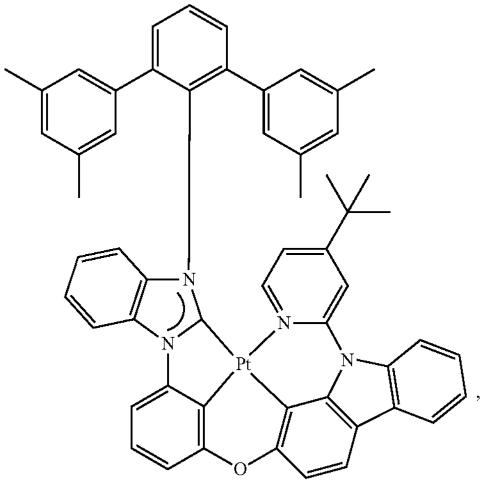
, -continued
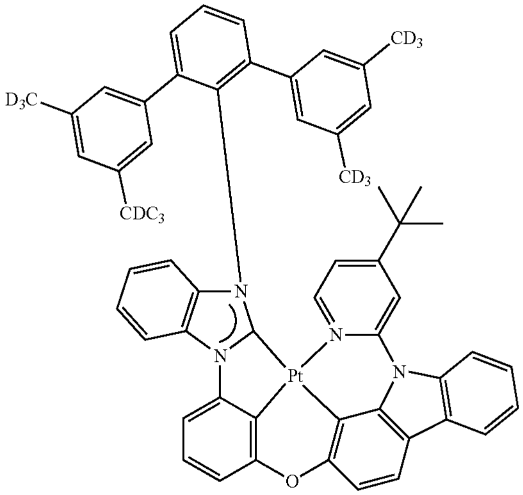
,
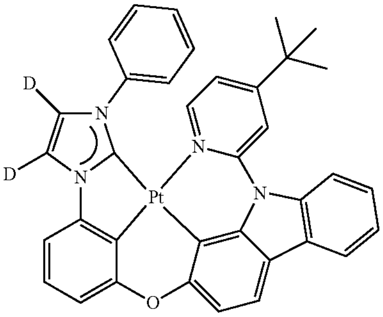
,
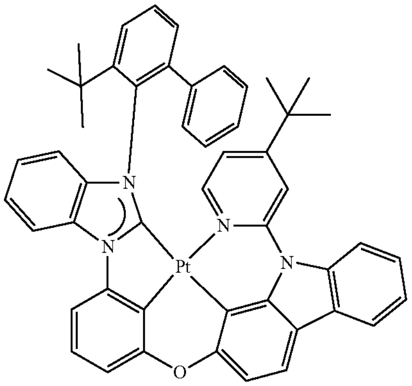
,
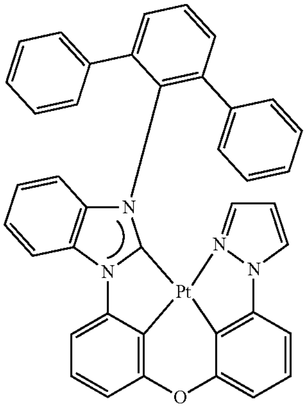
,
-continued
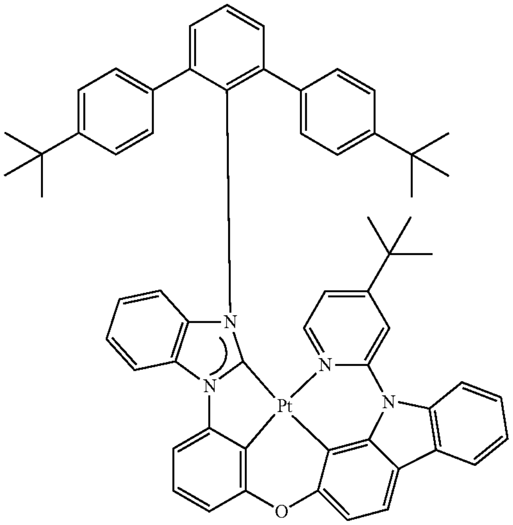
,
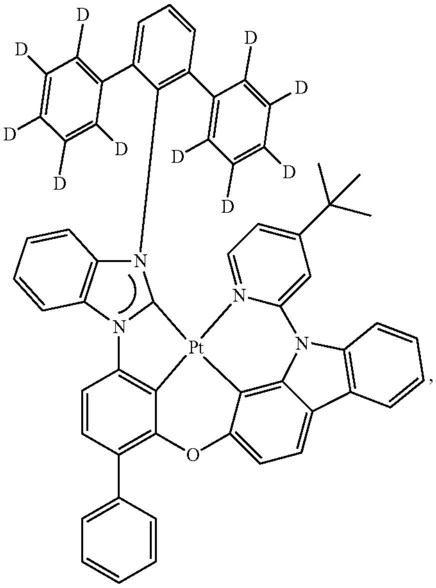
,
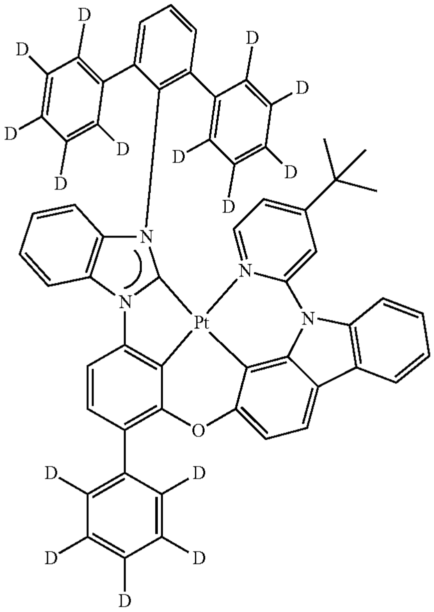
,

1033
-continued
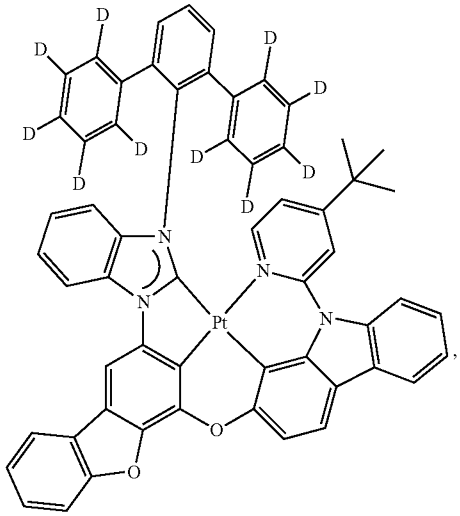
,
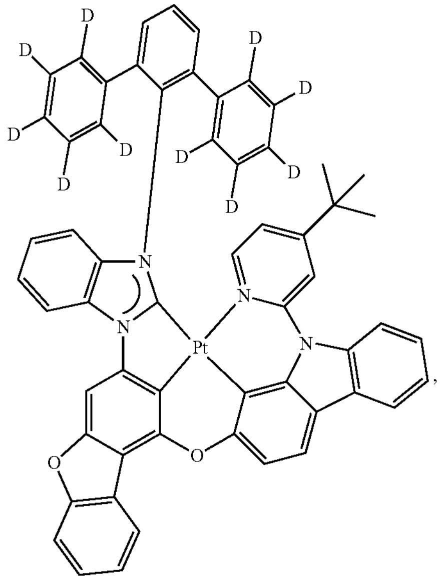
,
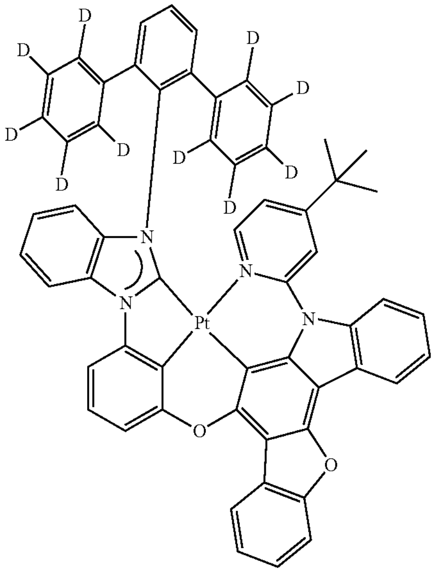
,
1034
-continued
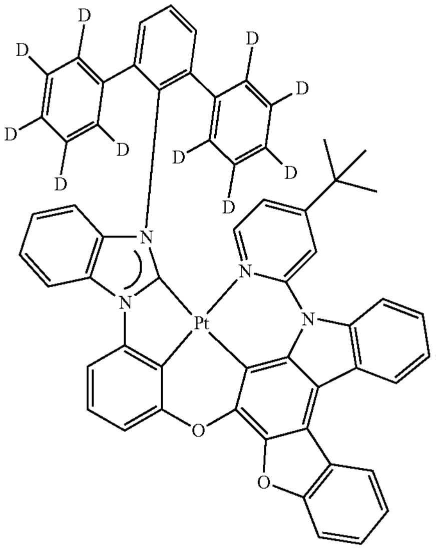
,
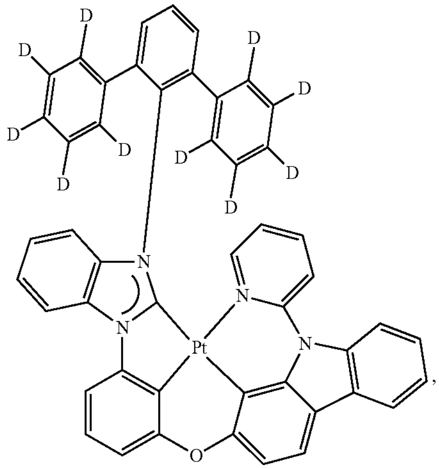
,
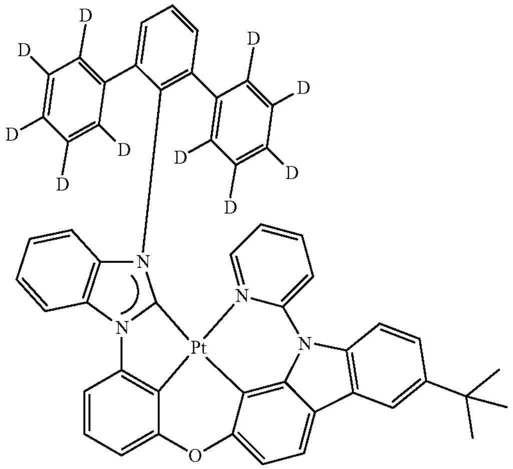
, -continued
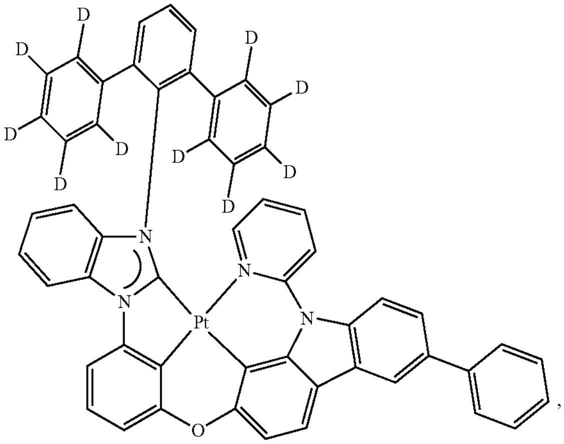
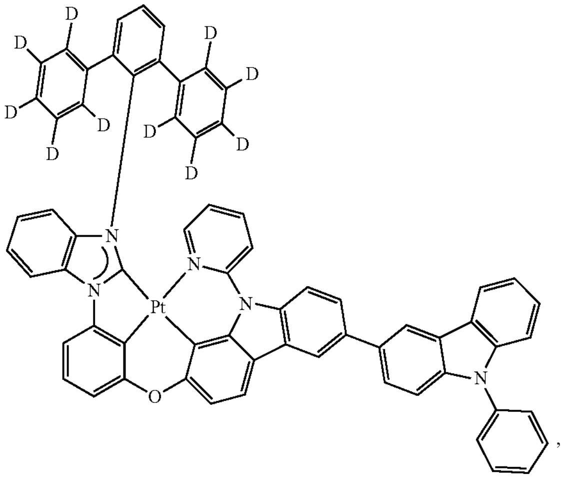
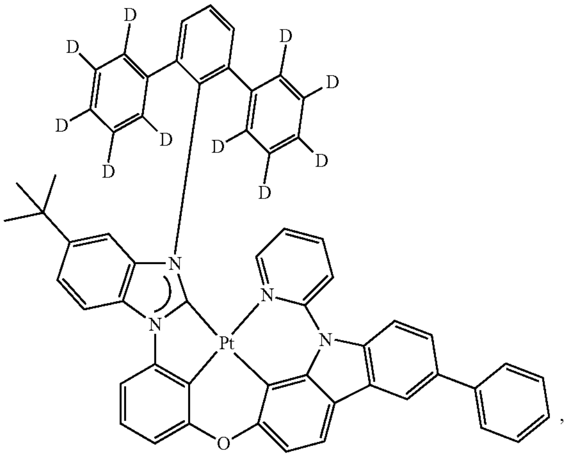
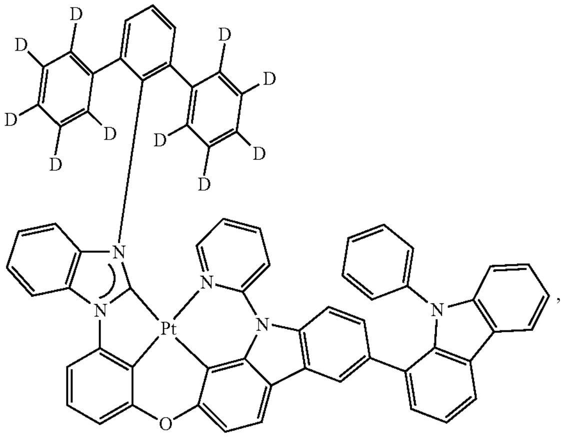
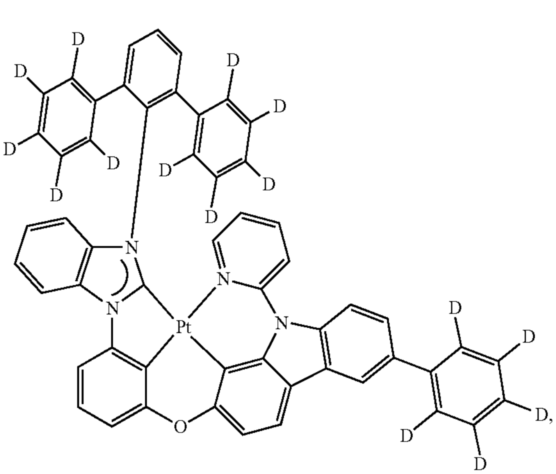
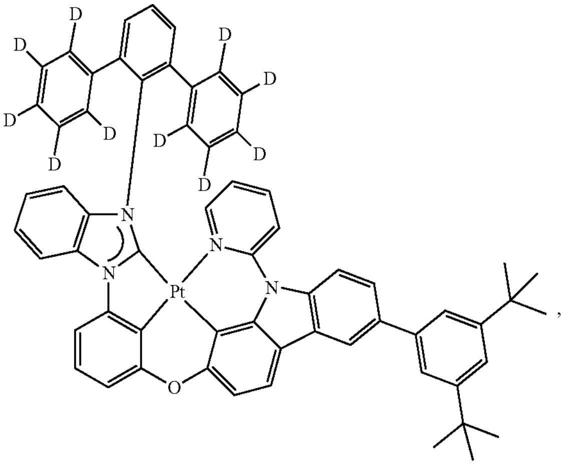

-continued
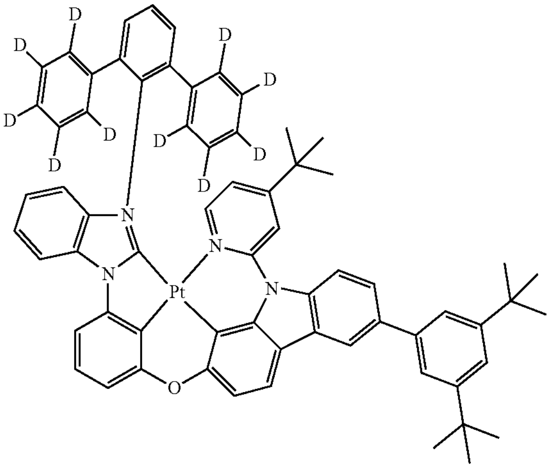
,
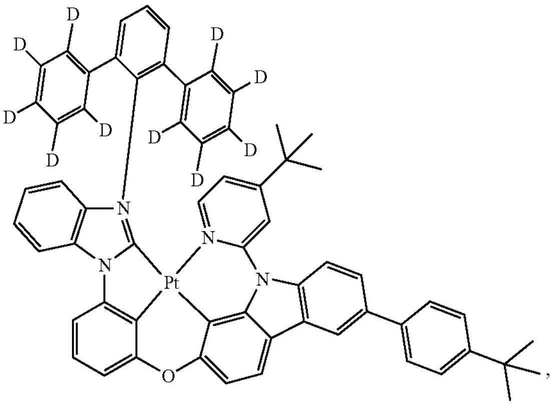
,
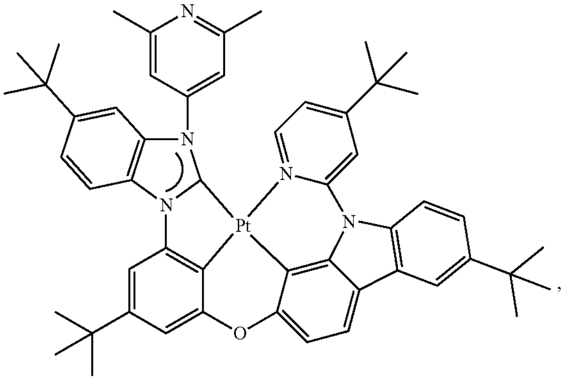
,
-continued
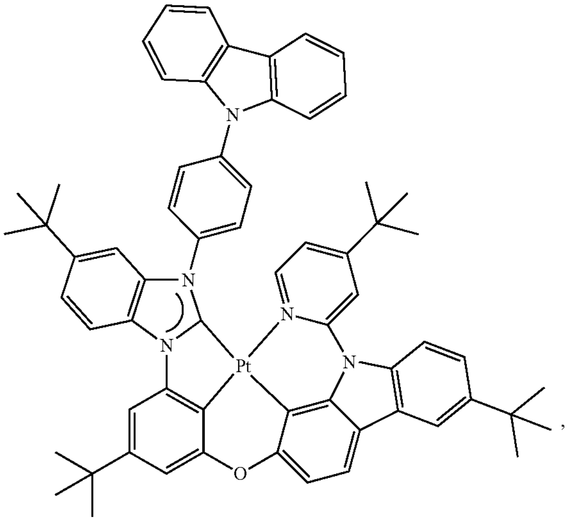
,
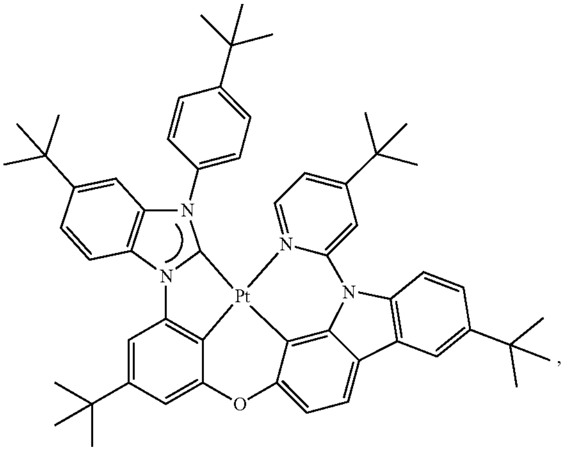
,

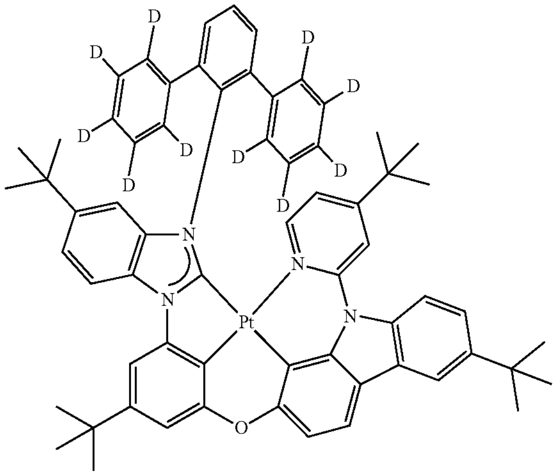,
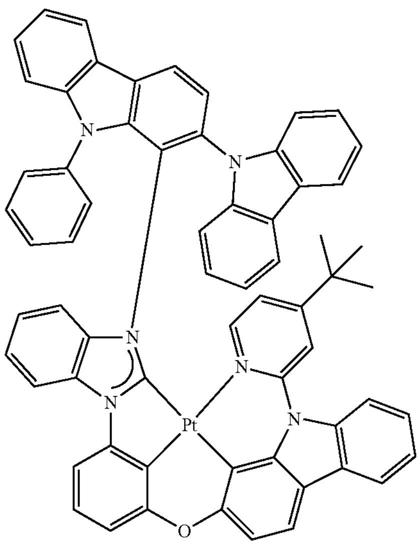,
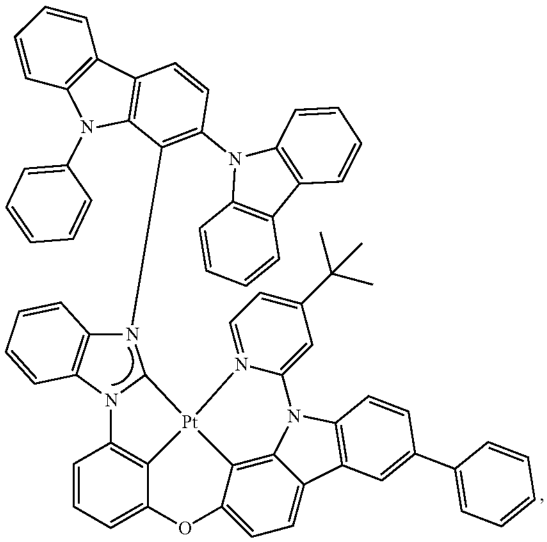,
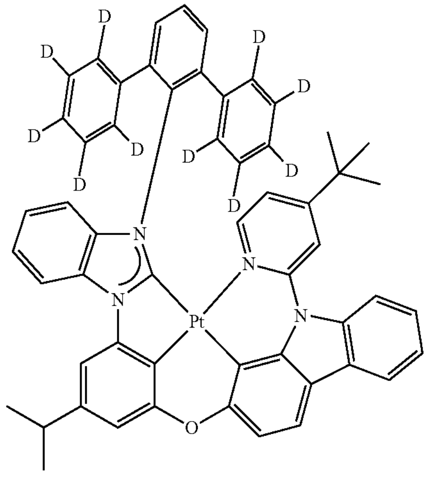,
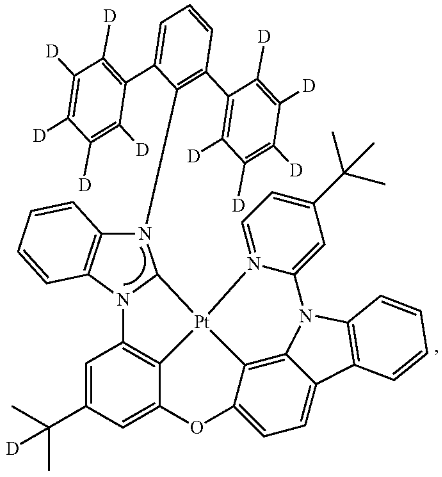,
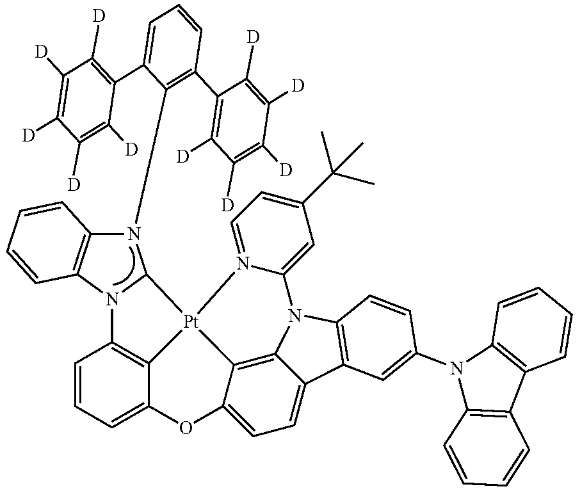, -continued
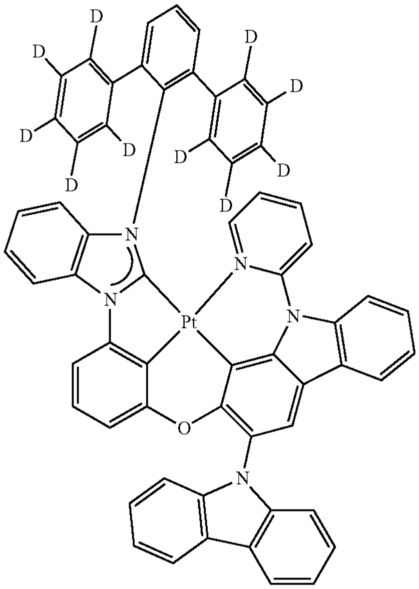
,
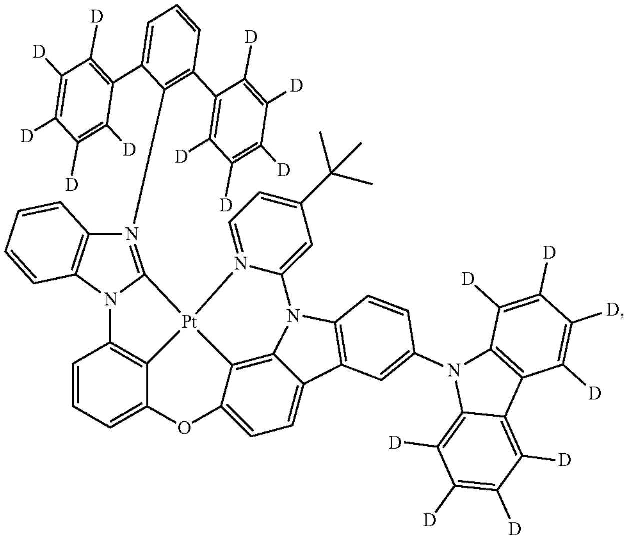
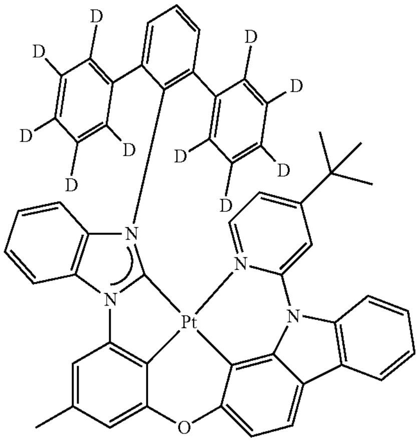
,
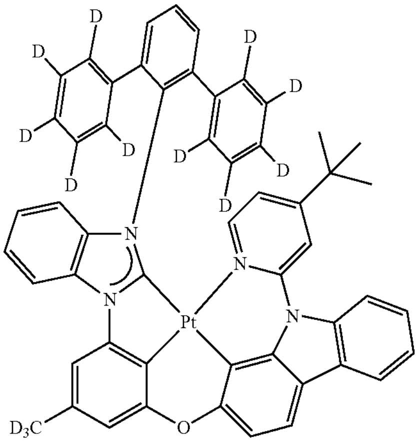
,
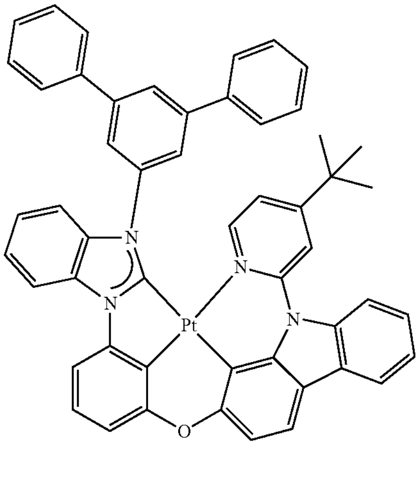
,
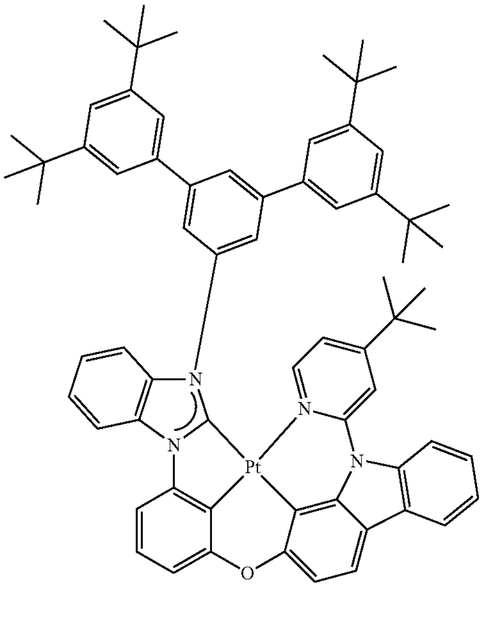
, -continued
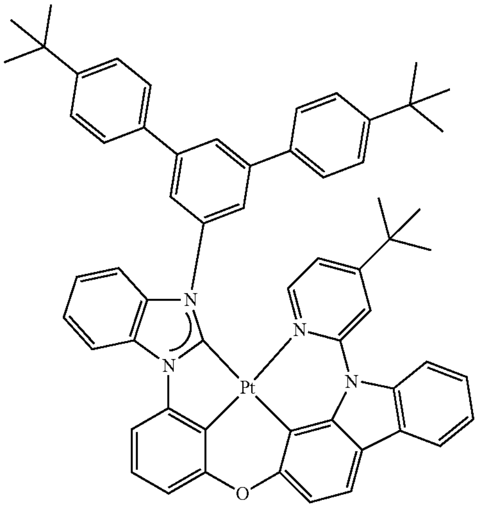
,
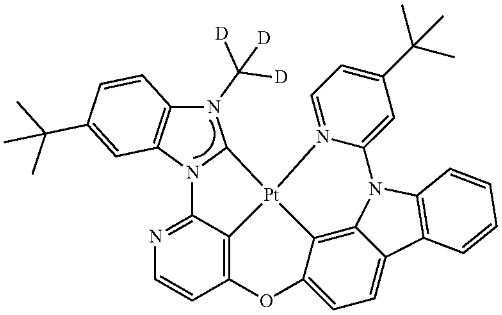
,
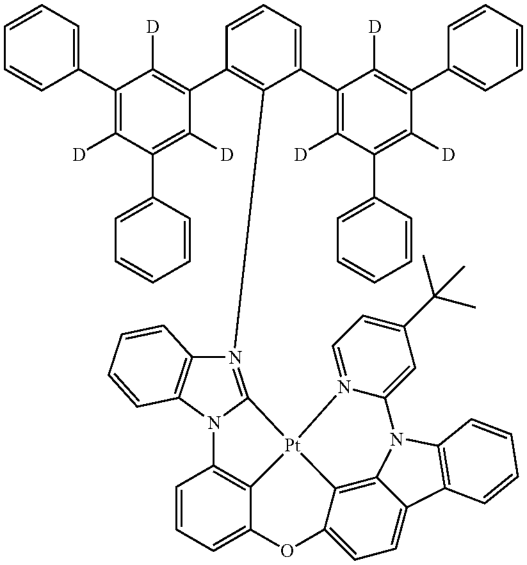
,
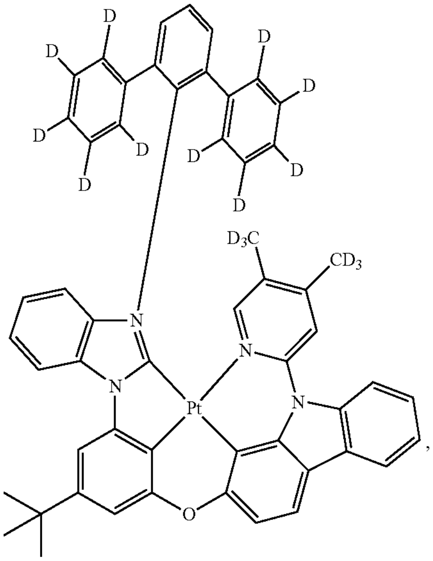
,
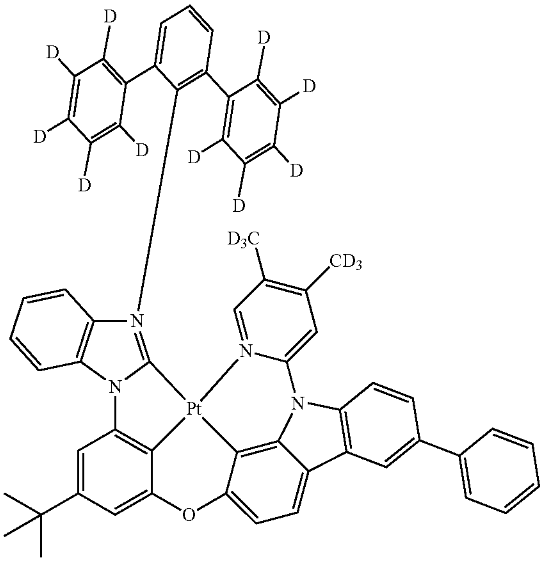
,
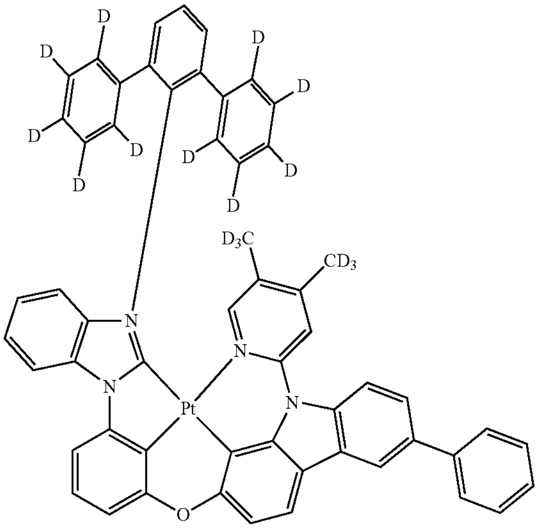
, -continued
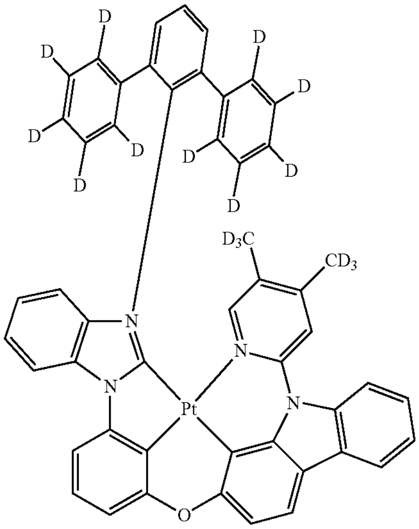
,
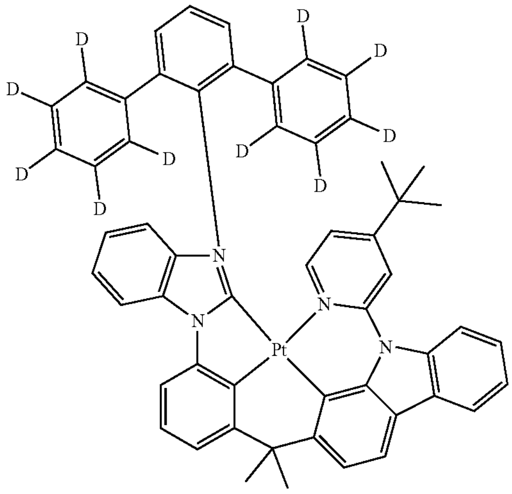
,
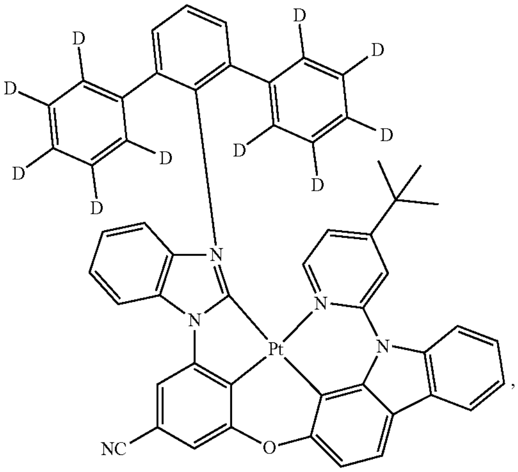
,
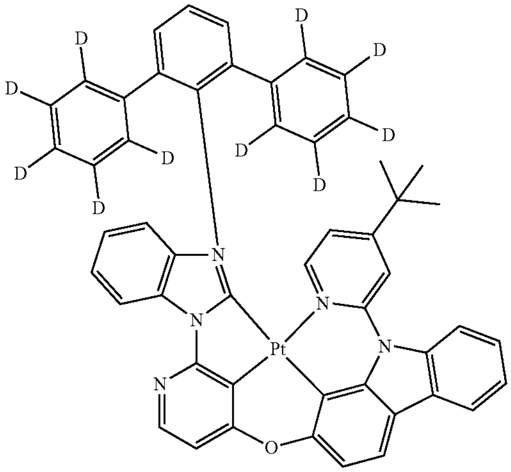
,
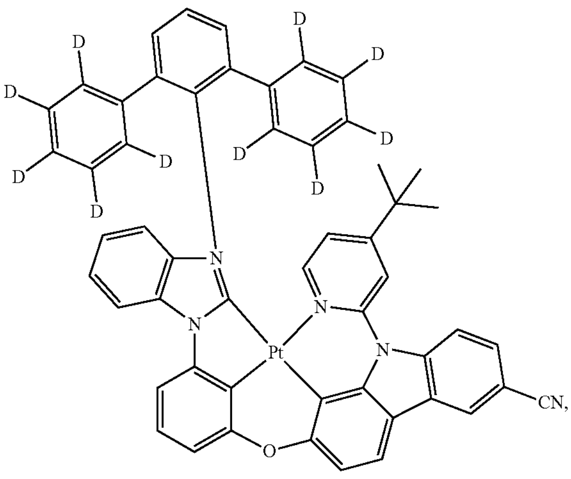
,
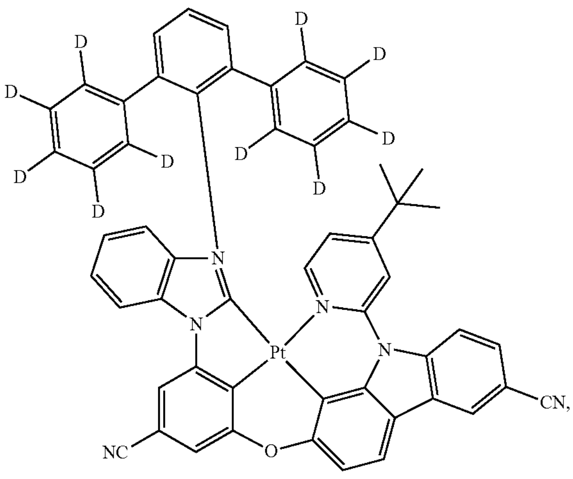
, -continued
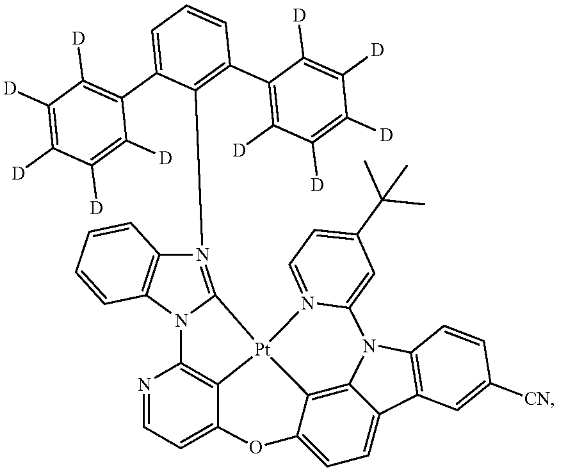
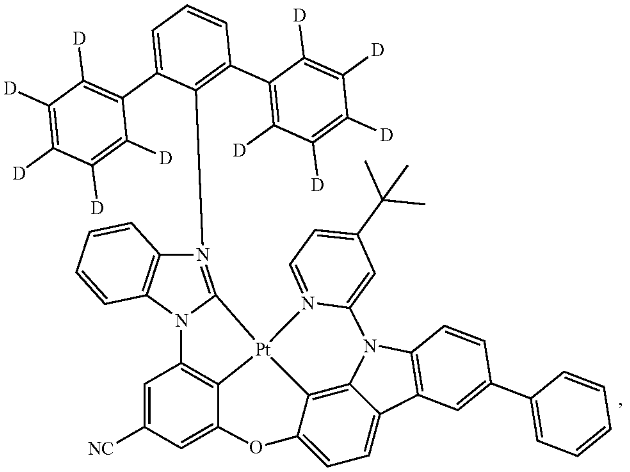
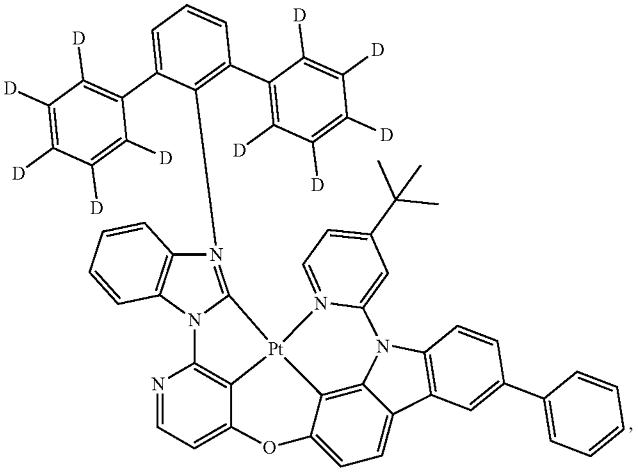
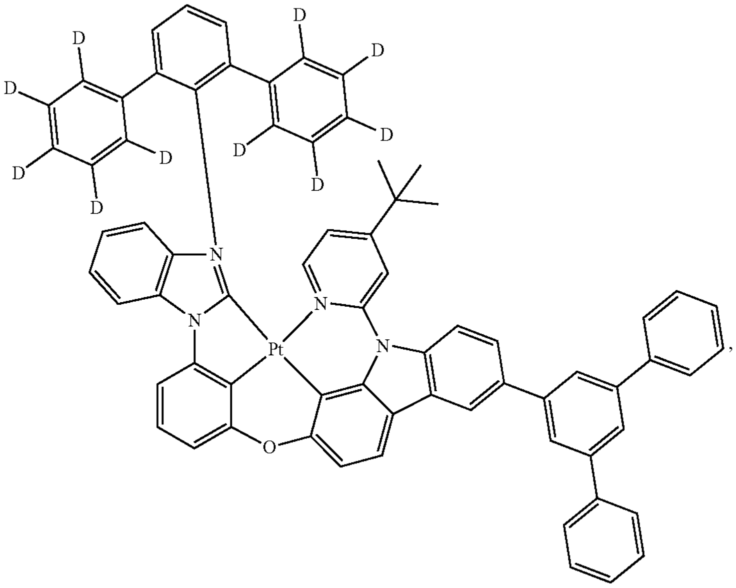

-continued
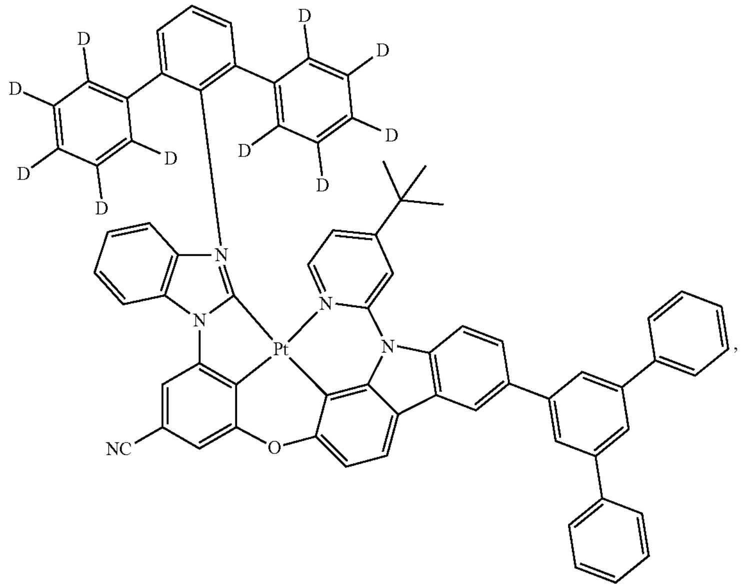
,
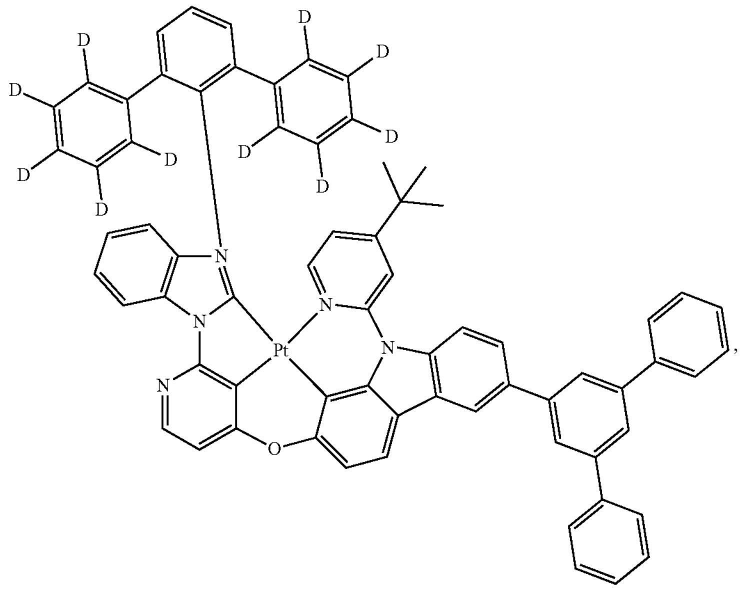
,

-continued
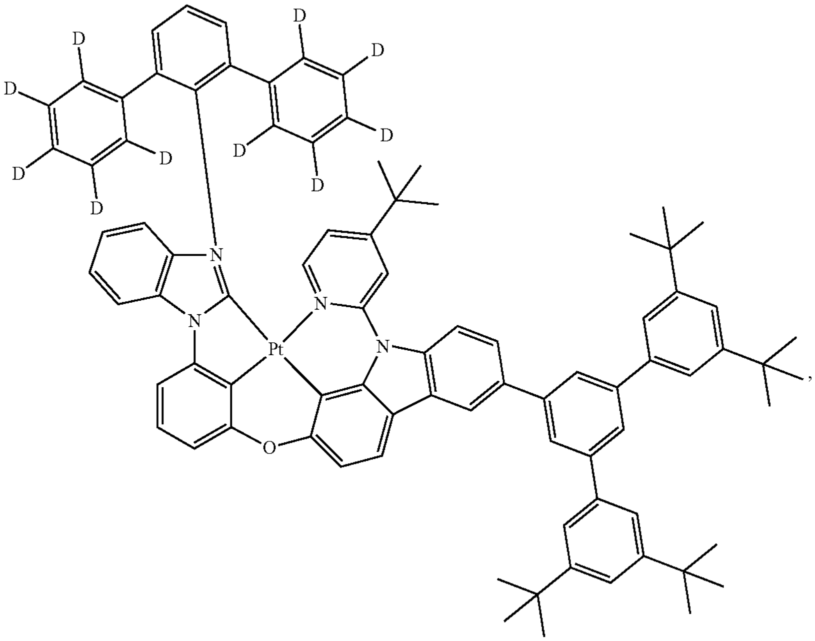
,
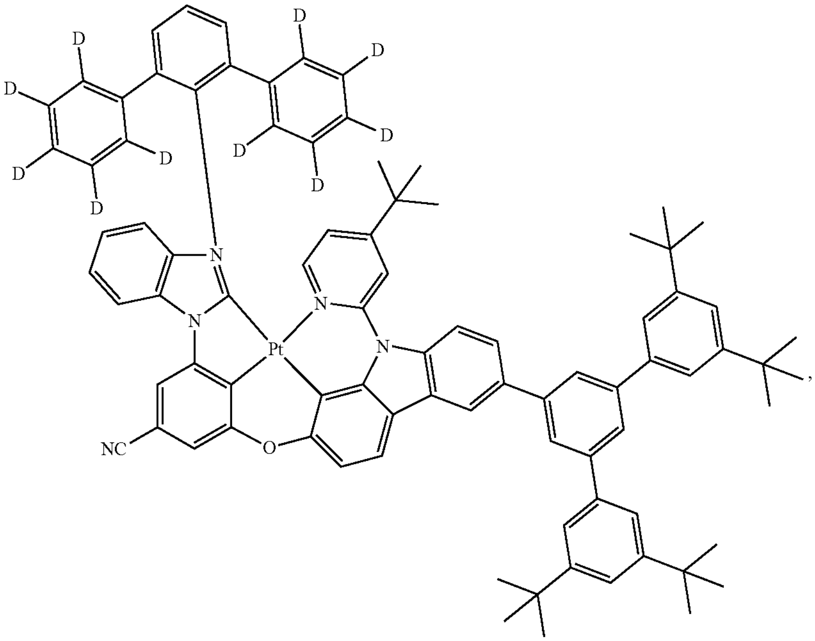
,

-continued
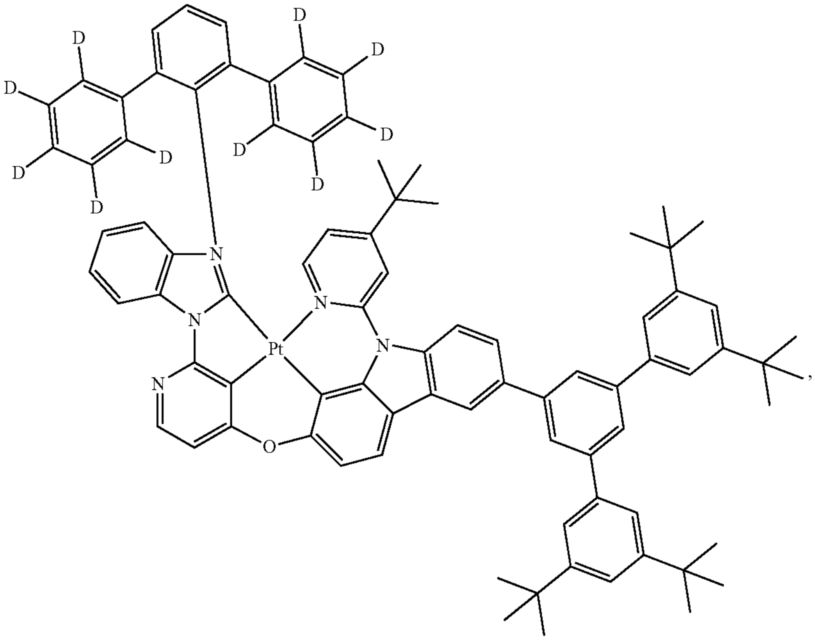
,
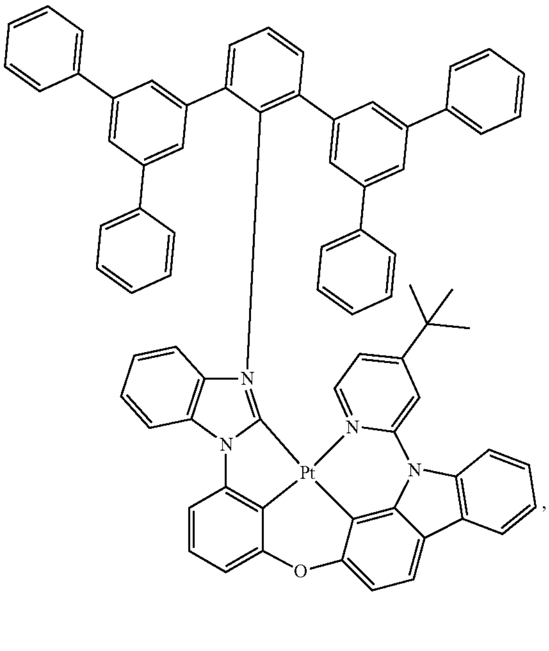
,
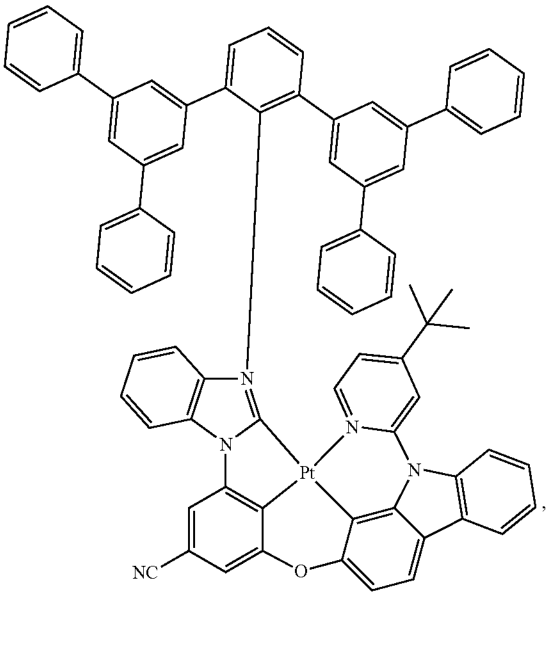
,

-continued
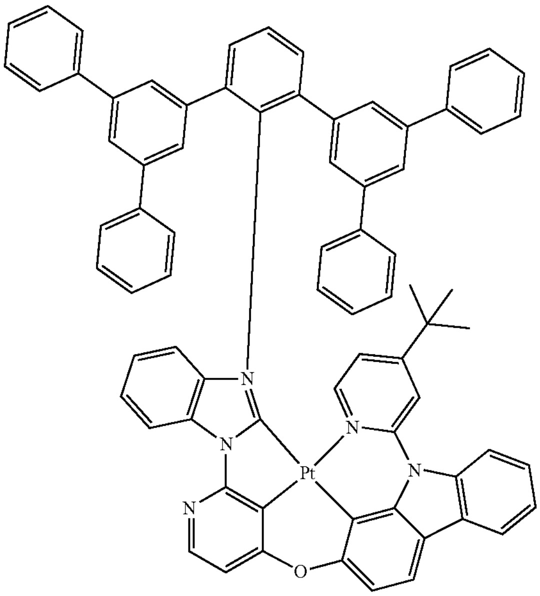
,
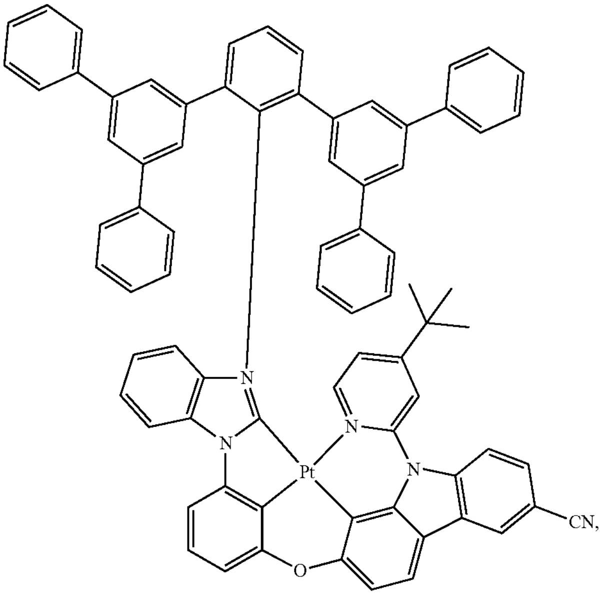
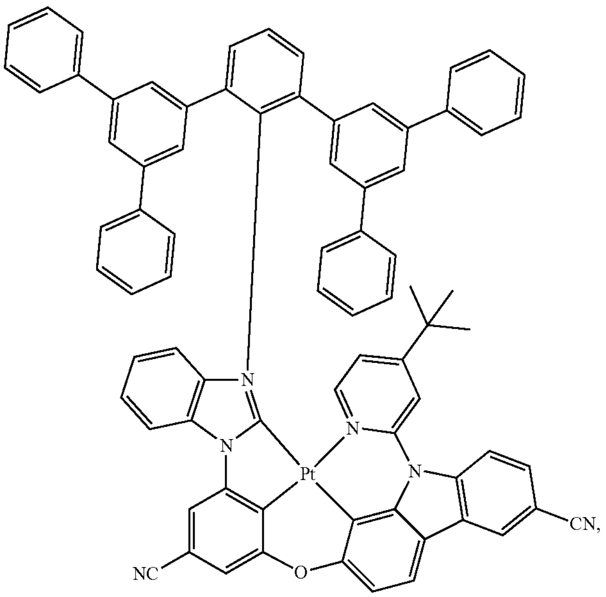

-continued
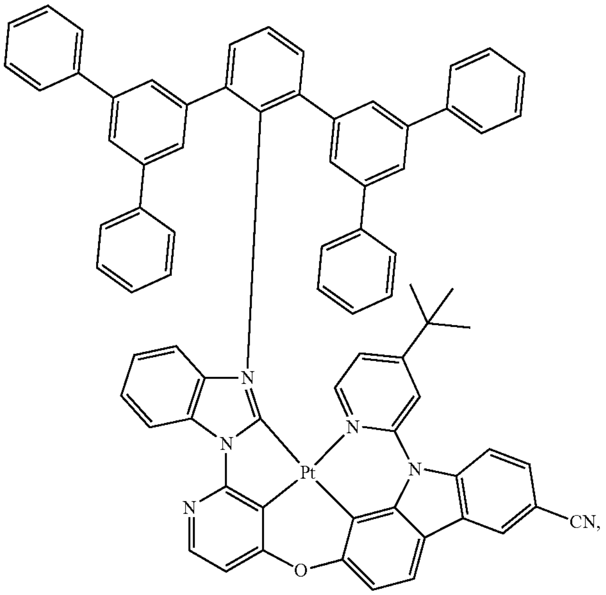
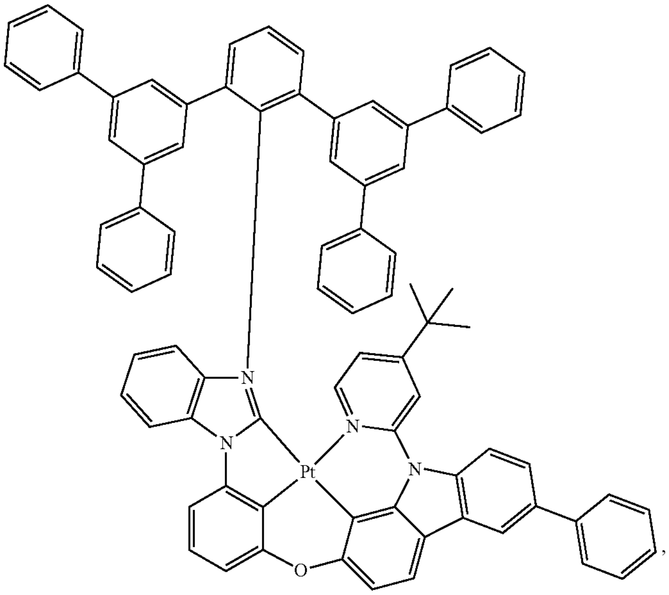
,

-continued
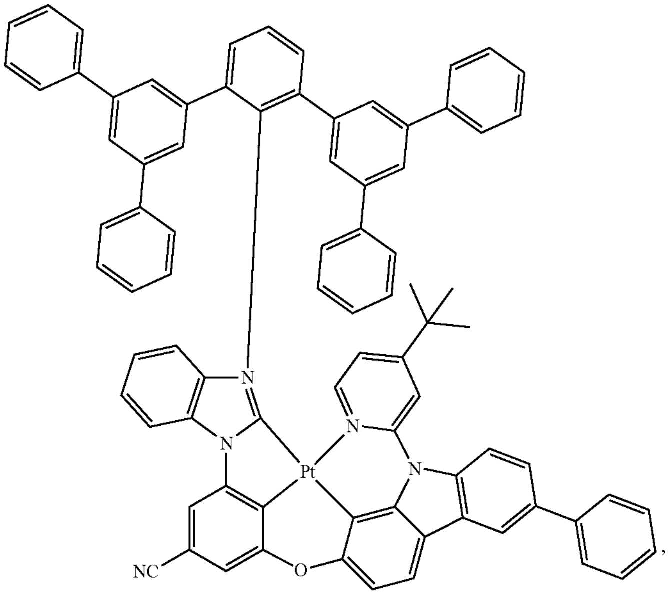
,
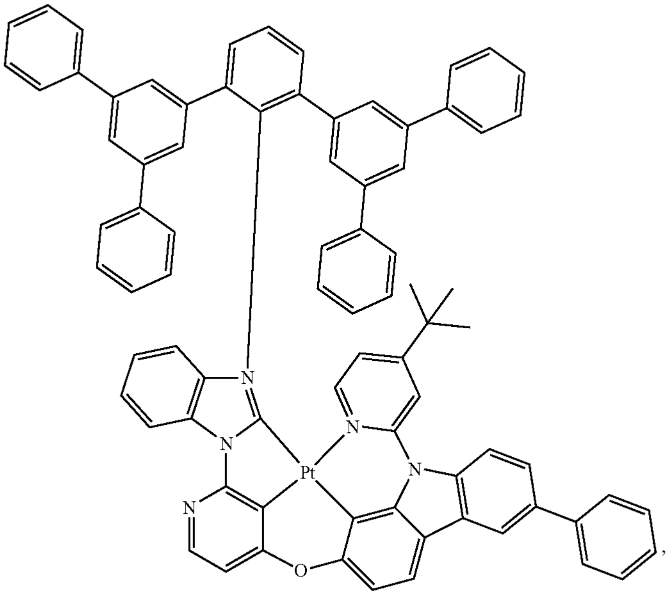
,

-continued
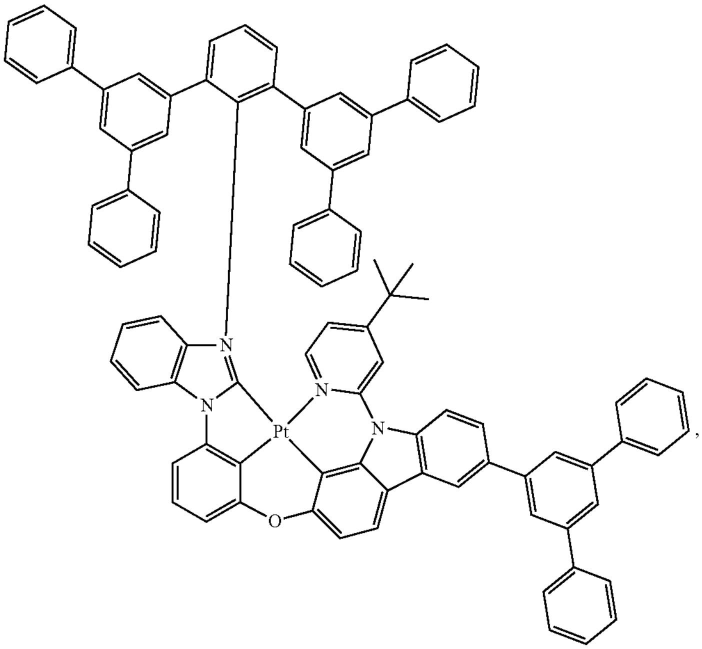
,
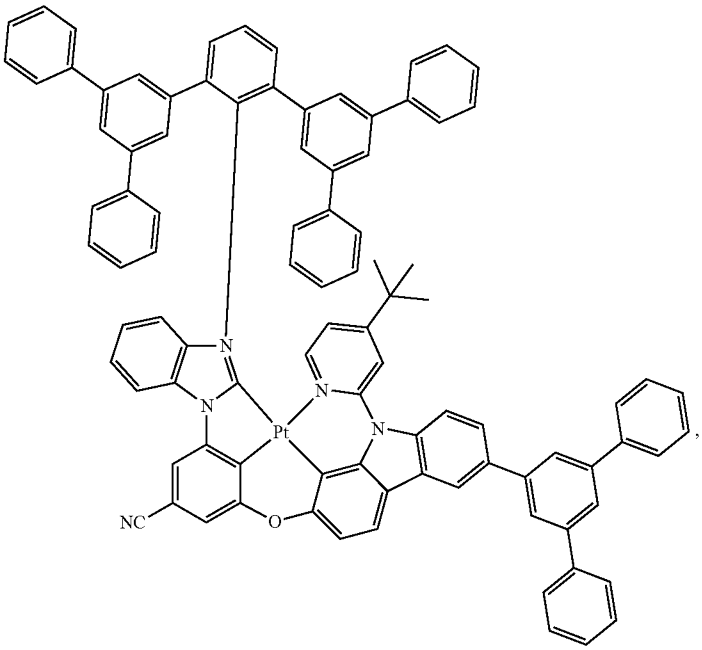
,

-continued
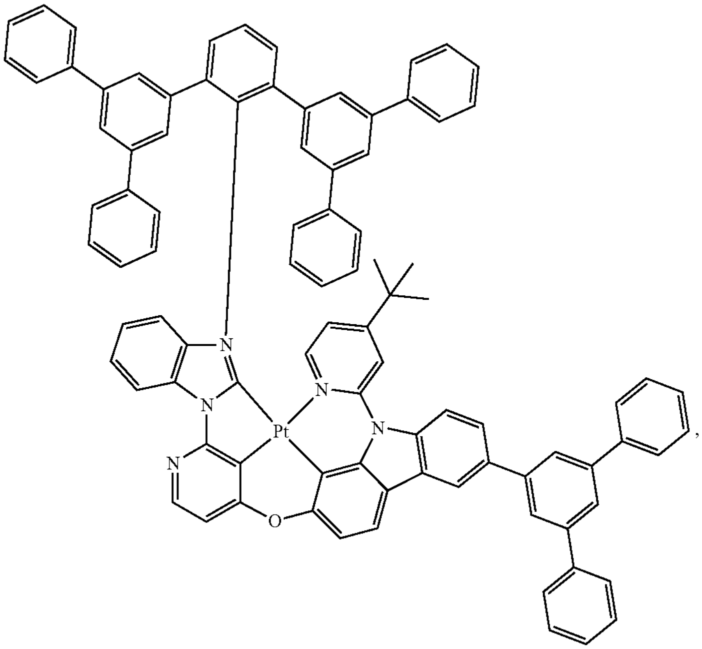
,
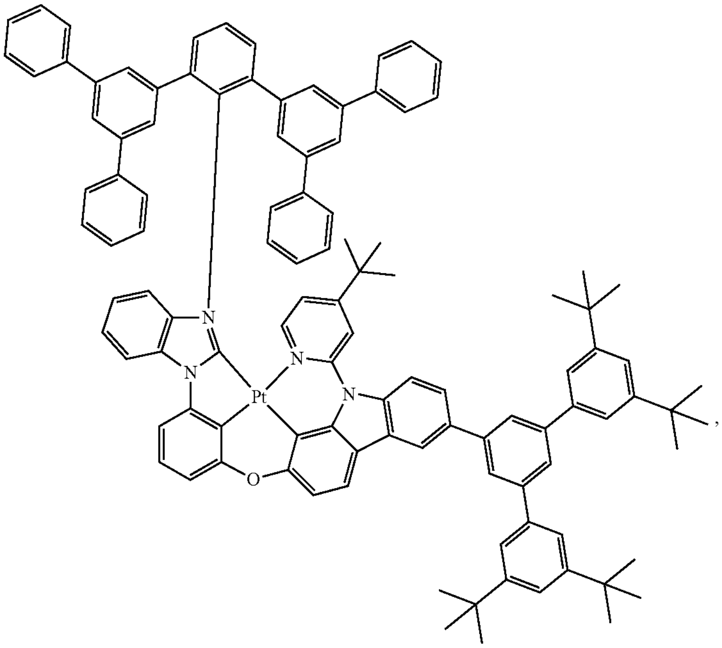
,

-continued
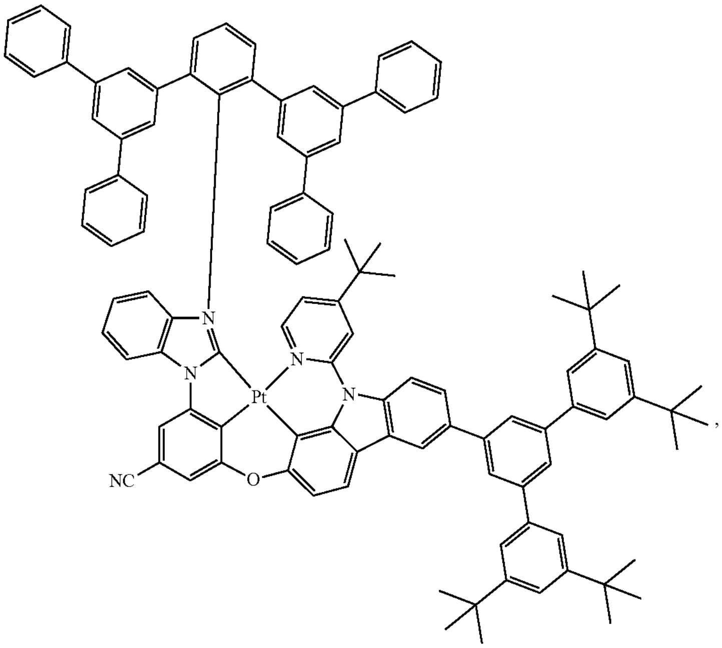
,
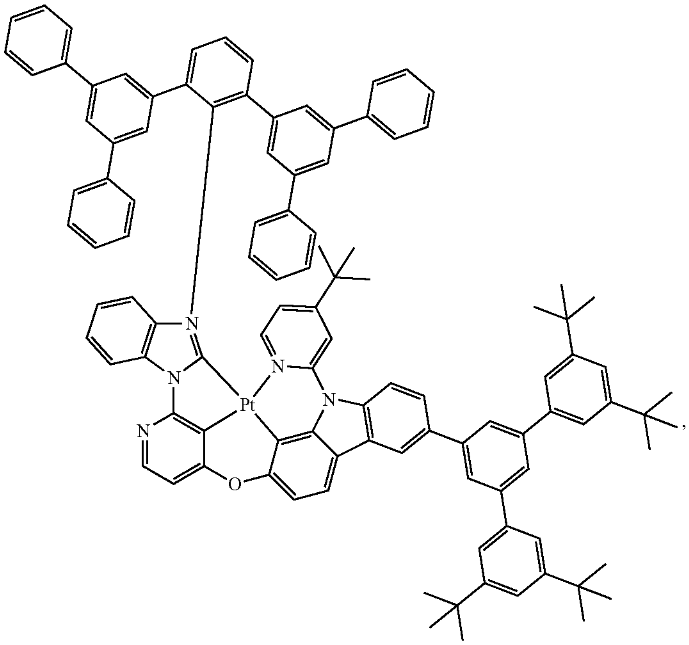
,

-continued
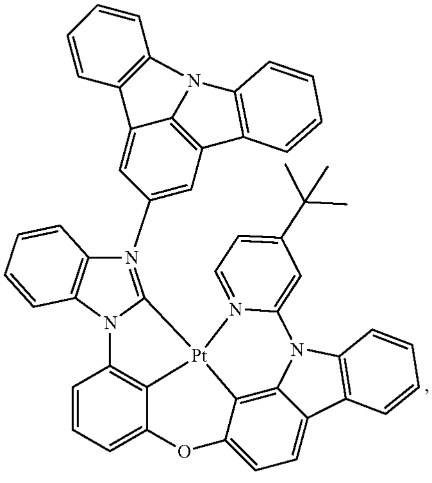
,
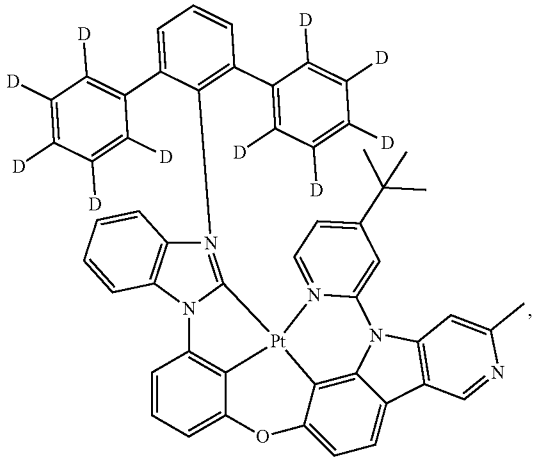
,
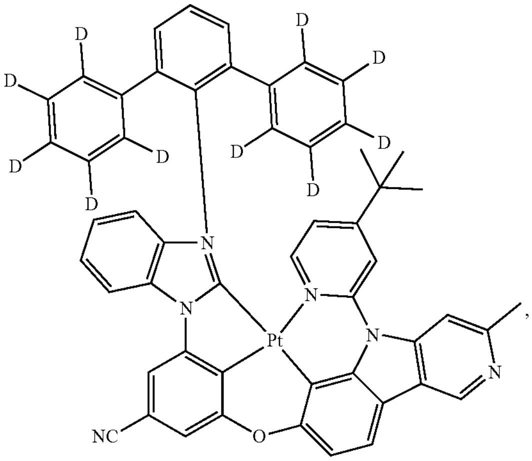
,
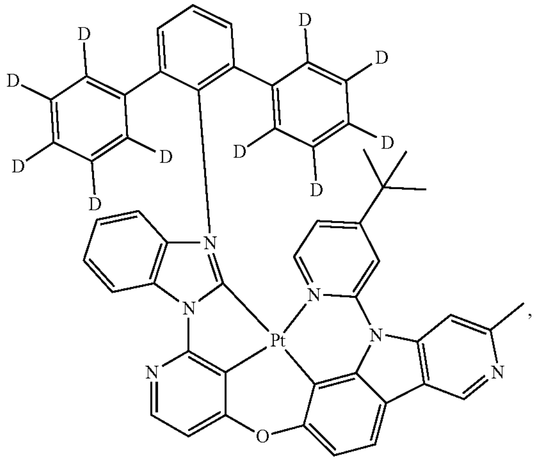
,
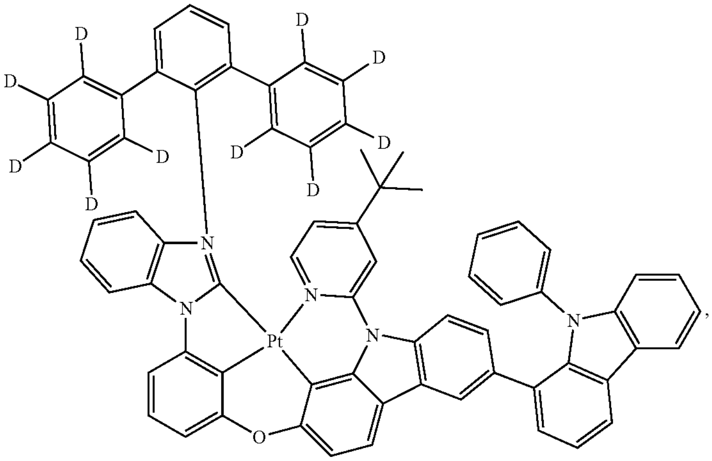
, -continued
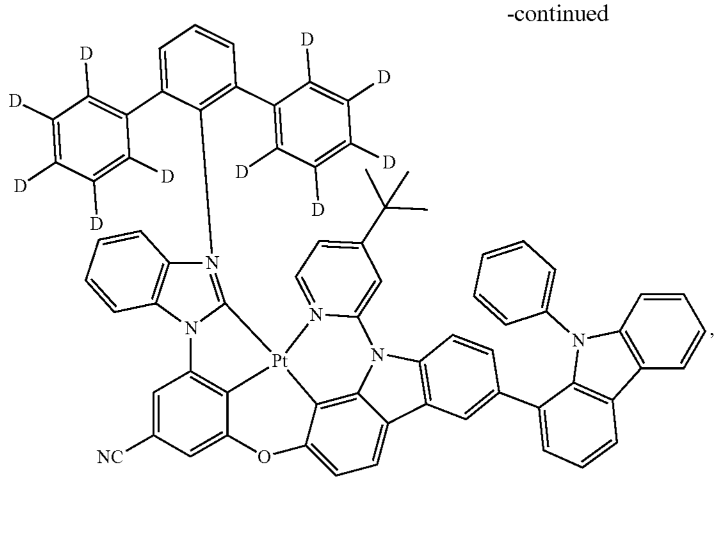
,
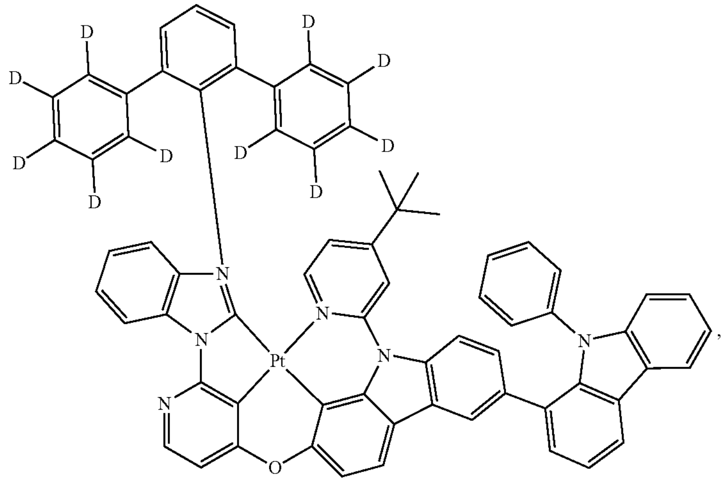
,
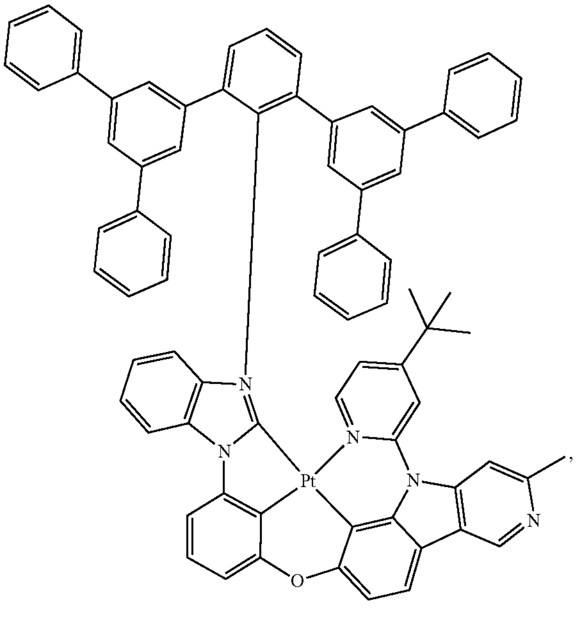
,
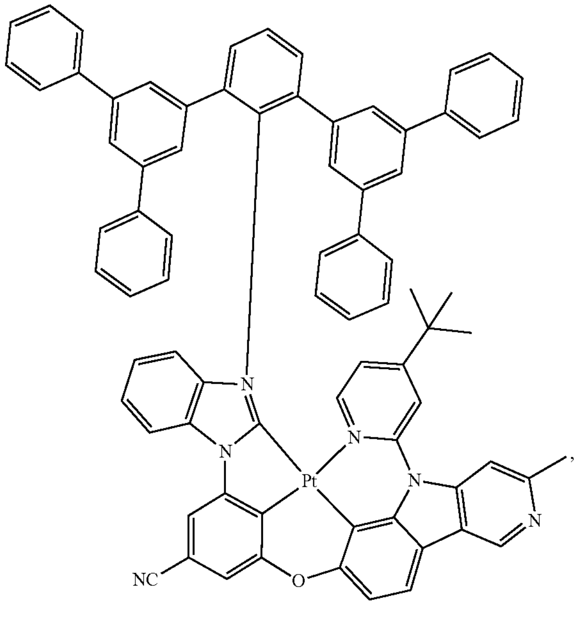
, -continued
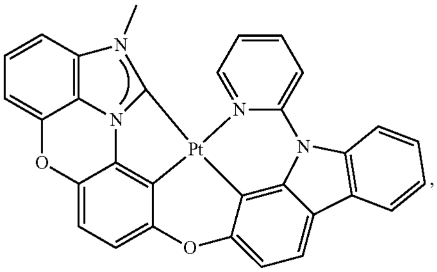,
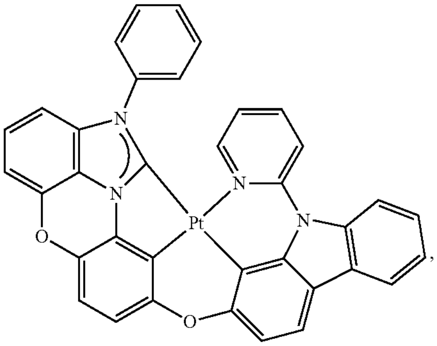,
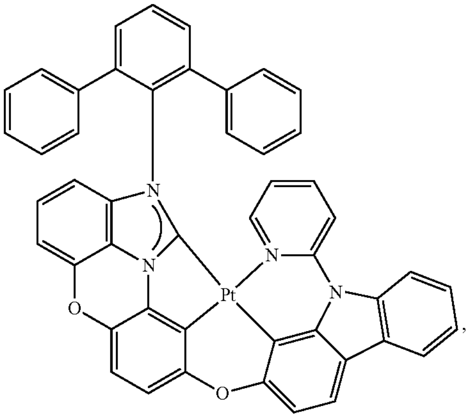,
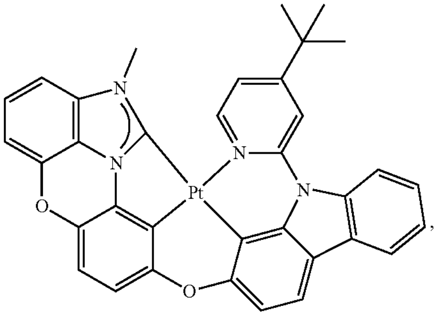,
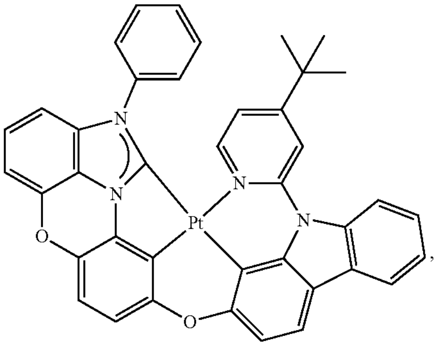,
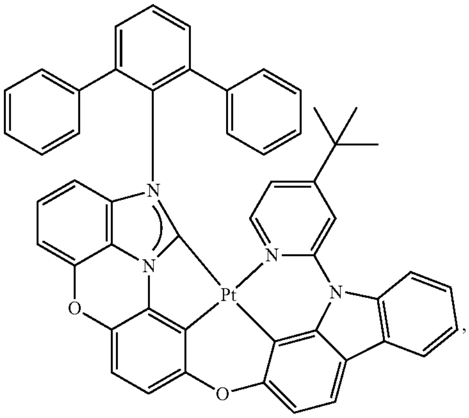, -continued
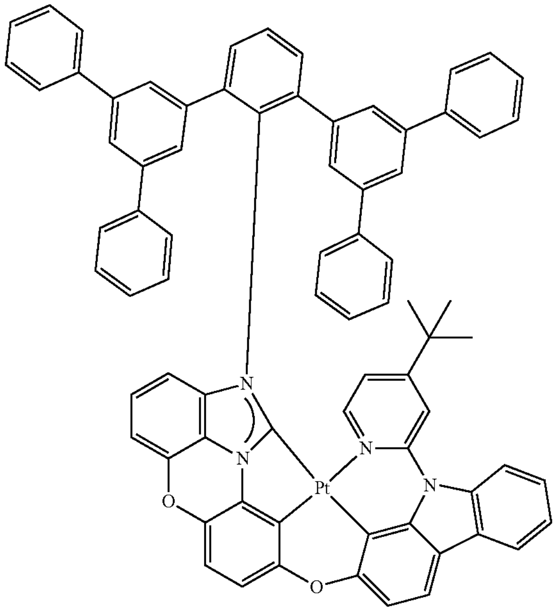
,
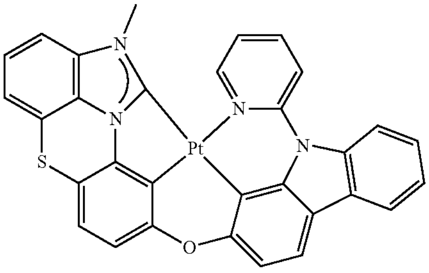
,
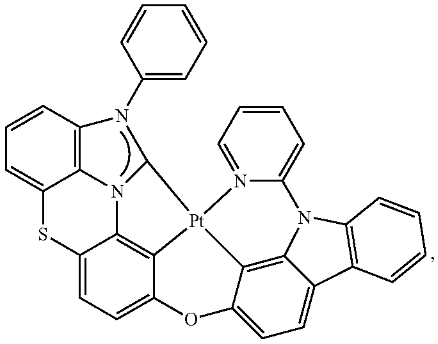
,
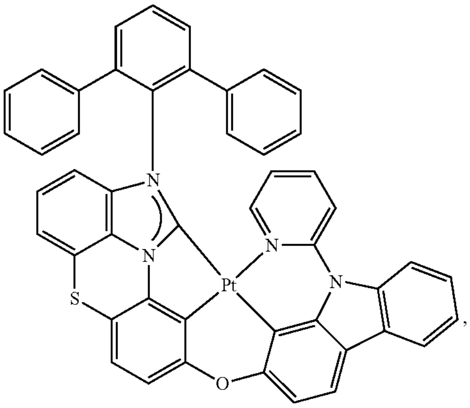
,
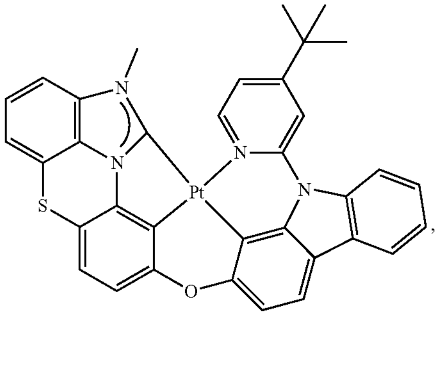
,
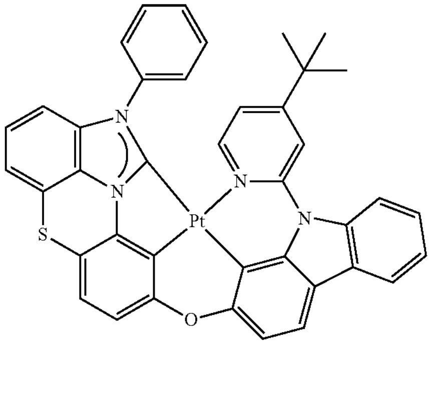
, -continued
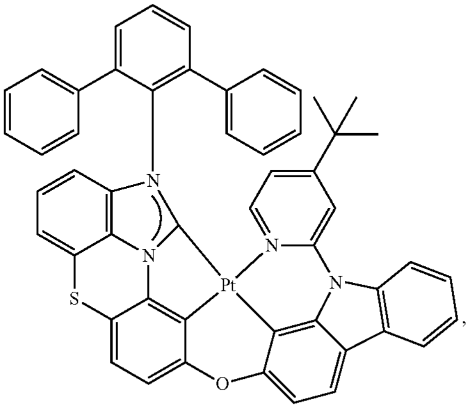,
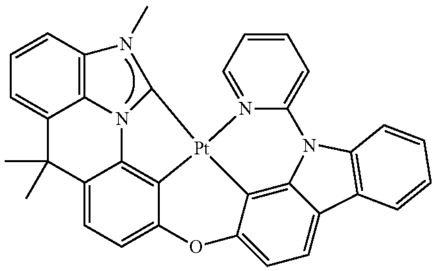,
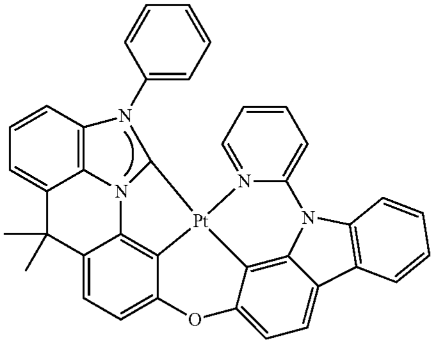,
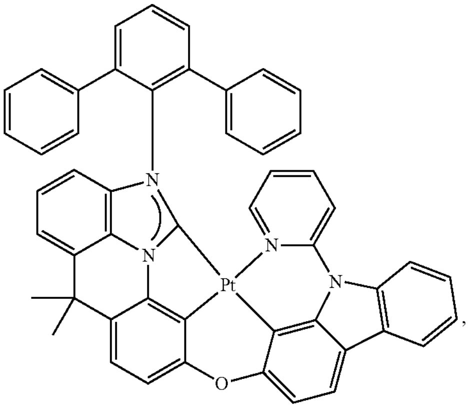,
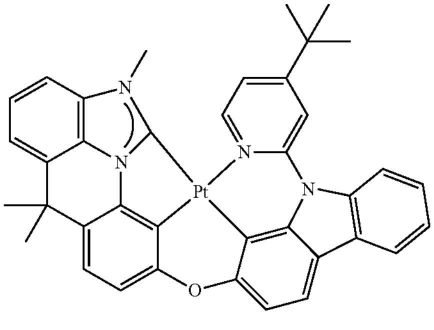,
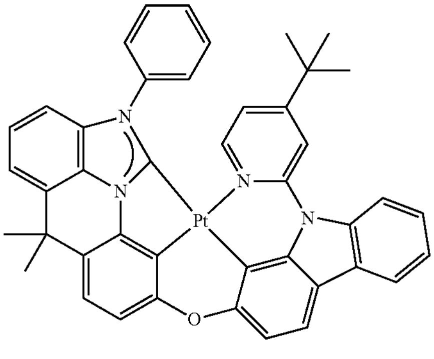, -continued
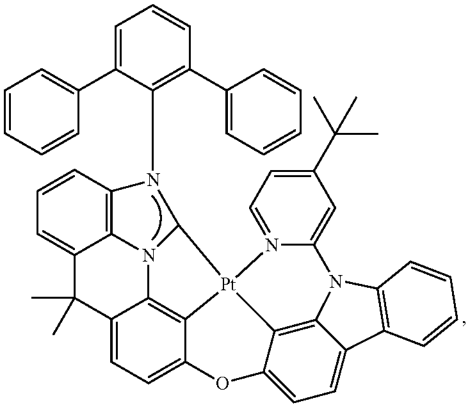
,
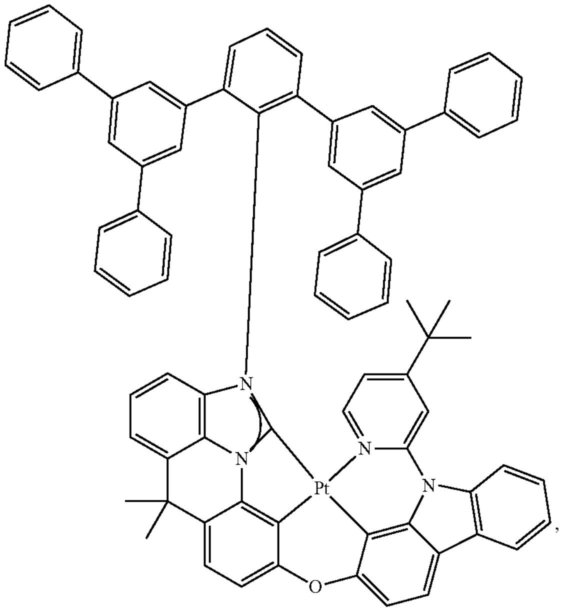
,
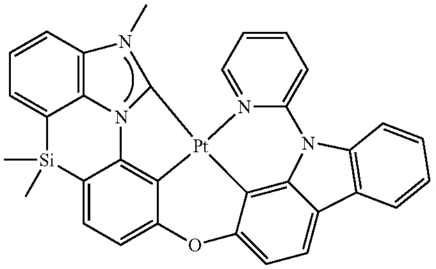
,
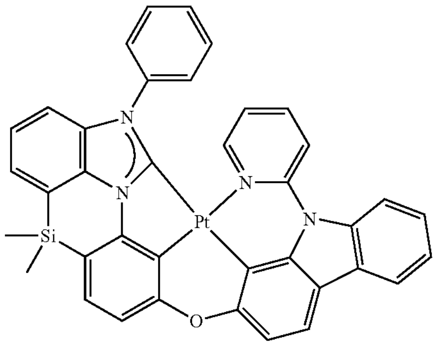
,
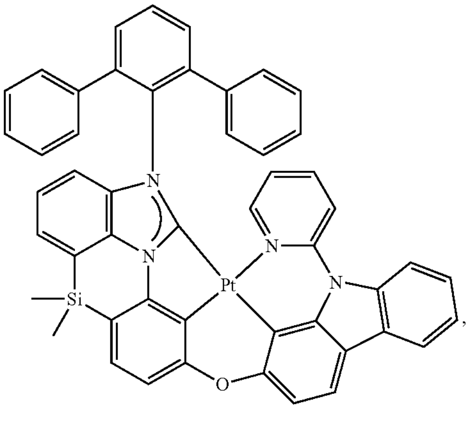
,
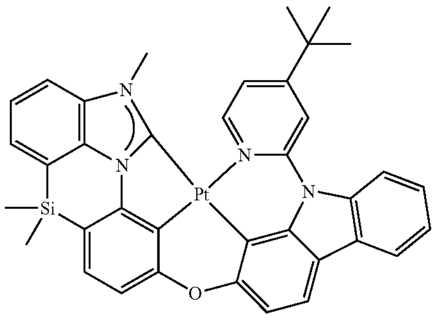
, -continued
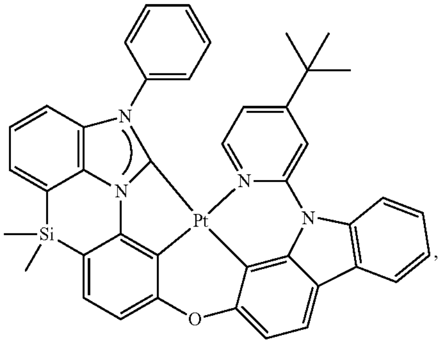,
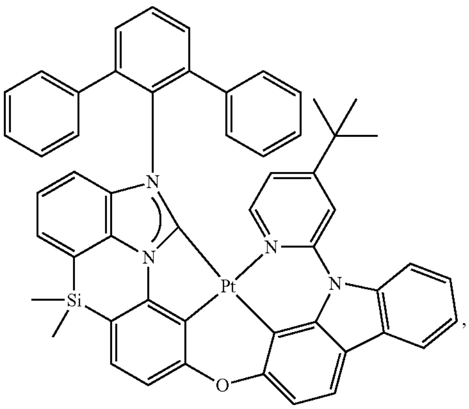,
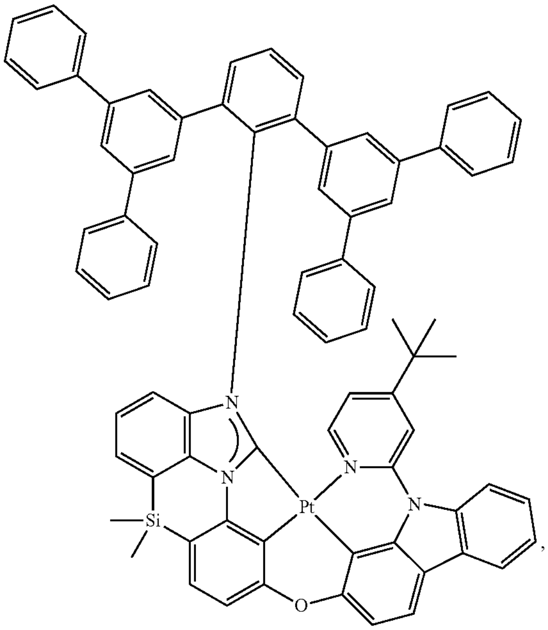,
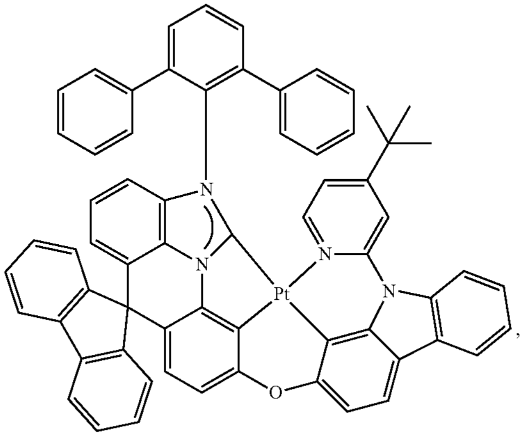,
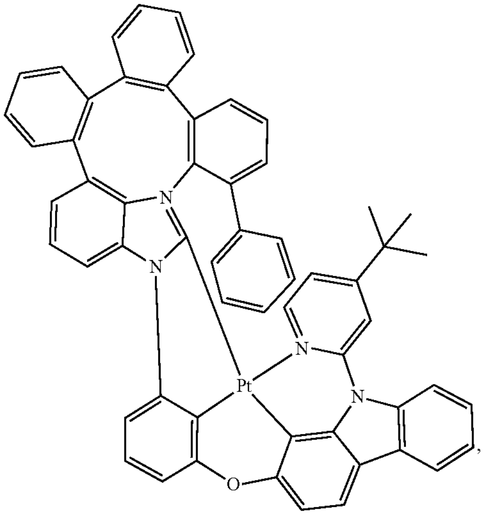,
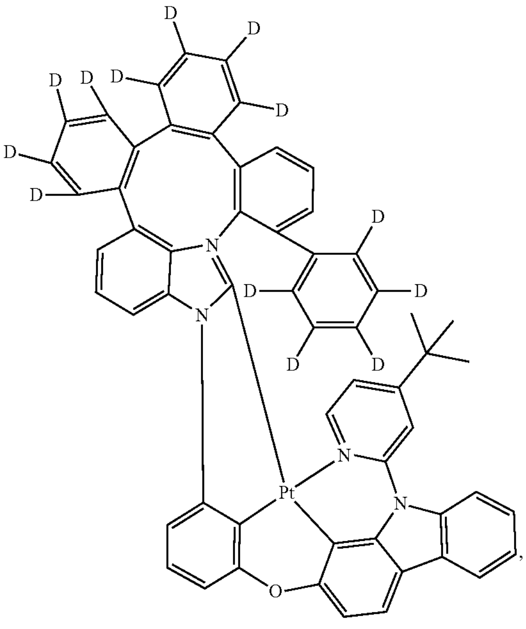, -continued
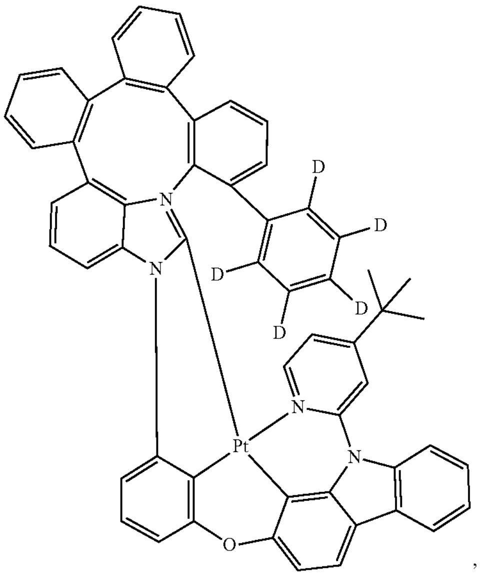
,
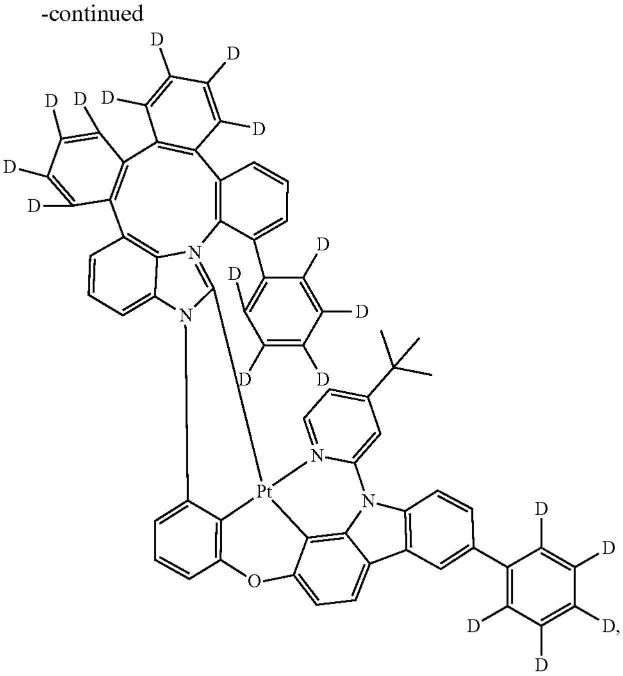
,
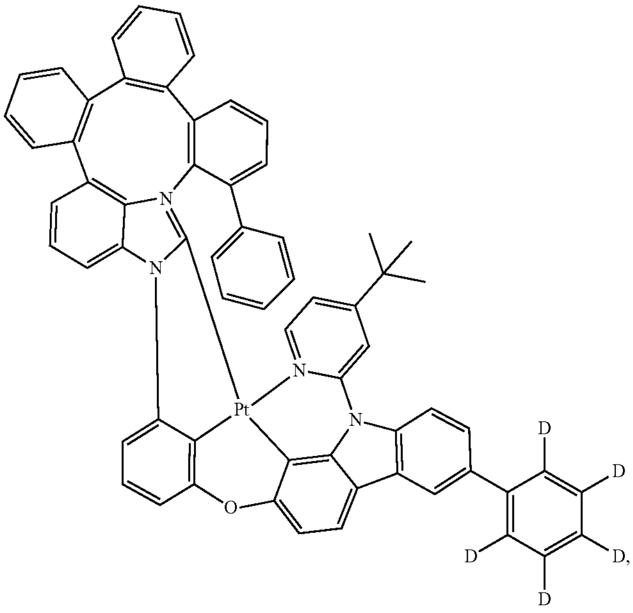
,
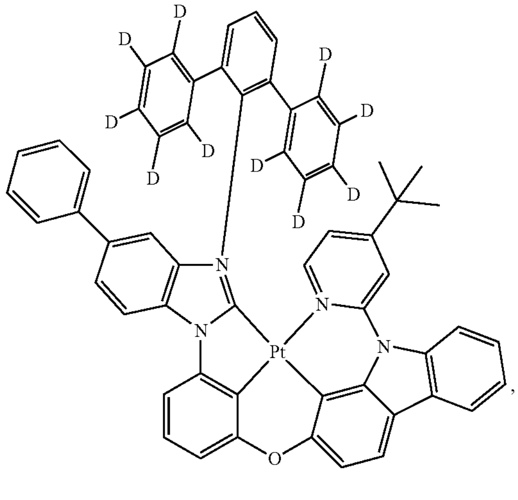
, -continued
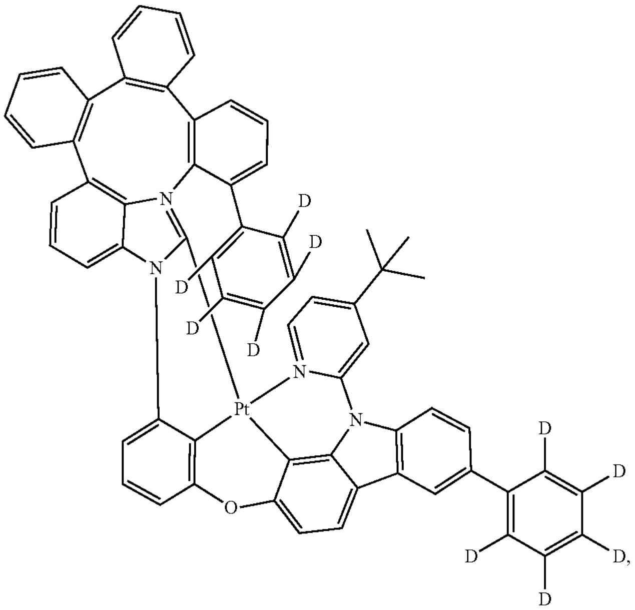
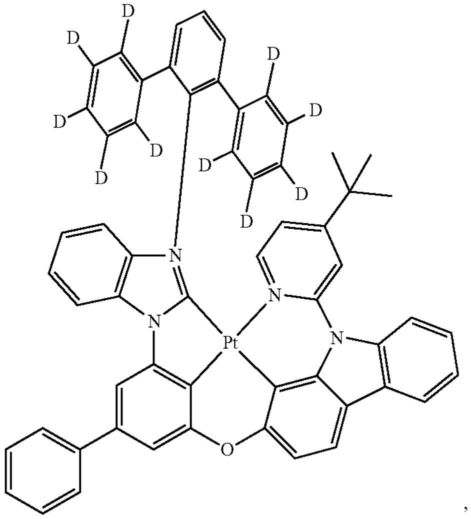
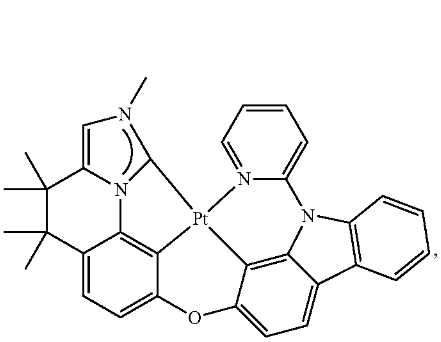
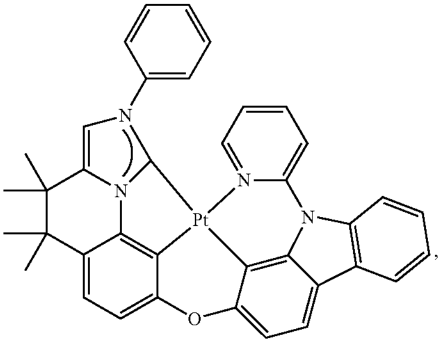
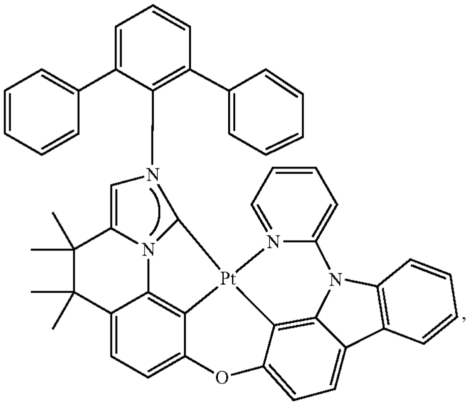
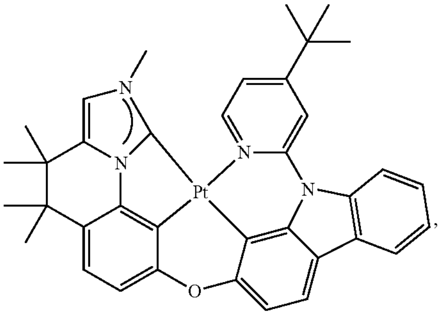

-continued
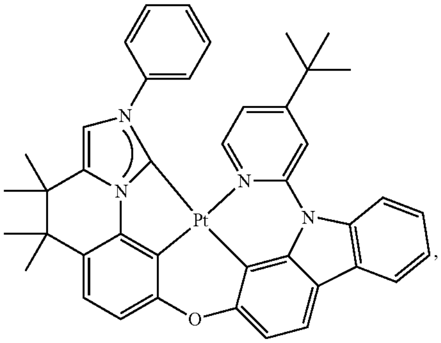,
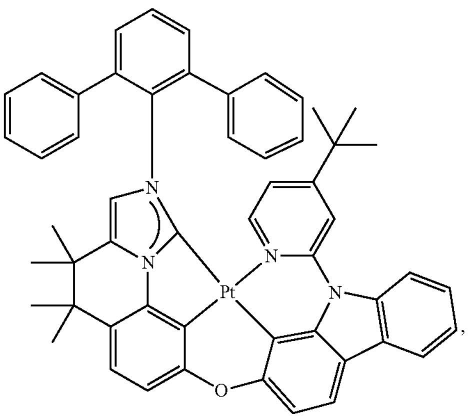,
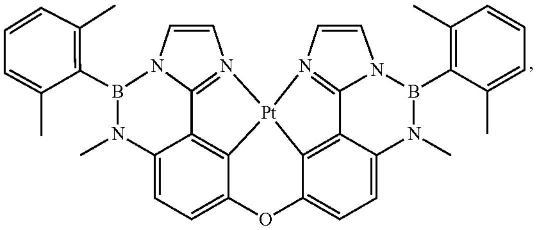,
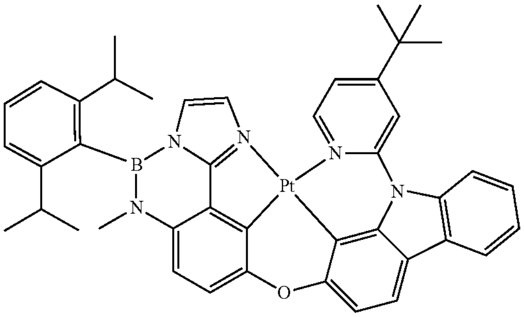,
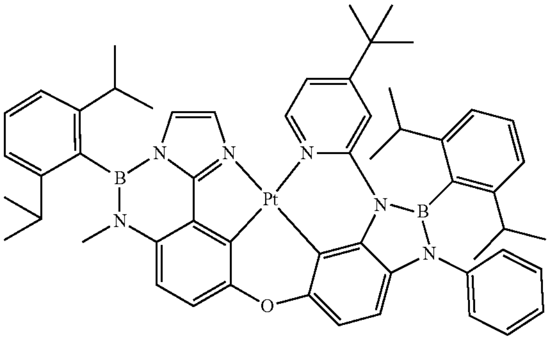,
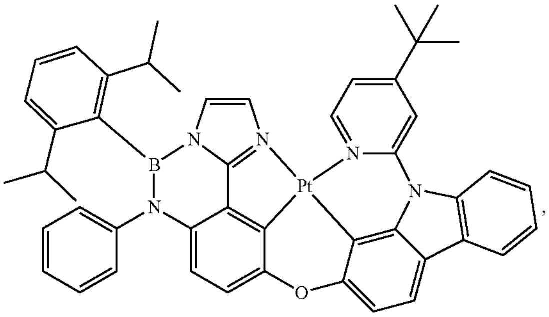,
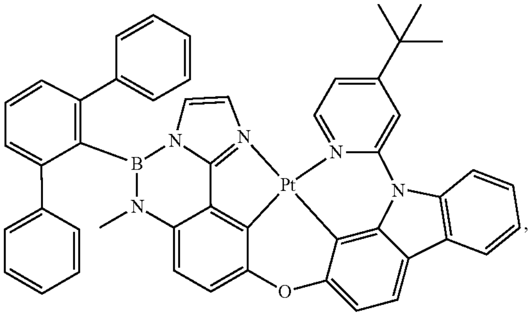, -continued
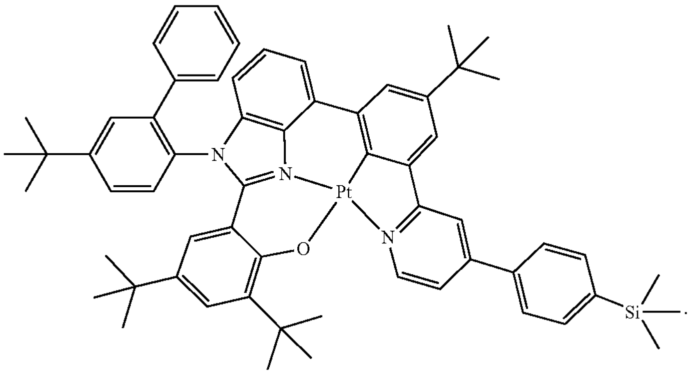
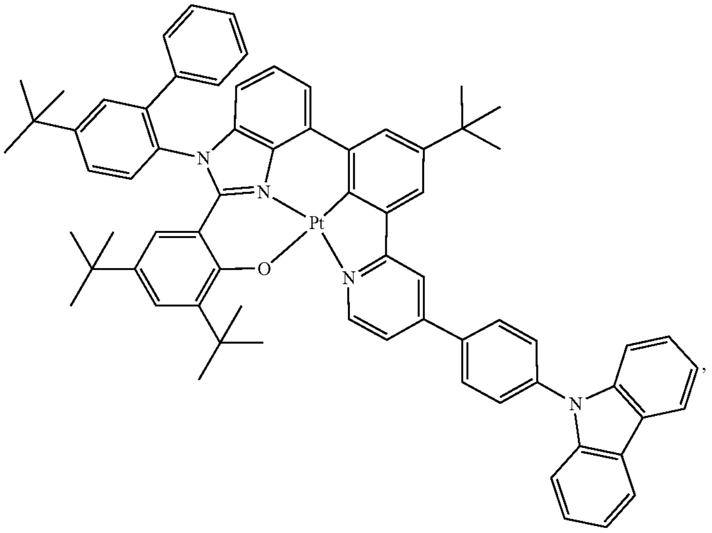
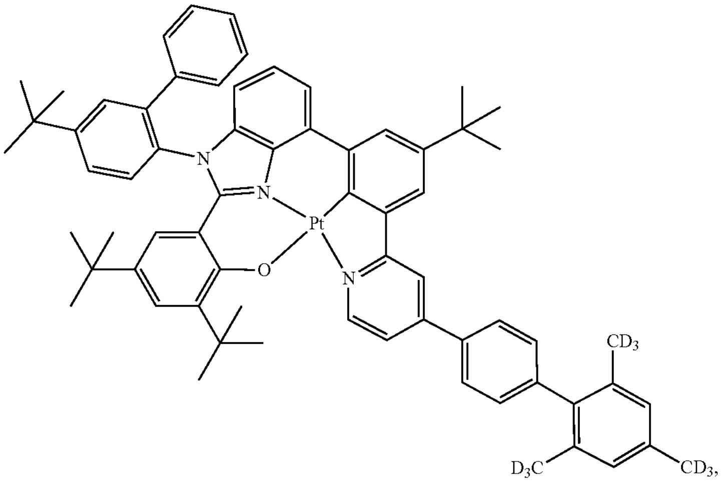

-continued
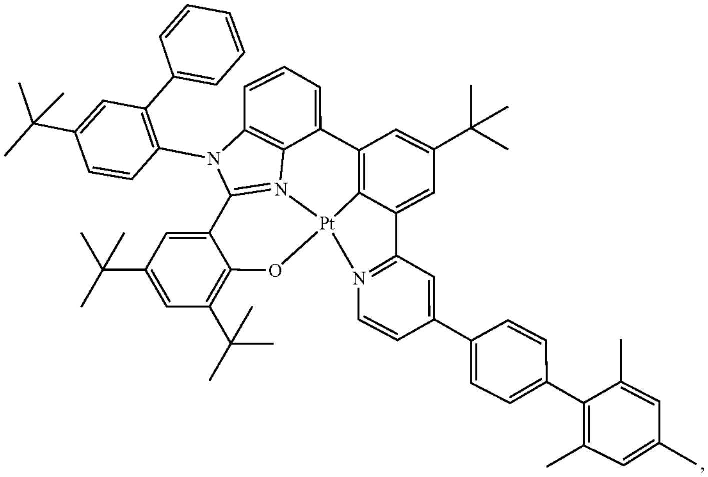
,
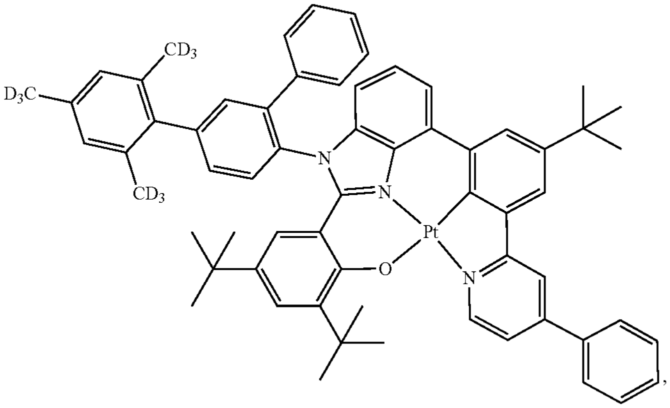
,
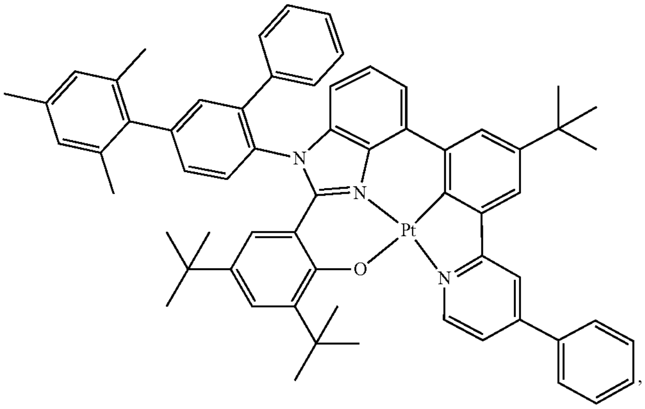
,
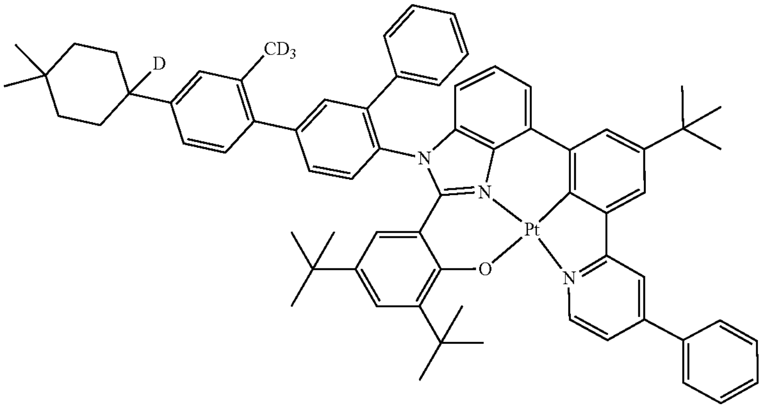
and

-continued

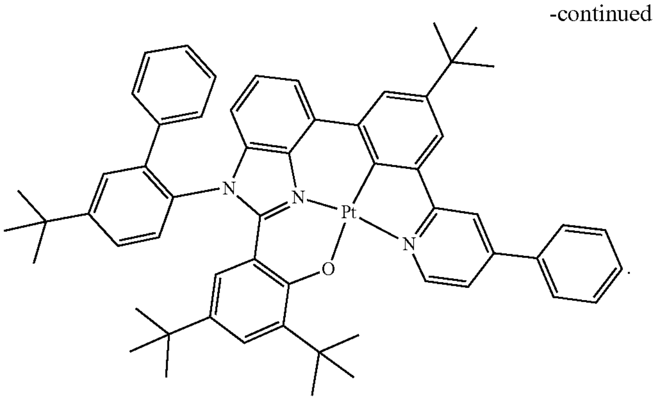

.

19. A consumer product comprising an OLED comprising:

an anode;

a cathode; and an emissive layer, disposed between the anode and the cathode, wherein the emissive layer comprises a phosphorescent dopant, a first host, and a second host, wherein the first host transports holes, the second host transports electrons, wherein the first host is fully or partially deuterated; and at least one of the following conditions is true:

(i) the second host does not comprise a carbazole or an indolocarbazole;

(ii) the second host has a HOMO level <−5.75 eV;

(iii) the second host has a HOMO level >−5.5 eV and is at least 25% deuterated;

(iv) the second host comprises biscarbazole or indolocarbazole moiety that is at least 60% deuterated;

(v) the first host comprises a hole transporting moiety that is at least 50% deuterated and the second host comprises an electron transporting moiety that is at least 50% deuterated; and (vi) the OLED has a lifetime represented by LT95, that is at least 75% higher than the lifetime LT95 of a comparative OLED, wherein the comparative OLED is constructed so that the only difference between the OLED and the comparative OLED is that the comparative OLED has a first host that is not deuterated, and wherein LT95 of a device is measured as a time to reduction of luminance of said device to 95% of its initial luminance at a constant current density of 80 $mA/cm^2$.

* * * * *